US009890152B2

(12) United States Patent
Bryan et al.

(10) Patent No.: US 9,890,152 B2
(45) Date of Patent: Feb. 13, 2018

(54) AMINOPYRIMIDINE COMPOUNDS AS INHIBITORS OF T790M CONTAINING EGFR MUTANTS

(71) Applicant: Genentech, Inc., South San Francisco, CA (US)

(72) Inventors: Marian C. Bryan, San Francisco, CA (US); Bryan Chan, San Carlos, CA (US); Emily Hanan, Redwood City, CA (US); Timothy Heffron, Burlingame, CA (US); Hans Purkey, Burlingame, CA (US); Richard Leonard Elliott, Harlow (GB); Robert Heald, Harlow (GB); Jamie Knight, Harlow (GB); Michael Lainchbury, Harlow (GB); Eileen M. Seward, Harlow (GB)

(73) Assignee: GENENTECH, INC., South San Francisco, CA (US)

( * ) Notice: Subject to any disclaimer, the term of this patent is extended or adjusted under 35 U.S.C. 154(b) by 0 days.

(21) Appl. No.: 14/745,159

(22) Filed: Jun. 19, 2015

(65) Prior Publication Data
US 2016/0016948 A1    Jan. 21, 2016

Related U.S. Application Data

(63) Continuation of application No. PCT/US2013/070788, filed on Nov. 19, 2013.

(60) Provisional application No. 61/728,487, filed on Nov. 20, 2012, provisional application No. 61/784,494, filed on Mar. 14, 2013, provisional application No. 61/866,164, filed on Aug. 15, 2013.

(51) Int. Cl.
*C07D 471/04* (2006.01)
*C07D 498/10* (2006.01)
*A61K 31/506* (2006.01)
*A61K 31/5377* (2006.01)
*C07D 498/08* (2006.01)
*A61K 31/541* (2006.01)
*A61K 31/538* (2006.01)
*C07D 491/107* (2006.01)
*C07D 519/00* (2006.01)
*A61K 31/5355* (2006.01)
*A61K 45/06* (2006.01)

(52) U.S. Cl.
CPC .......... *C07D 471/04* (2013.01); *A61K 31/506* (2013.01); *A61K 31/538* (2013.01); *A61K 31/5355* (2013.01); *A61K 31/5377* (2013.01); *A61K 31/541* (2013.01); *A61K 45/06* (2013.01); *C07D 491/107* (2013.01); *C07D 498/08* (2013.01); *C07D 498/10* (2013.01); *C07D 519/00* (2013.01)

(58) Field of Classification Search
CPC .............. C07D 471/04; C07D 491/107; A61K 31/506; A61K 31/5377
See application file for complete search history.

(56) References Cited

U.S. PATENT DOCUMENTS 7,547,779 B2    6/2009    Lee et al.

FOREIGN PATENT DOCUMENTS

WO    2011/079231 A1    6/2011

OTHER PUBLICATIONS

The European Communication, dated Mar. 29, 2017, in the related European Patent Application No. 17152475.4.
The International Search Report and Written Opinion, dated Jan. 24, 2014, in the related PCT Application No. PCT/US13/70788.
Zhou et al: "Novel mutant-selective EGFR kinase inhibitors against EGFR T790M", Nature, vol. 462, No. 7276, Dec. 24, 2009, pp. 1070-1074.
The English translation of the Japanese Office Action, dated Sep. 12, 2017, in the related Japanese Patent Application No. 2015-543116.

*Primary Examiner* — Jennifer M Kim

(57) ABSTRACT

This invention relates to novel compounds which are inhibitors of T790M containing EGFR mutants, to pharmaceutical compositions containing them, to processes for their preparation, and to their use in therapy for the prevention or treatment of cancer.

29 Claims, No Drawings

AMINOPYRIMIDINE COMPOUNDS AS INHIBITORS OF T790M CONTAINING EGFR MUTANTS

RELATED APPLICATIONS

This application is a continuation of International Application No. PCT/US2013/070788 having an international filing date of Nov. 19, 2013, the entire contents of which are incorporated herein by reference, and which claims benefit under 35 U.S.C. §119 to U.S. Provisional Patent Application No. 61/728,487, filed on Nov. 20, 2012, U.S. Provisional Patent Application No. 61/784,494, filed on Mar. 14, 2013, and U.S. Provisional Patent Application No. 61/866,164, filed on Aug. 15, 2013, the disclosures of which are incorporated herein by reference in their entireties.

FIELD OF INVENTION

This invention relates to novel compounds which are inhibitors of T790M containing EGFR mutants, to pharmaceutical compositions containing them, to processes for their preparation, and to their use in therapy for the prevention or treatment of cancer in a human.

BACKGROUND OF THE INVENTION

The HER family receptor tyrosine kinases are important mediators of cell growth, differentiation and survival. The receptor family includes four distinct members including epidermal growth factor receptor (EGFR, ErbB1, or HER1) HER2 (ErbB2), HER3 (ErbB3) and HER4 (ErbB4). Upon ligand binding the receptors form homo and heterodimers and subsequent activation of the intrinsic tyrosine kinase activity leads to receptor auto-phosphorylation and the activation of downstream signaling molecules (Yarden and Sliwkowski). De-regulation of EGFR by overexpression or mutation has been implicated in many types of human cancer including colorectal, pancreatic, gliomas, head and neck and lung cancer and several EGFR targeting agents have been developed over the years (Ciardiello, Hynes). Erlotinib (Tarceva®), a reversible inhibitor of the EGFR tyrosine kinase was approved by the United States Food and Drug Administration (FDA) for the treatment of recurrent NSCLC and pancreatic cancer. Other reversible EGFR tyrosine kinase inhibitors ("TKI") include gefitinib and lapatinib.

The most impressive single agent activity of EGFR tyrosine kinase inhibitors is observed in a subset of non-small cell lung cancer (NSCLC) patients whose tumors harbor somatic kinase domain mutations, whereas clinical benefit in wild-type EGFR patients is greatly diminished (Lynch 2004, Paez 2004). The most common somatic mutations of EGFR are exon 19 deletions with delta 746-750 the most prevalent mutation and the exon 21 amino acid substitutions with L858R the most frequent mutation (Sharma). Intriguingly, this is a subset of patients characterized by high prevalence of adenocarcinomas, females, never-smokers and Asians (Miller, Pao 2004).

Patients with EGFR-mutant lung cancer eventually develop disease progression after 10-14 months on EGFR tyrosine kinase inhibitors (Pao 2010). Over 50% of patients that progress on tyrosine kinase inhibitors acquire a secondary mutation in the kinase domain at position 790 that is known as the gatekeeper residue. Replacement of threonine by the bulkier residue methionine (T790M mutation) leads to an increase in the affinity for ATP relative to mutant forms of EGFR associated with clinical benefits from EGFR TKI treatment and to a reduced affinity for TKIs which taken together confers drug resistance (Yun). Similar gatekeeper mutations in the kinase domain that cause drug resistance are seen in Abl and Kit (Tamborini, Gorre). The present invention demonstrates the generation of selective molecules that specifically inhibit T790M containing EGFR mutants.

REFERENCES

Yarden, Y., Sliwkowski, M X. Untangling the ErbB signalling network. Nature Review Mol Cell Biol. 2001 February; 2(2):127-37.

Ciardiello, F., and Tortora, G. (2008). EGFR antagonists in cancer treatment. The New England journal of medicine 358, 1160-1174.

Hynes N E, MacDonald G. ErbB receptors and signaling pathways in cancer. Curr Opin Cell Biol. 2009 April; 21(2):177-84.

Lynch, T. J., Bell, D. W., Sordella, R., Gurubhagavatula, S., Okimoto, R. A., Brannigan, B. W., Harris, P. L., Haserlat, S. M., Supko, J. G., Haluska, F. G., et al. (2004). Activating mutations in the epidermal growth factor receptor underlying responsiveness of non-small-cell lung cancer to gefitinib. The New England journal of medicine 350, 2129-2139.

Paez, J. G., Janne, P. A., Lee, J. C., Tracy, S., Greulich, H., Gabriel, S., Herman, P., Kaye, F. J., Lindeman, N., Boggon, T. J., et al. (2004). EGFR mutations in lung cancer: correlation with clinical response to gefitinib therapy. Science (New York, N.Y. 304, 1497-1500.

Sharma S V, Bell D W, Settleman J, Haber D A. Epidermal growth factor receptor mutations in lung cancer. Nat Rev Cancer. 2007 March; 7(3):169-81.

Miller V A, Kris M G, Shah N, Patel J, Azzoli C, Gomez J, Krug L M, Pao W, Rizvi N, Pizzo B, Tyson L, Venkatraman E, Ben-Porat L, Memoli N, Zakowski M, Rusch V, Heelan R T. Bronchioloalveolar pathologic subtype and smoking history predict sensitivity to gefitinib in advanced non-small-cell lung cancer. J Clin Oncol. 2004 Mar. 15; 22(6):1103-9.

Pao W, Miller V, Zakowski M, Doherty J, Politi K, Sarkaria I, Singh B, Heelan R, Rusch V, Fulton L, Mardis E, Kupfer D, Wilson R, Kris M, Varmus H. EGF receptor gene mutations are common in lung cancers from "never smokers" and are associated with sensitivity of tumors to gefitinib and erlotinib. Proc Natl Acad Sci USA. 2004 Sep. 7; 101(36):13306-11.

Pao W, Chmielecki J. Rational, biologically based treatment of EGFR-mutant non-small-cell lung cancer. Nat Rev Cancer. 2010 November; 10(11):760-74.

Yun C H, Mengwasser K E, Toms A V, Woo M S, Greulich H, Wong K K, Meyerson M, Eck M J. The T790M mutation in EGFR kinase causes drug resistance by increasing the affinity for ATP. Proc Natl Acad Sci USA. 2008 Feb. 12; 105(6):2070-5.

Tamborini E, Bonadiman L, Greco A, Albertini V, Negri T, Gronchi A, Bertulli R, Colecchia M, Casali P G, Pierotti M A, Pilotti S. A new mutation in the KIT ATP pocket causes acquired resistance to imatinib in a gastrointestinal stromal tumor patient. Gastroenterology. 2004 July; 127 (1):294-9.

Gorre M E, Mohammed M, Ellwood K, Hsu N, Paquette R, Rao P N, Sawyers C L. Clinical resistance to STI-571 cancer therapy caused by BCR-ABL gene mutation or amplification. Science. 2001 Aug. 3; 293(5531):876-80.

SUMMARY OF THE INVENTION

This invention relates to a compound of Formula (I):

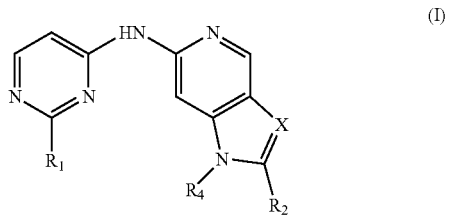

(I)

wherein,
X is $CR_3$ or N;
$R_1$ is $C_3$-$C_7$heterocycloalkyl, heteroaryl, aryl, —O($C_1$-$C_6$alkyl), —O($C_3$-$C_7$cycloalkyl) or —$NR_aR_b$, wherein said $C_3$-$C_7$heterocycloalkyl and heteroaryl may be further substituted with one to five $R_f$ groups;
$R_2$ is hydrogen, —$(CH_2)_m$aryl, —$(CH_2)_m$ heteroaryl, —$(CH_2)_mC_4$-$C_7$heterocycloalkyl, $C_1$-$C_6$alkyl, alkylamino, alkoxy or —$CH_2O(C_1$-$C_3$alkyl);
$R_3$ is hydrogen, $C_1$-$C_3$alkyl, CN, COOH, $C_3$-$C_7$cycloalkyl, heterocycloalkyl, —NHC(O)$C_1$-$C_6$alkyl, —$(CH_2)_mC(O)NR_aR_b$ or heteroaryl;
$R_4$ is hydrogen, $C_3$-$C_7$heterocycloalkyl, $C_3$-$C_7$cycloalkyl, $C_1$-$C_6$alkyl, —$(CH_2)_m$phenyl or —$(CH_2)_m$heteroaryl;
wherein each $R_a$ is independently H or $C_1$-$C_6$alkyl; each $R_b$ is independently H, $C_1$-$C_6$alkyl, alkoxy, amino, —$(CH_2)_mC_3$-$C_7$cycloalkyl, —$(CH_2)_mC_3$-$C_7$heterocycloalkyl or —$(CH_2)_m$heteroaryl, wherein said $C_3$-$C_7$heterocycloalkyl and heteroaryl may be further substituted with one to three groups selected from the group consisting of halo, hydroxy, $C_1$-$C_3$alkyl, amino, oxo, amide, sulfonyl, sulfoxide, sulfoximinyl, alkoxy, CN and acyl; $R_a$ and $R_b$ together may form a $C_3$-C7cycloalkyl, $C_3$-$C_7$heterocycloalkyl, or heteroaryl ring;
wherein each $R_f$ is independently selected from the group consisting of $C_1$-$C_3$alkyl, alkoxy, amino, hydroxyl, alkylamino, amide, urea, oxo, halo, pyrazolyl, imidazolyl, triazolyl, CN, —NHC(O)($C_1$-$C_3$alkyl), acyl, sulfonyl, sulfoxide, sulfoximinyl, sulfonamide, amide, —$(CH_2)_mC_3$-$C_7$heterocycloalkyl, —O($C_1$-$C_6$alkyl), —C(O)$OR_a$;
each m is independently 0, 1, 2 or 3;
or a pharmaceutically acceptable salt thereof.

This invention also relates to pharmaceutical compositions of compounds of Formula (I).

This invention also relates to a method of inhibiting T790M containing EGFR mutants.

This invention also relates to a method of treating cancer, use of compounds of Formula (I) in therapy, and use of compounds of Formula (I) in manufacturing a medicament for treating cancer.

This invention also relates to method of preparing compounds of Formula (I).

DETAILED DESCRIPTION OF THE INVENTION

Definitions

As used herein, unless defined otherwise, the term "acyl" refers to the group —C(O)R', where R' is alkyl, $C_3$-$C_6$cycloalkyl, or heterocyclyl, as each is defined herein.

As used herein, unless defined otherwise, the term "alkoxy" refers to the group —OR', where R' is $C_1$-$C_4$alkyl or $C_3$-$C_6$cycloalkyl as defined above. Examples of "alkoxy" include methoxy, ethyoxy, isopropoxy, propoxy, butoxy, t-butoxy, isobutoxy, cyclopropoxy, and cyclobutoxy, and halogenated forms thereof, e.g. fluoromethoxy and difluoromethoxy.

As used herein, unless defined or specified otherwise, the term "alkyl" (or "alkylene") refers to a straight or branched hydrocarbon chain having from one to twelve carbon atoms, which may be unsubstituted or substituted, saturated or unsaturated with multiple degrees of substitution, for example one, two or three, included within the present invention. Examples of substituents are selected from the group consisting of halo, trifluoromethyl, difluoromethyl, amino, alkylamino, cyano, sulfonyl, sulfonamide, sulfoxide, amide, hydroxy, alkoxy, ester, carboxylic acid and alkylthio. Examples of "alkyl" as used herein include, but are not limited to, methyl, ethyl, propyl, isopropyl, isobutyl, n-butyl, t-butyl, isopentyl, n-pentyl, and the like, as well as substituted versions thereof. Examples of substituted alkyl include but are not limited to, difluoromethyl and trifluoromethyl. Unsaturated alkyl can also be referred to as alkenyl or alkynyl, which may be substituted as described above. Examples of unsaturated alkyl include, but are not limited to, ethenyl or vinyl (—CH=$CH_2$), prop-1-enyl (—CH=$CHCH_3$), prop-2-enyl (—$CH_2$CH=$CH_2$), 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl, hexa-1,3-dienyl, ethynyl (—C≡CH), prop-1-ynyl (—C≡$CCH_3$), prop-2-ynyl (propargyl, —$CH_2$C≡CH), but-1-ynyl, but-2-ynyl and but-3-ynyl.

As used herein, the term "alkylamino" refers to the group —NR'R", wherein R' is H, $C_1$-$C_6$alkyl or $C_3$-$C_6$cycloalkyl, and R" is $C_1$-$C_6$alkyl or $C_3$-$C_6$cycloalkyl.

As used herein, unless defined otherwise, the term "amide" refers to the group —C(O)NR'R", wherein R' and R" are each independently H, $C_1$-$C_6$alkyl, or $C_3$-$C_6$cycloalkyl.

As used herein, unless defined otherwise, the term "aryl" refers to an aromatic, hydrocarbon, ring system. The ring system may be monocyclic or fused polycyclic (e.g., bicyclic, tricyclic, etc.), substituted or unsubstituted. In various embodiments, the monocyclic aryl ring is $C_5$-$C_{10}$, or $C_5$-$C_7$, or $C_5$-$C_6$, where these carbon numbers refer to the number of carbon atoms that form the ring system. A $C_6$ ring system, i.e. a phenyl ring, is an aryl group. In various embodiments, the polycyclic ring is a bicyclic aryl group, where examples of bicyclic aryl groups include are $C_8$-$C_{12}$, or $C_9$-$C_{10}$. A naphthyl ring, which has 10 carbon atoms, is a polycyclic aryl group. Examples of substituents for aryl are described below in the definition of "optionally substituted".

As used herein, unless defined otherwise, the term "cyano" refers to the group —CN.

As used herein, unless defined otherwise, "Cycloalkyl" refers to a non-aromatic, substituted or unsubstituted, saturated or partially unsaturated hydrocarbon ring group. Examples of substituents are described in the definition of "optionally substituted". In one example, the cycloalkyl group is 3 to 12 carbon atoms ($C_3$-$C_{12}$). In other examples, cycloalkyl is $C_3$-$C_8$, $C_3$-$C_{10}$ or $C_5$-$C_{10}$. In other examples, the cycloalkyl group, as a monocycle, is $C_3$-$C_8$, $C_3$-$C_6$ or $C_5$-$C_6$. In another example, the cycloalkyl group, as a bicycle, is $C_7$-$C_{12}$. In another example, the cycloalkyl group, as a spiro system, is $C_5$-$C_{12}$. Examples of monocyclic cycloalkyl include cyclopropyl, cyclobutyl, cyclopentyl, 1-cyclopent-1-enyl, 1-cyclopent-2-enyl, 1-cyclopent-3-enyl, cyclohexyl, perdeuteriocyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl and cyclododecyl. Exemplary arrangements of bicyclic cycloalkyls having 7 to 12 ring atoms include, but are not limited to, [4,4], [4,5], [5,5], [5,6] or [6,6] ring systems. Exemplary bridged bicyclic cycloalkyls include, but are not limited to, bicyclo[2.2.1]heptane, bicyclo[2.2.2]octane and bicyclo[3.2.2]nonane. Examples of spiro cycloalkyl include, spiro[2.2]pentane, spiro[2.3]hexane, spiro[2.4]heptane, spiro[2.5]octane and spiro[4.5]decane.

As used herein, unless defined otherwise, the term "ester" refers to the group —C(O)OR', where R' is $C_1$-$C_6$alkyl, or $C_3$-$C_6$cycloalkyl.

As used herein, unless defined otherwise, the term "heterocycle" "heterocycloalkyl" or "heterocyclyl" refers to unsubstituted and substituted mono- or polycyclic non-aromatic ring system containing 2 to 12 ring carbon atoms and 1 to 3 ring hetero atoms. Polycyclic ring systems can be fused bi- or tri-cyclic, spiro or bridged. Examples of heteroatoms include N, O, and S, including N-oxides, sulfur oxides, and dioxides. In one embodiment, the ring is three to eight-membered and is either fully saturated or has one or more degrees of unsaturation. Multiple degrees of substitution are included within the present definition. Examples of substituents are defined hereunder. Examples of "heterocyclic" groups include, but are not limited to tetrahydrofuranyl, pyranyl, 1,4-dioxanyl, 1,3-dioxanyl, piperidinyl, pyrrolidinyl, morpholinyl, azetidinyl, piperazinyl, pyrrolidinonyl, piperazinonyl, pyrazolidinyl, and their various tautomers.

As used herein, unless defined otherwise, the term "heteroaryl", unless defined otherwise, refers to an aromatic ring system containing 1 to 9 carbon(s) and at least one heteroatom. Examples of heteroatoms include N, O, and S. Heteroaryl may be monocyclic or polycyclic, substituted or unsubstituted. A monocyclic heteroaryl group may have 2 to 6 ring carbon atoms and 1 to 3 ring hetero atoms in the ring, while a polycyclic heteroaryl may contain 3 to 9 ring carbon atoms and 1 to 5 ring hetero atoms. A polycyclic heteroaryl ring may contain fused, spiro or bridged ring junctions, for example, bicyclic heteroaryl is a polycyclic heteroaryl. Bicyclic heteroaryl rings may contain from 8 to 12 member atoms. Monocyclic heteroaryl rings may contain from 5 to 8 member atoms (carbons and heteroatoms). Exemplary heteroaryl groups include but are not limited to: benzofuranyl, benzothiophenyl, furanyl, imidazolyl, indolyl, azaindolyl, azabenzimidazolyl, benzoxazolyl, benzthiazolyl, benzothiadiazolyl, benzotriazolyl, benzoimidazolyl, tetrazinyl, tetrazolyl, isothiazolyl, oxazolyl, isoxazolyl, pyrazinyl, pyrazolyl, pyridazinyl, pyridinyl, pyrimidinyl, pyrrolyl, quinolinyl, quinazolinyl, quinoxalinyl, triazinyl, thiazolyl and thiophenyl. Examples of substituents for heteroaryl are described below in the definition of "optionally substituted".

As used herein, unless defined otherwise, the term "urea" refers to the group —NR'C(O)NR", wherein R' and R" are each independently H, $C_1$-$C_6$alkyl, or $C_3$-$C_6$cycloalkyl.

As used herein, unless defined otherwise, the term "optionally" means that the subsequently described event(s) may or may not occur, and includes both event(s) that occur and event(s) that do not occur.

As used herein, unless defined otherwise, the phrase "optionally substituted" or variations thereof denote an optional substitution, including multiple degrees of substitution, with one or more substituent group, for example, one, two or three. The phrase should not be interpreted as duplicative of the substitutions herein described and depicted. Exemplary optional substituent groups include acyl, $C_1$-$C_6$alkyl, sulfonyl, amino, sulfonamide, sulfoxide, alkoxy, cyano, halo, urea, ester, carboxylic acid, amide, hydroxy, oxo, and nitro.

As used herein, unless defined otherwise, the term "treatment" refers to alleviating the specified condition, eliminating or reducing one or more symptoms of the condition, slowing or eliminating the progression of the condition As used herein, unless defined otherwise, the term "effective amount" means that amount of a drug or pharmaceutical agent that will elicit the biological or medical response of a tissue, system, animal, or human that is being sought, for instance, by a researcher or clinician.

As used herein, unless defined otherwise, the term "therapeutically effective amount" means any amount which, as compared to a corresponding subject who has not received such amount, results in treatment of a disease, disorder, or side effect, or a decrease in the rate of advancement of a disease or disorder. The term also includes within its scope amounts effective to enhance normal physiological function. For use in therapy, therapeutically effective amounts of a compound of Formula I, as well as salts thereof, may be administered as the raw chemical. Additionally, the active ingredient may be presented as a pharmaceutical composition.

This invention relates to a compound of Formula (I), or pharmaceutically acceptable salt thereof.

This invention relates to a compound of Formula (I), or pharmaceutically acceptable salt thereof.

This invention also relates to a compound of Formula (I), wherein X is N; or a pharmaceutically acceptable salt thereof.

This invention also relates to a compound of Formula (I), wherein X is $CR_3$; or a pharmaceutically acceptable salt thereof.

This invention also relates to any one of the above compounds, wherein $R_1$ is $C_3$-$C_7$heterocycloalkyl; or a pharmaceutically acceptable salt thereof.

This invention also relates to any one of the above compounds, wherein $R_1$ is heteroaryl; or a pharmaceutically acceptable salt thereof.

This invention also relates to any one of the above compounds, wherein $R_1$ is —$NR_aR_b$; or a pharmaceutically acceptable salt thereof.

This invention also relates to any one of the above compounds, wherein $R_2$ is $C_1$-$C_6$alkyl; or a pharmaceutically acceptable salt thereof.

This invention also relates to any one of the above compounds, wherein $R_2$ is hydrogen, —$(CH_2)_m$aryl, heteroaryl, $C_4$-$C_7$heterocycloalkyl, alkylamino, alkoxy or —$(CH_2)_mO(C_1$-$C_3$alkyl); or a pharmaceutically acceptable salt thereof.

This invention also relates to any one of the above compounds, wherein $R_4$ is hydrogen or $C_1$-$C_6$alkyl;

This invention also relates to any one of the above applicable compounds, wherein $R_3$ is hydrogen, $C_1$-$C_3$alkyl, heteroaryl or —$(CH_2)_mC(O)NR_aR_b$; or a pharmaceutically acceptable salt thereof.

This invention also relates to any one of the above applicable compounds, wherein $R_1$ is a $C_3$-$C_7$heterocycloalkyl selected from the group consisting of piperidinyl, piperizinyl, pyrazolyl and pyrrolidinyl, wherein said $C_3$-$C_7$heterocycloalkyl may be further substituted with one to five $R_f$ groups selected from $C_1$-$C_6$alkyl, alkoxy, halo, hydroxy, sulfonyl, and sulfonamide; or a pharmaceutically acceptable salt thereof.

This invention also relates to any one of the above applicable compounds, wherein $R_2$ is hydrogen or $C_1$-$C_3$alkyl; or a pharmaceutically acceptable salt thereof.

This invention also relates to any one of the above applicable compounds, wherein $R_3$ is hydrogen, $C_1$-$C_3$alkyl or —C(O)NH$_2$; or a pharmaceutically acceptable salt thereof.

This invention also relates to any one of the above applicable compounds, wherein $R_4$ is hydrogen or isopropyl; $R_f$ is F; or a pharmaceutically acceptable salt thereof.

This invention also relates to any one of the examples in the Experimental section.

Typically, but not absolutely, the salts of the present invention are pharmaceutically acceptable salts. Salts encompassed within the term "pharmaceutically acceptable salts" refer to non-toxic salts of the compounds of this invention. Salts of the disclosed compounds containing a basic amine or other basic functional group may be prepared by any method known in the art, including treatment of the free base with an inorganic acid, such as hydrochloric acid, hydrobromic acid, sulfuric acid, nitric acid, phosphoric acid, and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, pyranosidyl acid, such as glucuronic acid or galacturonic acid, alpha-hydroxy acid, such as citric acid or tartaric acid, amino acid, such as aspartic acid or glutamic acid, aromatic acid, such as benzoic acid or cinnamic acid, sulfonic acid, such as p-toluenesulfonic acid, methanesulfonic acid, ethanesulfonic acid or the like. Examples of pharmaceutically acceptable salts include sulfates, pyrosulfates, bisulfates, sulfites, bisulfites, phosphates, chlorides, bromides, iodides, acetates, propionates, decanoates, caprylates, acrylates, formates, isobutyrates, caproates, heptanoates, propiolates, oxalates, malonates succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, phenylacetates, phenylpropionates, phenylbutrates, citrates, lactates, γ-hydroxybutyrates, glycolates, tartrates mandelates, and sulfonates, such as xylenesulfonates, methanesulfonates, propanesulfonates, naphthalene-1-sulfonates and naphthalene-2-sulfonates.

Salts of the disclosed compounds containing a carboxylic acid or other acidic functional group can be prepared by reacting with a base. Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl) amine, procaine, dibenzylpiperidine, dehydroabietylamine, N,N'-bisdehydroabietylamine, glucamine, N-methylglucamine, collidine, choline, quinine, quinoline, and basic amino acid such as lysine and arginine.

Other salts, which are not pharmaceutically acceptable, may be useful in the preparation of compounds of this invention and these should be considered to form a further aspect of the invention. These salts, such as oxalic or trifluoroacetate, while not in themselves pharmaceutically acceptable, may be useful in the preparation of salts useful as intermediates in obtaining the compounds of the invention and their pharmaceutically acceptable salts.

The compound of Formula (I) may exist in solid or liquid form. In the solid state, it may exist in crystalline or noncrystalline form, or as a mixture thereof. The skilled artisan will appreciate that pharmaceutically acceptable solvates may be formed for crystalline or noncrystalline compounds. In crystalline solvates, solvent molecules are incorporated into the crystalline lattice during crystallization. Solvates may involve non-aqueous solvents such as, but not limited to, ethanol, isopropanol, DMSO, acetic acid, ethanolamine, or ethyl acetate, or they may involve water as the solvent that is incorporated into the crystalline lattice. Solvates wherein water is the solvent incorporated into the crystalline lattice are typically referred to as "hydrates." Hydrates include stoichiometric hydrates as well as compositions containing variable amounts of water. The invention includes all such solvates.

The skilled artisan will further appreciate that certain compounds of the invention that exist in crystalline form, including the various solvates thereof, may exhibit polymorphism (i.e. the capacity to occur in different crystalline structures). These different crystalline forms are typically known as "polymorphs." The invention includes all such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

The compound of Formula (I) or a salt thereof may exist in stereoisomeric forms (e.g., it contains one or more asymmetric carbon atoms). The individual stereoisomers (enantiomers and diastereomers) and mixtures of these are included within the scope of the present invention. Likewise, it is understood that a compound or salt of Formula (I) may exist in tautomeric forms other than that shown in the formula and these are also included within the scope of the present invention. It is to be understood that the present invention includes all combinations and subsets of the particular groups defined hereinabove. The scope of the present invention includes mixtures of stereoisomers as well as purified enantiomers or enantiomerically/diastereomerically enriched mixtures. It is to be understood that the present invention includes all combinations and subsets of the particular groups defined hereinabove.

The subject invention also includes isotopically-labelled compounds, which are identical to those recited in formula (I) and following, but for the fact that one or more atoms are replaced by an atom having an atomic mass or mass number different from the atomic mass or mass number usually found in nature. Examples of isotopes that can be incorporated into compounds of the invention and pharmaceutically acceptable salts thereof include isotopes of hydrogen, carbon, nitrogen, oxygen, phosphorous, sulphur, fluorine, iodine, and chlorine, such as 2H, 3H, 11C, 13C, 14C, 15N, 17O, 18O, 31P, 32P, 35S, 18F, 36Cl, 123I and 125I.

Compounds of the present invention and pharmaceutically acceptable salts of said compounds that contain the aforementioned isotopes and/or other isotopes of other atoms are within the scope of the present invention. Isotopically-labelled compounds of the present invention, for example those into which radioactive isotopes such as 3H, 14C are incorporated, are useful in drug and/or substrate tissue distribution assays. Tritiated, i.e., 3H, and carbon-14, i.e., 14C, isotopes are commonly used for their ease of preparation and detectability. 11C and 18F isotopes are useful in PET (positron emission tomography), and 125I isotopes are useful in SPECT (single photon emission computerized tomography), all useful in brain imaging. Further, substitution with heavier isotopes such as deuterium, i.e., 2H, can afford certain therapeutic advantages resulting from greater metabolic stability, for example increased in vivo half-life or reduced dosage requirements and, hence, may be preferred in some circumstances. Isotopically labelled compounds of formula I and following of this invention can generally be prepared by carrying out the procedures disclosed in the Schemes and/or in the Examples below, by substituting a readily available isotopically labelled reagent for a non-isotopically labelled reagent.

Pharmaceutical Compositions

The invention further provides a pharmaceutical composition (also referred to as pharmaceutical formulation) comprising a compound of Formula I or pharmaceutically acceptable salt thereof and one or more excipients (also referred to as carriers and/or diluents in the pharmaceutical arts). The excipients are acceptable in the sense of being compatible with the other ingredients of the formulation and not deleterious to the recipient thereof (i.e., the patient).

In accordance with another aspect of the invention there is provided a process for the preparation of a pharmaceutical composition comprising mixing (or admixing) a compound of Formula I or salt thereof with at least one excipient.

Pharmaceutical compositions may be in unit dose form containing a predetermined amount of active ingredient per unit dose. Such a unit may contain a therapeutically effective dose of the compound of Formula I or salt thereof or a fraction of a therapeutically effective dose such that multiple unit dosage forms might be administered at a given time to achieve the desired therapeutically effective dose. Preferred unit dosage formulations are those containing a daily dose or sub-dose, as herein above recited, or an appropriate fraction thereof, of an active ingredient. Furthermore, such pharmaceutical compositions may be prepared by any of the methods well-known in the pharmacy art.

The compounds of the invention may be administered by any acceptable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

Such compositions may be prepared by any method known in the art of pharmacy, for example, by bringing into association the active ingredient with the excipient(s). A typical formulation is prepared by mixing a compound of the present invention and a carrier or excipient. Examples of carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

When adapted for oral administration, pharmaceutical compositions may be in discrete units such as tablets or capsules; powders or granules; solutions or suspensions in aqueous or non-aqueous liquids; edible foams or whips; oil-in-water liquid emulsions or water-in-oil liquid emulsions. The compound or salt thereof of the invention or the pharmaceutical composition of the invention may also be incorporated into a candy, a wafer, and/or tongue tape formulation for administration as a "quick-dissolve" medicine.

For instance, for oral administration in the form of a tablet or capsule, the active drug component can be combined with an oral, non-toxic pharmaceutically acceptable inert carrier such as ethanol, glycerol, water, and the like. Powders or granules are prepared by comminuting the compound to a acceptable fine size and mixing with a similarly comminuted pharmaceutical carrier such as an edible carbohydrate, as, for example, starch or mannitol. Flavoring, preservative, dispersing, and coloring agents can also be present.

Capsules are made by preparing a powder mixture, as described above, and filling formed gelatin or non-gelatinous sheaths. Glidants and lubricants such as colloidal silica, talc, magnesium stearate, calcium stearate, solid polyethylene glycol can be added to the powder mixture before the filling operation. A disintegrating or solubilizing agent such as agar-agar, calcium carbonate, or sodium carbonate can also be added to improve the availability of the medicine when the capsule is ingested.

Moreover, when desired or necessary, binders, lubricants, disintegrating agents, and coloring agents can also be incorporated into the mixture. Examples of binders include starch, gelatin, natural sugars, such as glucose or beta-lactose, corn sweeteners, natural and synthetic gums such as acacia, tragacanth, sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methylcellulose, agar, bentonite, xanthan gum, and the like.

Tablets are formulated, for example, by preparing a powder mixture, granulating or slugging, adding a lubricant and disintegrant, and pressing into tablets. A powder mixture is prepared by mixing the compound, suitably comminuted, with a diluent or base as described above, and optionally, with a binder such as carboxymethylcellulose, and aliginate, gelatin, or polyvinyl pyrrolidone, a solution retardant such as paraffin, a resorption accelerator such as a quaternary salt, and/or an absorption agent such as bentonite, kaolin, or dicalcium phosphate. The powder mixture can be granulated by wetting a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compound or salt of the present invention can also be combined with a free-flowing inert carrier and compressed into tablets directly without going through the granulating or slugging steps. A clear opaque protective coating consisting of a sealing coat of shellac, a coating of sugar, or polymeric material, and a polish coating of wax can be provided. Dyestuffs can be added to these coatings to distinguish different dosages.

Oral fluids such as solutions, syrups, and elixirs can be prepared in dosage unit form so that a given quantity contains a predetermined amount of active ingredient. Syrups can be prepared by dissolving the compound or salt thereof of the invention in a suitably flavoured aqueous solution, while elixirs are prepared through the use of a non-toxic alcoholic vehicle. Suspensions can be formulated by dispersing the compound or salt of the invention in a non-toxic vehicle. Solubilizers and emulsifiers, such as ethoxylated isostearyl alcohols and polyoxyethylene sorbitol ethers, preservatives, flavor additives such as peppermint oil, natural sweeteners, saccharin, or other artificial sweeteners, and the like, can also be added.

Where appropriate, dosage unit formulations for oral administration can be microencapsulated. The formulation can also be prepared to prolong or sustain the release as, for example, by coating or embedding particulate material in polymers, wax, or the like.

In one embodiment, tablets and capsules are used for delivery of the pharmaceutical composition.

The present invention provides a method of treatment in a mammal, for example, a human, suffering from cancer, for example, lung cancer and pancreatic cancer. Such treatment comprises the step of administering a therapeutically effective amount of a compound of Formula I or salt thereof to said mammal, for example, a human. Treatment can also comprise the step of administering a therapeutically effective amount of a pharmaceutical composition containing a compound of Formula I or salt thereof to said mammal, for example, a human.

While it is possible that, for use in therapy, a therapeutically effective amount of a compound of Formula I or salt thereof may be administered as the raw chemical, it is typically presented as the active ingredient of a pharmaceutical composition or formulation.

The precise therapeutically effective amount of a compound or salt thereof of the invention will depend on a number of factors, including, but not limited to, the age and weight of the subject (patient) being treated, the precise disorder requiring treatment and its severity, the nature of the pharmaceutical formulation/composition, and route of administration, and will ultimately be at the discretion of the attending physician or veterinarian. Typically, a compound of Formula I or salt thereof will be given for the treatment in the range of about 0.1 to 100 mg/kg body weight of recipient (patient, mammal) per day and more usually in the range of 0.1 to 10 mg/kg body weight per day. Acceptable daily dosages may be from about 1 to about 1000 mg/day, and for example, from about 1 to about 100 mg/day. This amount may be given in a single dose per day or in a number (such as two, three, four, five, or more) of sub-doses per day such that the total daily dose is the same. An effective amount of a salt thereof may be determined as a proportion of the effective amount of the compound of Formula I per se. Similar dosages should be appropriate for treatment (including prophylaxis) of the other conditions referred herein for treatment. In general, determination of appropriate dosing can be readily arrived at by one skilled in medicine or the pharmacy art.

Indications and Methods of Treatment

The compounds of the present invention inhibit the activity of T790M containing EGFR mutants. The compositions and methods provided herein can potentially be useful for the treatment of cancer including tumors such as astrocytic, breast, cervical, colorectal, endometrial, esophageal, gastric, head and neck, hepatocellular, laryngeal, lung, oral, ovarian, prostate and thyroid carcinomas and sarcomas. More specifically, these compounds can potentially be used to treat: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, meduUoblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia (acute and chronic), acute lymphoblastic leukemia, chronic lymphocytic leukemia, myeloproliferative diseases, multiple myeloma, myelodysplasia syndrome), Hodgkin's disease, non-Hodgkin's lymphoma (malignant lymphoma); Skin: malignant melanoma, basal cell carcinoma, squamous cell carcinoma, Kaposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of or related to the above identified conditions.

In one embodiment, the compositions and methods provided herein are useful for the treatment of lung cancer and pancreatic cancer, most specifically, non-small cell lung cancer (NSCLC).

Combinations

When a compound of Formula (I) is administered for the treatment of cancer, the term "co-administering" and derivatives thereof as used herein refers to either simultaneous administration or any manner of separate sequential administration of a T790M inhibiting compound, as described herein, and a further active ingredient or ingredients, known to be useful in the treatment of cancer, including chemotherapy and radiation treatment. The term further active ingredient or ingredients, as used herein, includes any compound or therapeutic agent known to or that demonstrates advantageous properties when administered to a patient in need of treatment for cancer. If the administration is not simultaneous, the compounds are administered in a close time proximity to each other. Furthermore, it does not matter if the compounds are administered in the same dosage form, e.g. one compound may be administered topically and another compound may be administered orally.

Typically, any anti-neoplastic agent that has activity versus a susceptible tumor being treated may be co-administered in the treatment of cancer in the present invention. Examples of such agents can be found in Cancer Principles and Practice f Oncology by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Typical anti-neoplastic agents useful in the present invention include, but are not limited to, anti-microtubule agents such as diterpenoids and vinca alkaloids; platinum coordination complexes; alkylating agents such as nitrogen mustards, oxazaphosphorines, alkylsulfonates, nitrosoureas, and triazenes; antibiotic agents such as anthracyclins, actinomycins and bleomycins; topoisomerase II inhibitors such as epipodophyllotoxins; antimetabolites such as purine and pyrimidine analogues and anti-folate compounds; topoisomerase I inhibitors such as camptothecins; hormones and hormonal analogues; signal transduction pathway inhibitors; non-receptor tyrosine kinase angiogenesis inhibitors; immunotherapeutic agents; proapoptotic agents; and cell cycle signaling inhibitors.

Examples of a further active ingredient or ingredients for use in combination or co-administered with the present T790M inhibiting compounds are chemotherapeutic agents.

Anti-microtubule or anti-mitotic agents are phase specific agents active against the microtubules of tumor cells during M or the mitosis phase of the cell cycle. Examples of anti-microtubule agents include, but are not limited to, diterpenoids and vinca alkaloids.

Diterpenoids, which are derived from natural sources, are phase specific anti-cancer agents that operate at the $G_2/M$ phases of the cell cycle. It is believed that the diterpenoids stabilize the β-tubulin subunit of the microtubules, by binding with this protein. Disassembly of the protein appears then to be inhibited with mitosis being arrested and cell death following. Examples of diterpenoids include, but are not limited to, paclitaxel and its analog docetaxel.

Paclitaxel, 5β,20-epoxy-1,2α,4,7β,10β,13α-hexa-hydroxytax-11-en-9-one 4,10-diacetate 2-benzoate 13-ester with (2R,3S)—N-benzoyl-3-phenylisoserine; is a natural diterpene product isolated from the Pacific yew tree *Taxus brevifolia* and is commercially available as an injectable solution TAXOL®. It is a member of the taxane family of terpenes. It was first isolated in 1971 by Wani et al. J. Am. Chem, Soc., 93:2325. 1971), who characterized its structure by chemical and X-ray crystallographic methods. One mechanism for its activity relates to paclitaxel's capacity to bind tubulin, thereby inhibiting cancer cell growth. Schiff et al., Proc. Natl, Acad, Sci. USA, 77:1561-1565 (1980); Schiff et al., Nature, 277:665-667 (1979); Kumar, J. Biol, Chem, 256: 10435-10441 (1981). For a review of synthesis and anticancer activity of some paclitaxel derivatives see: D. G. I. Kingston et al., Studies in Organic Chemistry vol. 26, entitled "New trends in Natural Products Chemistry 1986", Attaur-Rahman, P. W. Le Quesne, Eds. (Elsevier, Amsterdam, 1986) pp 219-235.

Paclitaxel has been approved for clinical use in the treatment of refractory ovarian cancer in the United States (Markman et al., Yale Journal of Biology and Medicine, 64:583, 1991; McGuire et al., Ann. lntem, Med., 111:273, 1989) and for the treatment of breast cancer (Holmes et al., J. Nat. Cancer Inst., 83:1797, 1991.) It is a potential candidate for treatment of neoplasms in the skin (Einzig et. al., Proc. Am. Soc. Clin. Oncol., 20:46) and head and neck carcinomas (Forastire et. al., Sem. Oncol., 20:56, 1990). The compound also shows potential for the treatment of polycystic kidney disease (Woo et. al., Nature, 368:750. 1994), lung cancer and malaria. Treatment of patients with paclitaxel results in bone marrow suppression (multiple cell lineages, Ignoff, R. J. et. al, Cancer Chemotherapy Pocket Guide, 1998) related to the duration of dosing above a threshold concentration (50 nM) (Kearns, C. M. et. al., Seminars in Oncology, 3(6) p. 16-23, 1995).

Docetaxel, (2R,3S)—N-carboxy-3-phenylisoserine,N-tert-butyl ester, 13-ester with 5β-20-epoxy-1,2α,4,7β,10β, 13α-hexahydroxytax-11-en-9-one 4-acetate 2-benzoate, tri-hydrate; is commercially available as an injectable solution as TAXOTERE®. Docetaxel is indicated for the treatment of breast cancer. Docetaxel is a semisynthetic derivative of paclitaxel q.v., prepared using a natural precursor, 10-deacetyl-baccatin III, extracted from the needle of the European Yew tree. The dose limiting toxicity of docetaxel is neutropenia.

Vinca alkaloids are phase specific anti-neoplastic agents derived from the periwinkle plant. Vinca alkaloids act at the M phase (mitosis) of the cell cycle by binding specifically to tubulin. Consequently, the bound tubulin molecule is unable to polymerize into microtubules. Mitosis is believed to be arrested in metaphase with cell death following. Examples of vinca alkaloids include, but are not limited to, vinblastine, vincristine, and vinorelbine.

Vinblastine, vincaleukoblastine sulfate, is commercially available as VELBAN® as an injectable solution. Although, it has possible indication as a second line therapy of various solid tumors, it is primarily indicated in the treatment of testicular cancer and various lymphomas including Hodgkin's Disease; and lymphocytic and histiocytic lymphomas. Myelosuppression is the dose limiting side effect of vinblastine.

Vincristine, vincaleukoblastine, 22-oxo-, sulfate, is commercially available as ONCOVIN® as an injectable solution. Vincristine is indicated for the treatment of acute leukemias and has also found use in treatment regimens for Hodgkin's and non-Hodgkin's malignant lymphomas. Alopecia and neurologic effects are the most common side effect of vincristine and to a lesser extent myelosupression and gastrointestinal mucositis effects occur.

Vinorelbine, 3',4'-didehydro-4'-deoxy-C'-norvincaleukoblastine [R—(R*,R*)-2,3-dihydroxybutanedioate (1:2) (salt)], commercially available as an injectable solution of vinorelbine tartrate (NAVELBINE®), is a semisynthetic vinca alkaloid. Vinorelbine is indicated as a single agent or in combination with other chemotherapeutic agents, such as cisplatin, in the treatment of various solid tumors, for example, non-small cell lung, advanced breast, and hormone refractory prostate cancers. Myelosuppression is the most common dose limiting side effect of vinorelbine.

Platinum coordination complexes are non-phase specific anti-cancer agents, which are interactive with DNA. The platinum complexes enter tumor cells, undergo, aquation and form intra- and interstrand crosslinks with DNA causing adverse biological effects to the tumor. Examples of platinum coordination complexes include, but are not limited to, cisplatin and carboplatin.

Cisplatin, cis-diamminedichloroplatinum, is commercially available as PLATINOL® as an injectable solution. Cisplatin is primarily indicated in the treatment of metastatic testicular and ovarian cancer and advanced bladder cancer. The primary dose limiting side effects of cisplatin are nephrotoxicity, which may be controlled by hydration and diuresis, and ototoxicity.

Carboplatin, platinum, diammine [1,1-cyclobutane-dicarboxylate(2-)-O,O'], is commercially available as PARAPLATIN® as an injectable solution. Carboplatin is primarily indicated in the first and second line treatment of advanced ovarian carcinoma. Bone marrow suppression is the dose limiting toxicity of carboplatin.

Alkylating agents are non-phase anti-cancer specific agents and strong electrophiles. Typically, alkylating agents form covalent linkages, by alkylation, to DNA through nucleophilic moieties of the DNA molecule such as phosphate, amino, sulfhydryl, hydroxyl, carboxyl, and imidazole groups. Such alkylation disrupts nucleic acid function leading to cell death. Examples of alkylating agents include, but are not limited to, nitrogen mustards such as cyclophosphamide, melphalan, and chlorambucil; alkyl sulfonates such as busulfan; nitrosoureas such as carmustine; and triazenes such as dacarbazine.

Cyclophosphamide, 2-[bis(2-chloroethyl)amino]tetrahydro-2H-1,3,2-oxazaphosphorine 2-oxide monohydrate, is commercially available as an injectable solution or tablets as CYTOXAN®. Cyclophosphamide is indicated as a single agent or in combination with other chemotherapeutic agents, in the treatment of malignant lymphomas, multiple myeloma, and leukemias. Alopecia, nausea, vomiting and leukopenia are the most common dose limiting side effects of cyclophosphamide.

Melphalan, 4-[bis(2-chloroethyl)amino]-L-phenylalanine, is commercially available as an injectable solution or tablets as ALKERAN®. Melphalan is indicated for the palliative treatment of multiple myeloma and non-resectable epithelial carcinoma of the ovary. Bone marrow suppression is the most common dose limiting side effect of melphalan.

Chlorambucil, 4-[bis(2-chloroethyl)amino]benzenebutanoic acid, is commercially available as LEUKERAN® tablets. Chlorambucil is indicated for the palliative treatment of chronic lymphatic leukemia, and malignant lymphomas such as lymphosarcoma, giant follicular lymphoma, and Hodgkin's disease. Bone marrow suppression is the most common dose limiting side effect of chlorambucil.

Busulfan, 1,4-butanediol dimethanesulfonate, is commercially available as MYLERAN® TABLETS. Busulfan is indicated for the palliative treatment of chronic myelogenous leukemia. Bone marrow suppression is the most common dose limiting side effects of busulfan.

Carmustine, 1,3-[bis(2-chloroethyl)-1-nitrosourea, is commercially available as single vials of lyophilized material as BiCNU®. Carmustine is indicated for the palliative treatment as a single agent or in combination with other agents for brain tumors, multiple myeloma, Hodgkin's disease, and non-Hodgkin's lymphomas. Delayed myelosuppression is the most common dose limiting side effects of carmustine.

Dacarbazine, 5-(3,3-dimethyl-1-triazeno)-imidazole-4-carboxamide, is commercially available as single vials of material as DTIC-Dome®. Dacarbazine is indicated for the treatment of metastatic malignant melanoma and in combination with other agents for the second line treatment of Hodgkin's Disease. Nausea, vomiting, and anorexia are the most common dose limiting side effects of dacarbazine.

Antibiotic anti-neoplastics are non-phase specific agents, which bind or intercalate with DNA. Typically, such action results in stable DNA complexes or strand breakage, which disrupts ordinary function of the nucleic acids leading to cell death. Examples of antibiotic anti-neoplastic agents include, but are not limited to, actinomycins such as dactinomycin, anthrocyclins such as daunorubicin and doxorubicin; and bleomycins.

Dactinomycin, also know as Actinomycin D, is commercially available in injectable form as COSMEGEN®. Dactinomycin is indicated for the treatment of Wilm's tumor and rhabdomyosarcoma. Nausea, vomiting, and anorexia are the most common dose limiting side effects of dactinomycin.

Daunorubicin, (8S-cis-)-8-acetyl-10-[(3-amino-2,3,6-trideoxy-α-L-lyxo-hexopyranosyl)oxy]-7,8,9,10-tetrahydro-6,8,11-trihydroxy-1-methoxy-5,12 naphthacenedione hydrochloride, is commercially available as a liposomal injectable form as DAUNOXOME® or as an injectable as CERUBIDINE®. Daunorubicin is indicated for remission induction in the treatment of acute nonlymphocytic leukemia and advanced HIV associated Kaposi's sarcoma. Myelosuppression is the most common dose limiting side effect of daunorubicin.

Doxorubicin, (8S,10S)-10-[(3-amino-2,3,6-trideoxy-α-L-lyxo-hexopyranosyl)oxy]-8-glycoloyl, 7,8,9,10-tetrahydro-6,8,11-trihydroxy-1-methoxy-5,12 naphthacenedione hydrochloride, is commercially available as an injectable form as RUBEX® or ADRIAMYCIN RDF®. Doxorubicin is primarily indicated for the treatment of acute lymphoblastic leukemia and acute myeloblastic leukemia, but is also a useful component in the treatment of some solid tumors and lymphomas. Myelosuppression is the most common dose limiting side effect of doxorubicin.

Bleomycin, a mixture of cytotoxic glycopeptide antibiotics isolated from a strain of *Streptomyces verticillus*, is commercially available as BLENOXANE®. Bleomycin is indicated as a palliative treatment, as a single agent or in combination with other agents, of squamous cell carcinoma, lymphomas, and testicular carcinomas Pulmonary and cutaneous toxicities are the most common dose limiting side effects of bleomycin.

Topoisomerase II inhibitors include, but are not limited to, epipodophyllotoxins.

Epipodophyllotoxins are phase specific anti-neoplastic agents derived from the mandrake plant. Epipodophyllotoxins typically affect cells in the S and $G_2$ phases of the cell cycle by forming a ternary complex with topoisomerase II and DNA causing DNA strand breaks. The strand breaks accumulate and cell death follows. Examples of epipodophyllotoxins include, but are not limited to, etoposide and teniposide.

Etoposide, 4'-demethyl-epipodophyllotoxin 9[4,6-0-(R)-ethylidene-β-D-glucopyranoside], is commercially available as an injectable solution or capsules as VePESID® and is commonly known as VP-16. Etoposide is indicated as a single agent or in combination with other chemotherapy agents in the treatment of testicular and non-small cell lung cancers. Myelosuppression is the most common side effect of etoposide. The incidence of leucopenia tends to be more severe than thrombocytopenia.

Teniposide, 4'-demethyl-epipodophyllotoxin 9[4,6-0-(R)-thenylidene-β-D-glucopyranoside], is commercially available as an injectable solution as VUMON® and is commonly known as VM-26. Teniposide is indicated as a single agent or in combination with other chemotherapy agents in the treatment of acute leukemia in children. Myelosuppression is the most common dose limiting side effect of teniposide. Teniposide can induce both leucopenia and thrombocytopenia.

Antimetabolite neoplastic agents are phase specific antineoplastic agents that act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Examples of antimetabolite anti-neoplastic agents include, but are not limited to, fluorouracil, methotrexate, cytarabine, mecaptopurine, thioguanine, and gemcitabine.

5-fluorouracil, 5-fluoro-2,4-(1H,3H) pyrimidinedione, is commercially available as fluorouracil. Administration of 5-fluorouracil leads to inhibition of thymidylate synthesis and is also incorporated into both RNA and DNA. The result typically is cell death. 5-fluorouracil is indicated as a single agent or in combination with other chemotherapy agents in the treatment of carcinomas of the breast, colon, rectum, stomach and pancreas. Myelosuppression and mucositis are dose limiting side effects of 5-fluorouracil. Other fluoropyrimidine analogs include 5-fluoro deoxyuridine (floxuridine) and 5-fluorodeoxyuridine monophosphate.

Cytarabine, 4-amino-1-β-D-arabinofuranosyl-2 (1H)-pyrimidinone, is commercially available as CYTOSAR-U® and is commonly known as Ara-C. It is believed that cytarabine exhibits cell phase specificity at S-phase by inhibiting DNA chain elongation by terminal incorporation of cytarabine into the growing DNA chain. Cytarabine is indicated as a single agent or in combination with other chemotherapy agents in the treatment of acute leukemia. Other cytidine analogs include 5-azacytidine and 2',2'-difluorodeoxycytidine (gemcitabine). Cytarabine induces leucopenia, thrombocytopenia, and mucositis.

Mercaptopurine, 1,7-dihydro-6H-purine-6-thione monohydrate, is commercially available as PURINETHOL®. Mercaptopurine exhibits cell phase specificity at S-phase by inhibiting DNA synthesis by an as of yet unspecified mechanism. Mercaptopurine is indicated as a single agent or in combination with other chemotherapy agents in the treatment of acute leukemia. Myelosuppression and gastrointestinal mucositis are expected side effects of mercaptopurine at high doses. A useful mercaptopurine analog is azathioprine.

Thioguanine, 2-amino-1,7-dihydro-6H-purine-6-thione, is commercially available as TABLOID®. Thioguanine exhibits cell phase specificity at S-phase by inhibiting DNA synthesis by an as of yet unspecified mechanism. Thioguanine is indicated as a single agent or in combination with other chemotherapy agents in the treatment of acute leukemia. Myelosuppression, including leucopenia, thrombocytopenia, and anemia, is the most common dose limiting side effect of thioguanine administration. However, gastrointestinal side effects occur and can be dose limiting. Other purine analogs include pentostatin, erythrohydroxynonyladenine, fludarabine phosphate, and cladribine.

Gemcitabine, 2'-deoxy-2',2'-difluorocytidine monohydrochloride (β-isomer), is commercially available as GEMZAR®. Gemcitabine exhibits cell phase specificity at S-phase and by blocking progression of cells through the G1/S boundary. Gemcitabine is indicated in combination with cisplatin in the treatment of locally advanced non-small cell lung cancer and alone in the treatment of locally advanced pancreatic cancer. Myelosuppression, including leucopenia, thrombocytopenia, and anemia, is the most common dose limiting side effect of gemcitabine administration.

Methotrexate, N-[4[[(2,4-diamino-6-pteridinyl)methyl] methylamino]benzoyl]-L-glutamic acid, is commercially available as methotrexate sodium. Methotrexate exhibits cell phase effects specifically at S-phase by inhibiting DNA synthesis, repair and/or replication through the inhibition of dyhydrofolic acid reductase which is required for synthesis of purine nucleotides and thymidylate. Methotrexate is indicated as a single agent or in combination with other chemotherapy agents in the treatment of choriocarcinoma, meningeal leukemia, non-Hodgkin's lymphoma, and carcinomas of the breast, head, neck, ovary and bladder. Myelosuppression (leucopenia, thrombocytopenia, and anemia) and mucositis are expected side effect of methotrexate administration.

Camptothecins, including, camptothecin and camptothecin derivatives are available or under development as Topoisomerase I inhibitors. Camptothecins cytotoxic activity is believed to be related to its Topoisomerase I inhibitory activity. Examples of camptothecins include, but are not limited to irinotecan, topotecan, and the various optical forms of 7-(4-methylpiperazino-methylene)-10,11-ethylenedioxy-20-camptothecin described below.

Irinotecan HCl, (4S)-4,11-diethyl-4-hydroxy-9-[(4-piperidinopiperidino)carbonyloxy]-1H-pyrano[3',4',6,7]indolizino[1,2-b]quinoline-3,14(4H,12H)-dione hydrochloride, is commercially available as the injectable solution CAMPTOSAR®.

Irinotecan is a derivative of camptothecin which binds, along with its active metabolite SN-38, to the topoisomerase I-DNA complex. It is believed that cytotoxicity occurs as a result of irreparable double strand breaks caused by interaction of the topoisomerase I:DNA:irintecan or SN-38 ternary complex with replication enzymes. Irinotecan is indicated for treatment of metastatic cancer of the colon or rectum. The dose limiting side effects of irinotecan HCl are myelosuppression, including neutropenia, and GI effects, including diarrhea.

Topotecan HCl, (S)-10-[(dimethylamino)methyl]-4-ethyl-4,9-dihydroxy-1H-pyrano[3',4',6,7]indolizino[1,2-b] quinoline-3,14-(4H,12H)-dione monohydrochloride, is commercially available as the injectable solution HYCAMTIN®. Topotecan is a derivative of camptothecin which binds to the topoisomerase I-DNA complex and prevents religation of singles strand breaks caused by Topoisomerase I in response to torsional strain of the DNA molecule. Topotecan is indicated for second line treatment of metastatic carcinoma of the ovary and small cell lung cancer. The dose limiting side effect of topotecan HCl is myelosuppression, primarily neutropenia.

Also of interest, is the camptothecin derivative of formula A following, currently under development, including the racemic mixture (R,S) form as well as the R and S enantiomers:

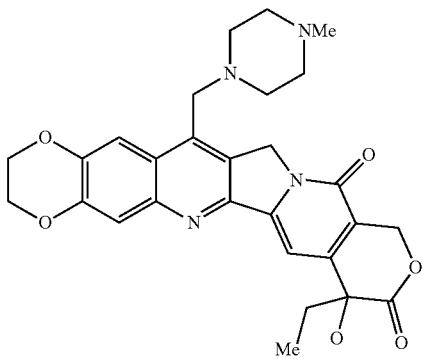

A known by the chemical name "7-(4-methylpiperazino-methylene)-10,11-ethylenedioxy-20(R,S)-camptothecin (racemic mixture) or "7-(4-methylpiperazino-methylene)-10,11-ethylenedioxy-20(R)-camptothecin (R enantiomer) or "7-(4-methylpiperazino-methylene)-10,11-ethylenedioxy-20(S)-camptothecin (S enantiomer). Such compound as well as related compounds are described, including methods of making, in U.S. Pat. Nos. 6,063,923; 5,342,947; 5,559,235; 5,491,237 and pending U.S. patent application Ser. No. 08/977,217 filed Nov. 24, 1997.

Hormones and hormonal analogues are useful compounds for treating cancers in which there is a relationship between the hormone(s) and growth and/or lack of growth of the cancer. Examples of hormones and hormonal analogues useful in cancer treatment include, but are not limited to, adrenocorticosteroids such as prednisone and prednisolone which are useful in the treatment of malignant lymphoma and acute leukemia in children; aminoglutethimide and other aromatase inhibitors such as anastrozole, letrazole, vorazole, and exemestane useful in the treatment of adrenocortical carcinoma and hormone dependent breast carcinoma containing estrogen receptors; progestrins such as megestrol acetate useful in the treatment of hormone dependent breast cancer and endometrial carcinoma; estrogens, androgens, and anti-androgens such as flutamide, nilutamide, bicalutamide, cyproterone acetate and 5α-reductases such as finasteride and dutasteride, useful in the treatment of prostatic carcinoma and benign prostatic hypertrophy; anti-estrogens such as tamoxifen, toremifene, raloxifene, droloxifene, iodoxyfene, as well as selective estrogen receptor modulators (SERMS) such those described in U.S. Pat. Nos. 5,681,835, 5,877,219, and 6,207,716, useful in the treatment of hormone dependent breast carcinoma and other susceptible cancers; and gonadotropin-releasing hormone (GnRH) and analogues thereof which stimulate the release of leutinizing hormone (LH) and/or follicle stimulating hormone (FSH) for the treatment prostatic carcinoma, for instance, LHRH agonists and antagagonists such as goserelin acetate and luprolide.

Signal transduction pathway inhibitors are those inhibitors, which block or inhibit a chemical process which evokes an intracellular change. As used herein this change is cell proliferation or differentiation. Signal transduction inhibitors useful in the present invention include inhibitors of receptor tyrosine kinases, non-receptor tyrosine kinases, SH2/SH3domain blockers, serine/threonine kinases, phosphotidyl inositol-3 kinases, myo-inositol signaling, and Ras oncogenes.

Several protein tyrosine kinases catalyse the phosphorylation of specific tyrosyl residues in various proteins involved in the regulation of cell growth. Such protein tyrosine kinases can be broadly classified as receptor or non-receptor kinases.

Receptor tyrosine kinases are transmembrane proteins having an extracellular ligand binding domain, a transmembrane domain, and a tyrosine kinase domain. Receptor tyrosine kinases are involved in the regulation of cell growth and are generally termed growth factor receptors. Inappropriate or uncontrolled activation of many of these kinases, i.e. aberrant kinase growth factor receptor activity, for example by over-expression or mutation, has been shown to result in uncontrolled cell growth. Accordingly, the aberrant activity of such kinases has been linked to malignant tissue growth. Consequently, inhibitors of such kinases could provide cancer treatment methods. Growth factor receptors include, for example, epidermal growth factor receptor (EGFR), platelet derived growth factor receptor (PDGFR), erbB2, erbB4, vascular endothelial growth factor receptor (VEGFR), tyrosine kinase with immunoglobulin-like and epidermal growth factor homology domains (TIE-2), insulin growth factor-I (IGFI) receptor, macrophage colony stimulating factor (cfms), BTK, ckit, cmet, fibroblast growth factor (FGF) receptors, Trk receptors (TrkA, TrkB, and TrkC), ephrin (eph) receptors, and the RET protooncogene. Several inhibitors of growth receptors are under development and include ligand antagonists, antibodies, tyrosine kinase inhibitors and anti-sense oligonucleotides. Growth factor receptors and agents that inhibit growth factor receptor function are described, for instance, in Kath, John C., Exp. Opin. Ther. Patents (2000) 10(6):803-818; Shawver et al DDT Vol 2, No. 2 February 1997; and Lofts, F. J. et al, "Growth factor receptors as targets", New Molecular Targets for Cancer Chemotherapy, ed. Workman, Paul and Kerr, David, CRC press 1994, London.

Tyrosine kinases, which are not growth factor receptor kinases are termed non-receptor tyrosine kinases. Non-receptor tyrosine kinases useful in the present invention, which are targets or potential targets of anti-cancer drugs, include cSrc, Lck, Fyn, Yes, Jak, cAbl, FAK (Focal adhesion kinase), Brutons tyrosine kinase, and Bcr-Abl. Such non-receptor kinases and agents which inhibit non-receptor tyrosine kinase function are described in Sinh, S. and Corey, S. J., (1999) Journal of Hematotherapy and Stem Cell Research 8 (5): 465-80; and Bolen, J. B., Brugge, J. S., (1997) Annual review of Immunology. 15: 371-404.

Erlotinib (Tareva®) is an EGFR inhibitor. Gefitinib (Iressa®) is another drug of this type. Erlotinib specifically targets the epidermal growth factor receptor (EGFR) tyrosine kinase, which is highly expressed and occasionally mutated in various forms of cancer. It binds in a reversible fashion to the adenosine triphosphate (ATP) binding site of the receptor. For the signal to be transmitted, two EGFR molecules need to come together to form a homodimer. These then use the molecule of ATP to trans-phosphorylate each other on tyrosine residues, which generates phosphotyrosine residues, recruiting the phosphotyrosine-binding proteins to EGFR to assemble protein complexes that transduce signal cascades to the nucleus or activate other cellular biochemical processes. By inhibiting the ATP, formation of phosphotyrosine residues in EGFR is not possible and the signal cascades are not initiated.

SH2/SH3 domain blockers are agents that disrupt SH2 or SH3 domain binding in a variety of enzymes or adaptor proteins including, PI3-K p85 subunit, Src family kinases, adaptor molecules (Shc, Crk, Nck, Grb2) and Ras-GAP. SH2/SH3 domains as targets for anti-cancer drugs are discussed in Smithgall, T. E. (1995), Journal of Pharmacological and Toxicological Methods. 34(3) 125-32.

Inhibitors of Serine/Threonine Kinases including MAP kinase cascade blockers which include blockers of Raf kinases (rafk), Mitogen or Extracellular Regulated Kinase (MEKs), and Extracellular Regulated Kinases (ERKs); and Protein kinase C family member blockers including blockers of PKCs (alpha, beta, gamma, epsilon, mu, lambda, iota, zeta). IkB kinase family (IKKa, IKKb), PKB family kinases, AKT kinase family members, and TGF beta receptor kinases. Such Serine/Threonine kinases and inhibitors thereof are described in Yamamoto, T., Taya, S., Kaibuchi, K., (1999), Journal of Biochemistry. 126 (5) 799-803; Brodt, P, Samani, A., and Navab, R. (2000), Biochemical Pharmacology, 60. 1101-1107; Massague, J., Weis-Garcia, F. (1996) Cancer Surveys. 27:41-64; Philip, P. A., and Harris, A. L. (1995), Cancer Treatment and Research. 78: 3-27, Lackey, K. et al Bioorganic and Medicinal Chemistry Letters, (10), 2000, 223-226; U.S. Pat. No. 6,268,391; and Martinez-Iacaci, L., et al, Int. J. Cancer (2000), 88(1), 44-52.

Inhibitors of Phosphotidyl inositol-3 Kinase family members including blockers of PI3-kinase, ATM, DNA-PK, and Ku are also useful in the present invention. Such kinases are discussed in Abraham, R. T. (1996), Current Opinion in Immunology. 8 (3) 412-8; Canman, C. E., Lim, D. S. (1998), Oncogene 17 (25) 3301-3308; Jackson, S. P. (1997), International Journal of Biochemistry and Cell Biology. 29 (7):935-8; and Zhong, H. et al, Cancer res, (2000) 60(6), 1541-1545.

Also useful in the present invention are Myo-inositol signaling inhibitors such as phospholipase C blockers and Myoinositol analogues. Such signal inhibitors are described in Powis, G., and Kozikowski A., (1994) New Molecular Targets for Cancer Chemotherapy ed., Paul Workman and David Kerr, CRC press 1994, London.

Another group of signal transduction pathway inhibitors are inhibitors of Ras Oncogene. Such inhibitors include inhibitors of farnesyltransferase, geranyl-geranyl transferase, and CAAX proteases as well as anti-sense oligonucleotides, ribozymes and immunotherapy. Such inhibitors have been shown to block ras activation in cells containing wild type mutant ras, thereby acting as antiproliferation agents. Ras oncogene inhibition is discussed in Scharovsky, O. G., Rozados, V. R., Gervasoni, S. I. Matar, P. (2000), Journal of Biomedical Science. 7(4) 292-8; Ashby, M. N. (1998), Current Opinion in Lipidology. 9 (2) 99-102; and BioChim. Biophys. Acta, (19899) 1423(3):19-30.

As mentioned above, antibody antagonists to receptor kinase ligand binding may also serve as signal transduction inhibitors. This group of signal transduction pathway inhibitors includes the use of humanized antibodies to the extracellular ligand binding domain of receptor tyrosine kinases. For example Imclone C225 EGFR specific antibody (see Green, M. C. et al, Monoclonal Antibody Therapy for Solid Tumors, Cancer Treat. Rev., (2000), 26(4), 269-286); Herceptin® erbB2 antibody (see Tyrosine Kinase Signalling in Breast cancer:erbB Family Receptor Tyrosine Kinases, Breast cancer Res., 2000, 2(3), 176-183); and 2CB VEGFR2 specific antibody (see Brekken, R. A. et al, Selective Inhibition of VEGFR2 Activity by a monoclonal Anti-VEGF antibody blocks tumor growth in mice, Cancer Res. (2000) 60, 5117-5124).

Non-receptor kinase angiogenesis inhibitors may also find use in the present invention. Inhibitors of angiogenesis related VEGFR and TIE2 are discussed above in regard to signal transduction inhibitors (both receptors are receptor tyrosine kinases). Angiogenesis in general is linked to erbB2/EGFR signaling since inhibitors of erbB2 and EGFR have been shown to inhibit angiogenesis, primarily VEGF expression. Thus, the combination of an erbB2/EGFR inhibitor with an inhibitor of angiogenesis makes sense. Accordingly, non-receptor tyrosine kinase inhibitors may be used in combination with the EGFR/erbB2 inhibitors of the present invention. For example, anti-VEGF antibodies, which do not recognize VEGFR (the receptor tyrosine kinase), but bind to the ligand; small molecule inhibitors of integrin (alpha$_v$ beta$_3$) that will inhibit angiogenesis; endostatin and angiostatin (non-RTK) may also prove useful in combination with the disclosed erb family inhibitors. (See Bruns C J et al (2000), Cancer Res., 60: 2926-2935; Schreiber A B, Winkler M E, and Derynck R. (1986), Science, 232: 1250-1253; Yen L et al. (2000), Oncogene 19: 3460-3469).

Agents used in immunotherapeutic regimens may also be useful in combination with the compounds of formula (I). There are a number of immunologic strategies to generate an immune response against erbB2 or EGFR. These strategies are generally in the realm of tumor vaccinations. The efficacy of immunologic approaches may be greatly enhanced through combined inhibition of erbB2/EGFR signaling pathways using a small molecule inhibitor. Discussion of the immunologic/tumor vaccine approach against erbB2/EGFR are found in Reilly R T et al. (2000), Cancer Res. 60: 3569-3576; and Chen Y, Hu D, Eling D J, Robbins J, and Kipps T J. (1998), Cancer Res. 58: 1965-1971.

Agents used in proapoptotic regimens (e.g., bcl-2 antisense oligonucleotides) may also be used in the combination of the present invention. Members of the Bcl-2 family of proteins block apoptosis. Upregulation of bcl-2 has therefore been linked to chemoresistance. Studies have shown that the epidermal growth factor (EGF) stimulates anti-apoptotic members of the bcl-2 family (i.e., mcl-1). Therefore, strategies designed to downregulate the expression of bcl-2 in tumors have demonstrated clinical benefit and are now in Phase II/III trials, namely Genta's G3139 bcl-2 antisense oligonucleotide. Such proapoptotic strategies using the antisense oligonucleotide strategy for bcl-2 are discussed in Water J S et al. (2000), J. Clin. Oncol. 18: 1812-1823; and Kitada S et al. (1994), Antisense Res. Dev. 4: 71-79.

Cell cycle signalling inhibitors inhibit molecules involved in the control of the cell cycle. A family of protein kinases called cyclin dependent kinases (CDKs) and their interaction with a family of proteins termed cyclins controls progression through the eukaryotic cell cycle. The coordinate activation and inactivation of different cyclin/CDK complexes is necessary for normal progression through the cell cycle. Several inhibitors of cell cycle signalling are under development. For instance, examples of cyclin dependent kinases, including CDK2, CDK4, and CDK6 and inhibitors for the same are described in, for instance, Rosania et al, Exp. Opin. Ther. Patents (2000) 10(2):215-230. Further, p21WAF1/CIP1 has been described as a potent and universal inhibitor of cyclin-dependent kinases (Cdks) (Ball et al., *Progress in Cell Cycle Res.*, 3: 125 (1997)). Compounds that are known to induce expression of p21WAF1/CIP1 have been implicated in the suppression of cell proliferation and as having tumor suppressing activity (Richon et al., *Proc. Nat Acad. Sci. U.S.A.* 97(18): 10014-10019 (2000)), and are included as cell cycle signaling inhibitors.

Modulators of the Retinoid Acid Receptor have been used to treat leukemias. The pathology of the leukemia is associated with the abnormal accumulation of immature progenitor cells that are sensitive to retinoc acid therapy. The majority of cases of acute promyelocytic leukemia (APL), also called acute myeloid leukemia subtype M3, involve a chromosomal translocation of chromosomes 15 and 17 that causes genetic fusion of the retinoic acid receptor (RAR) gene to the promyelocytic leukemia (PML) gene. This fusion PML-RAR protein is responsible for preventing immature myeloid cells from differentiating into more mature cells. This block in differentiation is and subsequent accumulation of less differentiated cells is thought to cause leukemia. ATRA, Tretinoin, acts on PML-RAR to lift this block, causing the immature promyelocytes to differentiate to normal mature blood cells thus decreasing promyelocytes and promoting a population of terminally differentiated cells with a restricted lifespan. Talazorole is an experimental drug in the same class as Tretinoin.

Epigenetic alterations have been implicated in virtually all types of human cancers. Cancer specific changes are often associated with silencing of tumor suppressor genes via histone modifications and modifications to DNA including DNA hypermethylation. Epigenetic pharmaceuticals control regulatory regions associated with tumor suppressor genes by causing conformational changes in histones and removing repressive modifications to DNA. These changes directly affect the formation and progression of cancer. Examples of epigenetic agents include histone deacetylase inhibitors and DNA methylation inhibitors.

Histone deacetylase inhibitors (HDAC inhibitors, HDI) are a class of compounds that interfere with the function of histone deacetylases Inhibitors of histone deacetylases have been shown to be useful in the treatment of cutaneous T-cell lymphoma. They are being investigated in the clinic for multiple other tumor types. Examples of HDAC inhibitors approved for use are Vorinostat and Romidepsin. These compounds are thought to inhibit the activity of HDACs and result in the accumulation of acetylation to histones promoting gene expression.

Azacitidine (INN) or 5-azacytidine, sold under the trade name Vidaza, is a chemical analogue of cytidine, a nucleoside present in DNA and RNA. Azacitidine and its deoxy derivative, decitabine (also known as 5-aza-2'deoxycytidine), are used in the treatment of myelodysplastic syndrome and are currently under study for other tumor indications. Azacitidine acts as a false substrate and potent inhibitor of DNA methyltransferases leading to reduction of DNA methylation. DNA methyltransferases incorporate azacitidine into DNA during replication and into RNA during transcription in the cell Inhibition of DNA methylation occurs through the formation of stable complexes between the molecule and DNA methyltransferases, thereby saturating cell methylation machinery. This results in a loss of DNA methylation and can affect the way cell regulation proteins, such as transcriptional machinery, are able to associate with the DNA.

Examples of such HDAC inhibitors include:

1. Vorinostat, including pharmaceutically acceptable salts thereof. Marks et al., Nature Biotechnology 25, 84 to 90 (2007); Stenger, Community Oncology 4, 384-386 (2007).

Vorinostat has the following chemical structure and name:

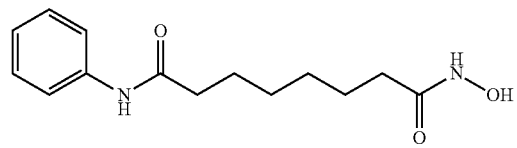 [SMILES: O=C(CCCCCCC(=O)Nc1ccccc1)NO]

N-hydroxy-N'-phenyl-octanediamide

2. Romidepsin, including pharmaceutically acceptable salts thereof.

Vinodhkumar et al., Biomedicine & Pharmacotherapy 62 (2008) 85-93.

Romidepsin, has the following chemical structure and name:

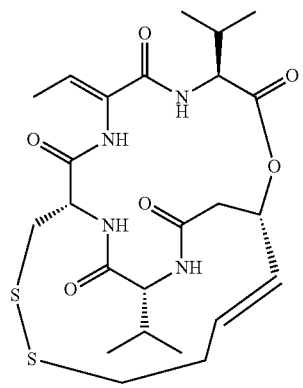 [SMILES: C/C=C1\NC(=O)[C@H]2CSSCC/C=C/[C@H](CC(=O)N[C@H](C(C)C)C(=O)N2)OC(=O)[C@H](C(C)C)NC1=O]

(1S,4S,7Z,10S,16E,21R)-7-ethylidene-4,21-di(propan-2-yl)-2-oxa-12,13-dithia-5,8,20,23-tetrazabicyclo[8.7.6]tricos-16-ene-3,6,9,19,22-pentone 3. Panobinostat, including pharmaceutically acceptable salts thereof. Drugs of the Future 32(4): 315-322 (2007).

Panobinostat, has the following chemical structure and name:

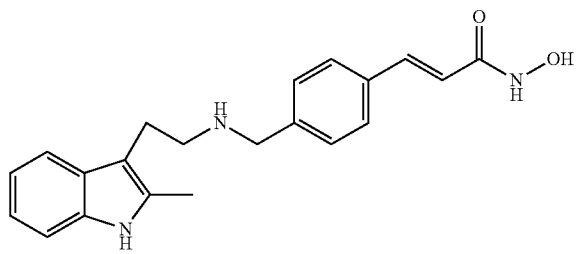 [SMILES: Cc1[nH]c2ccccc2c1CCNCc1ccc(/C=C/C(=O)NO)cc1]

(2E)-N-hydroxy-3-[4-({[2-(2-methyl-1H-indol-3-yl)ethyl]amino}methyl)phenyl]acrylamide 4. Valproic acid, including pharmaceutically acceptable salts thereof. Gottlicher, et al., EMBO J. 20(24): 6969-6978 (2001).

Valproic acid, has the following chemical structure and name:

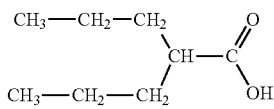

2-propylpentanoic acid

5. Mocetinostat (MGCD0103), including pharmaceutically acceptable salts thereof. Balasubramanian et al., Cancer Letters 280: 211-221 (2009).

Mocetinostat, has the following chemical structure and name:

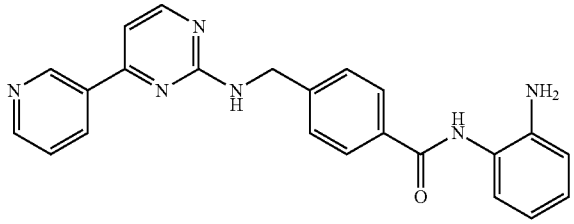 [SMILES: Nc1ccccc1NC(=O)c1ccc(CNc2nccc(-c3cccnc3)n2)cc1]

N-(2-Aminophenyl)-4-[[(4-pyridin-3-ylpyrimidin-2-yl)amino]methyl]benzamide

Further examples of such HDAC inhibitors are included in Bertrand European Journal of Medicinal Chemistry 45, (2010) 2095-2116.

Proteasome inhibitors are drugs that block the action of proteasomes, cellular complexes that break down proteins, like the p53 protein. Several proteasome inhibitors are marketed or are being studied in the treatment of cancer. Examples of proteasome inhibitors for use in combination herein include:

1. Bortezomib (Velcade®), including pharmaceutically acceptable salts thereof. Adams J, Kauffman M (2004), Cancer Invest 22 (2): 304-11.

Bortezomib has the following chemical structure and name.

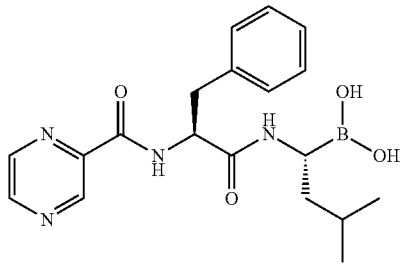 [SMILES: CC(C)C[C@H](NC(=O)[C@H](Cc1ccccc1)NC(=O)c1cnccn1)B(O)O]

[(1R)-3-methyl-1-({(2S)-3-phenyl-2-[(pyrazin-2-ylcarbonyl)amino]propanoyl}amino)butyl]boronic acid 2. Disulfiram, including pharmaceutically acceptable salts thereof.

Bouma et al. (1998). J. Antimicrob. Chemother. 42 (6): 817-20.

Disulfiram has the following chemical structure and name.

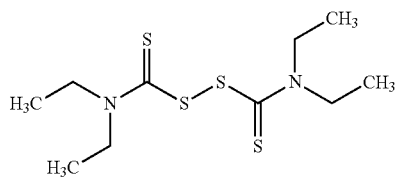 [SMILES: CCN(CC)C(=S)SSC(=S)N(CC)CC]

1,1',1'',1'''-[disulfanediylbis(carbonothioylnitrilo)]tetraethane

3. Epigallocatechin gallate (EGCG), including pharmaceutically acceptable salts thereof. Williamson et al., (December 2006), The Journal of Allergy and Clinical Immunology 118 (6): 1369-74.

Epigallocatechin gallate has the following chemical structure and name.

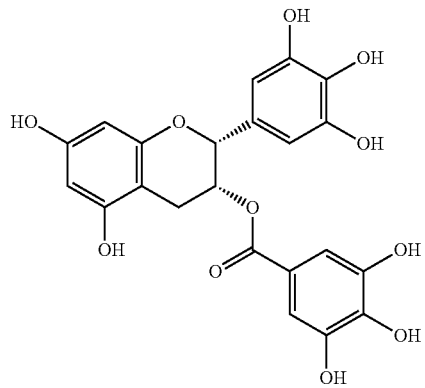 [SMILES: O=C(O[C@@H]1Cc2c(O)cc(O)cc2O[C@@H]1c1cc(O)c(O)c(O)c1)c1cc(O)c(O)c(O)c1]

[(2R,3R)-5,7-dihydroxy-2-(3,4,5-trihydroxyphenyl)chroman-3-yl]3,4,5-trihydroxybenzoate 4. Salinosporamide A, including pharmaceutically acceptable salts thereof. Feling et al., (2003), Angew. Chem. Int. Ed. Engl. 42 (3): 355-7.

Salinosporamide A has the following chemical structure and name.

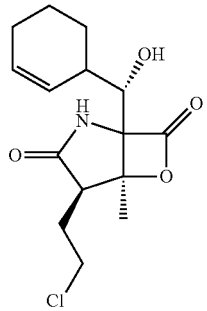

(4R,5S)-4-(2-chloroethyl)-1-((1S)-cyclohex-2-enyl (hydroxy)methyl)-5-methyl-6-oxa-2-azabicyclo3.2.0heptane-3,7-dione 5. Carfilzomib, including pharmaceutically acceptable salts thereof. Kuhn D J, et al, Blood, 2007, 110:3281-3290.

Carfilzomib has the following chemical structure and name.

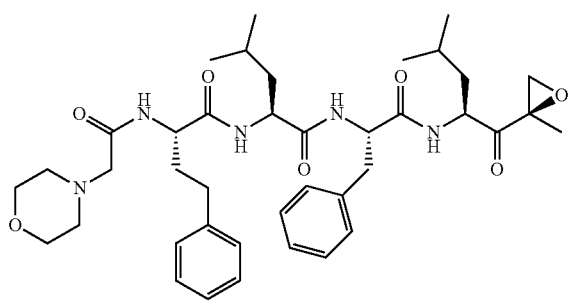 [SMILES: CC(C)C[C@H](NC(=O)[C@H](CCc1ccccc1)NC(=O)CN1CCOCC1)C(=O)N[C@@H](Cc1ccccc1)C(=O)N[C@@H](CC(C)C)C(=O)[C@@]1(C)CO1]

(S)-4-methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacet-amido)-4-phenylbutanamido)pentanamide The 70 kilodalton heat shock proteins (Hsp70s) and 90 kilodalton heat shock proteins (Hsp90s) are a families of ubiquitously expressed heat shock proteins. Hsp70s and Hsp90s are over expressed certain cancer types. Several Hsp70s and Hsp90s inhibitors are being studied in the treatment of cancer. Examples of Hsp70s and Hsp90s inhibitors for use in combination herein include:

1. 17-AAG(Geldanamycin), including pharmaceutically acceptable salts thereof. Jia W et al. Blood. 2003 Sep. 1; 102(5):1824-32.

17-AAG(Geldanamycin) has the following chemical structure and name.

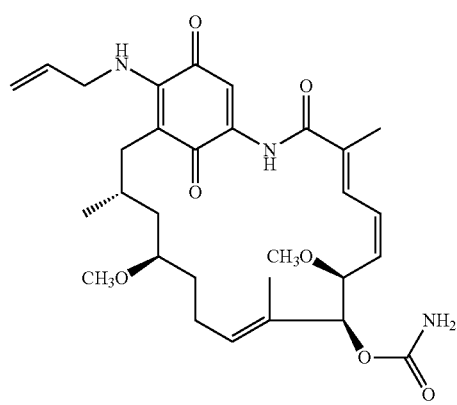

17-(Allylamino)-17-demethoxygeldanamycin

2. Radicicol, including pharmaceutically acceptable salts thereof (Lee et al., Mol Cell Endocrinol. 2002, 188, 47-54)

Radicicol has the following chemical structure and name.

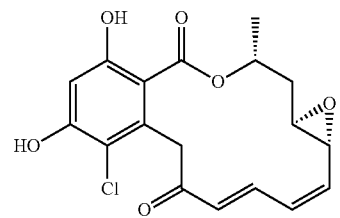

(1aR,2Z,4E,14R,15aR)-8-chloro-9,11-dihydroxy-14-methyl-15,15a-dihydro-1aH-benzo[c]oxireno[2,3-k][1]oxacyclotetradecine-6,12(7H,14H)-dione Inhibitors of cancer metabolism—Many tumor cells show a markedly different metabolism from that of normal tissues. For example, the rate of glycolysis, the metabolic process that converts glucose to pyruvate, is increased, and the pyruvate generated is reduced to lactate, rather than being further oxidized in the mitochondria via the tricarboxylic acid (TCA) cycle. This effect is often seen even under aerobic conditions and is known as the Warburg Effect.

Lactate dehydrogenase A (LDH-A), an isoform of lactate dehydrogenase expressed in muscle cells, plays a pivotal role in tumor cell metabolism by performing the reduction of pyruvate to lactate, which can then be exported out of the cell. The enzyme has been shown to be upregulated in many tumor types. The alteration of glucose metabolism described in the Warburg effect is critical for growth and proliferation of cancer cells and knocking down LDH-A using RNA-i has been shown to lead to a reduction in cell proliferation and tumor growth in xenograft models.

D. A. Tennant et. al., Nature Reviews, 2010, 267.
P. Leder, et. al., Cancer Cell, 2006, 9, 425.

High levels of fatty acid synthase (FAS) have been found in cancer precursor lesions. Pharmacological inhibition of FAS affects the expression of key oncogenes involved in both cancer development and maintenance.

Alli et al. Oncogene (2005) 24, 39-46. doi:10.1038

Inhibitors of cancer metabolism, including inhibitors of LDH-A and inhibitors of fatty acid biosynthesis (or FAS inhibitors), are acceptable for use in combination with the compounds of this invention.

In one embodiment, the cancer treatment method of the claimed invention includes the co-administration a compound of Formula (I) and/or a pharmaceutically acceptable salt thereof and at least one anti-neoplastic agent, such as one selected from the group consisting of anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, cell cycle signaling inhibitors; HDAC inhibitors, proteasome inhibitors; and inhibitors of cancer metabolism.

In another embodiment, the present invention relates to co-administering a compound of the present invention in combination with erlotinib for the treatment of cancer.

In another embodiment, the present invention relates to co-administering a compound of the present invention in combination with erlotinib for the treatment of non-small cell lung cancer.

In one embodiment, the present invention relates to a use of a combination of erlotinib and a compound of the present invention or a pharmaceutically acceptable salt thereof in preparation of a medicament for the treatment of cancer.

In one embodiment, the present invention relates to a use of a combination of erlotinib and a compound of the present invention or a pharmaceutically acceptable salt thereof in preparation of a medicament for the treatment of non-small cell lung cancer.

EXPERIMENTALS

General Experimental Conditions $^1$H NMR spectra were recorded at ambient temperature using either a Varian Unity Inova (400 MHz) spectrometer with a triple resonance 5 mm probe, an Avance III (300 MHz) spectrometer or a Bruker Ultrashield (400 MHz or 500 MHz) spectrometer. Chemical shifts are expressed in ppm relative to tetramethylsilane. The following abbreviations have been used: br=broad signal, s=singlet, d=doublet, dd=double doublet, t=triplet, q=quartet, m=multiplet.

Microwave experiments were carried out using a CEM Discover, Smith Synthesiser or a Biotage Initiator 60™, which uses a single-mode resonator and dynamic field tuning, both of which give reproducibility and control. Temperatures from 40-250° C. can be achieved and pressures of up to 30 bar can be reached.

High Pressure Liquid Chromatography-Mass Spectrometry (LCMS) experiments to determine retention times ($R_T$) and associated mass ions were performed using one of the following methods.

The spectrometers have an electrospray source operating in positive and negative ion mode. Additional detection was achieved using a Sedex 85 evaporative light scattering detector.

Method A:

Experiments performed on an Agilent 1100 HPLC with Agilent MSD mass spectrometer using ESI as ionization source using an Agilent ZORBAX SB-C18 100×3.0 mm column and a 0.7 ml/minute flow rate. The solvent system was a gradient starting with 98% water with 0.05% TFA (solvent A) and 2% acetonitrile with 0.05% TFA (solvent B), ramping up to 2% solvent A and 98% solvent B over 25.5 minutes. The final solvent system was held constant for a further 2.5 minutes.

Method B:

Experiments performed on an Agilent 1200 HPLC with Agilent MSD mass spectrometer using ESI as ionization source using an Agilent ZORBAX SB-C18 30×2.1 mm column and a 0.4 ml/minute flow rate. The solvent system was a gradient starting with 97% water with 0.05% TFA (solvent A) and 3% acetonitrile with 0.05% TFA (solvent B), ramping up to 5% solvent A and 95% solvent B over 7 minutes. The final solvent system was held constant for a further 1.5 minute.

Method C:

Experiments performed on a Waters Acquity UHPLC with Waters-LCT Premier XE mass spectrometer using ESI as ionization source using an Acquity UPLC BEH C18, 1.7 um, 2.1*50 mm column and a 0.6 ml/minute flow rate. The solvent system was a gradient starting with 98% water with 0.05% TFA (solvent A) and 2% acetonitrile with 0.05% TFA (solvent B), ramping up to 2% solvent A and 98% solvent B over 17 minutes. The final solvent system was held constant for a further 1.5 minutes.

Method D:

Experiments performed on a Waters Acquity UHPLC with Waters-LCT Premier XE mass spectrometer using ESI as ionization source using an Acquity UPLC BEH C18, 1.7 um, 2.1*50 mm column and a 0.6 ml/minute flow rate. The solvent system was a gradient starting with 98% water with 0.05% TFA (solvent A) and 2% acetonitrile with 0.05% TFA (solvent B), ramping up to 2% solvent A and 98% solvent B over 7.5 minutes. The final solvent system was held constant for a further 1.0 minutes.

Method E:

Experiments performed on a Waters Micromass ZQ2000 quadrupole mass spectrometer linked to a Waters Acquity UPLC system with a PDA UV detector.

LC Column-Acquity BEH C18 1.7 um 100×2.1 mm, maintained at 40° C. and a 0.4 mL/minute flow rate. The mobile phase consisted of formic acid 0.1% in water (solvent A) and formic acid 0.1% in acetonitrile (solvent B).

| Gradient - Time | flow mL/min | % A | % B |
| --- | --- | --- | --- |
| 0.00 | 0.4 | 95 | 5 |
| 0.40 | 0.4 | 95 | 5 |
| 6.00 | 0.4 | 5 | 95 |
| 6.80 | 0.4 | 5 | 95 |
| 7.00 | 0.4 | 95 | 5 |
| 8.00 | 0.4 | 95 | 5 |

Method F:

Experiments performed on a Waters Micromass ZQ2000 quadrupole mass spectrometer linked to a Waters Acquity UPLC system with a PDA UV detector.

LC Column-Acquity Shield RP18 1.7 μm, 100×2.1 mm or Acquity HSS T3 1.8 μm, 100×2.1 mm, maintained at 40° C. and a 0.4 mL/minute flow rate. The mobile phase consisted of formic acid 0.1% in water (solvent A) and formic acid 0.1% in acetonitrile (solvent B).

| Gradient - Time | flow mL/min | % A | % B |
| --- | --- | --- | --- |
| 0.00 | 0.4 | 95 | 5 |
| 0.40 | 0.4 | 95 | 5 |
| 6.00 | 0.4 | 5 | 95 |
| 6.80 | 0.4 | 5 | 95 |
| 7.00 | 0.4 | 95 | 5 |
| 8.00 | 0.4 | 95 | 5 |

Method G:

Experiments performed on an SHIMADZU 1100 HPLC with SHIMADZU MSD mass spectrometer using ESI as ionization source using an SHIMADU XR-ODS 50×3 0 mm column and a 0.9 ml/minute flow rate. The solvent system was a gradient starting with 95% water with 0.1% formic acid (solvent A) and 5% acetonitrile (solvent B), ramping up to 100% solvent B over 2 minutes. The final solvent system was held constant for a further 1.1 minutes.

Method H:

Experiments performed on an SHIMADZU 1100 HPLC with SHIMADZU MSD mass spectrometer using ESI as ionization source using an Phenomenex Gemini-NX C18 50×3.0 mm column and a 0.9 ml/minute flow rate. The solvent system was a gradient starting with 90% water with 0.04% NH3 (solvent A) and 10% acetonitrile (solvent B), ramping up to 35% solvent A and 65% solvent B over 4 minutes. The final solvent system was held constant for a further 0.2 minutes.

Method I:

Experiments performed on an SHIMADZU 1100 HPLC with SHIMADZU MSD mass spectrometer using ESI as ionization source using an SHIMADZU Shim-pack XR-ODS 50×2.0 mm column and a 0.7 ml/minute flow rate. The solvent system was a gradient starting with 95% water with 0.1% FA (solvent A) and 5% acetonitrile (solvent B), ramping up to 60% solvent A and 40% solvent B over 1 minutes. The final solvent system was held constant for a further 1 minute.

Method J:

Experiments performed on an SHIMADZU 1100 HPLC with SHIMADZU MSD mass spectrometer using ESI as ionization source using an SHIMADU XR-ODS 50×3 0 mm column and a 1 ml/minute flow rate. The solvent system was a gradient starting with 95% water with 0.05% TFA (solvent A) and 5% acetonitrile with 0.05% TFA (solvent B), ramping up to 5% solvent A and 95% solvent B over 4.2 minutes. The final solvent system was held constant for a further 1 minute.

Method K:

Experiments performed on an SHIMADZU 1100 HPLC with SHIMADZU MSD mass spectrometer using ESI as ionization source using an SHIMADU XR-ODS 50×3.0 mm column and a 1 ml/minute flow rate. The solvent system was a gradient starting with 95% water with 0.05% TFA (solvent A) and 5% acetonitrile with 0.05% TFA (solvent B), ramping up to 25% solvent A and 75% solvent B over 2 minutes. The final solvent system was held constant for a further 1.2 minutes.

Method L:

Experiments performed on an SHIMADZU 1100 HPLC with SHIMADZU MSD mass spectrometer using ESI as ionization source using an SHIMADU XR-ODS 50×3.0 mm column and a 1 ml/minute flow rate. The solvent system was a gradient starting with 95% water with 0.05% TFA (solvent A) and 5% acetonitrile with 0.05% TFA (solvent B), ramping up to 35% solvent A and 65% solvent B over 4.5 minutes. The final solvent system was held constant for a further 0.7 minutes.

Method M:

Experiments performed on an SHIMADZU 1100 HPLC with SHIMADZU MSD mass spectrometer using ESI as ionization source using an SHIMADU XR-ODS 50×3.0 mm column and a 1 ml/minute flow rate. The solvent system was a gradient starting with 95% water with 0.05% TFA (solvent A) and 5% acetonitrile with 0.05% TFA (solvent B), ramping up to 30% solvent A and 70% solvent B over 4 minutes. The final solvent system was held constant for a further 1.9 minutes.

Method N:

Experiments performed on an SHIMADZU 1100 HPLC with SHIMADZU MSD mass spectrometer using ESI as ionization source using an SHIMADU XR-ODS 50×3.0 mm column and a 1 ml/minute flow rate. The solvent system was a gradient starting with 95% water with 0.05% TFA (solvent A) and 5% acetonitrile with 0.05% TFA (solvent B), ramping up 100% solvent B over 2 minutes. The final solvent system was held constant for a further 1.1 minutes.

Method O:

Experiments performed on an Agilent 1100 HPLC with Agilent quadrupole LC/MSD SL mass spectrometer using ESI as ionization source using an Agilent XBridge C18 30×3.0 mm column and a 2 mL/min flow rate. The solvent system was a gradient starting with 98% water with 0.05% TFA (solvent A) and 2% acetonitrile with 0.05% TFA (solvent B), ramping up to 5% solvent A and 95% solvent B over 2.2 min. The final solvent system was held constant for a further 0.3 min.

Method P:

Experiments performed on a Waters Acquity UHPLC with Waters SQ mass spectrometer using ESI as ionization source using an Acquity UPLC BEH C18, 1.7 um, 2.1*50 mm column and a 0.7 mL/min flow rate. The solvent system was a gradient starting with 95% water with 0.05% TFA (solvent A) and 5% acetonitrile with 0.05% TFA (solvent B), ramping up to 5% solvent A and 95% solvent B over 1.4 min. The final solvent system was held constant for a further 0.3 min.

Method Q:

Experiments performed on a Shimadzu 1100 HPLC with Shimadzu MSD mass spectrometer using ESI as ionization source using a Shim-pack XR-ODS50×3.0 mm column and a 1 mL/min flow rate. The solvent system was a gradient starting with 95% water with 0.05% TFA (solvent A) and 5% acetonitrile with 0.05% TFA (solvent B), ramping up to 100% solvent B over 2.2 min. The final solvent system was held constant for a further 1 min.

Method R:

Experiments performed on a Shimadzu 1100 HPLC with Shimadzu MSD mass spectrometer using ESI as ionization source using a Shim-pack XBridge C18 50×3.0 mm column and a 1.1 mL/min flow rate. The solvent system was a gradient starting with 95% water with 0.05% ammonium bicarbonate (solvent A) and 5% acetonitrile (solvent B), ramping up to 95% solvent B over 2.2 min. The final solvent system was held constant for a further 1 min.

Method S:

Experiments performed on a Shimadzu 1100 HPLC with Shimadzu MSD mass spectrometer using ESI as ionization source using a Shimadzu Acquity UPLC BEH C18 50×2.1 mm column and a 0.7 mL/minute flow rate. The solvent system was a gradient starting with 95% water with 0.1% TFA (solvent A) and 5% acetonitrile with 0.05% TFA (solvent B), ramping up to 100% solvent B over 2 min. The final solvent system was held constant for a further 1.2 min.

Schemes

Compounds of the invention can be prepared as shown in Scheme A below. A 2-halo pyridine compound a reacts with amines to provide compound b. Reduction of the nitro group provides compounds c, which may be condensed with compounds of formula d to provide compounds e. Palladium-mediated coupling of compound e with 2-chloro-4-aminopyrimidine provides compound f. Direct displacement of the chloride with appropriately substituted amines or palladium-mediated coupling with aryl boronates or stanannes provide final compounds g and h.

Scheme A:

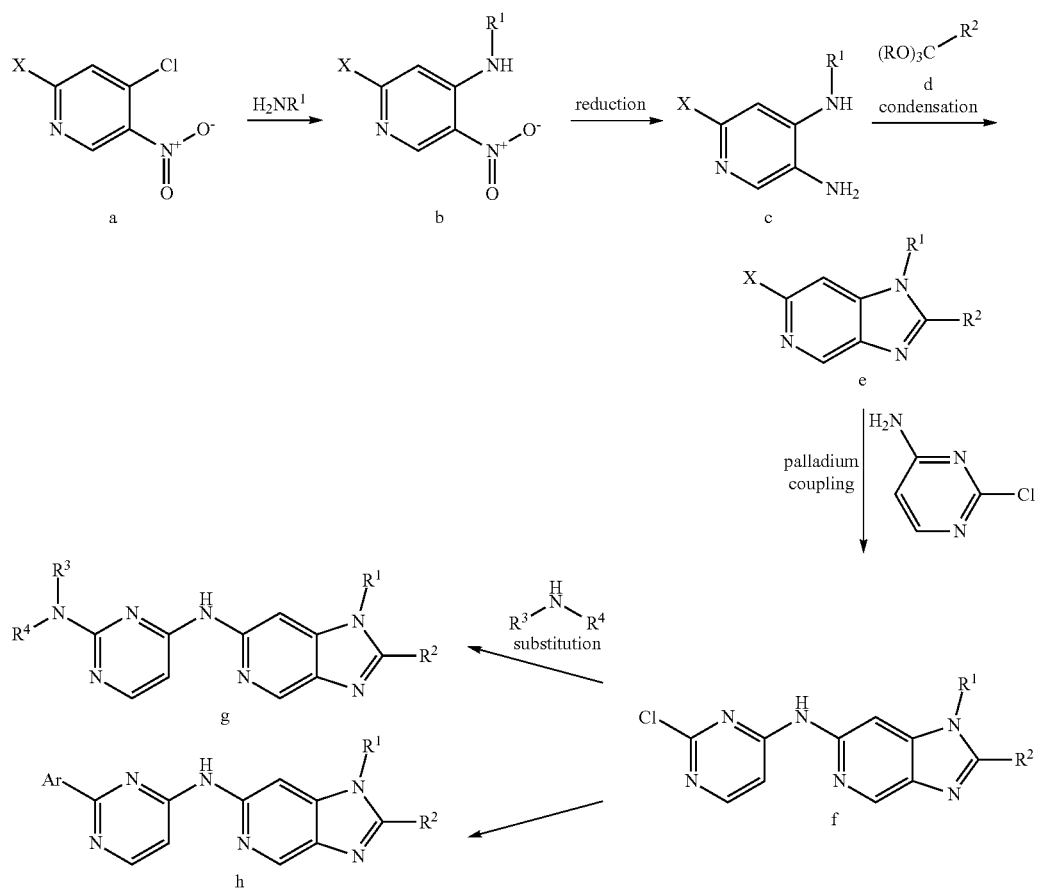

Alternatively, compounds of the invention can be prepared as shown in Scheme B below. 2-chloro-4-aminopyrimidine may be reacted with appropriately substituted amines or via palladium-mediated coupling with aryl boronates or stanannes to provide pyrimidines i with variable substitution at the 2-position. Compounds i and compound e may be reacted via a palladium-mediated coupling to form final compounds g or h.

Scheme B:

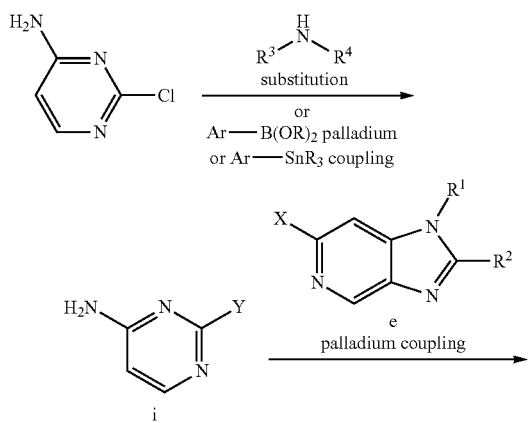

-continued

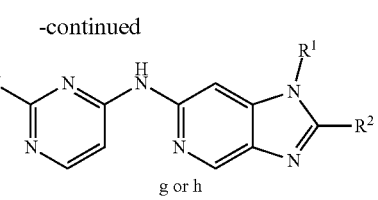

g or h

Compounds of the invention can be prepared as shown in Scheme C below. Iodination of 2-halo-azaindole j affords compound k. Alkylation of compound k with alkyl halides provide compound l. Compound l may be treated with n-BuLi and $CO_2$ to afford compound m. Coupling of an optionally substituted amine with compound m under standard amide bond formation conditions yields compound n. Palladium-mediated coupling of optionally substituted aminopyrimidine compound i with compound n affords the final compound o.

Scheme C:

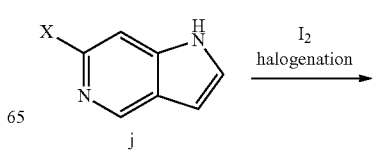

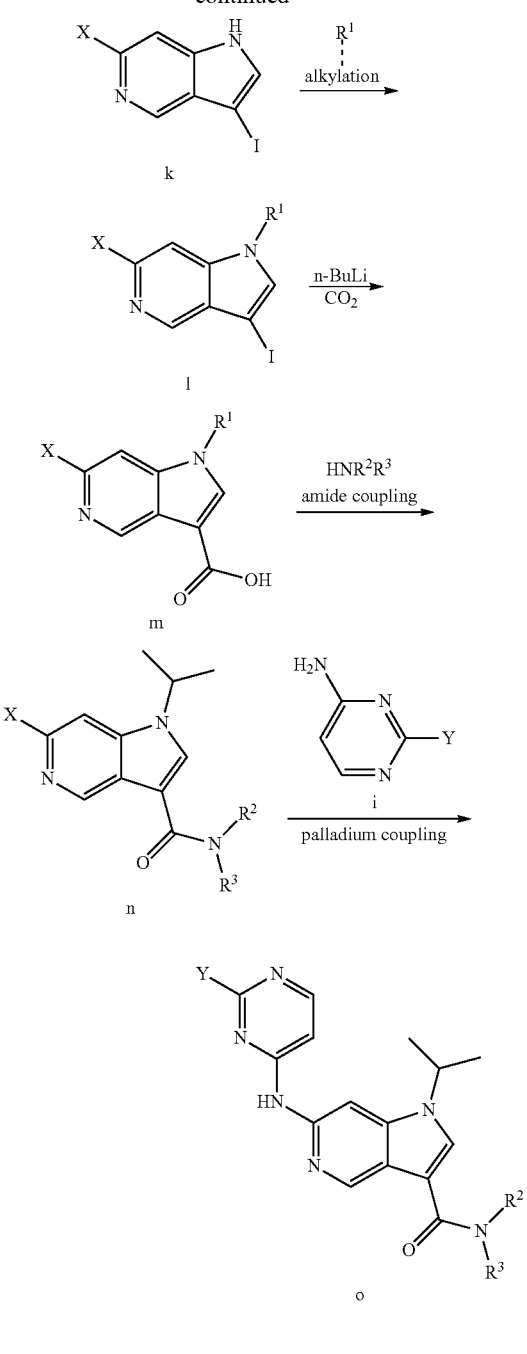

Example 1: N-(2-(4-Methoxypiperidin-1-yl)pyrimidin-4-yl)-2-(1H-pyrazol-4-yl)-1H-pyrrolo[3,2-c]pyridin-6-amine

Step 1: 4-((Trimethylsilyl)ethynyl)-1H-pyrazole

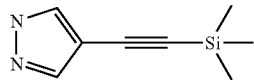

To a solution of 4-iodo-1H-pyrazole (11.0 g, 56.7 mmol) and ethynyl(trimethyl)silane (22.3 g, 227 mmol) in tetrahydrofuran (80 mL) was added diethylamine (80 mL, 758 mmol), bis(triphenylphosphine)palladium(II) dichloride (6.03 g, 8.51 mmol) and copper(I) iodide (1.62 g, 8.51 mmol), and the reaction mixture was stirred at room temperature for 18 h. The solvent was removed in vacuo and the resulting residue was dissolved in Et$_2$O (400 mL) and filtered. The filtrate was concentrated and the residue was purified by silica gel chromatography (gradient 0-100% Et$_2$O in heptane) to afford the title compound (5.1 g, 55%) as a brown oil. LCMS (ESI) [M+H]$^+$=165.2; $^1$H NMR (400 MHz, DMSO-d$_6$) δ 12.92 (s, 1H), 7.87 (s, 1H), 7.46 (s, 1H), 0.01 (d, J=6.4 Hz, 9H).

Step 2: 4-Ethynyl-1H-pyrazole

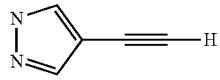

To a solution of 4-((trimethylsilyl)ethynyl-1H-pyrazole (5.0 g, 30 mmol) in tetrahydrofuran (50 mL) was added a solution of lithium hydroxide hydrate (1.9 g, 46 mmol) in water (10 mL). After stirring for 18 h at room temperature, the reaction mixture was neutralized with acetic acid and concentrated. The residue was partitioned between 1-butanol and water and the combined organic layers were concentrated to yield the title compound (2.8 g, quantitative). $^1$H NMR (400 MHz, DMSO-d$_6$) δ 13.08 (s, 1H), 7.84 (s, 2H), 3.93 (s, 1H).

Step 3: 2-Bromo-5-iodopyridin-4-amine

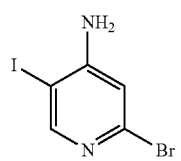

To a solution of 2-bromopyridin-4-amine (15.0 g, 86.7 mmol) and sodium acetate (14.2 g, 173.4 mmol) in glacial acetic acid (150 mL) was added a solution of iodine monochloride (4.9 mL, 95.4 mmol) in glacial acetic acid (70 mL). After heating for 18 h at 70° C., the reaction was cooled to room temperature and poured into water (800 mL). The aqueous solution was partitioned twice with EtOAc. The combined organic layers were washed with saturated aqueous Na$_2$CO$_3$, saturated aqueous Na$_2$S$_2$O$_3$, brine and dried over MgSO$_4$. The organic layer was filtered and concentrated in vacuo, and the resulting residue was purified by silica gel chromatography (gradient 10-60% EtOAc in heptane) to afford the title compound (8.9 g, 34%). LCMS (ESI)

[M+H]=300.0; ¹H NMR (400 MHz, DMSO-d₆) δ 8.16 (s, 1H), 6.77 (s, 1H), 6.50 (s, 2H).

Step 4:
N-(2-Bromo-5-iodopyridin-4-yl)methanesulfonamide

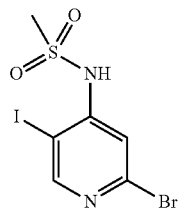

Methanesulfonyl chloride (2.15 mL, 27.3 mmol) in dichloromethane (8 mL) was added dropwise to a cold, 0° C., solution of 2-bromo-5-iodopyridin-4-amine (1.63 g, 5.45 mmol) and triethylamine (3.84 mL, 27.3 mmol) in dichloromethane (20 mL). The reaction mixture was allowed to warm to room temperature and stirred for 2 h. The solvent was removed in vacuo and the resulting residue was purified by silica gel chromatography (gradient 5-100% EtOAc in heptane) to afford the title compound (1.1 g, 44% yield) as an off-white solid which was dissolved in aqueous NaOH solution (10%, 15 mL) in tetrahydrofuran (15 mL) and stirred at room temperature for 16 hours. The reaction mixture was concentrated. Water was added and then acidified to pH 4 using an aqueous citric acid solution. The resulting solid was filtered and dried to afford the title compound (0.950 g, 46%). LCMS (ESI) [M+H]=379.0; ¹H NMR (400 MHz, DMSO-d₆) δ 8.62 (s, 1H), 7.52 (s, 1H), 3.26 (s, 3H).

Step 5: 6-Bromo-2-(1H-pyrazol-4-yl)-1H-pyrrolo[3,2-c]pyridine

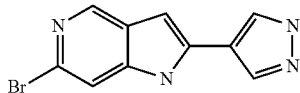 [SMILES: Brc1cc2[nH]c(-c3cn[nH]c3)cc2cn1]

A mixture of N-(2-bromo-5-iodopyridin-4-yl)methanesulfonamide (1500 mg, 4.0 mmol), 4-ethynyl-1H-pyrazole (440 mg, 4.8 mmol), bis(triphenylphosphine)palladium(II) dichloride (140 mg, 0.20 mmol), copper(I) iodide (38 mg, 0.20 mmol) and triethylamine (2.5 mL, 18 mmol) in DMF (35 mL) was heated at 100° C. for 3 h, and then cooled to 50° C. DBU (1.8 mL) was added and stirring continued at 50° C. for 30 min. After cooling to room temperature, the solution was diluted with saturated NH₄Cl and extracted twice with EtOAc. The combined organic layers were dried over MgSO₄, filtered and concentrated in vacuo. The resulting residue was purified by silica gel chromatography (gradient 5-100% EtOAc in heptane) to afford the title compound (350 mg, 33%). LCMS (ESI) [M+H]=263.0; ¹H NMR (400 MHz, DMSO-d₆) δ 13.13 (s, 1H), 11.92 (s, 1H), 8.51 (s, 1H), 8.26 (s, 1H), 8.01 (s, 1H), 7.48 (s, 1H), 6.72 (s, 1H)

Step 6: 6-Bromo-1-((2-(trimethylsilyl)ethoxy)methyl)-2-(1-((2-(trimethylsilyl)ethoxy)methyl)-1H-pyrazol-4-yl)-1H-pyrrolo[3,2-c]pyridine

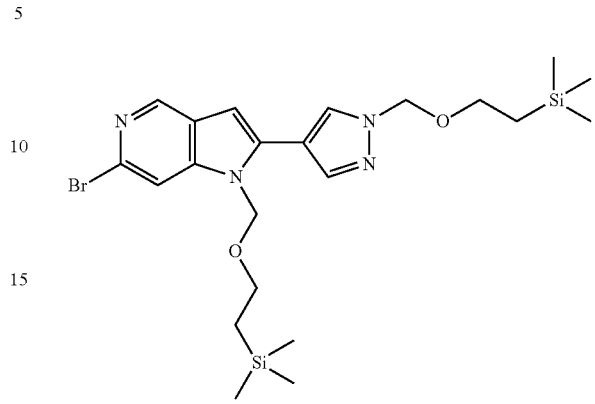

Sodium hydride (270 mg, 6.7 mmol) was added slowly to a solution of 6-bromo-2-(1H-pyrazol-4-yl)-1H-pyrrolo[3,2-c]pyridine (350 mg, 1.3 mmol) in THF (10 mL) at 0° C. and stirred for 30 minutes followed by addition of 2-(chloromethoxy)ethyltrimethylsilane (0.94 mL, 5.3 mmol). The reaction mixture was allowed to warm to room temperature and stirred for an additional 5 h. The reaction was quenched with H₂O (50 mL), and the aqueous layer was extracted twice with EtOAc. The combined organic layers were concentrated in vacuo and the resulting residue was purified by silica gel chromatography (gradient 0-50% EtOAc in heptane) to afford the title compound (250 mg, 36%). LCMS (ESI) [M+H]=524.0; ¹H NMR (500 MHz, DMSO-d₆) δ 8.60 (d, J=4.1 Hz, 1H), 8.36-8.33 (m, 1H), 8.01 (d, J=2.9 Hz, 2H), 6.85 (s, 1H), 5.64 (s, 2H), 5.48 (d, J=8.3 Hz, 2H), 3.61-3.48 (m, 4H), 0.94-0.76 (m, 4H), 0.01-0.00 (m, 18H).

Step 7: N-(2-(4-Methoxypiperidin-1-yl)pyrimidin-4-yl)-2-(1H-pyrazol-4-yl)-1H-pyrrolo[3,2-c]pyridin-6-amine

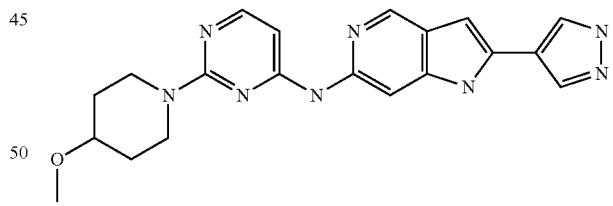

A mixture of 6-bromo-1-((2-(trimethylsilyl)ethoxy)methyl)-2-(1-((2-(trimethylsilyl)ethoxy)methyl)-1H-pyrazol-4-yl)-1H-pyrrolo[3,2-c]pyridine (125 mg, 0.239 mmol), 2-(4-methoxy-1-piperidyl)pyrimidin-4-amine (Example 3, step 2) (64.6 mg, 0.310 mmol), tris(dibenzylideneacetone)dipalladium (0) (10.9 mg, 0.012 mmol), Xantphos (14.2 mg, 0.024 mmol) and cesium carbonate (233 mg, 0.716 mmol) in 1,4-dioxane (1.5 mL) and 1,2-dimethoxyethane (1.5 mL) was added to a microwave tube. After purging with nitrogen for 5 minutes, the sealed tube was heated at 120° C. in a CEM microwave for 60 min. The reaction mixture was filtered through a pad of celite and the filtrate was concentrated in vacuo. The resulting residue was purified by silica gel chromatography (gradient 0-100% EtOAc in heptane) to afford the title compound (43 mg, 28%. LCMS (ESI) [M+H]=652.0) as an off-white solid which was dissolved in MeOH (1 mL) and 10% aqueous NaOH (0.1 mL), and stirred at room temperature for 30 min. The mixture was evaporated and the residue was purified by HPLC (C18 silica on a 20 min gradient 5-50% acetonitrile/0.1% NH$_4$OH in water) to afford the title compound (5.0 mg, 20%). LCMS (ESI): RT (min)=3.460, M+H=391.2, method=B; $^1$H NMR (400 MHz, DMSO-d$_6$) δ 9.46 (s, 1H), 8.44 (s, 1H), 8.07 (s, 2H), 7.96-7.87 (m, 2H), 6.63-6.53 (m, 2H), 4.24 (dt, J=13.0, 4.6 Hz, 2H), 3.52-3.35 (m, 2H), 3.30 (s, 3H), 1.97-1.85 (m, 2H), 1.51-1.36 (m, 2H).

Example 2: 1-Isopropyl-N-(2-(4-methoxypiperidin-1-yl)pyrimidin-4-yl)-2-(1H-pyrazol-4-yl)-1H-pyrrolo[3,2-c]pyridin-6-amine

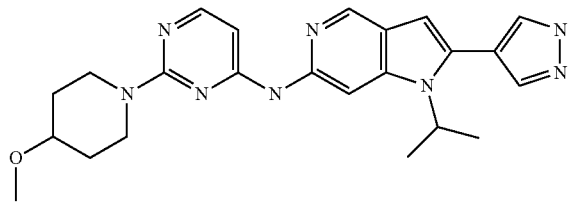 [SMILES: COC1CCN(c2nccc(Nc3cc4c(cn3)cc(-c3cn[nH]c3)n4C(C)C)n2)CC1]

Step 1: 4-Iodo-1-((2-(trimethylsilyl)ethoxy)methyl)-1H-pyrazole

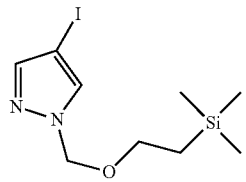

Into a 1 L 3-necked round-bottom flask purged and maintained with nitrogen, was added 4-iodo-1H-pyrazole (45.0 g, 232 mmol, 1.00 equiv) and N,N-dimethylformamide (500 mL). This was followed by addition of sodium hydride (10.2 g, 2.55 mmol, 1.10 equiv) in several batches at 0° C. The reaction mixture was stirred for 30 min at 0° C. in an ice/salt bath. To the reaction mixture was added [2-(chloromethoxy)ethyl]trimethylsilane (42.3 g, 254 mmol, 1.10 equiv) dropwise with stirring. The resulting solution was stirred for an additional 3 h at room temperature. The reaction mixture was quenched by addition of water/ice (250 mL), extracted with ethyl acetate (2×500 mL) and the organic layers were separated and combined. The combined organic layer was washed with brine, dried over anhydrous sodium sulfate and concentrated under vacuum to afford 4-iodo-1-[[2-(trimethylsilyl)ethoxy]methyl]-1H-pyrazole (80.0 g) as light yellow oil without further purification.

Step 2: 1-((2-(Trimethylsilyl)ethoxy)methyl)-4-(2-(trimethylsilyl)ethynyl)-1H-pyrazole

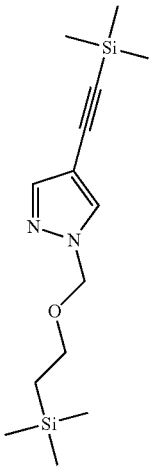

Into a 1 L 3-necked round-bottom flask purged and maintained with an inert atmosphere of nitrogen, was added 4-iodo-1-[[2-(trimethylsilyl)ethoxy]methyl]-1H-pyrazole (75.0 g, 231 mmol), CuI (880 mg, 4.62 mmol), dichlorobis(triphenylphosphine)palladium(II) (3.25 g, 4.63 mmol), triethylamine (93.5 g, 926 mmol), TMS-acetylene (56.7 g, 578 mmol) and tetrahydrofuran (500 mL). After being stirred for 5 h at room temperature, the reaction mixture was diluted with H$_2$O (300 mL) and ethyl acetate (1000 mL), filtered, washed with brine, dried over anhydrous sodium sulfate and concentrated under vacuum to afford 1-[[2-(trimethylsilyl)ethoxy]methyl]-4-[2-(trimethylsilyl)ethynyl]-1H-pyrazole (80.0 g) as brown oil. LCMS (ESI): R$_T$ (min)=1.912, [M+H]$^+$=295, method=K.

Step 3: 4-Ethynyl-1-((2-(trimethylsilyl)ethoxy)methyl)-1H-pyrazole

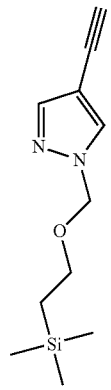

Into a 100 mL 3-necked round-bottom flask purged and maintained with nitrogen, was added 1-[[2-(trimethylsilyl)ethoxy]methyl]-4-[2-(trimethylsilyl)ethynyl]-1H-pyrazole (80.0 g, 272 mmol, 1.00 equiv) and tetrahydrofuran (100 mL). This was followed by addition of TBAF (1N in tetrahydrofuran, 300 mL) dropwise with stirring at room temperature. After being stirred for 4 h at room temperature, the reaction mixture was diluted with ethyl acetate (300 mL), washed with brine, dried over anhydrous sodium sulfate and concentrated under vacuum. The residue was purified by chromatography with ethyl acetate/petroleum ether (1:50) to afford the title compound (30.0 g, 50.0%) as yellow oil. LCMS (ESI): $R_T$ (min)=1.256, [M+H]$^+$=223, method=G. $^1$H NMR (300 MHz, CDCl$_3$) 7.68 (s, 1H), 7.59 (s, 1H), 5.34 (s, 2H), 3.50 (m, 2H), 2.99 (s, 1H), 0.85 (m, 2H), 0.03 (s, 9H).

Step 4: 6-Bromo-2-(1-((2-(trimethylsilyl)ethoxy)methyl)-1H-pyrazol-4-yl)-1H-pyrrolo[3,2-c]pyridine

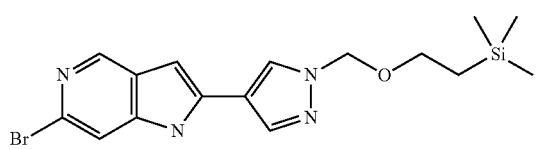 [SMILES: C[Si](C)(C)CCOCn1cc(-c2cc3cnc(Br)cc3[nH]2)cn1]

A mixture of N-(2-bromo-5-iodopyridin-4-yl)methanesulfonamide (5.9 g, 16.0 mmol), 4-ethynyl-1-((2-(trimethylsilyl)ethoxy)methyl)-1H-pyrazole (4.5 g, 20.0 mmol), bis(triphenylphosphine)palladium(II) dichloride (550 mg, 0.78 mmol), copper(I) iodide (150 mg, 0.78 mmol) and triethylamine (6.6 mL, 47.0 mmol) in DMF (50 mL) was heated at 100° C. for 3 h and then cooled to 50° C. DBU (7.1 mL) was added and stirring continued for an additional 30 minutes at 50° C. After stirring at room temperature for 18 h, the mixture was diluted with NH$_4$Cl aqueous solution, and extracted twice with EtOAc. The combined organic layers were dried over MgSO$_4$ and concentrated in vacuo. The resulting residue was purified by silica gel chromatography (gradient 0-100% EtOAc in heptane) to afford the title compound (2.1 g, 34%). LCMS (ESI) [M+H]$^+$=395.2; $^1$H NMR (400 MHz, DMSO-d$_6$) δ 8.57 (s, 1H), 8.41 (s, 1H), 8.09 (s, 1H), 7.53 (s, 1H), 6.80 (s, 1H), 5.51 (s, 2H), 3.67-3.55 (m, 2H), 0.97-0.74 (m, 2H), 0.00 (s, 9H).

Step 5: 6-Bromo-1-isopropyl-2-(1-((2-(trimethylsilyl)ethoxy)methyl)-1H-pyrazol-4-yl)-1H-pyrrolo[3,2-c]pyridine

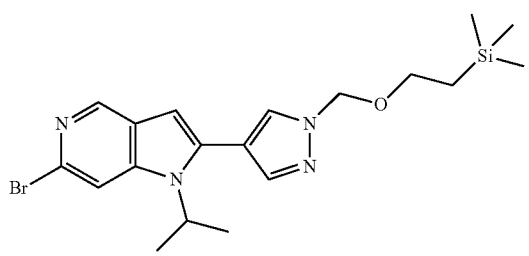 [SMILES: CC(C)n1c(-c2cnn(COCC[Si](C)(C)C)c2)cc2cnc(Br)cc21]

2-iodopropane (0.4 mL, 4.0 mmol) was added to a mixture of 6-bromo-2-(1-((2-(trimethylsilyl)ethoxy)methyl)-1H-pyrazol-4-yl)-1H-pyrrolo[3,2-c]pyridine (500 mg, 1.0 mmol), cesium carbonate (1000 mg, 4.0 mmol) in DMF (4 mL). After stirring at 90° C. for 48 h, the mixture was diluted with EtOAc (80 mL) and washed with water. The organic layer was concentrated in vacuo and the residue was purified by silica gel chromatography (gradient 0-40% EtOAc in heptane) to afford the title compound (240 mg, 40%). LCMS (ESI) [M+H]$^+$=437.4; $^1$H NMR (400 MHz, DMSO-d$_6$) δ 8.62 (s, 1H), 8.31 (s, 1H), 7.87 (d, J=9.9 Hz, 2H), 6.65 (s, 1H), 5.79 (s, 1H), 5.52 (s, 2H), 4.84-4.71 (m, 1H), 3.72-3.59 (m, 2H), 1.58 (d, J=6.9 Hz, 6H), 0.99-0.85 (m, 2H), 0.00 (s, 9H).

Step 6: 1-Isopropyl-N-(2-(4-methoxypiperidin-1-yl)pyrimidin-4-yl)-2-(1H-pyrazol-4-yl)-1H-pyrrolo[3,2-c]pyridin-6-amine

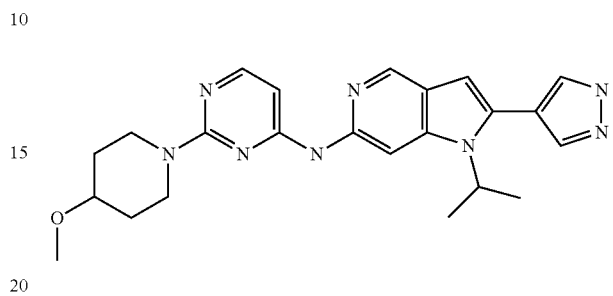

6-Bromo-1-isopropyl-2-(1-((2-(trimethylsilyl)ethoxy)methyl)-1H-pyrazol-4-yl)-1H-pyrrolo[3,2-c]pyridine (236 mg, 0.542 mmol), 2-(4-methoxy-1-piperidyl)pyrimidin-4-amine (Example 3, step 2) (169 mg, 0.813 mmol), tris(dibenzylideneacetone)dipalladium(0) (24.8 mg, 0.0271 mmol), Xantphos (32.3 mg, 0.054 mmol), cesium carbonate (442 mg, 1.36 mmol) and 1,4-dioxane (4 mL) was added to a pressure tube. After purging with nitrogen for 5 minutes, the sealed tube was heated at 120° C. for 20 h. The reaction mixture was filtered through a pad of celite and washed with EtOAc. The filtrate was concentrated in vacuo and the residue was purified by silica gel chromatography (gradient 0-100% EtOAc in heptane) to afford the title compound (110 mg, 36%, LCMS (ESI) [M+H]=563.6) as an off-white solid. The protected product was dissolved in 4N HCl in 1,4-dioxane (4 mL) and stirred at room temperature for 1 h. The mixture was concentrated and the residue was purified by preparatory HPLC (C18 silica on a 20 min gradient 5-50% acetonitrile/0.1% NH$_4$OH in water) to afford the title compound (19 mg, 22%). LCMS (ESI): RT (min)=3.581, [M+H]$^+$=433.3, method=B; $^1$H NMR (400 MHz, DMSO-d6) δ 13.21 (s, 1H), 9.56 (s, 1H), 8.50 (s, 1H), 8.33 (s, 1H), 7.93 (d, J=5.7 Hz, 1H), 6.45 (s, 2H), 4.72 (p, J=7.1 Hz, 1H), 4.33-4.24 (m, 2H), 3.50-3.34 (m, 2H), 3.30 (s, 3H), 1.91 (d, J=12.2 Hz, 2H), 1.57 (d, J=7.0 Hz, 6H), 1.43 (dq, J=8.2, 4.5, 3.9 Hz, 2H).

Example 3: (1-Isopropyl-1H-imidazo[4,5-c]pyridin-6-yl)-[2-(4-methoxypiperidin-1-yl)pyrimidin-4-yl]amine formate salt

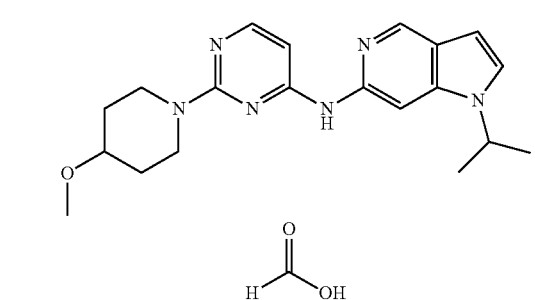

Step 1: (2-Chloro-5-nitropyridin-4-yl)isopropylamine

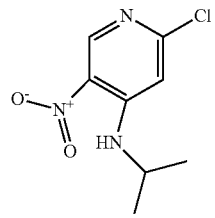

Isopropylamine (1.43 mL, 16.7 mmol) was added dropwise to a solution of 2,4-dichloro-5-nitropyridine (3 g, 13.9 mmol) and triethylamine (3.9 mL, 27.8 mmol) in THF (50 mL) at room temperature, resulting in a mild exotherm. The reaction mixture was stirred at room temperature for 3 h and then partitioned between water and EtOAc. The aqueous phase was washed with EtOAc and the combined organic phases were washed with brine, dried (MgSO$_4$) and concentrated in vacuo affording the title compound as a yellow solid (quantitative). $^1$H NMR (400 MHz, CDCl$_3$): δ 9.02 (1H, s), 8.08 (1H, s), 6.74 (1H, s), 3.88-3.72 (1H, m), 1.37 (6H, d, J=6.4 Hz).

Step 2: 2-(4-Methoxypiperidin-1-yl)pyrimidin-4-ylamine

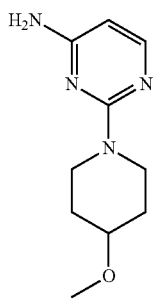

2-Chloropyrimidin-4-ylamine (3.5 g, 27.0 mmol), 4-methoxypiperidine hydrochloride (4.09 g, 27.0 mmol) and Cs$_2$CO$_3$ (26.4 g, 81.0 mmol) were suspended in DMF (60 mL) and heated at 120° C. for 18 h. The reaction mixture was partitioned between water and EtOAc. The aqueous phase was washed with EtOAc (×2) and the combined organic phases were washed with brine, dried (MgSO$_4$), and concentrated in vacuo affording the title compound as a solid (2.5 g). The aqueous phase was concentrated in vacuo and the slurry was extracted with EtOAc. The volatiles were removed in vacuo and the resulting residue was purified by chromatography (Si-PCC, gradient 0-100% EtOAc in cyclohexane) and then triturated with cyclohexane affording a second batch of the title compound (2.38 g, 87% combining the two batches). $^1$H NMR (400 MHz, CDCl$_3$) δ: 7.94 (1H, d, J=5.60 Hz), 5.74 (1H, d, J=5.60 Hz), 4.53 (2H s), 4.33-4.24 (2H, m), 3.47-3.37 (4H, m), 3.33-3.24 (2H, m), 1.98-1.87 (2H, m), 1.60-1.47 (2H, m).

Step 3: N$^4$-Isopropyl-N$^2$-[2-(4-methoxypiperidin-1-yl)pyrimidin-4-yl]-5-nitropyridine-2,4-diamine

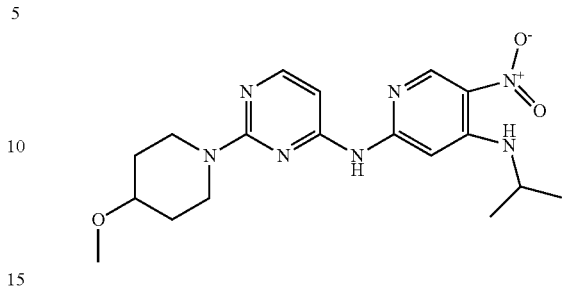

(2-Chloro-5-nitropyridin-4-yl)isopropylamine (517 mg, 2.4 mmol), 2-(4-methoxypiperidin-1-yl)pyrimidin-4-amine (500 mg, 2.4 mmol), XPhos (229 mg, 48 μmol), Pd$_2$(dba)$_3$ (109 mg, 12 μmol) and Cs$_2$CO$_3$ (1.56 g, 4.8 mmol) were suspended in 1,4 dioxane (10 mL). The reaction mixture was degassed with argon, sonicated and then heated under reflux for 3 h. The cooled reaction mixture was partitioned between water and EtOAc. The aqueous phase was washed with EtOAc (×2) and the combined organic phases were washed with brine, dried (MgSO$_4$), and concentrated in vacuo. The resulting dark brown solid was triturated with diethyl ether affording the title compound as a bright yellow solid (667 mg, 72%). $^1$H NMR (400 MHz, CDCl$_3$) δ: 9.02 (1H, s), 8.25 (1H, m), 8.11 (1H, d, J=5.5 Hz), 7.66 (1H, s), 7.30 (1H, s), 6.06 (1H, d, J=5.5 Hz), 4.33-4.20 (2H, m), 3.94-3.82 (1H, m), 3.56-3.44 (3H, m), 3.41 (3H, s), 2.00-1.89 (2H, m), 1.68-1.57 (2H, m), 1.37 (6H, d, J=6.38 Hz).

Step 4: N$^4$-Isopropyl-N$^2$-[2-(4-methoxypiperidin-1-yl)pyrimidin-4-yl]pyridine-2,4,5-triamine

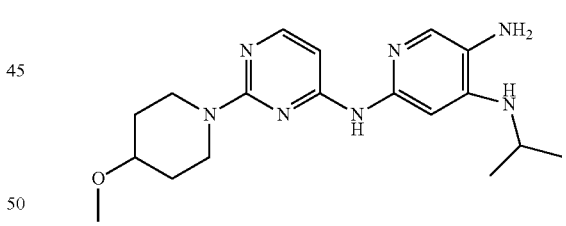

N$^4$-Isopropyl-N$^2$-[2-(4-methoxypiperidin-1-yl)pyrimidin-4-yl]-5-nitropyridine-2,4-diamine (2.18 g, 5.6 mmol) and Pd/C (10% by weight) (300 mg) were suspended in a mixture of EtOAc/MeOH (100 mL/10 mL) and stirred under a hydrogen atmosphere for 18 h. The reaction mixture was filtered and the filtrate was concentrated in vacuo. The resulting residue was purified by chromatography (Si-PCC, gradient 0-10% 2M NH$_3$/MeOH in DCM) to afford the title compound (1.84 g, 92%). $^1$H NMR (400 MHz, CDCl$_3$) δ 7.99 (1H, d, J=5.7 Hz), 7.61 (1H, s), 7.27 (1H, s), 7.18 (1H, s), 6.14 (1H, d, J=5.7 Hz), 4.37-4.2 (3H, m), 3.76-3.64 (1H, m), 3.50-3.33 (6H, m), 2.82 (2H, s), 1.99-1.89 (2H, m), 1.65-1.52 (2H, m), 1.28 (6H, d, J=6.3 Hz).

Step 5: (1-Isopropyl-1H-imidazo[4,5-c]pyridin-6-yl)-[2-(4-methoxypiperidin-1-yl)pyrimidin-4-yl]amine formate salt

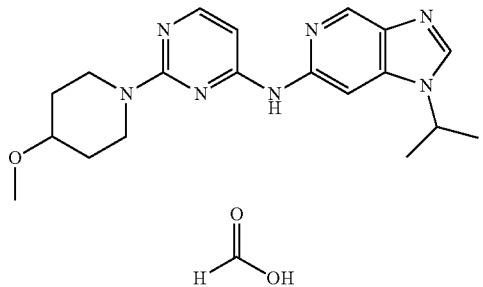

To a solution of N⁴-isopropyl-N²-[2-(4-methoxypiperidin-1-yl)pyrimidin-4-yl]pyridine-2,4,5-triamine (70 mg, 0.19 mmol) in trimethyl orthoformate (2 mL) was added formic acid (5 drops) and the reaction mixture was heated at 100° C. for 1 h. The volatiles were removed in vacuo and the resulting residue was purified by HPLC (C18 silica on a 20 min gradient 20-60% acetonitrile/0.1% NH₄OH in water followed by a 20 min gradient 5-50% acetonitrile/0.1% HCO₂H in water) to afford the title compound (19 mg, 27%). LCMS (ESI): R$_T$ 2.28 min, [M+H]⁺ 367.9, Method=E. ¹H NMR (400 MHz, DMSO): δ 9.74 (1H, s), 8.60 (1H, d, J=0.9 Hz), 8.35 (1H, s), 8.28 (1H, s), 8.14 (0.4H, s), 7.92 (1H, d, J=5.7 Hz), 6.33 (1H, d, J=5.7 Hz), 4.65-4.54 (1H, m), 4.24-4.12 (2H, m), 3.24 (3H, s), 2.46-2.25 (3H, m), 1.91-1.77 (2H, m), 1.51 (6H, d, J=6.8 Hz), 1.44-1.31 (2H, m).

Example 4: (2-Ethyl-1-isopropyl-1H-imidazo[4,5-c]pyridin-6-yl)-[2-(4-methoxypiperidin-1-yl)pyrimidin-4-yl]amine

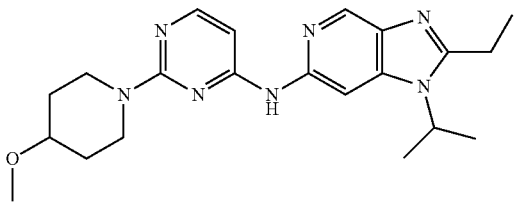 [SMILES: CCc1nc2cnc(Nc3ccnc(N4CCC(OC)CC4)n3)cc2n1C(C)C]

A mixture of N⁴-isopropyl-N²-[2-(4-methoxypiperidin-1-yl)pyrimidin-4-yl]pyridine-2,4,5-triamine (185 mg, 0.57 mmol), trimethyl orthopropionate (2 mL) and formic acid (5 drops) was heated at 180° C. under microwave irradiation for 7 h. The crude reaction mixture was purified by chromatography (Si-PCC, gradient 0-5% 2M NH₃/MeOH in DCM) followed by HPLC purification (C18 silica on 20 min gradient 10-90% acetonitrile/0.1% NH₄OH in water) to afford the title compound (113 mg, 55%). LCMS (ESI): R$_T$ 2.44 min, [M+H]⁺ 396.1, Method=E. ¹H NMR (400 MHz, CDCl₃): δ 8.62 (1H, s), 8.35 (1H, s), 8.00 (1H, d, J=5.64 Hz), 7.49 (1H, s), 6.01 (1H, d, J=5.7 Hz), 4.69-4.56 (1H, m), 4.39-4.28 (2H, m), 3.50-3.40 (3H, m), 3.37 (3H, s), 2.88 (2H, q, J=7.5 Hz), 1.98-1.89 (2H, m), 1.66-1.54 (8H, m), 1.43 (3H, t, J=7.5 Hz).

Example 5: (1-Isopropyl-2-methyl-1H-imidazo[4,5-c]pyridin-6-yl)-[2-(4-methoxypiperidin-1-yl)pyrimidin-4-yl]amine

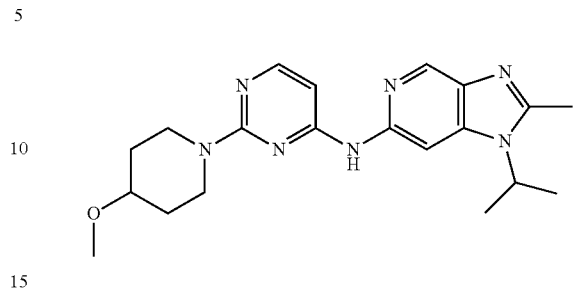

A mixture of N⁴-isopropyl-N²-[2-(4-methoxypiperidin-1-yl)pyrimidin-4-yl]pyridine-2,4,5-triamine (1.0 g, 2.81 mmol), trimethyl orthoacetate (7 mL) and formic acid (12 drops) was heated at 220° C. under microwave irradiation for 5 h and 30 min. The crude reaction mixture was purified by chromatography (Si-PCC, gradient 0-10% 2M NH₃/MeOH in DCM) to afford the title compound (963 mg, 90%). LCMS (ESI): R$_T$ 2.19 min, [M+H]⁺ 382.2, Method=E. ¹H NMR (400 MHz, CDCl₃): δ 8.58 (1H, s), 8.34 (1H, s), 8.00 (1H, d, J=5.6 Hz), 7.33 (1H, s), 6.00 (1H, d, J=5.6 Hz), 4.67-4.54 (1H, m), 4.38-4.28 (2H, m), 3.50-3.40 (3H, m), 3.38 (3H, s), 2.59 (3H, s), 1.99-1.90 (2H, m), 1.63 (6H, d, J=6.9 Hz), 1.62-1.55 (2H, m).

Example 6: 1-Isopropyl-N⁶-[2-(4-methoxypiperidin-1-yl)pyrimidin-4-yl]-N²-methyl-1H-imidazo[4,5-c]pyridine-2,6-diamine

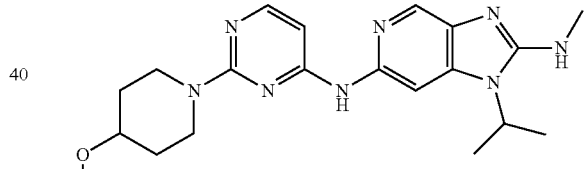

N⁴-Isopropyl-N²-[2-(4-methoxypiperidin-1-yl)pyrimidin-4-yl]pyridine-2,4,5-triamine (150 mg, 0.42 mmol) and methyl isothiocyanate (46 mg, 0.63 mmol) were dissolved in acetonitrile (7 mL) and heated at 70° C. for 18 h. (Benzotriazol-1-yloxy)tris(dimethylamino)phosphonium hexafluorophosphate (278 mg, 0.63 mmol) and DBU (128 mg, 0.84 mmol) were added and stirring at reflux temperature was continued for 16 h. The reaction mixture was partitioned between water and EtOAc. The aqueous phase was extracted with EtOAc (×2) and the combined organic phases were washed with brine, dried (MgSO₄), and concentrated in vacuo. The resulting residue was purified by HPLC (C18 silica on 20 min gradient 10-90% acetonitrile/0.1% NH₄OH in water) to afford the title compound (38 mg, 23%). LCMS (ESI): R$_T$ 1.91 min, [M+H]⁺ 397.2, Method=E. ¹H NMR (400 MHz, CDCl₃): δ 8.37 (1H, d, J=0.8 Hz), 8.08 (1H, s), 7.98 (1H, d, J=5.7 Hz), 7.28 (1H, s), 6.01 (1H, d, J=5.7 Hz), 4.38-4.22 (3H, m), 4.17-4.15 (1H, m), 3.49-3.38 (3H, m), 3.37 (3H, s), 3.13 (3H, d, J=4.9 Hz), 1.97-1.87 (2H, m), 1.65-1.3 (8H, m).

Example 7: [2-(2-Ethoxyethoxymethyl)-1-isopropyl-1H-imidazo[4,5-c]pyridin-6-yl]-[2-(4-methoxypiperidin-1-yl)pyrimidin-4-yl]amine

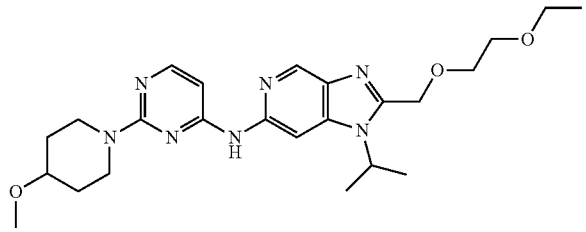 [SMILES: CCOCCOCc1nc2cnc(Nc3ccnc(N4CCC(OC)CC4)n3)cc2n1C(C)C]

Step 1:
2-Chloro-N-isopropyl-5-nitropyridin-4-amine

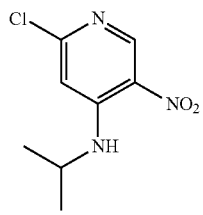

Into a 2000-mL 3-necked round-bottom flask was added a solution of 2,4-dichloro-5-nitropyridine (90.0 g, 466 mmol, 1.00 equiv) in tetrahydrofuran (1000 mL), triethylamine (70.0 g, 691 mmol, 1.48 equiv). This was followed by the addition of propan-2-amine (33.0 g, 558 mmol, 1.20 equiv) dropwise with stirring at 0° C. The resulting solution was stirred for 4 h at room temperature. The resulting mixture was concentrated under vacuum. The residue was triturated with H$_2$O (1000 mL). The solids were filtered and dried in an oven under reduced pressure to afford 2-chloro-5-nitro-N-(propan-2-yl)pyridin-4-amine the title compound (96 g, 95%) as a yellow solid. LCMS (ESI): R$_T$(min)=1.913, [M+H]$^+$=216, method=H.

Step 2: 6-Chloro-N$^4$-isopropylpyridine-3,4-diamine

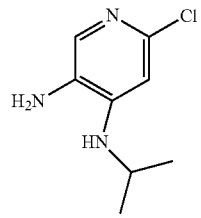

A suspension of 2-chloro-5-nitropyridin-4-yl)isopropylamine (1.01 g, 4.68 mmol) and Pt$_2$O (10 mg) in EtOAc (25 mL) was stirred at RT under a hydrogen atmosphere for 18 h. The reaction mixture was filtered and the filtrate was concentrated in vacuo to afford the title compound as a black solid (880 mg, quantitative). $^1$H NMR (400 MHz, CDCl$_3$) δ 7.64 (1H, s), 6.44 (1H, s), 4.22-4.13 (1H, m), 3.68-3.55 (1H, m), 3.49 (2H, s), 1.27 (6H, d, J=6.3 Hz).

Step 3: 6-Chloro-2-chloromethyl-1-isopropyl-1H-imidazo[4,5-c]pyridine

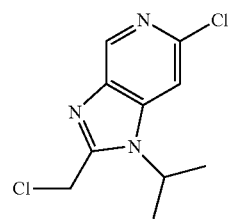

Chloroacetyl chloride (56 μL, 0.70 mmol) was added to a solution of 6-chloro-N$^4$-isopropylpyridine-3,4-diamine (100 mg, 0.54 mmol) and Et$_3$N (150 μL, 1.08 mmol) in DCM (1 mL) and the reaction mixture was stirred at RT for 30 min. The volatiles were removed in vacuo and the resulting residue was dissolved in AcOH (1 mL). The reaction mixture was heated at 70° C. for 48 h, then diluted with water and the pH adjusted to 8 by addition of NaOH (1N). The aqueous phase was washed with EtOAc (×2) and the combined organic layers were washed with brine, dried (MgSO$_4$) and evaporated. The resulting residue was purified by chromatography (Si-PCC, gradient 0-10% MeOH in DCM) to afford the title compound (53 mg, 40%). LCMS (ESI): [M+H]$^+$ 244.1.

Step 4: 6-Chloro-2-(2-ethoxyethoxymethyl)-1-isopropyl-1H-imidazo[4,5-c]pyridine

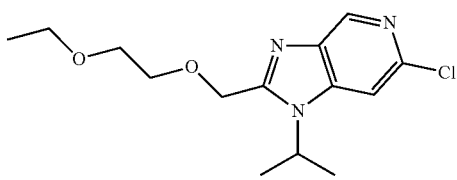 [SMILES: CCOCCOCc1nc2cnc(Cl)cc2n1C(C)C]

To a solution of 2-ethoxyethanol (23 μL, 0.24 mmol) in THF (2 mL) was added NaH (60% by weight in mineral oil, 11 mg, 0.28 mmol) and the reaction mixture was stirred at room temperature for 5 min. 6-Chloro-2-chloromethyl-1-isopropyl-1H-imidazo[4,5-c]pyridine (53 mg, 0.22 mmol) was added as a solution in THF (1 mL) and the reaction mixture was stirred at room temperature for 1 h, then diluted with water and extracted with EtOAc (×2). The combined organic layers were washed with brine, dried (MgSO$_4$) and concentrated in vacuo to afford the title compound (59 mg, 91%). LCMS (ESI): [M+H]$^+$ 298.2.

Step 5: [2-(2-Ethoxyethoxymethyl)-1-isopropyl-1H-imidazo[4,5-c]pyridin-6-yl]-[2-(4-methoxypiperidin-1-yl)pyrimidin-4-yl]amine

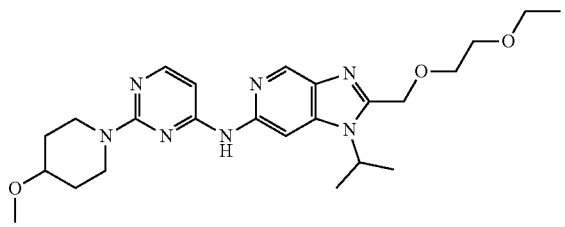 [SMILES: CCOCCOCc1nc2cnc(Nc3ccnc(N4CCC(OC)CC4)n3)cc2n1C(C)C]

6-Chloro-2-(2-ethoxyethoxymethyl)-1-isopropyl-1H-imidazo[4,5-c]pyridine (59 mg, 0.19 mmol), 2-(4-methoxypiperidin-1-yl)pyrimidin-4-amine (Example 3, Step 2) (38 mg, 0.18 mmol), XPhos (17 mg, 0.04 mmol), $Pd_2(dba)_3$ (8 mg, 9 μmol) and $Cs_2CO_3$ (118 mg, 0.36 mmol) were suspended in dioxane (2 mL). The reaction mixture was degassed with a steam of argon and sonicated and then heated at 100° C. for 3 h. The reaction mixture was partitioned between water and EtOAc. The aqueous phase was further extracted with EtOAc and the combined organic phases were washed with brine, dried ($MgSO_4$), and concentrated in vacuo. The resulting residue was purified by preparatory HPLC (column C18, 20 min gradient 10-50% acetonitrile/0.1% $HCO_2H$ in water) to afford the title compound (17 mg, 20%). LCMS (ESI): $R_T$ 2.74 min, [M+H]$^+$ 470.3, Method=E. $^1$H NMR (400 MHz, DMSO): δ 9.73 (1H, s), 8.58 (1H, d, J=0.9 Hz), 8.41 (1H, s), 7.92 (1H, d, J=5.6 Hz), 6.37 (1H, d, J=5.7 Hz), 4.89-4.78 (1H, m), 4.72 (2H, s), 4.26-4.14 (2H, m), 3.57-3.49 (2H, m), 3.48-3.19 (10H, m), 1.91-1.81 (2H, m), 1.54 (6H, d, J=6.9 Hz), 1.45-1.32 (2H, m), 1.03 (3H, t, J=6.9 Hz).

Example 8: [2-(2-Dimethylaminoethoxymethyl)-1-isopropyl-1H-imidazo[4,5-c]pyridin-6-yl]-[2-(4-methoxypiperidin-1-yl)pyrimidin-4-yl]amine

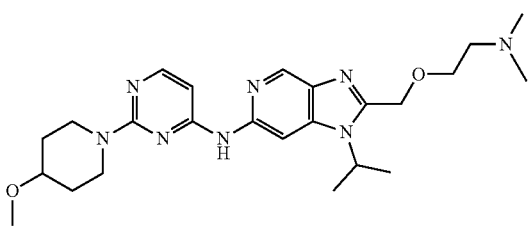 [SMILES: COC1CCN(c2nccc(Nc3cc4c(cn3)nc(COCCN(C)C)n4C(C)C)n2)CC1]

Step 1: [2-(6-Chloro-1-isopropyl-1H-imidazo[4,5-c]pyridin-2-ylmethoxy)ethyl]dimethylamine

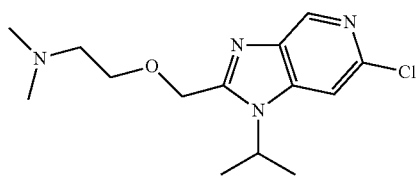 [SMILES: CC(C)n1c(COCCN(C)C)nc2cnc(Cl)cc21]

To a solution of 2-dimethylaminoethanol (54 μL, 0.54 mmol) in THF (2 mL) was added NaH (60% by weight in mineral oil, 27 mg, 0.68 mmol) and the reaction mixture was stirred at room temperature for 5 min. 6-Chloro-2-chloromethyl-1-isopropyl-1H-imidazo[4,5-c]pyridine (Example 7, step 3) (110 mg, 0.45 mmol) was added as a solution in THF (1 mL) and the reaction mixture was stirred at room temperature for 2 h, then diluted with water and extracted with EtOAc (×2). The combined organic layers were washed with brine, dried ($MgSO_4$) and concentrated in vacuo to afford the title compound (133 mg, quantitative). $^1$H NMR (400 MHz, $CDCl_3$) δ 8.79 (1H, s), 7.47 (1H, s), 5.03-4.91 (1H, m), 3.83 (2H, s), 3.58 (2H, t, J=5.7 Hz), 2.50 (2H, t, J=5.7 Hz), 2.24 (6H, s), 1.62 (6H, d, J=7.3 Hz).

Step 2: [2-(2-Dimethylaminoethoxymethyl)-1-isopropyl-1H-imidazo[4,5-c]pyridin-6-yl]-[2-(4-methoxypiperidin-1-yl)pyrimidin-4-yl]amine

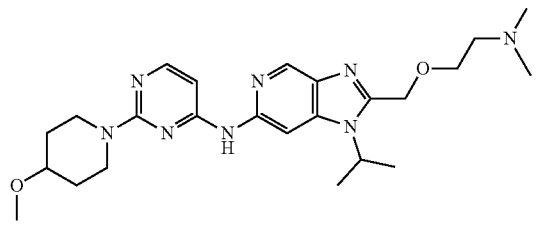 [SMILES: COC1CCN(c2nccc(Nc3cc4c(cn3)nc(COCCN(C)C)n4C(C)C)n2)CC1]

[2-(6-Chloro-1-isopropyl-1H-imidazo[4,5-c]pyridin-2-ylmethoxy)ethyl]dimethylamine (133 mg, 0.45 mmol), 2-(4-methoxypiperidin-1-yl)pyrimidin-4-amine (Example 3, step 2) (85 mg, 0.41 mmol), XPhos (39 mg, 0.08 mmol), $Pd_2(dba)_3$ (19 mg, 20.3 μmol) and $Cs_2CO_3$ (265 mg, 0.81 mmol) were suspended in dioxane (4 mL). The reaction mixture was degassed with a steam of argon and sonicated and then heated at 100° C. for 18 h. The reaction mixture was partitioned between water and EtOAc. The aqueous phase was further extracted with EtOAc and the combined organic phases were washed with brine, dried ($MgSO_4$), and concentrated in vacuo. The resulting residue was purified by chromatography (Si-PCC, gradient 0-10% MeOH in DCM followed by 10% 2M $NH_3$/MeOH in DCM) and then by preparatory HPLC (column C18, 20 min gradient 20-70% acetonitrile/0.1% $NH_4OH$ in water) to afford the title compound (114 mg, 60%). LCMS (ESI): $R_T$ 1.85 min, [M+H]$^+$ 469.3, Method=E. $^1$H NMR (400 MHz, DMSO): δ 9.73 (1H, s), 8.58 (1H, s), 8.41 (1H, s), 7.92 (1H, d, J=5.6 Hz), 6.37 (1H, d, J=5.7 Hz), 4.91-4.79 (1H, m), 4.70 (2H, s), 4.25-4.12 (2H, m), 3.51 (2H, t, J=5.8 Hz), 3.45-3.14 (6H, m), 2.38 (2H, t, J=5.8 Hz), 2.09 (6H, s), 1.92-1.81 (2H, m), 1.54 (6H, d, J=6.9 Hz), 1.46-1.32 (2H, m).

Example 9: (2-Dimethylaminomethyl-1-isopropyl-1H-imidazo[4,5-c]pyridin-6-yl)-[2-(4-methoxypiperidin-1-yl)pyrimidin-4-yl]amine formate salt

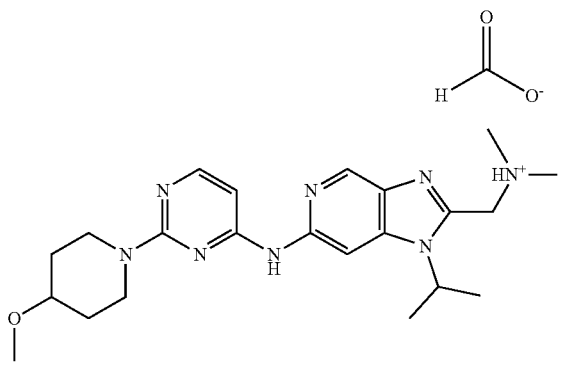

Step 1: (2-Chloromethyl-1-isopropyl-1H-imidazo[4,5-c]pyridin-6-yl)-[2-(4-methoxypiperidin-1-yl)pyrimidin-4-yl]amine

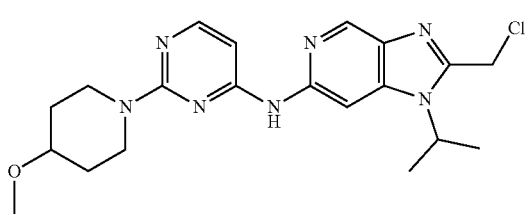

N⁴-Isopropyl-N²-[2-(4-methoxypiperidin-1-yl)pyrimidin-4-yl]pyridine-2,4,5-triamine (Example 3, step 4) (50 mg, 0.14 mmol) was dissolved in 2-chloro-1,1,1-trimethoxyethane (1 mL) and a catalytic amount of p-toluenesulfonic acid was added. The reaction mixture was heated at 100° C. for 1 h and then the volatiles were removed in vacuo. The resulting residue was purified by chromatography (Si-PCC, gradient 0-10% MeOH in DCM) to afford the title compound (50 mg, 86%). LCMS (ESI): [M+H]⁺ 416.3.

Step 2: (2-Dimethylaminomethyl-1-isopropyl-1H-imidazo[4,5-c]pyridin-6-yl)-[2-(4-methoxypiperidin-1-yl)pyrimidin-4-yl]amine formate salt

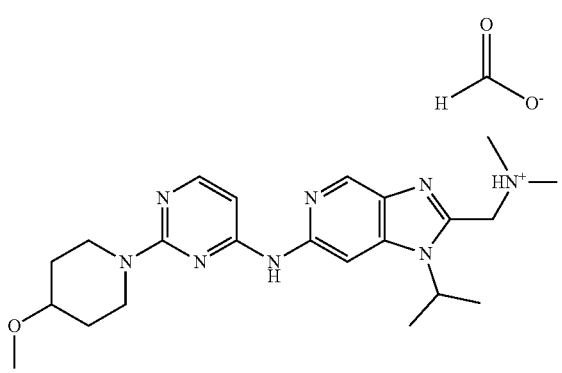

(2-Chloromethyl-1-isopropyl-1H-imidazo[4,5-c]pyridin-6-yl)-[2-(4-methoxypiperidin-1-yl)pyrimidin-4-yl]amine (50 mg, 0.12 mmol) in dimethyl amine (1M in MeOH, 2 mL) was heated at 120° C. for 20 min under microwave irradiation. The volatiles were removed in vacuo and the resulting residue was purified by preparatory HPLC (column C18, 20 min gradient 5-50% acetonitrile/0.1% HCO₂H in water) to afford the title compound (16 mg, 28%). LCMS (ESI): R$_T$ 1.74 min, [M+H]⁺ 425.0, Method=E. ¹H NMR (400 MHz, DMSO): δ 9.69 (1H, s), 8.53 (1H, s), 8.38 (1H, s), 8.10 (1H, s), 7.91 (1H, d, J=5.7 Hz), 6.36 (1H, d, J=5.7 Hz), 5.02-4.91 (1H, m), 4.26-4.13 (2H, m), 3.63 (2H, s), 3.49-3.08 (6H, m), 2.14 (6H, s), 1.90-1.81 (2H, m), 1.51 (6H, d, J=6.9 Hz), 1.45-1.32 (2H, m).

Example 10: {1-Isopropyl-6-[2-(4-methoxypiperidin-1-yl)pyrimidin-4-ylamino]-1H-imidazo[4,5-c]pyridin-2-yl}methanol

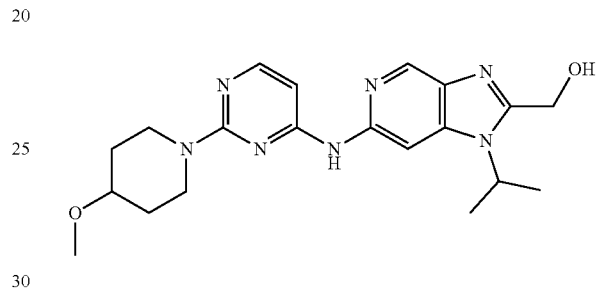

A solution of (2-chloromethyl-1-isopropyl-1H-imidazo[4,5-c]pyridin-6-yl)-[2-(4-methoxypiperidin-1-yl)pyrimidin-4-yl]amine (Example 9, step 1) (40 mg, 0.096 mmol) and KOAc (18 mg, 0.14 mmol) in DMF (1 mL) was heated at 100° C. for 45 min. The volatiles were removed in vacuo and the resulting residue was dissolved in a mixture MeOH (1 mL) and water (0.3 mL). LiOH monohydrate (6 mg, 0.14 mmol) was added and the reaction mixture was stirred at room temperature for 1 h. The volatiles were removed in vacuo and the resulting residue was purified by preparatory HPLC (column C18, 20 min gradient 5-50% acetonitrile/0.1% NH₄OH in water) to afford the title compound (20 mg, 52%). LCMS (ESI): R$_T$ 2.11 min, [M+H]⁺ 397.95, Method=E. ¹H NMR (400 MHz, DMSO-d₆): δ 9.70 (1H, s), 8.54 (1H, s), 8.39 (1H, s), 7.91 (1H, d, J=5.7 Hz), 6.36 (1H, d, J=5.7 Hz), 5.63 (1H, t, J=5.7 Hz), 4.97-4.83 (1H, m), 4.66 (2H, d, J=5.6 Hz), 4.25-4.15 (2H, m), 3.45-3.28 (3H, m), 3.24 (3H, s), 1.91-1.80 (2H, m), 1.53 (6H, d, J=6.9 Hz), 1.44-1.32 (2H, m).

Example 11: (1-Isopropyl-2-methoxy-1H-imidazo[4,5-c]pyridin-6-yl)-[2-(4-methoxypiperidin-1-yl)pyrimidin-4-yl]amine

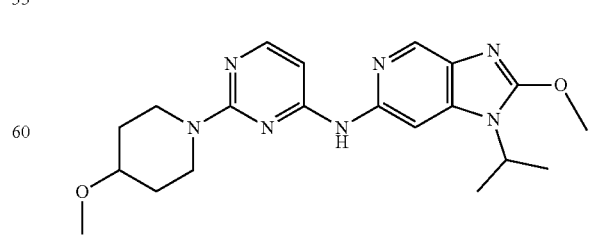

(1-Isopropyl-2-methoxy-1H-imidazo[4,5-c]pyridin-6-yl)-[2-(4-methoxypiperidin-1-yl)pyrimidin-4-yl]amine (11 mg, 19%) was prepared from N⁴-isopropyl-N²-[2-(4-methoxypiperidin-1-yl)pyrimidin-4-yl]pyridine-2,4,5-triamine (Example 3 Step 4, 50 mg, 0.14 mmol) according to a procedure analogous to that described for Example 4. LCMS (ESI): $R_T$ 2.60 min, [M+H]⁺ 398.2, Method=E. ¹H NMR (400 MHz, DMSO): δ 8.44 (1H, d, J=1.0 Hz), 8.20 (1H, s), 8.02 (1H, d, J=5.7 Hz), 7.34 (1H, s), 6.04 (1H, d, J=5.7 Hz), 4.72-4.57 (1H, m), 4.39-4.29 (2H, m), 4.20 (3H, s), 3.53-3.41 (3H, m), 3.40 (3H, s), 2.01-1.91 (2H, m), 1.71-1.58 (2H, m), 1.57 (6H, d, J=7.3 Hz).

Example 12: (1-Isopropyl-1H-imidazo[4,5-c]pyridin-6-yl)-[2-(1,4,6,7-tetrahydropyrazolo[4,3-c]pyridin-5-yl)pyrimidin-4-yl]amine

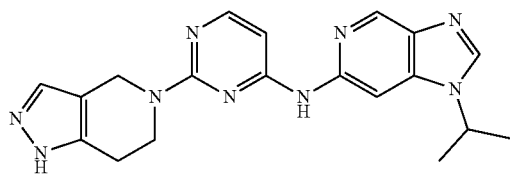 [SMILES: CC(C)n1cnc2cnc(Nc3ccnc(N4CCc5[nH]ncc5C4)n3)cc21]

Step 1:
(2-Bromo-5-nitropyridin-4-yl)isopropylamine

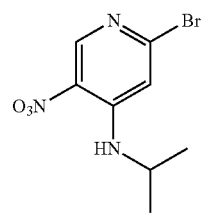

2,4-Dibromo-5-nitropyridine (10 g, 0.035 mol) was dissolved in THF (150 mL). Isopropylamine (4.6 mL, 0.053 mol) was added dropwise and the resulting bright yellow mixture was stirred for 30 min. Further isopropylamine (3.5 mL) was added and the reaction mixture was stirred for 30 min. The volatiles were removed in vacuo and the resulting residue was partitioned between DCM and water. The organic layer was dried (MgSO₄), filtered and evaporated in vacuo to give the title compound as a yellow solid (9.2 g, quantitative). LCMS (ESI): [M+H]⁺ 259.8.

Step 2: 6-Bromo-N⁴-isopropylpyridine-3,4-diamine

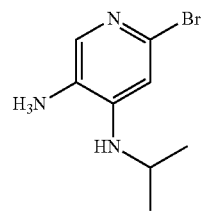

(2-Bromo-5-nitropyridin-4-yl)isopropylamine (9.2 g, 0.035 mol) was dissolved in AcOH (140 mL). Fe powder (7.9 g, 0.142 mol) was added slowly to the stirred mixture at room temperature. The reaction mixture showed a mild exotherm after 10 min and was cooled using an ice water bath to a maximum temperature of 40° C. Stirring at room temperature was continued for 18 h. The reaction mixture was diluted with EtOAc (300 mL), poured slowly onto Na₂CO₃ (1M aq., 1.5 L) and filtered through Hyflo washing thoroughly with EtOAc. The combined organic layers were separated, washed with brine, dried (MgSO₄), filtered and evaporated in vacuo to give a pink solid (7.83 g, quantitative). LCMS (ESI): [M+H]⁺ 231.

Step 3:
6-Bromo-1-isopropyl-1H-imidazo[4,5-c]pyridine

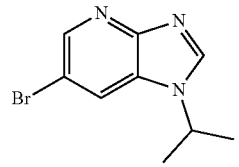

6-Bromo-N⁴-isopropylpyridine-3,4-diamine (7.8 g, 0.034 mol) was suspended in trimethyl orthoformate (69 mL) and formic acid (24 mL). The resulting mixture was heated at 110° C. for 12 h. The cooled solution was poured through an SCX cartridge. The cartridge was washed firstly with MeOH and the product eluted with 2M NH₃ in MeOH. The product containing fractions were combined and concentrated in vacuo and the resulting residue was purified by silica gel chromatography (PPC-ISCO, gradient 0-100% EtOAc in DCM) to afford the title compound as a beige solid (6.5 g, 80%). LCMS (ESI): [M+H]⁺ 239.9.

Step 4: (2-Chloropyrimidin-4-yl)-(1-isopropyl-1H-imidazo[4,5-c]pyridin-6-yl)amine

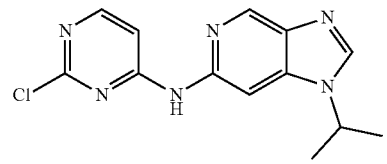 [SMILES: CC(C)n1cnc2cnc(Nc3ccnc(Cl)n3)cc21]

A mixture of 6-bromo-1-isopropyl-1H-imidazo[4,5-c]pyridine (1.2 g, 0.005 mol), 2-chloropyrimidin-4-ylamine (0.63 g, 0.0049 mol), Pd₂dba₃ (229 mg, 0.25 mmol), Xantphos (578 mg, 1 mmol), Cs₂CO₃ (3.25 g, 0.01 mol) in dioxane (40 mL) was degassed and purged with argon (×3). The resulting mixture was heated at reflux temperature for 12 h. The cooled mixture was diluted with DCM and filtered through Hyflo. The resulting orange solution was concentrated in vacuo and adsorbed onto diatomaceous earth and purified by chromatography on silica (PPC-ISCO gradient 0-5% 2M NH₃/MeOH in DCM). The appropriate fractions were concentrated in vacuo to afford the title compound as a white solid (720 mg, 48%). LCMS (ESI): [M+H]⁺ 288. ¹H NMR (400 MHz, CDCl₃): δ 8.8 (1H, d, J=0.9 Hz), 8.37 (1H, br s), 8.23 (1H, d, J=6.0 Hz), 8.14 (1H, br s), 8.01 (1H, s), 7.03 (1H, br s), 4.67 (1H, sept, J=6.6 Hz), 1.69 (6H, d, J=6.6 Hz)

Step 5: (1-Isopropyl-1H-imidazo[4,5-c]pyridin-6-yl)-[2-(1,4,6,7-tetrahydropyrazolo[4,3-c]pyridin-5-yl)pyrimidin-4-yl]amine

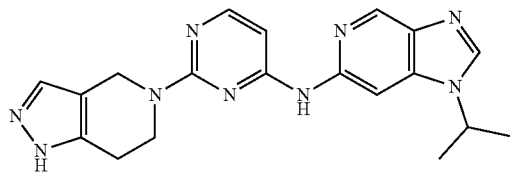 [SMILES: CC(C)n1cnc2cnc(Nc3ccnc(N4CCc5[nH]ncc5C4)n3)cc21]

A mixture of (2-chloropyrimidin-4-yl)-(1-isopropyl-1H-imidazo[4,5-c]pyridin-6-yl)amine (80 mg, 0.28 mmol), 4,5,6,7-tetrahydro-1H-pyrazolo[4,3-c]pyridine (65 mg, 0.33 mmol), triethylamine (0.18 mL, 1.32 mmol) in isopropyl alcohol (0.5 mL) was heated at 150° C. under microwave irradiation for 30 min. The cooled mixture was diluted with water and the resulting precipitate was collected by filtration. The solid thus obtained was crystallized from MeOH/EtOAc to give the title compound as a white solid (42 mg, 41%). LCMS (ESI): $R_T$ 2.05 min, [M+H]$^+$ 376.0, Method=E. $^1$H NMR (400 MHz, DMSO): δ 12.45 (1H, s), 9.79 (1H, s), 8.62 (1H, d, J=0.9 Hz), 8.41 (1H, s), 8.32 (1H, s), 7.96 (1H, d, J=5.7 Hz), 7.45 (0.6H, s, tautomer), 7.25 (0.4H, s, tautomer), 6.38 (1H, d, J=5.7 Hz), 4.87-4.54 (3H, m), 4.07 (2H, t, J=5.7 Hz), 2.77-2.66 (2H, m), 1.58 (6H, d, J=6.8 Hz).

Example 13: 1-[4-(1-Isopropyl-1H-imidazo[4,5-c]pyridin-6-ylamino)pyrimidin-2-yl]piperidin-4-ol

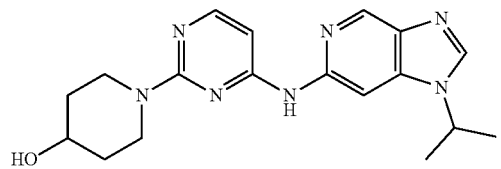 [SMILES: CC(C)n1cnc2cnc(Nc3ccnc(N4CCC(O)CC4)n3)cc21]

A mixture of (2-chloropyrimidin-4-yl)-(1-isopropyl-1H-imidazo[4,5-c]pyridin-6-yl)amine (Example 12, step 4) (75 mg, 0.26 mmol), piperidin-4-ol (31 mg, 0.30 mmol), triethylamine (0.07 mL) in isopropyl alcohol (0.5 mL) was heated at 150° C. under microwave irradiation on high absorbance for 30 min. The cooled reaction mixture was diluted with water and stirred for 10 min. The resulting precipitate was collected by filtration. The solid thus obtained was crystallized from MeOH/EtOAc to give the title compound as a white solid (70 mg, 76%). LCMS (ESI): $R_T$ 1.95 min, [M+H]$^+$ 354.1, Method=E. $^1$H NMR (400 MHz, CDCl$_3$): δ 8.73 (1H, d, J=1.0 Hz), 8.34 (1H, d, J=1.0 Hz), 8.02 (1H, d, J=5.6 Hz), 7.91 (1H, s), 7.48 (1H, s), 6.03 (1H, d, J=5.7 Hz), 4.62-4.49 (1H, m), 4.47-4.37 (2H, m), 4.02-3.90 (1H, m), 3.38 (2H, ddd, J=13.4, 9.7, 3.3 Hz), 2.01-1.90 (2H, m), 1.65-1.50 (9H, m).

Example 14: 8-[4-(1-Isopropyl-1H-imidazo[4,5-c]pyridin-6-ylamino)pyrimidin-2-yl]-1-oxa-3,8-diazaspiro[4.5]decan-2-one

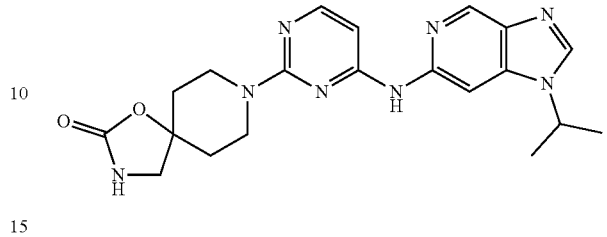

A mixture of (2-chloropyrimidin-4-yl)-(1-isopropyl-1H-imidazo[4,5-c]pyridin-6-yl)amine (Example 12, step 4) (80 mg, 0.268 mmol), 1-oxa-3,8-diazaspiro[4.5]decan-2-one (52 mg, 0.33 mmol), triethylamine (0.13 mL) in isopropyl alcohol (0.5 mL) was heated at 150° C. under microwave irradiation on high absorbance for 45 min. The cooled reaction mixture was diluted with water and the resulting precipitate was collected by filtration to afford the title compound as a white solid (61 mg, 54%). LCMS (ESI): $R_T$ 1.95 min, [M+H]$^+$ 409.1, Method=E. $^1$H NMR (400 MHz, DMSO-d$_6$): δ 9.78 (1H, s), 8.61 (1H, d, J=1.0 Hz), 8.32 (1H, s), 8.29 (1H, s), 7.94 (1H, d, J=5.7 Hz), 7.49 (1H, s), 6.38 (1H, d, J=5.7 Hz), 4.67-4.53 (1H, m), 4.14-4.04 (2H, m), 3.63-3.52 (2H, m), 3.24 (2H, s), 1.85-1.66 (4H, m), 1.52 (6H, d, J=6.7 Hz).

Example 15: [2-(5,6-Dihydro-8H-imidazo[1,2-a]pyrazin-7-yl)pyrimidin-4-yl]-(1-isopropyl-1H-imidazo[4,5-c]pyridin-6-yl)amine

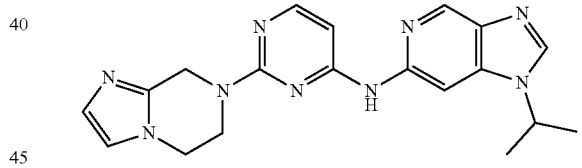

A mixture of (2-chloropyrimidin-4-yl)-(1-isopropyl-1H-imidazo[4,5-c]pyridin-6-yl)amine (Example 12, step 4) (70 mg, 0.24 mmol), 5,6,7,8-tetrahydroimidazo[1,2-a]pyrazine (44 mg, 0.36 mmol), triethylamine (0.15 mL) in isopropyl alcohol (0.5 mL) was heated at 150° C. under microwave irradiation on high absorbance for 2.5 h. The cooled reaction mixture was poured onto an SCX cartridge; the cartridge was washed with MeOH followed by elution of the product with 2M NH$_3$ in MeOH. The product containing fractions were concentrated in vacuo and the resulting residue was crystallised from MeOH/EtOAc to afford the title compound as a white solid (55 mg, 62%). LCMS (ESI): $R_T$ 1.72 min, [M+H]$^+$ 376.0, Method=E. $^1$H NMR (400 MHz, CDCl$_3$): δ 8.75 (1H, d, J=1.0 Hz), 8.29 (1H, s), 8.06 (1H, d, J=5.7 Hz), 7.95 (1H, s), 7.66 (1H, s), 7.02 (1H, d, J=1.3 Hz), 6.86 (1H, d, J=1.3 Hz), 6.22 (1H, d, J=5.7 Hz), 5.08 (2H, s), 4.79-4.67 (1H, m), 4.30 (2H, t, J=5.4 Hz), 4.07 (2H, t, J=5.4 Hz), 1.70 (6H, d, J=6.7 Hz).

Example 16: (1-Isopropyl-1H-imidazo[4,5-c]pyridin-6-yl)-[2-(4-methanesulfonylpiperazin-1-yl)pyrimidin-4-yl]-amine

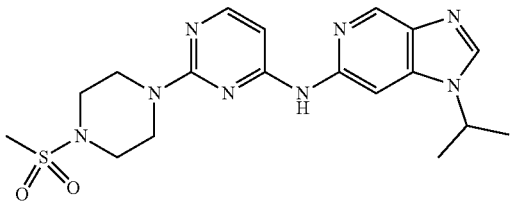 [SMILES: CC(C)n1cnc2cnc(Nc3ccnc(N4CCN(S(C)(=O)=O)CC4)n3)cc21]

A mixture of (2-chloropyrimidin-4-yl)-(1-isopropyl-1H-imidazo[4,5-c]pyridin-6-yl)amine (Example 12, step 4) (70 mg, 0.24 mmol), 1-methanesulfonylpiperazine (72 mg, 0.36 mmol), triethylamine (0.15 mL) in isopropyl alcohol (0.5 mL) was heated at 150° C. under microwave irradiation for 30 min. The cooled reaction mixture was diluted with water and the resulting precipitate was collected by filtration to afford the title compound as a white solid (75 mg, 75%). LCMS (ESI): $R_T$ 2.17 min, $[M+H]^+$ 417.1, Method=E. $^1$H NMR (400 MHz, CDCl$_3$): δ 8.75 (1H, d, J=1.0 Hz), 8.11 (1H, s), 8.04 (1H, d, J=5.7 Hz), 7.93 (1H, s), 7.49 (1H, s), 6.20 (1H, d, J=5.0 Hz), 4.60-4.47 (1H, m), 4.00 (4H, t, J=5.0 Hz), 3.28 (4H, t, J=5.0 Hz), 2.77 (3H, s), 1.63 (6H, d, J=6.9 Hz).

Example 17: (1-Isopropyl-1H-imidazo[4,5-c]pyridin-6-yl)-[2-(3-methoxyazetidin-1-yl)pyrimidin-4-yl]amine

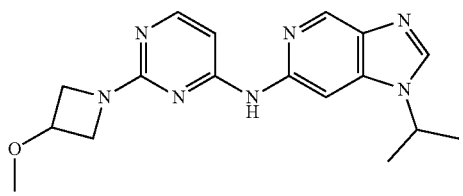 [SMILES: COC1CN(c2nccc(Nc3cc4c(cn3)ncn4C(C)C)n2)C1]

A mixture of (2-chloropyrimidin-4-yl)-(1-isopropyl-1H-imidazo[4,5-c]pyridin-6-yl)amine (Example 12, step 4) (37 mg, 0.13 mmol), 3-methoxyazetidine hydrochloride salt (19 mg, 0.15 mmol), Cs$_2$CO$_3$ (83 mg, 0.61 mmol) in isopropyl alcohol (0.5 mL) was heated at 60° C. for 3 h and then at room temperature for 18 h. The volatiles were removed in vacuo and the resulting residue was diluted with DCM. The resulting suspension was filtered and the filtrate was concentrated in vacuo. The resultant residue was purified by chromatography (Si-PCC, gradient 0-5% 2M NH$_3$/MeOH in DCM) and then crystallised from EtOAc/diethyl ether to afford the title compound (17 mg, 39%). LCMS (ESI): $R_T$ 2.14 min, $[M+H]^+$ 340.1, Method=E. $^1$H NMR (400 MHz, CDCl$_3$): δ 8.72 (1H, d, J=1.0 Hz), 8.49 (1H, s), 8.00 (1H, d, J=5.7 Hz), 7.91 (1H, s), 7.64 (1H, s), 6.08 (1H, d, J=5.7 Hz), 4.63-4.49 (1H, m), 4.37-4.28 (3H, m), 4.09-3.99 (2H, m), 3.34 (3H, s), 1.63 (6H, d, J=6.3 Hz).

Example 18: [2-(4-Methoxypiperidin-1-yl)pyrimidin-4-yl]-[1-(tetrahydrofuran-3-yl)-1H-imidazo[4,5-c]pyridin-6-yl]amine

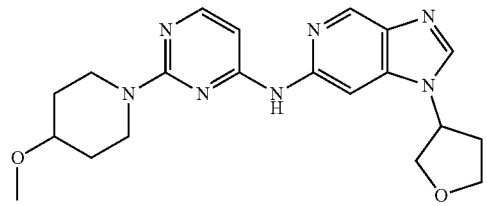 [SMILES: COC1CCN(c2nccc(Nc3cc4c(cn3)ncn4C3CCOC3)n2)CC1]

Step 1: (2-Chloro-5-nitropyridin-4-yl)(tetrahydrofuran-3-yl)amine

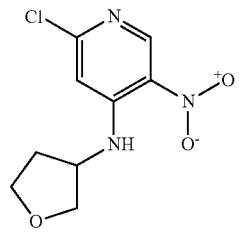 [SMILES: [O-]N([OH2+])c1cnc(Cl)cc1NC1CCOC1]

To a solution of 2,4-dichloro-5-nitropyridine (386 mg, 2.0 mmol), and triethylamine (417 µL, 3.0 mmol) in THF (6 mL) was added dropwise tetrahydrofuran-3-ylamine (208 mg, 2.4 mmol) and the reaction mixture was stirred for 1 h. An additional amount of tetrahydrofuran-3-ylamine (50 mg) was added and the reaction mixture was stirred for 1 h. The volatiles were removed in vacuo and the resulting residue was partitioned between water and EtOAc. The organic phase was dried (MgSO$_4$) and concentrated in vacuo to afford the title compound as a yellow solid (490 mg, quantitative). LCMS (ESI): $[M+H]^+$ 244.2.

Step 2: 6-Chloro-N$^4$-(tetrahydrofuran-3-yl)-pyridine-3,4-diamine

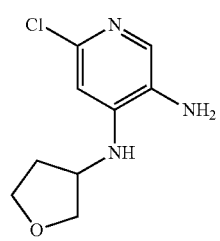 [SMILES: Nc1cnc(Cl)cc1NC1CCOC1]

To a solution of (2-chloro-5-nitropyridin-4-yl)(tetrahydrofuran-3-yl)amine (485 mg, 1.99 mmol) in AcOH (5 mL) was added Fe powder (440 mg, 8.0 mmol) portionwise. The reaction mixture was stirred at room temperature for 18 h and then diluted with EtOAc. The resulting suspension was filtered through celite and the filtrate was concentrated in vacuo. The resulting residue was dissolved in EtOAc and the solution was made basic by addition of Na$_2$CO$_3$ (1M aq.). The resultant mixture was extracted with EtOAc (×3) and the combined organic layers were washed with brine, dried (MgSO$_4$) and concentrated in vacuo to afford the title compound (297 mg, 70%). LCMS (ESI): [M+H]$^+$ 214.2.

Step 3: 6-Chloro-1-(tetrahydrofuran-3-yl)-1H-imidazo[4,5-c]pyridine

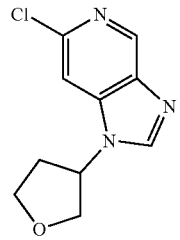 [SMILES: Clc1cc2c(cn1)ncn2C1CCOC1]

A mixture of 6-chloro-N$^4$-(tetrahydrofuran-3-yl)pyridine-3,4-diamine (290 mg, 1.35 mmol) in trimethyl orthoformate (10 mL) and formic acid (1 mL) was heated at 90° C. for 18 h under a nitrogen atmosphere. The cooled reaction mixture was loaded onto an SCX cartridge which was washed with DCM and MeOH and the product was eluted with 2M NH$_3$/MeOH. The product containing fractions were combined and concentrated in vacuo and the resulting residue was purified by chromatography (Si-PCC, gradient 0-6% MeOH in DCM) to afford the title compound as a pink solid (200 mg, 67%). LCMS (ESI): R$_T$ 2.00 min [M+H]$^+$ 224.2.

Step 4: [2-(4-Methoxypiperidin-1-yl)pyrimidin-4-yl]-[1-(tetrahydrofuran-3-yl)-1H-imidazo[4,5-c]pyridin-6-yl]amine

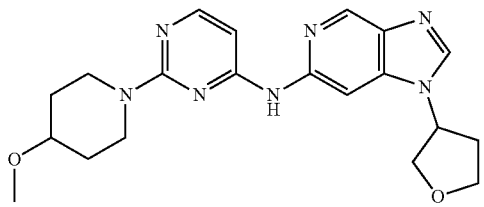 [SMILES: COC1CCN(c2nccc(Nc3cc4c(cn3)ncn4C3CCOC3)n2)CC1]

A mixture of 6-chloro-1-(tetrahydrofuran-3-yl)-1H-imidazo[4,5-c]pyridine (91 mg, 0.41 mmol), 2-(4-methoxypiperidin-1-yl)pyrimidin-4-ylamine (84 mg, 0.41 mmol), Pd$_2$dba$_3$ (19 mg, 0.02 mmol), Xphos (39 mg, 0.08 mmol), Cs$_2$CO$_3$ (265 mg, 0.8 mmol) in dioxane (2 mL) was purged with argon (×3) and heated at 120° C. in a sealed tube for 12 h. The cooled reaction mixture was diluted with DCM and filtered through celite. The filtrate was concentrated in vacuo and the resulting residue was purified by chromatography on silica (PPC-ISCO, gradient 0-5% 2M NH$_3$/MeOH in DCM) and crystallised from EtOAc/diethyl ether to afford the title compound as a white solid (60 mg, 38%). LCMS (ESI): R$_T$ 2.10 min [M+H]$^+$ 396.1, Method=E. $^1$H NMR (400 MHz, CDCl$_3$): δ 8.73 (1H, d, J=1.0 Hz), 8.25 (1H, d, J=1.0 Hz), 8.03 (1H, d, J=5.6 Hz), 7.96 (1H, s), 7.45 (1H, s), 6.08 (1H, d, J=5.6 Hz), 4.99-4.88 (1H, m), 4.33-4.21 (3H, m), 4.19-4.11 (1H, m), 4.07-3.93 (2H, m), 3.50-3.41 (3H, m), 3.38 (3H, s), 2.58-2.45 (1H, m), 2.29-2.19 (1H, m), 1.98-1.88 (2H, m), 1.65-1.55 (2H, m).

Example 19: [2-(4-Methoxypiperidin-1-yl)pyrimidin-4-yl]-[1-(tetrahydropyran-4-yl)-1H-imidazo[4,5-c]pyridin-6-yl]amine

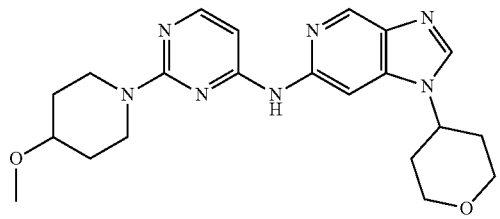 [SMILES: COC1CCN(c2nccc(Nc3cc4c(cn3)ncn4C3CCOCC3)n2)CC1]

Step 1: 2-Chloro-5-nitropyridin-4-yl)(tetrahydropyran-4-yl)amine

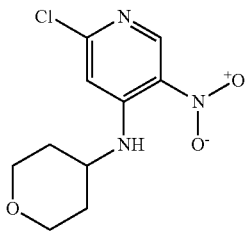 [SMILES: [O-]N([OH2+])c1cnc(Cl)cc1NC1CCOCC1]

To a solution of 2,4-dichloro-5-nitropyridine (386 mg, 2.0 mmol), and triethylamine (417 μL, 3.0 mmol) in THF (6 mL) was added dropwise tetrahydropyran-4-ylamine (242 mg, 2.4 mmol) over 10 min and the reaction mixture was stirred for 1 h. An additional amount of tetrahydropyran-4-ylamine (50 mg) was added and the stirring was continued for 1 h. The volatiles were removed in vacuo and the resulting residue was partitioned between water and EtOAc. The organic phase was dried (MgSO$_4$) and concentrated in vacuo to afford the title compound as a yellow solid (514 mg, quantitative). LCMS (ESI): [M+H]$^+$ 258.2.

Step 2: 6-Chloro-N$^4$-(tetrahydropyran-4-yl)pyridine-3,4-diamine

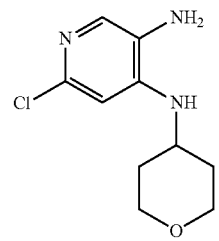 [SMILES: Nc1cnc(Cl)cc1NC1CCOCC1]

To a solution of 2-chloro-5-nitropyridin-4-yl)(tetrahydropyran-4-yl)amine (513 mg, 1.99 mmol) in AcOH (5 mL) was added Fe powder (440 mg, 8.0 mmol) portionwise. The reaction mixture was stirred at room temperature for 18 h and then diluted with EtOAc. The resulting suspension was filtered through celite and the filtrate was concentrated in vacuo. The resulting residue was dissolved in EtOAc and made basic by addition of NaHCO$_3$ (satd. aq. soln.). The resultant mixture was extracted with EtOAc (×3) and the combined organic layers were washed with brine, dried (MgSO$_4$) and concentrated in vacuo to afford the title compound as a red oil (453 mg, 80%). LCMS (ESI): [M+H]$^+$ 228.2.

Step 3: 6-Chloro-1-(tetrahydropyran-4-yl)-1H-imidazo[4,5-c]pyridine

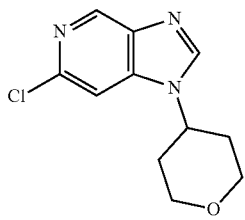 [SMILES: Clc1cc2c(cn1)ncn2C1CCOCC1]

A mixture of 6-chloro-N$^4$-(tetrahydropyran-4-yl)pyridine-3,4-diamine (355 mg, 1.55 mmol) in trimethyl orthoformate (10 mL) and formic acid (5 drops) was heated at 80° C. for 18 h. The cooled reaction mixture was loaded onto an SCX cartridge which was washed with MeOH and the product was eluted with 2M NH$_3$/MeOH. The product containing fractions were combined and concentrated in vacuo and the resulting residue was purified by chromatography (Si-PCC, gradient 0-5% MeOH in DCM) to afford the title compound as a pink solid (400 mg, 72%). LCMS (ESI): [M+H]$^+$ 238.2.

Step 4: [2-(4-Methoxypiperidin-1-yl)pyrimidin-4-yl]-[1-(tetrahydropyran-4-yl)-1H-imidazo[4,5-c]pyridin-6-yl]amine

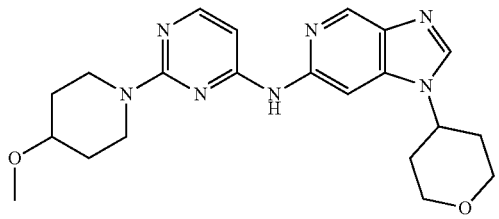 [SMILES: COC1CCN(c2nccc(Nc3cc4c(cn3)ncn4C3CCOCC3)n2)CC1]

A mixture of 6-chloro-1-(tetrahydropyran-4-yl)-1H-imidazo[4,5-c]pyridine (97 mg, 0.41 mmol), 2-(4-methoxypiperidin-1-yl)pyrimidin-4-amine (Example 3, step 2) (84 mg, 0.41 mmol), Pd$_2$dba$_3$ (19 mg, 0.02 mmol), XPhos (39 mg, 0.08 mmol), Cs$_2$CO$_3$ (265 mg, 0.8 mmol) in dioxane (2 mL) was purged with argon (×3) and heated at 120° C. in a sealed tube for 18 h. The cooled reaction mixture was diluted with DCM and filtered through celite. The filtrate was concentrated in vacuo and the resulting residue was purified by chromatography on silica (PPC-ISCO, gradient 0-5% 2M NH$_3$/MeOH in DCM) and crystallised from diethyl ether to afford the title compound as a cream solid (130 mg, 78%). LCMS (ESI): R$_T$ 2.16 min, [M+H]$^+$ 410.2, Method=E. $^1$H NMR (400 MHz, CDCl$_3$): δ 8.73 (1H, d, J=1.0 Hz), 8.35 (1H, d, J=1.0 Hz), 8.02 (1H, d, J=5.6 Hz), 7.91 (1H, s), 7.46 (1H, s), 6.01 (1H, d, J=5.6 Hz), 4.41-4.25 (3H, m), 4.18 (2H, dd, J=11.9, 4.3 Hz), 3.60-3.43 (5H, m), 3.37 (3H, s), 2.28-2.16 (2H, m), 2.13-2.05 (2H, m), 1.99-1.89 (2H, m), 1.66-1.56 (2H, m).

Example 20: (1-Ethyl-1H-imidazo[4,5-c]pyridin-6-yl)-[2-(4-methoxypiperidin-1-yl)pyrimidin-4-yl]amine

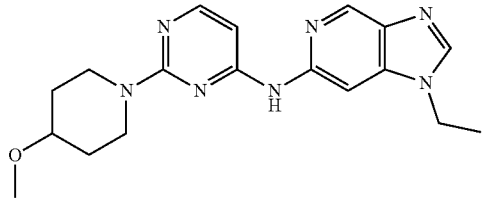 [SMILES: CCn1cnc2cnc(Nc3ccnc(N4CCC(OC)CC4)n3)cc21]

Step 1: 6-Chloro-1-ethyl-1H-imidazo[4,5-c]pyridine

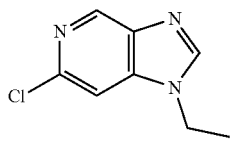

A mixture of 6-chloro-N$^4$-ethylpyridine-3,4-diamine (prepared using a procedure analogous to that described for Example 7, steps 1-2) (386 mg, 1.78 mmol) in trimethylorthoformate (10 mL) and formic acid (5 drops) was heated at 120° C. for 18 h. The cooled reaction mixture was loaded onto an SCX cartridge which was washed with MeOH while the product was eluted with 2M NH$_3$/MeOH. The product containing fractions were combined and concentrated in vacuo. The resulting residue was purified by chromatography (Si-PCC, gradient 0-100% EtOAc in DCM) and then crystallised from cyclohexane/diethyl ether to afford the title compound as a white solid (160 mg, 50%). LCMS (ESI): [M+H]$^+$ 182.1.

Step 2: (1-Ethyl-1H-imidazo[4,5-c]pyridin-6-yl)-[2-(4-methoxypiperidin-1-yl)pyrimidin-4-yl]amine

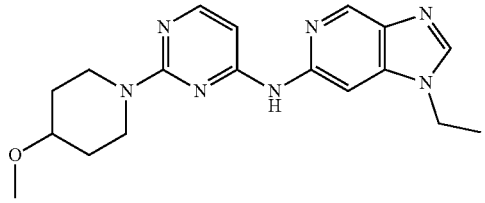 [SMILES: CCn1cnc2cnc(Nc3ccnc(N4CCC(OC)CC4)n3)cc21]

A mixture of 6-chloro-1-ethyl-1H-imidazo[4,5-c]pyridine (80 mg, 0.43 mmol), 2-(4-methoxypiperidin-1-yl)pyrimidin-4-amine (Example 3, step 2) (91 mg, 0.43 mmol), Pd$_2$dba$_3$ (20 mg, 0.02 mmol), XPhos (42 mg, 0.09 mmol), Cs$_2$CO$_3$ (285 mg, 0.9 mmol) in dioxane (2 mL) was purged with argon (×3) and heated at 130° C. in a sealed tube under microwave irradiation for 45 min and then thermally at 120° C. for 36 h. The cooled reaction mixture was diluted with DCM and filtered through celite. The filtrate was concentrated in vacuo and the resulting residue was purified by chromatography on silica (PPC-ISCO, gradient 0-5% 2M NH$_3$/MeOH in DCM) and crystallised from EtOAc/diethyl ether to afford the title compound (30 mg, 20%). LCMS (ESI): $R_T$ 2.12 min, [M+H]$^+$ 354.2, Method=E. $^1$H NMR (400 MHz, CDCl$_3$): δ 8.73 (1H, d, J=1.0 Hz), 8.33 (1H, s), 8.01 (1H, d, J=5.6 Hz), 7.83 (1H, s), 7.64 (1H, s), 6.02 (1H, d, J=5.7 Hz), 4.33-4.24 (2H, m), 4.19-4.12 (2H, m), 3.50-3.40 (3H, m), 3.37 (3H, s), 1.98-1.89 (2H, m), 1.67-1.55 (2H, m), 1.53 (3H, t, J=7.6 Hz).

Example 21: [2-(4-Methoxypiperidin-1-yl)pyrimidin-4-yl]-[1-methyl-2-(1H-pyrazol-4-yl)-1H-imidazo[4,5-c]pyridin-6-yl]amine

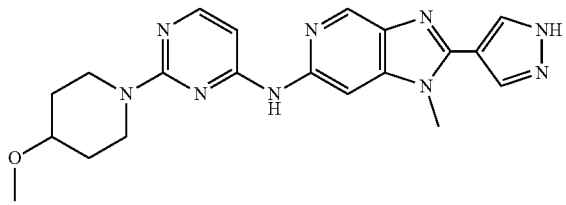 [SMILES: COC1CCN(c2nccc(Nc3cc4c(cn3)nc(-c3cn[nH]c3)n4C)n2)CC1]

Step 1: 6-Chloro-1-methyl-2-(1H-pyrazol-4-yl)-1H-imidazo[4,5-c]pyridine

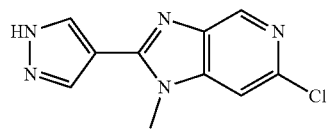 [SMILES: Cn1c(-c2cn[nH]c2)nc2cnc(Cl)cc21]

A mixture of 6-chloro-N$^4$-methylpyridine-3,4-diamine (prepared using a procedure analogous to that described for Example 7, steps 1-2) (92 mg, 0.58 mmol) and 1H-pyrazole-4-carboxylic acid (67 mg, 0.58 mmol) in polyphosphoric acid (~0.5 mL) was purged with argon and heated in a sealed vial at 150° C. for 18 h with stirring. The cooled mixture was diluted with water (1 mL) and taken to pH 7 by addition of NaOH (50% aq.). A solid precipitated which was isolated by filtration. The solid was suspended in MeOH and sonicated for 15 min. The MeOH was removed in vacuo. This process was repeated (×2) and the resulting solid was dried in vacuo to give a grey solid (130 mg, quant.). LCMS (ESI): [M+H]$^+$ 234/236 ($^{35}$Cl/$^{37}$Cl).

Step 2: 6-Chloro-1-methyl-2-[1-(2-trimethylsilanylethoxymethyl)-1H-pyrazol-4-yl]-1H-imidazo[4,5-c]pyridine

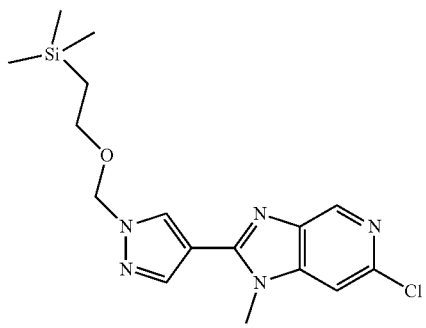 [SMILES: Cn1c(-c2cnn(COCC[Si](C)(C)C)c2)nc2cnc(Cl)cc21]

To a suspension of 6-chloro-1-methyl-2-(1H-pyrazol-4-yl)-1H-imidazo[4,5-c]pyridine (130 mg, 0.58 mmol) in THF (4 mL) under a nitrogen atmosphere was added NaH (60% dispersion in mineral oil, 27 mg, 0.696 mmol). DMF (0.5 mL) was added to facilitate dissolution. After 15 min stirring, a solution of 2-(trimethylsilyl)ethoxymethyl chloride (140 mg, 0.84 mmol) in THF (1 mL) was added and stirring was continued for 30 min. The reaction mixture was quenched by addition of water and then the volatiles were removed in vacuo. The resulting residue was partitioned between water and EtOAc, the organic phase was dried (MgSO$_4$) and concentrated in vacuo. The resulting residue was purified by chromatography on silica (PPC-ISCO, gradient 0-100% EtOAc in cyclohexane) to afford the title compound as a white solid (85 mg, 40%). LCMS (ESI): [M+H]$^+$ 364.2.

Step 3: [2-(4-Methoxypiperidin-1-yl)pyrimidin-4-yl]-{1-methyl-2-[1-(2-trimethylsilanylethoxymethyl)-1H-pyrazol-4-yl]-1H-imidazo[4,5-c]pyridin-6-yl}amine

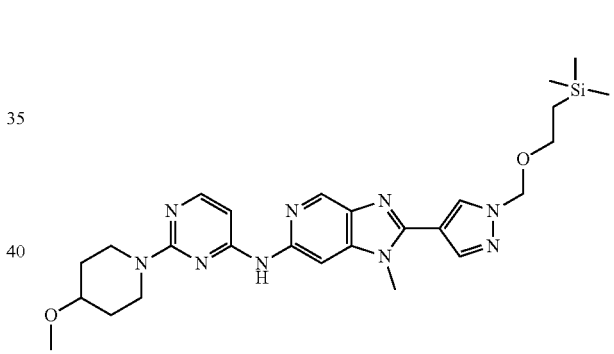

A mixture of 6-chloro-1-methyl-2-[1-(2-trimethylsilanylethoxymethyl)-1H-pyrazol-4-yl]-1H-imidazo[4,5-c]pyridine (45 mg, 0.2 mmol), 2-(4-methoxypiperidin-1-yl)pyrimidin-4-amine (Example 3, step 2) (79 mg, 0.2 mmol), Pd$_2$dba$_3$ (9 mg, 0.01 mmol), XPhos (19 mg, 0.04 mmol), Cs$_2$CO$_3$ (130 mg, 0.4 mmol) in dioxane (2 mL) was purged with argon (×3) and heated at 120° C. in a sealed tube for 18 h. The cooled reaction mixture was diluted with DCM and filtered through celite. The filtrate was concentrated in vacuo and the resulting residue was purified by chromatography on silica (PPC-ISCO, gradient 0-5% 2M NH$_3$/MeOH in DCM) to afford the title compound as a white solid (60 mg, 56%). $^1$H NMR (400 MHz, CDCl$_3$): δ 8.70 (1H, d, J=1.0 Hz), 8.28 (1H, s), 8.19 (1H, s), 8.08-8.03 (2H, m), 7.46 (1H, br s), 6.10 (1H, d, J=5.7 Hz), 5.54 (2H, s), 4.38-4.28 (2H, m), 3.90 (3H, s), 3.67-3.61 (2H, m), 3.57-3.47 (3H, m), 3.42 (3H, s), 2.3-1.94 (2H, m), 1.72-1.55 (2H, m), 0.98-0.96 (2H, m), 0.00 (9H, s).

Step 4: [2-(4-Methoxypiperidin-1-yl)pyrimidin-4-yl]-[1-methyl-2-(1H-pyrazol-4-yl)-1H-imidazo[4,5-c]pyridin-6-yl]amine

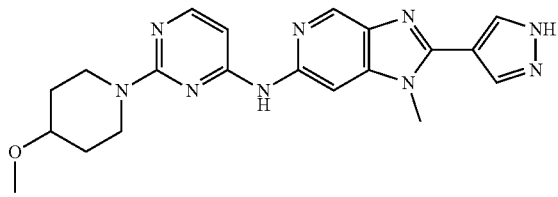 [SMILES: COC1CCN(c2nccc(Nc3cc4c(cn3)nc(-c3cn[nH]c3)n4C)n2)CC1]

A mixture of [2-(4-methoxypiperidin-1-yl)pyrimidin-4-yl]-{1-methyl-2-[1-(2-trimethylsilanylethoxymethyl)-1H-pyrazol-4-yl]-1H-imidazo[4,5-c]pyridin-6-yl}amine (55 mg, 0.1 mmol) in MeOH (2 mL) and HCl (6M aqueous solution, 1 mL) was heated at 70° C. for 18 h. The cooled reaction mixture was poured onto an SCX cartridge which was washed with MeOH and the product eluted with 2M NH$_3$ in MeOH. The product containing fractions were combined and concentrated in vacuo to afford the title compound as a white solid (25 mg, 62%). LCMS (ESI): R$_T$ 2.03 min, [M+H]$^+$ 405.9, Method=E. $^1$H NMR (400 MHz, DMSO): δ 13.38 (1H, s), 9.73 (1H, s), 8.53 (1H, d, J=1.0 Hz), 8.43 (1H, s), 8.25 (1H, s), 8.07 (1H, s), 7.92 (1H, d, J=5.7 Hz), 6.36 (1H, d, J=5.7 Hz), 4.24-4.14 (2H, m), 3.82 (3H, s), 3.46-3.28 (3H, m), 3.25 (3H, s), 1.92-1.82 (2H, m), 1.45-1.34 (2H, m).

Example 22: [2-(2-Fluorobenzyl)-3-methyl-3H-imidazo[4,5-c]pyridin-6-yl]-[2-(4-methoxypiperidin-1-yl)pyrimidin-4-yl]amine

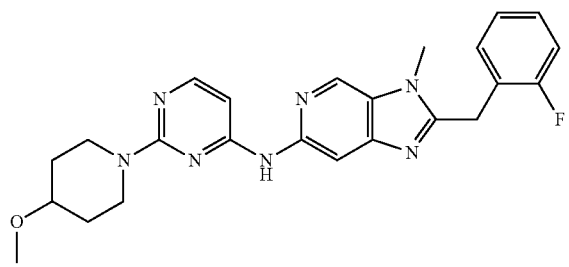 [SMILES: COC1CCN(c2nccc(Nc3cc4nc(Cc5ccccc5F)n(C)c4cn3)n2)CC1]

Step 1: N-(4-Amino-6-bromopyridin-3-yl)-2-(2-fluorophenyl)-N-methylacetamide

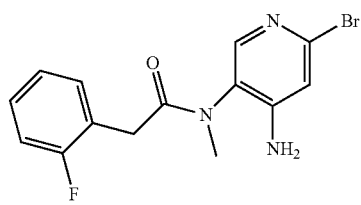 [SMILES: CN(C(=O)Cc1ccccc1F)c1cnc(Br)cc1N]

To a stirred suspension of 6-bromo-N$^3$-methylpyridine-3,4-diamine (prepared using a procedure analogous to that described for Example 12, steps 1-2) (136 mg, 0.67 mmol), (2-fluorophenyl)acetic acid (104 mg, 0.67 mmol) and HOAT (91 mg, 0.67 mmol) in DCM (3 mL) was added EDCI (193 mg, 1.01 mmol). The resulting solution was stirred for 1 h and then an additional aliquot of EDCI (100 mg) was added. Stirring was continued for 18 h. The mixture was diluted with DCM and water and the DCM extracts were combined, dried (MgSO$_4$) and evaporated. The resulting crude product was used in the following step without purification. LCMS (ESI): [M+H]$^+$ 338.0.

Step 2: 6-Bromo-2-(2-fluorobenzyl)-3-methyl-3H-imidazo[4,5-c]pyridine

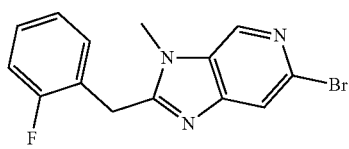 [SMILES: Cn1c(Cc2ccccc2F)nc2cc(Br)ncc21]

A mixture of N-(4-amino-6-bromopyridin-3-yl)-2-(2-fluorophenyl)-N-methylacetamide (0.67 mmol) in AcOH (4 mL) was heated at 90° C. for 18 h. The volatiles were removed in vacuo, azeotroping with toluene. The resulting residue was purified by chromatography on silica (PPC-ISCO, gradient 0-40% EtOAc in cyclohexane) to afford the title compound (66 mg, 30% over two steps). LCMS (ESI): [M+H]$^+$ 320.1.

Step 3: [2-(2-Fluorobenzyl)-3-methyl-3H-imidazo[4,5-c]pyridin-6-yl]-[2-(4-methoxypiperidin-1-yl)pyrimidin-4-yl]amine

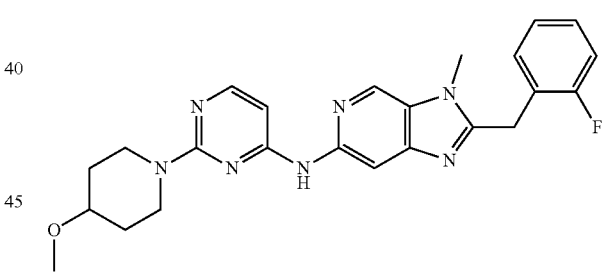

A mixture of 6-bromo-2-(2-fluorobenzyl)-3-methyl-3H-imidazo[4,5-c]pyridine (65 mg, 0.2 mmol), 2-(4-methoxypiperidin-1-yl)pyrimidin-4-ylamine (42 mg, 0.2 mmol), Pd$_2$dba$_3$ (11 mg, 0.01 mmol), XPhos (11 mg, 0.02 mmol), Cs$_2$CO$_3$ (203 mg, 0.62 mmol) in dioxane (2 mL) was purged with argon (×3) and heated at 90° C. in a sealed tube for 18 h. The cooled reaction mixture was diluted with DCM and filtered through celite. The filtrate was concentrated in vacuo and the resulting residue was purified by chromatography on silica (PPC-ISCO, gradient 0-8% MeOH in DCM) and crystallised from EtOAc/cyclohexane. The solid was collected to afford the title compound as an orange solid (50 mg, 36%). LCMS (ESI): R$_T$ 2.86 min, [M+H]$^+$ 448.0, Method=E. $^1$H NMR (400 MHz, CDCl$_3$): δ 8.38 (1H, d, J=1.0 Hz), 8.09 (1H, s), 8.04 (1H, d, J=5.7 Hz), 7.29-7.16 (3H, m), 7.13-7.05 (2H, m), 6.27 (1H, d, J=5.7 Hz), 4.40-4.31 (4H, m), 3.72 (3H, s), 3.50-3.34 (6H, m), 2.02-1.92 (2H, m), 1.64-1.54 (2H, m).

Example 23: [2-(4-Methoxypiperidin-1-yl)pyrimidin-4-yl]-[2-(1H-pyrazol-4-yl)-3H-imidazo[4,5-c]pyridin-6-yl]amine

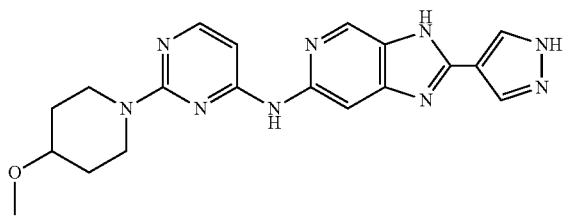 [SMILES: COC1CCN(c2nccc(Nc3cc4nc(-c5cn[nH]c5)[nH]c4cn3)n2)CC1]

Step 1: 6-Bromo-2-(1H-pyrazol-4-yl)-3H-imidazo[4,5-c]pyridine

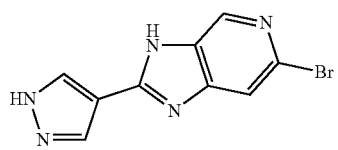 [SMILES: Brc1cc2nc(-c3cn[nH]c3)[nH]c2cn1]

A mixture of 6-bromopyridine-3,4-diamine (100 mg, 0.53 mmol) and 1H-pyrazole-4-carboxylic acid (60 mg, 0.53 mmol) in polyphosphoric acid (1 g) was heated in a sealed vial at 200° C. for 18 h. The reaction mixture was diluted with water and made basic by addition of NaOH (50% aq.) and a white precipitate formed. The solid thus formed was collected by filtration and washed with water to afford the title compound (150 mg, quant.). LCMS (ESI): [M+H]$^+$ 264.1.

Step 2: 6-Bromo-3-(2-trimethylsilanylethoxymethyl)-2-[1-(2-trimethylsilanylethoxymethyl)-1H-pyrazol-4-yl]-3H-imidazo[4,5-c]pyridine

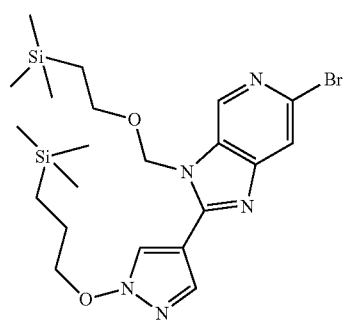 [SMILES: C[Si](C)(C)CCCOn1cc(-c2nc3cc(Br)ncc3n2COCC[Si](C)(C)C)cn1]

To a suspension of 6-bromo-2-(1H-pyrazol-4-yl)-3H-imidazo[4,5-c]pyridine (150 mg, 0.53 mmol) in THF (2 mL) under a nitrogen atmosphere was added NaH (60% dispersion in mineral oil, 63 mg, 1.6 mmol). DMF (2 mL) was added to facilitate dissolution. After effervescence had ceased, 2-(trimethylsilyl)ethoxymethyl chloride (265 mg, 1.6 mmol) was added and stirring was continued for 2 h. The reaction mixture was partitioned between water and EtOAc. The aqueous phase was further extracted with EtOAc (×3) and the combined organic phases were dried (MgSO$_4$) and concentrated in vacuo. The resulting residue was purified by chromatography on silica (PPC-ISCO, gradient 0-40% EtOAc in cyclohexane) to afford the title compound (a mixture of 2 regioisomers) as a yellow oil which solidified on standing (224 mg 81%). LCMS (ESI): [M+H]$^+$ 524.2.

Step 3: [2-(4-Methoxypiperidin-1-yl)pyrimidin-4-yl]-{3-(2-trimethylsilanylethoxymethyl)-2-[1-(2-trimethylsilanylethoxymethyl)-1H-pyrazol-4-yl]-3H-imidazo[4,5-c]pyridin-6-yl}amine

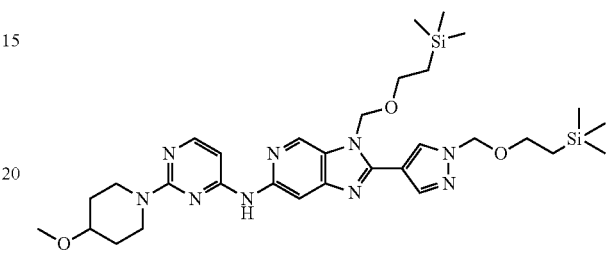

A mixture of 6-bromo-3-(2-trimethylsilanylethoxymethyl)-2-[1-(2-trimethylsilanylethoxymethyl)-1H-pyrazol-4-yl]-3H-imidazo[4,5-c]pyridine (120 mg, 0.23 mmol), 2-(4-methoxypiperidin-1-yl)pyrimidin-4-amine (Example 3, step 2) (53 mg, 0.25 mmol), Pd$_2$dba$_3$ (10 mg, 0.01 mmol), XPhos (22 mg, 0.046 mmol), Cs$_2$CO$_3$ (273 mg, 0.84 mmol) in dioxane (2 mL) was purged with argon (×3) and heated at 120° C. for 18 h. The cooled reaction mixture was diluted with DCM and filtered through celite. The filtrate was concentrated in vacuo and the resulting residue was purified by chromatography on silica (PPC-ISCO, gradient 0-10% MeOH in DCM, followed by 0-15% MeOH in EtOAc and by 0-10% 2M NH$_3$/MeOH in DCM) to afford the title compound (120 mg, 81%). LCMS (ESI): [M+H]$^+$ 652.4.

Step 4: [2-(4-Methoxypiperidin-1-yl)pyrimidin-4-yl]-[2-(1H-pyrazol-4-yl)-3H-imidazo[4,5-c]pyridin-6-yl]amine

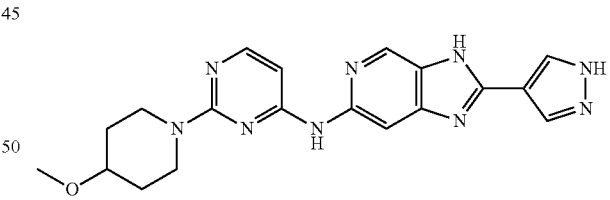

[2-(4-Methoxypiperidin-1-yl)pyrimidin-4-yl]-{3-(2-trimethylsilanylethoxymethyl)-2-[1-(2-trimethylsilanylethoxymethyl)-1H-pyrazol-4-yl]-3H-imidazo[4,5-c]pyridin-6-yl}amine (120 mg, 0.18 mmol) was suspended in MeOH (5 mL) and HCl (6M aqueous solution, 0.5 mL). The reaction mixture was stirred at RT for 3 h and then at 50° C. for a further 3 h. A solid precipitated on standing. The suspension thus obtained was dissolved in MeOH by the use of heat and sonication and the resulting solution was loaded onto an SCX cartridge. The cartridge was washed with MeOH while the product was eluted with 2M NH$_3$ in MeOH. The product containing fractions were combined and concentrated in vacuo and the resulting residue was purified by chromatography on silica (PPC-ISCO, gradient 0-10% 2M NH₃/MeOH in DCM) to afford the title compound as a white solid (55 mg, 76%). LCMS (ESI): R$_T$ 2.00 min, [M+H]⁺ 391.9, Method=E. ¹H NMR (400 MHz, DMSO-d₆): δ 13.29 (1H, s), 12.67 (1H, s), 9.61 (1H, s), 8.51 (1H, s), 8.43-8.09 (2H, br s), 8.03 (1H, s), 7.93 (1H, d, J=5.9 Hz), 6.58-6.50 (1H, m), 4.25-4.14 (2H, m), 3.48-3.30 (3H, m), 3.28 (3H, s), 1.93-1.84 (2H, m), 1.47-1.35 (2H, m).

Example 24: (1-Cyclopentyl-1H-pyrrolo[3,2-c]pyridin-6-yl)-[2-(4-methoxypiperidin-1-yl)pyrimidin-4-yl]amine

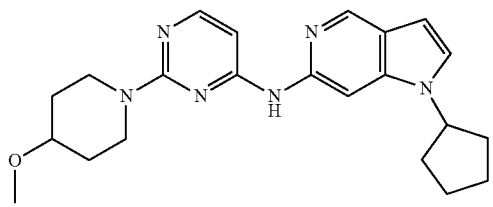 [SMILES: COC1CCN(c2nccc(Nc3cc4c(ccn4C4CCCC4)cn3)n2)CC1]

Step 1:
6-Chloro-1-cyclopentyl-1H-pyrrolo[3,2-c]pyridine

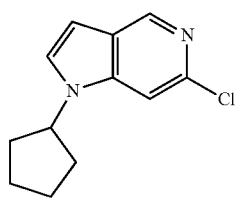 [SMILES: Clc1cc2c(ccn2C2CCCC2)cn1]

A mixture of 6-chloro-1H-pyrrolo[3,2-c]pyridine (100 mg, 0.65 mmol), iodocyclopentane (254 mg, 1.3 mmol) and Cs₂CO₃ (422 mg, 1.3 mmol) in DMF (1 mL) was heated at 80° C. for 18 h. The cooled reaction mixture was partitioned between water and EtOAc. The aqueous phase was further extracted with EtOAc and the combined organic phases were dried (MgSO₄) and concentrated in vacuo. The resulting residue was purified by chromatography on silica (PPC-ISCO, gradient 0-50% EtOAc in cyclohexane) to afford the title compound as a colourless oil (80 mg, 56%). ¹H NMR (400 MHz, CDCl₃): δ 8.64 (1H, s), 7.31 (1H, s), 7.21 (1H, d, J=3.3 Hz), 6.57 (1H, d, J=3.2 Hz), 4.76-4.65 (1H, m), 2.30-2.17 (2H, m), 1.97-1.72 (6H, m).

Step 2: (1-Cyclopentyl-1H-pyrrolo[3,2-c]pyridin-6-yl)-[2-(4-methoxypiperidin-1-yl)pyrimidin-4-yl]amine

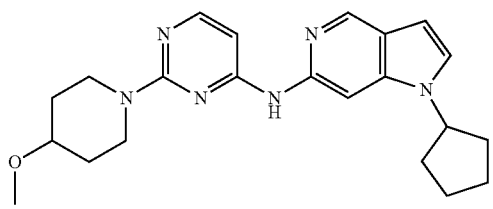 [SMILES: COC1CCN(c2nccc(Nc3cc4c(ccn4C4CCCC4)cn3)n2)CC1]

A mixture of 6-chloro-1-cyclopentyl-1H-pyrrolo[3,2-c]pyridine (76 mg, 0.35 mmol), 2-(4-methoxypiperidin-1-yl)pyrimidin-4-amine (Example 3, step 2) (72 mg, 0.35 mmol), Pd₂dba₃ (15 mg, 0.016 mmol), XPhos (33 mg, 0.027 mmol), Cs₂CO₃ (225 mg, 0.69 mmol) in dioxane (3.5 mL) was purged with argon (×3) and heated at 120° C. in a sealed tube for 30 min under microwave irradiation. The cooled reaction mixture was diluted with DCM and filtered through celite. The filtrate was concentrated in vacuo and the resulting residue was purified by chromatography on silica (PPC-ISCO, gradient 0-10% MeOH in EtOAc followed by 0-4% 2M NH₃/MeOH in DCM) and then by reverse phase HPLC to afford the title compound (22 mg, 16%). LCMS (ESI): R$_T$ 2.83 min, [M+H]⁺ 392.9, Method=E. ¹H NMR (400 MHz, CDCl₃): δ 8.53 (1H, s), 8.20 (1H, s), 7.99 (1H, d, J=5.7 Hz), 7.47 (1H, s), 7.11 (1H, d, J=3.4 Hz), 6.49 (1H, d, J=3.4 Hz), 6.03 (1H, d, J=5.7 Hz), 4.72-4.63 (1H, m), 4.37-4.27 (2H, m), 3.49-3.39 (3H, m), 3.38 (3H, s), 2.24-2.11 (2H, m), 1.98-1.70 (8H, m), 1.66-1.54 (2H, m).

Example 25: [2-(4-Methoxypiperidin-1-yl)pyrimidin-4-yl]-[3-methyl-2-(1H-pyrazol-4-yl)-3H-imidazo[4,5-c]pyridin-6-yl]amine dihydrochloride

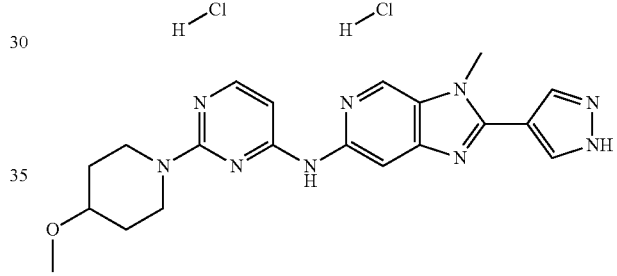

Step 1: 6-Bromo-3-methyl-2-(1H-pyrazol-4-yl)-3H-imidazo[4,5-c]pyridine

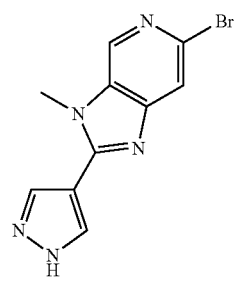 [SMILES: Cn1c(-c2cn[nH]c2)nc2cc(Br)ncc21]

A mixture of 6-bromo-N³-methylpyridine-3,4-diamine (54 mg, 0.27 mmol), 1H-pyrazole-4-carboxylic acid (30 mg, 0.27 mmol) and polyphosphoric acid (0.5 mL) was heated at 200° C. in a sealed tube for 5 h. After cooling, the reaction mixture was diluted with water and taken to pH 7 by addition of 50% aq. NaOH. A white suspension formed and the solid was collected by filtration affording the title compound (69 mg, 93%). LCMS (ESI): [M+H]⁺ 278.2.

Step 2: 6-Bromo-3-methyl-2-[1-(2-trimethylsilanylethoxymethyl)-1H-pyrazol-4-yl]-3H-imidazo[4,5-c]pyridine

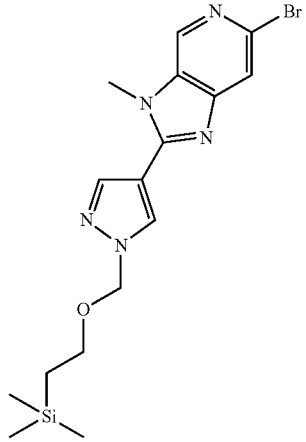 [SMILES: Cn1c(-c2cnn(COCC[Si](C)(C)C)c2)nc2cc(Br)ncc21]

To a suspension of 6-bromo-3-methyl-2-(1H-pyrazol-4-yl)-3H-imidazo[4,5-c]pyridine (67 mg, 0.24 mmol) in DMF (1 mL) under a nitrogen atmosphere was added NaH (60% dispersion in mineral oil, 20 mg, 0.48 mmol). After 10 min stirring, 2-(trimethylsilyl)ethoxymethyl chloride (80 mg, 0.48 mmol) was added and immediately a precipitate formed. The cooled reaction mixture was partitioned between water and DCM. The organic phase was dried (PTFE frit) and concentrated in vacuo. The resulting residue was purified by chromatography on silica (PPC-ISCO, gradient 0-100% EtOAc in cyclohexane) to afford the title compound as a solid (45 mg, 48%). LCMS (ESI): [M+H]+ 408.1.

Step 3: [2-(4-Methoxypiperidin-1-yl)pyrimidin-4-yl]-{3-methyl-2-[1-(2-trimethylsilanylethoxymethyl)-1H-pyrazol-4-yl]-3H-imidazo[4,5-c]pyridin-6-yl}amine

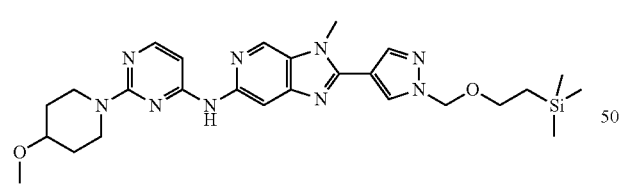

A mixture of 6-bromo-3-methyl-2-[1-(2-trimethylsilanylethoxymethyl)-1H-pyrazol-4-yl]-3H-imidazo[4,5-c]pyridine (45 mg, 0.11 mmol), 2-(4-methoxypiperidin-1-yl)pyrimidin-4-amine (Example 3, step 2) (24 mg, 0.12 mmol), Pd₂dba₃ (5 mg, 5 mol %), XPhos (10 mg, 20 mol %), Cs₂CO₃ (72 mg, 0.22 mmol) in dioxane (1 mL) was purged with argon (×3) and heated at 120° C. in a sealed tube for 18 h. The cooled reaction mixture was diluted with DCM and filtered through celite. The filtrate was concentrated in vacuo and the resulting residue was purified by chromatography on silica (PPC-ISCO, gradient 0-5% MeOH in DCM) to afford the title compound as a colourless glass (31 mg, 53%). LCMS (ESI): [M+H]+ 536.0.

Step 4: [2-(4-Methoxypiperidin-1-yl)pyrimidin-4-yl]-[3-methyl-2-(1H-pyrazol-4-yl)-3H-imidazo[4,5-c]pyridin-6-yl]amine dihydrochloride

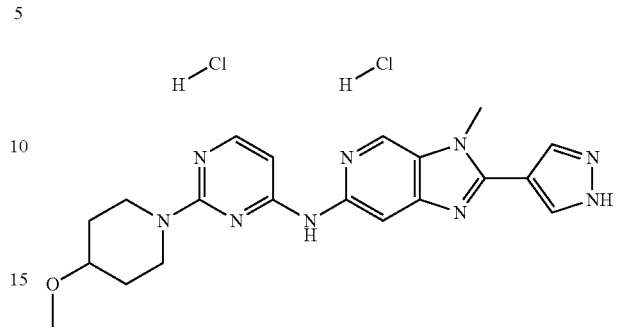

[2-(4-Methoxypiperidin-1-yl)pyrimidin-4-yl]-{3-methyl-2-[1-(2-trimethylsilanylethoxymethyl)-1H-pyrazol-4-yl]-3H-imidazo[4,5-c]pyridin-6-yl}amine (31 mg, 0.06 mmol) was suspended in MeOH (1 mL) and heated to obtain a solution. HCl (6M aqueous solution, 0.5 mL) was added and the reaction mixture was stirred for 2 h. A solid precipitated and was collected by filtration, then washed with water and dried in vacuo to afford the title compound as a white solid (22 mg, 80%). LCMS (ESI): R_T 2.01 min, [M]+ 405.9, Method=E. ¹H NMR (400 MHz, DMSO-d₆+TFA): δ 9.11 (1H, s), 8.73 (2H, s), 8.41 (1H, br s), 7.94 (1H, d, J=7.0 Hz), 6.61 (1H, br s), 4.14 (3H, s), 3.98-3.87 (2H, m), 3.67-3.55 (2H, m), 3.2-3.45 (1H, m), 3.25 (3H, s), 1.98-1.88 (2H, m), 1.68-1.53 (2H, m).

Example 26: (1-Cyclopentyl-1H-imidazo[4,5-c]pyridin-6-yl)-[2-(4-methoxy-piperidin-1-yl)-pyrimidin-4-yl]amine

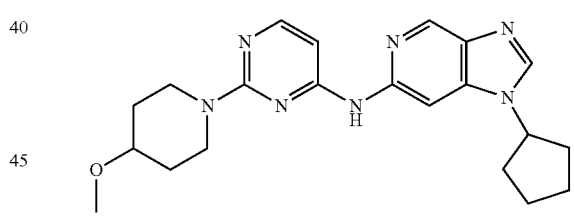

Step 1: (2-Chloro-5-nitropyridin-4-yl)cyclopentylamine

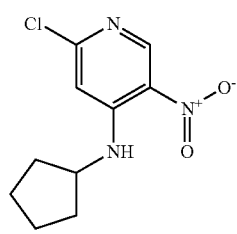 [SMILES: O=[N+]([O-])c1cnc(Cl)cc1NC1CCCC1]

(2-Chloro-5-nitropyridin-4-yl)cyclopentylamine (410 mg, 85%) was prepared from 2,4-dichloro-5-nitropyridine (386 mg, 2.0 mmol) and cyclopentylamine (170 mg, 2.0 mmol) according to a procedure analogous to that described for Example 18 Step 1. ¹H NMR (400 MHz, CDCl₃): δ 9.01 (1H, s), 8.17 (1H, s), 6.76 (1H, s), 3.99-3.87 (1H, m), 2.20-2.06 (2H, m), 1.88-1.58 (6H, m).

Step 2: 6-Chloro-N⁴-cyclopentylpyridine-3,4-diamine

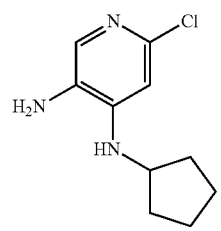 [SMILES: Nc1cnc(Cl)cc1NC1CCCC1]

To a solution of (2-chloro-5-nitropyridin-4-yl)cyclopentylamine (410 mg, 1.7 mmol) in EtOH (3 mL) were added H₂O (6 mL), NH₄Cl (363 mg, 6.8 mmol) and Fe powder (473 mg, 8.5 mmol). The reaction mixture was stirred at 78° C. for 20 h and then diluted with DCM. The resulting suspension was filtered through celite and the filtrate was made basic by addition of aq. NaHCO₃. The organic layer was washed with brine, dried (MgSO₄) and concentrated in vacuo to afford the title compound (290 mg, 80%). ¹H NMR (400 MHz, CDCl₃): δ 7.63 (1H, s), 6.47 (1H, s), 4.26 (1H, s), 3.83-3.71 (1H, m), 2.97 (2H, s), 2.13-1.99 (2H, m), 1.81-1.60 (4H, m), 1.59-1.45 (2H, m).

Step 3:
6-Chloro-1-cyclopentyl-1H-imidazo[4,5-c]pyridine

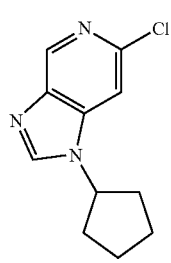 [SMILES: Clc1cc2c(cn1)ncn2C1CCCC1]

6-Chloro-1-cyclopentyl-1H-imidazo[4,5-c]pyridine (70 mg, 61%) was prepared 6-chloro-N⁴-cyclopentylpyridine-3,4-diamine (110 mg, 0.51 mmol) according to a procedure analogous to that described for Example 19 Step 3. ¹H NMR (400 MHz, CDCl₃): δ 8.85 (1H, d, J=0.9 Hz), 8.01 (1H, s), 7.40 (1H, d, J=0.9 Hz), 4.74-4.63 (1H, m), 2.38-2.25 (2H, m), 2.08-1.79 (6H, m).

Step 4: (1-Cyclopentyl-1H-imidazo[4,5-c]pyridin-6-yl)-[2-(4-methoxypiperidin-1-yl)-pyrimidin-4-yl]amine

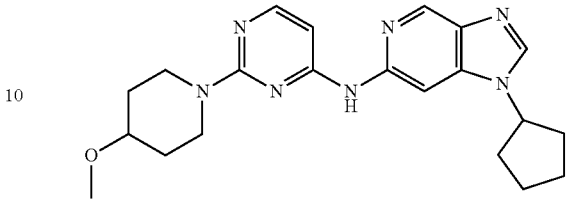

(1-Cyclopentyl-1H-imidazo[4,5-c]pyridin-6-yl)-[2-(4-methoxypiperidin-1-yl)-pyrimidin-4-yl]amine (30 mg, 15%) was prepared from 6-chloro-1-cyclopentyl-1H-imidazo[4,5-c]pyridine (110 mg, 0.496 mmol) and 2-(4-methoxypiperidin-1-yl)pyrimidin-4-amine (Example 3 Step 2, 103 mg, 0.496 mmol) according to a procedure analogous to that described for Example 22 Step 4. LCMS (ESI): R$_T$ 2.59 min, [M+H]⁺ 394.0, Method=E. ¹H NMR (400 MHz, CDCl₃): δ 8.72 (1H, d, J=1.0 Hz), 8.27 (1H, s), 8.02 (1H, d, J=5.6 Hz), 7.89 (1H, s), 7.47 (1H, s), 6.03 (1H, d, J=5.7 Hz), 4.69-4.58 (1H, m), 4.34-4.24 (2H, m), 3.50-3.39 (3H, m), 3.37 (3H, s), 2.30-2.20 (2H, m), 2.09-1.99 (2H, m), 1.97-1.76 (6H, m), 1.66-1.54 (2H, m).

Example A1:
6-Chloro-1-isopropyl-1H-pyrrolo[3,2-c]pyridine

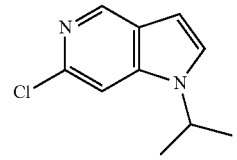

6-Chloro-1-isopropyl-1H-pyrrolo[3,2-c]pyridine (912 mg, 95%) was prepared from 6-chloro-1H-pyrrolo[3,2-c]pyridine (750 mg, 4.9 mmol) and 2-bromopropane (0.92 mL, 9.8 mmol) according to a procedure analogous to that described for Example 24 Step 1. LCMS (ESI): [M+H]⁺ 195.0. ¹H NMR (400 MHz, CDCl₃): δ 8.65 (1H, d, J=0.9 Hz), 7.30 (1H, s), 7.24 (1H, d, J=3.5 Hz), 6.59 (1H, d, J=3.5 Hz), 4.66-4.51 (1H, m), 1.54 (6H, d, J=6.9 Hz).

Example A2:
2-[(4-Aminopyrimidin-2-yl)methylamino]ethanol

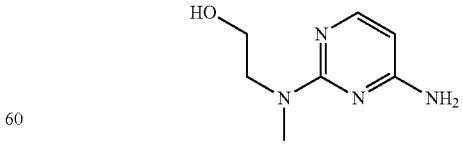

A mixture of 2-chloropyrimidin-4-ylamine (2.08 g, 16 mmol) and 2-methylaminoethanol (1.31 mL, 16 mmol) in dioxane (16 mL) was heated at 150° C. under microwave irradiation for 1 h. The reaction mixture was dissolved in 2M NH₃/MeOH and DCM was added. A solid was filtered and the filtrate was concentrated in vacuo. The resulting residue was purified by chromatography (silica, gradient 5-10% 2M NH$_3$/MeOH in DCM) to afford the title compound as a white solid (2.1 g, 78%). LCMS (ESI): [M+H]$^+$ 169.0. $^1$H NMR (400 MHz, CDCl$_3$) δ 7.87 (1H, d, J=5.7 Hz), 5.76 (1H, d, J=5.70 Hz), 5.14 (1H, br s), 4.66 (2H, s), 3.88-3.82 (2H, m), 3.74-3.68 (2H, m), 3.16 (3H, s).

Example A3:
6-Chloro-1-phenyl-1H-pyrrolo[3,2-c]pyridine

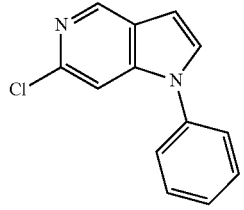 [SMILES: Clc1cc2c(ccn2-c2ccccc2)cn1]

A mixture of 2,2'-bipyridine (128 mg, 0.82 mmol) and Cu(OAc)$_2$ (148 mg, 0.82 mmol) in dichloroethane (4 mL) was heated at 70° C. under a nitrogen atmosphere for 5 min. 6-Chloro-1H-pyrrolo[3,2-c]pyridine (250 mg, 1.64 mmol), phenylboronic acid (400 mg, 3.28 mmol), Na$_2$CO$_3$ (348 mg, 3.28 mmol) and DCE (4 mL) were added and the reaction mixture was heated at 70° C. for 18 h. Additional amounts of 2,2'-bipyridine (64 mg), Cu(OAc)$_2$ (74 mg) and phenylboronic acid (200 mg) were added and stirring at 70° C. was continued for 18 h. The reaction mixture was diluted with EtOAc and filtered. The filtrate was washed with brine and the aqueous phase was further extracted with EtOAc (×2). The combined organic layers were dried (Na$_2$SO$_4$) and concentrated in vacuo. The resulting residue was purified by chromatography (Si-PCC, gradient 5-90% EtOAc in cyclohexane) to afford the title compound as a white solid (84 mg, 22%). LCMS (ESI): [M+H]$^+$ 228.9. $^1$H NMR (400 MHz, CDCl$_3$) δ 8.75 (1H, d, J=0.9 Hz), 7.62-7.54 (2H, m), 7.50-7.42 (4H, m), 7.38 (1H, d, J=3.4 Hz), 6.77 (1H, dd, J=3.4, 0.9 Hz).

Example A4:
1-(4-Aminopyrimidin-2-yl)piperidine-4-carboxylic acid amide

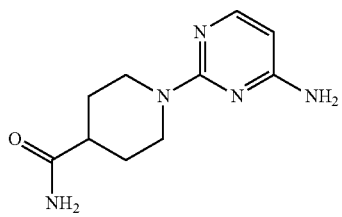 [SMILES: NC(=O)C1CCN(c2nccc(N)n2)CC1]

A mixture of 2-chloropyrimidin-4-ylamine (500 mg, 3.9 mmol), piperidine-4-carboxylic acid amide (495 mg, 3.9 mmol) and DIPEA (0.67 mL, 3.9 mmol) in dioxane (3.9 mL) was heated in a sealed tube at 100° C. for 18 h. The reaction mixture was diluted with MeOH and then concentrated. The resultant residue was purified by chromatography (Si-PCC, gradient 5-10% 2M NH$_3$/MeOH in DCM) to afford the title compound as a white solid (327 mg, 38%). LCMS (ESI): [M+H]$^+$ 222.0. $^1$H NMR (400 MHz, DMSO-d$_6$) δ 7.73 (1H, d, J=5.6 Hz), 7.25 (1H, s), 6.74 (1H, s), 6.34 (2H, s), 5.70 (1H, d, J=5.6 Hz), 4.60 (2H, d, J=13.1 Hz), 2.73 (2H, t, J=12.5 Hz), 2.36-2.25 (1H, m), 1.68 (2H, d, J=12.9 Hz), 1.46-1.34 (2H, m).

Example A5:
4-(4-Aminopyrimidin-2-yl)piperazin-2-one

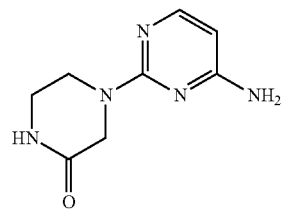 [SMILES: Nc1ccnc(N2CCNC(=O)C2)n1]

4-(4-Aminopyrimidin-2-yl)piperazin-2-one (300 mg, 40%) was prepared from 2-chloropyrimidin-4-ylamine (500 mg, 3.9 mmol) and piperazin-2-one (386 mg, 3.9 mmol) according to a procedure analogous to that described for Example A4. LCMS (ESI): [M+H]$^+$ 194.0. $^1$H NMR (400 MHz, DMSO-d$_6$) δ 7.98 (1H, s), 7.78 (1H, d, J=5.7 Hz), 6.50 (2H, s), 5.79 (1H, d, J=5.7 Hz), 4.10 (2H, s), 3.81 (2H, t, J=5.4 Hz), 3.25-3.17 (2H, m).

Example A6:
(4-Pyrazol-1-yl-piperidin-1-yl)pyrimidin-4-ylamine

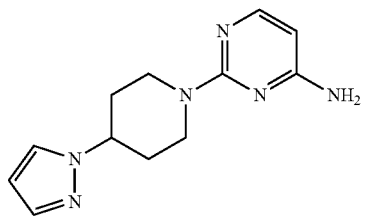 [SMILES: Nc1ccnc(N2CCC(n3cccn3)CC2)n1]

(4-Pyrazol-1-yl-piperidin-1-yl)pyrimidin-4-ylamine (259 mg, 55%) was prepared from 2-chloropyrimidin-4-ylamine (251 mg, 1.9 mmol) and 4-pyrazol-1-ylpiperidine di hydrochloride (434 mg, 1.9 mmol) according to a procedure analogous to that described for Example A4. LCMS (ESI): [M+H]$^+$ 245.0. $^1$H NMR (400 MHz, DMSO-d$_6$) δ 7.78-7.70 (2H, m), 7.41 (1H, d, J=1.7 Hz), 6.40 (2H, s), 6.21 (1H, t, J=2.0 Hz), 5.72 (1H, d, J=5.7 Hz), 4.74-4.66 (2H, m), 4.46-4.35 (1H, m), 2.94-2.83 (2H, m), 2.01-1.93 (2H, m), 1.83-1.70 (2H, m).

Example A7: 2-(4-Imidazol-1-ylpiperidin-1-yl)pyrimidin-4-ylamine

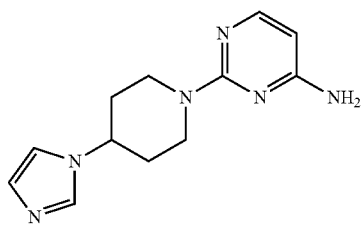 [SMILES: Nc1ccnc(N2CCC(n3ccnc3)CC2)n1]

2-(4-Imidazol-1-ylpiperidin-1-yl)pyrimidin-4-ylamine (232 mg, 68%) was prepared from 2-chloropyrimidin-4-ylamine (182 mg, 1.4 mmol) and 4-imidazol-1-ylpiperidine di hydrochloride (314 mg, 1.4 mmol) according to a procedure analogous to that described for Example A4. LCMS (ESI): [M+H]+ 245.0. $^1$H NMR (400 MHz, DMSO-d$_6$) δ 7.98 (1H, s), 7.75 (1H, d, J=5.8 Hz), 7.39 (1H, s), 7.02 (1H, s), 6.57 (2H, s), 5.77 (1H, d, J=5.8 Hz), 4.80-4.71 (2H, m), 4.42-4.30 (1H, m), 2.93-2.80 (2H, m), 2.05-1.94 (2H, m), 1.83-1.68 (2H, m).

Example A8: 2-(4-[1,2,4]Triazol-1-ylpiperidin-1-yl)pyrimidin-4-ylamine

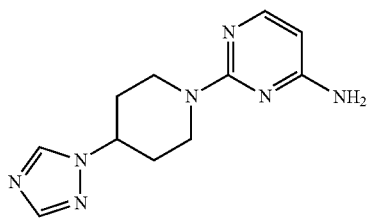 [SMILES: Nc1ccnc(N2CCC(n3cncn3)CC2)n1]

2-(4-[1,2,4]Triazol-1-ylpiperidin-1-yl)pyrimidin-4-ylamine (235 mg, 48%) was prepared from 2-chloropyrimidin-4-ylamine (258 mg, 2.0 mmol) and 4-[1,2,4]triazol-1-ylpiperidine di hydrochloride (449 mg, 2.0 mmol) according to a procedure analogous to that described for Example A4. LCMS (ESI): [M+H]+ 246.0. $^1$H NMR (400 MHz, DMSO-d$_6$) δ 8.58 (1H, s), 7.95 (1H, s), 7.76 (1H, d, J=5.7 Hz), 6.42 (2H, s), 5.74 (1H, d, J=5.7 Hz), 4.76-4.66 (2H, m), 4.60-4.50 (1H, m), 2.98-2.87 (2H, m), 2.08-1.99 (2H, m), 1.86-1.71 (2H, m).

Example A9: 2-(1-Oxa-8-azaspiro[4.5]dec-8-yl)pyrimidin-4-ylamine

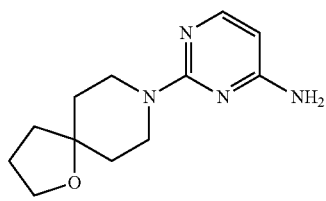 [SMILES: Nc1ccnc(N2CCC3(CCCO3)CC2)n1]

2-(1-Oxa-8-azaspiro[4.5]dec-8-yl)pyrimidin-4-ylamine (352 mg, 65%) was prepared from 2-chloropyrimidin-4-ylamine (300 mg, 2.3 mmol) and 1-oxa-8-azaspiro[4.5]decane hydrochloride (419 mg, 2.36 mmol) according to a procedure analogous to that described for Example A4. LCMS (ESI): [M+H]+ 235.1.

Example A10: 1-[4-(4-Aminopyrimidin-2-yl)piperazin-1-yl]ethanone

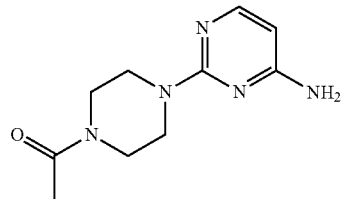 [SMILES: CC(=O)N1CCN(c2nccc(N)n2)CC1]

1-[4-(4-Aminopyrimidin-2-yl)piperazin-1-yl]ethanone (421 mg, 83%) was prepared from 2-chloropyrimidin-4-ylamine (300 mg, 2.3 mmol) and 1-piperazin-1-ylethanone (300 mg, 2.35 mmol) according to a procedure analogous to that described for Example A4. $^1$H NMR (400 MHz, DMSO-d$_6$): δ 7.75 (1H, d, J=5.7 Hz), 6.47 (2H, s), 5.76 (1H, d, J=5.7 Hz), 3.71-3.54 (4H, m), 3.49-3.39 (4H, m), 2.03 (3H, s).

Example A11: 2-[1-(4-Aminopyrimidin-2-yl)piperidin-4-yl]propan-2-ol

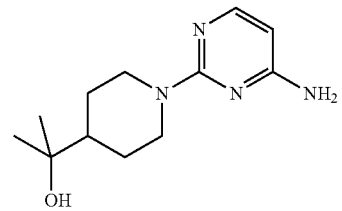 [SMILES: CC(C)(O)C1CCN(c2nccc(N)n2)CC1]

2-[1-(4-Aminopyrimidin-2-yl)piperidin-4-yl]propan-2-ol (quantitative yield) was prepared from 2-chloropyrimidin-4-ylamine (300 mg, 2.30 mmol) and 2-piperidin-4-ylpropan-2-ol (329 mg, 2.30 mmol) according to a procedure analogous to that described for Example A4. LCMS (ESI): [M+H]+ 237.2.

Example A12: 2-(4-Methoxy-4-methylpiperidin-1-yl)pyrimidin-4-ylamine

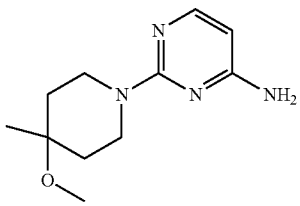 [SMILES: COC1(C)CCN(c2nccc(N)n2)CC1]

2-(4-Methoxy-4-methylpiperidin-1-yl)pyrimidin-4-ylamine (20 mg, 17%) was prepared from 2-chloropyrimidin-4-ylamine (70 mg, 0.54 mmol) and 4-methoxy-4-methylpiperidine (70 mg, 0.54 mmol) according to a procedure analogous to that described for Example A4. LCMS (ESI): [M+H]+ 223.1.

Example A13: 1-(4-Aminopyrimidin-2-yl)azetidine-3-carbonitrile

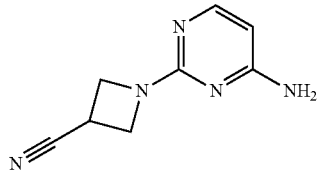 [SMILES: N#CC1CN(c2nccc(N)n2)C1]

1-(4-Aminopyrimidin-2-yl)azetidine-3-carbonitrile (293 mg, 53%) was prepared from 2-chloropyrimidin-4-ylamine (403 mg, 3.13 mmol) and azetidine-3-carbonitrile hydrochloride (371 mg, 3.13 mmol) according to a procedure analogous to that described for Example A4. LCMS (ESI): [M+H]$^+$ 176.2.

Example A14: 6-Bromo-1-(2,2,2-trifluoroethyl)-1H-imidazo[4,5-c]pyridine

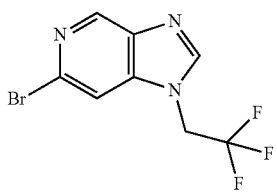 [SMILES: FC(F)(F)Cn1cnc2cnc(Br)cc21]

Step 1: (2-Bromo-5-nitropyridin-4-yl)-(2,2,2-trifluoroethyl)amine

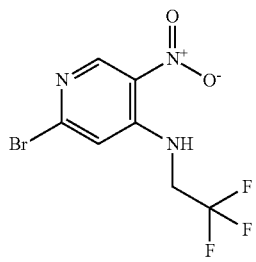 [SMILES: O=[N+]([O-])c1cnc(Br)cc1NCC(F)(F)F]

(2-Bromo-5-nitropyridin-4-yl)-(2,2,2-trifluoroethyl)amine (844 mg, 79%) was prepared from 2,4-dibromo-5-nitropyridine (1.0 g, 3.56 mmol) and 2,2,2-trifluoroethylamine (709 mg, 7.12 mmol) according to a procedure analogous to that described for Example 3. $^1$H NMR (400 MHz, CDCl$_3$): δ 9.04 (1H, s), 8.42 (1H, s), 7.04 (1H, s), 4.07-3.89 (2H, m).

Step 2: 6-Bromo-N$^4$-(2,2,2-trifluoroethyl)pyridine-3,4-diamine

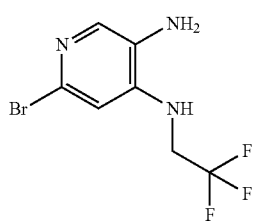 [SMILES: Nc1cnc(Br)cc1NCC(F)(F)F]

6-Bromo-N$^4$-(2,2,2-trifluoroethyl)pyridine-3,4-diamine (715 mg, 94%) was prepared from (2-bromo-5-nitropyridin-4-yl)-(2,2,2-trifluoroethyl)amine (844 mg, 2.81 mmol) according to a procedure analogous to that described for Example 12 Step 2. $^1$H NMR (400 MHz, DMSO-d$_6$): δ 7.46 (1H, s), 6.77 (1H, s), 6.17 (1H, t, J=6.7 Hz), 4.85 (2H, s), 4.19-3.99 (2H, m).

Step 3: 6-Bromo-1-(2,2,2-trifluoroethyl)-1H-imidazo[4,5-c]pyridine

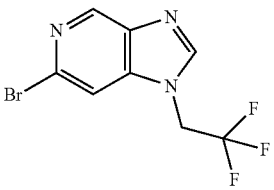

6-Bromo-1-(2,2,2-trifluoroethyl)-1H-imidazo[4,5-c]pyridine (400 mg, 54%) was prepared from 6-bromo-N$^4$-(2,2,2-trifluoroethyl)pyridine-3,4-diamine (715 mg, 2.65 mmol) according to a procedure analogous to that described for Example 3. LCMS (ESI): [M+H]$^+$ 280.0.

Example A15: 6-Chloro-1-cyclopropyl-1H-imidazo[4,5-c]pyridine

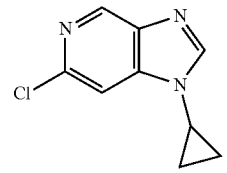 [SMILES: Clc1cc2c(cn1)ncn2C1CC1]

Step 1: (2-Chloro-5-nitropyridin-4-yl)cyclopropylamine

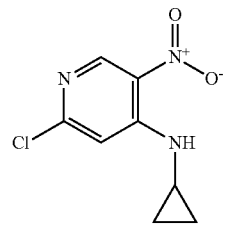 [SMILES: O=[N+]([O-])c1cnc(Cl)cc1NC1CC1]

(2-Chloro-5-nitropyridin-4-yl)cyclopropylamine (428 mg, 97%) was prepared from 2,4-dichloro-5-nitropyridine (400 mg, 2.07 mmol) and cyclopropylamine (158 µL, 2.28 mmol) according to a procedure analogous to that described for Example 3 Step 1. LCMS (ESI): [M+H]$^+$ 214.1.

Step 2: 6-Chloro-N⁴-cyclopropylpyridine-3,4-diamine

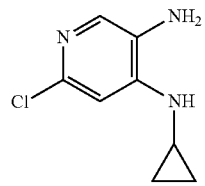 [SMILES: Nc1cnc(Cl)cc1NC1CC1]

6-Chloro-N⁴-cyclopropylpyridine-3,4-diamine (360 mg, 98%) was prepared from (2-chloro-5-nitropyridin-4-yl)cyclopropylamine (428 mg, 2.0 mmol) according to a procedure analogous to that described for Example 26 Step 2. LCMS (ESI): [M+H]⁺ 184.0.

Step 3:
6-Chloro-1-cyclopropyl-1H-imidazo[4,5-c]pyridine

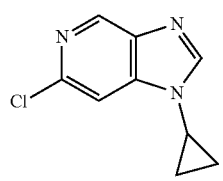 [SMILES: Clc1cc2c(cn1)ncn2C1CC1]

6-Chloro-1-cyclopropyl-1H-imidazo[4,5-c]pyridine (287 mg, 76%) was prepared from 6-chloro-N⁴-cyclopropylpyridine-3,4-diamine (360 mg, 1.96 mmol) according to a procedure analogous to that described for Example 20 Step 1. LCMS (ESI): [M+H]⁺ 194.0.

Example A16:
6-Chloro-1-cyclobutyl-1H-imidazo[4,5-c]pyridine

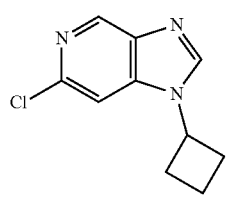 [SMILES: Clc1cc2c(cn1)ncn2C1CCC1]

Step 1:
(2-Chloro-5-nitropyridin-4-yl)cyclobutylamine

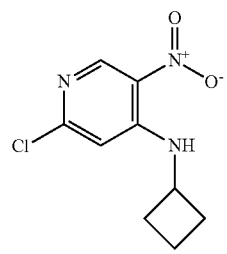 [SMILES: O=[N+]([O-])c1cnc(Cl)cc1NC1CCC1]

(2-Chloro-5-nitropyridin-4-yl)cyclobutylamine (471 mg, quantitative yield) was prepared from 2,4-dichloro-5-nitropyridine (400 mg, 2.07 mmol) and cyclobutylamine (195 µL, 2.28 mmol) according to a procedure analogous to that described for Example 3. LCMS (ESI): [M+H]⁺ 228.1.

Step 2: 6-Chloro-N⁴-cyclobutylpyridine-3,4-diamine

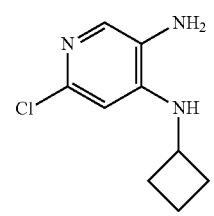 [SMILES: Nc1cnc(Cl)cc1NC1CCC1]

6-Chloro-N⁴-cyclobutylpyridine-3,4-diamine (409 mg, quantitative yield) was prepared from (2-chloro-5-nitropyridin-4-yl)cyclobutylamine (471 mg, 2.07 mmol) according to a procedure analogous to that described for Example 26 Step 2. LCMS (ESI): [M+H]⁺ 198.2.

Step 3:
6-Chloro-1-cyclobutyl-1H-imidazo[4,5-c]pyridine

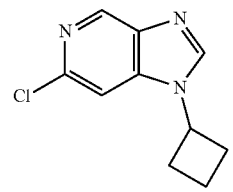 [SMILES: Clc1cc2c(cn1)ncn2C1CCC1]

6-Chloro-1-cyclobutyl-1H-imidazo[4,5-c]pyridine (300 mg, 70%) was prepared from 6-chloro-N⁴-cyclobutylpyridine-3,4-diamine (409 mg, 2.07 mmol) according to a procedure analogous to that described for Example 20 Step 1. LCMS (ESI): [M+H]⁺ 208.0.

Example A17:
6-Chloro-1-cyclohexyl-1H-imidazo[4,5-c]pyridine

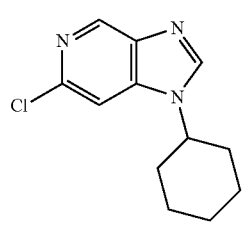 [SMILES: Clc1cc2c(cn1)ncn2C1CCCCC1]

83

Step 1:
(2-Chloro-5-nitropyridin-4-yl)cyclohexylamine

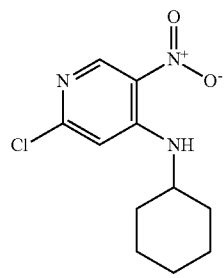 [SMILES: O=[N+]([O-])c1cnc(Cl)cc1NC1CCCCC1]

(2-Chloro-5-nitropyridin-4-yl)cyclohexylamine (529 mg, quantitative yield) was prepared from 2,4-dichloro-5-nitropyridine (400 mg, 2.07 mmol) and cyclohexylamine (261 μL, 2.28 mmol) according to a procedure analogous to that described for Example 3. LCMS (ESI): [M+H]$^+$ 256.0.

Step 2: 6-Chloro-N$^4$-cyclohexylpyridine-3,4-diamine

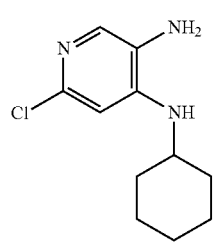 [SMILES: Nc1cnc(Cl)cc1NC1CCCCC1]

6-Chloro-N$^4$-cyclohexylpyridine-3,4-diamine (393 mg, 84%) was prepared from (2-chloro-5-nitropyridin-4-yl)cyclohexylamine (529 mg, 2.07 mmol) according to a procedure analogous to that described for Example 26 Step 2. LCMS (ESI): [M+H]$^+$ 226.2.

Step 3:
6-Chloro-1-cyclohexyl-1H-imidazo[4,5-c]pyridine

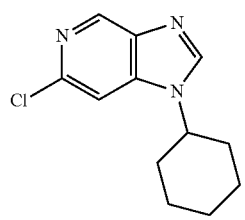 [SMILES: Clc1cc2c(cn1)ncn2C1CCCCC1]

6-Chloro-1-cyclohexyl-1H-imidazo[4,5-c]pyridine (320 mg, 78%) was prepared from 6-chloro-N$^4$-cyclohexylpyridine-3,4-diamine (393 mg, 1.74 mmol) according to a procedure analogous to that described for Example 20 Step 1. LCMS (ESI): [M+H]$^+$ 236.1.

84

Example A18:
1-sec-Butyl-6-chloro-1H-imidazo[4,5-c]pyridine

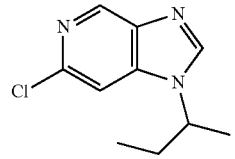

Step 1:
sec-Butyl-(2-chloro-5-nitropyridin-4-yl)amine

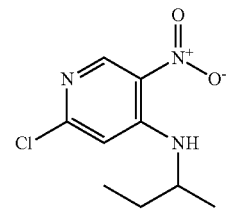

sec-Butyl-(2-chloro-5-nitropyridin-4-yl)amine (475 mg, quantitative yield) was prepared from 2,4-dichloro-5-nitropyridine (400 mg, 2.07 mmol) and sec-butylamine (230 μL, 2.28 mmol) according to a procedure analogous to that described for Example 3. LCMS (ESI): [M+H]$^+$ 230.1.

Step 2: N$^4$-sec-Butyl-6-chloropyridine-3,4-diamine

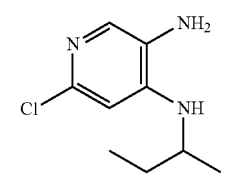

N$^4$-sec-Butyl-6-chloropyridine-3,4-diamine (390 mg, 94%) was prepared from sec-butyl-(2-chloro-5-nitropyridin-4-yl)amine (475 mg, 2.07 mmol) according to a procedure analogous to that described for Example 26 Step 2. LCMS (ESI): [M+H]$^+$ 200.2.

Step 3:
1-sec-Butyl-6-chloro-1H-imidazo[4,5-c]pyridine

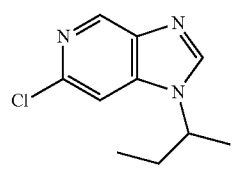

1-sec-Butyl-6-chloro-1H-imidazo[4,5-c]pyridine (287 mg, 70%) was prepared from N$^4$-sec-butyl-6-chloropyridine-3,4-diamine (390 mg, 1.95 mmol) according to a procedure analogous to that described for Example 20 Step 1. LCMS (ESI): [M+H]+ 210.0.

Example A19: 6-Chloro-1-(2,2,2-trifluoro-1-methylethyl)-1H-imidazo[4,5-c]pyridine

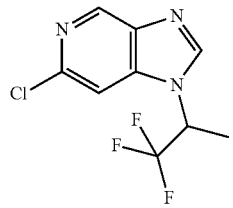 [SMILES: CC(n1cnc2cnc(Cl)cc21)C(F)(F)F]

Step 1: (2-Chloro-5-nitropyridin-4-yl)-(2,2,2-trifluoro-1-methylethyl)amine

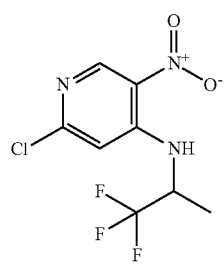 [SMILES: CC(Nc1cc(Cl)ncc1[N+](=O)[O-])C(F)(F)F]

(2-Chloro-5-nitropyridin-4-yl)-(2,2,2-trifluoro-1-methylethyl)amine (338 mg, 62%) was prepared from 2,4-dichloro-5-nitropyridine (386 mg, 2.0 mmol) and 2,2,2-trifluoro-1-methylethylamine (404 mg, 4.0 mmol) according to a procedure analogous to that described for Example 18 Step 1. $^1$H NMR (400 MHz, CDCl$_3$) δ 9.10 (1H, s), 8.26 (1H, d, J=8.9 Hz), 6.86 (1H, s), 4.32-4.18 (1H, m), 1.59 (3H, d, J=6.8 Hz).

Step 2: 6-Chloro-N$^4$-(2,2,2-trifluoro-1-methylethyl)pyridine-3,4-diamine

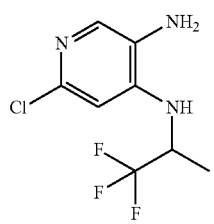

6-Chloro-N$^4$-(2,2,2-trifluoro-1-methylethyl)pyridine-3,4-diamine (250 mg, 85%) was prepared from (2-chloro-5-nitropyridin-4-yl)-(2,2,2-trifluoro-1-methylethyl)amine (330 mg, 1.22 mmol) according to a procedure analogous to that described for Example 18 Step 2. $^1$H NMR (400 MHz, CDCl$_3$) δ 7.75 (1H, s), 6.56 (1H, s), 4.48 (1H, d, J=8.7 Hz), 4.12-3.97 (1H, m), 3.03 (2H, s), 1.37 (3H, d, J=6.9 Hz).

Step 3: 6-Chloro-1-(2,2,2-trifluoro-1-methylethyl)-1H-imidazo[4,5-c]pyridine

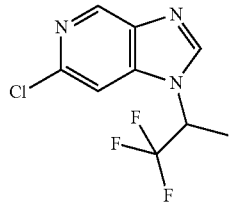 [SMILES: CC(n1cnc2cnc(Cl)cc21)C(F)(F)F]

6-Chloro-1-(2,2,2-trifluoro-1-methylethyl)-1H-imidazo[4,5-c]pyridine (240 mg, 92%) was prepared from 6-chloro-N$^4$-(2,2,2-trifluoro-1-methylethyl)pyridine-3,4-diamine (250 mg, 1.04 mmol) according to a procedure analogous to that described for Example 18 Step 3. $^1$H NMR (400 MHz, CDCl$_3$) δ 8.90 (1H, d, J=0.9 Hz), 8.07 (1H, s), 7.42 (1H, s), 4.89-4.90 (1H, m), 1.92 (3H, d, J=7.3 Hz).

Example A20: 1-tert-Butyl-6-chloro-2-methyl-1H-imidazo[4,5-c]pyridine

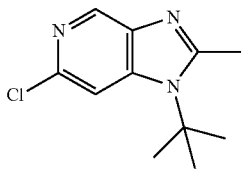

Step 1: tert-Butyl-(2-chloro-5-nitropyridin-4-yl)amine

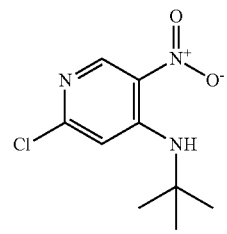

tert-Butyl-(2-chloro-5-nitropyridin-4-yl)amine (592 mg, quantitative) was prepared from 2,4-dichloro-5-nitropyridine (500 mg, 2.59 mmol) and tert-butylamine (378 mg, 5.18 mmol) according to a procedure analogous to that described for Example 18 Step 1. LCMS (ESI): [M+H]+ 230.0.

Step 2: N⁴-tert-Butyl-6-chloropyridine-3,4-diamine

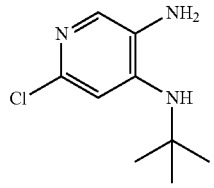

N⁴-tert-Butyl-6-chloropyridine-3,4-diamine (521 mg, quantitative) was prepared from tert-butyl-(2-chloro-5-nitropyridin-4-yl)amine (590 mg, 2.58 mmol) according to a procedure analogous to that described for Example 18 Step 2. LCMS (ESI): [M+H]⁺ 200.0.

Step 3: 1-tert-Butyl-6-chloro-2-methyl-1H-imidazo[4,5-c]pyridine

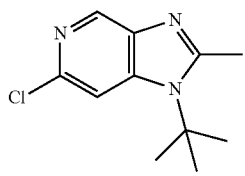

1-tert-Butyl-6-chloro-2-methyl-1H-imidazo[4,5-c]pyridine (180 mg, 64%) was prepared from N⁴-tert-butyl-6-chloropyridine-3,4-diamine (250 mg, 1.25 mmol) according to a procedure analogous to that described for Example 5. LCMS (ESI): [M+H]⁺ 223.9.

Example A21: 6-Chloro-1-(2-methoxy-1,1-dimethylethyl)-2-methyl-1H-imidazo[4,5-c]pyridine

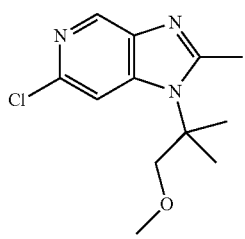 [SMILES: COCC(C)(C)n1c(C)nc2cnc(Cl)cc21]

Step 1: (2-Chloro-5-nitropyridin-4-yl)-(2-methoxy-1,1-dimethylethyl)amine

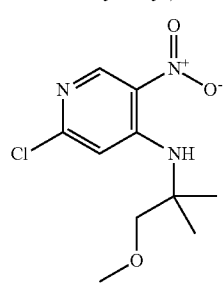

(2-Chloro-5-nitropyridin-4-yl)-(2-methoxy-1,1-dimethylethyl)amine (676 mg, quantitative) was prepared from 2,4-dichloro-5-nitropyridine (500 mg, 2.6 mmol) and 2-methoxy-1,1-dimethylethylamine (963 mg, 5.2 mmol) according to a procedure analogous to that described for Example 18 Step 1. ¹H NMR (400 MHz, CDCl₃) δ 9.00 (1H, s), 8.77 (1H, s), 6.98 (1H, s), 3.46 (3H, s), 3.40 (2H, s), 1.48 (6H, s).

Step 2: 6-Chloro-N⁴-(2-methoxy-1,1-dimethylethyl)pyridine-3,4-diamine

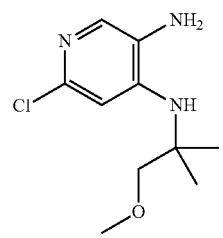

6-Chloro-N⁴-(2-methoxy-1,1-dimethylethyl)pyridine-3,4-diamine (617 mg, 97%) was prepared from (2-chloro-5-nitropyridin-4-yl)-(2-methoxy-1,1-dimethylethyl)amine (676 mg, 2.76 mmol) according to a procedure analogous to that described for Example 18 Step 2. LCMS (ESI): [M+H]⁺ 230.1.

Step 3: 6-Chloro-1-(2-methoxy-1,1-dimethylethyl)-2-methyl-1H-imidazo[4,5-c]pyridine

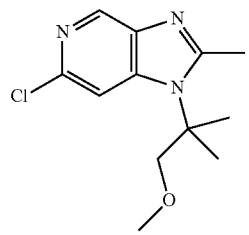 [SMILES: COCC(C)(C)n1c(C)nc2cnc(Cl)cc21]

6-Chloro-1-(2-methoxy-1,1-dimethylethyl)-2-methyl-1H-imidazo[4,5-c]pyridine (214 mg, 71%) was prepared from 6-chloro-N⁴-(2-methoxy-1,1-dimethylethyl)pyridine-3,4-diamine (270 mg, 1.17 mmol) according to a procedure analogous to that described for Example 5. LCMS (ESI): [M+H]⁺ 253.9.

Example A22: 4-[4-(1-Isopropyl-1H-imidazo[4,5-c]pyridin-6-ylamino)pyrimidin-2-yl]piperidinium chloride

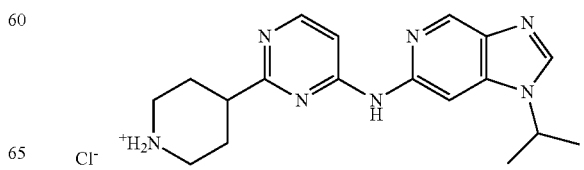

Step 1: 4-[4-(1-Isopropyl-1H-imidazo[4,5-c]pyridin-6-ylamino)pyrimidin-2-yl]piperidine-1-carboxylic acid tert-butyl ester

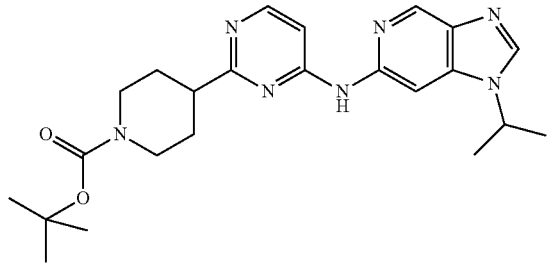 [SMILES: CC(C)n1cnc2cnc(Nc3ccnc(C4CCN(C(=O)OC(C)(C)C)CC4)n3)cc21]

A suspension of 4-[4-(1-isopropyl-1H-imidazo[4,5-c]pyridin-6-ylamino)pyrimidin-2-yl]-3,6-dihydro-2H-pyridine-1-carboxylic acid tert-butyl ester (Example 27, step 1) (135 mg, 0.31 mmol) and Pd/C (10 wt %, 100 mg) in EtOAc (10 mL) and MeOH (1 mL) was stirred at RT under a hydrogen atmosphere. Additional Pd/C (10 wt %, 100 mg) was added and stirring at RT was continued for 18 h. The reaction mixture was filtered and the filtrate was concentrated in vacuo to afford the title compound (88 mg, 65%). LCMS (ESI): [M+H]$^+$ 438.2.

Step 2: 4-[4-(1-Isopropyl-1H-imidazo[4,5-c]pyridin-6-ylamino)pyrimidin-2-yl]piperidinium chloride

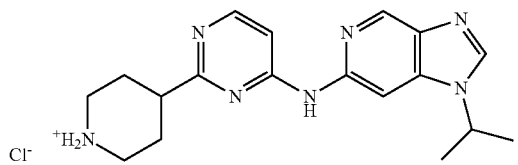 [SMILES: [Cl-] ; CC(C)n1cnc2cnc(Nc3ccnc(C4CC[NH2+]CC4)n3)cc21]

4-[4-(1-isopropyl-1H-imidazo[4,5-c]pyridin-6-ylamino)pyrimidin-2-yl]piperidinium chloride (75 mg, quantitative yield) was prepared from 4-[4-(1-isopropyl-1H-imidazo[4,5-c]pyridin-6-ylamino)pyrimidin-2-yl]piperidine-1-carboxylic acid tert-butyl ester (88 mg, 0.201 mmol) according to a procedure analogous to that described for Example 27 Step 2. LCMS (ESI): [M]$^+$ 338.0.

Example 27: (1-Isopropyl-1H-imidazo[4,5-c]pyridin-6-yl)-[2-(1-methanesulfonyl-1,2,3,6-tetrahydropyridin-4-yl)pyrimidin-4-yl]amine

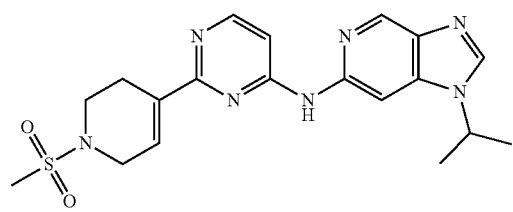 [SMILES: CC(C)n1cnc2cnc(Nc3ccnc(C4=CCN(S(C)(=O)=O)CC4)n3)cc21]

Step 1: 4-[4-(1-Isopropyl-1H-imidazo[4,5-c]pyridin-6-ylamino)pyrimidin-2-yl]-3,6-dihydro-2H-pyridine-1-carboxylic acid tert-butyl ester

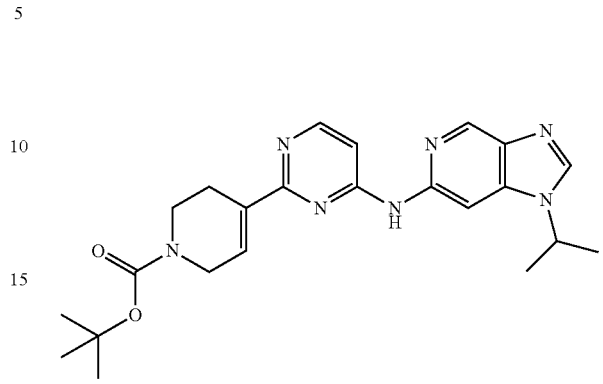

A solution of (2-chloropyrimidin-4-yl)-(1-isopropyl-1H-imidazo[4,5-c]pyridin-6-yl)amine (Example 12, step 4) (100 mg, 0.35 mmol), 4-(4,4,5,5-tetramethyl-[1,3,2]dioxaborolan-2-yl)-3,6-dihydro-2H-pyridine-1-carboxylic acid tert-butyl ester (161 mg, 0.52 mmol), Cs$_2$CO$_3$ (169 mg, 0.52 mmol) and Pd(PPh$_3$)$_4$ (40 mg, 0.04 mmol) in dioxane (3 mL) and water (0.1 mL) was degassed with a stream of argon and then heated at 100° C. for 3 h. The reaction mixture was partitioned between water and EtOAc and the aqueous phase was further extracted with EtOAc. The combined organic layers were washed with brine, dried (MgSO$_4$) and concentrated in vacuo. The resulting residue was purified by chromatography (Si-PCC, gradient 0-10% MeOH in DCM) to afford the title compound (142 mg, 93%). $^1$H NMR (400 MHz, CDCl$_3$) δ 8.78 (1H, d, J=1.0 Hz), 8.47 (1H, s), 8.36 (1H, d, J=5.8 Hz), 7.96 (1H, s), 7.74 (1H, s), 7.18 (1H, br. s), 6.71 (1H, d, J=5.8 Hz), 4.70-4.56 (1H, m), 4.18 (2H, br. s), 3.66 (2H, br. s), 2.81 (2H, br. s), 1.68 (6H, d, J=6.8 Hz), 1.49 (9H, s).

Step 2: 4-[4-(1-Isopropyl-1H-imidazo[4,5-c]pyridin-6-ylamino)pyrimidin-2-yl]-1,2,3,6-tetrahydropyridinium chloride

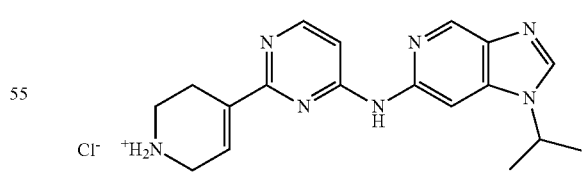

HCl (4N solution in dioxane) was added to a solution of 4-[4-(1-isopropyl-1H-imidazo[4,5-c]pyridin-6-ylamino)pyrimidin-2-yl]-3,6-dihydro-2H-pyridine-1-carboxylic acid tert-butyl ester (142 mg, 0.33 mmol) in MeOH (3 mL). The reaction mixture was stirred at room temperature for 1 h and then the volatiles were removed in vacuo to afford the title compound as an off-white solid. LCMS (ESI): [M]$^+$ 336.1.

Step 3: (1-Isopropyl-1H-imidazo[4,5-c]pyridin-6-yl)-[2-(1-methanesulfonyl-1,2,3,6-tetrahydropyridin-4-yl)pyrimidin-4-yl]amine

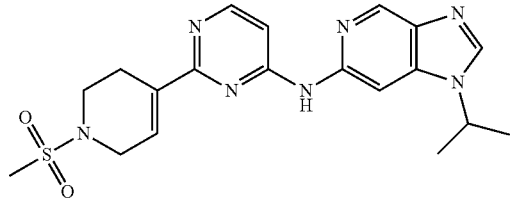 [SMILES: CC(C)n1cnc2cnc(Nc3ccnc(C4=CCN(S(C)(=O)=O)CC4)n3)cc21]

A suspension of 4-[4-(1-isopropyl-1H-imidazo[4,5-c]pyridin-6-ylamino)pyrimidin-2-yl]-1,2,3,6-tetrahydropyridinium chloride (60 mg, 0.16 mmol), triethylamine (68 µL, 0.49 mmol) and methanesulfonyl chloride (14 µL, 0.18 mmol) in THF (3 mL) was heated at 50° C. for 18 h. Additional amounts of triethylamine (34 µL) and methanesulfonyl chloride (19 µL) were added and heating at 50° C. was continued for 4 h. The cooled reaction mixture was partitioned between water and EtOAc and the aqueous phase was further extracted with EtOAc. The combined organic layers were washed with brine, dried (MgSO$_4$) and concentrated in vacuo. The resulting residue was purified by preparatory reverse-phase HPLC and lyophilized to afford the title compound (16 mg, 24%). LCMS (ESI): R$_T$ 2.35 min, [M+H]$^+$ 414.0, Method=E. $^1$H NMR (400 MHz, CDCl$_3$) δ 8.79 (1H, d, J=1.0 Hz), 8.37 (1H, d, J=5.8 Hz), 8.29 (1H, s), 7.98 (1H, s), 7.68 (1H, s), 7.24-7.18 (1H, m), 6.82 (1H, d, J=5.8 Hz), 4.68-4.55 (1H, m), 4.11-4.05 (2H, m), 3.55 (2H, t, J=5.7 Hz), 2.97-2.90 (2H, m), 2.88 (3H, s), 1.69 (6H, d, J=6.8 Hz).

Example 28: (1-Isopropyl-1H-imidazo[4,5-c]pyridin-6-yl)-(2-morpholin-4-ylpyrimidin-4-yl)amine

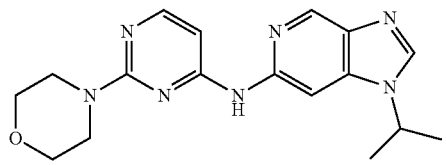 [SMILES: CC(C)n1cnc2cnc(Nc3ccnc(N4CCOCC4)n3)cc21]

A mixture of 2-chloropyrimidin-4-yl)-(1-isopropyl-1H-imidazo[4,5-c]pyridin-6-yl)amine (Example 12, step 4) (80 mg, 0.28 mmol), morpholine (0.03 mL, 0.3 mmol) and DIPEA (0.15 mL, 0.83 mmol) in isopropanol (0.5 mL) was heated at 150° C. under microwave irradiation for 30 min. Water (5 mL) was added and a precipitate formed. The solid thus formed was collected by filtration affording the title compound as a white solid (54 mg, 57%). LCMS (ESI): R$_T$ 2.05 min, [M+H]$^+$ 340.2, Method=E. $^1$H NMR (400 MHz, CDCl$_3$): δ 9.87 (1H, s), 8.68 (1H, d, J=0.9 Hz), 8.41 (1H, s), 8.35 (1H, s), 8.02 (1H, d, J=5.7 Hz), 6.47 (1H, d, J=5.7 Hz), 4.74-4.61 (1H, m), 3.78-3.67 (8H, m), 1.57 (6H, d, J=6.8 Hz).

Example 29: 4-(4-((1-isopropyl-1H-imidazo[4,5-c]pyridin-6-yl)amino)pyrimidin-2-yl)thiomorpholine 1-oxide

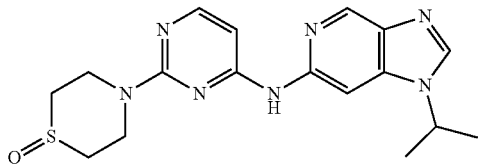 [SMILES: CC(C)n1cnc2cnc(Nc3ccnc(N4CCS(=O)CC4)n3)cc21]

And

Example 30: 4-(4-((1-isopropyl-1H-imidazo[4,5-c]pyridin-6-yl)amino)pyrimidin-2-yl)thiomorpholine 1,1-dioxide

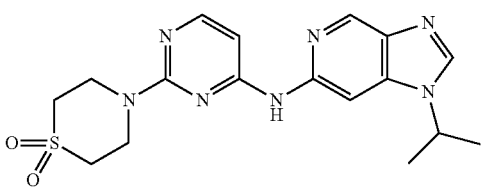 [SMILES: CC(C)n1cnc2cnc(Nc3ccnc(N4CCS(=O)(=O)CC4)n3)cc21]

meta-chloroperoxybenzoic acid (64 mg, 0.29 mmol) was added to a mixture of (1-isopropyl-1H-imidazo[4,5-c]pyridin-6-yl)-(2-thiomorpholin-4-ylpyrimidin-4-yl)amine (Example 137) (50 mg, 0.14 mmol) under a nitrogen atmosphere. The reaction mixture was stirred at room temperature for 1 h and then combined with a second batch of material (0.14 mmol) which had been subjected to the same reaction conditions. The combined reaction mixtures were washed with a saturated solution of sodium metabisulfite followed by a saturated solution of NaHCO$_3$. The organic layer was dried (MgSO$_4$) and concentrated in vacuo. The resulting residue was purified by column chromatography (Si-PCC, gradient 1-10% 2M NH$_3$/MeOH in DCM) followed by preparatory reverse-phase HPLC to afford the title compounds as white solids.

Example 29 (23 mg, 21%): LCMS (ESI): R$_T$ 1.82 min, [M+H]$^+$ 372.1, Method=E. $^1$H NMR (400 MHz, CDCl$_3$): δ 8.78 (1H, d, J=1.0 Hz), 8.13 (1H, s), 8.08 (1H, d, J=5.7 Hz), 7.96 (1H, s), 7.64 (1H, s), 6.25 (1H, d, J=5.7 Hz), 4.68-4.50 (3H, m), 4.30-4.19 (2H, m), 2.86-2.79 (4H, m), 1.66 (6H, d, J=6.7 Hz).

Example 30 (11 mg, 11%): LCMS (ESI): R$_T$ 2.12 min, [M+H]$^+$ 388.1, Method=E. $^1$H NMR (400 MHz, DMSO-d6): δ 9.93 (1H, s), 8.67 (1H, s), 8.35 (1H, s), 8.16 (1H, s), 8.04 (1H, d, J=5.7 Hz), 6.59 (1H, d, J=5.7 Hz), 4.70-4.57 (1H, m), 4.30-4.18 (4H, m), 3.23-3.13 (4H, m), 1.55 (6H, d, J=6.7 Hz).

Example 31: 3-{6-[2-(4-Methoxypiperidin-1-yl)pyrimidin-4-ylamino]pyrrolo[3,2-c]pyridin-1-yl}-2,2-dimethylpropionamide

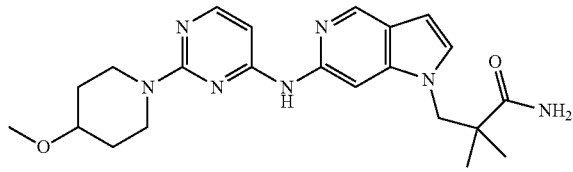 [SMILES: COC1CCN(c2nccc(Nc3cc4c(ccn4CC(C)(C)C(N)=O)cn3)n2)CC1]

Step 1: 3-(6-Chloropyrrolo[3,2-c]pyridin-1-yl)-2,2-dimethylpropionic acid ethyl ester

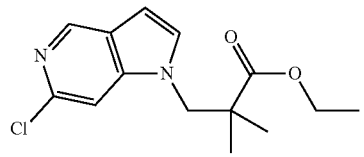 [SMILES: CCOC(=O)C(C)(C)Cn1ccc2cnc(Cl)cc21]

A mixture of 6-chloro-1H-pyrrolo[3,2-c]pyridine (509 mg, 3.3 mmol), 3-bromo-2,2-dimethylpropionic acid ethyl ester (1.4 g, 6.7 mmol) and Cs$_2$CO$_3$ (2.17 g, 6.7 mmol) in DMF (5 mL) was heated at 80° C. for 18 h. The volatiles were removed in vacuo and the resulting residue was purified by chromatography (Si-PCC, gradient 10-60% EtOAc in cyclohexane) to afford the title compound as a colorless oil (204 mg, 22%). $^1$H NMR (400 MHz, CDCl$_3$) δ 8.64 (1H, d, J=0.9 Hz), 7.28 (1H, s), 7.12 (1H, d, J=3.3 Hz), 6.57 (1H, dd, J=3.3, 0.9 Hz), 4.24 (2H, s), 4.17-4.08 (2H, m), 1.27-1.19 (9H, m).

Step 2: 3-{6-[2-(4-Methoxypiperidin-1-yl)pyrimidin-4-ylamino]pyrrolo[3,2-c]pyridin-1-yl}-2,2-dimethylpropionic acid ethyl ester

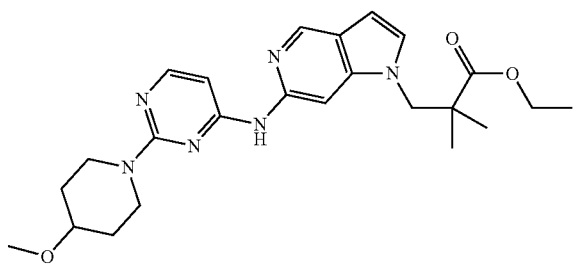 [SMILES: CCOC(=O)C(C)(C)Cn1ccc2cnc(Nc3ccnc(N4CCC(OC)CC4)n3)cc21]

3-{6-[2-(4-Methoxypiperidin-1-yl)pyrimidin-4-ylamino]pyrrolo[3,2-c]pyridin-1-yl}-2,2-dimethylpropionic acid ethyl ester (76 mg, 51%) was prepared from 3-(6-chloropyrrolo[3,2-c]pyridin-1-yl)-2,2-dimethylpropionic acid ethyl ester (92 mg, 0.33 mmol) and 2-(4-methoxypiperidin-1-yl)pyrimidin-4-ylamine (68 mg, 0.33 mmol) according to a procedure analogous to that described for Example 22 Step 3. LCMS (ESI): [M+H]$^+$ 453.1.

Step 3: 3-{6-[2-(4-Methoxypiperidin-1-yl)pyrimidin-4-ylamino]pyrrolo[3,2-c]pyridin-1-yl}-2,2-dimethylpropionic acid

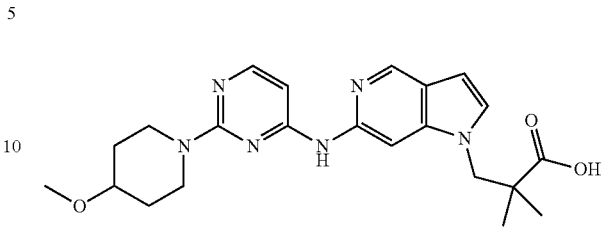

A mixture of 3-{6-[2-(4-methoxypiperidin-1-yl)pyrimidin-4-ylamino]pyrrolo[3,2-c]pyridin-1-yl}-2,2-dimethylpropionic acid ethyl ester (70 mg, 0.15 mmol) and LiOH (3M, 0.1 mL, 0.3 mmol) in MeOH (6 mL) and water (3 mL) was heated at 50° C. for 18 h. The volatiles were removed in vacuo and the resulting residue was partitioned between a saturated solution of NH$_4$Cl and DCM. The aqueous phase was further extracted with DCM (×4) and the combined organic layers were dried (Na$_2$SO$_4$) and concentrated in vacuo to afford the title compound as a white solid (64 mg, 98%). LCMS (ESI): [M+H]$^+$ 425.1.

Step 4: 3-{6-[2-(4-Methoxypiperidin-1-yl)pyrimidin-4-ylamino]pyrrolo[3,2-c]pyridin-1-yl}-2,2-dimethylpropionamide

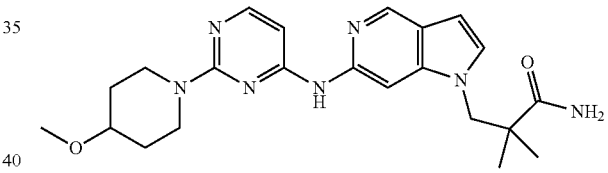

To a mixture of 3-{6-[2-(4-methoxypiperidin-1-yl)pyrimidin-4-ylamino]pyrrolo[3,2-c]pyridin-1-yl}-2,2-dimethylpropionic acid (64 mg, 0.15 mmol), NH$_4$Cl (16 mg, 0.2 mmol) and DIPEA (0.1 mL, 0.45 mmol) in DMF (1.5 mL) was added HATU (37 mg, 0.1 mmol) under a nitrogen atmosphere. After 1 h stirring at room temperature, additional HATU (37 mg, 0.1 mmol) was added and stirring was continued for 1 h. The reaction mixture was concentrated in vacuo and the resulting residue was partitioned between DCM and an aqueous solution of Na$_2$CO$_3$. The aqueous phase was further extracted with DCM and the combined organic layers were dried (Na$_2$SO$_4$) and concentrated in vacuo. The resultant residue was purified by chromatography (Si-PCC, gradient 1-10% 2M NH$_3$/MeOH in DCM) to afford the title compound as a white solid (18 mg, 28%). LCMS (ESI): R$_T$ 2.04 min, [M+H]$^+$ 423.9, Method=E. $^1$H NMR (400 MHz, CDCl$_3$) δ 8.52 (1H, d, J=0.9 Hz), 8.16 (1H, s), 8.02 (1H, d, J=5.7 Hz), 7.55 (1H, s), 7.10 (1H, d, J=3.3 Hz), 6.51 (1H, dd, J=3.3, 0.8 Hz), 6.13 (1H, d, J=5.7 Hz), 5.63-5.47 (2H, m), 4.41-4.33 (2H, m), 4.26 (2H, s), 3.54-3.44 (3H, m), 3.41 (3H, s), 2.05-1.92 (2H, m), 1.71-1.59 (2H, m), 1.28 (6H, s).

Example 32: ((R) or (S) 1-sec-Butyl-1H-imidazo[4,5-c]pyridin-6-yl)-[2-(4-methoxypiperidin-1-yl)pyrimidin-4-yl]amine (single unknown stereoisomer)

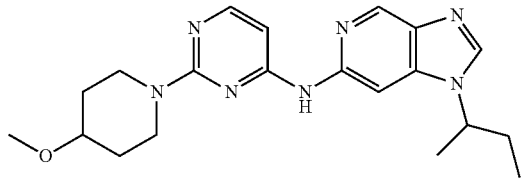 [SMILES: CCC(C)n1cnc2cnc(Nc3ccnc(N4CCC(OC)CC4)n3)cc21]

Example 32 was obtained from Example 153 (Table 1) by chiral separation using ChiralPak IA column (20 mm×250 mm) and a mixture of 10% EtOH, 10% TBME and 0.5% diethylamine in heptane (isocratic) at a flow rate of 18 mL/min. A stacked injection method was used (13×7.5 mg), giving the faster running enantiomer (41 mg, >99% ee). $^1$H NMR (400 MHz, DMSO-d$_6$) δ 9.80 (1H, s), 8.67 (1H, d, J=0.9 Hz), 8.40 (1H, s), 8.34 (1H, s), 7.97 (1H, d, J=5.6 Hz), 6.39 (1H, d, J=5.7 Hz), 4.4-4.36 (1H, m), 4.29-4.19 (2H, m), 3.52-3.35 (3H, m), 3.30 (3H, s), 2.04-1.86 (4H, m), 1.56 (3H, d, J=6.8 Hz), 1.50-1.39 (2H, m), 0.78 (3H, t, J=7.3 Hz).

Example 33: ((R) or (S) 1-sec-Butyl-1H-imidazo[4,5-c]pyridin-6-yl)-[2-(4-methoxypiperidin-1-yl)pyrimidin-4-yl]amine (single unknown stereoisomer)

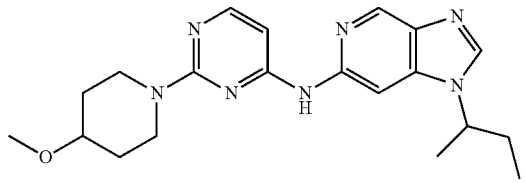 [SMILES: CCC(C)n1cnc2cnc(Nc3ccnc(N4CCC(OC)CC4)n3)cc21]

Example 33 was obtained from Example 153 (Table 1) by chiral separation using ChiralPak IA column (20 mm×250 mm) and a mixture of 10% EtOH, 10% TBME and 0.5% DEA in heptane (isocratic) at a flow rate of 18 mL/min. A stacked injection method was used (13×7.5 mg), giving the slower running enantiomer (38 mg, 93% ee). $^1$H NMR (400 MHz, DMSO-d$_6$) δ 9.80 (1H, s), 8.67 (1H, d, J=0.9 Hz), 8.40 (1H, s), 8.34 (1H, s), 7.97 (1H, d, J=5.6 Hz), 6.39 (1H, d, J=5.7 Hz), 4.4-4.36 (1H, m), 4.29-4.19 (2H, m), 3.52-3.35 (3H, m), 3.30 (3H, s), 2.04-1.86 (4H, m), 1.56 (3H, d, J=6.8 Hz), 1.50-1.39 (2H, m), 0.78 (3H, t, J=7.3 Hz).

Example 34: 1-[4-(1-Isopropyl-2-methyl-1H-imidazo[4,5-c]pyridin-6-ylamino)pyrimidin-2-yl]piperidine-3,4-diol

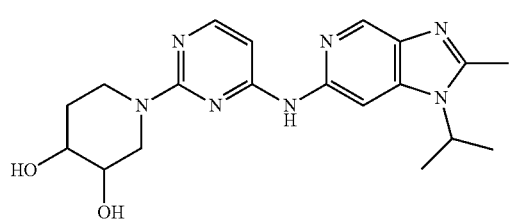 [SMILES: Cc1nc2cnc(Nc3ccnc(N4CCC(O)C(O)C4)n3)cc2n1C(C)C]

A suspension of [2-(3,6-dihydro-2H-pyridin-1-yl)pyrimidin-4-yl]-(1-isopropyl-2-methyl-1H-imidazo[4,5-c]pyridin-6-yl)amine (70 mg, 0.21 mmol), potassium osmate(VI) dihydrate (10 mg, 0.003 mmol), N-methylmorpholine N-oxide (49 mg, 0.42 mmol) in acetone (5 mL) and water (0.5 mL) was stirred for 18 h. Na$_2$S$_2$O$_5$ (1M solution in water, 2 mL) was added and the stirring was continued for 1 h. The resultant mixture was diluted with MeOH and DCM and loaded onto an SCX cartridge. The cartridge was washed with MeOH and the product eluted with 2M NH$_3$ in MeOH. The product containing fractions were concentrated in vacuo and the resultant residue was triturated with hot MeOH. The resultant suspension was cooled and filtered to afford the title compound as a beige solid (66 mg, 83%). LCMS (ESI): R$_T$ 1.76 min, [M+H]$^+$ 384.1, Method=E. $^1$H NMR (400 MHz, DMSO-d$_6$) δ 9.64 (1H, s), 8.48 (1H, d, J=0.9 Hz), 8.38 (1H, s), 7.92 (1H, d, J=5.6 Hz), 6.37 (1H, d, J=5.6 Hz), 4.78-4.65 (1H, m), 4.54 (2H, d, J=4.3 Hz), 3.90-3.62 (5H, m), 3.59-3.50 (1H, m), 2.55 (3H, s), 1.79-1.67 (1H, m), 1.63-1.49 (7H, m).

Example 35: N-(2-(8-Oxa-3-aza-bicyclo[3.2.1]octan-3-yl)pyrimidin-4-yl)-1-isopropyl-1H imidazo[4,5-c]pyridin-6-amine

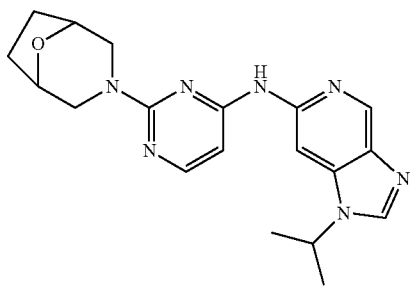 [SMILES: CC(C)n1cnc2cnc(Nc3ccnc(N4CC5CCC(C4)O5)n3)cc21]

Step 1: 2-(8-Oxa-3-azabicyclo[3.2.1]octan-3-yl)pyrimidin-4-amine

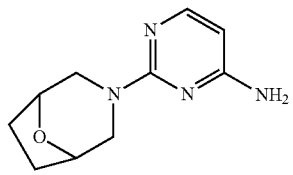 [SMILES: Nc1ccnc(N2CC3CCC(C2)O3)n1]

Into a 30 mL sealed tube was added a solution of 2-chloropyrimidin-4-amine (589 mg, 4.55 mmol) in N,N-dimethylformamide (10 mL), 8-oxa-3-azabicyclo[3.2.1]octane (745 mg, 6.58 mmol) and potassium carbonate (1.59 g, 11.5 mmol). The reaction mixture was irradiated with microwave radiation for 1 h at 120° C. The resulting solution was diluted with H$_2$O (20 mL). The resulting solution was extracted with ethyl acetate (3×30 mL). The combined organic layers were washed with brine (50 mL), dried over anhydrous sodium sulfate and concentrated under vacuum. The residue was purified by silica gel chromatography with dichloromethane/methanol (100:9.8) to afford 2-[8-oxa-3-azabicyclo[3.2.1]octan-3-yl]pyrimidin-4-amine (400 mg, 43%) as a white solid. LCMS (ESI): R$_T$ (min)=1.00, [M+H]$^+$=207, method=J.

Step 2: 6-chloro-1-isopropyl-1H-imidazo[4,5-c]pyridine

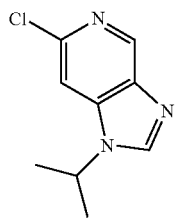

Into a 1000 mL 3-necked round-bottom flask was added a solution of 6-chloro-4-N-(propan-2-yl)pyridine-3,4-diamine (Example 7, step 2) (64.0 g, 344 mmol) in trimethylorthoformate (500 mL) and formic acid (10 mL). The resulting solution was stirred for 4 h at 80° C. The resulting mixture was concentrated under vacuum. The residue was purified by silica gel chromatography with ethyl acetate/petroleum ether (70:30) to afford 6-chloro-1-(propan-2-yl)-1H-imidazo[4,5-c]pyridine (51 g, 76%) as a brown solid. LCMS (ESI): $R_T$(min)=1.002, $[M+H]^+$=196, method=L; $^1$H NMR (300 MHz, DMSO-d6): δ 8.76 (s, 1H), 7.59 (s, 1H), 7.91 (s, 1H), 4.77-4.86 (m, 1H), 1.53-1.55 (d, J=6.6 Hz, 6H).

Step 3: N-(2-(8-Oxa-3-aza-bicyclo[3.2.1]octan-3-yl)pyrimidin-4-yl)-1-isopropyl-1H-imidazo[4,5-c]pyridin-6-amine

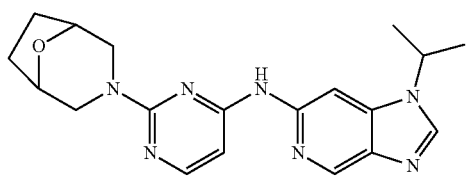 [SMILES: CC(C)n1cnc2cnc(Nc3ccnc(N4CC5CCC(C4)O5)n3)cc21]

Into a 30 mL sealed tube was added a solution of 6-chloro-1-isopropyl-1H-imidazo[4,5-c]pyridine (394 mg, 2.01 mmol) in 1,4-dioxane (15 mL), $Pd_2(dba)_3 \cdot CHCl_3$ (150 mg, 0.140 mmol), XantPhos (315 mg, 0.540 mmol), $Cs_2CO_3$ (2.20 g, 6.75 mmol), 2-8-oxa-3-azabicyclo[3.2.1]octan-3-ylpyrimidin-4-amine (410 mg, 1.99 mmol). The reaction mixture was heated under microwave irradiation for 45 min at 140° C. The reaction mixture was diluted with methanol (10 mL), solids were filtered out, and the filtrate was concentrated under vacuum. The crude product was purified by silica gel chromatography with dichloromethane/methanol (100:9.8) to afford 2-[8-oxa-3-azabicyclo[3.2.1]octan-3-yl]-N-[1-(propan-2-yl)-1H-imidazo[4,5-c]pyridin-6-yl]pyrimidin-4-amine (188.8 mg, 26%) as a yellow solid. LCMS (ESI): $R_T$ (min)=1.495, $[M+H]^+$=366.20, method=G; $^1$H NMR (300 MHz, DMSO-$d_6$) δ 9.84 (s, 1H), 8.65 (s, 1H), 8.44 (s, 1H), 8.33 (s, 1H), 7.98-7.95 (m, 1H), 6.43-6.41 (m, 1H), 4.72-4.63 (m, 1H), 4.43 (m, 2H), 4.22-4.17 (m, 2H), 3.17-3.10 (m, 2H), 1.85-1.68 (m, 4H), 1.57-1.50 (m, 6H).

Example 36: (R or S)—N-(2-(2-oxa-7-azaspiro[4.4]nonan-7-yl)pyrimidin-4-yl)-1-isopropyl-1H-imidazo[4,5-c]pyridin-6-amine (single unknown stereoisomer)

And

Example 37: (R or S)—N-(2-(2-Oxa-7-azaspiro[4.4]nonan-7-yl)pyrimidin-4-yl)-1-isopropyl-1H-imidazo[4,5-c]pyridin-6-amine (single unknown stereoisomer)

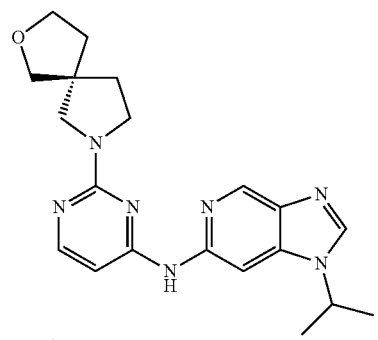

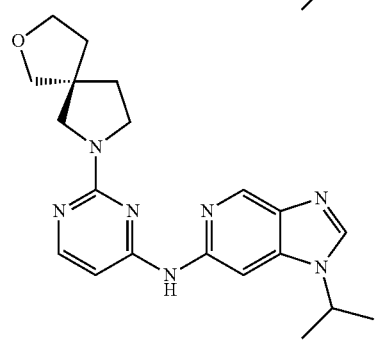

Step 1: 2-(2-Oxa-7-azaspiro[4.4]nonan-7-yl)pyrimidin-4-amine

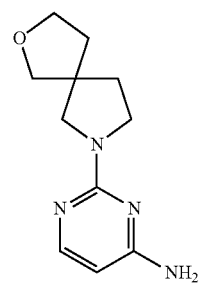 [SMILES: Nc1ccnc(N2CCC3(CCOC3)C2)n1]

A mixture of 2-chloropyrimidin-4-amine (76.1 mg, 0.587 mmol), 8-oxa-3-azaspiro[4.4]nonane hydrochloride (100 mg, 0.58054 mmol), cesium carbonate (396 mg, 1.20 mmol) and N,N-dimethylformamide (2.5 mL, 32 mmol) was heated at 120° C. for 24 hours. The reaction mixture was diluted with ethyl acetate, washed with water (2×) and brine, dried over magnesium sulfate, filtered, and evaporated in vacuo.

The crude product was purified via flash chromatography on silica gel (12 g silica, solvent gradient: 0-100% ethyl acetate in dichloromethane) to yield 76.4 mg (60%) of the title compound. LCMS (ESI): [M+H]⁺=221.4; ¹H NMR (400 MHz, DMSO-d₆): δ 7.70 (d, J=5.6 Hz, 1H), 6.28 (s, 1H), 5.69 (d, J=5.7 Hz, 1H), 3.84-3.71 (m, 2H), 3.58-3.51 (m, 2H), 3.50-3.35 (m, 3H), 3.27-3.21 (m, 1H), 1.93-1.76 (m, 4H).

Step 2: N-(2-(2-Oxa-7-azaspiro[4.4]nonan-7-yl)pyrimidin-4-yl)-1-isopropyl-1H-imidazo[4,5-c]pyridin-6-amine

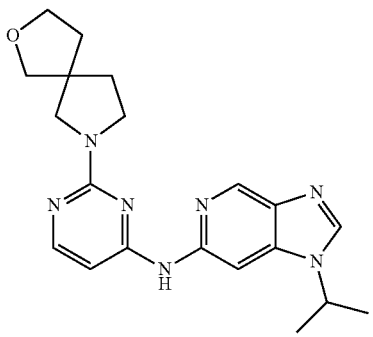 [SMILES: CC(C)n1cnc2cnc(Nc3ccnc(N4CCC5(CCOC5)C4)n3)cc21]

A mixture of 6-chloro-1-isopropyl1H-imidazo[4,5-c]pyridine (Example 35, step 2) (68.5 mg, 0.350 mmol), 2-(8-oxa-3-azaspiro[4.4]nonan-3-yl)pyrimidin-4-amine (75.4 mg, 0.342 mmol), tris(dibenylideneacetone)dipalladium chloroform complex (18.0 mg, 0.0169 mmol), 2-(dicyclohexylphosphino)-2',4',6'-triisopropyl-1,1'-biphenyl (19.4 mg, 0.0399 mmol), cesium carbonate (239.0 mg, 0.726 mmol) and 1,4-dioxane (1.5 mL) was heated in a sealed vial under nitrogen at 120° C. for 18 hours. The reaction mixture was diluted with ethyl acetate, washed with water (2×) and brine, dried over magnesium sulfate, filtered, and evaporated in vacuo. The crude product was purified via flash chromatography on silica gel (12 g silica, solvent gradient: 0-10% methanol in dichloromethane) followed by chiral SFC to separate the stereoisomers.

Example 36, Peak 1: 18.7 mg (14%), LCMS (ESI): R$_T$ (min)=3.363, M+H=380.3, method=B; ¹H NMR (400 MHz, DMSO-d₆) δ 9.77 (s, 1H), 8.69 (s, 1H), 8.64 (d, J=0.8 Hz, 1H), 8.31 (s, 1H), 7.94 (d, J=5.6 Hz, 1H), 6.33 (d, J=5.7 Hz, 1H), 4.72-4.62 (m, 1H), 3.91-3.76 (m, 2H), 3.71-3.49 (m, 6H), 2.07-1.87 (m, 4H), 1.56 (dd, J=6.8, 2.1 Hz, 6H).

Example 37, Peak 2: 17.3 mg (13%); LCMS (ESI): R$_T$ (min)=3.367, [M+H]⁺=380.2, method=B; ¹H NMR (400 MHz, DMSO-d₆) δ 9.77 (s, 1H), 8.69 (s, 1H), 8.64 (d, J=0.8 Hz, 1H), 8.31 (s, 1H), 7.94 (d, J=5.5 Hz, 1H), 6.33 (d, J=5.7 Hz, 1H), 4.73-4.61 (m, 1H), 3.89-3.76 (m, 2H), 3.71-3.50 (m, 6H), 2.06-1.86 (m, 4H), 1.56 (dd, J=6.8, 2.1 Hz, 6H).

Example 38: 1-Isopropyl-N-(2-(6-(methylsulfonyl)-2,6-diazaspiro[3.3]heptan-2-yl)pyrimidin-4-yl)-1H-imidazo[4,5-c]pyridin-6-amine

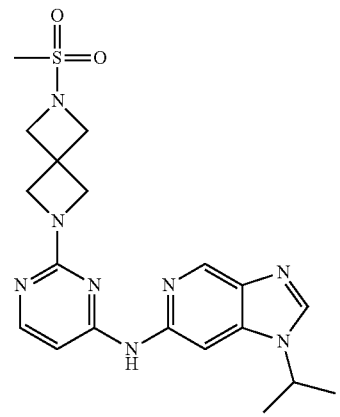 [SMILES: CC(C)n1cnc2cnc(Nc3ccnc(N4CC5(C4)CN(S(C)(=O)=O)C5)n3)cc21]

Step 1: tert-Butyl 6-(4-aminopyrimidin-2-yl)-2,6-diazaspiro[3.3]heptane-2-carboxylate

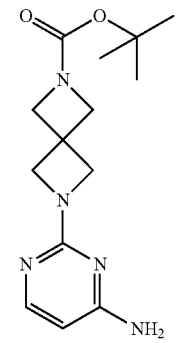 [SMILES: CC(C)(C)OC(=O)N1CC2(C1)CN(c1nccc(N)n1)C2]

A mixture of 2-chloropyrimidin-4-amine (46.6 mg, 0.36 mmol), 6-(tert-butoxycarbonyl)-6-aza-2-azoniaspiro[3.3]heptane oxalate (100 mg, 0.33 mmol), cesium carbonate (235.0 mg, 0.714 mmol) and N,N-dimethylformamide (2.0 mL) was heated at 120° C. for 18 hours. The reaction mixture was concentrated onto celite, and the crude product was purified via flash chromatography on silica gel (12 g silica, solvent gradient: 0-10% methanol in dichloromethane) to yield 45.4 mg (47%) of the desired product. LCMS (ESI): [M+H]⁺=292.4; ¹H NMR (400 MHz, DMSO-d₆): δ 7.69 (d, J=5.7 Hz, 1H), 6.44 (s, 2H), 5.75 (d, J=5.7 Hz, 1H), 4.00 (s, 4H), 3.98 (s, 4H), 1.37 (s, 9H).

Step 2: tert-Butyl 6-(4-((1-isopropyl-1H-imidazo[4,5-c]pyridin-6-yl)amino)pyrimidin-2-yl)-2,6-diazaspiro[3.3]heptane-2-carboxylate

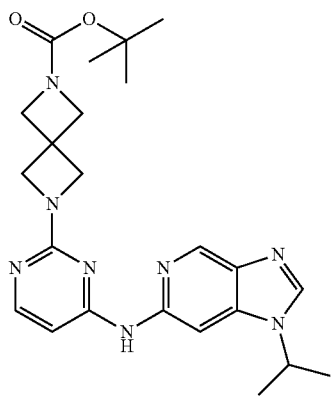 [SMILES: CC(C)n1cnc2cnc(Nc3ccnc(N4CC5(CN(C(=O)OC(C)(C)C)C5)C4)n3)cc21]

A mixture of 6-chloro-1-isopropyl1H-imidazo[4,5-c]pyridine (Example 35, step 2) (34.1 mg, 0.174 mmol), tert-butyl 6-(4-aminopyrimidin-2-yl)-2,6-diazaspiro[3.3]heptane-2-carboxylate (45.0 mg, 0.154 mmol), tris(dibenylideneacetone)dipalladium chloroform complex (7.5 mg, 0.0070 mmol), 2-(dicyclohexylphosphino)-2',4',6'-triisopropyl-1,1'-biphenyl (10.5 mg, 0.0216 mmol), cesium carbonate (130.4 mg, 0.396 mmol) and 1,4-dioxane (1.5 mL) was heated in a sealed vial under nitrogen at 120° C. for 4 days. The reaction mixture was diluted with ethyl acetate, washed with water (2×) and brine, dried over magnesium sulfate, filtered, and evaporated in vacuo. The crude product was purified via flash chromatography on silica gel (4 g silica, solvent gradient: 0-10% methanol in dichloromethane) to yield 51.7 mg (74%) of the title compound. LCMS (ESI): [M+H]$^+$=451.3; $^1$H NMR (400 MHz, DMSO-d$_6$): δ 9.81 (s, 1H), 8.64 (s, 1H), 8.48 (s, 1H), 8.32 (s, 1H), 7.94 (d, J=5.7 Hz, 1H), 6.50 (d, J=5.7 Hz, 1H), 4.73-4.61 (m, 1H), 4.18 (s, 4H), 3.26 (s, 4H), 1.59 (d, J=6.7 Hz, 6H), 1.39 (s, 9H).

Step 3: 1-Isopropyl-N-(2-(6-(methylsulfonyl)-2,6-diazaspiro[3.3]heptan-2-yl)pyrimidin-4-yl)-1H-imidazo[4,5-c]pyridin-6-amine

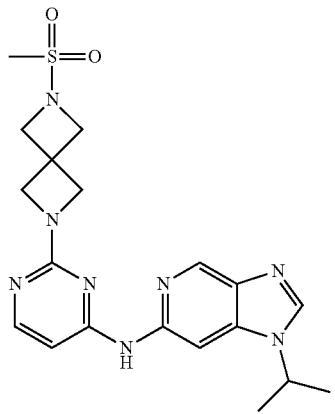 [SMILES: CC(C)n1cnc2cnc(Nc3ccnc(N4CC5(C4)CN(S(C)(=O)=O)C5)n3)cc21]

A mixture of tert-butyl 6-(4-((1-isopropyl-1H-imidazo[4,5-c]pyridin-6-yl)amino)pyrimidin-2-yl)-2,6-diazaspiro[3.3]heptane-2-carboxylate (51 mg, 0.11 mmol), dichloromethane (4.0 mL) and hydrogen chloride (4.0 mol/L in dioxane) (0.2 mL, 0.8 mmol) was stirred at room temperature for 4 hours and then concentrated under reduced pressure to yield N-(2-(2,6-diazaspiro[3.3]heptan-2-yl)pyrimidin-4-yl)-1-isopropyl-1H-imidazo[4,5-c]pyridin-6-amine hydrochloride. This material was dissolved in tetrahydrofuran (4.0 mL, 49 mmol) with triethylamine (0.05 mL, 0.4 mmol) and then treated with methanesulfonyl chloride (9.7 µL, 0.12 mmol). This mixture was stirred at room temperature for 3 hours, at which time additional methanesulfonyl chloride (3.0 µL) was added. After 2 hours, the reaction mixture was diluted with dichloromethane, washed with saturated aqueous sodium bicarbonate, dried over magnesium sulfate, filtered, and evaporated in vacuo. The crude product was purified via flash chromatography on silica gel (4 g silica, solvent gradient: 0-10% methanol in dichloromethane) followed by reverse-phase HPLC and lyophilized to yield to yield 7.6 mg (16%) of the title compound. LCMS (ESI): R$_T$ (min)=3.264, [M+H]$^+$=429.2, method=B; $^1$H NMR (400 MHz, DMSO-d$_6$) δ 9.83 (s, 1H), 8.64 (d, J=1.0 Hz, 1H), 8.50 (s, 1H), 8.33 (s, 1H), 7.95 (d, J=5.8 Hz, 1H), 6.51 (d, J=5.7 Hz, 1H), 4.78-4.62 (m, 1H), 4.22 (s, 4H), 4.12 (s, 4H), 3.02 (s, 3H), 1.59 (d, J=6.7 Hz, 6H).

Example 39: N$^4$-(1-isopropyl-1H-imidazo[4,5-c]pyridin-6-yl)-N2-(2-(methylsulfonyl)ethyl)pyrimidine-2,4-diamine

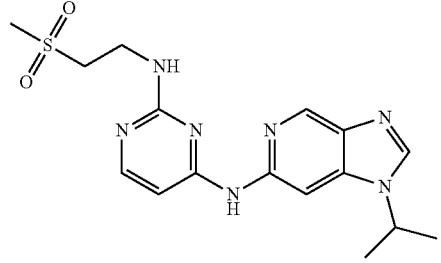 [SMILES: CC(C)n1cnc2cnc(Nc3ccnc(NCCS(C)(=O)=O)n3)cc21]

Step 1: N$^2$-(2-(Methylsulfonyl)ethyl)pyrimidine-2,4-diamine

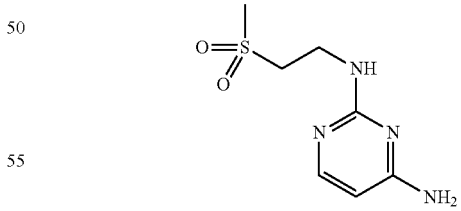

A mixture of 2-chloropyrimidin-4-amine (106.7 mg, 0.8236 mmol), 2-aminoethylmethylsulfone hydrochloride (155.2 mg, 0.9236 mmol), trifluoroacetic acid (0.05 mL, 0.6 mmol) and tert-butanol (2.0 mL, 21 mmol) was heated at 120° C. for 3 days. The reaction mixture was poured into 10 mL saturated aqueous sodium bicarbonate and extracted with dichloromethane (3×30 mL). The combined organic extracts were dried over magnesium sulfate, filtered, and concentrated in vacuo to yield 84.5 mg (47%) of the title compound, which was carried forward without purification. LCMS (ESI): [M+H]⁺=217.1.

Step 2: N⁴-(1-Isopropyl-1H-imidazo[4,5-c]pyridin-6-yl)-N²-(2-(methylsulfonyl)ethyl)pyrimidine-2,4-diamine

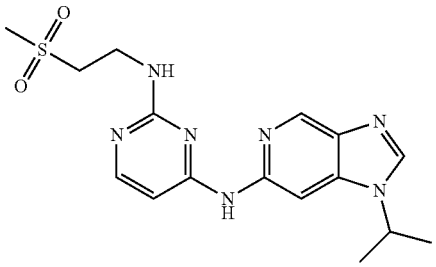 [SMILES: CC(C)n1cnc2cnc(Nc3ccnc(NCCS(C)(=O)=O)n3)cc21]

Using N²-(2-(methylsulfonyl)ethyl)pyrimidine-2,4-diamine and the procedures described for Example 36, the title compound was obtained in 4.6% yield (6.7 mg). LCMS (ESI): $R_T$ (min)=3.030, [M+H]⁺=376.2, method=B; ¹H NMR (400 MHz, DMSO-d₆) δ 9.72 (s, 1H), 8.64 (d, J=1.2 Hz, 1H), 8.41-8.31 (m, 2H), 7.93 (d, J=5.6 Hz, 1H), 6.90 (t, J=5.8 Hz, 1H), 6.51 (d, J=5.8 Hz, 1H), 4.82-4.66 (m, 1H), 3.77 (q, J=6.5 Hz, 2H), 3.42 (t, J=6.9 Hz, 2H), 3.02 (s, 3H), 1.55 (d, J=6.7 Hz, 6H).

Example 40: N⁴-(1-Isopropyl-1H-imidazo[4,5-c]pyridin-6-yl)-N²-(1-methyl-1H-pyrazol-4-yl)pyrimidine-2,4-diamine

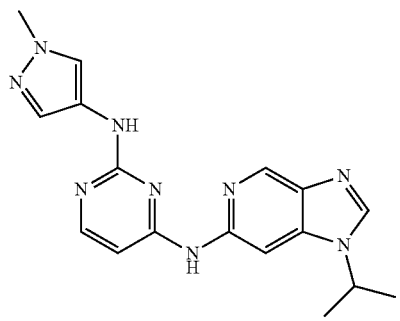 [SMILES: CC(C)n1cnc2cnc(Nc3ccnc(Nc4cnn(C)c4)n3)cc21]

Step 1: N²-(1-Methyl-1H-pyrazol-4-yl)pyrimidine-2,4-diamine

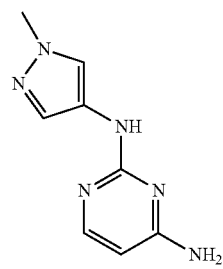

A mixture of 2-chloropyrimidin-4-amine (130.9 mg, 1.010 mmol), 1-methyl-1H-pyrazol-4-ylamine (169 mg, 1.7 mmol), trifluoroacetic acid (0.05 mL, 0.6 mmol) and tert-butanol (2.0 mL) was heated in a sealed vial at 110° C. for 4 hours. The reaction mixture was neutralized with ammonia/methanol and concentrated onto celite. The crude product was purified via flash chromatography on silica gel (12 g silica, solvent gradient: 0-10% methanol in dichloromethane) to yield 284.1 mg (65% purity, 96% yield) of the title compound. LCMS (ESI): [M+H]⁺=191.1; ¹H NMR (400 MHz, DMSO-d₆): δ 9.69 (s, 1H), 7.95 (s, 1H), 7.81 (s, 1H), 7.75 (d, J=6.7 Hz, 1H), 7.54 (s, 1H), 6.01 (d, J=6.7 Hz, 1H), 3.81 (s, 3H).

Step 2: N⁴-(1-Isopropyl-1H-imidazo[4,5-c]pyridin-6-yl)-N²-(1-methyl-1H-pyrazol-4-yl)pyrimidine-2,4-diamine

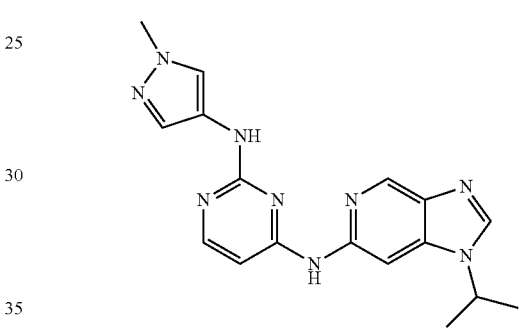

A mixture of 6-chloro-1-isopropyl-1H-imidazo[4,5-c]pyridine (Example 35, step 2) (216.7 mg, 1.1 mmol), N²-(1-methylpyrazol-4-yl)pyrimidine-2,4-diamine (284 mg, 0.97 mmol), tris(dibenylideneacetone)dipalladium chloroform complex (48.9 mg, 0.05 mmol), 2-(dicyclohexylphosphino)-2',4',6'-triisopropyl-1,1'-biphenyl (52.2 mg, 0.107 mmol), cesium carbonate (0.64 g, 1.96 mmol) and 1,4-dioxane (5.0 mL) was subjected to microwave irradiation at 130° C. for 2 hours. To the reaction mixture was added tris(dibenylideneacetone)dipalladium chloroform complex (54.1 mg, 0.0507 mmol) and 4,5-bis(diphenylphosphino)-9,9-dimethylxanthene (70.7 mg, 0.122 mmol). The reaction mixture was subjected to microwave irradiation at 130° C. for 1 hour and then 150° C. for 2 hours. The reaction mixture was diluted with ethyl acetate, washed with water (2×) and brine, dried over magnesium sulfate, filtered, and evaporated in vacuo. The crude product was purified via flash chromatography on silica gel (12 g silica, solvent gradient: 0-10% methanol in dichloromethane) to yield 118.7 mg, followed by reverse-phase HPLC and lyophilized to yield 44.2 mg (13%) of the title compound. LCMS (ESI): $R_T$ (min)=3.463, [M+H]⁺=350.2, method=B; ¹H NMR (400 MHz, DMSO-d₆) δ 9.71 (s, 1H), 8.88 (s, 1H), 8.67 (d, J=0.9 Hz, 1H), 8.39 (s, 1H), 8.02 (d, J=5.7 Hz, 1H), 7.85 (s, 1H), 7.54 (s, 1H), 6.71 (s, 1H), 4.79-4.59 (m, 1H), 3.78 (s, 3H), 1.53 (d, J=6.7 Hz, 6H).

Example 41: 1-Isopropyl-N-(2-(4-methoxypiperidin-1-yl)pyrimidin-4-yl)-2-(trifluoromethyl)-1H-imidazo[4,5-c]pyridin-6-amine

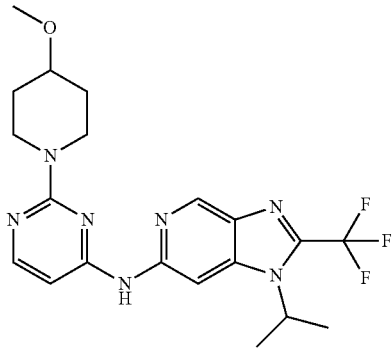 [SMILES: COC1CCN(c2nccc(Nc3cc4c(cn3)nc(C(F)(F)F)n4C(C)C)n2)CC1]

Step 1: 6-Chloro-1-isopropyl-2-(trifluoromethyl)-1H-imidazo[4,5-c]pyridine

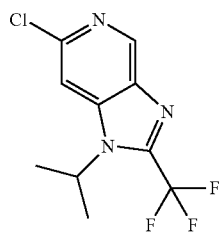 [SMILES: CC(C)n1c(C(F)(F)F)nc2cnc(Cl)cc21]

A mixture of triethylamine (0.40 mL, 2.8 mmol), trifluoroacetic acid (75 µL, 0.97 mmol), triphenylphosphine (604 mg, 2.30 mmol) and tetrachloromethane (4.0 mL) was stirred at room temperature for 10 minutes. A solution of 6-chloro-$N^4$-isopropyl-pyridine-3,4-diamine (Example 7, Step 2) (142.7 mg, 0.77 mmol) in tetrachloromethane (1 mL) was then added, and the reaction mixture heated at 80° C. for 10 hours. The reaction mixture was diluted with dichloromethane, washed with saturated aqueous sodium bicarbonate, dried over magnesium sulfate, filtered, and evaporated in vacuo. The crude product was purified via flash chromatography on silica gel (12 g Silicycle HP silica, solvent gradient: 0-100% ethyl acetate in heptanes) to yield 151.7 mg (75%) of the title compound. LCMS (ESI): [M+H]$^+$=264.2; $^1$H NMR (400 MHz, DMSO-d$_6$): δ 9.00 (d, J=0.9 Hz, 1H), 8.21 (d, J=1.0 Hz, 1H), 4.88 (p, J=6.9 Hz, 1H), 1.64 (d, J=6.8 Hz, 6H).

Step 2: 1-Isopropyl-N-(2-(4-methoxypiperidin-1-yl)pyrimidin-4-yl)-2-(trifluoromethyl)-1H-imidazo[4,5-c]pyridin-6-amine

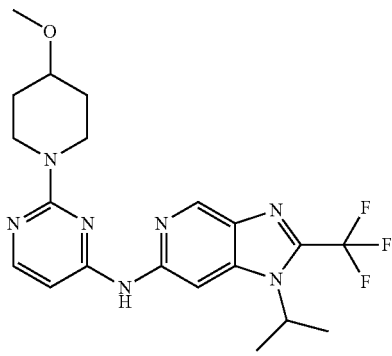 [SMILES: COC1CCN(c2nccc(Nc3cc4c(cn3)nc(C(F)(F)F)n4C(C)C)n2)CC1]

A mixture of 2-(4-methoxy-1-piperidyl)pyrimidin-4-amine (Example 3, step 2) (62.4 mg, 0.300 mmol), 6-chloro-1-isopropyl-2-(trifluoromethyl)imidazo[4,5-c]pyridine (70.8 mg, 0.269 mmol), tris(dibenylideneacetone)dipalladium chloroform complex (13.2 mg, 0.0124 mmol), 2-(dicyclohexylphosphino)-2',4',6'-triisopropyl-1,1'-biphenyl (21.4 mg, 0.0440 mmol), cesium carbonate (185.5 mg, 0.564 mmol) and 1,4-dioxane (1.5 mL) was heated in a sealed vial under nitrogen at 120° C. for 10 hours. The reaction mixture was diluted with ethyl acetate, washed with water (2×) and brine, dried over magnesium sulfate, filtered, and evaporated in vacuo. The crude product was purified via flash chromatography on silica gel (4 g Silicycle HP silica, solvent gradient: 0-10% methanol in dichloromethane) followed by reverse-phase HPLC and lyophilized to yield 64.5 mg (55%) of the title compound. LCMS (ESI): R$_T$ (min)=4.453, [M+H]$^+$=436.2, method=B; $^1$H NMR (400 MHz, DMSO-d$_6$) δ 10.00 (s, 1H), 8.89 (d, J=0.9 Hz, 1H), 8.58 (d, J=1.0 Hz, 1H), 8.01 (d, J=5.7 Hz, 1H), 6.45 (d, J=5.6 Hz, 1H), 4.86 (p, J=6.8 Hz, 1H), 4.33-4.17 (m, 2H), 3.54-3.34 (m, 3H), 3.30 (s, 3H), 1.99-1.83 (m, 2H), 1.66 (d, J=6.9 Hz, 5H), 1.52-1.37 (m, 2H).

Example 42: $N^4$-(1-Isopropyl-1H-imidazo[4,5-c]pyridin-6-yl)-$N^2$-(1H-pyrazol-4-yl)pyrimidine-2,4-diamine

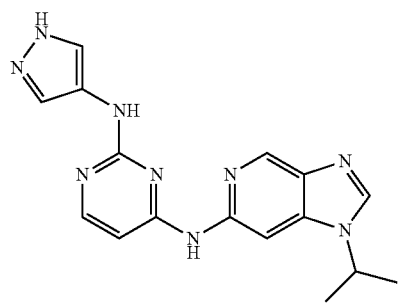 [SMILES: CC(C)n1cnc2cnc(Nc3ccnc(Nc4cn[nH]c4)n3)cc21]

A mixture of N-(2-chloropyrimidin-4-yl)-1-isopropyl-1H-imidazo[4,5-c]pyridin-6-amine (Example 12, Step 4) (51.1 mg, 0.177 mmol), 1H-pyrazol-4-amine (23.9 mg, 0.288 mmol), trifluoroacetic acid (10.0 µL, 0.129 mmol) and tert-butanol (1.5 mL, 16 mmol) was heated in a sealed vial at 100° C. for 2 days. The reaction mixture was diluted with dichloromethane, washed with saturated aqueous sodium bicarbonate, dried over magnesium sulfate, filtered, and evaporated in vacuo. The crude product (20.3 mg) was purified via reverse-phase HPLC and lyophilized to yield 4.6 mg (8%) of the title compound. LCMS (ESI): R$_T$ (min)=3.051, [M+H]$^+$=336.2, method=B; $^1$H NMR (400 MHz, DMSO-d$_6$) δ 12.43 (s, 1H), 9.72 (s, 1H), 8.83 (s, 1H), 8.66 (d, J=1.0 Hz, 1H), 8.38 (s, 1H), 8.01 (d, J=5.7 Hz, 1H), 6.67 (s, 1H), 4.62 (br s, 1H), 1.51 (d, J=6.6 Hz, 6H).

Example 43: 1-Isopropyl-N-(2-(4-(trifluoromethoxy)piperidin-1-yl)pyrimidin-4-yl)-1H-imidazo[4,5-c]pyridin-6-amine

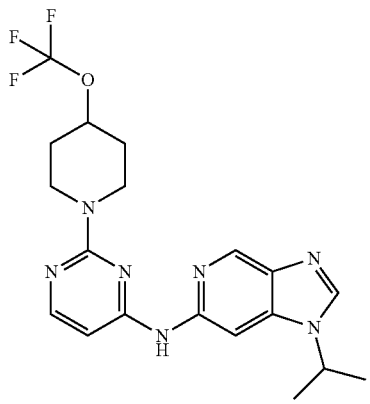 [SMILES: CC(C)n1cnc2cnc(Nc3ccnc(N4CCC(OC(F)(F)F)CC4)n3)cc21]

Step 1: tert-Butyl 4-(((methylthio)carbonothioyl)oxy)piperidine-1-carboxylate

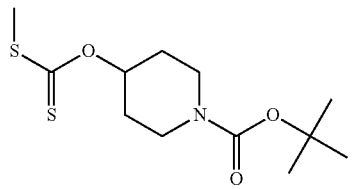 [SMILES: CSC(=S)OC1CCN(C(=O)OC(C)(C)C)CC1]

Into a 1000 mL 4-necked round-bottom flask purged and maintained with an inert atmosphere of nitrogen was placed sodium hydride (12.8 g, 373.33 mmol, 70% wt), dimethylacetamide (500 mL), followed by the addition of tert-butyl 4-hydroxypiperidine-1-carboxylate (50 g, 248.43 mmol) in several batches with stirring at 0° C. The mixture was stirred for 1 hour. To this was added carbon disulfide (75.6 g, 994.74 mmol) dropwise with stirring at 0° C. The mixture was stirred for 1 hour. To the mixture was added iodomethane (53.0 g, 373.24 mmol) dropwise with stirring at 0° C. The resulting solution was stirred at 0° C. for 1.5 h and quenched by the addition of 500 g of ice. The pH value of the solution was adjusted to 8 with saturated aqueous NaHCO$_3$. The resulting solution was extracted with 3×500 mL of ethyl acetate. The organic layers were combined and concentrated. The residue was purified on a silica gel column eluting with ethyl acetate: petroleum ether (1:10) to afford 60 g (83%) of the title compound.

Step 2: 4-(Trifluoromethoxy)piperidine

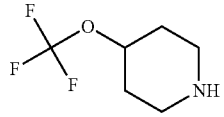 [SMILES: FC(F)(F)OC1CCNCC1]

Into a 1000 mL 4-necked round-bottom flask (PTFE) purged and maintained with an inert atmosphere of nitrogen was placed 1,3-dibromo-5,5-dimethylhydantoin (133 g, 468.31 mmol), dichloromethane (150 mL), followed by the addition of pyridine hydrofluoride (612 g, 4.33 mol, 70%) dropwise with stirring at −78° C. The mixture was stirred at −78° C. for 1 h. To this was added a solution of tert-butyl 4-[[(methylthio)carbonothioyl]oxy]piperidine-1-carboxylate (30 g, 102.94 mmol) in dichloromethane (500 mL) dropwise with stirring at −78° C. over 30 min. The resulting solution was stirred at −78° C. for 1 h and overnight at room temperature. The reaction was then quenched by the addition of 1 kg of ice. The pH value of the solution was adjusted to 10 with saturated aqueous potassium carbonate. The resulting solution was extracted with 4×1 L of ethyl acetate. The organic layers were combined, dried over anhydrous sodium sulfate and concentrated under vacuum to afford 50 g (crude) of 4-(trifluoromethoxy)piperidine as a yellow oil, which was carried forward without purification.

Step 3: tert-Butyl 4-(trifluoromethoxy)piperidine-1-carboxylate

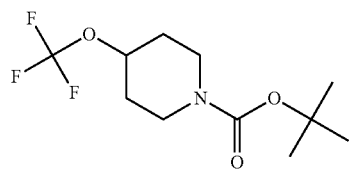 [SMILES: CC(C)(C)OC(=O)N1CCC(OC(F)(F)F)CC1]

Into a 3000-mL 4-necked round-bottom flask was placed 4-(trifluoromethoxy)piperidine (50 g, 295.60 mmol, 1.00 equiv), ethyl acetate (2000 mL) and di-tert-butyl dicarbonate (96.7 g, 443.07 mmol, 1.50 equiv). The resulting solution was stirred overnight at room temperature and concentrated under vacuum. The residue was purified on a silica gel column eluting with ethyl acetate: petroleum ether (1:10) to afford 16 g (20%) of the title compound as a light yellow solid.

Step 4: 4-(Trifluoromethoxy)piperidine hydrochloride

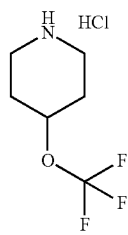 [SMILES: Cl ; FC(F)(F)OC1CCNCC1]

Into a 250-mL 3-necked round-bottom flask was placed tert-butyl 4-(trifluoromethoxy)piperidine-1-carboxylate (16 g, 59.42 mmol, 1.00 equiv) and dichloromethane (150 mL). To the above hydrogen chloride (gas) was introduced. The resulting solution was stirred at room temperature for 4 h, concentrated under vacuum and diluted with 200 mL of ether. The mixture was stirred at room temperature for 10 min. The solids were collected by filtration and washed with 1×50 mL of ether to afford 10 g (82%) of the title compound as a white solid. LCMS (ESI): [M−HCl+H]$^+$=170; $^1$H NMR (400 MHz, DMSO-d$_6$): δ 9.20 (s, 2H), 4.74 (m, 1H), 3.18 (m, 2H), 3.06 (d, 2H), 2.12 (m, 2H), 1.91 (m, 2H).

Step 5: 1-Isopropyl-N-(2-(4-(trifluoromethoxy)piperidin-1-yl)pyrimidin-4-yl)-1H-imidazo[4,5-c]pyridin-6-amine

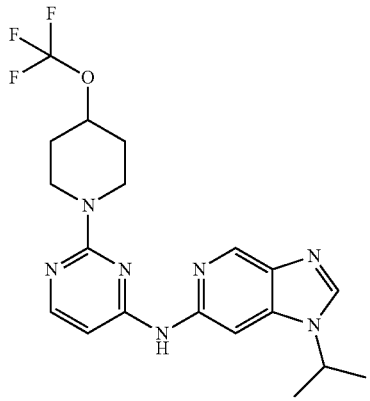 [SMILES: CC(C)n1cnc2cnc(Nc3ccnc(N4CCC(OC(F)(F)F)CC4)n3)cc21]

A mixture of (2-chloropyrimidin-4-yl)-(1-isopropyl-1H-imidazo[4,5-c]pyridin-6-yl)amine (Example 12, Step 4) (76.9 mg, 0.266 mmol), 4-(trifluoromethoxy)piperidine hydrochloride (83.2 mg, 0.384 mmol), triethylamine (0.20 mL, 1.4 mmol) and 2-propanol (2.0 mL) was heated under microwave irradiation at 150° C. for 30 minutes. The reaction mixture was diluted with dichloromethane, washed with saturated aqueous sodium bicarbonate, dried over magnesium sulfate, filtered, and evaporated in vacuo. The crude product was purified via reverse-phase HPLC and lyophilized to yield 64.9 mg (58%) of the title compound. LCMS (ESI): R$_T$ (min)=4.048, [M+H]$^+$=422.2, method=B; $^1$H NMR (400 MHz, DMSO-d$_6$) δ 9.81 (s, 1H), 8.66 (d, J=1.0 Hz, 1H), 8.33 (s, 2H), 7.99 (d, J=5.7 Hz, 1H), 6.44 (d, J=5.7 Hz, 1H), 4.74 (dt, J=8.7, 4.5 Hz, 1H), 4.70-4.62 (m, 1H), 4.32-4.17 (m, 2H), 3.58-3.46 (m, 2H), 2.06-1.99 (m, 2H), 1.76-1.65 (m, 2H), 1.56 (d, J=6.7 Hz, 6H).

Example 44: N-(2-((1R,5S,6s)-6-Amino-3-azabicyclo[3.1.0]hexan-3-yl)pyrimidin-4-yl)-1-isopropyl-1H-imidazo[4,5-c]pyridin-6-amine

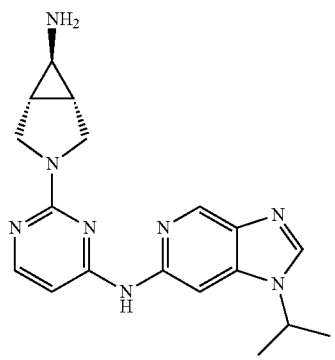 [SMILES: CC(C)n1cnc2cnc(Nc3ccnc(N4C[C@@H]5[C@@H](N)[C@@H]5C4)n3)cc21]

Step 1: (1R,5S,6s)-tert-Butyl 6-(((benzyloxy)carbonyl)amino)-3-azabicyclo[3.1.0]hexane-3-carboxylate

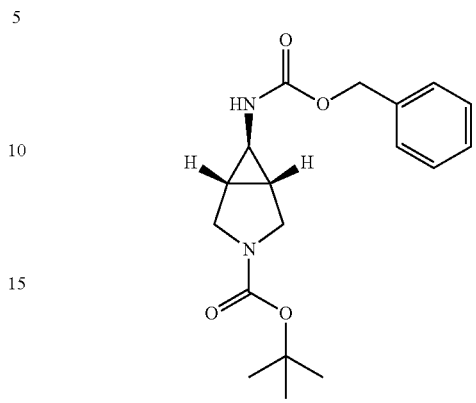

To a mixture of trans-tert-butyl 6-amino-3-azabicyclo[3.1.0]hexane-3-carboxylate (218.8 mg, 1.104 mmol) and cesium carbonate (723.9 mg, 2.20 mmol) in tetrahydrofuran (4.0 mL) was added benzyl chloroformate (0.20 mL, 1.3 mmol). The reaction mixture was then stirred at room temperature for 3 days. The reaction mixture was diluted with ethyl acetate, washed with water and brine, dried over magnesium sulfate, filtered, and evaporated in vacuo. The crude product was purified via flash chromatography on silica gel (12 g Silicycle HP silica, solvent gradient: 0-100% ethyl acetate in heptanes, TLC with CAM staining to identify relevant fractions) to yield 357.1 mg (97%) of the title compound. LCMS (ESI): [M+Na]$^+$=355.2; $^1$H NMR (400 MHz, DMSO-d$_6$): δ 7.49 (s, 1H), 7.41-7.26 (m, 5H), 5.01 (s, 2H), 3.44 (s, 1H), 3.42 (s, 1H), 3.34-3.30 (br s, 1H), 3.29-3.24 (br s, 1H), 2.15 (d, J=2.6 Hz, 1H), 1.63 (d, J=2.7 Hz, 2H), 1.37 (s, 9H).

Step 2: Benzyl (1R,5S,6s)-3-azabicyclo[3.1.0]hexan-6-ylcarbamate

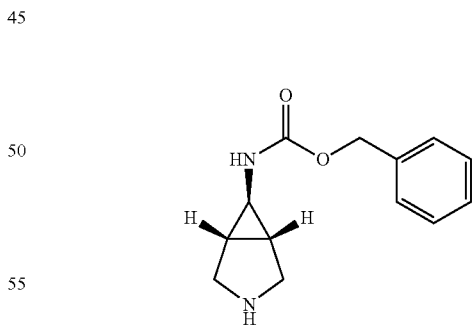

A mixture of tert-butyl (1R,5S,6s)-6-(benzyloxycarbonylamino)-3-azabicyclo[3.1.0]hexane-3-carboxylate (98 mg, 0.2948 mmol), hydrogen chloride (4.0 mol/L in dioxane) (0.75 mL, 3.0 mmol) and dichloromethane (4.0 mL, 62 mmol) was stirred at room temperature for 19 hours. The reaction mixture was evaporated under reduced pressure to provide a quantitative yield of the title compound, which was carried forward without purification. LCMS (ESI): [M+H]$^+$=233.4.

Step 3: Benzyl N-((1R,5S,6s)-3-(4-((1-isopropyl-1H-imidazo[4,5-c]pyridin-6-yl)amino)pyrimidin-2-yl)-3-azabicyclo[3.1.0]hexan-6-yl)carbamate

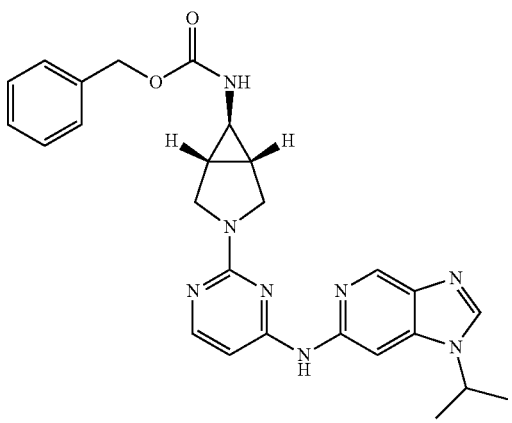 [SMILES: CC(C)n1cnc2cnc(Nc3ccnc(N4C[C@@H]5[C@H](C4)[C@H]5NC(=O)OCc4ccccc4)n3)cc21]

A mixture of (2-chloropyrimidin-4-yl)-(1-isopropyl-1H-imidazo[4,5-c]pyridin-6-yl)amine (Example 12, Step 4) (75.6 mg, 0.262 mmol), benzyl N-[(1R,5S,6s)-3-azabicyclo[3.1.0]hexan-6-yl]carbamate (0.29 mmol, 0.29 mmol), triethylamine (0.10 mL, 0.71 mmol) and 2-propanol (2.0 mL, 26 mmol) was heated under microwave irradiation at 150° C. for 30 minutes. 5 mL water was added and the desired product recovered via filtration as a tan solid (61.3 mg, 48% yield). LCMS (ESI): [M+H]$^+$=485.2; $^1$H NMR (400 MHz, DMSO-d$_6$): δ 9.77 (s, 1H), 8.64 (d, J=0.9 Hz, 1H), 8.57 (s, 1H), 8.32 (s, 1H), 7.93 (d, J=5.7 Hz, 1H), 7.54 (s, 1H), 7.40-7.26 (m, 5H), 6.38 (d, J=5.7 Hz, 1H), 5.02 (s, 2H), 4.69 (br s, 1H), 3.93-3.82 (m, 2H), 3.64-3.51 (m, 2H), 1.82 (s, 2H), 1.66-1.51 (m, 6H).

Step 4. N-(2-((1R,5S,6s)-6-Amino-3-azabicyclo[3.1.0]hexan-3-yl)pyrimidin-4-yl)-1-isopropyl-1H-imidazo[4,5-c]pyridin-6-amine

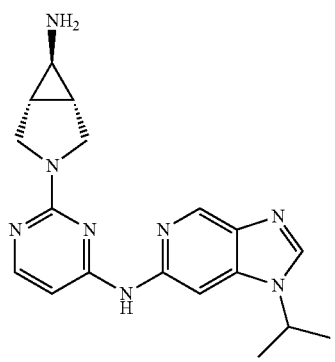 [SMILES: CC(C)n1cnc2cnc(Nc3ccnc(N4C[C@@H]5[C@@H](N)[C@@H]5C4)n3)cc21]

To a solution of benzyl N-[(1S,5R,6s)-3-[4-[(1-isopropyl-1H-imidazo[4,5-c]pyridin-6-yl)amino]pyrimidin-2-yl]-3-azabicyclo[3.1.0]hexan-6-yl]carbamate (60.3 mg, 0.124 mmol) in ethanol (3.0 mL, 52 mmol) under a nitrogen atmosphere was added palladium (10 wt. % on carbon) (19.7 mg, 0.0185 mmol). The reaction vessel was evacuated and backfilled with hydrogen, and then stirred at room temperature under a hydrogen balloon for 19 hours. Palladium (10 wt. % on carbon) (19.7 mg, 0.0185 mmol) was added and the reaction mixture heated under a hydrogen atmosphere at 50° C. for 7 hours. The reaction mixture was filtered through celite and evaporated. The crude product was purified via reverse phase HPLC and lyophilized to yield 9.5 mg (22%) of the title compound. LCMS (ESI): R$_T$ (min)=2.855, [M+H]$^+$=351.2, method=B; $^1$H NMR (400 MHz, DMSO-d$_6$) δ 9.74 (s, 1H), 8.63 (d, J=1.0 Hz, 1H), 8.59 (s, 1H), 8.32 (s, 1H), 7.91 (d, J=5.7 Hz, 1H), 6.35 (d, J=5.7 Hz, 1H), 4.75-4.63 (m, 1H), 3.75 (br s, 2H), 3.55 (br s, 2H), 2.00 (t, J=2.1 Hz, 1H), 1.60 (d, J=6.8 Hz, 5H), 1.57 (s, 2H).

Example 45: 1-Isopropyl-N-(2-((1R,5S,6s)-6-(methylamino)-3-azabicyclo[3.1.0]hexan-3-yl)pyrimidin-4-yl)-1H-imidazo[4,5-c]pyridin-6-amine

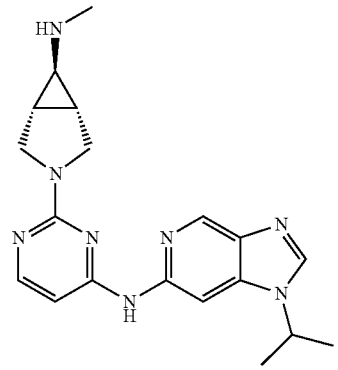 [SMILES: CN[C@H]1[C@@H]2CN(c3nccc(Nc4cc5c(cn4)ncn5C(C)C)n3)C[C@@H]21]

Step 1: (1R,5S,6s)-tert-Butyl 6-(((benzyloxy)carbonyl)(methyl)amino)-3-azabicyclo[3.1.0]hexane-3-carboxylate

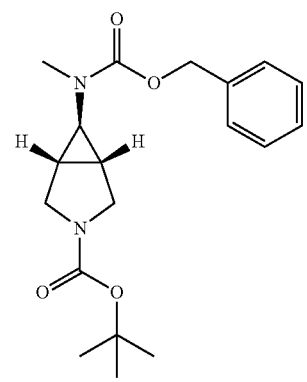 [SMILES: CN(C(=O)OCc1ccccc1)[C@H]1[C@@H]2CN(C(=O)OC(C)(C)C)C[C@@H]21]

To a solution of tert-butyl (1R,5S,6s)-6-(benzyloxycarbonylamino)-3-azabicyclo[3.1.0]hexane-3-carboxylate (Example 44, Step 1) (258 mg, 0.7762 mmol) in tetrahydrofuran (5.0 mL, 62 mmol) was added sodium hydride (60 wt % dispersion in mineral oil) (56 mg, 1.40 mmol). This mixture was stirred at room temperature for 30 minutes, followed by addition of iodomethane (63.0 μL, 1.01 mmol). The reaction mixture was stirred at room temperature for 16 hours. The reaction mixture was diluted with ethyl acetate, washed with water (2×) and brine, dried over magnesium sulfate, filtered, and evaporated in vacuo to yield 250.2 mg (93%) of the title compound. LCMS (ESI): [M+H-tBu]⁺=292.1; ¹H NMR (400 MHz, DMSO-d₆): δ 7.44-7.27 (m, 5H), 5.06 (s, 2H), 3.43 (d, J=10.9 Hz, 2H), 3.35-3.25 (m, 2H), 2.82 (s, 3H), 2.23 (t, J=2.3 Hz, 1H), 1.85 (d, J=1.6 Hz, 2H), 1.36 (s, 9H).

Step 2: 1-Isopropyl-N-(2-((1R,5S,6s)-6-(methylamino)-3-azabicyclo[3.1.0]hexan-3-yl)pyrimidin-4-yl)-1H-imidazo[4,5-c]pyridin-6-amine

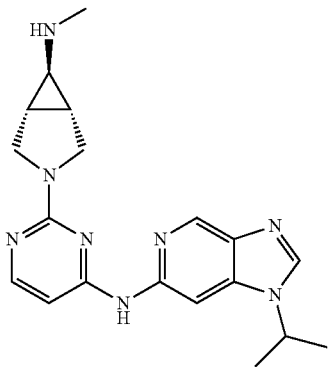 [SMILES: CN[C@H]1[C@@H]2CN(c3nccc(Nc4cc5c(cn4)ncn5C(C)C)n3)C[C@@H]21]

Using (1R,5S,6s)-tert-butyl 6-(((benzyloxy)carbonyl)(methyl)amino)-3-azabicyclo[3.1.0]hexane-3-carboxylate and following the procedures described for Example 44, the title compound was obtained in 3 steps and 52% yield (68.8 mg). LCMS (ESI): $R_T$ (min)=2.770, [M+H]⁺=365.2, method=B; ¹H NMR (400 MHz, DMSO-d₆) δ 9.75 (s, 1H), 8.64 (d, J=1.0 Hz, 1H), 8.61 (s, 1H), 8.32 (s, 1H), 7.91 (d, J=5.6 Hz, 1H), 6.35 (d, J=5.7 Hz, 1H), 4.76-4.64 (m, 1H), 3.77 (br s, 2H), 3.55 (br s, 2H), 2.30 (s, 3H), 1.82 (t, J=2.1 Hz, 1H), 1.63-1.61 (m, 2H), 1.60 (d, J=6.8 Hz, 6H).

Example 46: N-(2-(6,7-Dihydro-1H-pyrazolo[4,3-c]pyridin-5(4H)-yl)pyrimidin-4-yl)-1-isopropyl-2-methyl-1H-imidazo[4,5-c]pyridin-6-amine

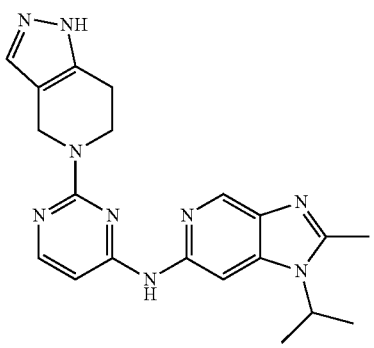 [SMILES: Cc1nc2cnc(Nc3ccnc(N4CCc5[nH]ncc5C4)n3)cc2n1C(C)C]

Step 1: 4-Chloro-5-nitropyridin-2-ol

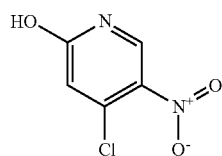

Into a 1 L 4-necked round-bottom flask purged and maintained with nitrogen, was added tetrahydrofuran (200 mL) Ammonia gas was bubbled into the solution at −70° C. to afford a saturated solution of ammonia. To the mixture was added t-BuOK (53.1 g, 0.473 mol) at −70° C., providing solution (I). Into another 5 L 4-necked round-bottom flask purged and maintained with nitrogen, was added a solution of 4-chloro-3-nitropyridine (30.0 g, 0.189 mol) in tetrahydrofuran (200 mL). To the mixture was added t-BuOOH (53.1 g, 0.473 mol) at 0° C. to afford a solution (II). Solution (II) was added dropwise into Solution (I) at −70° C., the resulting solution was stirred at −40° C. for 2 hours. The reaction mixture was quenched by addition of saturated aqueous ammonium chloride and concentrated under vacuum. The residue was triturated with water, and the solids were collected by filtration, washed with THF (50 mL) and dried under vacuum to afford 4-chloro-5-nitropyridin-2-ol (13.0 g, 39.0%) as a yellow solid. LCMS (ESI): $R_T$ (min)=0.535, [M+H]⁺=175, method=G. ¹HNMR (400 MHz, DMSO-d₆) 8.80 (s, 1H), 6.98 (br, 1H), 5.91 (s, 1H).

Step 2: 2,4-Dibromo-5-nitropyridine

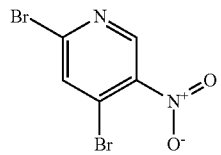 [SMILES: O=[N+]([O-])c1cnc(Br)cc1Br]

Into a 250 mL 3-necked round-bottom flask purged and maintained with nitrogen was added a solution of 4-chloro-5-nitropyridin-2-ol (11.5 g, 65.9 mmol) in CH₃CN (110 mL), followed by addition of POBr₃ (23.1 g). The resulting solution was stirred at 80° C. for 2 hours. The solids were filtered out and the filtrate was concentrated under vacuum. The residue was suspended in 500 mL of ice water. The resulting solids were collected by filtration and dried under vacuum to afford 2,4-dibromo-5-nitropyridine (7.66 g, 41.1%) as a light yellow solid, which was carried forward without purification.

Step 3: 2-Bromo-N-isopropyl-5-nitropyridin-4-amine

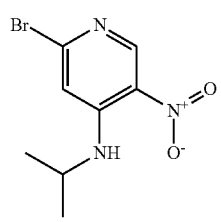

Into a 250 mL 3-necked round-bottom flask purged and maintained with nitrogen, was added 2,4-dibromo-5-nitropyridine (13.0 g, 4.60 mmol), tetrahydrofuran (100 mL) and triethylamine (7.00 g, 69.2 mmol). To the reaction mixture was added propan-2-amine (3.00 mL) dropwise with stirring at 0° C. After the mixture had stirred at room temperature for 4 h, the reaction mixture was concentrated under vacuum and the residue was suspended in H₂O (100 mL). The solids were collected by filtration and dried under vacuum to afford the title compound (12.0 g) as a yellow solid. LCMS (ESI): $R_T$ (min)=1.502, M+H$^+$=260, method=L.

Step 4: 6-Bromo-N$^4$-isopropylpyridine-3,4-diamine

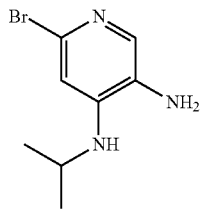

Into a 250 mL 3-necked round-bottom flask was added a solution 2-bromo-N-isopropyl-5-nitropyridin-4-amine (12.0 g, 46.1 mmol) in ethanol (100 mL) and acetic acid (3.00 mL). This was followed by addition of Fe powder (25.0 g, 0.446 mol) in several batches at 80° C. The reaction mixture was stirred at 80° C. for 4 h. The solids were filtered out and the filtrate was concentrated under vacuum. The resulting residue was dissolved in ethyl acetate (150 mL), washed with brine (2×100 mL), dried over anhydrous sodium sulfate and concentrated under vacuum to afford the title compound (10.0 g) as a brown solid. LCMS (ESI): $R_T$ (min)=1.580, [M+H]$^+$=230, method=H.

Step 5: (E)-Ethyl N-6-bromo-4-(isopropylamino) pyridin-3-ylacetimidate

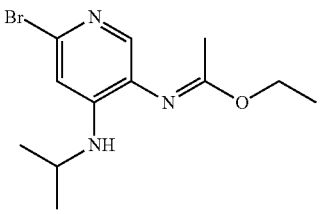 [SMILES: CCO/C(C)=N/c1cnc(Br)cc1NC(C)C]

Into a 500 mL round-bottom flask was added 6-bromo-N$^4$-isopropylpyridine-3,4-diamine (7.00 g, 30.4 mmol), 1,1,1-triethoxyethane (40.0 mL) and acetic acid (3.00 mL). The reaction mixture was heated at 80° C. overnight and then concentrated under vacuum. The residue was dissolved in ethyl acetate (50 mL), washed with brine (2×30 mL), dried over anhydrous sodium sulfate and concentrated under vacuum to afford the title compound (8.00 g, 88.1%) as brown oil. LCMS (ESI): $R_T$ (min)=1.324, [M+H]$^+$=300, method=J.

Step 6: 6-Bromo-1-isopropyl-2-methyl-1H-imidazo [4,5-c]pyridine

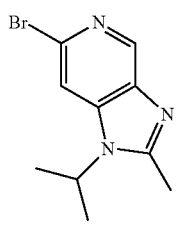

Into a 250 mL 3-necked round-bottom flask was added a solution of (E)-ethyl-N-6-bromo-4-(isopropylamino)pyridin-3-ylacetimidate (8.00 g, 26.6 mmol) in N,N-dimethylformamide (50 mL) and potassium carbonate (8.00 g, 57.9 mmol). The resulting solution was stirred at 100° C. overnight. The reaction mixture was diluted with H$_2$O (100 mL) and extracted with ethyl acetate (3×100 mL). The combined organic layers were washed with brine (2×100 mL), dried over anhydrous sodium sulfate and concentrated under vacuum. The residue was purified by silica gel chromatography with ethyl acetate/petroleum ether (3:1) to afford the title compound (3.20 g, 47.1%) as a brown solid. LCMS (ESI): $R_T$ (min)=1.103, [M+H]$^+$=254, method=G.

Step 7: N-(2-chloropyrimidin-4-yl)-1-isopropyl-2-methyl-1H-imidazo[4,5-c]pyridin-6-amine

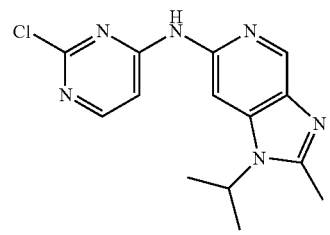 [SMILES: Cc1nc2cnc(Nc3ccnc(Cl)n3)cc2n1C(C)C]

Into a 250 mL 3-necked round-bottom flask purged and maintained with nitrogen, was added a solution of 6-bromo-1-isopropyl-2-methyl-1H-imidazo[4,5-c]pyridine (3.50 g, 13.0 mmol) in 1,4-dioxane (70.0 mL), 2-chloropyrimidin-4-amine (1.70 g, 13.1 mmol), XantPhos (1.70 g, 2.94 mmol), Pd$_2$(dba)$_3$CHCl$_3$ (1.70 g, 1.64 mmol) and Cs$_2$CO$_3$ (11.0 g, 33.7 mmol). The resulting mixture was stirred at 100° C. for 4 h. The mixture was cooled to room temperature, the solids were filtered out and the filtrate was concentrated under vacuum. The residue was purified by silica gel chromatography with dichloromethane/methanol (50:1) to afford the title compound (1.10 g, 26.1%) as a yellow solid. LCMS (ESI): $R_T$ (min)=1.215, [M+H]$^+$=303, method=I. $^1$HNMR (300 Hz, DMSO-d$_6$): δ 10.55 (s, 1H), 8.57 (s, 1H), 8.27-8.25 (d, J=5.7 Hz, 1H), 8.13 (s, 1H), 7.48 (s, 1H), 4.72-4.68 (m, 1H), 2.58 (s, 3H), 1.58-1.56 (d, 6H).

Step 8: N-(2-(6,7-dihydro-1H-pyrazolo[4,3-c]pyridin-5(4H)-yl)pyrimidin-4-yl)-1-isopropyl-2-methyl-1H-imidazo[4,5-c]pyridin-6-amine

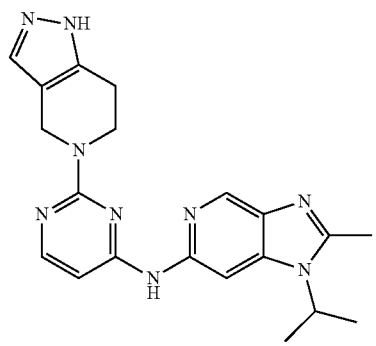 [SMILES: Cc1nc2cnc(Nc3ccnc(N4CCc5[nH]ncc5C4)n3)cc2n1C(C)C]

A mixture of N-(2-chloropyrimidin-4-yl)-1-isopropyl-2-methyl1H-imidazo[4,5-c]pyridin-6-amine (103.5 mg, 0.3418 mmol), 4,5,6,7-tetrahydro-1H-pyrazolo[4,3-C]pyridine (69.6 mg, 0.548 mmol), triethylamine (0.15 mL, 1.1 mmol) and 2-propanol (1.5 mL, 19 mmol) was heated under microwave irradiation at 150° C. for 60 minutes. The reaction mixture was diluted with dichloromethane, washed with saturated aqueous sodium bicarbonate, dried over magnesium sulfate, filtered, and evaporated in vacuo. The crude product was purified via reverse-phase HPLC and lyophilized to yield 67.7 mg (51%) of the title compound. LCMS (ESI): $R_T$ (min)=3.19, [M+H]$^+$=390.2, method=C; $^1$H NMR (400 MHz, DMSO-d$_6$) δ 12.49 (s, 1H), 9.71 (s, 1H), 8.51 (d, J=1.2 Hz, 1H), 8.39 (s, 1H), 7.99 (d, J=5.6 Hz, 1H), 7.46 (s, 1H), 6.47 (d, J=5.7 Hz, 1H), 4.80 (s, 2H), 4.78-4.69 (m, 1H), 4.12 (t, J=5.7 Hz, 2H), 2.75 (t, J=5.8 Hz, 2H), 2.58 (s, 3H), 1.64 (d, J=6.8 Hz, 6H).

Example 47: ((1R,5S,6r)-3-(4-((1-isopropyl-1H-imidazo[4,5-c]pyridin-6-yl)amino)pyrimidin-2-yl)-3-azabicyclo[3.1.0]hexan-6-yl)methanol

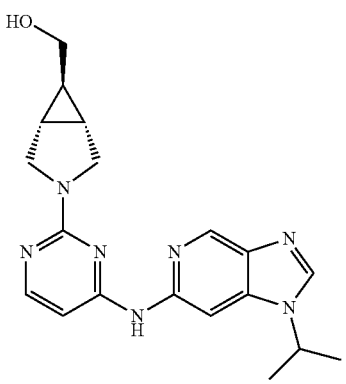 [SMILES: CC(C)n1cnc2cnc(Nc3ccnc(N4C[C@@H]5[C@@H](CO)[C@@H]5C4)n3)cc21]

Step 1: (1R,5S,6r)-tert-butyl 6-(hydroxymethyl)-3-azabicyclo[3.1.0]hexane-3-carboxylate

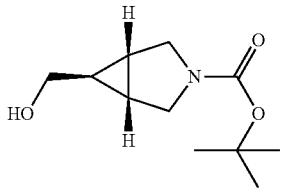

To a solution of (1R,5S,6r)-3-(tert-butoxycarbonyl)-3-azabicyclo[3.1.0]hexane-6-carboxylic acid (250.8 mg, 1.104 mmol) in tetrahydrofuran (5.0 mL, 62 mmol) was dropwise added borane-tetrahydrofuran complex (1.0 mol/L) in tetrahydrofuran (2.20 mL, 2.2 mmol). The reaction mixture was stirred at room temperature for 20 hours. To the reaction was added borane-tetrahydrofuran complex (1.0 mol/L) in tetrahydrofuran (2.20 mL, 2.2 mmol). After an additional 7 hours borane-tetrahydrofuran complex (1.0 mol/L) in tetrahydrofuran (3.0 mL, 3.0 mmol) was added and the reaction mixture stirred at room temperature for 3 days. The reaction mixture was diluted with dichloromethane, washed with water and brine, dried over magnesium sulfate, filtered, and evaporated in vacuo to provide a quantitative yield of the title compound which was carried forward without purification. LCMS (ESI): [M+H-tBu]$^+$=158.4; $^1$H NMR (400 MHz, DMSO-d$_6$): δ 4.45 (t, J=5.5 Hz, 1H), 3.47-3.34 (m, 3H), 3.29-3.25 (m, 2H), 3.26-3.18 (m, 2H), 1.41-1.38 (m, 2H), 1.37 (s, 9H).

Step 2: (1R,5S,6r)-3-azabicyclo[3.1.0]hexan-6-ylmethanol hydrochloride

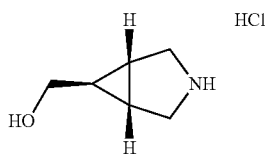

A mixture of tert-butyl (1S,5R,6r)-6-(hydroxymethyl)-3-azabicyclo[3.1.0]hexane-3-carboxylate (86 mg, 0.36292 mmol), hydrogen chloride (4.0 mol/L in dioxane) (1.0 mL, 4.0 mmol) and dichloromethane (2.5 mL, 39 mmol) was stirred at room temperature for 20 hours. The reaction mixture was concentrated under reduced pressure to provide a quantitative yield of the title compound which was carried forward without purification. $^1$H NMR (400 MHz, DMSO-d$_6$): δ 9.30 (br s, 1H), 8.94 (br s, 1H), 4.60 (t, J=5.5 Hz, 1H), 3.57 (s, 2H), 3.29-3.22 (m, 4H), 1.64-1.53 (m, 2H), 1.20-1.08 (m, 1H).

Step 3: ((1R,5S,6r)-3-(4-((1-isopropyl-1H-imidazo[4,5-c]pyridin-6-yl)amino)pyrimidin-2-yl)-3-azabicyclo[3.1.0]hexan-6-yl)methanol

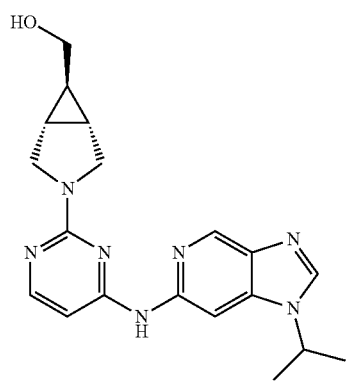

Using (1R,5S,6r)-3-azabicyclo[3.1.0]hexan-6-ylmethanol hydrochloride and following the procedures described for Example 43, the title compound was obtained in 65% yield (59.0 mg). LCMS (ESI): $R_T$ (min)=3.164, [M+H]$^+$=366.2, method=B; $^1$H NMR (400 MHz, DMSO-d$_6$) δ 9.74 (s, 1H), 8.64 (d, J=1.0 Hz, 1H), 8.58 (d, J=1.0 Hz, 1H), 8.32 (s, 1H), 7.92 (d, J=5.7 Hz, 1H), 6.37 (d, J=5.7 Hz, 1H), 4.75-4.63 (m, 1H), 4.49 (t, J=5.5 Hz, 1H), 3.90-3.74 (m, 2H), 3.55 (br s, 2H), 3.35 (t, J=5.9 Hz, 2H), 3.27 (s, 1H), 1.64-1.49 (m, 7H), 0.85-0.74 (m, 1H).

Example 48: 1-isopropyl-N-(2-((1R,5S,6r)-6-(methoxymethyl)-3-azabicyclo[3.1.0]hexan-3-yl)pyrimidin-4-yl)-1H-imidazo[4,5-c]pyridin-6-amine

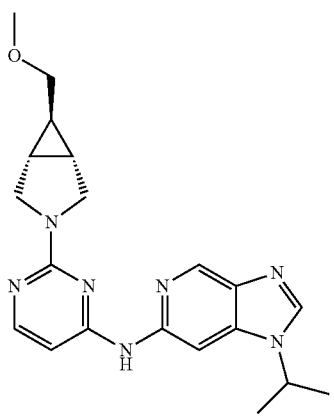 [SMILES: COC[C@@H]1[C@H]2CN(c3nccc(Nc4cc5c(cn4)ncn5C(C)C)n3)C[C@@H]12]

Step 1: (1R,5S,6r)-tert-butyl 6-(methoxymethyl)-3-azabicyclo[3.1.0]hexane-3-carboxylate

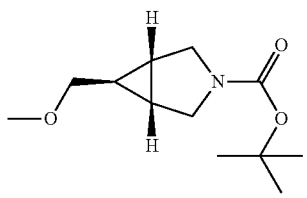 [SMILES: COC[C@@H]1[C@H]2CN(C(=O)OC(C)(C)C)C[C@@H]12]

A solution of tert-butyl (1S,5R,6r)-6-(hydroxymethyl)-3-azabicyclo[3.1.0]hexane-3-carboxylate (171 mg, 0.72162 mmol) in tetrahydrofuran (5.0 mL, 62 mmol) was treated with sodium hydride (60 wt % dispersion in mineral oil) (61 mg, 1.52513 mmol). This mixture was stirred at room temperature for 40 minutes and then treated with iodomethane (100.0 μL, 1.60 mmol) and stirred at room temperature for 24 hours. The reaction mixture was diluted with ethyl acetate, washed with water (2×) and brine, dried over magnesium sulfate, filtered, and evaporated in vacuo to yield the title compound (460.6 mg, 98%), which was carried forward without purification. LCMS (ESI): [M+H-tBu]+=172.4.

Step 2: 1-Isopropyl-N-(2-((1R,5S,6r)-6-(methoxymethyl)-3-azabicyclo[3.1.0]hexan-3-yl)pyrimidin-4-yl)-1H-imidazo[4,5-c]pyridin-6-amine

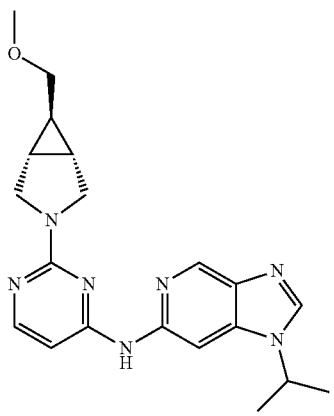 [SMILES: COC[C@@H]1[C@H]2CN(c3nccc(Nc4cc5c(cn4)ncn5C(C)C)n3)C[C@@H]12]

Using (1R,5S,6r)-tert-butyl 6-(methoxymethyl)-3-azabicyclo[3.1.0]hexane-3-carboxylate and following the procedures described for Example 43, the title compound was obtained in 62% yield (82.3 mg). LCMS (ESI): $R_T$ (min)=3.456, [M+H]+=380.2, method=B; $^1$H NMR (400 MHz, DMSO-$d_6$) δ 9.75 (s, 1H), 8.64 (d, J=1.0 Hz, 1H), 8.58 (d, J=1.0 Hz, 1H), 8.32 (s, 1H), 7.92 (d, J=5.6 Hz, 1H), 6.37 (d, J=5.7 Hz, 1H), 4.75-4.64 (m, 1H), 3.84 (br s, 2H), 3.55 (br s, 2H), 3.28 (d, J=6.8 Hz, 2H), 3.24 (s, 3H), 1.62 (m, 2H), 1.59 (d, J=6.8 Hz, 6H), 0.87 (m, 1H).

Example 49: $N^2$-(1-Benzyl-1H-pyrazol-3-yl)-N4-(1-isopropyl-1H-imidazo[4,5-c]pyridin-6-yl)pyrimidine-2,4-diamine

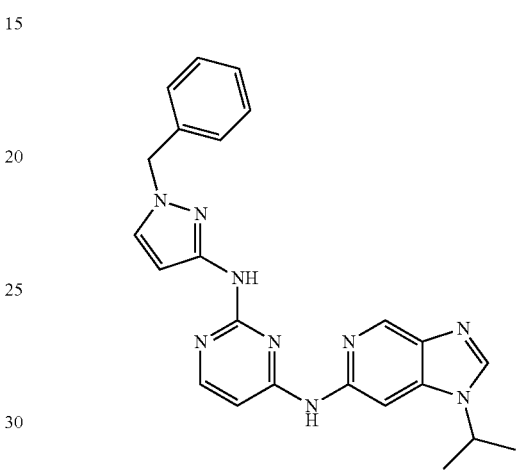

A mixture of (2-chloropyrimidin-4-yl)-(1-isopropyl-1H-imidazo[4,5-c]pyridin-6-yl)amine (Example 12, step 4) (68.8 mg, 0.238 mmol), 1-benzyl-1H-pyrazol-3-amine (72.7 mg, 0.399 mmol), trifluoroacetic acid (10.0 μL, 0.129 mmol) and tert-butanol (1.5 mL, 16 mmol) was heated at 100° C. for 5 hours. The reaction mixture was diluted with dichloromethane, washed with saturated aqueous sodium bicarbonate, dried over magnesium sulfate, filtered, and evaporated in vacuo to yield 152.1 mg crude product. 23 mg of the crude product was purified via reverse-phase HPLC and lyophilized to yield 8.6 mg of the title compound. LCMS (ESI): $R_T$ (min)=4.094, [M+H]+=426.2, method=B; $^1$H NMR (400 MHz, DMSO-$d_6$) δ 9.79 (s, 1H), 9.43 (s, 1H), 8.64 (d, J=1.0 Hz, 1H), 8.39 (s, 2H), 8.01 (d, J=5.8 Hz, 1H), 7.72 (d, J=2.3 Hz, 1H), 7.38-7.31 (m, 2H), 7.31-7.21 (m, 3H), 6.69 (d, J=2.2 Hz, 1H), 6.59 (d, J=5.8 Hz, 1H), 5.24 (s, 2H), 4.80 (br s, 1H), 1.48 (d, J=6.7 Hz, 6H).

Example 50: 3-((4-((1-Isopropyl-2-methyl-1H-imidazo[4,5-c]pyridin-6-yl)amino)pyrimidin-2-yl)amino)tetrahydrothiophene 1,1-dioxide

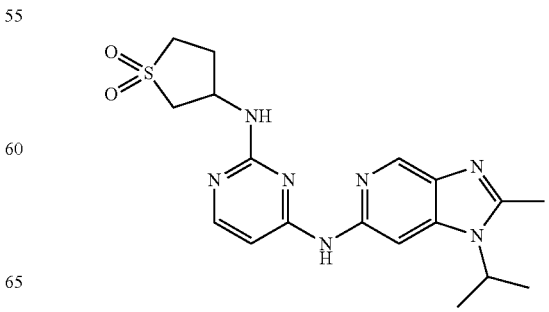

A mixture of N-(2-chloropyrimidin-4-yl)-1-isopropyl-2-methyl-1H-imidazo[4,5-c]pyridin-6-amine (Example 46, Step 7) (120.0 mg, 0.3963 mmol), 1,1-dioxidotetrahydrothien-3-ylamine (88.9 mg, 0.625 mmol), trifluoroacetic acid (10.0 μL, 0.129 mmol) and tert-butanol (1.5 mL, 16 mmol) was heated under microwave irradiation at 130° C. for 60 minutes. The reaction mixture was diluted with dichloromethane, washed with saturated aqueous sodium bicarbonate, dried over magnesium sulfate, filtered, and evaporated in vacuo to yield 150.4 mg crude product. The crude product was purified and stereoisomers separated via preparatory chiral SFC to yield the title compound as a single unknown stereoisomer. LCMS (ESI): $R_T$ (min)=3.094, [M+H]$^+$=402.2, method=B; $^1$H NMR (400 MHz, DMSO-d$_6$) δ 9.54 (s, 1H), 8.50 (d, J=0.9 Hz, 1H), 7.97-7.93 (m, 2H), 6.99 (s, 1H), 6.80 (d, J=5.8 Hz, 1H), 4.78-4.64 (m, 2H), 3.53 (dd, J=13.3, 7.5 Hz, 1H), 3.44-3.33 (m, 1H), 3.17-3.08 (m, 1H), 3.09-2.99 (m, 1H), 2.56 (s, 3H), 2.48-2.43 (m, 1H), 2.27-2.15 (m, 1H), 1.56 (dd, J=6.8, 1.5 Hz, 6H).

Example 51: 6-((2-(1-(Cyclopropylsulfonyl)-1H-pyrazol-4-yl)pyrimidin-4-yl)amino)-1-isopropyl-1H-pyrrolo[3,2-c]pyridine-3-carboxamide

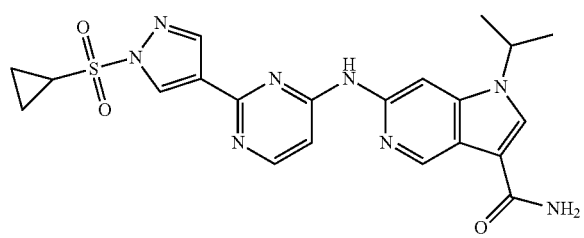 [SMILES: CC(C)n1cc(C(N)=O)c2cnc(Nc3ccnc(-c4cnn(S(=O)(=O)C5CC5)c4)n3)cc21]

Step 1:
6-Bromo-1-isopropyl-1H-pyrrolo[3,2-c]pyridine

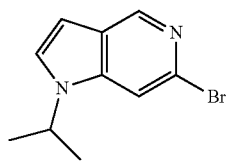

To a solution of 6-bromo-5-azaindole (1.0 g, 4.9 mmol) in DMF (8 mL) was added 60% sodium hydride (0.23 g, 5.8 mmol) at 0° C. The mixture was stirred 0° C. for 5 min prior to the addition of 2-bromopropane (0.7 mL, 7 mmol). The reaction was stirred at room temperature for 2 h. The reaction was then quenched by pouring onto saturated NH$_4$Cl. The product was extracted with EtOAc (3×). The combined extracts were washed with brine, dried over sodium sulfate, filtered and concentrated. The crude product was purified by flash chromatography on silica gel (solvent gradient: 0-100% EtOAc in heptane) to give the title compound (1.5 g, quant.).

Step 2: 6-Bromo-1-isopropyl-1H-pyrrolo[3,2-c]pyridine-3-carbaldehyde

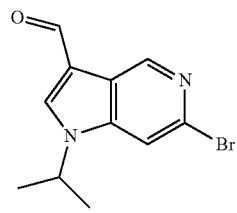

To cooled (0° C.) DMF (40 mL) was added POCl$_3$ (3.0 mL, 31 mmol). The reaction was stirred at 0° C. for 20 min. A solution of 6-bromo-1-isopropyl-1H-pyrrolo[3,2-c]pyridine (4.9 mmol) in DMF (1 mL) was added dropwise at room temperature. The reaction was stirred at 70° C. for 2 h. The mixture was then slowly neutralized by pouring onto a saturated sodium bicarbonate solution. The product was extracted with EtOAc (3×). The combined organic extracts were washed with sat. sodium bicarbonate and brine, dried over sodium sulfate, filtered and concentrated. The crude product was purified by flash chromatography on silica gel (solvent gradient: 0-100% EtOAc in heptane) to give the title compound (1.34 g, 80%).

Step 3: 6-Bromo-1-isopropyl-1H-pyrrolo[3,2-c]pyridine-3-carboxylic acid

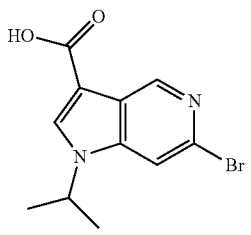

To a solution of 6-bromo-1-isopropyl-1H-pyrrolo[3,2-c]pyridine-3-carbaldehyde (1.3 g, 4.9 mmol) in t-BuOH (10 mL) was added 2-methyl-2-butene (2 M in THF, 4.1 mL, 49 mmol). A solution of sodium chlorite (1.1 g, 9.7 mmol) and monosodium phosphate (5.8 g, 49 mmol) in water (15 mL) was then added. The reaction was stirred at room temperature for 18 h. The mixture was then diluted with brine and extracted with EtOAc (3×). The combined extracts were washed with brine, dried over sodium sulfate, filtered and concentrated. The crude material (1.3 g, 94%) was used without further purification.

Step 4: 6-Bromo-1-isopropyl-1H-pyrrolo[3,2-c]pyridine-3-carboxamide

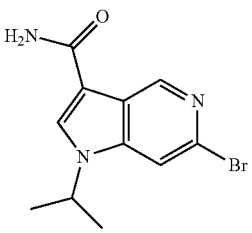 [SMILES: CC(C)n1cc(C(N)=O)c2cnc(Br)cc21]

To a solution of 6-bromo-1-isopropyl-1H-pyrrolo[3,2-c]pyridine-3-carboxylic acid (1.25 g, 4.4 mmol) in DMF (10 mL) was added DIPEA (1.2 mL, 6.6 mmol) and HBTU (2.64 g, 6.62 mmol). The mixture was stirred at room temperature for 15 min before the addition of ammonium hydroxide (10 mL). The resulting mixture was stirred vigorously for 1 h. The mixture was then diluted with brine and extracted with EtOAc (3×). The combined extracts were washed with brine, dried over sodium sulfate, filtered and concentrated. The crude material was purified by flash chromatography on silica gel (solvent gradient: 0-10% MeOH in DCM) to give the title compound (0.72 g, 58%).

Step 5: 6-((2-Chloropyrimidin-4-yl)amino)-1-isopropyl-1H-pyrrolo[3,2-c]pyridine-3-carboxamide

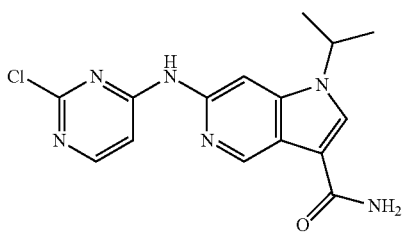 [SMILES: CC(C)n1cc(C(N)=O)c2cnc(Nc3ccnc(Cl)n3)cc21]

To a pressure tube was added 6-bromo-1-isopropyl-1H-pyrrolo[3,2-c]pyridine-3-carboxamide (0.15 g, 0.53 mmol), 4-amino-2-chloropyrimidine (70 mg, 0.53 mmol), Xantphos (32 mg, 0.053 mmol), Pd$_2$(dba)$_3$ (25 mg, 0.027 mmol), Cs$_2$CO$_3$ (0.35 g, 1.1 mmol) and dioxane (2 mL). The mixture was degassed by nitrogen bubbling for 20 min. The reaction vial was then sealed and stirred at 120° C. for 6 h. The reaction was then filtered and concentrated. The crude product was purified by flash chromatography on silica gel (solvent gradient: 0-10% MeOH in DCM) to give the title compound (0.70 g, 40%).

Step 6: 1-(Cyclopropylsulfonyl)-4-(4,4,5,5-tetramethyl-1,3,2-dioxaborolan-2-yl)-1H-pyrazole

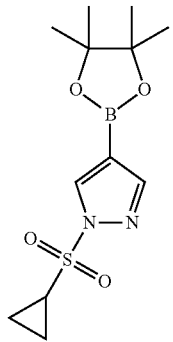 [SMILES: CC1(C)OB(c2cnn(S(=O)(=O)C3CC3)c2)OC1(C)C]

To a solution of 4-pyrazoleboronic acid pinacol ester (1.02 g, 5.26 mmol) in DMF (15 mL) was added sodium hydride (60%, 0.32 g, 8 mmol) and cyclopropylsufonyl chloride (0.8 g, 5.78 mmol). The reaction was stirred at room temperature for 5 h. The mixture was then diluted with brine and extracted with EtOAc (3×). The combined extracts were washed with brine, dried over sodium sulfate, filtered and concentrated. The crude material was purified by flash chromatography on silica gel (solvent gradient: 0-100% EtOAc in heptane) to give the title compound (0.8 g, 50%).

Step 7: 6-((2-(1-(Cyclopropylsulfonyl)-1H-pyrazol-4-yl)pyrimidin-4-yl)amino)-1-isopropyl-1H-pyrrolo[3,2-c]pyridine-3-carboxamide

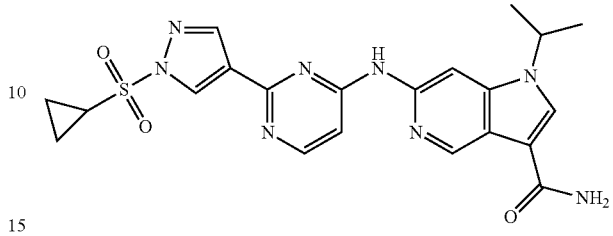

To a glass vial was added: 1-(cyclopropylsulfonyl)-4-(4,4,5,5-tetramethyl-1,3,2-dioxaborolan-2-yl)-1H-pyrazole (95 mg, 0.30 mmol), 6-((2-chloropyrimidin-4-yl)amino)-1-isopropyl-1H-pyrrolo[3,2-c]pyridine-3-carboxamide (50 mg, 0.15 mmol), Pd(Amphos)$_2$Cl$_2$ (5 mg, 0.008 mmol), a 2M solution of Na$_2$CO$_3$ (0.11 mL, 0.23 mmol) and acetonitrile (2.5 mL). The mixture was degassed by nitrogen bubbling for 20 min. The reaction vial was sealed and stirred at 100° C. in an oil bath for 1 h. The reaction mixture was cooled to room temperature, filtered and concentrated. The crude product was purified by reverse-phase HPLC and lyophilized to give the title compound (20 mg, 30%). LCMS (ESI): R$_T$ 4.13 min, [M+H]$^+$ 467.2, method=B; $^1$H NMR (400 MHz, DMSO-d$_6$) δ 10.27 (s, 1H), 9.08 (t, J=2.4 Hz, 1H), 8.70 (d, J=0.5 Hz, 1H), 8.50 (s, 1H), 8.47 (d, J=0.5 Hz, 1H), 8.37 (d, J=5.9 Hz, 1H), 8.23 (s, 1H), 7.49 (s, 1H), 7.11 (s, 1H), 6.97 (d, J=8.7 Hz, 1H), 6.63 (d, J=8.8 Hz, 1H), 4.80 (m, 1H), 1.56 (d, J=6.7 Hz, 6H), 1.40-1.31 (m, 2H), 1.30-1.23 (m, 2H).

Example 52: N-(2-(1-(Cyclopropylsulfonyl)-1H-pyrazol-4-yl)pyrimidin-4-yl)-1-isopropyl-2-methyl-1H-imidazo[4,5-c]pyridin-6-amine

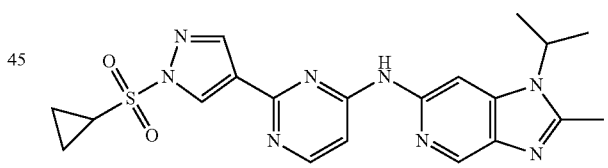

To a glass vial was added: 1-(cyclopropylsulfonyl)-4-(4,4,5,5-tetramethyl-1,3,2-dioxaborolan-2-yl)-1H-pyrazole (Example 51, step 6) (0.56 g, 1.8 mmol), N-(2-chloropyrimidin-4-yl)-1-isopropyl-2-methyl-1H-imidazo[4,5-c]pyridin-6-amine (Example 46, Step 7) (0.56 g, 1.8 mmol), Pd(Amphos)$_2$Cl$_2$ (65 mg, 0.092 mmol), a 2M solution of Na$_2$CO$_3$ (1.4 mL, 2.8 mmol) and acetonitrile (2.5 mL). The mixture was degassed by nitrogen bubbling for 20 min. The reaction vial was sealed and stirred at 100° C. in an oil bath for 3 h. The reaction mixture was cooled to room temperature, filtered and concentrated. The crude product was purified by reverse-phase HPLC and lyophilized to give the title compound (41 mg, 5%). LCMS (ESI): R$_T$ 4.77 min, [M+H]$^+$ 439.2, method=B; $^1$H NMR (400 MHz, DMSO-d$_6$) δ 10.16 (s, 1H), 8.66 (s, 1H), 8.56 (d, J=0.8 Hz, 1H), 8.47 (d, J=0.5 Hz, 1H), 8.39 (m, 2H), 7.24 (s, 1H), 4.78 (m, 1H), 2.58 (s, 3H), 1.63 (d, J=6.9 Hz, 6H), 1.38-1.21 (m, 4H).

Example 53: 1-Isopropyl-N-(2-(4-methoxyphenyl)pyrimidin-4-yl)-1H-imidazo[4,5-c]pyridin-6-amine

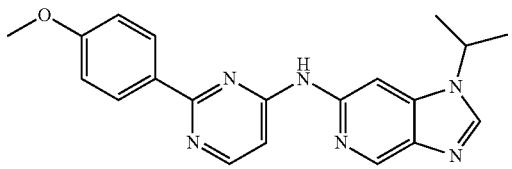 [SMILES: COc1ccc(-c2nccc(Nc3cc4c(cn3)ncn4C(C)C)n2)cc1]

Step 1: 2-(4-Methoxyphenyl)pyrimidin-4-amine

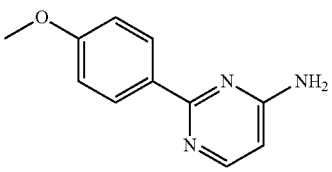

To a glass vial was added (4-methoxyphenyl)boronic acid (0.15 g, 1.0 mmol), 2-chloropyrimidin-4-amine (0.13 mg, 1.0 mmol), Pd(Amphos)$_2$Cl$_2$ (35 mg, 0.050 mmol), a 2M solution of Na$_2$CO$_3$ (0.75 mL, 1.5 mmol) and acetonitrile (2.5 mL). The mixture was degassed by nitrogen bubbling for 20 min. The reaction vial was sealed and stirred at 110° C. in an oil bath for 2 h. The reaction mixture was cooled to room temperature, filtered and concentrated. The crude product was purified by flash chromatography on silica to give the title compound (141 mg, 70%).

Step 2: 1-Isopropyl-N-(2-(4-methoxyphenyl)pyrimidin-4-yl)-1H-imidazo[4,5-c]pyridin-6-amine

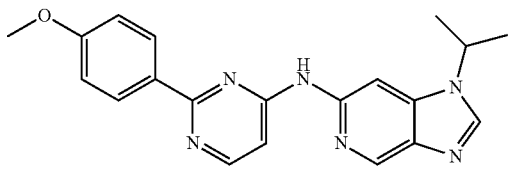

To a glass vial was added 2-(4-methoxyphenyl)pyrimidin-4-amine (0.14 g, 0.66 mmol), 6-chloro-1-isopropyl-imidazo[4,5-c]pyridine (Example 35, step 2) (0.13 g, 0.66 mmol), sodium t-butoxide (0.2 g, 2 mmol), t-BuOH (2.5 mL) and Chloro {[BrettPhos][2-(2-aminoethylphenyl]palladium (II)]}/[BrettPhos] admixture (molar PdP/P=1:1) (50 mg). The reaction was degassed by nitrogen bubbling for 15 min. The reaction vial was sealed and heated at 120° C. for 12 h in an oil bath. The reaction was then filtered, concentrated and purified by reverse-phase HPLC and lyophilized to give the title compound (129.6 mg, 54%). LCMS (ESI): R$_T$ 3.85 min, [M+H]$^+$ 361.2, method=B; $^1$H NMR (400 MHz, DMSO-d$_6$) δ 10.16 (s, 1H), 8.71 (s, 1H), 8.57 (s, 1H), 8.41 (d, J=5.8 Hz, 1H), 8.37 (m, 3H), 7.13 (d, J=5.7 Hz, 1H), 7.10-6.98 (m, 2H), 4.77 (m, 1H), 3.86 (s, 3H), 1.65 (d, J=6.8 Hz, 6H).

Example 54: 1-Isopropyl-N-(2-(6-methoxypyridin-3-yl)pyrimidin-4-yl)-1H-imidazo[4,5-c]pyridin-6-amine

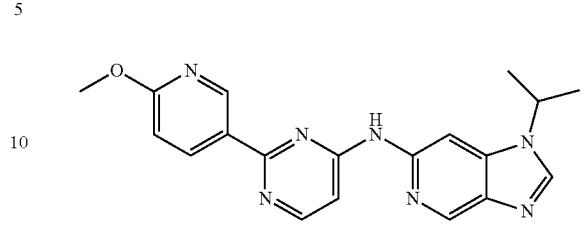

To a glass vial was added 2-(6-methoxy-3-pyridyl)pyrimidin-4-amine (0.14 g, 0.66 mmol), 6-chloro-1-isopropyl-imidazo[4,5-c]pyridine (Example 35, step 2) (0.13 g, 0.66 mmol), cesium carbonate (0.43 g, 2.0 mmol), 1,4-dioxane (3 mL), XPhos (32 mg, 0.066 mmol) and Pd$_2$(dba)$_3$ (31 mg, 0.33 mmol). The reaction was degassed by nitrogen bubbling for 15 min. The reaction vial was sealed and heated at 120° C. for 12 h in an oil bath. The reaction was then filtered, concentrated and purified by reverse-phase HPLC and lyophilized to give the title compound (129.6 mg, 54%). LCMS (ESI): R$_T$ 3.78 min, [M+H]$^+$ 362.2, method=B; $^1$H NMR (400 MHz, DMSO-d$_6$) δ 10.22 (s, 1H), 9.17 (d, J=2.3 Hz, 1H), 8.72 (s, 1H), 8.58 (m, 1H), 8.45 (d, J=3.3 Hz, 1H), 8.41 (m, 2H), 7.23 (d, J=5.6 Hz, 1H), 6.97 (d, J=8.7 Hz, 1H), 4.77 (m, 1H), 3.95 (s, 3H), 1.63 (d, J=6.8 Hz, 6H).

Example 55: N-(2'-Ethoxy-[2,5'-bipyrimidin]-4-yl)-1-isopropyl-1H-imidazo[4,5-c]pyridin-6-amine

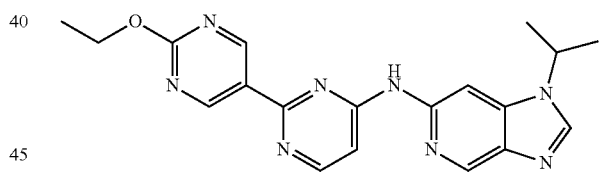

To a glass vial was added 2-methoxypyrimidine-5-boronic acid (0.105 g, 0.613 mmol), (2-chloropyrimidin-4-yl)-(1-isopropyl-1H-imidazo[4,5-c]pyridin-6-yl)amine (Example 12, Step 4) (0.176 mg, 0.613 mmol), Pd(Amphos)$_2$Cl$_2$ (22 mg, 0.031 mmol), a 2M solution of Na$_2$CO$_3$ (0.46 mL, 0.92 mmol) and acetonitrile (2.5 mL). The mixture was degassed by nitrogen bubbling for 20 min. The reaction vial was sealed and heated in a microwave at 140° C. for 20 min. Alternatively, the reaction was sealed and stirred at 100° C. in an oil bath for 2 h. The reaction mixture was cooled to room temperature, filtered and concentrated. The crude product was purified by reverse-phase HPLC and lyophilized to give the title compound (41 mg, 18%). LCMS (ESI): R$_T$ 3.91 min, [M+H]$^+$ 377.2, method=B; $^1$H NMR (400 MHz, DMSO-d$_6$) δ 10.31 (s, 1H), 9.40 (s, 2H), 8.73 (d, J=1.0 Hz, 1H), 8.46 (d, J=5.9 Hz, 1H), 8.39 (d, J=7.9 Hz, 2H), 7.30 (s, 1H), 4.85-4.71 (m, 1H), 4.46 (q, J=7.1 Hz, 2H), 1.61 (d, J=6.8 Hz, 6H), 1.38 (t, J=7.1 Hz, 3H).

Example 56: N-(2-(4-Isopropoxypiperidin-1-yl)pyrimidin-4-yl)-1-isopropyl-1H-imidazo[4,5-c]pyridin-6-amine

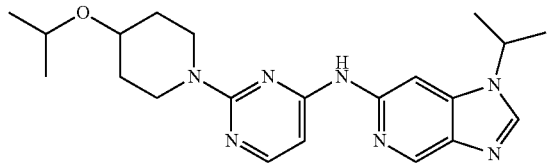 [SMILES: CC(C)OC1CCN(c2nccc(Nc3cc4c(cn3)ncn4C(C)C)n2)CC1]

A mixture of (2-chloropyrimidin-4-yl)-(1-isopropyl-1H-imidazo[4,5-c]pyridin-6-yl)amine (Example 12, Step 4) (100 mg, 0.35 mmol), 4-isopropoxypiperidine (50 mg, 0.35 mmol), DIPEA (90 mg, 0.70 mmol) in isopropyl alcohol (2 mL) was heated at 90° C. for 2 h. The cooled mixture was concentrated and purified by reverse-phase HPLC to give the title compound (27.8 mg, 20%). LCMS (ESI): $R_T$ 3.92 min, [M+H]$^+$ 396.3, method=B; $^1$H NMR (400 MHz, DMSO-d$_6$) δ 9.76 (s, 1H), 8.65 (d, J=0.9 Hz, 1H), 8.39 (s, 1H), 8.32 (s, 1H), 7.96 (d, J=5.6 Hz, 1H), 6.38 (d, J=5.6 Hz, 1H), 4.73-4.57 (m, 1H), 4.28 (m, 2H), 3.76 (m, 1H), 3.70-3.56 (m, 1H), 1.90-1.76 (m, 2H), 1.56 (d, J=6.8 Hz, 6H), 1.40 (m, 2H), 1.10 (d, J=6.1 Hz, 6H).

Example 57: N-Ethyl-1-isopropyl-6-((2-(4-methoxypiperidin-1-yl)pyrimidin-4-yl)amino)-1H-pyrrolo[3,2-c]pyridine-3-carboxamide

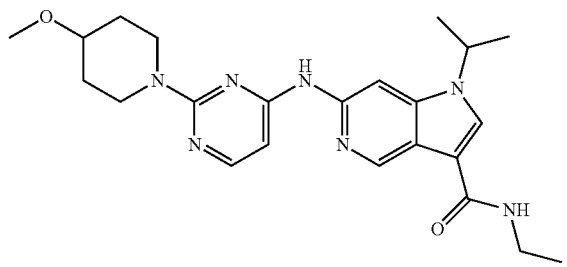 [SMILES: CCNC(=O)c1cn(C(C)C)c2cc(Nc3ccnc(N4CCC(OC)CC4)n3)ncc12]

Step 1: 6-Chloro-1-isopropyl-1H-pyrrolo[3,2-c]pyridine

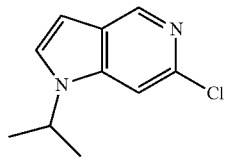

To a solution of 6-chloro-5-azaindole (0.50 g, 3.3 mmol) in DMF (8 mL) was added 60% sodium hydride (0.16 g, 3.9 mmol) at 0° C. The mixture was stirred 0° C. for 5 min prior to the addition of 2-bromopropane (0.47 mL, 4.9 mmol). The reaction was stirred at room temperature for 2 h. The reaction was then quenched by pouring onto saturated NH$_4$Cl. The product was extracted with EtOAc (3×). The combined extracts were washed with brine, dried over sodium sulfate, filtered and concentrated. The crude product was purified by flash chromatography on silica (solvent gradient: 0-100% EtOAc in heptane) to give the title compound (0.52 g, 82%).

Step 2: 6-Chloro-1-isopropyl-1H-pyrrolo[3,2-c]pyridine-3-carbaldehyde

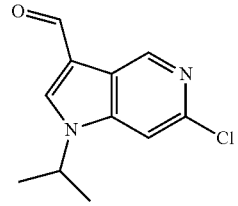

To cooled (0° C.) DMF (10 mL) was added POCl$_3$ (1.1 mL, 12 mmol). The reaction was stirred at 0° C. for 20 min. A solution of 6-chloro-1-isopropyl-1H-pyrrolo[3,2-c]pyridine (0.47 g, 2.43 mmol) in DMF (1 mL) was added dropwise at room temperature. The reaction was stirred at 60° C. for 2 h. The mixture was then slowly neutralized by pouring onto a saturated sodium bicarbonate solution. The product was extracted with EtOAc (3×). The combined organic extracts were washed with saturated sodium bicarbonate and brine, dried over sodium sulfate, filtered and concentrated. The crude product was purified by flash chromatography on silica (solvent gradient: 0-100% EtOAc in heptane) to give the title compound (0.52 g, 95%).

Step 3: 6-Chloro-1-isopropyl-1H-pyrrolo[3,2-c]pyridine-3-carboxylic acid

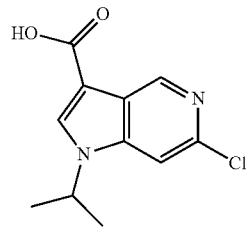

To a solution of 6-chloro-1-isopropyl-1H-pyrrolo[3,2-c]pyridine-3-carbaldehyde (0.52 g, 2.3 mmol) in t-BuOH (10 mL) was added 2-methyl-2-butene (2 M in THF, 12 mL, 23 mmol). A solution of sodium chlorite (0.53 g, 4.6 mmol) and monosodium phosphate (2.8 g, 23 mmol) in water (10 mL) was then added. The reaction was stirred at room temperature for 18 h. The mixture was then diluted with brine and extracted with EtOAc (3×). The combined extracts were washed with brine, dried over sodium sulfate, filtered and concentrated. The crude material (0.42 g, 76%) was used without further purification.

Step 4: 6-Chloro-N-ethyl-1-isopropyl-1H-pyrrolo[3,2-c]pyridine-3-carboxamide

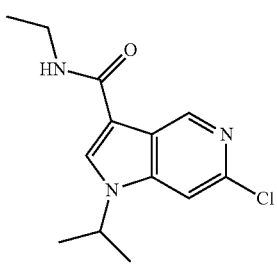 [SMILES: CCNC(=O)c1cn(C(C)C)c2cc(Cl)ncc12]

To a solution of 6-chloro-1-isopropyl-1H-pyrrolo[3,2-c]pyridine-3-carboxylic acid (0.20 g, 0.84 mmol) in DMF (5 mL) was added DIPEA (0.22 g, 1.7 mmol), HBTU (0.40 g, 1.0 mmol) and ethylamine hydrochloride (84 mg, 1.0 mmol). The resulting mixture was stirred at room temperature for 2 h. The mixture was then diluted with brine and extracted with EtOAc (3×). The combined extracts were washed with brine, dried over sodium sulfate, filtered and concentrated. The crude material was purified by flash chromatography on silica (solvent gradient: 0-5% MeOH in DCM) to provide the title compound (0.15 g, 67%).

Step 5: N-Ethyl-1-isopropyl-6-((2-(4-methoxypiperidin-1-yl)pyrimidin-4-yl)amino)-1H-pyrrolo[3,2-c]pyridine-3-carboxamide

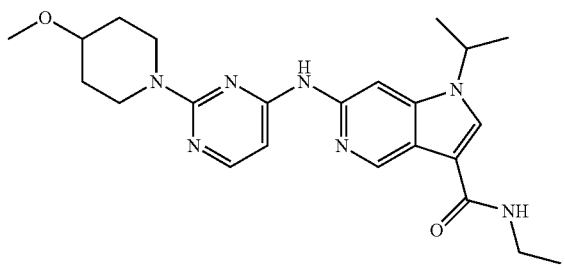 [SMILES: CCNC(=O)c1cn(C(C)C)c2cc(Nc3ccnc(N4CCC(OC)CC4)n3)ncc12]

To a glass vial was added 2-(4-methoxy-1-piperidyl)pyrimidin-4-amine (Example 3, step 2) (0.067 g, 0.32 mmol), 6-chloro-N-ethyl-1-isopropyl-pyrrolo[3,2-c]pyridine-3-carboxamide (0.086 g, 0.32 mmol), sodium t-butoxide (96 mg, 0.97 mmol), t-BuOH (2.5 mL) and Chloro{[BrettPhos][2-(2-aminoethylphenyl]palladium(II)]}/[BrettPhos] admixture (molar PdP/P=1:1) (50 mg). The reaction was degassed by nitrogen bubbling for 15 min. The reaction was sealed and heated at 120° C. for 12 h in an oil bath. The reaction was then filtered, concentrated and purified by reverse-phase HPLC to give the title compound (129.6 mg, 54%). LCMS (ESI): $R_T$ 3.50 min, [M+H]$^+$ 438.3, method=B; $^1$H NMR (400 MHz, DMSO-d$_6$) δ 9.75 (s, 1H), 9.02 (s, 1H), 8.34 (s, 1H), 8.13 (d, J=7.3 Hz, 2H), 7.96 (m, 2H), 6.34 (d, J=5.7 Hz, 1H), 4.60 (m, 1H), 4.24 (m, 2H), 2.89 (s, 1H), 2.73 (s, 1H), 2.07 (s, 1H), 1.91 (m, 2H), 1.51 (d, J=6.7 Hz, 6H), 1.48-1.37 (m, 2H), 1.14 (t, J=7.2 Hz, 3H).

Example 58: 1-Isopropyl-6-((2-(4-methoxypiperidin-1-yl)pyrimidin-4-yl)amino)-1H-pyrrolo[3,2-c]pyridine-3-carbonitrile

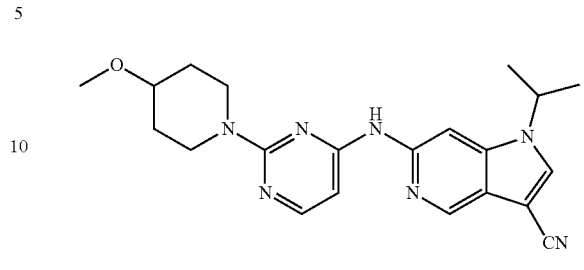

A mixture of 1-isopropyl-6-[[2-(4-methoxy-1-piperidyl)pyrimidin-4-yl]amino]pyrrolo[3,2-c]pyridine-3-carboxamide (Example 115) (58 mg, 0.14 mmol) and POCl$_3$ (10 mL) was stirred at 90° C. for 20 min. The reaction was concentrated. The crude product was purified by reverse-phase HPLC and lyophilized to give the title compound (22.3 mg, 40%). LCMS (ESI): $R_T$ 4.06 min, [M+H]$^+$ 392.2, method=B; $^1$H NMR (400 MHz, DMSO-d$_6$) δ 9.89 (s, 1H), 8.66 (s, 1H), 8.46 (d, J=6.5 Hz, 2H), 7.98 (d, J=5.6 Hz, 1H), 6.37 (d, J=5.6 Hz, 1H), 4.66 (m, 1H), 4.23 (m, 2H), 3.53-3.33 (m, 3H), 1.98-1.83 (m, 2H), 1.58-1.37 (m, 8H).

Example 59: 1-Isopropyl-N-(2-(4-methoxypiperidin-1-yl)pyrimidin-4-yl)-3-(5-methyl-1,3,4-oxadiazol-2-yl)-1H-pyrrolo[3,2-c]pyridin-6-amine

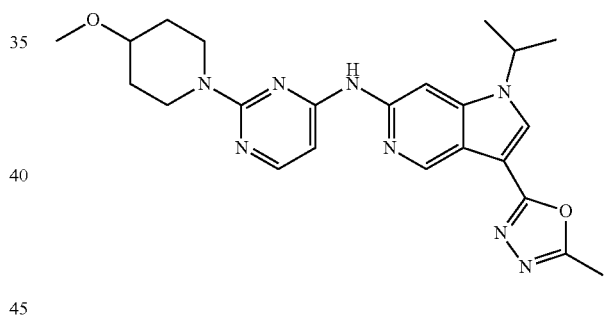

Step 1: N'-Acetyl-6-chloro-1-isopropyl-1H-pyrrolo[3,2-c]pyridine-3-carbohydrazide

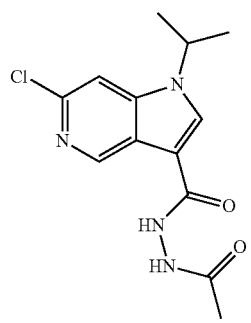 [SMILES: CC(=O)NNC(=O)c1cn(C(C)C)c2cc(Cl)ncc12]

A mixture of 6-chloro-1-isopropyl-pyrrolo[3,2-c]pyridine-3-carboxylic acid (Example 57, step 3) (0.358 g, 1.5 mmol), DIPEA (0.4 g, 3 mmol), HBTU (697 mg, 1.80 mmol) and acetic acid hydrazide (136 mg, 1.65 mmol) in DMF (5 mL) was stirred at room temperature for 18 h. The reaction was then diluted with brine. The product was extracted with EtOAc (3×). The combined extracts were washed with brine, dried over sodium sulfate, filtered and concentrated. The crude product was purified by flash chromatography on silica (solvent gradient: 0-100% EtOAc in heptane) to give the title compound (0.29 g, 66%).

Step 2: 2-(6-Chloro-1-isopropyl-1H-pyrrolo[3,2-c]pyridin-3-yl)-5-methyl-1,3,4-oxadiazole

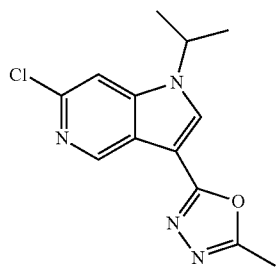 [SMILES: Cc1nnc(-c2cn(C(C)C)c3cc(Cl)ncc23)o1]

A mixture of N'-acetyl-6-chloro-1-isopropyl-1H-pyrrolo[3,2-c]pyridine-3-carbohydrazide (0.15 g, 0.51 mmol) and POCl$_3$ (5 mL) was stirred at 95° C. for 1 h. The reaction was then concentrated. The residue was neutralized by adding saturated sodium bicarbonate. The product extracted with EtOAc (3×). The combined extracts were washed with brine, dried over sodium sulfate, filtered and concentrated. The crude product was purified by flash chromatography on silica (solvent gradient: 0-5% MeOH in DCM) to give the title compound (0.091 g, 65%).

Step 3: 1-Isopropyl-N-(2-(4-methoxypiperidin-1-yl)pyrimidin-4-yl)-3-(5-methyl-1,3,4-oxadiazol-2-yl)-1H-pyrrolo[3,2-c]pyridin-6-amine

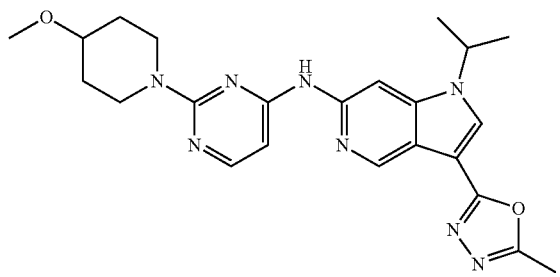

To a glass vial was added 2-(4-methoxy-1-piperidyl)pyrimidin-4-amine (Example 3, step 2) (0.067 g, 0.31 mmol), 2-(6-chloro-1-isopropyl-1H-pyrrolo[3,2-c]pyridin-3-yl)-5-methyl-1,3,4-oxadiazole (0.085 g, 0.31 mmol), sodium t-butoxide (91 mg, 0.92 mmol), t-BuOH (2.5 mL) and Chloro{[BrettPhos][2-(2-aminoethylphenyl]palladium (II)]}/[BrettPhos] admixture (molar PdP/P=1:1) (50 mg). The reaction was degassed by nitrogen bubbling for 15 min. The reaction vial was sealed and heated at 120° C. for 6 h in an oil bath. The reaction was then filtered, concentrated and purified by reverse-phase HPLC to give the title compound (31.5 mg, 23%). LCMS (ESI): R$_T$ 4.25 min, [M+H]$^+$ 449.3, method=B; $^1$H NMR (400 MHz, DMSO-d$_6$) δ 9.89 (s, 1H), 8.99 (d, J=0.9 Hz, 1H), 8.47 (s, 1H), 8.26 (s, 1H), 7.98 (d, J=5.6 Hz, 1H), 6.37 (d, J=5.7 Hz, 1H), 4.69 (m, 1H), 4.25 (m, 2H), 3.55-3.34 (m, 4H), 2.58 (s, 3H), 1.91 (d, J=9.9 Hz, 2H), 1.56 (d, J=6.7 Hz, 6H), 1.52-1.37 (m, 2H).

Example 60: 6-((2-(6,7-Dihydro-1H-pyrazolo[4,3-c]pyridin-5(4H)-yl)pyrimidin-4-yl)amino)-1-isopropyl-1H-pyrrolo[3,2-c]pyridine-3-carboxamide

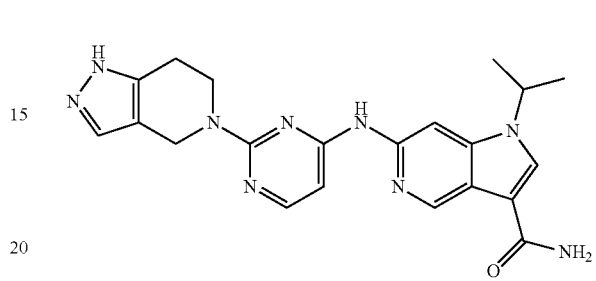

A mixture of 6-[(2-chloropyrimidin-4-yl)amino]-1-isopropyl-pyrrolo[3,2-c]pyridine-3-carboxamide (Example 51, step 5) (11.4 mg, 0.027 mmol), 4-ethoxypiperidine (27 mg, 0.21 mmol), DIPEA (27 mg, 0.21 mmol) in 2-propanol (3 mL) was stirred at 100° C. for 2 h. The reaction mixture was concentrated and the product was purified by reverse-phase HPLC to give the title compound (11.4 mg, 13%). LCMS (ESI): R$_T$ 3.38 min, [M+H]$^+$ 418.2, method=B; $^1$H NMR (400 MHz, DMSO-d$_6$) δ 12.48 (s, 1H), 9.81 (s, 1H), 9.02 (d, J=0.9 Hz, 1H), 8.41 (s, 1H), 8.19 (s, 1H), 7.98 (d, J=5.7 Hz, 1H), 7.46 (s, 2H), 6.96 (s, 1H), 6.38 (d, J=5.7 Hz, 1H), 4.81 (s, 2H), 4.76-4.55 (m, 1H), 4.11 (t, J=5.7 Hz, 2H), 2.78 (s, 2H), 1.57 (d, J=6.7 Hz, 6H).

Example 61: 1-(4-((1-Isopropyl-2-methyl-1H-imidazo[4,5-c]pyridin-6-yl)amino)pyrimidin-2-yl)-N-methyl-1H-imidazole-4-carboxamide

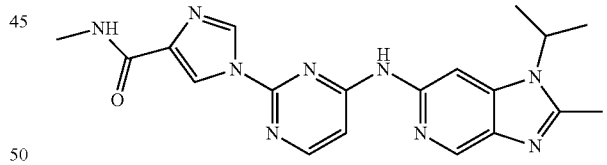

Step 1: 1-[4-[(1-Isopropyl-2-methyl-imidazo[4,5-c]pyridin-6-yl)amino]pyrimidin-2-yl]imidazole-4-carboxylic acid

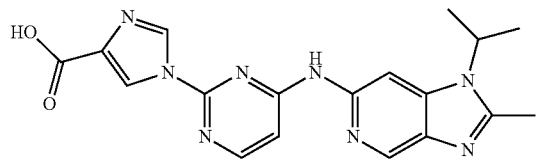

A mixture of methyl 1H-imidazole-4-carboxylate (64 mg, 0.51 mmol) and N-(2-chloropyrimidin-4-yl)-1-isopropyl-2-methyl-1H-imidazo[4,5-c]pyridin-6-amine (Example 46, step 7) (140 mg, 0.46 mmol), cesium carbonate (140 mg, 0.46 mmol) in t-BuOH was heated under microwave irradiation at 150° C. for 30 min. The reaction was filtered and concentrated to give the title compound (0.31 g, quant.). The crude material was used in the following step without purification.

Step 2: 1-(4-((1-Isopropyl-2-methyl-1H-imidazo[4,5-c]pyridin-6-yl)amino)pyrimidin-2-yl)-N-methyl-1H-imidazole-4-carboxamide

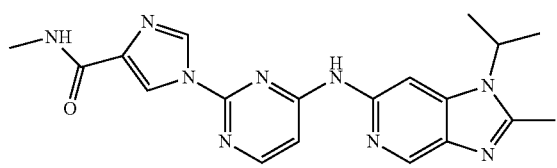

A mixture of crude 1-[4-[(1-isopropyl-2-methyl-imidazo[4,5-c]pyridin-6-yl)amino]pyrimidin-2-yl]imidazole-4-carboxylic acid (0.10 g, 0.26 mmol), DIPEA (0.14 mL, 0.79 mmol), HBTU (210 mg, 0.53 mmol) was stirred at room temperature for 30 min. A 40 wt % aqueous solution of methylamine was added and the reaction was stirred for 30 min. The reaction was then concentrated and the product was purified by reverse-phase HPLC to give the title compound (7.7 mg, 7.4%). LCMS (ESI): $R_T$ 3.68 min, [M+H]$^+$ 392.2, method=B; $^1$H NMR (400 MHz, DMSO-d$_6$) δ 10.50 (s, 1H), 8.60 (s, 1H), 8.55 (d, J=1.3 Hz, 1H), 8.38 (d, J=5.9 Hz, 1H), 8.27 (d, J=1.3 Hz, 2H), 8.13 (d, J=4.8 Hz, 1H), 7.30 (s, 1H), 4.79 (m, 2H), 2.77 (d, J=4.8 Hz, 3H), 2.60 (s, 3H), 1.64 (d, J=6.9 Hz, 6H).

Example 62: 5-(4-((1-Isopropyl-1H-imidazo[4,5-c]pyridin-6-yl)amino)pyrimidin-2-yl)pyridin-2-ol

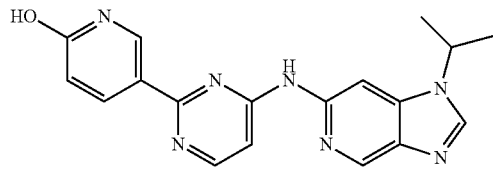 [SMILES: CC(C)n1cnc2cnc(Nc3ccnc(-c4ccc(O)nc4)n3)cc21]

To a solution of 1-isopropyl-N-[2-(6-methoxy-3-pyridyl)pyrimidin-4-yl]imidazo[4,5-c]pyridin-6-amine (Example 54) (30 mg, 0.083 mmol) in acetonitrile (5 mL) was added TMSI (0.1 mL). The reaction was stirred at 50° C. for 4 h. The reaction was concentrated and purified by reverse-phase HPLC to give the title compound (3.7 mg, 13%). LCMS (ESI): $R_T$ 3.20 min, [M+H]$^+$ 348.2, method=B.

Example 63: N-(2-(1H-Imidazol-1-yl)ethyl)-1-isopropyl-6-(2-(4-methoxypiperidin-1-yl)pyrimidin-4-ylamino)-1H-pyrrolo[3,2-c]pyridine-3-carboxamide

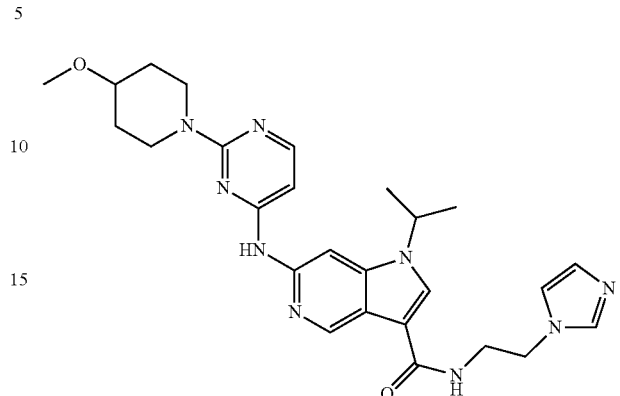

Step 1: 6-Chloro-3-iodo-1H-pyrrolo[3,2-c]pyridine

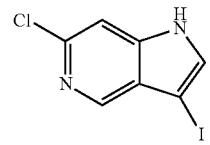 [SMILES: Clc1cc2[nH]cc(I)c2cn1]

Into a 100 mL 3-necked round-bottom flask was added a solution of 6-chloro-1H-pyrrolo[3,2-c]pyridine (1.00 g, 6.55 mmol) in N,N-dimethylformamide (10 mL), potassium hydroxide (1.40 g, 24.9 mmol). The reaction mixture was stirred for 20 min at room temperature, then I$_2$ (1.66 g, 6.54 mmol, 1.00) was added to the solution. The reaction mixture was stirred for additional 30 min at room temperature. The reaction mixture was diluted with H$_2$O (50 mL) and the solids were collected by filtration. The solids were dried under reduced pressure overnight to afford 6-chloro-3-iodo-1H-pyrrolo[3,2-c]pyridine (1.70 g, 93.0%) as a yellow solid. LCMS (ESI): $R_T$ (min)=1.321, [M+H]$^+$=279, method=N.

Step 2: 6-Chloro-3-iodo-1-isopropyl-1H-pyrrolo[3,2-c]pyridine

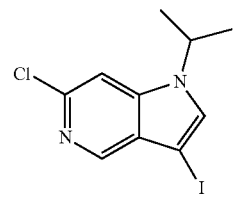

Into a 100 mL 3-necked round-bottom flask purged and maintained with an inert atmosphere of nitrogen, was added a solution of 6-chloro-3-iodo-1H-pyrrolo[3,2-c]pyridine (1.70 g, 6.10 mmol) in N,N-dimethylformamide (20.0 mL) followed by sodium hydride (600 mg, 25.0 mmol). This was followed by addition of 2-iodopropane (2.20 g, 12.9 mmol) dropwise with stirring at 0° C. The reaction mixture was stirred for 16 h at room temperature. The reaction was then quenched by addition of water (50 mL). The resulting solution was extracted with ethyl acetate (3×50 mL) and the organic layers were separated and combined. The combined organic layer was washed with brine (100 mL), dried over anhydrous sodium sulfate and concentrated under vacuum. The residue was purified by silica gel chromatography with ethyl acetate/petroleum ether (1:7) to afford the title compound (1.40 g, 72.0%) as a yellow solid. LCMS (ESI): $R_T$ (min)=1.549, [M+H]$^+$=321, method=M.

Step 3: 6-Chloro-1-isopropyl-1H-pyrrolo[3,2-c]pyridine-3-carboxylic acid

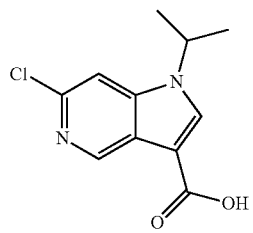 [SMILES: CC(C)n1cc(C(=O)O)c2cnc(Cl)cc21]

Into a 500 mL 3-necked round-bottom flask purged and maintained with an inert atmosphere of nitrogen, was added a solution of 6-chloro-3-iodo-1-isopropyl-1H-pyrrolo[3,2-c]pyridine (14.0 g, 43.6 mmol) in tetrahydrofuran (150 mL). This was followed by addition of n-BuLi (30 mL, 2.5M solution in heptanes) dropwise with stirring at −78° C. After being stirred for 30 min at −78° C., to the reaction mixture was added $CO_2$ (solid) in several batches at −78° C. The resulting solution was stirred for an additional 60 min while the temperature was maintained at −78° C. The reaction mixture was quenched by addition of saturated ammonium chloride (50 mL). The resulting solution was diluted with $H_2O$ (200 mL), extracted with ethyl acetate (2×300 mL) and the organic layers were separated and combined. The combined organic layer was washed with brine (500 mL), dried over anhydrous sodium sulfate and concentrated under vacuum to afford the title compound (7.00 g, 67.0%) as a yellow solid. LCMS (ESI): $R_T$ (min)=1.254, [M+H]$^+$=239, method=M; $^1$H NMR (300 MHz, DMSO-d6) δ 12.58 (s, 1H), 8.95 (s, 1H), 8.35 (s, 1H), 7.89 (s, 1H), 4.92-4.83 (m, 1H), 1.50-1.43 (m, 6H).

Step 4: N-(2-(1H-Imidazol-1-yl)ethyl)-6-chloro-1-isopropyl-1H-pyrrolo[3,2-c]pyridine-3-carboxamide

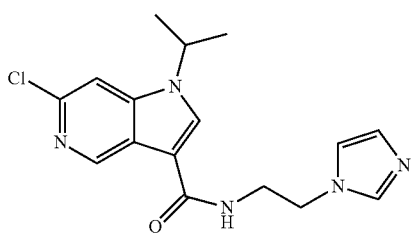 [SMILES: CC(C)n1cc(C(=O)NCCn2ccnc2)c2cnc(Cl)cc21]

Into a 25 mL vial was added a solution of 6-chloro-1-isopropyl-1H-pyrrolo[3,2-c]pyridine-3-carboxylic acid (300 mg, 1.26 mmol) in N,N-dimethylformamide (5 mL), 2-(1H-imidazol-1-yl)ethan-1-amine (280 mg, 2.52 mmol), HBTU (600 mg, 1.58 mmol) and DIPEA (500 mg, 3.87 mmol). The reaction mixture was stirred for 3 h at room temperature. The solids were filtered out and the filtrate was concentrated under vacuum. The crude product was purified by silica gel chromatography with dichloromethane/methanol (100:10) to afford the title compound (500 mg) as yellow oil. LCMS (ESI): $R_T$ (min)=0.604, [M+H]$^+$=332, method=G.

Step 5: N-(2-(1H-Imidazol-1-yl)ethyl)-1-isopropyl-6-(2-(4-methoxypiperidin-1-yl)pyrimidin-4-ylamino)-1H-pyrrolo[3,2-c]pyridine-3-carboxamide

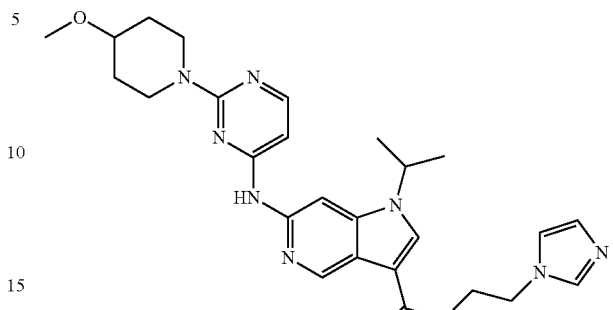

Into a 30 mL sealed tube was added a solution of N-(2-(1H-imidazol-1-yl)ethyl)-6-chloro-1-isopropyl-1H-pyrrolo[3,2-c]pyridine-3-carboxamide (300 mg, 0.900 mmol) in 1,4-dioxane (10 mL), 2-(4-methoxypiperidin-1-yl)pyrimidin-4-amine (Example 3, step 2) (189 mg, 0.910 mmol), XantPhos (105 mg, 0.180 mmol), Pd$_2$(dba)$_3$.CHCl$_3$ (93.0 mg, 0.0900 mmol) and Cs$_2$CO$_3$ (870 mg, 2.67 mmol). The reaction mixture was heated under microwave radiation for 75 min at 140° C. The solids were filtered out and the filtrate was concentrated under vacuum. The residue was purified by silica gel chromatography with dichloromethane/methanol (10:1) to afford the title compound (57.4 mg, 13.0%) as a light yellow solid. LCMS (ESI): $R_T$ (min)=1.816, [M+H]$^+$=504.45, method=J; $^1$H NMR (300 MHz, DMSO-d6) δ 9.81 (s, 1H), 8.99 (s, 1H), 8.37 (s, 1H), 8.19-8.17 (m, 1H), 8.12 (s, 1H), 7.96-7.95 (m, 1H), 7.63 (s, 1H), 7.20 (s, 1H), 6.89 (s, 1H), 6.35-6.33 (m, 1H), 4.64-4.57 (m, 1H), 4.26-4.15 (m, 4H), 3.60-3.56 (m, 2H), 3.48-3.30 (m, 6H), 1.93-1.90 (m, 2H), 1.52-1.50 (m, 6H), 1.47-1.23 (m, 2H).

Example 64: N-Ethyl-1-isopropyl-6-((2-(4-methoxypiperidin-1-yl)pyrimidin-4-yl)amino)-1H-pyrrolo[3,2-c]pyridine-3-carboxamide

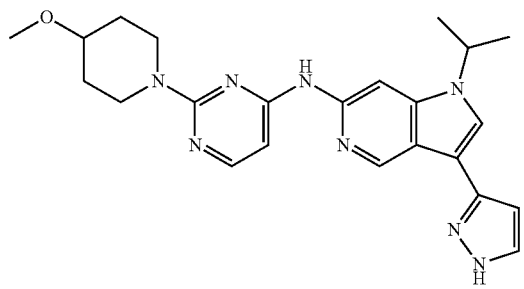 [SMILES: COC1CCN(c2nccc(Nc3cc4c(cn3)c(-c3cc[nH]n3)cn4C(C)C)n2)CC1]

Step 1: 6-Chloro-1-isopropyl-3-(1H-pyrazol-3-yl)-1H-pyrrolo[3,2-c]pyridine

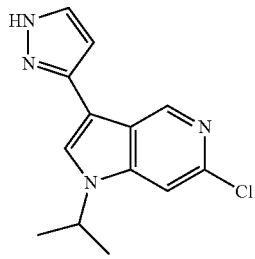 [SMILES: CC(C)n1cc(-c2cc[nH]n2)c2cnc(Cl)cc21]

To a glass vial was added 6-chloro-3-iodo-1-isopropyl-1H-pyrrolo[3,2-c]pyridine (Example 63, step 2) (0.15 g, 0.47 mmol), 3-(4,4,5,5-tetramethyl-1,3,2-dioxaborolan-2-yl)-1H-pyrazole (0.11 g, 0.56 mmol), bis(di-tert-butyl(4-dimethylaminophenyl)phosphine)dichloropalladium(II) (35 mg, 0.047 mmol), a 2M solution of sodium carbonate (0.5 mL, 0.94 mmol) and acetonitrile (2.5 mL). The reaction vial was sealed and stirred at 100° C. for 1 h. The reaction was filtered, concentrated and purified by flash chromatography on silica gel (solvent gradient: 0-100% EtOAc in heptane) to give the title compound (0.12 g, 98%).

Step 2: N-Ethyl-1-isopropyl-6-((2-(4-methoxypiperidin-1-yl)pyrimidin-4-yl)amino)-1H-pyrrolo[3,2-c]pyridine-3-carboxamide

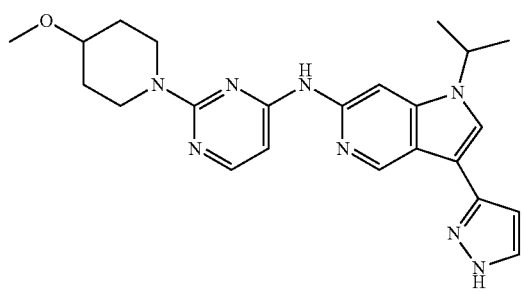 [SMILES: COC1CCN(c2nccc(Nc3cc4c(cn3)c(-c3cc[nH]n3)cn4C(C)C)n2)CC1]

To a glass vial was added 2-(4-methoxy-1-piperidyl)pyrimidin-4-amine (Example 3, step 2) (0.056 g, 0.27 mmol), 6-chloro-1-isopropyl-3-(1H-pyrazol-3-yl)-1H-pyrrolo[3,2-c]pyridine (0.070 g, 0.27 mmol), sodium t-butoxide (80 mg, 0.81 mmol), t-BuOH (2.5 mL) and Chloro{[BrettPhos][2-(2-aminoethylphenyl)palladium(II)]}/[BrettPhos] admixture (molar PdP/P=1:1) (50 mg). The reaction was degassed by nitrogen bubbling for 15 min. The reaction vial was sealed and heated at 120° C. for 3 h in an oil bath. The reaction was then filtered, concentrated and purified by preparatory reverse-phase HPLC to give the title compound (19.8 mg, 17%). LCMS (ESI): $R_T$ 3.95 min, $[M+H]^+$ 433.3, method=B; $^1$H NMR (400 MHz, DMSO-$d_6$) δ 12.68 (s, 1H), 9.71 (s, 1H), 9.05 (s, 1H), 8.33 (s, 1H), 7.95 (d, J=5.7 Hz, 1H), 7.85 (s, 1H), 7.73 (s, 1H), 6.64 (d, J=2.1 Hz, 1H), 6.36 (d, J=5.7 Hz, 1H), 4.61 (m, 1H), 4.26 (m, 2H), 3.57-3.35 (m, 3H), 2.05-1.83 (m, 2H), 1.53 (d, J=6.7 Hz, 6H), 1.49-1.35 (m, 2H).

Each compound in Table 1 below was prepared following a similar experimental procedure (using appropriately substituted reagents) as described in another Example herein, such Example being referenced in the Synthesis Method column.

TABLE 1

| Example | Structure/Name | Synthesis Method/ Example # | LCMS $R_T$ (min), $M + H^+$, method | $^1$H NMR (ppm) |
|---|---|---|---|---|
| 65 | 1-isopropyl-N-(2-(3-methoxypyrrolidin-1-yl)pyrimidin-4-yl)-1H-imidazo[4,5-c]pyridin-6-amine | 35 | 1.156, 354, N | $^1$H NMR (400 MHz, DMSO-$d_6$) δ 9.80 (s, 1H), 8.68-8.65 (d, 2H), 8.33 (s, 1H), 7.95-7.94 (d, 1H), 6.36-6.34 (d, 1H), 4.71-4.65 (m, 1H), 4.09 (m, 1H), 3.67-3.54 (m, 4H), 3.32 (s, 3H), 2.07 (s, 2H). 1.58-1.56 (m, J = 6.6 Hz, 6H) |
| 66 | 1-(4-(1-isopropyl-1H-imidazo[4,5-c]pyridin-6-ylamino)pyrimidin-2-yl)piperidine-3-carboxamide | 35 | 1.725, 381.20, I | $^1$H NMR (400 MHz, DMSO-$d_6$) 9.84 (s, 1H), 8.66 (s, 1H), 8.40 (s, 1H), 8.35 (s, 1H), 8.34-7.98 (d, 1H), 7.37 (s, 1H), 6.86 (s, 1H), 6.39-6.38 (d, 1H), 4.72-4.55 (m, 3H), 3.00-2.94 (t, 1H), 2.89-2.83 (t, 1H), 2.34-2.29 (m, 1H), 1.92-1.95 (d, 1H), 1.75-1.61 (m, 2H), 1.59-1.52 (m, 6H), 1.49-1.39 (m, 1H) |

TABLE 1-continued

| Example | Structure/Name | Synthesis Method/ Example # | LCMS $R_T$ (min), M + H$^+$, method | $^1$H NMR (ppm) |
|---|---|---|---|---|
| 67 | N-(1-(4-(1-isopropyl-1H-imidazo[4,5-c]pyridin-6-ylamino)pyrimidin-2-yl)azetidin-3-yl)acetamide | 35 | 1.450, 367.25, L | $^1$H NMR (300 MHz, DMSO-d$_6$) δ 9.88 (s, 1H), 8.64 (s, 1H), 8.55 (s, 1H), 8.53 (s, 1H), 8.32 (s, 1H), 7.96-7.94 (d, 1H), 6.49-6.47 (d, 1H), 4.67-4.63 (m, 1H), 4.60-4.56 (m, 1H), 4.34-4.28 (t, 2H), 3.89-3.85 (m, 2H), 1.84 (s, 3H), 1.57-1.54 (d, J = 6.7 Hz, 6H) |
| 68 | 1-(5-(4-(1-isopropyl-1H-imidazo[4,5-c]pyridin-6-ylamino)pyrimidin-2-yl)-hexahydropyrrolo[3,4-c]pyrrol-2(1H)-yl)ethanone | 35 | 1.476, 407.30, M | $^1$NMR (400 MHz, DMSO-d$_6$) δ 9.82 (s, 1H), 8.67 (s, 1H), 8.64 (s, 1H), 8.32 (s, 1H), 7.96-7.94 (d, 1H), 6.36-6.35 (d, 1H), 4.71-4.67 (m, 1H), 3.78-3.73 (m, 2H), 3.58-3.33 (m, 5H), 3.09-2.98 (m, 2H), 1.94 (s, 3H), 1.58-1.55 (m, 6H) |
| 69 | 1-isopropyl-N-(2-(5-(methylsulfonyl)-hexahydropyrrolo[3,4-c]pyrrol-2(1H)-yl)pyrimidin-4-yl)-1H-imidazo[4,5-c]pyridin-6-amine | 35 | 1.078, 443.30, M | $^1$H NMR (400 MHz, DMSO-d$_6$) δ 9.83 (s, 1H), 8.66 (s, 1H), 8.65 (s, 1H), 8.33 (s, 1H), 7.96-7.95 (d, 1H), 6.38-6.36 (d, 1H), 4.69 (m, 1H), 3.90-3.70 (m, 2H), 3.57-3.51 (m, 4H), 3.18-3.10 (m, 4H), 2.64 (s, 3H), 1.58-1.56 (d, J = 6.7 Hz, 6H) |
| 70 | 4-(4-(1-isopropyl-1H-imidazo[4,5-c]pyridin-6-ylamino)pyrimidin-2-yl)piperazine-1-carboxamide | 35 | 1.719, 382.20, I | $^1$H NMR (300 MHz, DMSO-d$_6$) δ 9.85 (s, 1H), 8.66 (s, 1H), 8.39 (s, 1H), 8.33 (s, 1H), 8.00-7.98 (d, 1H), 6.45-6.43 (d, 1H), 6.09 (s, 2H), 4.71-4.66 (m, 1H), 3.75-3.72 (m, 4H), 3.41-3.38 (m, 4H), 1.59-1.57 (d, J = 6.8 Hz, 6H) |

TABLE 1-continued

| Example | Structure/Name | Synthesis Method/ Example # | LCMS $R_T$ (min), M + H[+], method | $^1$H NMR (ppm) |
|---|---|---|---|---|
| 71 | 1-isopropyl-N-(2-(7-(methylsulfonyl)-2,7-diazaspiro[4.4]nonan-2-yl)pyrimidin-4-yl)-1H-imidazo[4,5-c]pyridin-6-amine | 35 | 3.023, 457.05, J | $^1$H NMR (300 MHz, DMSO-$d_6$) δ 9.81 (s, 1H), 8.67 (s, 1H), 8.64 (s, 1H), 8.32 (s, 1H), 7.95-7.93 (d, 1H), 6.35-6.33 (d, 1H), 4.71-4.62 (m, 1H), 3.62 (m, 4H), 3.35-3.43 (m, 2H), 3.39-3.27 (m, 2H), 2.95 (s, 3H), 2.07-1.88 (m, 4H), 1.59-1.56 (m, 6H) |
| 72 | 1-isopropyl-N-(2-(3-methoxypiperidin-1-yl)pyrimidin-4-yl)-1H-imidazo[4,5-c]pyridin-6-amine | 35 | 1.436, 368.20, L | $^1$H NMR (300 MHz, DMSO-$d_6$) δ 9.81 (s, 1H), 8.66 (s, 1H), 8.41 (s, 1H), 8.35 (s, 1H), 7.97-7.95 (d, 1H), 6.38-6.37 (d, 1H), 4.70-4.61 (m, 1H), 4.21-4.16 (m, 1H), 4.04-3.98 (m, 1H), 3.53-3.43 (m, 2H), 3.33 (s, 1 H), 3.27 (s, 3H), 2.02-1.96 (m, 1H), 1.76-1.73 (m, 1H), 1.52-1.58 (m, 8H) |
| 73 | 1-(1-(4-(1-isopropyl-1H-imidazo[4,5-c]pyridin-6-ylamino)pyrimidin-2-yl)piperidin-4-yl)urea | 35 | 1.876, 396.20, H | $^1$H NMR (400 MHz, DMSO-$d_6$) δ 9.88 (s, 1H), 8.66 (s, 1H), 8.41 (s, 1H), 8.35 (s, 1H), 7.98-7.96 (d, 1H), 6.40-6.39 (s, 1H), 6.01-5.99 (m, 1H), 5.38 (s, 2H), 4.69-4.62 (m, 1H), 4.53-4.50 (d, 2H), 3.66-3.64 (m, 1H), 3.15-3.09 (m, 2H), 1.85-1.82 (m, 2H), 1.57-1.55 (d, J = 6.6 Hz, 6H), 1.41-1.27 (m, 2H) |
| 74 | 1-(4-(1-isopropyl-1H-imidazo[4,5-c]pyridin-6-ylamino)pyrimidin-2-yl)-4-methylpiperidine-4-carboxamide | 35 | 1.773, 395, L | $^1$H NMR (400 MHz, DMSO-$d_6$) δ 9.80 (s, 1H), 8.65 (s, 1H), 8.43 (s, 1H), 8.33 (s, 1H), 7.97-7.95 (d, 1H), 7.26 (s, 1H), 6.93 (s, 1H), 6.38-6.36 (d, 1H), 4.69-4.62 (m, 1H), 4.11-4.08 (m, 2H), 3.45-3.40 (m, 2H), 2.04-2.01 (m, 2H), 1.59-1.57 (d, 6H), 1.40-1.31 (m, 2H), 1.15 (s, 3H) |

TABLE 1-continued

| Example | Structure/Name | Synthesis Method/ Example # | LCMS $R_T$ (min), M + H+, method | 1H NMR (ppm) |
|---|---|---|---|---|
| 75 | 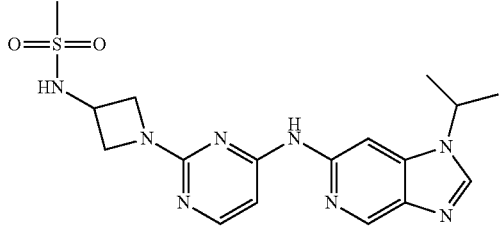 [SMILES: CC(C)n1cnc2cnc(Nc3ccnc(N4CC(NS(C)(=O)=O)C4)n3)cc21]<br>N-(1-(4-(1-isopropyl-1H-imidazo[4,5-c]pyridin-6-ylamino)pyrimidin-2-yl)azetidin-3-yl)methanesulfonamide | 35 | 1.275, 403.10, H | 1H NMR (300 MHz, DMSO-d6) δ 9.91 (s, 1H), 8.65 (s, 1H), 8.58 (s, 1H), 8.33 (s, 1H), 7.96-7.94 (d, 1H), 7.83 (s, 1H), 6.48-6.46 (d, 1H), 4.70-4.62 (m, 1H), 4.40-4.35 (m, 3H), 3.96 (m, 2H), 2.95 (s, 3H), 1.57-1.55 (d, J = 6.7 Hz, 6H) |
| 76 | 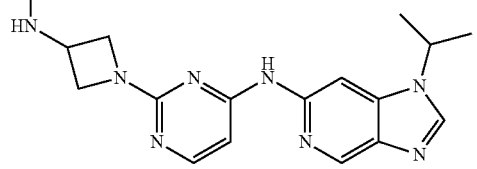<br>1-(1-(4-(1-isopropyl-1H-imidazo[4,5-c]pyridin-6-ylamino)pyrimidin-2-yl)azetidin-3-yl)urea | 35 | 1.143, 368.15, H | 1H NMR (300 MHz, DMSO-d6) δ 9.87 (s, 1H), 8.64 (s, 1H), 8.57 (s, 1H), 8.32 (s, 1H), 7.95-7.93 (d, 1H), 6.70-6.67 (d, 1H), 6.47-6.45 (d, 1H), 5.58 (s, 2H), 4.68-4.63 (m, 1H), 4.47-4.45 (m, 1H), 4.31-4.26 (m, 2H), 3.84-3.80 (m, 2H), 1.57-1.55 (d, J = 6.7 Hz, 6H) |
| 77 | 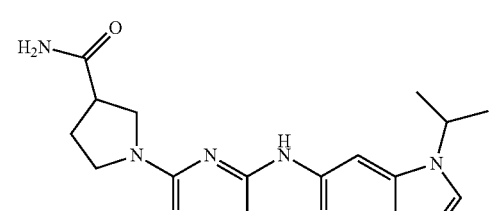<br>1-(4-(1-isopropyl-1H-imidazo[4,5-c]pyridin-6-ylamino)pyrimidin-2-yl)pyrrolidine-3-carboxamide | 35 | 0.966, 367.15, G | 1H NMR (400 MHz, DMSO-d6) δ 9.81 (s, 1H), 8.76 (s, 1H), 8.64 (s, 1H), 8.32 (s, 1H), 7.95-7.94 (d, 1H), 7.49 (s, 1H), 7.02 (s, 1H), 6.33-6.31 (d, 1H), 4.68-4.62 (m, 1H), 3.87-3.50 (m, 4H), 3.08-3.02 (m, 1H), 2.19-2.05 (m, 2H), 1.56-1.53 (m, 6H) |
| 78 | 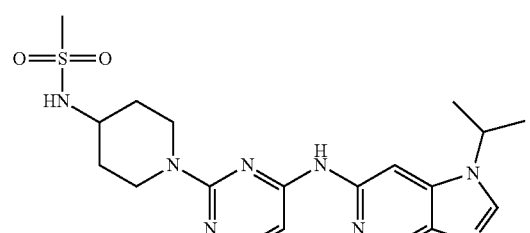<br>N-(1-(4-(1-isopropyl-1H-imidazo[4,5-c]pyridin-6-ylamino)pyrimidin-2-yl)piperidin-4-yl)methanesulfonamide | 35 | 1.401, 431.15, H | 1H NMR (300 MHz, DMSO-d6) δ 9.82 (s, 1H), 8.66 (s, 1H), 8.38 (s, 1H), 8.34 (s, 1H), 7.98-7.96 (d, 1H), 7.14-7.11 (d, 1H), 6.40-6.39 (d, 1H), 4.67-4.63 (m, 1H), 4.57-4.53 (d, 2H), 3.47-3.45 (m, 1H), 3.17-3.06 (m, 2H), 2.96 (s, 3H), 1.92-1.89 (m, 2H), 1.57-1.55 (d, J = 6.7 Hz, 6H), 1.47-1.23 (m, 2H) |

TABLE 1-continued

| Example | Structure/Name | Synthesis Method/ Example # | LCMS R_T (min), M + H+, method | 1H NMR (ppm) |
|---|---|---|---|---|
| 79 | N-(2-(3-aminoazetidin-1-yl)pyrimidin-4-yl)-1-isopropyl-1H-imidazo[4,5-c]pyridin-6-amine | 35 | 0.891, 325.15, L | 1H NMR (300 MHz, DMSO-d6) δ 9.82 (s, 1H), 8.64 (s, 1H), 8.60 (s, 1H), 8.32 (s, 1H), 7.93-7.91 (d, 1H), 6.46-6.40 (d, 1H), 4.70-4.61 (m, 1H), 4.24-4.19 (m, 2H), 3.83-3.77 (m, 1H), 3.70-3.66 (m, 2H), 2.35 (s, 1H), 1.58-1.56 (d, J = 6.8 Hz, 6H) |
| 80 | 1-(4-(1-isopropyl-1H-imidazo[4,5-c]pyridin-6-ylamino)pyrimidin-2-yl)-N,N-dimethylpyrrolidine-3-carboxamide | 35 | 1.050, 395.20, G | 1H NMR (400 MHz, DMSO-d6) δ 9.81 (s, 1H), 8.70 (s, 1H), 8.64 (s, 1H), 8.32 (s, 1H), 7.95-7.94 (d, 1H), 6.34-6.33 (d, 1H), 4.67-4.60 (m, 1H), 3.86-3.65 (m, 3H), 3.55-3.52 (m, 2H), 3.09 (s, 3H), 2.87 (s, 3H), 2.22-2.07 (m, 2H), 1.54-1.52 (d, J = 6.7 Hz, 6H) |
| 81 | 1-isopropyl-N-(2-(4-(oxetan-3-yl)piperazin-1-yl)pyrimidin-4-yl)-1H-imidazo[4,5-c]pyridin-6-amine | 35 | 1.257, 395.15, K | 1H NMR (300 MHz, DMSO-d6) δ 9.83 (s, 1H), 8.65 (s, 1H), 8.37 (s, 1H), 8.33 (s, 1H), 7.99-7.97 (d, 1H), 6.44-6.42 (d, 1H), 4.70-4.48 (m, 5H), 3.80-3.77 (m, 4H), 3.48-3.44 (m, 1H), 2.35-2.32 (m, 4H), 1.56-1.53 (m, 6H) |
| 82 | N4-(1-isopropyl-1H-imidazo[4,5-c]pyridin-6-yl)-N2-(3-methoxypropyl)pyrimidine-2,4-diamine | 35 | 1.396, 342.15, G | 1H NMR (300 MHz, CDCl3) δ 8.76 (s, 1H), 8.42 (s, 1H), 7.96-7.96 (d, 2H), 7.75 (s, 1H), 6.14-6.12 (d, 1H), 5.60 (s, 1H), 4.67-4.58 (m, 1H), 3.66-3.51 (m, 4H), 3.34 (s, 3H), 1.97-1.89 (m, 2H), 1.67-1.64 (d, J = 6.7 Hz, 6H) |
| 83 | 4-(4-(1-isopropyl-1H-imidazo[4,5-c]pyridin-6-ylamino)pyrimidin-2-yl)-1-methylpiperazine-2-carboxamide | 35 | 0.947, 396.25, M | 1H NMR (400 MHz, CD3OD) δ 8.66 (s, 1H), 8.39 (s, 1H), 8.34 (s, 1H), 8.00-7.99 (d, 1H), 6.39-6.41 (d, 1H), 4.88-4.61 (m, 3H), 3.23-3.14 (m, 2H), 3.01-2.97 (m, 1H), 2.88-2.70 (m, 1H), 2.34 (s, 3H), 2.31-2.28 (m, 1H), 1.71-1.63 (m, 6H) |

TABLE 1-continued

| Example | Structure/Name | Synthesis Method/ Example # | LCMS R$_T$ (min), M + H$^+$, method | $^1$H NMR (ppm) |
|---|---|---|---|---|
| 84 | N4-(1-isopropyl-1H-imidazo[4,5-c]pyridin-6-yl)-2,5'-bipyrimidine-2',4-diamine | 35 | 1.095, 348.15, G | $^1$H NMR (300 MHz, DMSO-d$_6$) δ 9.13 (s, 2H), 8.71 (s, 1H), 8.39-8.37 (m, 3H), 7.19-7.15 (m, 3H), 4.80-4.71 (m, 1H), 1.93 (s, 1H), 1.54-1.51 (d, J = 6.7 Hz, 6H) |
| 85 | 3-(4-(1-isopropyl-1H-imidazo[4,5-c]pyridin-6-ylamino)pyrimidin-2-ylamino)-2,2-dimethylpropanamide | 35 | 1.295, 369.20, H | $^1$H NMR (300 MHz, DMSO-d$_6$) δ 9.76 (s, 1H), 8.64 (s, 1H), 8.43 (s, 1H), 8.37 (s, 1H), 7.89-7.87 (d, 1H), 7.19 (s, 1H), 6.94 (s, 1H), 6.41-6.34 (m, 2H), 4.74-4.70 (m, 1H), 3.51-3.50 (d, 2H), 1.56-1.54 (m, 6H), 1.15 (s, 6H) |
| 86 | 3-(4-(1-isopropyl-1H-imidazo[4,5-c]pyridin-6-ylamino)pyrimidin-2-yloxy)propan-1-ol | 35 | 1.518, 329.15, M | $^1$H NMR (300 MHz, DMSO-d$_6$) δ 10.17 (s, 1H), 8.68 (s, 1H), 8.38 (s, 1H), 8.35 (s, 1H), 8.13-8.11 (d, 1H), 6.89-6.88 (d, 1H), 4.71-4.63 (m, 1H), 4.57-4.54 (m, 1H), 4.42-4.38 (m, 2H), 3.58-3.56 (m, 2H), 1.91-1.87 (m, 2H), 1.56-1.54 (d, J = 6.7 Hz, 6H) |
| 87 | 7-(4-(1-isopropyl-1H-imidazo[4,5-c]pyridin-6-ylamino)pyrimidin-2-yl)-tetrahydro-1H-oxazolo[3,4-a]pyrazin-3(5H)-one | 35 | 1.214, 395.20, M | $^1$H NMR (300 MHz, DMSO-d$_6$) δ 9.91 (s, 1H), 8.66 (s, 1H), 8.36 (s, 1H), 8.27 (s, 1H), 8.02-8.00 (d, 1H), 6.49-6.48 (d, 1H), 4.88-4.83 (m, 1H), 4.75-4.65 (m, 2H), 4.46-4.41 (m, 1H), 4.04-4.00 (m, 1H), 3.89 (m, 1H), 3.68-3.64 (m, 1H), 3.08-2.81 (m, 3H), 1.56-1.54 (d, J = 6.7 Hz, 6H) |

TABLE 1-continued

| Example | Structure/Name | Synthesis Method/ Example # | LCMS R$_T$ (min), M + H$^+$, method | $^1$H NMR (ppm) |
|---|---|---|---|---|
| 88 | 2-(1-(4-(1-isopropyl-1H-imidazo[4,5-c]pyridin-6-ylamino)pyrimidin-2-yl)piperidin-4-yloxy)acetamide | 35 | 1.328, 411.15, H | $^1$H NMR (300 MHz, DMSO-d$_6$) δ 9.82 (s, 1H), 8.65 (s, 1H), 8.41 (s, 1H), 8.34 (s, 1H), 7.98-7.96 (d, 1H), 7.27 (s, 1H), 7.16 (s, 1H), 6.38-6.37 (d, 1H), 4.67-4.63 (m, 1H), 4.30-4.25 (m, 2H), 3.88 (s, 2H), 3.64-3.62 (m, 1H), 3.40 (m, 2H), 1.94-1.91 (m, 2H), 1.58-1.59 (d, J = 6.6 Hz, 6H), 1.53-1.50 (m, 2H) |
| 89 | 3-(4-(1-isopropyl-1H-imidazo[4,5-c]pyridin-6-ylamino)pyrimidin-2-ylamino)propanamide | 35 | 1.175, 341.05, H | $^1$H NMR (300 MHz, DMSO-d$_6$) δ 9.74 (s, 1H), 8.63 (s, 1H), 8.54 (s, 1H), 8.36 (s, 1H), 7.89-7.87 (d, 1H), 7.35 (s, 1H), 6.85 (s, 1H), 6.77-6.73 (m, 1H), 6.38-6.35 (d, 1H), 4.70 (m, 1H), 3.56-3.43 (m, 2H), 2.43-2.38 (m, 2H), 1.55-1.52 (d, J = 6.7 Hz, 6H) |
| 90 | 3-(4-(1-isopropyl-1H-imidazo[4,5-c]pyridin-6-ylamino)pyrimidin-2-yloxy)-2,2-dimethylpropan-1-ol | 35 | 1.908, 357.20, M | $^1$H NMR (300 MHz, DMSO-d$_6$) δ 10.21 (s, 1H), 8.69 (s, 1H), 8.39 (s, 2H), 8.12-8.10 (d, 1H), 6.89-6.87 (m, 1H), 4.72-4.65 (m, 2H), 4.10 (s, 2H), 3.30-3.29 (m, 2H), 1.57-1.55 (d, J = 6.7 Hz, 6H), 0.95 (s, 6H) |
| 91 | 1-isopropyl-2-methyl-N-(2-(1-(methylsulfonyl)-1H-pyrazol-4-yl)pyrimidin-4-yl)-1H-imidazo[4,5-c]pyridin-6-amine | 52 | 3.91, 413.2, B | n/a |
| 92 | 1-isopropyl-2-methyl-N-(2-(3-(methylsulfonyl)phenyl)pyrimidin-4-yl)-1H-imidazo[4,5-c]pyridin-6-amine | 52 | 3.96, 423.2, B | $^1$H NMR (400 MHz, DMSO-d$_6$) δ 10.21 (s, 1H), 8.87 (t, J = 1.7 Hz, 1H), 8.75-8.68 (m, 1H), 8.58 (d, J = 0.7 Hz, 1H), 8.52 (d, J = 5.9 Hz, 1H), 8.27 (s, 1H), 8.16-8.07 (m, 1H), 7.83 (t, J = 7.8 Hz, 1H), 7.50 (s, 1H), 4.76 (m, 1H), 2.59 (s, 4H), 1.61 (d, J = 6.9 Hz, 6H). |

TABLE 1-continued

| Example | Structure/Name | Synthesis Method/ Example # | LCMS R$_T$ (min), M + H$^+$, method | $^1$H NMR (ppm) |
|---|---|---|---|---|
| 93 | 1-isopropyl-N-(2-(1-((2-methoxyethyl)sulfonyl)-1H-pyrazol-4-yl)pyrimidin-4-yl)-2-methyl-1H-imidazo[4,5-c]pyridin-6-amine | 52 | 3.78, 457.2, B | n/a |
| 94 | 4-((1-isopropyl-1H-imidazo[4,5-c]pyridin-6-yl)amino)-[2,5'-bipyrimidin]-2'-ol | 53 | 2.96, 349.2, B | $^1$H NMR (400 MHz, DMSO-d$_6$) δ 10.21 (s, 1H), 9.04 (s, 2H), 8.71 (d, J = 0.9 Hz, 1H), 8.45-8.28 (m, 3H), 7.20 (s, 1H), 6.24 (s, 1H), 4.75 (m, 1H), 1.60 (d, J = 6.7 Hz, 6H). |
| 95 | 2-(4-(4-((1-isopropyl-1H-imidazo[4,5-c]pyridin-6-yl)amino)pyrimidin-2-yl)-1H-pyrazol-1-yl)ethanol | 53 | 3.47, 365.2 B | $^1$H NMR (400 MHz, DMSO-d$_6$) δ 10.08 (s, 1H), 8.70 (d, J = 1.0 Hz, 1H), 8.47 (s, 1H), 8.38 (s, 1H), 8.31 (d, J = 5.8 Hz, 1H), 8.28 (d, J = 0.5 Hz, 1H), 8.03 (d, J = 0.6 Hz, 1H), 7.07 (d, J = 5.8 Hz, 1H), 4.97 (t, J = 5.2 Hz, 1H), 4.76 (m, 1H), 4.22 (t, J = 5.4 Hz, 2H), 3.78 (m, 2H), 1.62 (d, J = 6.7 Hz, 6H). |
| 96 | N-(2-(1H-pyrazol-4-yl)pyrimidin-4-yl)-1-isopropyl-1H-imidazo[4,5-c]pyridin-6-amine | 55 | 3.60, 321.2 B | |
| 97 | N-(2-(1-(cyclopropylsulfonyl)-1H-pyrazol-4-yl)pyrimidin-4-yl)-1-isopropyl-1H-imidazo[4,5-c]pyridin-6-amine | 55 | 3.91, 425.2, B | H NMR (400 MHz, DMSO-d$_6$) δ 10.27 (s, 1H), 8.70 (m, 2H), 8.48 (t, J = 5.6 Hz, 2H), 8.40 (d, J = 5.7 Hz, 2H), 7.18 (d, J = 5.1 Hz, 1H), 4.80 (m, 1H), 1.62 (d, J = 6.7 Hz, 5H), 1.41-1.20 (m, 4H). |

TABLE 1-continued

| Example | Structure/Name | Synthesis Method/ Example # | LCMS $R_T$ (min), M + H+, method | ¹H NMR (ppm) |
|---|---|---|---|---|
| 98 | 1-isopropyl-N-(2-(1-isopropyl-1H-pyrazol-4-yl)pyrimidin-4-yl)-1H-imidazo[4,5-c]pyridin-6-amine | 55 | 4.01, 363.2, B | ¹H NMR (400 MHz, DMSO-d₆) δ 8.70 (d, J = 0.9 Hz, 1H), 8.46 (s, 1H), 8.39 (s, 1H), 8.35-8.27 (m, 2H), 8.06-7.94 (m, 1H), 7.07 (d, J = 5.7 Hz, 1H), 4.78 (m, 1H), 4.58 (m, 1H), 1.61 (d, J = 6.8 Hz, 6H), 1.48 (d, J = 6.7 Hz, 6H). |
| 99 | 1-isopropyl-N-(2'-methoxy-[2,5'-bipyrimidin]-4-yl)-1H-imidazo[4,5-c]pyridin-6-amine | 55 | 3.70, 363.2, B | ¹H NMR (400 MHz, DMSO-d₆) δ 10.31 (s, 1H), 9.42 (s, 2H), 8.73 (d, J = 0.9 Hz, 1H), 8.47 (d, J = 5.9 Hz, 1H), 8.38 (d, J = 15.9 Hz, 2H), 7.32 (s, 1H), 4.78 (m, 1H), 4.02 (s, 3H), 1.61 (d, J = 6.8 Hz, 6H). |
| 100 | N-(2-(4-ethoxypiperidin-1-yl)pyrimidin-4-yl)-1-isopropyl-1H-imidazo[4,5-c]pyridin-6-amine | 56 | 3.64, 382.3, B | ¹H NMR (400 MHz, DMSO-d₆) δ 9.77 (s, 1H), 8.65 (d, J = 0.9 Hz, 1H), 8.39 (s, 1H), 8.32 (s, 1H), 7.96 (d, J = 5.7 Hz, 1H), 6.38 (d, J = 5.7 Hz, 1H), 4.77-4.55 (m, 1H), 4.29 (m, 2H), 3.62-3.44 (m, 3H), 1.96-1.82 (m, 2H), 1.56 (d, J = 6.8 Hz, 5H), 1.48-1.32 (m, 2H), 1.13 (t, J = 7.0 Hz, 3H). |
| 101 | N-(2-(1-oxa-7-azaspiro[4.4]nonan-7-yl)pyrimidin-4-yl)-1-isopropyl-1H-imidazo[4,5-c]pyridin-6-amine (single unknown stereoisomer) | 36 | 3.481, 380.2, B | ¹H NMR (400 MHz, DMSO-d₆) δ 9.76 (s, 1H), 8.67 (s, 1H), 8.64 (d, J = 0.9 Hz, 1H), 8.31 (s, 1H), 7.93 (d, J = 5.6 Hz, 1H), 6.33 (d, J = 5.6 Hz, 1H), 4.74-4.62 (m, 1H), 3.85-3.46 (m, 6H), 2.06-1.87 (m, 6H), 1.57 (d, J = 6.8 Hz, 6H). |

TABLE 1-continued

| Example | Structure/Name | Synthesis Method/ Example # | LCMS $R_T$ (min), M + H+, method | ¹H NMR (ppm) |
|---|---|---|---|---|
| 102 | 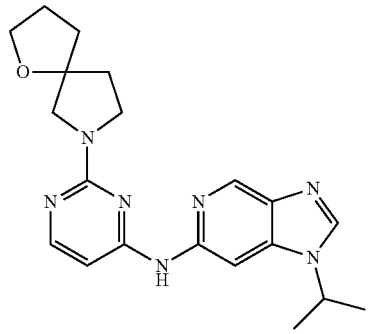 [SMILES: CC(C)n1cnc2cnc(Nc3ccnc(N4CCC5(CCCO5)C4)n3)cc21]

N-(2-(1-oxa-7-azaspiro[4.4]nonan-7-yl)pyrimidin-4-yl)-1-isopropyl-1H-imidazo[4,5-c]pyridin-6-amine (single unknown stereoisomer) | 36 | 3.491, 380.2, B | ¹H NMR (400 MHz, DMSO-d₆) δ 9.76 (s, 1H), 8.67 (s, 1H), 8.64 (d, J = 0.8 Hz, 1H), 8.31 (s, 1H), 7.93 (d, J = 5.6 Hz, 1H), 6.33 (d, J = 5.7 Hz, 1H), 4.73-4.61 (m, 1H), 3.87-3.46 (m, 6H), 2.08-1.85 (m, 6H), 1.57 (dd, J = 6.7, 1.8 Hz, 6H). |
| 103 | 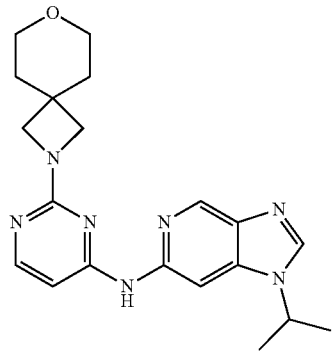 [SMILES: CC(C)n1cnc2cnc(Nc3ccnc(N4CC5(CCOCC5)C4)n3)cc21]

N-(2-(7-oxa-2-azaspiro[3.5]nonan-2-yl)pyrimidin-4-yl)-1-isopropyl-1H-imidazo[4,5-c]pyridin-6-amine | 36 | 3.373, 380.2, B | ¹H NMR (400 MHz, DMSO-d₆) δ 9.81 (s, 1H), 8.65 (s, 2H), 8.64 (s, 2H), 8.31 (s, 1H), 7.93 (d, J = 5.7 Hz, 1H), 6.41 (d, J = 5.7 Hz, 1H), 4.77-4.63 (m, 1H), 3.84 (s, 4H), 3.56 (br s, 4H), 1.77 (t, J = 5.2 Hz, 4H), 1.59 (d, J = 6.7 Hz, 6H). |
| 104 | 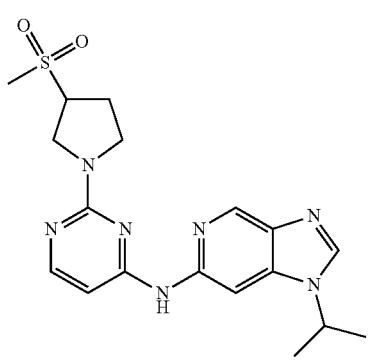 [SMILES: CC(C)n1cnc2cnc(Nc3ccnc(N4CCC(S(C)(=O)=O)C4)n3)cc21]

1-isopropyl-N-(2-(3-(methylsulfonyl)pyrrolidin-1-yl)pyrimidin-4-yl)-1H-imidazo[4,5-c]pyridin-6-amine (single unknown stereoisomer) | 36 | 3.182, 402.2, B | ¹H NMR (400 MHz, DMSO-d₆) δ 9.84 (s, 1H), 8.64 (s, 2H), 8.33 (s, 1H), 7.97 (d, J = 5.6 Hz, 1H), 6.41 (d, J = 5.7 Hz, 1H), 4.65 (p, J = 6.7 Hz, 1H), 4.17-4.07 (m, 1H), 4.02-3.90 (m, 2H), 3.84-3.70 (m, 1H), 3.71-3.58 (m, 1H), 3.07 (s, 3H), 2.45-2.37 (m, 2H), 1.56 (t, J = 6.5 Hz, 6H). |

TABLE 1-continued

| Example | Structure/Name | Synthesis Method/ Example # | LCMS R$_T$ (min), M + H$^+$, method | $^1$H NMR (ppm) |
|---|---|---|---|---|
| 105 | 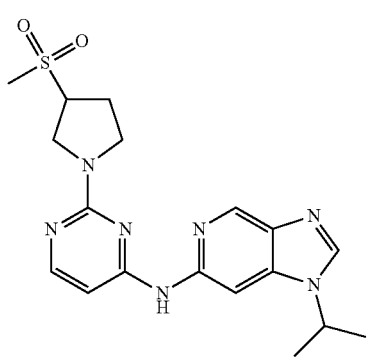 [SMILES: CC(C)n1cnc2cnc(Nc3ccnc(N4CCC(S(C)(=O)=O)C4)n3)cc21]<br>1-isopropyl-N-(2-(3-(methylsulfonyl)pyrrolidin-1-yl)pyrimidin-4-yl)-1H-imidazo[4,5-c]pyridin-6-amine (single unknown stereoisomer) | 36 | 3.140, 402.2, B | $^1$H NMR (400 MHz, DMSO-d$_6$) δ 9.84 (s, 1H), 8.65 (s, 2H), 8.33 (s, 1H), 7.97 (d, J = 5.6 Hz, 1H), 6.41 (d, J = 5.7 Hz, 1H), 4.65 (p, J = 6.7 Hz, 1H), 4.20-4.04 (m, 1H), 4.02-3.89 (m, 2H), 3.84-3.72 (m, 1H), 3.70-3.56 (m, 1H), 3.07 (s, 3H), 2.45-2.37 (m, 2H), 1.56 (t, J = 6.5 Hz, 6H). |
| 106 | 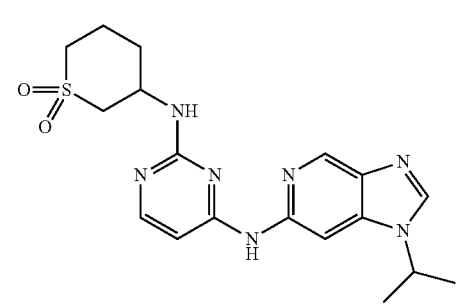 [SMILES: CC(C)n1cnc2cnc(Nc3ccnc(NC4CCCS(=O)(=O)C4)n3)cc21]<br>3-((4-((1-isopropyl-1H-imidazo[4,5-c]pyridin-6-yl)amino)pyrimidin-2-yl)amino)tetrahydro-2H-thiopyran 1,1-dioxide | 39 | 3.080, 402.2, B | $^1$H NMR (400 MHz, DMSO-d$_6$) δ 9.69 (s, 1H), 8.64 (d, J = 1.0 Hz, 1H), 8.39 (s, 1H), 8.21 (s, 1H), 7.93 (d, J = 5.7 Hz, 1H), 6.83 (s, 1H), 6.53 (d, J = 5.8 Hz, 1H), 4.76 (p, J = 6.7 Hz, 1H), 4.38 (d, J = 10.0 Hz, 1H), 3.39 (d, J = 13.8 Hz, 1H), 3.28-3.25 (m, 1H), 3.13-3.05 (m, 2H), 2.16-2.05 (m, 1H), 2.01 (d, J = 13.9 Hz, 1H), 1.81 (s, 1H), 1.65-1.50 (m, 7H). |
| 107 | 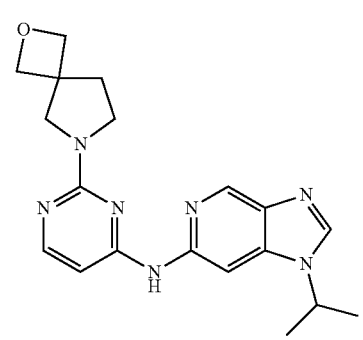 [SMILES: CC(C)n1cnc2cnc(Nc3ccnc(N4CCC5(COC5)C4)n3)cc21]<br>N-(2-(2-oxa-6-azaspiro[3.4]octan-6-yl)pyrimidin-4-yl)-1-isopropyl-1H-imidazo[4,5-c]pyridin-6-amine | 36 | 3.694, 366.2, B | $^1$H NMR (400 MHz, DMSO-d$_6$) δ 9.78 (s, 1H), 8.70 (s, 1H), 8.64 (d, J = 0.9 Hz, 1H), 8.33 (s, 1H), 7.94 (d, J = 5.7 Hz, 1H), 6.34 (d, J = 5.7 Hz, 1H), 4.81-4.66 (m, 1H), 4.63-4.49 (m, 4H), 3.86 (s, 2H), 3.56 (s, 2H), 2.26 (t, J = 6.9 Hz, 2H), 1.61 (d, J = 6.7 Hz, 6H). |

TABLE 1-continued

| Example | Structure/Name | Synthesis Method/ Example # | LCMS R$_T$ (min), M + H$^+$, method | $^1$H NMR (ppm) |
|---|---|---|---|---|
| 108 | 3-((4-((1-isopropyl-1H-imidazo[4,5-c]pyridin-6-yl)amino)pyrimidin-2-yl)amino)cyclobutanol | 36 | 3.462, 340.2, B | $^1$H NMR (400 MHz, DMSO-d$_6$) δ 9.68 (s, 1H), 8.63 (d, J = 0.8 Hz, 1H), 8.49 (s, 1H), 8.37 (d, J = 2.0 Hz, 1H), 7.86 (d, J = 5.6 Hz, 1H), 7.04 (s, 1H), 6.34 (s, 1H), 5.06 (s, 0.5H), 4.98 (s, 0.5H), 4.83-4.62 (m, 1H), 4.55 (s, 0.5H), 4.32 (s, 0.5H), 4.00-3.87 (m, 1H), 3.88-3.77 (m, 1H), 2.71-2.56 (m, 1H), 2.26-2.18 (m, 1H), 1.94-1.79 (m, 1H), 1.58 (dd, J = 6.7, 3.0 Hz, 6H). |
| 109 | 3-((4-((1-isopropyl-1H-imidazo[4,5-c]pyridin-6-yl)amino)pyrimidin-2-yl)amino)tetrahydrothiophene 1,1-dioxide (single unknown stereoisomer) | 39 | 3.470, 388.2, B | $^1$H NMR (400 MHz, DMSO-d$_6$) δ 9.73 (s, 1H), 8.65 (d, J = 0.9 Hz, 1H), 8.38 (s, 1H), 8.20 (s, 1H), 7.94 (d, J = 5.7 Hz, 1H), 7.14 (s, 1H), 6.57 (d, J = 5.7 Hz, 1H), 4.78-4.64 (m, 2H), 3.56 (dd, J = 13.3, 7.5 Hz, 1H), 3.44-3.36 (m, 1H), 3.28-3.25 (m, 1H), 3.18-3.08 (m, 1H), 3.08-2.99 (m, 1H), 2.55-2.46 (m, 1H), 2.28-2.18 (m, 1H), 1.55 (dd, J = 6.7, 2.9 Hz, 6H). |
| 110 | 2-(difluoromethyl)-1-isopropyl-N-(2-(4-methoxypiperidin-1-yl)pyrimidin-4-yl)-1H-imidazo[4,5-c]pyridin-6-amine | 40 | 4.167, 418.3, B | $^1$H NMR (400 MHz, DMSO-d$_6$) δ 9.91 (s, 1H), 8.80 (d, J= 1.0 Hz, 1H), 8.53 (d, J = 1.0 Hz, 1H), 8.00 (d, J = 5.6 Hz, 1H), 7.43 (t, J = 52.0 Hz, 1H), 6.43 (d, J = 5.6 Hz, 1H), 4.94 (p, J = 6.9 Hz, 1H), 4.34-4.17 (m, 2H), 3.54-3.45 (m, 1H), 3.45-3.36 (m, 2H), 3.30 (s, 3H), 1.98-1.84 (m, 2H), 1.63 (d, J = 6.9 Hz, 6H), 1.53-1.35 (m, 2H). |

TABLE 1-continued

| Example | Structure/Name | Synthesis Method/ Example # | LCMS $R_T$ (min), M + H+, method | ¹H NMR (ppm) |
|---|---|---|---|---|
| 111 | 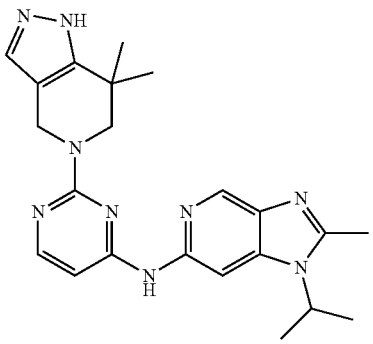 [SMILES: Cc1nc2cnc(Nc3ccnc(N4Cc5cn[nH]c5C(C)(C)C4)n3)cc2n1C(C)C]<br>N-(2-(7,7-dimethyl-6,7-dihydro-1H-pyrazolo[4,3-c]pyridin-5(4H)-yl)pyrimidin-4-yl)-1-isopropyl-2-methyl-1H-imidazo[4,5-c]pyridin-6-amine | 46 | 3.534, 418.3, B | ¹H NMR (400 MHz, DMSO-d₆) δ 12.55 (d, J = 78.6 Hz, 1H), 9.67 (s, 1H), 8.51 (d, J = 0.9 Hz, 1H), 8.34 (s, 1H), 7.99 (d, J = 5.6 Hz, 1H), 7.34 (d, J = 61.9 Hz, 1H), 6.50 (d, J = 5.7 Hz, 1H), 4.86-4.67 (m, 3H), 3.87 (s, 2H), 2.58 (s, 3H), 1.65 (d, J = 6.9 Hz, 6H), 1.25 (s, 6H). |
| 112 | 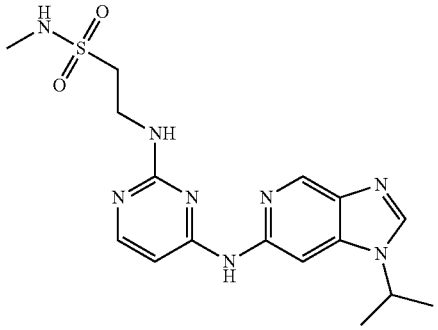 [SMILES: CNS(=O)(=O)CCNc1nccc(Nc2cc3c(cn2)ncn3C(C)C)n1]<br>2-((4-((1-isopropyl-1H-imidazo[4,5-c]pyridin-6-yl)amino)pyrimidin-2-yl)amino)-N-methylethanesulfonamide | 43 | 3.028, 391.2, B | ¹H NMR (400 MHz, DMSO-d₆) δ 9.72 (s, 1H), 8.64 (d, J = 1.1 Hz, 1H), 8.37 (s, 2H), 7.93 (d, J = 5.7 Hz, 1H), 6.97 (s, 1H), 6.81 (t, J = 5.9 Hz, 1H), 6.49 (d, J = 5.7 Hz, 1H), 4.79-4.68 (m, 1H), 3.77-3.64 (m, 2H), 3.36-3.32 (m, 2H), 2.58 (s, 3H), 1.55 (d, J = 6.7 Hz, 6H). |
| 113 | 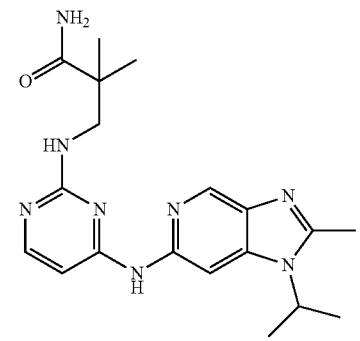 [SMILES: Cc1nc2cnc(Nc3ccnc(NCC(C)(C)C(N)=O)n3)cc2n1C(C)C]<br>3-((4-((1-isopropyl-2-methyl-1H-imidazo[4,5-c]pyridin-6-yl)amino)pyrimidin-2-yl)amino)-2,2-dimethylpropanamide | 46 | 3.50, 383.2, C | ¹H NMR (400 MHz, DMSO-d₆) δ 9.56 (s, 1H), 8.48 (d, J = 0.8 Hz, 1H), 8.30 (s, 1H), 7.88 (d, J = 5.7 Hz, 1H), 7.19 (s, 1H), 6.94 (s, 1H), 6.52 (d, J = 5.7 Hz, 1H), 6.00 (s, 1H), 4.72 (p, J = 6.9 Hz, 1H), 3.46 (d, J = 5.9 Hz, 2H), 2.56 (s, 3H), 1.57 (d, J = 6.9 Hz, 6H), 1.14 (s, 6H). |

TABLE 1-continued

| Example | Structure/Name | Synthesis Method/ Example # | LCMS R$_T$ (min), M + H$^+$, method | $^1$H NMR (ppm) |
|---|---|---|---|---|
| 114 | 1-isopropyl-6-((2-(4-methoxypiperidin-1-yl)pyrimidin-4-yl)amino)-N-(1-methylpiperidin-4-yl)-1H-pyrrolo[3,2-c]pyridine-3-carboxamide | 57 | 3.27, 507.4, B | $^1$H NMR (400 MHz, DMSO-d$_6$) δ 9.74 (s, 1H), 9.01 (s, 1H), 8.34 (s, 1H), 8.18 (s, 1H), 7.95 (d, J = 5.7 Hz, 1H), 7.78 (d, J = 7.7 Hz, 1H), 6.34 (d, J = 5.7 Hz, 1H), 4.60 (m, 1H), 4.24 (m, 2H), 3.81-3.61 (m, 1H), 3.57-3.43 (m, 1H), 3.39 (m, 2H), 2.78 (m, 2H), 2.18 (s, 3H), 1.94 (m, 4H), 1.81 (d, J = 9.7 Hz, 2H), 1.62-1.37 (m, 9H). |
| 115 | 1-isopropyl-6-((2-(4-methoxypiperidin-1-yl)pyrimidin-4-yl)amino)-1H-pyrrolo[3,2-c]pyridine-3-carboxamide | 57 | 3.54, 411.3, B | $^1$H NMR (400 MHz, DMSO-d$_6$) δ 9.76 (s, 1H), 9.01 (s, 1H), 8.35 (s, 1H), 8.16 (s, 1H), 7.95 (d, J = 5.7 Hz, 1H), 7.46 (s, 1H), 6.95 (s, 1H), 6.34 (d, J = 5.7 Hz, 1H), 4.60 (m, 1H), 4.24 (m, 2H), 3.59-3.43 (m, 1H), 3.38 (m, 2H), 1.99-1.83 (m, 2H), 1.62-1.34 (m, 8H). |
| 116 | 1-isopropyl-6-((2-(4-methoxypiperidin-1-yl)pyrimidin-4-yl)amino)-1H-pyrrolo[3,2-c]pyridine-3-carboxylic acid | 57 | 3.31, 410.3, B | $^1$H NMR (400 MHz, DMSO-d$_6$) δ 9.80 (s, 1H), 8.89 (s, 1H), 8.40 (s, 1H), 8.10 (s, 1H), 7.96 (d, J = 5.7 Hz, 1H), 6.35 (d, J = 5.7 Hz, 1H), 4.63 (m, 1H), 4.24 (m, 2H), 3.46 (m, 1H), 3.44-3.34 (m, 2H), 2.02-1.85 (m, 2H), 1.53 (d, J = 6.7 Hz, 5H), 1.43 (m, 2H). |

TABLE 1-continued

| Example | Structure/Name | Synthesis Method/ Example # | LCMS R$_T$ (min), M + H$^+$, method | $^1$H NMR (ppm) |
|---|---|---|---|---|
| 117 | 1-isopropyl-6-((2-(4-methoxypiperidin-1-yl)pyrimidin-4-yl)amino)-N-(tetrahydro-2H-pyran-4-yl)-1H-pyrrolo[3,2-c]pyridine-3-carboxamide | 57 | 3.63, 494.3, B | $^1$H NMR (400 MHz, DMSO-d$_6$) δ 9.74 (s, 1H), 9.01 (d, J = 0.8 Hz, 1H), 8.34 (s, 1H), 8.18 (s, 1H), 7.95 (d, J = 5.6 Hz, 1H), 7.84 (d, J = 7.7 Hz, 1H), 6.35 (d, J = 5.7 Hz, 1H), 4.61 (m, 1H), 4.24 (m, 2H), 4.14-3.96 (m, 1H), 3.96-3.82 (m, 2H), 3.53-3.34 (m, 5H), 1.97-1.86 (m, 2H), 1.81 (m, 2H), 1.64-1.36 (m, 10H). |
| 118 | (1-isopropyl-6-((2-(4-methoxypiperidin-1-yl)pyrimidin-4-yl)amino)-1H-pyrrolo[3,2-c]pyridin-3-yl)(morpholino)methanone | 57 | 3.56, 480.3, B | $^1$H NMR (400 MHz, DMSO-d$_6$) δ 9.74 (s, 1H), 8.68 (d, J = 0.9 Hz, 1H), 8.35 (s, 1H), 7.95 (d, J = 5.6 Hz, 1H), 7.82 (s, 1H), 6.35 (d, J = 5.7 Hz, 1H), 4.61 (m, 1H), 4.20 (m, 2H), 3.65 (m, 5H), 3.59-3.31 (m, 6H), 2.90 (m, 1H), 2.33 (t, J = 7.3 Hz, 1H), 1.89 (s, 2H), 1.67 (m, 1H), 1.53 (m, 4H), 1.42 (m, 3H), 1.17 (d, J = 11.4 Hz, 2H). |
| 119 | (1-isopropyl-6-((2-(4-methoxypiperidin-1-yl)pyrimidin-4-yl)amino)-1H-pyrrolo[3,2-c]pyridin-3-yl)(pyrrolidin-1-yl)methanone | 57 | 3.78, 464.3, B | $^1$H NMR (400 MHz, DMSO-d$_6$) δ 9.74 (s, 1H), 8.98 (d, J = 0.9 Hz, 1H), 8.35 (s, 1H), 7.95 (d, J = 5.7 Hz, 1H), 7.88 (s, 1H), 6.34 (d, J = 5.7 Hz, 1H), 4.64 (m, 1H), 4.32-4.20 (m, 2H), 3.80-3.34 (m, 8H), 1.90 (s, 7H), 1.54 (d, J = 6.7 Hz, 6H), 1.51-1.35 (m, 3H), 1.17 (d, J = 12.2 Hz, 1H). |

TABLE 1-continued

| Example | Structure/Name | Synthesis Method/ Example # | LCMS $R_T$ (min), M + H$^+$, method | $^1$H NMR (ppm) |
|---|---|---|---|---|
| 120 | N,1-diisopropyl-6-((2-(4-methoxypiperidin-1-yl)pyrimidin-4-yl)amino)-1H-pyrrolo[3,2-c]pyridine-3-carboxamide | 57 | 3.80, 452.3, B | $^1$H NMR (400 MHz, DMSO-d$_6$) δ 9.75 (s, 1H), 9.02 (d, J = 0.7 Hz, 1H), 8.34 (s, 1H), 8.17 (s, 1H), 7.95 (d, J = 5.6 Hz, 1H), 7.75 (d, J = 7.7 Hz, 1H), 6.34 (d, J = 5.7 Hz, 1H), 4.60 (m, 1H), 4.25 (mz, 2H), 4.11 (m, 1H), 3.55-3.44 (m, 1H), 3.44-3.33 (m, 2H), 1.91 (m, 2H), 1.58-1.38 (m, 8H), 1.18 (d, J = 6.6 Hz, 6H). |
| 121 | N-(2-hydroxyethyl)-1-isopropyl-6-((2-(4-methoxypiperidin-1-yl)pyrimidin-4-yl)amino)-1H-pyrrolo[3,2-c]pyridine-3-carboxamide | 57 | 3.34, 454.3, B | $^1$H NMR (400 MHz, DMSO-d$_6$) δ 9.76 (s, 1H), 9.01 (d, J = 0.8 Hz, 1H), 8.35 (s, 1H), 8.18 (s, 1H), 7.99 (t, J = 5.7 Hz, 1H), 7.95 (d, J = 5.6 Hz, 1H), 6.34 (d, J = 5.6 Hz, 1H), 4.72 (s, 1H), 4.60 (m, 1H), 4.23 (m, 2H), 3.59-3.32 (m, 6H), 1.90 (s, 2H), 1.57-1.36 (m, 7H). |
| 122 | (4-ethylpiperazin-1-yl)(1-isopropyl-6-((2-(4-methoxypiperidin-1-yl)pyrimidin-4-yl)amino)-1H-pyrrolo[3,2-c]pyridin-3-yl)methanone | 57 | 3.28, 507.4, B | $^1$H NMR (400 MHz, DMSO-d$_6$) δ 9.74 (s, 1H), 8.65 (d, J = 0.9 Hz, 1H), 8.35 (s, 1H), 7.95 (d, J = 5.6 Hz, 1H), 7.79 (s, 1H), 6.35 (d, J = 5.7 Hz, 1H), 4.62 (m, 1H), 4.32-4.18 (m, 2H), 3.76-3.59 (m, 3H), 3.53-3.42 (m, 1H), 3.44-3.34 (m, 2H), 2.38 (m, 5H), 1.89 (s, 2H), 1.57-1.38 (m, 6H), 1.02 (t, J = 7.2 Hz, 3H). |
| 123 | 6-((2-(4-ethoxypiperidin-1-yl)pyrimidin-4-yl)amino)-1-isopropyl-1H-pyrrolo[3,2-c]pyridine-3-carboxamide | 57 | 3.55, 424.3, B | $^1$H NMR (400 MHz, DMSO-d$_6$) δ 9.77 (s, 1H), 9.01 (d, J = 0.9 Hz, 1H), 8.35 (s, 1H), 8.17 (s, 1H), 7.95 (d, J = 5.7 Hz, 1H), 7.48 (s, 1H), 6.96 (s, 1H), 6.34 (d, J = 5.7 Hz, 1H), 4.67-4.51 (m, 1H), 4.39-4.23 (m, 2H), 3.63-3.46 (m, 3H), 1.98-1.85 (m, 2H), 1.51 (d, J = 6.7 Hz, 6H), 1.46-1.37 (m, 2H), 1.13 (t, J = 7.0 Hz, 3H). |

TABLE 1-continued

| Example | Structure/Name | Synthesis Method/ Example # | LCMS R$_T$ (min), M + H$^+$, method | $^1$H NMR (ppm) |
|---|---|---|---|---|
| 124 | 6-((2-(4-isopropoxypiperidin-1-yl)pyrimidin-4-yl)amino)-1-isopropyl-1H-pyrrolo[3,2-c]pyridine-3-carboxamide | 57 | 3.70, 438.3, B | $^1$H NMR (400 MHz, DMSO-d$_6$) δ 9.76 (s, 1H), 9.01 (d, J = 0.9 Hz, 1H), 8.35 (s, 1H), 8.16 (s, 1H), 7.94 (d, J = 5.6 Hz, 1H), 7.46 (s, 1H), 6.93 (s, 1H), 6.34 (d, J = 5.7 Hz, 1H), 4.60 (m, 1H), 4.28 (m, 2H), 3.82-3.70 (m, 1H), 3.70-3.56 (m, 1H), 1.85 (d, J = 9.5 Hz, 2H), 1.51 (d, J = 6.7 Hz, 6H), 1.39 (m, 2H), 1.10 (d, J = 6.1 Hz, 6H). |
| 125 | 6-((2-(4-cyclopropoxypiperidin-1-yl)pyrimidin-4-yl)amino)-1-isopropyl-1H-pyrrolo[3,2-c]pyridine-3-carboxamide | 57 | 3.49, 436.3, B | n/a |
| 126 | 6-((2-((1,1-dioxidotetrahydrothiophen-3-yl)amino)pyrimidin-4-yl)amino)-1-isopropyl-1H-pyrrolo[3,2-c]pyridine-3-carboxamide | 57 | 3.32, 430.2, B | n/a |
| 127 | 2-{[4-(1-Isopropyl-1H-pyrrolo[3,2-c]pyridin-6-ylamino)pyrimidin-2-yl]methylamino}ethanol | 18 | 1.94, 326.9, E | $^1$H NMR (400 MHz, CDCl$_3$) δ 8.59 (1H, d, J =1.0 Hz), 8.26 (1H, s), 7.96 (1H, d, J = 5.8 Hz), 7.52 (1H, s), 7.18 (1H, d, J = 3.4 Hz), 6.55 (1H, d, J = 3.4 Hz), 6.11 (1H, d, J = 5.8 Hz), 4.70-4.57 (1H, m), 3.96-3.89 (2H, m), 3.86-3.80 (2H, m), 3.33 (3H, s), 1.56 (6H, d, J = 6.8 Hz). |

TABLE 1-continued

| Example | Structure/Name | Synthesis Method/ Example # | LCMS R$_T$ (min), M + H$^+$, method | $^1$H NMR (ppm) |
|---|---|---|---|---|
| 128 | 2-{Methyl-[4-(1-phenyl-1H-pyrrolo[3,2-c]pyridin-6-ylamino)pyrimidin-2-yl]amino}ethanol | 18 | 2.51, 360.9, E | $^1$H NMR (400 MHz, CDCl$_3$) δ 8.63 (1H, s), 8.42 (1H, s), 7.90 (1H, d, J = 5.7 Hz), 7.55-7.46 (5H, m), 7.44-7.36 (1H, m), 7.26 (1H, d, J = 3.5 Hz), 6.70 (1H, d, J = 3.5 Hz), 6.01 (1H, d, J = 5.8 Hz), 3.80-3.70 (2H, m), 3.69-3.62 (2H, m), 2.98 (3H, s), 1.61 (1H, s). |
| 129 | (1-Isopropyl-1H-pyrrolo[3,2-c]pyridin-6-yl)-[2-(4-methoxypiperidin-1-yl)pyrimidin-4-yl]amine formate salt | 18 | 2.44, 366.9, E | $^1$H NMR (400 MHz, DMSO-d$_6$) δ 9.61 (1H, s), 8.52 (1H, d, J = 0.9 Hz), 8.29 (1H, s), 8.15 (0.8H, s), 7.93 (1H, d, J = 5.7 Hz), 7.45 (1H, d, J = 3.3 Hz), 6.51 (1H, d, J = 3.3 Hz), 6.35 (1H, d, J = 5.7 Hz), 4.65-4.51 (1H, m), 4.28-4.18 (2H, m), 3.50-3.41 (1H, m), 3.40-3.31 (2H, m), 3.29 (3H, s), 1.95-1.84 (2H, m), 1.48 (6H, d, J = 6.7 Hz), 1.45-1.36 (2H, m). |
| 130 | (1-Isopropyl-1H-imidazo[4,5-c]pyridin-6-yl)-(2-piperidin-1-yl-pyrimidin-4-yl)amine | 18 | 2.44, 338.1, E | $^1$H NMR (400 MHz, CDCl$_3$) δ 8.75 (1H, d, J = 1.0 Hz), 8.45 (1H, d, J = 1.0 Hz), 8.05 (1H, d, J = 5.6 Hz), 7.93 (1H, s), 7.45 (1H, s), 6.00 (1H, d, J = 5.3 Hz), 4.65-4.52 (1H, m), 3.89-3.81 (4H, m), 1.77-1.61 (12H, m). |
| 131 | 1-[4-(1-Isopropyl-1H-imidazo[4,5-c]pyridin-6-ylamino)pyrimidin-2-yl]piperidine-4-carboxylic acid amide | 18 | 1.86, 381.2, E | $^1$H NMR (400 MHz, CDCl$_3$) δ 8.74 (1H, d, J = 1.00 Hz), 8.32 (1H, d, J = 1.0 Hz), 8.03 (1H, d, J = 5.6 Hz), 7.92 (1H, s), 7.51 (1H, s), 6.07 (1H, d, J = 5.7 Hz), 5.54-5.36 (2H, br), 4.84 (2H, d, J = 13.4 Hz), 4.63-4.49 (1H, m), 3.02 (2H, td, J = 12.6, 2.7 Hz), 2.51-2.39 (1H, m), 2.01-1.92 (2H, m), 1.82-1.70 (2H, m), 1.64 (6H, d, J = 6.8 Hz). |
| 132 | 4-[4-(1-Isopropyl-1H-imidazo[4,5-c]pyridin-6-ylamino)pyrimidin-2-yl]piperazin-2-one | 18 | 1.83, 353.1, E | $^1$H NMR (400 MHz, DMSO-d$_6$) δ 9.90 (1H, s), 8.66 (1H, d, J = 1.0 Hz), 8.44 (1H, s), 8.35 (1H, s), 8.07 (1H, s), 8.01 (1H, d, J = 5.7 Hz), 6.47 (1H, d, J = 5.7 Hz), 4.78-4.63 (1H, m), 4.24 (2H, s), 3.93 (2H, t, J = 5.3 Hz), 3.34-3.24 (2H, m), 1.56 (6H, d, J = 6.7 Hz). |

TABLE 1-continued

| Example | Structure/Name | Synthesis Method/ Example # | LCMS $R_T$ (min), $M + H^+$, method | $^1$H NMR (ppm) |
|---|---|---|---|---|
| 133 | (1-Isopropyl-1H-imidazo[4,5-c]pyridin-6-yl)-[2-(4-pyrazol-1-ylpiperidin-1-yl)pyrimidin-4-yl]amine | 18 | 2.37, 404.2, E | $^1$H NMR (400 MHz, CDCl$_3$) δ 8.77 (1H, d, J = 1.0 Hz), 8.33 (1H, d, J = 1.0 Hz), 8.07 (1H, d, J = 5.7 Hz), 7.94 (1H, s), 7.59 (1H, s), 7.53 (1H, g, J = 2.4 Hz), 7.45 (1H, d, J = 2.4 Hz), 6.28 (1H, t, J = 2.1 Hz), 6.12 (1H, d, J = 5.7 Hz), 4.99 (2H, d, J = 13.6 Hz), 4.63-4.52 (1H, m), 4.52-4.38 (1H, m), 3.18-3.08 (2H, m), 2.28-2.20 (2H, m), 2.12-2.98 (2H, m), 1.64 (6H, d, J = 6.9 Hz). |
| 134 | [2-(4-Imidazol-1-yl-piperidin-1-yl)pyrimidin-4-yl]-(1-isopropyl-1H-imidazo[4,5-c]pyridin-6-yl)amine | 18 | 1.60, 404.2, E | $^1$H NMR (400 MHz, CDCl$_3$) δ 8.77 (1H, s), 8.22 (1H, s), 8.07 (1H, d, J = 5.7 Hz), 7.93 (1H, s), 7.66 (1H, s), 7.58 (1H, s), 7.08 (1H, s), 6.97 (1H, s), 6.18 (1H, d, J = 5.7 Hz), 5.06-4.96 (2H, m), 4.63-4.47 (1H, m), 4.31-4.17 (1H, m), 3.10-3.00 (2H, m), 2.20-2.11 (2H, m), 2.03-1.89 (2H, m), 1.64 (6H, d, J = 8.0 Hz). |
| 135 | (1-Isopropyl-1H-imidazo[4,5-c]pyridin-6-yl)-[2-(4-[1,2,4]triazol-1-ylpiperidin-1-yl)pyrimidin-4-yl]amine | 1 | 2.02, 405.2, E | $^1$H NMR (400 MHz, CDCl$_3$) δ 8.78 (1H, d, J = 1.0 Hz), 8.25 (1H, s), 8.13 (1H, s), 8.08 (1H, d, J = 5.7 Hz), 7.97 (1H, s), 7.94 (1H, s), 7.59 (1H, s), 6.18 (1H, d, J = 5.7 Hz), 5.04-4.94 (2H, m), 4.63-4.44 (2H, m), 3.21-3.11 (2H, m), 2.31-2.22 (2H, m), 2.15-2.01 (2H, m), 1.65 (6H, d, J = 7.3 Hz). |
| 136 | (1-Isopropyl-1H-imidazo[4,5-c]pyridin-6-yl)-(2-[1,2]oxazinan-2-ylpyrimidin-4-yl)amine | 28 | 2.26, 340.1, E | $^1$H NMR (400 MHz, CDCl$_3$) δ 8.76 (1H, d, J = 1.0 Hz), 8.45 (1H, s), 8.17 (1H, d, J = 5.7 Hz), 7.94 (1H, s), 7.74 (1H, s), 6.33 (1H, d, J = 5.7 Hz), 4.67-4.54 (1H, m), 4.18-4.12 (2H, m), 4.06-3.99 (2H, m), 1.90-1.79 (4H, m), 1.66 (6H, d, J = 7.3 Hz). |

TABLE 1-continued

| Example | Structure/Name | Synthesis Method/ Example # | LCMS R$_T$ (min), M + H$^+$, method | $^1$H NMR (ppm) |
|---|---|---|---|---|
| 137 | (1-Isopropyl-1H-imidazo[4,5-c]pyridin-6-yl)-(2-thiomorpholin-4-ylpyrimidin-4-yl)amine | 28 | 2.36, 356.3, E | $^1$H NMR (400 MHz, CDCl$_3$) δ 8.75 (1H, d, J = 1.0 Hz), 8.22 (1H, d, J = 1.0 Hz), 8.03 (1H, d, J = 5.6 Hz), 7.93 (1H, s), 7.61 (1H, s), 6.10 (1H, d, J = 5.7 Hz), 4.61-4.48 (1H, m), 4.23-4.16 (4H, m), 2.70-2.63 (4H, m), 1.64 (6H, d, J = 6.6 Hz). |
| 138 | {1-[4-(1-isopropyl-1H-imidazo[4,5-c]pyridin-6-ylamino)pyrimidin-2-yl]piperidin-4-ylmethyl}dimethylamtnonium formate | 28 | 1.63, 395.1, E | $^1$H NMR (400 MHz, DMSO-d$_6$) δ 9.77 (1H, s), 8.65 (1H, d, J = 0.9 Hz), 8.42 (1H, s), 8.33 (1H, s), 7.96 (1H, d, J = 5.6 Hz), 6.36 (1H, d, J = 5.7 Hz), 4.73-4.61 (3H, m), 2.97-2.84 (2H, m), 2.13 (6H, s), 2.08 (2H, d, J = 6.7 Hz), 1.81-1.68 (3H, m), 1.57 (6H, d, J = 6.8 Hz), 1.15-0.99 (2H, m). |
| 139 | 2-{1-[4-(1-Isopropyl-1H-imidazo[4,5-c]pyridin-6-ylamino)pyrimidin-2-yl]piperidin-4-yl}ethanol | 28 | 2.17, 382.1, E | $^1$H NMR (400 MHz, CDCl$_3$) δ 8.75 (1H, s), 8.41 (1H, s), 8.04 (1H, d, J = 5.6 Hz), 7.94 (1H, s), 7.53 (1H, s), 6.03 (1H, d, J = 5.6 Hz), 4.85-4.76 (2H, m), 4.65-4.52 (1H, m), 3.76 (2H, t, J = 6.5 Hz), 3.00-2.88 (2H, m), 1.84-1.75 (3H, m), 1.67 (6H, d, J = 6.9 Hz), 1.61-1.53 (2H, m), 1.44 (1H, s), 1.36-1.22 (2H, m). |
| 140 | 2-{[4-(1-Cyclopentyl-1H-pyrrolo[3,2-c]pyridin-6-ylamino)pyrimidin-2-yl]methylamino}ethanol formate salt | 18 | 2.26, 352.9, E | $^1$H NMR (400 MHz, CDCl$_3$) δ 10.44 (1H, br s), 8.62-8.47 (2H, m), 8.37 (1H, s), 7.93 (1H, d, J = 5.8 Hz), 7.20 (1H, d, J = 3.9 Hz), 6.57 (1H, d, J = 3.4 Hz), 6.22 (1H, d, J = 5.8 Hz), 4.81-4.68 (1H, m), 3.92-3.84 (2H, m), 3.83-3.76 (2H, m), 3.28 (3H, s), 2.27-2.13 (2H, m), 1.96-1.70 (6H, m). |

TABLE 1-continued

| Example | Structure/Name | Synthesis Method/ Example # | LCMS R<sub>T</sub> (min), M + H<sup>+</sup>, method | $^1$H NMR (ppm) |
|---|---|---|---|---|
| 141 | (1-Isopropyl-1H-imidazo[4,5-c]pyridin-6-yl)-[2-(1-oxa-8-azaspiro[4.5]dec-8-yl)pyrimidin-4-yl]amine formate salt | 20 | 2.51, 394.2, E | $^1$H NMR (400 MHz, CDCl$_3$) δ 8.71 (1H, d, J = 1.0 Hz), 8.50 (1H, s), 8.47-8.28 (1H, br m), 8.06 (1H, d, J = 5.7 Hz), 7.98 (1H, s), 6.09 (1H, d, J = 5.7 Hz), 4.65-4.52 (1H, m), 4.26-4.17 (2H, m), 3.91 (2H, t, J = 6.8 Hz), 3.75-3.65 (2H, m), 2.05-1.92 (2H, m), 1.78-1.60 (12H, m). |
| 142 | 1-{4-[4-(1-Isopropyl-1H-imidazo[4,5-c]pyridin-6-ylamino)pyrimidin-2-yl]piperazin-1-yl}ethanone formate salt | 20 | 1.97, 381.2, E | $^1$H NMR (400 MHz, CDCl$_3$) δ 8.75 (1H, d, J = 1.0 Hz), 8.24 (1H, s), 8.07 (1H, d, J = 5.7 Hz), 7.96 (1H, s), 7.74 (1H, s), 6.20 (1H, d, J = 5.7 Hz), 4.63-4.51 (1H, m), 3.95-3.85 (4H, m), 3.76-3.70 (2H, m), 3.59-3.53 (2H, m), 2.17 (3H, s), 1.67 (6H, d, J = 6.8 Hz). |
| 143 | 2-{1-[4-(1-Isopropyl-1H-imidazo[4,5-c]pyridin-6-ylamino)-pyrimidin-2-yl]-piperidin-4-yl}-propan-2-ol | 20 | 2.28, 396.2, E | $^1$H NMR (400 MHz, CDCl$_3$) δ 8.76 (1H, d, J = 1.0 Hz), 8.41 (1H, d, J = 1.0 Hz), 8.05 (1H, d, J = 5.6 Hz), 7.94 (1H, s), 7.52 (1H, s), 6.04 (1H, d, J = 5.6 Hz), 4.97-4.89 (2H, m), 4.66-4.53 (1H, m), 2.89 (2H, td, J = 12.8, 2.5 Hz), 1.86 (2H, d, J = 12.8 Hz), 1.69-1.56 (7H, m), 1.45-1.32 (2H, m), 1.31 (1H, s), 1.22 (6H, s). |
| 144 | (1-Isopropyl-1H-imidazo[4,5-c]pyridin-6-yl)-[2-(4-methoxy-4-methylpiperidin-1-yl)pyrimidin-4-yl]amine | 20 | 2.46, 382.1, E | $^1$H NMR (400 MHz, DMSO-d$_6$) δ 9.78 (1H, s), 8.65 (1H, d, J = 1.0 Hz), 8.42 (1H, s), 8.33 (1H, s), 7.96 (1H, d, J = 5.6 Hz), 6.37 (1H, d, J = 5.7 Hz), 4.98-4.59 (1H, m), 4.27-4.17 (2H, m), 3.39-3.27 (2H, m), 3.16 (3H, s), 1.78-1.69 (2H, m), 1.60-1.41 (8H, m), 1.15 (3H, s). |

TABLE 1-continued

| Example | Structure/Name | Synthesis Method/ Example # | LCMS R$_T$ (min), M + H$^+$, method | $^1$H NMR (ppm) |
|---|---|---|---|---|
| 145 | 1-[4-(1-Isopropyl-1H-imidazo[4,5-c]pyridin-6-ylamino)pyrimidin-2-yl]azetidine-3-carbonitrile | 20 | 2.05, 335.1, E | $^1$H NMR (400 MHz, DMSO-d$_6$) δ 9.94 (1H, s), 8.65 (1H, d, J = 1.0 Hz), 8.44 (1H, s), 8.34 (1H, s), 7.98 (1H, d, J = 5.8 Hz), 6.57 (1H, d, J = 5.8 Hz), 4.76-4.61 (1H, m), 4.37 (2H, t, J = 8.5 Hz), 4.24-4.15 (2H, m), 3.91-3.82 (1H, m), 1.57 (6H, d, J = 6.7 Hz). |
| 146 | 1-[4-(1-Isopropyl-1H-imidazo[4,5-c]pyridin-6-ylamino)pyrimidin-2-yl]azetidin-3-ol | 13 | 1.85, 326.0, E | $^1$H NMR (400 MHz, DMSO-d$_6$) δ 9.83 (1H, s), 8.63 (1H, d, J = 1.0 Hz), 8.56 (1H, s), 8.31 (1H, s), 7.93 (1H, d, J = 5.7 Hz), 6.43 (1H, d, J = 5.7 Hz), 5.66 (1H, d, J = 6.4 Hz), 4.72-4.61 (1H, m), 4.60-4.51 (1H, m), 4.26 (2H, t, J = 7.7 Hz), 3.85-3.77 (2H, m), 1.57 (6H, d, J = 6.7 Hz). |
| 147 | N$^4$-(1-Isopropyl-1H-imidazo[4,5-c]pyridin-6-yl)-N$^2$-(R)-tetrahydrofuran-3-ylpyrimidine-2,4-diamine | 13 | 2.00, 340.0, E | $^1$H NMR (400 MHz, DMSO-d$_6$) δ 9.71 (1H, s), 8.64 (1H, d, J = 1.0 Hz), 8.41 (1H, s), 8.37 (1H, s), 7.90 (1H, d, J = 5.7 Hz), 7.03 (1H, br s), 6.42 (1H, d, J = 5.7 Hz), 4.69 (1H, br s), 4.58-4.45 (1H, m), 3.99-3.92 (1H, m), 3.91-3.84 (1H, m), 3.77-3.69 (1H, m), 3.56-3.49 (1H, m), 2.25-2.14 (1H, m), 1.98-1.87 (1H, m), 1.55 (6H, d, J = 6.7 Hz). |
| 148 | 1-[4-(1-Isopropyl-1H-imidazo[4,5-c]pyridin-6-ylamino)pyrimidin-2-yl]piperidine-4-carbonitrile | 13 | 2.20, 363.2, E | $^1$H NMR (400 MHz, DMSO-d$_6$) δ 9.86 (1H, s), 8.67 (1H, d, J = 0.9 Hz), 8.38-8.32 (2H, m), 8.00 (1H, d, J = 5.7 Hz), 6.44 (1H, d, J = 5.7 Hz), 4.73-4.59 (1H, m), 4.17-4.07 (2H, m), 3.63-3.51 (2H, m), 3.20-3.11 (1H, m), 2.01-1.91 (2H, m), 1.82-1.68 (2H, m), 1.58 (6H, d, J = 6.8 Hz). |
| 149 | [2-(4-Methoxypiperidin-1-yl)-pyrimidin-4-yl]-[1-(2,2,2-trifluoroethyl)-1H-imidazo[4,5-c]pyridin-6-yl]amine formate salt | 18 | 2.48, 408.1, E | $^1$H NMR (400 MHz, DMSO-d$_6$) δ 9.88 (1H, s), 8.70 (1H, d, J = 0.9 Hz), 8.47 (1H, s), 8.30 (1H, s), 8.14 (1H, s), 7.97 (1H, d, J = 5.6 Hz), 6.35 (1H, d, J = 5.6 Hz), 5.36-5.23 (2H, m), 4.26-4.15 (2H, m), 3.49-3.20 (6H, m), 1.93-1.82 (2H, m), 1.50-1.36 (2H, m). |

TABLE 1-continued

| Example | Structure/Name | Synthesis Method/ Example # | LCMS R$_T$ (min), M + H$^+$, method | $^1$H NMR (ppm) |
|---|---|---|---|---|
| 150 | 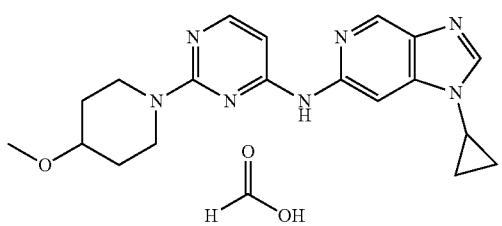<br>(1-Cyclopropyl-1H-imidazo[4,5-c]pyridin-6-yl)-[2-(4-methoxypiperidin-1-yl)pyrimidin-4-yl]amine formate salt | 18 | 2.27, 366.2, E | $^1$H NMR (400 MHz, DMSO-d$_6$) δ 9.84 (1H, s), 8.65 (1H, d, J = 1.0 Hz), 8.50 (1H, s), 8.30-8.15 (2H, m), 7.98 (1H, d, J = 5.6 Hz), 6.38 (1H, d, J = 5.7 Hz), 4.33-4.23 (2H, m), 3.55-3.22 (4H, m), 3.30 (3H, s), 1.99-1.87 (2H, m), 1.51-1.37 (2H, m), 1.08 (4H, d, J = 5.34 Hz). |
| 151 | 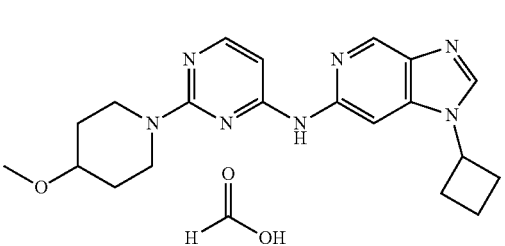<br>(1-Cyclobutyl-1H-imidazo[4,5-c]pyridin-6-yl)-[2-(4-methoxypiperidin-1-yl)pyrimidin-4-yl]amine formate salt | 18 | 2.42, 380.2, E | $^1$H NMR (400 MHz, DMSO-d$_6$) δ 9.77 (1H, s), 8.65 (1H, d, J = 1.0 Hz), 8.39 (1H, s), 8.15 (0.4H, s), 8.29 (1H, s), 7.97 (1H, d, J = 5.7 Hz), 6.40 (1H, d, J = 5.7 Hz), 4.92-4.80 (1H, m), 4.28-4.17 (2H, m), 3.54-3.32 (4H, m), 3.29 (3H, s), 2.61-2.52 (3H, m), 1.96-1.85 (4H, m), 1.50-1.37 (2H, m). |
| 152 | 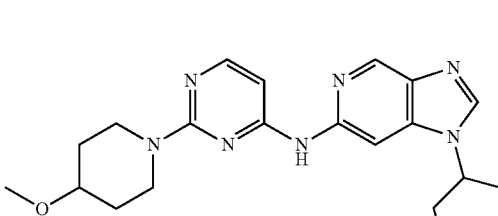<br>(1-Cyclohexyl-1H-imidazo[4,5-c]pyridin-6-yl)-[2-(4-methoxypiperidin-1-yl)pyrimidin-4-yl]amine | 18 | 2.78, 408.2, E | $^1$H NMR (400 MHz, DMSO-d$_6$) δ 9.79 (1H, s), 8.66 (1H, d, J = 0.9 Hz), 8.39-8.30 (2H, m), 7.98 (1H, d, J = 5.6 Hz), 6.37 (1H, d, J = 5.7 Hz), 4.29-4.15 (3H, m), 3.53-3.37 (3H, m), 3.30 (3H, s), 2.13-2.03 (2H, m), 1.96-1.79 (7H, m), 1.54-1.37 (4H, m), 1.36-1.20 (1H, m). |
| 153 | 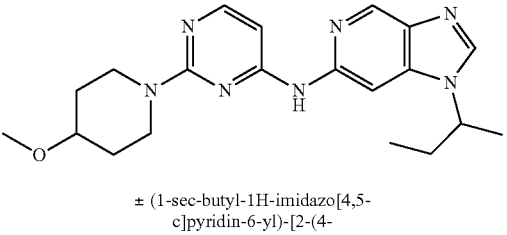<br>± (1-sec-butyl-1H-imidazo[4,5-c]pyridin-6-yl)-[2-(4-methoxypiperidin-1-yl)pyrimidin-4-yl]amine | 18 | 2.46, 382.1, E | $^1$H NMR (400 MHz, DMSO-d$_6$) δ 9.78 (1H, s), 8.65 (1H, d, J = 0.9 Hz), 8.37 (1H, s), 8.32 (1H, s), 7.96 (1H, d, J = 5.7 Hz), 6.37 (1H, d, J = 5.7 Hz), 4.46-4.33 (1H, m), 4.28-4.17 (2H, m), 3.49-3.33 (3H, m), 3.28 (3H, s), 2.03-1.82 (4H, m), 1.54 (3H, d, J = 6.8 Hz), 1.49-1.35 (2H, m), 0.76 (3H, t, J = 7.3 Hz). |

TABLE 1-continued

| Example | Structure/Name | Synthesis Method/ Example # | LCMS $R_T$ (min), M + H+, method | ¹H NMR (ppm) |
|---|---|---|---|---|
| 154 | 1-Isopropyl-1H-imidazo[4,5-c]pyridin-6-yl)-[2-(1,4,6,7-tetrahydroimidazo[4,5-c]pyridin-5-yl)pyrimidin-4-yl]amine | 12 | 1.68, 376.1, E | ¹H NMR (400 MHz, DMSO-d₆ + TFA) δ 9.39 (1H, s), 9.12 (1H, d, J = 0.9 Hz), 9.05 (1H, s), 8.38 (1H, s), 8.18 (1H, d, J = 7.0 Hz), 6.87 (1H, br. s), 5.02-4.88 (3H, m), 4.23-4.11 (2H, m), 2.99-2.91 (2H, m), 1.67 (6H, d, J = 6.8 Hz). |
| 155 | {2-[4-(1,1-Dioxo-1lambda⁶-isothiazolidin-2-yl)piperidin-1-yl]pyrimidin-4-yl}-(1-isopropyl-1H-imidazo[4,5-c]pyridin-6-yl)amine formate salt | 12 | 2.23, 457.1, E | ¹H NMR (400 MHz, DMSO-d₆) δ 9.81 (1H, s), 8.66 (1H, d, J = 0.9 Hz), 8.39 (1H, s), 8.34 (1H, s), 8.17 (1H, s), 7.98 (1H, d, J = 5.7 Hz), 6.40 (1H, d, J = 5.7 Hz), 4.76-4.60 (3H, m), 3.64-3.51 (2H, m), 3.25-3.13 (4H, m), 3.08-2.98 (1H, m), 2.24-2.13 (2H, m), 1.88-1.78 (2H, m), 1.74-1.60 (2H, m), 1.56 (6H, d, J = 6.9 Hz). |
| 156 | (1-Isopropyl-1H-imidazo[4,5-c]pyridin-6-yl)-{2-[4-(2-methoxyethoxy)piperidin-1-yl]pyrimidin-4-yl}amine | 12 | 2.35, 412.2, E | ¹H NMR (400 MHz, DMSO-d₆) δ 9.78 (1H, s), 8.64 (1H, d, J = 1.0 Hz), 8.39 (1H, s), 8.32 (1H, s), 7.96 (1H, d, J = 5.7 Hz), 6.37 (1H, d, J = 5.7 Hz), 4.70-4.57 (1H, m), 4.32-4.20 (2H, m), 3.62-3.53 (3H, m), 3.48-3.41 (2H, m), 3.38-3.27 (2H, m), 3.24 (3H, s), 1.95-1.85 (2H, m), 1.56 (6H, d, J = 6.8 Hz), 1.49-1.36 (2H, m). |
| 157 | [2-(4-Methoxypiperidin-1-yl)pyrimidin-4-yl]-[1-(2,2,2-trifluoro-1-methylethyl)-1H-imidazo[4,5-c]pyridin-6-yl]amine formate salt | 18 | 2.61, 422.1, E | ¹H NMR (400 MHz, DMSO-d₆) δ 9.85 (1H, s), 8.70 (1H, d, J = 0.9 Hz), 8.50 (1H, s), 8.44 (1H, s), 8.14 (1H, s), 7.97 (1H, d, J = 5.6 Hz), 6.36 (1H, d, J = 5.7 Hz), 5.65-5.48 (1H, m), 4.27-4.11 (2H, m), 3.51-3.29 (3H, m), 3.28 (3H, s), 1.92-1.79 (5H, m), 1.50-1.32 (2H, m). |

TABLE 1-continued

| Example | Structure/Name | Synthesis Method/ Example # | LCMS R$_T$ (min), M + H$^+$, method | $^1$H NMR (ppm) |
|---|---|---|---|---|
| 158 | 2-{1-[4-(1-Isopropyl-1H-imidazo[4,5-c]pyridin-6-ylamino)pyrimidin-2-yl]piperidin-4-yl}isobutyramide | 12 | 2.19, 423.2, E | $^1$H NMR (400 MHz, DMSO-d$_6$) δ 9.78 (1H, s), 8.66 (1H, d, J = 0.9 Hz), 8.42 (1H, s), 8.34 (1H, s), 7.97 (1H, d, J = 5.6 Hz), 7.02 (1H, s), 6.83 (1H, s), 6.38 (1H, d, J = 5.7 Hz), 4.81 (2H, d, J = 12.8 Hz), 4.71-4.61 (1H, m), 2.80 (2H, t, J = 12.6 Hz), 1.89-1.78 (1H, m), 1.65-1.52 (8H, m), 1.28-1.12 (2H, m), 1.01 (6H, s). |
| 159 | (1-Isopropyl-1H-imidazo[4,5-c]pyridin-6-yl)-[2-(3-methyl-3,4,6,7-tetrahydroimidazo[4,5-c]pyridin-5-yl)pyrimidin-4-yl]amine | 12 | 1.71, 390.2, E | $^1$H NMR (400 MHz, DMSO-d$_6$) δ 9.85 (1H, s), 8.67 (1H, d, J = 1.0 Hz), 8.42-8.34 (2H, m), 8.02 (1H, d, J = 5.7 Hz), 7.46 (1H, s), 6.49 (1H, d, J = 5.7 Hz), 4.78 (2H, s), 4.75-4.64 (1H, m), 4.11 (2H, t, J = 5.6 Hz), 3.58 (3H, s), 2.68-2.60 (2H, m), 1.59 (6H, d, J = 6.7 Hz). |
| 160 | [2-(3,6-Dihydro-2H-pyridin-1-yl)-pyrimidin-4-yl]-(1-isopropyl-2-methyl-1H-imidazo[4,5-c]pyridin-6-yl)amine | 46 | 2.35, 350.1, E | $^1$H NMR (400 MHz, DMSO-d$_6$) δ 9.72 (1H, s), 8.50 (1H, d, J = 0.9 Hz), 8.45 (1H, s), 7.97 (1H, d, J = 5.7 Hz), 6.42 (1H, d, J = 5.7 Hz), 5.96-5.87 (1H, m), 5.86-5.78 (1H, m), 4.79-4.66 (1H, m), 4.23-4.17 (2H, m), 3.92 (2H, t, J = 5.6 Hz), 2.56 (3H, s), 2.24-2.15 (2H, m), 1.58 (6H, d, J = 6.9 Hz). |
| 161 | {2-[4-(2-Dimethylaminoethoxy)piperidin-1-yl]pyrimidin-4-yl}-(1-isopropyl-1H-imidazo[4,5-c]pyridin-6-yl)amine | 28 | 1.72, 425.2, E | $^1$H NMR (400 MHz, DMSO-d$_6$) δ 9.78 (1H, s), 8.64 (1H, d, J = 0.9 Hz), 8.39 (1H, s), 8.32 (1H, s), 7.96 (1H, d, J = 5.6 Hz), 6.37 (1H, d, J = 5.7 Hz), 4.70-4.58 (1H, m), 4.29-4.19 (2H, m), 3.60-3.48 (3H, m), 3.40-3.26 (2H, m), 2.40 (2H, t, J = 6.1 Hz), 2.15 (6H, s), 1.95-1.83 (2H, m), 1.56 (6H, d, J = 6.8 Hz), 1.48-1.36 (2H, m). |

TABLE 1-continued

| Example | Structure/Name | Synthesis Method/ Example # | LCMS $R_T$ (min), M + H+, method | 1H NMR (ppm) |
|---|---|---|---|---|
| 162 | {2-[4-(2-Dimethylaminoethyl)-piperidin-1-yl]pyrimidin-4-yl}-(1-isopropyl-1H-imidazo[4,5-c]pyridin-6-yl)amine | 28 | 1.73, 409.2, E | 1H NMR (400 MHz, DMSO-$d_6$) δ 9.76 (1H, s), 8.64 (1H, d, J = 0.9 Hz), 8.42 (1H, s), 8.32 (1H, s), 7.94 (1H, d, J = 5.6 Hz), 6.34 (1H, d, J = 5.7 Hz), 4.72-4.57 (3H, m), 2.93-2.80 (2H, m), 2.23 (2H, t, J = 7.3 Hz), 2.10 (6H, s), 1.72 (2H, d, J = 12.8 Hz), 1.64-1.49 (7H, m), 1.40-1.30 (2H, m), 1.18-1.00 (2H, m). |
| 163 | (1-tert-butyl-2-methyl-1H-imidazo[4,5-c]pyridin-6-yl)-[2-(4-methoxypiperidin-1-yl)pyrimidin-4-yl]amine | 18 | 2.35, 396.1, E | 1H NMR (400 MHz, DMSO-$d_6$) δ 9.65 (1H, s), 8.49 (1H, s), 8.44 (1H, s), 7.95 (1H, d, J = 5.7 Hz), 6.47 (1H, d, J = 5.7 Hz), 4.29-4.18 (2H, m), 3.48-3.40 (1H, m), 3.39-3.30 (2H, m), 3.29 (3H, s), 2.73 (3H, s), 1.95-1.85 (2H, m), 1.79 (9H, s), 1.47-1.36 (2H, m). |
| 164 | [1-(2-Methoxy-1,1-dimethylethyl)-2-methyl-1H-imidazo[4,5-c]pyridin-6-yl]-[2-(4-methoxypiperidin-1-yl)pyrimidin-4-yl]amine | 18 | 2.42, 426.2, E | 1H NMR (400 MHz, DMSO-$d_6$) δ 9.63 (1H, s), 8.48 (1H, s), 8.37 (1H, s), 7.95 (1H, d, J = 5.7 Hz), 6.49 (1H, d, J = 5.6 Hz), 4.29-4.18 (2H, m), 3.78 (2H, s), 3.49-3.39 (1H, m), 3.38-3.30 (2H, m), 3.29 (3H, s), 3.19 (3H, s), 2.70 (3H, s), 1.96-1.84 (2H, m), 1.79 (6H, s), 1.47-1.35 (2H, m). |
| 165 | (1-Isopropyl-1H-imidazo[4,5-c]pyridin-6-yl)-[2-(1-methanesulfonylpiperidin-4-yl)pyrimidin-4-yl]amine | 27 | 2.18, 416.1, E | 1H NMR (400 MHz, CDCl$_3$) δ 8.77 (1H, s), 8.66 (1H, s), 8.30 (1H, d, J = 5.9 Hz), 7.97 (1H, s), 7.82 (1H, s), 6.69 (1H, d, J = 5.9 Hz), 4.73-4.60 (1H, m), 4.00-3.90 (2H, m), 3.00-2.89 (1H, m), 2.87-2.79 (5H, m), 2.24-2.10 (4H, m), 1.71 (6H, d, J = 6.8 Hz). |

Each compound in Table 2. below was prepared following one of the following two general synthetic methods (using appropriately substituted reagents) as described below, such method being referenced in the Synthesis Method column:

General Method A:

The appropriately substituted amine (1 equiv., 0.13 mmol) was weighed out into a 1 dram conical vial. To this vial was added N-(2-chloropyrimidin-4-yl)-1-isopropyl-imidazo[4,5-c]pyridin-6-amine (0.667 equiv., 0.087 mmol) dissolved in boiling isopropanol to a concentration of approximately 35 mM. Triethylamine (2 equiv., 0.26 mmol) was then added. The reaction was allowed to proceed at 110° C. overnight or until UPLC analysis indicated complete conversion. The reaction mixture was concentrated under reduced pressure. Any Boc-protected materials were optionally deprotected by shaking in 4M HCl for 2 hours, and acidic solvent then removed under reduced pressure. Following the removal of all volatiles the crude products were dissolved in dichloromethane (2 mL) and washed with sodium bicarbonate (2×1 mL). The organic portion was separated and concentrated under reduced pressure. The crude product was purified via reverse-phase HPLC and lyophilized to yield the desired product.

General Method B:

The appropriately substituted amine (1 equiv., 0.13 mmol) was weighed out into a 1 dram conical vial. To this vial was added N-(2-chloropyrimidin-4-yl)-1-isopropyl-imidazo[4,5-c]pyridin-6-amine (0.667 equiv., 0.087 mmol) dissolved in boiling isopropanol to a concentration of approximately 35 mM. Triethylamine (2 equiv., 0.26 mmol) was then added. The reaction mixtures were subjected to microwave irradiation at 220° C. and 300 psi (or the maximum for the instrument) for 30 minutes. The reaction mixture was concentrated under reduced pressure. Following the removal of all volatiles the crude products were dissolved in dichloromethane (2 mL) and washed with sodium bicarbonate (2×1 mL). The organic portion was separated and concentrated under reduced pressure. The crude product was purified via reverse-phase HPLC and lyophilized to yield the desired product.

TABLE 2

| Example | Structure/Name | Synthesis Method/ Example # | LCMS RT (min), M + H+, method | $^1$H NMR (ppm) |
|---|---|---|---|---|
| 166 | 1-((4-((1-isopropyMH-imidazo [4,5-c] pyridin-6-yl)amino)pyrimidin-2-yl)amino)-2-methylpropan-2-ol | B | 3.519, 342.2, B | $^1$H NMR (400 MHz, DMSO-d$_6$) δ 9.69 (s, 1H), 8.64 (d, J = 0.9 Hz, 1H), 8.48 (s, 1H), 8.36 (s, 1H), 7.88 (d, J = 5.7 Hz, 1H), 6.39 (s, 2H), 4.79-4.71 (m, 1H), 3.36 (d, J = 5.7 Hz, 2H), 3.27 (s, 1H), 1.55 (d, J = 6.7 Hz, 6H), 1.15 (s, 6H). |
| 167 | N2-(cyclopropylmethyl)-N4-(1-isopropyl-1H-imidazo[4,5-c]pyridin-6-yl)pyrimidin-2,4-diamine | B | 3.924, 324.2, B | $^1$H NMR (400 MHz, DMSO-d$_6$) δ 9.68 (s, 1H), 8.63 (d, J = 1.0 Hz, 1H), 8.57 (s, 1H), 8.35 (s, 1H), 7.87 (d, J = 5.6 Hz, 1H), 6.87 (s, 1H), 6.34 (d, J = 5.8 Hz, 1H), 4.71 (br s, 1H), 3.24 (m, 2H), 1.57 (d, J = 6.7 Hz, 6H), 1.17 (br s, 1H), 0.54-0.38 (m, 2H), 0.32-0.17 (m, 2H). |
| 168 | 1-(4-((1-isopropyl-1H-imidazo[4,5-c]pyridin-6-yl)amino)pyrimidin-2-yl)piperidin-3-ol | A | 3.493, 354.2, B | $^1$H NMR (400 MHz, DMSO-d$_6$) δ 9.75 (s, 1H), 8.65 (d, J = 0.9 Hz, 1H), 8.44 (s, 1H), 8.33 (s, 1H), 7.95 (d, J = 5.6 Hz, 1H), 6.35 (d, J = 5.6 Hz, 1H), 4.82 (s, 1H), 4.68 (p, J = 6.7 Hz, 1H), 4.49 (dd, J = 12.5, 4.2 Hz, 1H), 4.35 (d, J = 12.9 Hz, 1H), 3.55-3.41 (m, 1H), 3.11-2.99 (m, 1H), 2.90 (dd, J = 12.5, 9.1 Hz, 1H), 1.98-1.87 (m, 1H), 1.79-1.69 (m, 1H), 1.56 (dd, J = 6.8, 4.6 Hz, 6H), 1.49-1.38 (m, 2H). |

TABLE 2-continued

| Example | Structure/Name | Synthesis Method/ Example # | LCMS RT (min), M + H+, method | 1H NMR (ppm) |
|---|---|---|---|---|
| 169 | 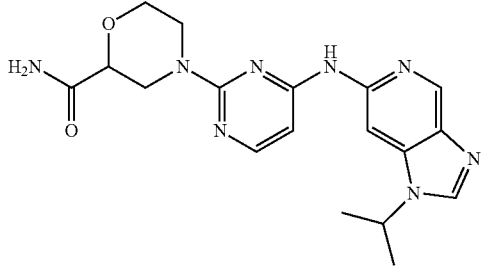<br>4-(4-((1-isopropyl-1H-imidazo[4,5-c]pyridin-6-yl)amino)pyrimidin-2-yl)morpholine-2-carboxamide | A | 3.332, 383.2, B | n/a |
| 170 | 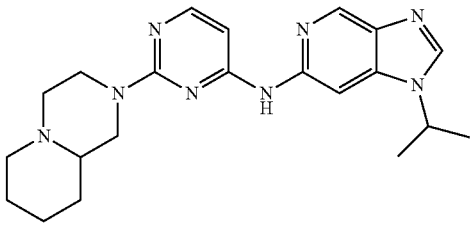<br>N-(2-(hexahydro-1H-pyrido[1,2-a]pyrazin-2(6H)-yl)pyrimidin-4-yl)-1-isopropyl-1H-imidazo[4,5-c]pyridin-6-amine | A | 3.278, 393.3, B | 1H NMR (400 MHz, DMSO-$d_6$) δ 9.78 (s, 1H), 8.65 (s, 1H), 8.36 (s, 1H), 8.34 (s, 1H), 7.97 (d, J = 5.7 Hz, 1H), 6.42 (d, J = 5.6 Hz, 1H), 4.65 (p, J = 6.8 Hz, 1H), 4.57 (d, J = 12.6 Hz, 1H), 4.51-4.41 (m, 1H), 3.05-2.93 (m, 1H), 2.84-2.73 (m, 2H), 2.60 (dd, J = 12.6, 10.5 Hz, 1H), 2.11 (td, J = 11.7, 3.2 Hz, 1H), 2.01-1.90 (m, 1H), 1.84 (t, J = 10.3 Hz, 1H), 1.77-1.67 (m, 1H), 1.62-1.45 (m, 9H), 1.31-1.16 (m, 2H). |
| 171 | 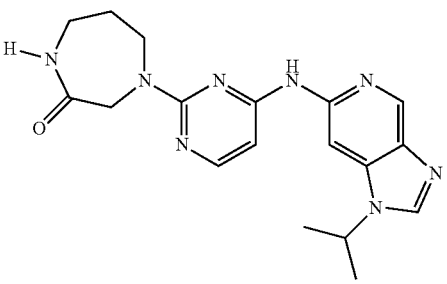<br>4-(4-((1-isopropyl-1H-imidazo[4,5-c]pyridin-6-yl)amino)pyrimidin-2-yl)-1,4-diazepan-2-one | A | 1.84, 367.2, D | n/a |
| 172 | 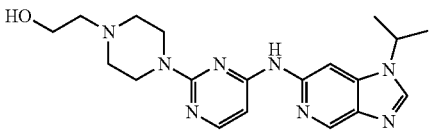<br>2-(4-(4-((1-isopropyl-1H-imidazo[4,5-c]pyridin-6-yl)amino)pyrimidin-2-yl)piperazin-1-yl)ethanol | A | 2.994, 383.2, B | 1H NMR (400 MHz, DMSO-$d_6$) δ 9.79 (s, 1H), 8.65 (d, J = 1.2 Hz, 1H), 8.40 (d, J = 1.0 Hz, 1H), 8.32 (s, 1H), 7.97 (d, J = 5.7 Hz, 1H), 6.41 (d, J = 5.6 Hz, 1H), 4.66 (p, J = 6.8 Hz, 1H), 4.41 (s, 1H), 3.76 (t, J = 5.0 Hz, 4H), 3.55 (t, J = 6.2 Hz, 2H), 3.29-3.24 (m, 2H), 2.49-2.47 (m, 2H), 2.45 (t, J = 6.2 Hz, 2H), 1.56 (d, J = 6.7 Hz, 6H). |

TABLE 2-continued

| Example | Structure/Name | Synthesis Method/ Example # | LCMS RT (min), M + H+, method | 1H NMR (ppm) |
|---|---|---|---|---|
| 173 | N4-(1-isopropyl-1H-imidazo[4,5-c]pyridin-6-yl)-N2-methyl-N2-((tetrahydrofuran-2-yl)methyl)pyrimidine-2,4-diamine | A | 3.762, 368.2, B | 1H NMR (400 MHz, DMSO-d6) δ 9.79-9.64 (m, 1H), 8.64 (s, 1H), 8.46 (s, 1H), 8.34 (s, 1H), 7.95 (d, J = 5.6 Hz, 1H), 6.37 (d, J = 5.7 Hz, 1H), 4.67 (p, J = 6.7 Hz, 1H), 4.09 (p, J = 6.3 Hz, 1H), 3.83-3.56 (m, 4H), 3.22 (s, 3H), 1.97-1.71 (m, 3H), 1.54 (dd, J = 6.8, 1.4 Hz, 7H). |
| 174 | 1-isopropyl-N-(2-(4-(2-methoxyethyl)piperazin-1-yl)pyrimidin-4-yl)-1H-imidazo[4,5-c]pyridin-6-amine | A | 1.44, 397.2, D | 1H NMR (400 MHz, DMSO-d6) δ 9.79 (s, 1H), 8.65 (s, 1H), 8.40 (s, 1H), 8.32 (s, 1H), 7.97 (d, J = 5.6 Hz, 1H), 6.41 (d, J = 5.7 Hz, 1H), 4.66 (p, J = 6.8 Hz, 1H), 3.75 (t, J = 5.0 Hz, 4H), 3.48 (t, J = 5.8 Hz, 2H), 3.25 (s, 3H), 2.56-2.52 (m, 2H), 1.56 (d, J = 6.7 Hz, 6H). |
| 175 | 3-((4-((1-isopropyl-1H-imidazo[4,5-c]pyridin-6-yl)amino)pyrimidin-2-yl)amino)cyclohexanol | B | 3.577, 368.2, B | 1H NMR (400 MHz, DMSO-d6) δ 9.60 (s, 1H), 8.63 (d, J = 0.9 Hz, 1H), 8.38 (s, 1H), 8.31 (s, 1H), 7.87 (d, J = 5.7 Hz, 1H), 6.57 (d, J = 35.4 Hz, 1H), 6.40 (d, J = 5.7 Hz, 1H), 4.79-4.57 (m, 2H), 3.85 (br s, 1H), 3.49 (d, J = 4.2 Hz, 1H), 2.09 (d, J = 12.2 Hz, 1H), 1.87-1.68 (m, 3H), 1.56 (d, J = 6.7 Hz, 6H), 1.35-1.05 (m, 4H). |
| 176 | N-(2-(2-azabicyclo[2.1.1]hexan-2-yl)pyrimidin-4-yl)-1-isopropyl-1H-imidazo[4,5-c]pyridin-6-amine | A | 2.16, 336.2, D | 1H NMR (400 MHz, DMSO-d6) δ 9.75 (s, 1H), 8.64 (d, J = 1.2 Hz, 1H), 8.58 (s, 1H), 8.32 (s, 1H), 7.94 (d, J = 5.7 Hz, 1H), 6.39 (d, J = 5.7 Hz, 1H), 4.83 (d, J = 7.0 Hz, 1H), 4.69 (p, J = 6.7 Hz, 1H), 3.54 (s, 2H), 3.00-2.90 (m, 1H), 2.04-1.90 (m, 2H), 1.58 (d, J = 6.8 Hz, 6H), 1.39 (dd, J = 4.4, 1.9 Hz, 2H). |

TABLE 2-continued

| Example | Structure/Name | Synthesis Method/ Example # | LCMS RT (min), M + H+, method | 1H NMR (ppm) |
|---|---|---|---|---|
| 177 | 1-((1-(4-((1-isopropyl-1H-imidazo[4,5-c]pyridin-6-yl)amino)pyrimidin-2-yl)piperidin-4-yl)methyl)pyrrolidin-2-one | A | 2.03, 435.3, D | 1H NMR (400 MHz, DMSO-d6) δ 9.76 (s, 1H), 8.65 (d, J = 0.9 Hz, 1H), 8.40 (s, 1H), 8.32 (s, 1H), 7.96 (d, J = 5.6 Hz, 1H), 6.36 (d, J = 5.7 Hz, 1H), 4.72-4.53 (m, 3H), 3.36 (t, J = 7.0 Hz, 2H), 3.08 (d, J = 7.3 Hz, 2H), 2.92 (td, J = 12.7, 2.7 Hz, 2H), 2.23 (t, J = 8.0 Hz, 2H), 2.00-1.84 (m, 3H), 1.71-1.60 (m, 2H), 1.55 (d, J = 6.7 Hz, 6H), 1.20-1.01 (m, 2H). |
| 178 | 1-(4-((4-((1-isopropyl-1H-imidazo[4,5-c]pyridin-6-yl)amino)pyrimidin-2-yl)amino)piperidin-1-yl)ethanone | B | 3.480, 395.3, B | n/a |
| 179 | 4-(4-((1-isopropyl-1H-imidazo[4,5-c]pyridin-6-yl)amino)pyrimidin-2-yl)-N,2-dimethylmorpholine-2-carboxamide | A | 3.571, 411.3, B | n/a |
| 180 | tert-butyl 4-(4-((1-isopropyl-1H-imidazo[4,5-c]pyridin-6-yl)amino)pyrimidin-2-yl)-2-methylpiperazine-1-carboxylate | A | 4.461, 453.3, B | 1H NMR (400 MHz, DMSO-d6) δ 9.82 (s, 1H), 8.66 (d, J = 1.3 Hz, 1H), 8.35 (s, 2H), 7.98 (d, J = 5.7 Hz, 1H), 6.44 (d, J = 5.7 Hz, 1H), 4.69 (p, J = 6.8 Hz, 1H), 4.49 (d, J = 12.6 Hz, 1H), 4.44-4.35 (m, 1H), 4.22 (d, J = 6.3 Hz, 1H), 3.88-3.73 (m, 1H), 3.24 (dd, J = 13.2, 4.1 Hz, 1H), 3.16 (t, J = 10.9 Hz, 1H), 3.09-2.98 (m, 1H), 1.57 (dd, J = 6.7, 4.3 Hz, 6H), 1.43 (s, 9H), 1.09 (d, J = 6.7 Hz, 3H). |

TABLE 2-continued

| Example | Structure/Name | Synthesis Method/ Example # | LCMS RT (min), M + H+, method | 1H NMR (ppm) |
|---|---|---|---|---|
| 181 | tert-butyl 4-(4-((1-isopropyl-1H-imidazo[4,5-c]pyridin-6-yl)amino)pyridin-2-yl)piperazine-1-carboxylate | A | 4.241, 439.3, B | n/a |
| 182 | 1-isopropyl-N-(2-(7-methoxy-2-azabicyclo[2.2.1]heptan-2-yl)pyrimidin-4-yl)-1H-imidazo[4,5-c]pyridin-6-amine | A | 2.30, 380.2, D | n/a |
| 183 | 1-(4-((1-isopropyl-1H-imidazo[4,5-c]pyridin-6-yl)amino)pyrimidin-2-yl)-N-methylpyrrolidine-3-carboxamide | A | 3.369, 381.2, B | 1H NMR (400 MHz, DMSO-d6) δ 9.77 (s, 1H), 8.71 (s, 1H), 8.63 (d, J = 1.2 Hz, 1H), 8.30 (s, 1H), 7.99-7.89 (m, 2H), 6.33 (d, J = 5.7 Hz, 1H), 4.63 (q, J = 6.8 Hz, 1H), 3.84 (s, 1H), 3.74 (s, 1H), 3.59 (s, 2H), 3.03 (q, J = 8.0 Hz, 1H), 2.63 (d, J = 4.6 Hz, 3H), 2.21-2.02 (m, 2H), 1.53 (dd, J = 6.8, 3.6 Hz, 6H). |
| 184 | 1-(4-4-((1-isopropyl-1H-imidazo[4,5-c]pyridin-6-yl)amino)pyrimidin-2-yl)-1,4-diazepan-1-yl)ethanone | A | 1.65, 395.2, D | 1H NMR (400 MHz, DMSO-d6) δ 9.78 (d, J = 9.6 Hz, 1H), 8.65 (t, J = 1.2 Hz, 1H), 8.37 (d, J = 14.9 Hz, 2H), 3.92 (t, J = 5.3 Hz, 1H), 3.87-3.77 (m, 3H), 3.64 (d, J = 6.9 Hz, 2H), 3.44 (dt, J = 16.5, 6.0 Hz, 2H), 3.31 (s, 22H), 1.99 (s, 1H), 1.90 (s, 2H), 1.81 (s, 2H), 1.56 (dd, J = 6.7, 2.8 Hz, 6H). |

TABLE 2-continued

| Example | Structure/Name | Synthesis Method/ Example # | LCMS RT (min), M + H+, method | 1H NMR (ppm) |
|---|---|---|---|---|
| 185 | N-(2-3,3-difluoropyrrolidin-1-yl)pyrimidin-4-yl)-1-isopropyl-1H-imidazo[4,5-c]pyridine-6-amine | A | 2.39, 360.2, D | n/a |
| 186 | 3-(4-((1-isopropyl-1H-imidazo[4,5-c]pyridine-6-yl)amino)pyrimidin-2-yl)-3-azabicyclo[3.1.0]hexane-6-carboxamide | A | 3.25, 379.2, B | 1H NMR (400 MHz, DMSO-d6) δ 9.67 (s, 1H), 8.62 (d, J = 3.9 Hz, 2H), 8.29 (d, J = 18.3 Hz, 1H), 7.88 (d, J = 5.7 Hz, 1H), 7.25 (s, 1H), 6.66 (s, 1H), 6.32 (d, J = 5.6 Hz, 1H), 4.68 (m, 1H), 4.10 (s, 1H), 3.64 (s, 1H), 1.93 (dd, J = 8.4, 3.1 Hz, 2H), 1.72 (t, J = 8.2 Hz, 1H), 1.59 (d, J = 6.7 Hz, 6H). |
| 187 | 1-(4-((1-isopropyl-1H-imidazo[4,5-c]pyridin-6-yl)amino)pyrimidin-2-yl)piperidin-4-yl)methanol | A | 3.53, 368.2, B | 1H NMR (400 MHz, DMSO-d6) δ 9.75 (s, 1H), 8.65 (d, J = 0.9 Hz, 1H), 8.43 (s, 1H), 8.32 (s, 1H), 7.96 (d, J = 5.6 Hz, 1H), 6.36 (d, J = 5.6 Hz, 1H), 4.76-4.58 (m, 3H), 4.46 (s, 1H), 2.89 (td, J = 12.6, 2.6 Hz, 2H), 1.78-1.60 (m, 3H), 1.57 (d, J = 6.7 Hz, 6H), 1.13 (qd, J = 12.3, 4.2 Hz, 2H). |
| 188 | N-(2-(5-oxa-2-azaspiro[3.5]nonan-2-yl)pyrimidin-4-yl)-1-isopropyl-1H-imidazo[4,5-c]pyridin-6-amine | A | 3.93, 380.2, B | 1H NMR (400 MHz, DMSO-d6) δ 9.84 (s, 1H), 8.67-8.58 (m, 2H), 8.32 (s, 1H), 7.94 (d, J = 5.7 Hz, 1H), 6.44 (d, J = 5.8 Hz, 1H), 4.73 (h, J = 6.7 Hz, 1H), 3.98-3.87 (m, 4H), 3.61 (t, J = 5.2 Hz, 2H), 1.77 (t, J = 5.9 Hz, 2H), 1.67-1.45 (m, 8H). |

TABLE 2-continued

| Example | Structure/Name | Synthesis Method/ Example # | LCMS RT (min), M + H+, method | 1H NMR (ppm) |
|---|---|---|---|---|
| 189 | N-(2-(4-cyclopropylpiperazin-1-yl)pyrimidin-4-yl)-1-isopropyl-1H-imidazo[4,5-c]pyridin-6-amine | A | 1.65, 379.2, D | 1H NMR (400 MHz, DMSO-d6) δ 9.78 (s, 1H), 8.65 (d, J = 0.9 Hz, 1H), 8.35 (d, J = 19.7 Hz, 2H), 7.97 (d, J = 5.7 Hz, 1H), 6.42 (d, J = 5.7 Hz, 1H), 4.67 (p, J = 6.8 Hz, 1H), 3.72 (t, J = 5.0 Hz, 5H), 2.61 (t, J = 5.1 Hz, 5H), 1.66 (tt, J = 6.7, 3.7 Hz, 1H), 1.56 (d, J = 6.8 Hz, 7H), 0.50-0.34 (m, 5H). |
| 190 | N-(2-(3,4-difluoropyrrolidin-1-yl)pyrimidin-4-yl)-1-isopropyl-1H-imidazo[4,5-c]pyridin-6-amine | A | 3.74, 360.2, B | 1H NMR (400 MHz, DMSO-d6) δ 9.88 (s, 1H), 8.65 (d, J = 1.0 Hz, 1H), 8.57 (s, 1H), 8.33 (s, 1H), 7.99 (d, J = 5.7 Hz, 1H), 6.46 (d, J = 5.7 Hz, 1H), 5.58-5.29 (m, 2H), 4.71 (p, J = 6.7 Hz, 1H), 4.12-3.85 (m, 2H), 3.82-3.63 (m, 2H), 1.57 (d, J = 6.7 Hz, 6H). |
| 191 | N-(2-(5-fluoro-2-azabicyclo[2.2.1]heptan-2-yl)pyrimidin-4-yl)-1-isopropyl-1H-imidazo[4,5-c]pyridin-6-amine | A | 2.08, 268.2, D | 1H NMR (400 MHz, DMSO-d6) δ 9.76 (s, 1H), 8.64 (d, J = 0.9 Hz, 1H), 8.32 (s, 1H), 7.94 (d, J = 5.7 Hz, 1H), 6.36 (d, J = 5.7 Hz, 1H), 5.43-5.21 (m, 1H), 4.70-4.53 (m, 2H), 3.89-3.64 (m, 1H), 2.95 (s, 1H), 2.14 (br s, 1H), 1.92-1.79 (m, 1H), 1.73-1.62 (m, 1H), 1.61-1.43 (m, 7H). |
| 192 | 7-(4-((1-isopropyl-1H-imidazo[4,5-c]pyridin-6-yl)amino)pyrimidin-2-yl)-2,7-diazaspiro[4.4]nonan-1-one | A | 1.63, 393.2, D | 1H NMR (400 MHz, DMSO-d6) δ 9.79 (s, 1H), 8.71 (s, 1H), 8.63 (d, J = 1.0 Hz, 1H), 8.27 (d, J = 25.6 Hz, 1H), 7.95 (d, J = 5.7 Hz, 1H), 7.81 (s, 1H), 6.33 (d, J = 5.7 Hz, 1H), 4.64 (p, J = 6.6 Hz, 1H), 3.81 (s, 1H), 3.65 (s, 3H), 3.25 (q, J = 6.7 Hz, 2H), 2.21-2.05 (m, 3H), 1.92 (s, 1H), 1.53 (dd, J = 6.9, 4.2 Hz, 6H). |

TABLE 2-continued

| Example | Structure/Name | Synthesis Method/ Example # | LCMS RT (min), M + H+, method | ¹H NMR (ppm) |
|---|---|---|---|---|
| 193 | N4-(1-isopropyl-1H-imidazo[4,5-c]pyridin-6-yl)-N2-(2-methoxy-2-methylpropyl)pyrimidine-2,4-diamine | B | 3.75, 356.2, B | ¹H NMR (400 MHz, DMSO-d₆) δ 9.69 (s, 1H), 8.64 (d, J = 1.1 Hz, 1H), 8.47 (s, 1H), 8.36 (s, 1H), 7.88 (d, J = 5.6 Hz, 1H), 6.39 (d, J = 5.6 Hz, 1H), 6.26 (s, 1H), 4.73 (s, 1H), 3.45 (d, J = 6.0 Hz, 2H), 3.16 (s, 2H), 1.56 (d, J = 6.7 Hz, 6H), 1.16 (s, 6H). |
| 194 | N-(2-(hexahydrofuro[3,2-c]pyridin-5(6H)-yl)pyrimidin-4-yl)-1-isopropyl-1H-imidazo[4,5-c]pyridin-6-amine | A | 2.04, 380.2, D | n/a |
| 195 | N-(2-(hexahydrofuro[3,4-c]pyridin-5(3H)-yl)pyrimidin-4-yl)-1-isopropyl-1H-imidazo[4,5-c]pyridin-6-amine | A | 2.00, 380.2, D | ¹H NMR (400 MHz, DMSO-d₆) δ 9.77 (s, 1H), 8.65 (d, J = 1.1 Hz, 1H), 8.43 (s, 1H), 8.32 (d, J = 4.2 Hz, 1H), 7.95 (d, J = 5.6 Hz, 1H), 6.36 (d, J = 5.7 Hz, 1H), 4.64 (hept, J = 6.7 Hz, 1H), 3.94 (ddd, J = 16.3, 11.0, 3.7 Hz, 2H), 3.84-3.71 (m, 3H), 3.62-3.48 (m, 2H), 3.42 (dd, J = 8.4, 5.8 Hz, 1H), 2.42 (ddt, J = 19.6, 13.0, 6.6 Hz, 2H), 1.90-1.77 (m, 1H), 1.56 (dd, J = 6.7, 1.3 Hz, 6H). |
| 196 | 3-(4-((1-isopropyl-1H-imidazo[4,5-c]pyridin-6-yl)amino)pyrimidin-2-yl)-N-methyl-3-azabicyclo[3.1.0]hexane-6-carboxamide | A | 1.73, 393.2, D | ¹H NMR (400 MHz, DMSO-d₆) δ 9.79 (s, 1H), 8.64 (d, J = 1.0 Hz, 1H), 8.55 (s, 1H), 8.32 (s, 1H), 7.92 (dd, J = 12.6, 5.2 Hz, 2H), 6.40 (d, J = 5.7 Hz, 1H), 4.68 (p, J = 6.7 Hz, 1H), 3.89 (d, J = 11.0 Hz, 2H), 3.59 (s, 2H), 2.59 (d, J = 4.6 Hz, 3H), 2.02 (s, 2H), 1.58 (d, J = 6.7 Hz, 6H), 1.44 (t, J = 3.1 Hz, 1H). |

TABLE 2-continued

| Example | Structure/Name | Synthesis Method/ Example # | LCMS RT (min), M + H+, method | 1H NMR (ppm) |
|---|---|---|---|---|
| 197 | 1-(4-((1-isopropyl-1H-imidazo[4,5-c]pyridin-6-yl)amino)pyrimidin-2-yl)-N-methylazetidine-3-carboxamide | A | 3.28, 367.2, B | n/a |
| 198 | (1-(45-((1-isopropyl-1H-imidazo[4,5-c]pyridin-6-yl)amino)pyrimidin-2-yl)azetidin-3-yl)(morpholino)methanone | A | 3.51, 423.3, B | 1H NMR (400 MHz, DMSO-d$_6$) δ 9.86 (s, 1H), 8.64 (d, J = 1.0 Hz, 1H), 8.58 (s, 1H), 8.32 (s, 1H), 7.95 (d, J = 5.7 Hz, 1H), 6.45 (d, J = 5.8 Hz, 1H), 4.68 (p, J = 6.8 Hz, 1H), 4.21 (dt, J = 14.1, 8.0 Hz, 4H), 3.88-3.76 (m, 1H), 3.58 (q, J = 4.7 Hz, 5H), 3.48 (t, J = 4.8 Hz, 2H), 3.38-3.24 (m, 2H), 1.56 (d, J = 6.7 Hz, 6H). |
| 199 | 2-(1-(4-((1-isopropyl-1H-imidazo[4,5-c]pyridin-6-yl)amino)pyrimidin-2-yl)piperidin-4-yl)-N,N-dimethylacetamide | A | 3.72, 423.3, B | 1H NMR (400 MHz, DMSO-d$_6$) δ 9.75 (s, 1H), 8.65 (d, J = 1.0 Hz, 1H), 8.41 (d, J = 2.0 Hz, 1H), 8.32 (s, 1H), 7.96 (d, J = 5.7 Hz, 1H), 6.36 (d, J = 5.7 Hz, 1H), 4.71-4.59 (m, 4H), 2.95 (s, 5H), 2.82 (s, 3H), 2.26 (d, J = 6.8 Hz, 2H), 1.75 (d, J = 11.7 Hz, 2H), 1.56 (dd, J = 6.8, 5.1 Hz, 8H), 1.18 (tt, J = 12.3, 6.2 Hz, 2H). |
| 200 | 1-(4-((1-isopropyl-1H-imidazo[4,5-c]pyridin-6-yl)amino)pyrimidin-2-yl)azepan-4-ol | A | 3.47, 368.2, B | n/a |

TABLE 2-continued

| Example | Structure/Name | Synthesis Method/ Example # | LCMS RT (min), M + H+, method | 1H NMR (ppm) |
|---|---|---|---|---|
| 201 | tert-butyl (1-(4-((1-isopropyl-1H-imidazo[4,5-c]pyridin-6-yl)amino)pyrimidin-2-yl)pyrollidin-3-yl)methyl)carbamate | A | 4.38, 453.3, B | 1H NMR (400 MHz, DMSO-$d_6$) δ 9.80 (s, 1H), 8.71 (s, 1H), 8.64 (d, J = 1.1 Hz, 1H), 8.30 (s, 1H), 7.95 (d, J = 5.6 Hz, 1H), 6.34 (d, J = 5.7 Hz, 1H), 4.79 (s, 1H), 4.66 (p, J = 6.7 Hz, 1H), 3.78 (s, 2H), 3.47 (s, 2H), 2.78 (s, 3H), 2.12 (d, J = 8.7 Hz, 1H), 1.53 (dd, J = 6.8, 3.4 Hz, 6H), 1.42 (s, 9H). |
| 202 | 1-(4-((1-isopropyl-1H-imidazo[4,5-c]pyridin-6-yl)amino)pyrimidin-2-yl)-N,4-dimethylpiperidine-4-carboxamide | A | 3.60, 409.3, B | 1H NMR (400 MHz, DMSO-$d_6$) δ 9.75 (s, 1H), 8.65 (d, J = 0.9 Hz, 1H), 8.43-8.37 (m, 1H), 8.32 (s, 1H), 7.96 (d, J = 5.7 Hz, 1H), 7.59 (q, J = 4.4 Hz, 1H), 6.38 (d, J = 5.7 Hz, 1H), 4.67 (h, J = 6.7 Hz, 1H), 4.02 (ddd, J = 13.2, 6.5, 3.9 Hz, 2H), 3.47 (ddd, J = 12.9, 9.1, 3.3 Hz, 2H), 2.62 (d, J = 4.4 Hz, 3H), 2.02 (ddd, J = 13.2, 6.4, 3.5 Hz, 2H), 1.58 (d, J = 6.8 Hz, 6H), 1.39 (ddd, J = 13.2, 9.0, 3.8 Hz, 2H), 1.14 (s, 3H). |
| 203 | 1-(4-((1-isopropyl-1H-imidazo[4,5-c]pyridin-6-yl)amino)pyrimidin-2-yl)-yl)pyrrolidin-2-yl)methanol | A | 3.49, 354.2, B | 1H NMR (400 MHz, DMSO-$d_6$) δ 9.75 (s, 1H), 8.64 (d, J = 1.0 Hz, 1H), 8.33 (s, 1H), 8.25 (s, 1H), 7.93 (d, J = 5.7 Hz, 1H), 6.36 (d, J = 5.7 Hz, 1H), 4.72 (s, 1H), 3.71-3.63 (m, 1H), 3.40 (t, J = 9.1 Hz, 1H), 2.03-1.87 (m, 4H), 1.54 (dd, J = 7.1, 4.1 Hz, 6H). |
| 204 | N2-((1-ethylpyrrolidin-3-yl)methyl)-N4-(1-isopropyl-1H-imidazo[4,5-c]pyridin-6-yl)-N2-methylpyrimidine-2,4-diamine | A | 3.23, 395.3, B | 1H NMR (400 MHz, DMSO-$d_6$) δ 9.70 (s, 1H), 8.64 (d, J = 1.0 Hz, 1H), 8.46 (s, 1H), 8.32 (d, J = 19.3 Hz, 3H), 7.95 (d, J = 5.6 Hz, 1H), 6.37 (d, J = 5.7 Hz, 1H), 4.68 (p, J = 6.8 Hz, 1H), 3.63 (d, J = 6.8 Hz, 1H), 3.17 (s, 3H), 2.63-2.51 (m, 1H), 2.44-2.33 (m, 1H), 1.92-1.79 (m, 1H), 1.55 (t, J = 6.7 Hz, 6H), 1.45 (dt, J = 13.2, 6.7 Hz, 1H), 0.94 (t, J = 7.3 Hz, 3H). |

TABLE 2-continued

| Example | Structure/Name | Synthesis Method/ Example # | LCMS RT (min), M + H+, method | 1H NMR (ppm) |
|---|---|---|---|---|
| 205 | 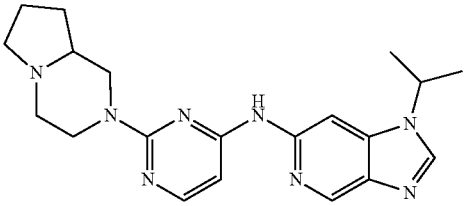<br>N-(2-(hexahydropyrrolo[1,2-a]pyrazin-2(1H)-yl)pyrimidin-4-yl)-1-isopropyl-1H-imidazo[4,5-c]pyridin-6-amine | A | 3.11, 379.2, B | n/a |
| 206 | 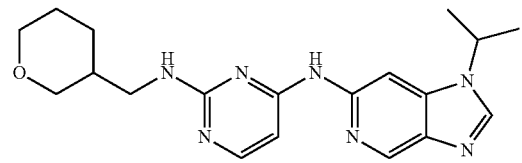<br>N4-(1-isopropyl-1H-imidazo[4,5-c]pyridin-6-yl)-N2-((tetrahydro-2H-pyran-3-yl)methyl)pyrimidine-2,4-diamine | B | 3.69, 368.2, B | 1H NMR (400 MHz, DMSO-$d_6$) δ 9.63 (s, 1H), 8.63 (d, J = 1.0 Hz, 1H), 8.42 (s, 1H), 8.36 (s, 1H), 8.28 (s, 1H), 7.88 (d, J = 5.7 Hz, 1H), 6.78 (s, 1H), 6.39 (d, J = 5.7 Hz, 1H), 4.70 (s, 1H), 3.84 (dd, J = 10.6, 3.6 Hz, 1H), 3.72 (dt, J = 11.0, 3.9 Hz, 1H), 3.36-3.22 (m, 2H), 3.14 (dd, J = 11.1, 9.1 Hz, 1H), 1.93-1.78 (m, 2H), 1.56 (d, J = 6.7 Hz, 7H), 1.47 (tq, J = 10.8, 3.9 Hz, 1H), 1.26 (dtd, J = 14.0, 10.3, 4.1 Hz, 1H). |
| 207 | 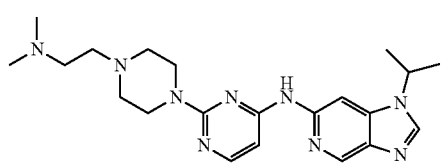<br>N-(2-(4-(2-(dimethylamino)ethyl)piperazin-1-yl)pyrimidin-4-yl)-1-isopropyl-1H-imidazo[4,5-c]pyridin-6-amine | A | 3.20, 410.3, B | 1H NMR (400 MHz, DMSO-$d_6$) δ 9.79 (s, 1H), 8.65 (d, J = 0.8 Hz, 1H), 8.39 (s, 1H), 8.30 (d, J = 13.3 Hz, 3H), 7.97 (d, J = 5.6 Hz, 1H), 6.41 (d, J = 5.7 Hz, 1H), 4.66 (p, J = 6.7 Hz, 1H), 3.75 (t, J = 5.0 Hz, 4H), 2.51-2.38 (m, 8H), 2.19 (s, 6H), 1.56 (d, J = 6.8 Hz, 6H). |
| 208 | 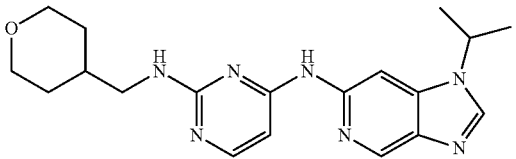<br>N4-(1-isopropyl-1H-imidazo[4,5-c]pyridin-6-yl)-N2-((tetrahydro-2H-pyran-4-yl)methyl)pyrimidine-2,4-diamine | B | 3.60, 368.2, B | 1H NMR (400 MHz, DMSO-$d_6$) δ 9.63 (s, 1H), 8.63 (d, J = 0.9 Hz, 1H), 8.44 (s, 1H), 8.36 (s, 1H), 8.25 (s, 1H), 7.87 (d, J = 5.6 Hz, 1H), 6.79 (t, J = 5.8 Hz, 1H), 6.38 (d, J = 5.6 Hz, 1H), 4.69 (s, 1H), 3.85 (ddd, J = 11.5, 4.6, 1.8 Hz, 2H), 3.26 (td, J = 11.6, 2.1 Hz, 4H), 2.50-2.45 (m, 1H), 1.83 (ddp, J = 11.2, 7.1, 3.2 Hz, 1H), 1.66 (dd, J = 12.9, 3.2 Hz, 2H), 1.56 (d, J = 6.7 Hz, 6H), 1.22 (qd, J = 12.1, 4.5 Hz, 2H). |

TABLE 2-continued

| Example | Structure/Name | Synthesis Method/ Example # | LCMS RT (min), M + H+, method | 1H NMR (ppm) |
|---|---|---|---|---|
| 209 | 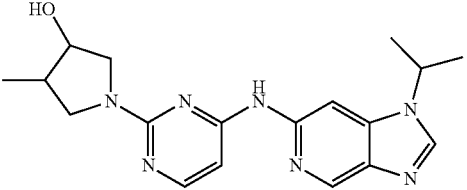<br>1-(4-((1-isopropyl-1H-imidazo[4,5-c]pyridin-6-yl)amino)pyrimidin-2-yl)-4-methylpyrrolidin-3-ol | A | 1.73, 354.2, D | n/a |
| 210 | 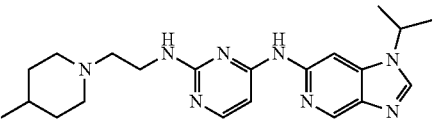<br>N4-(1-isopropyl-1H-imidazo[4,5-c]pyridin-6-yl)-N2-(2-(4-methylpiperidin-1-yl)ethyl)pyrimidine-2,4-diamine | B | 3.43, 395.3, B | n/a |
| 211 | 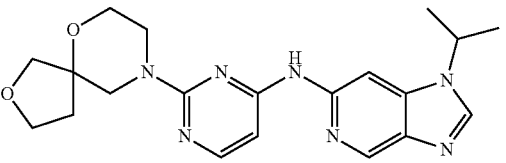<br>N-(2-(2,6-dioxa-9-azaspiro[4.5]decan-9-yl)pyrimidin-4-yl)-1-isopropyl-1H-imidazo[4,5-c]pyridin-6-amine | A | 1.88, 396.2, D | 1H NMR (400 MHz, DMSO-$d_6$) δ 9.84 (s, 1H), 8.66 (d, J = 0.9 Hz, 1H), 8.35 (s, 1H), 8.30 (s, 1H), 8.00 (d, J = 5.6 Hz, 1H), 6.49 (d, J = 5.7 Hz, 1H), 4.64 (p, J = 6.8 Hz, 1H), 3.86-3.61 (m, 9H), 2.09-1.97 (m, 1H), 1.87 (dt, J = 12.9, 7.8 Hz, 1H), 1.55 (dd, J = 6.7, 3.1 Hz, 6H). |
| 212 | 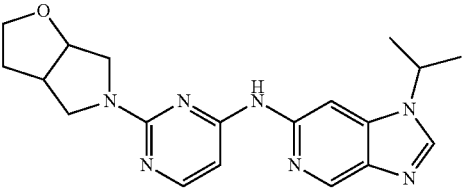<br>1-isopropyl-N-(2-(tetrahydro-2H-furo[2,3-c]pyrrol-5(3H)-yl)pyrimidin-4-yl)-1H-imidazo[4,5-c]pyridin-6-amine | A | 1.98, 366.2, D | 1H NMR (400 MHz, DMSO-$d_6$) δ 9.78 (s, 1H), 8.64 (t, J = 1.5 Hz, 2H), 8.32 (s, 1H), 8.27 (s, 1H), 7.94 (d, J = 5.6 Hz, 1H), 6.37 (d, J = 5.7 Hz, 1H), 4.69 (m, 1H), 4.54 (t, J = 5.3 Hz, 1H), 3.96-3.71 (m, 4H), 3.64 (dd, J = 12.4, 4.8 Hz, 1H), 3.40 (m, 1H), 3.02 (m, 1H), 2.12 (m, 1H), 1.82 (m, 1H), 1.58 (d, J = 6.7 Hz, 6H). |

TABLE 2-continued

| Example | Structure/Name | Synthesis Method/ Example # | LCMS RT (min), M + H+, method | 1H NMR (ppm) |
|---|---|---|---|---|
| 213 | N-(2-(6-oxa-2-azaspiro[3.5]nonan-2-yl)pyrimidin-4-yl)-1-isopropyl-1H-imidazo[4,5-c]pyridin-6-amine | A | 3.75, 380.2, B | 1H NMR (400 MHz, DMSO-$d_6$) δ 9.81 (s, 1H), 8.63 (d, J = 7.8 Hz, 2H), 8.29 (d, J = 10.8 Hz, 1H), 7.93 (d, J = 5.7 Hz, 1H), 6.43 (d, J = 5.7 Hz, 1H), 4.68 (h, J = 6.8 Hz, 1H), 3.83-3.70 (m, 4H), 3.64 (s, 2H), 3.54 (t, J = 5.1 Hz, 2H), 1.83 (t, J = 5.9 Hz, 2H), 1.58 (d, J = 6.7 Hz, 8H). |
| 214 | 7-(4-((1-isopropyl-1H-imidazo[4,5-c]pyridin-6-yl)amino)pyrimidin-2-yl)-7-azabicyclo[2.2.1]heptane-2-carboxamide | A | 2.01, 393.2, D | n/a |
| 215 | 1-(4-((1-isopropyl-1H-imidazo[4,5-c]pyridin-6-yl)amino)pyrimidin-2-yl)-3-methylpyrrolidin-3-ol | A | 1.83, 354.2, D | 1H NMR (400 MHz, DMSO-$d_6$) δ 9.74 (s, 1H), 8.72 (s, 1H), 8.64 (d, J = 1.2 Hz, 1H), 8.30 (d, J = 10.5 Hz, 2H), 7.93 (d, J = 5.7 Hz, 1H), 6.30 (d, J = 5.7 Hz, 1H), 4.72-4.64 (m, 1H), 1.90 (t, J = 8.4 Hz, 2H), 1.58 (dd, J = 7.0, 4.1 Hz, 6H), 1.37 (s, 3H). |
| 216 | N-(2-(3-azabicyclo[3.1.0]hexan-3-yl)pyrimidin-4-yl)-1-isopropyl-1H-imidazo[4,5-c]pyridin-6-amine | A | 2.17, 336.1, D | 1H NMR (400 MHz, DMSO-$d_6$) δ 9.74 (s, 1H), 8.66-8.57 (m, 2H), 8.32 (s, 1H), 7.92 (d, J = 5.7 Hz, 1H), 6.36 (d, J = 5.7 Hz, 1H), 4.69 (p, J = 6.7 Hz, 1H), 3.84 (d, J = 10.7 Hz, 2H), 3.54 (s, 2H), 1.68 (dt, J = 7.2, 3.3 Hz, 2H), 1.59 (d, J = 6.8 Hz, 6H), 0.75 (td, J = 7.8, 4.5 Hz, 1H), 0.19 (q, J = 4.2 Hz, 1H). |

TABLE 2-continued

| Example | Structure/Name | Synthesis Method/ Example # | LCMS RT (min), M + H+, method | 1H NMR (ppm) |
|---|---|---|---|---|
| 217 | N-(2-(2-azabicyclo[3.1.0]hexan-2-yl)pyrimidin-4-yl)-1-isopropyl-1H-imidazo[4,5-c]pyridin-6-amine | A | 2.18, 336.1, D | 1H NMR (400 MHz, DMSO-d6) δ 9.76 (s, 4H), 8.66-8.58 (m, 7H), 8.31 (s, 5H), 8.20 (s, 1H), 7.94 (d, J = 5.7 Hz, 4H), 6.52 (s, 3H), 6.38 (d, J = 5.6 Hz, 4H), 4.62 (p, J = 6.7 Hz, 4H), 3.90 (d, J = 10.7 Hz, 4H), 3.77 (td, J = 6.2, 2.4 Hz, 4H), 3.15 (s, 6H), 2.20 (ddd, J = 15.0, 9.2, 5.5 Hz, 4H), 2.09-1.98 (m, 4H), 1.68 (t, J = 7.1 Hz, 5H), 1.53 (dd, J = 6.7, 3.6 Hz, 27H), 0.73 (dt, J = 8.8, 5.7 Hz, 4H), 0.63-0.55 (m, 4H). |
| 218 | 1-isopropyl-N-(2-(tetrahydro-1H-furo[3,4-c]pyrrol-5(3H)-yl)pyrimidin-4-yl)-1H-imidazo[4,5-c]pyridin-6-amine | A | 1.87, 366.2, D | 1H NMR (400 MHz, DMSO-d6) δ 9.77 (s, 2H), 8.67-8.60 (m, 3H), 8.31 (s, 2H), 7.95 (d, J = 5.6 Hz, 2H), 6.66 (s, 1H), 6.37 (d, J = 5.7 Hz, 2H), 4.68 (h, J = 6.8 Hz, 2H), 3.82 (ddd, J = 34.2, 9.6, 6.4 Hz, 7H), 3.55 (ddd, J = 24.0, 10.0, 3.3 Hz, 9H), 3.04 (dp, J = 7.2, 4.1, 3.7 Hz, 4H), 1.57 (d, J = 6.7 Hz, 12H). |
| 219 | N-(2-(3-(aminomethyl)pyrrolidin-1-yl)pyrimidin-4-yl)-1-isopropyl-1H-imidazo[4,5-c]pyridin-6-amine | A | 2.77, 353.2, B | 1H NMR (400 MHz, DMSO-d6) δ 9.74 (s, 2H), 8.71 (d, J = 18.6 Hz, 2H), 8.63 (s, 1H), 8.31 (s, 2H), 7.93 (dd, J = 5.7, 1.5 Hz, 2H), 6.31 (dd, J = 7.7, 5.7 Hz, 2H), 4.67 (ddd, J = 10.0, 8.5, 4.9 Hz, 2H), 3.67 (s, 4H), 3.51 (s, 1H), 3.04 (t, J = 6.3 Hz, 1H), 2.62 (dd, J = 12.2, 7.0 Hz, 2H), 2.29 (d, J = 7.5 Hz, 1H), 2.07 (dt, J = 11.4, 5.7 Hz, 2H), 1.70 (q, J = 10.2, 9.2 Hz, 2H), 1.56 (dt, J = 6.8, 2.2 Hz, 13H). |
| 220 | N-(2-(4-(aminomethyl)piperidin-1-yl)pyrimidin-4-yl)-1-isopropyl-1H-imidazo[4,5-c]pyridin-6-amine | A | 3.08, 367.3, B | 1H NMR (400 MHz, DMSO-d6) δ 9.75 (s, 1H), 8.65 (s, 1H), 8.43 (s, 1H), 8.32 (s, 1H), 7.96 (d, J = 5.6 Hz, 1H), 6.36 (d, J = 5.8 Hz, 1H), 4.76-4.59 (m, 3H), 2.89 (td, J = 12.5, 11.1, 5.7 Hz, 3H), 1.74 (dd, J = 24.1, 11.8 Hz, 2H), 1.57 (d, J = 6.8 Hz, 6H), 1.10 (qd, J = 12.3, 4.0 Hz, 2H). |

TABLE 2-continued

| Example | Structure/Name | Synthesis Method/ Example # | LCMS RT (min), M + H+, method | 1H NMR (ppm) |
|---|---|---|---|---|
| 221 | 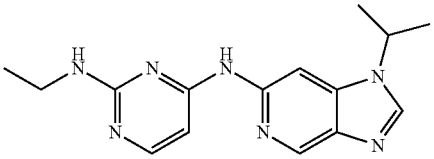<br>N2-ethyl-N4-(1-isopropyl-1H-imidazo[4,5-c]pyridin-6-yl)pyrimidine-2,4-diamine | B | 3.43, 298.2, B | 1H NMR (400 MHz, DMSO-d6) δ 9.66 (s, 1H), 8.63 (d, J = 1.0 Hz, 1H), 8.54 (s, 1H), 8.34 (s, 1H), 7.87 (d, J = 5.7 Hz, 1H), 6.78 (s, 1H), 6.34 (d, J = 5.6 Hz, 1H), 4.69 (s, 1H), 3.39 (p, J = 7.0 Hz, 2H), 1.56 (d, J = 6.7 Hz, 6H), 1.19 (t, J = 7.1 Hz, 3H). |
| 222 | 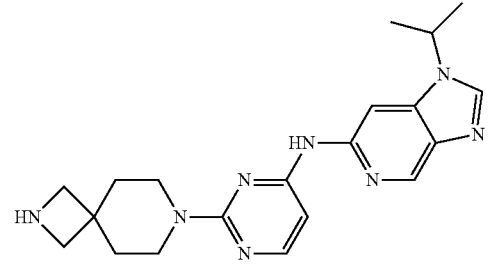<br>N-(2-(2,7-diazaspiro[3.5]nonan-7-yl)pyrimidin-4-yl)-1-isopropyl-1H-imidazo[4,5-c]pyridin-6-amine | A | 3.02, 379.3, B | 1H NMR (400 MHz, DMSO-d6) δ 9.76 (s, 1H), 8.65 (d, J = 1.1 Hz, 1H), 8.42-8.37 (m, 1H), 8.33 (s, 1H), 7.96 (d, J = 5.7 Hz, 1H), 6.38 (d, J = 5.6 Hz, 1H), 4.66 (p, J = 6.7 Hz, 1H), 3.60 (s, 1H), 3.30 (s, 3H), 1.77-1.66 (m, 4H), 1.58 (d, J = 6.7 Hz, 6H). |
| 223 | 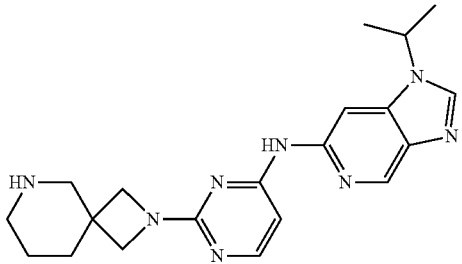<br>N-(2-(2,7-diazaspiro[3.5]nonan-2-yl)pyrimidin-4-yl)-1-isopropyl-1H-imidazo[4,5-c]pyridin-6-amine | A | 3.17, 379.2, B | 1H NMR (400 MHz, DMSO-d6) δ 9.79 (s, 1H), 8.63 (s, 2H), 8.31 (s, 1H), 7.92 (d, J = 5.7 Hz, 1H), 6.41 (d, J = 5.7 Hz, 1H), 4.68 (h, J = 6.7 Hz, 1H), 3.77 (d, J = 8.2 Hz, 2H), 3.69 (d, J = 8.2 Hz, 2H), 2.80 (s, 2H), 2.62 (t, J = 5.2 Hz, 2H), 1.71 (t, J = 6.0 Hz, 2H), 1.58 (d, J = 6.8 Hz, 6H), 1.43 (q, J = 5.8, 5.3 Hz, 2H). |
| 224 | 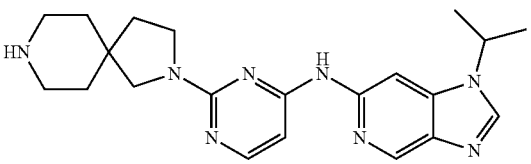<br>N-(2-(2,8-diazaspiro[4.5]decan-2-yl)pyrimidin-4-yl)-1-isopropyl-1H-imidazo[4,5-c]pyridin-6-amine | A | 3.11, 393.3, B | 1H NMR (400 MHz, DMSO-d6) δ (s, 1H), 8.70-8.61 (m, 2H), 8.33 1H), 7.93 (d, J = 5.7 Hz, 1H), 6.32 (d, J = 5.6 Hz 1H) 4.67 (p, J = 6.7 Hz, 1H), 3.59 (s, 2H), 3.45 (s, 2H), 2.70 (ddd, J = 29.1, 13.1, 6.4 Hz, 3H), 1.83 (t, J = 7.0 Hz, 2H), 1.53 (dd, J = 38.4, 6.0 Hz, 10H). |

TABLE 2-continued

| Example | Structure/Name | Synthesis Method/ Example # | LCMS RT (min), M + H+, method | 1H NMR (ppm) |
|---|---|---|---|---|
| 225 | N-(2-(1,8-diazaspiro[4.6]undecan-8-yl)pyrimidin-4-yl)-1-isopropyl-1H-imidazo[4,5-c]pyridin-6-amine | A | 3.26, 407.3, B | n/a |
| 226 | N-(2-(2,6-diazaspiro[4.5]decan-2-yl)pyrimidin-4-yl)-1-isopropyl-1H-imidazo[4,5-c]pyridin-6-amine | A | 3.15, 393.3, B | 1H NMR (400 MHz, DMSO-d$_6$) δ 9.74 (s, 1H), 8.70-8.61 (m, 2H), 8.33 (s, 1H), 7.93 (d, J = 5.7 Hz, 1H), 6.32 (d, J = 5.7 Hz, 1H), 4.66 (h, J = 6.8 Hz, 1H), 3.59 (s, 3H), 3.45 (s, 2H), 2.72 (tq, J = 17.7, 6.1, 5.5 Hz, 4H), 1.84 (t, J = 7.0 Hz, 2H), 1.58 (d, J = 6.7 Hz, 7H), 1.48 (t, J = 5.5 Hz, 4H). |
| 227 | N-(2-(3,9-diazaspiro[5.5]undecan-3-yl)pyrimidin-4-yl)-1-isopropyl-1H-imidazo[4,5-c]pyridin-6-amine | A | 3.10, 407.3, B | 1H NMR (400 MHz, DMSO-d$_6$) δ 9.74 (s, 1H), 8.64 (d, J = 0.9 Hz, 1H), 8.43 (s, 1H), 8.32 (s, 1H), 7.96 (d, J = 5.7 Hz, 1H), 6.35 (d, J = 5.7 Hz, 1H), 4.66 (p, J = 6.7 Hz, 1H), 3.77 (dd, J = 6.9, 4.5 Hz, 4H), 2.71-2.63 (m, 4H), 1.60-1.37 (m, 16H). |
| 228 | N-(2-(1,7-diazaspiro[3.5]nonan-7-yl)pyrimidin-4-yl)-1-isopropyl-1H-imidazo[4,5-c]pyridin-6-amine | A | 3.28, 379.3, B | 1H NMR (400 MHz, DMSO-d$_6$) δ 9.78 (s, 2H), 8.65 (d, J = 0.9 Hz, 2H), 8.49 (s, 2H), 8.33 (s, 2H), 7.98 (d, J = 5.7 Hz, 2H), 6.59 (s, 1H), 6.39 (d, J = 5.6 Hz, 2H), 5.52 (s, 3H), 4.68 (h, J = 6.8 Hz, 2H), 4.18 (s, 4H), 3.90 (t, J = 5.7 Hz, 5H), 3.06 (q, J = 6.7 Hz, 2H), 2.65 (t, J = 7.1 Hz, 3H), 2.19-2.05 (m, 8H), 1.59 (d, J = 6.7 Hz, 14H). |

| Example | Structure/Name | Synthesis Method/ Example # | LCMS RT (min), M + H+, method | 1H NMR (ppm) |
|---|---|---|---|---|
| 229 | 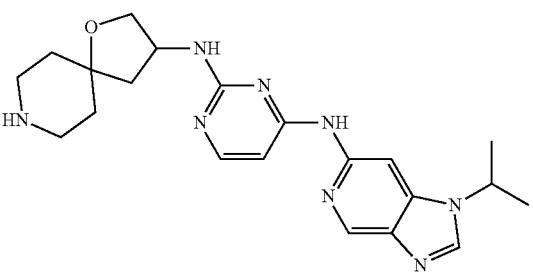<br>N4-(1-isopropyl-1H-imidazo[4,5-c]pyridin-6-yl)-N2-(1-oxa-8-azaspiro[4.5]decan-3-yl)pyrimidine-2,4-diamine | B | 3.17, 409.3, B | 1H NMR (400 MHz, DMSO-$d_6$) δ 9.75 (s, 1H), 8.65 (d, J = 1.0 Hz, 1H), 8.39 (s, 1H), 8.32 (s, 1H), 7.96 (d, J = 5.7 Hz, 1H), 6.38 (d, J = 5.7 Hz, 1H), 4.65 (p, J = 6.8 Hz, 1H), 4.03-3.80 (m, 3H), 3.66 (tdd, J = 13.0, 8.5, 4.3 Hz, 2H), 3.51 (p, J = 6.3 Hz, 1H), 3.36 (dd, J = 8.4, 6.2 Hz, 1H), 2.11-1.95 (m, 1H), 1.75-1.61 (m, 2H), 1.61-1.40 (m, 10H). |
| 230 | 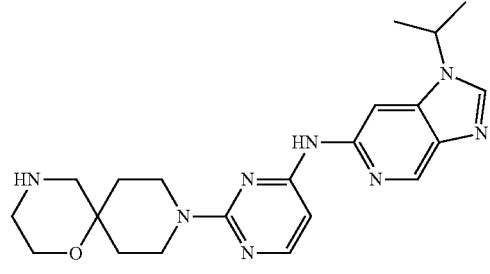<br>N-(2-(1-oxa-4,9-diazaspiro[5.5]undecan-9-yl)pyrimidin-4-yl)-1-isopropyl-1H-imidazo[4,5-c]pyridin-6-amine | A | 3.26, 409.3, D | 1H NMR (400 MHz, DMSO-$d_6$) δ 9.75 (s, 1H), 8.65 (d, J = 1.0 Hz, 1H), 8.42 (s, 1H), 8.32 (s, 1H), 7.96 (d, J = 5.6 Hz, 1H), 6.37 (d, J = 5.7 Hz, 1H), 4.66 (p, J = 6.7 Hz, 1H), 4.21 (dt, J = 12.9, 4.3 Hz, 2H), 3.61-3.54 (m, 2H), 3.42-3.31 (m, 2H), 2.66 (dd, J = 5.7, 3.9 Hz, 2H), 2.58 (s, 2H), 1.91 (d, J = 13.5 Hz, 2H), 1.61-1.41 (m, 8H). |
| 231 | 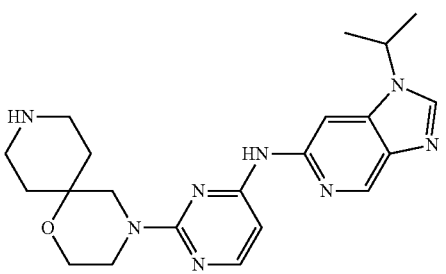<br>N-(2-(1-oxa-4,9-diazaspiro[5.5]undecan-4-yl)pyrimidin-4-yl)-1-isopropyl-1H-imidazo[4,5-c]pyridin-6-amine | A | 3.23, 409.3, B | 1H NMR (400 MHz, DMSO-$d_6$) δ 9.79 (s, 1H), 8.66 (d, J = 0.9 Hz, 1H), 8.33 (d, J = 18.9 Hz, 2H), 7.98 (d, J = 5.7 Hz, 1H), 6.44 (d, J = 5.7 Hz, 1H), 4.65 (p, J = 6.7 Hz, 1H), 3.80-3.68 (m, 4H), 3.65 (s, 2H), 2.73 (q, J = 9.8, 8.6 Hz, 2H), 2.67-2.57 (m, 2H), 1.66 (d, J = 13.5 Hz, 2H), 1.56 (d, J = 6.7 Hz, 6H), 1.42 (ddd, J = 13.0, 9.4, 3.9 Hz, 2H). |

TABLE 2-continued

| Example | Structure/Name | Synthesis Method/ Example # | LCMS RT (min), M + H+, method | 1H NMR (ppm) |
|---|---|---|---|---|
| 232 | 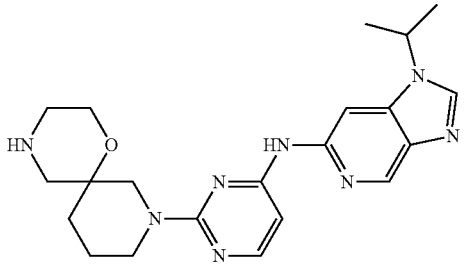<br>N-(2-(1-oxa-4,8-diazaspiro[5.5]undecan-8-yl)pyrimidin-4-yl)-1-isopropyl-1H-imidazo[4,5-c]pyridin-6-amine | A | 3.24, 409.3, B | 1H NMR (400 MHz, DMSO-d6) δ 9.71 (s, 3H), 8.65 (d, J = 0.8 Hz, 3H), 8.37 (d, J = 23.1 Hz, 7H), 7.95 (d, J = 5.6 Hz, 3H), 6.35 (d, J = 5.7 Hz, 3H), 4.71 (q, J = 5.9, 5.0 Hz, 2H), 4.53 (d, J = 13.4 Hz, 3H), 4.19 (s, 3H), 3.94 (s, 1H), 3.68 (dt, J = 11.4, 5.6 Hz, 3H), 3.47-3.24 (m, 7H), 2.66-2.55 (m, 10H), 2.53 (s, 1H), 1.68 (s, 9H), 1.56 (t, J = 6.8 Hz, 22H), 1.47 (s, 5H). |
| 233 | 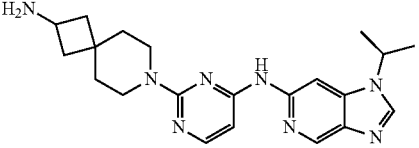<br>N-(2-(2-amino-7-azaspiro[3.5]nonan-7-yl)pyrimidin-4-yl)-1-isopropyl-1H-imidazo[4,5-c]pyridin-6-amine | A | 3.23, 393.3, B | 1H NMR (400 MHz, DMSO-d6) δ 9.74 (d, J = 2.5 Hz, 1H), 8.65 (s, 1H), 8.40 (s, 1H), 8.32 (s, 1H), 8.01-7.91 (m, 1H), 6.40-6.33 (m, 1H), 4.73-4.60 (m, 1H), 3.79-3.63 (m, 5H), 2.22-2.10 (m, 2H), 1.70 (dd, J = 11.4, 8.3 Hz, 1H), 1.61-1.38 (m, 13H). |
| 234 | 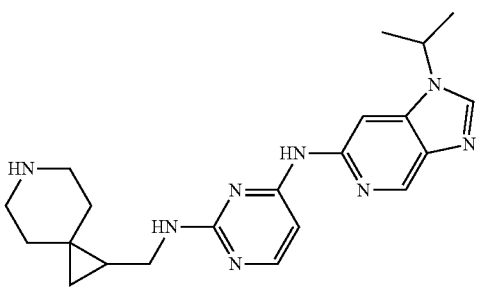<br>N2-(6-azaspiro[2.5]octan-1-ylmethyl)-N4-(1-isopropyl-1H-imidazo[4,5-c]pyridin-6-yl)pyrimidine-2,4-diamine | B | 3.31, 393.2, B | 1H NMR (400 MHz, DMSO-d6) δ 9.66 (s, 2H), 8.67-8.60 (m, 2H), 8.50 (s, 2H), 8.33 (d, J = 15.0 Hz, 2H), 7.88 (d, J = 5.6 Hz, 2H), 6.70-6.58 (m, 2H), 6.40-6.34 (m, 2H), 4.69 (s, 3H), 2.79-2.66 (m, 1H), 2.61 (s, 1H), 1.55 (t, J = 7.1 Hz, 14H), 1.38 (s, 2H), 1.30 (s, 2H), 1.00 (s, 4H), 0.42 (dd, J = 8.4, 4.2 Hz, 2H), 0.15 (dd, J = 5.7, 3.7 Hz, 2H). |
| 235 | 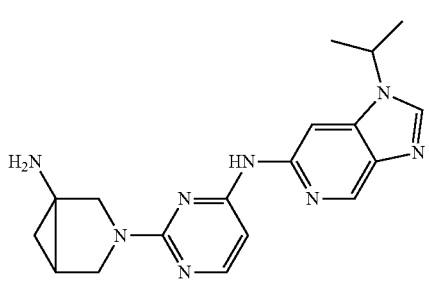<br>N-(2-(1-amino-3-azabicyclo[3.1.0]hexan-3-yl)pyrimidin-4-yl)-1-isopropyl-1H-imidazo[4,5-c]pyridin-6-amine | A | 2.95, 351.2, B | n/a |

TABLE 2-continued

| Example | Structure/Name | Synthesis Method/ Example # | LCMS RT (min), M + H+, method | 1H NMR (ppm) |
|---|---|---|---|---|
| 236 | N-(2-(hexahydropyrrolo[3,4-b]pyrrol-5(1H)-yl)pyrimidin-4-yl)-1-isopropyl-1H-imidazo[4,5-c]pyridin-6-amine | A | 2.88, 365.2, B | n/a |
| 237 | N-(2-(9-oxa-3,7-diazabicyclo[3.3.1]nonan-3-yl)pyrimidin-4-yl)-1-isopropyl-1H-imidazo[4,5-c]pyridin-6-amine | A | 3.16, 381.2, B | 1H NMR (400 MHz, DMSO-d6) δ 9.81 (s, 1H), 8.65 (d, J = 1.1 Hz, 1H), 8.49 (s, 1H), 8.32 (s, 1H), 8.00 (d, J = 5.6 Hz, 1H), 6.43 (d, J = 5.7 Hz, 1H), 4.67 (h, J = 6.7 Hz, 1H), 4.49 (d, J = 13.0 Hz, 2H), 3.79 (t, J = 4.1 Hz, 2H), 3.43-3.32 (m, 2H), 3.16-3.07 (m, 2H), 2.89 (d, J = 13.2 Hz, 2H), 1.55 (d, J = 6.8 Hz, 6H). |
| 238 | N-(2-(1-(aminomethyl)-2-azabicyclo[2.1.1]hexan-2-yl)pyrimidin-4-yl)-1-isopropyl-1H-imidazo[4,5-c]pyridin-6-amine | A | 3.23, 365.2, B | 1H NMR (400 MHz, DMSO-d6) δ 9.67 (s, 1H), 8.64 (d, J = 0.9 Hz, 1H), 8.50 (s, 1H), 8.33 (s, 1H), 7.89 (d, J = 5.7 Hz, 1H), 6.37 (d, J = 5.7 Hz, 1H), 4.71 (p, J = 6.7 Hz, 1H), 3.68 (s, 2H), 2.83 (t, J = 3.1 Hz, 1H), 1.85 (s, 2H), 1.60-1.50 (m, 8H). |
| 239 | (1R,5S,6r)-3-(4-((1-isopropyl-1H-imidazo[4,5-c]pyridin-6-yl)amino)pyrimidin-2-yl)-3-azabicyclo[3.1.0]hexane-6-carboxamide | A | 1.68, 379.2, D | 1H NMR (400 MHz, DMSO-d6) δ 9.78 (s, 1H), 8.64 (d, J = 1.0 Hz, 1H), 8.56 (s, 1H), 8.32 (s, 1H), 7.93 (d, J = 5.7 Hz, 1H), 7.45 (s, 1H), 6.82 (s, 1H), 6.40 (d, J = 5.6 Hz, 1H), 4.68 (p, J = 6.8 Hz, 1H), 3.91 (d, J = 11.0 Hz, 2H), 2.01 (s, 2H), 1.59 (d, J = 6.7 Hz, 6H), 1.45 (t, J = 3.1 Hz, 1H). |

Each compound in Table 3. below was prepared following a similar experimental procedure (using appropriately substituted reagents) as described in another Example herein, such Example being referenced in the Synthesis Method column.

TABLE 3

| Example | Structure/Name | Synthesis Method/ Example # | LCMS RT (min), M + H+, method | ¹H NMR (ppm) |
|---|---|---|---|---|
| 240 | N-(2-(2-aminopyridin-4-yl)pyrimidin-4-yl)-1-isopropyl-1H-imidazo[4,5-c]pyridin-6-amine | 35 | 1.498 347.15 O | 1H NMR (300 MHz, DMSO-d6) δ 10.31(s, 1H), 8.73 (s, 1H), 8.50-8.47 (m, 2H), 8.40 (s, 1H), 8.08-8.06 (d, J = 5.4 Hz, 1H), 7.42-7.38 (m, 2H), 7.27-7.26 (m, 1H), 6.08 (s, 2H), 4.78-4.74 (m, 1H), 1.62-1.60 (m, 6H) |
| 241 | 1-isopropyl-N-(2-(3-(methoxymethyl)piperazin-1-yl)pyrimidin-4-yl)-1H-imidazo[4,5-c]pyridin-6-amine | 35 | 1.083 383.2 K | 1H NMR (300 MHz, DMSO-d6) δ 9.80 (s, 1H), 8.65 (s, 1H), 8.37-8.34 (m, 2H), 7.97-7.96 (m, 1H), 6.41-6.39 (m, 1H), 4.67-4.63 (m, 1H), 4.53-4.44 (m, 2H), 3.39-3.26 (m, 5H), 2.97-2.90 (m, 2H), 2.79-2.77 (m, 1H), 2.70-2.37 (m, 3H), 1.57-1.53 (m, 6H) |
| 242 | 3-(4-(1-isopropyl-1H-imidazo[4,5-c]pyridin-6-ylamino)pyrimidin-2-yloxy)-2,2-dimethylpropanamide | 35 | 1.335 370.10 J | 1H NMR (300 MHz, DMSO-d6) δ 10.22 (s, 1H), 8.69 (s, 1H), 8.39-8.37 (m, 2H), 8.12-8.10 (m, 1H), 7.21 (s, 1H), 6.96 (m, 2H), 4.70 (m, 1H), 4.31 (s, 2H), 1.56-1.54 (m, 6H), 1.21 (s, 6H) |
| 243 | N-(3-hydroxypropyl)-1-isopropyl-6-(2-(4-methoxypiperidin-1-yl)pyrimidin-4-ylamino)-1H-pyrrolo[3,2-c]pyridine-3-carboxamide | 63 | 1.566 468.15 J | 1H NMR (300 MHz, DMSO-d6) δ 9.83 (s, 1H), 9.01 (s, 1H), 8.35 (s, 1H), 8.15 (s, 1H), 8.03-7.94 (m, 2H), 6.34-6.33 (m, 1H), 4.62-4.49 (m, 2H), 4.26-4.21 (m, 2H), 3.51-3.29 (m, 10H), 1.93-1.89 (m, 2H), 1.72-1.66 (m, 2H), 1.52-1.42 (m, 8H) |

| Example | Structure/Name | Synthesis Method/ Example # | LCMS RT (min), M + H⁺, method | ¹H NMR (ppm) |
|---|---|---|---|---|
| 244 | 1-isopropyl-6-(2-(4-methoxypiperidin-1-yl)pyrimidin-4-ylamino)-N-(3-morpholinopropyl)-1H-pyrrolo[3,2-c]pyridine-3-carboxamide | 63 | 1.087 537.35 I | 1H NMR (300 MHz, DMSO-d6) δ 9.80 (s, 1H), 9.01 (s, 1H), 8.36 (s, 1H), 8.13 (s, 1H), 7.96-7.94 (m, 2H), 6.34-6.32 (m, 1H), 4.63-4.56 (m, 1H), 4.26-4.22 (m, 2H), 3.59-3.56 (m, 4H), 3.47-3.29 (m, 8H), 2.37-2.34 (m, 6H), 1.93-1.89 (m, 2H), 1.71-1.66 (m, 2H), 1.52-1.43 (m, 8H) |
| 245 | 1-isopropyl-6-(2-(4-methoxypiperidin-1-yl)pyrimidin-4-ylamino)-N-(2-(4-methylpiperazin-1-yl)ethyl)-1H-pyrrolo[3,2-c]pyridine-3-carboxamide | 63 | 1.596 536.25 J | 1H NMR (400 MHz, DMSO-d6) δ 9.80 (s, 1H), 9.01 (s, 1H), 8.36 (s, 1H), 8.13 (s, 1H), 7.96-7.93 (m, 2H), 6.34-6.33 (m, 1H), 4.64-4.57 (m, 1H), 4.27-4.23 (m, 2H), 3.48-3.29 (m, 9H), 2.51-2.33 (m, 8H), 2.15 (s, 3H), 1.92-1.90 (m, 2H), 1.76-1.45 (m, 8H) |
| 246 | 1-isopropyl-6-(2-(4-methoxypiperidin-1-yl)pyrimidin-4-ylamino)-N-(2-(pyrrolidin-1-yl)ethyl)-1H-pyrrolo[3,2-c]pyridine-3-carboxamide | 63 | 1.68 507.35 I | 1H NMR (300 MHz, DMSO-d6) δ 9.81 (s, 1H), 9.16 (s, 1H), 8.36 (s, 1H), 8.15 (s, 1H), 7.99-7.94 (m, 2H), 6.34-6.32 (m, 1H), 4.62-4.58 (m, 1H), 4.26-4.22 (m, 2H), 3.47-3.29 (m, 12H), 2.59-2.54 (m, 2H), 1.93-1.89 (m, 2H), 1.70-1.67 (m, 4H), 1.52-1.44 (m, 8H) |

TABLE 3-continued

| Example | Structure/Name | Synthesis Method/ Example # | LCMS RT (min), M + H+, method | 1H NMR (ppm) |
|---|---|---|---|---|
| 247 | 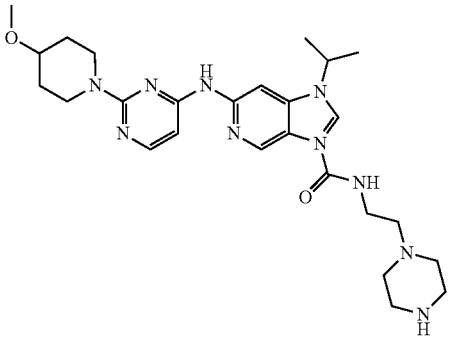<br>1-isopropyl-6-(2-(4-methoxypiperidin-1-yl)pyrimidin-4-ylamino)-N-(2-(piperazin-1-yl)ethyl)-1H-pyrrolo[3,2-c]pyridine-3-carboxamide | 63 | 1.668<br>522.25<br>J | 1H NMR (400 MHz, DMSO-d6) δ 9.81 (s, 1H), 9.01 (s, 1H), 8.37 (s, 1H), 8.13 (s, 1H), 7.96-7.93 (m, 2H), 6.34-6.33 (m, 1H), 4.64-4.57 (m, 1H), 4.26-4.23 (m, 2H), 3.48-3.18 (m, 8H), 2.70-2.68 (m, 4H), 2.51-2.30 (m, 6H), 1.92-1.90 (m, 2H) 1.52-1.47 (m, 8H) |
| 248 | 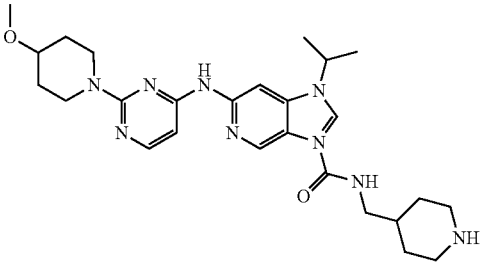<br>1-isopropyl-6-(2-(4-methoxypiperidin-1-yl)pyrimidin-4-ylamino)-N-(piperidin-4-ylmethyl)-1H-pyrrolo[3,2-c]pyridine-3-carboxamide | 63 | 1.54<br>507.35<br>I | 1H NMR (300 MHz, DMSO-d6) δ 9.80 (s, 1H), 9.01 (s, 1H), 8.35 (s, 1H), 8.17 (s, 1H), 8.05-7.90 (m, 2H), 6.34-6.32 (m, 1H), 4.62-4.57 (m, 1H), 4.26-4.22 (m, 2H), 3.35-3.12 (m, 8H), 2.94-2.91 (m, 2H), 2.45-2.37 (m, 2H), 1.92-1.90 (m, 2H), 1.60-1.50 (m, 11H), 1.06-1.03 (m, 2H) |
| 249 | 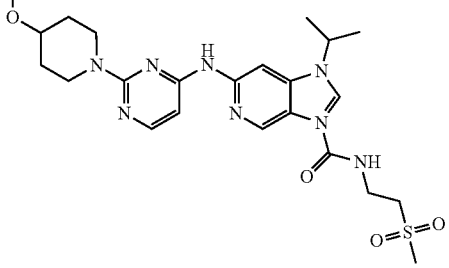<br>1-isopropyl-6-(2-(4-methoxypiperidin-1-yl)pyrimidin-4-ylamino)-N-(2-(methylsulfonyl)ethyl)-1H-pyrrolo[3,2-c]pyridine-3-carboxamide | 63 | 1.609<br>516.15<br>J | 1H NMR (300 MHz, DMSO-d6) δ 9.82 (s, 1H), 9.01 (s, 1H), 8.37-8.31 (m, 2H), 8.15 (s, 1H), 7.96-7.94 (m, 1H), 6.34-6.33 (m, 1H), 4.61 (m, 1H), 4.27-4.22 (m, 2H), 3.68-3.64 (m, 2H), 3.41-3.33 (m, 5H), 3.29 (s, 3H), 3.05 (s, 3H), 1.92-1.89 (m, 2H), 1.52-1.41 (m, 8H) |

| Example | Structure/Name | Synthesis Method/ Example # | LCMS RT (min), M + H+, method | 1H NMR (ppm) |
|---|---|---|---|---|
| 250 | 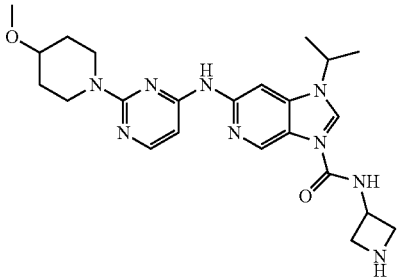<br>N-(azetidin-3-yl)-1-isopropyl-6-(2-(4-methoxypiperidin-1-yl)pyrimidin-4-ylamino)-1H-pyrrolo[3,2-c]pyridine-3-carboxamide | 63 | 1.583<br>465.25<br>I | 1H NMR (300 MHz, DMSO-d6) δ 9.80 (s, 1H), 9.00 (s, 1H), 8.62 (s, 1H), 8.36-8.24 (m, 2H), 7.96-7.94 (m, 1H), 6.34-6.32 (m, 1H), 4.77-4.56 (m, 2H), 4.26-4.22 (m, 2H), 3.79-3.40 (m, 11H), 1.92-1.89 (m, 2H), 1.53-1.41 (m, 8H) |

Example A23: Cyano(hydroxymethyl)methylacetic acid ethyl ester

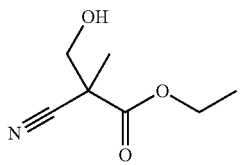

A mixture of ethyl 2-cyanopropionate (2.238 g, 17.6 mmol), paraformaldehyde (0.87 g, 26.4 mmol) and potassium carbonate (7.3 g, 52.8 mmol) in ethanol (100 mL) was stirred at room temperature for 2.5 h, then filtered through a Celite pad. The filtrate was concentrated in vacuo and the residue partitioned between EtOAc and water. The aqueous phase was extracted with additional EtOAc, and the combined organic extracts were dried over anhydrous sodium sulfate, filtered and concentrated in vacuo. The residue was purified by chromatography on silica (solvent gradient 10-50% EtOAc in cyclohexane) to afford the title compound as a colorless oil (1.633 g, 59%). 1H NMR (400 MHz, CDCl3): δ 4.31 (2H, q, J=7.1 Hz), 3.97-3.86 (2H, m), 2.37 (1H, t, J=7.1 Hz), 1.60 (3H, s), 1.35 (3H, t, J=7.1 Hz).

Example A24: 3-Amino-2-(2,2-dimethylpropionyloxymethyl)-2-methylpropionic acid ethyl ester hydrochloride

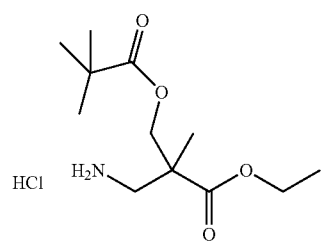 [SMILES: Cl ; CCOC(=O)C(C)(CN)COC(=O)C(C)(C)C]

Step 1: Cyano-(2,2-dimethylpropionyloxymethyl)methylacetic acid ethyl ester

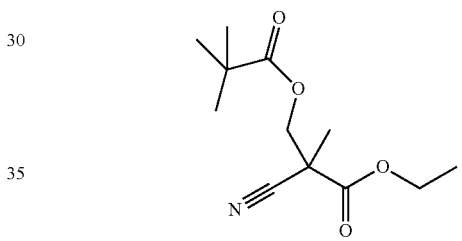

To a solution of cyano(hydroxymethyl)methylacetic acid ethyl ester (0.5 g, 3.18 mmol) in dichloromethane (8 mL) at 0° C. was added trimethylacetyl chloride (0.47 mL, 3.82 mmol) and N,N-diisopropylethylamine (0.827 mL, 4.77 mmol). The reaction mixture was stirred for 3 h at room temperature, then diluted with dichloromethane, washed successively with 1M HCl and saturated aqueous sodium bicarbonate, dried over anhydrous sodium sulphate and concentrated in vacuo. The residue was purified by chromatography (silica, gradient 5-20% EtOAc in cyclohexane) to afford the title compound as a colorless oil (0.693 g, 90%). 1H NMR (400 MHz, CDCl3): δ 4.37 (1H, d, J=11.0 Hz), 4.31 (1H, d, J=11.0 Hz), 4.30 (2H, q, J=7.1 Hz), 1.63 (3H, s), 1.35 (3H, t, J=7.1 Hz), 1.23 (9H, s).

Step 2: 3-Amino-2-(2,2-dimethylpropionyloxymethyl)-2-methylpropionic acid ethyl ester hydrochloride

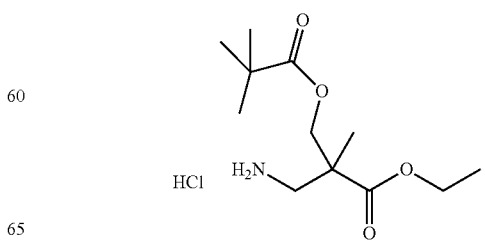

A mixture of cyano-(2,2-dimethylpropionyloxymethyl)methylacetic acid ethyl ester (0.136 g, 0.564 mmol), platinum(IV) oxide (12 mg, 0.05 mmol), ethanol (6 mL) and 4M HCl in dioxane (0.25 mL) was stirred under a balloon of hydrogen for 3 h, then filtered through a Celite pad. The filtrate was concentrated in vacuo to afford the title compound as a colourless gum (quantitative). $^1$H NMR (400 MHz, DMSO-$d_6$): δ 8.19 (3H, br s), 4.17-4.09 (4H, m), 3.15-2.98 (2H, m), 1.24 (3H, s), 1.20 (3H, t, J=7.1 Hz), 1.12 (9H, s).

Example A25:
3-Amino-2-hydroxy-2-methylpropionic acid ethyl ester

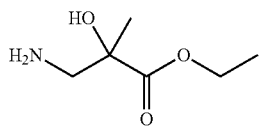

To a solution of 2-hydroxy-2-methyl-3-nitropropionic acid ethyl ester (*J. Am. Chem. Soc.*, 2008, 130, 13862) (0.5 g, 2.822 mmol) in acetic acid (35 mL) was added zinc dust (7.38 g, 113 mmol) portion-wise over 10 min. The mixture was stirred in a bath at 15° C. for 6.5 h, then filtered through a Celite pad. The filtrate was concentrated in vacuo, co-concentrated in vacuo with toluene and the residue was purified by chromatography on silica (gradient 2-12% 2M ammonia in methanol in dichloromethane) to afford the title compound as a colorless oil (0.378 g, 91%). $^1$H NMR (400 MHz, CDCl$_3$): δ 4.25 (2H, q, J=7.1 Hz), 3.04 (1H, d, J=13.1 Hz), 2.76 (1H, d, J=13.1 Hz), 2.73 (3H, br s), 1.36 (3H, s), 1.31 (3H, t, J=7.1 Hz).

Example A26: 2,2-Dimethyl-3-(2,2,2-trifluoroacetylamino)propionic acid ethyl ester

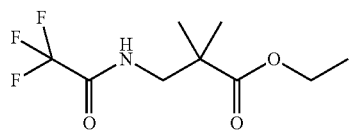 [SMILES: CCOC(=O)C(C)(C)CNC(=O)C(F)(F)F]

To a solution of 3-amino-2,2-dimethylpropionic acid ethyl ester (0.5 g, 3.44 mmol) in dichloromethane (10 mL) at 0° C. was added N,N-diisopropylethylamine (0.895 mL, 5.165 mmol) followed by trifluoroacetic anhydride (0.574 mL, 4.13 mmol) dropwise over 5 min. The mixture was stirred at 0° C. for 2.5 h, then washed with 1M HCl, dried over anhydrous sodium sulfate and concentrated in vacuo to afford the title compound as a colorless oil (quantitative). $^1$H NMR (400 MHz, CDCl$_3$): δ 7.10 (1H, br s), 4.18 (2H, q, J=7.1 Hz), 3.44 (2H, d, J=6.4 Hz), 1.28 (3H, t, J=7.1 Hz), 1.23 (6H, s).

Example A27: 2,2-Dimethyl-3-[methyl-(2,2,2-trifluoroacetyl)amino]propionic acid ethyl ester

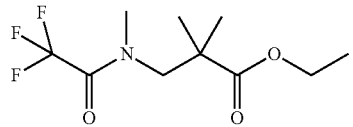 [SMILES: CCOC(=O)C(C)(C)CN(C)C(=O)C(F)(F)F]

To a solution of 2,2-dimethyl-3-(2,2,2-trifluoroacetylamino)propionic acid ethyl ester (0.877 mg, 3.44 mmol) in THF (10 mL) at 0° C. was added iodomethane (0.279 mL, 4.47 mmol) followed by sodium hydride (60% dispersion in oil, 0.413 g, 10.3 mmol) portion-wise over 10 min. The mixture was stirred at room temperature for 4 h, and then added to a mixture of 1M HCl and diethyl ether at 0° C. The aqueous phase was extracted with additional diethyl ether, and the combined organic extracts were dried over anhydrous sodium sulfate and concentrated in vacuo. The residue was purified by chromatography (silica, gradient 5-20% EtOAc in cyclohexane) to afford the title compound as a colorless oil (0.669 g, 76% 2 steps). $^1$H NMR (400 MHz, CDCl$_3$): δ 4.18 (2H, q, J=7.1 Hz), 3.72 (2H, s), 3.11 (3H, q, J=1.7 Hz), 1.30 (3H, t, J=7.1 Hz), 1.24 (6H, s).

Example A28:
2,2-Dimethyl-3-methylaminopropionic acid ethyl ester

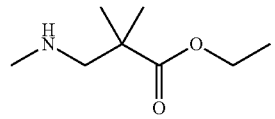

A solution of 2,2-dimethyl-3-[methyl-(2,2,2-trifluoroacetyl)amino]propionic acid ethyl ester (0.669 g, 2.62 mmol) in 2M ammonia in methanol (20 mL) was stirred at room temperature for 3 h, then 7M ammonia in methanol (10 mL) was added and stirring continued for 18 h. The reaction mixture was concentrated in vacuo and the residue purified by chromatography on silica (solvent gradient 1-7% 2M ammonia in methanol in dichloromethane) to afford the title compound as a colorless oil (0.32 g, 77%). $^1$H NMR (400 MHz, CDCl$_3$): δ 4.16 (2H, q, J=7.1 Hz), 2.65 (2H, s), 2.45 (3H, s), 1.27 (3H, t, J=7.1 Hz), 1.22 (6H, s), 1.15 (1H, br s).

Example A29: 2-Cyano-4-(2,2-dimethylpropionyloxy)-2-methylbutyric acid ethyl ester

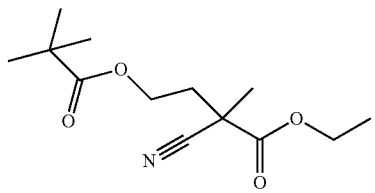 [SMILES: CCOC(=O)C(C)(C#N)CCOC(=O)C(C)(C)C]

To a solution of ethyl 2-cyanopropionate (0.636 g, 5 mmol) in dimethylformamide (3 mL) at 0° C. was added sodium hydride (60% dispersion in oil, 0.22 g, 5.5 mmol) portion-wise over 5 min. The mixture was stirred for 10 min at room temperature, then re-cooled to 0° C. while a solution of 2,2-dimethylpropionic acid 2-bromoethyl ester (US 2012/0202785) (1.254 g, 6 mmol) in dimethylformamide (2 mL) was added. The reaction mixture was stirred for 16 h at room temperature, then diluted with EtOAc, washed successively with 1M HCl, water and brine, dried over anhydrous sodium sulfate and concentrated in vacuo. The residue was purified by chromatography on silica (gradient 5-20% EtOAc in cyclohexane) to afford the title compound as a colorless oil (1.048 g, 82%). $^1$H NMR (400 MHz, CDCl$_3$): δ 4.33-4.18 (4H, m), 2.35 (1H, dt, J=14.5, 6.5 Hz), 2.13 (1H, dt, J=14.5, 6.3 Hz), 1.66 (3H, s), 1.34 (3H, t, J=7.1 Hz), 1.21 (9H, s).

Example A30: 2-Aminomethyl-4-(2,2-dimethylpropionyloxy)-2-methylbutyric acid ethyl ester

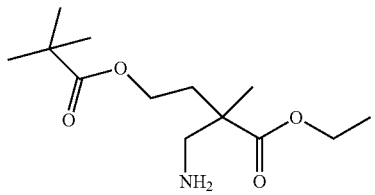 [SMILES: CCOC(=O)C(C)(CN)CCOC(=O)C(C)(C)C]

A mixture of 2-cyano-4-(2,2-dimethylpropionyloxy)-2-methylbutyric acid ethyl ester (0.5 g, 1.96 mmol), platinum (IV) oxide (30 mg, 0.13 mmol), ethanol (20 mL) and 4M HCl in dioxane (1 mL) was stirred under a balloon of hydrogen for 4 h, then filtered through a Celite pad. The filtrate was concentrated in vacuo, and the residue purified by chromatography on silica (solvent gradient: 2-6% 2M ammonia in methanol in dichloromethane) to afford the title compound as a colorless gum (0.384 g, 76%). $^1$H NMR (400 MHz, CDCl$_3$): δ 4.17 (2H, q, J=7.1 Hz), 4.13-4.07 (2H, m), 2.89 (1H, d, J=13.2 Hz), 2.74 (1H, d, J=13.2 Hz), 2.03 (1H, dt, J=14.1, 6.7 Hz), 1.81 (1H, dt, J=14.0, 6.8 Hz), 1.27 (3H, t, J=7.1 Hz), 1.20 (3H, s), 1.19 (11H, s).

Example A31: (E)-2,2-Dimethyl-4-(4,4,5,5-tetramethyl-[1,3,2]dioxaborolan-2-yl)but-3-enoic acid ethyl ester

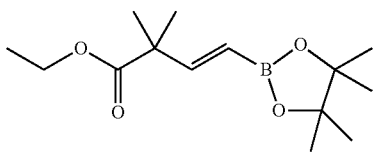 [SMILES: CCOC(=O)C(C)(C)/C=C/B1OC(C)(C)C(C)(C)O1]

A mixture of ethyl 2,2-dimethyl-3-butenoate (*J. Org. Chem.*, 2000, 65, 8402) (0.462 g, 3.25 mmol), vinylboronic acid pinacol ester (0.20 g, 1.3 mmol), Grubbs Catalyst, 2$^{nd}$ Generation (55 mg, 0.065 mmol) and dichloromethane (13 mL) was heated under reflux for 16 h. A further portion of Grubbs Catalyst, 2$^{nd}$ Generation (55 mg, 0.065 mmol) was added and heating continued for 24 h. The reaction mixture was purified by chromatography on silica (solvent gradient: 0-10% ethyl acetate in dichloromethane) to afford the title compound as a colorless oil (0.089 g, 27%). $^1$H NMR (400 MHz, CDCl$_3$): δ 6.74 (1H, d, J=18.3 Hz), 5.50 (1H, d, J=18.3 Hz), 4.12 (2H, q, J=7.1 Hz), 1.30 (6H, s), 1.27 (12H, s), 1.24 (3H, t, J=7.1 Hz).

Example A32: [(E)-1,1-Dimethyl-3-(4,4,5,5-tetramethyl-[1,3,2]dioxaborolan-2-yl)allyl]carbamic acid tert-butyl ester

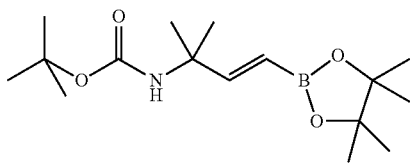 [SMILES: CC(C)(/C=C/B1OC(C)(C)C(C)(C)O1)NC(=O)OC(C)(C)C]

The title compound (118.5 mg, 53%) was prepared from (1,1-dimethylallyl)carbamic acid tert-butyl ester (WO2007/115058) (0.2 g, 1.08 mmol) and vinylboronic acid pinacol ester (0.111 g, 0.72 mmol) according to a procedure analogous to that described for Example A31. $^1$H NMR (400 MHz, CDCl$_3$): δ 6.64 (1H, d, J=18.2 Hz), 5.47 (1H, d, J=18.2 Hz), 4.56 (1H, br s), 1.42 (9H, s), 1.37 (6H, s), 1.27 (12H, s).

Example A33: Dimethyl-(5-tributylstannanylthiazol-2-yl)amine

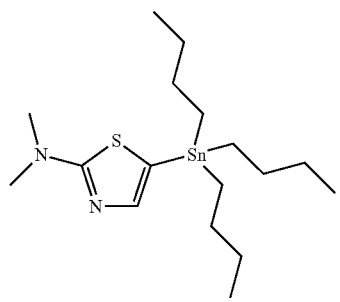 [SMILES: CCC[CH2][Sn]([CH2]CCC)([CH2]CCC)[c]1cnc(N(C)C)s1]

n-Butyllithium (2.5M in hexanes, 1.34 mL, 3.35 mmol) was added to a solution of 2-dimethylaminothiazole (*J. Chem. Soc., Perkin Trans.* 1, 1983, 341) (0.39 g, 3.04 mmol) in THF (10 mL) at −78° C. The mixture was stirred at −78° C. for 30 min, and a solution of tributyltin chloride (0.817 mL, 3.35 mmol) in THF (3 mL) was added. The reaction mixture was allowed to warm to 0° C. over 90 min. Saturated ammonium chloride was added and the mixture was extracted twice with EtOAc. The combined organic phases were washed with brine, dried over anhydrous sodium sulfate and concentrated in vacuo to afford the title compound as a pale yellow oil (quantitative). $^1$H NMR (400 MHz, CDCl$_3$): δ 7.10 (1H, s), 3.12 (6H, s), 1.59-1.51 (6H, m), 1.39-1.27 (6H, m), 1.08-1.04 (6H, m), 0.89 (9H, t, J=7.3 Hz).

Example A34: 2-Ethyl-5-tributylstannanylthiazole

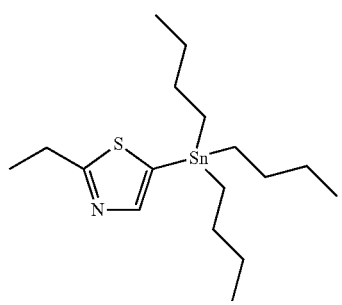 [SMILES: CCC[CH2][Sn]([CH2]CCC)([CH2]CCC)[c]1cnc(CC)s1]

The title compound (1.1 g, 100%) was prepared from 2-ethylthiazole (0.3 g, 2.63 mmol) according to a procedure analogous to that described for Example A33. $^1$H NMR (400 MHz, CDCl$_3$): δ 7.59 (1H, s), 3.10 (2H, q, J=7.6 Hz), 1.59-1.51 (6H, m), 1.41 (3H, t, J=7.6 Hz), 1.38-1.28 (6H, m), 1.13-1.09 (6H, m), 0.89 (9H, t, J=7.3 Hz).

Example A35: (trans)-3-Hydroxy-4-methoxypiperidine and (trans)-4-Hydroxy-3-methoxypiperidine

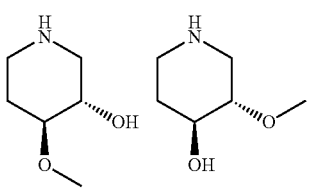

Step 1: (trans)-3-Hydroxy-4-methoxypiperidine-1-carboxylic acid benzyl ester and (trans)-4-Hydroxy-3-methoxypiperidine-1-carboxylic acid benzyl ester

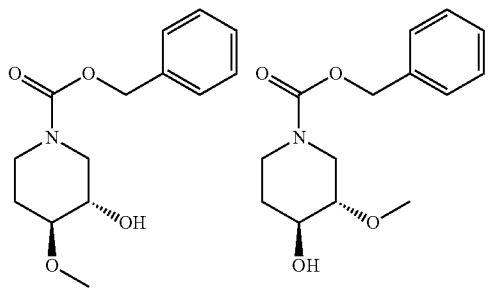

To a mixture of 7-oxa-3-azabicyclo[4.1.0]heptane-3-carboxylic acid benzyl ester (1.9 g, 8.15 mmol), in methanol (17 mL) was added slowly ceric ammonium nitrate (0.447 mg, 0.815 mmol); the reaction mixture became a deep orange colour. The mixture was stirred under nitrogen for 12 h. The mixture was evaporated onto diatomaceous earth and the product was purified by chromatography on silica (eluent: EtOAc in cyclohexane) to give the product as colorless oil, a mixture of regioisomers. (1.45 g, 67%). LCMS (ESI): [M+H]$^+$ 265.

Step 2: (trans)-3-Hydroxy-4-methoxypiperidine and (trans)-4-Hydroxy-3-methoxypiperidine

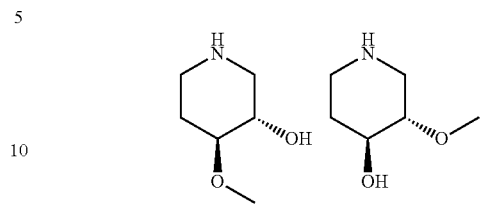

A mixture of (trans)-3-hydroxy-4-methoxypiperidine-1-carboxylic acid benzyl ester and (trans)-4-hydroxy-3-methoxypiperidine-1-carboxylic acid benzyl ester (1.2 g, 4.5 mmol) was dissolved in industrial methylated spirits (30 mL) and the mixture was purged with argon. Pd—C (10%, 100 mg) was added as a slurry in industrial methylated spirits (5 mL) and the mixture was stirred under an atmosphere of hydrogen for 2 h. The mixture was purged with argon, filtered to remove the catalyst and the resulting solution was concentrated in vacuo to give colorless oil that crystallised on standing as a mixture of regioisomers. LCMS (ESI): [M+H]$^+$ 132.

Example A36: 4-Dimethylaminomethyl-4-hydroxypiperidine-1-carboxylic acid tert-butyl ester

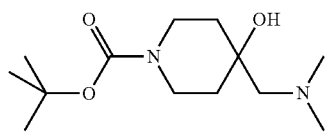 [SMILES: CN(C)CC1(O)CCN(C(=O)OC(C)(C)C)CC1]

tert-Butyl 1-oxa-6-azaspiro[2.5]octane-6-carboxylate (427 mg, 2.0 mmol) in dimethylamine (2M solution in methanol) (4 mL) was stirred at room temperature for 64 h. The reaction mixture was concentrated in vacuo. The residue was taken up in aqueous sodium bicarbonate and extracted with ethyl acetate (2×25 mL). The organic extracts were combined, dried over magnesium sulfate and concentrated in vacuo. The crude material was purified by chromatography on silica (solvent gradient: 1-10% 2M methanolic ammonia in dichloromethane) to give a colorless oil (428 mg, 83%). LCMS (ESI): [M-$^t$Bu]$^+$ 203.

Example A37: 4-Dimethylaminomethyl-4-methoxypiperidine-1-carboxylic acid tert-butyl ester

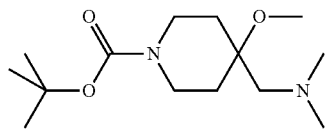

Sodium hydride (60% dispersion in oil) (131 mg, 3.28 mmol) was added to a solution of 4-dimethylaminomethyl-4-hydroxypiperidine-1-carboxylic acid tert-butyl ester (424 mg, 1.64 mmol) in tetrahydrofuran (5 mL) and the resulting mixture was stirred at room temperature for 45 min. Methyl iodide (0.11 mL, 1.72 mmol) was added and the reaction mixture was stirred at room temperature for 3 h. The reaction mixture was quenched with slow addition of water and then diluted with aqueous sodium bicarbonate (70 mL). The aqueous mixture was extracted with ethyl acetate (4×15 mL). The organic extracts were combined, washed with brine, dried over magnesium sulfate and concentrated in vacuo. The crude residue was purified by chromatography on silica (solvent gradient: 1-5% 2M methanolic ammonia in dichloromethane) to give a colorless oil (329 mg, 76%). $^1$H NMR (400 MHz, CDCl$_3$) δ 3.84-3.64 (m, 2H), 3.19 (s, 3H), 3.14-3.01 (m, 2H), 2.31-2.28 (m, 8H), 1.81-1.75 (m, 2H), 1.48-1.41 (m, 2H), 1.45 (s, 9H).

Example A38: (4-Methoxypiperidin-4-ylmethyl)dimethylamine

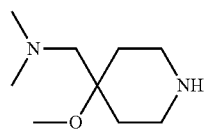

Trifluoroacetic acid (2.5 mL) was added to a solution of 4-dimethylaminomethyl-4-methoxypiperidine-1-carboxylic acid tert-butyl ester (337 mg, 1.2 mmol) in dichloromethane (10 mL) and stirred at room temperature for 20 min. The reaction mixture was diluted with methanol and loaded onto an SCX cartridge. The title compound was washed with methanol and then eluted with 2M ammonia in methanol. The basic fraction was concentrated in vacuo to give a colorless oil. LCMS (ESI): [M+H]$^+$ 173.

Example A39: 4-Hydroxy-4-methoxymethylpiperidine-1-carboxylic acid tert-butyl ester

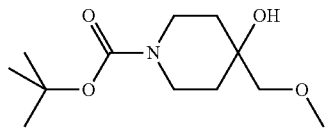

Sodium methoxide (122 mg, 2.3 mmol) was added to a solution of tert-butyl 1-oxa-6-azaspiro[2.5]octane-6-carboxylate (400 mg, 1.9 mmol) in anhydrous methanol (1.9 mL) and the reaction solution was stirred at room temperature for 64 h. The reaction mixture was concentrated in vacuo. The crude reaction was taken up in aqueous ammonium chloride and extracted with ethyl acetate (2×). The organic extracts were combined, dried over magnesium sulfate and concentrated in vacuo. The crude was purified by chromatography on silica (solvent gradient: 5-50% ethyl acetate in cyclohexane) to give a colorless oil (413 mg, 90%). LCMS (ESI): [M+Na]$^+$ 268.

Example A40: 4-Methoxy-4-methoxymethylpiperidine

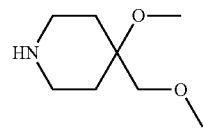

4-Methoxy-4-methoxymethylpiperidine was synthesised from 4-hydroxy-4-methoxymethylpiperidine-1-carboxylic acid tert-butyl ester following procedures analogous to those described for Example A37 and A38. This gave a colorless oil. LCMS (ESI): [M+H]$^+$ 160.

Example A41: 4-(2-Hydroxyethyl)-4-methoxypiperidine-1-carboxylic acid tert-butyl ester

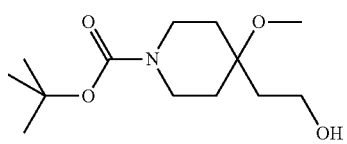 [SMILES: COC1(CCO)CCN(C(=O)OC(C)(C)C)CC1]

Borane dimethyl sulfide complex (3.8 mL, 40 mmol) was added to 4-methoxy-4-vinylpiperidine-1-carboxylic acid tert-butyl ester (Monatshefte fuer Chemie, 2004, 135 (7), 899-909) (4.8 g, 20 mmol) in tetrahydrofuran (90 mL) over 2 min at 0° C. After 15 min the reaction mixture was warmed to room temperature and stirred for a further 30 min. The reaction mixture was cooled to 0° C. and 6M sodium hydroxide (33 mL, 200 mmol) was added dropwise, followed by a slow addition of hydrogen peroxide solution (30 wt. % in water) (23 mL, 200 mmol). The reaction mixture was stirred for 30 min and then quenched with aqueous sodium metabisulfite and concentrated in vacuo to remove the volatile organic extracts. The resulting aqueous mixture was extracted with ethyl acetate (2×). The organic extracts were combined, washed with brine (50 mL), dried over sodium sulfate and concentrated in vacuo. The crude residue was purified by chromatography on silica (solvent gradient: 50-100% ethyl acetate in dichloromethane) to give a colorless oil (1.68 g, 33%). LCMS (ESI): [M+H]$^+$ 260.

Example A42: 2-(4-Methoxypiperidin-4-yl)ethanol

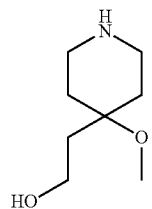

2-(4-Methoxypiperidin-4-yl)ethanol was synthesised from 4-(2-hydroxyethyl)-4-methoxypiperidine-1-carboxylic acid tert-butyl ester in a procedure analogous to that described for Example A38. This gave a colorless oil. $^1$H NMR (400 MHz, CDCl$_3$) δ 3.78 (t, J=6.5 Hz, 2H), 3.21 (s, 3H), 3.18-3.09 (m, 4H), 2.03-1.97 (m, 2H), 1.91-1.83 (m, 2H), 1.81 (t, J=6.5 Hz, 2H).

Example A43: 4-(2-Methanesulfonyloxyethyl)-4-methoxypiperidine-1-carboxylic acid tert-butyl ester

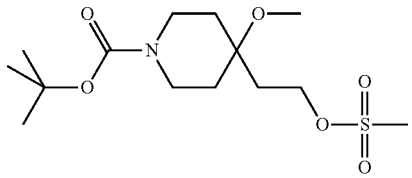 [SMILES: COC1(CCOS(C)(=O)=O)CCN(C(=O)OC(C)(C)C)CC1]

Methanesulfonyl chloride (0.13 mL, 1.70 mmol) was added dropwise to a solution of 4-(2-hydroxyethyl)-4-methoxypiperidine-1-carboxylic acid tert-butyl ester (400 mg, 1.54 mmol) and N,N-diisopropylethylamine (0.40 mL, 2.31 mmol) in tetrahydrofuran (4 mL) at 0° C. The reaction mixture was allowed to warm to room temperature and stirred for 90 min. The reaction mixture was quenched with aqueous ammonium hydroxide and then concentrated in vacuo. The residue was taken up in aqueous sodium bicarbonate and extracted with ethyl acetate (2×). The organic extracts were combined, washed with brine (15 mL), dried over sodium sulfate and concentrated in vacuo to give a colorless oil (511 mg, 98%). LCMS (ESI): [M+Na]$^+$ 360.

Example A44: 4-(2-Dimethylaminoethyl)-4-methoxypiperidine-1-carboxylic acid tert-butyl ester

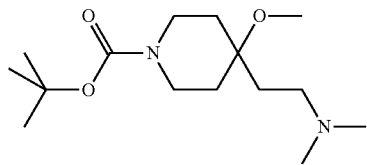

4-(2-Methanesulfonyloxyethyl)-4-methoxypiperidine-1-carboxylic acid tert-butyl ester (221 mg, 0.65 mmol) in dimethylamine (2M solution in tetrahydrofuran) (2 mL) was heated at 65° C. in a sealed tube. The reaction mixture was diluted with methanol and loaded onto an SCX cartridge. The title compound was washed with methanol and eluted with 2M ammonia in methanol. The basic fraction was concentrated in vacuo to give a pale yellow oil (187 mg, 69%). LCMS (ESI): [M+H]$^+$ 257.

Example A45: [2-(4-Methoxypiperidin-4-yl)ethyl]dimethylamine

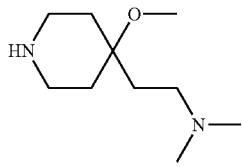

[2-(4-Methoxypiperidin-4-yl)ethyl]dimethylamine was synthesized from 4-(2-dimethylaminoethyl)-4-methoxypiperidine-1-carboxylic acid tert-butyl ester in a procedure analogous to that described for Example A38. This gave a pale yellow oil. LCMS (ESI): [M+H]$^+$ 187.

Example A46: 4-(2-Azidoethyl)-4-methoxypiperidine-1-carboxylic acid tert-butyl ester

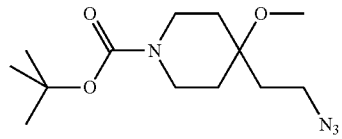 [SMILES: COC1(CCN=[N+]=[N-])CCN(C(=O)OC(C)(C)C)CC1]

Sodium azide (64 mg, 1.0 mmol) was added to a solution of 4-(2-methanesulfonyloxyethyl)-4-methoxypiperidine-1-carboxylic acid tert-butyl ester (302 mg, 0.9 mmol) in N,N-dimethylformamide (1.5 mL) and stirred at 40° C. for 16 h. The reaction mixture was diluted with dichloromethane and purified by column chromatography on silica (solvent gradient: 10-50% ethyl acetate/dichloromethane) to give a colorless oil (201 mg, 79%). LCMS (ESI): [M+H]$^+$ 285.

Example A47: 2-(4,5,6,7-Tetrahydropyrazolo[4,3-c]pyridin-2-yl)ethanol hydrochloride and 2-(4,5,6,7-Tetrahydropyrazolo[4,3-c]pyridin-1-yl)ethanol hydrochloride

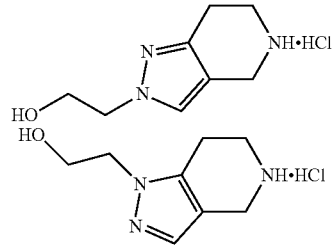

Step 1: 3-[1-Dimethylaminometh-(Z)-ylidene]-4-oxopiperidine-1-carboxylic acid tert-butyl ester

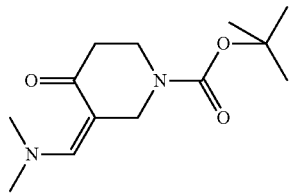 [SMILES: CN(C)/C=C1/CN(C(=O)OC(C)(C)C)CCC1=O]

4-Oxopiperidine-1-carboxylic acid tert-butyl ester (2 g, 10.0 mmol) was dissolved in dimethylformamide dimethyl acetal (10 mL) and the reaction mixture heated at reflux for 16 h. The reaction was cooled to room temperature, concentrated in vacuo and the resultant residue subjected to silica gel chromatography (solvent: 100% EtOAc) to yield the title compound as an oil (0.46 g, 18%). $^1$H NMR 400 MHz δ (CDCl$_3$): 7.49 (1H, s), 4.55 (2H, s), 3.60 (2H, d, J=6.5 Hz), 3.11 (6H, s), 2.44 (2H, t, J=6.5 Hz), 1.48 (9H, s).

Step 2: 2-(2-Hydroxyethyl)-2,4,6,7-tetrahydropyrazolo[4,3-c]pyridine-5-carboxylic acid tert-butyl ester and 1-(2-Hydroxyethyl)-1,4,6,7-tetrahydropyrazolo[4,3-c]pyridine-5-carboxylic acid tert-butyl ester

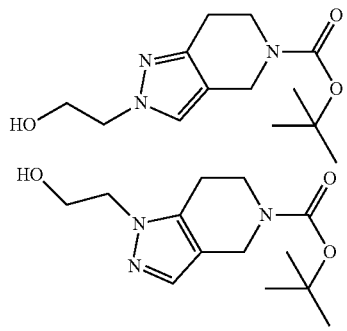

To a solution of 3-[1-dimethylaminometh-(Z)-ylidene]-4-oxopiperidine-1-carboxylic acid tert-butyl ester (455 mg, 1.78 mmol) in industrial methylated spirits (10 mL) was added 2-hydroxyethylhydrazine (163 mg, 2.15 mmol) and the reaction mixture heated at reflux for 4 h. The reaction mixture was concentrated in vacuo and the resultant residue subjected to silica gel chromatography (solvent: 100% EtOAc) to yield the title compound as a 1:1.3 mixture of regioisomers. (0.45 g, 94%). $^1$H NMR 400 MHz δ (CDCl$_3$): 7.32 (1H, s), 7.20 (1.3H, s), 4.46 (2.6H, s), 4.43 (2H, s), 4.18 (2.6H, t, J=4.8 Hz), 4.10-4.07 (2H, m), 4.02-3.92 (4.6H, m), 3.77-3.64 (4.6H, m), 3.31 (1H, br s), 3.13 (1.3H, br s), 2.75 (2.6H, t, J=4.8 Hz), 2.68 (2H, t, J=4.9 Hz), 1.48 (20.7H, s).

Step 3: 2-(4,5,6,7-Tetrahydropyrazolo[4,3-c]pyridin-2-yl)ethanol hydrochloride and 2-(4,5,6,7-Tetrahydropyrazolo[4,3-c]pyridin-1-yl)ethanol hydrochloride

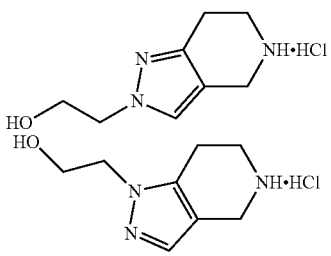

A mixture of 2-(2-hydroxyethyl)-2,4,6,7-tetrahydropyrazolo[4,3-c]pyridine-5-carboxylic acid tert-butyl ester and 1-(2-hydroxyethyl)-1,4,6,7-tetrahydropyrazolo[4,3-c]pyridine-5-carboxylic acid tert-butyl ester (200 mg, 0.75 mmol) in methanol (1 mL) was treated with HCl in dioxane (4N, 2 mL). The reaction was stirred at room temperature for 1 h before being concentrated in vacuo to give a mixture of the title products as a white solid. (152 mg, 100%). $^1$H NMR 400 MHz δ (DMSO-d$_6$): 9.30 (4.6H, br s), 7.60 (1.3H, s), 7.36 (1H, s), 4.15-4.01 (9.2H, m), 3.77-3.62 (4.6H, m), 3.40 (4.6H, m), 2.97 (2H, t, J=6.1 Hz), 2.85 (2.6H, t, J=6.1 Hz).

Example A48: (2-Chloropyrimidin-4-yl)-(1-isopropyl-2-methoxymethyl-1H-imidazo[4,5-c]pyridin-6-yl)amine

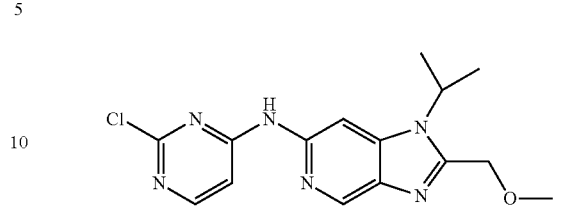

Step 1: N-(6-Bromo-4-isopropylaminopyridin-3-yl)-2-methoxyacetamide

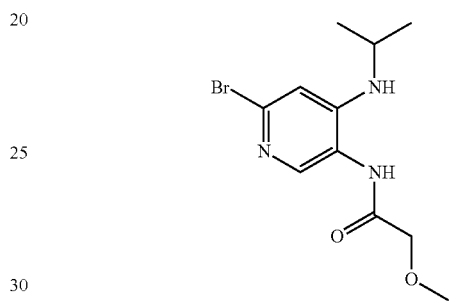

To a solution of 6-bromo-N$^4$-isopropylpyridine-3,4-diamine (Example 12, Step 2) (200 mg, 0.88 mmol) and triethylamine (243 µL, 1.75 mmol) in dichloromethane (3 mL) at 0° C. was added dropwise methoxyacetyl chloride (104 µL, 1.14 mmol) and the reaction mixture was stirred at room temperature for 30 min. The reaction mixture was diluted with water and extracted with dichloromethane (3×). The combined organic extracts were washed with brine, dried over anhydrous magnesium sulfate and concentrated in vacuo to give the title compound (263 mg, 100%). $^1$H NMR 400 MHz (CDCl$_3$) δ 8.01 (1H, br s), 7.89 (1H, s), 6.72 (1H, s), 4.95-4.81 (1H, m), 4.10 (2H, s), 3.53 (3H, s), 1.26 (6H, d, J=6.3 Hz).

Step 2: 6-Bromo-1-isopropyl-2-methoxymethyl-1H-imidazo[4,5-c]pyridine

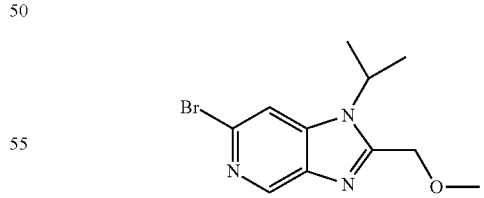

A solution of N-(6-bromo-4-isopropylaminopyridin-3-yl)-2-methoxyacetamide (263 mg, 0.88 mmol) and potassium carbonate (157 mg, 1.14 mmol) in N,N-dimethylformamide (5 mL) was heated at 100° C. for 16 h. The reaction mixture was diluted with water and the product extracted with EtOAc (3×). The combined organic extracts were washed with brine, dried over anhydrous magnesium sulfate and concentrated in vacuo. The resultant residue was subjected to silica gel chromatography (solvent gradient: 0-10% methanol in EtOAc) to yield the title compound as an off white solid (143 mg, 57%). LCMS (ESI): [M+H]+=284.

Step 3: (2-Chloropyrimidin-4-yl)-(1-isopropyl-2-methoxymethyl-1H-imidazo[4,5-c]pyridin-6-yl)amine

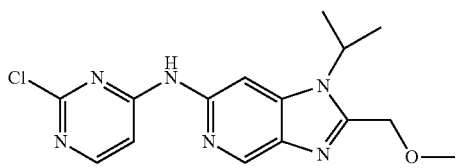 [SMILES: COCc1nc2cnc(Nc3ccnc(Cl)n3)cc2n1C(C)C]

6-Bromo-1-isopropyl-2-methoxymethyl-1H-imidazo[4,5-c]pyridine (143 mg, 0.50 mmol), 4-amino-2-chloropyrimidine (65 mg, 0.50 mmol), tris(dibenzylideneacetone)dipalladium(0) (23 mg, 25 μmol), 4,5-bis(diphenylphosphino)-9,9-dimethylxanthene (58 mg, 0.10 mmol), cesium carbonate (328 mg, 1.00 mmol) and dioxane (5 mL) were sealed in a vial and the mixture degassed with argon. The reaction mixture was heated at 100° C. for 3 h. The reaction mixture was diluted with water and the product extracted with EtOAc (3×). The combined organic extracts were washed with brine, dried over anhydrous magnesium sulfate and concentrated in vacuo. The resultant residue was subjected to silica gel chromatography (solvent gradient: 0-10% methanol in EtOAc) to yield the title compound as an off white solid (113 mg, 67%). LCMS (ESI): [M+H]+=333.

Example A49: (2-Chloropyrimidin-4-yl)-[1-isopropyl-2-(tetrahydropyran-2-yloxymethyl)-1H-imidazo[4,5-c]pyridin-6-yl]amine

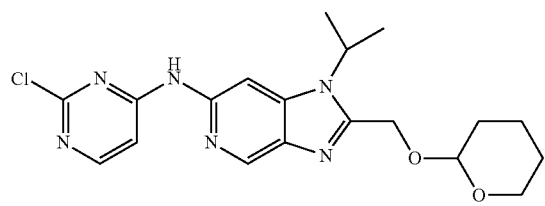

Step 1: Acetic acid (6-bromo-4-isopropylaminopyridin-3-ylcarbamoyl)methyl ester

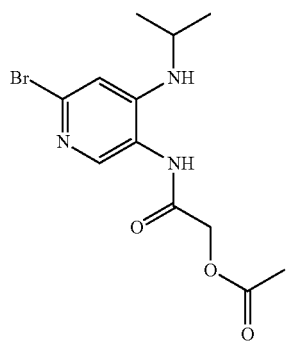 [SMILES: CC(=O)OCC(=O)Nc1cnc(Br)cc1NC(C)C]

Acetoxyacetyl chloride (1.8 mL, 16.9 mmol) was added dropwise to a solution of 6-bromo-N4-isopropylpyridine-3,4-diamine (Example 12, Step 2) (3 g, 13.0 mmol) and triethylamine (3.6 mL, 26.0 mmol) in dichloromethane at 0° C. and the resultant mixture was stirred at 0° C. for 15 min. The reaction mixture was diluted with water and the product extracted with dichloromethane (3×). The combined organic extracts were washed with brine, dried over anhydrous magnesium sulfate and concentrated in vacuo to give the crude title product as a yellow oil. LCMS (ESI): [M+H]+=330.

Step 2: (6-Bromo-1-isopropyl-1H-imidazo[4,5-c]pyridin-2-yl)methanol

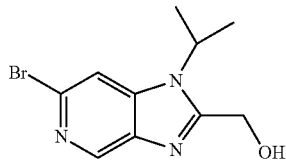

A suspension of acetic acid (6-bromo-4-isopropylaminopyridin-3-ylcarbamoyl)methyl ester (4.28 g, 13.0 mmol) and potassium carbonate (2.34 g, 16.9 mmol) in N,N-dimethylformamide (30 mL) was heated at 120° C. for 5 h. The reaction mixture was cooled to room temperature and diluted with water and the product extracted with EtOAc (3×). The combined organic extracts were washed with brine, dried over anhydrous magnesium sulfate and concentrated in vacuo. The resultant residue was dissolved in methanol (20 mL) and water (5 mL) and lithium hydroxide monohydrate (200 mg, 4.8 mmol) added. The reaction mixture was stirred at room temperature for 16 h. To the reaction mixture was acidified with HCl (1N) until pH 5, followed by saturated aqueous sodium bicarbonate until pH 8. The product was extracted with EtOAc (3×) and the combined organic extracts were washed with brine, dried over anhydrous magnesium sulfate and concentrated in vacuo. The resultant residue was subjected to silica gel chromatography (solvent gradient: 0-5% methanol in EtOAc) to yield the title compound as an off-white solid (1.53 g, 43%). LCMS (ESI): [M+H]+=270.

Step 3: 6-Bromo-1-isopropyl-2-(tetrahydropyran-2-yloxymethyl)-1H-imidazo[4,5-c]pyridine

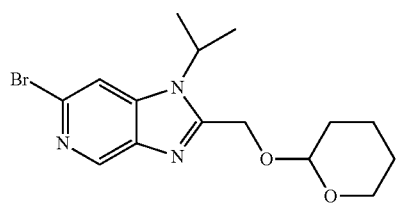 [SMILES: CC(C)n1c(COC2CCCCO2)nc2cnc(Br)cc21]

To a solution of (6-bromo-1-isopropyl-1H-imidazo[4,5-c]pyridin-2-yl)methanol (1.53 g, 5.77 mmol) in tetrahydrofuran (20 mL) was added 3,4-dihydropyran (790 μL, 8.66 mmol) and p-toluenesulfonic acid (98 mg, 0.58 mmol) and the resultant mixture heated at reflux for 1 h. 3,4-Dihydropyran (0.4 mL, 4.3 mmol) was added and heating continued for 16 h. The reaction mixture was diluted with saturated aqueous sodium bicarbonate and the product extracted with EtOAc (3x). The combined organic extracts were washed with brine, dried over anhydrous magnesium sulfate and concentrated in vacuo. The resultant residue was subjected to silica gel chromatography (solvent gradient: 0-5% methanol in EtOAc) to yield the title compound as an off-white solid (1.89 g, 94%). LCMS (ESI): [M+H]$^+$=354.

Step 4: (2-Chloropyrimidin-4-yl)-[1-isopropyl-2-(tetrahydropyran-2-yloxymethyl)-1H-imidazo[4,5-c]pyridin-6-yl]-amine

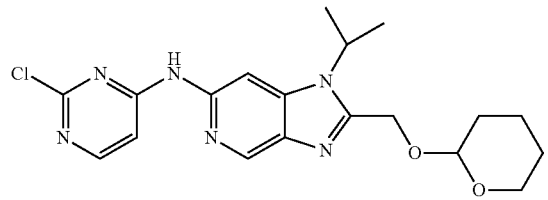 [SMILES: CC(C)n1c(COC2CCCCO2)nc2cnc(Nc3ccnc(Cl)n3)cc21]

6-Bromo-1-isopropyl-2-(tetrahydropyran-2-yloxymethyl)-1H-imidazo[4,5-c]pyridine (1.89 g, 5.34 mmol), 4-amino-2-chloropyrimidine (691 mg, 5.34 mmol), tris(dibenzylideneacetone)dipalladium(0) (244 mg, 0.27 mmol), 4,5-bis(diphenylphosphino)-9,9-dimethylxanthene (617 mg, 1.07 mmol), cesium carbonate (3.48 g, 10.67 mmol) and dioxane (50 mL) were sealed in a vial and the mixture degassed with argon. The reaction mixture was heated at 100° C. for 1 h. The reaction mixture was diluted with water and the product extracted with EtOAc (3x). The combined organic extracts were washed with brine, dried over anhydrous magnesium sulfate and concentrated in vacuo. The resultant residue was subjected to silica gel chromatography (solvent gradient: 0-5% methanol in EtOAc) to yield the title compound as an off-white solid (1.68 g, 78%). LCMS (ESI): [M+H]$^+$=403.

Example A50: (2-Chloropyrimidin-4-yl)-(4,4-dimethyl-3,4-dihydro-2H-1-oxa-4a,7,9-triazafluoren-6-yl)amine

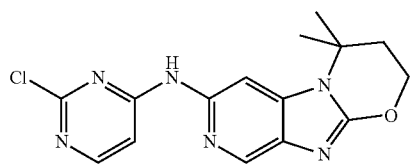 [SMILES: CC1(C)CCOc2nc3cnc(Nc4ccnc(Cl)n4)cc3n21]

Step 1: 3-(2-Bromo-5-nitropyridin-4-ylamino)-3-methylbutan-1-ol

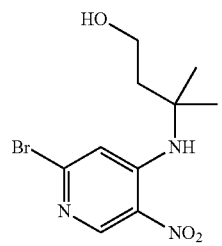

To a solution of 2,4-dibromo-5-nitropyridine (0.5 g, 1.77 mmol) in tetrahydrofuran (10 mL) was added 3-amino-3-methylbutan-1-ol (220 mg, 2.12 mmol) and the reaction mixture heated at reflux for 16 h. The reaction mixture was diluted with water and the product extracted with EtOAc (3x). The combined organic extracts were washed with brine, dried over anhydrous magnesium sulfate and concentrated in vacuo. The resultant residue was subjected to silica gel chromatography (solvent gradient: 0-100% EtOAc in pentane) to yield the title compound as a yellow solid (480 mg, 89%). $^1$H NMR 400 MHz δ (CDCl$_3$): 8.96 (1H, s), 8.71 (1H, br s), 7.12 (1H, s), 3.89-3.82 (2H, m), 2.07 (2H, t, J=6.4 Hz), 1.55 (6H, s), 1.45 (1H, t, J=4.6 Hz).

Step 2: (2-Bromo-5-nitropyridin-4-yl)-[1,1-dimethyl-3-(tetrahydropyran-2-yloxy)propyl]amine

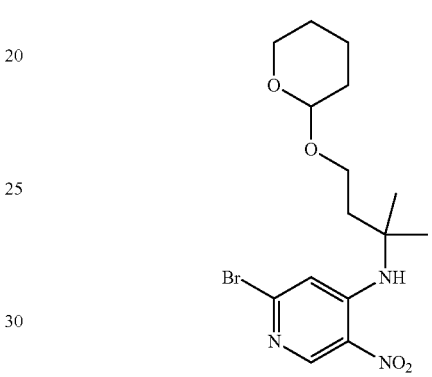

To a solution of 3-(2-bromo-5-nitropyridin-4-ylamino)-3-methylbutan-1-ol (480 mg, 1.58 mmol) in tetrahydrofuran (15 mL) was added 3,4-dihydropyran (360 μL, 3.95 mmol) and p-toluenesulfonic acid (27 mg, 0.16 mmol) and the resultant mixture heated at reflux for 16 h. The reaction mixture was diluted with saturated aqueous sodium bicarbonate and the product extracted with EtOAc (3x). The combined organic extracts were washed with brine, dried over anhydrous magnesium sulfate and concentrated in vacuo. The resultant residue was subjected to silica gel chromatography (solvent gradient: 0-100% EtOAc in pentane) to yield the title compound (0.61 g, 100%). LCMS (ESI): [M+H]$^+$=388.

Step 3: 6-Bromo-N$^4$-[1,1-dimethyl-3-(tetrahydropyran-2-yloxy)propyl]pyridine-3,4-diamine

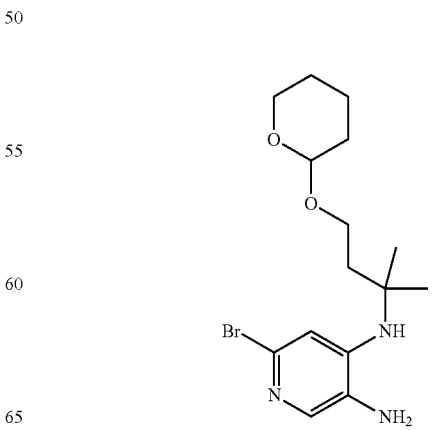

To a solution of (2-bromo-5-nitropyridin-4-yl)-[1,1-dimethyl-3-(tetrahydropyran-2-yloxy)-propyl]amine (0.71 g, 1.84 mmol) in industrial methylated spirits (5 mL) was added platinum (IV) oxide (36 mg, 0.16 mmol). The reaction mixture was stirred at room temperature under an atmosphere of hydrogen for 1 h. The reaction mixture was concentrated in vacuo. The resultant residue was subjected to silica gel chromatography (solvent gradient: 0-100% EtOAc in cyclohexane) to yield the title compound as an orange oil (373 mg, 57%). LCMS (ESI): [M+H]$^+$=358.

Step 4: 6-Bromo-1-[1,1-dimethyl-3-(tetrahydropyran-2-yloxy)-propyl]-1,3-dihydroimidazo[4,5-c]pyridin-2-one

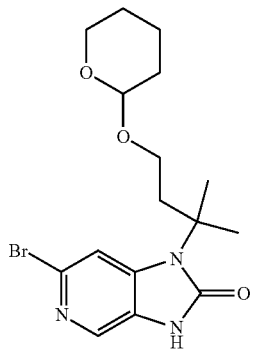 [SMILES: CC(C)(CCOC1CCCCO1)n1c(=O)[nH]c2cnc(Br)cc21]

Phosgene solution (20% in toluene) (0.82 mL, 1.56 mmol) was added drop-wise to a solution of 6-bromo-N$^4$-[1,1-dimethyl-3-(tetrahydropyran-2-yloxy)propyl]pyridine-3,4-diamine (373 mg, 1.04 mmol) and triethylamine (290 µL, 2.08 mmol) in tetrahydrofuran (5 mL) causing a thick white precipitate to form. The reaction mixture was stirred at room temperature for 10 min, diluted with water and the product extracted with EtOAc (3×). The combined organic extracts were washed with brine, dried over anhydrous magnesium sulfate and concentrated in vacuo. The solid was triturated with diethyl ether to yield the title compound as an off-white solid (0.30 g, 74%). LCMS (ESI): [M+H]$^+$=382.

Step 5: 6-Bromo-1-(3-hydroxy-1,1-dimethylpropyl)-1,3-dihydroimidazo[4,5-c]pyridin-2-one

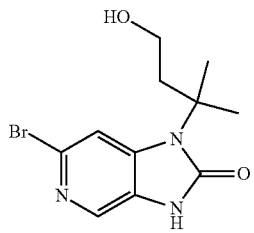 [SMILES: CC(C)(CCO)n1c(=O)[nH]c2cnc(Br)cc21]

6-Bromo-1-[1,1-dimethyl-3-(tetrahydropyran-2-yloxy)propyl]-1,3-dihydroimidazo[4,5-c]pyridin-2-one (297 mg, 0.77 mmol) was dissolved in hydrochloric acid in methanol (10 mL, 1.25 M) and the reaction mixture was stirred at room temperature for 3 h. The reaction mixture was basified with saturated aqueous sodium bicarbonate to pH 8 and the product was extracted with EtOAc (3×). The combined organic extracts were washed with brine, dried over anhydrous magnesium sulfate and concentrated in vacuo. The solid was triturated with diethyl ether to yield the title compound as an off-white solid (0.21 g, 90%). LCMS (ESI): [M+H]$^+$=300 & 302.

Step 6: 6-Bromo-4,4-dimethyl-3,4-dihydro-2H-1-oxa-4a,7,9-triazafluorene

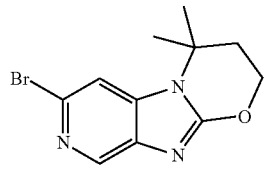 [SMILES: CC1(C)CCOc2nc3cnc(Br)cc3n21]

Diisopropyl azodicarboxylate (196 µL, 0.99 mmol) was added drop-wise to a suspension of 6-bromo-1-(3-hydroxy-1,1-dimethylpropyl)-1,3-dihydroimidazo[4,5-c]pyridin-2-one (213 mg, 0.71 mmol) and triphenylphosphine (279 mg, 1.06 mmol) in tetrahydrofuran (5 mL) and the reaction mixture was stirred at room temperature for 1 h until the solids dissolved. The reaction mixture was diluted with hydrochloric acid (10 mL, 1 M) and the solution washed with EtOAc (10 mL). The aqueous fraction was basified with saturated aqueous sodium bicarbonate solution to pH 8. The product was extracted with EtOAc (3×). The combined organic extracts were washed with brine, dried over anhydrous magnesium sulfate and concentrated in vacuo. The resultant residue was subjected to silica gel chromatography (solvent gradient: 0-10% methanol in dichloromethane) to yield the title compound as an off-white solid (69 mg, 34%). $^1$H NMR 400 MHz δ (CDCl$_3$): 8.55 (1H, s), 7.45 (1H, s), 4.52 (2H, t, J=5.4 Hz), 2.23 (2H, t, J=5.4 Hz), 1.73 (6H, s).

Step 7: (2-Chloropyrimidin-4-yl)-(4,4-dimethyl-3,4-dihydro-2H-1-oxa-4a,7,9-triazafluoren-6-yl)amine

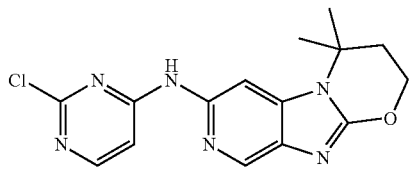 [SMILES: CC1(C)CCOc2nc3cnc(Nc4ccnc(Cl)n4)cc3n21]

6-Bromo-4,4-dimethyl-3,4-dihydro-2H-1-oxa-4a,7,9-triazafluorene (69 mg, 0.24 mmol), 4-amino-2-chloropyrimidine (32 mg, 0.24 mmol), tris(dibenzylideneacetone)dipalladium(0) (11 mg, 12 µmol), 4,5-bis(diphenylphosphino)-9,9-dimethylxanthene (28 mg, 49 µmol), cesium carbonate (160 mg, 0.49 mmol) and dioxane (3 mL) were sealed in a vial and the mixture degassed with argon. The reaction mixture was heated at 100° C. for 16 h. The reaction mixture was diluted with water and the product extracted with EtOAc (3×). The combined organic extracts were washed with brine, dried over anhydrous magnesium sulfate and concentrated in vacuo. The resultant residue was subjected to silica gel chromatography (solvent gradient: 0-10% methanol in EtOAc) to yield the title compound as an off-white solid (34 mg, 42%). LCMS (ESI): [M+H]$^+$=331.

Example A51: (R)-6-Bromo-1-sec-butyl-2-[(R)-1-(tetrahydropyran-2-yloxy)ethyl]-1H-imidazo[4,5-c]pyridine

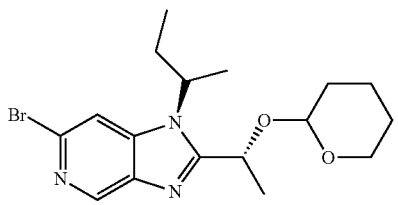

Step 1: (2-Bromo-5-nitropyridin-4-yl)-((R)-sec-butyl)amine

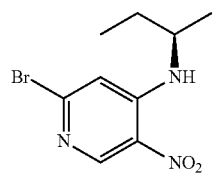

To a solution of 2,4-dibromo-5-nitropyridine (1 g, 3.50 mmol) in tetrahydrofuran (5 mL) was added (R)-sec-butylamine (429 µL, 4.26 mmol) and triethylamine (1 mL, 7.10 mmol) and the reaction mixture was stirred at room temperature for 1 h. The reaction mixture was diluted with water and the product extracted with EtOAc (3×). The combined organic extracts were washed with brine, dried over anhydrous magnesium sulfate and concentrated in vacuo to yield the title compound as a yellow solid (903 mg, 93%). LCMS (ESI): [M+H]$^+$=274 (100%).

Step 2: 6-Bromo-N$^4$—((R)-sec-butyl)pyridine-3,4-diamine

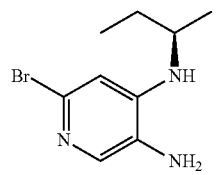

To a solution of (2-bromo-5-nitropyridin-4-yl)-((R)-sec-butyl)amine (903 mg, 3.29 mmol) in industrial methylated spirits (20 mL) was added acetic acid (1 mL), water (0.5 mL) and iron powder (738 mg, 13.2 mmol) and the resultant mixture was stirred at room temperature for 2 h. The reaction mixture was filtered through Celite and the filtrate diluted with water. The product was extracted with EtOAc (3×) and the combined organic extracts washed with brine, dried over anhydrous magnesium sulfate and concentrated in vacuo. This gave the title compound as a brown solid (750 mg, 93%). LCMS (ESI): [M+H]$^+$=244.

Step 3: (R)-1-((R)-6-Bromo-1-sec-butyl-1H-imidazo[4,5-c]pyridin-2-yl)ethanol

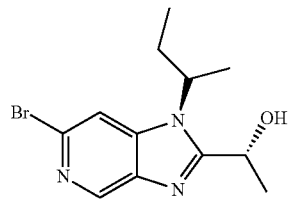

To a solution of (R)-lactamide (410 mg, 4.60 mmol) in dichloromethane (15 mL) was added triethyloxonium tetrafluoroborate (963 mg, 5.1 mmol) and the reaction mixture was stirred at room temperature for 2 h. The reaction mixture was concentrated in vacuo and the resultant residue dissolved in ethanol (15 mL). 6-Bromo-N$^4$—((R)-sec-butyl)pyridine-3,4-diamine (750 mg, 3.1 mmol) was added and the reaction mixture heated at reflux for 4 h. The reaction mixture was diluted with water and the product extracted with EtOAc (3×). The combined organic extracts were washed with brine, dried over anhydrous magnesium sulfate and concentrated in vacuo. The resultant residue was subjected to silica gel chromatography (solvent gradient: 0-5% methanol in EtOAc) to yield the title compound as an off-white solid (214 mg, 23%). LCMS (ESI): [M+H]$^+$=298.

Step 4: (R)-6-Bromo-1-sec-butyl-2-[(R)-1-(tetrahydropyran-2-yloxy)ethyl]-1H-imidazo[4,5-c]pyridine

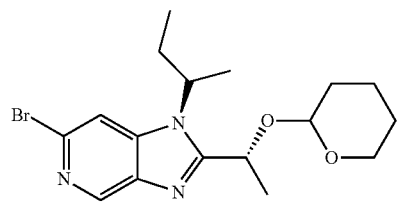

To a solution of (R)-1-((R)-6-bromo-1-sec-butyl-1H-imidazo[4,5-c]pyridin-2-yl)ethanol (214 mg, 0.71 mmol) in tetrahydrofuran (10 mL) was added 3,4-dihydropyran (262 µL, 2.87 mmol) and p-toluenesulfonic acid (catalytic) and the resultant mixture heated at reflux for 4 h. Further aliquots of 3,4-dihydropyran (612 µL, 6.7 mmol) and p-toluenesulfonic acid (catalytic) were added and heating continued for 48 h. The reaction mixture was diluted with saturated aqueous sodium bicarbonate and the product extracted with EtOAc (3×). The combined organic extracts were washed with brine, dried over anhydrous magnesium sulfate and concentrated in vacuo. The resultant residue was subjected to silica gel chromatography (solvent gradient: 0-100% EtOAc in pentane) to yield the title compound (0.16 g, 58%). LCMS (ESI): [M+H]$^+$=382.

Example A52: 2-(1-Ethanesulfonyl-1H-pyrazol-4-yl)pyrimidin-4-ylamine

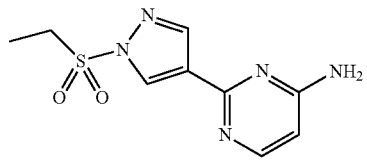 [SMILES: CCS(=O)(=O)n1cc(-c2nccc(N)n2)cn1]

Step 1: 1-(Ethanesulfonyl)-4-(4,4,5,5-tetramethyl-1,3,2-dioxaborolan-2-yl)-1H-pyrazole

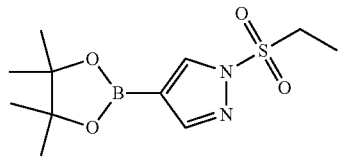 [SMILES: CCS(=O)(=O)n1cc(B2OC(C)(C)C(C)(C)O2)cn1]

To a reaction vessel was placed a solution of 4-(tetramethyl-1,3,2-dioxaborolan-2-yl)-1H-pyrazole (20.0 g, 103 mmol) in dichloromethane (270 mL) and triethylamine (34.6 g, 342 mmol). The reaction mixture was cooled to 0° C. and ethanesulfonyl chloride (19.9 g, 155 mmol) was added. The reaction mixture was stirred for 12 h at room temperature. The reaction was filtered and the solution was concentrated in vacuo. The residue was purified by silica gel chromatography (solvent: 20% ethyl acetate in petroleum ether) to afford the title compound as yellow oil (19 g, 64%).

Step 2: 2-(1-Ethanesulfonyl-1H-pyrazol-4-yl)pyrimidin-4-ylamine

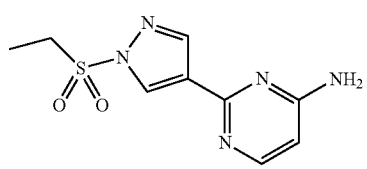 [SMILES: CCS(=O)(=O)n1cc(-c2nccc(N)n2)cn1]

1-(Ethanesulfonyl)-4-(4,4,5,5-tetramethyl-1,3,2-dioxaborolan-2-yl)-1H-pyrazole (1 g, 3.49 mmol), 2-chloro-4-aminopyrimidine (412 mg, 3.18 mmol), bis(di-tert-butyl(4-dimethylaminophenyl)phosphine)dichloropalladium(II) (225 mg, 0.32 mmol) and cesium carbonate (1.35 g, 4.13 mmol) were suspended in dioxane (7 mL) and water (1 mL). The reaction mixture was degassed with argon, and heated at 100° C. for 45 min. The reaction mixture was diluted with water and the product extracted with EtOAc (3×). The combined organic extracts were washed with brine, dried over anhydrous magnesium sulfate and concentrated in vacuo. The resultant residue was subjected to silica gel chromatography (solvent gradient: 0-5% methanol in EtOAc) to yield the title compound (0.57 g, 71%). LCMS (ESI): $[M+H]^+=254$.

Example A53: (R)-6-Bromo-1-sec-butyl-2-[(S)-1-(tetrahydropyran-2-yloxy)ethyl]-1H-imidazo[4,5-c]pyridine

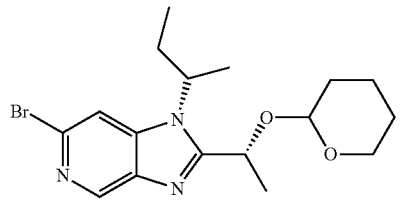

Step 1: (2-Bromo-5-nitropyridin-4-yl)-((S)-sec-butyl)amine

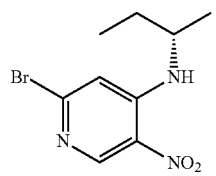

To a solution of 2,4-dibromo-5-nitropyridine (1 g, 3.50 mmol) in tetrahydrofuran (5 mL) was added (S)-sec-butylamine (429 μL, 4.26 mmol) and triethylamine (1 mL, 7.10 mmol) and the reaction mixture was stirred at room temperature for 1 h. The reaction mixture was diluted with water and the product extracted with EtOAc (3×). The combined organic extracts were washed with brine, dried over anhydrous magnesium sulfate and concentrated in vacuo to yield the title compound as a yellow solid (903 mg, 93%). LCMS (ESI): $[M+H]^+=274$.

Step 2: 6-Bromo-$N^4$—((S)-sec-butyl)pyridine-3,4-diamine

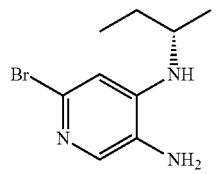

To a solution of (2-bromo-5-nitropyridin-4-yl)-((S)-sec-butyl)amine (903 mg, 3.29 mmol) in industrial methylated spirits (20 mL) was added acetic acid (1 mL), water (0.5 mL) and iron powder (738 mg, 13.2 mmol) and the resultant mixture was stirred at room temperature for 2 h. The reaction mixture was filtered through celite and the filtrate diluted with water. The product was extracted with EtOAc (3×) and the combined organic extracts washed with brine, dried over anhydrous magnesium sulfate and concentrated in vacuo to yield the title compound as a brown solid (670 mg, 83%). LCMS (ESI): $[M+H]^+=244$.

Step 3: (R)-1-((S)-6-Bromo-1-sec-butyl-1H-imidazo[4,5-c]pyridin-2-yl)ethanol

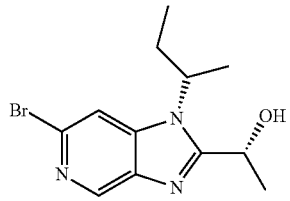

To a solution of (R)-lactamide (367 mg, 4.10 mmol) in dichloromethane (15 mL) was added triethyloxonium tetrafluoroborate (860 mg, 4.53 mmol) and the reaction mixture was stirred at room temperature for 2 h. The reaction mixture was concentrated in vacuo and the resultant residue dissolved in ethanol (15 mL). 6-Bromo-$N^4$—((S)-sec-butyl)pyridine-3,4-diamine (670 mg, 2.74 mmol) was added and the reaction mixture heated at reflux for 16 h. The reaction mixture was diluted with water and the product extracted with EtOAc (3×). The combined organic extracts were washed with brine, dried over anhydrous magnesium sulfate and concentrated in vacuo. The resultant residue was subjected to silica gel chromatography (solvent gradient: 0-5% methanol in EtOAc) to yield the title compound as an off-white solid (300 mg, 37%). $^1$H NMR 400 MHz δ (CDCl$_3$): 8.78 (1H, s), 7.58 (1H, s), 5.19-5.05 (1H, m), 4.66-4.53 (1H, m), 2.13-1.92 (2H, m), 1.75 (3H, d, J=6.9 Hz), 1.60 (3H, d, J=7.5 Hz), 0.86 (3H, t, J=7.5 Hz).

Step 4: (R)-6-Bromo-1-sec-butyl-2-[(S)-1-(tetrahydropyran-2-yloxy)ethyl]-1H-imidazo[4,5-c]pyridine

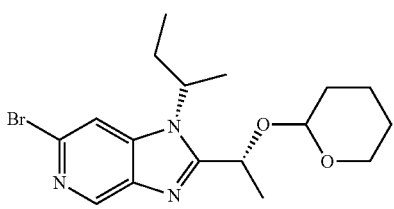

To a solution of (R)-1-((S)-6-bromo-1-sec-butyl-1H-imidazo[4,5-c]pyridin-2-yl)-ethanol (300 mg, 1.00 mmol) in tetrahydrofuran (10 mL) was added 3,4-dihydropyran (367 µL, 4.00 mmol) and p-toluenesulfonic acid (catalytic) and the resultant mixture heated at reflux for 4 h. Further aliquots of 3,4-dihydropyran (612 µL, 6.7 mmol) and p-toluenesulfonic acid (catalytic) were added and heating continued for 48 h. The reaction mixture was diluted with saturated aqueous sodium bicarbonate and the product extracted with EtOAc (3×). The combined organic extracts were washed with brine, dried over anhydrous magnesium sulfate and concentrated in vacuo. The resultant residue was subjected to silica gel chromatography (solvent gradient: 0-100% EtOAc in pentane) to yield the title compound (227 mg, 59%). LCMS (ESI): [M+H]$^+$=382.

Example A54: 6-Chloro-1-isopropyl-2-[2-(tetrahydropyran-2-yloxy)ethoxy]-1H-imidazo[4,5-c]pyridine and 6-Bromo-1-isopropyl-2-[2-(tetrahydropyran-2-yloxy)ethoxy]-1H-imidazo[4,5-c]pyridine

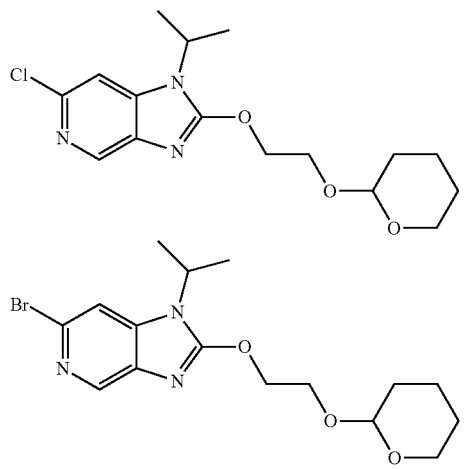

Step 1: 6-Bromo-1-isopropyl-1,3-dihydro-imidazo[4,5-c]pyridin-2-one

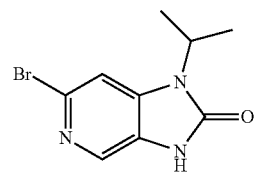

Phosgene (20% in toluene) (3.4 mL, 6.52 mmol,) was added dropwise to a solution of 6-bromo-$N^4$-isopropylpyridine-3,4-diamine (Example 12, Step 2) (1 g, 4.35 mmol) and triethylamine (1.21 mL, 8.69 mmol) in tetrahydrofuran (30 mL) causing a thick white precipitate to form. The reaction mixture was stirred at room temperature for 30 min, diluted with water and the product extracted with EtOAc (3×). The combined organic extracts were washed with brine, dried over anhydrous magnesium sulfate and concentrated in vacuo to yield the title compound as an off white solid (1.02 g, 92%). $^1$H NMR 400 MHz δ (CDCl$_3$): 9.55 (1H, br s), 8.13 (1H, s), 7.24 (1H, s), 4.69 (1H, sept, J=6.9 Hz), 1.54 (6H, d, J=6.9 Hz).

Step 2: 6-Bromo-2-chloro-1-isopropyl-1H-imidazo[4,5-c]pyridine and 2-Bromo-6-chloro-1-isopropyl-1H-imidazo[4,5-c]pyridine

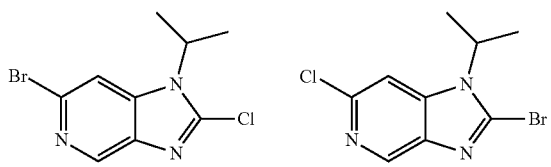

6-Bromo-1-isopropyl-1,3-dihydro-imidazo[4,5-c]pyridin-2-one (300 mg, 1.17 mmol) was dissolved in phosphorus (V) oxychloride (5 mL) and the reaction mixture heated at reflux for 48 h. The reaction mixture was concentrated in vacuo and the resultant residue dissolved in EtOAc. The solution was washed with saturated aqueous sodium bicarbonate and the product extracted with EtOAc (3×). The combined organic extracts were washed with brine, dried over anhydrous magnesium sulfate and concentrated in vacuo to give the title compounds as ~2:1 mixture. LCMS (ESI): [M+H]$^+$=274, 276, 278.

Step 3: 6-Chloro-1-isopropyl-2-[2-(tetrahydropyran-2-yloxy)ethoxy]-1H-imidazo[4,5-c]pyridine and 6-Bromo-1-isopropyl-2-[2-(tetrahydropyran-2-yloxy)ethoxy]-1H-imidazo[4,5-c]pyridine

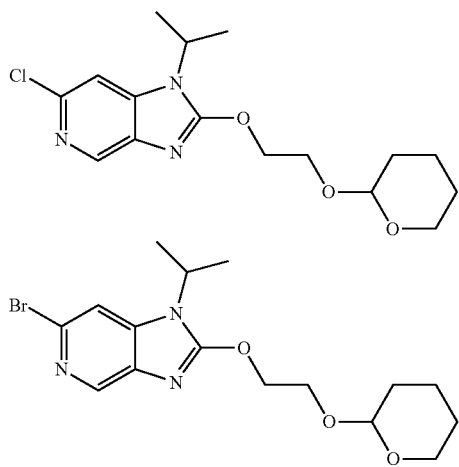

A mixture of 6-bromo-2-chloro-1-isopropyl-1H-imidazo[4,5-c]pyridine and 2-bromo-6-chloro-1-isopropyl-1H-imidazo[4,5-c]pyridine (220 mg, 0.80 mmol) and 2-(tetrahydropyran-2-yloxy)ethanol (176 mg, 1.20 mmol) and cesium carbonate (522 mg, 1.60 mmol) in N,N-dimethylformamide (6 mL) was heated in a sealed tube at 100° C. for 16 h. The reaction mixture was diluted with water and the product extracted with EtOAc (3×). The combined organic extracts were washed with brine, dried over anhydrous magnesium sulfate and concentrated in vacuo. The resultant residue was subjected to silica gel chromatography (solvent gradient: 0-100% EtOAc in cyclohexane) to yield the title compounds as an approximate 2:1 mixture of bromide:chloride (226 mg, 78%). LCMS (ESI): [M+H]$^+$=384 and [M+H]$^+$=340.

Example A55: 6-Chloro-1-isopropyl-2-(2-methoxyethoxy)-1H-imidazo[4,5-c]pyridine and 6-Bromo-1-isopropyl-2-(2-methoxyethoxy)-1H-imidazo[4,5-c]pyridine

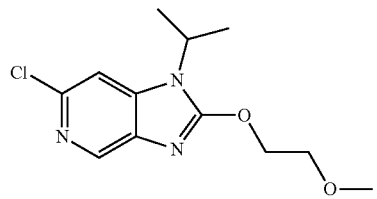

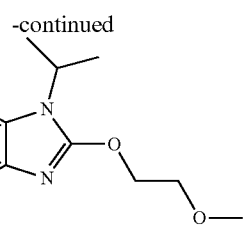

A mixture of 6-bromo-2-chloro-1-isopropyl-1H-imidazo[4,5-c]pyridine and 2-bromo-6-chloro-1-isopropyl-1H-imidazo[4,5-c]pyridine (Example A54, Step 2) (70 mg, ~0.25 mmol), 2-methoxyethanol (30 μL, 0.38 mmol) and cesium carbonate (166 mg, 0.51 mmol) in N,N-dimethylformamide (3 mL) was heated at 100° C. for 16 h. The reaction mixture was diluted with water and the product extracted with EtOAc (3×). The combined organic extracts were washed with brine, dried over anhydrous magnesium sulfate and concentrated in vacuo. The resultant residue was subjected to silica gel chromatography (solvent gradient: 0-10% methanol in EtOAc) to yield the title compounds as an approximate 3:2 mixture of bromide:chloride (49 mg, 66%). LCMS (ESI): [M+H]$^+$=314 and [M+H]$^+$=270.

Example A56: (6-Chloro-1-isopropyl-1H-imidazo[4,5-c]pyridin-2-yl)-(2-methoxyethyl)amine

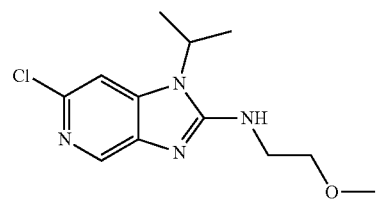 [SMILES: COCCNc1nc2cnc(Cl)cc2n1C(C)C]

2,6-Dichloro-1-isopropyl-1H-imidazo[4,5-c]pyridine (Example 284, Step 2) (250 mg, 1.1 mmol) and 2-methoxyethylamine (0.66 mL, 7.60 mmol) were dissolved in dimethylacetamide (3 mL) and the reaction mixture heated at 95° C. for 2 h. The reaction mixture was diluted with water and the product extracted with EtOAc (3×). The combined organic extracts were washed with brine, dried over anhydrous magnesium sulfate and concentrated in vacuo. The resultant residue was subjected to silica gel chromatography (solvent gradient: 0-10% methanol in EtOAc) to yield the title compound as an off-white solid (264 mg, 90%). $^1$H NMR 400 MHz δ (CDCl$_3$): 8.34 (1H, s), 7.15 (1H, s), 4.77-4.69 (1H, m), 4.32 (1H, sept, J=6.9 Hz), 3.76-3.69 (2H, m), 3.68-3.63 (2H, m), 3.42 (3H, s), 1.59 (6H, d, J=6.9 Hz).

Example A57: (6-Chloro-1-isopropyl-1H-imidazo[4,5-c]pyridin-2-yl)dimethylamine

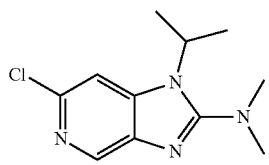 [SMILES: CC(C)n1c(N(C)C)nc2cnc(Cl)cc21]

2,6-Dichloro-1-isopropyl-1H-imidazo[4,5-c]pyridine (Example 284, Step 2) (100 mg, 0.44 mmol) and 2-methoxyethylamine (0.25 mL, 2.88 mmol) were dissolved in dimethylformamide (3 mL) and the reaction mixture heated at 95° C. for 48 h. The reaction mixture was diluted with water and the product extracted with EtOAc (3×). The combined organic extracts were washed with brine, dried over anhydrous magnesium sulfate and concentrated in vacuo. The resultant residue was subjected to silica gel chromatography (solvent gradient: 0-5% methanol in EtOAc) to yield the title compound (44 mg, 42%), derived from thermal decomposition of dimethylformamide. LCMS (ESI): [M+H]$^+$=239.

Example A58: 6-Bromo-4,4-dimethyl-3,4-dihydro-1H-2-oxa-4a,7,9-triazafluorene

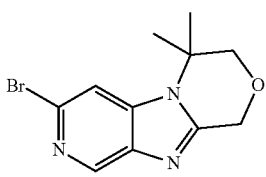 [SMILES: CC1(C)COCc2nc3cnc(Br)cc3n21]

Step 1: Acetic acid 2-(2-bromo-5-nitropyridin-4-ylamino)-2-methylpropyl ester

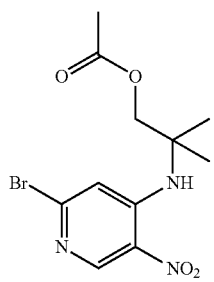

To a solution of 2-(2-bromo-5-nitropyridin-4-ylamino)-2-methylpropan-1-ol (0.97 g, 3.36 mmol) and triethylamine (0.94 mL, 6.73 mmol) in tetrahydrofuran (15 mL) at 0° C. was added acetyl chloride (251 μL, 3.55 mmol) and the reaction mixture was stirred at room temperature for 1 h. The reaction mixture was diluted with water and the product extracted with EtOAc (3×). The combined organic extracts were washed with brine, dried over anhydrous magnesium sulfate and concentrated in vacuo to yield the title compound as a yellow solid (1.1 g, 100%). $^1$H NMR 400 MHz δ (CDCl$_3$): 8.98 (1H, s), 7.17 (1H, s), 4.18 (2H, s), 2.15 (3H, s), 1.54 (6H, s).

Step 2: Acetic acid 2-(5-amino-2-bromopyridin-4-ylamino)-2-methylpropyl ester

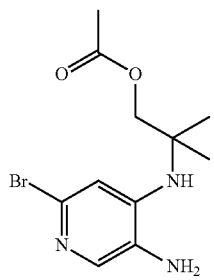 [SMILES: CC(=O)OCC(C)(C)Nc1cc(Br)ncc1N]

A mixture of acetic acid 2-(2-bromo-5-nitropyridin-4-ylamino)-2-methylpropyl ester (1.1 g, 3.30 mmol) and platinum (IV) oxide (100 mg, 0.44 mmol) in EtOAc (30 mL) was stirred at room temperature under an atmosphere of hydrogen for 16 h. The reaction mixture was concentrated in vacuo and the resultant residue subjected to silica gel chromatography (solvent gradient: 0-10% methanol in EtOAc) to yield the title compound (809 mg, 80%). $^1$H NMR 400 MHz δ (CDCl$_3$): 7.64 (1H, s), 6.80 (1H, s), 4.68 (1H, br s), 4.14 (2H, s), 2.98 (2H, br s), 2.12 (3H, s), 1.43 (6H, s).

Step 3: Acetic acid 2-[5-(2-acetoxyacetylamino)-2-bromopyridin-4-ylamino]-2-methylpropyl ester

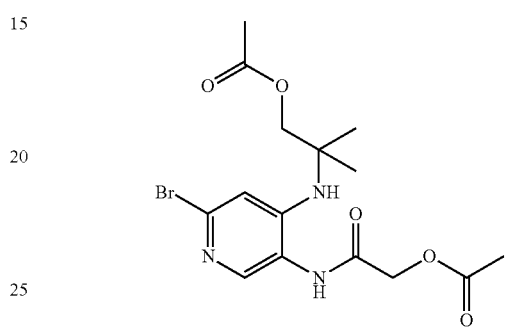

To a solution of acetic acid 2-(5-amino-2-bromopyridin-4-ylamino)-2-methylpropyl ester (300 mg, 0.99 mmol) and triethylamine (0.28 mL, 1.98 mmol) in tetrahydrofuran (5 mL) was added acetic acid chlorocarbonylmethyl ester (117 μL, 1.09 mmol) and the reaction mixture was stirred at room temperature for 1 h. The reaction mixture was diluted with water and the product extracted with EtOAc (3×). The combined organic extracts were washed with brine, dried over anhydrous magnesium sulfate and concentrated in vacuo. The resultant residue was subjected to silica gel chromatography (solvent gradient: 0-5% methanol in EtOAc) to yield the title compound (211 mg, 53%). LCMS (ESI): [M+H]$^+$=402.

Step 4: Acetic acid 2-(2-acetoxymethyl-6-bromoimidazo[4,5-c]pyridin-1-yl)-2-methylpropyl ester

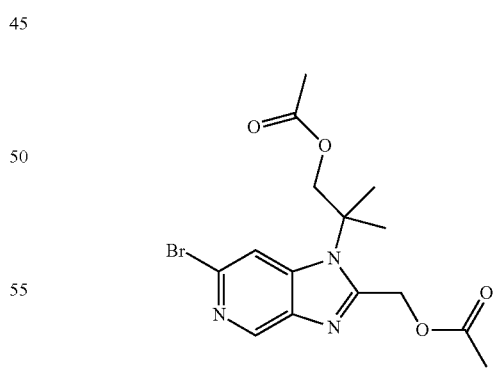

Acetic acid 2-[5-(2-acetoxyacetylamino)-2-bromopyridin-4-ylamino]-2-methylpropyl ester (267 mg, 0.66 mmol) was dissolved in acetic acid (3 mL) and the reaction mixture heated at reflux for 16 h. The reaction mixture was concentrated in vacuo and the resultant residue dissolved in EtOAc (10 mL). The solution was washed with saturated aqueous sodium bicarbonate and extracted with EtOAc (3×). The combined organic extracts were washed with brine, dried over anhydrous magnesium sulfate and concentrated in vacuo to yield the title compound (195 mg, 76%). LCMS (ESI): [M+H]⁺=384.

Step 5: 2-(6-Bromo-2-hydroxymethylimidazo[4,5-c]pyridin-1-yl)-2-methylpropan-1-ol

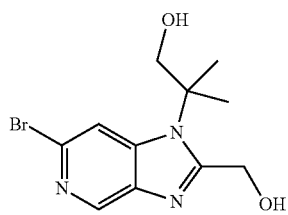 [SMILES: CC(C)(CO)n1c(CO)nc2cnc(Br)cc21]

To a solution of acetic acid 2-(2-acetoxymethyl-6-bromoimidazo[4,5-c]pyridin-1-yl)-2-methylpropyl ester (195 mg, 0.51 mmol) in methanol (5 mL) and water (1 mL) was added lithium hydroxide monohydrate (47 mg, 1.16 mmol) and the reaction mixture was stirred at room temperature for 2 h. The reaction mixture was concentrated to ~⅓ volume and the solution extracted with EtOAc (3×). The combined organic extracts were washed with brine, dried over anhydrous magnesium sulfate and concentrated in vacuo to yield the title compound (133 mg, 87%). LCMS (ESI): [M+H]⁺=300 & 302.

Step 6: 6-Bromo-4,4-dimethyl-3,4-dihydro-1H-2-oxa-4a,7,9-triazafluorene

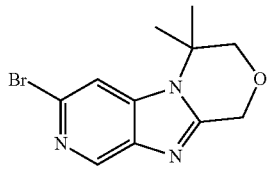 [SMILES: CC1(C)COCc2nc3cnc(Br)cc3n21]

To a mixture of 2-(6-bromo-2-hydroxymethylimidazo[4,5-c]pyridin-1-yl)-2-methylpropan-1-ol (120 mg, 0.38 mmol) and triphenylphosphine (126 mg, 0.48 mmol) in tetrahydrofuran (3 mL) was added diisopropyl azodicarboxylate (86 μL, 0.44 mmol) and the reaction mixture was stirred at room temperature for 4 d. The reaction mixture was concentrated in vacuo, dissolved in diethyl ether and washed with aqueous hydrochloric acid (1M, 10 mL). The aqueous fraction was basified with saturated aqueous sodium bicarbonate solution to pH 8. The product was extracted with EtOAc (3×). The combined organic extracts were washed with brine, dried over anhydrous magnesium sulfate and concentrated in vacuo. The resultant residue was subjected to silica gel chromatography (solvent gradient: 0-10% methanol in EtOAc) to yield the title compound (56 mg, 49%). LCMS (ESI): [M+H]⁺=282.

Example A59: 6-Bromo-2-methyl-1-(tetrahydropyran-4-ylmethyl)-1H-imidazo[4,5-c]pyridine

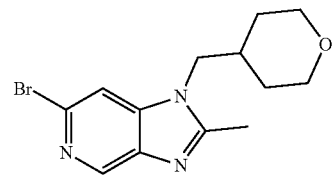 [SMILES: Cc1nc2cnc(Br)cc2n1CC1CCOCC1]

Step 1: (2-Bromo-5-nitropyridin-4-yl)-(tetrahydropyran-4-ylmethyl)amine

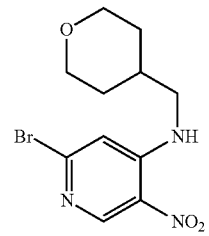 [SMILES: O=[N+]([O-])c1cnc(Br)cc1NCC1CCOCC1]

To a solution of 2,4-dibromo-5-nitropyridine (1 g, 3.50 mmol) in tetrahydrofuran (15 mL) was added (tetrahydro-2H-pyran-4-yl)methanamine (449 mg, 3.91 mmol) and triethylamine (1 mL, 7.10 mmol) and the reaction mixture was stirred at room temperature for 90 min. The reaction mixture was diluted with water and the product extracted with EtOAc (3×). The combined organic extracts were washed with brine, dried over anhydrous magnesium sulfate and concentrated in vacuo to yield the title compound as a yellow solid (1.01 g, 90%). LCMS (ESI): [M+H]⁺=316.

Step 2: 6-Bromo-N⁴-(tetrahydropyran-4-ylmethyl)pyridine-3,4-diamine

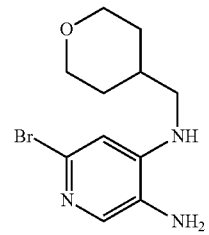 [SMILES: Nc1cnc(Br)cc1NCC1CCOCC1]

To a solution of (2-bromo-5-nitropyridin-4-yl)-(tetrahydropyran-4-ylmethyl)amine (1.01 g, 3.19 mmol), acetic acid (1 mL) and water (0.5 mL) in industrial methylated spirits (20 mL) was added iron powder (1.07 g, 19 mmol). The reaction mixture was stirred at room temperature for 2 h then 50° C. for 1 h. The reaction mixture was cooled to room temperature, diluted with EtOAc (5 mL) and basified with saturated aqueous sodium bicarbonate to pH 8. The slurry was filtered through celite and the filtrate extracted with EtOAc (3×). The combined organic extracts were washed with brine, dried over anhydrous magnesium sulfate and concentrated in vacuo to yield the title compound as a yellow solid (900 mg, 98%). LCMS (ESI): [M+H]⁺=286.

Step 3: 6-Bromo-2-methyl-1-(tetrahydropyran-4-ylmethyl)-1H-imidazo[4,5-c]pyridine

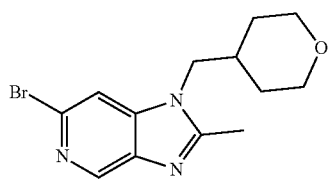 [SMILES: Cc1nc2cnc(Br)cc2n1CC1CCOCC1]

A solution of 6-bromo-N⁴-(tetrahydropyran-4-ylmethyl)pyridine-3,4-diamine (300 mg, 1.05 mmol) and ethyl acetimidate hydrochloride (142 mg, 1.15 mmol) in ethanol (5 mL) were heated at reflux for 3 h. Ethyl acetimidate hydrochloride (40 mg, 0.32 mmol) was added and heating continued for 2 h. The reaction mixture was diluted with saturated aqueous sodium bicarbonate and the product extracted with EtOAc (3×). The combined organic extracts were washed with brine, dried over anhydrous magnesium sulfate and concentrated in vacuo. The resultant residue was triturated with EtOAc to yield the title compound as a pale brown solid (220 mg, 68%). LCMS (ESI): [M+H]⁺=310, 312.

Example A60: 6-Chloro-2-(tetrahydropyran-2-yloxymethyl)-1-((R)-2,2,2-trifluoro-1-methylethyl)-1H-imidazo[4,5-c]pyridine

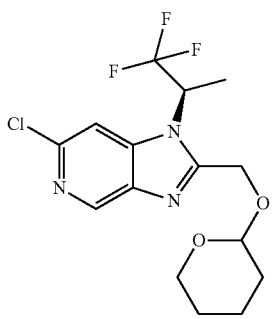 [SMILES: C[C@@H](n1c(COC2CCCCO2)nc2cnc(Cl)cc21)C(F)(F)F]

Step 1: (2-Chloro-5-nitropyridin-4-yl)-((R)-2,2,2-trifluoro-1-methylethyl)amine

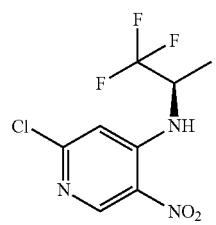

A solution of 2,4-dichloro-5-nitropyridine (4 g, 20.72 mmol), (R)-trifluoromethyl-2-aminopropane (4.69 g, 41.44 mmol) and triethylamine (5.8 mL, 41.4 mmol) in tetrahydrofuran were heated in a sealed vessel at 55° C. for 6 d. The reaction mixture was diluted with water and the product extracted with EtOAc (3×). The combined organic extracts were washed with brine, dried over anhydrous magnesium sulfate and concentrated in vacuo. The resultant residue was subjected to silica gel chromatography (solvent gradient: 0-30% EtOAc in cyclohexane) to yield the title compound as an orange oil (3.95 g, 70%). LCMS (ESI): [M+H]⁺=270.

Step 2: 6-Chloro-N⁴—((R)-2,2,2-trifluoro-1-methylethyl)pyridine-3,4-diamine

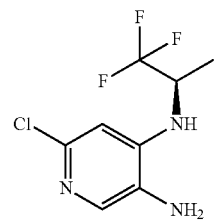

To a solution of (2-chloro-5-nitropyridin-4-yl)-((R)-2,2,2-trifluoro-1-methylethyl)amine (3.95 g, 14.70 mmol), acetic acid (4 mL) and water (2 mL) in industrial methylated spirits (80 mL) was added iron powder (4.92 g, 0.089 mol). The reaction mixture was stirred at room temperature for 1 h. The reaction mixture was diluted with EtOAc (5 mL) and basified with saturated aqueous sodium bicarbonate to pH 8. The slurry was filtered through celite and the filtrate extracted with EtOAc (3×). The combined organic extracts were washed with brine, dried over anhydrous magnesium sulfate and concentrated in vacuo to yield the title compound as a brown solid (3.32 g, 95%). LCMS (ESI): [M+H]⁺=240.

Step 3: Acetic acid [6-chloro-4-((R)-2,2,2-trifluoro-1-methylethylamino)pyridin-3-ylcarbamoyl]methyl ester

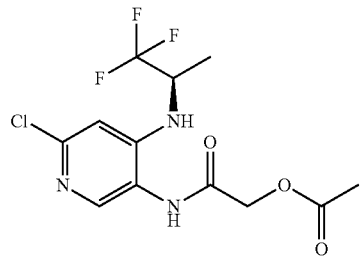 [SMILES: CC(=O)OCC(=O)Nc1cnc(Cl)cc1N[C@H](C)C(F)(F)F]

To a solution of 6-chloro-N⁴—((R)-2,2,2-trifluoro-1-methylethyl)pyridine-3,4-diamine (1 g, 4.17 mmol) and triethylamine (1.16 mL, 8.34 mmol) in tetrahydrofuran (15 mL) at 0° C. was added dropwise acetoxyacetyl chloride (471 μL, 4.38 mmol) and the reaction mixture was stirred at room temperature for 2 h. The reaction mixture was diluted with water and the product extracted with dichloromethane (3×). The combined organic extracts were washed with brine, dried over anhydrous magnesium sulfate and concentrated in vacuo. The resultant residue was subjected to silica gel chromatography (solvent gradient: 0-3% methanol in EtOAc) to yield the title compound (832 mg, 59%). LCMS (ESI): [M+H]⁺=340.

Step 4: Acetic acid 6-chloro-1-((R)-2,2,2-trifluoro-1-methylethyl)-1H-imidazo[4,5-c]pyridin-2-ylmethyl ester

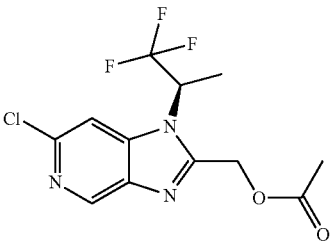 [SMILES: CC(=O)OCc1nc2cnc(Cl)cc2n1[C@H](C)C(F)(F)F]

Acetic acid [6-chloro-4-((R)-2,2,2-trifluoro-1-methylethylamino)pyridin-3-ylcarbamoyl]methyl ester (832 mg, 2.40 mmol) was dissolved in acetic acid (5 mL) and the reaction mixture heated at reflux for 16 h. The reaction mixture was concentrated in vacuo and the resultant residue dissolved in EtOAc (10 mL). The solution was washed with saturated aqueous sodium bicarbonate and extracted with EtOAc (3×). The combined organic extracts were washed with brine, dried over anhydrous magnesium sulfate and concentrated in vacuo to yield the title compound (732 mg, 93%). LCMS (ESI): [M+H]$^+$=322 and 324.

Step 5: 6-Chloro-2-(tetrahydropyran-2-yloxymethyl)-1-((R)-2,2,2-trifluoro-1-methylethyl)-1H-imidazo[4,5-c]pyridine

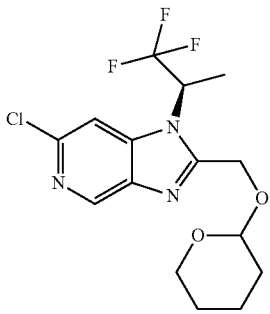 [SMILES: C[C@@H](n1c(COC2CCCCO2)nc2cnc(Cl)cc21)C(F)(F)F]

To a solution of acetic acid 6-chloro-1-((R)-2,2,2-trifluoro-1-methylethyl)-1H-imidazo[4,5-c]pyridin-2-ylmethyl ester (550 mg, 1.71 mmol) in methanol (10 mL) was added lithium hydroxide monohydrate (108 mg, 2.56 mmol) and water (1 mL). The resultant mixture was stirred at room temperature for 30 min. The mixture was acidified with HCl (1N) to pH 5 followed by basification with saturated aqueous sodium bicarbonate to pH 8. The solution was extracted with EtOAc (3×) and the combined organic extracts washed with brine, dried over anhydrous magnesium sulfate and concentrated in vacuo. The resultant residue was dissolved in tetrahydrofuran (15 mL) and 3,4-dihydropyran (624 μL, 6.84 mmol) and p-toluenesulfonic acid (33 mg, 0.17 mmol) was added. The reaction mixture was stirred at reflux for 5 d, diluted with water and the product extracted with EtOAc (3×). The combined organic extracts were washed with brine, dried over anhydrous magnesium sulfate and concentrated in vacuo. The resultant residue was subjected to silica gel chromatography (solvent gradient: 0-100% EtOAc in cyclohexane) to yield the title compound (586 mg, 94%). LCMS (ESI): [M+H]$^+$=364.

Example A61: 6-Chloro-2-[(R)-1-(tetrahydropyran-2-yloxy)ethyl]-1-((R)-2,2,2-trifluoro-1-methylethyl)-1H-imidazo[4,5-c]pyridine

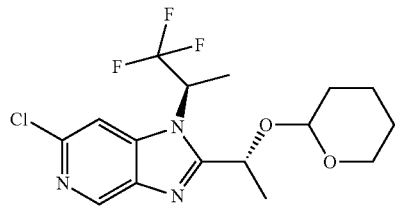 [SMILES: C[C@@H](OC1CCCCO1)c1nc2cnc(Cl)cc2n1[C@H](C)C(F)(F)F]

Step 1: (R)-1-[6-Chloro-1-((R)-2,2,2-trifluoro-1-methylethyl)-1H-imidazo[4,5-c]pyridin-2-yl]ethanol

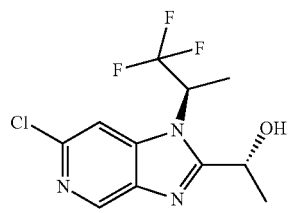 [SMILES: C[C@@H](O)c1nc2cnc(Cl)cc2n1[C@H](C)C(F)(F)F]

To a solution of (R)-lactamide (1.23 g, 13.8 mmol) in dichloromethane (40 mL) was added triethyloxonium tetrafluoroborate (2.88 g, 15.1 mmol) and the reaction mixture was stirred at room temperature for 2 h. The reaction mixture was concentrated in vacuo and the resultant residue dissolved in ethanol (50 mL). 6-Chloro-N$^4$—((R)-2,2,2-trifluoro-1-methylethyl)pyridine-3,4-diamine (Example A60, Step 2) (2.13 g, 9.18 mmol) was added and the reaction mixture heated at reflux for 1 h. The reaction mixture was diluted with water and the product extracted with EtOAc (3×). The combined organic extracts were washed with brine, dried over anhydrous magnesium sulfate and concentrated in vacuo. The resultant residue was subjected to silica gel chromatography (solvent gradient: 0-100% EtOAc in cyclohexane) to yield the title compound (2.05 g, 78%). LCMS (ESI): [M+H]$^+$=294.

Step 2: 6-Chloro-2-[(R)-1-(tetrahydropyran-2-yloxy)ethyl]-1-((R)-2,2,2-trifluoro-1-methylethyl)-1H-imidazo[4,5-c]pyridine

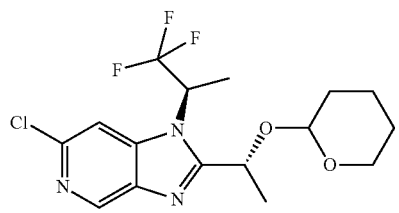 [SMILES: C[C@@H](OC1CCCCO1)c1nc2cnc(Cl)cc2n1[C@H](C)C(F)(F)F]

To a solution of (R)-1-[6-chloro-1-((R)-2,2,2-trifluoro-1-methylethyl)-1H-imidazo[4,5-c]pyridin-2-yl]ethanol (2.03 g, 6.91 mmol) in tetrahydrofuran (30 mL) was added 3,4-dihydropyran (2.5 mL, 27.6 mmol) and p-toluenesulfonic acid (131 mg, 0.69 mmol) and the resultant mixture heated at reflux for 5 d. The reaction mixture was cooled to room temperature, diluted with saturated aqueous sodium bicarbonate and extracted with EtOAc (3×). The combined organic extracts were washed with brine, dried over anhydrous magnesium sulfate and concentrated in vacuo. The resultant residue was subjected to silica gel chromatography (solvent gradient: 0-100% EtOAc in pentane) to yield the title compound (2.03 g, 78%). LCMS (ESI): [M+H]$^+$=378.

Example A62: 2-(1-Cyclopropanesulfonyl-1H-pyrazol-4-yl)pyrimidin-4-ylamine

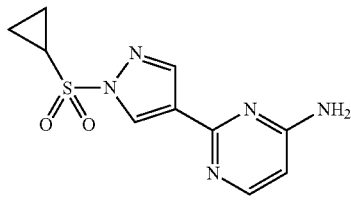 [SMILES: Nc1ccnc(-c2cnn(S(=O)(=O)C3CC3)c2)n1]

1-Cyclopropanesulfonyl-4-(4,4,5,5-tetramethyl-[1,3,2]dioxaborolan-2-yl)-1H-pyrazole (2 g, 6.7 mmol) (Example 51 step 6), 2-chloro-4-aminopyrimidine (0.79 g, 6.1 mmol), bis(di-tert-butyl(4-dimethylaminophenyl)phosphine)dichloropalladium(II) (432 mg, 0.61 mmol) and cesium carbonate (2.58 g, 7.9 mmol) were suspended in dioxane (15 mL) and water (2.5 mL). The reaction mixture was degassed with argon, and heated at 100° C. for 1.5 h. The reaction mixture was diluted with water and the product extracted with EtOAc (3×). The combined organic extracts were washed with brine, dried over anhydrous magnesium sulfate and concentrated in vacuo. The resultant residue was subjected to silica gel chromatography (solvent gradient: 0-100% EtOAc in cyclohexane) to yield the title compound (1.09 g, 67%). LCMS (ESI): [M+H]$^+$=266.

Example A63: (−)-2-((3R,4S)-3-Fluoro-4-methoxypiperidin-1-yl)pyrimidin-4-ylamine

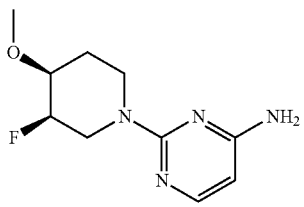 [SMILES: CO[C@H]1CCN(c2nccc(N)n2)C[C@H]1F]

Step 1: (3R,4S)-3-Fluoro-4-methoxypiperidine-1-carboxylic acid tert-butyl ester

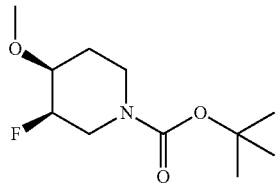 [SMILES: CO[C@H]1CCN(C(=O)OC(C)(C)C)C[C@H]1F]

To a solution of (−)-(3R,4S)-3-fluoro-4-hydroxypiperidine-1-carboxylic acid tert-butyl ester (WO2011/36576) (500 mg, 2.28 mmol) in tetrahydrofuran (10 mL) was added sodium hydride (60% dispersion in mineral oil) (109 mg, 2.74 mmol) and the reaction mixture was stirred at room temperature for 10 min. Dimethyl sulphate (0.26 mL, 2.74 mmol) was added and the reaction mixture was stirred at room temperature for 3 h. The reaction mixture was diluted with water and the product extracted with ethyl acetate (3×). The combined organic extracts were washed with brine, dried over anhydrous magnesium sulfate and concentrated in vacuo. The resultant residue was subjected to flash chromatography on silica (solvent gradient: 0-100% ethyl acetate in cyclohexane) to yield the title compound (530 mg, 100%). $^1$H NMR 400 MHz δ (CDCl$_3$): 4.81-4.58 (1H, m), 4.06-3.97 (1H, m), 3.89-3.64 (1H, m), 3.50-3.38 (4H, m), 3.37-3.20 (1H, m), 3.17-3.04 (1H, m), 1.94-1.82 (1H, m), 1.78-1.67 (1H, m), 1.46 (9H, s).

Step 2: (−)-2-((3R,4S)-3-Fluoro-4-methoxypiperidin-1-yl)pyrimidin-4-ylamine

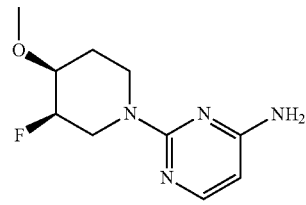 [SMILES: CO[C@H]1CCN(c2nccc(N)n2)C[C@H]1F]

(3R,4S)-3-Fluoro-4-methoxypiperidine-1-carboxylic acid tert-butyl ester (530 mg, 2.27 mmol) was dissolved in HCl in dioxane (4N, 5 mL) and the reaction stirred at 40° C. for 2 h. The reaction mixture was concentrated in vacuo. The resultant residue was suspended in isopropyl alcohol (5 mL) and 2-chloro-4-aminopyrimidine (294 mg, 2.27 mmol) and triethylamine (0.95 mL, 6.82 mmol) added. The reaction mixture was heated in a sealed reaction vessel at 120° C. for 16 h. The reaction mixture was cooled to room temperature, evaporated to dryness and subjected to chromatography on silica (solvent gradient: 25-100% ethyl acetate in cyclohexane) to yield the title compound (353 mg, 69%). LCMS (ESI): [M+H]$^+$=227; [α]$_D$ −9.2° (c 3.5 in dichloromethane).

Example A64: (−)-(3R,4S)-1-(4-Aminopyrimidin-2-yl)-3-fluoropiperidin-4-ol

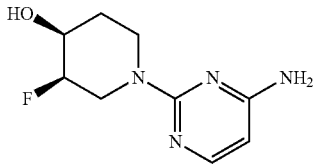 [SMILES: Nc1ccnc(N2CC[C@H](O)[C@H](F)C2)n1]

(−)-(3R,4S)-3-Fluoro-4-hydroxypiperidine-1-carboxylic acid tert-butyl ester (WO2011/36576) (500 mg, 2.27 mmol), was dissolved in HCl in dioxane (4N, 5 mL) and the reaction stirred at 40° C. for 90 min. The reaction mixture was concentrated in vacuo. The resultant residue was suspended in isopropyl alcohol (5 mL) and 2-chloro-4-aminopyrimidine (294 mg, 2.27 mmol) and triethylamine (0.95 mL, 6.82 mmol) were added. The reaction mixture was heated in a sealed reaction vessel at 130° C. for 16 h, cooled to room temperature, evaporated to dryness and subjected to chromatography on silica (solvent gradient: 0-10% methanol in ethyl acetate) to yield the title compound (383 mg, 79%). LCMS (ESI): [M+H]$^+$=213; [α]$_D$ −6.8 (c 3.5, methanol)

Example A65: (+)-2-((3S,4R)-3-Fluoro-4-methoxypiperidin-1-yl)pyrimidin-4-ylamine

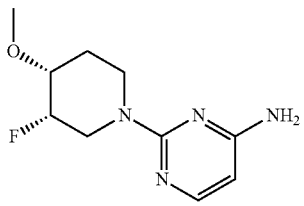 [SMILES: CO[C@@H]1CCN(c2nccc(N)n2)C[C@@H]1F]

Step 1: (3S,4R)-3-Fluoro-4-methoxypiperidine-1-carboxylic acid tert-butyl ester

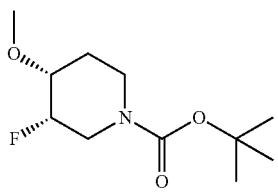 [SMILES: CO[C@@H]1CCN(C(=O)OC(C)(C)C)C[C@@H]1F]

To a solution of (+)-(3S,4R)-3-fluoro-4-hydroxypiperidine-1-carboxylic acid tert-butyl ester (WO2011/36576) (500 mg, 2.28 mmol) in tetrahydrofuran (10 mL) was added sodium hydride (60% dispersion in mineral oil) (109 mg, 2.74 mmol) and the reaction mixture was stirred at room temperature for 10 min. Dimethyl sulphate (0.26 mL, 2.74 mmol) was added and the reaction mixture was stirred at room temperature for 3 h. The reaction mixture was diluted with water and the product extracted with ethyl acetate (3×). The combined organic extracts were washed with brine, dried over anhydrous magnesium sulfate and concentrated in vacuo. The resultant residue was subjected to chromatography on silica (solvent gradient: 0-100% ethyl acetate in cyclohexane) to yield the title compound (530 mg, 100%). $^1$H NMR 400 MHz δ (CDCl$_3$): 4.81-4.56 (1H, m), 4.07-3.94 (1H, m), 3.89-3.62 (1H, m), 3.49-3.36 (4H, m), 3.37-3.20 (1H, m), 3.17-2.99 (1H, m), 1.94-1.82 (1H, m), 1.78-1.63 (1H, m), 1.46 (9H, s).

Step 2: (+)-2-((3S,4R)-3-Fluoro-4-methoxypiperidin-1-yl)pyrimidin-4-ylamine

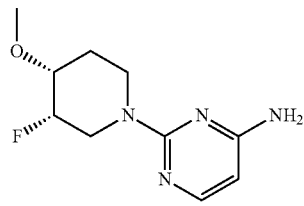 [SMILES: CO[C@@H]1CCN(c2nccc(N)n2)C[C@@H]1F]

(3S,4R)-3-Fluoro-4-methoxypiperidine-1-carboxylic acid tert-butyl ester (530 mg, 2.27 mmol), was dissolved in HCl in dioxane (4N, 5 mL) and the reaction stirred at 40° C. for 2 h. The reaction mixture was concentrated in vacuo. The resultant residue was suspended in isopropyl alcohol (5 mL) and 2-chloro-4-aminopyrimidine (294 mg, 2.27 mmol) and triethylamine (0.95 mL, 6.82 mmol) added. The reaction mixture was heated in a sealed reaction vessel at 120° C. for 16 h. The reaction mixture was subjected to flash chromatography (solvent gradient: 25-100% ethyl acetate in cyclohexane) to yield the title compound (373 mg, 72%). LCMS (ESI): [M+H]$^+$=227. [α]$_D$ +14.0° (c 3.0 in dichloromethane)

Example A66: (+)-(3S,4R)-1-(4-Aminopyrimidin-2-yl)-3-fluoropiperidin-4-ol

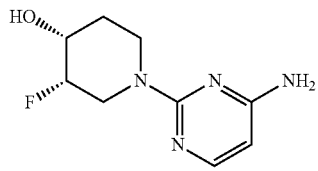 [SMILES: Nc1ccnc(N2CC[C@@H](O)[C@@H](F)C2)n1]

(+)-(3S,4R)-3-fluoro-4-hydroxypiperidine-1-carboxylic acid tert-butyl ester (500 mg, 2.27 mmol), was dissolved in HCl in dioxane (4N, 5 mL) and the reaction stirred at 40° C. for 90 min. The reaction mixture was concentrated in vacuo. The resultant residue was suspended in isopropyl alcohol (5 mL) and 2-chloro-4-aminopyrimidine (294 mg, 2.27 mmol) and triethylamine (0.95 mL, 6.82 mmol) added. The reaction mixture was heated in a sealed vial at 130° C. for 16 h. The reaction mixture was evaporated to dryness, adsorbed onto diatomaceous earth and subjected to flash chromatography (SiO$_2$, eluting with 0-10% methanol in ethyl acetate) to yield the title compound (378 mg, 78%). LCMS (ESI): [M+H]$^+$=213; [α]$_D$+9.0° (c 3.5 in methanol).

Example A67: (6-Bromo-1-isopropyl-1H-imidazo[4,5-c]pyridin-2-yl)ethylamine

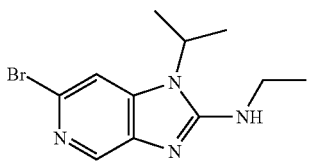 [SMILES: CCNc1nc2cnc(Br)cc2n1C(C)C]

A reaction vessel was charged with 6-bromo-N⁴-isopropylpyridine-3,4-diamine (Example 12, Step 2) (300 mg, 1.30 mmol), ethyl isothiocyanate (171 µl, 1.96 mmol) and acetonitrile (15 ml). The reaction mixture was heated under reflux for 24 h. The reaction mixture was allowed to cool to room temperature and (benzotriazol-1-yloxy)tris(dimethylamino)phosphonium hexafluorophosphate (864.9 mg, 1.96 mmol) and 1,8-diazabicyclo[5.4.0]undec-7-ene (390 µL, 2.61 mmol) were added. The reaction mixture was heated under reflux for 24 h. The reaction mixture was allowed to cool to room temperature and partitioned between EtOAc and distilled water. The organic layer was separated, dried over anhydrous magnesium sulfate and concentrated in vacuo. The residue was purified by chromatography on silica (solvent: 10% 2M methanolic ammonia in EtOAc) to afford the title compound (86.2 mg, 23%). LCMS (ESI): [M+H]⁺ 284.2.

Example A68: (±)-6-Bromo-1-isopropyl-2-[2-(tetrahydropyran-2-yloxy)ethoxymethyl]-1H-imidazo[4,5-c]pyridine

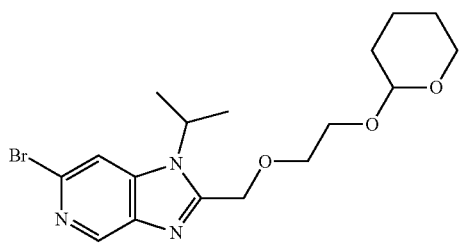 [SMILES: CC(C)n1c(COCCOC2CCCCO2)nc2cnc(Br)cc21]

A reaction vessel was charged with (6-bromo-1-isopropyl-1H-imidazo[4,5-c]pyridin-2-yl)methanol (Example 251, step 5) (200 mg, 0.743 mmol) and dissolved in dimethylformamide (7 mL). The reaction mixture was cooled to 0° C. and sodium hydride (35.6 mg, 0.892 mmol) was added. The reaction mixture was stirred at 0° C. for 10 min. and 2-(2-bromoethoxy)tetrahydropyran (137.5 µl, 0.892 mmol) was added. The reaction mixture was allowed to warm from 0° C. to room temperature and stirred at room temperature for 24 h. The reaction mixture was partitioned between EtOAc and distilled water. The organic layer was separated, dried over anhydrous magnesium sulfate and concentrated in vacuo. The residue was further purified by chromatography on silica (solvent gradient: 0-10% methanol in EtOAc) to afford the title compound (196.1 mg, 66%). LCMS (ESI): [M+H]⁺ 399.3.

Example A69: 6-Bromo-1-isopropyl-2-(2,2,2-trifluoroethyl)-1H-imidazo[4,5-c]pyridine

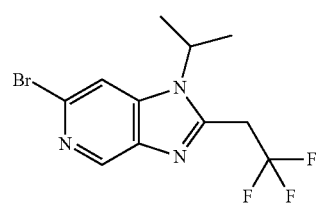 [SMILES: CC(C)n1c(CC(F)(F)F)nc2cnc(Br)cc21]

A reaction vessel was charged with 3,3,3-trifluoropropionic acid (116 µl, 1.30 mmol), triethylamine (500 µl, 3.59 mmol), triphenylphosphine (855 mg, 3.26 mmol) and carbon tetrachloride (5 ml). The reaction mixture was stirred at room temperature for 10 min and 6-bromo-N⁴-isopropylpyridine-3,4-diamine (Example 12, Step 2) (250 mg, 1.09 mmol) was added as a solution in carbon tetrachloride (2 ml). The reaction mixture was heated at 80° C. for 24 h. The reaction mixture was allowed to cool to room temperature and partitioned between dichloromethane and distilled water. The organic layer was separated, dried over anhydrous magnesium sulfate and concentrated in vacuo. The residue was further purified by chromatography on silica (solvent gradient: 0-50% EtOAc in cyclohexanes) to afford the title compound (175.2 mg, 50%). LCMS (ESI): [M+H]⁺ 323.1.

Example A70: [1-(4-Aminopyrimidin-2-yl)-4-methoxypiperidin-4-yl]methanol

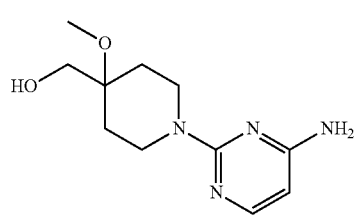 [SMILES: COC1(CO)CCN(c2nccc(N)n2)CC1]

A reaction vessel was charged with 2-chloropyrimidin-4-ylamine (578 mg, 4.46 mmol), (4-methoxypiperidin-4-yl)methanol (648 mg, 4.46 mmol), N,N-diisopropylethylamine (875 µl, 5.05 mmol) and ethanol (12 ml). The reaction mixture was heated under microwave irradiation at 150° C. for 1 h, cooled to room temperature and diluted with methanol. The reaction mixture was purified by passage of the methanolic solution through an SCX-2 cartridge, the cartridge was washed with methanol and the product was eluted with 2M NH₃ in methanol to afford the title compound (920 mg, 87%). LCMS (ESI): [M+H]⁺ 239.3

Example A71: 3-(4-Aminopyrimidin-2-ylamino)-2,2-dimethylpropionic acid ethyl ester

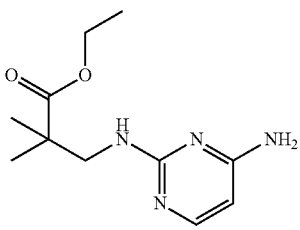 [SMILES: CCOC(=O)C(C)(C)CNc1nccc(N)n1]

The title compound (87 mg, 37%) was prepared from 2-chloropyrimidin-4-ylamine (127 mg, 0.98 mmol) and 3-amino-2,2-dimethylpropionic acid ethyl ester (WO2011106276) (143 mg, 0.98 mmol) according to a procedure analogous to that described for Example A70. LCMS (ESI): [M+H]$^+$ 239.3

Example A72: 6-Bromo-1-isopropyl-2-[1-(tetrahydropyran-2-yloxy)ethyl]-1H-imidazo[4,5-c]pyridine

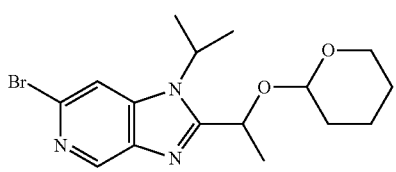 [SMILES: CC(OC1CCCCO1)c1nc2cnc(Br)cc2n1C(C)C]

Step 1: (±)-1-(6-Bromo-1-isopropyl-1H-imidazo[4,5-c]pyridin-2-yl)ethanol

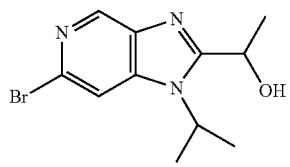 [SMILES: CC(O)c1nc2cnc(Br)cc2n1C(C)C]

A reaction vessel was charged with (±)-lactamide (968 mg, 10.86 mmol), triethyloxonium tetrafluoroborate (2.06 g, 10.86 mmol) and tetrahydrofuran (35 ml). The reaction mixture was stirred at room temperature for 90 min and concentrated in vacuo. The residue was dissolved in ethanol (31 ml) and charged with 6-bromo-N$^4$-isopropylpyridine-3,4-diamine (Example 12, Step 2) (1.0 g, 4.34 mmol). The reaction mixture was heated at 75° C. for 24 h, allowed to cool to room temperature and partitioned between EtOAc and 1M aqueous HCl. The acidic layer was separated, neutralized with saturated sodium hydrogen carbonate and extracted with EtOAc. The organic layer was separated, dried over anhydrous magnesium sulfate and concentrated in vacuo to afford the title compound (757.2 mg, 62%). LCMS (ESI): [M+H]$^+$ 285.2.

Step 2: 6-Bromo-1-isopropyl-2-[1-(tetrahydropyran-2-yloxy)-ethyl]-1H-imidazo[4,5-c]pyridine

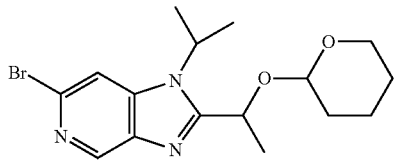 [SMILES: CC(OC1CCCCO1)c1nc2cnc(Br)cc2n1C(C)C]

A reaction vessel was a charged with (±)-1-(6-bromo-1-isopropyl-1H-imidazo[4,5-c]pyridin-2-yl)ethanol (757.2 mg, 2.67 mmol), dihydropyran (488 µl, 5.35 mmol), p-toluenesulfonic acid (45.5 mg, 0.267 mmol) and tetrahydrofuran (23.0 ml). The reaction mixture was heated under reflux for 24 h, allowed to cool to room temperature, and partitioned between EtOAc and distilled water. The organic layer was separated, dried over anhydrous magnesium sulfate and concentrated in vacuo. The residue was further purified by chromatography on silica (solvent gradient: 0-10% methanol in EtOAc) to afford the title compound (778.3 mg, 79%). LCMS (ESI): [M+H]$^+$ 369.2.

Example A73: 6-Bromo-1-isopropyl-2-[(R)-1-(tetrahydropyran-2-yloxy)ethyl]-1H-imidazo[4,5-c]pyridine

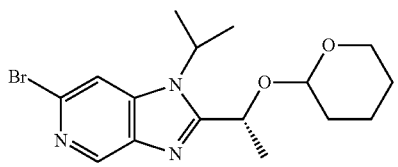 [SMILES: CC(C)n1c([C@@H](C)OC2CCCCO2)nc2cnc(Br)cc21]

The title compound (442.5 mg, 69%) was prepared from (R)-lactamide (428.1 mg, 4.81 mmol) according to a procedure analogous to that described for Example A72. LCMS (ESI): [M+H]$^+$ 369.2.

Example A74: 6-Bromo-1-isopropyl-2-[(S)-1-(tetrahydropyran-2-yloxy)ethyl]-1H-imidazo[4,5-c]pyridine

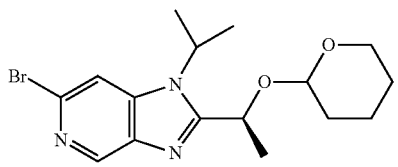 [SMILES: CC(C)n1c([C@H](C)OC2CCCCO2)nc2cnc(Br)cc21]

The title compound (1.55 g, 95%) was prepared from (S)-lactamide (1.0 g, 11.22 mmol), according to a procedure analogous to that described for Example A72. LCMS (ESI): [M+H]$^+$ 369.2.

Example A75: (±)-6-Bromo-1-isopropyl-2-[1-methyl-1-(tetrahydropyran-2-yloxy)ethyl]-1H-imidazo[4,5-c]pyridine

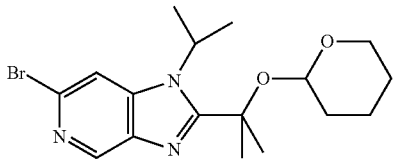 [SMILES: CC(C)n1c(C(C)(C)OC2CCCCO2)nc2cnc(Br)cc21]

The title compound (641.6 mg, 53%) was prepared from 2-hydroxy-2-methylpropionamide (1.0 g, 9.70 mmol) according to a procedure analogous to that described for Example A72. LCMS (ESI): [M+H]$^+$ 383.3.

Example A76: 6-Bromo-2-cyclopropyl-1-isopropyl-1H-imidazo[4,5-c]pyridine

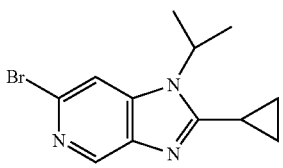 [SMILES: CC(C)n1c(C2CC2)nc2cnc(Br)cc21]

The title compound (1.58 g, 76%) was prepared from cyclopropanecarboxylic acid amide (1.0 g, 11.75 mmol) according to a procedure analogous to that described for Example A72. LCMS (ESI): [M+H]$^+$ 281.2.

Example A77: (±)-6-Bromo-1-isopropyl-2-(tetrahydrofuran-2-yl)-1H-imidazo[4,5-c]pyridine

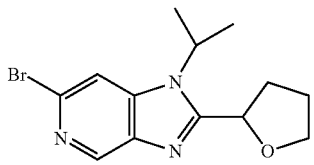 [SMILES: CC(C)n1c(C2CCCO2)nc2cnc(Br)cc21]

The title compound (973 mg, 78%) was prepared from tetrahydrofuran-2-carboxylic acid amide (738.2 mg, 6.41 mmol) (1.0 g, 11.75 mmol) according to a procedure analogous to that described for Example A72. LCMS (ESI): [M+H]$^+$ 311.2.

Example A78: (±)-6-Bromo-1-isopropyl-2-(1-methoxyethyl)-1H-imidazo[4,5-c]pyridine

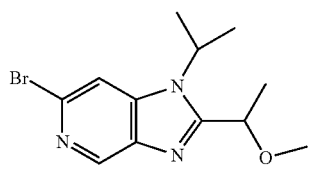 [SMILES: COC(C)c1nc2cnc(Br)cc2n1C(C)C]

The title compound (1.41 g, 77%) was prepared from (±)-2-methoxypropionamide (1 g, 9.69 mmol) according to a procedure analogous to that described for Example A72. LCMS (ESI): [M+H]$^+$ 299.2.

Example A79: [(S)-1-(6-Bromo-1-isopropyl-1H-imidazo[4,5-c]pyridin-2-yl)-ethyl]carbamic acid tert-butyl ester

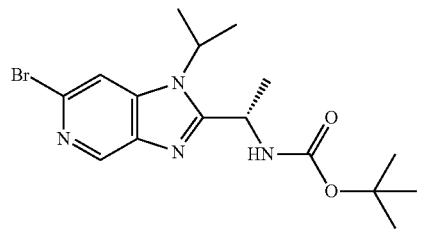 [SMILES: CC(C)n1c([C@H](C)NC(=O)OC(C)(C)C)nc2cnc(Br)cc21]

The title compound (591 mg, 46%) was prepared from ((S)-1-carbamoylethyl)carbamic acid tert-butyl ester (1.0 g, 5.32 mmol) according to a procedure analogous to that described for Example A72. LCMS (ESI): [M+H]$^+$ 384.3.

Example A80: [(R)-1-(6-Bromo-1-isopropyl-1H-imidazo[4,5-c]pyridin-2-yl)-ethyl]carbamic acid tert-butyl ester

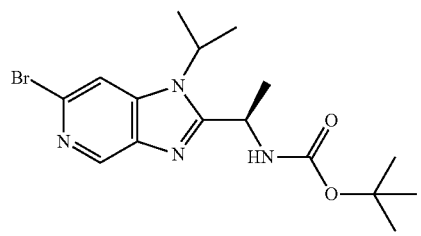 [SMILES: CC(C)n1c([C@@H](C)NC(=O)OC(C)(C)C)nc2cnc(Br)cc21]

The title compound (700.6 mg, 54%) was prepared from ((R)-1-carbamoylethyl)carbamic acid tert-butyl ester (1.0 g, 5.32 mmol) according to a procedure analogous to that described for Example A72. LCMS (ESI): [M+H]$^+$ 384.3.

Example A81: 6-Bromo-2-((S)-2,2-dimethyl-[1,3]dioxolaN-4-yl)-1-isopropyl-1H-imidazo[4,5-c]pyridine

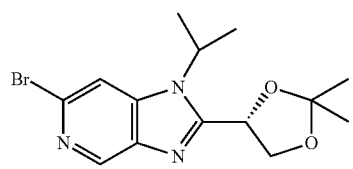 [SMILES: CC(C)n1c([C@H]2COC(C)(C)O2)nc2cnc(Br)cc21]

The title compound (113.2 mg, 26%) was prepared from (S)-2,2-dimethyl-[1,3]dioxolane-4-carboxylic acid amide (286.2 mg, 1.97 mmol) according to a procedure analogous to that described for Example A72. LCMS (ESI): [M+H]$^+$ 341.2.

Example A82: 6-Chloro-2-(tetrahydropyran-2-yloxymethyl)-1-((S)-2,2,2-trifluoro-1-methylethyl)-1H-imidazo[4,5-c]pyridine

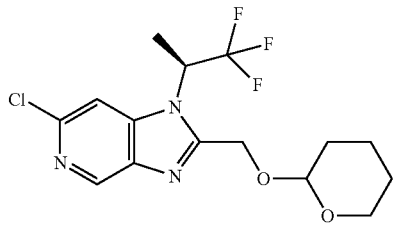 [SMILES: C[C@H](n1c(COC2CCCCO2)nc2cnc(Cl)cc21)C(F)(F)F]

Step 1: (2-Chloro-5-nitropyridin-4-yl)-((S)-2,2,2-trifluoro-1-methylethyl)amine

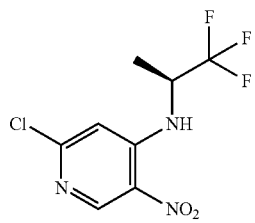 [SMILES: C[C@H](Nc1cc(Cl)ncc1[N+](=O)[O-])C(F)(F)F]

A reaction vessel was charged with 2,4-dichloro-5-nitropyridine (1 g, 5.18 mmol), (S)-2,2,2-trifluoro-1-methylethylamine (703 mg, 6.22 mmol), N,N-diisopropylethylamine (1.44 ml, 10.36 mmol) and tetrahydrofuran (10 ml). The reaction mixture was heated at 55° C. for 7 d. The reaction mixture was allowed to cool to room temperature, and partitioned between EtOAc and distilled water. The organic layer was separated, dried over anhydrous magnesium sulfate and concentrated in vacuo. The residue was further purified by chromatography on silica (solvent gradient: 0-50% EtOAc in cyclohexane) to afford the title compound (3.86 g, 92%). LCMS (ESI): [M+H]$^+$ 270.6.

Step 2: 6-Chloro-N$^4$—((S)-2,2,2-trifluoro-1-methylethyl)pyridine-3,4-diamine

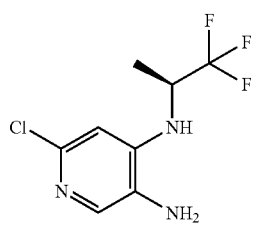

A reaction vessel was charged with (2-chloro-5-nitropyridin-4-yl)-((S)-2,2,2-trifluoro-1-methylethyl)amine (3.86 g, 14.32 mmol) industrial methylated spirits (80 ml), distilled water (2 ml) and acetic acid (4 ml). The reaction mixture was cooled to 0° C. and iron powder (4.81 g, 85.9 mmol) was added portionwise. The reaction mixture was allowed to warm to room temperature and stirred for 24 h. The reaction mixture was filtered in vacuo and the residue partitioned between EtOAc and saturated sodium hydrogen carbonate. The organic layer was separated, dried over anhydrous magnesium sulfate and concentrated in vacuo to afford the title compound (3.37 g, quant.). LCMS (ESI): [M+H]$^+$ 240.6.

Step 3: Acetic acid [6-chloro-4-((S)-2,2,2-trifluoro-1-methylethylamino)pyridin-3-ylcarbamoyl]methyl ester

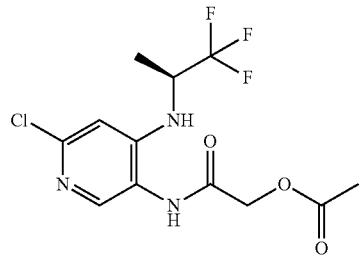 [SMILES: CC(=O)OCC(=O)Nc1cnc(Cl)cc1N[C@@H](C)C(F)(F)F]

A reaction vessel was charged with 6-chloro-N$^4$—((S)-2,2,2-trifluoro-1-methylethyl)pyridine-3,4-diamine (1.0 g, 4.17 mmol), and tetrahydrofuran (10 ml). The reaction mixture was cooled to 0° C. and triethylamine (1.16 ml, 8.34 mmol) was added. Acetic acid chlorocarbonylmethyl ester (417 µl, 4.38 mmol) was added dropwise and the reaction mixture was allowed to warm to room temperature over 2 h. The reaction mixture was partitioned between EtOAc and saturated sodium hydrogen carbonate. The organic layer was separated, dried over anhydrous magnesium sulfate and concentrated in vacuo. The residue was purified by chromatography on silica (solvent gradient: 0-10% methanol in EtOAc) to afford the title compound (944 mg, 67%). LCMS (ESI): [M+H]$^+$ 340.7.

Step 4: Acetic acid 6-chloro-1-((S)-2,2,2-trifluoro-1-methylethyl)-1H-imidazo[4,5-c]pyridin-2-ylmethyl ester

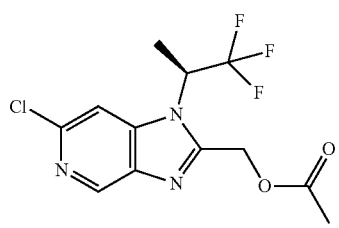 [SMILES: CC(=O)OCc1nc2cnc(Cl)cc2n1[C@@H](C)C(F)(F)F]

A reaction vessel was charged with acetic acid [6-chloro-4-((S)-2,2,2-trifluoro-1-methylethylamino)pyridin-3-ylcarbamoyl]methyl ester (944 mg, 2.77 mmol), acetic acid (6 ml) and N,N-dimethylformamide (20 ml). The reaction mixture was stirred at room temperature and was heated at 118° C. for 24 h. The reaction mixture was cooled to room temperature and partitioned between EtOAc and saturated sodium hydrogen carbonate. The organic layer was separated, dried over anhydrous magnesium sulfate and concentrated in vacuo to afford the title compound (894 mg, quant). LCMS (ESI): [M+H]$^+$ 322.7.

Step 5: [6-Chloro-1-((S)-2,2,2-trifluoro-1-methyl-ethyl)-1H-imidazo[4,5-c]pyridin-2-yl]methanol

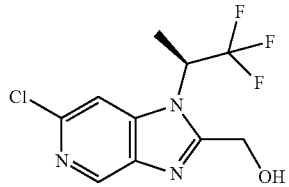 [SMILES: C[C@H](n1c(CO)nc2cnc(Cl)cc21)C(F)(F)F]

A reaction vessel was charged with acetic acid 6-chloro-1-((S)-2,2,2-trifluoro-1-methylethyl)-1H-imidazo[4,5-c]pyridin-2-ylmethyl ester (894 mg, 2.78 mmol) and dissolved in methanol (15 ml) and distilled water (2 ml). The reaction mixture was stirred at room temperature for 5 h. The reaction mixture was quenched with 1M aqueous HCl and basified with saturated sodium hydrogen carbonate. The organic layer was separated, dried over anhydrous magnesium sulfate and concentrated in vacuo to afford the title compound (778 mg, quant). LCMS (ESI): [M+H]$^+$ 280.7.

Step 6: 6-Chloro-2-(tetrahydropyran-2-yloxymethyl)-1-((S)-2,2,2-trifluoro-1-methylethyl)-1H-imidazo[4,5-c]pyridine

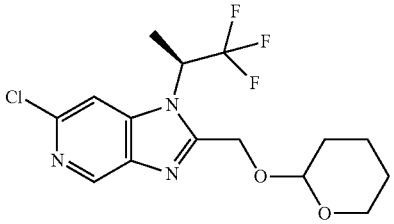 [SMILES: C[C@H](n1c(COC2CCCCO2)nc2cnc(Cl)cc21)C(F)(F)F]

A reaction vessel was charged with [6-chloro-1-((S)-2,2,2-trifluoro-1-methylethyl)-1H-imidazo[4,5-c]pyridin-2-yl]methanol (778 mg, 2.78 mmol), dihydropyran (1.02 ml, 11.12 mmol), p-toluenesulfonic acid (53 mg, 0.1 mmol) and tetrahydrofuran (25 ml). The reaction mixture was heated under reflux for 24 h. The reaction mixture was allowed to cool to room temperature, and partitioned between EtOAc and distilled water. The organic layer was separated, dried over anhydrous magnesium sulfate and concentrated in vacuo. The residue was further purified by chromatography on silica (solvent gradient: 0-50% EtOAc in cyclohexane) to afford the title compound (805.6 mg, 80%). LCMS (ESI): [M+H]$^+$ 364.8.

Example A83: 6-Chloro-2-[(R)-1-(tetrahydropyran-2-yloxy)ethyl]-1-((S)-2,2,2-trifluoro-1-methylethyl)-1H-imidazo[4,5-c]pyridine

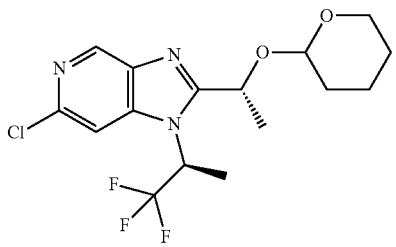 [SMILES: C[C@H](n1c([C@@H](C)OC2CCCCO2)nc2cnc(Cl)cc21)C(F)(F)F]

The title compound (968.5 mg, quant.) was prepared from (R)-lactamide (587 mg, 6.59 mmol) according to a procedure analogous to that described for Example A72. LCMS (ESI): [M+H]$^+$ 378.8.

Example A84: (±)-cis-2-(3-Fluoro-4-methoxypiperidin-1-yl)pyrimidin-4-ylamine

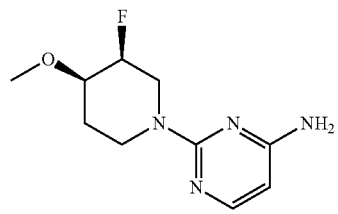 [SMILES: CO[C@@H]1CCN(c2nccc(N)n2)C[C@@H]1F]

A reaction vessel was charged with 2-chloropyrimidin-4-ylamine (499 mg, 3.86 mmol), (f)-cis-3-fluoro-4-methoxypiperidine hydrochloride (WO2009054468) (654 mg, 3.86 mmol), cesium carbonate (3.76 g, 11.56 mmol) and N,N-dimethylformamide (8 mL). The reaction mixture was heated at 120° C. for 24 h, allowed to cool to room temperature, and concentrated in vacuo. The residue was purified directly by chromatography on silica (solvent gradient: 0-50% EtOAc in cyclohexane) to afford the title compound (533.4 mg, 62%). LCMS (ESI): [M+H]$^+$ 227.3.

Example A85: (±)-cis-1-(4-Aminopyrimidin-2-yl)-3-fluoropiperidin-4-ol

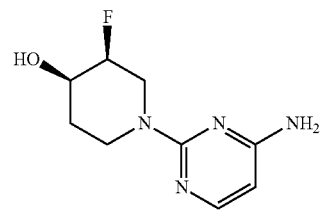 [SMILES: Nc1ccnc(N2CC[C@@H](O)[C@@H](F)C2)n1]

A suspension of (cis)-3-fluoropiperidinol hydrochloride (17.7 g, 0.114 mol), 2-chloro-4-aminopyrimidine (14.7 g, 0.114 mol) and triethylamine (48 mL, 0.342 mol) in isopropanol was heated in a sealed stainless steel vessel at 110° C. for 2 days. The cooled reaction mixture was triturated with brine to dissolve triethylammonium chloride. The precipitate was isolated by filtration, washed with water and acetonitrile and dried in vacuo to give the product as a white solid (16.3 g, 67%). $^1$H NMR (DMSO-d$_6$): 7.72 (1H, d, J=5.64 Hz), 6.38 (2H, s), 5.70 (1H, d, J=5.6 Hz), 5.03 (1H, d, J=5.11 Hz), 4.48-4.61 (1H, m), 4.35-4.45 (1H, m), 4.17 (1H, dt, J=13.2, 4.8 Hz), 3.69-3.83 (1H, m), 3.33-3.44 (1H, m), 3.12-3.23 (1H, m), 1.52-1.67 (2H, m).

Example A86: 2-Methyl-2-(4-(4,4,5,5-tetramethyl-1,3,2-dioxaborolan-2-yl)-1H-pyrazol-1-yl)propanamide

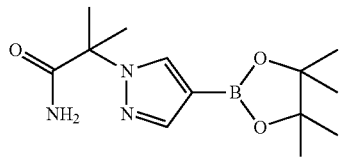 [SMILES: CC(C)(C(N)=O)n1cc(B2OC(C)(C)C(C)(C)O2)cn1]

To a mixture of 4-(4,4,5,5-tetramethyl-1,3,2-dioxaborolan-2-yl)-1H-pyrazole (252.4 mg, 1.30 mmol) and cesium carbonate (866.3 mg, 2.63 mmol) in N,N-dimethylformamide (4.0 mL) was added dropwise 2-bromo-2-methylpropanamide (403.7 mg, 2.36 mmol). The resulting mixture was stirred at room temperature for 15 h and was then heated at 50° C. for 6 h. The reaction mixture was then cooled to room temperature, diluted with EtOAc, washed with a mixture of 2:1:1 water:brine:saturated sodium bicarbonate (3×) and brine, dried over magnesium sulfate, and filtered through a plug of silica gel, rinsing with additional EtOAc. The filtrate was evaporated in vacuo and the crude product was purified via flash chromatography on silica gel (solvent gradient: 0-100% EtOAc in heptanes) to yield the title compound (91.6 mg, 25%). LCMS (ESI): [M+H]$^+$=280.4; $^1$H NMR (400 MHz, DMSO-d$_6$) δ 7.97 (s, 1H), 7.63 (s, 1H), 7.12 (s, 1H), 6.79 (s, 1H), 1.69 (s, 6H), 1.26 (s, 12H).

Example A87: 2-(4-(4,4,5,5-tetramethyl-1,3,2-dioxaborolan-2-yl)-1H-pyrazol-1-yl)propanenitrile

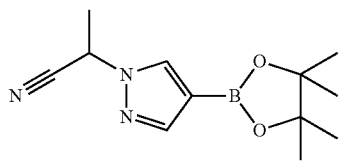 [SMILES: CC(C#N)n1cc(B2OC(C)(C)C(C)(C)O2)cn1]

To a mixture of 4-(4,4,5,5-tetramethyl-1,3,2-dioxaborolan-2-yl)-1H-pyrazole (260.6 mg, 1.34 mmol) and cesium carbonate (664.6 mg, 2.02 mmol) in N,N-dimethylformamide (3.0 mL) was added dropwise 2-bromopropionitrile (156.0 μL, 1.75 mmol). The resulting mixture was stirred at room temperature for 18 h. The reaction mixture was diluted with EtOAc, washed with a mixture of 2:1:1 water:brine:saturated sodium bicarbonate (3×) and brine, dried over magnesium sulfate, and filtered through a plug of silica gel, rinsing with additional EtOAc. The filtrate was concentrated in vacuo to yield the title compound (325.2 mg, 98%). LCMS (ESI): [M+H]$^+$=248.4; $^1$H NMR (400 MHz, DMSO-d$_6$) δ 8.12 (s, 1H), 7.73 (s, 1H), 5.86 (q, J=7.1 Hz, 1H), 1.79 (d, J=7.1 Hz, 3H), 1.26 (s, 12H).

Example A88: N,2-Dimethyl-2-(4-(4,4,5,5-tetramethyl-1,3,2-dioxaborolan-2-yl)-1H-pyrazol-1-yl)propanamide

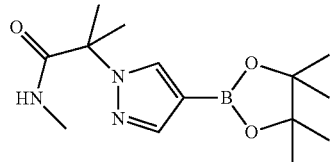 [SMILES: CNC(=O)C(C)(C)n1cc(B2OC(C)(C)C(C)(C)O2)cn1]

To a solution of 4-(4,4,5,5-tetramethyl-1,3,2-dioxaborolan-2-yl)-1H-pyrazole (252.1 mg, 1.30 mmol) and N,N-dimethylformamide (5.0 mL) in an oven-dried flask was added sodium hydride (60 wt % dispersion in mineral oil) (69.1 mg, 1.73 mmol). The reaction mixture was stirred at room temperature for 20 min, and then N-methyl-2-bromoisobutyramide (292.3 mg, 1.59 mmol) was added. Stirring was continued at room temperature for 4 h, followed by the addition of sodium hydride (60 wt % dispersion in mineral oil) (69.1 mg, 1.73 mmol). The reaction mixture was stirred at room temperature for an additional 20 h and then diluted with EtOAc, washed with water (2×) and brine, dried over magnesium sulfate, filtered, and concentrated in vacuo. The crude product was purified via flash chromatography on silica gel (solvent gradient: 20-100% EtOAc in heptanes) to yield the title compound (216.3 mg, 75% pure, 43% yield). LCMS (ESI): [M+H]$^+$=294.4; $^1$H NMR (400 MHz, DMSO-d$_6$) δ 7.97 (s, 1H), 7.64 (s, 1H), 7.24 (s, 1H), 2.54 (d, J=4.5 Hz, 3H), 1.68 (s, 6H), 1.26 (s, 12H).

Example A89: 3,3-Dimethylpiperidin-4-amine dihydrochloride

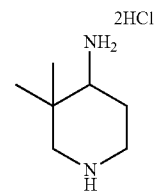

Step 1: tert-Butyl 4-amino-3,3-dimethylpiperidine-1-carboxylate

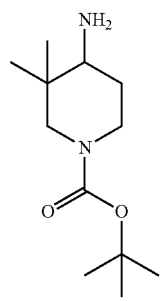 [SMILES: CC(C)(C)OC(=O)N1CCC(N)C(C)(C)C1]

A mixture of tert-butyl 3,3-dimethyl-4-oxo-piperidine-1-carboxylate (108.2 mg, 0.4760 mmol) and ammonia (7.0 N solution in methanol) (2.0 mL, 14 mmol) was stirred at room temperature for 16 h. Sodium borohydride (81.5 mg, 2.13 mmol) was then added and the mixture was stirred at room temperature for 3 h. The reaction mixture was concentrated under reduced pressure to remove the majority of the solvent, diluted with saturated aqueous sodium bicarbonate, and extracted with dichloromethane (3×). The combined organic extracts were dried over magnesium sulfate, filtered, and concentrated in vacuo to yield the title compound (105.6 mg, 63% yield, 65% pure), which was taken on without further purification. LCMS (ESI): [M+H-tButyl]$^+$=173.4.

Step 2: 3,3-Dimethylpiperidin-4-amine dihydrochloride

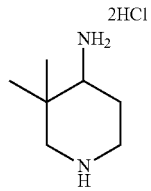

To a solution of tert-butyl 4-amino-3,3-dimethyl-piperidine-1-carboxylate (65% pure, 105.6 mg, 0.30 mmol) in dichloromethane (3.0 mL) was added hydrogen chloride (4.0 M in dioxane) (1.0 mL, 4.0 mmol). The reaction mixture was stirred at room temperature for 15 h. The reaction mixture was concentrated in vacuo to provide the title compound as the dihydrochloride salt (quant. yield), which was taken on without further purification. LCMS (ESI): [M+H]$^+$=129.4.

Example 251: (6-(2-(3-Amino-1-(cyclopropylmethyl)-1H-pyrazol-4-yl)pyrimidin-4-ylamino)-1-isopropyl-1H-imidazo[4,5-c]pyridin-2-yl)methanol

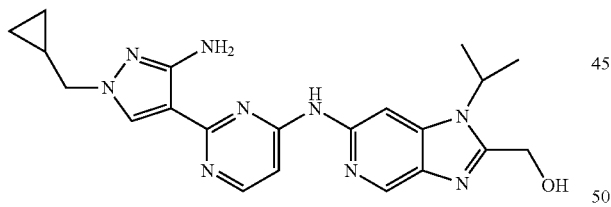

Step 1: 4-Bromo-3-nitro-1H-pyrazole

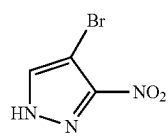

To a stirred suspension of 3-nitro-1H-pyrazole (10.0 g, 88.4 mmol) in acetic acid (100 mL) was added bromine (4.80 mL, 93.7 mmol). The resulting solution was stirred for 12 h at room temperature. The mixture was diluted with water and the pH was adjusted to 8 with aqueous sodium hydroxide. The resulting solution was extracted with ethyl acetate and the organic layer was washed with brine, dried over anhydrous sodium sulfate and concentrated in vacuo. The residue was purified by chromatography on silica (solvent: 10% methanol in dichloromethane) to afford the title compound as a white solid (8.5 g, 50%). $^1$H NMR (400 MHz, DMSO-d$_6$): δ 14.36 (br, 1H), 8.35 (s, 1H).

Step 2: 4-Bromo-1-(cyclopropylmethyl)-3-nitro-1H-pyrazole

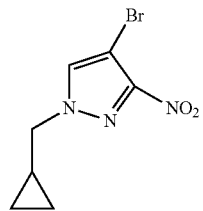 [SMILES: O=[N+]([O-])c1nn(CC2CC2)cc1Br]

To a stirred suspension of 4-bromo-3-nitro-1H-pyrazole (3.0 g, 15.6 mmo) in N,N-dimethylformamide (22 mL) was added sodium hydride (60 wt % dispersion in mineral oil)(1.25 g, 52.1 mmol) and (bromomethyl)cyclopropane (4.20 g, 31.1 mmol). The resulting solution was stirred for 5 h at room temperature. The reaction was then quenched with the addition of water. The aqueous phase was extracted with EtOAc (3×) and the combined organic phases were washed with brine, dried over anhydrous magnesium sulfate and concentrated in vacuo. The residue was purified by chromatography on silica (solvent: 10% EtOAc in petroleum ether) to afford the title compound as a yellow solid (700 mg, 18%). LCMS (ESI): R$_T$ (min)=1.461, [M+H]$^+$=246 & 248, Method=M.

Step 3: 1-(Cyclopropylmethyl)-3-nitro-1H-pyrazol-4-ylboronic acid

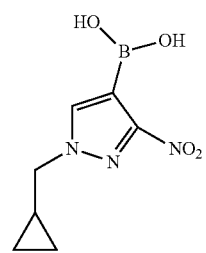 [SMILES: O=[N+]([O-])c1nn(CC2CC2)cc1B(O)O]

To a stirred suspension of 4-bromo-1-(cyclopropylmethyl)-3-nitro-1H-pyrazole (500 mg, 2.03 mmol) in 2-methyloxolane (8 mL) was added 4,4,5,5-tetramethyl-2-(tetramethyl-1,3,2-dioxaborolan-2-yl)-1,3,2-dioxaborolane (620 mg, 2.44 mmol), [1,1'-bis(diphenylphosphino)ferrocene]dichloropalladium(II), complex with dichloromethane (166 mg, 0.20 mmol) and potassium acetate (998 mg, 10.2 mmol). The resulting solution was stirred for 12 h at 95° C., cooled to room temperature, filtered, concentrated in vacuo and the residue purified by chromatography on silica (solvent: 50% EtOAc in petroleum ether) to afford the title compound as a white solid (250 mg, 58%). LCMS (ESI): R$_T$ (min)=1.694, [M+H]$^+$=212, Method=M.

Step 4: 2-(6-Bromo-4-(isopropylamino)pyridin-3-ylamino)-2-oxoethyl acetate

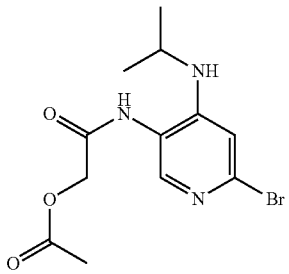 [SMILES: CC(=O)OCC(=O)Nc1cnc(Br)cc1NC(C)C]

To a solution of 6-bromo-4-N-(propan-2-yl)pyridine-3,4-diamine (Example 46, step 4) (9.00 g, 39.1 mmol) in dichloromethane (50 mL) at 0° C. was added triethylamine (7.90 g, 78.1 mmol) followed by 2-chloro-2-oxoethyl acetate (6.40 g, 46.9 mmol) dropwise with stirring. The resulting solution was stirred for 1 h at 0° C. and diluted with water (10 mL). The resulting solution was washed with brine (2×), dried over anhydrous sodium sulfate and concentrated in vacuo to afford the title compound as a brown crude solid (12 g, 67%). LCMS (ESI): $R_T$ (min)=1.060, $[M+H]^+$=330 & 332, Method=L.

Step 5: (6-Bromo-1-isopropyl-1H-imidazo[4,5-c]pyridin-2-yl)methanol

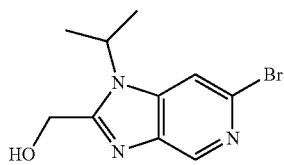

To a solution of 2-(6-bromo-4-(isopropylamino)pyridin-3-ylamino)-2-oxoethyl acetate (190 g, 575 mmol) in N,N-dimethylformamide (1.8 L) was added potassium carbonate (273 g, 1.98 mol). The resulting solution was stirred for 4 h at 120° C. The reaction was cooled to room temperature, diluted with water and extracted with EtOAc (4×). The combined organic extracts were washed with brine, dried over anhydrous sodium sulfate, filtered and concentrated in vacuo. The product was then oven-dried to afford the title compound as a white solid (88 g, 57%). The crude product was used in next step without further purification. LCMS (ESI): $R_T$ (min)=0.857, $[M+H]^+$=270 & 272, Method=L.

Step 6: 6-Bromo-1-isopropyl-2-((tetrahydro-2H-pyran-2-yloxy)methyl)-1H-imidazo[4,5-c]pyridine

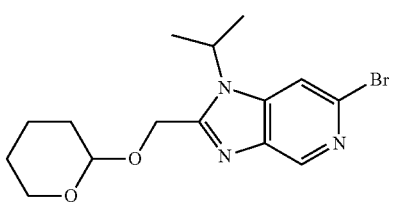 [SMILES: CC(C)n1c(COC2CCCCO2)nc2cnc(Br)cc21]

To a solution of (6-bromo-1-isopropyl-1H-imidazo[4,5-c]pyridin-2-yl]methanol (3.00 g, 11.1 mmol) in tetrahydrofuran (100 mL) was added p-toluenesulfonic acid (190 mg, 1.11 mmol) and 3,4-dihydro-2H-pyran (2.10 g, 25.0 mmol). The resulting solution was stirred for 12 h at 60° C. The reaction was cooled to room temperature, diluted with saturated aqueous sodium bicarbonate, and extracted with EtOAc (3×). The combined organic extracts were washed with brine, dried over anhydrous sodium sulfate and concentrated in vacuo. The residue was purified by chromatography on silica (solvent gradient: 0-100% EtOAc in petroleum ether) to afford the title compound as a white solid (2.0 g, 51%). LCMS (ESI): $R_T$ (min)=2.546, $[M+H]^+$=354, Method=L.

Step 7: N-(2-Chloropyrimidin-4-yl)-1-isopropyl-2-((tetrahydro-2H-pyran-2-yloxy)methyl)-1H-imidazo[4,5-c]pyridin-6-amine

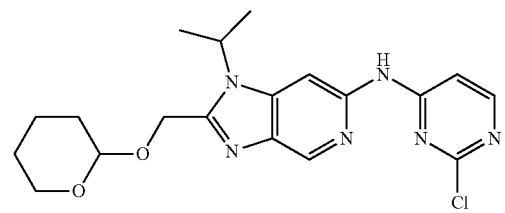 [SMILES: CC(C)n1c(COC2CCCCO2)nc2cnc(Nc3ccnc(Cl)n3)cc21]

A mixture of 6-bromo-1-isopropyl-2-((tetrahydro-2H-pyran-2-yloxy)methyl)-1H-imidazo[4,5-c]pyridine (3.00 g, 8.47 mmol), 2-chloropyrimidin-4-amine (1.09 g, 8.41 mmol), tris(dibenzylideneacetone)dipalladium(0) (389 mg, 0.42 mmol), 4,5-bis(diphenylphosphino)-9,9-dimethylxanthene (960 mg, 1.69 mmol), cesium carbonate (5.50 g, 2.00 equiv) and 1.4-dioxane (30 mL) was stirred for 1 h at 100° C. The reaction was cooled to room temperature, filtered and concentrated in vacuo. The residue was purified by chromatography on silica (solvent gradient: 0-100% EtOAc in petroleum ether) to afford the title compound as a light yellow solid (3.1 g, 91%). LCMS (ESI): $R_T$ (min)=1.602, $[M+H]^+$=403, Method=M; $^1$H NMR (400 MHz, DMSO-d$_6$): δ 10.60 (s, 1H), 8.70 (s, 1H), 8.27-8.26 (d, J=6.0 Hz, 1H), 8.24 (br, 1H), 7.45 (br, 1H), 4.95-4.91 (d, J=12.4 Hz, 1H), 4.90-4.84 (m, 1H), 4.76-4.73 (d, J=12.4 Hz, 2H), 3.80-3.75 (m. 1H), 3.53-3.50 (m, 1H), 1.75-1.65 (m, 2H), 1.61-1.59 (d, J=6.8 Hz, 6H), 1.50-1.48 (m, 4H).

Step 8: N-(2-(1-(Cyclopropylmethyl)-3-nitro-1H-pyrazol-4-yl)pyrimidin-4-yl)-1-isopropyl-2-((tetrahydro-2H-pyran-2-yloxy)methyl)-1H-imidazo[4,5-c]pyridin-6-amine

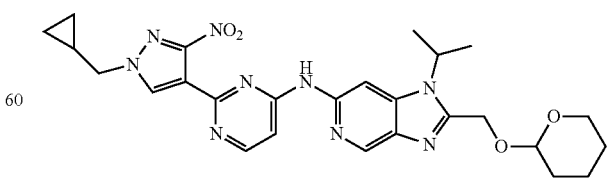

To a reaction vessel was added [1-(cyclopropylmethyl)-3-nitro-1H-pyrazol-4-yl]boronic acid (200 mg, 0.95 mmol), N-(2-chloropyrimidin-4-yl)-1-isopropyl-2-((tetrahydro-2H- pyran-2-yloxy)methyl)-1H-imidazo[4,5-c]pyridin-6-amine (380 mg, 0.94 mmol), bis(di-tert-butyl(4-dimethylaminophenyl)phosphine)dichloropalladium(II) (70 mg, 0.10 mmol), sodium carbonate (250 mg, 2.34 mmol), acetonitrile (12 mL), N,N-dimethylformamide (1 mL) and water (0.5 mL). The reaction mixture was subjected to microwave irradiation for 30 min at 130° C. The reaction was cooled to room temperature, filtered and concentrated in vacuo. The residue was purified by silica gel chromatography (solvent: 10% methanol in dichloromethane) to the title compound as a yellow solid (190 mg, 38%). LCMS (ESI): $R_T$ (min)=2.258, [M+H]$^+$=534, Method=M.

Step 9: N-(2-(3-Amino-1-(cyclopropylmethyl)-1H-pyrazol-4-yl)pyrimidin-4-yl)-1-isopropyl-2-((tetrahydro-2H-pyran-2-yloxy)methyl)-1H-imidazo[4,5-c]pyridin-6-amine

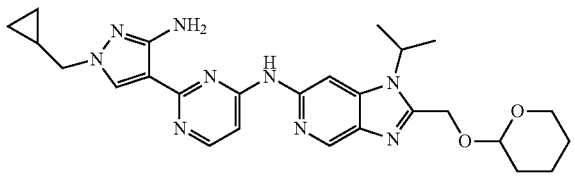 [SMILES: CC(C)n1c(COC2CCCCO2)nc2cnc(Nc3ccnc(-c4cn(CC5CC5)nc4N)n3)cc21]

To a reaction vessel was added N-(2-(1-(cyclopropylmethyl)-3-nitro-1H-pyrazol-4-yl)pyrimidin-4-yl)-1-isopropyl-2-((tetrahydro-2H-pyran-2-yloxy)methyl)-1H-imidazo[4,5-c]pyridin-6-amine (160 mg, 0.30 mmol), iron powder (67.0 mg, 1.20 mmol), ammonium chloride (93.0 mg, 1.74 mmol), water (1.5 mL), acetic acid (1 mL) and ethanol (10 mL). The reaction mixture was stirred for 4.5 h at 80° C., cooled to room temperature, filtered and concentrated in vacuo to afford the title compound as brown oil (210 mg) which was carried forward without purification. LCMS (ESI): $R_T$ (min)=1.485, [M+H]$^+$=504, Method=M.

Step 10: (6-(2-(3-Amino-1-(cyclopropylmethyl)-1H-pyrazol-4-yl)pyrimidin-4-ylamino)-1-isopropyl-1H-imidazo[4,5-c]pyridin-2-yl)methanol

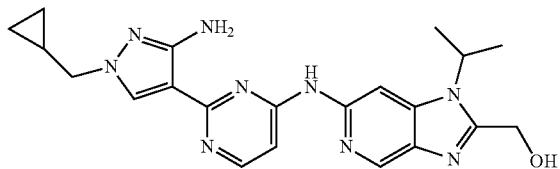 [SMILES: CC(C)n1c(CO)nc2cnc(Nc3ccnc(-c4cn(CC5CC5)nc4N)n3)cc21]

To a reaction vessel was added N-(2-(3-amino-1-(cyclopropylmethyl)-1H-pyrazol-4-yl)pyrimidin-4-yl)-1-isopropyl-2-((tetrahydro-2H-pyran-2-yloxy)methyl)-1H-imidazo[4,5-c]pyridin-6-amine (0.30 mmol, crude from previous step), trifluoroacetic acid (2 mL, 26.9 mmol) and ethanol (5 mL). The reaction mixture was stirred for 1 h at 80° C. The reaction was cooled to room temperature, quenched by the addition of water, and the pH was adjusted to 8 with aqueous sodium carbonate. The resulting solution was extracted with EtOAc and the organic layer was washed with brine, dried over anhydrous sodium sulfate and concentrated in vacuo. The residue was purified via reverse-phase HPLC and lyophilized to afford the title compound as a white solid (21.1 mg, 17% over 2 steps). LCMS (ESI): $R_T$ (min)=1.721, [M+H]$^+$=420, Method=M; $^1$H NMR (400 MHz, DMSO-d$_6$): δ 9.89 (s, 1H), 8.64 (s, 1H), 8.28 (d, J=6.0 Hz, 1H), 7.96 (s, 1H), 7.88 (s, 1H), 7.33 (s, 1H), 5.83 (s, 2H), 5.71-5.68 (m, 1H), 4.99-4.92 (m, 1H), 4.72 (d, J=6.0 Hz, 2H), 3.76 (d, J=6.8 Hz, 2H), 1.60 (d, J=6.8 Hz, 6H), 1.27-1.20 (m, 1H), 0.56-0.52 (m, 2H), 0.54-0.52 (m, 2H).

Example 252: N-(4-Cyanocyclohexyl)-6-((2-(1-(cyclopropylsulfonyl)-1H-pyrazol-4-yl)pyrimidin-4-yl)amino)-1-isopropyl-1H-pyrrolo[3,2-c]pyridine-3-carboxamide

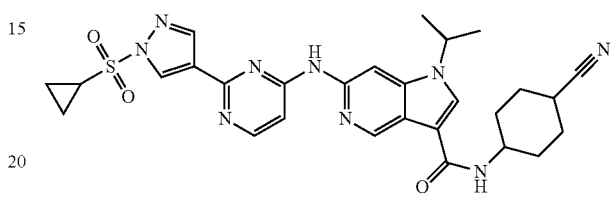

Step 1: 6-Bromo-N-(4-cyanocyclohexyl)-1-isopropyl-1H-pyrrolo[3,2-c]pyridine-3-carboxamide

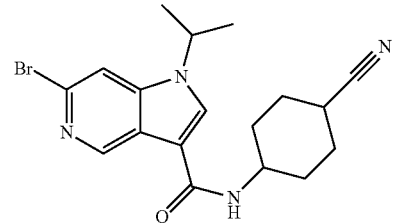 [SMILES: CC(C)n1cc(C(=O)NC2CCC(C#N)CC2)c2cnc(Br)cc21]

To a reaction vessel was added 4-aminocyclohexane-1-carbonitrile (300 mg, 2.42 mmol), HBTU (549 mg, 1.45 mmol), N,N-diisopropylethylamine (312 mg, 2.41 mmol), 6-bromo-1-isopropyl-1H-pyrrolo[3,2-c]pyridine-3-carboxylic acid (Example 51, Step 3)(342 mg, 1.21 mmol) and N,N-dimethylformamide (10 mL). The reaction mixture was stirred for 2 h at room temperature, diluted with water and extracted with ethyl acetate (3×). The combined organic layers were washed with brine, dried over anhydrous sodium sulfate and concentrated in vacuo. The residue was purified by silica gel chromatography (solvent gradient: 0-33% ethyl acetate in hexanes) to afford the title compound as a light yellow solid (340 mg, 72%). LCMS (ESI): $R_T$ (min)=1.223, [M+H]$^+$=389, Method=S.

Step 2: N-(4-Cyanocyclohexyl)-6-((2-(1-(cyclopropylsulfonyl)-1H-pyrazol-4-yl)pyrimidin-4-yl)amino)-1-isopropyl-1H-pyrrolo[3,2-c]pyridine-3-carboxamide

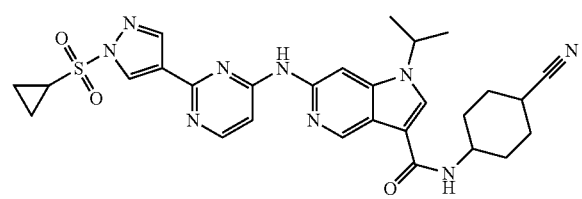 [SMILES: CC(C)n1cc(C(=O)NC2CCC(C#N)CC2)c2cnc(Nc3ccnc(-c4cnn(S(=O)(=O)C5CC5)c4)n3)cc21]

To a reaction vessel was added 6-bromo-N-(4-cyanocyclohexyl)-1-isopropyl-1H-pyrrolo[3,2-c]pyridine-3-carboxamide (300 mg, 0.77 mmol), 4,5-bis(diphenylphosphino)-9,9-dimethylxanthene (87 mg, 0.15 mmol), tris(dibenzylideneacetone)dipalladium(0) (70.5 mg, 0.08 mmol), cesium carbonate (502 mg, 1.54 mmol), 2-(1-cyclopropanesulfonyl-1H-pyrazol-4-yl)pyrimidin-4-ylamine (Example A62) (205 mg, 0.770 mmol) and dioxane (8 mL). The reaction mixture was stirred for 2 h at 100° C. under an inert atmosphere of nitrogen. The reaction was filtered and concentrated in vacuo. The crude product was purified via reverse-phase HPLC and lyophilized to afford the title compound as a white solid (15.4 mg, 3%). LCMS (ESI): $R_T$ (min)=2.063, [M+H]$^+$=574.10, Method=R; $^1$H NMR (300 MHz, DMSO-d$_6$, ppm): δ 10.28 (s, 1H), 9.07 (s, 1H), 8.70 (s, 1H), 8.50 (s, 1H), 8.47 (s, 1H), 8.37 (d, J=6 Hz, 1H), 8.27 (s, 1H), 7.95 (d, J=6 Hz, 1H), 7.11 (d, J=6 Hz, 1H), 4.81 (m, 1H), 3.88 (m, 1H), 3.27 (m, 1H), 3.13 (m, 1H), 1.92 (m, 4H), 1.70 (m, 4H), 1.57 (d, J=6 Hz, 6H), 1.34 (m, 2H), 1.29 (m, 2H).

Example 253: 2-(3-(6-(2-(1-(Cyclopropylsulfonyl)-1H-pyrazol-4-yl)pyrimidin-4-ylamino)-1-isopropyl-1H-pyrrolo[3,2-c]pyridin-3-yl)-4-methyl-1H-pyrazol-1-yl)ethanol

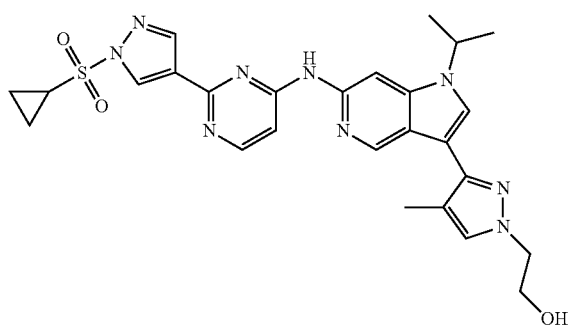 [SMILES: Cc1cn(CCO)nc1-c1cn(C(C)C)c2cc(Nc3ccnc(-c4cnn(S(=O)(=O)C5CC5)c4)n3)ncc12]

Step 1: 3-Iodo-4-methyl-1H-pyrazole

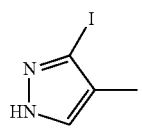

To a reaction vessel was added 4-methyl-1H-pyrazol-3-amine hydrochloride (1.00 g, 7.49 mmol), acetic acid (20 mL) and water (5 mL) followed by aqueous sodium nitrite (3.76 M)(2 mL, 7.52 mmol) dropwise with stirring at 0° C. To the resulting reaction mixture was added sulfuric acid (0.2 mL), potassium iodide (3.74 g, 22.5 mmol) and iodine (3.82 g, 15.0 mmol) and the reaction mixture was stirred for 3 h at 55° C. The reaction was then quenched by addition of ice water and the pH was adjusted to 7 with ammonia (15M in water). The resulting solution was extracted with EtOAc and the organic layer was washed with brine, dried over anhydrous sodium sulphate and concentrated in vacuo to afford the title compound as a light yellow solid (1 g, 47%). LCMS (ESI): $R_T$ (min)=1.264, [M+H]$^+$=209, Method=N.

Step 2: 3-iodo-4-methyl-1-(2-(tetrahydro-2H-pyran-2-yloxy)ethyl)-1H-pyrazole

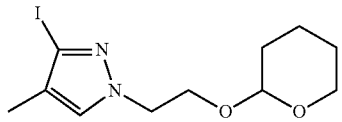 [SMILES: Cc1cn(CCOC2CCCCO2)nc1I]

To a reaction vessel was added 3-iodo-4-methyl-1H-pyrazole (1.40 g, 6.73 mmol), 2-(2-bromoethoxy)oxane (2.80 g, 13.4 mmol), cesium carbonate (4.39 g, 13.5 mmol) and acetonitrile (30 mL). The reaction mixture was stirred overnight at room temperature, filtered and concentrated in vacuo. The residue was purified by silica gel chromatography (solvent: 33% EtOAc in petroleum ether) to afford the title compound as yellow oil (1.6 g, 71%). LCMS (ESI): $R_T$ (min)=1.377, [M+H]$^+$=337, Method=M.

Step 3: 4-Methyl-1-(2-(tetrahydro-2H-pyran-2-yloxy)ethyl)-3-(tributylstannyl)-1H-pyrazole

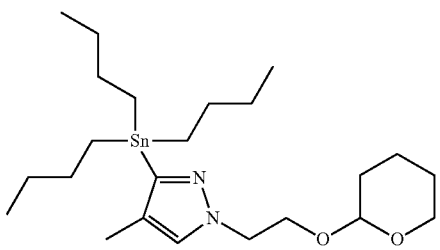 [SMILES: CCC[CH2][Sn]([CH2]CCC)([CH2]CCC)[c]1nn(CCOC2CCCCO2)cc1C]

To a reaction vessel under nitrogen containing 3-iodo-4-methyl-1-(2-(tetrahydro-2H-pyran-2-yloxy)ethyl)-1H-pyrazole (1.60 g, 4.76 mmol) in tetrahydrofuran (20 mL) at −78° C. was added n-butyllithium (2.3 mL, 2.5 M) dropwise, followed by tributylchlorostannane (1.86 g, 5.71 mmol) dropwise. The resulting solution was stirred for 2 h at room temperature. The pH was adjusted to 7-8 with aqueous sodium bicarbonate and the reaction was extracted with EtOAc. The organic layer was washed with brine, dried over anhydrous sodium sulfate and concentrated in vacuo. The residue was purified by silica gel chromatography (solvent: 25% EtOAc in petroleum ether) to the title compound as yellow oil (1.2 g, 50%). LCMS (ESI): $R_T$ (min)=1.719, [M+H]$^+$=499, Method=N.

Step 4: 2-Bromo-5-methylpyridine-1-oxide

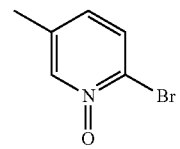

A mixture of 2-bromo-5-methylpyridine (300 g, 1.74 mol), meta-chloroperoxybenzoic acid (450 g, 2.61 mol) in dichloromethane (2 L) was stirred overnight at room temperature under nitrogen. The pH was adjusted to 8 with aqueous sodium bicarbonate and the reaction was extracted with dichloromethane (3×). The combined organic extracts were washed with brine, dried over anhydrous sodium sulfate and concentrated in vacuo to afford the title compound as a yellow solid (310 g, 95%). LCMS (ESI): $R_T$ (min)=0.907, $[M+H]^+$=188, Method=R.

Step 5: 2-Bromo-5-methyl-4-nitropyridine-1-oxide

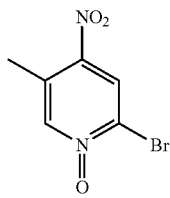

To a reaction flask containing a solution of 2-bromo-5-methylpyridine-1-oxide (100 g, 532 mmol) in concentrated sulfuric acid (100 mL) was added a mixture of fuming nitric acid in sulphuric acid (1:1, 200 mL) dropwise with stirring at 60° C. The resulting solution was stirred for 1 h at 90° C., cooled to room temperature and quenched by the addition of ice water. The reaction was filtered and the filtrate was extracted with EtOAc. The organic layer was washed with saturated aqueous sodium carbonate and brine, dried over anhydrous sodium sulfate and concentrated in vacuo to afford the title compound as a yellow solid (80 g, 65%). LCMS (ESI): $R_T$ (min)=1.284, $[M+H]^+$=233 & 235, Method=R.

Step 6: (E)-2-Bromo-5-(2-(dimethylamino)vinyl)-4-nitropyridine-1-oxide

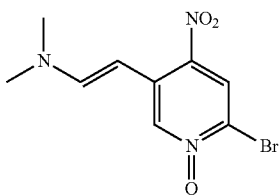 [SMILES: CN(C)/C=C/c1c[n+]([O-])c(Br)cc1[N+](=O)[O-]]

To a reaction vessel was added 2-bromo-5-methyl-4-nitropyridine-1-oxide (90.0 g, 386 mmol), N,N-dimethylformamide (450 mL) and N,N-dimethylformamide dimethyl acetal (450 mL). The resulting solution was stirred for 4 h at 120° C. The reaction was cooled to 0° C. and the product was isolated by filtration and dried to afford the title compound as a black solid (45 g, 40%). LCMS (ESI): $R_T$ (min)=1.794, $[M+H]^+$=288 & 290, Method=R.

Step 7: 6-Bromo-1H-pyrrolo[3,2-c]pyridine

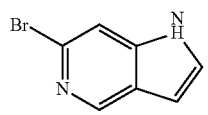

To a reaction vessel was added (E)-2-bromo-5-(2-(dimethylamino)vinyl)-4-nitropyridine-1-oxide (40.0 g, 138 mmol), iron powder (31.2 g, 557 mmol) and acetic acid (800 mL). The reaction mixture was stirred for 5 h at 100° C., filtered and concentrated in vacuo. The pH was adjusted to 8 with aqueous sodium carbonate and extracted with ethyl acetate. The organic portion was washed with brine, dried over anhydrous sodium sulfate and concentrated in vacuo. The residue was purified by silica gel chromatography (solvent: 33% ethyl acetate in petroleum ether) to afford the title compound as a white solid (10 g, 37%). $^1$HNMR (300 Hz, DMSO-$d_6$): δ 11.65 (s, 1H), 8.62 (s, 1H), 7.65 (s, 1H), 7.49 (s, 1H), 6.61 (s, 1H).

Step 8: 6-Bromo-3-iodo-1H-pyrrolo[3,2-c]pyridine

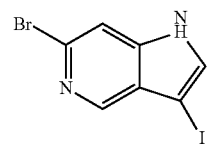 [SMILES: Brc1cc2[nH]cc(I)c2cn1]

A mixture of 6-bromo-1H-pyrrolo[3,2-c]pyridine (3.00 g, 12.2 mmol) and potassium hydroxide (3.00 g, 53.5 mmol) in N,N-dimethylformamide (30 mL) was stirred for 30 min at room temperature. Iodine (3.90 g, 15.4 mmol) was added and the reaction was stirred for an additional 30 min at room temperature. The reaction mixture was diluted with water and the product was isolated by filtration and dried under reduced pressure to afford the title compound as a yellow solid (3.5 g, 89%). LCMS (ESI): $R_T$ (min)=1.232, $[M+H]^+$=323, Method=R.

Step 9: 6-Bromo-3-iodo-1-isopropyl-1H-pyrrolo[3,2-c]pyridine

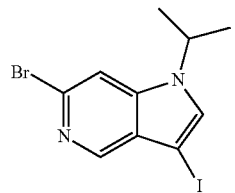

To a reaction vessel was added a solution of 6-bromo-3-iodo-1H-pyrrolo[3,2-c]pyridine (3.50 g, 10.8 mmol) in N,N-dimethylformamide (30 mL), sodium hydride (60 wt % dispersion in mineral oil) (900 mg, 37.5 mmol) and 2-iodopropane (3.70 g, 21.8 mmol) at 0° C. The reaction mixture was stirred for 16 h at room temperature, quenched by addition of water and extracted with ethyl acetate (3×). The combined organic layers were washed with brine, dried over anhydrous sodium sulfate and concentrated in vacuo. The residue was purified by silica gel chromatography (10% ethyl acetate in petroleum ether) to afford the title compound as a white solid (3 g, 76%). LCMS (ESI): $R_T$ (min)=2.323, $[M+H]^+$=365, Method=R.

Step 10: 6-Bromo-1-isopropyl-3-(4-methyl-1-(2-(tetrahydro-2H-pyran-2-yloxy)ethyl)-1H-pyrazol-3-yl)-1H-pyrrolo[3,2-c]pyridine

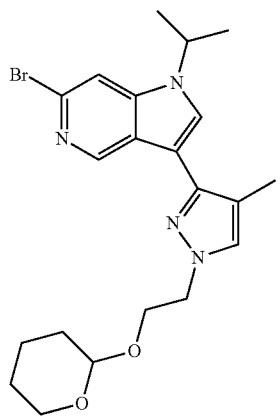 [SMILES: Cc1cn(CCOC2CCCCO2)nc1-c1cn(C(C)C)c2cc(Br)ncc12]

To a reaction vessel under nitrogen was added 4-methyl-1-(2-(tetrahydro-2H-pyran-2-yloxy)ethyl)-3-(tributylstannyl)-1H-pyrazole (1.20 g, 2.40 mmol), 6-bromo-3-iodo-1-isopropyl-1H-pyrrolo[3,2-c]pyridine (1.00 g, 2.74 mmol), tetrakis(triphenylphosphine)palladium(0) (283 mg, 0.240 mmol), copper (I) thiophene-2-carboxylate (464 mg, 2.43 mmol) and 1,4-dioxane (8 mL). The reaction vessel was sealed and irradiated in the microwave for 90 min at 100° C. The reaction was then quenched by addition of water and extracted with ethyl acetate (2×). The combined organic extracts were washed with brine, dried over anhydrous sodium sulfate and concentrated in vacuo. The residue was purified by silica gel chromatography (solvent: 50% ethyl acetate in petroleum ether) to the title compound as a yellow oil (206 mg, 19%). LCMS (ESI): $R_T$ (min)=1.405, [M+H]$^+$=447 & 449, Method=N.

Step 11: N-(2-(1-(Cyclopropylsulfonyl)-1H-pyrazol-4-yl)pyrimidin-4-yl)-1-isopropyl-3-(4-methyl-1-(2-(tetrahydro-2H-pyran-2-yloxy)ethyl)-1H-pyrazol-3-yl)-1H-pyrrolo[3,2-c]pyridin-6-amine

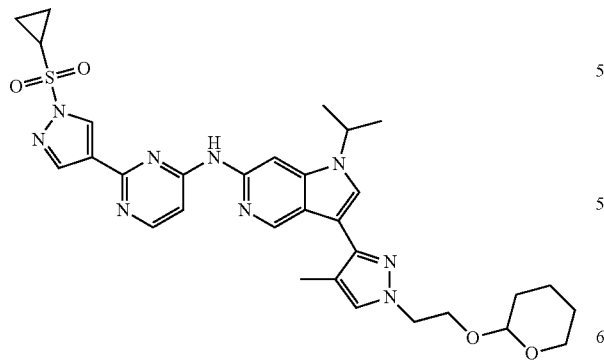

To a reaction vessel was added 6-bromo-1-isopropyl-3-(4-methyl-1-(2-(tetrahydro-2H-pyran-2-yloxy)ethyl)-1H-pyrazol-3-yl)-1H-pyrrolo[3,2-c]pyridine (200 mg, 0.450 mmol), 2-(1-cyclopropanesulfonyl-1H-pyrazol-4-yl)pyrimidin-4-ylamine (Example A62) (142 mg, 0.540 mmol), tris(dibenzylideneacetone)dipalladium(0) (42 mg, 0.050 mmol), 4,5-bis(diphenylphosphino)-9,9-dimethylxanthene (52 mg, 0.090 mmol), cesium carbonate (364 mg, 1.12 mmol) and 1,4-dioxane (4 mL). The reaction mixture was stirred for 2 h at 100° C. in an inert atmosphere of nitrogen. Upon cooling to room temperature, the reaction was filtered and concentrated in vacuo. The residue was purified by silica gel chromatography (solvent: 20% methanol in dichloromethane) to afford the title compound as a yellow solid (150 mg, 53%). LCMS (ESI): $R_T$ (min)=1.377, [M+H]$^+$=632, Method=M.

Step 12: 2-(3-(6-(2-(1-(Cyclopropylsulfonyl)-1H-pyrazol-4-yl)pyrimidin-4-ylamino)-1-isopropyl-1H-pyrrolo[3,2-c]pyridin-3-yl)-4-methyl-1H-pyrazol-1-yl)ethanol

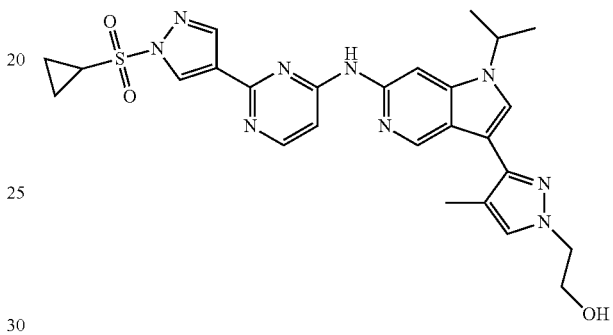

To a reaction vessel was added N-(2-(1-(cyclopropylsulfonyl)-1H-pyrazol-4-yl)pyrimidin-4-yl)-1-isopropyl-3-(4-methyl-1-(2-(tetrahydro-2H-pyran-2-yloxy)ethyl)-1H-pyrazol-3-yl)-1H-pyrrolo[3,2-c]pyridin-6-amine (150 mg, 0.240 mmol) and HCl (4M in 1,4-dioxane)(15 mL). The reaction mixture was stirred for 15 min at room temperature. The pH was adjusted to 7-8 with aqueous sodium bicarbonate and extracted with ethyl acetate. The organic layer was washed with brine, dried over anhydrous sodium sulfate and concentrated in vacuo. The residue was purified via reverse-phase HPLC and lyophilized to afford the title compound as an off-white solid (19 mg, 15%). LCMS (ESI): $R_T$ (min)=2.004, [M+H]$^+$=548.15, Method=N; $^1$H NMR (300 MHz, DMSO-$d_6$): δ 10.22 (s, 1H), 9.13 (s, 1H), 8.71 (s, 1H), 8.46 (s, 1H). 8.38-8.36 (d, J=6.0 Hz, 2H), 7.62 (s, 1H), 7.56 (s, 1H), 7.16 (s, 1H), 4.93-4.85 (m, 1H), 4.83-4.79 (m, 1H), 4.16 (m, 2H), 3.80-3.78 (d, J=5.1 Hz, 2H), 3.33-3.26 (m, 1H), 2.22 (s, 3H), 1.61-1.59 (d, J=6.6 Hz, 6H), 1.39-1.26 (m, 4H)

Example 254: N-(2-(1H-pyrazol-4-yl)pyrimidin-4-yl)-1-isopropyl-3-(2H-1,2,3-triazol-4-yl)-1H-pyrrolo[3,2-c]pyridin-6-amine

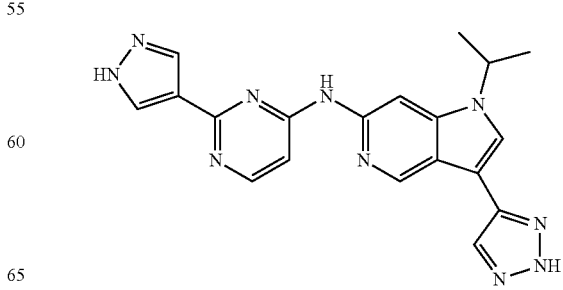

Step 1: 6-Bromo-1-isopropyl-3-((trimethylsilyl)ethynyl)-1H-pyrrolo[3,2-c]pyridine

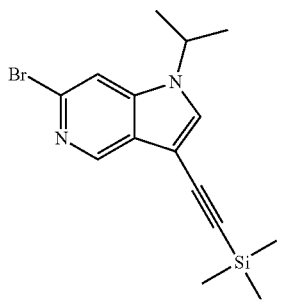 [SMILES: CC(C)n1cc(C#C[Si](C)(C)C)c2cnc(Br)cc21]

To a reaction vessel was added 6-bromo-3-iodo-1-isopropyl-1H-pyrrolo[3,2-c]pyridine (Example 253, Step 9) (3.00 g, 8.22 mmol), bis(triphenylphosphine)palladium(II) chloride (75 mg, 0.11 mmol), copper (I) iodide (40 mg, 0.21 mmol), triethylamine (3.50 g, 34.6 mmol), ethynyltrimethylsilane (810 mg, 8.25 mmol) and tetrahydrofuran (50 mL). The reaction mixture was stirred for 3 h at room temperature under nitrogen, concentrated in vacuo and purified by silica gel chromatography (eluent: 5% ethyl acetate in petroleum ether) to afford the title compound as a yellow oil (2.3 g, 83%). LCMS (ESI): $R_T$ (min)=1.744, $[M+H]^+$=335, Method=M.

Step 2: 6-Bromo-3-ethynyl-1-isopropyl-1H-pyrrolo[3,2-c]pyridine

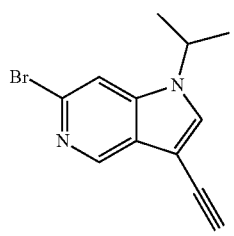

To a reaction vessel purged and maintained under nitrogen was added a solution of 6-bromo-1-isopropyl-3-((trimethylsilyl)ethynyl)-1H-pyrrolo[3,2-c]pyridine (1.00 g, 2.98 mmol) in tetrahydrofuran (10 mL), followed by tetrabutylammonium fluoride (0.1M, 0.5 mL) dropwise with stirring at −40° C. The resulting solution was stirred for 3 h at room temperature, concentrated in vacuo, and purified by silica gel chromatography (eluent: 6% ethyl acetate in petroleum ether) to afford the title compound as a brown oil (250 mg, 32%). LCMS (ESI): $R_T$ (min)=1.509, $[M+H]^+$=263, Method=M.

Step 3: 3-(2-Benzyl-2H-1,2,3-triazol-4-yl)-6-bromo-1-isopropyl-1H-pyrrolo[3,2-c]pyridine

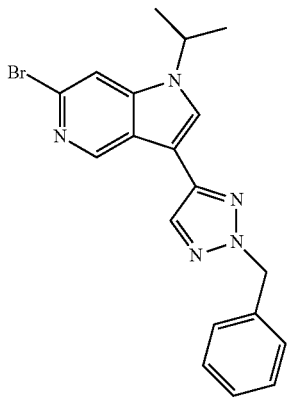 [SMILES: CC(C)n1cc(-c2cnn(Cc3ccccc3)n2)c2cnc(Br)cc21]

To a reaction vessel was added 6-bromo-3-ethynyl-1-isopropyl-1H-pyrrolo[3,2-c]pyridine (230 mg, 0.870 mmol), (azidomethyl)benzene (180 mg, 1.35 mmol), copper (I) iodide (160 mg, 0.84 mmol), L-sodium ascorbate (12 mg), N,N-dimethylformamide (10 mL) and water (4 mL). The reaction mixture was stirred for 4 h at room temperature. The reaction mixture was diluted with 50 mL of water, extracted with 3×50 mL of ethyl acetate, washed with brine, dried over anhydrous sodium sulfate and concentrated in vacuo. The residue was purified by silica gel chromatography with ethyl acetate/petroleum ether (3/7) to afford the title compound as a yellow oil (90 mg, 26%). LCMS (ESI): $R_T$ (min)=1.452, $[M+H]^+$=396 & 398, Method=M.

Step 4: 3-(2-Benzyl-2H-1,2,3-triazol-4-yl)-N-(2-(1-(cyclopropylsulfonyl)-1H-pyrazol-4-yl)pyrimidin-4-yl)-1-isopropyl-1H-pyrrolo[3,2-c]pyridin-6-amine

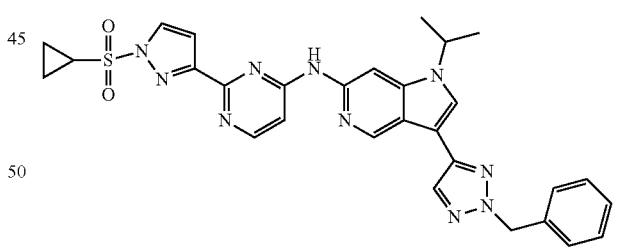

To a reaction vessel was added 3-(2-benzyl-2H-1,2,3-triazol-4-yl)-6-bromo-1-isopropyl-1H-pyrrolo[3,2-c]pyridine (150 mg, 0.38 mmol), 2-(1-cyclopropanesulfonyl-1H-pyrazol-4-yl)pyrimidin-4-ylamine (Example A62) (130 mg, 0.49 mmol), tris(dibenzylideneacetone)dipalladium (50 mg, 0.05 mmol), (9,9-dimethyl-9H-xanthene-4,5-diyl)bis(diphenylphosphine) (56 mg, 0.10 mmol), cesium carbonate (550 mg, 1.69 mmol) and 1,4-dioxane (10 mL). The reaction mixture was stirred for 3 h at 100° C. under nitrogen. Upon cooling to room temperature, the reaction was filtered and the resulting solution was diluted with water, extracted with ethyl acetate (2×), washed with brine, dried over anhydrous sodium sulfate and concentrated in vacuo. The residue was purified by silica gel chromatography (eluent: 5% methanol in dichloromethane) to afford the title compound as a yellow solid (130 mg, 59%). LCMS (ESI): $R_T$ (min)=1.343, [M+H]$^+$=581, Method=M.

Step 5: N-(2-(1H-pyrazol-4-yl)pyrimidin-4-yl)-1-isopropyl-3-(2H-1,2,3-triazol-4-yl)-1H-pyrrolo[3,2-c]pyridin-6-amine

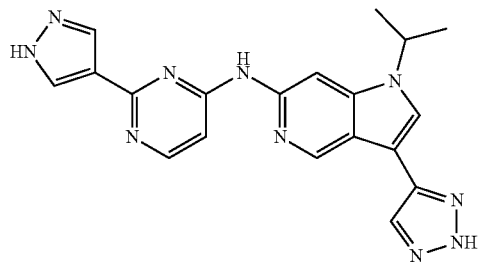 [SMILES: CC(C)n1cc(-c2cn[nH]n2)c2cnc(Nc3ccnc(-c4cn[nH]c4)n3)cc21]

To a reaction vessel was added 3-(2-benzyl-2H-1,2,3-triazol-4-yl)-N-(2-(1-(cyclopropylsulfonyl)-1H-pyrazol-4-yl)pyrimidin-4-yl)-1-isopropyl-1H-pyrrolo[3,2-c]pyridin-6-amine (130 mg, 0.22 mmol), aluminium trichloride (143 mg, 1.08 mmol) and toluene (6 mL). The reaction mixture was stirred for 20 h at 60° C., cooled to room temperature, and filtered to collect the precipitate. The precipitate was purified via reverse-phase HPLC and lyophilized to afford the title compound as a light yellow solid (8.3 mg, 10%). LCMS (ESI): $R_T$ (min)=2.178, [M+H]$^+$=387.0, Method=N. $^1$H NMR (400 MHz, DMSO-d$_6$): δ 13.19 (s, 1H), 10.07 (s, 1H), 9.07 (s, 1H), 8.45 (s, 1H), 8.30 (d, J=6.0 Hz, 1H), 8.25 (s, 1H), 8.20 (br, 1H), 8.04 (s, 1H), 7.07 (d, J=4.4 Hz, 1H), 6.53 (s, 1H), 4.80-4.77 (m, 1H), 1.60 (d, J=6.8 Hz, 6H).

Example 255: 2-(4-(6-(2-(1-(Ethylsulfonyl)-1H-pyrazol-4-yl)pyrimidin-4-ylamino)-1-isopropyl-1H-pyrrolo[3,2-c]pyridin-3-yl)-1H-pyrazol-1-yl)-N-(oxetan-3-yl)acetamide

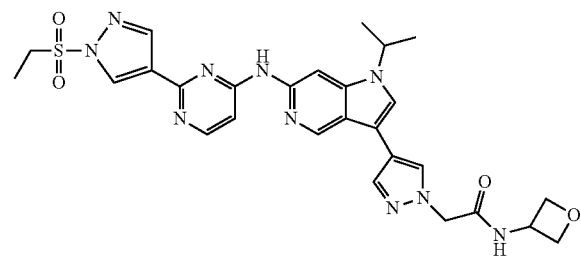 [SMILES: CCS(=O)(=O)n1cc(-c2nccc(Nc3cc4c(cn3)c(-c3cnn(CC(=O)NC5COC5)c3)cn4C(C)C)n2)cn1]

Step 1: Ethyl 2-(4-(4,4,5,5-tetramethyl-1,3,2-dioxaborolan-2-yl)-1H-pyrazol-1-yl)acetate

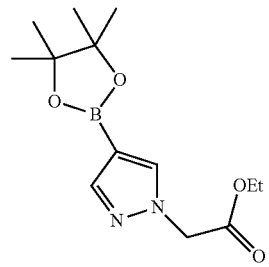 [SMILES: CCOC(=O)Cn1cc(B2OC(C)(C)C(C)(C)O2)cn1]

To a reaction vessel was added 4-(tetramethyl-1,3,2-dioxaborolan-2-yl)-1H-pyrazole (1 g, 5.15 mmol), ethyl 2-bromoacetate (940 mg, 5.63 mmol), cesium carbonate (2.68 g, 8.23 mmol) and N,N-dimethylformamide (10 mL). The reaction mixture was stirred overnight at 60° C. under an inert atmosphere of nitrogen. Upon cooling to room temperature, the solution was diluted with water, extracted with ethyl acetate (3×), and the combined organic layers were washed with brine, dried over anhydrous sodium sulfate and concentrated in vacuo. The residue was purified by silica gel chromatography (solvent gradient: 0-5% ethyl acetate in petroleum ether) to afford ethyl 2-(4-(4,4,5,5-tetramethyl-1,3,2-dioxaborolan-2-yl)-1H-pyrazol-1-yl)acetate as yellow oil (800 mg, 55%).

Step 2: Ethyl 2-(4-(6-bromo-1-isopropyl-1H-pyrrolo[3,2-c]pyridin-3-yl)-1H-pyrazol-1-yl)acetate

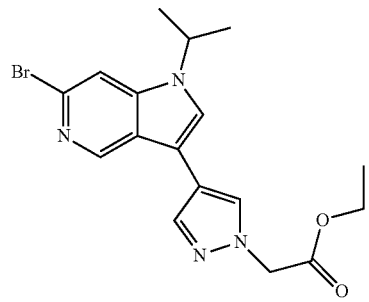 [SMILES: CCOC(=O)Cn1cc(-c2cn(C(C)C)c3cc(Br)ncc23)cn1]

To a reaction vessel was added ethyl 2-(4-(4,4,5,5-tetramethyl-1,3,2-dioxaborolan-2-yl)-1H-pyrazol-1-yl)acetate (3.70 g, 13.2 mmol), tetrakis(triphenylphosphine)palladium (0) (760 mg, 0.660 mmol), sodium carbonate (2.80 g, 26.4 mmol), 6-bromo-3-iodo-1-isopropyl-1H-pyrrolo[3,2-c]pyridine (Example 253, Step 9) (4.80 g, 13.1 mmol), acetonitrile (50 mL) and water (5 mL). The reaction mixture was stirred for 4 h at 80° C. under an inert atmosphere of nitrogen. The reaction was diluted with water, extracted with ethyl acetate (3×), and the combined organic layers were washed with brine, dried over anhydrous sodium sulfate and concentrated in vacuo. The residue was purified by silica gel chromatography (solvent gradient: 0-33% ethyl acetate in petroleum ether) to afford the title compound as a yellow solid (1.2 g, 23%). LCMS (ESI): $R_T$ (min)=1.310, [M+H]$^+$=391, Method=M.

Step 3: Ethyl 2-(4-(6-(2-chloropyrimidin-4-ylamino)-1-isopropyl-1H-pyrrolo[3,2-c]pyridin-3-yl)-1H-pyrazol-1-yl)acetate

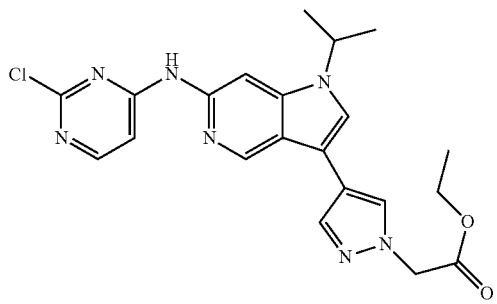 [SMILES: CCOC(=O)Cn1cc(-c2cn(C(C)C)c3cc(Nc4ccnc(Cl)n4)ncc23)cn1]

To a reaction vessel was added ethyl 2-(4-(6-bromo-1-isopropyl-1H-pyrrolo[3,2-c]pyridin-3-yl)-1H-pyrazol-1-yl)acetate (1.80 g, 4.60 mmol), tris(dibenzylideneacetone)dipalladium(0) (0.84 g, 0.092 mmol), 4,5-bis(diphenylphosphino)-9,9-dimethylxanthene (0.44 g, 0.076 mmol), 2-chloropyrimidin-4-amine (600 mg, 4.63 mmol), cesium carbonate (3.00 g, 9.20 mmol) and 1,4-dioxane (30 mL). The reaction mixture was stirred for 2 h at 90° C. under an inert atmosphere of nitrogen. The reaction was cooled to room temperature, extracted with ethyl acetate, and the organic layer was washed with brine, dried over anhydrous sodium sulfate and concentrated in vacuo. The residue was purified by silica gel chromatography (solvent: 10% methanol in dichloromethane) to afford the title compound as a yellow solid (1 g, 49%). LCMS (ESI): $R_T$ (min)=1.229, [M+H]$^+$=440, Method=M.

Step 4: 2-(4-[6-[(2-Chloropyrimidin-4-yl)amino]-1-(propan-2-yl)-1H-pyrrolo[3,2-c]pyridin-3-yl]-1H-pyrazol-1-yl)acetic acid

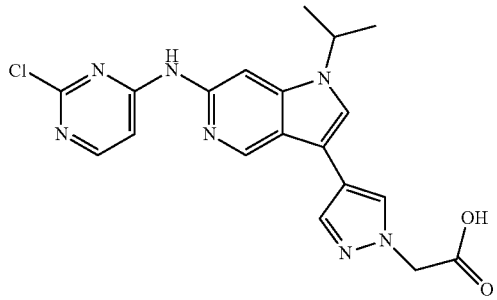 [SMILES: CC(C)n1cc(-c2cnn(CC(=O)O)c2)c2cnc(Nc3ccnc(Cl)n3)cc21]

To a reaction vessel was added ethyl 2-(4-(6-(2-chloropyrimidin-4-ylamino)-1-isopropyl-1H-pyrrolo[3,2-c]pyridin-3-yl)-1H-pyrazol-1-yl)acetate (1.00 g, 2.27 mmol), lithium hydroxide (100 mg, 4.18 mmol), water (4 mL) and ethanol (20 mL). The reaction mixture was stirred for 30 min at 60° C. and the pH was adjusted to 6 with acetic acid. The precipitate was collected by filtration and dried in an oven to afford the title compound as a yellow solid (0.5 g, 53%). LCMS (ESI): $R_T$ (min)=1.109, [M+H]$^+$=412, Method=G.

Step 5: 2-(4-[6-[(2-Chloropyrimidin-4-yl)amino]-1-(propan-2-yl)-1H-pyrrolo[3,2-c]pyridin-3-yl]-1H-pyrazol-1-yl)-N-(oxetan-3-yl)acetamide

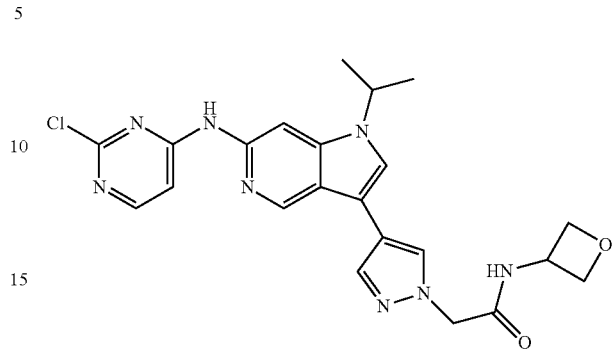

To a reaction vessel was added 2-(4-[6-[(2-chloropyrimidin-4-yl)amino]-1-(propan-2-yl)-1H-pyrrolo[3,2-c]pyridin-3-yl]-1H-pyrazol-1-yl)acetic acid (130 mg, 0.320 mmol), HBTU (180 mg, 0.47 mmol), N,N-diisopropylethylamine (61 mg, 0.47 mmol), oxetan-3-amine (69 mg, 0.94 mmol) and N,N-dimethylformamide (5 mL). The reaction mixture was stirred for 2 h at room temperature under an inert atmosphere of nitrogen, diluted with water, and extracted with ethyl acetate. The organic layer was washed with brine, dried over anhydrous sodium sulfate and concentrated in vacuo to afford the title compound as a yellow solid (120 mg, 81%). The crude product was used in next step without further purification. LCMS (ESI): $R_T$ (min)=1.030 min, [M+H]$^+$=467, Method=N.

Step 6: 2-[4-[6-([2-[1-(Ethanesulfonyl)-1H-pyrazol-4-yl]pyrimidin-4-yl]amino)-1-(propan-2-yl)-1H-pyrrolo[3,2-c]pyridin-3-yl]-1H-pyrazol-1-yl]-N-(oxetan-3-yl)acetamide

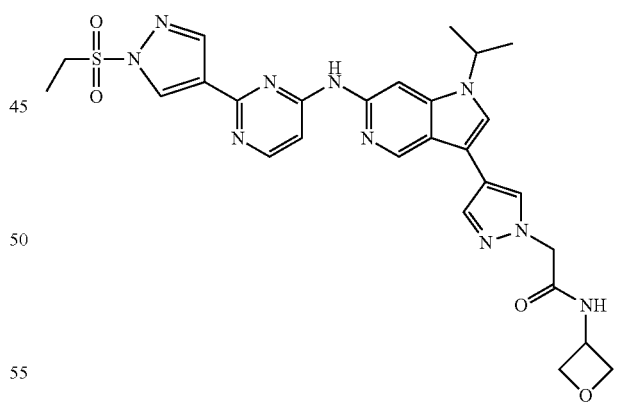

To a reaction vessel was added 2-(4-[6-[(2-chloropyrimidin-4-yl)amino]-1-(propan-2-yl)-1H-pyrrolo[3,2-c]pyridin-3-yl]-1H-pyrazol-1-yl)-N-(oxetan-3-yl)acetamide (130 mg, 0.28 mmol), tetrakis(triphenylphosphine)palladium(0) (32 mg, 0.030 mmol), sodium carbonate (59 mg, 0.56 mmol), 1-(ethylsulfonyl)-4-(4,4,5,5-tetramethyl-1,3,2-dioxaborolan-2-yl)-1H-pyrazole (Example A52, Step 1) (120 mg, 0.42 mmol), dioxane (3 mL) and water (0.3 mL). The reaction mixture was stirred for 4 h at 90° C. under an inert atmosphere of nitrogen. The reaction mixture was diluted with water, extracted with ethyl acetate, and the organic layer was washed with brine, dried over sodium sulfate and concentrated in vacuo. The crude product was purified via reverse-phase HPLC and lyophilized to afford the title compound as a light yellow solid (48.6 mg, 29%). LCMS (ESI): $R_T$ (min)=1.518, $[M+H]^+$=591.10, Method=R; $^1$H NMR (400 MHz, DMSO-$d_6$) δ 10.23 (s, 1H), 8.96 (d, J=6.8 Hz, 1H), 8.83 (s, 1H), 8.69 (s, 1H), 8.49 (s, 1H), 8.48 (s, 1H), 8.37 (d, J=6.0 Hz, 1H), 8.20 (s, 1H), 7.90 (s, 1H), 7.80 (s, 1H), 7.12 (s, 1H), 4.85-4.72 (m, 6H), 4.46 (m, 2H), 3.84 (m, 2H), 1.56 (s, 6H), 1.16 (m, 3H).

Example 256: 4-(6-(2-(1-(Cyclopropylsulfonyl)-1H-pyrazol-4-yl)pyrimidin-4-ylamino)-1-isopropyl-1H-pyrrolo[3,2-c]pyridin-3-yl)pyrrolidin-2-one

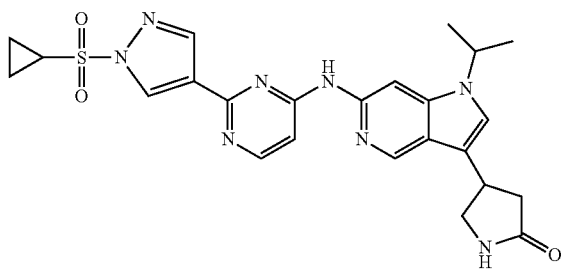 [SMILES: CC(C)n1cc(C2CNC(=O)C2)c2cnc(Nc3ccnc(-c4cnn(S(=O)(=O)C5CC5)c4)n3)cc21]

Step 1: 4-(6-Bromo-1H-pyrrolo[3,2-c]pyridin-3-yl)pyrrolidin-2-one

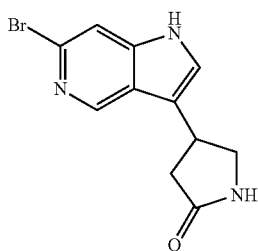 [SMILES: O=C1CC(c2c[nH]c3cc(Br)ncc23)CN1]

To a reaction vessel was added 6-bromo-1H-pyrrolo[3,2-c]pyridine (Example 253, Step 7) (268 mg, 1.36 mmol), tert-butyl 2-oxo-2,5-dihydro-1H-pyrrole-1-carboxylate (500 mg, 2.73 mmol) and acetic acid (4 mL). The reaction mixture was stirred overnight at 105° C. The reaction was cooled to room temperature, concentrated in vacuo and the residue was dissolved in ethyl acetate (10 mL). The desired product was isolated by filtration and dried in an oven to afford the title compound as a brown solid (150 mg, 39%). LCMS (ESI): $R_T$ (min)=0.931, $[M+H]^+$=280, Method=R.

Step 2: 4-[6-Bromo-1-(propan-2-yl)-1H-pyrrolo[3,2-c]pyridin-3-yl]pyrrolidin-2-one

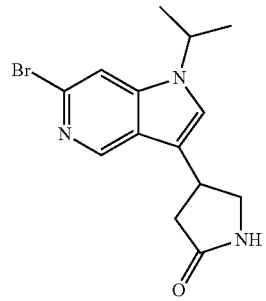 [SMILES: CC(C)n1cc(C2CNC(=O)C2)c2cnc(Br)cc21]

To a reaction vessel was added 4-(6-bromo-1H-pyrrolo[3,2-c]pyridin-3-yl)pyrrolidin-2-one (50 mg, 0.18 mmol), cesium carbonate (116 mg, 0.36 mmol) and N,N-dimethylformamide (2 mL). The reaction mixture was stirred for 30 min and 2-iodopropane (63.7 mg, 0.380 mmol) was added. The reaction mixture was stirred for 2 h at 80° C., cooled to room temperature, diluted with water, and extracted with ethyl acetate (3×). The combined organic layers were washed with brine, dried over anhydrous sodium sulfate and concentrated in vacuo. The residue was purified by silica gel chromatography (solvent gradient: 0-100% ethyl acetate in petroleum ether) to afford the title compound as a light yellow oil (30 mg, 52%). LCMS (ESI): $R_T$ (min)=1.101, $[M+H]^+$=322 & 324, Method=N.

Step 3: 4-[6-([2-[1-(Cyclopropanesulfonyl)-1H-pyrazol-4-yl]pyrimidin-4-yl]amino)-1-(propan-2-yl)-1H-pyrrolo[3,2-c]pyridin-3-yl]pyrrolidin-2-one

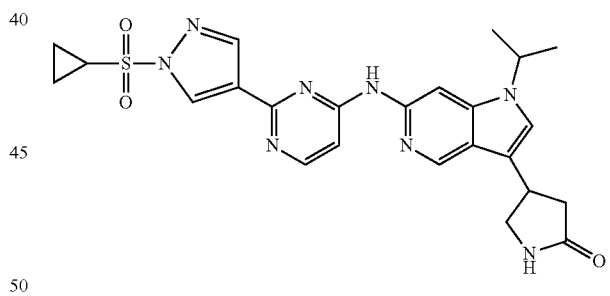

To a reaction vessel was added 4-[6-bromo-1-(propan-2-yl)-1H-pyrrolo[3,2-c]pyridin-3-yl]pyrrolidin-2-one (50 mg, 0.16 mmol), tris(dibenzylideneacetone)dipalladium(0) (14 mg, 0.020 mmol), 4,5-bis(diphenylphosphino)-9,9-dimethylxanthene (17.5 mg, 0.03 mmol), cesium carbonate (101 mg, 0.30 mmol), 2-(1-cyclopropanesulfonyl-1H-pyrazol-4-yl)pyrimidin-4-ylamine (Example A62) (41 mg, 0.15 mmol) and 1,4-dioxane (5 mL). The reaction mixture was stirred for 2 h at 100° C., cooled to room temperature, filtered and concentrated in vacuo. The crude product was purified via reverse-phase HPLC and lyophilized to afford the title compound as a white solid (23.8 mg, 30%). LCMS (ESI): $R_T$ (min)=1.543, $[M+H]^+$=507.05, Method=R. $^1$H NMR (300 MHz, DMSO-$d_6$): δ 10.21 (s, 1H), 8.67 (s, 1H), 8.56 (s, 1H), 8.51-8.38 (m, 3H), 8.08 (s, 1H), 7.45 (s, 1H), 7.17 (s, 1H), 4.99-4.93 (m, 1H), 4.79-4.64 (m, 1H), 3.32-3.31 (m, 2H), 2.39-2.28 (m, 2H), 2.17-2.01 (m, 1H), 1.52 (d, J=3 Hz, 6H), 1.51 (s, 2H), 1.50-1.37 (m, 2H).

Example 257: N-(2-(1-(Cyclopropylsulfonyl)-1H-pyrazol-4-yl)pyrimidin-4-yl)-2-methyl-1-(1,1,1-trifluoropropan-2-yl)-1H-imidazo[4,5-c]pyridin-6-amine

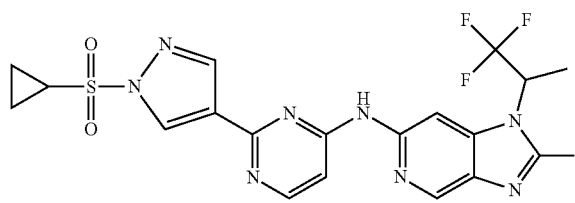 [SMILES: Cc1nc2cnc(Nc3ccnc(-c4cnn(S(=O)(=O)C5CC5)c4)n3)cc2n1C(C)C(F)(F)F]

Step 1: (E)-6-Bromo-N³-(2-ethoxypropylidene)-N⁴-(1,1,1-trifluoropropan-2-yl)pyridine-3,4-diamine

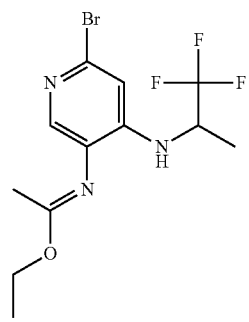 [SMILES: CCO/C(C)=N/c1cnc(Br)cc1NC(C)C(F)(F)F]

6-bromo-4-N-(1,1,1-trifluoropropan-2-yl)pyridine-3,4-diamine (prepared analogously to Example A60, step 2) (200 mg, 0.70 mmol) was dissolved in 1,1,1-triethoxyethane (10 mL) and acetic acid (1 mL) and stirred for 16 h at 80° C. The mixture was cooled to room temperature and concentrated in vacuo to afford the title compound as a yellow oil (23.8 mg, 30%). LCMS (ESI): $R_T$ (min)=1.300, [M+H]⁺=354 & 356, Method=L.

Step 2: 6-Bromo-2-methyl-1-(1,1,1-trifluoropropan-2-yl)-1H-imidazo[4,5-c]pyridine

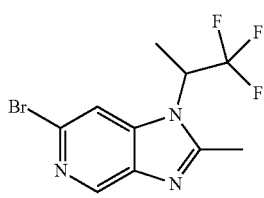 [SMILES: Cc1nc2cnc(Br)cc2n1C(C)C(F)(F)F]

To a reaction vessel was added (E)-6-bromo-N³-(2-ethoxypropylidene)-N⁴-(1,1,1-trifluoropropan-2-yl)pyridine-3,4-diamine (300 mg, 0.85 mmol), potassium carbonate (1.00 g, 7.24 mmol) and N,N-dimethylformamide (10 mL). The reaction mixture was stirred for 16 h at 100° C. Upon cooling to room temperature, the reaction mixture was diluted with water and extracted with ethyl acetate (3×). The combined organic layers were washed with brine, dried over anhydrous sodium sulfate and concentrated in vacuo. The residue was purified by silica gel chromatography (solvent: 30% ethyl acetate in petroleum ether) to afford the title compound as a yellow oil (120 mg, 48%). LCMS (ESI): $R_T$ (min)=1.376, [M+H]⁺=308, Method=M.

Step 3: 2-Chloro-N-[2-methyl-1-(1,1,1-trifluoropropan-2-yl)-1H-imidazo[4,5-c]pyridin-6-yl]pyrimidin-4-amine

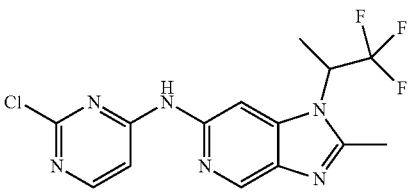 [SMILES: Cc1nc2cnc(Nc3ccnc(Cl)n3)cc2n1C(C)C(F)(F)F]

To a reaction vessel was added 6-bromo-2-methyl-1-(1,1,1-trifluoropropan-2-yl)-1H-imidazo[4,5-c]pyridine (120 mg, 0.39 mmol), 2-chloropyrimidin-4-amine (52 mg, 0.40 mmol), 4,5-bis(diphenylphosphino)-9,9-dimethylxanthene (45 mg, 0.080 mmol), tris(dibenzylideneacetone)dipalladium(0) (38 mg, 0.04 mmol), cesium carbonate (397 mg, 1.22 mmol) and 1,4-dioxane (5 mL). The reaction mixture was stirred for 2 h at 100° C. Upon cooling to room temperature, the reaction was filtered and concentrated in vacuo. The residue was purified by silica gel chromatography (solvent: 75% ethyl acetate in petroleum ether) to afford the title compound as a white solid (60 mg, 43%). LCMS (ESI): $R_T$ (min)=0.814, [M+H]⁺=357, Method=S.

Step 4: N-(2-(1-(Cyclopropylsulfonyl)-1H-pyrazol-4-yl)pyrimidin-4-yl)-2-methyl-1-(1,1,1-trifluoropropan-2-yl)-1H-imidazo[4,5-c]pyridin-6-amine

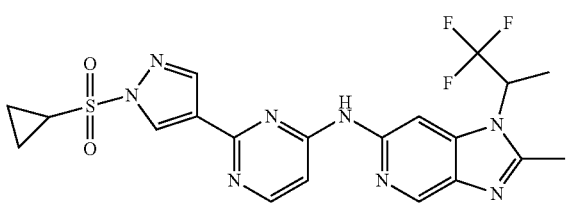 [SMILES: Cc1nc2cnc(Nc3ccnc(-c4cnn(S(=O)(=O)C5CC5)c4)n3)cc2n1C(C)C(F)(F)F]

To a reaction vessel was added 2-chloro-N-[2-methyl-1-(1,1,1-trifluoropropan-2-yl)-1H-imidazo[4,5-c]pyridin-6-yl]pyrimidin-4-amine (60 mg, 0.17 mmol), 1-(cyclopropylsulfonyl)-4-(4,4,5,5-tetramethyl-1,3,2-dioxaborolan-2-yl)-1H-pyrazole (Example 51, Step 6) (62 mg, 0.21 mmol), tetrakis(triphenylphosphine)palladium(0) (23 mg, 0.02 mmol), sodium carbonate (72 mg, 0.68 mmol), 1,4-dioxane (4 mL) and water (0.4 mL). The reaction mixture was irradiated in the microwave for 60 min at 100° C. Upon cooling to room temperature, the reaction was filtered and concentrated in vacuo. The crude product was purified via reverse-phase HPLC and lyophilized to afford the title compound as a white solid (19.8 mg, 24%). LCMS (ESI): $R_T$ (min)=2.369, [M+H]⁺=493, Method L; ¹H NMR (300 MHz, DMSO-$d_6$): δ 10.26 (s, 1H), 8.63-8.58 (m, 2H), 8.45-8.33 (m, 3H), 7.29 (m, 1H), 5.73-5.57 (m, 1H), 3.25-3.24 (m, 1H), 2.62 (s, 3H), 1.92-1.90 (d, J=6.8 Hz, 3H), 1.33-1.15 (m, 4H).

Example 258: 1-Isopropyl-2-methyl-N-(2-(1-(pyrrolidin-3-ylsulfonyl)-1H-pyrazol-4-yl)pyrimidin-4-yl)-1H-imidazo[4,5-c]pyridin-6-amine

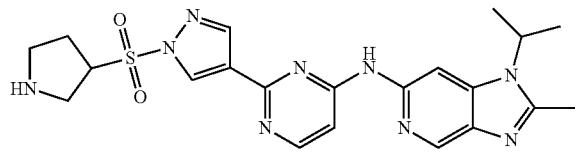 [SMILES: Cc1nc2cnc(Nc3ccnc(-c4cnn(S(=O)(=O)C5CCNC5)c4)n3)cc2n1C(C)C]

Step 1: tert-Butyl 3-[4-(tetramethyl-1,3,2-dioxaborolan-2-yl)-1H-pyrazole-1-sulfonyl]pyrrolidine-1-carboxylate

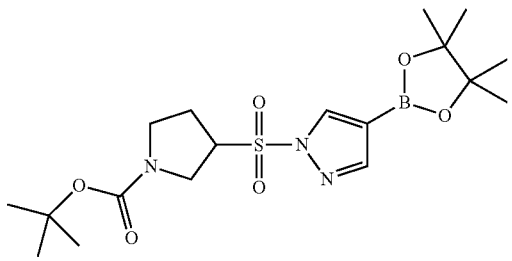 [SMILES: CC(C)(C)OC(=O)N1CCC(S(=O)(=O)n2cc(B3OC(C)(C)C(C)(C)O3)cn2)C1]

To a reaction vessel was added 4-(tetramethyl-1,3,2-dioxaborolan-2-yl)-1H-pyrazole (790 mg, 4.07 mmol), cesium carbonate (3.60 g, 11.0 mmol), tert-butyl 3-(chlorosulfonyl)pyrrolidine-1-carboxylate (1 g, 3.71 mmol) and acetonitrile (30 mL). The reaction mixture was stirred overnight at room temperature. The reaction was filtered and concentrated in vacuo. The residue was purified by silica gel chromatography (solvent gradient: 0-10% methanol in dichloromethane) to afford the title compound as a yellow solid (800 mg, 50%). LCMS (ESI): $R_T$ (min)=0.932, $[M+H]^+$=428, Method=S.

Step 2: tert-Butyl 3-[4-(4-[[2-methyl-1-(propan-2-yl)-1H-imidazo[4,5-c]pyridin-6-yl]amino]pyrimidin-2-yl)-1H-pyrazole-1-sulfonyl]pyrrolidine-1-carboxylate

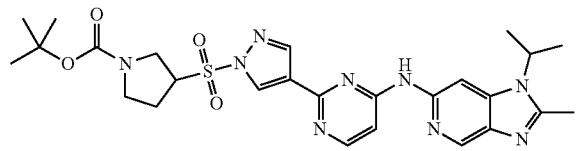 [SMILES: Cc1nc2cnc(Nc3ccnc(-c4cnn(S(=O)(=O)C5CCN(C(=O)OC(C)(C)C)C5)c4)n3)cc2n1C(C)C]

To a reaction vessel was added tert-butyl 3-[4-(tetramethyl-1,3,2-dioxaborolan-2-yl)-1H-pyrazole-1-sulfonyl]pyrrolidine-1-carboxylate (500 mg, 1.17 mmol), N-(2-chloropyrimidin-4-yl)-1-isopropyl-2-methyl-1H-imidazo[4,5-c]pyridin-6-amine (Example 46, Step 7) (354 mg, 1.17 mmol), tetrakis(triphenylphosphine)palladium(0) (135 mg, 0.120 mmol), sodium carbonate (372 mg, 3.51 mmol), 1,4-dioxane (15 mL) and water (1.5 mL). The reaction mixture was subjected to microwave radiation for 1 h at 100° C. The reaction was cooled to room temperature, filtered and concentrated in vacuo. The residue was purified by silica gel chromatography (solvent gradient: 0-10% methanol in dichloromethane) to afford the title compound as a light yellow solid (500 mg, 75%). LCMS (ESI): $R_T$ (min)=0.777, $[M+H]^+$=568, Method=S.

Step 3: 1-Isopropyl-2-methyl-N-(2-(1-(pyrrolidin-3-ylsulfonyl)-1H-pyrazol-4-yl)pyrimidin-4-yl)-1H-imidazo[4,5-c]pyridin-6-amine

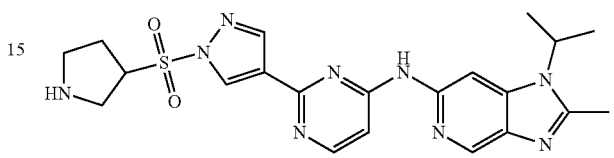

tert-Butyl 3-[4-(4-[[2-methyl-1-(propan-2-yl)-1H-imidazo[4,5-c]pyridin-6-yl]amino]pyrimidin-2-yl)-1H-pyrazole-1-sulfonyl]pyrrolidine-1-carboxylate (500 mg, 0.88 mmol) was dissolved in dichloromethane (10 mL) and trifluoroacetic acid (3 mL). The resulting solution was stirred for 40 min at room temperature and concentrated in vacuo. The crude product was purified via reverse-phase HPLC and lyophilized to afford the title compound as a white solid (38.7 mg, 9%). LCMS (ESI): $R_T$ (min)=1.133, $[M+H]^+$=468.00, Method=L; $^1$H NMR (400 MHz, DMSO-$d_6$): δ10.20 (s, 1H), 8.68 (s, 1H), 8.56 (s, 1H), 8.49-8.38 (m, 3H), 7.23 (s, 1H), 4.80-4.76 (m, 1H), 4.33-4.27 (m, 1H), 3.29-3.02 (m, 3H), 2.76 (s, 2H), 2.58 (s, 3H), 2.07-2.03 (m, 2H), 1.63 (d, J=6 Hz, 6H).

Example 259: 1-(3-(4-(4-(1-Isopropyl-2-methyl-1H-imidazo[4,5-c]pyridin-6-ylamino)pyrimidin-2-yl)-1H-pyrazol-1-ylsulfonyl)pyrrolidin-1-yl)ethanone

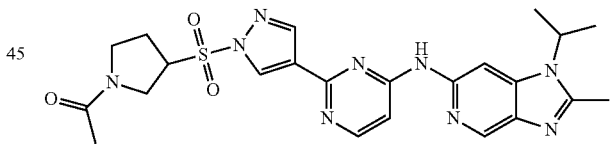

To a reaction vessel was added 1-isopropyl-2-methyl-N-(2-(1-(pyrrolidin-3-ylsulfonyl)-1H-pyrazol-4-yl)pyrimidin-4-yl)-1H-imidazo[4,5-c]pyridin-6-amine (Example 258) (150 mg, 0.32 mmol), triethylamine (97 mg, 0.96 mmol), acetyl chloride (25 mg, 0.32 mmol) and tetrahydrofuran (10 mL). The reaction mixture was stirred for 40 min at 0° C. The resulting mixture was concentrated in vacuo and purified by silica gel chromatography (solvent gradient: 0-10% methanol in dichloromethane) to afford the title compound as a white solid (13.6 mg, 8%). LCMS (ESI): $R_T$ (min)=1.264, $[M+H]^+$=510.05, Method=L; $^1$H NMR (400 MHz, DMSO-$d_6$): δ10.20 (s, 1H), 8.73-8.68 (m, 1H), 8.57-8.52 (m, 2H), 8.39 (s, 2H), 7.24 (s, 1H), 4.77-4.66 (m, 2H), 3.94-3.81 (m, 2H), 3.58-3.51 (m, 2H), 2.58-2.42 (m, 3H), 2.28 (s, 2H), 1.93-1.88 (m, 3H), 1.62 (s, 6H).

Example 260: 1-Isopropyl-2-methyl-N-(2-(1-(oxetan-3-ylsulfonyl)-1H-pyrazol-4-yl)pyrimidin-4-yl)-1H-imidazo[4,5-c]pyridin-6-amine

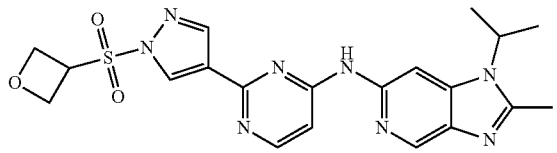 [SMILES: Cc1nc2cnc(Nc3ccnc(-c4cnn(S(=O)(=O)C5COC5)c4)n3)cc2n1C(C)C]

Step 1: 1-(Oxetan-3-ylsulfanyl)ethan-1-one

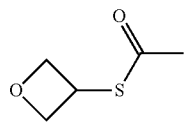

To a reaction vessel was added 3-iodooxetane (2.5 g, 13.6 mmol), potassium ethanethioate (4.60 g, 34.0 mmol) and N,N-dimethylformamide (8 mL). The reaction mixture was stirred overnight at room temperature. The resulting solution was extracted with ethyl acetate and the organic layer was washed with brine, dried over anhydrous sodium sulfate and concentrated in vacuo. The residue was purified by silica gel chromatography (solvent: 10% ethyl acetate in petroleum ether) to afford the title compound as a light yellow oil (1.3 g, 72%).

Step 2: Oxetane-3-sulfonyl chloride

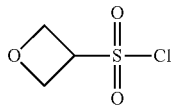

To a reaction vessel purged and maintained with an inert atmosphere of nitrogen containing N-chlorosuccinimide (2.00 g, 15.0 mmol) and acetonitrile (8 mL) at 0° C. was added hydrogen chloride (7N in water)(0.3 mL) dropwise with stirring followed by a dropwise solution of 1-(oxetan-3-ylsulfanyl)ethan-1-one (500 mg, 3.78 mmol) in acetonitrile (2 mL). The resulting solution was stirred for 20 min at 0° C., concentrated in vacuo and co-evaporated with ether to afford the title compound as a colorless oil (0.5 g). The crude product was used in next step without further purification.

Step 3: tert-Butyl 2-chloropyrimidin-4-yl(1-isopropyl-2-methyl-1H-imidazo[4,5-c]pyridin-6-yl)carbamate

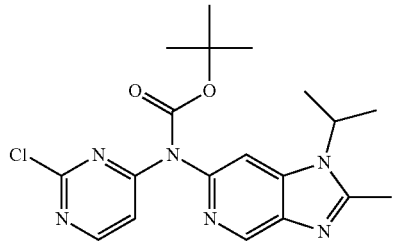 [SMILES: Cc1nc2cnc(N(C(=O)OC(C)(C)C)c3ccnc(Cl)n3)cc2n1C(C)C]

To a reaction vessel was added N-(2-chloropyrimidin-4-yl)-1-isopropyl-2-methyl-1H-imidazo[4,5-c]pyridin-6-amine (Example 46, Step 7) (500 mg, 1.65 mmol), triethylamine (500 mg, 4.94 mmol), 4-dimethylaminopyridine (20 mg, 0.160 mmol), di-tert-butyl dicarbonate (1.00 g, 4.58 mmol) and dichloromethane (10 mL). The reaction mixture was stirred for 16 h at room temperature. The resulting solution was diluted with 50 mL of water, extracted with 3×50 mL of ethyl acetate, washed with brine, dried over anhydrous sodium sulfate and concentrated in vacuo. The residue was purified by silica gel chromatography with ethyl acetate/petroleum ether (4:1) to afford the title compound as a light yellow solid (0.6 g, 90%). LCMS (ESI): $R_T$ (min)=1.310, [M+H]$^+$=403, Method=M.

Step 4: tert-Butyl-2-(1H-pyrazol-4-yl)pyrimidin-4-yl(1-isopropyl-2-methyl-1H-imidazo[4,5-c]pyridin-6-yl)carbamate

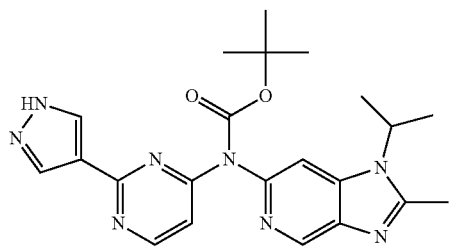 [SMILES: Cc1nc2cnc(N(C(=O)OC(C)(C)C)c3ccnc(-c4cn[nH]c4)n3)cc2n1C(C)C]

To a reaction vessel was added tert-butyl 2-chloropyrimidin-4-yl(1-isopropyl-2-methyl-1H-imidazo[4,5-c]pyridin-6-yl)carbamate (1.00 g, 2.48 mmol), 4-(tetramethyl-1,3,2-dioxaborolan-2-yl)-1H-pyrazole (570 mg, 2.94 mmol), tetrakis(triphenylphosphine)palladium(0) (300 mg, 0.26 mmol), sodium carbonate (790 mg, 7.45 mmol), 1,4-dioxane (20 mL) and water (2 mL). The reaction mixture was irradiated with microwave radiation for 90 min at 100° C. The reaction was filtered and concentrated in vacuo. The residue was purified by silica gel chromatography (solvent: 10% methanol in dichloromethane) to afford the title compound as a white solid (700 mg, 65%). LCMS (ESI): $R_T$ (min)=1.196, [M+H]$^+$=435, Method=M.

311

Step 5: tert-Butyl 1-isopropyl-2-methyl-1H-imidazo[4,5-c]pyridin-6-yl(2-(1-(oxetan-3-ylsulfonyl)-1H-pyrazol-4-yl)pyrimidin-4-yl)carbamate

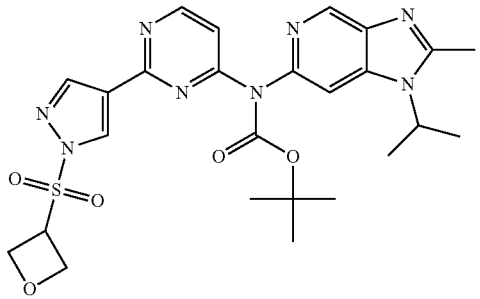 [SMILES: Cc1nc2cnc(N(C(=O)OC(C)(C)C)c3ccnc(-c4cnn(S(=O)(=O)C5COC5)c4)n3)cc2n1C(C)C]

To a reaction vessel purged and maintained under an inert atmosphere of nitrogen, was placed oxetane-3-sulfonyl chloride (210 mg, 1.34 mmol), triethylamine (200 mg, 1.98 mmol) and dichloromethane (10 mL). This was followed by the addition of tert-butyl-2-(1H-pyrazol-4-yl)pyrimidin-4-yl (1-isopropyl-2-methyl-1H-imidazo[4,5-c]pyridin-6-yl)carbamate (300 mg, 0.69 mmol) dropwise with stirring. The reaction mixture was stirred for 3 h at 0° C. The reaction mixture was washed with brine, dried over anhydrous sodium sulfate and concentrated in vacuo to afford the title compound as a yellow solid (200 mg, 52%). LCMS (ESI): $R_T$ (min)=1.269, $[M+H]^+$=555, Method=R.

Step 6: 1-Isopropyl-2-methyl-N-(2-(1-(oxetan-3-ylsulfonyl)-1H-pyrazol-4-yl)pyrimidin-4-yl)-1H-imidazo[4,5-c]pyridin-6-amine

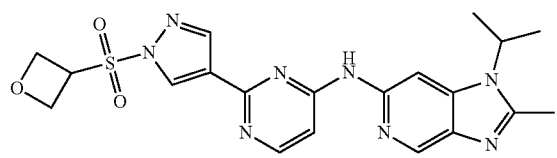 [SMILES: Cc1nc2cnc(Nc3ccnc(-c4cnn(S(=O)(=O)C5COC5)c4)n3)cc2n1C(C)C]

To a reaction vessel was added tert-butyl 1-isopropyl-2-methyl-1H-imidazo[4,5-c]pyridin-6-yl(2-(1-(oxetan-3-ylsulfonyl)-1H-pyrazol-4-yl)pyrimidin-4-yl)carbamate (200 mg, 0.36 mmol), trifluoroacetic acid (1 mL) and dichloromethane (1 mL). The reaction mixture was stirred for 30 min at room temperature. Saturated aqueous sodium bicarbonate was added and the resulting solution was extracted with ethyl acetate. The organic layer was washed with brine, dried over anhydrous sodium sulfate and concentrated in vacuo. The crude product was purified via reverse-phase HPLC and lyophilized to afford the title compound as a white solid (60 mg, 37%). LCMS (ESI): $R_T$ (min)=2.052, $[M+H]^+$=455.05, Method=R; $^1$H NMR (400 MHz, DMSO-$d_6$): δ10.20 (s, 1H), 8.72 (s, 1H), 8.57 (s, 1H), 8.50 (s, 1H), 8.41-8.38 (m, 2H), 7.25 (s, 1H), 5.38-5.31 (m, 1H), 4.93-4.75 (m, 5H), 2.68 (s, 3H), 1.62 (s, 6H).

312

Example 261: (1-Isopropyl-6-(2-(4-methoxypiperidin-1-yl)pyrimidin-4-ylamino)-1H-imidazo[4,5-c]pyridin-2-yl)(4-methylpiperazin-1-yl)methanone

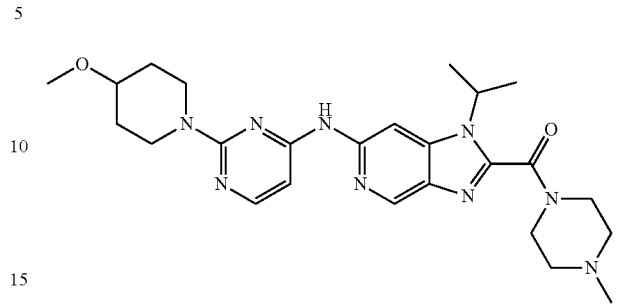

Step 1: 6-Bromo-1-isopropyl-1H-imidazo[4,5-c]pyridine-2-carboxylic acid

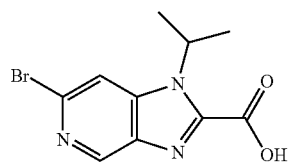 [SMILES: CC(C)n1c(C(=O)O)nc2cnc(Br)cc21]

To a reaction vessel was added 6-bromo-1-isopropyl-1H-imidazo[4,5-c]pyridin-2-yl)methanol (Example 251, Step 5) (1 g, 3.70 mmol), potassium permanganate (5.9 g, 37 mmol), acetone (20 mL) and water (7 mL). The reaction mixture was stirred for 2 h at room temperature, quenched by the addition of methanol and filtered. The resulting mixture was concentrated in vacuo to afford the title compound as a yellow solid (2 g, 76%). The crude product was used in next step without further purification. LCMS (ESI): $R_T$ (min)=1.201, $[M+H]^+$=284, Method=R.

Step 2: (6-Bromo-1-isopropyl-1H-imidazo[4,5-c]pyridin-2-yl)(4-methylpiperazin-1-yl)methanone

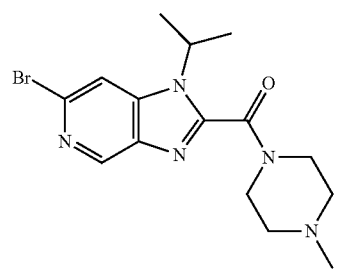 [SMILES: CC(C)n1c(C(=O)N2CCN(C)CC2)nc2cnc(Br)cc21]

To a reaction vessel was added 6-bromo-1-isopropyl-1H-imidazo[4,5-c]pyridine-2-carboxylic acid (500 mg, 1.76 mmol), 1-methylpiperazine (5.4 g, 53.91 mmol), benzotriazol-1-yl-oxytripyrrolidinophosphonium hexafluorophosphate (2.8 g, 3.00 equiv), N,N-diisopropylethylamine (464 mg, 3.59 mmol) and N,N-dimethylformamide (10 mL). The reaction mixture was stirred overnight at room temperature, diluted with water and extracted with ethyl acetate (3×). The combined organic layers were washed with brine, dried over anhydrous sodium sulfate and concentrated in vacuo to afford the title compound as yellow oil (400 mg, 62%). LCMS (ESI): R$_T$ (min)=1.083, [M+H]$^+$=366, Method=M.

Step 3: (1-Isopropyl-6-(2-(4-methoxypiperidin-1-yl)pyrimidin-4-ylamino)-1H-imidazo[4,5-c]pyridin-2-yl)(4-methylpiperazin-1-yl)methanone

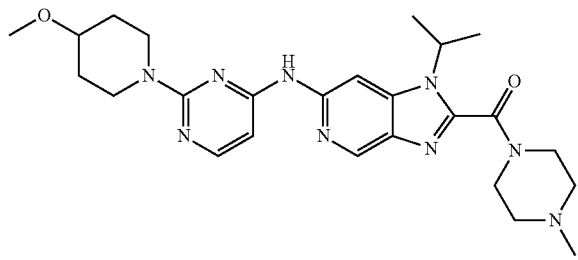

To a reaction vessel was added (6-bromo-1-isopropyl-1H-imidazo[4,5-c]pyridin-2-yl)(4-methylpiperazin-1-yl)methanone (200 mg, 0.55 mmol, 1.00 equiv), tris(dibenzylideneacetone)dipalladium chloroform complex (25.9 mg, 0.05 equiv), 4,5-bis(diphenylphosphino)-9,9-dimethylxanthene (28.9 mg, 0.05 equiv), 2-(4-methoxy-1-piperidyl)pyrimidin-4-amine (Example 3, step 2) (137 mg, 0.66 mmol, 1.20 equiv), cesium carbonate (815 mg, 5.00 equiv) and 1,4-dioxane (5 mL). The reaction mixture was heated under microwave irradiation for 1 h at 140° C. The reaction was filtered and concentrated in vacuo. The crude product was purified via reverse-phase HPLC and lyophilized to afford the title compound as a white solid (13.1 mg, 5%). LCMS (ESI): R$_T$ (min)=1.100, [M+H]$^+$=494, Method=K; $^1$H NMR (300 MHz, DMSO-d$_6$): δ 9.89 (s, 1H), 8.73 (s, 1H), 8.50 (s, 1H), 8.00-7.98 (d, J=5.7 Hz, 1H), 6.42-6.34 (d, J=5.4 Hz, 1H), 4.76-4.67 (m, 1H), 4.26-4.23 (m, 2H), 3.72 (m, 2H), 3.52-3.44 (m, 3H), 3.44-3.36 (m, 2H), 3.29 (s, 3H), 2.43-2.42 (m, 2H), 2.33-2.28 (m, 2H), 2.22 (s, 3H), 1.93-1.89 (m, 2H), 1.59-1.57 (d, J=6.9 Hz, 6H), 1.50-1.35 (m, 2H).

Example 262: 2-Chloro-6-(2-(1-(cyclopropylsulfonyl)-1H-pyrazol-4-yl)pyrimidin-4-ylamino)-1-isopropyl-N-(tetrahydro-2H-pyran-4-yl)-1H-pyrrolo[3,2-c]pyridine-3-carboxamide

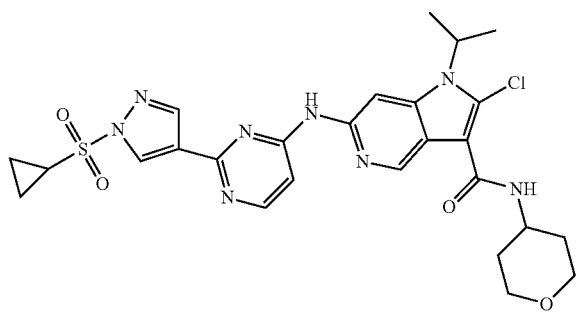 [SMILES: CC(C)n1c(Cl)c(C(=O)NC2CCOCC2)c2cnc(Nc3ccnc(-c4cnn(S(=O)(=O)C5CC5)c4)n3)cc21]

Step 1: 6-Bromo-2-chloro-1-isopropyl-N-(tetrahydro-2H-pyran-4-yl)-1H-pyrrolo[3,2-c]pyridine-3-carboxamide

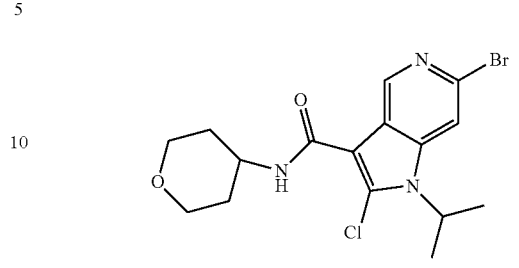

To a reaction vessel purged and maintained under an inert atmosphere of nitrogen containing a solution of 6-bromo-1-isopropyl-N-(tetrahydro-2H-pyran-4-yl)-1H-pyrrolo[3,2-c]pyridine-3-carboxamide (prepared using a method analogous to that described for Example 51, steps 1-4) (100 mg, 0.27 mmol) in tetrahydrofuran (3 mL) at −78° C. was added lithium diisopropylamide (0.82 mL, 3.00 equiv) dropwise with stirring. The resulting solution was stirred for 30 min at −78° C. To the reaction mixture was added perchloroethane (323 mg, 4.00 equiv) in 3 batches over 10 min at −78° C. The resulting solution was stirred at −78° C. for 10 min followed by 1 h at room temperature. The reaction was then quenched with water and extracted with ethyl acetate (3×). The combined organic extracts were washed with brine, dried over sodium sulfate and concentrated in vacuo to afford the title compound as a white solid (80 mg, 73%). LCMS (ESI): R$_T$ (min)=0.965, [M+H]$^+$=400 & 402, Method=L.

Step 2: 2-Chloro-6-(2-(1-(cyclopropylsulfonyl)-1H-pyrazol-4-yl)pyrimidin-4-ylamino)-1-isopropyl-N-(tetrahydro-2H-pyran-4-yl)-1H-pyrrolo[3,2-c]pyridine-3-carboxamide

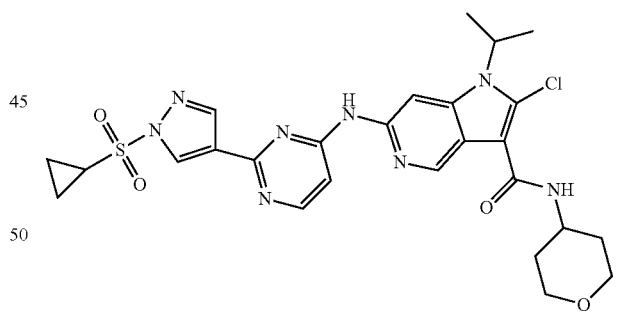

To a reaction vessel was added 6-bromo-2-chloro-1-isopropyl-N-(tetrahydro-2H-pyran-4-yl)-1H-pyrrolo[3,2-c]pyridine-3-carboxamide (60 mg, 0.15 mmol), 2-(1-cyclopropanesulfonyl-1H-pyrazol-4-yl)pyrimidin-4-ylamine (Example A62) (52.0 mg, 0.20 mmol), tris(dibenzylideneacetone)dipalladium (17.9 mg, 0.02 mmol), 4,5-bis(diphenylphosphino)-9,9-dimethylxanthene (22.5 mg, 0.04 mmol), cesium carbonate (127 mg, 0.39 mmol) and 1,4-dioxane (3 mL). The reaction mixture was stirred for 3 h at 100° C. The reaction was cooled to room temperature, filtered, and concentrated in vacuo. The crude product was purified via reverse-phase HPLC and lyophilized to afford the title compound as a white solid (20.4 mg, 23%). LCMS (ESI): R$_T$ (min)=1.579, [M+H]⁺=585.20, Method=M; ¹H NMR (400 MHz, DMSO-d₆): δ10.28 (s, 1H), 8.77 (s, 1H), 8.68 (s, 1H), 8.48 (s, 2H), 8.41 (d, J=5.6 Hz, 1H), 7.95 (d, J=8 Hz, 1H), 7.25 (s, 1H), 5.02-5.06 (m, 1H), 4.06-4.02 (m, 1H), 3.90-3.87 (m, 2H), 3.45-3.32 (m, 2H), 3.29-3.25 (m, 1H), 1.84-1.82 (m, 2H), 1.68-1.57 (m, 8H), 1.37-1.34 (m, 4H).

Example 263: N-(2-(1-(Cyclopropylsulfonyl)-1H-pyrazol-4-yl)pyrimidin-4-yl)-2-(difluoromethyl)-1-isopropyl-1H-imidazo[4,5-c]pyridin-6-amine

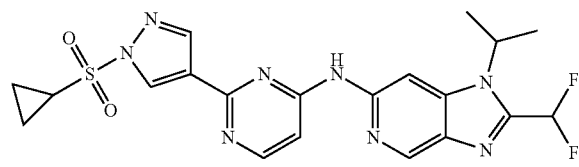 [SMILES: CC(C)n1c(C(F)F)nc2cnc(Nc3ccnc(-c4cnn(S(=O)(=O)C5CC5)c4)n3)cc21]

Step 1: 6-Bromo-2-(difluoromethyl)-1-isopropyl-1H-imidazo[4,5-c]pyridine

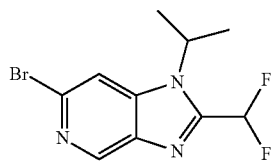 [SMILES: CC(C)n1c(C(F)F)nc2cnc(Br)cc21]

To a reaction vessel was added triphenylphosphine (17.0 g, 64.8 mmol), 2,2-difluoroacetic acid (2.5 g, 26.0 mmol), triethylamine (7.30 g, 72.1 mmol), 6-bromo-N4-isopropylpyridine-3,4-diamine (Example 46, Step 4) (5.00 g, 21.7 mmol) and carbon tetrachloride (50 mL). The reaction mixture was stirred overnight at 80° C. under an inert atmosphere of nitrogen. The reaction mixture was diluted with water, extracted with ethyl acetate, and the organic layer was washed with brine, dried over anhydrous sodium sulfate and concentrated in vacuo. The residue was purified by chromatography with 25% ethyl acetate in petroleum ether to afford the title compound as a yellow solid (4 g, 63%).

Step 2: 2-Chloro-N-[2-(difluoromethyl)-1-(propan-2-yl)-1H-imidazo[4,5-c]pyridin-6-yl]pyrimidin-4-amine

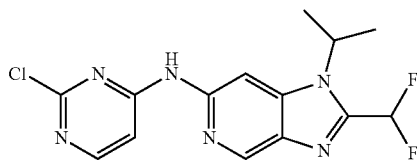 [SMILES: CC(C)n1c(C(F)F)nc2cnc(Nc3ccnc(Cl)n3)cc21]

To a reaction vessel was added 6-bromo-2-(difluoromethyl)-1-isopropyl-1H-imidazo[4,5-c]pyridine (1.0 g, 3.45 mmol), tris(dibenzylideneacetone)dipalladium chloroform complex (160 mg, 0.05 equiv), 4,5-bis(diphenylphosphino)-9,9-dimethylxanthene (0.1 g, 0.05 equiv), 2-chloropyrimidin-4-amine (400 mg, 3.09 mmol), cesium carbonate (2.30 g, 7.06 mmol) and 1,4-dioxane (20 mL). The reaction mixture was stirred for 5 h at 100° C. The reaction mixture was diluted with water and extracted with ethyl acetate. The organic layer was washed with brine, dried over sodium sulfate and concentrated in vacuo to afford the title compound as a yellow solid (0.5 g, 43%). The crude product was used in next step without further purification. LCMS (ESI): R_T (min)=2.083, [M+H]⁺=339, Method=R.

Step 3: 2-[1-(Cyclopropanesulfonyl)-1H-pyrazol-4-yl]-N-[2-(difluoromethyl)-1-(propan-2-yl)-1H-imidazo[4,5-c]pyridin-6-yl]pyrimidin-4-amine

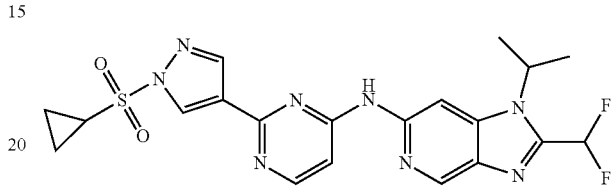

To a reaction vessel was added 2-chloro-N-[2-(difluoromethyl)-1-(propan-2-yl)-1H-imidazo[4,5-c]pyridin-6-yl]pyrimidin-4-amine (300 mg, 0.89 mmol), tetrakis(triphenylphosphine)palladium(0) (50 mg, 0.04 mmol), sodium carbonate (0.19 g, 1.79 mmol), 1-(cyclopropanesulfonyl)-4-(tetramethyl-1,3,2-dioxaborolan-2-yl)-1H-pyrazole (Example 51, Step 6) (320 mg, 1.07 mmol), dioxane (5 mL) and water (0.5 mL). The reaction mixture was stirred overnight at 90° C. under an inert atmosphere of nitrogen. The resulting solution was diluted with water, extracted with ethyl acetate, and the organic layer was washed with brine, dried over anhydrous sodium sulfate and concentrated in vacuo. The residue was purified by silica gel chromatography (solvent: 30% ethyl acetate in petroleum ether) to afford the title compound as an off-white solid (200 mg, 48%). LCMS (ESI): R_T(min)=2.488, [M+H]⁺=475.20, Method=R; ¹HN MR (400 MHz, DMSO-d₆): δ10.40 (s, 1H), 8.87 (s, 1H), 8.69 (s, 1H), 8.61 (s, 1H), 8.49 (s, 1H), 8.44 (d, J=4.2 Hz, 1H), 7.47 (m, 1H), 7.25 (d, J=4 Hz, 1H), 5.00 (m, 1H), 3.26 (m, 1H), 1.70 (s, 6H), 1.33 (m, 2H), 1.27 (m, 2H).

Example 264: 6-(2-(1-(Cyclopropylsulfonyl)-1H-pyrazol-4-yl)pyrimidin-4-ylamino)-1-isopropyl-1H-imidazo[4,5-c]pyridine-2-carbaldehyde

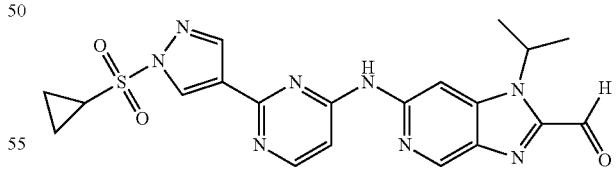

To a reaction vessel was added N-(2-(1-(cyclopropylsulfonyl)-1H-pyrazol-4-yl)pyrimidin-4-yl)-1-isopropyl-2-methyl-1H-imidazo[4,5-c]pyridin-6-amine (Example 52) (200 mg, 0.44 mmol), 2-iodoxybenzoic acid (184 mg, 1.85 mmol,) and DMSO (3 mL). The reaction mixture was stirred for 6 h at room temperature. The resulting solution was diluted with water and filtered. The crude precipitate was purified by silica gel chromatography (solvent: 20% ethyl acetate in petroleum ether) to afford the title compound as a yellow solid (13.4 mg, 7%). LCMS (ESI): R_T (min)=2.158,

[M+H]$^+$=453.05, Method=R; $^1$H NMR (300 MHz, CDCl$_3$): δ10.07 (s, 1H), 8.99 (s, 1H), 8.71 (s, 1H), 8.63 (s, 1H), 8.49 (s, 1H), 8.45 (d, J=5.7 Hz, 1H), 7.93 (br, 1H), 6.84 (d, J=5.7 Hz, 1H), 5.94-5.85 (m, 1H), 2.89-2.80 (m, 1H), 1.78 (d, J=6.9 Hz, 6H), 1.56-1.51 (m, 2H), 1.29-1.22 (m, 2H).

Example 265: (6-(2-(1-(Cyclopropylsulfonyl)-1H-pyrazol-4-yl)pyrimidin-4-ylamino)-1-(pentan-2-yl)-1H-imidazo[4,5-c]pyridin-2-yl)methanol

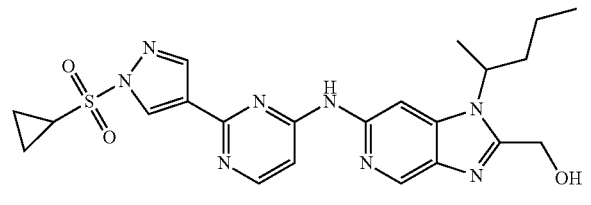 [SMILES: CCCC(C)n1c(CO)nc2cnc(Nc3ccnc(-c4cnn(S(=O)(=O)C5CC5)c4)n3)cc21]

Step 1: 2-Bromo-5-nitro-N-(pentan-2-yl)pyridin-4-amine

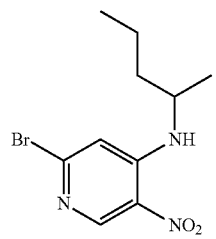 [SMILES: CCCC(C)Nc1cc(Br)ncc1[N+](=O)[O-]]

To a reaction vessel was added 2,4-dibromo-5-nitropyridine (5.89 g, 20.9 mmol), pentan-2-amine (2.00 g, 22.9 mmol), triethylamine (5.8 mL, 41.73 mmol) and tetrahydrofuran (30 mL). The reaction mixture was stirred for 8 h at room temperature. The reaction was quenched by the addition of water and extracted with ethyl acetate (3×). The combined organic layers were washed with brine, dried over anhydrous sodium sulfate and concentrated in vacuo to afford the title compound as a yellow solid (5.66 g, 94%). The crude product was used in the next step without further purification.

Step 2: 6-Bromo-4-N-(pentan-2-yl)pyridine-3,4-diamine

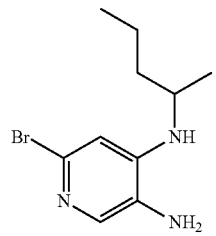

To a reaction vessel was added 2-bromo-5-nitro-N-(pentan-2-yl)pyridin-4-amine (3 g, 10.4 mmol), platinum(IV) oxide (400 mg, 1.76 mmol) and tetrahydrofuran (20 mL). The reaction mixture was stirred for 2 h under a hydrogen atmosphere (1 atm) at room temperature. The reaction was filtered and concentrated in vacuo to afford the title compound as a dark red oil (2.7 g, 99%). The crude product was used in the next step without further purification. LCMS (ESI): R$_T$ (min)=1.133, [M+H]$^+$=258, Method=N.

Step 3: 2-(6-Bromo-4-(pentan-2-ylamino)pyridin-3-ylamino)-2-oxoethyl acetate

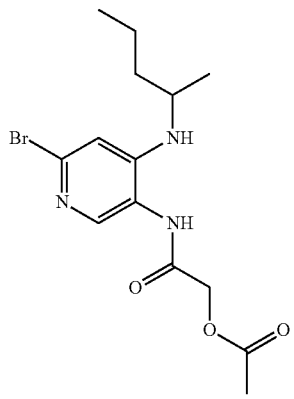 [SMILES: CCCC(C)Nc1cc(Br)ncc1NC(=O)COC(C)=O]

To a reaction vessel was added 6-bromo-4-N-(pentan-2-yl)pyridine-3,4-diamine (2.71 g, 10.5 mmol), triethylamine (3 mL, 21.58 mmol), 2-chloro-2-oxoethyl acetate (1.43 g, 10.5 mmol) and dichloromethane (20 mL). The reaction was stirred for 1 h at 0° C., quenched by the addition of water and extracted with dichloromethane (2×). The combined organic layers were washed with brine, dried over anhydrous sodium sulfate and concentrated in vacuo. The residue was purified by silica gel chromatography (solvent: 50% ethyl acetate in petroleum ether) to afford the title compound as a white solid (1 g, 27%). LCMS (ESI): R$_T$ (min)=1.195, [M+H]$^+$=358, Method=N.

Step 4: (6-Bromo-1-(pentan-2-yl)-1H-imidazo[4,5-c]pyridin-2-yl)methyl acetate

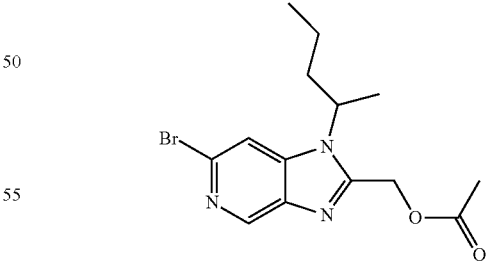

2-(6-Bromo-4-(pentan-2-ylamino)pyridin-3-ylamino)-2-oxoethyl acetate (1 g, 2.79 mmol) was dissolved in acetic acid (10 mL) and heated under microwave irradiation for 4 h at 120° C. The reaction was quenched by the addition of water and extracted with dichloromethane (3×). The combined organic layers were washed with brine, dried over anhydrous sodium sulphate and concentrated in vacuo to afford the title compound as a white solid (610 mg, 64%).

The crude product was used in the next step without further purification. LCMS (ESI): $R_T$ (min)=1.411, [M+H]$^+$=340, Method=M.

Step 5: (6-Bromo-1-(pentan-2-yl)-1H-imidazo[4,5-c]pyridin-2-yl)methanol

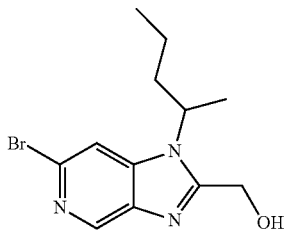 [SMILES: CCCC(C)n1c(CO)nc2cnc(Br)cc21]

To a reaction vessel was added (6-bromo-1-(pentan-2-yl)-1H-imidazo[4,5-c]pyridin-2-yl)methyl acetate (610 mg, 1.79 mmol), sodium hydroxide (144 mg, 4.49 mmol), water (1 mL) and methanol (10 mL). The reaction mixture was stirred for 30 min at room temperature. The reaction was quenched by the addition of water and extracted with dichloromethane (3×). The combined organic extracts were washed with brine, dried over anhydrous sodium sulfate and concentrated in vacuo to afford the title compound as a white solid (500 mg, 93%). The crude product was used in the next step without further purification. LCMS (ESI): $R_T$ (min)=0.914, [M+H]$^+$=298, Method=M.

Step 6: (6-(2-(1-(Cyclopropylsulfonyl)-1H-pyrazol-4-yl)pyrimidin-4-ylamino)-1-(pentan-2-yl)-1H-imidazo[4,5-c]pyridin-2-yl)methanol

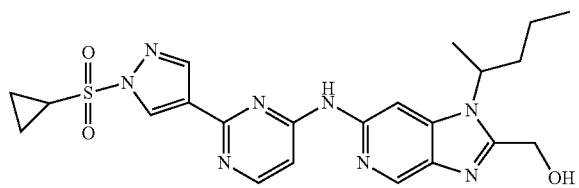 [SMILES: CCCC(C)n1c(CO)nc2cnc(Nc3ccnc(-c4cnn(S(=O)(=O)C5CC5)c4)n3)cc21]

To a reaction vessel was added (6-bromo-1-(pentan-2-yl)-1H-imidazo[4,5-c]pyridin-2-yl)methanol (440 mg, 1.48 mmol), 2-(1-cyclopropanesulfonyl-1H-pyrazol-4-yl)pyrimidin-4-ylamine (Example A62) (392 mg, 1.48 mmol), tris(dibenzylideneacetone)dipalladium(0) (136 mg, 0.15 mmol), 4,5-bis(diphenylphosphino)-9,9-dimethylxanthene (171 mg, 0.30 mmol), cesium carbonate (966 mg, 2.96 mmol) and dioxane (10 mL). The reaction mixture was heated at 100° C. for 90 min under an inert atmosphere of nitrogen. The reaction was then quenched by the addition of water and extracted with dichloromethane (3×). The combined organic layers were washed with brine, dried over anhydrous sodium sulfate and concentrated in vacuo. The residue was purified by silica gel chromatography (solvent: 10% methanol in dichloromethane) to afford the title compound as a white solid (160 mg, 22%). LCMS (ESI): $R_T$ (min)=2.406, [M+H]$^+$=483, Method=N; $^1$H NMR (300 Hz, CDCl$_3$): δ 8.80 (s, 1H), 8.68 (s, 1H), 8.48 (s, 1H), 8.40-8.38 (d, J=6.0 Hz, 2H), 7.98 (s, 1H), 6.89-6.87 (d, J=5.7 Hz, 1H), 4.92 (s, 2H), 4.62-4.59 (m, 1H), 3.88 (s, 1H), 2.86-2.81 (m, 1H), 2.22-2.17 (m, 1H), 2.04-1.96 (m, 1H), 1.76-1.73 (d, J=6.9 Hz, 3H), 1.56-1.50 (m, 2H), 1.37-1.32 (m, 1H), 1.26-1.11 (m, 3H), 0.89 (m, 3H)

Example 266: (trans)-N-{1-[4-(1-Isopropyl-2-methyl-1H-imidazo[4,5-c]pyridin-6-ylamino)pyrimidin-2-yl]-4-methoxypiperidin-3-yl}methanesulfonamide formate salt

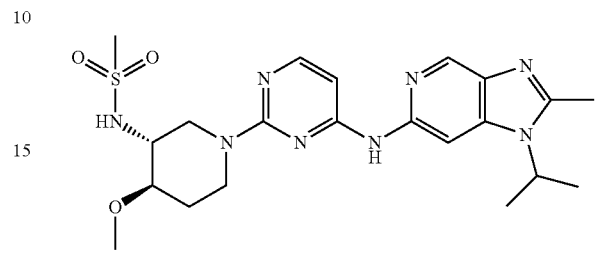

Step 1: (trans)-3-Azido-4-methoxypiperidine-1-carboxylic acid tert-butyl ester

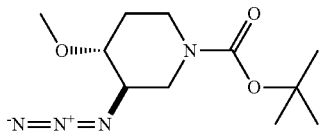

Methyl iodide (328 μL, 5.27 mmol) was added to a solution of (trans)-3-azido-4-hydroxypiperidine-1-carboxylic acid tert-butyl ester (Bioorganic & Medicinal Chemistry Letters 2008, 18, 5063-5065) (1.16 g, 4.79 mmol) in tetrahydrofuran (16 mL). After cooling to 0° C., sodium hydride (60% in mineral oil) (230 mg, 5.75 mmol) was slowly added and the reaction mixture was stirred at 0° C. for 15 min, then warmed to room temperature and stirred at room temperature for 18 h. The crude mixture was quenched by addition of methanol and diluted with dichloromethane. The organic phase was washed with water, dried over magnesium sulfate and concentrated in vacuo. The resulting yellow oil was purified by chromatography on silica (solvent gradient: 0-30% EtOAc in cyclohexane) to afford the title compound (0.92 g, 75%) as a colorless oil. LCMS (ESI): [M+H]$^+$ 257.2.

Step 2: (trans)-3-Amino-4-methoxypiperidine-1-carboxylic acid tert-butyl ester

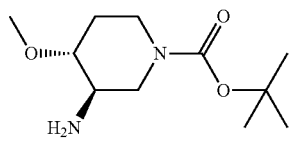

A mixture of (trans)-3-azido-4-methoxypiperidine-1-carboxylic acid tert-butyl ester (300 mg, 1.17 mmol) in industrial methylated spirits (10 mL) was stirred under a hydrogen atmosphere for 4 h in the presence of 10% palladium on carbon (20 mg, catalytic). The reaction mixture was filtered through celite, rinsing with additional industrial methylated spirits, and the filtrate was concentrated in vacuo to afford the title compound (310 mg, quantitative). LCMS (ESI): [M+H]⁺ 231.1.

Step 3: (trans)-3-Methanesulfonylamino-4-methoxypiperidine-1-carboxylic acid tert-butyl ester

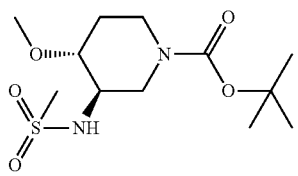 [SMILES: CO[C@@H]1CCN(C(=O)OC(C)(C)C)C[C@H]1NS(C)(=O)=O]

Triethylamine (281 µl, 2.02 mmol) was added to a solution of (trans)-3-amino-4-methoxypiperidine-1-carboxylic acid tert-butyl ester (310 mg, 1.35 mmol) in dichloromethane (5 mL) at 0° C. under a nitrogen atmosphere followed by methanesulfonyl chloride (136 µL, 1.75 mmol). The reaction mixture was slowly warmed to room temperature and stirred for 18 h. The crude mixture was diluted with a saturated aqueous solution of sodium bicarbonate and further extracted with dichloromethane. The organic layer was dried over magnesium sulfate and concentrated in vacuo to afford the title compound as a yellow oil (460 mg, quantitative). LCMS (ESI): [M+H]⁺ 309.1.

Step 4: N-((trans)-4-Methoxypiperidin-3-yl)methanesulfonamide

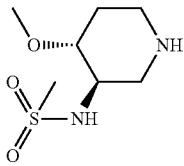

A solution of (trans)-3-methanesulfonylamino-4-methoxypiperidine-1-carboxylic acid tert-butyl ester (460 mg, 1.49 mmol) in dichloromethane (15 mL) was treated with trifluoroacetic acid (3.75 mL) and stirred at room temperature under a nitrogen atmosphere for 18 h. The mixture was concentrated under reduced pressure and the resultant residue was purified by SCX eluting first with methanol and then with 2M ammonia in methanol to afford the title compound as a brown oil (230 mg, 74%). LCMS (ESI): [M+H]⁺ 209.0.

Step 5: (trans)-N-{1-[4-(1-Isopropyl-2-methyl-1H-imidazo[4,5-c]pyridin-6-ylamino)pyrimidin-2-yl]-4-methoxypiperidin-3-yl}methanesulfonamide formate salt

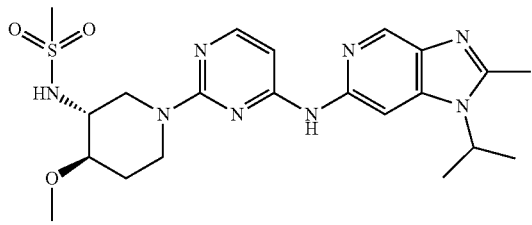 [SMILES: CO[C@@H]1CCN(c2nccc(Nc3cc4c(cn3)nc(C)n4C(C)C)n2)C[C@H]1NS(C)(=O)=O]

A mixture of (2-chloropyrimidin-4-yl)-(1-isopropyl-2-methyl-1H-imidazo[4,5-c]pyridin-6-yl)amine (Example 46, Step 7) (120 mg, 0.305 mmol), (trans)-N-(4-methoxypiperidin-3-yl)methanesulfonamide (70 mg, 0.336 mmol) and triethylamine (0.6 mL) in isopropyl alcohol (120 mL) was heated in a sealed reaction vessel at 110° C. for 18 h under an argon atmosphere. After cooling to room temperature, the volatiles were concentrated in vacuo and the resultant residue was purified by reverse phase HPLC to afford the title compound as a formate salt (87 mg, 60%). LCMS (ESI): R$_T$ 2.14 min [M+H]⁺ 475.1, Method F; ¹H NMR (400 MHz, DMSO-d₆): 9.68 (1H, s), 8.49 (1H, d, J=0.9 Hz), 8.24 (1H, s), 8.14 (1H, s), 7.96 (1H, d, J=5.7 Hz), 7.35 (1H, d, J=7.9 Hz), 6.55-6.47 (1H, m), 4.76-4.64 (1H, m), 4.56-4.39 (2H, m), 3.35 (3H, s), 3.32-2.94 (4H, m), 2.91 (3H, s), 2.55 (3H, s), 2.21-2.11 (1H, m), 1.60-1.52 (6H, m), 1.39-1.28 (1H, m).

Example 267: (trans)-[2-(3-Amino-4-methoxypiperidin-1-yl)pyrimidin-4-yl]-(1-isopropyl-2-methyl-1H-imidazo[4,5-c]pyridin-6-yl)amine

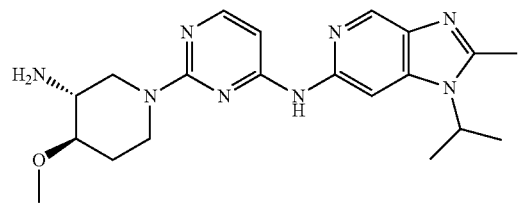 [SMILES: CO[C@@H]1CCN(c2nccc(Nc3cc4c(cn3)nc(C)n4C(C)C)n2)C[C@H]1N]

Step 1: (trans)-3-Azido-4-methoxypiperidine

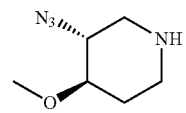

A solution of (trans)-3-azido-4-methoxypiperidine-1-carboxylic acid tert-butyl ester (263 mg, 0.78 mmol) in dichloromethane (1.25 mL) was treated with trifluoroacetic acid (2 mL) at 0° C. and slowly warmed to room temperature. After 3 h, the reaction mixture was concentrated in vacuo. The resulting residue was purified by SCX cartridge eluting first with methanol and then with 2M ammonia in methanol to afford the title compound as a colourless oil (112 mg, 92%). ¹H NMR (400 MHz, DMSO-d₆): δ 3.31 (3H, s), 3.32-3.28 (1H, m), 3.20-3.06 (1H, m), 2.97 (1H, ddd, J=12.4, 4.8, 1.6 Hz), 2.82-2.89 (1H, m), 2.34 (1H, td, J=12.4, 2.7 Hz), 2.20 (1H, dd, J=12.4, 10.2 Hz), 2.02-2.04 (1H, m), 1.18 (1H, tdd, J=12.2, 10.4, 4.3 Hz).

Step 2: (trans)-[2-(3-Azido-4-methoxypiperidin-1-yl)pyrimidin-4-yl]-(1-isopropyl-2-methyl-1H-imidazo[4,5-c]pyridin-6-yl)amine

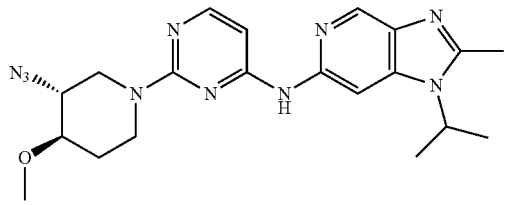 [SMILES: CO[C@@H]1CCN(c2nccc(Nc3cc4c(cn3)nc(C)n4C(C)C)n2)C[C@H]1N=[N+]=[N-]]

A mixture of (trans)-3-azido-4-methoxypiperidine (54 mg, 0.347 mmol), (2-chloropyrimidin-4-yl)-(1-isopropyl-2-methyl-1H-imidazo[4,5-c]pyridin-6-yl)amine (Example 46, Step 7) (100 mg, 0.33 mmol), triethylamine (92 µL) in isopropyl alcohol (0.6 mL) was heated at 150° C. under microwave irradiation for 30 min under argon atmosphere. The reaction mixture was concentrated in vacuo and the resulting residue was purified by silica gel chromatography (solvent gradient 0-5% methanol in dichloromethane) to afford the title compound as a beige solid (113 mg, 81%). LCMS (ESI): [M+H]$^+$ 423.1.

Step 3: (trans)-[2-(3-Amino-4-methoxypiperidin-1-yl)pyrimidin-4-yl]-(1-isopropyl-2-methyl-1H-imidazo[4,5-c]pyridin-6-yl)amine

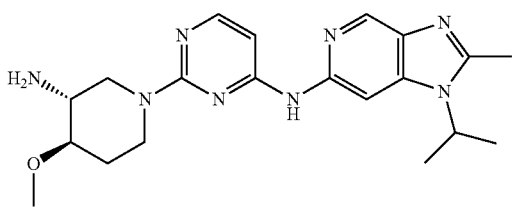 [SMILES: CO[C@@H]1CCN(c2nccc(Nc3cc4c(cn3)nc(C)n4C(C)C)n2)C[C@H]1N]

A solution of [2-((trans)-3-azido-4-methoxypiperidin-1-yl)pyrimidin-4-yl]-(1-isopropyl-2-methyl-1H-imidazo[4,5-c]pyridin-6-yl)amine (110 mg, 0.26 mmol) in industrial methylated spirits (4 mL) was treated with 10% palladium on carbon (20 mg) under a hydrogen atmosphere for 18 h at room temperature. The reaction mixture was purged with nitrogen and filtered through a pad of celite, rinsing with additional industrial methylated spirits. The resultant residue was purified by silica gel chromatography (solvent gradient 0-8% 2M ammonia in methanol in dichloromethane) to afford the title compound as white foam (36 mg, 35%). LCMS (ESI): R$_T$ 1.66 min, [M+H]$^+$ 397.1, Method F; $^1$H NMR (400 MHz, DMSO-d$_6$): δ 9.68 (1H, s), 8.51 (1H, d, J=0.9 Hz), 8.33 (1H, s), 7.96 (1H, d, J=5.7 Hz), 6.45 (1H, d, J=5.7 Hz), 4.80-4.68 (1H, m), 4.57-4.46 (2H, m), 3.35 (3H, s), 3.19-3.01 (2H, m), 2.89-2.79 (1H, m), 2.64-2.54 (4H, m), 2.14-2.05 (1H, m), 1.69-1.52 (8H, m), 1.34-1.22 (1H, m).

Example 268: [1-(1-Cyclopropylethyl)-2-methyl-1H-imidazo[4,5-c]pyridin-6-yl]-[2-(4-methoxypiperidin-1-yl)pyrimidin-4-yl]amine

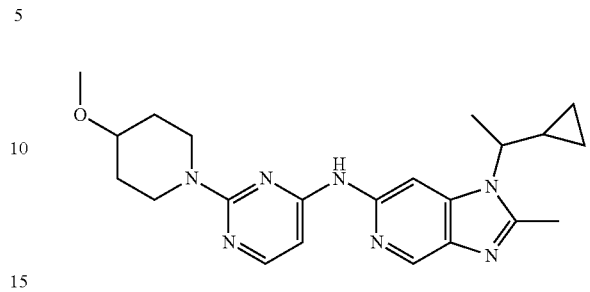

Step 1: (2-Chloro-5-nitropyridin-4-yl)-(1-cyclopropylethyl)amine

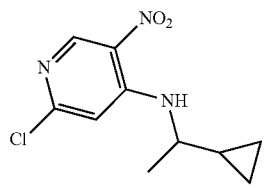 [SMILES: CC(Nc1cc(Cl)ncc1[N+](=O)[O-])C1CC1]

Diisopropylethylamine (1.14 mL, 6.5 mmol) was added to a mixture of 2,4-dichloro-5-nitropyridine (0.5 g, 2.6 mmol) and 1-cyclopropylethylamine hydrochloride (632 mg, 5.2 mmol) in tetrahydrofuran (8 mL). The reaction mixture was stirred at room temperature for 4 h. Additional diisopropylethylamine (0.5 mL) was added and stirring was continued for 18 h. The reaction mixture was concentrated in vacuo and the resultant residue was partitioned between water and dichloromethane. The organic layer was dried over magnesium sulfate and concentrated in vacuo. The resultant residue was purified by silica gel chromatography (solvent gradient: 0-30% EtOAc in cyclohexane) to afford the title compound as a yellow solid (392 mg, 62%). LCMS (ESI): [M+H]$^+$ 242.0.

Step 2: 6-Chloro-N$^4$-(1-cyclopropylethyl)pyridine-3,4-diamine

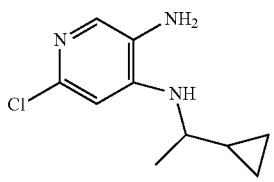

6-Chloro-N$^4$-(1-cyclopropylethyl)pyridine-3,4-diamine (354 mg, 61%) was prepared from (2-chloro-5-nitropyridin-4-yl)-(1-cyclopropylethyl)amine (392 mg, 1.63 mmol) according to a procedure analogous to that described in Example 12, Step 2. LCMS (ESI): [M+H]$^+$ 212.0

Step 3: 6-Chloro-1-(1-cyclopropylethyl)-2-methyl-1H-imidazo[4,5-c]pyridine

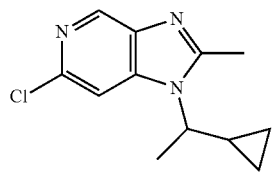 [SMILES: Cc1nc2cnc(Cl)cc2n1C(C)C1CC1]

6-Chloro-N⁴-(1-cyclopropylethyl)pyridine-3,4-diamine (0.354 mg, 1.67 mmol), triethylorthoformate (3 mL, excess) and formic acid (15 drops) were heated in a sealed reaction vessel at 220° C. for 5 h under microwave irradiation. The cooled mixture was purified by SCX cartridge eluting first with methanol and then with 2M ammonia in methanol followed by silica gel chromatography (solvent gradient: 10-75% EtOAc in cyclohexane) to yield the title compound as a brown solid (165 mg, 42%). LCMS (ESI): [M+H]⁺ 236.0

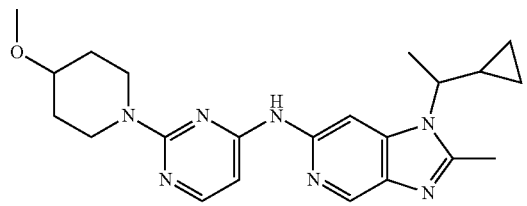 [SMILES: COC1CCN(c2nccc(Nc3cc4c(cn3)nc(C)n4C(C)C3CC3)n2)CC1]

Step 4: [1-(1-Cyclopropylethyl)-2-methyl-1H-imidazo[4,5-c]pyridin-6-yl]-[2-(4-methoxypiperidin-1-yl)pyrimidin-4-yl]amine 2-(4-methoxy-1-piperidyl)pyrimidin-4-amine (Example 3, step 2) (84 mg, 0.402 mmol), 2-dicyclohexylphosphino-2',4',6'-triisopropylbiphenyl (37 mg, 0.077 mmol), tris(dibenzylideneacetone)dipalladium(0) (18 mg, 19 µmol) and cesium carbonate (249 mg, 0.77 mmol) were suspended in dioxane (2 mL). The reaction mixture was purged with argon and heated at 100° C. for 3 h. The reaction mixture was cooled to room temperature and passed through a plug of silica, eluting the product with a solvent gradient of 0-10% methanol in dichloromethane. The resulting residue was purified further by preparatory HPLC to afford the title compound (22 mg, 14%). LCMS (ESI): $R_T$ 2.48 min, [M+H]⁺ 408.2, Method=F. ¹H NMR (400 MHz, DMSO-d₆) δ 9.71 (1H, s), 8.51 (1H, s), 8.45 (1H, br s), 7.95 (1H, d, J=5.6 Hz), 6.40 (1H, br d, J=5.6 Hz), 4.25-4.20 (2H, m), 3.79-3.71 (1H, m), 3.49-3.43 (1H, m), 3.41-3.35 (2H, m), 3.29 (3H, s), 2.51 (3H, s), 1.92-1.85 (2H, m), 1.63 (3H, d, J=7.0 Hz), 1.61-1.55 (1H, m), 1.47-1.38 (2H, m), 0.71-0.65 (1H, m), 0.56-0.50 (1H, m), 0.46-0.39 (1H, m), 0.28-0.22 (1H, m).

Example 269: (2-Cyclohexylpyrimidin-4-yl)-(1-isopropyl-1H-imidazo[4,5-c]pyridin-6-yl)amine

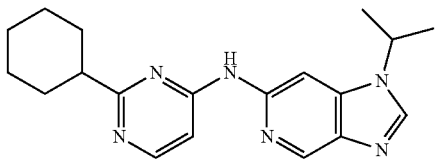 [SMILES: CC(C)n1cnc2cnc(Nc3ccnc(C4CCCCC4)n3)cc21]

Step 1: (2-Cyclohex-1-enylpyrimidin-4-yl) (1-isopropyl-1H-imidazo[4,5-c]pyridin-6-yl)amine A mixture of (2-chloropyrimidin-4-yl)-(1-isopropyl-1H-imidazo[4,5-c]pyridin-6-yl)amine (Example 12, Step 4) (100 mg, 0.35 mmol), 1-cyclohexen-1-ylboronic acid pinacol ester (112 µL, 0.52 mmol), tetrakis(triphenylphosphine)palladium(0) (20 mg, 5 mol %) and cesium carbonate (170 mg, 0.52 mmol) in dioxane (3 mL) and water (0.5 mL) was degassed and purged with nitrogen. The resulting mixture was heated at 120° C. under microwave irradiation for 45 min. The reaction mixture was diluted with methanol and loaded onto an SCX cartridge. The cartridge was washed with methanol and then eluted with 2M ammonia in methanol. The product fractions were concentrated in vacuo. The resulting residue was purified by chromatography (solvent gradient: 1-10% 2M ammonia in methanol in dichloromethane) to give an off-white solid (89 mg, 77%) LCMS (ESI): [M+H]⁺ 335.

Step 2: (2-Cyclohexylpyrimidin-4-yl) (1-isopropyl-1H-imidazo[4,5-c]pyridin-6-yl)amine

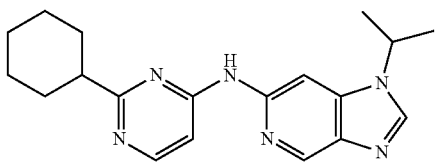 [SMILES: CC(C)n1cnc2cnc(Nc3ccnc(C4CCCCC4)n3)cc21]

A mixture of (2-cyclohex-1-enylpyrimidin-4-yl) (1-isopropyl-1H-imidazo[4,5-c]pyridin-6-yl)amine (85 mg, 0.27 mmol) and 10% palladium on carbon (85 mg) in industrial methylated spirit (20 mL) was stirred under a hydrogen atmosphere for 16 h, then filtered through a celite pad. The filtrate was concentrated in vacuo and the residue was purified by reverse phase HPLC to give a colorless solid (45 mg, 53%). LCMS (ESI): $R_T$ 2.70 min [M+H]⁺ 337, Method F; ¹H NMR (400 MHz, DMSO-d₆) δ 10.06 (s, 1H), 8.68 (s, 1H), 8.64 (s, 1H), 8.34 (s, 1H), 8.26 (d, J=5.7 Hz, 1H), 7.02 (d, J=5.7 Hz, 1H), 4.76-4.66 (m, 1H), 2.74-2.67 (m, 1H), 2.06-2.00 (m, 2H), 1.84-1.60 (m, 5H), 1.60 (d, J=6.5 Hz, 6H), 1.45-1.34 (m, 2H), 1.30-1.19 (m, 1H).

Example 270: {2-[4-(2-Aminoethyl)-4-methoxypiperidin-1-yl]pyrimidin-4-yl}(1-isopropyl-2-methyl-1H-imidazo[4,5-c]pyridin-6-yl)amine

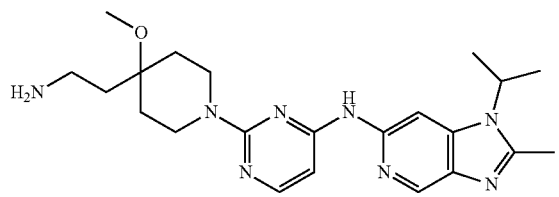 [SMILES: COC1(CCN)CCN(c2nccc(Nc3cc4c(cn3)nc(C)n4C(C)C)n2)CC1]

Step 1: 4-(2-Azidoethyl)-4-methoxypiperidine

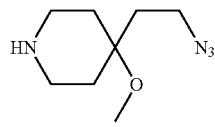

4-(2-Azidoethyl)-4-methoxypiperidine was synthesised from 4-(2-azidoethyl)-4-methoxypiperidine-1-carboxylic acid tert-butyl ester in a procedure analogous to that described for Example A38. This gave a colorless oil. $^1$H NMR (400 MHz, CDCl$_3$) δ 3.35 (t, J=7.4 Hz, 2H), 3.20-3.09 (m, 4H), 3.17 (s, 3H), 1.98-1.92 (m, 2H), 1.87-1.79 (m, 2H), 1.81 (t, J=7.4 Hz, 2H).

Step 2: {2-[4-(2-Azidoethyl)-4-methoxypiperidin-1-yl]pyrimidin-4-yl}(1-isopropyl-2-methyl-1H-imidazo[4,5-c]pyridin-6-yl)amine

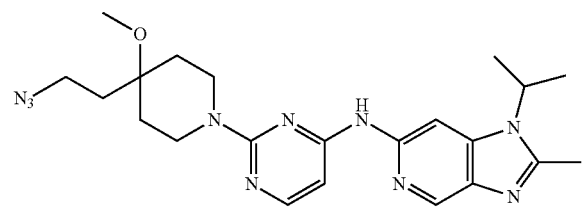 [SMILES: COC1(CCN=[N+]=[N-])CCN(c2nccc(Nc3cc4c(cn3)nc(C)n4C(C)C)n2)CC1]

{2-[4-(2-Azidoethyl)-4-methoxypiperidin-1-yl]pyrimidin-4-yl}(1-isopropyl-2-methyl-1H-imidazo[4,5-c]pyridin-6-yl)amine was synthesized from N-(2-chloropyrimidin-4-yl)-1-isopropyl-2-methyl-1H-imidazo[4,5-c]pyridin-6-amine and 4-(2-azidoethyl)-4-methoxypiperidine in a procedure analogous to that described for Example 46. This gave a colorless solid. LCMS (ESI): [M+H]$^+$ 451.

Step 3: {2-[4-(2-Aminoethyl)-4-methoxypiperidin-1-yl]pyrimidin-4-yl}(1-isopropyl-2-methyl-1H-imidazo[4,5-c]pyridin-6-yl)amine

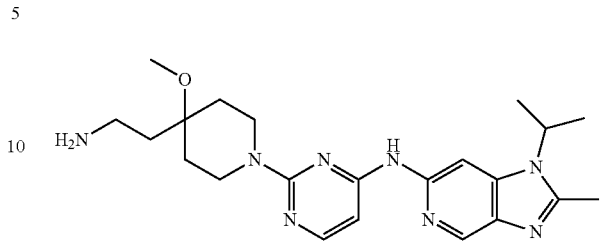

A mixture of {2-[4-(2-azidoethyl)-4-methoxypiperidin-1-yl]pyrimidin-4-yl}(1-isopropyl-2-methyl-1H-imidazo[4,5-c]pyridin-6-yl)amine (148 mg, 3.28 mmol) and 10% palladium on carbon (15 mg) in industrial methylated spirit (15 mL) was stirred under a hydrogen atmosphere for 16 h, then filtered through a celite pad. The filtrate was concentrated in vacuo and the residue was purified by chromatography on silica (solvent gradient: 5-10% 2M ammonia in methanol in dichloromethane) to give a colourless solid (94 mg, 68%). LCMS (ESI): R$_T$ 1.73 min [M+H]$^+$ 425, Method F; $^1$H NMR (400 MHz, DMSO-d$_6$): δ 9.67 (s, 1H), 8.50 (s, 1H), 8.39 (s, 1H), 7.94 (d, J=5.6 Hz, 1H), 6.39 (d, J=5.7 Hz, 1H), 4.76-4.66 (m, 1H), 4.34-4.29 (m, 2H), 3.29-3.20 (m, 2H), 3.14 (s, 3H), 2.59-2.55 (m, 2H), 2.56 (s, 3H), 1.77-1.72 (m, 2H), 1.60-1.54 (m, 2H), 1.55 (d, J=6.8 Hz, 6H), 1.48-1.41 (m, 2H).

Example 271: [2-(4-Aminomethyl-4-methoxypiperidin-1-yl)pyrimidin-4-yl](1-isopropyl-2-methyl-1H-imidazo[4,5-c]pyridin-6-yl)amine

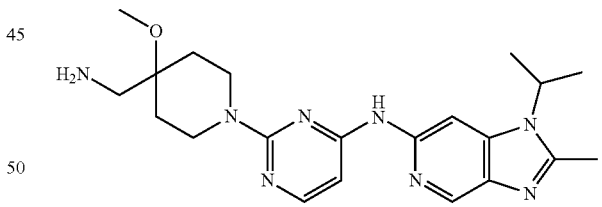

[2-(4-Aminomethyl-4-methoxypiperidin-1-yl)pyrimidin-4-yl](1-isopropyl-2-methyl-1H-imidazo[4,5-c]pyridin-6-yl)amine was synthesized from N-(2-chloropyrimidin-4-yl)-1-isopropyl-2-methyl-1H-imidazo[4,5-c]pyridin-6-amine and 4-azidomethyl-4-methoxypiperidine (WO2005/79805) in a procedure analogous to that described for Example 270. This gave an off-white solid. LCMS (ESI): R$_T$ 1.69 min [M+H]$^+$ 411, Method F; $^1$H NMR (400 MHz, DMSO-d$_6$): δ 9.68 (s, 1H), 8.50 (s, 1H), 8.40 (s, 1H), 7.95 (d, J=5.7 Hz, 1H), 6.40 (d, J=5.7 Hz, 1H), 4.77-4.66 (m, 1H), 4.37-4.31 (m, 2H), 3.29-3.21 (m, 2H), 3.16 (s, 3H), 2.66 (s, 2H), 2.56 (s, 3H), 1.79-1.74 (m, 2H), 1.56 (d, J=6.9 Hz, 6H), 1.50-1.42 (m, 2H).

Example 272: {6-[2-(1-Cyclopropanesulfonyl-1H-pyrazol-4-yl)pyrimidin-4-ylamino]-1-isopropyl-1H-imidazo[4,5-c]pyridin-2-yl}methanol

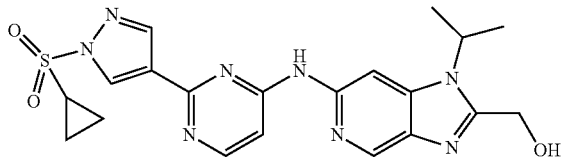 [SMILES: CC(C)n1c(CO)nc2cnc(Nc3ccnc(-c4cnn(S(=O)(=O)C5CC5)c4)n3)cc21]

Step 1: [2-(1-Cyclopropanesulfonyl-1H-pyrazol-4-yl)-pyrimidin-4-yl]-[1-isopropyl-2-(tetrahydro-yran-2-yloxymethyl)-1H-imidazo[4,5-c]pyridin-6-yl]-amine

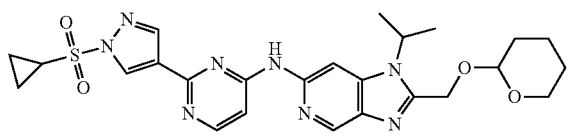 [SMILES: CC(C)n1c(COC2CCCCO2)nc2cnc(Nc3ccnc(-c4cnn(S(=O)(=O)C5CC5)c4)n3)cc21]

(2-Chloropyrimidin-4-yl)-[1-isopropyl-2-(tetrahydropyran-2-yloxymethyl)-1H-imidazo[4,5-c]pyridin-6-yl]amine (Intermediate A49) (1.59 g, 3.95 mmol), N-cyclopropylsulfonyl-4-pyrazoleboronic acid pinacol ester (Example 51, step 6) (1.41 g, 4.74 mmol), tetrakistriphenylphosphine palladium (456 mg, 0.39 mmol) and cesium carbonate (1.67 g, 5.13 mmol) were dissolved in dioxane (50 mL) and water (5 mL). The mixture was degassed with argon and the reaction mixture heated at reflux for 2.5 h. The reaction mixture was diluted with water and the product extracted with EtOAc (3×). The combined organic extracts were washed with brine, dried over anhydrous magnesium sulfate and concentrated in vacuo. The resultant residue was subjected to silica gel chromatography (solvent gradient: 0-4% methanol in EtOAc) to yield the title compound (1.94 g, 90%). LCMS (ESI): [M+H]$^+$=539.

Step 2: {6-[2-(1-Cyclopropanesulfonyl-1H-pyrazol-4-yl)pyrimidin-4-ylamino]-1-isopropyl-1H-imidazo[4,5-c]pyridin-2-yl}methanol

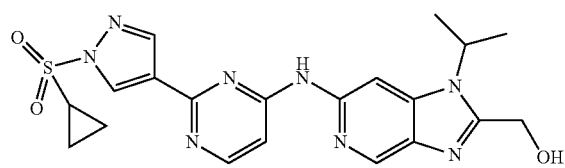 [SMILES: CC(C)n1c(CO)nc2cnc(Nc3ccnc(-c4cnn(S(=O)(=O)C5CC5)c4)n3)cc21]

[2-(1-Cyclopropanesulfonyl-1H-pyrazol-4-yl)pyrimidin-4-yl]-[1-isopropyl-2-(tetrahydropyran-2-yloxymethyl)-1H-imidazo[4,5-c]pyridin-6-yl]amine (1.91 g, 3.54 mmol) was dissolved in HCl (1.25M in methanol) (15 mL) and the reaction mixture was stirred at room temperature for 3 h, followed by 40° C. for 1 h. The reaction mixture was diluted with saturated aqueous sodium bicarbonate and the product extracted with EtOAc (3×). The combined organic extracts were washed with brine, dried over anhydrous magnesium sulfate and concentrated in vacuo. The resultant residue was subjected to silica gel chromatography (solvent gradient: 0-10% methanol in EtOAc). The product was then refluxed in water for 1 h, cooled to room temperature and collected by filtration to yield the title compound (977 mg, 61%). LCMS (ESI) R$_T$ 2.73 min [M+H]$^+$ 455, Method F; $^1$H NMR (400 MHz, DMSO-d$_6$) δ 10.22 (1H, s), 8.67 (1H, s), 8.66 (1H, s), 8.48 (1H, s), 8.47 (1H, br s), 8.40 (1H, d, J=5.9 Hz), 7.28-7.20 (1H, m), 5.70 (1H, t, J=5.5 Hz), 5.00 (1H, sept, J=6.9 Hz), 4.74 (2H, d, J=5.5 Hz), 3.29-3.21 (1H, m), 1.65 (6H, d, J=6.9 Hz), 1.37-1.22 (4H, m).

Example 273: (1-Isopropyl-6-((2-((1R,5R,8r)-8-methoxy-3-azabicyclo[3.2.1]octan-3-yl)pyrimidin-4-yl)amino)-1H-imidazo[4,5-c]pyridin-2-yl)methanol

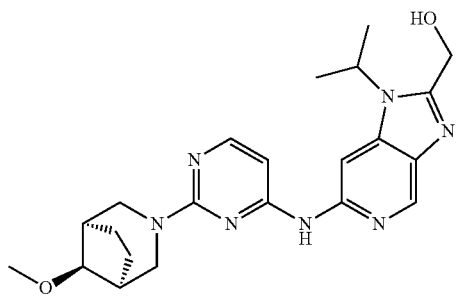 [SMILES: CO[C@H]1[C@@H]2CC[C@H]1CN(c1nccc(Nc3cc4c(cn3)nc(CO)n4C(C)C)n1)C2]

A mixture of N-(2-chloropyrimidin-4-yl)-1-isopropyl-2-((tetrahydro-2H-pyran-2-yloxy)methyl)-1H-imidazo[4,5-c]pyridin-6-amine (155.8 mg, 0.3867 mmol), (1S,5R,8r)-8-methoxy-3-azabicyclo[3.2.1]octane hydrochloride (84.6 mg, 0.476 mmol), triethylamine (0.20 mL, 1.4 mmol), and 2-propanol (1.5 mL) was heated at 150° C. under microwave irradiation for 30 minutes. The reaction mixture was diluted with dichloromethane, washed with water and brine, dried over magnesium sulfate, filtered, and evaporated in vacuo. The resulting residue was dissolved in methanol (3.0 mL) and treated with hydrogen chloride (4.0 mol/L solution in dioxane, 1.0 mL, 4.0 mmol). This mixture was stirred at room temperature for 3 hours, and then concentrated to dry. The reaction mixture was diluted with dichloromethane, washed with saturated aqueous sodium bicarbonate, dried over magnesium sulfate, filtered, and evaporated in vacuo. The crude product was purified via reverse-phase HPLC and lyophilized to yield 103.9 mg (63%) of the title compound. LCMS (ESI) R$_T$ 3.299 min [M+H]$^+$ 424.3, Method B; $^1$H NMR (400 MHz, DMSO-d$_6$) δ 9.73 (s, 1H), 8.63-8.52 (m, 2H), 7.95 (d, J=5.6 Hz, 1H), 6.37 (d, J=5.6 Hz, 1H), 5.72-5.61 (m, 1H), 4.95 (p, J=6.9 Hz, 1H), 4.71 (d, J=5.5 Hz, 2H), 4.16 (d, J=12.0 Hz, 2H), 3.61 (t, J=4.9 Hz, 1H), 3.37 (s, 3H), 3.27-3.23 (m, 1H), 2.30 (s, 2H), 1.78-1.67 (m, 2H), 1.57 (d, J=6.9 Hz, 6H), 1.54-1.45 (m, 2H).

Example 274: {6-[2-(4-Aminomethyl-4-methoxypiperidin-1-yl)pyrimidin-4-ylamino]-1-isopropyl-1H-imidazo[4,5-c]pyridin-2-yl}methanol

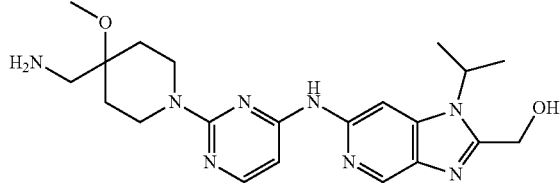 [SMILES: COC1(CN)CCN(c2nccc(Nc3cc4c(cn3)nc(CO)n4C(C)C)n2)CC1]

{6-[2-(4-Aminomethyl-4-methoxypiperidin-1-yl)pyrimidin-4-ylamino]-1-isopropyl-1H-imidazo[4,5-c]pyridin-2-yl}methanol was synthesized from N-(2-chloropyrimidin-4-yl)-1-isopropyl-2-((tetrahydro-2H-pyran-2-yloxy)methyl)-1H-imidazo[4,5-c]pyridin-6-amine (Example 251, step 7) and 4-azidomethyl-4-methoxypiperidine (WO2005/79805) following procedures analogous to those described for Example 270 and Example 273. This gave an off-white solid. LCMS (ESI): $R_T$ 1.65 min [M+H]$^+$ 427, Method F; $^1$H NMR (400 MHz, CDCl$_3$): δ 8.65 (s, 1H), 8.41 (s, 1H), 8.04 (d, J=5.7 Hz, 1H), 7.49 (s, 1H), 6.04 (d, J=5.7 Hz, 1H), 4.89 (s, 2H), 4.85-4.77 (m, 1H), 4.50-4.44 (m, 2H), 3.41-3.34 (m, 2H), 3.25 (s, 3H), 2.71 (s, 2H), 1.90-1.85 (m, 2H), 1.67 (d, J=6.9 Hz, 6H), 1.52-1.45 (m, 2H)

Example 275: (2-Cyclohex-1-enylpyrimidin-4-yl)-(1-isopropyl-2-methyl-1H-imidazo[4,5-c]pyridin-6-yl)amine

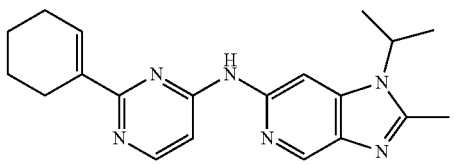 [SMILES: Cc1nc2cnc(Nc3ccnc(C4=CCCCC4)n3)cc2n1C(C)C]

A mixture of N-(2-chloropyrimidin-4-yl)-1-isopropyl-2-methyl-1H-imidazo[4,5-c]pyridin-6-amine (Example 46, step 7) (151 mg, 0.5 mmol), 1-cyclohexen-1-ylboronic acid pinacol ester (156 µL, 0.75 mmol), tetrakis(triphenylphosphine)palladium(0) (29 mg, 0.25 µmol, 5 mol %) and cesium carbonate (325 mg, 1.0 mmol) in dioxane (5 mL) and water (0.5 mL) was heated at 120° C. under microwave irradiation for 45 min. The reaction mixture was diluted with methanol and loaded onto an SCX cartridge. The cartridge was washed with methanol and then eluted with 2M ammonia in methanol. The product fraction was concentrated in vacuo. The resulting residue was purified by chromatography (silica, gradient 1-7% methanol in dichloromethane) to give an off-white solid which was recrystallized from ethyl acetate (79 mg, 77%). LCMS (ESI): $R_T$ 1.73 min: [M+H]$^+$ 349.2 Method F. $^1$H NMR (400 MHz, DMSO-d$_6$) δ 9.97 (1H, s), 8.63 (1H, s), 8.53 (1H, d, J=0.9 Hz), 8.29 (1H, d, J=5.6 Hz), 7.25-7.30 (1H, m), 7.00 (1H, br d, J=5.6 Hz) 4.74 (1H, septet, 6.9 Hz), 2.57-2.62 (2H, m), 2.57 (3H, s), 2.23-2.31 (2H, m), 1.70-1.78 (2H, m), 1.62-1.69 (2H, m) 1.57 (6H, d, J=6.9 Hz)

Example 276: 4-(1-Isopropyl-2-methyl-1H-imidazo[4,5-c]pyridin-6-ylamino)pyrimidine-2-carbonitrile

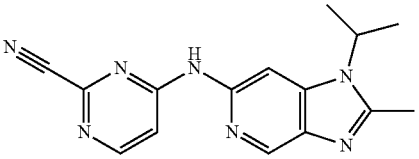 [SMILES: Cc1nc2cnc(Nc3ccnc(C#N)n3)cc2n1C(C)C]

A mixture of N-(2-chloropyrimidin-4-yl)-1-isopropyl-2-methyl-1H-imidazo[4,5-c]pyridin-6-amine (Example 46, Step 7) (605 mg, 2.0 mmol), sodium cyanide (118 mg, 2.4 mmol), 1,4-diazabicyclo[2.2.2]octane (224 mg, 2.00 mmol), in DMSO (3 mL) and water (1 mL) was heated at 80° C. under nitrogen for 12 h. The mixture was diluted with water and a solid precipitated. The solid was isolated by filtration. The aqueous filtrate was extracted with EtOAc and the organic extract was combined with the solid material. The solid was dissolved in methanol, adsorbed onto diatomaceous earth and purified on silica eluting with 1-7% methanol in dichloromethane to afford the product which was triturated in ethyl acetate to give a cream solid (580 mg, quantitative). LCMS (ESI): $R_T$ 2.63 min, [M+H]$^+$=294.1, Method F. $^1$H NMR (400 MHz, DMSO-d$_6$) δ 10.64 (1H, s), 8.58 (1H, d, J=0.9 Hz), 8.45 (1H, d, J=5.6 Hz), 8.05 (1H, br s), 7.75 (1H, br s), 4.74 (1H, septet, J=6.9 Hz), 2.58 (3H, s), 1.58 (6H, d, J=6.9 Hz).

Example 277: 2-{6-[4-(1-Isopropyl-2-methyl-1H-imidazo[4,5-c]pyridin-6-ylamino)pyrimidin-2-yl]-4,5,6,7-tetrahydropyrazolo[3,4-c]pyridin-1-yl}ethanol

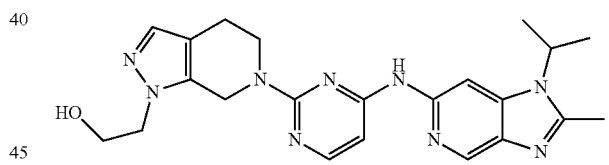

N-(2-Chloropyrimidin-4-yl)-1-isopropyl-2-methyl-1H-imidazo[4,5-c]pyridin-6-amine (Example 46, Step 7) (100 mg, 0.33 mmol), 2-(4,5,6,7-tetrahydropyrazolo[4,3-c]pyridin-1-yl)ethanol (87 mg, 0.43 mmol), N,N-diisopropylethylamine (230 µL, 1.32 mmol) and n-butanol (2 mL) were heated in a sealed vessel at 110° C. for 16 h. The reaction mixture was loaded onto an SCX-2 cartridge, washed with methanol and the product eluted with ammonia in methanol (2N). The solvent was concentrated in vacuo and the residue subjected to silica gel chromatography (solvent gradient: 0-10% methanol in EtOAc). The product was further purified by supercritical fluid chromatography to give the title compound (16 mg). LCMS (ESI): $R_T$=2.02 min, [M+H]$^+$ 434, Method F. $^1$H NMR (400 MHz, CDCl$_3$) δ 8.74 (1H, s), 8.63 (1H, s), 8.27 (1H, d, J=5.8 Hz), 7.95 (1H, s), 7.79 (1H, br s), 6.66 (1H, d, J=5.8 Hz), 4.64 (1H, sept, J=6.8 Hz), 3.94-3.89 (2H, m), 2.97-2.89 (1H, m), 2.85-2.76 (5H, m), 2.21-2.07 (4 h, m), 1.68 (6H, d, J=6.8 Hz).

Example 278: 2-{6-[4-(1-Isopropyl-2-methyl-1H-imidazo[4,5-c]pyridin-6-ylamino)pyrimidin-2-yl]-4,5,6,7-tetrahydropyrazolo[3,4-c]pyridin-2-yl}ethanol

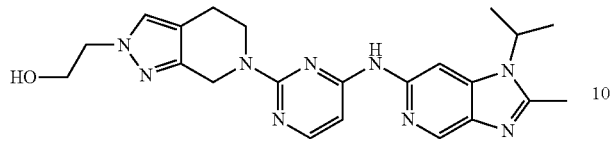

The title compound was separated from the crude reaction product during the purification of 2-{6-[4-(1-isopropyl-2-methyl-1H-imidazo[4,5-c]pyridin-6-ylamino)-pyrimidin-2-yl]-4,5,6,7-tetrahydro-pyrazolo[3,4-c]pyridin-1-yl}ethanol (Example 277) by super critical fluid chromatography. LCMS (ESI): $R_T$=2.03 min, [M+H]$^+$ 434, Method F. $^1$H NMR (400 MHz, CDCl$_3$) δ 8.58 (1H, s), 8.34 (1H, s), 8.03 (1H, d, J=5.7 Hz), 7.49 (1H, s), 7.20 (1H, s), 6.07 (1H, d, J=5.7 Hz), 4.85 (2H, s), 4.65 (1H, sept, J=6.9 Hz), 4.21 (2H, t, J=5.8 Hz), 4.17 (2H, t, J=4.8 Hz), 3.95 (2H, t, J=4.8 Hz), 2.86 (2H, t, J=5.8 Hz), 2.60 (3H, s), 1.69 (6H, d, J=6.9 Hz).

Example 279: [2-(1-Cyclopropanesulfonyl-1H-pyrazol-4-yl)-pyrimidin-4-yl]-(1-isopropyl-2-methoxymethyl-1H-imidazo[4,5-c]pyridin-6-yl)amine

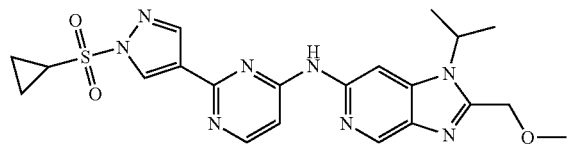 [SMILES: COCc1nc2cnc(Nc3ccnc(-c4cnn(S(=O)(=O)C5CC5)c4)n3)cc2n1C(C)C]

(2-Chloropyrimidin-4-yl)-(1-isopropyl-2-methoxymethyl-1H-imidazo[4,5-c]pyridin-6-yl)amine (Example A48) (65 mg, 0.19 mmol), N-cyclopropylsulfonyl-4-pyrazoleboronic acid pinacol ester (Example 51, step 6) (87 mg, 0.28 mmol), tetrakistriphenylphosphine palladium (23 mg, 19 µmol) and cesium carbonate (95 mg, 0.29 mmol) were dissolved in dioxane (2 mL) and water (0.2 mL). The mixture was degassed with argon and the reaction mixture heated at reflux for 1 h. The reaction mixture was diluted with water and the product extracted with EtOAc (3×). The combined organic extracts were washed with brine, dried over anhydrous magnesium sulfate and concentrated in vacuo. The resultant residue was subjected to silica gel chromatography (solvent gradient: 0-3% methanol in EtOAc) to yield the title compound (36 mg, 39%). LCMS (ESI): $R_T$=3.21 min, [M+H]$^+$ 469, Method F; $^1$H NMR (400 MHz, DMSO-d$_6$) δ 10.21 (1H, s), 8.70 (1H, s), 8.67 (1H, s), 8.50 (1H, br s), 8.48 (1H, s), 8.41 (1H, d, J=5.8 Hz), 7.28-7.19 (1H, m), 4.90 (1H, sept, J=6.9 Hz), 4.72 (2H, s), 3.32 (3H, s), 3.30-3.21 (1H, m), 1.64 (6H, d, J=6.9 Hz), 1.37-1.22 (4H, m).

Example 280: [2-(1-Cyclopropanesulfonyl-1H-pyrazol-4-yl)-pyrimidin-4-yl]-(3,3-dimethyl-2,3-dihydro-1-oxa-3a,6,8-triazacyclopenta[a]inden-5-yl)-amine

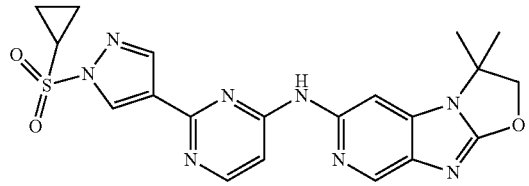 [SMILES: CC1(C)COc2nc3cnc(Nc4ccnc(-c5cnn(S(=O)(=O)C6CC6)c5)n4)cc3n21]

Step 1: 2-(2-Bromo-5-nitropyridin-4-ylamino)-2-methylpropan-1-ol

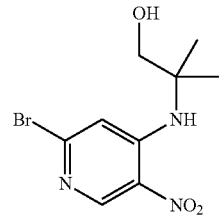 [SMILES: CC(C)(CO)Nc1cc(Br)ncc1[N+](=O)[O-]]

To a solution of 2,4-dibromo-5-nitropyridine (1 g, 3.5 mmol) in tetrahydrofuran (30 mL) was added 2-amino-2-methylpropanol (0.5 mL, 5.32 mmol) and the reaction mixture heated at 50° C. for 3 h. A further aliquot of 2-amino-2-methylpropanol (1.0 mL, 10.64 mmol) was added and heating continued for 16 h. The reaction mixture was cooled to room temperature, concentrated in vacuo and the resultant residue subjected to silica gel chromatography (solvent gradient: 0-100% EtOAc in pentane) to yield the title compound as a yellow solid (1.02 g, 100%). $^1$H NMR (400 MHz, CDCl$_3$) δ 8.96 (1H, s), 8.73 (1H, br s), 7.15 (1H, s), 3.71 (2H, d, J=5.1 Hz), 1.92 (1H, t, J=5.1 Hz), 1.50 (6H, s).

Step 2: (2-Bromo-5-nitropyridin-4-yl)-[2-(tert-butyldimethylsilanyloxy)-1,1-dimethylethyl]amine

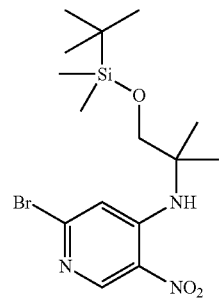 [SMILES: CC(C)(CO[Si](C)(C)C(C)(C)C)Nc1cc(Br)ncc1[N+](=O)[O-]]

To a solution of 2-(2-bromo-5-nitropyridin-4-ylamino)-2-methylpropan-1-ol (1 g, 3.45 mmol) in tetrahydrofuran (15 mL) was added tert-butyldimethylsilyl chloride (0.57 mL, 3.79 mmol), imidazole (0.28 g, 4.13 mmol) and 4-dimethylaminopyridine (catalytic). The reaction mixture was stirred at room temperature for 72 h. The reaction mixture was diluted with water and the product extracted with dichloromethane (3×). The combined organic extracts were washed with brine, dried over anhydrous magnesium sulfate and concentrated in vacuo. The resultant residue was subjected to silica gel chromatography (solvent gradient: 0-100% EtOAc in pentane) to yield the title compound as a colorless oil (1.08 g, 77%). $^1$H NMR (400 MHz, CDCl$_3$) δ 8.96 (1H, s), 8.83 (1H, br s), 7.14 (1H, s), 3.56 (2H, s), 1.44 (6H, s), 0.93 (9H, s), 0.12 (6H, s).

Step 3: 6-Bromo-N$^4$-[2-(tert-butyldimethylsilanyloxy)-1,1-dimethylethyl]pyridine-3,4-diamine

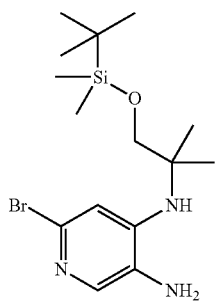 [SMILES: CC(C)(CO[Si](C)(C)C(C)(C)C)Nc1cc(Br)ncc1N]

To a solution of (2-bromo-5-nitropyridin-4-yl)-[2-(tert-butyldimethylsilanyloxy)-1,1-dimethylethyl]amine (1.08 g, 2.67 mmol) in industrial methylated spirits (20 mL) was added platinum (IV) oxide (100 mg, 0.44 mmol). The reaction mixture was stirred at room temperature under an atmosphere of hydrogen for 2 h. The reaction mixture was filtered and the filtrate concentrated in vacuo. The resultant residue was subjected to silica gel chromatography (solvent gradient: 0-100% EtOAc in pentane) to yield the title compound as an orange oil (740 mg, 80%). LCMS (ESI): [M+H]$^+$=374.

Step 4: 6-Bromo-1-[2-(tert-butyldimethylsilanyloxy)-1,1-dimethylethyl]-1,3-dihydro-imidazo[4,5-c]pyridin-2-one

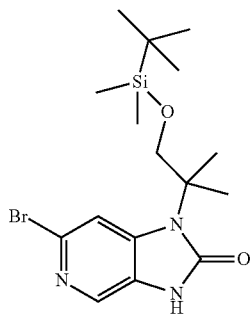 [SMILES: CC(C)(CO[Si](C)(C)C(C)(C)C)n1c(=O)[nH]c2cnc(Br)cc21]

Phosgene solution (1.1 mL, 20% in toluene, 2.08 mmol) was added drop-wise to a solution of 6-bromo-N$^4$-[2-(tert-butyldimethylsilanyloxy)-1,1-dimethylethyl]pyridine-3,4-diamine (520 mg, 1.39 mmol) and triethylamine (387 µL, 2.7 mmol) in tetrahydrofuran (15 mL) at 0° C. causing a thick white precipitate to form. The reaction mixture was stirred at room temperature for 20 min. The reaction mixture was diluted with water and the product extracted with EtOAc (3×). The combined organic extracts were washed with brine, dried over anhydrous magnesium sulfate and concentrated in vacuo to yield the title compound as an off-white solid (0.55 g, 99%). LCMS (ESI): [M+H]$^+$=400.

Step 5: 6-Bromo-1-(2-hydroxy-1,1-dimethylethyl)-1,3-dihydroimidazo[4,5-c]pyridin-2-one

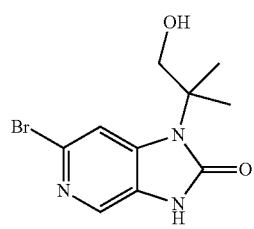

A solution of 6-bromo-1-[2-(tert-butyldimethylsilanyloxy)-1,1-dimethylethyl]-1,3-dihydro-imidazo[4,5-c]pyridin-2-one (550 mg, 1.37 mmol) and tetrabutylammonium fluoride (1 M in tetrahydrofuran) (2.75 mL, 2.75 mmol) in tetrahydrofuran (5 mL) was stirred at room temperature for 16 h. A further aliquot of tetrabutylammonium fluoride (1 M in tetrahydrofuran) (2 mL, 2.00 mmol) was added and stirring continued for 24 h. The reaction mixture was diluted with water and the product extracted with EtOAc (3×). The combined organic extracts were washed with brine, dried over anhydrous magnesium sulfate and concentrated in vacuo to give a dark brown solid. The product was triturated with EtOAc to give the title compound as an off-white solid (288 mg, 73%). LCMS (ESI): [M+H]$^+$=286.

Step 6: 5-Bromo-3,3-dimethyl-2,3-dihydro-1-oxa-3a,6,8-triazacyclopenta[a]indene

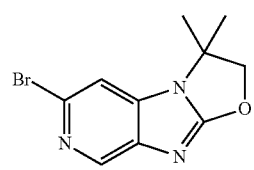

Diisopropyl azodicarboxylate (277 µL, 1.41 mmol) was added drop-wise to a solution of 6-bromo-1-(2-hydroxy-1,1-dimethylethyl)-1,3-dihydroimidazo[4,5-c]pyridin-2-one (288 mg, 1.0 mmol) and triphenylphosphine (396 mg, 1.51 mmol) in tetrahydrofuran (10 mL) and the reaction mixture was stirred at room temperature for 30 min. The reaction mixture was concentrated in vacuo and the resultant residue subjected to silica gel chromatography (solvent gradient: 0-10% methanol in dichloromethane). The product was dissolved in dichloromethane (5 mL) and the solution washed with aqueous hydrochloric acid (10 mL, 1 M). The aqueous fraction was basified with saturated aqueous sodium bicarbonate solution to pH 8. The product was extracted with EtOAc (3×) and the combined organic extracts were washed with brine, dried over anhydrous magnesium sulfate and concentrated in vacuo to give the title compound as a white solid (218 mg, 79%). LCMS (ESI): [M+H]$^+$=268.

Step 7: [2-(1-Cyclopropanesulfonyl-1H-pyrazol-4-yl)-pyrimidin-4-yl]-(3,3-dimethyl-2,3-dihydro-1-oxa-3a,6,8-triazacyclopenta[a]inden-5-yl)-amine

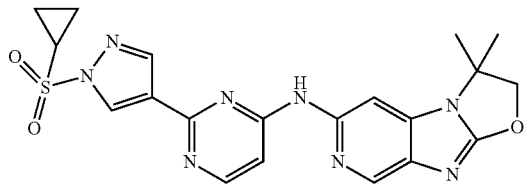 [SMILES: CC1(C)COc2nc3cnc(Nc4ccnc(-c5cnn(S(=O)(=O)C6CC6)c5)n4)cc3n21]

5-Bromo-3,3-dimethyl-2,3-dihydro-1-oxa-3a,6,8-triazacyclopenta[a]indene (35 mg, 0.13 mmol), 2-(1-cyclopropanesulfonyl-1H-pyrazol-4-yl)-pyrimidin-4-ylamine (Example A62) (35 mg, 0.13 mmol), tris(dibenzylideneacetone)dipalladium(0) (6 mg, 6.5 μmol), 4,5-bis(diphenylphosphino)-9,9-dimethylxanthene (15 mg, 26 μmol), cesium carbonate (85 mg, 0.26 mmol) and dioxane (3 mL) were sealed in a vial and the mixture degassed with argon. The reaction mixture was heated at 100° C. for 16 h. The reaction mixture was diluted with water and the product extracted with EtOAc (3×). The combined organic extracts were washed with brine, dried over anhydrous magnesium sulfate and concentrated in vacuo. The resultant residue was subjected to reverse phase HPLC to yield the title compound (10 mg, 17%). LCMS (ESI): $R_T$=2.78 min, [M+H]$^+$ 453, Method F. $^1$H NMR (400 MHz, DMSO-d$_6$) δ 10.15 (1H, s), 8.63 (1H, s), 8.44 (1H, s), 8.38 (1H, d, Hz), 8.36 (1H, s), 8.21 (1H, br s), 7.19-7.10 (1H, m), 4.94 (2H, s), 3.29-3.21 (1H, m), 1.70 (6H, s), 1.36-1.20 (4H, m).

Example 281: (R)-1-{1-((R)-sec-Butyl)-6-[2-(1-ethanesulfonyl-1H-pyrazol-4-yl)-pyrimidin-4-ylamino]-1H-imidazo[4,5-c]pyridin-2-yl}ethanol

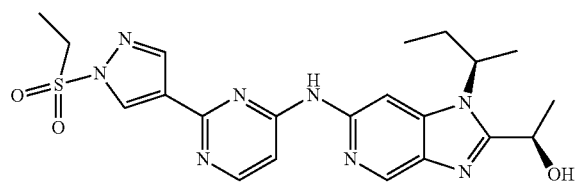 [SMILES: CC[C@@H](C)n1c([C@@H](C)O)nc2cnc(Nc3ccnc(-c4cnn(S(=O)(=O)CC)c4)n3)cc21]

Step 1: {1-((R)-sec-Butyl)-2-[(R)-1-(tetrahydropyran-2-yloxy)ethyl]-1H-imidazo[4,5-c]pyridin-6-yl}[2-(1-ethanesulfonyl-1H-pyrazol-4-yl)-pyrimidin-4-yl]amine

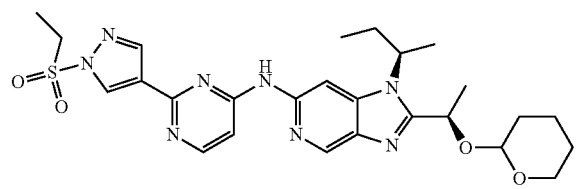 [SMILES: CC[C@@H](C)n1c([C@@H](C)OC2CCCCO2)nc2cnc(Nc3ccnc(-c4cnn(S(=O)(=O)CC)c4)n3)cc21]

(R)-6-Bromo-1-sec-butyl-2-[(R)-1-(tetrahydropyran-2-yloxy)ethyl]-1H-imidazo[4,5-c]pyridine (Example A51) (80 mg, 0.21 mmol), 2-(1-ethanesulfonyl-1H-pyrazol-4-yl)-pyrimidin-4-ylamine (Example A52) (53 mg, 0.21 mmol), tris(dibenzylideneacetone)dipalladium(0) (10 mg, 0.01 mmol), 4,5-bis(diphenylphosphino)-9,9-dimethylxanthene (24 mg, 0.04 mmol), cesium carbonate (136 mg, 0.42 mmol) and dioxane (3 mL) were sealed in a vial and the mixture degassed by bubbling argon through the solution whilst under sonication. The reaction mixture was heated at 100° C. for 1.75 h. The reaction mixture was diluted with water and the product extracted with EtOAc (3×). The combined organic extracts were washed with brine, dried over anhydrous magnesium sulfate and concentrated in vacuo. The resultant residue was subjected to silica gel chromatography (solvent gradient: 0-10% methanol in EtOAc) to yield the title compound (50 mg, 43%). LCMS (ESI): [M+H]$^+$=555.

Step 2: (R)-1-{1-((R)-sec-Butyl)-6-[2-(1-ethanesulfonyl-1H-pyrazol-4-yl)pyrimidin-4-ylamino]-1H-imidazo[4,5-c]pyridin-2-yl}ethanol

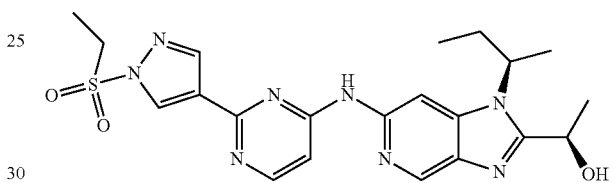

{1-((R)-sec-Butyl)-2-[(R)-1-(tetrahydropyran-2-yloxy)ethyl]-1H-imidazo[4,5-c]pyridin-6-yl}-[2-(1-ethanesulfonyl-1H-pyrazol-4-yl)pyrimidin-4-yl]amine (50 mg, 90 μL), was dissolved in HCl (1.25M in methanol) (5 mL) and the reaction mixture was stirred at room temperature for 4 h, then at 40° C. for 1 h. The reaction mixture was diluted with saturated aqueous sodium bicarbonate and the product extracted with EtOAc (3×). The combined organic extracts were washed with brine, dried over anhydrous magnesium sulfate and concentrated in vacuo. The resultant residue was subjected to reverse phase HPLC to yield the title compound (38 mg, 89%). LCMS (ESI): $R_T$=2.95 min, [M+H]$^+$ 471, Method F; $^1$H NMR 400 MHz δ (CDCl$_3$): 8.68 (2H, s), 8.46 (2H, s), 8.35 (1H, d, J=5.8 Hz), 8.29 (1H, br s), 6.80 (1H, d, J=5.8 Hz), 5.08 (1H, q, J=6.5 Hz), 4.55-4.45 (1H, m), 3.55 (2H, q, J=7.4 Hz), 2.31-2.18 (1H, m), 2.14-2.02 (1H, m), 1.73 (3H, d, J=7.2 Hz), 1.68 (3H, d, J=6.6 Hz), 1.28 (3H, t, J=7.4 Hz), 0.84 (3H, t, J=7.3 Hz).

Example 282: 2-{6-[2-(1-Cyclopropanesulfonyl-1H-pyrazol-4-yl)pyrimidin-4-ylamino]-1-isopropyl-1H-imidazo[4,5-c]pyridin-2-yloxy}ethanol

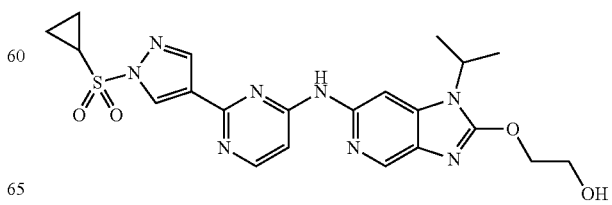

Step 1: [2-(1-Cyclopropanesulfonyl-1H-pyrazol-4-yl)pyrimidin-4-yl]-{1-isopropyl-2-[2-(tetrahydropyran-2-yloxy)ethoxy]-1H-imidazo[4,5-c]pyridin-6-yl}amine

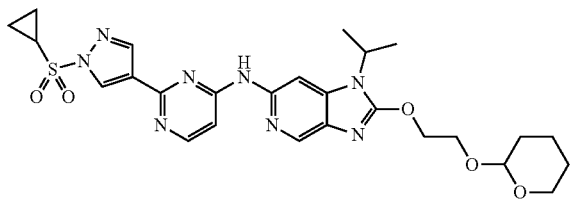 [SMILES: CC(C)n1c(OCCOC2CCCCO2)nc2cnc(Nc3ccnc(-c4cnn(S(=O)(=O)C5CC5)c4)n3)cc21]

A mixture of 6-chloro-1-isopropyl-2-[2-(tetrahydropyran-2-yloxy)ethoxy]-1H-imidazo[4,5-c]pyridine and 6-bromo-1-isopropyl-2-[2-(tetrahydropyran-2-yloxy)ethoxy]-1H-imidazo[4,5-c]pyridine (Example A54) (226 mg, ~0.62 mmol), 2-(1-cyclopropanesulfonyl-1H-pyrazol-4-yl)-pyrimidin-4-ylamine (Example A62) (182 mg, 0.68 mmol), 4,5-bis(diphenylphosphino)-9,9-dimethylxanthene (18 mg, 0.03 mmol), 2-dicyclohexylphosphino-2',4',6'-triisopropylbiphenyl (15 mg, 0.03 mmol), tris(dibenzylideneacetone)dipalladium(0) (14 mg, 0.02 mmol) and cesium carbonate (400 mg, 1.2 mmol) were suspended in dioxane (5 mL) and the resultant mixture degassed with argon. The reaction mixture was heated at 100° C. for 90 min, cooled to room temperature, diluted with water and extracted with EtOAc (3×). The combined organic extracts were washed with brine, dried over anhydrous magnesium sulfate and concentrated in vacuo. The resultant residue was subjected to silica gel chromatography (solvent gradient: 0-10% methanol in EtOAc) to yield the title compound as an off-white solid (58 mg, 16%). LCMS (ESI): [M+H]$^+$=569.

Step 2: 2-{6-[2-(1-Cyclopropanesulfonyl-1H-pyrazol-4-yl)pyrimidin-4-ylamino]-1-isopropyl-1H-imidazo[4,5-c]pyridin-2-yloxy}ethanol

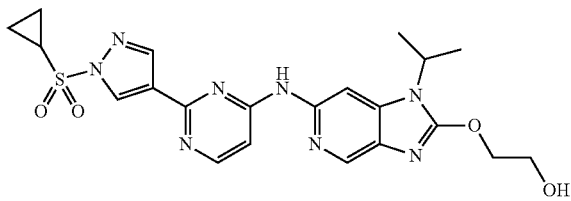 [SMILES: CC(C)n1c(OCCO)nc2cnc(Nc3ccnc(-c4cnn(S(=O)(=O)C5CC5)c4)n3)cc21]

[2-(1-Cyclopropanesulfonyl-1H-pyrazol-4-yl)pyrimidin-4-yl]-{1-isopropyl-2-[2-(tetrahydropyran-2-yloxy)ethoxy]-1H-imidazo[4,5-c]pyridin-6-yl}amine (58 mg, 0.10 mmol) was dissolved in hydrochloric acid (1.25M in methanol) (5 mL) and the reaction mixture was stirred at room temperature for 2 h. The reaction mixture was diluted with saturated aqueous sodium bicarbonate and the product extracted with EtOAc (3×). The combined organic extracts were washed with brine, dried over anhydrous magnesium sulfate and concentrated in vacuo. The resultant residue was subjected to preparative HPLC to yield the title compound as a white solid (19 mg, 38%). LCMS (ESI): R$_T$=2.72 min, [M+H]$^+$ 485, Method F; $^1$H NMR 400 MHz δ (CDCl$_3$): 8.63 (1H, s), 8.43 (1H, s), 8.39-8.32 (3H, m), 6.84 (1H, d, J=5.8 Hz), 4.74-4.65 (3H, m), 4.07-4.01 (2H, m), 2.84-2.76 (1H, m), 1.65 (6H, d, J=6.9 Hz), 1.52-1.47 (2H, m), 1.24-1.16 (2H, m).

Example 283: N$^6$-[2-(1-Cyclopropanesulfonyl-1H-pyrazol-4-yl)-pyrimidin-4-yl]-1-isopropyl-N$^2$,N$^2$-dimethyl-1H-imidazo[4,5-c]pyridine-2,6-diamine

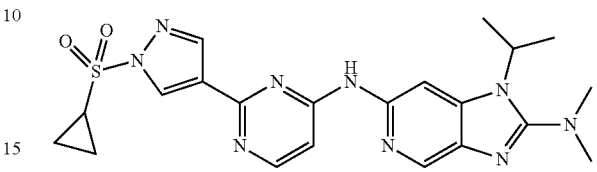

(6-Chloro-1-isopropyl-1H-imidazo[4,5-c]pyridin-2-yl)dimethylamine (Example A57) (49 mg, 0.18 mmol), 2-(1-cyclopropanesulfonyl-1H-pyrazol-4-yl)-pyrimidin-4-ylamine (Example A62) (48 mg, 0.18 mmol), 2-dicyclohexylphosphino-2',4',6'-triisopropylbiphenyl (18 mg, 0.04 mmol), tris(dibenzylideneacetone)dipalladium(0) (8 mg, 0.01 mmol) and cesium carbonate (120 mg, 0.26 mmol) were suspended in dioxane (3 mL) and the resultant mixture degassed with argon. The reaction mixture was heated at 100° C. for 90 min, cooled to room temperature, diluted with water and extracted with EtOAc (3×). The combined organic extracts were washed with brine, dried over anhydrous magnesium sulfate and concentrated in vacuo. The resultant residue was subjected to reverse phase HPLC to yield the title compound (18 mg, 21%). LCMS (ESI): R$_T$=2.96 min, [M+H]$^+$ 468, Method F; $^1$H NMR 400 MHz δ (CDCl$_3$): 8.66 (1H, s), 8.49 (1H, s), 8.46 (1H, s), 8.34 (1H, d, J=5.8 Hz), 8.26 (1H, br s), 7.98 (1H, br s), 6.82 (1H, d, J=5.8 Hz), 4.68 (1H, sept, J=6.9 Hz), 2.95 (6H, s), 2.84-2.77 (1H, m), 1.68 (6H, d, J=6.9 Hz), 1.53-1.46 (2H, m), 1.22-1.15 (2H, m).

Example 284: [2-(Azetidin-3-yloxy)-1-isopropyl-1H-imidazo[4,5-c]pyridin-6-yl]-[2-(1-cyclopropanesulfonyl-1H-pyrazol-4-yl)pyrimidin-4-yl]amine

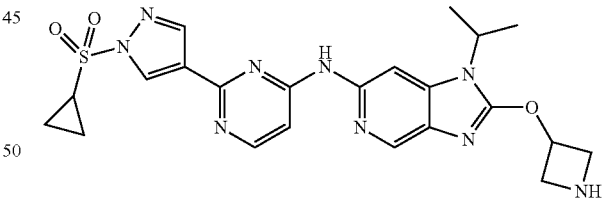

Step 1: 6-Chloro-1-isopropyl-1,3-dihydroimidazo[4,5-c]pyridin-2-one

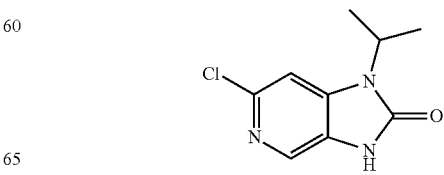

Phosgene solution (9.9 mL, 20% in toluene, 18.8 mmol) was added drop-wise to a solution of 6-chloro-N⁴-isopropylpyridine-3,4-diamine (2.33 m, 12.5 mmol) and triethylamine (3.49 mL, 25.0 mmol) in tetrahydrofuran (75 mL) causing a thick white precipitate to form. The reaction mixture was stirred at room temperature for 15 min, diluted with water, and the product extracted with EtOAc (3×). The combined organic extracts were washed with brine, dried over anhydrous magnesium sulfate and concentrated in vacuo to yield the title compound as an off-white solid (2.53 g, 94%). LCMS (ESI): [M+H]⁺=212.

Step 2:
2,6-Dichloro-1-isopropyl-1H-imidazo[4,5-c]pyridine

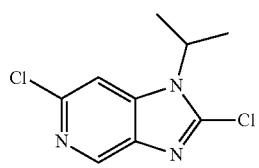

6-Chloro-1-isopropyl-1,3-dihydroimidazo[4,5-c]pyridin-2-one (2.53 g, 11.95 mmol) was suspended in phosphorus oxychloride (20 mL) and the reaction mixture heated at reflux for 4 d, during which the solids dissolved. The reaction mixture was concentrated in vacuo and the residue diluted with EtOAc. The solution was poured slowly into water and the resultant mixture made basic to pH 10 by addition of sodium hydroxide solution (2 M). The product was extracted with EtOAc (3×). The combined organic extracts were washed with brine, dried over anhydrous magnesium sulfate and concentrated in vacuo. The resultant residue was subjected to silica gel chromatography (solvent gradient: 0-100% EtOAc in cyclohexane) to yield the title compound as an off white solid (1.34 g, 49%). LCMS (ESI): [M+H]⁺=230 & 232 & 234.

Step 3: 3-(6-Chloro-1-isopropyl-1H-imidazo[4,5-c]pyridin-2-yloxy)azetidine-1-carboxylic acid tert-butyl ester

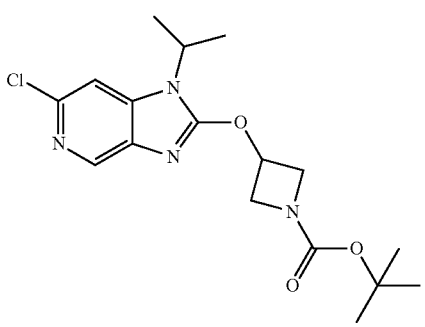 [SMILES: CC(C)n1c(OC2CN(C(=O)OC(C)(C)C)C2)nc2cnc(Cl)cc21]

A mixture of 2,6-dichloro-1-isopropyl-1H-imidazo[4,5-c]pyridine (200 mg, 0.87 mmol), 3-hydroxyazetidine-1-carboxylic acid tert-butyl ester (226 mg, 1.30 mmol) and cesium carbonate (566 mg, 1.74 mmol) in dimethylformamide (5 mL) was heated at 100° C. for 2 h. The reaction mixture was diluted with water and the product extracted with EtOAc (3×). The combined organic extracts were washed with brine, dried over anhydrous magnesium sulfate and concentrated in vacuo. The resultant residue was subjected to silica gel chromatography (solvent gradient: 0-100% EtOAc in cyclohexane) to yield the title compound as an off-white solid (272 mg, 87%). LCMS (ESI): [M+H]⁺=367 & 369.

Step 4: 3-{6-[2-(1-Cyclopropanesulfonyl-1H-pyrazol-4-yl)-pyrimidin-4-ylamino]-1-isopropyl-1H-imidazo[4,5-c]pyridin-2-yloxy}azetidine-1-carboxylic acid tert-butyl ester

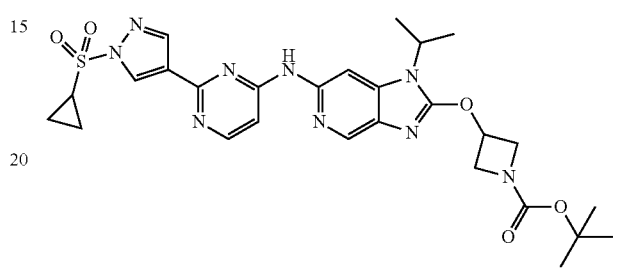

3-(6-Chloro-1-isopropyl-1H-imidazo[4,5-c]pyridin-2-yloxy)azetidine-1-carboxylic acid tert-butyl ester (272 mg, 0.74 mmol), 2-(1-cyclopropanesulfonyl-1H-pyrazol-4-yl)-pyrimidin-4-ylamine (Example A62) (216 mg, 0.82 mmol), 2-dicyclohexylphosphino-2',4',6'-triisopropylbiphenyl (71 mg, 0.15 mmol), Tris(dibenzylideneacetone)dipalladium(0) (34 mg, 0.04 mmol) and cesium carbonate (483 mg, 1.48 mmol) were suspended in dioxane (5 mL) and the resultant mixture degassed with argon. The reaction mixture was heated at 100° C. for 4 h, cooled to room temperature, diluted with water and extracted with EtOAc (3×). The combined organic extracts were washed with brine, dried over anhydrous magnesium sulfate and concentrated in vacuo. The resultant residue was subjected to silica gel chromatography (solvent gradient: 0-10% methanol in EtOAc) to yield the title compound (125 mg, 28%) LCMS (ESI): [M+H]⁺=596.

Step 5: [2-(Azetidin-3-yloxy)-1-isopropyl-1H-imidazo[4,5-c]pyridin-6-yl]-[2-(1-cyclopropanesulfonyl-1H-pyrazol-4-yl)-pyrimidin-4-yl]amine

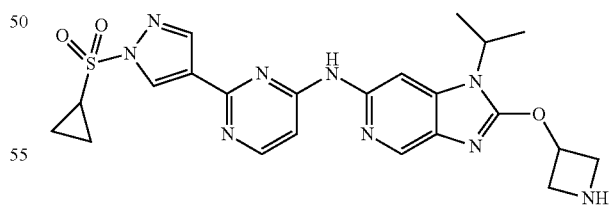

To a solution of 3-{6-[2-(1-cyclopropanesulfonyl-1H-pyrazol-4-yl)-pyrimidin-4-ylamino]-1-isopropyl-1H-imidazo[4,5-c]pyridin-2-yloxy}-azetidine-1-carboxylic acid tert-butyl ester (125 mg, 0.21 mmol) in dichloromethane (1 mL) was added trifluoroacetic acid (1 mL) and the reaction mixture was stirred at room temperature for 1 h. The reaction was basified with saturated aqueous sodium bicarbonate to pH 8 and the product extracted with EtOAc (3×). The combined organic extracts were washed with brine, dried over anhydrous magnesium sulfate and concentrated in vacuo. The resultant residue was subjected to purification by reverse phase HPLC to yield the title compound (11 mg, 11%). LCMS (ESI): R$_T$=2.29 min, [M+H]$^+$ 496, Method F; $^1$H NMR 400 MHz δ (CDCl$_3$): 8.64 (1H, s), 8.44 (1H, s), 8.43 (1H, s), 8.33 (1H, d, J=5.9 Hz), 8.17 (1H, br s), 7.99 (1H, br s), 6.82 (1H, d, J=5.8 Hz), 5.63 (1H, quin, J=6.0 Hz), 4.70 (1H, sept, J=6.9 Hz), 4.14-4.06 (2H, m), 3.90-3.82 (2H, m), 2.94-2.69 (2H, m), 1.65 (6H, d, J=6.9 Hz), 1.53-1.46 (2H, m), 1.22-1.15 (2H, m).

Example 285: [2-(Azetidin-3-yloxy)-1-isopropyl-1H-imidazo[4,5-c]pyridin-6-yl]-[2-(1H-pyrazol-4-yl)pyrimidin-4-yl]amine

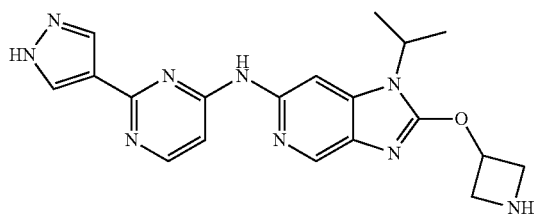 [SMILES: CC(C)n1c(OC2CNC2)nc2cnc(Nc3ccnc(-c4cn[nH]c4)n3)cc21]

To a solution of 3-{6-[2-(1-cyclopropanesulfonyl-1H-pyrazol-4-yl)-pyrimidin-4-ylamino]-1-isopropyl-1H-imidazo[4,5-c]pyridin-2-yloxy}azetidine-1-carboxylic acid tert-butyl ester (Example 284, step 4) (147 mg, 0.25 mmol) in methanol (5 mL) was added HCl (4M in dioxane) (5 mL) and the reaction mixture was stirred at room temperature for 20 min. The reaction mixture was concentrated in vacuo and the resultant residue subjected to purification by reverse phase HPLC to yield the title compound (15 mg, 16%). LCMS (ESI): R$_T$=1.65 min, [M+H]$^+$ 392, Method F; $^1$H NMR 400 MHz δ (DMSO-d$_6$): 9.84 (1H, s), 8.32 (1H, s), 8.24 (1H, d, J=5.8 Hz), 8.20-7.97 (3H, m), 7.16-7.06 (1H, m), 5.44 (1H, quin, J=6.1 Hz), 4.65 (1H, sept, J=6.9 Hz), 3.81-3.73 (2H, m), 3.62-3.54 (2H, m), 1.53 (6H, d, J=6.9 Hz).

Example 286: [(R)-6-[2-(1-Cyclopropanesulfonyl-1H-pyrazol-4-yl)pyrimidin-4-ylamino]-1-(2,2,2-trifluoro-1-methylethyl)-1H-imidazo[4,5-c]pyridin-2-yl]methanol

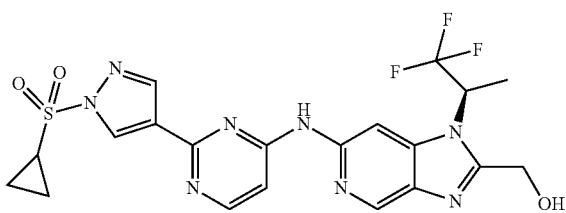 [SMILES: C[C@@H](n1c(CO)nc2cnc(Nc3ccnc(-c4cnn(S(=O)(=O)C5CC5)c4)n3)cc21)C(F)(F)F]

Step 1: [2-(1-Cyclopropanesulfonyl-1H-pyrazol-4-yl)-pyrimidin-4-yl]-[(R)-2-(tetrahydropyran-2-yloxymethyl)-1-(2,2,2-trifluoro-1-methylethyl)-1H-imidazo[4,5-c]pyridin-6-yl]amine

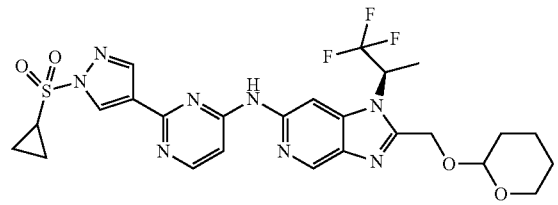 [SMILES: C[C@@H](n1c(COC2CCCCO2)nc2cnc(Nc3ccnc(-c4cnn(S(=O)(=O)C5CC5)c4)n3)cc21)C(F)(F)F]

6-Chloro-2-(tetrahydropyran-2-yloxymethyl)-1-((R)-2,2,2-trifluoro-1-methylethyl)-1H-imidazo[4,5-c]pyridine (Example A60) (137 mg, 0.38 mmol), 2-(1-cyclopropanesulfonyl-1H-pyrazol-4-yl)-pyrimidin-4-ylamine (Example A62) (100 mg, 0.38 mmol), 2-dicyclohexylphosphino-2',4',6'-triisopropylbiphenyl (36 mg, 0.08 mmol), tris(dibenzylideneacetone)dipalladium(0) (17 mg, 0.02 mmol) and cesium carbonate (246 mg, 0.75 mmol) were suspended in dioxane (3.5 mL) and the resultant mixture degassed with argon. The reaction mixture was heated at 100° C. for 1 h, cooled to room temperature, diluted with water and extracted with EtOAc (3×). The combined organic extracts were washed with brine, dried over anhydrous magnesium sulfate and concentrated in vacuo. The resultant residue was subjected to silica gel chromatography (solvent gradient: 0-5% methanol in EtOAc) to yield the title compound (90 mg, 40%) LCMS (ESI): [M+H]$^+$=593.

Step 2: [(R)-6-[2-(1-Cyclopropanesulfonyl-1H-pyrazol-4-yl)pyrimidin-4-ylamino]-1-(2,2,2-trifluoro-1-methylethyl)-1H-imidazo[4,5-c]pyridin-2-yl]methanol

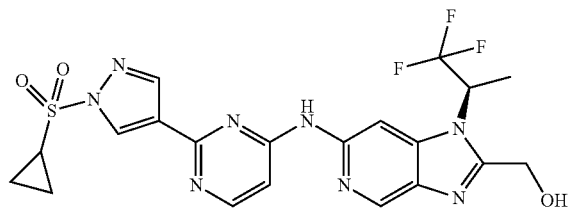 [SMILES: C[C@@H](n1c(CO)nc2cnc(Nc3ccnc(-c4cnn(S(=O)(=O)C5CC5)c4)n3)cc21)C(F)(F)F]

[2-(1-Cyclopropanesulfonyl-1H-pyrazol-4-yl)-pyrimidin-4-yl]-[(R)-2-(tetrahydropyran-2-yloxymethyl)-1-(2,2,2-trifluoro-1-methylethyl)-1H-imidazo[4,5-c]pyridin-6-yl]amine (90 mg, 0.15 mmol) was dissolved in hydrochloric acid (1.25M in methanol) (5 mL) and the reaction mixture was stirred at room temperature for 1 h. The reaction mixture was diluted with saturated aqueous sodium bicarbonate and the product extracted with EtOAc (3×). The combined organic extracts were washed with brine, dried over anhydrous magnesium sulfate and concentrated in vacuo. The resultant residue was subjected to preparative HPLC to yield the title compound as a white solid (47 mg, 61%). LCMS (ESI): R$_T$=3.19 min, [M+H]$^+$ 509, Method F; $^1$H NMR 400 MHz δ (CDCl$_3$): 8.69 (1H, s), 8.63 (1H, s), 8.43 (1H, s), 8.40 (1H, br s), 8.38 (1H, d, J=5.8 Hz), 7.98 (1H, br s), 6.84 (1H, d, J=5.8 Hz), 5.35 (1H, quin, J=7.7 Hz), 4.95 (1H, d, J=14.2), 4.91 (1H, d, J=14.2 Hz), 2.85-2.76 (1H, m), 1.99 (3H, d, J=7.2 Hz), 1.55-1.44 (2H, m), 1.24-1.13 (2H, m).

Example 287: (1-Isopropyl-1H-imidazo[4,5-c]pyridin-6-yl)-[2-(1-methanesulfonylpiperidin-4-yl)pyrimidin-4-yl]amine

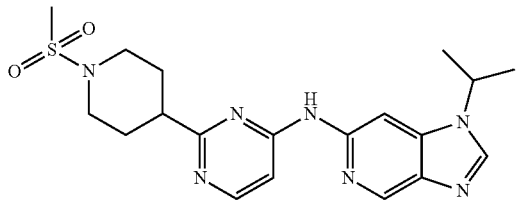 [SMILES: CC(C)n1cnc2cnc(Nc3ccnc(C4CCN(S(C)(=O)=O)CC4)n3)cc21]

To a suspension of 4-[4-(1-isopropyl-1H-imidazo[4,5-c]pyridin-6-ylamino)pyrimidin-2-yl]piperidinium chloride (Example A22) (45 mg, 0.12 mmol) in dimethylformamide (3 mL) was added triethylamine (50 µL, 0.36 mmol) and methanesulfonyl chloride (19 µL, 0.24 mmol) and the reaction mixture was stirred at room temperature for 2 h. The reaction mixture was diluted with saturated aqueous sodium bicarbonate and the product extracted with EtOAc (3×). The combined organic extracts were washed with brine, dried over anhydrous magnesium sulfate and concentrated in vacuo. The resultant residue was subjected to preparative HPLC to yield the title compound (10 mg, 20%). LCMS (ESI): $R_T$=2.18 min, [M+H]$^+$ 416, Method F; $^1$H NMR 400 MHz δ (CDCl$_3$): 8.74 (1H, s), 8.63 (1H, s), 8.27 (1H, d, J=5.8 Hz), 7.95 (1H, s), 7.79 (1H, br s), 6.66 (1H, d, J=5.8 Hz), 4.64 (1H, sept, J=6.8 Hz), 3.94-3.89 (2H, m), 2.97-2.89 (1H, m), 2.85-2.76 (5H, m), 2.21-2.07 (4 h, m), 1.68 (6H, d, J=6.8 Hz).

Example 288: (R)-1-[6-[2-((3R,4S)-3-Fluoro-4-methoxypiperidin-1-yl)-pyrimidin-4-ylamino]-1-((S)-2,2,2-trifluoro-1-methylethyl)-1H-imidazo[4,5-c]pyridin-2-yl]ethanol

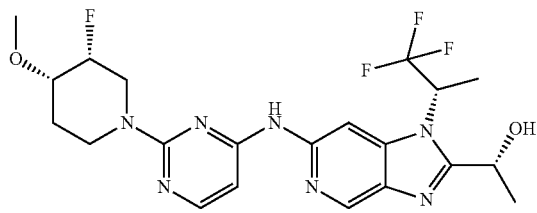 [SMILES: CO[C@H]1CCN(c2nccc(Nc3cc4c(cn3)nc([C@@H](C)O)n4[C@@H](C)C(F)(F)F)n2)C[C@H]1F]

Step 1: [2-((3R,4S)-3-Fluoro-4-methoxypiperidin-1-yl)-pyrimidin-4-yl]-[2-[(R)-1-(tetrahydropyran-2-yloxy)-ethyl]-1-((S)-2,2,2-trifluoro-1-methylethyl)-1H-imidazo[4,5-c]pyridin-6-yl]amine

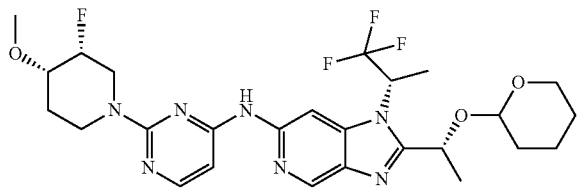 [SMILES: CO[C@H]1CCN(c2nccc(Nc3cc4c(cn3)nc([C@@H](C)OC3CCCCO3)n4[C@@H](C)C(F)(F)F)n2)C[C@H]1F]

6-Chloro-2-[(R)-1-(tetrahydropyran-2-yloxy)ethyl]-1-((S)-2,2,2-trifluoro-1-methylethyl)-1H-imidazo[4,5-c]pyridine (Example A83) (175 mg, 0.46 mmol), (−)-2-((3R,4S)-3-fluoro-4-methoxypiperidin-1-yl)pyrimidin-4-ylamine (Example A63) (100 mg, 0.44 mmol), 2-dicyclohexylphosphino-2',4',6'-triisopropylbiphenyl (42 mg, 0.09 mmol), tris(dibenzylideneacetone)dipalladium(0) (20 mg, 0.02 mmol) and cesium carbonate (288 mg, 0.88 mmol) were suspended in dioxane (5 mL) and the resultant mixture degassed with argon. The reaction mixture was heated at 100° C. for 90 min. The reaction mixture was cooled to room temperature, diluted with water and the product extracted with ethyl acetate (3×). The combined organic extracts were washed with brine, dried over anhydrous magnesium sulfate and concentrated in vacuo. The resultant residue was subjected to flash chromatography (solvent gradient: 0-4% methanol in ethyl acetate) to yield the title compound (135 mg, 53%) LCMS (ESI): [M+H]$^+$=568.

Step 2: (R)-1-[6-[2-((3R,4S)-3-Fluoro-4-methoxypiperidin-1-yl)pyrimidin-4-ylamino]-1-((S)-2,2,2-trifluoro-1-methylethyl)-1H-imidazo[4,5-c]pyridin-2-yl]ethanol

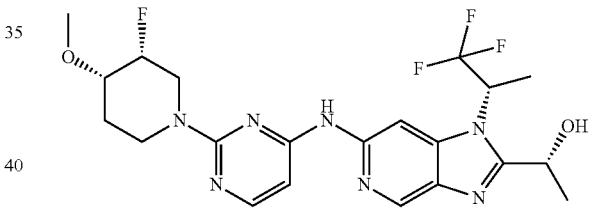

[2-((3R,4S)-3-Fluoro-4-methoxypiperidin-1-yl)-pyrimidin-4-yl]-[2-[(R)-1-(tetrahydropyran-2-yloxy)-ethyl]-1-((S)-2,2,2-trifluoro-1-methylethyl)-1H-imidazo[4,5-c]pyridin-6-yl]amine (135 mg, 0.24 mmol) was dissolved in hydrochloric acid in methanol (5 mL, 1.25 M) and the reaction mixture was stirred at room temperature for 2 h. The reaction mixture was diluted with saturated aqueous sodium bicarbonate and the product extracted with ethyl acetate (3×). The combined organic extracts were washed with brine, dried over anhydrous magnesium sulfate and concentrated in vacuo. The resultant residue was subjected to preparative HPLC to yield the title compound as a white solid (37 mg, 32%). LCMS (ESI): $R_T$ 2.58 min, [M+H]$^+$ 484, Method F; $^1$H NMR 400 MHz δ (CDCl$_3$): 8.71 (1H, s), 8.38 (1H, br s), 8.04 (1H, d, J=5.8 Hz), 7.44 (1H, br s), 6.09 (1H, d, J=5.8 Hz), 5.59 (1H, quin, J=7.7 Hz), 5.11 (1H, q, J=9.7 Hz), 4.92-4.87 (0.5H, m), 4.79-4.76 (0.5H, m), 4.70-4.61 (1H, m), 4.40-4.32 (1H, m), 3.72-3.52 (2H, m), 3.50 (3H, s), 3.49-3.41 (1H, m) 2.06-1.95 (1H, m), 1.92 (3H, d, J=6.9 Hz), 1.84 (3H, d, J=6.6 Hz), 1.79-1.47 (1H, m).

Example 289: (3R,4S)-3-Fluoro-1-{4-[2-((R)-1-hydroxyethyl)-1-((S)-2,2,2-trifluoro-1-methylethyl)-1H-imidazo[4,5-c]pyridin-6-ylamino]pyrimidin-2-yl}-piperidin-4-ol

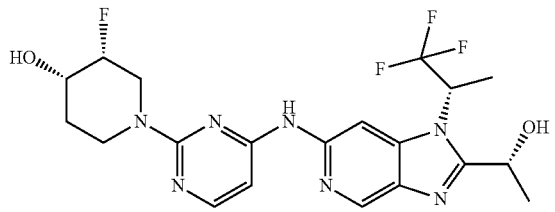 [SMILES: C[C@H](n1c([C@@H](C)O)nc2cnc(Nc3ccnc(N4CC[C@H](O)[C@H](F)C4)n3)cc21)C(F)(F)F]

Step 1: (3R,4S)-3-Fluoro-1-{4-[2-[(R)-1-(tetrahydropyran-2-yloxy)ethyl]-1-((S)-2,2,2-trifluoro-1-methylethyl)-1H-imidazo[4,5-c]pyridin-6-ylamino]pyrimidin-2-yl}piperidin-4-ol

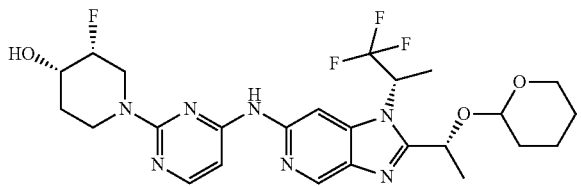 [SMILES: C[C@H](n1c([C@@H](C)OC2CCCCO2)nc2cnc(Nc3ccnc(N4CC[C@H](O)[C@H](F)C4)n3)cc21)C(F)(F)F]

6-Chloro-2-[(R)-1-(tetrahydropyran-2-yloxy)ethyl]-1-((S)-2,2,2-trifluoro-1-methylethyl)-1H-imidazo[4,5-c]pyridine (Example A83) (200 mg, 0.53 mmol), (−)-(3R,4S)-1-(4-aminopyrimidin-2-yl)-3-fluoropiperidin-4-ol (Example A64) (112 mg, 0.53 mmol), 2-dicyclohexylphosphino-2',4',6'-triisopropylbiphenyl (50 mg, 0.119 mmol), tris(dibenzylideneacetone)dipalladium(0) (24 mg, 0.03 mmol) and cesium carbonate (345 mg, 1.06 mmol) were suspended in dioxane (5 mL) and the resultant mixture degassed with argon. The reaction mixture was heated at 100° C. for 1 h. The reaction mixture was diluted with water and the product extracted with ethyl acetate (3×15 mL). The combined organic extracts were washed with brine, dried over anhydrous magnesium sulfate and concentrated in vacuo. The resultant residue was subjected to flash chromatography on silica (solvent gradient: 0-10% methanol in ethyl acetate) to yield the title compound (160 mg, 55%) LCMS (ESI): [M+H]$^+$=554.

Step 2: (3R,4S)-3-Fluoro-1-{4-[2-((R)-1-hydroxyethyl)-1-((S)-2,2,2-trifluoro-1-methylethyl)-1H-imidazo[4,5-c]pyridin-6-ylamino]pyrimidin-2-yl}-piperidin-4-ol

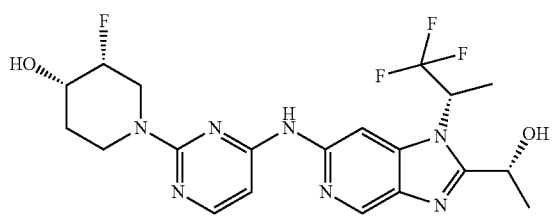 [SMILES: C[C@H](n1c([C@@H](C)O)nc2cnc(Nc3ccnc(N4CC[C@H](O)[C@H](F)C4)n3)cc21)C(F)(F)F]

(3R,4S)-3-Fluoro-1-{4-[2-[(R)-1-(tetrahydropyran-2-yloxy)ethyl]-1-((S)-2,2,2-trifluoro-1-methylethyl)-1H-imidazo[4,5-c]pyridin-6-ylamino]pyrimidin-2-yl}piperidin-4-ol (160 mg, 0.29 mmol) was dissolved in hydrochloric acid in methanol (5 mL, 1.25 M) and the reaction mixture was stirred at room temperature for 3 h. The reaction mixture was diluted with saturated aqueous sodium bicarbonate and the product extracted with ethyl acetate (3×15 mL). The combined organic extracts were washed with brine, dried over anhydrous magnesium sulfate and concentrated in vacuo. The resultant residue was subjected to preparative HPLC to yield the title compound as a white solid (53 mg, 39%). LCMS (ESI): R$_T$ 2.28 min, [M+H]$^+$ 470, Method F; $^1$H NMR 400 MHz δ (d$_6$-DMSO): 9.80 (1H, br s), 8.63 (1H, s), 8.32 (1H, br s), 7.93 (1H, d, J=5.9 Hz), 6.44 (1H, br s), 5.91 (1H, d, J=6.2 Hz), 5.90-5.78 (1H, m), 5.07 (1H, d, J=5.3), 4.98 (1H, quin, J=6.6 Hz), 4.69-4.65 (0.5H, m), 4.58-4.49 (1.5H, m), 4.34-4.26 (1H, m), 3.86-3.72 (1H, m), 3.49-3.40 (1H, m), 1.81 (3H, d, J=7.1 Hz), 1.68-1.60 (3H, m), 1.58 (3H, d, J=6.6 Hz).

Example 290: (R)-1-[6-[2-((3S,4R)-3-Fluoro-4-methoxypiperidin-1-yl)-pyrimidin-4-ylamino]-1-((S)-2,2,2-trifluoro-1-methylethyl)-1H-imidazo[4,5-c]pyridin-2-yl]ethanol

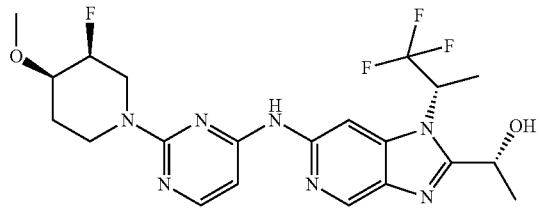 [SMILES: CO[C@@H]1CCN(c2nccc(Nc3cc4c(cn3)nc([C@@H](C)O)n4[C@@H](C)C(F)(F)F)n2)C[C@@H]1F]

Step 1: [2-((3S,4R)-3-Fluoro-4-methoxypiperidin-1-yl)-pyrimidin-4-yl]-[2-[(R)-1-(tetrahydropyran-2-yloxy)-ethyl]-1-((S)-2,2,2-trifluoro-1-methylethyl)-1H-imidazo[4,5-c]pyridin-6-yl]amine

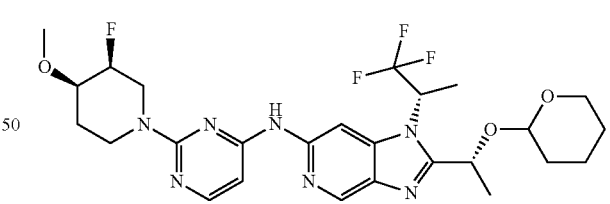

6-Chloro-2-[(R)-1-(tetrahydropyran-2-yloxy)ethyl]-1-((S)-2,2,2-trifluoro-1-methylethyl)-1H-imidazo[4,5-c]pyridine (Example A83) (175 mg, 0.46 mmol), (+)-2-((3S,4R)-3-fluoro-4-methoxypiperidin-1-yl)-pyrimidin-4-ylamine (Example A65) (100 mg, 0.44 mmol), 2-dicyclohexylphosphino-2',4',6'-triisopropylbiphenyl (42 mg, 0.09 mmol), tris(dibenzylideneacetone)dipalladium(0) (20 mg, 0.02 mmol) and cesium carbonate (288 mg, 0.88 mmol) were suspended in dioxane (5 mL) and the resultant mixture degassed with argon. The reaction mixture was heated at 100° C. for 90 min, cooled to room temperature, diluted with water and the product extracted with ethyl acetate (3×15 mL). The combined organic extracts were washed with brine, dried over anhydrous magnesium sulfate and concentrated in vacuo. The resultant residue was subjected to flash chromatography on silica (solvent gradient: 0-4% methanol in ethyl acetate) to yield the title compound (119 mg, 48%) LCMS (ESI): [M+H]+=568.

Step 2: (R)-1-[6-[2-((3S,4R)-3-Fluoro-4-methoxypiperidin-1-yl)-pyrimidin-4-ylamino]-1-((S)-2,2,2-trifluoro-1-methylethyl)-1H-imidazo[4,5-c]pyridin-2-yl]ethanol

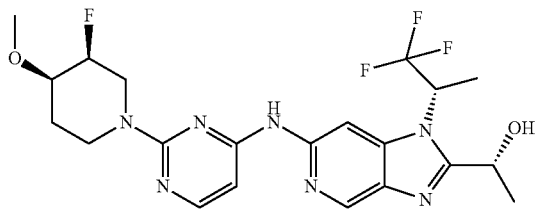 [SMILES: CO[C@@H]1CCN(c2nccc(Nc3cc4c(cn3)nc([C@@H](C)O)n4[C@@H](C)C(F)(F)F)n2)C[C@@H]1F]

[2-((3S,4R)-3-Fluoro-4-methoxypiperidin-1-yl)-pyrimidin-4-yl]-[2-[(R)-1-(tetrahydropyran-2-yloxy)-ethyl]-1-((S)-2,2,2-trifluoro-1-methylethyl)-1H-imidazo[4,5-c]pyridin-6-yl]amine (119 mg, 0.21 mmol) was dissolved in hydrochloric acid in methanol (5 mL, 1.25 M) and the reaction mixture was stirred at room temperature for 2 h. The reaction mixture was diluted with saturated aqueous sodium bicarbonate and the product extracted with ethyl acetate (3×15 mL). The combined organic extracts were washed with brine, dried over anhydrous magnesium sulfate and concentrated in vacuo. The resultant residue was subjected to preparative HPLC to yield the title compound as a white solid (37 mg, 32%). LCMS (ESI): $R_T$=2.57 min, [M+H]+ 484, Method F; $^1$H NMR 400 MHz δ (CDCl$_3$): 8.69 (1H, s), 8.31 (1H, br s), 8.01 (1H, d, J=5.8 Hz), 7.37 (1H, br s), 6.08 (1H, d, J=5.8 Hz), 5.57 (1H, quin, J=7.7 Hz), 5.08 (1H, q, J=9.7 Hz), 4.84-4.79 (0.5H, m), 4.72-4.68 (0.5H, m), 4.50-4.41 (1H, m), 4.23-4.14 (1H, m), 3.84-3.70 (1H, m), 3.63-3.52 (2H, m), 3.47 (3H, s), 2.03-1.92 (1H, m), 1.89 (3H, d, J=6.9 Hz), 1.82 (3H, d, J=6.6 Hz), 1.80-1.74 (1H, m).

Example 291: (3S,4R)-3-Fluoro-1-{4-[2-((R)-1-hydroxyethyl)-1-((S)-2,2,2-trifluoro-1-methylethyl)-1H-imidazo[4,5-c]pyridin-6-ylamino]pyrimidin-2-yl}-piperidin-4-ol

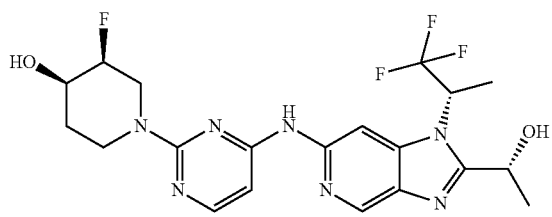 [SMILES: C[C@H](n1c([C@@H](C)O)nc2cnc(Nc3ccnc(N4CC[C@@H](O)[C@@H](F)C4)n3)cc21)C(F)(F)F]

Step 1: (3S,4R)-3-Fluoro-1-{4-[2-[(R)-1-(tetrahydropyran-2-yloxy)ethyl]-1-((S)-2,2,2-trifluoro-1-methylethyl)-1H-imidazo[4,5-c]pyridin-6-ylamino]pyrimidin-2-yl}piperidin-4-ol

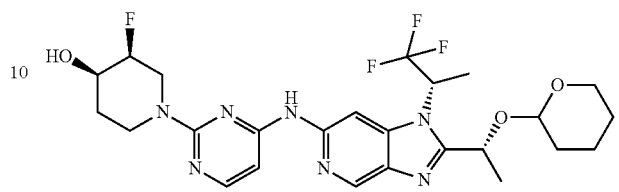

6-Chloro-2-[(R)-1-(tetrahydropyran-2-yloxy)ethyl]-1-((S)-2,2,2-trifluoro-1-methylethyl)-1H-imidazo[4,5-c]pyridine (Example A83) (200 mg, 0.53 mmol), (+)-(3S,4R)-1-(4-aminopyrimidin-2-yl)-3-fluoropiperidin-4-ol (Example A66) (112 mg, 0.53 mmol), 2-dicyclohexylphosphino-2',4',6'-triisopropylbiphenyl (50 mg, 0.119 mmol), tris(dibenzylideneacetone)dipalladium(0) (24 mg, 0.03 mmol) and cesium carbonate (345 mg, 1.06 mmol) were suspended in dioxane (5 mL) and the resultant mixture degassed with argon. The reaction mixture was heated at 100° C. for 1 h. The reaction mixture was diluted with water and the product extracted with ethyl acetate (3×15 mL). The combined organic extracts were washed with brine, dried over anhydrous magnesium sulfate and concentrated in vacuo. The resultant residue was subjected to flash chromatography on silica (solvent gradient: 0-10% methanol in ethyl acetate) to yield the title compound (150 mg, 44%) LCMS (ESI): [M+H]+=554.

Step 2: (3S,4R)-3-Fluoro-1-{4-[2-((R)-1-hydroxyethyl)-1-((S)-2,2,2-trifluoro-1-methylethyl)-1H-imidazo[4,5-c]pyridin-6-ylamino]pyrimidin-2-yl}piperidin-4-ol

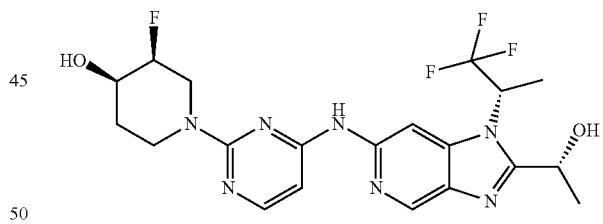

(3S,4R)-3-Fluoro-1-{4-[2-[(R)-1-(tetrahydropyran-2-yloxy)ethyl]-1-((S)-2,2,2-trifluoro-1-methylethyl)-1H-imidazo[4,5-c]pyridin-6-ylamino]pyrimidin-2-yl}piperidin-4-ol (150 mg, 0.27 mmol) was dissolved in hydrochloric acid in methanol (5 mL, 1.25 M) and the reaction mixture was stirred at room temperature for 3 h. The reaction mixture was diluted with saturated aqueous sodium bicarbonate and the product extracted with ethyl acetate (3×15 mL). The combined organic extracts were washed with brine, dried over anhydrous magnesium sulfate and concentrated in vacuo. The resultant residue was subjected to preparative HPLC to yield the title compound as a white solid (53 mg, 39%). LCMS (ESI): $R_T$=2.28 min, [M+H]+ 470, Method F; $^1$H NMR 400 MHz δ (d$_6$-DMSO): 9.80 (1H, br s), 8.63 (1H, s), 8.31 (1H, br s), 7.93 (1H, d, J=5.9 Hz), 6.44 (1H, br s), 5.91 (1H, d, J=6.2 Hz), 5.90-5.76 (1H, m), 5.11-5.04 (1H, m), 4.98 (1H, quin, J=6.6 Hz), 4.68-4.64 (0.5H, m), 4.56-4.44 (1.5H, m), 4.34-4.24 (1H, m), 3.86-3.72 (1H, m), 3.53-3.40 (1H, m), 1.81 (3H, d, J=7.1 Hz), 1.71-1.60 (3H, m), 1.58 (3H, d, J=6.6 Hz).

Example 292: 1-[4-(1-Isopropyl-2-methyl-1H-imidazo[4,5-c]pyridin-6-ylamino)pyrimidin-2-yl]piperidine-3-carbonitrile

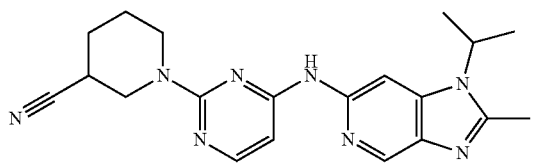 [SMILES: Cc1nc2cnc(Nc3ccnc(N4CCCC(C#N)C4)n3)cc2n1C(C)C]

A microwave reaction vessel was charged with (2-chloropyrimidin-4-yl)-(1-isopropyl-2-methyl-1H-imidazo[4,5-c]pyridin-6-yl)amine (Example 46, Step 7) (0.075 g, 0.248 mmol), (±)-piperidine-3-carbonitrile (0.031 g, 0.285 mmol), triethylamine (70 µL) and isopropyl alcohol (0.5 ml). The reaction mixture was heated under microwave irradiation for 30 min. at 150° C., cooled to room temperature, concentrated in vacuo, triturated with diethyl ether and filtered in vacuo. The solid collected was further purified by reverse phase HPLC to afford the title compound (30.2 mg, 32%). LCMS (ESI): $R_T$ 2.19 min [M+H]$^+$ 377.1, Method F; $^1$H NMR (400 MHz, DMSO-d$_6$) δ 9.71 (1H, s), 8.47 (1H, s), 8.25 (1H, s), 7.94 (1H, d, J=5.7 Hz), 6.45 (1H, d, J=5.7 Hz), 4.72-4.65 (1H, m), 4.13-4.03 (1H, m), 3.93-3.85 (2H, m), 3.69-3.62 (1H, m), 3.08-3.03 (1H, m), 2.52 (3H, s), 1.97-1.82 (2H, m), 1.70-1.55 (2H, m), 2.53, 2.51 (6H, 2×d, J=6.7 Hz).

Example 293: N$^6$-[2-(1-Cyclopropanesulfonyl-1H-pyrazol-4-yl)pyrimidin-4-yl]-1-isopropyl-N$^2$-methyl-1H-imidazo[4,5-c]pyridine-2,6-diamine

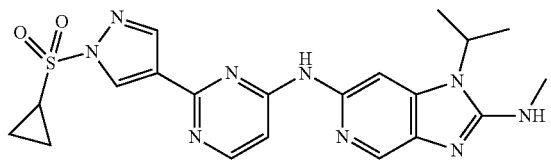 [SMILES: CNc1nc2cnc(Nc3ccnc(-c4cnn(S(=O)(=O)C5CC5)c4)n3)cc2n1C(C)C]

Step 1: (6-Bromo-1-isopropyl-1H-imidazo[4,5-c]pyridin-2-yl)methylamine

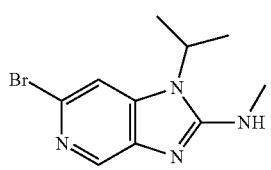

A reaction vessel was charged with 6-bromo-N$^4$-isopropylpyridine-3,4-diamine (Example 12, Step 2) (600 mg, 2.61 mmol), methyl isothiocyanate (286 mg, 3.91 mmol) and dissolved in acetonitrile (30 ml). The reaction mixture was heated under reflux for 24 h. The reaction mixture was allowed to cool to room temperature and (benzotriazol-1-yloxy)tris(dimethylamino)phosphonium hexafluorophosphate (1.72 g, 3.91 mmol) and 1,8-diazabicyclo[5.4.0]undec-7-ene (780 µL, 5.21 mmol) were added. The reaction mixture was heated under reflux for 24 h. The reaction mixture was allowed to cool to room temperature and was partitioned between EtOAc and distilled water. The organic layer was separated, dried over anhydrous magnesium sulfate and concentrated in vacuo. The residue was purified by chromatography on silica (solvent: 10% methanol in dichloromethane) to afford the title compound (646.1 mg, 92%). LCMS (ESI): [M+H]$^+$ 370.1.

Step 2: N$^6$-[2-(1-Cyclopropanesulfonyl-1H-pyrazol-4-yl)pyrimidin-4-yl]-1-isopropyl-N$^2$-methyl-1H-imidazo[4,5-c]pyridine-2,6-diamine

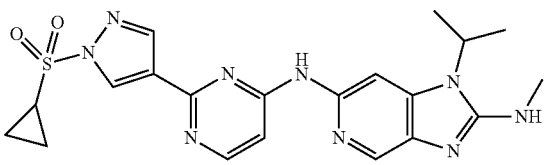 [SMILES: CNc1nc2cnc(Nc3ccnc(-c4cnn(S(=O)(=O)C5CC5)c4)n3)cc2n1C(C)C]

A reaction vessel was charged with (6-bromo-1-isopropyl-1H-imidazo[4,5-c]pyridin-2-yl)methylamine (100 mg, 0.371 mmol), 2-(1-cyclopropanesulfonyl-1H-pyrazol-4-yl)pyrimidin-4-ylamine (Example A62) (98.6 mg, 0.371 mmol), 4,5-bis(diphenylphosphino)-9,9-dimethylxanthene (42.9 mg, 0.074 mmol), tris(dibenzylideneacetone)dipalladium(0) (17.0 mg, 0.019 mmol), cesium carbonate (242.0 mg, 0.743 mmol) and dioxane (4.0 ml). The reaction mixture was degassed under argon and heated under reflux for 24 h. The reaction mixture was allowed to cool to room temperature, filtered in vacuo and the filtrate partitioned between EtOAc and distilled water. The organic layer was separated, dried over anhydrous magnesium sulfate and concentrated in vacuo. The residue was purified by chromatography on silica (solvent gradient: 0-10% methanol in dichloromethane) and reverse phase HPLC to afford the title compound (32 mg, 19%). LCMS (ESI): $R_T$ 2.63 min, [M+H]$^+$ 454.2, Method F; $^1$H NMR (400 MHz, DMSO-d$_6$) δ 9.94 (1H, s), 8.63 (1H, s), 8.44 (1H, s), 8.34 (1H, d, J=5.9 Hz), 8.20 (1H, s), 8.18 (1H, s), 8.05 (1H, brs), 7.29 (1H, brs), 6.82 (1H, q, J=4.6 Hz), 4.61 (1H, sept, J=6.9 Hz), 3.24-3.17 (1H, m), 2.92 (3H, d, J=4.5 Hz), 1.49 (6H, d, J=7.0 Hz), 1.31-1.17 (4H, m).

Example 294: (±)-1-{6-[2-(1-Cyclopropanesulfonyl-1H-pyrazol-4-yl)pyrimidin-4-ylamino]-1-isopropyl-1H-imidazo[4,5-c]pyridin-2-yl}ethanol

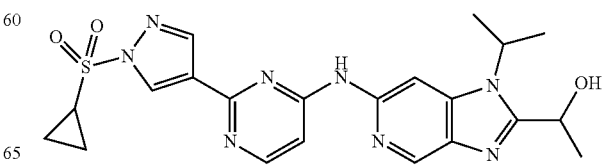

Step 1: (2-Chloropyrimidin-4-yl)-{1-isopropyl-2-[1-(tetrahydropyran-2-yloxy)ethyl]-1H-imidazo[4,5-c]pyridin-6-yl}amine

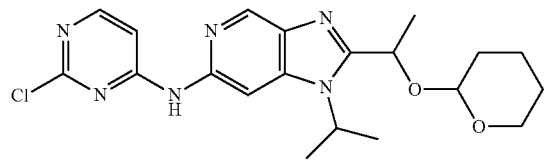 [SMILES: CC(OC1CCCCO1)c1nc2cnc(Nc3ccnc(Cl)n3)cc2n1C(C)C]

A reaction vessel was charged with 6-bromo-1-isopropyl-2-[1-(tetrahydropyran-2-yloxy)-ethyl]-1H-imidazo[4,5-c]pyridine (Example A72) (788.3 mg, 2.11 mmol), 2-chloropyrimidin-4-ylamine (274.0 mg, 2.11 mmol), 4,5-bis(diphenylphosphino)-9,9-dimethylxanthene (244.6 mg, 0.423 mmol), tris(dibenzylideneacetone)dipalladium(0) (96.7 mg, 0.106 mmol), cesium carbonate (1.38 g, 4.23 mmol) and dissolved in dioxane (21.0 ml). The reaction mixture was degassed and placed under argon. The reaction mixture was stirred at room temperature and was heated under reflux for 24 h. The reaction mixture was allowed to cool to room temperature, filtered in vacuo and the filtrate partitioned between EtOAc and distilled water. The organic layer was separated, dried over anhydrous magnesium sulfate and concentrated in vacuo. The residue was purified by chromatography on silica (solvent gradient: 0-10% methanol in EtOAc) to afford the title compound (208.0 mg, 21%). LCMS (ESI): [M+H]+ 417.9.

Step 2: [2-(1-Cyclopropanesulfonyl-1H-pyrazol-4-yl)-pyrimidin-4-yl]-{1-isopropyl-2-[1-(tetrahydropyran-2-yloxy)ethyl]-1H-imidazo[4,5-c]pyridin-6-yl}amine

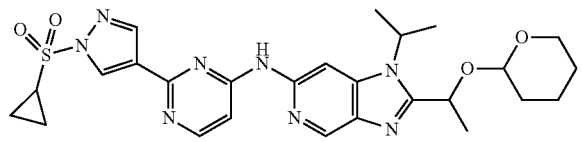 [SMILES: CC(OC1CCCCO1)c1nc2cnc(Nc3ccnc(-c4cnn(S(=O)(=O)C5CC5)c4)n3)cc2n1C(C)C]

A reaction vessel was charged with (2-chloropyrimidin-4-yl)-{1-isopropyl-2-[1-(tetrahydropyran-2-yloxy)ethyl]-1H-imidazo[4,5-c]pyridin-6-yl}amine (208 mg, 0.5 mmol), 1-cyclopropanesulfonyl-4-(4,4,5,5-tetramethyl-[1,3,2]dioxaborolan-2-yl)-1H-pyrazole (Example 51, Step 6) (179 mg, 0.6 mmol), tetrakis(triphenylphosphine)palladium(0) (57.8 mg, 0.05 mmol), cesium carbonate (212.0 mg, 0.65 mmol), dioxane (7.0 ml) and distilled water (30 µl). The reaction mixture was degassed and placed under argon. The reaction mixture was heated under reflux for 24 h, allowed to cool to room temperature, filtered and the filtrate partitioned between EtOAc and distilled water. The organic layer was separated, dried over anhydrous magnesium sulfate and concentrated in vacuo. The residue was purified by chromatography on silica (solvent gradient: 0-10% methanol in dichloromethane) to afford the title compound (143.5 mg, 52%). LCMS (ESI): [M+H]+ 553.7.

Step 3: (±)-1-{6-[2-(1-Cyclopropanesulfonyl-1H-pyrazol-4-yl)pyrimidin-4-ylamino]-1-isopropyl-1H-imidazo[4,5-c]pyridin-2-yl}ethanol

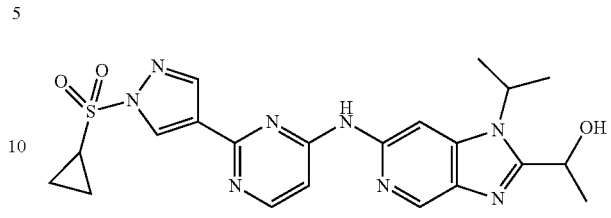

A reaction vessel was charged with [2-(1-cyclopropanesulfonyl-1H-pyrazol-4-yl)pyrimidin-4-yl]-{1-isopropyl-2-[1-(tetrahydropyran-2-yloxy)ethyl]-1H-imidazo[4,5-c]pyridin-6-yl}amine (143.5 mg, 0.259 mmol) and HCl (1.25 M in methanol) (5 ml) and stirred at room temperature for 2 h. The reaction mixture was partitioned between EtOAc and saturated sodium hydrogen carbonate. The organic layer was separated, dried over anhydrous magnesium sulfate and concentrated in vacuo. The residue was purified by reverse phase HPLC to afford the title compound (121.7 mg, quant.). LCMS (ESI): $R_T$ 2.88 min, [M+H]+ 469.2, Method F; $^1$H NMR (400 MHz, DMSO-$d_6$) δ 10.14 (1H, s), 8.62 (2H, s), 8.42 (1H, s), 8.40 (1H, bs), 8.34 (1H, d, J=6.1 Hz), 7.21-7.19 (1H, m), 5.67 (1H, d, J=4.5 Hz), 5.13-5.06 (1H, m), 5.02-4.99 (1H, m), 3.22-3.17 (1H, m), 1.60, 1.58 (6H, 2×d, J=6.4 Hz), 1.55 (3H, d, J=6.8 Hz), 1.30-1.17 (4H, m).

Example 295: [2-(2-Ethylaminothiazol-5-yl)pyrimidin-4-yl](1-isopropyl-2-methyl-1H-imidazo[4,5-c]pyridin-6-yl)amine

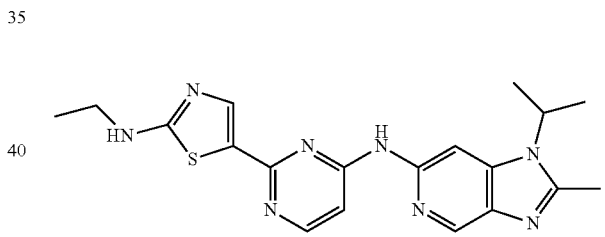

Step 1: Ethyl-(5-(tributylstannanyl)thiazol-2-yl)carbamic acid tert-butyl ester

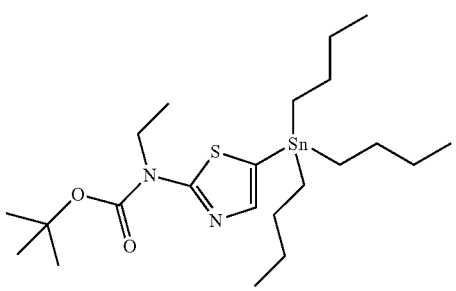 [SMILES: CCC[CH2][Sn]([CH2]CCC)([CH2]CCC)[c]1cnc(N(CC)C(=O)OC(C)(C)C)s1]

A reaction vessel was charged with diisopropylamine (584.2 µl, 4.13 mmol) and tetrahydrofuran (11 ml). The reaction mixture was cooled to −40° C. N-Butyllithium (2.5M in hexanes) (1.65 ml, 4.13 mmol) was added dropwise and the reaction mixture stirred at between −40 and −20° C. for 30 min. The reaction mixture was cooled to −78° C. and a solution of ethylthiazol-2-yl-carbamic acid tert-butyl ester (786.6 mg, 3.44 mmol) in tetrahydrofuran (11 ml) was added. The mixture was stirred at −78° C. for 40 min and a solution of tributyltin chloride (1.12 ml, 4.13 mmol) in tetrahydrofuran (5 ml) was added. The reaction mixture was allowed to warm to room temperature over 2 h. Saturated ammonium chloride solution was added and the reaction mixture was partitioned between water and EtOAc. The combined organic layers were washed with brine, dried over anhydrous magnesium sulfate and concentrated in vacuo to afford the title compound (1.78 g, quant.). $^1$H NMR (400 MHz, CDCl$_3$) δ: 7.28 (1H, s), 4.12 (2H, q, J=7.3 Hz), 1.59 (9H, s), 1.29 (3H, t, J=7.3 Hz).

Step 2: Ethyl-{5-[4-(1-isopropyl-2-methyl-1H-imidazo[4,5-c]pyridin-6-ylamino)pyrimidin-2-yl]-thiazol-2-yl}carbamic acid tert-butyl ester

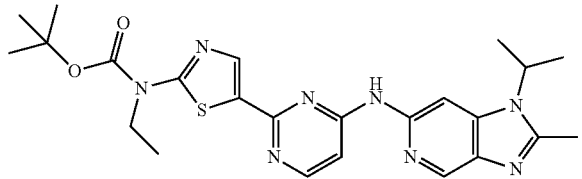 [SMILES: CCN(C(=O)OC(C)(C)C)c1ncc(-c2nccc(Nc3cc4c(cn3)nc(C)n4C(C)C)n2)s1]

A reaction vessel was charged with (2-chloropyrimidin-4-yl)-(1-isopropyl-2-methyl-1H-imidazo[4,5-c]pyridin-6-yl)amine (180 mg, 0.594 mmol), ethyl-(5-tributylstannanylthiazol-2-yl)carbamic acid tert-butyl ester (460.4 mg, 0.892 mmol), tetrakis(triphenylphosphine)palladium(0) (68.7 mg, 0.059 mmol), dioxane (1.8 ml) and toluene (1.8 ml). The reaction mixture was degassed, placed under argon and heated under microwave irradiation at 140° C. for 1 h. The reaction mixture was cooled to room temperature, diluted with dichloromethane (30 ml), treated with potassium fluoride (1 g, 17 mmol), and stirred for 10 min at room temperature. The reaction mixture was purified by chromatography on silica (solvent gradient: 0-10% methanol in EtOAc) to afford the title compound (309.1 mg, quant). LCMS (ESI): [M+H]$^+$ 495.6.

Step 3: [2-(2-Ethylaminothiazol-5-yl)pyrimidin-4-yl](1-isopropyl-2-methyl-1H-imidazo[4,5-c]pyridin-6-yl)amine

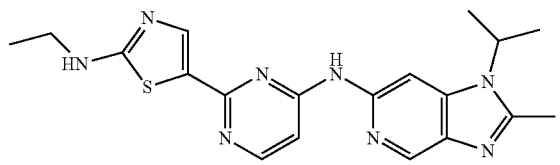 [SMILES: CCNc1ncc(-c2nccc(Nc3cc4c(cn3)nc(C)n4C(C)C)n2)s1]

A reaction vessel was charged with ethyl-{5-[4-(1-isopropyl-2-methyl-1H-imidazo[4,5-c]pyridin-6-ylamino)pyrimidin-2-yl]thiazol-2-yl}carbamic acid tert-butyl ester (294 mg, 0.594 mmol) and dichloromethane (4 ml). TFA (1 ml) was added and the reaction mixture was stirred at room temperature for 1 h. The reaction mixture was partitioned between dichloromethane and saturated sodium hydrogen carbonate. The organic layer was separated, dried over anhydrous magnesium sulfate and concentrated in vacuo. The residue was purified by reverse phase HPLC to afford the title compound (85.4 mg, 36%). LCMS (ESI): RT 2.44 min, [M+H]$^+$ 395.0, Method F; $^1$H NMR (400 MHz, DMSO-d$_6$) δ 9.95 (1H, s), 8.50 (1H, d, J=0.8 Hz), 8.33 (1H, bs), 8.17 (1H, d, J=6.1 Hz), 8.10 (1H, t, J=5.4 Hz), 7.84 (1H, s), 7.00-6.96 (1H, m), 4.75-4.68 (1H, m), 3.26-3.21 (2H, m), 2.53 (3H, s), 1.61 (6H, d, J=6.8 Hz), 1.17 (3H, t, J=7.0 Hz).

Example 296: cis-3-Fluoro-1-{4-[2-((R)-1-hydroxyethyl)-1-((S)-2,2,2-trifluoro-1-methylethyl)-1H-imidazo[4,5-c]pyridin-6-ylamino]pyrimidin-2-yl}piperidin-4-ol

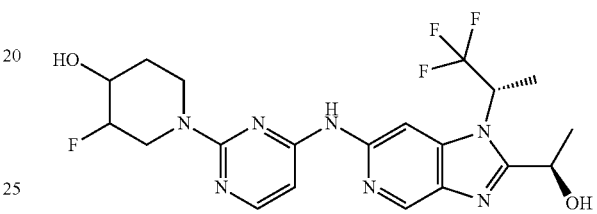

Step 1: cis-3-Fluoro-1-{4-[2-[(R)-1-(tetrahydropyran-2-yloxy)ethyl]-1-((S)-2,2,2-trifluoro-1-methylethyl)-1H-imidazo[4,5-c]pyridin-6-ylamino]pyrimidin-2-yl}piperidin-4-ol

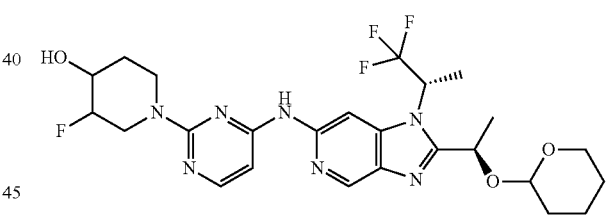

A reaction vessel was charged with 6-chloro-2-[(R)-1-(tetrahydropyran-2-yloxy)ethyl]-1-((S)-2,2,2-trifluoro-1-methylethyl)-1H-imidazo[4,5-c]pyridine (Example A83) (310.3 mg, 0.904 mmol), (±)-cis-1-(4-aminopyrimidin-2-yl)-3-fluoropiperidin-4-ol (Example A85) (190 mg, 1.16 mmol), 2-dicyclohexylphosphino-2',4',6'-triisopropylbiphenyl (78.2 mg, 0.164 mmol), tris(dibenzylideneacetone)dipalladium(0) (37.6 mg, 0.041 mmol), cesium carbonate (535 mg, 1.64 mmol) and dioxane (6.5 ml). The reaction mixture was degassed, placed under argon and heated at 110° C. for 5 h. The reaction mixture was allowed to cool to room temperature, filtered in vacuo and the filtrate partitioned between EtOAc and distilled water. The organic layer was separated, dried over anhydrous magnesium sulfate and concentrated in vacuo. The residue was purified by chromatography on silica (solvent gradient: 0-10% methanol in EtOAc) to afford the title compound (222.1 mg, 49%) as a mixture of isomers. LCMS (ESI): [M+H]$^+$ 554.6.

Step 2: cis-3-Fluoro-1-{4-[2-((R)-1-hydroxyethyl)-1-((S)-2,2,2-trifluoro-1-methylethyl)-1H-imidazo[4,5-c]pyridin-6-ylamino]pyrimidin-2-yl}piperidin-4-ol

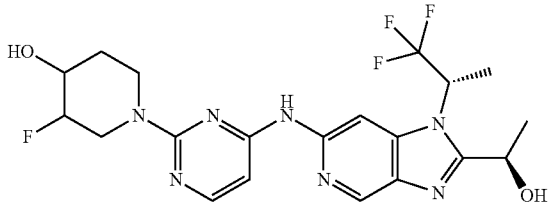 [SMILES: C[C@H](n1c([C@@H](C)O)nc2cnc(Nc3ccnc(N4CCC(O)C(F)C4)n3)cc21)C(F)(F)F]

A reaction vessel was charged with 3-fluoro-1-{4-[2-[(R)-1-(tetrahydropyran-2-yloxy)-ethyl]-1-((S)-2,2,2-trifluoro-1-methylethyl)-1H-imidazo[4,5-c]pyridin-6-ylamino]pyrimidin-2-yl}piperidin-4-ol (222.1 mg, 0.399 mmol) and HCl (1.25 M in methanol) (9 ml) and stirred at room temperature for 1 h. The reaction mixture was partitioned between EtOAc and saturated sodium hydrogen carbonate. The organic layer was separated, dried over anhydrous magnesium sulfate and concentrated in vacuo. The residue was purified by chromatography on silica (solvent gradient: 0-10% methanol in EtOAc) to afford the title compound as a mixture of 2 diastereoisomers (120.4 mg, 64%). LCMS (ESI): $R_T$ 2.24 min, [M+H]$^+$ 470.2, Method F; $^1$H NMR (400 MHz, CDCl$_3$) δ 8.72 (2H, 2×s), 8.36, 8.34 (2H, 2×s), 8.05 (2H, 2×d, J=5.7 Hz), 7.38 (2H, 2×s), 6.11, 6.09 (2H, 2×d, J=5.7 Hz), 5.63-5.56 (2H, m), 5.14-5.08 (2H, m), 4.82-4.75 (1H, m), 4.70-4.63 (1H, m), 4.53-4.46 (1H, m), 4.35-4.20 (2H, m), 4.13-3.96 (4H, m), 3.89-3.74 (2H, m), 3.64-3.58 (1H, m), 2.22 (2H, 2×d, J=7.3 Hz), 2.09, 2.08 (2H, 2×d, J=6.6 Hz), 2.00-1.85 (4H, m), 1.92 (6H, 2×d, J=7.1 Hz), 1.85 (6H, 2×d, J=6.7 Hz).

Example 297: (R)-1-[6-[2-(cis-3-Fluoro-4-methoxypiperidin-1-yl)pyrimidin-4-ylamino]-1-((R)-2,2,2-trifluoro-1-methylethyl)-1H-imidazo[4,5-c]pyridin-2-yl]ethanol

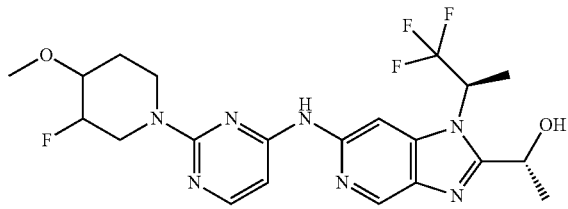 [SMILES: COC1CCN(c2nccc(Nc3cc4c(cn3)nc([C@@H](C)O)n4[C@H](C)C(F)(F)F)n2)CC1F]

Step 1: [2-(cis-3-Fluoro-4-methoxypiperidin-1-yl)-pyrimidin-4-yl]-[2-[(R)-1-(tetrahydropyran-2-yloxy)ethyl]-1-((R)-2,2,2-trifluoro-1-methylethyl)-1H-imidazo[4,5-c]pyridin-6-yl]amine

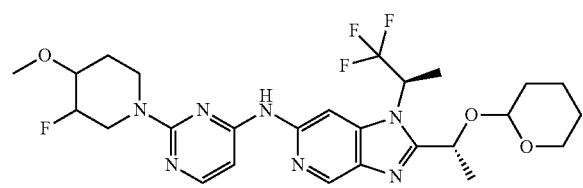 [SMILES: COC1CCN(c2nccc(Nc3cc4c(cn3)nc([C@@H](C)OC3CCCCO3)n4[C@H](C)C(F)(F)F)n2)CC1F]

A reaction vessel was charged with 6-chloro-2-[(R)-1-(tetrahydropyran-2-yloxy)ethyl]-1-((R)-2,2,2-trifluoro-1-methylethyl)-1H-imidazo[4,5-c]pyridine (Example A61) (400 mg, 1.058 mmol), (±)-cis-2-(3-fluoro-4-methoxypiperidin-1-yl)pyrimidin-4-ylamine (Example A84) (264 mg, 1.16 mmol), 2-dicyclohexylphosphino-2',4',6'-triisopropylbiphenyl (101 mg, 0.212 mmol), tris(dibenzylideneacetone)dipalladium(0) (48.5 mg, 0.052 mmol), cesium carbonate (690 mg, 2.12 mmol) and dioxane (8 ml). The reaction mixture was degassed, placed under argon and heated at 110° C. for 3 h. The reaction mixture was allowed to cool to room temperature, filtered in vacuo and the filtrate partitioned between EtOAc and distilled water. The organic layer was separated, dried over anhydrous magnesium sulfate and concentrated in vacuo. The residue was purified by chromatography on silica (solvent gradient: 0-10% methanol in EtOAc) to afford the title compound (398.5 mg, 66%). LCMS (ESI): [M+H]$^+$ 568.6.

Step 2: (R)-1-[6-[2-(cis-3-Fluoro-4-methoxypiperidin-1-yl)pyrimidin-4-ylamino]-1-((R)-2,2,2-trifluoro-1-methylethyl)-1H-imidazo[4,5-c]pyridin-2-yl]ethanol

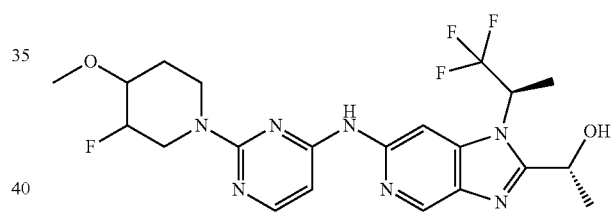

A reaction vessel was charged with [2-(cis-3-fluoro-4-methoxypiperidin-1-yl)pyrimidin-4-yl]-[2-[(R)-1-(tetrahydropyran-2-yloxy)ethyl]-1-((R)-2,2,2-trifluoro-1-methylethyl)-1H-imidazo[4,5-c]pyridin-6-yl]amine (398.5 mg, 0.702 mmol) and HCl (1.25 M in methanol) (16 ml) and stirred at room temperature for 1 h. The reaction mixture was partitioned between EtOAc and saturated sodium hydrogen carbonate. The organic layer was separated, dried over anhydrous magnesium sulfate and concentrated in vacuo. The residue was purified by chromatography on silica (solvent gradient: 0-10% methanol in EtOAc) to afford the title compound as an inseparable mixture of 2 diastereoisomers (214.4 mg, 63%). LCMS (ESI): $R_T$ 2.48 min, [M+H]$^+$ 484.1, Method F; $^1$H NMR (400 MHz, CDCl$_3$) δ 8.70 (2H, 2×d, J=1.1 Hz), 8.36, 8.32 (2H, 2×s), 8.06, 8.05 (2H, 2×d, J=5.6 Hz), 7.38, 7.37 (2H, 2×s), 6.11, 6.09 (2H, 2×d, J=5.7 Hz), 5.53-5.43 (2H, m), 5.20-5.12 (2H, m), 4.91-4.82 (1H, m), 4.79-4.70 (1H, m), 4.66-4.58 (1H, m), 4.50-4.42 (1H, m), 4.37-4.28 (1H, m), 4.23-4.15 (1H, m), 3.88-3.53 (6H, m), 3.51, 3.50 (6H, 2×s), 2.75 (2H, bs), 2.05-1.95 (2H, m), 1.91, 1.89 (6H, 2×d, J=7.1 Hz), 1.86-1.80 (2H, m), 1.77, 1.75 (6H, 2×d, J=6.7 Hz).

Example 298: 3-[4-(1-Isopropyl-2-methyl-1H-imidazo[4,5-c]pyridin-6-ylamino)pyrimidin-2-ylamino]propionamide

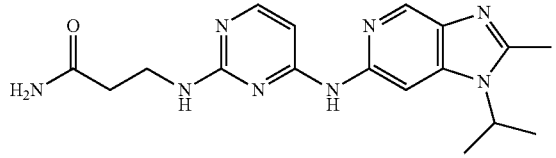 [SMILES: Cc1nc2cnc(Nc3ccnc(NCCC(N)=O)n3)cc2n1C(C)C]

Step 1: 3-[4-(1-Isopropyl-2-methyl-1H-imidazo[4,5-c]pyridin-6-ylamino)pyrimidin-2-ylamino]propionic acid tert-butyl ester

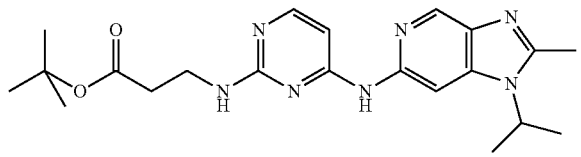 [SMILES: Cc1nc2cnc(Nc3ccnc(NCCC(=O)OC(C)(C)C)n3)cc2n1C(C)C]

A mixture of N-(2-chloropyrimidin-4-yl)-1-isopropyl-2-methyl-1H-imidazo[4,5-c]pyridin-6-amine (Example 46, Step 7) (55.7 mg, 0.184 mmol), 3-aminopropionic acid tert-butyl ester hydrochloride (66.9 mg, 0.368 mmol) and N,N-diisopropylethylamine (0.127 mL, 0.736 mmol) in isopropanol (3 mL) was heated at 150° C. under microwave irradiation for 5 h. The reaction mixture was concentrated in vacuo. The resulting residue was partitioned between dichloromethane and aqueous saturated sodium bicarbonate. The aqueous phase was extracted with additional dichloromethane, and the combined organic extracts were dried over anhydrous sodium sulfate and concentrated in vacuo. The residue was purified by chromatography (silica, gradient 2-10% 2M ammonia in methanol in dichloromethane) to afford the title compound as a colourless gum (51.1 mg, 67%). LCMS (ESI): [M+H]$^+$ 412.

Step 2: 3-[4-(1-Isopropyl-2-methyl-1H-imidazo[4,5-c]pyridin-6-ylamino)pyrimidin-2-ylamino]propionic acid

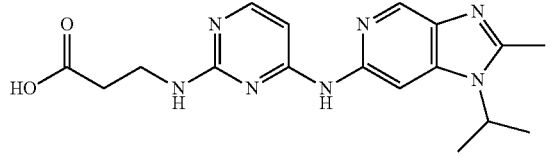 [SMILES: Cc1nc2cnc(Nc3ccnc(NCCC(=O)O)n3)cc2n1C(C)C]

To a solution of 3-[4-(1-isopropyl-2-methyl-1H-imidazo[4,5-c]pyridin-6-ylamino)pyrimidin-2-ylamino]propionic acid tert-butyl ester (51 mg, 0.124 mmol) in dichloromethane (1 mL) at 0° C. was added TFA (1.5 mL). The mixture was allowed to warm to room temperature and stirred for 2 h. Toluene was added and the reaction mixture was concentrated in vacuo (2×). The residue was dissolved in acetonitrile and loaded on to an SCX cartridge. The cartridge was washed successively with acetonitrile and 5% aqueous ammonia in acetonitrile, then eluted with 2M ammonia in methanol to give the title compound as a colorless solid (39.3 mg, 85%). LCMS (ESI): [M+H]$^+$ 356.

Step 3: 3-[4-(1-Isopropyl-2-methyl-1H-imidazo[4,5-c]pyridin-6-ylamino)pyrimidin-2-ylamino]propionamide

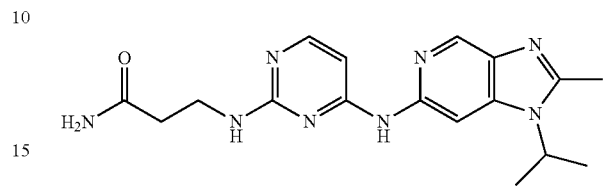

To a mixture of 3-[4-(1-isopropyl-2-methyl-1H-imidazo[4,5-c]pyridin-6-ylamino)pyrimidin-2-ylamino]propionic acid (39 mg, 0.105 mmol), ammonium chloride (5.6 mg, 0.105 mmol) and N,N-diisopropylethylamine (0.055 mL, 0.317 mmol) in dimethylformamide (1 mL) at 0° C. was added 1-[bis(dimethylamino)methylene]-1H-1,2,3-triazolo[4,5-b]pyridinium 3-oxid hexafluorophosphate (60.2 mg, 0.158 mmol) portion-wise over 5 min. The mixture was stirred at room temperature for 1.5 h, then concentrated in vacuo. The resulting residue was purified by chromatography (silica, gradient 3-21% 2M ammonia in methanol in dichloromethane) followed by mass-directed auto purification to afford the title compound as a colorless solid (7.2 mg, 19%). LCMS (ESI): R$_T$ 1.70 min, [M+H]$^+$ 355.1, Method F; $^1$H NMR (400 MHz, DMSO-d$_6$) δ 9.59 (1H, br s), 8.48 (1H, s), 8.38 (1H, br s), 7.88 (1H, d, J=5.7 Hz), 7.33 (1H, br s), 6.83 (1H, br s), 6.48 (1H, br s), 4.71 (1H, septet, J=6.9 Hz), 3.58-3.53 (2H, m), 2.56 (3H, s), 2.39 (2H, t, J=7.1 Hz), 1.55 (6H, d, J=6.9 Hz).

Example 299: 2-{[4-(1-Isopropyl-2-methyl-1H-imidazo[4,5-c]pyridin-6-ylamino)pyrimidin-2-ylamino]methyl}-2-methylbutyric acid

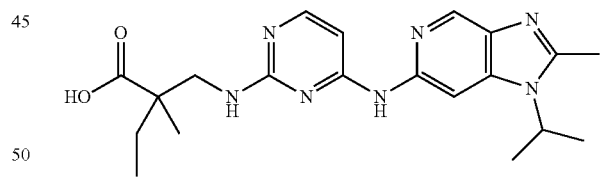 [SMILES: CCOC(=O)C(C)(CC)CNc1nccc(Nc2cc3c(cn2)nc(C)n3C(C)C)n1]

Step 1: 2-{[4-(1-Isopropyl-2-methyl-1H-imidazo[4,5-c]pyridin-6-ylamino)pyrimidin-2-ylamino]methyl}-2-methylbutyric acid ethyl ester

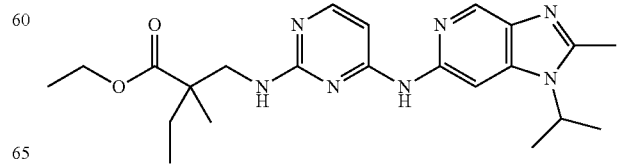

A mixture of N-(2-chloropyrimidin-4-yl)-1-isopropyl-2-methyl-1H-imidazo[4,5-c]pyridin-6-amine (Example 46, Step 7) (150 mg, 0.495 mmol), 2-aminomethyl-2-methylbutyric acid ethyl ester (WO2009/067547) (237 mg, 1.49 mmol) and N,N-diisopropylethylamine (0.172 mL, 1.0 mmol) in isopropanol (5 mL) was heated at 150° C. under microwave irradiation for 8 h. The reaction mixture was concentrated in vacuo. The resulting residue was partitioned between dichloromethane and saturated aqueous sodium carbonate. The aqueous phase was extracted with additional dichloromethane, and the combined organic extracts were dried over anhydrous sodium sulfate and concentrated in vacuo. The residue was purified by chromatography on silica (solvent gradient: 2-10% 2M methanolic ammonia in dichloromethane) to afford the title compound as a colorless gum (quantitative). LCMS (ESI): [M+H]$^+$ 426.

Step 2: 2-{[4-(1-Isopropyl-2-methyl-1H-imidazo[4,5-c]pyridin-6-ylamino)pyrimidin-2-ylamino]methyl}-2-methylbutyric acid

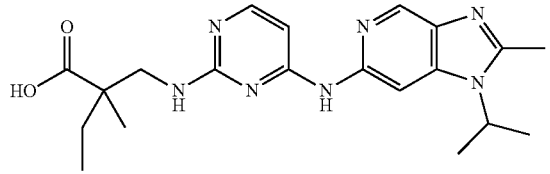 [SMILES: CCC(C)(CNc1nccc(Nc2cc3c(cn2)nc(C)n3C(C)C)n1)C(=O)O]

To a solution of 2-{[4-(1-isopropyl-2-methyl-1H-imidazo[4,5-c]pyridin-6-ylamino)pyrimidin-2-ylamino]methyl}-2-methylbutyric acid ethyl ester (0.196 mg, 0.495 mmol) in THF (3 mL) and methanol (0.75 mL) was added a solution of lithium hydroxide monohydrate (62.4 mg, 1.49 mmol) in water (1.5 mL). The mixture was heated at 120° C. under microwave irradiation for 3 h, then concentrated in vacuo. The resulting residue was dissolved in water (5 mL) and treated with 1M HCl (1.5 mL). The resulting precipitate was collected by filtration, washed with water and dried in vacuo. Further purification by chromatography on silica (solvent gradient: 5-40% 2M methanolic ammonia in dichloromethane) gave the title compound as a white solid (123 mg, 63%, 2 steps). LCMS (ESI): R$_T$ 2.27 min, [M+H]$^+$ 398.2, Method F; $^1$H NMR (400 MHz, DMSO-d$_6$) δ 9.56 (1H, s), 8.49 (1H, s), 8.29 (1H, br s), 7.88 (1H, d, J=5.7 Hz), 6.53 (1H, d, J=5.4 Hz), 6.13 (1H, br s), 4.72 (1H, septet, J=6.9 Hz), 3.60 (1H, dd, J=13.1, 5.9 Hz), 3.48 (1H, dd, J=13.2, 5.6 Hz), 2.56 (3H, s), 1.70-1.61 (1H, m), 1.56 (6H, d, J=6.9 Hz), 1.53-1.44 (1H, m), 1.10 (3H, s), 0.83 (3H, t, J=7.5 Hz).

Example 300: 2-{[4-(1-Isopropyl-2-methyl-1H-imidazo[4,5-c]pyridin-6-ylamino)pyrimidin-2-ylamino]methyl}-2-methylbutyramide

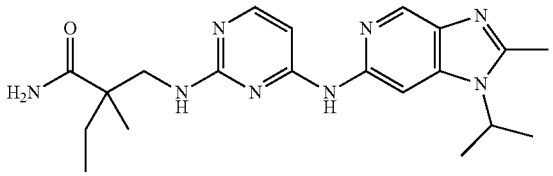 [SMILES: CCC(C)(CNc1nccc(Nc2cc3c(cn2)nc(C)n3C(C)C)n1)C(N)=O]

The title compound (27.6 mg, 67%) was prepared from 2-{[4-(1-isopropyl-2-methyl-1H-imidazo[4,5-c]pyridin-6-ylamino)pyrimidin-2-ylamino]methyl}-2-methylbutyric acid (Example 299, Step 1) (41 mg, 0.10 mmol) according to a procedure analogous to that described for Example 298, Step 3. LCMS (ESI): R$_T$ 2.05 min, [M+H]$^+$ 397.1, Method F; $^1$H NMR (400 MHz, DMSO-d$_6$) δ 9.57 (1H, s), 8.48 (1H, s), 8.30 (1H, br s), 7.88 (1H, d, J=5.6 Hz), 7.18 (1H, br s), 7.00 (1H, br s), 6.52 (1H, br d, J=6.5 Hz), 5.93 (1H, br s), 4.72 (1H, septet, J=6.9 Hz), 3.54 (1H, dd, J=13.0, 5.9 Hz), 3.41 (1H, dd, J=13.0, 5.8 Hz), 2.56 (3H, s), 1.69-1.59 (1H, m), 1.57 (6H, d, J=6.9 Hz), 1.52-1.43 (1H, m), 1.10 (3H, s), 0.81 (3H, t, J=7.4 Hz).

Example 301: 2-Hydroxy-3-[4-(1-isopropyl-2-methyl-1H-imidazo[4,5-c]pyridin-6-ylamino)pyrimidin-2-ylamino]propionamide

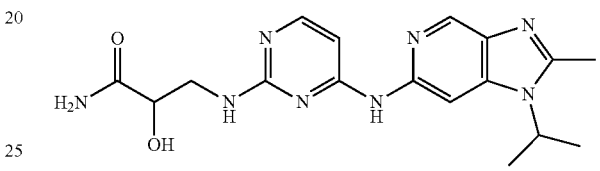

Step 1: 2-Hydroxy-3-[4-(1-isopropyl-2-methyl-1H-imidazo[4,5-c]pyridin-6-ylamino)pyrimidin-2-ylamino]propionic acid ethyl ester and 2-Hydroxy-3-[4-(1-isopropyl-2-methyl-1H-imidazo[4,5-c]pyridin-6-ylamino)pyrimidin-2-ylamino]propionic acid isopropyl ester

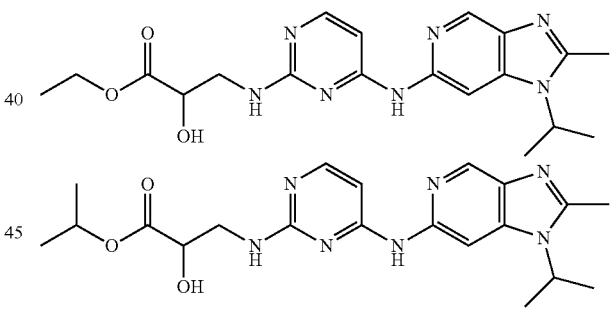

A mixture of N-(2-chloropyrimidin-4-yl)-1-isopropyl-2-methyl-1H-imidazo[4,5-c]pyridin-6-amine (Example 46, Step 7) (150 mg, 0.495 mmol), 3-amino-2-hydroxypropionic acid ethyl ester hydrochloride (J. Med. Chem., 2008, 15, 5387) (253 mg, 1.49 mmol) and N,N-diisopropylethylamine (0.516 mL, 2.98 mmol) in isopropanol (5 mL) was heated at 150° C. under microwave irradiation for 9 h. The reaction mixture was concentrated in vacuo. The resulting residue was partitioned between 8% methanol in dichloromethane and saturated aqueous sodium bicarbonate. The aqueous phase was extracted with additional dichloromethane, and the combined organic extracts were washed with water, then dried over anhydrous sodium sulfate and concentrated in vacuo. The residue was purified by chromatography on silica (solvent gradient: 2-12% 2M methanolic ammonia in dichloromethane) to afford a mixture of the title compounds as a colorless gum (75.5 mg, 38%). LCMS (ESI): [M+H]$^+$ 400 & 414.

Step 2: 2-Hydroxy-3-[4-(1-isopropyl-2-methyl-1H-imidazo[4,5-c]pyridin-6-ylamino)pyrimidin-2-ylamino]propionic acid

To a solution of the mixture of 2-hydroxy-3-[4-(1-isopropyl-2-methyl-1H-imidazo[4,5-c]pyridin-6-ylamino)pyrimidin-2-ylamino]propionic acid ethyl and isopropyl esters (75.5 mg, 0.189 mmol) in THF (1 mL) and methanol (0.25 mL) was added a solution of lithium hydroxide monohydrate (23.8 mg, 0.566 mmol) in water (0.5 mL). The mixture was heated at 120° C. under microwave irradiation for 2 h, then concentrated in vacuo. The resulting residue was dissolved in water (1 mL), treated with 1M HCl (0.566 mL) and concentrated in vacuo. The residue was purified by chromatography on silica (solvent gradient: 10-50% 2M methanolic ammonia in dichloromethane) to give the title compound as a cream solid (57.2 mg, 81%). LCMS (ESI): [M+H]$^+$ 372.

Step 3: 2-Hydroxy-3-[4-(1-isopropyl-2-methyl-1H-imidazo[4,5-c]pyridin-6-ylamino)pyrimidin-2-ylamino]propionamide

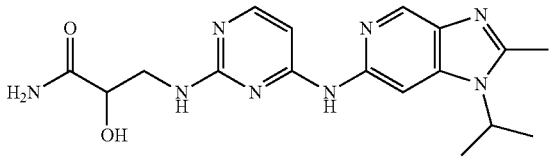 [SMILES: Cc1nc2cnc(Nc3ccnc(NCC(O)C(N)=O)n3)cc2n1C(C)C]

To a mixture of 2-hydroxy-3-[4-(1-isopropyl-2-methyl-1H-imidazo[4,5-c]pyridin-6-ylamino)pyrimidin-2-ylamino] propionic acid (57 mg, 0.153 mmol), benzotriazol-1-ol ammonium salt (WO2006/100119) (46.7 mg, 0.307 mmol) and N,N-diisopropylethylamine (0.08 mL, 0.46 mmol) in N,N-dimethylformamide (1 mL) was added N-(3-dimethylaminopropyl)-N'-ethylcarbodiimide hydrochloride (43.7 mg, 0.23 mmol). The mixture was stirred at room temperature for 4 h, then further portions of benzotriazol-1-ol ammonium salt (46.7 mg, 0.307 mmol), N,N-diisopropylethylamine (0.08 mL, 0.46 mmol) and N-(3-dimethylaminopropyl)-N'-ethylcarbodiimide hydrochloride (43.7 mg, 0.23 mmol) were added. The mixture was stirred for 2 days, diluted with methanol and loaded on to an SCX cartridge. The cartridge was washed with methanol and the desired product was eluted with 1M ammonia in methanol and concentrated in vacuo. The resulting residue was purified by chromatography on silica (solvent gradient: 3-18% 2M methanolic ammonia in dichloromethane) to afford the title compound as a white solid (34.7 mg, 61%). LCMS (ESI): R$_T$ 1.64 min, [M+H]$^+$ 371.1, Method F; $^1$H NMR (400 MHz, DMSO-d$_6$) δ 9.63 (1H, s), 8.49 (1H, s), 8.37 (1H, br s), 7.89 (1H, d, J=5.7 Hz), 7.28 (1H, br s), 7.24 (1H, br s), 6.53 (1H, br s), 6.32 1H, br t, J=5.2 Hz), 4.72 (1H, septet, J=6.9 Hz), 4.06 (1H, br s), 3.64 (1H, dt, J=12.9, 4.5 Hz), 3.52 (1H, br s), 2.56 (3H, s), 1.56 (6H, d, J=6.9 Hz).

Example 302: 3-[4-(1-Isopropyl-2-methyl-1H-imidazo[4,5-c]pyridin-6-ylamino)pyrimidin-2-ylamino]-2,2-dimethylpropionic acid

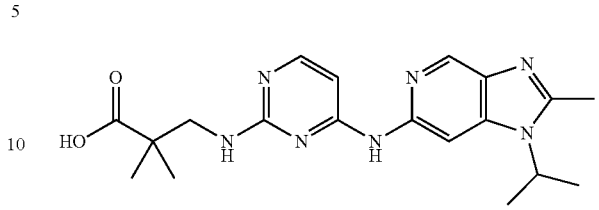

Step 1: 3-[4-(1-Isopropyl-2-methyl-1H-imidazo[4,5-c]pyridin-6-ylamino)pyrimidin-2-ylamino]-2,2-dimethylpropionic acid ethyl ester

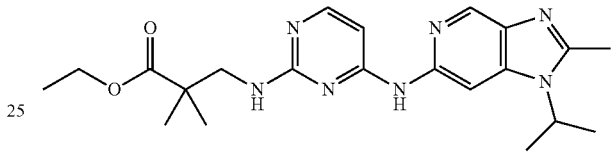

A mixture of N-(2-chloropyrimidin-4-yl)-1-isopropyl-2-methyl-1H-imidazo[4,5-c]pyridin-6-amine (Example 46, Step 7) (1.0 g, 3.3 mmol), 3-amino-2,2-dimethylpropionic acid ethyl ester (WO2009/067547) (0.5 g, 3.44 mmol) and N,N-diisopropylethylamine (0.629 mL, 3.63 mmol) in isopropanol (20 mL) was heated at 150° C. under microwave irradiation for 10 h. The reaction mixture was concentrated in vacuo. The resulting residue was purified by chromatography on silica (solvent gradient: 2%-8% 2M methanolic ammonia in dichloromethane) to afford the title compound as an off-white foam (1.305 g, 96%). LCMS (ESI): [M+H]$^+$ 412.

Step 2: 3-[4-(1-Isopropyl-2-methyl-1H-imidazo[4,5-c]pyridin-6-ylamino)pyrimidin-2-ylamino]-2,2-dimethylpropionic acid

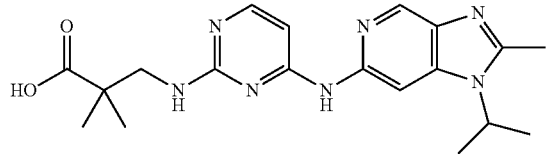 [SMILES: Cc1nc2cnc(Nc3ccnc(NCC(C)(C)C(=O)O)n3)cc2n1C(C)C]

A solution of 3-[4-(1-isopropyl-2-methyl-1H-imidazo[4,5-c]pyridin-6-ylamino)pyrimidin-2-ylamino]-2,2-dimethylpropionic acid ethyl ester (1.132 g, 2.75 mmol) in 6M HCl (20 mL) was heated at 120° C. under microwave irradiation for 1 h and then concentrated in vacuo. The resulting residue was treated with aqueous ammonia, concentrated in vacuo and purified by chromatography on silica (solvent gradient: 5-40% 2M methanolic ammonia in dichloromethane) to give the title compound as a white solid (1.02 g, 97%). LCMS (ESI): R$_T$ 2.12 min, [M+H]$^+$ 384.2, Method F; $^1$H NMR (400 MHz, DMSO-d$_6$) δ 9.58 (1H, s), 8.49 (1H, s), 8.29 (1H, br s), 7.88 (1H, d, J=5.7 Hz), 6.54 (1H, d, J=5.7 Hz), 6.17 (1H, br s), 4.72 (1H, septet, J=6.9 Hz), 3.54 (2H, d, J=6.0 Hz), 2.56 (3H, s), 1.57 (6H, d, J=6.9 Hz), 1.16 (6H, s).

Example 303: 2-Hydroxymethyl-3-[4-(1-isopropyl-2-methyl-1H-imidazo[4,5-c]pyridin-6-ylamino)pyrimidin-2-ylamino]-2-methylpropionamide

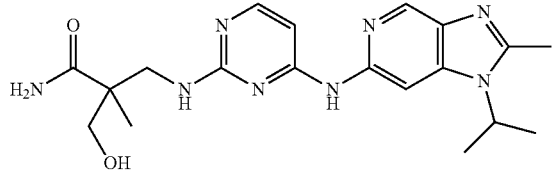 [SMILES: Cc1nc2cnc(Nc3ccnc(NCC(C)(CO)C(N)=O)n3)cc2n1C(C)C]

Step 1: 2-(2,2-Dimethylpropionyloxymethyl)-3-[4-(1-isopropyl-2-methyl-1H-imidazo[4,5-c]pyridin-6-ylamino)pyrimidin-2-ylamino]-2-methylpropionic acid ethyl ester

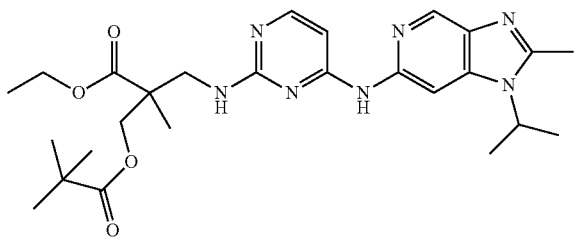 [SMILES: CCOC(=O)C(C)(CNc1nccc(Nc2cc3c(cn2)nc(C)n3C(C)C)n1)COC(=O)C(C)(C)C]

A mixture of N-(2-chloropyrimidin-4-yl)-1-isopropyl-2-methyl-1H-imidazo[4,5-c]pyridin-6-amine (Example 46, Step 7) (0.15 g, 0.495 mmol), 3-amino-2-(2,2-dimethylpropionyloxymethyl)-2-methylpropionic acid ethyl ester hydrochloride (Example A24, Step 2) (0.5636 mmol) and N,N-diisopropylethylamine (0.214 mL, 1.238 mmol) in isopropanol (4.5 mL) was heated at 150° C. under microwave irradiation for 10 h. The reaction mixture was concentrated in vacuo. The resulting residue was purified by chromatography (silica, gradient 1-7% 2M ammonia in methanol in dichloromethane) to afford the title compound as a white solid (0.166 g, 65%). LCMS (ESI): [M+H]+ 512.

Step 2: 2-Hydroxymethyl-3-[4-(1-isopropyl-2-methyl-1H-imidazo[4,5-c]pyridin-6-ylamino)pyrimidin-2-ylamino]-2-methylpropionic acid

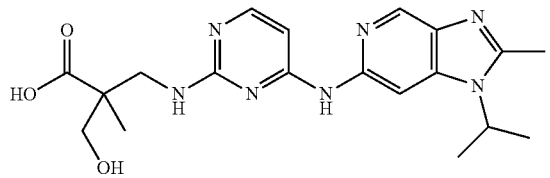 [SMILES: Cc1nc2cnc(Nc3ccnc(NCC(C)(CO)C(=O)O)n3)cc2n1C(C)C]

A solution of 2-(2,2-dimethylpropionyloxymethyl)-3-[4-(1-isopropyl-2-methyl-1H-imidazo[4,5-c]pyridin-6-ylamino)pyrimidin-2-ylamino]-2-methylpropionic acid ethyl ester (165 mg, 0.322 mmol) in 3M HCl (5 mL) was heated at 110° C. under microwave irradiation for 1 h, then concentrated in vacuo. The resulting residue was treated with aqueous ammonia, concentrated in vacuo, and purified by chromatography (silica, gradient 5-45% 2M ammonia in methanol in dichloromethane) to give the title compound as a white solid (84.6 mg, 66%). LCMS (ESI): [M+H]+ 400.

Step 3: 2-Hydroxymethyl-3-[4-(1-isopropyl-2-methyl-1H-imidazo[4,5-c]pyridin-6-ylamino)pyrimidin-2-ylamino]-2-methylpropionamide

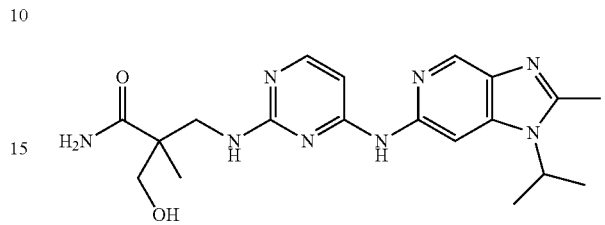

To a mixture of 2-hydroxymethyl-3-[4-(1-isopropyl-2-methyl-1H-imidazo[4,5-c]pyridin-6-ylamino)pyrimidin-2-ylamino]-2-methylpropionic acid (79 mg, 0.198 mmol), ammonium chloride (21.2 mg, 0.396 mmol) and N,N-diisopropylethylamine (0.137 mL, 0.792 mmol) in dimethylformamide (1.5 mL) at 0° C. was added 1-[bis(dimethylamino)methylene]-1H-1,2,3-triazolo[4,5-b]pyridinium 3-oxid hexafluorophosphate (113 mg, 0.297 mmol) portionwise over 10 min. The mixture was stirred at room temperature for 0.5 h, then aqueous ammonia (0.1 mL) was added and the reaction mixture concentrated in vacuo. The resulting residue was purified by chromatography (silica, gradient 2-14% 2M ammonia in methanol in dichloromethane) to afford the title compound as a colorless solid (24.1 mg, 31%). LCMS (ESI): $R_T$ 1.75 min, [M+H]+ 399.2, Method F; $^1$H NMR (400 MHz, DMSO-$d_6$) δ 9.60 (1H, s), 8.49 (1H, s), 8.25 (1H, br s), 7.88 (1H, d, J=5.8 Hz), 7.17 (1H, br s), 6.99 (1H, br s), 6.57 (1H, br d, J=5.6 Hz), 6.18 (1H, t, J=5.9 Hz), 5.21 (1H, br s), 4.72 (1H, septet, J=6.9 Hz), 3.56-3.43 (4H, m), 2.56 (3H, s), 1.56 (6H, d, J=6.9 Hz), 1.06 (3H, s).

Example 304: (1-Isopropyl-2-methyl-1H-imidazo[4,5-c]pyridin-6-yl)-[2-(3-methoxy-3-methylbut-1-ynyl)pyrimidin-4-yl]amine

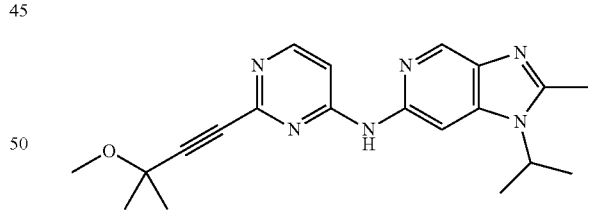

A mixture of N-(2-chloropyrimidin-4-yl)-1-isopropyl-2-methyl-1H-imidazo[4,5-c]pyridin-6-amine (Example 46, Step 7) (0.15 g, 0.495 mmol), 3-methoxy-3-methylbut-1-yne (58.2 mg, 0.594 mmol), bis(triphenylphosphine)palladium (II) dichloride (34.8 mg, 0.05 mmol), triphenylphosphine (26.1 mg, 0.1 mmol), copper(I) iodide (18.9 mg, 0.1 mmol), triethylamine (0.207 mL, 1.49 mmol) and dimethylformamide (3.5 mL) was heated at 120° C. under microwave irradiation for 3 h. The cooled reaction mixture was partitioned between EtOAc and water. The aqueous phase was extracted with additional EtOAc, and the combined organic extracts were washed with water and brine, dried over anhydrous sodium sulphate, and concentrated in vacuo. The residue was purified by chromatography (silica, gradient 2-6% 2M ammonia in methanol in dichloromethane; gradient 1-8% methanol in methyl acetate) to give the title compound as a colorless gum (96.5 mg, 54%). LCMS (ESI): $R_T$ 2.77 min, $[M+H]^+$ 365.2, Method F; $^1$H NMR (400 MHz, DMSO-$d_6$) δ 10.27 (1H, s), 8.54 (1H, s), 8.31 (1H, br s), 8.30 (1H, d, J=6.0 Hz), 7.37 (1H, br s), 4.72 (1H, septet, J=6.9 Hz), 3.35 (3H, s), 2.57 (3H, s), 1.58 (6H, d, J=6.9 Hz), 1.50 (6H, s).

Example 305: (1-Isopropyl-2-methyl-1H-imidazo[4,5-c]pyridin-6-yl)-[2-(3-methoxy-3-methylbutyl)pyrimidin-4-yl]amine

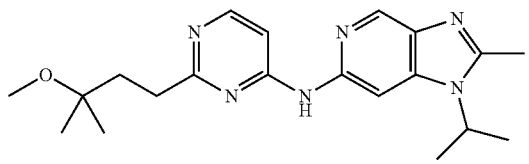

A mixture of (1-isopropyl-2-methyl-1H-imidazo[4,5-c]pyridin-6-yl)-[2-(3-methoxy-3-methylbut-1-ynyl)pyrimidin-4-yl]amine (Example 304) (0.104 g, 0.285 mmol) and 10% Pd/C (20 mg) in EtOH (10 mL) was stirred under a balloon of hydrogen for 16 h, then filtered through a Celite pad. The filtrate was concentrated in vacuo and the residue was purified by chromatography (silica, gradient 2-18% methanol in methyl acetate) followed by mass-directed auto purification to afford the title compound as a colorless solid (39.3 mg, 37%). LCMS (ESI): $R_T$ 2.36 min, $[M+H]^+$ 369.2, Method F. $^1$H NMR (400 MHz, DMSO-$d_6$) δ 9.97 (1H, s), 8.52 (1H, s), 8.48 (1H, br s), 8.24 (1H, d, J=5.9 Hz), 7.15 (1H, br d), 4.72 (1H, septet, J=6.9 Hz), 3.12 (3H, s), 2.77-2.72 (2H, m), 2.56 (3H, s), 1.95-1.91 (2H, m), 1.59 (6H, d, J=6.9 Hz), 1.15 (6H, s).

Example 306: 1-[4-(1-Isopropyl-2-methyl-1H-imidazo[4,5-c]pyridin-6-ylamino)pyrimidin-2-yl]-3-methylpyrrolidine-3-carboxylic acid amide

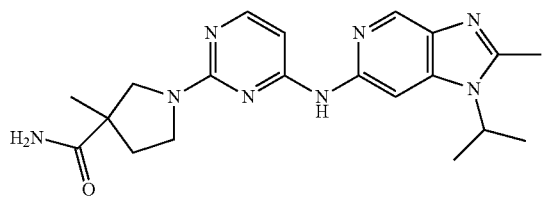 [SMILES: Cc1nc2cnc(Nc3ccnc(N4CCC(C)(C(N)=O)C4)n3)cc2n1C(C)C]

Step 1: 1-[4-(1-Isopropyl-2-methyl-1H-imidazo[4,5-c]pyridin-6-ylamino)pyrimidin-2-yl]-3-methylpyrrolidine-3-carboxylic acid ethyl ester

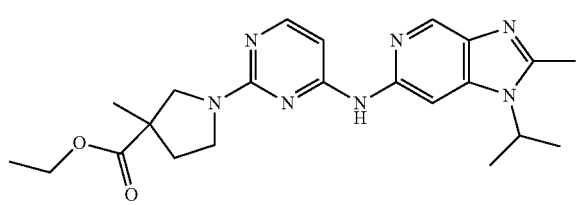 [SMILES: CCOC(=O)C1(C)CCN(c2nccc(Nc3cc4c(cn3)nc(C)n4C(C)C)n2)C1]

A mixture of N-(2-chloropyrimidin-4-yl)-1-isopropyl-2-methyl-1H-imidazo[4,5-c]pyridin-6-amine (Example 46, Step 7) (0.15 g, 0.495 mmol), 2-aminomethyl-4-(2,2-dimethylpropionyloxy)-2-methylbutyric acid ethyl ester (Example A30) (0.154 g, 0.594 mmol) and N,N-diisopropylethylamine (0.129 mL, 0.743 mmol) in isopropanol (4.5 mL) was heated at 150° C. under microwave irradiation for 10 h. The reaction mixture was concentrated in vacuo. The resulting residue was partitioned between dichloromethane and saturated aqueous sodium bicarbonate. The aqueous phase was extracted with additional dichloromethane, and the combined organic extracts were washed with water, dried over anhydrous sodium sulfate and concentrated in vacuo. Purification by chromatography (silica, gradient 2-8% 2M ammonia in methanol in dichloromethane) afforded the title compound as a colorless gum (quantitative). LCMS (ESI): $[M+H]^+$ 424.

Step 2: 1-[4-(1-Isopropyl-2-methyl-1H-imidazo[4,5-c]pyridin-6-ylamino)pyrimidin-2-yl]-3-methylpyrrolidine-3-carboxylic acid

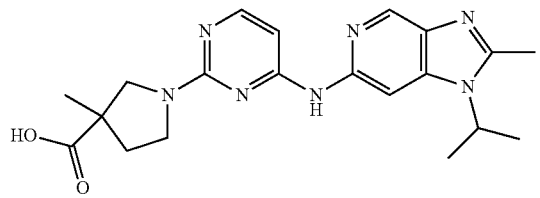 [SMILES: Cc1nc2cnc(Nc3ccnc(N4CCC(C)(C(=O)O)C4)n3)cc2n1C(C)C]

A solution of 1-[4-(1-isopropyl-2-methyl-1H-imidazo[4,5-c]pyridin-6-ylamino)pyrimidin-2-yl]-3-methylpyrrolidine-3-carboxylic acid ethyl ester (0.495 mmol) in 3M HCl (5 mL) was heated at 110° C. under microwave irradiation for 1 h, then concentrated in vacuo. The resulting residue was treated with aqueous ammonia, concentrated in vacuo and purified by chromatography (silica, gradient 5-35% 2M ammonia in methanol in dichloromethane) to give the title compound as a white solid (0.18 g, 92%, 2 steps). LCMS (ESI): $[M+H]^+$ 396.

Step 3: 1-[4-(1-Isopropyl-2-methyl-1H-imidazo[4,5-c]pyridin-6-ylamino)pyrimidin-2-yl]-3-methylpyrrolidine-3-carboxylic acid amide

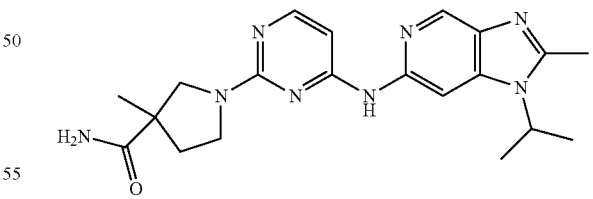

To a mixture of 1-[4-(1-isopropyl-2-methyl-1H-imidazo[4,5-c]pyridin-6-ylamino)pyrimidin-2-yl]-3-methylpyrrolidine-3-carboxylic acid (90 mg, 0.227 mmol), ammonium chloride (24.4 mg, 0.455 mmol) and N,N-diisopropylethylamine (0.158 mL, 0.91 mmol) in N,N-dimethylformamide (2 mL) at 0° C. was added 1-[bis(dimethylamino)methylene]-1H-1,2,3-triazolo[4,5-b]pyridinium 3-oxid hexafluorophosphate (130 mg, 0.34 mmol) portion-wise over 15 min. The mixture was stirred at room temperature for 1.5 h, then diluted with acetonitrile (8 mL) and water (0.5 mL) to give a clear solution which was loaded onto an SCX cartridge. The cartridge was washed with acetonitrile in water (9:1), and the desired product was eluted with aqueous ammonia in acetonitrile (1:9) followed by 2M ammonia in methanol. Upon concentration in vacuo, the resulting residue was purified by chromatography (silica, gradient 2-14% 2M ammonia in methanol in dichloromethane) to afford the title compound as a white solid (62.6 mg, 70%). LCMS (ESI): $R_T$ 1.90 min, [M+H]$^+$ 395.3, Method F; $^1$H NMR (400 MHz, DMSO-d$_6$) δ 9.68 (1H, s), 8.65 (1H, br s), 8.49 (1H, s), 7.92 (1H, d, J=5.7 Hz), 7.34 (1H, br s), 6.98 (1H, br s), 6.35 (1H, br d, J=5.3 Hz), 4.72 (1H, septet, J=6.9 Hz), 4.06 (1H, br s), 3.60 (2H, br s), 3.39 (1H, br d, J=10.6 Hz), 2.56 (3H, s), 2.39-2.30 (1H, m), 1.91-1.84 (1H, m), 1.57 & 1.56 (6H, 2d, J=6.9 Hz), 1.31 (3H, s).

Example 307: (1-Isopropyl-2-methyl-1H-imidazo[4,5-c]pyridin-6-yl)-[((E)-2-pent-1-enyl)pyrimidin-4-yl]amine

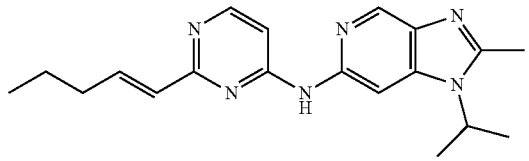 [SMILES: CCC/C=C/c1nccc(Nc2cc3c(cn2)nc(C)n3C(C)C)n1]

A mixture of N-(2-chloropyrimidin-4-yl)-1-isopropyl-2-methyl-1H-imidazo[4,5-c]pyridin-6-amine (Example 46, Step 7) (0.10 g, 0.33 mmol), 1-penten-1-ylboronic acid (0.112 g, 0.98 mmol), [1,1'-bis(diphenylphosphino)ferrocene]dichloropalladium(II), complex with dichloromethane (54 mg, 0.066 mmol), dimethoxyethane (2 mL) and 2M sodium carbonate in water (0.5 mL) was heated at 100° C. in a sealed vial for 16 h. The reaction mixture was partitioned between dichloromethane and water. The aqueous phase was extracted with additional dichloromethane, and the combined organic extracts were washed with water, dried over anhydrous sodium sulfate and concentrated in vacuo. The resulting residue was purified by chromatography (silica, gradient 2-10% 2M ammonia in methanol in dichloromethane) followed by mass-directed auto purification to afford the title compound as a colorless foam (71.9 mg, 65%). LCMS (ESI): $R_T$ 2.69 min, [M+H]$^+$ 337.1, Method F; $^1$H NMR (400 MHz, DMSO-d$_6$) δ 9.98 (1H, s), 8.53 (1H, s), 8.48 (1H, br s), 8.27 (1H, d, J=5.9 Hz), 7.12 (1H, br d, J=5.7 Hz), 7.09 (1H, dt, J=15.6, 7.2 Hz), 6.39 (1H, dt, J=15.6, 1.3 Hz), 4.74 (1H, septet, J=6.9 Hz), 2.57 (3H, s), 2.27 (2H, dq, J=7.1, 1.3 Hz), 1.60 (6H, d, J=6.9 Hz), 1.52 (2H, sextet, J=7.3 Hz), 0.95 (3H, t, J=7.3 Hz).

Example 308: (E)-4-[4-(1-Isopropyl-2-methyl-1H-imidazo[4,5-c]pyridin-6-ylamino)pyrimidin-2-yl]-2-methylbut-3-en-2-ol

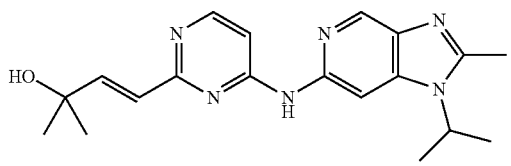 [SMILES: Cc1nc2cnc(Nc3ccnc(/C=C/C(C)(C)O)n3)cc2n1C(C)C]

A mixture of N-(2-chloropyrimidin-4-yl)-1-isopropyl-2-methyl-1H-imidazo[4,5-c]pyridin-6-amine (Example 46, Step 7) (0.10 g, 0.33 mmol), 3-methyl-3-hydroxybuten-1-ylboronic acid ester (J. Org. Chem., 2003, 68, 6031) (0.137 g, 0.66 mmol), [1,1'-bis(diphenylphosphino)ferrocene]dichloropalladium (II), complex with dichloromethane (54 mg, 0.066 mmol), dimethoxyethane (2 mL) and 2M sodium carbonate in water (0.5 mL) was heated at 100° C. in a sealed vial for 64 h. The reaction mixture was partitioned between dichloromethane and water. The aqueous phase was extracted with additional dichloromethane, and the combined organic extracts were washed with water, dried over anhydrous sodium sulfate and concentrated in vacuo. The resulting residue was purified by chromatography (silica, gradient 2-12% 2M ammonia in methanol in dichloromethane) to afford the title compound as a colorless solid (91.9 mg, 79%). LCMS (ESI): $R_T$ 2.13 min, [M+H]$^+$ 353.1, Method F; $^1$H NMR (400 MHz, DMSO-d$_6$) δ 9.99 (1H, s), 8.54 (1H, s), 8.43 (1H, br s), 8.29 (1H, d, J=5.9 Hz), 7.15 (1H, br s), 7.14 (1H, d, J=15.7 Hz), 6.51 (1H, d, J=15.7 Hz), 4.86 (1H, s), 4.74 (1H, septet, J=6.9 Hz), 2.57 (3H, s), 1.61 (6H, d, J=6.9 Hz), 1.31 (6H, s).

Example 309: (1-Isopropyl-2-methyl-1H-imidazo[4,5-c]pyridin-6-yl)-(2-pyridin-3-ylpyrimidin-4-yl)amine

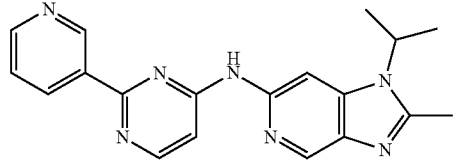 [SMILES: Cc1nc2cnc(Nc3ccnc(-c4cccnc4)n3)cc2n1C(C)C]

A mixture of N-(2-chloropyrimidin-4-yl)-1-isopropyl-2-methyl-1H-imidazo[4,5-c]pyridin-6-amine (Example 46, Step 7) (50 mg, 0.165 mmol), 3-pyridineboronic acid (40.6 mg, 0.33 mmol), [1,1'-bis(diphenylphosphino)ferrocene]dichloropalladium(II), complex with dichloromethane (27 mg, 0.033 mmol), dimethoxyethane (1 mL) and 2M sodium carbonate in water (0.25 mL) was heated at 100° C. in a sealed vial for 16 h. The reaction mixture was diluted with methanol (25 mL), a mixture of water (3 mL) and 1M HCl (0.5 mL) was added and the solution loaded on to an SCX cartridge. The cartridge was washed with methanol in water (4:1), followed by methanol, and the desired product was eluted with 0.5M ammonia in methanol. Upon concentration in vacuo, the resulting residue was purified by chromatography (silica, gradient 2%-7% 2M ammonia in methanol in dichloromethane) to afford the title compound as a cream solid (42.6 mg, 75%). LCMS (ESI): $R_T$ 2.22 min, [M+H]$^+$ 346.2, Method F; $^1$H NMR (400 MHz, DMSO-d$_6$) δ 10.25 (1H, s), 9.55 (1H, d, J=2.0 Hz), 8.73 (1H, dd, J=4.8, 1.7 Hz), 8.67 (1H, dt, J=8.0, 2.0 Hz), 8.58 (1H, s), 8.50 (1H, br s), 8.49 (1H, d, J=5.8 Hz), 7.57 (1H, dd, J=7.9, 4.8 Hz), 7.32 (1H, br s), 4.77 (1H, septet, J=6.9 Hz), 2.59 (3H, s), 1.63 (6H, d, J=6.9 Hz).

Example 310: (E)-4-[4-(1-Isopropyl-2-methyl-1H-imidazo[4,5-c]pyridin-6-ylamino)pyrimidin-2-yl]-2,2-dimethylbut-3-enoic acid amide

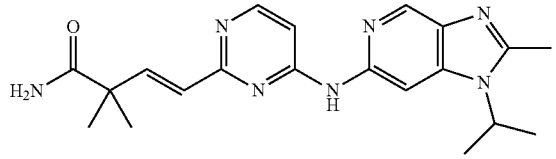 [SMILES: Cc1nc2cnc(Nc3ccnc(/C=C/C(C)(C)C(N)=O)n3)cc2n1C(C)C]

Step 1: (E)-4-[4-(1-Isopropyl-2-methyl-1H-imidazo[4,5-c]pyridin-6-ylamino)pyrimidin-2-yl]-2,2-dimethylbut-3-enoic acid ethyl ester

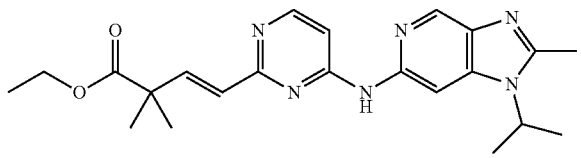 [SMILES: CCOC(=O)C(C)(C)/C=C/c1nccc(Nc2cc3c(cn2)nc(C)n3C(C)C)n1]

The title compound (64 mg, 42%) was prepared from N-(2-chloropyrimidin-4-yl)-1-isopropyl-2-methyl-1H-imidazo[4,5-c]pyridin-6-amine (Example 46, Step 7) (112 mg, 0.37 mmol) and (E)-2,2-dimethyl-4-(4,4,5,5-tetramethyl-[1,3,2]dioxaborolan-2-yl)but-3-enoic acid ethyl ester (Example A31) (113 mg, 0.421 mmol), according to a procedure analogous to that described for Example 307. LCMS (ESI): [M+H]$^+$ 409.

Steps 2 and 3: (E)-4-[4-(1-Isopropyl-2-methyl-1H-imidazo[4,5-c]pyridin-6-ylamino)pyrimidin-2-yl]-2,2-dimethylbut-3-enoic acid amide

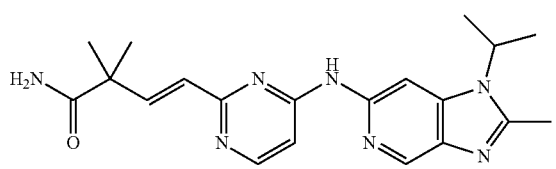 [SMILES: Cc1nc2cnc(Nc3ccnc(/C=C/C(C)(C)C(N)=O)n3)cc2n1C(C)C]

The title compound (16.5 mg, 33%%) was prepared from (E)-4-[4-(1-isopropyl-2-methyl-1H-imidazo[4,5-c]pyridin-6-ylamino)pyrimidin-2-yl]-2,2-dimethylbut-3-enoic acid ethyl ester (53.9 mg, 0.132 mmol) according to procedures analogous to those described for Example 300, Step 2 and 298, Step 3. LCMS (ESI): R$_T$ 2.13 min, [M+H]$^+$ 380.1, Method F; $^1$H NMR (400 MHz, DMSO-d$_6$) δ 10.01 (1H, s), 8.53 (1H, s), 8.44 (1H, br s), 8.30 (1H, d, J=5.9 Hz), 7.20 (1H, d, J=15.9 Hz), 7.16 (1H, br s), 7.10 (1H, br s), 6.95 (1H, br s), 6.41 (1H, d, J=15.9 Hz), 4.73 (1H, septet, J=6.9 Hz), 2.57 (3H, s), 1.59 (6H, d, J=6.9 Hz), 1.32 (6H, s).

Example 311: (1-Isopropyl-2-methyl-1H-imidazo[4,5-c]pyridin-6-yl)-[2-(3-methyl-3H-imidazol-4-yl)pyrimidin-4-yl]amine

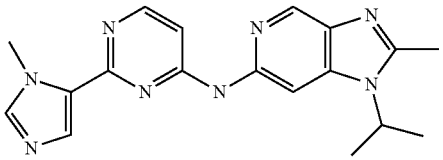 [SMILES: Cc1nc2cnc(Nc3ccnc(-c4cncn4C)n3)cc2n1C(C)C]

A mixture of N-(2-chloropyrimidin-4-yl)-1-isopropyl-2-methyl-1H-imidazo[4,5-c]pyridin-6-amine (Example 46, Step 7) (60 mg, 0.2 mmol), 1-methyl-5-tributylstannanyl-1H-imidazole (0.11 g, 0.3 mmol), tetrakis(triphenylphosphine)palladium(0) (18.3 mg, 0.016 mmol), dioxane (0.6 mL) and toluene (0.6 mL) was heated at 140° C. under microwave irradiation for 4 h. The reaction mixture was diluted with dichloromethane (30 mL), potassium fluoride (1 g) was added, and the mixture was stirred for 10 min. The mixture was then loaded on to a silica cartridge. The cartridge was eluted with a gradient of 2-10% 2M ammonia in methanol in dichloromethane to provide the crude product upon concentration in vacuo. Further chromatography (silica, gradient 10-40% methanol in EtOAc) afforded the title compound as a white solid (29 mg, 42%). LCMS (ESI): R$_T$ 1.83 min, [M+H]$^+$ 349.0, Method F; $^1$H NMR (400 MHz, DMSO-d$_6$) δ 10.02 (1H, s), 8.56 (1H, s), 8.37 (1H, d, J=5.9 Hz), 8.22 (1H, br s), 7.78 (1H, s), 7.72 (1H, d, J=1.2 Hz), 7.31 (1H, br s), 4.75 (1H, septet, J=6.9 Hz), 4.02 (3H, s), 2.58 (3H, s), 1.60 (6H, d, J=6.9 Hz).

Example 312: (1-Isopropyl-2-methyl-1H-imidazo[4,5-c]pyridin-6-yl)-[2-(2-methylaminothiazol-5-yl)pyrimidin-4-yl]amine

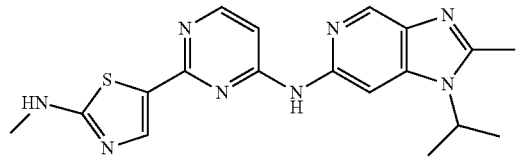

Step 1: {5-[4-(1-Isopropyl-2-methyl-1H-imidazo[4,5-c]pyridin-6-ylamino)pyrimidin-2-yl]thiazol-2-yl}methylcarbamic acid tert-butyl ester

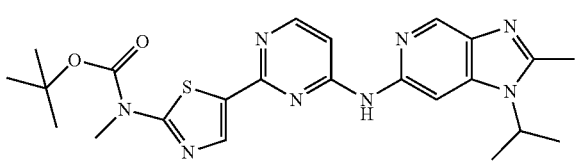 [SMILES: Cc1nc2cnc(Nc3ccnc(-c4cnc(N(C)C(=O)OC(C)(C)C)s4)n3)cc2n1C(C)C]

A mixture of N-(2-chloropyrimidin-4-yl)-1-isopropyl-2-methyl-1H-imidazo[4,5-c]pyridin-6-amine (Example 46, Step 7) (60 mg, 0.2 mmol), methyl-(5-tributylstannanylthiazol-2-yl)carbamic acid tert-butyl ester (Org. Lett., 2002, 4, 4209) (0.151 g, 0.3 mmol), tetrakis(triphenylphosphine)

palladium(0) (18.3 mg, 0.016 mmol), dioxane (0.6 mL) and toluene (0.6 mL) was heated at 140° C. under microwave irradiation for 1 h. The reaction mixture was diluted with dichloromethane (30 mL), potassium fluoride (1 g) was added, and the resulting mixture was stirred for 10 min followed by being loaded on to a silica cartridge. The cartridge was eluted with a gradient of 2-10% 2M ammonia in methanol in dichloromethane to afford the title compound as a colorless gum (89.6 mg, 93%). LCMS (ESI): [M+H]$^+$ 481.

Step 2: (1-Isopropyl-2-methyl-1H-imidazo[4,5-c]pyridin-6-yl)-[2-(2-methylaminothiazol-5-yl)pyrimidin-4-yl]amine

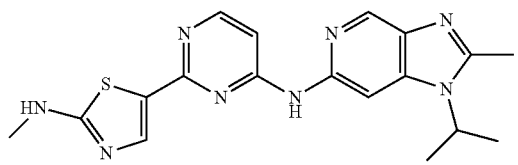

To a solution of {5-[4-(1-isopropyl-2-methyl-1H-imidazo[4,5-c]pyridin-6-ylamino)pyrimidin-2-yl]thiazol-2-yl}methylcarbamic acid tert-butyl ester (89.6 mg, 0.186 mmol) in dichloromethane (4 mL) at 0° C. was added TFA (1 mL). The mixture was allowed to warm to room temperature and stirred for 3 h. Toluene was added and the reaction mixture was concentrated in vacuo (2×). The residue was dissolved in methanol and loaded on to an SCX cartridge. The cartridge was washed successively with methanol, and the desired product was eluted with 0.5M ammonia in methanol. Upon concentration in vacuo, the residue was purified by chromatography (silica, gradient 2-10% 2M ammonia in methanol in dichloromethane) to afford the title compound as a white solid (54.7 mg, 77%). LCMS (ESI): $R_T$ 2.24 min, [M+H]$^+$ 381.0, Method F; $^1$H NMR (400 MHz, DMSO-d$_6$) δ 10.01 (1H, s), 8.54 (1H, s), 8.40 (1H, br s), 8.22 (1H, d, J=5.9 Hz), 8.05 (1H, q, J=4.7 Hz), 7.90 (1H, s), 7.02 (1H, br s), 4.77 (1H, septet, J=6.9 Hz), 2.89 (3H, d, J=4.7 Hz), 2.58 (3H, s), 1.66 (6H, d, J=6.9 Hz).

Example 313: 5-[4-(1-Isopropyl-2-methyl-1H-imidazo[4,5-c]pyridin-6-ylamino)pyrimidin-2-yl]pyridine-2-carboxylic acid amide

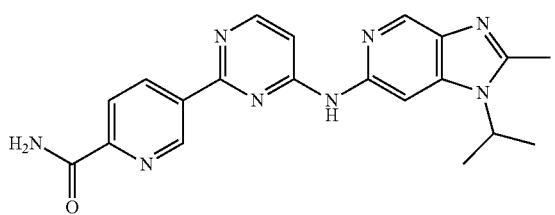 [SMILES: Cc1nc2cnc(Nc3ccnc(-c4ccc(C(N)=O)nc4)n3)cc2n1C(C)C]

Step 1: 5-[4-(1-Isopropyl-2-methyl-1H-imidazo[4,5-c]pyridin-6-ylamino)pyrimidin-2-yl]pyridine-2-carboxylic acid

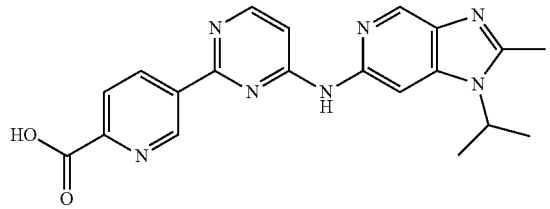

The title compound (64 mg, 42%) was prepared from N-(2-chloropyrimidin-4-yl)-1-isopropyl-2-methyl-1H-imidazo[4,5-c]pyridin-6-amine (Example 46, Step 7) (100 mg, 0.33 mmol) and 2-methoxycarbonylpyridine-5-boronic acid (89.6 mg, 0.495 mmol), according to a procedure analogous to that described for Example 309. LCMS (ESI): [M+H]$^+$ 390.

Step 2: 5-[4-(1-Isopropyl-2-methyl-1H-imidazo[4,5-c]pyridin-6-ylamino)pyrimidin-2-yl]pyridine-2-carboxylic acid amide

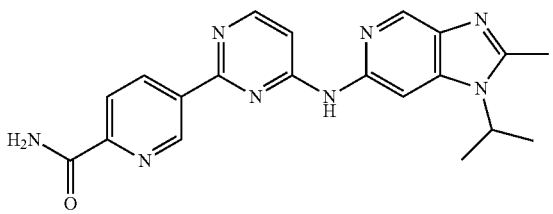 [SMILES: Cc1nc2cnc(Nc3ccnc(-c4ccc(C(N)=O)nc4)n3)cc2n1C(C)C]

To a mixture of 5-[4-(1-isopropyl-2-methyl-1H-imidazo[4,5-c]pyridin-6-ylamino)pyrimidin-2-yl]pyridine-2-carboxylic acid (60 mg, 0.154 mmol), ammonium chloride (16.5 mg, 0.308 mmol) and N,N-diisopropylethylamine (0.107 mL, 0.616 mmol) in dimethylformamide (1.5 mL) at 0° C. was added 1-[bis(dimethylamino)methylene]-1H-1,2,3-triazolo[4,5-b]pyridinium 3-oxid hexafluorophosphate (88 mg, 0.231 mmol) portion-wise over 5 min. The mixture was stirred at room temperature for 2 h and then water (0.1 mL) was added. The mixture was diluted with methanol (15 mL) and 0.5M HCl (2 mL) and loaded on to an SCX cartridge. The cartridge was washed with methanol and the product eluted with 1M ammonia in methanol followed by 2M ammonia in methanol and dichloromethane (1:1). Upon concentration in vacuo, the residue was purified by chromatography (silica, gradient 2-15% 2M ammonia in methanol in dichloromethane) to afford the title compound as a cream solid (23.8 mg, 40%). LCMS (ESI): $R_T$ 2.37 min, [M+H]$^+$ 389.2, Method F; $^1$H NMR (400 MHz, DMSO-d$_6$) δ 10.29 (1H, s), 9.54 (1H, d, J=1.9 Hz), 8.82 (1H, dd, J=8.1, 2.1 Hz), 8.59 (1H, s), 8.53 (1H, d, J=5.9 Hz), 8.41 (1H, br s), 8.22 (1H, br s), 8.18 (1H, d, J=8.1 Hz), 7.76 (1H, br s), 7.41 (1H, br s), 4.77 (1H, septet, J=6.9 Hz), 2.59 (3H, s), 1.64 (6H, d, J=6.9 Hz).

Example 314: (1-Isopropyl-2-methyl-1H-imidazo[4,5-c]pyridin-6-yl)-[2-(6-methylaminopyridin-3-yl)pyrimidin-4-yl]amine

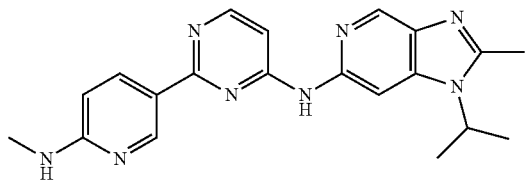

Step 1: {5-[4-(1-Isopropyl-2-methyl-1H-imidazo[4,5-c]pyridin-6-ylamino)pyrimidin-2-yl]pyridin-2-yl}methylcarbamic acid tert-butyl ester

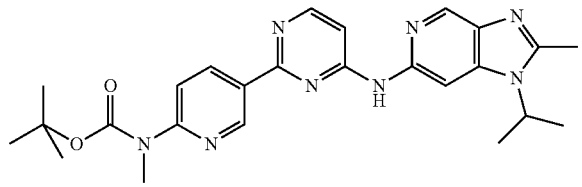 [SMILES: Cc1nc2cnc(Nc3ccnc(-c4ccc(N(C)C(=O)OC(C)(C)C)nc4)n3)cc2n1C(C)C]

The title compound was prepared from N-(2-chloropyrimidin-4-yl)-1-isopropyl-2-methyl-1H-imidazo[4,5-c]pyridin-6-amine (Example 46, Step 7) (0.05 g, 0.165 mmol) and methyl-[5-(4,4,5,5-tetramethyl-[1,3,2]dioxaborolan-2-yl)pyridin-2-yl]carbamic acid tert-butyl ester (0.11 g, 0.33 mmol) according to a procedure analogous to that described for Example 307. LCMS (ESI): [M+H]$^+$ 475.

Step 2: (1-Isopropyl-2-methyl-1H-imidazo[4,5-c]pyridin-6-yl)-[2-(6-methylaminopyridin-3-yl)pyrimidin-4-yl]amine

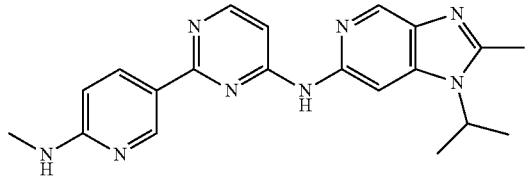

The title compound as a white solid (43.3 mg, 83%) was prepared from {5-[4-(1-isopropyl-2-methyl-1H-imidazo[4,5-c]pyridin-6-ylamino)pyrimidin-2-yl]pyridin-2-yl}methylcarbamic acid tert-butyl ester (66.5 mg, 0.14 mmol) according to a procedure analogous to that described for Example 312, Step 2. LCMS (ESI): R$_T$ 1.99 min [M+H]$^+$ 375.1, Method F; $^1$H NMR (400 MHz, DMSO-d$_6$) δ 10.01 (1H, s), 9.06 (1H, d, J=2.2 Hz), 8.55 (1H, s), 8.50 (1H, br s), 8.34 (1H, d, J=5.8 Hz), 8.31 (1H, dd, J=8.8, 2.3 Hz), 7.12 (1H, br s), 6.97 (1H, q, J=4.9 Hz), 6.52 (1H, d, J=8.8 Hz), 4.77 (1H, septet, J=6.9 Hz), 2.86 (1H, d, J=4.8 Hz), 2.58 (3H, s), 1.63 (6H, d, J=6.9 Hz).

Example 315: N-{5-[4-(1-Isopropyl-2-methyl-1H-imidazo[4,5-c]pyridin-6-ylamino)pyrimidin-2-yl]thiazol-2-yl}-N-methylacetamide

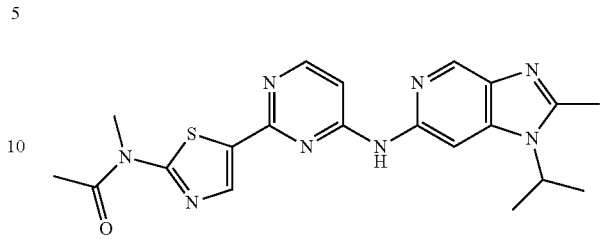

To a solution of (1-isopropyl-2-methyl-1H-imidazo[4,5-c]pyridin-6-yl)-[2-(2-methylaminothiazol-5-yl)pyrimidin-4-yl]amine (Example 312) (60 mg, 0.157 mmol) in N,N-dimethylformamide (1 mL) was added acetic acid (0.0108 mL, 0.189 mmol) and N,N-diisopropylethylamine (0.082 mL, 0.474 mmol). 1-[Bis(dimethylamino)methylene]-1H-1,2,3-triazolo[4,5-b]pyridinium 3-oxid hexafluorophosphate (90 mg, 0.236 mmol) was added portion-wise over 5 min. The mixture was stirred at room temperature for 3 h, then diluted with dichloromethane (15 mL) and loaded on to a silica cartridge. The cartridge was eluted with a gradient of 2-12% 2M ammonia in methanol in dichloromethane. Further chromatography (silica, gradient 5-30% methanol in EtOAc) afforded the title compound as a white solid (51.6 mg, 77%). LCMS (ESI): R$_T$ 2.77 min, [M+H]$^+$ 423.1, Method F; $^1$H NMR (400 MHz, DMSO-d$_6$) δ 10.14 (1H, s), 8.56 (1H, d, J=0.8 Hz), 8.40 (1H, br s), 8.33 (1H, d, J=5.9 Hz), 8.25 (1H, s), 7.19 (1H, br s), 4.81 (1H, septet, J=6.9 Hz), 3.70 (3H, s), 2.59 (3H, s), 2.44 (3H, s), 1.67 (6H, d, J=6.9 Hz).

Example 316: [2-(2-Benzenesulfonyl-3-methyl-3H-imidazol-4-yl)pyrimidin-4-yl]-(1-isopropyl-2-methyl-1H-imidazo[4,5-c]pyridin-6-yl)amine

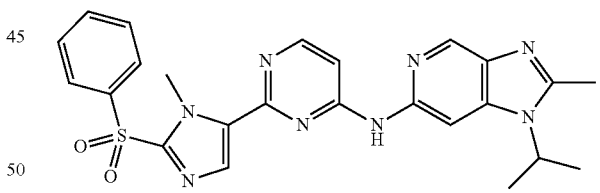

The title compound as a white solid (120 mg, 74%) was prepared from N-(2-chloropyrimidin-4-yl)-1-isopropyl-2-methyl-1H-imidazo[4,5-c]pyridin-6-amine (Example 46, Step 7) (100 mg, 0.33 mmol) and 2-benzenesulfonyl-1-methyl-5-tributylstannanyl-1H-imidazole (*Bioorg. Med. Chem. Lett.*, 2000, 10, 1543) (0.253 g, 0.495 mmol) according to a procedure analogous to that described for Example 312, Step 1. LCMS (ESI): R$_T$ 3.17 min, [M+H]$^+$ 489.2, Method F; $^1$H NMR (400 MHz, DMSO-d$_6$) δ 10.20 (1H, br s), 8.58 (1H, s), 8.44 (1H, d, J=5.9 Hz), 8.08 (1H, br s), 8.03-8.00 (2H, m), 7.83-7.78 (2H, m), 7.73-7.68 (2H, m), 7.46 (1H, br s), 4.74 (1H, septet, J=6.9 Hz), 4.32 (3H, s), 2.59 (3H, s), 1.55 (6H, d, J=6.9 Hz).

Example 317: [2-(2-Dimethylaminothiazol-5-yl)pyrimidin-4-yl]-(1-isopropyl-2-methyl-1H-imidazo[4,5-c]pyridin-6-yl)amine

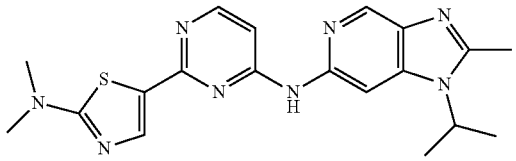

The title compound as a pale yellow solid (104 mg, 80%) was prepared from N-(2-chloropyrimidin-4-yl)-1-isopropyl-2-methyl-1H-imidazo[4,5-c]pyridin-6-amine (Example 46, Step 7) (100 mg, 0.33 mmol) and dimethyl-(5-tributylstannanylthiazol-2-yl)amine (Example A33) (207 mg, 0.495 mmol) according to a procedure analogous to that described for Example 312 Step 1. LCMS (ESI): $R_T$ 2.44 min, [M+H]$^+$ 395.1, Method F. $^1$H NMR (400 MHz, DMSO-d$_6$) δ 10.11 (1H, br s), 8.56 (1H, s), 8.39 (1H, br s), 8.24 (1H, d, J=5.9 Hz), 7.99 (1H, s), 7.01 (1H, br s), 4.77 (1H, septet, J=6.9 Hz), 3.14 (6H, s), 2.59 (3H, s), 1.66 (6H, d, J=6.9 Hz).

Example 318: 1-[4-(1-Isopropyl-2-methyl-1H-imidazo[4,5-c]pyridin-6-ylamino)pyrimidin-2-yl]imidazolidin-4-one

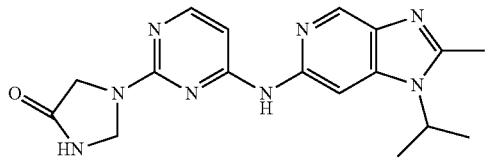 [SMILES: Cc1nc2cnc(Nc3ccnc(N4CNC(=O)C4)n3)cc2n1C(C)C]

A mixture of N-(2-chloropyrimidin-4-yl)-1-isopropyl-2-methyl-1H-imidazo[4,5-c]pyridin-6-amine (Example 46, Step 7) (200 mg, 0.66 mmol), imidazolidin-4-one (569 mg, 6.6 mmol), copper(I) iodide (50 mg, 0.26 mmol), trans-4-hydroxy-L-proline (34 mg, 0.26 mmol) and potassium phosphate (280 mg, 1.32 mmol) in DMSO (3 mL) was heated at 80° C. for 1.5 h. The reaction mixture was diluted with methanol and the resulting precipitate was collected by filtration. Purification by chromatography (silica, gradient 0-20% 2M ammonia in methanol in dichloromethane) afforded the title compound as a white solid (130 mg, 56%). LCMS (ESI): $R_T$ 1.83 min, [M+H]$^+$ 353.1, Method F; $^1$H NMR (400 MHz, DMSO-d$_6$) δ 9.86 (1H, s), 8.71 (1H, br s), 8.51 (1H, s), 8.49 (1H, br s), 8.00 (1H, d, J=5.8 Hz), 6.55 (1H, br d, J=5.6 Hz), 4.92 (2H, br s), 4.75 (1H, septet, J=6.9 Hz), 3.98 (2H, br s), 2.56 (3H, s), 1.58 (6H, d, J=6.9 Hz).

Example 319: N-(2-(4-methoxypiperidin-1-yl)pyrimidin-4-yl)-3H-imidazo[4,5-c]pyridin-6-amine

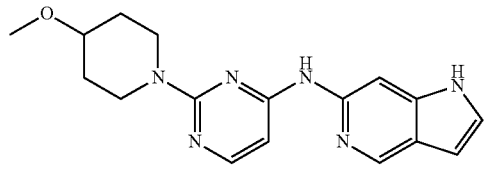 [SMILES: COC1CCN(c2nccc(Nc3cc4[nH]ccc4cn3)n2)CC1]

Step 1: 6-Chloro-1-((2-(trimethylsilyl)ethoxy)methyl)-1H-pyrrolo[3,2-c]pyridine

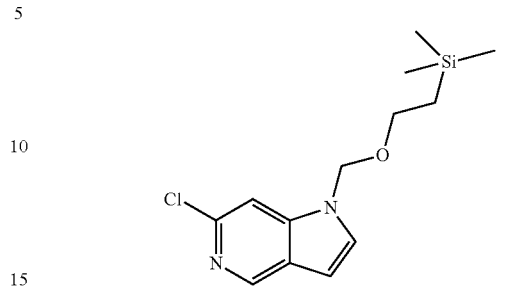

To a solution of 6-chloro-1H-pyrrolo[3,2-c]pyridine (280 mg, 1.8 mmol) in N,N-dimethylformamide (5 mL) was added sodium hydride (60 wt % dispersion in mineral oil) (150 mg, 3.7 mmol) at 0° C. The solution was stirred for 10 minutes and then 2-(chloromethoxy)ethyl-trimethyl-silane (340 mg, 2.0 mmol) was added slowly. The reaction was allowed to warm to room temperature for 1 h. The mixture was diluted with brine and extracted with EtOAc (3×). The combined organic extracts were washed with brine, dried over anhydrous magnesium sulfate, filtered and concentrated in vacuo. The crude material was purified by flash chromatography on silica gel (solvent gradient: 0-100% EtOAc in heptane) to afford the title compound (345 mg, 66%); $^1$H NMR (400 MHz, DMSO-d$_6$) δ 8.76 (d, J=0.9 Hz, 1H), 7.84 (t, J=0.9 Hz, 1H), 7.74 (d, J=3.3 Hz, 1H), 6.79 (dd, J=3.4, 0.9 Hz, 1H), 5.70 (s, 2H), 3.62-3.49 (m, 2H), 0.98-0.87 (m, 2H), 0.00 (s, 9H).

Step 2: N-(2-(4-Methoxypiperidin-1-yl)pyrimidin-4-yl)-1-((2-(trimethylsilyl)ethoxy)methyl)-1H-pyrrolo[3,2-c]pyridin-6-amine

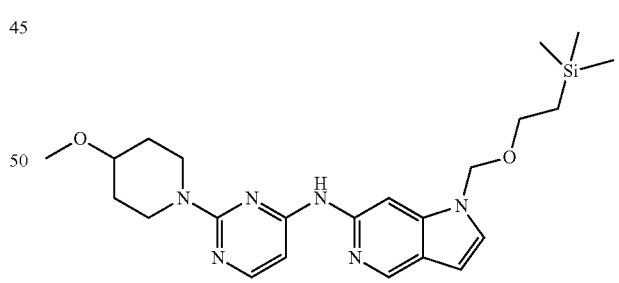

To a glass reaction vessel was added 6-chloro-1-((2-(trimethylsilyl)ethoxy)methyl)-1H-pyrrolo[3,2-c]pyridine (200 mg, 0.71 mmol), 2-(4-methoxy-1-piperidyl)pyrimidin-4-amine (Example 3, Step 2) (150 mg, 0.71 mmol), sodium tert-butoxide (210 mg, 2.1 mmol) in tert-butanol (3.0 mL) and Chloro{[BrettPhos][2-(2-aminoethylphenyl]palladium (II)]}/[BrettPhos] admixture (molar PdP/P=1:1)(50 mg). The reaction vessel was purged with nitrogen for 5 min, sealed and heated at 110° C. for 2 h. The reaction was then filtered and concentrated in vacuo to give the title compound (300 mg, 93%). LCMS (ESI): [M+H]$^+$ 455.6.

Step 3: N-(2-(4-Methoxypiperidin-1-yl)pyrimidin-4-yl)-1-((2-(trimethylsilyl)ethoxy)methyl)-1H-pyrrolo[3,2-c]pyridin-6-amine

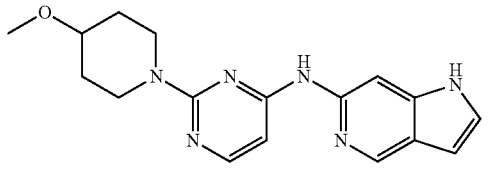 [SMILES: COC1CCN(c2nccc(Nc3cc4[nH]ccc4cn3)n2)CC1]

A mixture of N-(2-(4-methoxypiperidin-1-yl)pyrimidin-4-yl)-1-((2-(trimethylsilyl)ethoxy)methyl)-1H-pyrrolo[3,2-c]pyridin-6-amine (300 mg, 0.66 mmol) and HCl in 1,4 dioxane (4N, 5 mL) was stirred at room temperature for 1 h. The reaction mixture was concentrated in vacuo to yield crude (6-((2-(4-methoxypiperidin-1-yl)pyrimidin-4-yl)amino)-1H-pyrrolo[3,2-c]pyridin-1-yl)methanol. This was brought up in methanol (3 mL) to which was added 10% NaOH in water (1.0 mL). The mixture was stirred for 30 min at room temperature, concentrated in vacuo, purified by reverse-phase HPLC and lyophilized to give the title compound (34 mg, 16%). LCMS (ESI): [M+H]+ 325.2; $^1$H NMR (400 MHz, DMSO-$d_6$) δ 11.35 (s, 1H), 9.49 (s, 1H), 8.53 (d, J=0.8 Hz, 1H), 8.09-7.86 (m, 1H), 7.32 (dd, J=3.2, 2.0 Hz, 1H), 6.58-6.41 (m, 2H), 4.22 (dt, J=13.2, 4.7 Hz, 2H), 3.57-3.34 (m, 2H), 3.17 (s, 3H), 1.96-1.85 (m, 2H), 1.51-1.36 (m, 2H).

Example 320: N-(2-(4-Methoxypiperidin-1-yl)pyrimidin-4-yl)-3H-imidazo[4,5-c]pyridin-6-amine

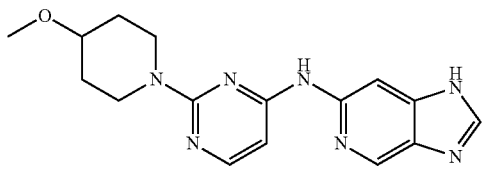 [SMILES: COC1CCN(c2nccc(Nc3cc4[nH]cnc4cn3)n2)CC1]

Step 1: 5-Chloro-3-((2-(trimethylsilyl)ethoxy)methyl)-3H-imidazo[4,5-b]pyridine

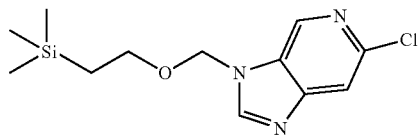 [SMILES: C[Si](C)(C)CCOCn1cnc2cc(Cl)ncc21]

5-Chloro-3-((2-(trimethylsilyl)ethoxy)methyl)-3H-imidazo[4,5-b]pyridine was prepared in a method analogous to Example 319, Step 1. LCMS (ESI) [M+H]+=284.3; $^1$H NMR (400 MHz, DMSO-$d_6$) δ 8.90 (d, J=0.9 Hz, 1H), 8.69 (s, 1H), 7.99 (d, J=1.0 Hz, 1H), 5.77 (s, 2H), 3.66-3.53 (m, 2H), 0.92 (m, J=8.6, 7.5, 3.2 Hz, 2H), 0.00 (s, J=1.1 Hz, 9H).

Step 2: N-(2-(4-Methoxypiperidin-1-yl)pyrimidin-4-yl)-3H-imidazo[4,5-c]pyridin-6-amine

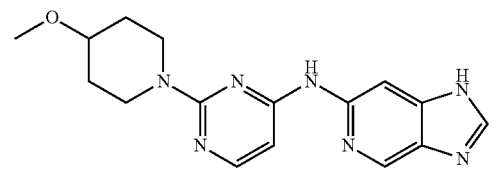 [SMILES: COC1CCN(c2nccc(Nc3cc4[nH]cnc4cn3)n2)CC1]

To a glass reaction vessel was added 5-chloro-3-((2-(trimethylsilyl)ethoxy)methyl)-3H-imidazo[4,5-b]pyridine (200 mg, 0.71 mmol), 2-(4-methoxy-1-piperidyl)pyrimidin-4-amine (Example 3, Step 2) (100 mg, 0.71 mmol), sodium tert-butoxide (200 mg, 2.0 mmol) in tert-butanol (3.0 mL) and Chloro{[BrettPhos][2-(2-aminoethylphenyl]palladium (II)]}/[BrettPhos] admixture (molar PdP/P=1:1) (50 mg). The reaction was degassed by nitrogen bubbling for 5 min. The reaction vial was sealed and heated at 120° C. After 2 h, the reaction was filtered, concentrated in vacuo, purified by reverse-phase HPLC and lyophilized to give the title compound (13 mg, 6%). LCMS (ESI): [M+H]+ 326.2; $^1$H NMR (400 MHz, DMSO-$d_6$) δ 9.64 (s, 1H), 8.63 (d, J=1.0 Hz, 1H), 8.25 (s, 1H), 8.19 (s, 1H), 7.95 (d, J=5.6 Hz, 1H), 6.50 (d, J=5.7 Hz, 1H), 4.21 (dt, J=13.2, 4.8 Hz, 2H), 3.57-3.37 (m, 2H), 3.17 (s, 3H), 1.90 (m, J=18.2, 8.3, 4.4 Hz, 2H), 1.43 (m, J=12.7, 8.8, 3.8 Hz, 2H).

Examples 321 and 322: (+)-1-(sec-Butyl)-6-((2-(1-(cyclopropylsulfonyl)-1H-pyrazol-4-yl)pyrimidin-4-yl)amino)-N-(tetrahydro-2H-pyran-4-yl)-1H-pyrrolo[3,2-c]pyridine-3-carboxamide and (−)-1-(sec-butyl)-6-((2-(1-(cyclopropylsulfonyl)-1H-pyrazol-4-yl)pyrimidin-4-yl)amino)-N-(tetrahydro-2H-pyran-4-yl)-1H-pyrrolo[3,2-c]pyridine-3-carboxamide

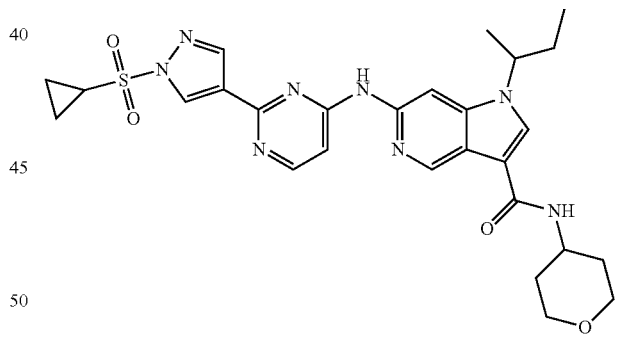

Step 1: (+/−)-6-Bromo-1-(sec-butyl)-1H-pyrrolo[3,2-c]pyridine-3-carboxylic acid

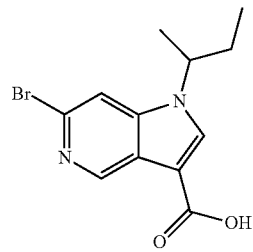 [SMILES: CCC(C)n1cc(C(=O)O)c2cnc(Br)cc21]

The title compound was prepared using a procedure analogous to that described in Example 51.

Step 2: (+/−)-6-Bromo-1-(sec-butyl)-N-(tetrahydro-2H-pyran-4-yl)-1H-pyrrolo[3,2-c]pyridine-3-carboxamide

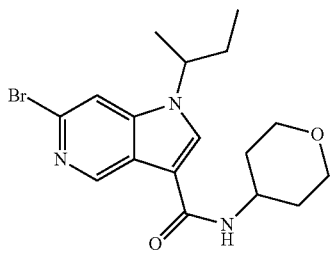

To a solution of (±)-6-bromo-1-(sec-butyl)-1H-pyrrolo[3,2-c]pyridine-3-carboxylic acid (0.70 g, 2.4 mmol) in N,N-dimethylformamide (25 mL) was added N,N-diisopropylethylamine (0.5 mL, 3.1 mmol), O-(benzotriazol-1-yl)-N,N,N',N'-tetramethyluronium hexafluorophosphate (1.2 g, 3.1 mmol) and tetrahydropyran-4-amine (0.3 g, 2.8 mmol). The reaction was stirred at room temperature for 1 h. The reaction was diluted with saturated sodium bicarbonate and the product was extracted with EtOAc (3×). The combined organic extracts were washed with brine, dried over sodium sulfate, filtered and concentrated in vacuo. The crude product was purified by silica gel flash chromatography (solvent gradient: 0-10% methanol in dichloromethane) to give the title compound (0.83 g, 93%). LCMS (ESI): [M+H]$^+$=382.

Step 3: (+)-1-(sec-Butyl)-6-((2-(1-(cyclopropylsulfonyl)-1H-pyrazol-4-yl)pyrimidin-4-yl)amino)-N-(tetrahydro-2H-pyran-4-yl)-1H-pyrrolo[3,2-c]pyridine-3-carboxamide and (−)-1-(sec-butyl)-6-((2-(1-(cyclopropylsulfonyl)-1H-pyrazol-4-yl)pyrimidin-4-yl)amino)-N-(tetrahydro-2H-pyran-4-yl)-1H-pyrrolo[3,2-c]pyridine-3-carboxamide

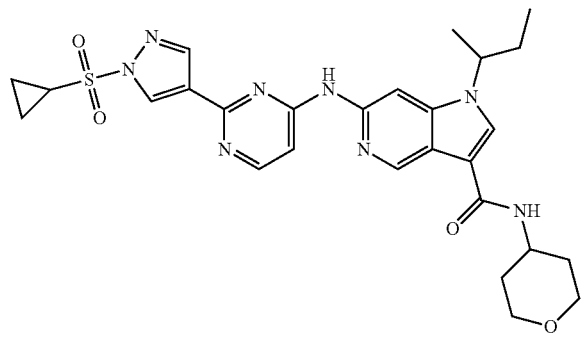 [SMILES: CCC(C)n1cc(C(=O)NC2CCOCC2)c2cnc(Nc3ccnc(-c4cnn(S(=O)(=O)C5CC5)c4)n3)cc21]

A microwave reaction vessel was charged (+/−)-6-bromo-1-(sec-butyl)-N-(tetrahydro-2H-pyran-4-yl)-1H-pyrrolo[3,2-c]pyridine-3-carboxamide (0.22 g, 0.66 mmol), 2-(1-(cyclopropylsulfonyl)-1H-pyrazol-4-yl)pyrimidin-4-amine (Example A62) (0.17 g, 0.66 mmol), 2-dicyclohexylphosphino-2',4',6'-triisopropylbiphenyl (64 mg, 0.13 mmol), tris(dibenzylideneacetone)dipalladium(0) (30 mg, 0.033 mmol), cesium carbonate (0.43 mg, 1.3 mmol) and 1,4-dioxane (3 mL). The reaction was sealed and degassed by nitrogen bubbling for 20 min. The reaction was stirred at 100° C. for 3 h. The reaction mixture was then filtered and concentrated in vacuo. The crude product was purified by supercritical fluid chromatography to give the two enantiomers of the titled compound (73.6 mg, 19.8%). Enantiomer 1 (38.1 mg): LCMS (ESI): R$_T$ (min)=9.56, [M+H]=565.3, method=A; $^1$H NMR (400 MHz, DMSO) δ 10.22 (s, 1H), 9.08 (s, 1H), 8.69 (s, 1H), 8.47 (s, 1H), 8.44 (s, 1H), 8.37 (d, J=6.0 Hz, 1H), 8.21 (s, 1H), 7.87 (d, J=7.6 Hz, 1H), 7.14 (s, 1H), 4.55 (m, 1H), 4.02 (m, 1H), 3.91 (d, J=11.4 Hz, 2H), 3.41 (m, 2H), 2.01-1.88 (m, 2H), 1.83 (d, J=13.0 Hz, 2H), 1.55 (d, J=6.7 Hz, 5H), 1.39-1.20 (m, 4H), 0.80 (t, J=7.3 Hz, 3H). Enantiomer 2 (35.5 mg): LCMS (ESI): R$_T$(min)=9.55, [M+H]=565.3, method=A; $^1$H NMR (400 MHz, DMSO) δ 10.21 (s, 1H), 9.08 (s, 1H), 8.69 (s, 1H), 8.47 (s, 1H), 8.43 (s, 1H), 8.37 (d, J=5.9 Hz, 1H), 8.21 (s, 1H), 7.87 (d, J=7.1 Hz, 1H), 7.14 (s, 1H), 4.55 (m, 1H), 4.01 (s, 1H), 3.91 (d, J=10.7 Hz, 2H), 3.41 (t, J=11.0 Hz, 2H), 2.02-1.88 (m, 2H), 1.83 (d, J=13.1 Hz, 2H), 1.55 (d, J=6.7 Hz, 5H), 1.30 m, 4H), 0.80 (t, J=7.3 Hz, 3H).

Examples 323 and 324: 1-(sec-butyl)-6-((2-((3S,4R)-3-fluoro-4-hydroxypiperidin-1-yl)pyrimidin-4-yl)amino)-N-(tetrahydro-2H-pyran-4-yl)-1H-pyrrolo[3,2-c]pyridine-3-carboxamide (Isomer 1) and 1-(sec-butyl)-6-((2-((3S,4R)-3-fluoro-4-hydroxypiperidin-1-yl)pyrimidin-4-yl)amino)-N-(tetrahydro-2H-pyran-4-yl)-1H-pyrrolo[3,2-c]pyridine-3-carboxamide (Isomer 2)

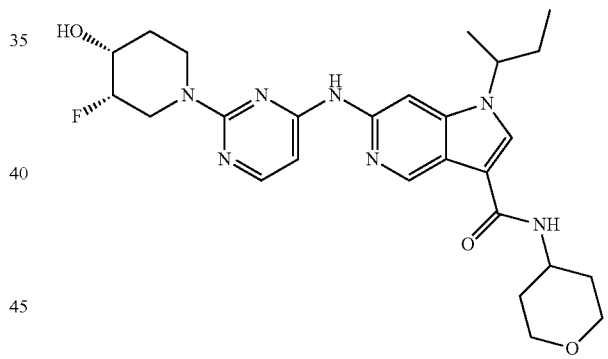

To a microwave reaction vessel was added 6-bromo-1-(sec-butyl)-N-(tetrahydro-2H-pyran-4-yl)-1H-pyrrolo[3,2-c]pyridine-3-carboxamide (Example 321, Step 2)(0.18 g, 0.47 mmol), (+)-(3S,4R)-1-(4-aminopyrimidin-2-yl)-3-fluoropiperidin-4-ol (Example A66) (0.10 g, 0.47 mmol), sodium tert-butoxide (0.14 g, 1.4 mmol), Chloro{[BrettPhos][2-(2-aminoethylphenyl]palladium(II)]}/[BrettPhos] admixture (molar PdP/P=1:1, 60 mg) and tert-butanol (4 mL). The reaction was degassed by nitrogen bubbling for 20 min. The reaction was sealed and stirred at 120° C. for 90 min. The reaction was filtered and concentrated in vacuo. The crude product was purified by supercritical fluid chromatography to give the two stereoisomers of the title compound (55 mg, 23%). Stereoisomer 1 (18.2 mg): LCMS (ESI): R$_T$(min)=3.3, [M+H]=512.3, method=B; $^1$H NMR (400 MHz, DMSO) δ 9.77 (s, 1H), 9.02 (s, 1H), 8.32 (s, 1H), 8.16 (s, 1H), 7.95 (d, J=5.6 Hz, 1H), 7.84 (d, J=7.6 Hz, 1H), 6.36 (d, J=5.6 Hz, 1H), 5.10 (d, J=5.1 Hz, 1H), 4.67 (d, J=49.4 Hz, 1H), 4.49 (m, 1H), 4.38 (m, 1H), 4.24 (s, 1H), 4.08-3.95 (m, 1H), 3.88 (m, 3H), 3.60 (m, 1H), 3.40 (t, J=10.9 Hz, 3H), 1.83 (m, 6H), 1.55 (m, 2H), 1.48 (d, J=6.7 Hz, 3H), 0.80 (t, J=7.3 Hz, 3H). Stereoisomer 2 (18.4 mg); LCMS (ESI): $R_T$ (min)=3.27, [M+H]=512.3, method=B; $^1$H NMR (400 MHz, DMSO) δ 9.77 (s, 1H), 9.02 (d, J=0.7 Hz, 1H), 8.33 (s, 1H), 8.16 (s, 1H), 7.95 (d, J=5.7 Hz, 1H), 7.84 (d, J=7.5 Hz, 1H), 6.36 (d, J=5.5 Hz, 1H), 5.10 (d, J=5.1 Hz, 1H), 4.67 (d, J=49.4 Hz, 1H), 4.57-4.44 (m, 1H), 4.38 (m, 1H), 4.27 (s, 1H), 4.01 (m, 1H), 3.88 (t, J=13.7 Hz, 3H), 3.60 (m, 1H), 3.40 (m, 3H), 1.98-1.77 (m, 4H), 1.70 (m, 2H), 1.62-1.46 (m, 3H), 0.79 (t, J=7.3 Hz, 3H).

Examples 325 and 326: 1-(sec-butyl)-6-((2-((3S,4R)-3-fluoro-4-methoxypiperidin-1-yl)pyrimidin-4-yl)amino)-N-(1-(oxetan-3-yl)piperidin-4-yl)-1H-pyrrolo[3,2-c]pyridine-3-carboxamide (Isomer 1) and 1-(sec-butyl)-6-((2-((3S,4R)-3-fluoro-4-methoxypiperidin-1-yl)pyrimidin-4-yl)amino)-N-(1-(oxetan-3-yl)piperidin-4-yl)-1H-pyrrolo[3,2-c]pyridine-3-carboxamide (Isomer 2)

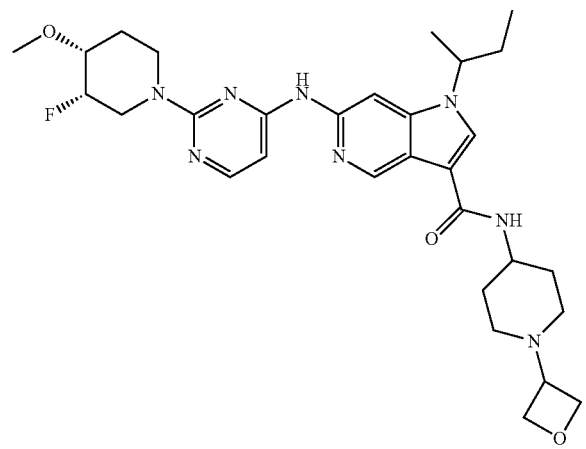 [SMILES: CCC(C)n1cc(C(=O)NC2CCN(C3COC3)CC2)c2cnc(Nc3ccnc(N4CC[C@@H](OC)[C@@H](F)C4)n3)cc21]

Step 1: (+/−)-tert-Butyl 4-(6-bromo-1-(sec-butyl)-1H-pyrrolo[3,2-c]pyridine-3-carboxamido)piperidine-1-carboxylate

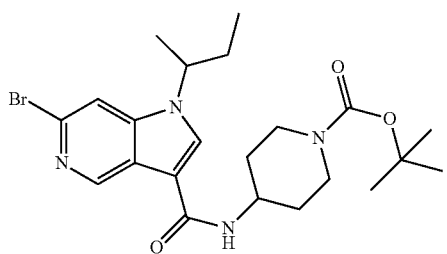 [SMILES: CCC(C)n1cc(C(=O)NC2CCN(C(=O)OC(C)(C)C)CC2)c2cnc(Br)cc21]

To a solution of (+/−)-6-bromo-1-(sec-butyl)-1H-pyrrolo[3,2-c]pyridine-3-carboxylic acid (Example 321, Step 1) (0.80 g, 2.7 mmol) in N,N-dimethylformamide (10 mL) was added N,N-diisopropylethylamine (0.6 mL, 3.5 mmol), O-(benzotriazol-1-yl)-N,N,N',N'-tetramethyluronium hexafluorophosphate (1.4 g, 3.5 mmol) and tert-butyl 4-aminopiperidine-1-carboxylate (0.54 g, 2.7 mmol). The reaction was stirred at room temperature for 1 h, diluted with saturated sodium bicarbonate and extracted with EtOAc (3×). The combined extracts were washed with brine, dried over sodium sulfate, filtered and concentrated in vacuo. The crude product was purified by silica gel flash chromatography (solvent gradient: 0-10% methanol in dichloromethane) to give the title compound (1.2 g, 93%). LCMS (ESI): [M+H]$^+$=479.3.

Step 2: (+/−)-6-Bromo-1-(sec-butyl)-N-(1-(oxetan-3-yl)piperidin-4-yl)-1H-pyrrolo[3,2-c]pyridine-3-carboxamide

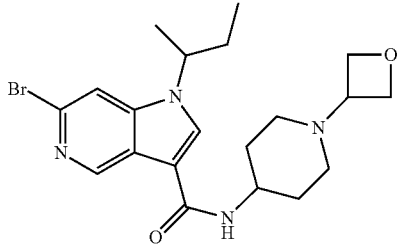 [SMILES: CCC(C)n1cc(C(=O)NC2CCN(C3COC3)CC2)c2cnc(Br)cc21]

To a solution of (+/−)-tert-butyl 4-(6-bromo-1-(sec-butyl)-1H-pyrrolo[3,2-c]pyridine-3-carboxamido)piperidine-1-carboxylate (1.2 g, 2.6 mmol) in 1,4-dioxane (15 mL) was added HCl (4M in 1,4-dioxane, 15 mL). The reaction was stirred at room temperature for 16 h and concentrated in vacuo. To the residue was added dichloroethane (50 mL), N,N-diisopropylethylamine (0.9 mL, 5.2 mmol) and 3-oxetanone (0.6 g, 8 mmol). The reaction was stirred at room temperature for 10 min before the addition of sodium triacetoxyborohydride (1.6 g, 7.7 mmol). The reaction was stirred overnight at room temperature. The reaction was diluted with saturated sodium bicarbonate and the product was extracted with dichloromethane (3×). The combined organic extracts were washed with brine, dried over sodium sulfate, filtered and concentrated in vacuo. The crude product was purified by silica gel flash chromatography (solvent gradient: 0-10% methanol in dichloromethane) to give the title compound (0.6 g, 50%). LCMS (ESI): [M+H]$^+$=435.2.

Step 3: 1-(sec-butyl)-6-((2-(3S,4R)-3-fluoro-4-methoxypiperidin-1-yl)pyrimidin-4-yl)amino)-N-(1-(oxetan-3-yl)piperidin-4-yl)-1H-pyrrolo[3,2-c]pyridine-3-carboxamide (Isomer 1) and 1-(sec-butyl)-6-((2-((3S,4R)-3-fluoro-4-methoxypiperidin-1-yl)pyrimidin-4-yl)amino)-N-(1-(oxetan-3-yl)piperidin-4-yl)-1H-pyrrolo[3,2-c]pyridine-3-carboxamide (Isomer 2)

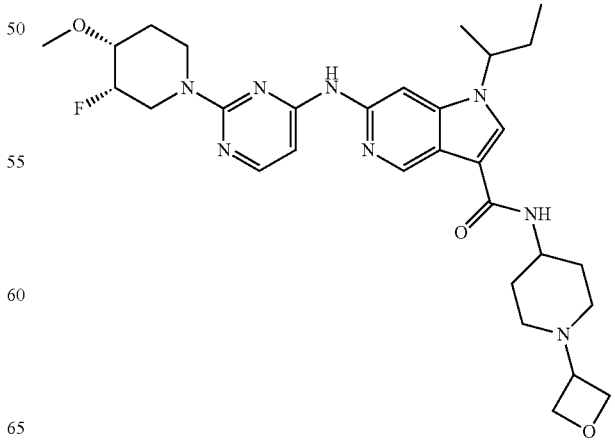

To a microwave reaction vessel was added (+/−)-6-bromo-1-(sec-butyl)-N-(1-(oxetan-3-yl)piperidin-4-yl)-1H-pyrrolo[3,2-c]pyridine-3-carboxamide (0.20 g, 0.46 mmol), (+)-2-((3S,4R)-3-fluoro-4-methoxypiperidin-1-yl)pyrimidin-4-ylamine (Example A65) (0.10 g, 0.46 mmol), sodium tert-butoxide (0.14 g, 1.4 mmol), chloro{[BrettPhos][2-(2-aminoethylphenyl]palladium(II)]}/[BrettPhos] admixture (molar PdP/P=1:1, 60 mg) and tert-butanol (4 mL). The reaction was degassed by nitrogen bubbling for 20 min. The reaction was sealed and stirred at 120° C. for 90 min. The reaction was filtered and concentrated in vacuo. The crude product was purified by supercritical fluid chromatography to give the two stereoisomers of the title compound (93.6 mg, 35%): Stereoisomer 1 (43.3 mg): LCMS (ESI): RT (min)=3.11, [M+H]=581.3, method=B; $^1$H NMR (400 MHz, DMSO) δ 9.82 (s, 1H), 9.01 (d, J=0.7 Hz, 1H), 8.31 (s, 1H), 8.16 (s, 1H), 7.95 (d, J=5.7 Hz, 1H), 7.85 (d, J=7.7 Hz, 1H), 6.37 (d, J=5.6 Hz, 1H), 4.93 (d, J=46.9 Hz, 1H), 4.64 (s, 1H), 4.54 (m, 2H), 4.48-4.28 (m, 4H), 3.78 (m, 1H), 3.55 (m, 2H), 2.73 (m, 2H), 1.84 (m, 7H), 1.64-1.39 (m, 5H), 0.78 (t, J=7.3 Hz, 3H). Stereoisomer 2 (50.3 mg); LCMS (ESI): RT (min)=3.16, [M+H]=581.3, method=B; $^1$H NMR (400 MHz, DMSO) δ 9.82 (s, 1H), 9.01 (d, J=0.7 Hz, 1H), 8.31 (s, 1H), 8.16 (s, 1H), 7.95 (d, J=5.7 Hz, 1H), 7.85 (d, J=7.7 Hz, 1H), 6.37 (d, J=5.6 Hz, 1H), 4.93 (d, J=46.9 Hz, 1H), 4.64 (s, 1H), 4.54 (m, 2H), 4.48-4.28 (m, 4H), 3.78 (m, 1H), 3.55 (m, 2H), 2.73 (m, 2H), 1.84 (m, 7H), 1.64-1.39 (m, 5H), 0.78 (t, J=7.3 Hz, 3H).

Example 327: N-(6-((2-(1-(Cyclopropylsulfonyl)-1H-pyrazol-4-yl)pyrimidin-4-yl)amino)-1-isopropyl-1H-pyrrolo[3,2-c]pyridin-3-yl)acetamide

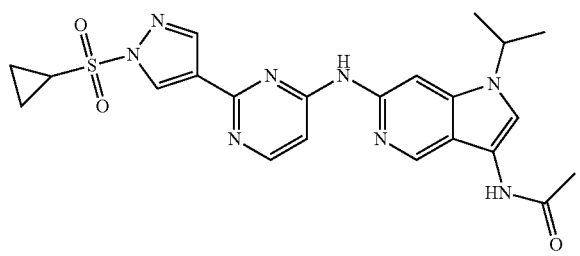 [SMILES: CC(=O)Nc1cn(C(C)C)c2cc(Nc3ccnc(-c4cnn(S(=O)(=O)C5CC5)c4)n3)ncc12]

Step 1: N-(6-Chloro-1-isopropyl-1H-pyrrolo[3,2-c]pyridin-3-yl)acetamide

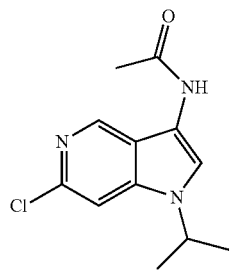 [SMILES: CC(=O)Nc1cn(C(C)C)c2cc(Cl)ncc12]

To a microwave reaction vessel was added 6-chloro-3-iodo-1-isopropyl-1H-pyrrolo[3,2-c]pyridine (Example 63, Step 2) (0.10 g, 0.40 mmol), acetamide (44 mg, 0.75 mmol), trans-N,N'-dimethylcyclohexane-1,2-diamine (45 mg, 0.31 mmol), copper (I) iodide (60 mg, 0.31 mmol), potassium triphosphate (0.3 g, 0.62 mmol) and 1,4-dioxane (3 mL). The reaction was degassed by nitrogen bubbling for 20 min, sealed and stirred at 100° C. for 2.5 h. The mixture was filtered and concentrated in vacuo. The crude product was purified by silica gel chromatography (solvent gradient: 0-5% methanol in dichloromethane) to give the title compound (0.1 g, 60%). LCMS (ESI): M+H=252.

Step 2: N-(6-((2-(1-(Cyclopropylsulfonyl)-1H-pyrazol-4-yl)pyrimidin-4-yl)amino)-1-isopropyl-1H-pyrrolo[3,2-c]pyridin-3-yl)acetamide

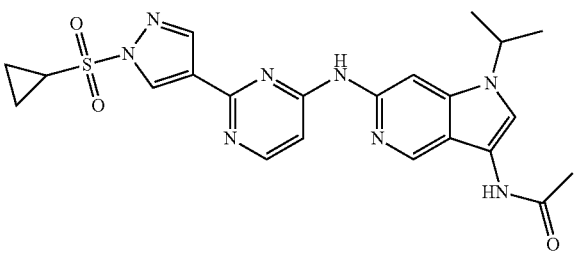 [SMILES: CC(=O)Nc1cn(C(C)C)c2cc(Nc3ccnc(-c4cnn(S(=O)(=O)C5CC5)c4)n3)ncc12]

To a microwave reaction vessel was added N-(6-chloro-1-isopropyl-1H-pyrrolo[3,2-c]pyridin-3-yl)acetamide (0.20 g, 0.79 mmol), 2-(1-(cyclopropylsulfonyl)-1H-pyrazol-4-yl)pyrimidin-4-ylamine (Example A62) (210 mg, 0.79 mmol, 2-dicyclohexylphosphino-2',4',6'-triisopropylbiphenyl (77 mg, 0.16 mmol), tris(dibenzylideneacetone)dipalladium(0) (36 mg, 0.040 mmol), cesium carbonate (0.52 g, 1.6 mmol) and 1,4-dioxane (3 mL). The reaction was degassed by nitrogen bubbling for 20 min, sealed and stirred at 100° C. for 90 min. The mixture was filtered and concentrated in vacuo. The crude product was purified by supercritical fluid chromatography to give the title compound (68.5 mg, 18%). LCMS (ESI): RT (min)=4.36, [M+H]=481.2, method=B; 1H NMR (400 MHz, DMSO) δ 10.17 (s, 1H), 10.09 (s, 1H), 8.81 (d, J=0.8 Hz, 1H), 8.68 (d, J=0.5 Hz, 1H), 8.47 (d, J=0.5 Hz, 1H), 8.36 (d, J=5.9 Hz, 2H), 7.77 (s, 1H), 7.12 (s, 1H), 4.82-4.67 (m, 1H), 2.11 (s, 3H), 1.51 (d, J=6.7 Hz, 6H), 1.39-1.20 (m, 4H).

Example 328: N-(6-((2-(1-(Cyclopropylsulfonyl)-1H-pyrazol-4-yl)pyrimidin-4-yl)amino)-1-isopropyl-1H-pyrrolo[3,2-c]pyridin-3-yl)-2-hydroxyacetamide

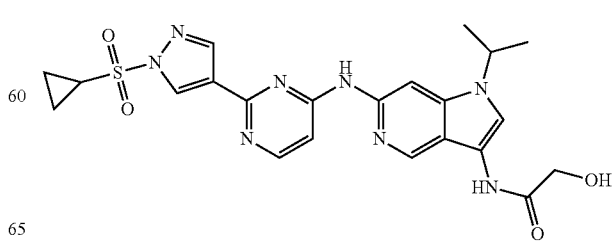

Step 1: 2-(Benzyloxy)-N-(6-chloro-1-isopropyl-1H-pyrrolo[3,2-c]pyridin-3-yl)acetamide

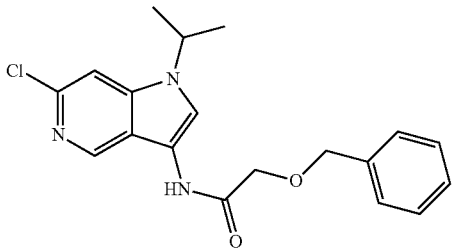 [SMILES: CC(C)n1cc(NC(=O)COCc2ccccc2)c2cnc(Cl)cc21]

The title compound was prepared according to a similar procedure as described in Example 327. LCMS (ESI): M+H=358.

Step 2: 2-(Benzyloxy)-N-(6-((2-(1-(cyclopropylsulfonyl)-1H-pyrazol-4-yl)pyrimidin-4-yl)amino)-1-isopropyl-1H-pyrrolo[3,2-c]pyridin-3-yl)acetamide

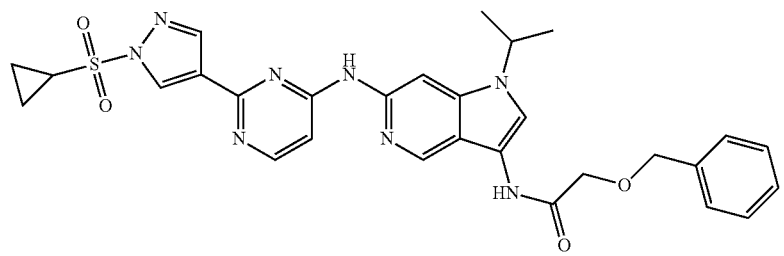 [SMILES: CC(C)n1cc(NC(=O)COCc2ccccc2)c2cnc(Nc3ccnc(-c4cnn(S(=O)(=O)C5CC5)c4)n3)cc21]

A microwave reaction vessel was charged 2-(benzyloxy)-N-(6-chloro-1-isopropyl-1H-pyrrolo[3,2-c]pyridin-3-yl)acetamide (1.0 g, 2.8 mmol), 2-(1-cyclopropanesulfonyl-1H-pyrazol-4-yl)pyrimidin-4-ylamine (Example A62) (0.74 g, 2.8 mmol), 2-dicyclohexylphosphino-2',4',6'-triisopropylbiphenyl (270 mg, 0.56 mmol), tris(dibenzylideneacetone)dipalladium(0) (130 mg, 0.14 mmol), cesium carbonate (1.8 g, 5.6 mmol) and 1,4-dioxane (3 mL). The reaction was sealed and degassed by nitrogen bubbling for 20 min and stirred at 100° C. for 3.5 h. The reaction mixture was then filtered and concentrated in vacuo. The crude product was purified by silica gel flash chromatography (solvent gradient: 0-5% methanol in dichloromethane) to give the title compound (0.3 g, 20%). LCMS (ESI): [M+H]⁺=587.

Step 3: N-(6-((2-(1-(cyclopropylsulfonyl)-1H-pyrazol-4-yl)pyrimidin-4-yl)amino)-1-isopropyl-1H-pyrrolo[3,2-c]pyridin-3-yl)-2-hydroxyacetamide

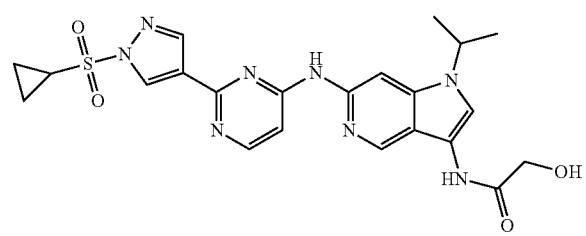 [SMILES: CC(C)n1cc(NC(=O)CO)c2cnc(Nc3ccnc(-c4cnn(S(=O)(=O)C5CC5)c4)n3)cc21]

A mixture of 2-(benzyloxy)-N-(6-((2-(1-(cyclopropylsulfonyl)-1H-pyrazol-4-yl)pyrimidin-4-yl)amino)-1-isopropyl-1H-pyrrolo[3,2-c]pyridin-3-yl)acetamide (0.08 g, 0.1 mmol) and 20% palladium hydroxide on carbon (20%, 80 mg) in ethanol was bubbled through with hydrogen for 20 min and then stirred under hydrogen for 15 h. The reaction was then filtered through celite and concentrated in vacuo. The crude product was purified by supercritical fluid chromatography to give the title compound (26.3 mg, 40%). LCMS (ESI): RT (min)=4.22, [M+H]⁺=497.2, method=B; ¹H NMR (400 MHz, DMSO) δ 10.17 (s, 1H), 9.83 (s, 1H), 8.81 (d, J=0.8 Hz, 1H), 8.68 (s, 1H), 8.52-8.44 (m, 1H), 8.36 (d, J=5.9 Hz, 2H), 7.76 (s, 1H), 7.12 (s, 1H), 5.52 (t, J=6.0 Hz, 1H), 4.75 (m, 1H), 4.08 (d, J=6.0 Hz, 2H), 1.52 (d, J=6.7 Hz, 6H), 1.39-1.22 (m, 4H).

Example 329: N⁴-(1-Isopropyl-2-methyl-1H-imidazo[4,5-c]pyridin-6-yl)-N²-(2-methyl-2-(4H-1,2,4-triazol-3-yl)propyl)pyrimidine-2,4-diamine

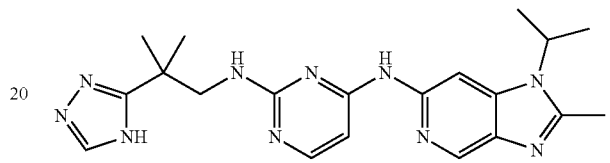

A mixture of 3-((4-((1-isopropyl-2-methyl-1H-imidazo[4,5-c]pyridin-6-yl)amino)pyrimidin-2-yl)amino)-2,2-dimethylpropanamide (Example 113) (0.2 g, 0.50 mmoL) and N,N-dimethylformamide-dimethyl acetal (2 mL) was stirred at 85° C. for 2 h. The mixture was then cooled to room temperature and concentrated in vacuo. To the residue was added 40% hydrazine in water (1.0 mL) and acetic acid (0.5 mL). The reaction was stirred at 65° C. for 1 h, cooled to room temperature and concentrated in vacuo. The crude product was purified by reverse phase-HPLC to give the title compound (16 mg, 7%). LCMS (ESI): RT (min)=3.42, [M+H]⁺=407.3, method=B; ¹H NMR (400 MHz, DMSO) δ 13.73 (s, 1H), 9.57 (s, 1H), 8.47 (s, 1H), 8.34 (s, 1H), 7.87 (m, 2H), 6.51 (m, 1H), 6.45-6.04 (m, 2H), 4.70 (m, 1H), 3.63 (s, 2H), 2.55 (s, 3H), 1.53 (d, J=5.7 Hz, 6H), 1.34 (s, 6H).

Example 330: N-(2-(1-(Cyclopropylsulfonyl)-1H-pyrazol-4-yl)pyrimidin-4-yl)-1-isopropyl-3-morpholino-1H-pyrrolo[3,2-c]pyridin-6-amine

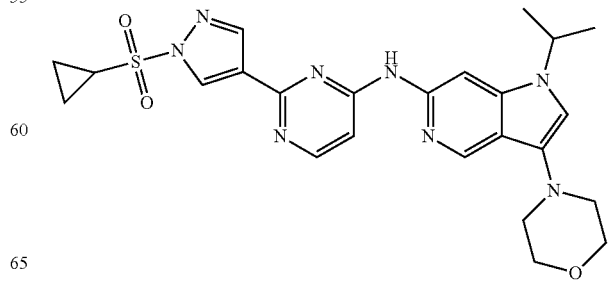

Step 1: 4-(6-Chloro-1-isopropyl-1H-pyrrolo[3,2-c]pyridin-3-yl)morpholine

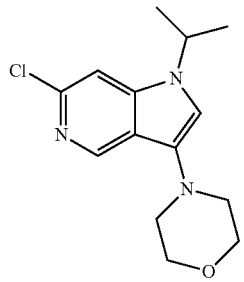 [SMILES: CC(C)n1cc(N2CCOCC2)c2cnc(Cl)cc21]

To a microwave reaction vessel was charged 6-chloro-3-iodo-1-isopropyl-1H-pyrrolo[3,2-c]pyridine (Example 63, Step 2) (0.60 g, 1.9 mmol), morpholine (0.49 g, 5.6 mmol), 2-dicyclohexylphosphino-2',4',6'-triisopropylbiphenyl (91 mg, 0.19 mmol), tris(dibenzylideneacetone)dipalladium(0) (86 mg, 0.094 mmol), cesium carbonate (1.3 g, 4.1 mmol) and 1,4-dioxane (2 mL). The reaction was sealed, degassed by nitrogen bubbling for 20 min, and stirred at 100° C. for 2 h. The reaction mixture was then filtered and concentrated in vacuo. The crude product was purified by silica gel flash chromatography (solvent gradient: 0-10% methanol in dichloromethane) to give the title compound (0.08 g, 15%). LCMS (ESI): M+H=281.

Step 2: N-(2-(1-(Cyclopropylsulfonyl)-1H-pyrazol-4-yl)pyrimidin-4-yl)-1-isopropyl-3-morpholino-1H-pyrrolo[3,2-c]pyridin-6-amine

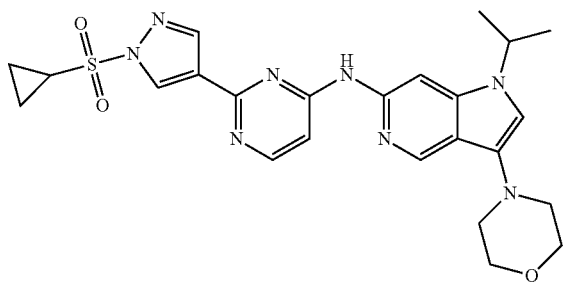 [SMILES: CC(C)n1cc(N2CCOCC2)c2cnc(Nc3ccnc(-c4cnn(S(=O)(=O)C5CC5)c4)n3)cc21]

To a microwave reaction vessel was charged 4-(6-chloro-1-isopropyl-1H-pyrrolo[3,2-c]pyridin-3-yl)morpholine (0.080 g, 0.29 mmol), 2-(1-cyclopropanesulfonyl-1H-pyrazol-4-yl)pyrimidin-4-ylamine (Example A62) (0.076 g, 0.29 mmol), 2-dicyclohexylphosphino-2',4',6'-triisopropylbiphenyl (28 mg, 0.06 mmol), tris(dibenzylideneacetone)dipalladium(0) (13 mg, 0.014 mmol), cesium carbonate (0.19 g, 0.57 mmol) and 1,4-dioxane (3 mL). The reaction was sealed, degassed by nitrogen bubbling for 20 min and stirred at 100° C. for 90 min. The reaction mixture was then filtered and concentrated in vacuo. The crude product was purified by reverse phase HPLC to give the title compound (16 mg, 11%). LCMS (ESI): [M+H]⁺=509.2, method=B; ¹H NMR (400 MHz, DMSO) δ 10.13 (s, 1H), 8.67 (d, J=0.5 Hz, 1H), 8.64 (d, J=0.8 Hz, 1H), 8.46 (d, J=0.5 Hz, 1H), 8.36 (s, 1H), 8.33 (m, 1H), 7.12 (s, 1H), 6.95 (s, 1H), 4.67 (m, 1H), 3.87-3.75 (m, 4H), 3.29-3.23 (m, 1H), 3.10-2.98 (m, 4H), 1.50 (d, J=6.7 Hz, 6H), 1.38-1.23 (m, 4H).

Example 331: 2-(4-(6-((2-(1-(Cyclopropylsulfonyl)-1H-pyrazol-4-yl)pyrimidin-4-yl)amino)-1-isopropyl-1H-pyrrolo[3,2-c]pyridin-3-yl)-1H-pyrazol-1-yl)acetamide

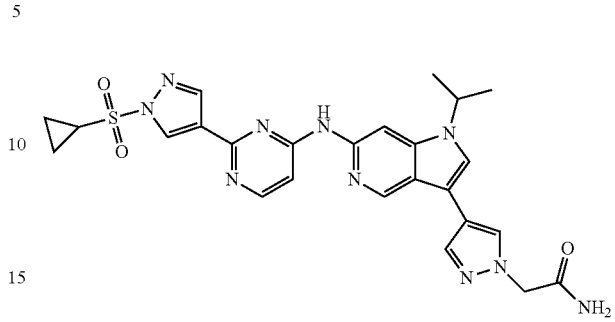

Step 1: 2-(4-(6-Bromo-1-isopropyl-1H-pyrrolo[3,2-c]pyridin-3-yl)-1H-pyrazol-1-yl)acetamide

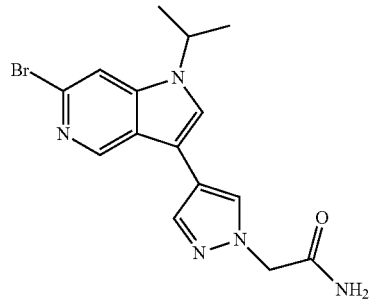 [SMILES: CC(C)n1cc(-c2cnn(CC(N)=O)c2)c2cnc(Br)cc21]

A mixture of 6-bromo-3-iodo-1-isopropyl-1H-pyrrolo[3,2-c]pyridine (Example 253, step 9) (1.5 g, 4.1 mmol), 2-(4-(4,4,5,5-tetramethyl-1,3,2-dioxaborolan-2-yl)-1H-pyrazol-1-yl)acetamide (1.2 g, 4.5 mmol), 2M aqueous sodium carbonate (3.1 mL, 6.2 mmol), and bis(di-tert-butyl(4-dimethylaminophenyl)phosphine)dichloropalladium(II) (0.3 g, 0.41 mmol) in acetonitrile (2.5 mL) was degassed for 20 min and stirred at 100° C. for 3 h. The reaction mixture was filtered and concentrated in vacuo. The crude product was purified by silica gel chromatography (solvent gradient: 0-10% methanol in dichloromethane) to give the title compound (0.375 g, 25%). LCMS (ESI): [M+H]⁺=362.

Step 2: 2-(4-(6-((2-(1-(Cyclopropylsulfonyl)-1H-pyrazol-4-yl)pyrimidin-4-yl)amino)-1-isopropyl-1H-pyrrolo[3,2-c]pyridin-3-yl)-1H-pyrazol-1-yl)acetamide

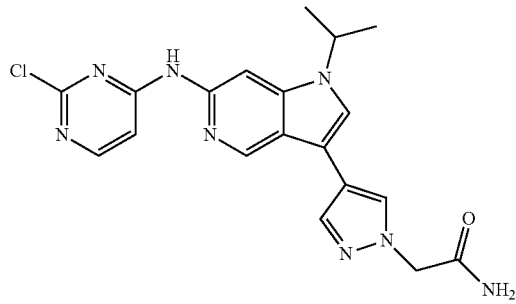 [SMILES: CC(C)n1cc(-c2cnn(CC(N)=O)c2)c2cnc(Nc3ccnc(Cl)n3)cc21]

A mixture of 2-(4-(6-bromo-1-isopropyl-1H-pyrrolo[3,2-c]pyridin-3-yl)-1H-pyrazol-1-yl)acetamide (0.117 g, 0.323 mmol), 4-amino-2-chloropyrimidine (43 mg, 0.323 mmol), cesium carbonate (211 mg, 0.646 mmol), 4,5-bis(diphenylphosphino)-9,9-dimethylxanthene (19 mg, 0.032 mmol), tris(dibenzylideneacetone)dipalladium(0) (15 mg, 0.016 mmol) in 1,4-dioxane (5 mL) was degassed by nitrogen bubbling for 20 min. The reaction was sealed and stirred at 120° C. for 3 h. The reaction was filtered and concentrated in vacuo and the crude product was purified by silica gel chromatography (solvent gradient: 0-10% methanol in dichloromethane) to give the title compound (40 mg, 30%). LCMS (ESI): [M+H]$^+$=411.

Step 3: 2-(4-(6-((2-(1-(Cyclopropylsulfonyl)-1H-pyrazol-4-yl)pyrimidin-4-yl)amino)-1-isopropyl-1H-pyrrolo[3,2-c]pyridin-3-yl)-1H-pyrazol-1-yl)acetamide

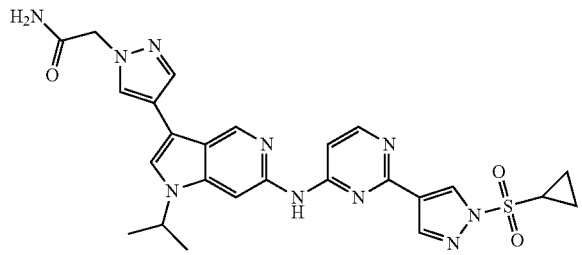 [SMILES: CC(C)n1cc(-c2cnn(CC(N)=O)c2)c2cnc(Nc3ccnc(-c4cnn(S(=O)(=O)C5CC5)c4)n3)cc21]

A mixture of 2-(4-(6-((2-(1-(cyclopropylsulfonyl)-1H-pyrazol-4-yl)pyrimidin-4-yl)amino)-1-isopropyl-1H-pyrrolo[3,2-c]pyridin-3-yl)-1H-pyrazol-1-yl)acetamide (40 mg, 0.097 mmol), 1-cyclopropylsulfonyl-4-(4,4,5,5-tetramethyl-1,3,2-dioxaborolan-2-yl)pyrazole (Example 51, Step 6)(1.2 g, 4.5 mmol), sodium carbonate (2M in water) (0.7 mL, 0.15 mmol), and 4,5-bis(diphenylphosphino)-9,9-dimethylxanthene (36 mg, 0.12 mmol) in acetonitrile (2.5 mL) was degassed for 20 min and stirred at 100° C. for 3 h. The reaction mixture was filtered and concentrated in vacuo. The crude product was purified by reverse phase HPLC to give the title compound (20 mg, 40%). LCMS (ESI): R$_T$=4.74 min, [M+H]$^+$=547.2, method=B; $^1$H NMR (400 MHz, DMSO) δ 10.20 (s, 1H), 8.83 (d, J=0.8 Hz, 1H), 8.70 (s, 1H), 8.47 (s, 1H), 8.44 (s, 1H), 8.37 (d, J=5.9 Hz, 1H), 8.19 (s, 1H), 7.90 (d, J=0.6 Hz, 1H), 7.78 (s, 1H), 7.44 (s, 1H), 7.26 (s, 1H), 6.49 (s, 1H), 4.89-4.67 (m, 3H), 1.57 (m, 6H), 1.40-1.19 (m, 4H).

Example 332: (+/−)-1-(1-(4-((1-Isopropyl-2-methyl-1H-imidazo[4,5-c]pyridin-6-yl)amino)pyrimidin-2-yl)-1H-imidazol-4-yl)ethanol

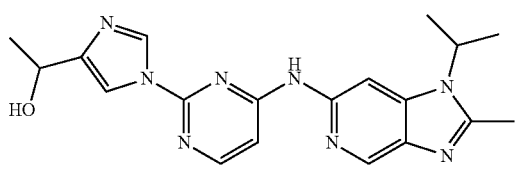 [SMILES: Cc1nc2cnc(Nc3ccnc(-n4cnc(C(C)O)c4)n3)cc2n1C(C)C]

A mixture of N-(2-chloropyrimidin-4-yl)-1-isopropyl-2-methyl-1H-imidazo[4,5-c]pyridin-6-amine (Example 46, Step 7) (215 mg, 0.71 mmol), 4-acetylimidazole (0.1 g, 0.89 mmol) and cesium carbonate (0.44 g, 1.3 mmol) in tert-butanol (2.5 mL) was irradiated in a microwave at 150° C. for 30 min. The reaction was diluted with saturated sodium bicarbonate and extracted with EtOAc (3×). The combined organic extracts were washed with brine, dried over sodium sulfate, filtered and concentrated in vacuo. The crude product was filtered through a silica gel cartridge eluting with EtOAc and concentrated in vacuo. To the residue was added 10 mL of methanol and sodium borohydride (50 mg, 1.3 mmol) at 0° C. The reaction was stirred at room temperature for 15 min, diluted with saturated sodium bicarbonate and extracted with EtOAc (3×). The combined organic extracts were washed with brine, dried over sodium sulfate, filtered and concentrated in vacuo. The crude product was purified by reverse phase HPLC to give the title compound (0.31 g, 92%). LCMS (ESI): R$_T$=3.53 min, [M+H]$^+$=379.2, method=B; $^1$H NMR (400 MHz, DMSO) δ 10.39 (s, 1H), 8.59 (d, J=0.8 Hz, 1H), 8.43 (d, J=1.3 Hz, 1H), 8.34 (d, J=5.9 Hz, 1H), 8.21 (s, 1H), 7.70 (t, J=1.1 Hz, 1H), 7.27 (s, 1H), 5.04 (d, J=4.8 Hz, 1H), 4.87-4.64 (m, 2H), 2.59 (s, 3H), 1.62 (d, J=6.9 Hz, 6H), 1.39 (d, J=6.5 Hz, 3H).

Example 333: 1-Isopropyl-N-(2-(4-methoxypiperidin-1-yl)pyrimidin-4-yl)-3-(methylsulfonyl)-1H-pyrrolo[3,2-c]pyridin-6-amine

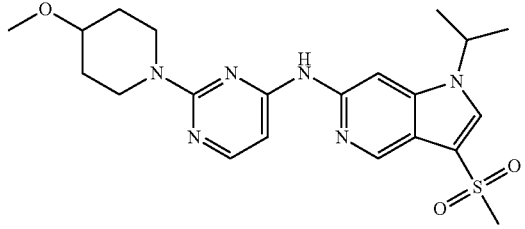 [SMILES: COC1CCN(c2nccc(Nc3cc4c(cn3)c(S(C)(=O)=O)cn4C(C)C)n2)CC1]

Step 1: 6-Chloro-1-isopropyl-3-(methylsulfonyl)-1H-pyrrolo[3,2-c]pyridine

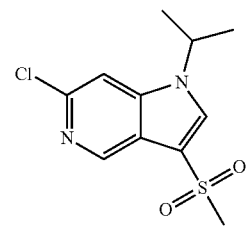 [SMILES: CC(C)n1cc(S(C)(=O)=O)c2cnc(Cl)cc21]

To a mixture of 6-chloro-3-iodo-1-isopropyl-1H-pyrrolo[3,2-c]pyridine (Example 63, Step 2) (0.25 g, 0.78 mmol), methanesulfonic acid (0.37 g, 3.9 mmol), copper(I) trifluoromethanesulfonate benzene complex (87 mg, 0.16 mmol), N,N'-dimethylethylenediamine (28 mg, 0.31 mmol) in dimethyl sulfoxide (4 mL) was degassed for 20 min by nitrogen bubbling. The reaction was then sealed and stirred at 110° C. for 15 h. The reaction was diluted with saturated sodium bicarbonate and extracted with EtOAc (3×). The combined organic extracts were washed with brine, dried over sodium sulfate, filtered and concentrated in vacuo. The crude product was purified by silica gel chromatography (solvent gradient: 0-100% EtOAc in heptane) to give the title compound (0.12 g, 56%). LCMS (ESI): M+H=273.

Step 2: 1-Isopropyl-N-(2-(4-methoxypiperidin-1-yl) pyrimidin-4-yl)-3-(methylsulfonyl)-1H-pyrrolo[3,2-c]pyridin-6-amine

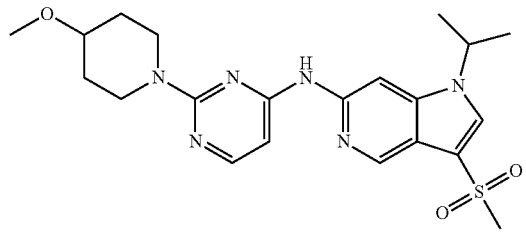 [SMILES: COC1CCN(c2nccc(Nc3cc4c(cn3)c(S(C)(=O)=O)cn4C(C)C)n2)CC1]

To a microwave reaction vessel was added 6-chloro-1-isopropyl-3-(methylsulfonyl)-1H-pyrrolo[3,2-c]pyridine (0.20 g, 0.7 mmol), 2-(4-methoxy-1-piperidyl)pyrimidin-4-amine (Example 3, Step 2) (0.20 g, 0.7 mmol), sodium tert-butoxide (0.2 g, 2 mmol), chloro{[BrettPhos][2-(2-aminoethylphenyl]palladium(II)]}/[BrettPhos] admixture (molar PdP/P=1:1, 50 mg) and tert-butanol (2.5 mL). The reaction was degassed by nitrogen bubbling for 20 min, sealed and stirred at 120° C. for 3 h. The reaction was filtered and concentrated in vacuo. The crude product was purified by reverse phase HPLC to give the title compound (39 mg, 10%). LCMS (ESI): $R_T$=4.25 min, [M+H]$^+$=445.2, method=B; $^1$H NMR (400 MHz, DMSO) δ 9.92 (s, 1H), 8.77 (d, J=0.9 Hz, 1H), 8.46 (s, 1H), 7.98 (d, J=5.7 Hz, 1H), 6.80 (m, 1H), 6.37 (d, J=5.7 Hz, 1H), 4.67 (m, 1H), 4.29-4.16 (m, 2H), 3.52-3.33 (m, 3H), 1.89 (s, 2H), 1.54 (m, 6H), 1.50-1.40 (m, 2H).

Example 334: (6-((2-(1-(1-Fluorovinyl)-1H-pyrazol-4-yl)pyrimidin-4-yl)amino)-1-isopropyl-1H-imidazo[4,5-c]pyridin-2-yl)methanol

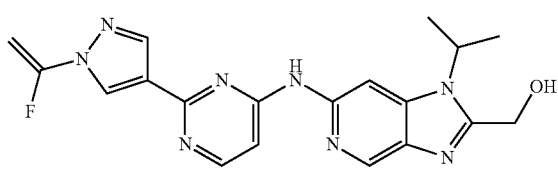 [SMILES: C=C(F)n1cc(-c2nccc(Nc3cc4c(cn3)nc(CO)n4C(C)C)n2)cn1]

Step 1: 1-(1-Fluorovinyl)-4-(4,4,5,5-tetramethyl-1,3,2-dioxaborolan-2-yl)-1H-pyrazole

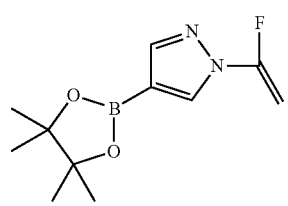 [SMILES: C=C(F)n1cc(B2OC(C)(C)C(C)(C)O2)cn1]

To a mixture of 4-(4,4,5,5-tetramethyl-1,3,2-dioxaborolan-2-yl)-1H-pyrazole (0.80 g, 4.1 mmol) and cesium carbonate (1.3 g, 4.1 mmol) in N,N-dimethylformamide was bubbled through with 1-chloro-1,1-difluoroethane for 15 min. The reaction was sealed and stirred under an atmosphere of 1-chloro-1,1-difluoroethane at 80° C. for 1 h. The reaction was diluted with brine and extracted with EtOAc (3×). The combined extracts were washed with brine, dried over sodium sulfate, filtered and concentrated in vacuo. The crude product was purified by silica gel chromatography (solvent gradient: 0-100% EtOAc in heptane) to give the title compound (0.6 g, 60%). LCMS (ESI): [M+H]$^+$=239.

Step 2: (6-((2-(1-(1-Fluorovinyl)-1H-pyrazol-4-yl)pyrimidin-4-yl)amino)-1-isopropyl-1H-imidazo[4,5-c]pyridin-2-yl)methanol

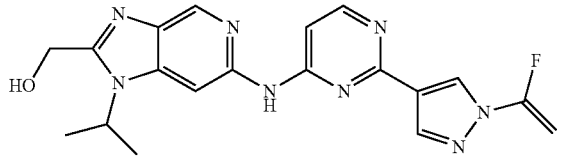 [SMILES: C=C(F)n1cc(-c2nccc(Nc3cc4c(cn3)nc(CO)n4C(C)C)n2)cn1]

The title compound was prepared according to a procedure similar to Example 52 using 1-(1-fluorovinyl)-4-(4,4,5,5-tetramethyl-1,3,2-dioxaborolan-2-yl)-1H-pyrazole. LCMS (ESI): $R_T$=4.27 min, [M+H]$^+$=395.2, method=B; $^1$H NMR (400 MHz, DMSO) δ 10.16 (s, 1H), 8.65 (d, J=0.8 Hz, 1H), 8.57 (d, J=1.3 Hz, 1H), 8.46 (s, 1H), 8.37 (d, J=5.9 Hz, 1H), 8.33 (d, J=3.3 Hz, 1H), 7.23 (s, 1H), 5.70 (s, 1H), 5.14 (m, 1H), 5.01 (m, 1H), 4.86 (m, 1H), 4.74 (s, 2H), 1.64 (d, J=6.9 Hz, 6H).

Example 335: 6-((2-(1-(Cyclopropylsulfonyl)-1H-pyrazol-4-yl)pyrimidin-4-yl)amino)-1-isopropyl-2-methyl-N-(tetrahydro-2H-pyran-4-yl)-1H-pyrrolo[3,2-c]pyridine-3-carboxamide

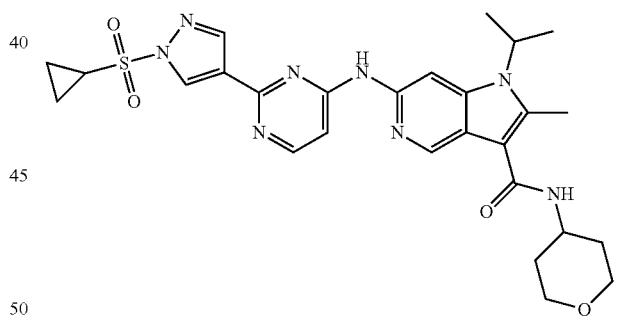

Step 1: 6-Bromo-1-isopropyl-2-methyl-1H-pyrrolo[3,2-c]pyridine-3-carboxylic acid

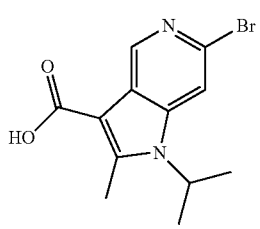

To solution of 6-bromo-1-isopropyl-1H-pyrrolo[3,2-c]pyridine-3-carboxylic acid (Example 51, Step 3) (1.36 g, 4.8 mmol) in tetrahydrofuran (10 mL) was added lithium diisopropylamide (5.9 mL, 1.8 M in heptane/ethylbenzene/THF, 10.6 mmol) at −78° C. The reaction was stirred at −78° C. for 20 min before the addition of iodomethane (0.75 mL, 12 mmol). The reaction was stirred at −78° C. for 20 min and allowed to warm to room temperature. The reaction was then diluted with saturated ammonium chloride and extracted with EtOAc (3×). The combined organic extracts were washed with brine, dried over sodium sulfate and concentrated to give a 2:5 mixture of the title compound and the starting material. The crude product was taken on to the next step without purification. LCMS (ESI): [M+H]$^+$=297.

Step 2: 6-Bromo-1-isopropyl-2-methyl-N-(tetrahydro-2H-pyran-4-yl)-1H-pyrrolo[3,2-c]pyridine-3-carboxamide

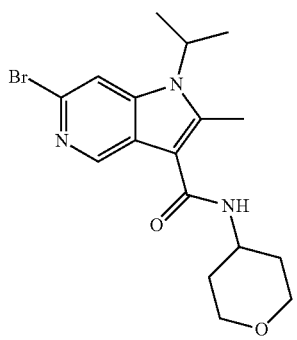 [SMILES: Cc1c(C(=O)NC2CCOCC2)c2cnc(Br)cc2n1C(C)C]

A mixture of 6-bromo-1-isopropyl-2-methyl-1H-pyrrolo[3,2-c]pyridine-3-carboxylic acid (1.3 g, 4.4 mmol), 4-aminotetrahydropyran (0.54 g, 5.2 mmol), O-(benzotriazol-1-yl)-N,N,N',N'-tetramethyluronium hexafluorophosphate (2 g, 5.2 mmol) and N,N-diisopropylethylamine (2.3 mL, 13 mmol) in N,N-dimethylformamide was stirred at room temperature for 15 h. The reaction was diluted with saturated sodium bicarbonate and extracted with EtOAc (3×). The combined organic extracts were washed with brined, dried over sodium sulfate, filtered and concentrated in vacuo. The crude product was purified by silica gel chromatography (solvent gradient: 0-100% EtOAc in heptane) to give the title compound (0.8 g, 50%). LCMS (ESI): [M+H]$^+$=380.

Step 3: 6-((2-(1-(Cyclopropylsulfonyl)-1H-pyrazol-4-yl)pyrimidin-4-yl)amino)-1-isopropyl-2-methyl-N-(tetrahydro-2H-pyran-4-yl)-1H-pyrrolo[3,2-c]pyridine-3-carboxamide

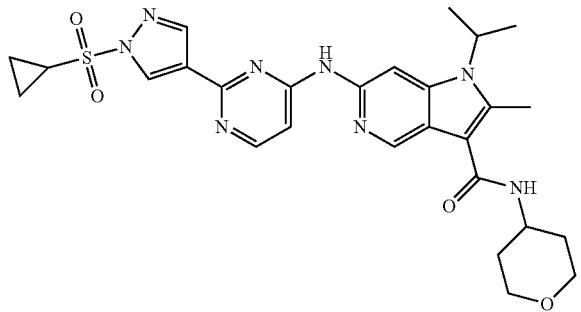 [SMILES: Cc1c(C(=O)NC2CCOCC2)c2cnc(Nc3ccnc(-c4cnn(S(=O)(=O)C5CC5)c4)n3)cc2n1C(C)C]

To a microwave reaction vessel was added 6-bromo-1-isopropyl-2-methyl-N-(tetrahydro-2H-pyran-4-yl)-1H-pyrrolo[3,2-c]pyridine-3-carboxamide (0.5 g, 1 mmol), 2-(1-cyclopropanesulfonyl-1H-pyrazol-4-yl)pyrimidin-4-ylamine (Example A62) (0.3 g, 1 mmol), cesium carbonate (0.9 g, 3 mmol), 2-dicyclohexylphosphino-2',4',6'-triisopropylbiphenyl (0.1 g, 0.3 mmol), tris(dibenzylideneacetone)dipalladium(0) (0.06 g, 0.07 mmol) and 1,4-dioxane (3 mL). The reaction was degassed by nitrogen bubbling for 20 min, sealed and stirred at 100° C. for 3 h. The reaction mixture was filtered and concentrated in vacuo. The crude product was purified by supercritical fluid chromatography to give the title compound (20.8 mg, 3%). LCMS (ESI): R$_T$=4.47 min, [M+H]$^+$=565.3, method=B; $^1$H NMR (400 MHz, DMSO) δ 10.12 (s, 1H), 8.73-8.63 (m, 2H), 8.48 (s, 1H), 8.38 (d, J=5.9 Hz, 2H), 7.83 (d, J=7.8 Hz, 1H), 7.29 (s, 1H), 4.81 (m, 1H), 4.14-3.96 (m, 1H), 3.89 (m, 2H), 2.60 (s, 3H), 1.93-1.77 (m, 2H), 1.64 (d, J=7.0 Hz, 6H), 1.37-1.23 (m, 4H).

Example 336: N-(2-(5-Chloro-1-(cyclopropylmethyl)-1H-pyrazol-4-yl)pyrimidin-4-yl)-1-isopropyl-2-methyl-1H-imidazo[4,5-c]pyridin-6-amine

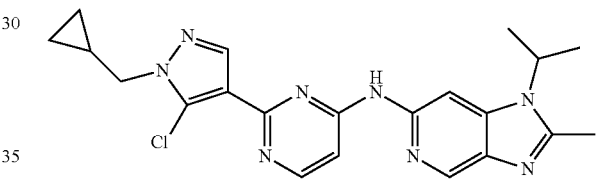

Step 1: tert-butyl N-tert-butoxycarbonyl-N-(2-chloropyrimidin-4-yl)carbamate

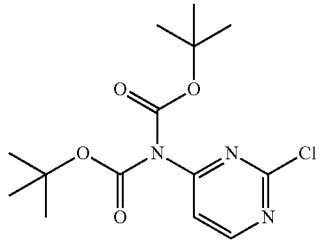 [SMILES: CC(C)(C)OC(=O)N(C(=O)OC(C)(C)C)c1ccnc(Cl)n1]

To a mixture of 2-chloropyrimidin-4-amine (4.1 g, 32 mmol) in 2-methyltetrahydrofuran (150 mL) was added di-tert-butyl dicarbonate (15 g, 66 mmol) and 4-N,N-dimethylpyridine (0.2 g, 1.6 mmol). The reaction was stirred overnight at room temperature. The reaction mixture was concentrated in vacuo and the residue was purified by silica gel chromatography (solvent gradient: 0-50% EtOAc in heptane) to afford the title compound (10 g, quant.). LCMS (ESI): [M+H]$^+$=330.

Step 2: tert-Butyl N-tert-butoxycarbonyl-N-[2-[pyrazol-4-yl]pyrimidin-4-yl]carbamate

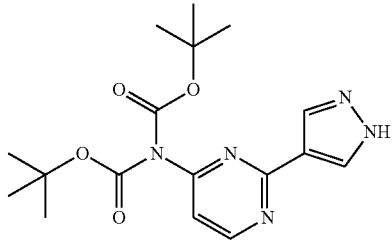 [SMILES: CC(C)(C)OC(=O)N(C(=O)OC(C)(C)C)c1ccnc(-c2cn[nH]c2)n1]

To a microwave tube was added tert-butyl N-tert-butoxycarbonyl-N-(2-chloropyrimidin-4-yl)carbamate (2.6 g, 7.9 mmol), 4-(4,4,5,5-tetramethyl-1,3,2-dioxaborolan-2-yl)-1H-pyrazole in acetonitrile (1.8 g, 9.5 mmol), 2M aqueous sodium carbonate (7.9 mL, 16 mmol), bis(di-tert-butyl(4-dimethylaminophenyl)phosphine)dichloropalladium(II) (0.59 g, 0.79 mmol) and acetonitrile (10 mL). The reaction was degassed by nitrogen bubbling for 20 minutes. The reaction was sealed and stirred at 100° C. for 2 hours. The reaction was diluted with water and the product was extracted with EtOAc (3×). The combined extracts were washed with brine, dried over sodium sulfate, filtered and concentrated. The crude product was purified by silica gel chromatography (0-100% EtOAc in heptane) to give the title compound (0.45 g, 22%). LCMS (ESI): [M+H]$^+$=262.

Step 3: tert-Butyl N-tert-butoxycarbonyl-N-[2-[1-(cyclopropylmethyl)pyrazol-4-yl]pyrimidin-4-yl]carbamate

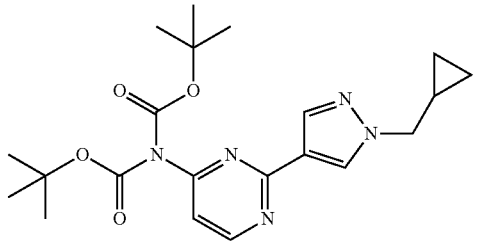 [SMILES: CC(C)(C)OC(=O)N(C(=O)OC(C)(C)C)c1ccnc(-c2cnn(CC3CC3)c2)n1]

A mixture of tert-butyl N-tert-butoxycarbonyl-N-[2-(1H-pyrazol-4-yl)pyrimidin-4-yl]carbamate (0.40 g, 1.1 mmol), cesium carbonate (0.4 g, 1.2 mmol) and bromomethylcyclopropane (0.12 mL, 1.2 mmol) in N,N-dimethylformamide (5 mL) was stirred at room temperature for 4 hours. The reaction was diluted with saturated sodium bicarbonate and extracted with EtOAc (3×). The combined organic extracts were washed with brine, dried over sodium sulfate, filtered and concentrated in vacuo. The crude product was purified by silica gel chromatography (solvent gradient: 0-100% EtOAc in heptane) to give the title compound (0.20 g, 43%). LCMS (ESI): [M+H]$^+$=416.

Step 4: 2-(5-Chloro-1-(cyclopropylmethyl)-1H-pyrazol-4-yl)pyrimidin-4-amine

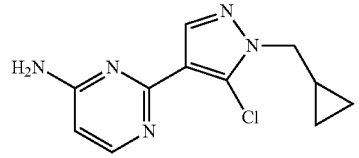 [SMILES: Nc1ccnc(-c2cnn(CC3CC3)c2Cl)n1]

To a solution of tert-butyl N-tert-butoxycarbonyl-N-[2-[1-(cyclopropylmethyl)pyrazol-4-yl]pyrimidin-4-yl]carbamate (0.2 g, 0.4 mmol) in N,N-dimethylformamide (3 mL) was added N-chlorosuccinimide (0.1 g, 0.7 mmol). The reaction was stirred at 60° C. for 2 h. The reaction was then diluted with saturated aqueous sodium bicarbonate and extracted with EtOAc (3×). The combined organic extracts were washed with brine, dried over sodium sulfate, filtered and concentrated in vacuo. The crude product was then filtered through a pad of silica gel, eluting with EtOAc, and concentrated to give tert-butyl N-tert-butoxycarbonyl-N-[2-[3-chloro-1-(cyclopropylmethyl)pyrazol-4-yl]pyrimidin-4-yl]carbamate (0.2 g) as a crude mixture. To the residue was added HCl (10 mL, 4M in 1,4-dioxane) and stirred at 60° C. for 1 h. The reaction was then diluted with saturated sodium bicarbonate and extracted with EtOAc (3×). The combined extracts were washed with brine, dried over sodium sulfate, filtered and concentrated in vacuo. The crude product was purified by silica gel chromatography (solvent gradient: 0-15% methanol in dichloromethane) to give the title compound (0.18 g, quant.). LCMS [M+H]$^+$=250.2.

Step 5: N-(2-(5-Chloro-1-(cyclopropylmethyl)-1H-pyrazol-4-yl)pyrimidin-4-yl)-1-isopropyl-2-methyl-1H-imidazo[4,5-c]pyridin-6-amine

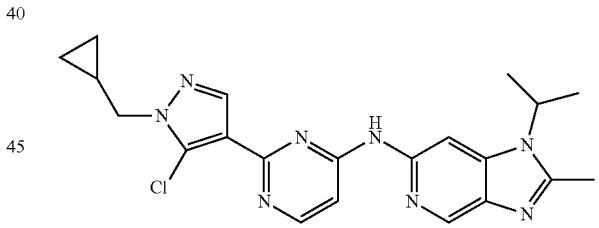

To a microwave reaction vessel was added 6-bromo-1-isopropyl-2-methyl-1H-imidazo[4,5-c]pyridine (Example 46, Step 6) (0.15 g, 0.60 mmol), 2-(5-chloro-1-(cyclopropylmethyl)-1H-pyrazol-4-yl)pyrimidin-4-amine (0.15 g, 0.60 mmol), cesium carbonate (0.39 g, 1.2 mmol), 2-dicyclohexylphosphino-2',4',6'-triisopropylbiphenyl (58 mg, 0.12 mmol), tris(dibenzylideneacetone)dipalladium(0) (28 mg, 0.030 mmol) and 1,4-dioxane (3 mL). The reaction was degassed by nitrogen bubbling for 20 min, sealed and stirred at 120° C. for 2.5 h. The reaction mixture was filtered and concentrated in vacuo. The crude product was purified by supercritical fluid chromatography to give the title compound (9 mg, 3.6%). LCMS (ESI): R$_T$=4.60 min, [M+H]$^+$=423.2, method=B; $^1$H NMR (400 MHz, DMSO) δ 9.98 (s, 1H), 8.55 (d, J=0.7 Hz, 1H), 8.38 (d, J=5.9 Hz, 1H), 8.27 (s, 1H), 8.15 (s, 1H), 7.30 (s, 1H), 4.74 (m, 1H), 4.11 (d, J=7.0 Hz, 2H), 2.58 (s, 3H), 1.59 (d, J=6.9 Hz, 6H), 1.28 (m, 1H), 0.64-0.35 (m, 4H).

399

Example 337: 1-Isopropyl-2-methyl-N-(2-(4-(methylsulfonyl)-1H-imidazol-1-yl)pyrimidin-4-yl)-1H-imidazo[4,5-c]pyridin-6-amine

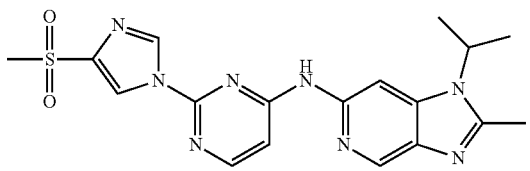

And

Example 338: 1-Isopropyl-2-methyl-N-(2-(4-(methylsulfinyl)-1H-imidazol-1-yl)pyrimidin-4-yl)-1H-imidazo[4,5-c]pyridin-6-amine

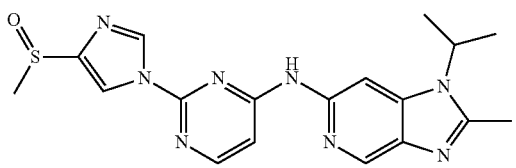 [SMILES: Cc1nc2cnc(Nc3ccnc(-n4cnc(S(C)=O)c4)n3)cc2n1C(C)C]

To a solution of 1-isopropyl-2-methyl-N-(2-(4-(methylthio)-1H-imidazol-1-yl)pyrimidin-4-yl)-1H-imidazo[4,5-c]pyridin-6-amine (Example 422) (0.10 g, 0.263 mmol) in dichloromethane (3 mL) was added TFA (0.02 mL, 0.3 mmol) and 3-chloroperbenzoic acid (0.12 g, 0.53 mmol). The reaction was stirred at room temperature for 14 h. The reaction was concentrated and two products separated and purified by reverse phase-HPLC to give both of the title compounds:

Example 337 (79 mg, 79%): LCMS (ESI): RT=3.98 min, [M+H]$^+$=413.2, method=B; 1H NMR (400 MHz, DMSO) δ 10.67 (s, 1H), 8.71 (s, 1H), 8.60 (s, 1H), 8.38 (m, 2H), 8.18 (br s, 1H), 7.36 (br s, 1H), 4.78 (m, 1H), 3.22 (s, 3H), 2.60 (s, 3H), 1.62 (d, 6H).

Example 338 (9.5 mg, 10%): LCMS (ESI): RT=3.70 min, [M+H]$^+$=397.2. 1H NMR (400 MHz, DMSO) δ 10.51 (s, 1H), 8.69 (d, J=1.3 Hz, 1H), 8.60 (d, J=0.9 Hz, 1H), 8.39 (d, J=5.9 Hz, 1H), 8.32 (d, J=1.3 Hz, 1H), 8.18 (s, 1H), 7.37 (s, 1H), 4.78 (m, 1H), 2.89 (s, 3H), 2.59 (s, 3H), 1.61 (m, 6H).

Examples 339 and 340: 1-((R)-sec-butyl)-6-((2-((3R,4S)-3-fluoro-4-methoxypiperidin-1-yl)pyrimidin-4-yl)amino)-N-(tetrahydro-2H-pyran-4-yl)-1H-pyrrolo[3,2-c]pyridine-3-carboxamide and 1-((S)-sec-butyl)-6-((2-((3R,4S)-3-fluoro-4-methoxypiperidin-1-yl)pyrimidin-4-yl)amino)-N-(tetrahydro-2H-pyran-4-yl)-1H-pyrrolo[3,2-c]pyridine-3-carboxamide

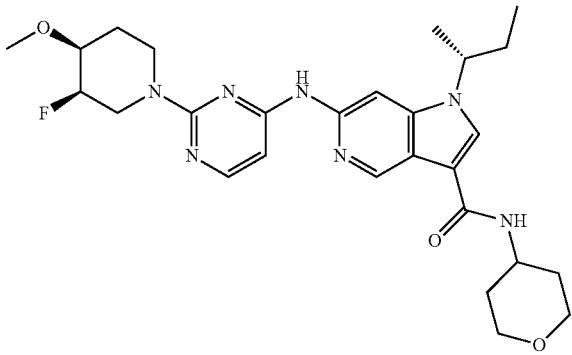

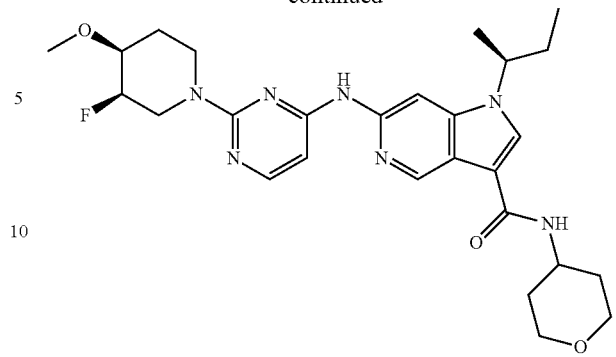

Step 1: (+/−)-6-Bromo-1-(sec-butyl)-1H-pyrrolo[3,2-c]pyridine

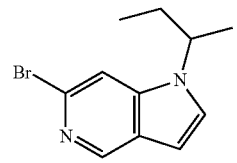

To a solution of 6-bromo-5-azaindole (1.0 g, 4.9 mmol) in N,N-dimethylformamide (8 mL) was added sodium hydride (60 wt % dispersion in mineral oil) (0.23 g, 5.8 mmol) at 0° C. The mixture was stirred 0° C. for 5 min prior to the addition of 2-bromobutane (0.7 mL, 6.4 mmol) followed by stirring at room temperature for 2 h. The reaction was then quenched by pouring onto saturated aqueous ammonium chloride. The product was extracted with EtOAc (3×). The combined organic extracts were washed with brine, dried over sodium sulfate, filtered and concentrated in vacuo. The crude product was purified by flash chromatography on silica gel (solvent gradient: 0-100% EtOAc in heptane) to afford the title compound (1.5 g, quant.). LCMS (ESI): [M+H]$^+$=253.

Step 2: (+/−)-6-Bromo-1-(sec-butyl)-1H-pyrrolo[3,2-c]pyridine-3-carbaldehyde

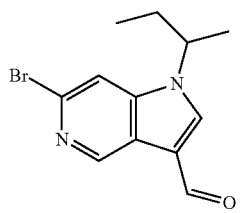 [SMILES: CCC(C)n1cc(C=O)c2cnc(Br)cc21]

To N,N-dimethylformamide (100 mL) at 0° C. was added phosphoryl chloride (15 mL, 160 mmol). The reaction was stirred at 0° C. for 20 min, warmed to room temperature and a solution of (+/−)-6-bromo-1-(sec-butyl)-1H-pyrrolo[3,2-c]pyridine (8.0 g, 32 mmol) in N,N-dimethylformamide (10 mL) was added dropwise. The reaction was stirred at 70° C. for 2 h. The mixture was then slowly neutralized by pouring onto a saturated aqueous sodium bicarbonate solution. The product was extracted with EtOAc (3×). The combined organic extracts were washed with saturated sodium bicarbonate and brine, dried over sodium sulfate, filtered and concentrated in vacuo. The crude product was purified by flash chromatography on silica gel (solvent gradient: 0-100% EtOAc in heptane) to afford the title compound (6.7 g, 75%). LCMS (ESI): [M+H]$^+$=281.

Step 3: (+/−)-6-Bromo-1-(sec-butyl)-1H-pyrrolo[3,2-c]pyridine-3-carboxylic acid

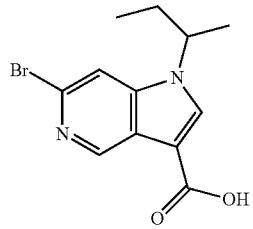 [SMILES: CCC(C)n1cc(C(=O)O)c2cnc(Br)cc21]

To a solution of (+/−)-6-bromo-1-(sec-butyl)-1H-pyrrolo[3,2-c]pyridine-3-carbaldehyde (6.0 g, 21 mmol) in tert-butanol (50 mL) was added 2-methyl-2-butene (2 M solution in tetrahydrofuran, 18 mL, 36 mmol). A solution of sodium chlorite (4.8 g, 43 mmol) and monosodium phosphate (26 g, 210 mmol) in water (15 mL) was then added. The reaction was stirred at room temperature for 18 h. The mixture was then diluted with brine and acidified to pH 2 with the addition of 1M HCl in water. The product was then extracted with EtOAc (3×). The combined organic extracts were washed with brine, dried over sodium sulfate, filtered and concentrated in vacuo. The crude material (7.7 g, quant.) was used without further purification. LCMS (ESI): [M+H]$^+$=297; $^1$H NMR (400 MHz, CDCl$_3$) δ 9.17 (d, J=17.2 Hz, 1H), 7.98 (s, 1H), 7.53 (s, 1H), 4.45-4.27 (m, 1H), 1.99-1.83 (m, 2H), 1.64-1.52 (m, 4H), 0.96-0.77 (m, 4H).

Step 4: (+/−)-6-Bromo-1-(sec-butyl)-N-(tetrahydro-2H-pyran-4-yl)-1H-pyrrolo[3,2-c]pyridine-3-carboxamide

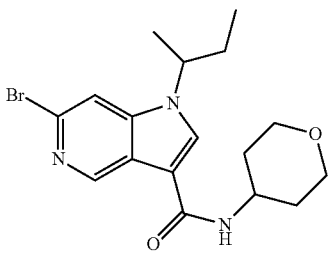 [SMILES: CCC(C)n1cc(C(=O)NC2CCOCC2)c2cnc(Br)cc21]

To a solution of (+/−)-6-bromo-1-(sec-butyl)-1H-pyrrolo[3,2-c]pyridine-3-carboxylic acid (0.70 g, 2.4 mmol) in N,N-dimethylformamide (25 mL) was added N,N-diisopropylethylamine (0.5 mL, 3.1 mmol), O-(benzotriazol-1-yl)-N,N,N',N'-tetramethyluronium hexafluorophosphate (1.2 g, 3.1 mmol) and tetrahydropyran-4-amine (0.3 g, 2.8 mmol). The reaction was stirred at room temperature for 1 h and then diluted with saturated sodium bicarbonate. The product was extracted with EtOAc (3×) and the combined organic extracts were washed with brine, dried over sodium sulfate, filtered and concentrated in vacuo. The crude product was purified by silica gel flash chromatrography (solvent gradient: 0-10% methanol in dichloromethane) to give the title compound (0.83 g, 93%). LCMS (ESI): [M+H]$^+$=382.

Step 5: 1-((R)-sec-butyl)-6-((2-((3R,4S)-3-fluoro-4-methoxypiperidin-1-yl)pyrimidin-4-yl)amino)-N-(tetrahydro-2H-pyran-4-yl)-1H-pyrrolo[3,2-c]pyridine-3-carboxamide and 1-((S)-sec-butyl)-6-((2-((3R,4S)-3-fluoro-4-methoxypiperidin-1-yl)pyrimidin-4-yl)amino)-N-(tetrahydro-2H-pyran-4-yl)-1H-pyrrolo[3,2-c]pyridine-3-carboxamide

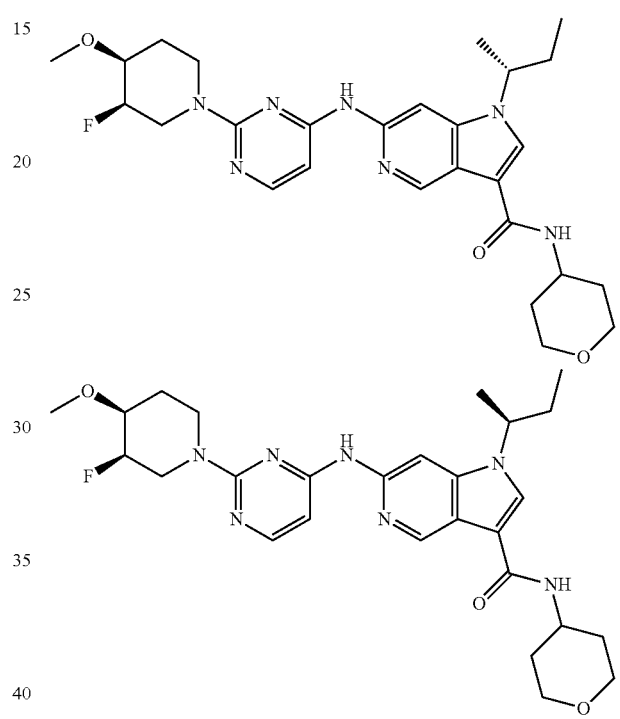

To a microwave reaction vessel was added (+/−)-6-bromo-1-(sec-butyl)-N-(tetrahydro-2H-pyran-4-yl)-1H-pyrrolo[3,2-c]pyridine-3-carboxamide (0.16 g, 0.48 mmol), (−)-2-((3R,4S)-3-fluoro-4-methoxypiperidin-1-yl)pyrimidin-4-ylamine (Example A63) (0.11 g, 0.48 mmol), sodium tert-butoxide (0.11 g, 0.48 mmol), chloro{[BrettPhos][2-(2-aminoethylphenyl]palladium(II)]}/[BrettPhos] admixture (molar PdP/P=1:1, 60 mg) and tert-butanol (4 mL). The reaction was degassed by nitrogen bubbling for 15 min, sealed and stirred at 120° C. for 90 min. The reaction was cooled to room temperature, filtered and concentrated in vacuo. The crude products were separated and purified by chiral supercritical fluid chromatography to give the two stereoisomers of the title compound (84.1 mg, 34%).

Stereoisomer 1 (Example 339) (40.7 mg): LCMS (ESI): R$_T$=3.65 min, [M+H]$^+$=526.3, method=B; $^1$H NMR (400 MHz, DMSO) δ 9.82 (s, 1H), 9.02 (d, J=0.7 Hz, 1H), 8.32 (s, 1H), 8.17 (s, 1H), 7.95 (d, J=5.7 Hz, 1H), 7.88 (d, J=7.6 Hz, 1H), 6.37 (d, J=5.7 Hz, 1H), 4.93 (d, J=51.2 Hz, 1H), 4.66 (m, 1H), 4.38 (m, 2H), 4.09-3.94 (m, 1H), 3.90 (m, 2H), 3.55 (m, 2H), 1.96-1.63 (m, 6H), 1.64-1.46 (m, 5H), 0.78 (t, J=7.3 Hz, 3H).

Stereoisomer 2 (Example 340) (43.4 mg): LCMS (ESI): R$_T$=3.69 min, [M+H]$^+$=526.3, method=B; $^1$H NMR (400 MHz, DMSO) δ 9.82 (s, 1H), 9.02 (d, J=0.7 Hz, 1H), 8.31

(s, 1H), 8.17 (s, 1H), 7.96 (d, J=5.7 Hz, 1H), 7.88 (d, J=7.7 Hz, 1H), 6.37 (d, J=5.6 Hz, 1H), 4.93 (d, J=49.3 Hz, 1H), 4.64 (s, 1H), 4.38 (m, 2H), 4.09-3.95 (m, 1H), 3.90 (d, J=9.9 Hz, 2H), 3.57 (m, 2H), 1.97-1.69 (m, 6H), 1.61-1.44 (m, 5H), 0.79 (t, J=7.3 Hz, 3H).

Example 341: 1-(4-(4-((1-Isopropyl-2-methyl-1H-imidazo[4,5-c]pyridin-6-yl)amino)pyrimidin-2-yl)-1H-pyrazol-1-yl)-2-methylpropan-2-ol

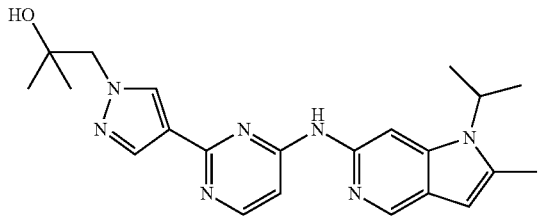 [SMILES: Cc1cc2cnc(Nc3ccnc(-c4cnn(CC(C)(C)O)c4)n3)cc2n1C(C)C]

Step 1: 2-Methyl-1-(4-(4,4,5,5-tetramethyl-1,3,2-dioxaborolan-2-yl)-1H-pyrazol-1-yl)propan-2-ol

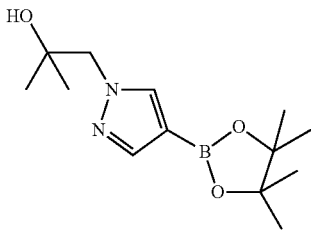 [SMILES: CC(C)(O)Cn1cc(B2OC(C)(C)C(C)(C)O2)cn1]

To a suspension of 4,4,5,5-tetramethyl-2-(1H-pyrazol-4-yl)-1,3,2-dioxaborolane (10.0 g, 51.5 mmol) in isobutylene oxide (5.0 mL) and methanol (2.5 mL) was added cesium carbonate (4.8 g, 15 mmol). The reaction mixture was heated in a sealed vessel at 110° C. for 90 min. The mixture was then cooled to room temperature, diluted with diethyl ether, and washed with water (2×). The organic portion was washed with brine, dried over anhydrous magnesium sulfate, filtered and concentrated in vacuo to produce the title compound as a white solid which was carried forward without further purification (7.05 g, 51% yield). LCMS (ESI): [M+H]⁺=267.2; ¹H NMR (400 MHz, CDCl₃) δ 7.81 (s, 1H), 7.69 (s, 1H), 4.07 (s, 2H), 3.93 (s, 1H), 1.32 (s, 12H), 1.15 (s, 6H).

Step 2: 1-(4-(4-((1-Isopropyl-2-methyl-1H-imidazo[4,5-c]pyridin-6-yl)amino)pyrimidin-2-yl)-1H-pyrazol-1-yl)-2-methylpropan-2-ol

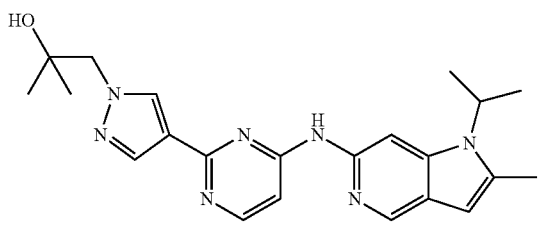 [SMILES: Cc1cc2cnc(Nc3ccnc(-c4cnn(CC(C)(C)O)c4)n3)cc2n1C(C)C]

A mixture of N-(2-chloropyrimidin-4-yl)-1-isopropyl-2-methyl-imidazo[4,5-c]pyridin-6-amine (Example 46, Step 7) (263.7 mg, 0.671 mmol), 2-methyl-1-[4-(4,4,5,5-tetramethyl-1,3,2-dioxaborolan-2-yl)-1H-pyrazol-1-yl]propan-2-ol (369.6 mg, 1.347 mmol), bis(di-tert-butyl(4-dimethylaminophenyl)phosphine)dichloropalladium(II) (48.5 mg, 0.069 mmol), potassium carbonate (200.8 mg, 1.453 mmol), dioxane (2.5 mL) and water (0.25 mL) was heated under microwave irradiation at 120° C. for 2 h. Bis(di-tert-butyl(4-dimethylaminophenyl)phosphine)dichloropalladium(II) (34.1 mg, 0.048 mmol) and 2-methyl-1-[4-(4,4,5,5-tetramethyl-1,3,2-dioxaborolan-2-yl)-1H-pyrazol-1-yl]propan-2-ol (359.3 mg, 1.350 mmol) were added and the mixture was heated under microwave irradiation at 130° C. for 70 min. The reaction mixture was diluted with EtOAc, washed with water (2×) and brine, dried over magnesium sulfate, filtered, and concentrated in vacuo. The crude product was purified via flash chromatography on silica gel (solvent gradient: 0-10% methanol in dichloromethane) followed by reverse-phase HPLC and lyophilized to yield the title compound (72.7 mg, 26%). LCMS (ESI): R$_T$ (min)=6.40, [M+H]⁺=407.5, method=C; ¹H NMR (400 MHz, DMSO-d₆) δ 10.00 (s, 1H), 8.55 (d, J=0.8 Hz, 1H), 8.37 (s, 1H), 8.31 (d, J=5.9 Hz, 1H), 8.24 (s, 1H), 8.03 (s, 1H), 7.17 (s, 1H), 4.81 (s, 1H), 4.76 (p, J=7.0 Hz, 1H), 4.08 (s, 2H), 2.58 (s, 3H), 1.63 (d, J=6.8 Hz, 6H), 1.10 (s, 6H).

Example 342: 2-(4-(4-((1-Isopropyl-2-methyl-1H-imidazo[4,5-c]pyridin-6-yl)amino)pyrimidin-2-yl)-1H-pyrazol-1-yl)-2-methylpropan-1-ol

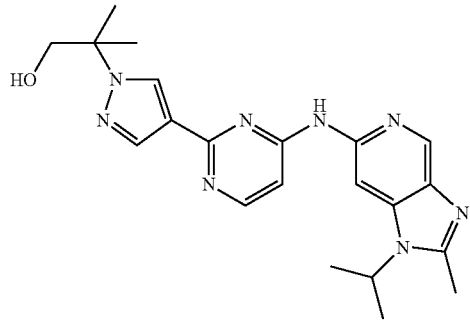 [SMILES: Cc1nc2cnc(Nc3ccnc(-c4cnn(C(C)(C)CO)c4)n3)cc2n1C(C)C]

Step 1: Ethyl 2-methyl-2-(4-(4,4,5,5-tetramethyl-1,3,2-dioxaborolan-2-yl)-1H-pyrazol-1-yl)propanoate

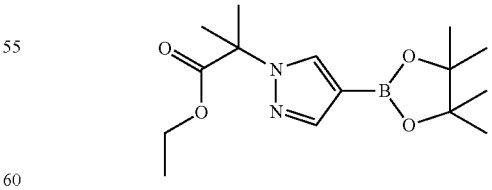

To a solution of 4,4,5,5-tetramethyl-2-(1H-pyrazol-4-yl)-1,3,2-dioxaborolane (5.00 g, 0.026 mol) and cesium carbonate (10.07 g, 0.031 mol) in N,N-dimethylformamide (50 mL) was added ethyl 2-bromoisobutyrate (4.16 mL, 0.028 mol). The reaction mixture was heated at 110° C. overnight and then cooled to room temperature. Water was added and the aqueous phase was extracted with EtOAc (3×). The organic layers were combined, dried with anhydrous magnesium sulfate, and concentrated in vacuo to yield the title compound (6.7 g, 84%), which was carried forward without further purification. $^1$H NMR (400 MHz, CDCl$_3$) δ 7.88 (s, 1H), 7.83 (s, 1H), 4.16 (q, J=7.2 Hz, 2H), 1.84 (s, 6H), 1.33 (s, 12H), 1.20 (t, J=7.1 Hz, 3H).

Step 2: Ethyl 2-(4-(4-((1-isopropyl-2-methyl-1H-imidazo[4,5-c]pyridin-6-yl)amino)pyrimidin-2-yl)-1H-pyrazol-1-yl)-2-methylpropanoate

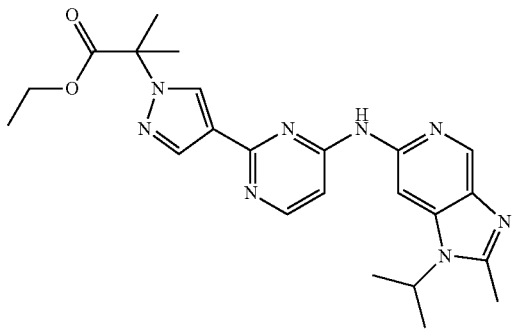 [SMILES: CCOC(=O)C(C)(C)n1cc(-c2nccc(Nc3cc4c(cn3)nc(C)n4C(C)C)n2)cn1]

Using ethyl 2-methyl-2-(4-(4,4,5,5-tetramethyl-1,3,2-dioxaborolan-2-yl)-1H-pyrazol-1-yl)propanoate and following a similar procedure to that described for Example 341, the title product was obtained (126.6 mg, 70%). LCMS (ESI): [M+H]$^+$=449.4.

Step 3: 2-(4-(4-((1-Isopropyl-2-methyl-1H-imidazo[4,5-c]pyridin-6-yl)amino)pyrimidin-2-yl)-1H-pyrazol-1-yl)-2-methylpropan-1-ol

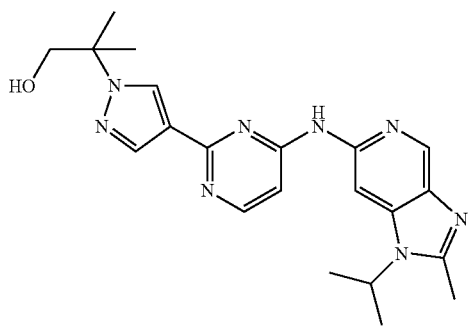 [SMILES: Cc1nc2cnc(Nc3ccnc(-c4cnn(C(C)(C)CO)c4)n3)cc2n1C(C)C]

To a solution of ethyl 2-(4-(4-((1-isopropyl-2-methyl-imidazo[4,5-c]pyridin-6-yl)amino)pyrimidin-2-yl)-1H-pyrazol-1-yl)-2-methyl-propanoate (126.6 mg, 0.20 mmol) in tetrahydrofuran (3.0 mL) was added lithium aluminum hydride (1.0 M in tetrahydrofuran) (0.40 mL, 0.40 mmol). The reaction mixture was stirred at room temperature for 30 min, and then quenched by the sequential dropwise addition of water (15 μL), 15% aqueous sodium hydroxide (15 μL), and water (50.0 μL). The resulting mixture was stirred at room temperature for 30 min, and then dried over magnesium sulfate, filtered, and concentrated in vacuo. The crude product was purified via reverse-phase HPLC and lyophilized to yield the title compound (7.5 mg, 9%). LCMS (ESI): R$_T$ (min)=3.733, [M+H]$^+$=407.3, method=B; $^1$H NMR (400 MHz, DMSO-d$_6$) δ 9.94 (s, 1H), 8.54 (d, J=0.9 Hz, 1H), 8.36 (s, 1H), 8.30 (d, J=5.8 Hz, 1H), 8.27 (s, 1H), 8.06 (s, 1H), 7.22-7.13 (m, 1H), 4.76 (p, J=6.9 Hz, 1H), 3.62 (s, 2H), 2.58 (s, 3H), 1.62 (d, J=6.9 Hz, 6H), 1.52 (s, 6H).

Example 343: 3-((4-((1-Isopropyl-2-methyl-1H-imidazo[4,5-c]pyridin-6-yl)amino)pyrimidin-2-yl)thio)-2,2-dimethylpropanamide

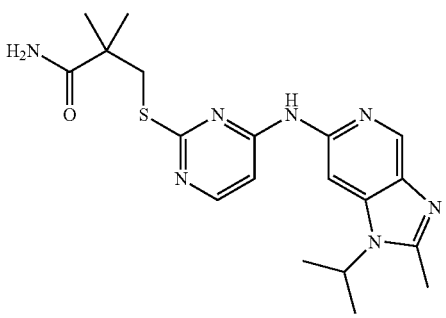 [SMILES: Cc1nc2cnc(Nc3ccnc(SCC(C)(C)C(N)=O)n3)cc2n1C(C)C]

Step 1: Ethyl 3-((4-aminopyrimidin-2-yl)thio)-2,2-dimethylpropanoate

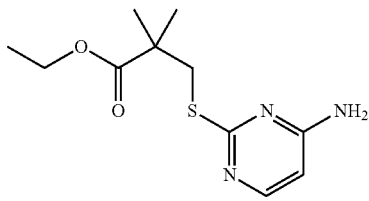 [SMILES: CCOC(=O)C(C)(C)CSc1nccc(N)n1]

A mixture of 4-amino-1H-pyrimidine-2-thione (401.1 mg, 3.154 mmol), ethyl 3-chloro-2,2-dimethyl-propanoate (537.0 mg, 3.262 mmol), potassium carbonate (653.9 mg., 4.731 mmol) and N,N-dimethylformamide (10.0 mL) was stirred at 90° C. for 16 h. The reaction mixture was diluted with EtOAc, washed with water and brine, dried over magnesium sulfate, filtered, and concentrated in vacuo. The crude product was purified via flash chromatography on silica gel (solvent gradient: 0-100% EtOAc in dichloromethane) to yield the title compound as a light yellow oil (393.2 mg, 49%). LCMS (ESI): [M+H]$^+$=256.2; $^1$H NMR (400 MHz, DMSO-d$_6$) δ 7.88 (d, J=5.8 Hz, 1H), 6.88 (s, 2H), 6.12 (d, J=5.8 Hz, 1H), 4.04 (q, J=7.1 Hz, 2H), 3.37 (s, 2H), 1.19 (s, 6H), 1.14 (t, J=7.1 Hz, 3H).

Step 2: Ethyl 3-((4-((1-isopropyl-2-methyl-1H-imidazo[4,5-c]pyridin-6-yl)amino)pyrimidin-2-yl)thio)-2,2-dimethylpropanoate

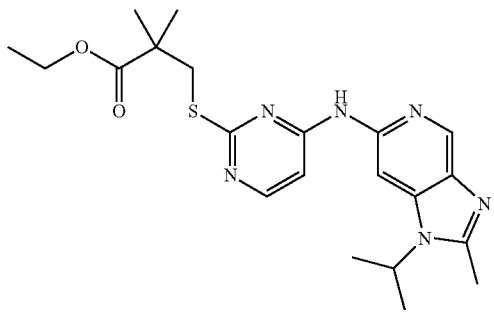 [SMILES: CCOC(=O)C(C)(C)CSc1nccc(Nc2cc3c(cn2)nc(C)n3C(C)C)n1]

A reaction vessel containing a mixture of 6-bromo-1-isopropyl-2-methyl-imidazo[4,5-c]pyridine (Example 46, Step 6) (123.4 mg, 0.4856 mmol), ethyl 3-((4-aminopyrimidin-2-yl)thio)-2,2-dimethyl-propanoate (107.3 mg, 0.4203 mmol), copper(I) iodide (87.2 mg, 0.458 mmol), trans-N,N'-dimethylcyclohexane-1,2-diamine (137.0 µL, 0.843 mmol), cesium carbonate (280.4 mg, 0.852 mmol) and 1,4-dioxane (4.0 mL) was purged with nitrogen and then heated at 90° C. for 1.5 h. The reaction mixture was cooled to room temperature, diluted with EtOAc, washed with water (2×) and brine, dried over magnesium sulfate, filtered, and concentrated in vacuo. The crude product was purified via flash chromatography on silica gel (solvent gradient: 20-100% EtOAc in dichloromethane) to yield 53.9 mg (30%) of the title compound. LCMS (ESI): [M+H]⁺=429.2.

Step 3: 3-((4-((1-Isopropyl-2-methyl-1H-imidazo[4,5-c]pyridin-6-yl)amino)pyrimidin-2-yl)thio)-2,2-dimethylpropanoic acid

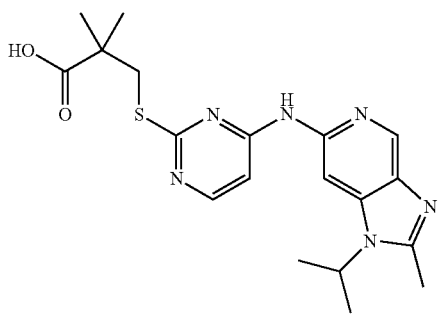 [SMILES: Cc1nc2cnc(Nc3ccnc(SCC(C)(C)C(=O)O)n3)cc2n1C(C)C]

A mixture of ethyl 3-((4-((1-isopropyl-2-methyl-1H-imidazo[4,5-c]pyridin-6-yl)amino)pyrimidin-2-yl)thio)-2,2-dimethylpropanoate (53.9 mg, 0.126 mmol), tetrahydrofuran (2.0 mL, 25 mmol) and lithium hydroxide (1.0 M solution in water) (0.5 mL, 0.5 mmol) was stirred at room temperature for 4 h, at 50° C. for 20 h, and then heated under microwave irradiation at 100° C. for 4 h. The reaction mixture was neutralized with 10% aqueous citric acid and extracted with dichloromethane (2×). The combined dichloromethane portions were washed with brine, dried over magnesium sulfate, filtered, and concentrated in vacuo to provide a quantitative yield of the title compound, which was carried forward without purification. LCMS (ESI): [M+H]⁺=401.2.

Step 4: 3-((4-((1-Isopropyl-2-methyl-1H-imidazo[4,5-c]pyridin-6-yl)amino)pyrimidin-2-yl)thio)-2,2-dimethylpropanamide

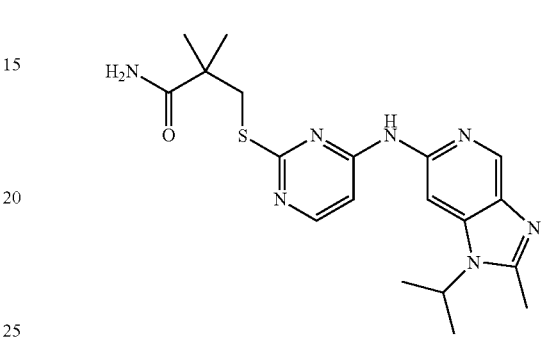

A mixture of 3-((4-((1-isopropyl-2-methyl-1H-imidazo[4,5-c]pyridin-6-yl)amino)pyrimidin-2-yl)thio)-2,2-dimethylpropanoic acid (0.126 mmol, 0.126 mmol), 1-[bis(dimethylamino)methylene]-1H-1,2,3-triazolo[4,5-b]pyridinium 3-oxid hexafluorophosphate (66.9 mg, 0.172 mmol), ammonium chloride (18.7 mg, 0.350 mmol), N,N-diisopropylethylamine (0.15 mL, 0.86 mmol), 4-dimethylaminopyridine (3 mg., 0.025 mmol) and N,N-dimethylformamide (2.0 mL) was stirred at room temperature for 3 h. The reaction mixture was diluted with EtOAc, washed with water (2×) and brine, dried over magnesium sulfate, filtered, and concentrated in vacuo. The crude product was purified via reverse-phase HPLC and lyophilized to yield 23.3 mg (46% yield over 2 steps) of the title compound. LCMS (ESI): R$_T$ (min)=4.069, [M+H]⁺=400.2, method=B; ¹H NMR (400 MHz, DMSO-d₆) δ 10.01 (s, 1H), 8.53 (d, J=0.9 Hz, 1H), 8.16 (d, J=5.9 Hz, 1H), 8.10 (s, 1H), 7.20 (s, 1H), 7.15 (s, 1H), 6.88 (s, 1H), 4.71 (p, J=6.9 Hz, 1H), 3.41 (s, 2H), 2.56 (s, 3H), 1.57 (d, J=6.9 Hz, 6H), 1.18 (s, 6H).

Example 344: 1-Isopropyl-2-methyl-N-(2-(1-(pyrrolidin-3-ylmethyl)-1H-pyrazol-4-yl)pyrimidin-4-yl)-1H-imidazo[4,5-c]pyridin-6-amine

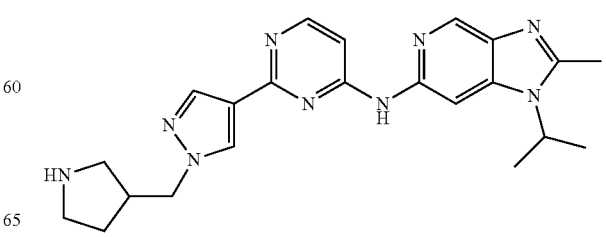

Step 1: tert-Butyl 3-((4-(4,4,5,5-tetramethyl-1,3,2-dioxaborolan-2-yl)-1H-pyrazol-1-yl)methyl)pyrrolidine-1-carboxylate

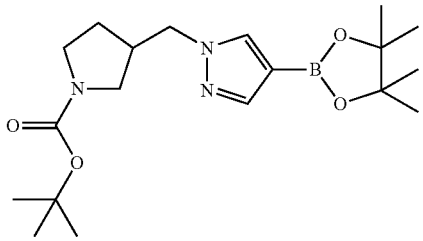 [SMILES: CC(C)(C)OC(=O)N1CCC(Cn2cc(B3OC(C)(C)C(C)(C)O3)cn2)C1]

A mixture of 4-(4,4,5,5-tetramethyl-1,3,2-dioxaborolan-2-yl)-1H-pyrazole (111.3 mg, 0.574 mmol), tert-butyl 3-(bromomethyl)pyrrolidine-1-carboxylate (200.0 mg, 0.734 mmol), cesium carbonate (285 mg, 0.866 mmol) and N,N-dimethylformamide (5.0 mL, 64 mmol) was stirred at 50° C. for 16 h. The reaction mixture was concentrated onto celite, and the crude product was purified via flash chromatography on silica gel (solvent gradient: 0-50% EtOAc in heptanes) to yield 133.6 mg (62%) of the title compound. LCMS (ESI): [M+H]$^+$=378.4; $^1$H NMR (400 MHz, DMSO-d$_6$) δ 7.95 (s, 1H), 7.59 (s, 1H), 4.14 (d, J=7.2 Hz, 2H), 3.35-3.31 (m, 1H), 3.29-3.24 (m, 1H), 3.22-3.13 (m, 1H), 3.03-2.92 (m, 1H), 2.74-2.57 (m, 1H), 1.89-1.76 (m, 1H), 1.64-1.48 (m, 1H), 1.38 (s, 9H), 1.25 (s, 12H).

Step 2: tert-Butyl 3-((4-(4-((1-isopropyl-2-methyl-1H-imidazo[4,5-c]pyridin-6-yl)amino)pyrimidin-2-yl)-1H-pyrazol-1-yl)methyl)pyrrolidine-1-carboxylate

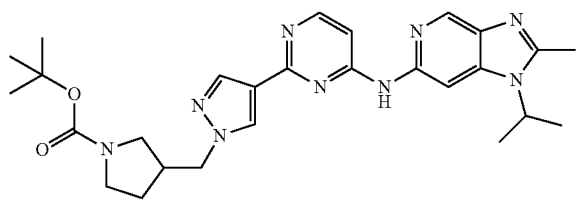 [SMILES: Cc1nc2cnc(Nc3ccnc(-c4cnn(CC5CCN(C(=O)OC(C)(C)C)C5)c4)n3)cc2n1C(C)C]

A mixture of N-(2-chloropyrimidin-4-yl)-1-isopropyl-2-methyl-imidazo[4,5-c]pyridin-6-amine (Example 46, Step 7) (102.0 mg, 0.3099 mmol), tert-butyl 3-((4-(4-4,4,5,5-tetramethyl-1,3,2-dioxaborolan-2-yl)-1H-pyrazol-1-yl)methyl)pyrrolidine-1-carboxylate (133.0 mg, 0.3525 mmol), [1,1'-bis(diphenylphosphino)ferrocene]palladium (II) chloride, complex with dichloromethane (1:1) (25.0 mg, 0.031 mmol), cesium carbonate (222.9 mg, 0.677 mmol), 1,2-dimethoxyethane (2.0 mL, 19 mmol) and water (0.2 mL, 10 mmol) was heated under microwave irradiation at 140° C. for 3 h. The reaction mixture was diluted with EtOAc, washed with water and brine, dried over magnesium sulfate, filtered, and concentrated in vacuo. The crude product was purified via flash chromatography on silica gel (solvent gradient: 0-10% methanol in dichloromethane) to yield 54.7 mg (34%) of the title compound. LCMS (ESI): [M+H]$^+$=518.3.

Step 3: 1-Isopropyl-2-methyl-N-(2-(1-(pyrrolidin-3-ylmethyl)-1H-pyrazol-4-yl)pyrimidin-4-yl)-1H-imidazo[4,5-c]pyridin-6-amine

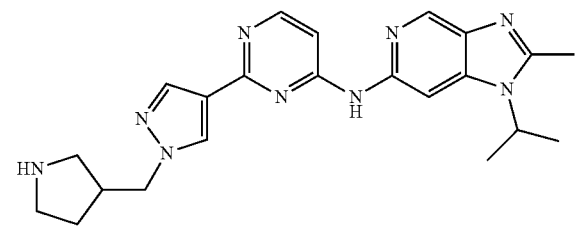 [SMILES: Cc1nc2cnc(Nc3ccnc(-c4cnn(CC5CCNC5)c4)n3)cc2n1C(C)C]

To a solution of tert-butyl 3-((4-(4-((1-isopropyl-2-methyl-1H-imidazo[4,5-c]pyridin-6-yl)amino)pyrimidin-2-yl)-1H-pyrazol-1-yl)methyl)pyrrolidine-1-carboxylate (54.7 mg, 0.106 mmol) in dichloromethane (3.0 mL, 47 mmol) and methanol (1.0 mL, 20 mmol) was added hydrogen chloride (4.0 M in dioxane) (0.5 mL, 2 mmol). The reaction mixture was stirred at room temperature for 1.5 h, and then concentrated in vacuo. The crude product was purified via reverse-phase HPLC followed by preparatory supercritical fluid chromatography to yield 5.22 mg (12%) of the title compound. LCMS (ESI): R$_T$ (min)=3.451, [M+H]$^+$=418.3, method=B; $^1$H NMR (400 MHz, DMSO-d$_6$) δ 9.96 (s, 1H), 8.55 (s, 1H), 8.40-8.25 (m, 3H), 8.05 (d, J=3.2 Hz, 1H), 7.17 (s, 1H), 4.76 (p, J=6.7 Hz, 1H), 4.26-4.08 (m, 2H), 3.06 (s, 2H), 2.94-2.70 (m, 2H), 2.58 (d, J=3.2 Hz, 4H), 1.78 (s, 1H), 1.63 (d, J=6.6 Hz, 6H), 1.43 (d, J=10.9 Hz, 1H).

Example 345: N-(2-(1-(Cyclopropylsulfonyl)-1H-pyrazol-4-yl)pyrimidin-4-yl)-3-(3,5-dimethyl-1H-pyrazol-4-yl)-1-isopropyl-1H-pyrrolo[3,2-c]pyridin-6-amine

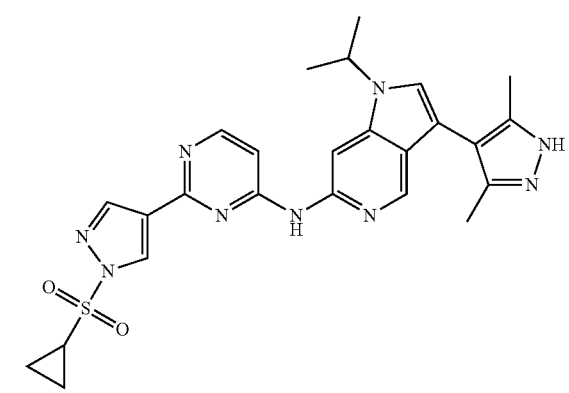 [SMILES: Cc1n[nH]c(C)c1-c1cn(C(C)C)c2cc(Nc3ccnc(-c4cnn(S(=O)(=O)C5CC5)c4)n3)ncc12]

Step 1: 6-Bromo-3-(3,5-dimethyl-1H-pyrazol-4-yl)-1-isopropyl-1H-pyrrolo[3,2-c]pyridine

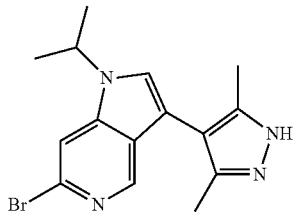 [SMILES: Cc1n[nH]c(C)c1-c1cn(C(C)C)c2cc(Br)ncc12]

A mixture of 6-bromo-3-iodo-1-isopropyl-1H-pyrrolo[3,2-c]pyridine (Example 253, Step 9) (310.6 mg, 0.851 mmol), 3,5-dimethylpyrazole-4-boronic acid, pinacol ester (255.9 mg, 1.118 mmol), [1,1'-bis(diphenylphosphino)ferrocene]palladium(II) chloride, complex with dichloromethane (1:1) (71.2 mg, 0.0872 mmol), sodium carbonate (2.0 mol/L) in water (0.85 mL, 1.7 mmol), and acetonitrile (3.0 mL, 57 mmol) was degassed with nitrogen and heated in a sealed vial at 100° C. for 26 h. The reaction mixture was filtered and concentrated onto celite. The crude product was purified via flash chromatography on silica gel (solvent gradient: 0-10% methanol in dichloromethane) to yield 186.0 mg (66%) of the title compound. LCMS (ESI): [M+H]$^+$=333.0; $^1$H NMR (400 MHz, DMSO-d$_6$) δ 12.29 (s, 1H), 8.35 (s, 1H), 7.86 (s, 1H), 7.57 (s, 2H), 4.84 (p, J=6.7 Hz, 1H), 2.12 (s, 6H), 1.48 (d, J=6.6 Hz, 6H).

Step 2: N-(2-(1-(Cyclopropylsulfonyl)-1H-pyrazol-4-yl)pyrimidin-4-yl)-3-(3,5-dimethyl-1H-pyrazol-4-yl)-1-isopropyl-1H-pyrrolo[3,2-c]pyridin-6-amine

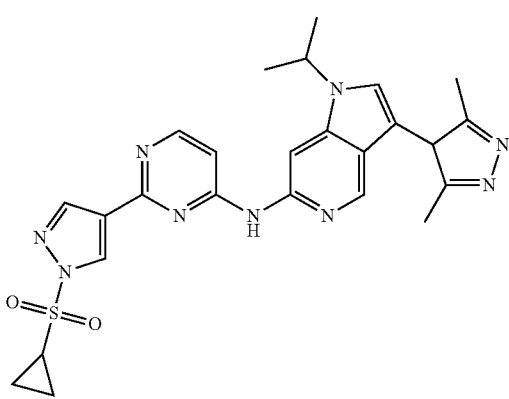 [SMILES: CC1=NN=C(C)C1c1cn(C(C)C)c2cc(Nc3ccnc(-c4cnn(S(=O)(=O)C5CC5)c4)n3)ncc12]

A mixture of 6-bromo-3-(3,5-dimethyl-1H-pyrazol-4-yl)-1-isopropyl-pyrrolo[3,2-c]pyridine (186 mg, 0.558 mmol), 2-(1-cyclopropanesulfonyl-1H-pyrazol-4-yl)pyrimidin-4-ylamine (Example A62) (154.6 mg, 0.583 mmol), 4,5-bis(diphenylphosphino)-9,9-dimethylxanthene (86.5 mg, 0.149 mmol), palladium(II) acetate (25.2 mg, 0.112 mmol), cesium carbonate (392.4 mg, 1.19 mmol) and 1,4-dioxane (2.5 mL, 29 mmol) was heated under an atmosphere of nitrogen at 100° C. for 4 h. The reaction mixture was cooled to room temperature, filtered through a PFTE frit, and concentrated onto celite. The crude product was purified via flash chromatography on silica gel (solvent gradient: 0-10% methanol in dichloromethane) followed by preparatory supercritical fluid chromatography to yield 18.8 mg (6%) of the title compound. LCMS (ESI): R$_T$ (min)=3.820, [M+H]$^+$=518.2, method=B; $^1$H NMR (400 MHz, DMSO-d$_6$) δ 12.25 (s, 1H), 10.12 (s, 1H), 8.69 (s, 1H), 8.47 (s, 1H), 8.41-8.35 (m, 3H), 7.42 (s, 1H), 7.16 (s, 1H), 4.78 (p, J=6.7 Hz, 1H), 3.27-3.23 (m, 1H), 2.17 (s, 6H), 1.58 (d, J=6.7 Hz, 6H), 1.40-1.32 (m, 2H), 1.32-1.21 (m, 2H).

Example 346: N-(2-(1-(cyclopropylsulfonyl)-1H-pyrazol-4-yl)pyrimidin-4-yl)-1-isopropyl-3-(4-methyl-1H-pyrazol-5-yl)-1H-pyrrolo[3,2-c]pyridin-6-amine

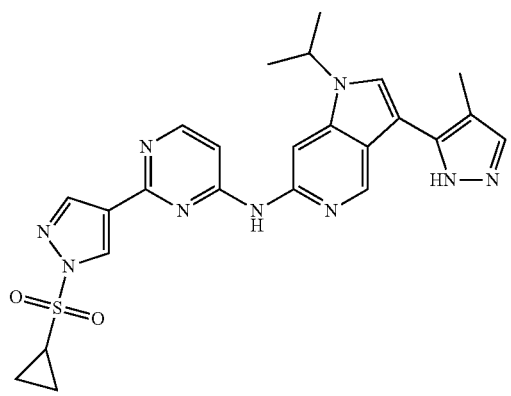 [SMILES: Cc1cn[nH]c1-c1cn(C(C)C)c2cc(Nc3ccnc(-c4cnn(S(=O)(=O)C5CC5)c4)n3)ncc12]

Step 1: N-(2-(1-(cyclopropylsulfonyl)-1H-pyrazol-4-yl)pyrimidin-4-yl)-1-isopropyl-3-(4-methyl-1-(tetrahydro-2H-pyran-2-yl)-1H-pyrazol-5-yl)-1H-pyrrolo[3,2-c]pyridin-6-amine

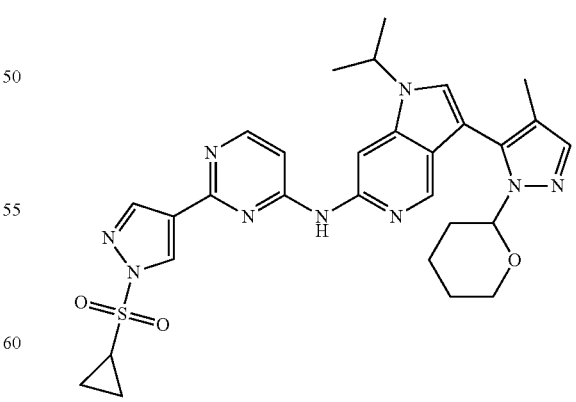

The title compound was prepared following procedures analogous to those described for Example 345. LCMS (ESI): [M+H]$^+$=588.0.

Step 2: N-(2-(1-(cyclopropylsulfonyl)-1H-pyrazol-4-yl)pyrimidin-4-yl)-1-isopropyl-3-(4-methyl-1H-pyrazol-5-yl)-1H-pyrrolo[3,2-c]pyridin-6-amine

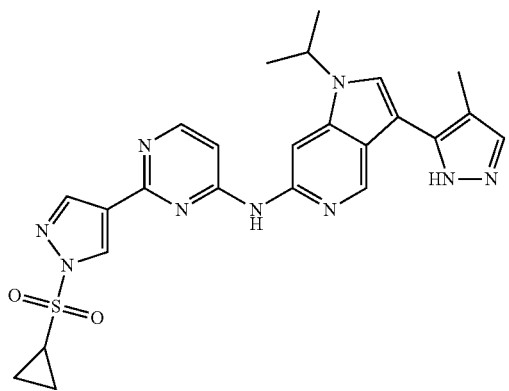 [SMILES: Cc1cn[nH]c1-c1cn(C(C)C)c2cc(Nc3ccnc(-c4cnn(S(=O)(=O)C5CC5)c4)n3)ncc12]

A mixture of N-(2-(1-(cyclopropylsulfonyl)-1H-pyrazol-4-yl)pyrimidin-4-yl)-1-isopropyl-3-(4-methyl-1-(tetrahydro-2H-pyran-2-yl)-1H-pyrazol-5-yl)-1H-pyrrolo[3,2-c]pyridin-6-amine (198 mg, 0.1685 mmol), hydrogen chloride (4.0 mol/L in dioxane) (1.0 mL, 4.0 mmol), and methanol (3.0 mL, 70 mmol) was stirred at room temperature for 3 h. The reaction mixture was concentrated to dry, and the crude product was purified via reverse-phase HPLC and lyophilized to yield 10.8 mg (13%) of the title compound. LCMS (ESI): $R_T$ (min)=4.319, [M+H]$^+$=504.2, method=B; $^1$H NMR (400 MHz, DMSO-d$_6$) δ 12.49 (s, 1H), 10.21 (s, 1H), 9.16 (s, 1H), 8.70 (s, 1H), 8.48 (s, 1H), 8.37 (d, J=5.9 Hz, 1H), 7.64 (s, 1H), 7.58 (s, 1H), 7.13 (s, 1H), 4.88-4.74 (m, 1H), 3.27-3.23 (m, 1H), 2.24 (s, 3H), 1.60 (d, J=6.7 Hz, 6H), 1.36 (dq, J=8.2, 3.7 Hz, 2H), 1.27 (dt, J=5.9, 3.7 Hz, 2H).

Example 347: 1-(4-((1-Isopropyl-3-(4-methyl-1H-pyrazol-5-yl)-1H-pyrrolo[3,2-c]pyridin-6-yl)amino)pyrimidin-2-yl)-3,3-dimethylpiperidin-4-ol

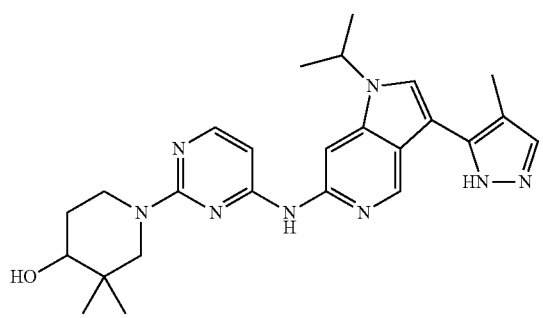 [SMILES: Cc1cn[nH]c1-c1cn(C(C)C)c2cc(Nc3ccnc(N4CCC(O)C(C)(C)C4)n3)ncc12]

Step 1: 4-Methyl-1-(tetrahydro-2H-pyran-2-yl)-1H-pyrazole

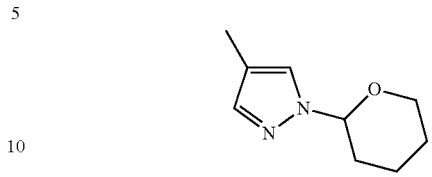

Trifluoroacetic acid (40.0 μL, 0.519 mmol) was added to a solution of 4-methylpyrazole (0.901 g, 11.0 mmol) in dihydropyran (2.0 mL, 22 mmol). The reaction mixture was stirred at 90° C. for 20 h. The mixture was cooled to room temperature, and then quenched with sodium hydride (60 wt % dispersion in mineral oil)(92 mg, 2.3 mmol). After stirring at room temperature for 10 min, the solvent was removed in vacuo. The residue was suspended in dichloromethane, and filtered through a short plug of silica that was rinsed with dichloromethane. The filtrate was evaporated in vacuo to afford the title compound (1.5213 g, 83%). LCMS (ESI): [M+H]$^+$=167.4; $^1$H NMR (400 MHz, DMSO-d$_6$) δ 7.60 (s, 1H), 7.27 (s, 1H), 5.29 (d, J=9.9 Hz, 1H), 3.89 (d, J=11.2 Hz, 1H), 3.64-3.51 (m, 1H), 2.00 (overlapping s and m, 4H), 1.88 (dd, J=27.1, 13.0 Hz, 1H), 1.64 (m, 1H), 1.51 (m, 2H).

Step 2: 4-Methyl-1-(tetrahydro-2H-pyran-2-yl)-5-(tributylstannyl)-1H-pyrazole

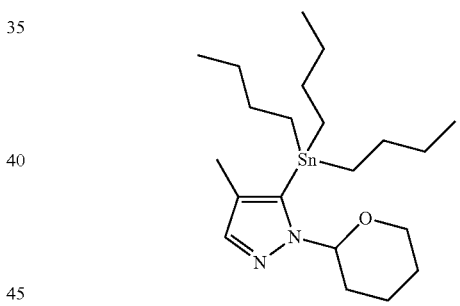

To a solution of 4-methyl-1-(tetrahydro-2H-pyran-2-yl)-1H-pyrazole (0.258 g, 1.55 mmol) in tetrahydrofuran (6 mL, 70 mmol) at −78° C. was added n-butyllithium (2.5 M in hexane)(0.80 mL). The reaction was stirred at −78° C. for 50 min, and then tributyltin chloride (0.60 mL, 2.2 mmol) was added. The reaction was kept at −78° C. for 2 h and then quenched with saturated aqueous ammonium chloride and warmed to room temperature. The reaction mixture was diluted with water and extracted with EtOAc. The organic portion was dried with anhydrous magnesium sulfate, filtered, and concentrated in vacuo. The crude product was purified via flash chromatography on silica gel (solvent gradient: 0-50% EtOAc in heptanes) to afford the title compound (520.6 mg, 74%). LCMS (ESI): [M+H]$^+$=457.2; $^1$H NMR (400 MHz, DMSO-d$_6$) δ 7.31 (s, 1H), 5.11 (d, J=8.3 Hz, 1H), 3.81 (d, J=11.4 Hz, 1H), 3.59-3.48 (m, 1H), 2.23 (dd, J=20.7, 9.4 Hz, 1H), 2.04 (s, 3H), 1.97 (d, J=12.8 Hz, 1H), 1.90 (d, J=13.3 Hz, 1H), 1.48 (m, 9H), 1.30 (dd, J=14.5, 7.3 Hz, 6H), 1.20-0.97 (m, 6H), 0.86 (t, J=7.3 Hz, 9H).

Step 3: 6-Bromo-1-isopropyl-3-(4-methyl-1-(tetrahydro-2H-pyran-2-yl)-1H-pyrazol-5-yl)-1H-pyrrolo[3,2-c]pyridine

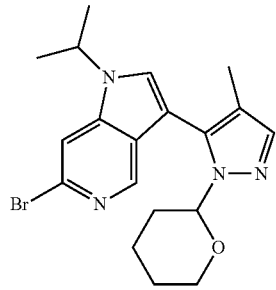 [SMILES: Cc1cnn(C2CCCCO2)c1-c1cn(C(C)C)c2cc(Br)ncc12]

A mixture of 6-bromo-3-iodo-1-isopropyl-1H-pyrrolo[3,2-c]pyridine (Example 253, Step 9) (148.5 mg, 0.4068 mmol), 4-methyl-1-(tetrahydro-2H-pyran-2-yl)-5-(tributylstannyl)-1H-pyrazole (230.0 mg, 0.4799 mmol), tetrakis(triphenylphosphine)palladium(0) (52.5 mg, 0.0454 mmol), copper(I) thiophene-2-carboxylate (85.3 mg, 0.429 mmol), and 1,4-dioxane (2.0 mL, 23 mmol) was purged with nitrogen and heated under microwave irradiation at 100° C. for 1 h. The reaction mixture was diluted with dichloromethane, filtered through a PFTE frit, and concentrated onto silica. The crude product was purified via flash chromatography on silica gel (solvent gradient: 0-10% methanol in dichloromethane) to yield the title compound (128.1 mg, 78%). LCMS (ESI): [M+H]$^+$=403.2.

Step 4: 1-(4-Aminopyrimidin-2-yl)-3,3-dimethylpiperdin-4-ol

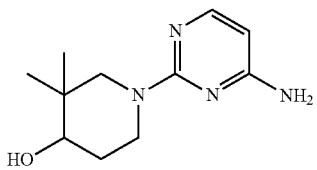 [SMILES: CC1(C)CN(c2nccc(N)n2)CCC1O]

To a reaction vessel was added 2-chloropyrimidin-4-amine (1.0 g, 8.0 mmol), 3,3-dimethylpiperidin-4-ol (1.0 g, 9.0 mmol), triethylamine (3.0 g, 30 mmol), and 2-propanol (5 mL). The vessel was sealed and heated under microwave irradiation at 150° C. for 45 min. The reaction mixture was cooled to room temperature, diluted with saturated aqueous sodium bicarbonate and extracted with dichloromethane. The organic layer was dried over magnesium sulfate, filtered and concentrated in vacuo to afford the title compound (1.24 g, 70%). LCMS (ESI): [M+H]$^+$=223.2; $^1$H NMR (300 MHz, DMSO-$d_6$) δ 7.69 (d, J=5.6 Hz, 1H), 6.28 (s, 2H), 5.64 (d, J=5.6 Hz, 1H), 4.55 (d, J=4.7 Hz, 1H), 4.33-4.22 (m, 1H), 4.02 (dd, J=12.8, 1.7 Hz, 1H), 3.25 (dd, J=9.4, 4.6 Hz, 1H), 3.08-2.96 (m, 1H), 2.75 (d, J=13.0 Hz, 1H), 1.66-1.54 (m, 1H), 1.47-1.35 (m, 1H), 0.87 (s, 3H), 0.74 (s, 3H).

Step 5: 1-(4-((1-Isopropyl-3-(4-methyl-1H-pyrazol-5-yl)-1H-pyrrolo[3,2-c]pyridin-6-yl)amino)pyrimidin-2-yl)-3,3-dimethylpiperidin-4-ol

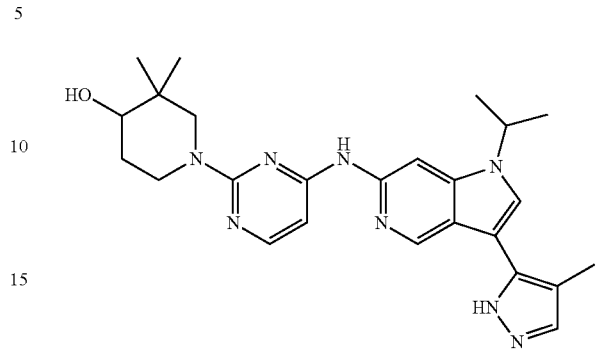

A mixture of 6-bromo-1-isopropyl-3-(4-methyl-1-(tetrahydro-2H-pyran-2-yl)-1H-pyrazol-5-yl)-1H-pyrrolo[3,2-c]pyridine (105.4 mg, 0.2613 mmol), 1-(4-aminopyrimidin-2-yl)-3,3-dimethylpiperidin-4-ol (71.7 mg, 0.323 mmol), chloro{[BrettPhos][2-(2-aminoethylphenyl)Palladium(II)]}/[BrettPhos] admixture (17.7 mg, 0.0133 mmol), sodium tert-butoxide (83.0 mg, 0.864 mmol) and tert-butanol (1.5 mL, 16 mmol) was heated in a sealed vial under a nitrogen atmosphere at 100° C. for 2 h. The reaction mixture was filtered through a PFTE frit, diluted with EtOAc, washed with water and brine, dried over magnesium sulfate, and concentrated in vacuo. The resulting material was combined with hydrogen chloride (4.0 mol/L in dioxane) (1.0 mL, 4.0 mmol) and methanol (3.0 mL, 70 mmol) and this mixture was stirred at room temperature for 4 h. The reaction mixture was concentrated in vacuo, and the crude product was purified via reverse-phase HPLC and lyophilized to yield 13.5 mg (11%) of the title compound. LCMS (ESI): R$_T$ (min)=3.504, [M+H]$^+$=461.3, method=B; $^1$H NMR (400 MHz, DMSO-$d_6$) δ 9.66 (s, 1H), 8.99 (s, 1H), 8.33 (s, 1H), 8.17 (s, OH), 7.91 (d, J=5.7 Hz, 1H), 7.60 (s, 1H), 7.53 (s, 1H), 6.31 (d, J=5.7 Hz, 1H), 4.74-4.58 (m, 2H), 4.46-4.34 (m, 1H), 4.16-4.04 (m, 1H), 3.40-3.34 (m, 2H), 3.00 (d, J=12.9 Hz, 1H), 2.21 (s, 3H), 1.77-1.67 (m, 1H), 1.55 (dd, J=6.7, 1.4 Hz, 6H), 0.95 (s, 3H), 0.82 (s, 3H).

Example 348: 2-(3-(6-((2-((3R,4S)-3-Fluoro-4-methoxypiperidin-1-yl)pyrimidin-4-yl)amino)-1-isopropyl-1H-pyrrolo[3,2-c]pyridin-3-yl)-4-methyl-1H-pyrazol-1-yl)ethanol

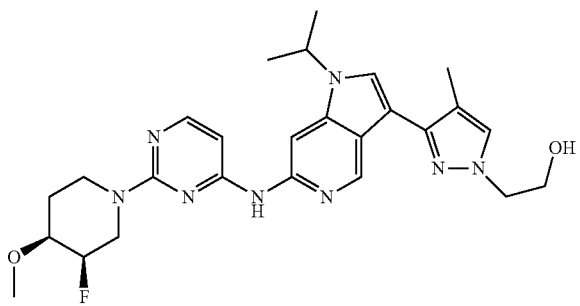 [SMILES: CO[C@H]1CCN(c2nccc(Nc3cc4c(cn3)c(-c3nn(CCO)cc3C)cn4C(C)C)n2)C[C@H]1F]

417

Step 1: N-(2-((3R,4S)-3-Fluoro-4-methoxypiperidin-1-yl)pyrimidin-4-yl)-1-isopropyl-3-(4-methyl-1H-pyrazol-5-yl)-1H-pyrrolo[3,2-c]pyridin-6-amine

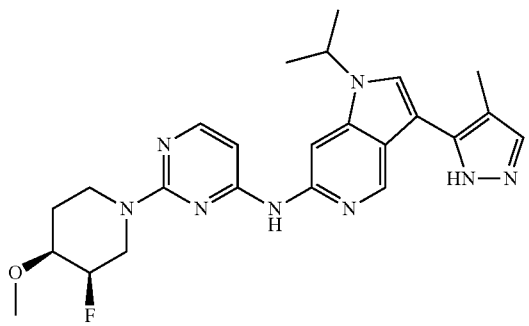 [SMILES: CO[C@H]1CCN(c2nccc(Nc3cc4c(cn3)c(-c3[nH]ncc3C)cn4C(C)C)n2)C[C@H]1F]

The title compound was prepared using 6-bromo-1-isopropyl-3-(4-methyl-1-(tetrahydro-2H-pyran-2-yl)-1H-pyrazol-5-yl)-1H-pyrrolo[3,2-c]pyridine (Example 347, Step 3) and (−)-2-((3R,4S)-3-Fluoro-4-methoxypiperidin-1-yl)pyrimidin-4-ylamine (Example A63) (74.5 mg, 0.329 mmol), and following the procedures analogous to those described for Example 347, Step 4. LCMS (ESI): [M+H]$^+$=465.2.

Step 2: 2-(3-(6-((2-((3R,4S)-3-Fluoro-4-methoxypiperidin-1-yl)pyrimidin-4-yl)amino)-1-isopropyl-1H-pyrrolo[3,2-c]pyridin-3-yl)-4-methyl-1H-pyrazol-1-yl)ethanol

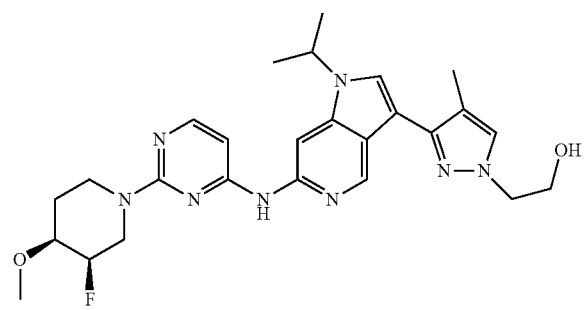 [SMILES: CO[C@H]1CCN(c2nccc(Nc3cc4c(cn3)c(-c3nn(CCO)cc3C)cn4C(C)C)n2)C[C@H]1F]

A mixture of N-(2-((3R,4S)-3-fluoro-4-methoxypiperidin-1-yl)pyrimidin-4-yl)-1-isopropyl-3-(4-methyl-1H-pyrazol-5-yl)-1H-pyrrolo[3,2-c]pyridin-6-amine (38.1 mg, 0.0820 mmol), 2-bromoethanol (9.0 μL, 0.13 mmol), cesium carbonate (55.4 mg, 0.168 mmol) and N,N-dimethylformamide (2.0 mL, 26 mmol) was heated at 70° C. for 16 h. 2-Bromoethanol (9.0 μL, 0.13 mmol) was added and the reaction mixture maintained at 70° C. for an additional 24 h. The reaction mixture was diluted with EtOAc, washed with water (2×) and brine, dried over magnesium sulfate, filtered, and concentrated in vacuo. The crude product was purified via reverse-phase HPLC and lyophilized to yield the title compound (9.1 mg, 22%). LCMS (ESI): R$_T$ (min)=3.720, [M+H]$^+$=509.3, method=B; $^1$H NMR (400 MHz, DMSO-d$_6$) δ 9.75 (s, 1H), 9.07 (d, J=0.9 Hz, 1H), 8.30 (s, 1H), 7.95 (d, J=5.7 Hz, 1H), 7.58 (s, 1H), 7.55 (d, J=0.9 Hz, 1H), 6.40 (d, J=5.7 Hz, 1H), 5.04-4.85 (m, 2H), 4.72-4.60 (m, 2H), 4.47-4.36 (m, 1H), 4.15 (t, J=5.7 Hz, 2H), 3.82-3.74 (m, 2H), 3.66-3.49 (m, 2H), 3.37 (s, 3H), 3.30-3.25 (m, 1H), 2.20 (s, 3H), 1.85-1.70 (m, 2H), 1.55 (dd, J=6.7, 4.2 Hz, 6H).

418

Example 349: 3-(6-((2-(4-Methoxypiperidin-1-yl)pyrimidin-4-yl)amino)-2-methyl-1H-imidazo[4,5-c]pyridin-1-yl)butanenitrile

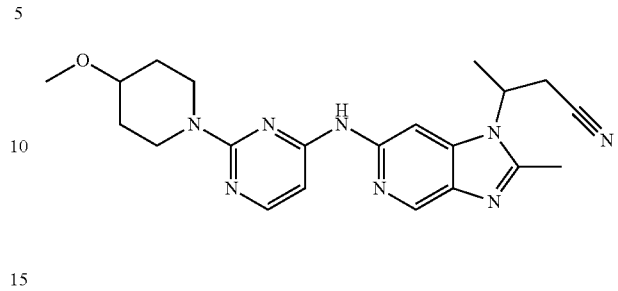

Step 1: 3-((2-Bromo-5-nitropyridin-4-yl)amino)butanenitrile

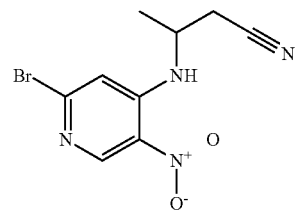

2,4-Dibromo-5-nitro-pyridine (1.0 g, 3.55 mmol) and 3-aminobutanenitrile (328.3 mg, 3.90 mmol) were dissolved in n-butanol (20 mL). Triethylamine (0.59 mL, 4.26 mmol) was added drop-wise and the resulting mixture was stirred for 24 h at room temperature. The reaction was concentrated in vacuo and the resulting residue was partitioned between ethyl acetate and water. The organic layer was dried over anhydrous sodium sulfate, filtered and concentrated in vacuo. The crude material was purified by flash chromatography on silica gel (solvent gradient: 30-60% ethyl acetate in heptanes) and concentrated in vacuo to give the title compound (600 mg, 60%). LCMS (ESI): [M+H]$^+$ 287.2; $^1$H NMR (400 MHz, DMSO-d$_6$) δ 8.84 (s, 1H), 8.18 (d, J=9.1 Hz, 1H), 7.49 (s, 1H), 4.49-4.37 (m, 1H), 2.94 (qd, J=16.7, 6.2 Hz, 2H), 1.32 (d, J=6.4 Hz, 3H).

Step 2: 3-((5-Amino-2-bromopyridin-4-yl)amino)butanenitrile

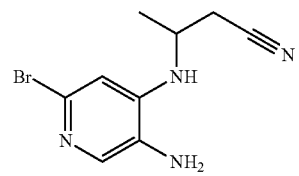

3-((2-Bromo-5-nitropyridin-4-yl)amino)butanenitrile (250 mg, 0.88 mmol) was dissolved in ethanol (15 mL). Iron powder (196 mg, 3.51 mmol) and ammonium chloride (235 mg, 4.38 mmol) were added slowly followed by water (10 mL) and the mixture was heated at 70° C. for 3 h. The reaction mixture was filtered and concentrated in vacuo to give the title compound as a light purple solid (224 mg, quantitative). LCMS (ESI): [M+H]$^+$ 256.2.

Step 3: 3-(6-Bromo-2-methyl-1H-imidazo[4,5-c]pyridin-1-yl)butanenitrile

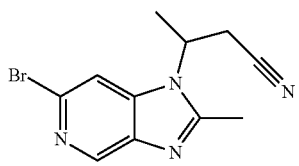 [SMILES: Cc1nc2cnc(Br)cc2n1C(C)CC#N]

3-((5-amino-2-bromopyridin-4-yl)amino)butanenitrile (130 mg, 0.51 mmol) and ethyl acetimidate hydrochloride (126 mg, 1.02 mmol) were brought up in ethanol (4 mL) and heated at 85° C. for 18 h. The reaction was cooled to room temperature, neutralized with 2N ammonia in ethanol and concentrated in vacuo. The crude material was purified by flash chromatography on silica gel (solvent gradient: 0-10% ethyl acetate in heptanes) and concentrated in vacuo to afford the title compound (60 mg, 40%). LCMS (ESI): [M+H]+ 281.2.

Step 4: 3-(6-((2-(4-Methoxypiperidin-1-yl)pyrimidin-4-yl)amino)-2-methyl-1H-imidazo[4,5-c]pyridin-1-yl)butanenitrile

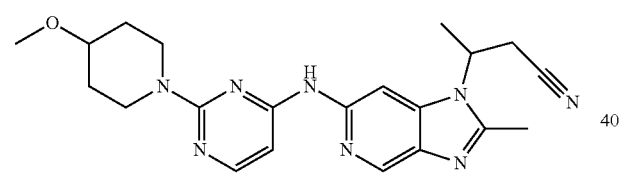

To a microwave reaction vessel was added 3-(6-bromo-2-methyl-1H-imidazo[4,5-c]pyridin-1-yl)butanenitrile (300.0 mg, 1.07 mmol), 2-(4-methoxy-1-piperidyl)pyrimidin-4-amine (Example 3, Step 2) (157 mg, 0.75 mmol), bis(dibenzylideneacetone)palladium (46.3 mg, 0.081 mmol), cesium carbonate (700 mg, 2.15 mmol), 2-(dicyclohexylphosphino)2',4',6'-triisopropylbiphenyl (53.9 mg, 0.107 mmol) and 1,4-dioxane (1.0 mL). The reaction vessel was sealed and heated at 120° C. under microwave irradiation for 30 min. The reaction mixture was cooled to room temperature, filtered, and concentrated in vacuo. The crude product was purified by reverse-phase HPLC and lyophilized to give the title compound (8.3 mg, 2%). LCMS (ESI): R$_T$ 0.44 min, [M+H]+ 407.2, method=B; $^1$H NMR (400 MHz, DMSO-d6) δ 9.72 (s, 1H), 8.54 (d, J=0.8 Hz, 1H), 8.29 (s, 1H), 7.96 (d, J=5.7 Hz, 1H), 6.42 (d, J=5.6 Hz, 1H), 5.04-4.93 (m, 1H), 4.25-4.20 (m, 2H), 3.50-3.36 (m, 2H), 3.29 (s, 3H), 3.27-3.23 (m, 2H), 2.61 (s, 3H), 1.96-1.88 (m, 2H), 1.67 (d, J=7.0 Hz, 3H), 1.52-1.32 (m, 2H).

Examples 350 and 351: (cis)-3-(6-((2-(4-methoxypiperidin-1-yl)pyrimidin-4-yl)amino)-2-methyl-1H-imidazo[4,5-c]pyridin-1-yl)cyclopentanecarbonitrile and (trans)-3-(6-((2-(4-methoxypiperidin-1-yl)pyrimidin-4-yl)amino)-2-methyl-1H-imidazo[4,5-c]pyridin-1-yl)cyclopentanecarbonitrile

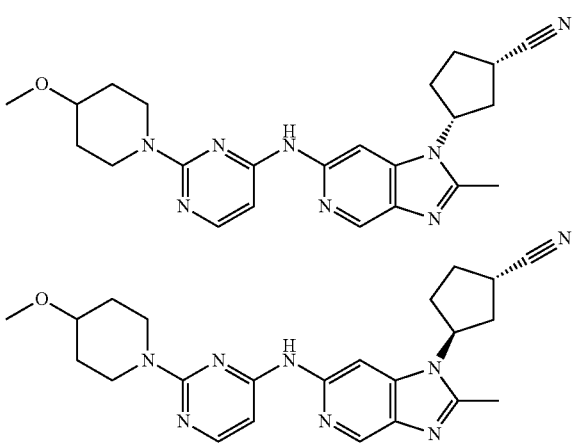

Step 1: 3-((2-Bromo-5-nitropyridin-4-yl)amino)cyclopentanecarbonitrile

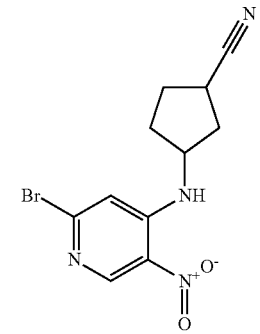

3-((2-Bromo-5-nitropyridin-4-yl)amino)cyclopentanecarbonitrile (710 mg, 60%) was prepared in a method analogous to Example 349, Step 1. LCMS (ESI): [M+H]+ 312.2; $^1$H NMR (400 MHz, CDCl$_3$) δ 8.97 (s, 1H), 8.10 (s, 1H), 6.91 (s, 1H), 4.25-4.12 (m, 1H), 3.14-3.02 (m, 1H), 2.57-2.38 (m, 2H), 2.38-2.26 (m, 1H), 2.15-2.05 (m, 2H), 1.85-1.71 (m, 1H).

Step 2: 3-((5-Amino-2-bromopyridin-4-yl)cyclopentanecarbonitrile

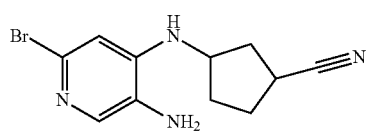

3-((5-Amino-2-bromopyridin-4-yl)cyclopentanecarbonitrile (580 mg, 90%) was prepared from 3-((2-bromo-5-nitropyridin-4-yl)amino)cyclopentanecarbonitrile in a method analogous to Example 349, Step 2. LCMS (ESI): [M+H]+ 282.2.

Step 3: 3-(6-Bromo-2-methyl-1H-imidazo[4,5-c]pyridin-1-yl)cyclopentanecarbonitrile

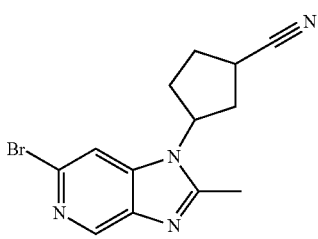 [SMILES: Cc1nc2cnc(Br)cc2n1C1CCC(C#N)C1]

3-(6-Bromo-2-methyl-1H-imidazo[4,5-c]pyridin-1-yl)cyclopentanecarbonitrile (250 mg, 21%) was prepared from 3-((5-amino-2-bromopyridin-4-yl)cyclopentanecarbonitrile in a method analogous to Example 349, Step 3. LCMS (ESI): [M+H]+ 307.2.

Step 4: (cis)-3-(6-((2-(4-methoxypiperidin-1-yl)pyrimidin-4-yl)amino)-2-methyl-1H-imidazo[4,5-c]pyridin-1-yl)cyclopentanecarbonitrile and (trans)-3-(6-((2-(4-methoxypiperidin-1-yl)pyrimidin-4-yl)amino)-2-methyl-1H-imidazo[4,5-c]pyridin-1-yl)cyclopentanecarbonitrile

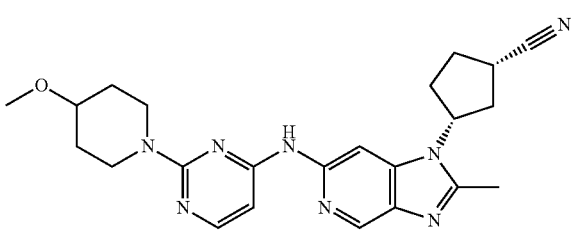

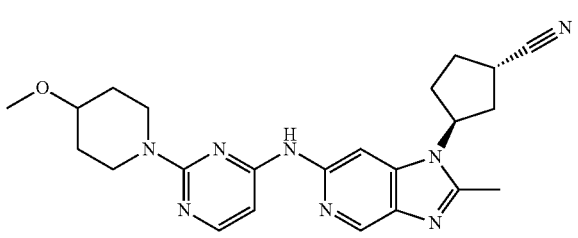

The title compounds were prepared in a method analogous to Example 349, with the cis and trans stereoisomers separated on preparatory HPLC. Example 350 (11 mg, 6%): LCMS (ESI): R$_T$ 0.44 min, [M+H]+ 433.2, method=B; $^1$H NMR (400 MHz, DMSO-d$_6$) δ 9.55 (s, 1H), 8.20 (s, 1H), 7.99 (d, J=5.7 Hz, 1H), 7.74 (s, 1H), 6.82 (s, 1H), 4.91-4.86 (m, 1H), 4.30-4.20 (m, 2H), 3.47-3.38 (m, 1H), 3.36-3.20 (m, 5H), 3.17 (s, 1H), 2.57 (s, 3H), 2.32-2.16 (m, 4H), 1.90-1.85 (m, 2H), 1.43-1.30 (m, 2H). Example 351 (11 mg, 6%): LCMS (ESI): R$_T$ 0.43 min, [M+H]+ 433.2, method=B; $^1$H NMR (400 MHz, DMSO-d$_6$) δ 9.49 (s, 1H), 8.53 (s, 1H), 8.18 (s, 1H), 7.99 (d, J=5.2, 3.1 Hz, 1H), 7.69 (s, 1H), 6.77 (s, 1H), 5.11-4.99 (m, 1H), 4.26-4.16 (m, 2H), 3.54-3.38 (m, 2H), 3.35-3.23 (m, 5H), 3.19-3.14 (m, 1H), 2.59 (s, 3H), 2.40-1.95 (m, 4H), 1.92-1.78 (m, 1H), 1.43-1.31 (m, 2H).

Example 352: 3-(6-((2-(4-Methoxypiperidin-1-yl)pyrimidin-4-yl)amino)-2-methyl-1H-imidazo[4,5-c]pyridin-1-yl)butanamide

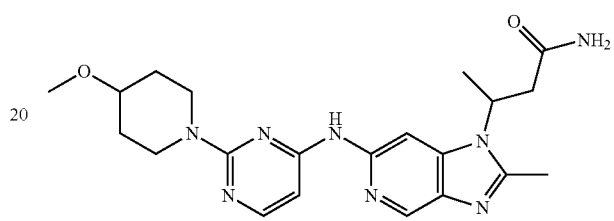

Step 1: 3-((2-Chloro-5-nitropyridin-4-yl)amino)butanamide

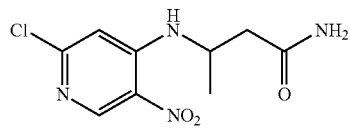 [SMILES: CC(CC(N)=O)Nc1cc(Cl)ncc1[N+](=O)[O-]]

2,4-Dichloro-5-nitro-pyridine (472 mg, 2.45 mmol) and 3-aminobutanamide (250 mg, 2.45 mmol) were brought up in n-butanol (20 mL). Triethylamine (0.41 mL, 2.94 mmol) was added drop-wise and the resulting mixture was stirred for 24 h at room temperature. The resulting precipitate was filtered and dried in vacuo to give the title compound (700 mg, 100%). LCMS (ESI): [M+H]+ 259.2; $^1$H NMR (400 MHz, DMSO-d$_6$) δ 8.87 (s, 1H), 7.16 (s, 1H), 7.01 (s, 1H), 4.29-4.17 (m, 1H), 2.50-2.39 (m, 2H), 1.24 (d, J=6.4 Hz, 3H).

Step 2: 3-((5-Amino-2-chloropyridin-4-yl)amino)butanamide

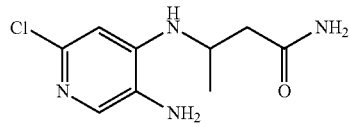

3-((5-Amino-2-chloropyridin-4-yl)amino)butaneamide (230 mg, 40%) was prepared from 3-((2-chloro-5-nitropyridin-4-yl)amino)butanenitrile in a method analogous to Example 349, Step 2. LCMS (ESI): [M+H]+=229.2.

Step 3: 3-(6-Chloro-2-methyl-1H-imidazo[4,5-c]pyridin-1-yl)butanenitrile

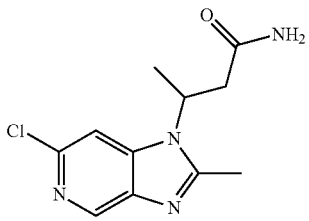 [SMILES: Cc1nc2cnc(Cl)cc2n1C(C)CC(N)=O]

3-(6-Chloro-2-methyl-1H-imidazo[4,5-c]pyridin-1-yl)butanamide (140 mg, 55%) was prepared from 3-((5-amino-2-chloropyridin-4-yl)amino)butanamide (230 mg, 1.01 mmol) in a method analogous to Example 349, Step 3. LCMS (ESI): [M+H]$^+$=253.3; $^1$H NMR (400 MHz, DMSO-d$_6$) δ 8.57 (s, 1H), 7.74 (s, 1H), 5.01-4.87 (m, 1H), 2.90 (dd, J=15.2, 9.3 Hz, 1H), 2.74 (dd, J=15.3, 5.8 Hz, 1H), 2.62 (s, 3H), 1.54 (d, J=7.0 Hz, 3H).

Step 4: 3-(6-((2-(4-Methoxypiperidin-1-yl)pyrimidin-4-yl)amino)-2-methyl-1H-imidazo[4,5-c]pyridin-1-yl)butanamide

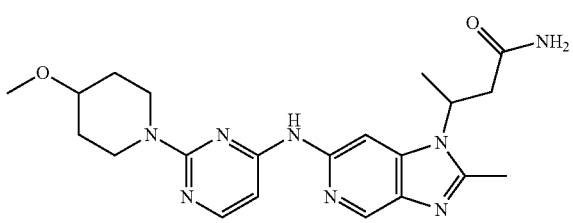 [SMILES: COC1CCN(c2nccc(Nc3cc4c(cn3)nc(C)n4C(C)CC(N)=O)n2)CC1]

3-(6-((2-(4-Methoxypiperidin-1-yl)pyrimidin-4-yl)amino)-2-methyl-1H-imidazo[4,5-c]pyridin-1-yl)butanenitrile (3.8 mg, 1%) was prepared from 3-(6-chloro-2-methyl-1H-imidazo[4,5-c]pyridin-1-yl)butanamide (280.0 mg, 1.11 mmol) in a method analogous to Example 349, Step 4. LCMS (ESI): R$_T$ 2.96 min, [M+H]$^+$ 425.3, method=B; $^1$H NMR (500 MHz, DMSO-d$_6$) δ 9.74 (s, 1H), 8.48 (s, 1H), 8.41 (s, 1H), 7.95 (d, J=5.7 Hz, 1H), 6.39 (d, J=5.7 Hz, 1H), 5.01-4.89 (m, 1H), 4.32-4.16 (m, 2H), 3.46-3.36 (m, 3H), 3.30 (s, 4H), 2.95 (dd, J=15.3, 9.5 Hz, 1H), 2.70 (dd, J=15.4, 5.1 Hz, 1H), 2.58 (s, 3H), 1.98-1.85 (m, 2H), 1.58 (d, J=7.0 Hz, 3H), 1.53-1.37 (m, 2H).

Example 353: 4-(1-(6-((2-(4-Methoxypiperidin-1-yl)pyrimidin-4-yl)amino)-2-methyl-1H-imidazo[4,5-c]pyridin-1-yl)ethyl)benzonitrile

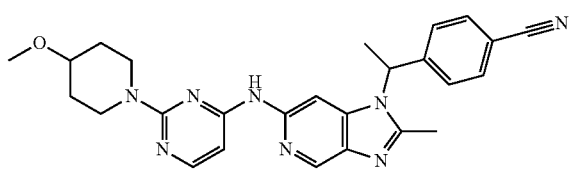 [SMILES: COC1CCN(c2nccc(Nc3cc4c(cn3)nc(C)n4C(C)c3ccc(C#N)cc3)n2)CC1]

Step 1: 4-(1-((2-Chloro-5-nitropyridin-4-yl)amino)ethyl)benzonitrile

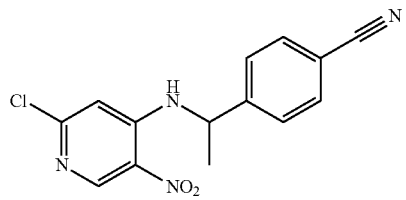 [SMILES: CC(Nc1cc(Cl)ncc1[N+](=O)[O-])c1ccc(C#N)cc1]

4-(1-((2-Chloro-5-nitropyridin-4-yl)amino)ethyl)benzonitrile (900 mg, 60%) was prepared from 2,4-dichloro-5-nitro-pyridine (1.0 g, 5.18 mmol) and 4-(1-aminoethyl)benzonitrile (833.25 mg, 5.70 mmol) in a method analogous to Example 349, Step 1. LCMS (ESI): [M+H]$^+$ 303.2; $^1$H NMR (400 MHz, DMSO-d$_6$) δ 8.89 (s, 1H), 8.47 (d, J=7.3 Hz, 1H), 7.90-7.78 (m, 2H), 7.78-7.62 (m, 2H), 6.86 (s, 1H), 5.17 (p, J=6.9 Hz, 1H), 1.60 (d, J=6.8 Hz, 3H).

Step 2: 4-(1-((5-Amino-2-chloropyridin-4-yl)amino)ethyl)benzonitrile

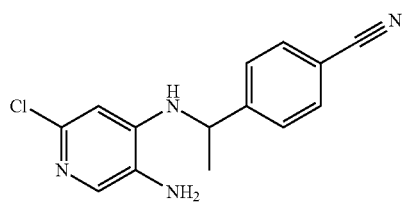

4-(1-((5-Amino-2-chloropyridin-4-yl)amino)ethyl)benzonitrile (230 mg, 30%) was prepared from 4-(1-((2-chloro-5-nitropyridin-4-yl)amino)ethyl)benzonitrile (900 mg, 3.0 mmol) in a method analogous to Example 349, Step 2. LCMS (ESI): [M+H]$^+$=273.3.

Step 3: 4-(1-(6-Chloro-2-methyl-1H-imidazo[4,5-c]pyridin-1-yl)ethyl)benzonitrile

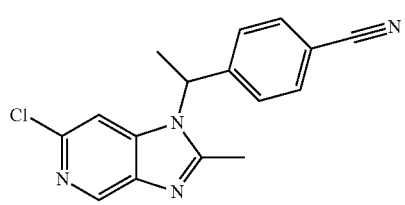 [SMILES: Cc1nc2cnc(Cl)cc2n1C(C)c1ccc(C#N)cc1]

4-(1-(6-Chloro-2-methyl-1H-imidazo[4,5-c]pyridin-1-yl)ethyl)benzonitrile (350 mg, 60%) was prepared from 4-(1-((5-amino-2-chloropyridin-4-yl)amino)ethyl)benzonitrile (500 mg, 2.0 mmol) in a method analogous to Example 349, Step 3. LCMS (ESI): [M+H]$^+$=297.3. $^1$H NMR (400 MHz, DMSO-d$_6$) δ 8.63 (s, 1H), 7.85 (d, 2H), 7.45 (d, J=8.1 Hz, 2H), 7.35 (s, 1H), 6.07 (q, J=7.1 Hz, 1H), 2.57 (s, 3H), 1.95 (d, J=7.1 Hz, 4H).

Step 4: 4-(1-(6-((2-(4-Methoxypiperidin-1-yl)pyrimidin-4-yl)amino)-2-methyl-1H-imidazo[4,5-c]pyridine-1-yl)ethyl)benzonitrile

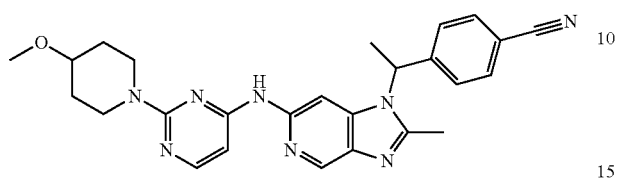

4-(1-(6-((2-(4-Methoxypiperidin-1-yl)pyrimidin-4-yl)amino)-2-methyl-1H-imidazo[4,5-c]pyridine-1-yl)ethyl)benzonitrile (57 mg, 24%) was prepared from 4-(1-(6-chloro-2-methyl-1H-imidazo[4,5-c]pyridin-1-yl)ethyl)benzonitrile (150.0 mg, 0.505 mmol) in a method analogous to Example 349, Step 4. LCMS (ESI): $R_T$ 3.58 min, $[M+H]^+$ 469.3, method=B; $^1$H NMR (400 MHz, DMSO-$d_6$) δ 9.62 (d, J=2.6 Hz, 1H), 8.57 (s, 1H), 7.92 (d, J=5.7 Hz, 1H), 7.89 (s, 1H), 7.85 (d, J=8.4 Hz, 2H), 7.34 (d, J=8.2 Hz, 2H), 6.42 (d, J=5.6 Hz, 1H), 6.00 (q, J=7.1 Hz, 1H), 4.03-3.93 (m, 2H), 3.53-3.31 (m, 2H), 3.29 (s, 3H), 3.20-3.06 (m, 2H), 2.49 (s, 1H), 1.98 (d, J=7.1 Hz, 3H), 1.73-1.64 (m, 2H), 1.32-1.15 (m, 2H).

Example 354: 4-(1-(6-((2-(4-Methoxypiperidin-1-yl)pyrimidin-4-yl)amino)-2-methyl-1Himidazo[4,5-c]pyridin-1-yl)ethyl)benzamide

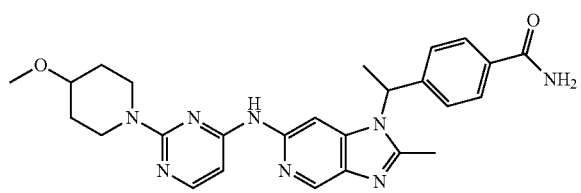 [SMILES: COC1CCN(c2nccc(Nc3cc4c(cn3)nc(C)n4C(C)c3ccc(C(N)=O)cc3)n2)CC1]

To a solution of 4-(1-(6-((2-(4-methoxypiperidin-1-yl)pyrimidin-4-yl)amino)-2-methyl-1H-imidazo[4,5-c]pyridine-1-yl)ethyl)benzonitrile (Example 353) (40 mg, 0.085 mmol) in formic acid (3 mL) was added aqueous hydrochloric acid (12 mol/L)(6 mL, 73 mmol). The reaction vessel was then sealed, heated at 70° C. for 2 h, cooled to room temperature and concentrated in vacuo. The crude product was purified by reverse-phase HPLC and lyophilized to afford the title compound (6.1 mg, 14%). LCMS (ESI): $R_T$ 3.16 min, $[M+H]^+$ 487.3, method=B; $^1$H NMR (400 MHz, DMSO-$d_6$) δ 9.60 (s, 1H), 8.55 (s, 1H), 7.90 (d, J=5.6 Hz, 2H), 7.88-7.82 (m, 2H), 7.32 (s, 1H), 7.22 (d, J=8.2 Hz, 2H), 6.40 (d, J=5.7 Hz, 1H), 5.94 (q, J=7.2 Hz, 1H), 4.05-3.97 (m, 2H), 3.37-3.29 (m, 1H), 3.25 (s, 4H), 3.19-3.07 (m, 2H), 2.53 (s, 3H), 1.98 (d, J=7.1 Hz, 3H), 1.71 (s, 2H), 1.24 (d, J=3.1 Hz, 2H).

Example 355: 1-(1H-Indazol-4-ylmethyl)-N-[2-(4-methoxy-1-piperidyl)pyrimidin-4-yl]-2-methyl-imidazo[4,5-c]pyridin-6-amine

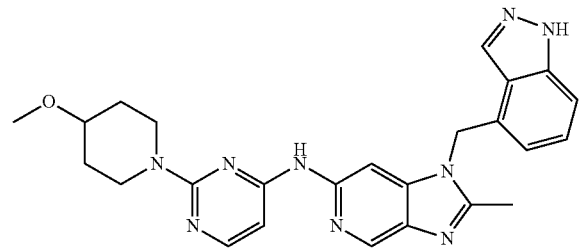 [SMILES: COC1CCN(c2nccc(Nc3cc4c(cn3)nc(C)n4Cc3cccc4[nH]ncc34)n2)CC1]

Step 1: 2-Chloro-5-nitro-N-[(1-tetrahydropyran-2-ylindazol-4-yl)methyl]pyridin-4-amine

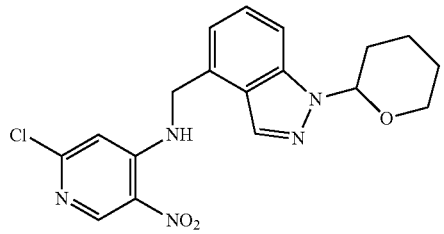 [SMILES: O=[N+]([O-])c1cnc(Cl)cc1NCc1cccc2c1cnn2C1CCCCO1]

To a round-bottom flask was added a solution of 2,4-dichloro-5-nitropyridine (0.26 g, 1.35 mmol) in tetrahydrofuran (3 mL) and triethylamine (0.27 g, 2.69 mmol). This was followed by the addition of (1-tetrahydropyran-2-ylindazol-4-yl)methanamine (WO 2013026914)(0.311 g, 1.35 mmol) in one portion with stirring at 0° C. The resulting solution was stirred for 4 h at room temperature. The resulting mixture was concentrated in vacuo to afford the title compound (0.52 g, 99%) as a yellow solid which was used without further purification. LCMS (ESI): $R_T$ (min)=1.28, $[M+H]^+$=388, method=I.

Step 2: 6-Chloro-$N^4$-[(1-tetrahydropyran-2-ylindazol-4-yl)methyl]pyridine-3,4-diamine

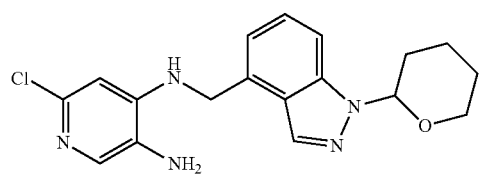 [SMILES: Nc1cnc(Cl)cc1NCc1cccc2c1cnn2C1CCCCO1]

To a round bottom flask was added 2-chloro-5-nitro-N-[(1-tetrahydropyran-2-ylindazol-4-yl)methyl]pyridin-4-amine (0.160 g, 0.413 mmol), ammonium chloride (0.11 g, 2.06 mmol), iron powder (0.092 g, 1.65 mmol), ethanol (1.92 mL) and water (0.483 mL). The mixture was heated to 70° C. for 2 h. The reaction was cooled to room temperature, filtered through a pad of celite and concentrated in vacuo. The resulting residue was dissolved in ethyl acetate (10 mL) and stirred for 15 min. Anhydrous magnesium sulfate was added to the solution and stirring continued for an additional 10 min. The suspension was filtered through a pad of celite and concentrated in vacuo afford the title compound (0.13 g, 88%) as a brown solid. LCMS (ESI): $R_T$ (min)=0.93, $[M+H]^+$=358, method=I.

Step 3: 6-Chloro-2-methyl-1-[(1-tetrahydropyran-2-ylindazol-4-yl)methyl]imidazo[4,5-c]pyridine

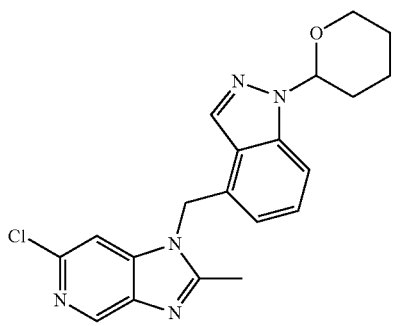 [SMILES: Cc1nc2cnc(Cl)cc2n1Cc1cccc2c1cnn2C1CCCCO1]

To a reaction vessel was added 6-chloro-$N^4$-[(1-tetrahydropyran-2-ylindazol-4-yl)methyl]pyridine-3,4-diamine (0.29 g, 0.81 mmol), ethylacetimidate hydrochloride (0.12 g, 0.97 mmol) and ethanol (4 mL.) The reaction vessel was sealed and heated at 85° C. for 18 h. The reaction was cooled to room temperature, neutralized with 2N ammonia in ethanol and concentrated in vacuo. The residue was purified by silica gel chromatography (eluent: 10% methanol in dichloromethane) to afford the title compound (0.22 g, 72%) as a tan solid. LCMS (ESI): $R_T$ (min)=0.98, $[M+H]^+$=382, method=I.

Step 4: 1-(1H-Indazol-4-ylmethyl)-N-[2-(4-methoxy-1-piperidyl)pyrimidin-4-yl]-2-methyl-imidazo[4,5-c]pyridin-6-amine

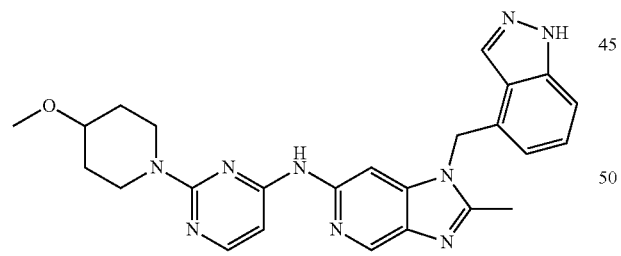

To a microwave reaction vessel was added 6-chloro-2-methyl-1-[(1-tetrahydropyran-2-ylindazol-4-yl)methyl]imidazo[4,5-c]pyridine (43 mg, 0.1126 mmol), 2-(4-methoxy-1-piperidyl)pyrimidin-4-amine (Example 3, step 2) (35.17 mg, 0.169 mmol), chloro {[BrettPhos][2-(2-aminoethylphenyl)palladium(II)]}/[BrettPhos] admixture (molar PdP/P=1: 1) (4.5 mg, 0.006 mmol), 2-(dicyclohexylphosphino)3,6-dimethoxy-2',4',6'-triisopropyl-1,1'-biphenyl (6.2 mg, 0.011 mmol), cesium carbonate (81 mg, 0.248 mmol) and 1,4-dioxane (1 mL). The vial was sealed, purged with nitrogen and subjected to microwave irradiation for 60 min at 120° C. The reaction was filtered through a pad of celite and was purified by silica gel chromatography (eluent: 10% methanol in dichloromethane) to afford N-[2-(4-methoxy-1-piperidyl)pyrimidin-4-yl]-2-methyl-1-[(1-tetrahydropyran-2-ylindazol-4-yl)methyl]imidazo[4,5-c]pyridin-6-amine (39 mg), which was brought up in 1,4-dioxane (1 mL) and treated with HCl (4 N in 1,4-dioxane)(0.07 mL, 0.282 mmol). The mixture was heated to 100° C. for 2 h and then purified by reverse phase HPLC to afford the title compound (8.3 mg, 25%). LCMS (ESI): $R_T$ 3.24 min, $[M+H]^+$ 470.3, Method=E; $^1$H NMR (400 MHz, DMSO-$d_6$) δ 9.73 (s, 1H), 8.60 (d, J=0.9 Hz, 1H), 8.22 (s, 1H), 8.00 (s, 1H), 7.89 (d, J=5.6 Hz, 1H), 7.48 (d, J=8.4 Hz, 1H), 7.24 (dd, J=8.4, 7.0 Hz, 1H), 6.37 (d, J=7.1 Hz, 1H), 6.31 (d, J=5.6 Hz, 1H), 5.77 (s, 2H), 3.87 (d, J=12.7 Hz, 2H), 3.10 (s, 3H), 2.91 (t, J=11.2 Hz, 2H), 2.45 (s, 3H), 1.36 (s, 2H), 1.09-0.87 (m, 2H).

Example 356: 1-Benzyl-N-[2-(4-methoxy-1-piperidyl)pyrimidin-4-yl]-2-methyl-imidazo[4,5-c]pyridin-6-amine

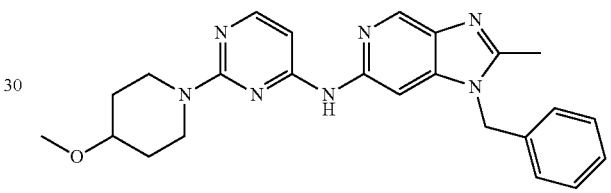

Step 1: N-Benzyl-2-chloro-5-nitropyridin-4-amine

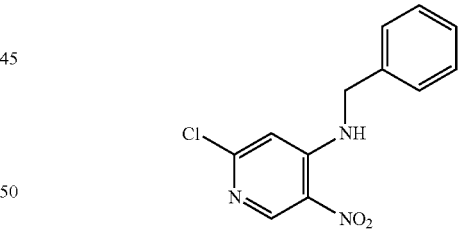

To a round bottom flask was added a solution of 2,4-dichloro-5-nitropyridine (0.115 g, 0.60 mmol) in tetrahydrofuran (32 mL) and triethylamine (0.12 g, 1.19 mmol) followed by dropwise addition of benzylamine (0.064 g, 0.60 mmol) with stirring at 0° C. The resulting solution was stirred for 1 h at room temperature, concentrated in vacuo and purified by silica gel chromatography (eluent: 10% methanol in dichloromethane) to afford the title compound (0.112 g, 71%) as a yellow solid. LCMS (ESI): $R_T$ (min)=1.24, $[M+H]^+$=264, method=I; $^1$H NMR (300 MHz, DMSO-$d_6$) δ 9.07 (t, J=6.3 Hz, 1H), 8.89 (s, 1H), 7.40-7.35 (m, 4H), 7.35-7.22 (m, 1H), 6.94 (s, 1H), 4.69 (d, J=6.3 Hz, 2H).

Step 2: N⁴-Benzyl-6-chloropyridine-3,4-diamine

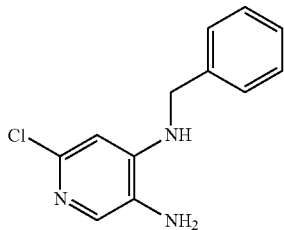 [SMILES: O=[N+]([O-])c1cnc(Cl)cc1NCc1ccccc1]

To a round bottom flask was added N-benzyl-2-chloro-5-nitro-pyridin-4-amine (0.112 g, 0.425 mmol), ammonium chloride (0.113 g, 2.12 mmol), iron powder (0.094 g, 1.7 mmol), ethanol (2 mL) and water (0.5 mL). The mixture was heated to 70° C. for 2 h. The reaction was cooled to room temperature, filtered through a pad of celite and concentrated in vacuo. The resulting residue was dissolved in ethyl acetate (10 mL) and stirred for 15 min. Anhydrous magnesium sulfate was added to the solution and stirring continued for an additional 10 min. The suspension was filtered through a pad of celite and concentrated to afford the title compound (0.10 g, 100%) as a brown solid. LCMS (ESI): $R_T$ (min)=0.83, [M+H]⁺=234, method=I.

Step 3: 1-Benzyl-6-chloro-2-methyl-1H-imidazo[4,5-c]pyridine

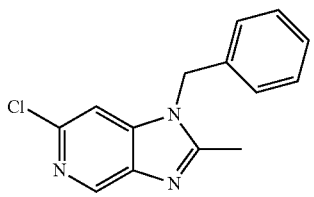 [SMILES: Cc1nc2cnc(Cl)cc2n1Cc1ccccc1]

To a reaction vessel was added N⁴-benzyl-6-chloropyridine-3,4-diamine (0.10 g, 0.43 mmol), ethylacetimidate hydrochloride (0.063 g, 0.51 mmol) and ethanol (4 mL.) The vessel was sealed and heated at 85° C. for 18 h. The reaction was cooled to room temperature, neutralized with 2N ammonia in ethanol and concentrated in vacuo. The residue was purified by silica gel chromatography (eluent: 10% methanol in dichloromethane) to afford the title compound (0.073 g, 66%) as a tan solid. LCMS (ESI): $R_T$ (min)=0.94, [M+H]⁺=258, method=I.

Step 4: 1-Benzyl-N-[2-(4-methoxy-1-piperidyl)pyrimidin-4-yl]-2-methyl-imidazo[4,5-c]pyridin-6-amine

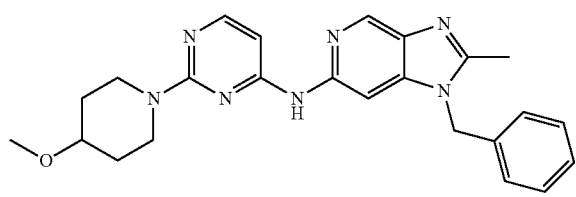 [SMILES: COC1CCN(c2nccc(Nc3cc4c(cn3)nc(C)n4Cc3ccccc3)n2)CC1]

To a microwave reaction vessel was added 1-benzyl-6-chloro-2-methyl-1H-imidazo[4,5-c]pyridine (73 mg, 0.28 mmol), 2-(4-methoxy-1-piperidyl)pyrimidin-4-amine (Example 3, Step 2) (88.5 mg, 0.43 mmol), chloro{[BrettPhos][2-(2-aminoethylphenyl]palladium(II)]}/[BrettPhos] admixture (molar PdP/P=1:1) (11.3 mg, 0.014 mmol), 2-(dicyclohexylphosphino)3,6-dimethoxy-2',4',6'-triisopropyl-1,1'-biphenyl (15.5 mg, 0.028 mmol), cesium carbonate (184 mg, 0.567 mmol) and 1,4-dioxane (1 mL). The vessel was sealed, purged with nitrogen and subjected to microwave irradiation for 60 min at 120° C. The reaction was filtered through a pad of celite and purified by silica gel chromatography (eluent: 10% methanol in dichloromethane) followed by reverse phase HPLC to afford the title compound (22.1 mg, 18%). LCMS (ESI): $R_T$ 3.53 min, [M+H]⁺ 430.2, Method=E; ¹H NMR (400 MHz, DMSO-d₆) δ 9.72 (s, 1H), 8.56 (d, J=0.9 Hz, 1H), 8.22 (s, 1H), 7.92 (d, J=5.6 Hz, 1H), 7.42-7.25 (m, 3H), 7.14-7.04 (m, 2H), 6.35 (d, J=5.7 Hz, 1H), 5.42 (s, 2H), 4.02 (d, J=13.5 Hz, 2H), 3.21 (s, 3H), 3.17 (td, J=9.7, 4.9 Hz, 2H), 2.47 (s, 3H), 1.64 (d, J=11.8 Hz, 2H), 1.21 (d, J=9.1 Hz, 2H).

Example 357: 1-[(1S)-1-(1H-Benzimidazol-5-yl)ethyl]-N-[2-(4-methoxy-1-piperidyl)pyrimidin-4-yl]-2-methyl-imidazo[4,5-c]pyridin-6-amine

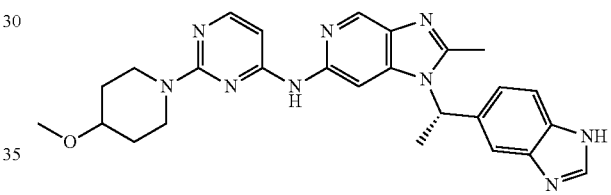

Step 1: (S)—N-(1-(1H-Benzo[d]imidazol-5-yl)ethyl)-2-chloro-5-nitropyridin-4-amine

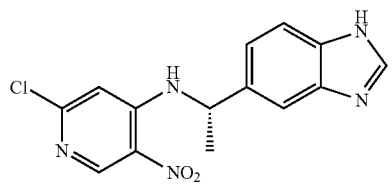 [SMILES: C[C@H](Nc1cc(Cl)ncc1[N+](=O)[O-])c1ccc2[nH]cnc2c1]

To a round bottom flask was added a solution of 2,4-dichloro-5-nitropyridine (0.50 g, 2.59 mmol) in tetrahydrofuran (10 mL) and triethylamine (0.52 g, 5.18 mmol) followed by the addition of (1S)-1-(1-(tetrahydro-2H-pyran-2-yl)-1H-benzo[d]imidazol-5-yl)ethanamine (WO 2013026914)(0.635 g, 2.59 mmol) with stirring at 0° C. The resulting solution was stirred for 4 h at room temperature, concentrated in vacuo and purified by silica gel chromatography (eluent: 10% methanol in dichloromethane) to afford the title compound (0.80 g, 97%) as a yellow solid. LCMS (ESI): $R_T$ (min)=0.84, [M+H]⁺=318, method=I; ¹H NMR (400 MHz, DMSO-d₆) δ 8.88 (s, 1H), 8.50 (d, J=7.0 Hz, 1H), 8.21 (s, 1H), 7.69 (s, 1H), 7.58 (d, J=8.3 Hz, 1H), 7.31 (dd, J=8.3, 1.6 Hz, 1H), 6.96 (s, 1H), 5.15 (t, J=6.8 Hz, 1H), 3.17 (d, J=4.4 Hz, 2H), 1.63 (d, J=6.7 Hz, 3H).

Step 2: (S)—N⁴-(1-(1H-Benzo[d]imidazol-5-yl)ethyl)-6-chloropyridine-3,4-diamine

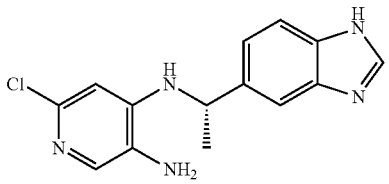 [SMILES: C[C@H](Nc1cc(Cl)ncc1N)c1ccc2[nH]cnc2c1]

To a round bottom flask was added (S)—N-(1-(1H-benzo[d]imidazol-5-yl)ethyl)-2-chloro-5-nitropyridin-4-amine (0.80 g, 2.52 mmol), ammonium chloride (0.673 g, 12.59 mmol), iron powder (0.562 g, 10.07 mmol), ethanol (12 mL) and water (1 mL). The mixture was heated to 70° C. for 2 h, cooled to room temperature, filtered through a pad of celite and concentrated in vacuo. The resulting residue was dissolved in ethyl acetate (10 mL) and stirred for 15 min. Anhydrous magnesium sulfate was added to the solution and stirring continued for an additional 10 min. The suspension was filtered through a pad of celite, concentrated and purified by silica gel chromatography (eluent: 10% methanol in dichloromethane) to afford the title compound (0.37 g, 43%) as a brown solid. LCMS (ESI): $R_T$ (min)=0.46, [M+H]⁺=288, method=I; ¹H NMR (400 MHz, DMSO-d₆) δ 8.16 (s, 1H), 7.62-7.47 (m, 2H), 7.37 (s, 1H), 7.21 (d, J=8.6 Hz, 1H), 6.08 (d, J=11.0 Hz, 2H), 4.93 (s, 2H), 4.70 (t, J=6.7 Hz, 1H), 3.08 (d, J=8.0 Hz, 2H), 1.52 (d, J=6.7 Hz, 3H), 1.18 (t, J=7.3 Hz, 2H).

Step 3: (S)-1-(1-(1H-benzo[d]imidazol-5-yl)ethyl)-6-chloro-2-methyl-1H-imidazo[4,5-c]pyridine

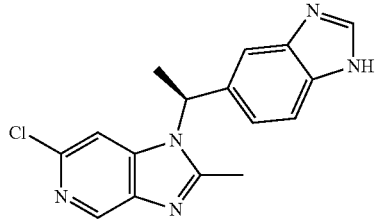 [SMILES: Cc1nc2cnc(Cl)cc2n1[C@@H](C)c1ccc2[nH]cnc2c1]

To a reaction vessel was added (S)—N⁴-(1-(1H-benzo[d]imidazol-5-yl)ethyl)-6-chloropyridine-3,4-diamine (0.19 g, 0.66 mmol), ethylacetimidate hydrochloride (0.815 g, 6.6 mmol) and ethanol (10 mL.) The reaction vessel was sealed and heated at 85° C. for 18 h. The reaction was cooled to room temperature, neutralized with 2N ammonia in ethanol and concentrated in vacuo. The residue was purified by silica gel chromatography (eluent: 10% methanol in dichloromethane) to afford the title compound (0.12 g, 58%) as a tan solid. LCMS (ESI): $R_T$ (min)=0.61, [M+H]⁺=312, method=I.

Step 4: 1-[(1S)-1-(1H-Benzimidazol-5-yl)ethyl]-N-[2-(4-methoxy-1-piperidyl)pyrimidin-4-yl]-2-methyl-imidazo[4,5-c]pyridin-6-amine

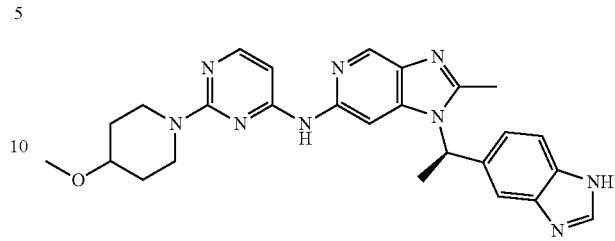

To a reaction vessel was added (S)-1-(1-(1H-benzo[d]imidazol-5-yl)ethyl)-6-chloro-2-methyl-1H-imidazo[4,5-c]pyridine (43 mg, 0.1126 mmol), 2-(4-methoxy-1-piperidyl)pyrimidin-4-amine (Example 3, Step 2) (35.17 mg, 0.169 mmol), chloro{[BrettPhos][2-(2-aminoethylphenyl]palladium(II)]}/[BrettPhos] admixture (molar PdP/P=1:1) (50 mg, 0.062 mmol, 0.45 equiv), sodium tert-butoxide (40 mg, 0.414 mmol, 3.0 equiv) and tert-butanol (5 mL). The suspension was purged with nitrogen, sealed, and heated at 125° C. for 1 h. The reaction was cooled to room temperature, filtered through a pad of celite, concentrated in vacuo and purified by reverse phase HPLC to afford the title compound (4.9 mg, 7%). LCMS (ESI): $R_T$ 3.38 min, [M+H]⁺ 484.3, Method=E; ¹H NMR (400 MHz, DMSO-d₆) δ 9.59 (s, 1H), 8.55 (s, 1H), 8.18 (s, 1H), 8.01 (s, 1H), 7.88 (d, J=5.7 Hz, 1H), 7.55 (d, J=8.4 Hz, 1H), 7.33 (s, 1H), 7.02 (dd, J=8.5, 1.8 Hz, 1H), 6.37 (d, J=5.7 Hz, 2H), 5.99 (d, J=7.2 Hz, 1H), 4.06-3.93 (m, 2H), 3.19 (s, 3H), 3.19-2.99 (m, 3H), 2.03 (d, J=7.1 Hz, 3H), 1.63 (s, 2H), 1.20 (d, J=10.5 Hz, 2H).

Example 358: 1-((1H-Benzo[d]imidazol-4-yl)methyl)-N-(2-(4-methoxypiperidin-1-yl)pyrimidin-4-yl)-2-methyl-1H-imidazo[4,5-c]pyridin-6-amine

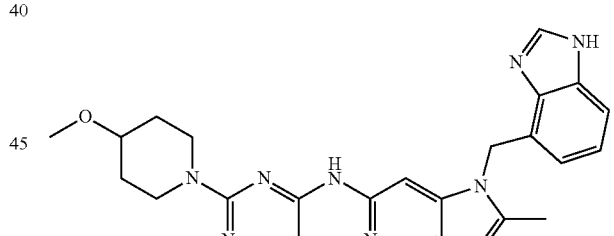

And

Example 359: 1-((1H-Benzo[d]imidazol-5-yl)methyl)-N-(2-(4-methoxypiperidin-1-yl)pyrimidin-4-yl)-2-methyl-1H-imidazo[4,5-c]pyridin-6-amine

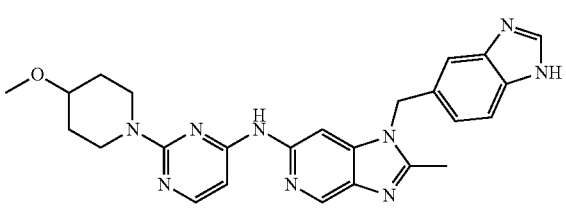 [SMILES: COC1CCN(c2nccc(Nc3cc4c(cn3)nc(C)n4Cc3ccc4[nH]cnc4c3)n2)CC1]

Step 1: N-((1H-Benzo[d]imidazol-4-yl)methyl)-2-chloro-5-nitropyridin-4-amine and N-((1H-benzo[d]imidazol-5-yl)methyl)-2-chloro-5-nitropyridin-4-amine

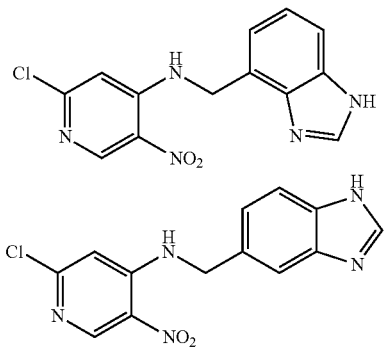

To a round bottom flask was added a solution of 2,4-dichloro-5-nitropyridine (0.41 g, 2.13 mmol, 1.00 equiv) in tetrahydrofuran (3 mL) and triethylamine (0.43 g, 4.25 mmol, 2 equiv). This was followed by the addition of a 1:1 mixture of (1-(tetrahydro-2H-pyran-2-yl)-1H-benzo[d]imidazol-4-yl)methanamine and (1-(tetrahydro-2H-pyran-2-yl)-1H-benzo[d]imidazol-5-yl)methanamine (WO 2013026914)(0.492 g, 213 mmol) with stirring at 0° C. The resulting solution was stirred for 1 h at room temperature, concentrated in vacuo and purified by silica gel chromatography (eluent: 10% methanol in dichloromethane) to afford a mixture of N-((1H-benzo[d]imidazol-4-yl)methyl)-2-chloro-5-nitropyridin-4-amine and N-((1H-benzo[d]imidazol-5-yl)methyl)-2-chloro-5-nitropyridin-4-amine (0.55 g, 85%) as a yellow solid. LCMS (ESI): $R_T$ (min)=1.04, 1.08, [M+H]$^+$=304.3, method=I.

Step 2: $N^4$-((1H-Benzo[d]imidazol-4-yl)methyl)-6-chloropyridine-3,4-diamine and $N^4$-((1H-benzo[d]imidazol-5-yl)methyl)-6-chloropyridine-3,4-diamine

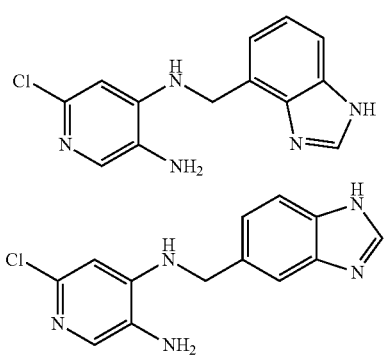

To a round bottom flask was added a mixture of N-((1H-benzo[d]imidazol-4-yl)methyl)-2-chloro-5-nitropyridin-4-amine and N-((1H-benzo[d]imidazol-5-yl)methyl)-2-chloro-5-nitropyridin-4-amine (0.55 g, 1.81 mmol), ammonium chloride (0.484 g, 9.06 mmol), iron (0.404 g, 7.24 mmol), ethanol (8.5 mL) and water (2.1 mL). The mixture was heated to 70° C. for 2 h. The reaction was cooled to room temperature, filtered through a pad of celite and concentrated in vacuo. The residue was dissolved in ethyl acetate (10 mL) and stirred for 15 min. Anhydrous magnesium sulfate was added to the solution and stirring continued for an additional 10 min. The suspension was filtered through a pad of celite and concentrated to afford a mixture of $N^4$-((1H-benzo[d]imidazol-4-yl)methyl)-6-chloropyridine-3,4-diamine and $N^4$-((1H-benzo[d]imidazol-5-yl)methyl)-6-chloropyridine-3,4-diamine (0.32 g, 65%) as a brown solid. LCMS (ESI): $R_T$ (min)=0.62, 0.69 [M+H]$^+$=274.3, method=I.

Step 3: 1-((1H-Benzo[d]imidazol-4-yl)methyl)-6-chloro-2-methyl-1H-imidazo[4,5-c]pyridine and 1-((1H-benzo[d]imidazol-5-yl)methyl)-6-chloro-2-methyl-1H-imidazo[4,5-c]pyridine

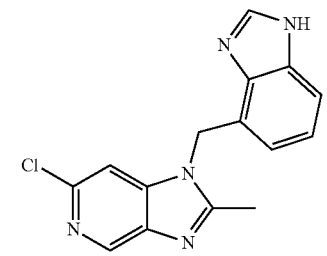

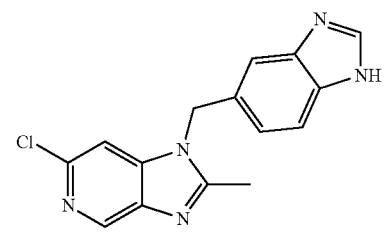

To a reaction vessel was added a mixture of $N^4$-((1H-benzo[d]imidazol-4-yl)methyl)-6-chloropyridine-3,4-diamine and $N^4$-((1H-benzo[d]imidazol-5-yl)methyl)-6-chloropyridine-3,4-diamine (0.32 g, 1.2 mmol), ethylacetimidate hydrochloride (0.220 g, 1.8 mmol) and ethanol (12 mL.) The reaction vessel was sealed and heated at 85° C. for 18 h. The reaction was cooled to room temperature, neutralized with 2N ammonia in ethanol and concentrated in vacuo. The residue was purified by silica gel chromatography (eluent: 10% methanol in dichloromethane) to afford a mixture of 1-((1H-benzo[d]imidazol-4-yl)methyl)-6-chloro-2-methyl-1H-imidazo[4,5-c]pyridine and 1-((1H-benzo[d]imidazol-5-yl)methyl)-6-chloro-2-methyl-1H-imidazo[4,5-c]pyridine (0.14 g, 40%) as a tan solid. LCMS (ESI): $R_T$ (min)=0.77, 0.82, [M+H]$^+$=298.3, method=I.

Step 4: 1-((1H-Benzo[d]imidazol-4-yl)methyl)-N-(2-(4-methoxypiperidin-1-yl)pyrimidin-4-yl)-2-methyl-1H-imidazo[4,5-c]pyridin-6-amine

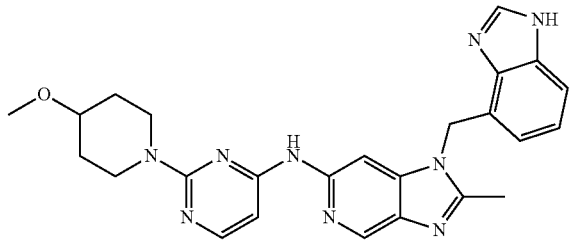 [SMILES: COC1CCN(c2nccc(Nc3cc4c(cn3)nc(C)n4Cc3cccc4[nH]cnc34)n2)CC1]

And 1-((1H-Benzo[d]imidazol-5-yl)methyl)-N-(2-(4-methoxypiperidin-1-yl)pyrimidin-4-yl)-2-methyl-1H-imidazo[4,5-c]pyridin-6-amine

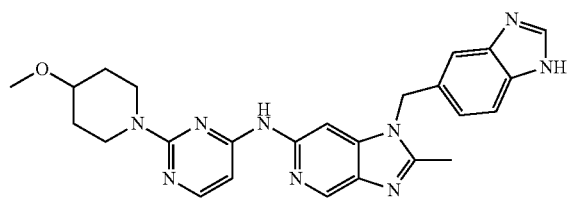 [SMILES: COC1CCN(c2nccc(Nc3cc4c(cn3)nc(C)n4Cc3ccc4[nH]cnc4c3)n2)CC1]

To a reaction vessel was added a mixture of 1-((1H-benzo[d]imidazol-4-yl)methyl)-6-chloro-2-methyl-1H-imidazo[4,5-c]pyridine and 1-((1H-benzo[d]imidazol-5-yl)methyl)-6-chloro-2-methyl-1H-imidazo[4,5-c]pyridine (70 mg, 0.235 mmol), 2-(4-methoxy-1-piperidyl)pyrimidin-4-amine (Example 3, step 2) (54 mg, 0.259 mmol), chloro{[BrettPhos][2-(2-aminoethylphenyl]palladium(II)]}/[BrettPhos] admixture (molar PdP/P=1:1) (50 mg, 0.062 mmol), sodium tert-butoxide (68 mg, 0.705 mmol) and tert-butanol (5 mL). The reaction vessel was purged with nitrogen and heated to 125° C. for 1.5 h. The reaction was cooled to room temperature, filtered through a pad of celite, concentrated and the two products purified by reverse phase HPLC to afford the title compounds: 1-((1H-Benzo[d]imidazol-5-yl)methyl)-N-(2-(4-methoxypiperidin-1-yl)pyrimidin-4-yl)-2-methyl-1H-imidazo[4,5-c]pyridin-6-amine (2.4 mg, 2.1%). LCMS (ESI): $R_T$ 2.83 min, [M+H]$^+$ 470.3, Method=E. 1-((1H-benzo[d]imidazol-4-yl)methyl)-N-(2-(4-methoxypiperidin-1-yl)pyrimidin-4-yl)-2-methyl-1H-imidazo[4,5-c]pyridin-6-amine (7.5 mg, 6.8%). LCMS (ESI): $R_T$ 2.82 min, [M+H]$^+$ 470.3, Method=E; $^1$H NMR (400 MHz, DMSO-d$_6$) δ 9.96 (s, 1H), 8.60 (s, 1H), 8.25 (d, J=9.1 Hz, 2H), 7.91 (d, J=5.8 Hz, 1H), 7.20 (s, 1H), 7.03 (dd, J=8.2, 1.7 Hz, 1H), 6.55-6.44 (m, 1H), 6.39 (d, J=5.9 Hz, 1H), 5.54 (s, 2H), 4.02-3.90 (m, 2H), 3.10 (s, 3H), 1.53 (s, 2H), 1.14 (d, J=8.7 Hz, 2H).

Example 360: 1-Isopropyl-2-methyl-N-(2-(3-methylisothiazol-5-yl)pyrimidin-4-yl)-1H-imidazo[4,5-c]pyridin-6-amine

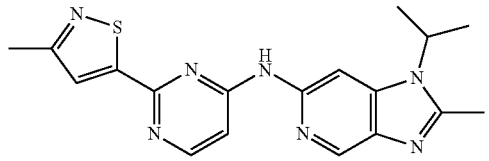

A reaction vial containing tributyl-(3-methylisothiazol-5-yl)stannane (153 mg, 0.393 mmol), N-(2-chloropyrimidin-4-yl)-1-isopropyl-2-methyl-1H-imidazo[4,5-c]pyridin-6-amine (Example 46, Step 7) (79.4 mg, 0.262 mmol), bis(di-tert-butyl(4-dimethylaminophenyl)phosphine) dichloropalladium(II) (22.3 mg, 0.0315 mmol), and N,N-dimethylacetamide (1.5 mL, 16 mmol) was subjected to microwave irradiation at 130° C. for 30 minutes followed by an additional 45 minutes at 130° C. The reaction mixture was filtered through celite and concentrated in vacuo. The crude material was purified by flash chromatography on silica gel (solvent gradient: 0-7% methanol in dichloromethane) followed by reverse-phase HPLC and lyophilized to give the title compound (13.8 mg, 14%) as a white solid. LCMS (ESI): $R_T$ 4.56 min, [M+H]$^+$ 366.2, method=B; $^1$H NMR (400 MHz, DMSO-d$_6$) δ 10.29 (s, 1H), 8.58 (d, J=1.1 Hz, 1H), 8.42 (d, J=6.0 Hz, 1H), 8.37 (s, 1H), 7.78 (s, 1H), 7.30 (s, 1H), 4.79 (p, J=6.9 Hz, 1H), 2.59 (s, 3H), 2.51 (s, 3H), 1.66 (d, J=6.9 Hz, 6H).

Example 361: (5-(4-((1-Isopropyl-2-methyl-1H-imidazo[4,5-c]pyridin-6-yl)amino)pyrimidin-2-yl)thiazol-2-yl)methanol

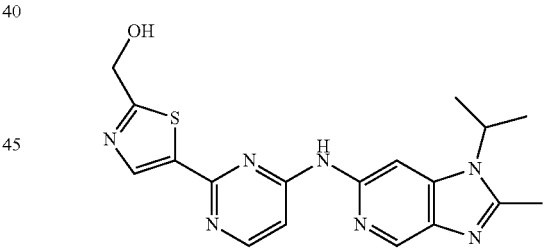

To a microwave vial was added N-(2-chloropyrimidin-4-yl)-1-isopropyl-2-methyl-1H-imidazo[4,5-c]pyridin-6-amine (Example 46, Step 7)(50 mg, 0.165 mmol), thiazol-2-ylmethanol (57 mg, 0.495 mmol), and palladium (II) acetate (2 mg, 0.008 mmol). The mixture was degassed by nitrogen bubbling for 20 min. Potassium phosphate tribasic (71 mg, 0.330 mmol), butyldi-1-adamantylphosphine (6 mg, 0.0165 mmol) and 1-methyl-2-pyrrolidinone (0.7 mL) were added and the reaction vessel was sealed and stirred for 15 min at room temperature followed by 125° C. for 24 h. The reaction was then cooled to room temperature, diluted with water and extracted with dichloromethane (3×). The combined organic layers were washed with brine, dried over anhydrous sodium sulfate, filtered, and concentrated in vacuo. The crude product was purified by reverse-phase HPLC and lyophilized to give the title compound (13.6 mg, 22%). LCMS (ESI): $R_T$ 4.13 min, [M+H]$^+$ 382.2, method=B; ¹H NMR (400 MHz, DMSO-d₆) δ 10.17 (s, 1H), 8.54 (d, J=1.3 Hz, 1H), 8.28 (s, 1H), 8.18 (d, J=5.8 Hz, 1H), 7.83 (d, J=3.3 Hz, 1H), 7.75 (d, J=3.2 Hz, 1H), 7.09 (s, 1H), 5.71 (s, 2H), 4.72 (p, J=6.9 Hz, 1H), 2.57 (s, 3H), 1.55 (d, J=6.9 Hz, 6H).

Example 362: N-(2-(3,5-Dimethyl-1H-pyrazol-4-yl)pyrimidin-4-yl)-1-isopropyl-2-methyl-1H-imidazo[4,5-c]pyridin-6-amine

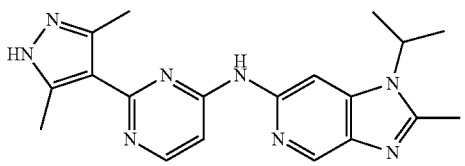 [SMILES: Cc1n[nH]c(C)c1-c1nccc(Nc2cc3c(cn2)nc(C)n3C(C)C)n1]

To a microwave vial was added N-(2-chloropyrimidin-4-yl)-1-isopropyl-2-methyl-1H-imidazo[4,5-c]pyridin-6-amine (Example 46, Step 7) (70 mg, 0.231 mmol), 3,5-dimethylpyrazole-4-boronic acid, pinacol ester (106 mg, 0.462 mmol), [1,1'-bis(diphenylphosphino)ferrocene]palladium(II) chloride, complex with dichloromethane (1:1) (38 mg, 0.046 mmol), sodium carbonate (2.0 mol/L in water) (491 μL, 0.983 mmol), and 1,4-dioxane (3 mL). The vial was sealed and subjected to microwave irradiation at 130° C. for 40 minutes. The reaction mixture was cooled to room temperature, diluted with ethyl acetate, washed with water (2×) and brine, dried over anhydrous sodium sulfate, filtered, and concentrated in vacuo. The crude product was purified by reverse-phase HPLC and lyophilized to give the title compound (16.1 mg, 19%) as a light pink solid. LCMS (ESI): R_T 3.45 min, [M+H]⁺ 363.2, method=B; ¹H NMR (400 MHz, DMSO-d₆) δ 10.17 (s, 1H), 8.54 (d, J=1.3 Hz, 1H), 8.28 (s, 1H), 8.18 (d, J=5.8 Hz, 1H), 7.83 (d, J=3.3 Hz, 1H), 7.75 (d, J=3.2 Hz, 1H), 7.09 (s, 1H), 5.71 (s, 3H), 4.72 (p, J=6.9 Hz, 1H), 3.27 (s, 3H), 2.57 (s, 3H), 1.55 (d, J=6.9 Hz, 6H).

Example 363: N-(2-(3-Amino-1-methyl-1H-pyrazol-4-yl)pyrimidin-4-yl)-1-isopropyl-2-methyl-1H-imidazo[4,5-c]pyridin-6-amine

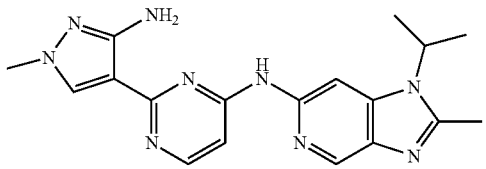

Step 1: (1-Methyl-3-nitro-1H-pyrazol-4-yl)boronic acid

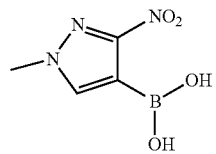

To a reaction vessel was added 4-bromo-1-methyl-3-nitro-pyrazole (500 mg, 2.427 mmol), potassium acetate (1254 mg, 12.136 mmol), bis(pinacolato)diboron (1300 mg, 4.854 mmol), 1,1'-bis(diphenylphosphino)ferrocene-palladium(II)dichloride, dichloromethane complex (104 mg, 0.121 mmol) and 2-methyltetrahydrofuran (12 mL) and the reaction was heated to 90° C. After 7 h, the reaction was cooled to room temperature, filtered through celite, and concentrated in vacuo. The crude material was purified by flash chromatography on silica gel (solvent gradient: 0-100% EtOAc in heptanes) to provide the title compound (83.7 mg, 20%) as an off-white solid. LCMS (ESI) [M+H]⁺=172.0; ¹H NMR (400 MHz, DMSO-d₆) δ 8.19 (s, 2H), 7.86 (s, 1H), 3.93 (s, 3H).

Step 2: 1-Isopropyl-2-methyl-N-(2-(1-methyl-3-nitro-1H-pyrazol-4-yl)pyrimidin-4-yl)-1H-imidazo[4,5-c]pyridin-6-amine

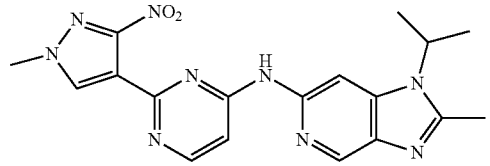

1-Isopropyl-2-methyl-N-(2-(1-methyl-3-nitro-1H-pyrazol-4-yl)pyrimidin-4-yl)-1H-imidazo[4,5-c]pyridin-6-amine was prepared in a method analogous to Example 51, Step 7. LCMS (ESI) [M+H]⁺=394.2.

Step 3: N-(2-(3-Amino-1-methyl-1H-pyrazol-4-yl)pyrimidin-4-yl)-1-isopropyl-2-methyl-1H-imidazo[4,5-c]pyridin-6-amine

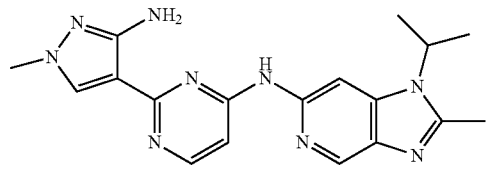

A mixture of iron powder (13.4 mg, 0.240 mmol), ammonium chloride (18.6 mg, 0.347 mmol), and 1-isopropyl-2-methyl-N-(2-(1-methyl-3-nitro-1H-pyrazol-4-yl)pyrimidin-4-yl)-1H-imidazo[4,5-c]pyridin-6-amine (23.5 mg, 0.060 mmol) in water (300 μL) and ethanol (900 μL) was heated at 80° C. for 2 h. The reaction mixture was cooled to room temperature, filtered, concentrated in vacuo and purified by reverse-phase HPLC and lyophilized to give the title compound (5.1 mg, 23%). LCMS (ESI): R_T 3.27 min, [M+H]⁺ 364.2, method=B; ¹H NMR (400 MHz, DMSO-d₆) δ 9.85 (s, 1H), 8.55 (d, J=0.9 Hz, 1H), 8.26 (d, J=5.8 Hz, 1H), 7.91 (d, J=5.5 Hz, 2H), 7.24 (s, 1H), 5.78 (s, 2H), 4.74 (p, J=6.9 Hz, 1H), 3.66 (s, 3H), 2.58 (s, 3H), 1.60 (d, J=6.9 Hz, 6H).

Example 364: N-(2-(3-(1H-Pyrazol-5-yl)piperdine-1-yl)pyrimidin-4-yl)-1-isopropyl-2-methyl-1H-imidazo[4,5-c]pyridin-6-amine

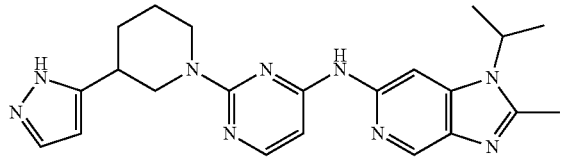 [SMILES: Cc1nc2cnc(Nc3ccnc(N4CCCC(c5ccn[nH]5)C4)n3)cc2n1C(C)C]

To a glass reaction vessel was added 3-(1H-pyrazol-5-yl)piperidine (103.5 mg, 0.68 mmol), N-(2-chloropyrimidin-4-yl)-1-isopropyl-2-methyl-1H-imidazo[4,5-c]pyridin-6-amine (Example 46, Step 7) (207.3 mg, 0.68 mmol), potassium carbonate (191.1 mg, 1.37 mmol) and 1-methyl-2-pyrrolidinone (5.0 mL). The reaction vessel was sealed and stirred at 80° C. overnight. The reaction mixture was cooled to room temperature, diluted with water, extracted with dichloromethane, and the organic layer was dried over magnesium sulfate, filtered and concentrated in vacuo. The crude product was purified by reverse-phase HPLC and lyophilized to give the title compound (67.2 mg, 23.5%). LCMS (ESI): $R_T$ 4.07 min, [M+H]$^+$ 418.3, method=B; $^1$H NMR (400 MHz, DMSO-$d_6$) δ 12.51 (s, 1H), 9.65 (s, 1H), 8.49 (d, J=0.9 Hz, 1H), 8.29 (s, 1H), 7.96 (d, J=5.6 Hz, 1H), 6.46 (d, J=5.8 Hz, 1H), 6.13 (s, 1H), 4.83-4.69 (m, 2H), 4.67-4.59 (m, 1H), 3.27 (s, 2H), 3.03 (t, J=12.9 Hz, 2H), 2.54 (s, 3H), 2.11-2.00 (m, 1H), 1.72 (dt, J=20.8, 11.9 Hz, 2H), 1.44 (dd, J=14.4, 6.9 Hz, 6H).

Example 365: 1-Isopropyl-2-methyl-N-(2-(1-methyl-1H-pyrazol-4-yl)pyrimidin-4-yl)-1H-imidazo[4,5-c]pyridin-6-amine

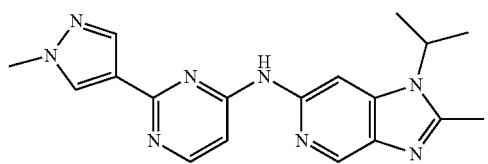

To a microwave reaction vial was added 1-methyl-4-(4,4,5,5-tetramethyl-1,3,2-dioxaborolan-2-yl)pyrazole (82.5 mg, 0.396 mmol), N-(2-chloropyrimidin-4-yl)-1-isopropyl-2-methyl-1H-imidazo[4,5-c]pyridin-6-amine (Example 46, Step 7) (100.0 mg, 0.33 mmol), tetrakis(triphenylphosphine)palladium(0) (38.2 mg, 0.033 mmol, 1M potassium acetate in water (1.0 mL) and acetonitrile (1.0 mL). The reaction vial was sealed and heated at 130° C. under microwave irradiation for 20 min. The reaction mixture was cooled to room temperature, diluted with water and extracted with ethyl acetate. The organic layer was washed with brine, dried over magnesium sulfate, filtered and concentrated in vacuo. The crude product was purified by reverse-phase HPLC and lyophilized to give the title compound (35.7 mg, 31%). LCMS (ESI): $R_T$ 3.76 min, [M+H]$^+$ 349.2, method=B; $^1$H NMR (400 MHz, DMSO-$d_6$) δ 10.00 (s, 1H), 8.55 (d, J=0.9 Hz, 1H), 8.41 (s, 1H), 8.30 (d, J=5.8 Hz, 1H), 8.25 (s, 1H), 8.02 (d, J=0.7 Hz, 1H), 7.14 (s, 1H), 4.76 (p, J=6.9 Hz, 1H), 3.92 (s, 3H), 2.58 (s, 3H), 1.63 (d, J=6.9 Hz, 6H).

Example 366: 1-Isopropyl-N-(2-isoxazol-4-yl)pyrimidin-4-yl)-2-methyl-1H-imidazo[4,5-c]pyridin-6-amine

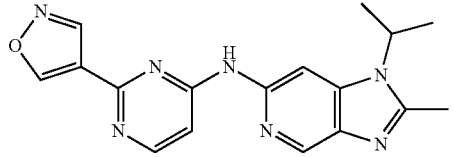 [SMILES: Cc1nc2cnc(Nc3ccnc(-c4cnoc4)n3)cc2n1C(C)C]

To a microwave vial was added 4-(4,4,5,5-tetramethyl-1,3,2-dioxaborolan-2-yl)isoxazole (51.2 mg, 0.26 mmol), N-(2-chloropyrimidin-4-yl)-1-isopropyl-2-methyl-1H-imidazo[4,5-c]pyridin-6-amine (Example 46, Step 7) (53.0 mg, 0.175 mmol), bis(di-tert-butyl(4-dimethylaminophenyl)phosphine)dichloropalladium(II) (13.05 mg, 0.0175 mmol), 1M sodium carbonate in water (0.35 mL) and acetonitrile (2.0 mL). The reaction vial was purged with nitrogen for 5 minutes, sealed and heated at 100° C. for 24 hours. The reaction mixture was cooled to room temperature, diluted with water, extracted with ethyl acetate, and the organic wash was dried over magnesium sulfate, filtered and concentrated in vacuo. The crude material was purified by flash chromatography on silica gel (solvent gradient: 0-50% methanol in dichloromethane) followed by reverse-phase HPLC and lyophilized to give the title compound (8.3 mg, 14%). LCMS (ESI): $R_T$ 3.99 min, [M+H]$^+$ 336.2, method=B; $^1$H NMR (400 MHz, DMSO-$d_6$) δ 11.02 (s, 1H), 9.11 (s, 1H), 8.79 (s, 1H), 8.60 (d, J=0.8 Hz, 1H), 8.03 (s, 1H), 6.70 (s, 1H), 4.89 (s, 1H), 2.61 (s, 3H), 1.55 (d, J=6.9 Hz, 6H).

Example 367: N-(2-(2H-1,2,3-triazol-2-yl)pyrimidin-4-yl)-1-isopropyl-2-methyl-1H-imidazo[4,5-c]pyridine-6-amine

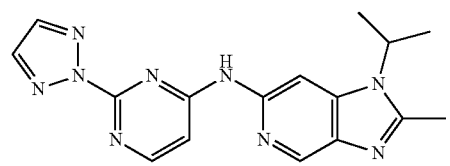 [SMILES: Cc1nc2cnc(Nc3ccnc(-n4nccn4)n3)cc2n1C(C)C]

To a reaction vessel was added 1H-1,2,3-triazole (45.61 mg, 0.66 mmol), N-(2-chloropyrimidin-4-yl)-1-isopropyl-2-methyl-1H-imidazo[4,5-c]pyridin-6-amine (Example 46, Step 7) (200 mg, 0.66 mmol), potassium carbonate (91.29 mg, 0.66 mmol) and 1-methyl-2-pyrrolidinone (5.0 mL). The reaction vessel was sealed and heated at 80° C. for 72 h. The reaction mixture was cooled to room temperature, diluted with water, extracted with dichloromethane and concentrated in vacuo. The crude material was purified by flash chromatography on silica gel (solvent gradient: 0-10% methanol in dichloromethane) followed by reverse-phase HPLC and lyophilized to give the title compound (46.3 mg, 14%). LCMS (ESI): $R_T$ 4.07 min, [M+H]$^+$ 336.2, method=B; $^1$H NMR (400 MHz, DMSO-$d_6$) δ 10.59 (s, 1H), 9.10 (s, 1H), 8.56 (d, J=0.9 Hz, 1H), 8.43 (d, J=5.9 Hz, 1H), 8.20 (s, 1H), 7.22 (s, 1H), 4.77 (p, J=6.8 Hz, 1H), 2.58 (s, 3H), 1.69 (d, J=6.9 Hz, 6H).

Example 368: 1-Isopropyl-2-methyl-N-(2-(3-methyl-1H-1,2,4-triazol-5-yl)pyrimidin-4-yl)-1H-imidazo[4,5-c]pyridine-6-amine

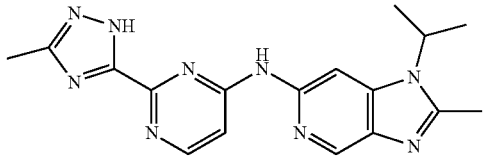

Step 1: 4-((1-Isopropyl-2-methyl-1H-imidazo[4,5-c]pyridine-6-yl)amino)pyrimidine-2-carbonitrile

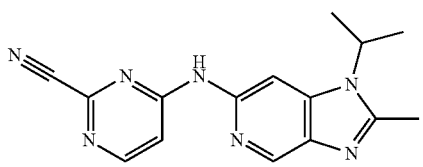 [SMILES: Cc1nc2cnc(Nc3ccnc(C#N)n3)cc2n1C(C)C]

To a reaction vessel was added N-(2-chloropyrimidin-4-yl)-1-isopropyl-2-methyl-1H-imidazo[4,5-c]pyridin-6-amine (Example 46, Step 7) (689 mg, 2.275 mmol), potassium cyanide (183 mg, 2.73 mmol), 1,4-diazabicyclo[2.2.2]octane (26.9 mg, 0.23 mmol), dimethylsulfoxide (5.8 g, 74 mmol) and water (0.45 mL, 24.75 mmol). The reaction vessel was sealed and heated at 60° C. for 1 h. The reaction mixture was cooled to room temperature, diluted with water and extracted with ethyl acetate. The organic layer was washed with brine, dried over magnesium sulfate, filtered and concentrated in vacuo. The crude material was purified by flash chromatography on silica gel (solvent gradient: 0-50% methanol in dichloromethane) and concentrated in vacuo to give the title compound (667.4 mg, 100%).

Step 2: 4-((1-Isopropyl-2-methyl-1H-imidazo[4,5-c]pyridine-6-yl)amino)pyrimidine-2-carboxamide

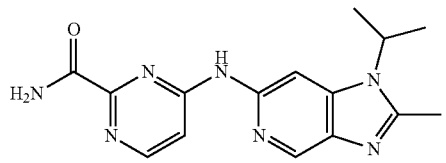 [SMILES: Cc1nc2cnc(Nc3ccnc(C(N)=O)n3)cc2n1C(C)C]

To 4-((1-isopropyl-2-methyl-1H-imidazo[4,5-c]pyridine-6-yl)amino)pyrimidine-2-carbonitrile (667.4 mg, 2.275 mmol) in dimethyl sulfoxide (2.26 mL, 31.86 mmol) and water (2.0 mL) was added potassium carbonate (635.3 mg, 4.55 mmol) and hydrogen peroxide (50% aqueous)(0.66 mL, 11.38 mmol). The reaction was stirred for 3 h at room temperature and concentrated in vacuo. The crude material was purified by flash chromatography on silica gel (solvent gradient: 0-50% methanol in dichloromethane) and concentrated in vacuo to give the title compound (908.2 mg, 100%).

Step 3: (E)-N-(1-(dimethylamino)ethylidene)-4-((1-isopropyl-2-methyl-1H-imidazo[4,5-c]pyridin-6-yl)amino)pyrimidine-2-carboxamide

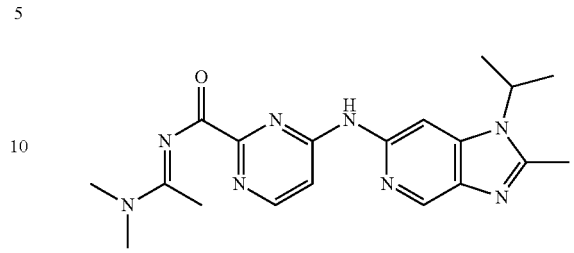

To 4-((1-isopropyl-2-methyl-1H-imidazo[4,5-c]pyridine-6-yl)amino)pyrimidine-2-carboxamide (225 mg, 0.564 mmol) in toluene (30 mL) was added N,N-dimethylacetamide dimethyl acetal (0.35 mL, 2.2 mmol). The reaction flask was affixed with a reflux condenser and the reaction was heated at 95° C. for 20 h. The crude material was concentrated in vacuo to give the title compound (214 mg, quantitative yield).

Step 4: 1-Isopropyl-2-methyl-N-(2-(3-methyl-1H-1,2,4-triazol-5-yl)pyrimidin-4-yl)-1H-imidazo[4,5-c]pyridine-6-amine

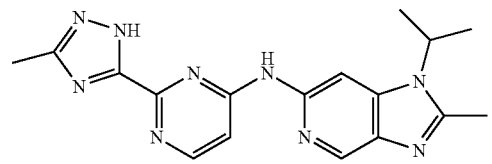

(E)-N-(1-(dimethylamino)ethylidene)-4-((1-isopropyl-2-methyl-1H-imidazo[4,5-c]pyridin-6-yl)amino)pyrimidine-2-carboxamide (107 mg, 0.28 mmol) was brought up in acetic acid (3.0 mL) and cooled to 0° C. Hydrazine (10.12 mg, 0.31 mmol) was added and the reaction was slowly heated to 95° C. and maintained at this temperature for 5 h. The crude material was purified by flash chromatography on silica gel (solvent gradient: 0-20% methanol in dichloromethane) followed by reverse-phase HPLC and lyophilized to give the title compound (7.2 mg, 7%). LCMS (ESI): $R_T$ 3.78 min, [M+H]$^+$ 350.2, method=B; $^1$H NMR (400 MHz, DMSO-d6) δ 10.27 (s, 1H), 9.13 (s, 1H), 8.53 (s, 1H), 8.47-8.39 (m, 1H), 7.20 (s, 1H), 4.76 (p, J=7.0 Hz, 1H), 2.57 (s, 3H), 2.42 (s, 3H), 1.70 (d, J=6.9 Hz, 6H).

Each compound in Table 4. below was prepared following a similar experimental procedure (using appropriately substituted reagents) as described in another Example herein, such Example being referenced in the Synthesis Method column (e.g., a compound in Table 4 that is prepared following a similar experimental procedure as described in Example 12 will have "12" noted in the Synthesis Method column)

TABLE 4

| Example | Structure/Name | Synthesis Method/ Example # | LCMS $R_T$ (min), [M + H]$^+$, method | $^1$H NMR (ppm) |
|---|---|---|---|---|
| 369 | 1-(sec-butyl)-N-ethyl-6-((2-((3S,4R)-3-fluoro-4-hydroxypiperidin-1-yl)pyrimidin-4-yl)amino)-1H-pyrrolo[3,2-c]pyridine-3-carboxamide (diastereoisomer 1) | 323 | 3.22, 456.2, B | $^1$H NMR (400 MHz, DMSO-d$_6$) δ 9.78 (s, 1H), 9.02 (s, 1H), 8.33 (s, 1H), 8.10 (s, 1H), 7.95 (m, 2H), 6.35 (m, 1H), 5.10 (d, J = 5.0 Hz, 1H), 4.67 (d, J = 49.1 Hz, 1H), 4.58-4.45 (m, 1H), 4.44-4.20 (m, 2H), 3.86 (m, 1H), 3.60 (m, 1H), 3.48-3.33 (m, 1H), 1.95-1.82 (m, 2H), 1.70 (d, J = 4.9 Hz, 2H), 1.49 (d, J = 6.7 Hz, 3H), 1.15 (t, J = 7.2 Hz, 3H), 0.78 (t, J = 7.3 Hz, 3H). |
| 370 | 1-(sec-butyl)-N-ethyl-6-((2-((3S,4R)-3-fluoro-4-hydroxypiperidin-1-yl)pyrimidin-4-yl)amino)-1H-pyrrolo[3,2-c]pyridine-3-carboxamide (diastereoisomer 2) | 323 | 3.26, 456.2, B | $^1$H NMR (400 MHz, DMSO-d$_6$) δ 9.77 (s, 1H), 9.02 (d, J = 0.7 Hz, 1H), 8.32 (s, 1H), 8.10 (s, 1H), 7.96 m, 2H), 6.36 (m, 1H), 5.10 (d, J = 5.1 Hz, 1H), 4.67 (d, J = 49.1 Hz, 1H), 4.55-4.44 (m, 1H), 4.37 (m, 1H), 4.24 (s, 1H), 3.86 (m, 1H), 3.60 (m, 1H), 3.39 (s, 1H), 1.96-1.83 (m, 2H), 1.70 (d, J = 5.2 Hz, 2H), 1.48 (d, J = 6.7 Hz, 3H), 1.15 (t, J = 7.2 Hz, 3H), 0.79 (t, J = 7.3 Hz, 3H). |
| 371 | (±)-1-(sec-butyl)-6-((2-(1-(cyclopropylsulfonyl)-1H-pyrazol-4-yl)pyrimidin-4-yl)amino-N-(1-(oxetan-3-yl)piperidin-4-yl)-1H-pyrrolo[3,2-c]pyridine-3-carboxamide | 321 | 3.65, 620, B | $^1$H NMR (400 MHz, DMSO-d$_6$) δ 10.28 (s, 1H), 9.07 (d, J = 0.8 Hz, 1H), 8.74-8.65 (m, 1H), 8.54-8.43 (m, 2H), 8.38 (d, J = 5.9 Hz, 1H), 8.22 (s, 1H), 7.88 (d, J = 7.6 Hz, 1H), 7.12 (s, 1H), 4.54 (t, J = 6.5 Hz, 3H), 4.44 (t, J = 6.1 Hz, 2H), 3.86-3.70 (m, 1H), 3.48-3.36 (m, 1H), 3.3 (m, 1H), 2.80-2.69 (m, 2H), 2.01-1.81 (m, 6H), 1.55 (d, J = 6.7 Hz, 5H), 1.39-1.22 (m, 4H), 0.80 (t, J = 7.3 Hz, 3H). |

TABLE 4-continued

| Example | Structure/Name | Synthesis Method/ Example # | LCMS $R_T$ (min), [M + H]+, method | $^1$H NMR (ppm) |
|---|---|---|---|---|
| 372 | 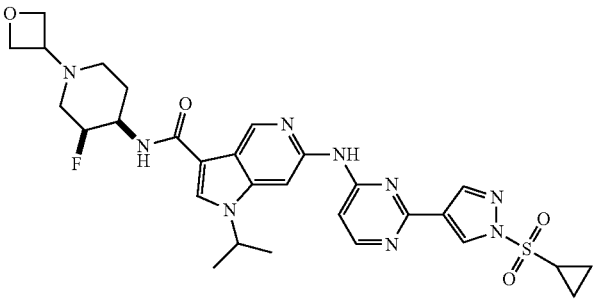<br>(±)-6-((2-(1-(cyclopropylsulfonyl)-1H-pyrazol-4-yl)pyrimidin-4-yl)amino)-N-((cis)-3-fluoro-1-(oxetan-3-yl)piperidin-4-yl)-1-isopropyl-1H-pyrrolo[3,2-c]pyridine-3-carboxamide | 321 | 3.58, 624.3, B | $^1$H NMR (400 MHz, DMSO-$d_6$) δ 10.8 (s, 1H), 9.08 (s, 1H), 8.87 (s, 1H), 8.71 (s, 1H), 8.48 (s, 1H), 8.44 (s, 1H), 8.39 (s, 1H), 8.38 (d, 1H), 8.06 (d, 1H), 7.11 (s, 1H), 4.82 (m, 2H), 4.56 (m, 2H), 4.55 (m, 1H), 4.42 (m, 1H), 4.40 (m, 2H), 3.51 (m, 1H), 3.01 (m, 1H), 2.80 (m, 1H), 1.93-2.1 (m, 2H), 1.57 (m, 1H), 1.57 (m, 1H), 1.57 (m, 4H), 1.26-1.36 (m, 4H). |
| 373 | 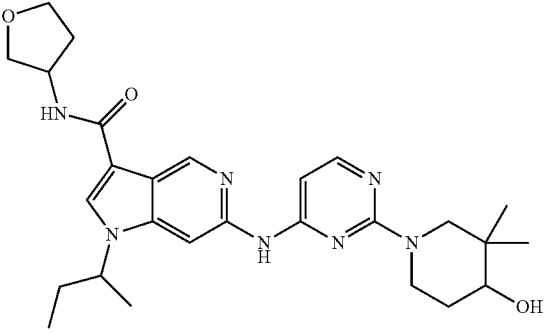 [SMILES: CCC(C)n1cc(C(=O)NC2CCOC2)c2cnc(Nc3ccnc(N4CCC(O)C(C)(C)C4)n3)cc21]<br>1-(sec-butyl)-6-((2-(4-hydroxy-3,3-dimethylpiperidin-1-yl)pyrimidin-4-yl)amino)-N-(tetrahydrofuran-3-yl)-1H-pyrrolo[3,2-c]pyridine-3-carboxamide<br>(mixture of diastereoisomers) | 323 | 3.36, 508.3, B | n/a |
| 374 | 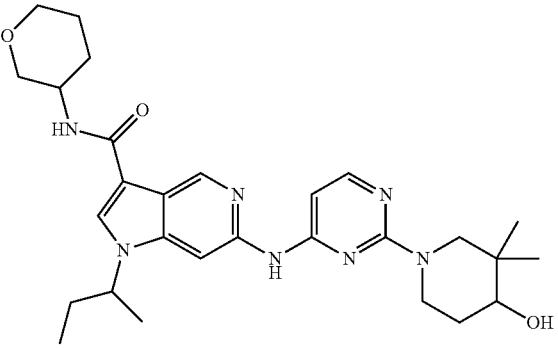 [SMILES: CCC(C)n1cc(C(=O)NC2CCCOC2)c2cnc(Nc3ccnc(N4CCC(O)C(C)(C)C4)n3)cc21]<br>1-(sec-butyl)-6-((2-(4-hydroxy-3,3-dimethylpiperidin-1-yl)pyrimidin-4-yl)amino)-N-(tetrahydro-2H-pyran-3-yl)-1H-pyrrolo[3,2-c]pyridine-3-carboxamide<br>(mixture of diastereoisomer) | 323 | 7.08, 522.4, B | n/a |

TABLE 4-continued

| Example | Structure/Name | Synthesis Method/ Example # | LCMS R$_T$ (min), [M + H]$^+$, method | $^1$H NMR (ppm) |
|---|---|---|---|---|
| 375 | 1-(sec-butyl)-6-((2-((3S,4R)-3-fluoro-4-methoxypiperidin-1-yl)pyrimidin-4-yl)amino)-N-(tetrahydro-2H-pyran-4-yl)-1H-pyrrolo[3,2-c]pyridine-3-carboxamide (diastereoisomer 1) | 339 | 8.21, 526.3, A | $^1$H NMR (400 MHz, DMSO-d$_6$) δ 9.82 (s, 1H), 9.02 (d, J = 0.8 Hz, 1H), 8.31 (s, 1H), 8.17 (s, 1H), 7.95 (d, J = 5.7 Hz, 1H), 7.88 (d, J = 7.6 Hz, 1H), 6.37 (d, J = 5.7 Hz, 1H), 4.93 (d, J = 46.5 Hz, 1H), 4.64 (s, 1H), 4.38 (m, 2H), 4.11-3.94 (m, 1H), 3.90 (d, J = 9.5 Hz, 2H), 3.59 (m, 2H), 1.85 (m, 6H), 1.52 (m, 5H), 0.79 (t, J = 7.3 Hz, 3H). |
| 376 | 1-(sec-butyl)-6-((2-((3S,4R)-3-fluoro-4-methoxypiperidin-1-yl)pyrimidin-4-yl)amino)-N-(tetrahydro-2H-pyran-4-yl)-1H-pyrrolo[3,2-c]pyridine-3-carboxamide (diastereoisomer 2) | 339 | 8.16, 526.3, A | $^1$H NMR (400 MHz, DMSO-d$_6$) δ 9.82 (s, 1H), 9.02 (d, J = 0.6 Hz, 1H), 8.32 (s, 1H), 8.17 (s, 1H), 7.95 (d, J = 5.7 Hz, 1H), 7.88 (d, J = 7.6 Hz, 1H), 6.37 (d, J = 5.6 Hz, 1H), 4.93 (d, J = 49.4 Hz, 1H), 4.64 (s, 1H), 4.38 (m, 2H), 4.12-3.95 (m, 1H), 3.90 (d, J = 9.7 Hz, 2H), 3.55 (m, 2H), 1.84 (m, 6H), 1.65-1.40 (m, 5H), 0.78 (t, J = 7.3 Hz, 3H). |
| 377 | 6-((2-(1-(N,N-dimethylsulfamoyl)-1H-pyrazol-4-yl)pyrimidin-4-yl)amino)-N-ethyl-1-isopropyl-1H-pyrrolo[3,2-c]pyridine-3-carboxamide | 321 | 4.79, 498.3, A | $^1$H NMR (400 MHz, DMSO-d$_6$) δ 10.24 (s, 1H), 9.08 (d, J = 0.9 Hz, 1H), 8.64 (d, J = 0.5 Hz, 1H), 8.49 (s, 1H), 8.42 (d, J = 0.4 Hz, 1H), 8.37 (d, J = 5.9 Hz, 1H), 8.19 (s, 1H), 8.01 (t, J = 5.5 Hz, 1H), 7.11 (s, 1H), 4.80 (m, 1H), 2.93 (s, 6H), 1.57 (d, J = 6.7 Hz, 6H), 1.15 (t, J = 7.2 Hz, 3H). |

TABLE 4-continued

| Example | Structure/Name | Synthesis Method/ Example # | LCMS R$_T$ (min), [M + H]$^+$, method | $^1$H NMR (ppm) |
|---|---|---|---|---|
| 378 | 6-((2-(1-(N,N-dimethylsulfamoyl)-1H-pyrazol-4-yl)pyrimidin-4-yl)amino)-1-isopropyl-N-(oxetan-3-yl)-1H-pyrrolo[3,2-c]pyridine-3-carboxamide | 321 | 4.22, 526.3, A | $^1$H NMR (400 MHz, DMSO-d$_6$) δ 10.30 (s, 1H), 9.00 (d, J = 0.9 Hz, 1H), 8.64 (d, J = 0.5 Hz, 1H), 8.54 (s, 1H), 8.42 (d, J = 0.5 Hz, 1H), 8.37 (d, J = 5.9 Hz, 1H), 7.99 (s, 1H), 7.11 (s, 1H), 4.81 (m, 2H), 4.38 (m, 1H), 4.36-4.25 (m, 1H), 4.25-4.15 (m, 1H), 3.70-3.56 (m, 1H), 3.55-3.39 (m, 1H), 2.93 (s, 6H), 1.57 (m, 6H). |
| 379 | 6-((2-(1-(cyclopropylsulfonyl)-1H-pyrazol-4-yl)pyrimidin-4-yl)amino)-1-isopropyl-N-(oxetan-3-yl)-1H-pyrrolo[3,2-c]pyridine-3-carboxamide | 321 | 4.75, 554.3, A | $^1$H NMR (400 MHz, DMSO-d$_6$) δ 10.24 (s, 1H), 9.07 (d, J = 0.9 Hz, 1H), 8.64 (s, 1H), 8.49 (s, 1H), 8.42 (d, J = 0.4 Hz, 1H), 8.37 (d, J = 5.9 Hz, 1H), 8.24 (s, 1H), 7.88 (d, J = 7.6 Hz, 1H), 7.12 (s, 1H), 4.80 (m, 1H), 4.10-3.95 (m, 1H), 3.91 (m, 2H), 3.41 (m, 2H), 1.86-1.76 (m, 2H), 1.64-1.47 (m, 8H). |
| 380 | 6-((2-((3S,4R)-3-fluoro-4-methoxypiperidin-1-yl)pyrimidin-4-yl)amino)-1-isopropyl-N-(tetrahydro-2H-pyran-4-yl)-1H-pyrrolo[3,2-c]pyridine-3-carboxamide | 323 | 7.94, 512.3, A | $^1$H NMR (400 MHz, DMSO-d$_6$) δ 9.78 (s, 1H), 9.02 (s, 1H), 8.31 (s, 1H), 8.19 (s, 1H), 7.95 (d, J = 5.7 Hz, 1H), 7.85 (d, J = 7.6 Hz, 1H), 6.38 (d, J = 5.6 Hz, 1H), 4.93 (d, J = 49.3 Hz, 1H), 4.62 (m, 2H), 4.38 (m, 1H), 4.01 (m, 1H), 3.90 (m, 2H), 3.64-3.35 (m, 7H), 1.81 (d, J = 13.1 Hz, 4H), 1.63-1.45 (m, 8H). |

TABLE 4-continued

| Example | Structure/Name | Synthesis Method/ Example # | LCMS $R_T$ (min), [M + H]+, method | ¹H NMR (ppm) |
|---|---|---|---|---|
| 381 | 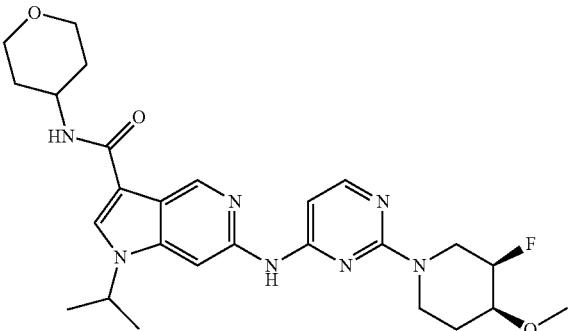<br>6-((2-((3R,4S)-3-fluoro-4-methoxypiperidin-1-yl)pyrimidin-4-yl)amino)-1-isopropyl-N-(tetrahydro-2H-pyran-4-yl)-1H-pyrrolo[3,2-c]pyridine-3-carboxamide | 323 | 3.31, 512.3, B | ¹H NMR (400 MHz, DMSO-d₆) δ 9.77 (s, 1H), 9.02 (s, 1H), 8.31 (s, 1H), 8.19 (s, 1H), 7.95 (d, J = 5.6 Hz, 1H), 7.85 (d, J = 7.9 Hz, 1H), 6.38 (d, J = 5.5 Hz, 1H), 4.93 (d, J = 50.9 Hz, 1H), 4.72-4.57 (m, 2H), 4.36 (m, 1H), 4.00 (m, 1H), 3.90 (m, 2H), 3.65-3.35 (m, 7H), 1.81 (m, 4H), 1.53 (m, 8H). |
| 382 | 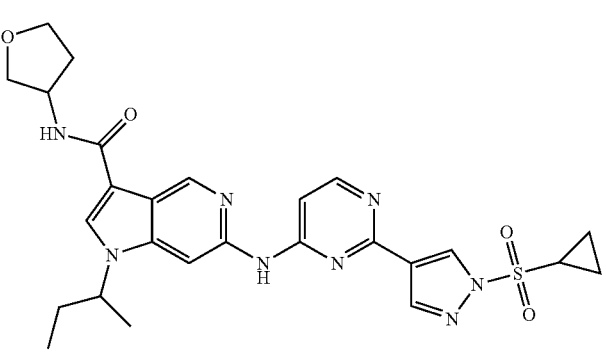 [SMILES: CCC(C)n1cc(C(=O)NC2CCOC2)c2cnc(Nc3ccnc(-c4cnn(S(=O)(=O)C5CC5)c4)n3)cc21]<br>1-(sec-butyl)-6-((2-(1-(cyclopropylsulfonyl)-1H-pyrazol-4-yl)pyrimidin-4-yl)amino)-N-(tetrahydrofuran-3-yl)-1H-pyrrolo[3,2-c]pyridine-3-carboxamide<br>(mixture of diastereoisomers) | 321 | 4.01, 551.3, B | ¹H NMR (400 MHz, DMSO-d₆) δ 10.25 (s, 1H), 9.08 (s, 1H), 8.69 (s, 1H), 8.46 (d, J = 9.7 Hz, 2H), 8.38 (d, J = 5.9 Hz, 1H), 8.26 (s, 1H), 8.11 (s, 1H), 7.12 (s, 1H), 4.61-4.44 (m, 2H), 3.95-3.84 (m, 2H), 3.74 (m, 1H), 3.62 (m, 1H), 2.19 (m, 1H), 2.03-1.82 (m, 3H), 1.55 (d, J = 6.7 Hz, 3H), 1.42-1.18 (m, 4H), 0.80 (t, J = 7.3 Hz, 3H). |
| 383 | 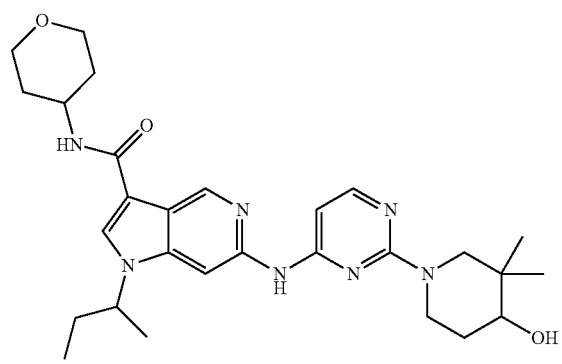 [SMILES: CCC(C)n1cc(C(=O)NC2CCOCC2)c2cnc(Nc3ccnc(N4CCC(O)C(C)(C)C4)n3)cc21]<br>1-(sec-butyl)-6-((2-(4-hydroxy-3,3-dimethylpiperidin-1-yl)pyrimidin-4-yl)amino)-N-(tetrahydro-2H-pyran-4-yl)-1H-pyrrolo[3,2-c]pyridine-3-carboxamide<br>(mixture of diastereoisomers) | 323 | 6.77, 522.4, A | ¹H NMR (400 MHz, DMSO-d₆) δ 9.70 (s, 1H), 9.01 (s, 1H), 8.33 (d, J = 5.0 Hz, 1H), 8.16 (s, 1H), 7.92 (d, J = 5.6 Hz, 1H), 7.85 (d, J = 7.7 Hz, 1H), 6.31 (d, J = 5.6 Hz, 1H), 4.65 (d, J = 4.7 Hz, 1H), 4.38 (m, 2H), 4.21-3.97 (m, 2H), 3.90 (d, J = 9.7 Hz, 2H), 2.99 (m, 1H), 2.00-1.81 (m, 3H), 1.69 (s, 1H), 1.65-1.33 (m, 6H), 0.94 (d, J = 3.0 Hz, 3H), 0.88-0.63 (m, 5H). |

TABLE 4-continued

| Example | Structure/Name | Synthesis Method/ Example # | LCMS $R_T$ (min), [M + H]$^+$, method | $^1$H NMR (ppm) |
|---|---|---|---|---|
| 384 | 1-(sec-butyl)-6-((2-(4-hydroxy-3,3-dimethylpiperidin-1-yl)pyrimidin-4-yl)amino)-N-(tetrahydro-2H-pyran-4-yl)-1H-pyrrolo[3,2-c]pyridine-3-carboxamide (mixture of diastereoisomers) | 323 | 6.78, 522.4, A | N/A |
| 385 | (±)-6-((2-(4-hydroxy-3,3-dimethylpiperidin-1-yl)pyrimidin-4-yl)amino)-1-isopropyl-N-(tetrahydro-2H-pyran-4-yl)-1H-pyrrolo[3,2-c]pyridine-3-carboxamide | 63 | 3.31, 508.3, B | $^1$H NMR (400 MHz, DMSO-d$_6$) δ 9.70 (s, 1H), 9.01 (s, 1H), 8.33 (s, 2H), 8.19 (s, 1H), 7.91 (d, J = 5.7 Hz, 1H), 7.85 (d, J = 7.9 Hz, 1H), 6.31 (d, J = 5.8 Hz, 1H), 4.71-4.59 (m, 1H), 4.38 (m, 1H), 4.09 (m, 1H), 4.01 (m, 1H), 3.90 (m, 2H), 2.99 (m, 1H), 1.81 (m, 2H), 1.70 (s, 1H), 1.54 (m, 8H), 0.93 (s, 3H), 0.81 (s, 3H). |
| 386 | 6-((2-(1-(cyclopropylsulfonyl)-1H-pyrazol-4-yl)pyrimidin-4-yl)amino)-1-isopropyl-N-(oxetan-3-yl)-1H-pyrrolo[3,2-c]pyridine-3-carboxamide | 321 | 4.54, 523.2, B | $^1$H NMR (400 MHz, DMSO-d$_6$) δ 10.27 (s, 1H), 9.05 (d, J = 0.9 Hz, 1H), 8.72-8.66 (m, 2H), 8.49 (t, J = 7.0 Hz, 2H), 8.38 (d, J = 5.9 Hz, 1H), 8.30 (s, 1H), 7.12 (s, 1H), 5.05 (m, 1H), 4.85-4.76 (m, 3H), 4.59 (m, 2H), 1.58 (d, J = 6.6 Hz, 6H), 1.39-1.24 (m, 4H). |
| 387 | N-(6-((2-(1-(cyclopropylsulfonyl)-1H-pyrazol-4-yl)pyrimidin-4-yl)amino)-1-isopropyl-1H-pyrrolo[3,2-c]pyridin-3-yl)-N-methylacetamide | 325 | 4.45, 495.2, B | $^1$H NMR (400 MHz, DMSO-d$_6$) δ 10.23 (s, 1H), 8.69 (s, 1H), 8.53 (s, 1H), 8.51-8.41 (m, 2H), 8.38 (d, J = 5.9 Hz, 1H), 7.69 (s, 1H), 7.15 (s, 1H), 4.84-4.68 (m, 1H), 3.22 (s, 3H), 1.85 (s, 3H), 1.54 (d, J = 6.7 Hz, 6H), 1.38-1.30 (m, 2H), 1.26 (m 2H). |

TABLE 4-continued

| Example | Structure/Name | Synthesis Method/ Example # | LCMS R$_T$ (min), [M + H]$^+$, method | $^1$H NMR (ppm) |
|---|---|---|---|---|
| 388 | 1-isopropyl-N-(oxetan-3-yl)-6-((2-(1-(pyrrolidin-1-ylsulfonyl)-1H-pyrazol-4-yl)pyrimidin-4-yl)amino)-1H-pyrrolo[3,2-c]pyridine-3-carboxamide | 321 | 4.46, 552.6, B | $^1$H NMR (400 MHz, DMSO-d$_6$) δ 10.31 (s, 1H), 9.00 (d, J = 0.9 Hz, 1H), 8.65 (d, J = 0.4 Hz, 1H), 8.57 (s, 1H), 8.40 (d, J = 0.4 Hz, 1H), 8.37 (d, J = 6.0 Hz, 1H), 7.99 (s, 1H), 7.10 (s, 1H), 4.80 (m, 2H), 4.38 (m, 1H), 4.35-4.25 (m, 1H), 4.25-4.15 (m, 1H), 3.64 (m, 1H), 3.53-3.39 (m, 6H), 1.81-1.73 (m, 4H), 1.61-1.53 (m, 6H). |
| 389 | 1-(sec-butyl)-6-((2-((3R,4S)-3-fluoro-4-hydroxypiperidin-1-yl)pyrimidin-4-yl)amino)-N-(1-(oxetan-3-yl)piperidin-4-yl)-1H-pyrrolo[3,2-c]pyridine-3-carboxamide (mixture of 2 diastereoisomers) | 321 | 3.04, 567.3, B | $^1$H NMR (400 MHz, DMSO-d$_6$) δ 9.77 (s, 1H), 9.01 (s, 1H), 8.32 (s, 1H), 8.15 (s, 1H), 7.95 (d, J = 5.7 Hz, 1H), 7.82 (d, J = 7.5 Hz, 1H), 6.36 (m, 1H), 5.11 (s, 1H), 4.67 (m, 1H), 4.46 (m, 4H), 4.26 (s, 1H), 3.84 (m, 2H), 3.60 (m, 1H), 3.51-3.33 (m, 2H), 2.74 (s, 1H), 1.95-1.37 (m, 9H), 0.79 (m, 2H). |
| 390 | N-(6-((2-(1-(cyclopropylsulfonyl)-1H-pyrazol-4-yl)pyrimidin-4-yl)amino)-1-isopropyl-1H-pyrrolo[3,2-c]pyridin-3-yl)-2-hydroxy-N-methylacetamide | 328 | 4.60, 511.2, B | $^1$H NMR (400 MHz, DMSO-d$_6$) δ 10.24 (s, 1H), 8.83-8.63 (m, 1H), 8.53 (s, 1H), 8.47 (d, J = 0.4 Hz, 2H), 8.38 (d, J = 5.9 Hz, 1H), 7.70 (s, 1H), 7.13 (s, 1H), 4.87-4.68 (m, 1H), 4.49 (m, 1H), 3.85 (m, 2H), 3.26 (s, 3H), 1.53 (d, J = 6.7 Hz, 6H), 1.39-1.21 (m, 4H). |

TABLE 4-continued

| Example | Structure/Name | Synthesis Method/ Example # | LCMS R$_T$ (min), [M + H]$^+$, method | $^1$H NMR (ppm) |
|---|---|---|---|---|
| 391 | N-(6-((2-(1-(cyclopropylsulfonyl)-1H-pyrazol-4-yl)pyrimidin-4-yl)amino)-1-isopropyl-1H-pyrrolo[3,2-c]pyridin-3-yl)-2-hydroxy-2-methylpropanamide | 325 | 3.89, 525.2, B | $^1$H NMR (400 MHz, DMSO-d$_6$) δ 10.17 (s, 1H), 9.60 (s, 1H), 8.80 (d, J = 0.7 Hz, 1H), 8.68 (s, 1H), 8.47 (s, 1H), 8.36 (d, J = 5.9 Hz, 2H), 7.78 (s, 1H), 7.11 (s, 1H), 5.64 (s, 1H), 4.75 (m, 1H), 1.52 (d, J = 6.7 Hz, 6H), 1.40 (s, 6H), 1.36-1.23 (m, 4H). |
| 392 | N-(2-(1-(ethylsulfonyl)-1H-pyrazol-4-yl)pyrimidin-4-yl)-1-isopropyl-3-(1-(2-(methylsulfonyl)ethyl)-1H-pyrazol-4-yl)-1H-pyrrolo[3,2-c]pyridin-6-amine | 331 | 4.75, 584.2, B | N/A |
| 393 | 2-(4-(6-((2-(1-(cyclopropylsulfonyl)-1H-pyrazol-4-yl)pyrimidin-4-yl)amino)-1-isopropyl-1H-pyrrolo[3,2-c]pyridin-3-yl)-1H-pyrazol-1-yl)ethanol | 331 | 4.80, 534.2, B | $^1$H NMR (400 MHz, DMSO-d$_6$) δ 10.18 (s, 1H), 8.84 (d, J = 0.8 Hz, 1H), 8.69 (d, J = 0.4 Hz, 1H), 8.47 (d, J = 0.6 Hz, 1H), 8.41 (s, 1H), 8.37 (d, J = 5.9 Hz, 1H), 8.17 (d, J = 0.4 Hz, 1H), 7.87 (d, J = 0.7 Hz, 1H), 7.75 (s, 1H), 7.16 (s, 1H), 4.91 (m, 1H), 4.86-4.62 (m, 1H), 4.20 (m, 2H), 3.80 (m, 2H), 1.56 (d, J = 6.7 Hz, 6H), 1.35 (m, 2H), 1.27 (m, 2H). |
| 394 | 1-isopropyl-2-methyl-N-(2-(1-((1-methyl-1H-pyrazol-3-yl)sulfonyl)-1H-pyrazol-4-yl)pyrimidin-4-yl)-1H-imidazo[4,5-c]pyridin-6-amine | 52 | 4.41, 479.2, B | $^1$H NMR (400 MHz, DMSO-d$_6$) δ 10.17 (s, 1H), 8.75 (d, J = 0.6 Hz, 1H), 8.56 (d, J = 0.8 Hz, 1H), 8.43 (s, 1H), 8.40 (d, J = 0.6 Hz, 1H), 8.37 (d, J = 5.9 Hz, 1H), 8.02 (d, J = 2.4 Hz, 1H), 7.22 (s, 1H), 7.03 (d, J = 2.4 Hz, 1H), 4.79 (m, 1H), 3.93 (s, 3H), 2.59 (s, 3H), 1.66 (d, J = 6.9 Hz, 6H). |

TABLE 4-continued

| Example | Structure/Name | Synthesis Method/ Example # | LCMS R_T (min), [M + H]+, method | 1H NMR (ppm) |
|---|---|---|---|---|
| 395 | N-(2-(1-(cyclopropylmethyl)-1H-pyrazol-4-yl)pyrimidin-4-yl)-1-isopropyl-2-methyl-1H-imidazo[4,5-c]pyridin-6-amine | 52 | 3.98, 389.3, B | 1H NMR (400 MHz, DMSO-d$_6$) δ 9.95 (s, 1H), 8.55 (d, J = 0.8 Hz, 1H), 8.35 (s, 1H), 8.33-8.25 (m, 2H), 8.04 (d, J = 0.5 Hz, 1H), 7.19 (s, 1H), 4.80-4.70 (m, 1H), 4.04 (d, J = 7.1 Hz, 2H), 2.58 (s, 3H), 1.62 (d, J = 6.9 Hz, 6H), 1.36-1.20 (m, 1H), 0.62-0.51 (m, 2H), 0.46-0.30 (m, 2H). |
| 396 | 6-((2-(1-(cyclopropylsulfonyl)-1H-pyrazol-yl)pyrimidin-4-yl)amino)-1-isopropyl-N-(tetrahydro-2H-pyran-4-yl)-1H-pyrrolo[3,2-c]pyridine-3-carboxamide | 51 | 4.79, 551.3, B | 1H NMR (400 MHz, DMSO-d$_6$) δ 10.26 (s, 1H), 9.08 (d, J = 0.9 Hz, 1H), 8.70 (s, 1H), 8.48 (s, 2H), 8.38 (d, J = 5.9 Hz, 1H), 8.25 (s, 1H), 7.88 (d, J = 7.7 Hz, 1H), 7.13 (s, 1H), 4.80 (m, 1H), 4.02 (m, 1H), 3.91 (m, 2H), 3.41 (m, 2H), 1.82 (m, 2H), 1.57 (d, J = 6.6 Hz, 6H), 1.39-1.23 (m, 4H). |
| 397 | 4-(4-((1-isopropyl-2-methyl-1H-imidazo[4,5-c]pyridin-6-yl)amino)pyrimidin-2-yl)-N,N-dimethyl-1H-pyrazole-1-sulfonamide | 52 | 4.44, 442.2, D | 1H NMR (400 MHz, DMSO-d$_6$) δ 10.15 (s, 1H), 8.60 (d, J = 0.5 Hz, 1H), 8.56 (d, J = 0.9 Hz, 1H), 8.42 (m, 2H), 8.38 (m, 1H), 7.22 (s, 1H), 4.83-4.69 (m, 1H), 2.92 (s, 6H), 2.58 (s, 3H), 1.63 (d, J = 6.9 Hz, 6H). |
| 398 | (±)-1-isopropyl-2-methyl-N-(2-(1-(pyrrolidin-3-yl)-1H-pyrazol-4-yl)pyrimidin-4-yl)-1H-imidazo[4,5-c]pyridin-6-amine | 52 | 3.41, 404.3, B | n/a |
| 399 | 1-isopropyl-2-methyl-N-(2-(3-methyl-1H-pyrazol-4-yl)pyrimidin-4-yl)-1H-imidazo[4,5-c]pyridin-6-amine | 52 | 4.51, 349.2, B | n/a |

TABLE 4-continued

| Example | Structure/Name | Synthesis Method/ Example # | LCMS $R_T$ (min), $[M+H]^+$, method | $^1$H NMR (ppm) |
|---|---|---|---|---|
| 400 | N-(2-(1-(cyclopropylsulfonyl)-3-methyl-1H-pyrazol-4-yl)pyrimidin-4-yl)-1-isopropyl-2-methyl-1H-imidazo[4,5-c]pyridin-6-amine | 52 | 4.39, 453.2, B | n/a |
| 401 | 1-isopropyl-N-(2-(4-methoxypiperidin-1-yl)pyrimidin-4-yl)-3-(1H-pyrazol-4-yl)-1H-pyrrolo[3,2-c]pyridin-6-amine | 64 | 3.98, 433.3, B | $^1$H NMR (400 MHz, DMSO-d$_6$) δ 9.65 (s, 1H), 8.79 (d, J = 0.8 Hz, 1H), 8.29 (s, 1H), 8.04 (s, 2H), 7.94 (d, J = 5.7 Hz, 1H), 7.69 (s, 1H), 6.38 (d, J = 5.7 Hz, 1H), 4.59 (m, 1H), 4.40-4.22 (m, 2H), 3.53-3.44 (m, 1H), 3.43-3.35 (m, 2H), 1.91 (m, 2H), 1.56-1.38 (m, 8H). |
| 402 | 2-(4-(1-isopropyl-6-((2-(4-methoxypiperidin-1-yl)pyrimidin-4-yl)amino)-1H-pyrrolo[3,2-c]pyridin-3-yl)-1H-pyrazol-1-yl)ethanol | 64 | 4.22, 477.3, B | $^1$H NMR (400 MHz, DMSO-d$_6$) δ 9.67 (s, 1H), 8.77 (d, J = 0.8 Hz, 1H), 8.30 (s, 1H), 8.15 (d, J = 0.6 Hz, 1H), 7.94 (d, J = 5.6 Hz, 1H), 7.85 (d, J = 0.7 Hz, 1H), 7.69 (s, 1H), 6.37 (d, J = 5.7 Hz, 1H), 4.91 (s, 1H), 4.59 (m, 1H), 4.33-4.22 (m, 2H), 4.19 (m, 2H), 3.79 (m, 2H), 3.51-3.33 (m, 4H), 1.91 (m, 2H), 1.55-1.37 (m, 8H). |
| 403 | 3-(1H-imidazol-4-yl)-1-isopropyl-N-(2-(4-methoxypiperidin-1-yl)pyrimidin-4-yl)-1H-pyrrolo[3,2-c]pyridin-6-amine | 64 | 4.16, 433.3, B | $^1$H NMR (400 MHz, DMSO-d$_6$) δ 9.75 (s, 1H), 8.58 (d, J = 0.8 Hz, 1H), 8.38 (s, 1H), 8.03 (d, J = 0.9 Hz, 1H), 7.96 (d, J = 5.7 Hz, 1H), 7.52 (s, 1H), 7.16 (d, J = 0.9 Hz, 1H), 6.35 (d, J = 5.7 Hz, 1H), 5.12 (d, J = 9.6 Hz, 1H), 4.65 (m, 1H), 4.35-4.20 (m, 2H), 4.07 (d, J = 11.1 Hz, 1H), 3.62-3.34 (m, 4H), 1.92 (m, 3H), 1.55 (m, 6H). |

TABLE 4-continued

| Example | Structure/Name | Synthesis Method/ Example # | LCMS R$_T$ (min), [M + H]$^+$, method | $^1$H NMR (ppm) |
|---|---|---|---|---|
| 404 | (±)-N-(2-(1-(((1,4-dioxan-2-yl)methyl)sulfonyl)-1H-pyrazol-4-yl)pyrimidin-4-yl)-1-isopropyl-2-methyl-1H-imidazo[4,5-c]pyridin-6-amine | 52 | 4.35, 499.2, B | $^1$H NMR (400 MHz, DMSO-d$_6$) δ 10.17 (s, 1H), 8.64 (d, J = 0.6 Hz, 1H), 8.56 (d, J = 0.8 Hz, 1H), 8.46 (d, J = 0.5 Hz, 1H), 8.38 (d, J = 5.9 Hz, 1H), 8.17 (s, 1H), 7.22 (s, 1H), 4.79 (m, 1H), 4.04 (m, 1H), 3.94 (m, 2H), 3.66 (m, 1H), 3.54 (t, J = 8.7 Hz, 3H), 2.59 (s, 3H), 1.65 (d, J = 6.8 Hz, 6H). |
| 405 | N-(2-(1-((2-ethoxyethyl)sulfonyl)-1H-pyrazol-4-yl)pyrimidin-4-yl)-1-isopropyl-2-methyl-1H-imidazo[4,5-c]pyridin-6-amine | 52 | 4.41, 471.2, B | $^1$H NMR (400 MHz, DMSO-d$_6$) δ 10.16 (s, 1H), 8.61 (d, J = 0.5 Hz, 1H), 8.56 (d, J = 0.8 Hz, 1H), 8.44 (d, J = 0.6 Hz, 2H), 8.38 (d, J = 5.9 Hz, 1H), 7.22 (s, 1H), 4.89-4.71 (m, 1H), 4.05 (t, J = 5.4 Hz, 2H), 3.71 (t, J = 5.4 Hz, 2H), 3.25 (m, 2H), 2.59 (s, 3H), 1.64 (d, J = 6.9 Hz, 6H), 0.86 (t, J = 7.0 Hz, 3H). |
| 406 | (±)-1-isopropyl-2-methyl-N-(2-(1-((tetrahydrofuran-3-yl)sulfonyl)-1H-pyrazol-4-yl)pyrimidin-4-yl)-1H-imidazo[4,5-c]pyridin-6-amine | 52 | 4.56, 469.2, B | $^1$H NMR (400 MHz, DMSO-d$_6$) δ 8.70 (d, J = 0.4 Hz, 1H), 8.57 (d, J = 0.8 Hz, 1H), 8.53-8.48 (m, 1H), 8.44 (s, 2H), 8.39 (d, J = 5.9 Hz, 1H), 7.24 (s, 1H), 4.79 (m, 1H), 4.75-4.63 (m, 1H), 4.17 (m, 1H), 3.90 (m, 1H), 3.76 (m, 1H), 3.64 (m, 1H), 2.59 (s, 3H), 2.38-2.26 (m, 2H), 1.69-1.57 (m, 6H). |
| 407 | N-(2-(1-((1-ethyl-1H-pyrazol-4-yl)sulfonyl)-1H-pyrazol-4-yl)pyrimidin-4-yl)-1-isopropyl-2-methyl-1H-imidazo[4,5-c]pyridin-6-amine | 52 | 4.62, 493.2, B | $^1$H NMR (400 MHz, DMSO-d$_6$) δ 10.19 (s, 1H), 8.79 (s, 1H), 8.75 (d, J = 0.5 Hz, 1H), 8.57 (d, J = 0.8 Hz, 1H), 8.47-8.34 (m, 3H), 8.12 (d, J = 0.6 Hz, 1H), 7.22 (s, 1H), 4.91-4.66 (m, 1H), 4.21 (m, 2H), 2.59 (s, 3H), 1.65 (d, J = 6.9 Hz, 6H), 1.37 (m, 3H). |

TABLE 4-continued

| Example | Structure/Name | Synthesis Method/ Example # | LCMS $R_T$ (min), [M + H]$^+$, method | $^1$H NMR (ppm) |
|---|---|---|---|---|
| 408 | (6-((2-(1-(difluoromethyl)-1H-pyrazol-4-yl)pyrimidin-4-yl)amino)-1-isopropyl-1H-imidazo[4,5-c]pyridin-2-yl)methanol | 52 | 3.99, 401.2, B | $^1$H NMR (400 MHz, DMSO-d$_6$) δ 10.15 (s, 1H), 8.73-8.67 (m, 1H), 8.66 (d, J = 0.9 Hz, 1H), 8.43 (s, 1H), 8.38 (d, J = 5.9 Hz, 1H), 8.33 (s, 1H), 7.91 (t, J = 59.1 Hz, 1H), 7.26 (s, 1H), 5.69 (t, J = 5.6 Hz, 1H), 5.08-4.91 (m, 1H), 4.74 (d, J = 5.6 Hz, 2H), 1.64 (d, J = 6.9 Hz, 6H). |
| 409 | 1-isopropyl-N-(2-(1-(isopropylsulfonyl)-1H-pyrazol-4-yl)pyrimidin-4-yl)-2-methyl-1H-imidazo[4,5-c]pyridin-6-amine | 52 | 4.46, 441.2, B | $^1$H NMR (400 MHz, DMSO-d$_6$) δ 10.21 (s, 1H), 8.65 (d, J = 0.4 Hz, 1H), 8.57 (d, J = 0.8 Hz, 1H), 8.50 (d, J = 0.4 Hz, 1H), 8.45 (s, 1H), 8.39 (d, J = 5.9 Hz, 1H), 7.22 (s, 1H), 4.79 (m, 1H), 4.09-3.92 (m, 1H), 2.59 (s, 3H), 1.63 (d, J = 6.9 Hz, 6H), 1.28 (d, J = 6.8 Hz, 6H). |
| 410 | 2-(4-(1-isopropyl-6-((2-(4-methoxypiperidin-1-yl)pyrimidin-4-yl)amino)-1H-pyrrolo[3,2-c]pyridin-3-yl)-1H-pyrazol-1-yl)acetamide | 64 | 4.03, 490.3, B | $^1$H NMR (400 MHz, DMSO-d$_6$) δ 9.74 (s, 1H), 9.01 (d, J = 0.7 Hz, 1H), 8.34 (s, 1H), 7.94 (d, J = 5.7 Hz, 1H), 7.86 (s, 1H), 7.73 (d, J = 2.3 Hz, 1H), 7.47 (s, 1H), 7.29 (s, 1H), 6.64 (d, J = 2.3 Hz, 1H), 6.36 (d, J = 5.6 Hz, 1H), 4.81 (s, 2H), 4.61 (m, 1H), 4.26 (m, 2H), 3.53-3.42 (m, 1H), 3.30 (s, 3H), 1.91 (s, 2H), 1.53 (d, J = 6.7 Hz, 6H), 1.49-1.39 (m, 2H). |
| 411 | 2-(3-(1-isopropyl-6-((2-(4-methoxypiperidin-1-yl)pyrimidin-4-yl)amino)-1H-pyrrolo[3,2-c]pyridin-3-yl)-1H-pyrazol-1-yl)acetamide | 64 | 4.03, 490.3, B | $^1$H NMR (400 MHz, DMSO-d$_6$) δ 9.74 (s, 1H), 9.01 (d, J = 0.8 Hz, 1H), 8.34 (s, 1H), 7.94 (d, J = 5.7 Hz, 1H), 7.85 (s, 1H), 7.73 (d, J = 2.3 Hz, 1H), 7.47 (s, 1H), 7.29 (s, 1H), 6.64 (d, J = 2.3 Hz, 1H), 6.36 (d, J = 5.7 Hz, 1H), 4.81 (s, 2H), 4.70-4.49 (m, 1H), 4.35-4.15 (m, 2H), 3.52-3.43 (m, 1H), 3.37 (m, 2H), 1.92 (d, J = 8.8 Hz, 2H), 1.50 (m, 6H), 1.50-1.33 (m, 2H). |

TABLE 4-continued

| Example | Structure/Name | Synthesis Method/ Example # | LCMS $R_T$ (min), [M + H]+, method | $^1$H NMR (ppm) |
|---|---|---|---|---|
| 412 | 1-isopropyl-N-(2-(4-methoxypiperidin-1-yl)pyrimidin-4-yl)-3-(1-(2-morpholinoethyl)-1H-pyrazol-4-yl)-1H-pyrrolo[3,2-c]pyridin-6-amine | 64 | 4.05, 547, B | $^1$H NMR (400 MHz, DMSO-d$_6$) δ 9.68 (s, 1H), 8.77 (d, J = 0.8 Hz, 1H), 8.30 (s, 1H), 8.21 (d, J = 0.6 Hz, 1H), 7.95 (d, J = 5.7 Hz, 1H), 7.83 (d, J = 0.7 Hz, 1H), 7.69 (s, 1H), 6.37 (d, J = 5.7 Hz, 1H), 4.66-4.49 (m, 1H), 4.36-4.18 (m, 4H), 3.63-3.53 (m, 4H), 3.53-3.36 (m, 3H), 2.77 (t, J = 6.6 Hz, 2H), 2.47-2.38 (m, 4H), 1.99-1.82 (m, 2H), 1.51 (d, J = 6.7 Hz, 6H), 1.45 (m, 2H). |
| 413 | 2-(4-(4-((1-isopropyl-2-methyl-1H-imidazo[4,5-c]pyridin-6-yl)amino)pyrimidin-2-yl)-1H-pyrazol-1-yl)acetamide | 52 | 3.32, 392.2, B | $^1$H NMR (400 MHz, DMSO-d$_6$) δ 9.98 (s, 1H), 8.55 (s, 1H), 8.40 (s, 1H), 8.34 (m, 1H), 8.26 (s, 1H), 8.03 (s, 1H), 7.56 (s, 1H), 7.29 (s, 1H), 7.16 (s, 1H), 4.85 (s, 2H), 4.82-4.72 (m, 1H), 2.58 (s, 3H), 1.62 (d, J = 6.9 Hz, 6H). |
| 414 | 1-isopropyl-2-methyl-N-(2-(1-(1-(2,2,2-trifluoroethyl)azetidin-3-yl)-1H-pyrazol-4-yl)pyrimidin-4-yl)-1H-imidazo[4,5-c]pyridin-6-amine | 52 | 2.17, 472.0, D | $^1$H NMR (400 MHz, DMSO-d$_6$) δ 9.97 (s, 1H), 8.55 (d, J = 0.8 Hz, 1H), 8.45 (s, 1H), 8.39-8.26 (m, 2H), 8.18-8.04 (m, 1H), 7.19 (d, J = 5.3 Hz, 1H), 5.27-5.08 (m, 1H), 4.76 (m, 1H), 3.90 (t, J = 7.7 Hz, 2H), 3.73 (m, 2H), 3.37 (q, J = 10.1 Hz, 2H), 2.58 (s, 3H), 1.62 (d, J = 6.9 Hz, 6H). |
| 415 | N$^4$-(1-isopropyl-2-methyl-1H-imidazo[4,5-c]pyridin-6-yl)-N$^2$-(1-methyl-1H-pyrazol-3-yl)pyrimidine-2,4-diamine | 42 | 3.88, 364.2, B | $^1$H NMR (400 MHz, DMSO-d$_6$) δ 9.58 (s, 1H), 9.07 (s, 1H), 8.51 (d, J = 0.8 Hz, 1H), 8.03 (d, J = 5.7 Hz, 1H), 7.99 (s, 1H), 7.51 (d, J = 2.2 Hz, 1H), 6.91 (d, J = 5.7 Hz, 1H), 6.63 (d, J = 2.2 Hz, 1H), 4.74 (m, 1H), 3.74 (s, 3H), 2.57 (s, 3H), 1.52 (d, J = 6.9 Hz, 6H). |

TABLE 4-continued

| Example | Structure/Name | Synthesis Method/ Example # | LCMS R_T (min), [M + H]+, method | 1H NMR (ppm) |
|---|---|---|---|---|
| 416 | N-(2-(1-(azetidin-3-yl)-1H-pyrazol-4-yl)pyrimidin-4-yl)-1-isopropyl-2-methyl-1H-imidazo[4,5-c]pyridin-6-amine | 52 | 3.49, 390.2, B | 1H NMR (400 MHz, DMSO-d6) δ 9.98 (s, 1H), 8.55 (d, J = 0.9 Hz, 1H), 8.39 (d, J = 9.4 Hz, 2H), 8.31 (d, J = 5.9 Hz, 1H), 8.10 (s, 1H), 7.17 (s, 1H), 5.30-5.18 (m, 1H), 4.76 (m, 1H), 3.93 (t, J = 7.7 Hz, 2H), 3.78 (t, J = 8.1 Hz, 2H), 2.58 (s, 3H), 1.63 (d, J = 6.9 Hz, 6H). |
| 417 | (±)-3-((4-((1-isopropyl-2-methyl-1H-imidazo[4,5-c]pyridin-6-yl)amino)pyrimidin-2-yl)amino)-2,2-dimethylbutanamide | 42 | 3.00, 397.3, B | 1H NMR (400 MHz, DMSO-d6) δ 9.53 (s, 1H), 8.48 (d, J = 0.7 Hz, 1H), 8.30 (s, 1H), 7.87 (d, J = 5.6 Hz, 1H), 7.08 (m, 2H), 6.56-6.32 (m, 2H), 4.73 (m, 1H), 4.13 (s, 1H), 2.56 (s, 3H), 1.57 (t, J = 6.7 Hz, 6H), 1.15 (, 9H). |
| 418 | 1-(4-((2-(hydroxymethyl)-1-isopropyl-1H-imidazo[4,5-c]pyridin-6-yl)amino)pyrimidin-2-yl)-4-methylpiperidin-4-ol | 42 | 2.96, 398.2, B | 1H NMR (400 MHz, DMSO-d6) δ 9.70 (s, 1H), 8.59 (s, 1H), 8.46, 7.95 (d, 1H), 6.38 (d, 1H), 5.67 (s, 1H), 4.96 (m, 1H), 4.71 (s, 2H), 4.36 (s, 1H), 4.22 (m, 2H), 3.47 (m, 2H), 1.57 (m, 8H), 1.17 (s, 3H) |
| 419 | (±)-N-(2-(3-ethylmorpholino)pyrimidin-4-yl)-1-isopropyl-2-methyl-1H-imidazo[4,5-c]pyridin-6-amine | 42 | 4.06, 483.2, B | 1H NMR (400 MHz, DMSO-d6) δ 9.68 (s, 1H), 8.50 (d, J = 0.7 Hz, 1H), 8.31 (s, 1H), 7.97 (d, J = 5.6 Hz, 1H), 6.44 (d, J = 5.5 Hz, 1H), 4.70 (m, 1H), 4.57 (s, 1H), 4.39 (d, J = 11.0 Hz, 1H), 3.99-3.74 (m, 2H), 3.59-3.41 (m, 2H), 3.17 (m, 1H), 2.56 (s, 3H), 1.83-1.65 (m, 2H), 1.55 (m, 6H), 0.82 (t, J = 7.5 Hz, 3H). |
| 420 | N2-(2-(1H-pyrazol-4-yl)ethyl)-N4-(1-isopropyl-2-methyl-1H-imidazo[4,5-c]pyridin-6-yl)pyrimidine-2,4-diamine | 42 | 3.41, 378.3, B | 1H NMR (400 MHz, DMSO-d6) δ 12.63 (s, 1H), 9.55 (s, 1H), 8.47 (s, 1H), 8.35 (s, 1H), 7.88 (d, 1H), 7.43 (d, 2H), 6.49 (m, 2H), 4.62 (m, 1H), 3.53 (m, 2H), 2.75, (t, 2H), 2.54 (s, 3H), 1.42 (d, 6H) |

TABLE 4-continued

| Example | Structure/Name | Synthesis Method/ Example # | LCMS $R_T$ (min), [M + H]$^+$, method | $^1$H NMR (ppm) |
|---|---|---|---|---|
| 421 | N-(2-(4-methoxypiperidin-1-yl)pyrimidin-4-yl)-1-(2-(methylsulfonyl)ethyl)-1H-pyrrolo[3,2-c]pyridin-6-amine | 42 | 3.58, 431.2, B | $^1$H NMR (400 MHz, DMSO) δ 9.63 (s, 1H), 8.54 (d, J = 0.9 Hz, 1H), 8.23 (s, 1H), 7.94 (d, J = 5.6 Hz, 1H), 7.40 (d, J = 3.3 Hz, 1H), 6.56 (m, 1H), 6.39 (d, J = 5.6 Hz, 1H), 4.53 (t, J = 6.9 Hz, 2H), 4.25 (m, 2H), 3.71 (t, J = 6.8 Hz, 2H), 3.51-3.32 (m, 3H), 2.85 (s, 3H), 1.94 (m, 2H), 1.44 (m, 2H). |
| 422 | 1-isopropyl-2-methyl-N-(2-(4-(methylthio)-1H-imidazol-1-yl)pyrimidin-4-yl)-1H-imidazo[4,5-c]pyridin-6-amine | 42 | 4.25, 381.2, B | $^1$H NMR (400 MHz, DMSO-d$_6$) δ 10.41 (s, 1H), 8.59 (d, J = 0.9 Hz, 1H), 8.52 (d, J = 1.3 Hz, 1H), 8.35 (s, 1H), 7.76 (d, J = 1.3 Hz, 1H), 7.31 (s, 1H), 6.80 (m, 1H), 4.92-4.66 (m, 1H), 2.59 (s, 3H), 2.44 (s, 3H), 1.61 (d, J = 6.9 Hz, 6H). |
| 423 | 2-(1-(4-(((1-isopropyl-2-methyl-1H-imidazo[4,5-c]pyridin-6-yl)amino)pyrimidin-2-yl)-1H-imidazol-4-yl)propan-2-ol | 42 | 3.69, 393.2, B | $^1$H NMR (400 MHz, DMSO-d$_6$) δ 10.37 (s, 1H), 8.59 (d, J = 0.8 Hz, 1H), 8.41 (d, J = 1.4 Hz, 1H), 8.33 (d, J = 5.9 Hz, 1H), 8.18 (s, 1H), 7.68 (d, J = 1.3 Hz, 1H), 7.29 (s, 1H), 4.93-4.56 (m, 2H), 2.59 (s, 3H), 1.62 (d, J = 6.9 Hz, 6H), 1.44 (s, 6H). |
| 424 | 2-(4-(4-(((1-isopropyl-2-methyl-1H-imidazo[4,5-c]pyridin-6-yl)amino)pyrimidin-2-yl)-1H-pyrazol-1-yl)-2-methylpropanamide | 341 | 3.661, 420.3, B | $^1$H NMR (400 MHz, DMSO-d$_6$) δ 9.97 (s, 1H), 8.55 (d, J = 1.2 Hz, 1H), 8.39-8.26 (m, 3H), 8.09 (s, 1H), 7.21 (s, 2H), 7.00 (s, 1H), 4.76 (p, J = 6.9 Hz, 1H), 2.58 (s, 3H), 1.76 (s, 6H), 1.62 (d, J = 6.9 Hz, 6H). |
| 425 | 2-(4-(4-(((1-isopropyl-2-methyl-1H-imidazo[4,5-c]pyridin-6-yl)amino)pyrimidin-2-yl)-1H-pyrazol-1-yl)propanenitrile | 341 | 3.932, 388.2, B | $^1$H NMR (400 MHz, DMSO-d$_6$) δ 10.01 (s, 1H), 8.55 (d, J = 0.9 Hz, 1H), 8.46 (s, 1H), 8.33 (d, J = 5.8 Hz, 1H), 8.30 (s, 1H), 8.17 (s, 1H), 7.32-7.17 (m, 1H), 5.94 (q, J = 7.1 Hz, 1H), 4.76 (p, J = 6.9 Hz, 1H), 2.58 (s, 3H), 1.86 (d, J = 7.1 Hz, 3H), 1.62 (d, J = 6.9 Hz, 6H). |

TABLE 4-continued

| Example | Structure/Name | Synthesis Method/ Example # | LCMS R$_T$ (min), [M + H]$^+$, method | $^1$H NMR (ppm) |
|---|---|---|---|---|
| 426 | 2-(4-(4-((1-isopropyl-2-methyl-1H-imidazo[4,5-c]pyridin-6-yl)amino)pyrimidin-2-yl)-1H-pyrazol-1-yl)-N,2-dimethylpropanamide | 341 | 3.733, 434.3, B | $^1$H NMR (400 MHz, DMSO-d$_6$) δ 9.97 (s, 1H), 8.55 (d, J = 1.2 Hz, 1H), 8.37-8.27 (m, 3H), 8.09 (s, 1H), 7.43 (d, J = 4.7 Hz, 1H), 7.21 (s, 1H), 4.76 (p, J = 6.9 Hz, 1H), 2.62-2.55 (m, 6H), 1.76 (s, 6H), 1.62 (d, J = 6.9 Hz, 6H). |
| 427 | 1-(4-((1-isopropyl-2-methyl-1H-imidazo[4,5-c]pyridin-6-yl)amino)pyrimidin-2-yl)-3,3-dimethylpiperidin-4-ol | 46 | 3.672, 396.3, B | $^1$H NMR (400 MHz, DMSO-d$_6$) δ 9.60 (s, 1H), 8.50 (d, J = 0.9 Hz, 1H), 8.31 (s, 1H), 7.92 (d, J = 5.7 Hz, 1H), 6.40 (d, J = 5.6 Hz, 1H), 4.72 (p, J = 6.9 Hz, 1H), 4.65-4.60 (m, 1H), 4.46-4.36 (m, 1H), 4.09 (dd, J = 12.8, 1.6 Hz, 1H), 3.37-3.31 (m, 1H), 3.27 (s, 1H), 2.96 (d, J = 12.9 Hz, 1H), 2.56 (s, 3H), 1.75-1.65 (m, 1H), 1.57 (dd, J = 7.0, 1.4 Hz, 6H), 1.54-1.45 (m, 1H), 0.92 (s, 3H), 0.79 (s, 3H). |
| 428 | N-(2-(4-amino-3,3-dimethylpiperidin-1-yl)pyrimidin-4-yl)-1-isopropyl-2-methyl-1H-imidazo[4,5-c]pyridin-6-amine | 46 | 3.260, 395.3, B | $^1$H NMR (400 MHz, DMSO-d$_6$) δ 9.60 (s, 1H), 8.49 (d, J = 0.9 Hz, 1H), 8.33 (s, 1H), 7.92 (d, J = 5.6 Hz, 1H), 6.39 (d, J = 5.7 Hz, 1H), 4.77-4.68 (m, 1H), 4.63 (d, J = 13.1 Hz, 1H), 4.31 (dd, J = 12.9, 1.8 Hz, 1H), 3.11-3.00 (m, 1H), 2.71 (d, J = 12.9 Hz, 1H), 2.56 (s, 3H), 2.52 (d, J = 4.2 Hz, 1H), 1.66-1.60 (m, 1H), 1.57 (dd, J = 6.9, 2.4 Hz, 6H), 1.40 (dt, J = 13.0, 6.7 Hz, 1H), 0.92 (s, 3H), 0.74 (s, 3H). |

TABLE 4-continued

| Example | Structure/Name | Synthesis Method/ Example # | LCMS R$_T$ (min), [M + H]$^+$, method | $^1$H NMR (ppm) |
|---|---|---|---|---|
| 429 | N-(2-(1-(azetidin-3-ylmethyl)-1H-pyrazol-4-yl)pyrimidin-4-yl)-1-isopropyl-2-methyl-1H-imidazo[4,5-c]pyridin-6- | 344 | 3.358, 404.2, B | $^1$H NMR (400 MHz, DMSO-d$_6$) δ 9.95 (s, 1H), 8.54 (d, J = 0.9 Hz, 1H), 8.34 (s, 1H), 8.30 (d, J = 5.9 Hz, 1H), 8.27 (s, 1H), 8.04 (d, J = 0.7 Hz, 1H), 7.18 (s, 1H), 4.76 (p, J = 6.9 Hz, 1H), 4.39 (d, J = 7.3 Hz, 2H), 3.63 (t, J = 8.2 Hz, 2H), 3.45 (t, J = 7.4 Hz, 2H), 3.16-3.08 (m, 1H), 2.58 (s, 3H), 1.63 (d, J = 6.9 Hz, 6H). |
| 430 | N-(2-(1-(3-aminopropyl)-1H-pyrazol-4-yl)pyrimidin-4-yl)-1-isopropyl-2-methyl-1H-imidazo[4,5-c]pyridin-6-amine | 344 | 6.065, 460.2, B | $^1$H NMR (400 MHz, DMSO-d$_6$) δ 9.96 (s, 1H), 8.54 (d, J = 0.9 Hz, 1H), 8.39 (s, 1H), 8.31-8.24 (m, 2H), 8.03 (s, 1H), 7.14 (d, J = 5.8 Hz, 1H), 4.82-4.67 (m, 1H), 4.23 (t, J = 6.9 Hz, 2H), 2.58 (s, 3H), 2.54-2.51 (m, 2H), 1.87 (t, J = 6.8 Hz, 2H), 1.63 (d, J = 6.9 Hz, 7H). |
| 431 | 1-isopropyl-2-methyl-N-(2-(1-((3-methyloxetan-3-yl)methyl)-1H-pyrazol-4-yl)pyrimidin-4-yl)-1H-imidazo[4,5-c]pyridin-6-amine | 344 | 3.602, 419.2, B | $^1$H NMR (400 MHz, DMSO-d$_6$) δ 9.95 (s, 1H), 8.55 (d, J = 0.9 Hz, 1H), 8.36-8.26 (m, 3H), 8.06 (s, 1H), 7.22 (d, J = 5.8 Hz, 1H), 4.75 (p, J = 6.9 Hz, 1H), 4.63 (d, J = 5.9 Hz, 2H), 4.42 (s, 2H), 4.26 (d, J = 5.9 Hz, 2H), 2.58 (s, 3H), 1.62 (d, J = 6.9 Hz, 6H), 1.17 (s, 3H). |

TABLE 4-continued

| Example | Structure/Name | Synthesis Method/ Example # | LCMS R$_T$ (min), [M + H]$^+$, method | $^1$H NMR (ppm) |
|---|---|---|---|---|
| 432 | 3-(4-(4-((1-isopropyl-2-methyl-1H-imidazo[4,5-c]pyridin-6-yl)amino)pyrimidin-2-yl)-1H-pyrazol-1-yl)tetrahydrothiophene 1,1-dioxide | 344 | 3.366, 453.2, B | $^1$H NMR (400 MHz, DMSO-d$_6$) δ 9.98 (s, 1H), 8.55 (s, 1H), 8.43 (s, 1H), 8.33 (d, J = 5.9 Hz, 2H), 8.30 (s, 1H), 8.13 (s, 1H), 7.23 (d, J = 6.0 Hz, 1H), 5.42-5.29 (m, 1H), 4.76 (p, J = 6.9 Hz, 1H), 3.78 (dd, J = 13.7, 8.2 Hz, 1H), 3.55 (dd, J = 13.7, 7.5 Hz, 1H), 3.50-3.44 (m, 1H), 3.31-3.25 (m, 1H), 2.76-2.66 (m, 1H), 2.65-2.56 (m, 4H), 1.62 (d, J = 6.9 Hz, 6H). |
| 433 | (1R,5S,8r)-3-(4-((2-(hydroxymethyl)-1-isopropyl-1H-imidazo[4,5-c]pyridin-6-yl)amino)pyrimidin-2-yl)-3-azabicyclo[3.2.1]octan-8-ol | 273 | 3.063, 410.2, B | $^1$H NMR (400 MHz, DMSO-d$_6$) δ 9.70 (s, 1H), 8.70-8.44 (m, 2H), 7.94 (d, J = 5.6 Hz, 1H), 6.35 (d, J = 5.6 Hz, 1H), 5.68-5.62 (m, 1H), 5.11-5.03 (m, 1H), 4.95 (p, J = 6.9 Hz, 1H), 4.71 (d, J = 5.6 Hz, 2H), 4.15 (d, J = 12.0 Hz, 2H), 3.93 (q, J = 4.6 Hz, 1H), 3.39 (d, J = 12.1 Hz, 2H), 2.03 (s, 2H), 1.76-1.64 (m, 2H), 1.57 (d, J = 6.9 Hz, 6H), 1.51-1.41 (m, 2H). |
| 434 | N-(2-(1-(cyclopropylsulfonyl)-1H-pyrazol-4-yl)pyrimidin-4-yl)-3-(1,4-dimethyl-1H-pyrazol-5-yl)-1-isopropyl-1H-pyrrolo[3,2-c]pyridin-6-amine | 345 | 4.121, 518.2, B | n/a |

TABLE 4-continued

| Example | Structure/Name | Synthesis Method/ Example # | LCMS $R_T$ (min), [M + H]+, method | $^1$H NMR (ppm) |
|---|---|---|---|---|
| 435 | 2-(3-(6-(2-(1-(cyclopropylsulfonyl)-1H-pyrazol-4-yl)pyrimidin-4-ylamino)-1-isopropyl-1H-pyrrolo[3,2-c]pyridin-3-yl)-5-methyl-1H-pyrazol-1-yl)ethanol | 253 | 2.181, 548, R | $^1$H NMR (400 MHz, DMSO-$d_6$) δ 10.21 (s, 1H), 9.06 (s, 1H), 8.70 (s, 1H), 8.47 (s, 1H), 8.45 (s, 1H), 8.36 (d, J = 5.6 Hz, 1H), 7.81 (s, 1 H), 7.15 (s, 1H), 6.39 (s, 1H), 4.90-4.87 (m, 1H), 4.81-4.74 (m, 1H), 4.12-4.10 (m, 2H), 3.80-3.75 (m, 2H), 3.33-3.28 (m, 1H), 2.32 (s, 3H), 1.56 (d, J = 6.8 Hz, 6H), 1.38-1.33 (m, 2H), 1.29-1.23 (m, 2H) |
| 436 | 2-(5-(6-(2-(1-(cyclopropylsulfonyl)-1H-pyrazol-4-yl)pyrimidin-4-ylamino)-1-isopropyl-1H-pyrrolo[3,2-c]pyridin-3-yl)-3-methyl-1H-pyrazol-1-yl)ethanol | 253 | 1.656, 548, R | $^1$H NMR (400 MHz, DMSO-$d_6$) δ 10.27 (s, 1H), 8.71 (s, 1H), 8.62 (s, 1H), 8.50 (s, 1H), 8.48 (s, 1H), 8.38 (d, J = 6.0 Hz, 1H), 7.85 (s, 1H), 7.13 (s, 1H), 6.29 (s, 1H), 4.98-4.95 (m, 1H), 4.88-4.78 (m, 1H), 4.13-4.11 (m, 2H), 3.81-3.78 (m, 2H), 3.32-3.26 (m, 1H), 2.22 (s, 3H), 1.59 (d, J = 6.8 Hz, 6H), 1.38-1.33 (m, 2H), 1.28-1.25 (m, 2H). |
| 437 | 2-(4-(6-(2-(1-(cyclopropylsulfonyl)-1H-pyrazol-4-yl)pyrimidin-4-ylamino)-1-isopropyl-1H-pyrrolo[3,2-c]pyridin-3-yl)-3-methyl-1H-pyrazol-1-yl)ethanol | 253 | 1.577, 548, M | $^1$H NMR (300 MHz, DMSO-$d_6$) δ 10.20 (s, 1H), 8.70 (s, 2H), 8.48 (s, 1H), 8.43 (s, 1H), 8.37 (d, J = 6 Hz, 1H), 8.06 (s, 1H), 7.50 (s, 1H), 7.15 (d, J = 6 Hz, 1H), 4.91-4.87 (m, 1H), 4.80-4.76 (m, 1H), 4.15-4.11 (m, 2H), 3.80-3.75 (m, 2H), 3.29 (s, 1H), 2.32 (s, 3H), 1.60 (d, J = 6.6 Hz, 3H), 1.56 (d, J = 6.6 Hz, 3H), 1.39-1.32 (m, 2H), 1.30-1.23 (m, 2H) |

TABLE 4-continued

| Example | Structure/Name | Synthesis Method/ Example # | LCMS $R_T$ (min), $[M + H]^+$, method | $^1$H NMR (ppm) |
|---|---|---|---|---|
| 438 | 2-(4-(6-(2-(1-(cyclopropylsulfonyl)-1H-pyrazol-4-yl)pyrimidin-4-ylamino)-1-isopropyl-1H-pyrrolo[3,2-c]pyridin-3-yl)-5-methyl-1H-pyrazol-1-yl)ethanol | 253 | 1.691, 548, M | $^1$H NMR (300 MHz, DMSO-$d_6$): δ 10.19 (s, 1H), 8.70 (s, 1H), 8.62 (s, 1H), 8.36-8.38 (m, 3H), 7.71 (d, J = 6 Hz, 1H), 7.48 (s, 1H), 7.16 (s, 1H), 4.92-4.89 (m, 1H), 4.80-4.76 (m, 1H), 4.18-4.14 (m, 2H), 3.78-3.73 (m, 2H), 3.32 (s, 1H), 2.39 (s, 3H), 1.58 (d, J = 6 Hz, 6H), 1.36-1.26 (m, 4H). |
| 439 | 2-(4-(6-(2-(1-(cyclopropylsulfonyl)-1H-pyrazol-4-yl)pyrimidin-4-ylamino)-1-isopropyl-1H-pyrrolo[3,2-c]pyridin-3-yl)-1H-pyrazol-1-yl)propane-1,3-diol | 253 | 1.501, 564, R | $^1$H NMR (300 MHz, DMSO-$d_6$) δ 10.26 (s, 1H), 8.88 (s, 1H), 8.71 (s, 1H), 8.49 (s, 1H), 8.39 (d, J = 6 Hz, 2H), 8.17 (s, 1H), 7.90 (s, 1H), 7.80 (s, 1H), 7.16 (s, 1H), 4.90 (s, 2H), 4.82-4.73 (m, 1H), 4.34-4.26 (m, 1H), 3.80 (d, J = 6.0 Hz, 4H), 3.33-3.25 (m, 1H), 1.56 (d, J = 6.6 Hz, 6H), 1.39-1.33 (m, 2H), 1.32-1.26 (m, 2H). |

TABLE 4-continued

| Example | Structure/Name | Synthesis Method/ Example # | LCMS R$_T$ (min), [M + H]$^+$, method | $^1$H NMR (ppm) |
|---|---|---|---|---|
| 440 | 3-((4-(6-(2-(1-(cyclopropylsulfonyl)-1H-pyrazol-4-yl)pyrimidin-4-ylamino)-1-isopropyl-1H-pyrrolo[3,2-c]pyridin-3-yl)-1H-pyrazol-1-yl)methyl)oxetan-3-ol | 253 | 2.252, 576.15, R | $^1$H NMR (400 MHz, DMSO-d$_6$): δ 10.21 (s, 1H), 8.83 (s, 1H), 8.70 (s, 1H), 8.48 (s, 1H), 8.43 (br, 1H), 8.37 (d, J = 6 Hz, 1H), 8.18 (s, 1H), 7.91 (s, 1H), 7.78 (s, 1H), 7.16 (br, 1H), 6.08 (s, 1H), 4.78 (m, 1H), 4.62 (d, J = 6.8 Hz, 2H), 4.44 (s, 4H), 3.32 (s, 1H), 1.57 (d, J = 6.4 Hz, 6H), 1.31 (m, 2H), 1.21 (m, 2H). |
| 441 | N-(2-(1-(cyclopropylsulfonyl)-1H-pyrazol-4-yl)pyrimidin-4-yl)-1-isopropyl-3-(1-(oxetan-3-yl)-1H-pyrazol-4-yl)-1H-pyrrolo[3,2-c]pyridin-6-amine | 253 | 1.523, 546.05, L | $^1$H NMR (400 MHz, DMSO-d$_6$): δ 10.21 (s, 1H), 8.88 (s, 1H), 8.70 (s, 1H), 8.48 (s, 1H), 8.44-8.37 (m, 3H), 8.03 (s, 1H), 7.82 (s, 1H), 7.16 (s, 1H), 5.63 (m, 1H), 5.00-4.94 (m, 4H), 4.78 (m, 1H), 3.27 (m, 1H), 1.56 (s, 6H), 1.38-1.20 (m, 4H). |
| 442 | N-(2-(1-(cyclopropylsulfonyl)-1H-pyrazol-4-yl)pyrimidin-4-yl)-1-isopropyl-3-(5,6,7,8-tetrahydroimidazo[1,2-a]pyrazin-2-yl)-1H-pyrrolo[3,2-c]pyridin-6-amine | 253 | 1.633, 545.15, H | $^1$H NMR (400 MHz, DMSO-d$_6$): δ 10.22 (s, 1H), 8.97 (s, 1H), 8.70 (s, 1H), 8.48 (s, 1H), 8.43 (br, 1H), 8.37 (d, J = 6 Hz, 1H), 7.70 (s, 1H), 7.47 (s, 1H), 7.15 (s, 1H), 4.76 (m, 1H), 3.95-3.89 (m, 4H), 3.30-3.27 (m, 1H), 3.08 (m, 2H), 2.76 (br, 1H), 1.55 (m, 6H), 1.35-1.29 (m, 2H), 1.28-1.26 (m, 2H). |

TABLE 4-continued

| Example | Structure/Name | Synthesis Method/ Example # | LCMS $R_T$ (min), $[M+H]^+$, method | $^1$H NMR (ppm) |
|---|---|---|---|---|
| 443 | 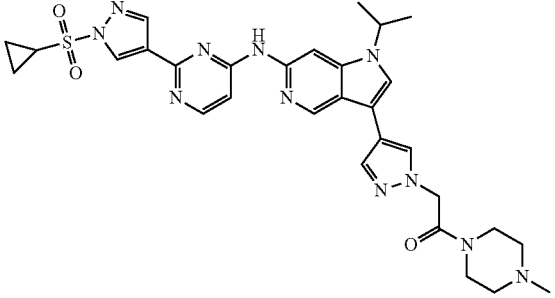 [SMILES: CC(C)n1cc(-c2cnn(CC(=O)N3CCN(C)CC3)c2)c2cnc(Nc3ccnc(-c4cnn(S(=O)(=O)C5CC5)c4)n3)cc21]<br>2-(4-(6-(2-(1-(cyclopropylsulfonyl)-1H-pyrazol-4-yl)pyrimidin-4-ylamino)-1-isopropyl-1H-pyrrolo[3,2-c]pyridin-3-yl)-1H-pyrazol-1-yl)-1-(4-methylpiperazin-1-yl)ethanone | 255 | 1.627, 630, R | $^1$H NMR (300 MHz, DMSO-$d_6$) δ 10.22 (s, 1H), 8.82 (s, 1H), 8.70 (s, 1H), 8.48 (s, 2H), 8.37 (d, J = 6 Hz, 1H), 8.15 (s, 1H), 7.88 (s, 1H), 7.78 (s, 1H), 7.14 (d, J = 6 Hz, 1H), 5.16 (s, 2H), 4.80-4.75 (m, 1H), 3.53 (s, 2H), 3.51 (s, 2H), 3.28 (s, 1H), 2.35 (s, 2H), 2.30 (s, 2H), 2.20 (s, 3H), 1.56 (d, J = 6.6 Hz, 6H), 1.33-1.37 (m, 2H), 1.30-1.22 (m, 2H) |
| 444 | 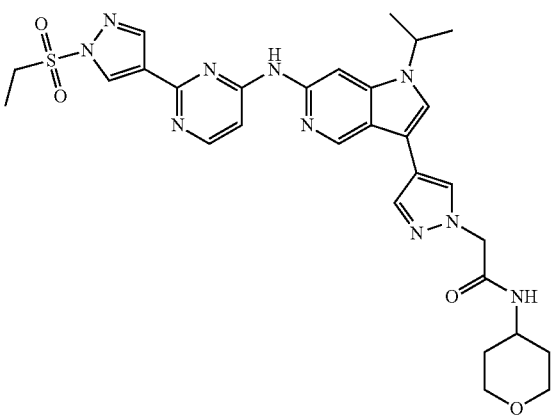 [SMILES: CCS(=O)(=O)n1cc(-c2nccc(Nc3cc4c(cn3)c(-c3cnn(CC(=O)NC5CCOCC5)c3)cn4C(C)C)n2)cn1]<br>2-(4-(6-(2-(1-(ethylsulfonyl)-1H-pyrazol-4-yl)pyrimidin-4-ylamino)-1-isopropyl-1H-pyrrolo[3,2-c]pyridin-3-yl)-1H-pyrazol-1-yl)-H-(tetrahydro-2H-pyran-4-yl)acetamide | 255 | 1.53, 619.1, R | $^1$H NMR (400 MHz, DMSO-$d_6$): δ 10.24 (s, 1H), 8.83 (s, 1H), 8.70 (s, 1H), 8.49 (s, 1H), 8.48 (br, 1H), 8.37 (d, J = 6 Hz, 1H), 8.21 (s, 1H), 8.20 (s, 1H), 7.90 (s, 1H), 7.80 (s, 1H), 7.14 (s, 1H), 4.81 (s, 2H), 4.77 (m, 1H), 3.87-3.78 (m, 5H), 3.37 (m, 2H), 1.75-1.72 (m, 2H), 1.57 (s, 6H), 1.48-1.43 (m, 2H), 1.42 (m, 3H). |
| 445 | 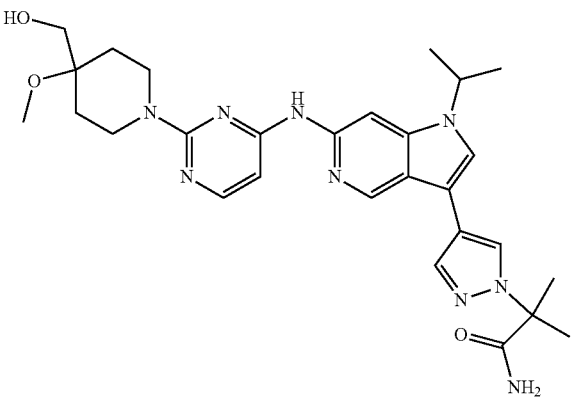 [SMILES: COC1(CO)CCN(c2nccc(Nc3cc4c(cn3)c(-c3cnn(C(C)(C)C(N)=O)c3)cn4C(C)C)n2)CC1]<br>2-(4-(6-(2-(4-(hydroxymethyl)-4-methoxypiperidin-1-yl)pyrimidin-4-ylamino)-1-isopropyl-1H-pyrrolo[3,2-c]pyridin-3-yl)-1H-pyrazol-1-yl)-2-methylpropanamide | 255 | 1.834, 548.45, M | $^1$H NMR (400 MHz, DMSO-$d_6$): δ 9.68 (s, 1H), 8.84 (s, 1H), 8.33 (s, 1H), 8.23 (s, 1H), 7.95 (s, 1H), 7.94 (s, 1H), 7.75 (s, 1H), 7.19 (s, 1H), 6.73 (s, 1H), 6.37 (s, 1H), 4.63-4.55 (m, 2H), 4.37-4.34 (m, 2H), 3.38 (d, J = 5.6 Hz, 2H), 3.25-3.21 (m, 5H), 1.77 (s, 6H), 1.73 (m, 2H), 1.52-1.47 (m, 8H). |

TABLE 4-continued

| Example | Structure/Name | Synthesis Method/ Example # | LCMS R_T (min), [M + H]+, method | 1H NMR (ppm) |
|---|---|---|---|---|
| 446 | 2-(4-(6-(2-(4-(hydroxymethyl)-4-methoxypiperidin-1-yl)pyrimidin-4-ylamino)-1-isopropyl-1H-pyrrolo[3,2-c]pyridin-3-yl)-1H-pyrazol-1-yl)acetamide | 255 | 2.011, 520.3, H | 1H NMR (400 MHz, DMSO-d6): δ 9.70 (s, 1H), 8.77 (s, 1H), 8.35 (s, 1H), 8.17 (s, 1H), 7.94 (d, J = 5.6 Hz, 1H), 7.88 (s, 1H), 7.72 (s, 1H), 7.45 (s, 1H), 7.27 (s, 1H), 6.34 (d, J = 6.0 Hz, 1H), 4.79 (s, 2H), 4.63-4.55 (m, 2H), 4.37-4.34 (m, 2H), 3.40 (m, 2H), 3.31-3.21 (m, 5H), 1.75-1.69 (m, 2H), 1.52-1.48 (m, 8H). |
| 447 | N-ethyl-2-(4-(6-(2-(1-(ethylsulfonyl)-1H-pyrazol-4-yl)pyrimidin-4-ylamino)-1-isopropyl-1H-pyrrolo[3,2-c]pyridin-3-yl)-1H-pyrazol-1-yl)acetamide | 255 | 1.593, 563.1, R | 1H NMR (400 MHz, DMSO-d6): δ 10.24 (s, 1H), 8.83 (s, 1H), 8.70 (s, 1H), 8.49 (s, 1H), 8.48 (br, 1H), 8.37 (d, J = 5.6 Hz, 1H), 8.20 (s, 1H), 8.08 (m, 1H), 7.91 (s, 1H), 7.80 (s, 1H), 7.13 (s, 1H), 4.80 (s, 2H), 4.76 (m, 1H), 3.84 (m, 2H), 3.13 (m, 2H), 1.57 (s, 6H), 1.16 (m, 3H), 1.05 (m, 3H). |
| 448 | 6-(2-(1-(ethylsulfonyl)-1H-pyrazol-4-yl)pyrimidin-4-ylamino)-1-isopropyl-N-(oxetan-3-yl)-1H-pyrrolo[3,2-c]pyridine-3-carboxamide | 252 | 1.352, 511, N | 1H NMR (400 MHz, CDCl3) δ 9.05 (s, 1H), 8.71 (s, 1H), 8.48-8.47 (m, 2H), 8.38 (d, J = 6.0 Hz, 1H), 7.85 (s, 1H), 7.75 (s, 1H), 6.77 (d, J = 5.6 Hz, 1H), 6.40 (d, J = 12 Hz, 1H), 5.33-5.27 (m, 1H), 5.08-5.04 (m, 2H), 4.77-4.70 (m, 1H), 4.68-4.64 (m, 2H), 3.62-3.56 (m, 2H), 1.67 (d, J = 6.8 Hz, 6H), 1.34-1.30 (m, 3H). |

TABLE 4-continued

| Example | Structure/Name | Synthesis Method/ Example # | LCMS $R_T$ (min), [M + H]$^+$, method | $^1$H NMR (ppm) |
|---|---|---|---|---|
| 449 | 1-isopropyl-6-(2-(4-methoxypiperidin-1-yl)pyrimidin-4-ylamino)-N-(1-(oxetan-3-yl)piperidin-4-yl)-1H-pyrrolo[3,2-c]pyridine-3-carboxamide | 252 | 1.064, 549, L | $^1$H NMR (300 MHz, DMSO-d$_6$): δ 9.79 (s, 1H), 9.00 (s, 1H), 8.35 (s, 1H), 8.19 (s, 1H), 7.95-7.87 (m, 2H), 6.33 (s, 1H), 4.55-4.45 (m, 5H), 4.24 (d, J = 6 Hz, 2H), 3.78 (s, 1H), 3.50 (m, 1H), 3.33-3.28 (m, 4H), 2.73 (s, 2H), 1.88 (s, 6H), 1.51-1.45 (m, 11H), 1.23 (s, 1H). |
| 450 | 6-(2-(1-(cyclopropylsulfonyl)-1H-pyrazol-4-yl)pyrimidin-4-ylamino)-N-((1s,3S,4R)-3,4-dihydroxycyclopentyl)-1-isopropyl-1H-pyrrolo[3,2-c]pyridine-3-carboxamide | 252 | 4.605, 567, L | $^1$H NMR (400 MHz, DMSO-d$_6$): δ 10.29 (s, 1H), 9.07 (s, 1H), 8.70 (s, 1H), 8.51 (s, 1H), 8.48 (s, 1H), 8.37 (d, J = 4 Hz, 1H), 8.31 (s, 1H), 7.95 (d, J = 8 Hz, 1H), 7.10 (s, 1H), 4.83-4.77 (m, 1H), 4.53 (d, J = 4 Hz, 2H), 4.19-4.13 (m, 1H), 3.81-3.80 (d, J = 4 Hz, 2H), 3.29-3.26 (m, 1H), 2.19-2.12 (m, 2H), 1.67-1.60 (m, 2H), 1.55 (d, J = 4 Hz, 6H), 1.35 (s, 2H), 1.25 (d, J = 8 Hz, 2H). |
| 451 | 6-(2-(1-(cyclopropylsulfonyl)-1H-pyrazol-4-yl)pyrimidin-4-ylamino)-N-((1r,3R,4S)-3,4-dihydroxycyclopentyl)-1-isopropyl-1H-pyrrolo[3,2-c]pyridine-3-carboxamide | 252 | 2.340, 567, L | $^1$H NMR (400 MHz, DMSO-d$_6$): δ 10.30 (s, 1H), 9.07 (s, 1H), 8.70 ( s, 1H), 8.51 (s, 1H), 8.48 (s, 1H), 8.37 (d, J = 4 Hz, 1H), 8.21 (s, 1H), 7.92 (d, J = 8 Hz, 1H), 7.10 (s, 1H), 4.82-4.79 (m, 1H), 4.45-4.44 (m, 3H), 4.03 (s, 2H), 3.33 (s, 1H), 1.98 (s, 2H), 1.71-1.69 (m, 2H), 1.56 (d, J = 8 Hz, 6H), 1.27-1.25 (m, 4H). |
| 452 | 6-(2-(1-(cyclopropylsulfonyl)-1H-pyrazol-4-yl)pyrimidin-4-ylamino)-1-isopropyl-N-(2-(methylsulfonyl)ethyl)-1H-pyrrolo[3,2-c]pyridine-3-carboxamide | 252 | 2.448, 573, M | $^1$H NMR (300 MHz, DMSO-d$_6$) δ 10.30 (s, 1H), 9.08 (s, 1H), 8.71 (s, 1H), 8.48-8.22 (m, 5H), 7.11 (s, 1H), 4.82 (s, 1H), 3.81 (s, 2H), 3.69-3.58 (m, 3H), 3.06 (s, 3H), 1.57 (s, 6H), 1.35-1.07 (m, 4H) |

TABLE 4-continued

| Example | Structure/Name | Synthesis Method/ Example # | LCMS R$_T$ (min), [M + H]$^+$, method | $^1$H NMR (ppm) |
|---|---|---|---|---|
| 453 | 6-(2-(1-(cyclopropylsulfonyl)-1H-pyrazol-4-yl)pyrimidin-4-ylamino)-1-isopropyl-N-(tetrahydrofuran-3-yl)-1H-pyrrolo[3,2-c]pyridine-3-carboxamide | 252 | 1.605, 537, R | $^1$H NMR (300 MHz, DMSO-d$_6$) δ 10.31 (s, 1H), 9.08 (s, 1H), 8.71 (s, 1H), 8.51 (s, 1H), 8.48 (s, 1H), 8.38 (d, J = 6.0 Hz, 1H), 8.31 (s, 1H), 8.14 (d, J = 6.6 Hz, 1H), 7.11 (d, J = 5.4 Hz, 1H), 4.84-4.79 (m, 1H), 4.51-4.49 (m, 1H), 3.90-3.85 (m, 2H), 3.78-3.71 (m, 1H), 3.63-3.59 (m, 1H), 3.32-3.26 (m, 1H), 2.22-2.16 (m, 1H), 1.93-1.89 (m, 1H), 1.57 (d, J = 6.6 Hz, 6H), 1.36-1.33 (m, 2H), 1.30-1.25 (m, 2H). |
| 454 | 6-(2-(1-(cyclopropylsulfonyl)-1H-pyrazol-4-yl)pyrimidin-4-ylamino)-N-(4-hydroxycyclohexyl)-1-isopropyl-1H-pyrrolo[3,2-c]pyridine-3-carboxamide | 252 | 2.105, 565, R | $^1$H NMR (400 MHz, DMSO-d$_6$) δ 10.28 (s, 1H), 9.07 (s, 1H), 8.70 (s, 1H), 8.49 (d, J = 9.2 Hz, 2H), 8.38 (d, J = 6.0 Hz, 1H), 8.24 (s, 1H), 7.77 (d, J = 8.0 Hz, 1H), 7.11 (s, 1H), 4.84-4.77 (m, 1H), 4.57 (d, J = 4.4 Hz, 1H), 3.75-3.73 (m, 1H), 3.42 (d, J = 4.0 Hz, 1H), 3.33-3.26 (m, 1H), 1.87 (d, J = 11.2 Hz, 4H), 1.56 (d, J = 6.4 Hz, 6H), 1.39-1.22 (m, 8H). |
| 455 | 6-((2-(1-(cyclopropylsulfonyl)-1H-pyrazol-4-yl)pyrimidin-4-yl)amino)-1-isopropyl-N-(1-oxidotetrahydro-2H-thiopyran-4-yl)-1H-pyrrolo[3,2-c]pyridine-3-carboxamide | 252 | 2.264, 583, R | $^1$H NMR (400 MHz, DMSO-d$_6$) δ 10.30 (s, 1H), 9.06 (s, 1H), 8.71 (s, 1H), 8.52 (s, 1H), 8.48 (s, 1H), 8.38 (d, J = 6 Hz, 1H), 8.24 (s, 1H), 7.86 (d, J = 8 Hz, 1H), 7.12 (s, 1H), 4.84-4.80 (m, 1H), 4.11-4.09 (m, 1H), 3.30-3.22 (m, 3H), 2.82-2.76 (m, 2H), 2.25-2.21 (m, 2H), 1.76-1.73 (m, 2H), 1.57 (d, J = 6.8 Hz, 6H), 1.36-1.34 (m, 2H), 1.29-1.27 (m, 2H) |

TABLE 4-continued

| Example | Structure/Name | Synthesis Method/ Example # | LCMS $R_T$ (min), $[M + H]^+$, method | $^1$H NMR (ppm) |
|---|---|---|---|---|
| 456 | 6-((2-(1-(cyclopropylsulfonyl)-1H-pyrazol-4-yl)pyrimidin-4-yl)amino)-1-isopropyl-N-(1-oxidotetrahydro-2H-thiopyran-4-yl)-1H-pyrrolo[3,2-c]pyridine-3-carboxamide | 252 | 1.351, 583, R | $^1$H NMR (400 MHz, DMSO-d$_6$) δ 10.29 (s, 1H), 9.08 (s, 1H), 8.71 (s, 1H), 8.50 (s, 1H), 8.48 (s, 1H), 8.38 (d, J = 6 Hz, 1H), 8.30 (s, 1H), 8.09 (d, J = 8 Hz, 1H), 7.11 (s, 1H), 4.85-4.78 (m, 1H), 4.08-4.00 (m, 1H), 3.29-3.27 (m, 1H), 2.98-2.95 (m, 2H), 2.84-2.77 (m, 2H), 2.25-2.16 (m, 2H), 1.85-1.82 (m, 2H), 1.57 (d, J = 6.8 Hz, 6H), 1.38-1.32 (m, 2H), 1.29-1.22 (m, 2H). |
| 457 | 6-((2-(1-(cyclopropylsulfonyl)-1H-pyrazol-4-yl)pyrimidin-4-yl)amino)-N-(1,1-dioxidotetrahydro-2H-thiopyran-4-yl)-1-isopropyl-1H-pyrrolo[3,2-c]pyridine-3-carboxamide | 252 | 2.464, 599, R | $^1$H NMR (400 MHz, DMSO-d$_6$) δ 10.30 (s, 1H), 9.07 (s, 1H), 8.71 (s, 1H), 8.52 (s, 1H), 8.48 (s, 1H), 8.38 (d, J = 6 Hz, 1H), 8.25 (s, 1H), 8.02 (d, J = 8 Hz, 1H), 7.12 (s, 1H), 4.84-4.80 (m, 1H), 4.24-4.22 (m, 1H), 3.38-3.27 (m, 3H), 3.16-3.12 (m, 2H), 2.19-2.16 (m, 2H), 2.11-2.05 (m, 2H), 1.57 (d, J = 6.8 Hz, 6H), 1.36-1.34 (m, 2H), 1.29-1.26 (m, 2H). |

TABLE 4-continued

| Example | Structure/Name | Synthesis Method/ Example # | LCMS $R_T$ (min), [M + H]+, method | $^1$H NMR (ppm) |
|---|---|---|---|---|
| 458 | 6-(2-(1-(cyclopropylsulfonyl)-1H-pyrazol-4-yl)pyrimidin-4-ylamino)-1-isopropyl-N-(tetrahydro-2H-thiopyran-4-yl)-1H-pyrrolo[3,2-c]pyridine-3-carboxamide | 252 | 1.598, 567, L | $^1$H NMR (400 MHz, DMSO-d$_6$) δ 10.29 (s, 1H), 9.07 (s, 1H), 8.71 (s, 1H), 8.51 (s, 1H), 8.48 (s, 1H), 8.38 (d, J = 6 Hz, 1H), 8.26 (s, 1H), 7.93 (d, J = 8 Hz, 1H), 7.11 (s, 1H), 4.85-4.78 (m, 1H), 3.90-3.82 (m, 1H), 3.29-3.26 (m, 1H), 2.77-2.67 (m, 4H), 2.17-2.13 (m, 2H), 1.69-1.62 (m, 2H), 1.59 (d, J = 8.8 Hz, 6H), 1.38-1.31 (m, 2H), 1.29-1.24 (m, 2H). |
| 459 | 6-(2-(1-(cyclopropylsulfonyl)-1H-pyrazol-4-yl)pyrimidin-4-ylamino)-1-isopropyl-N-(tetrahydro-2H-pyran-3-yl)-1H-pyrrolo[3,2-c]pyridine-3-carboxamide | 252 | 1.931, 551, R | $^1$H NMR (400 MHz, DMSO-d$_6$) δ 10.32 (s, 1H), 9.08 (s, 1H), 8.71 (s, 1H), 8.53 (s, 1H), 8.48 (s, 1H), 8.38 (d, J = 6 Hz, 1H), 8.30 (s, 1H), 7.84 (d, J = 8 Hz, 1H), 7.10 (s, 1H), 4.85-4.79 (m, 1H), 3.94-3.76 (m, 3H), 3.39-3.27 (m, 2H), 3.20-3.15 (m, 1H), 1.96 (s, 1H), 1.74 (s, 1H), 1.64-1.56 (m, 8H), 1.41-1.28 (m, 4H). |

TABLE 4-continued

| Example | Structure/Name | Synthesis Method/ Example # | LCMS R$_T$ (min), [M + H]$^+$, method | $^1$H NMR (ppm) |
|---|---|---|---|---|
| 460 | 4-(6-(2-(1-(cyclopropylsulfonyl)-1H-pyrazol-4-yl)pyrimidin-4-ylamino)-1-isopropyl-1H-pyrrolo[3,2-c]pyridin-3-yl)-1-(2-hydroxyethyl)pyrrolidin-2-one | 256 | 1.507, 551, R | $^1$H NMR (400 MHz, DMSO-d$_6$): δ 10.20 (s, 1H), 8.68 (s, 1H), 8.48-8.35 (m, 4H), 7.55 (s, 1H), 7.15 (s, 1H), 5.07 (m, 1H), 4.75-4.71 (m, 1H), 4.62-4.61 (m, 1H), 3.48-3.39 (m, 2H), 3.29-3.26 (m, 2H), 2.67-2.63 (m, 1H), 2.45-2.40 (m, 2H), 2.12-1.99 (m, 2H), 1.55-1.51 (m, 6H), 1.27 (d, J = 4 Hz, 2H), 1.25-1.21 (m, 2H). |
| 461 | N-(2-(1-(cyclopropylsulfonyl)-1H-pyrazol-4-yl)pyrimidin-4-yl)-2-methyl-1H-imidazo[4,5-c]pyridin-6-amine | 257 | 1.436, 397, H | $^1$H NMR (400 MHz, DMSO-d$_6$): δ 9.93 (s, 1H), 8.65 (s, 1H), 8.50 (s, 1H), 8.41 (s, 1H), 8.48 (s, 1H), 8.32 (d, J = 6.0 Hz, 1H), 7.97 (s, 1H), 7.32 (s, 1H), 3.31-3.25 (m, 1H), 2.47 (s, 3H), 1.38-1.34 (m, 2H), 1.30-1.23 (m, 2H). |
| 462 | 3-(4-(1-isopropyl-2-methyl-1H-imidazo[4,5-c]pyridin-6-ylamino)pyrimidin-2-ylamino)-N,N,2,2-tetramethylpropanamide | 50 | 1.600, 411, R | $^1$H NMR (300 MHz, DMSO-d$_6$) δ 9.59 (s, 1H), 8.49 (s, 1H), 8.29 (s, 1H), 7.88 (d, J = 5.7 Hz, 1H), 6.52 (d, J = 5.4 Hz, 1H), 6.01 (s, 1H), 4.76-4.67 (m, 1H), 3.55 (d, J = 6.0 Hz, 2H), 2.96 (s, 6H), 2.51-2.50 (m, 3H), 1.56 (d, J = 3.6 Hz, 6H), 1.24 (s, 6H). |
| 463 | 3-(4-(1-isopropyl-2-methyl-1H-imidazo[4,5-c]pyridin-6-ylamino)pyrimidin-2-ylamino)-N,2,2-trimethylpropanamide | 50 | 1.018, 397, N | $^1$H NMR (300 MHz, DMSO-d$_6$) δ 9.60 (s, 1H), 8.47 (s, 1H), 8.30 (s, 1H), 7.87 (d, J = 5.1 Hz, 1H), 7.62 (d, J = 4.5 Hz, 1H), 6.51 (d, J = 4.5 Hz, 1H), 6.08 (s, 1H), 4.75-4.70 (m, 1H), 3.46 (d, J = 5.7 Hz, 2H), 2.58-2.56 (m, 6H), 1.56 (d, J = 6.9 Hz, 6H), 1.13 (s, 6H). |

TABLE 4-continued

| Example | Structure/Name | Synthesis Method/ Example # | LCMS R_T (min), [M + H]+, method | 1H NMR (ppm) |
|---|---|---|---|---|
| 464 | (2-(4-(4-(1-isopropyl-2-methyl-1H-imidazo[4,5-c]pyridin-6-ylamino)pyrimidin-2-yl)-1H-pyrazol-1-ylsulfonyl)cyclopropyl)methanol | 258 | 1.216, 469, L | 1H NMR (300 MHz, acetone-d$_6$): δ 9.18 (s, 1H), 8.68 (s, 1H), 8.53 (s, 1H), 8.47 (s, 1H), 8.43-8.40 (m, 2 H), 7.38 (d, J = 5.1 Hz, 1H), 4.92-4.87 (m, 1H), 3.95-3.88 (m, 1H), 3.65-3.58 (m, 2H), 3.04-3.01 (m, 1H), 2.63 (s, 3H), 2.12-2.10 (m, 1H), 1.75 (d, J = 6.9 Hz, 6H), 1.58-1.55 (m, 1H), 1.38-1.36 (m, 1H). |
| 465 | 4-(4-(4-(1-isopropyl-2-methyl-1H-imidazo[4,5-c]pyridin-6-ylamino)pyrimidin-2-yl)-1H-pyrazol-1-ylsulfonyl)pyrrolidin-2-one | 260 | 1.049, 482, R | 1H NMR (300 MHz, DMSO-d$_6$): δ 10.20 (s, 1H), 8.73 (s, 1H), 8.57 (s, 1H), 8.50 (m, 1H), 8.41-8.39 (d, J = 6.0 Hz, 2H), 7.93 (s, 1H), 7.24 (s, 1H), 4.89-4.73 (m, 2H), 3.67-3.65 (d, J = 6.0 Hz, 2H), 2.80-2.71 (m, 1H), 2.63-2.50 (m, 4H), 1.64-1.62 (d, J = 6.9 Hz, 6H) |
| 466 | 1-(3-(4-(4-(1-isopropyl-2-methyl-1H-imidazo[4,5-c]pyridin-6-ylamino)pyrimidin-2-yl)-1H-pyrazol-1-ylsulfonyl)azetidin-1-yl)ethanone | 259 | 1.345, 496, R | 1H NMR (400 MHz, DMSO-d$_6$) δ 10.21 (s, 1H), 8.75 (s, 1H), 8.57 (s, 1H), 8.52 (s, 1H) 8.40 (d, J = 5.6 Hz, 2H), 7.25 (s, 1H), 4.77-4.93 (m, 2H), 4.50 (s, 2H), 4.23-4.15 (m, 2H), 2.59 (s, 3H), 1.77 (s, 3H), 1.64-1.62 (m, 6H) |
| 467 | N-(2-(1-(azetidin-3-ylsulfonyl)-1H-pyrazol-4-yl)pyrimidin-4-yl)-1-isopropyl-2-methyl-1H-imidazo[4,5-c]pyridin-6-amine | 258 | 1.811, 454, M | 1H NMR (400 MHz, DMSO-d$_6$) δ 10.20 (s, 1H), 8.67 (s, 1H), 8.57 (s, 1H), 8.48-8.38 (m, 3H), 7.23 (s, 1H), 5.00-4.92 (m, 1H), 4.82-4.75 (m, 1H), 3.85-3.82 (m, 2H), 3.73-3.69 (m, 2H), 3.00 (s, 1H), 2.59 (s, 3H), 1.64-1.63 (d, J = 6.8 Hz, 6H) |
| 468 | 1-isopropyl-2-methyl-N-(2-(1-(1-methylazetidin-3-ylsulfonyl)-1H-pyrazol-4-yl)pyrimidin-4-yl)-1H-imidazo[4,5-c]pyridin-6-amine | 259 | 1.392, 468, R | 1H NMR (300 MHz, DMSO-d$_6$) δ 10.20 (s, 1H), 8.68 (s, 1H), 8.57 (s, 1H), 8.48 (s, 1H), 8.43 (s, 1H), 8.39 (d, J = 5.7 Hz, 1H), 7.23 (d, J = 4.2 Hz, 1H), 4.71-4.83 (m, 2H), 3.55-3.47 (m, 4H), 2.59 (s, 3H), 2.19 (s, 3H), 1.63 (d, J = 6.9 Hz, 6H). |

TABLE 4-continued

| Example | Structure/Name | Synthesis Method/ Example # | LCMS R$_T$ (min), [M + H]$^+$, method | $^1$H NMR (ppm) |
|---|---|---|---|---|
| 469 | 2-(difluoromethyl)-1-isopropyl-N-(2-(1-(isopropylsulfonyl)-1H-pyrazol-4-yl)pyrimidin-4-yl)-1H-imidazo[4,5-c]pyridin-6-amine | 263 | 2.196, 477.25, R | $^1$H NMR (400 MHz, DMSO-d$_6$): δ 10.42 (s, 1H), 8.87 (s, 1H), 8.67 (s, 1H), 8.62 (s, 1H), 8.51 (s, 1H), 8.45 (d, J = 6 Hz, 1H), 7.46 (m, 1H), 7.24 (d, J = 4.4 Hz, 1H), 5.03-4.96 (m, 1H), 3.99-4.06 (m, 1H), 1.69 (s, 6H), 1.28 (s, 6H) |
| 470 | 3-(4-(4-(2-(hydroxymethyl)-1-isopropyl-1H-imidazo[4,5-c]pyridin-6-ylamino)pyrimidin-2-yl)-1H-pyrazol-1-yl)-2,2-dimethylpropan-1-ol | 251 | 1.193, 437, N | $^1$H NMR (400 MHz, DMSO-d$_6$): δ 10.04 (s, 1H), 8.65 (s, 1H), 8.44 (s, 1H), 8.31 (d, J = 4 Hz, 1H), 8.21 (s, 1H), 8.04 (s, 1H), 7.18 (s, 1H), 5.71 (s, 1H), 5.02-4.96 (m, 1H), 4.80 (d, J = 4 Hz, 1H), 4.73 (d, J = 4 Hz, 2H), 4.04 (s, 2H), 3.15 (m, 2H), 1.65 (d, J = 4 Hz, 6H), 0.85 (s, 6H) |
| 471 | 3-(4-(4-(2-(hydroxymethyl)-1-isopropyl-1H-imidazo[4,5-c]pyridin-6-ylamino)pyrimidin-2-yl)-1H-pyrazol-1-yl)-2,2-dimethylpropanamide | 251 | 1.126, 450, R | $^1$H NMR (400 MHz, DMSO-d$_6$): δ 10.04 (s, 1H), 8.65 (s, 1H), 8.38 (s, 1H), 8.31 (d, J = 4 Hz, 1H), 8.17 (s, 1H), 8.02 (s, 1H), 7.23 (s, 2H), 7.03 (s, 1H), 5.72 (s, 1H), 5.00-4.97 (m, 1H), 4.73 (d, J = 4 Hz, 2H), 4.28 (s, 2H), 1.65 (d, J = 4 Hz, 6H), 1.11 (s, 6H) |
| 472 | 3-(6-(2-(1-(cyclopropylsulfonyl)-1H-pyrazol-4-yl)pyrimidin-4-ylamino)-2-(hydroxymethyl)-1H-imidazo[4,5-c]pyridin-1-yl)-3-methylbutan-1-ol | 265 | 1.505, 499, N | $^1$H NMR (400 MHz, CDCl$_3$) δ 8.68-8.67 (d, J = 4.0 Hz, 2H), 8.64 (s, 1H), 8.48 (s, 1H), 8.37-8.36 (d, J = 5.6 Hz, 1H), 7.80 (s, 1H), 6.77-6.76 (d, J = 5.2 Hz, 1H), 5.01 (s, 2H), 4.50 (s, 1H), 3.62 (m, 2H), 2.86-2.80 (m, 1H), 2.51 (m, 2H), 2.00 (s, 6H), 1.55-1.52 (m, 2H), 1.29-1.26 (m, 2H) |

TABLE 4-continued

| Example | Structure/Name | Synthesis Method/ Example # | LCMS $R_T$ (min), [M + H]+, method | 1H NMR (ppm) |
|---|---|---|---|---|
| 473 | (6-(2-(1-(cyclopropylsulfonyl)-1H-pyrazol-4-yl)pyrimidin-4-ylamino)-1-((1R,2R)-2-methylcyclopentyl)-1H-imidazo[4,5-c]pyridin-2-yl)methanol | 265 | 1.429, 495, N | 1H NMR (400 MHz, CDCl3): δ 8.78 (s, 1H), 8.65 (s, 1H), 8.42 (m, 2H), 8.30 (s, 1H), 7.97 (s, 1H), 7.04-7.05 (d, J = 5.6 Hz, 1H), 4.88-4.93 (m, 3H), 2.85-2.81 (m, 1H), 2.59-2.42 (m, 3H), 2.08-2.02 (m, 2H), 1.76-1.72 (m, 1H), 1.61-1.51 (m, 3H), 1.25-1.19 (m, 2H), 1.70-1.68 (d, J = 6.8 Hz, 3H) |
| 474 | (6-(2-(1-(cyclopropylsulfonyl)-1H-pyrazol-4-yl)pyrimidin-4-ylamino)-1-((1R,2R)-2-methylcyclopentyl)-1H-imidazo[4,5-c]pyridin-2-yl)methanol | 265 | 1.140, 495, S | 1H NMR (400 MHz, CDCl3) δ 8.78 (s, 1H), 8.64 (s, 1H), 8.39 (m, 2H), 8.01 (s, 2H), 6.97-6.96 (d, J = 5.6 Hz, 1H), 4.93 (s, 2H), 4.36-4.31 (m, 1H), 4.05 (s, 1H), 2.85-2.81 (m, 1H), 2.63-2.60 (m, 1H), 2.34-2.30 (m, 2H), 2.28-2.14 (m, 1H), 1.95-1.86 (m, 2H), 1.55-1.50 (m, 2H), 1.49-1.41 (m, 1H), 1.26-1.18 (m, 2H), 1.03-1.02 (d, J = 6.4 Hz, 3H) |
| 475 | (6-(2-(1-(cyclopropylsulfonyl)-1H-pyrazol-4-yl)pyrimidin-4-ylamino)-1-phenyl-1H-imidazo[4,5-c]pyridin-2-yl)methanol | 265 | 2.027, 489, S | 1H NMR (300 MHz, DMSO-d6): δ 10.32 (s, 1H), 8.77 (s, 1H), 8.52 (s, 1H), 8.38-8.36 (d, J = 6.0 Hz, 1H), 8.11 (s, 1H), 7.96 (s, 1H), 7.77-7.59 (m, 5H), 7.18-7.16 (d, J = 4.8 Hz, 1H), 5.59 (m, 1H), 4.62-4.60 (d, J = 5.7 Hz, 2H), 3.28-3.20 (m, 1H), 1.39-1.25 (m, 4H) |
| 476 | 4-(6-(2-(1-(cyclopropylsulfonyl)-1H-pyrazol-4-yl)pyrimidin-4-ylamino)-2-(hydroxymethyl)-1H-imidazo[4,5-c]pyridin-1-yl)-1-methylpyrrolidin-2-one | 265 | 0.963, 510, L | 1H NMR (300 MHz, DMSO-d6): δ 10.25 (s, 1H), 8.71 (s, 1H), 8.65 (s, 1H), 8.44-8.41 (m, 2H), 7.71-7.69 (d, J = 5.7 Hz, 1H), 7.49 (s, 1H), 5.85 (s, 1H), 5.58-5.55 (m, 1H), 4.76 (s, 2H), 3.96-3.90 (m, 1H), 3.73-3.68 (m, 1H), 3.32-3.25 (m, 1H), 2.98-2.70 (m, 5H), 1.39-1.24 (m, 4H) |

TABLE 4-continued

| Example | Structure/Name | Synthesis Method/ Example # | LCMS R_T (min), [M + H]+, method | 1H NMR (ppm) |
|---|---|---|---|---|
| 477 | (6-(2-(1-(cyclopropylsulfonyl)-1H-pyrazol-4-yl)pyrimidin-4-ylamino)-1-(1-methylcyclopentyl)-1H-imidazo[4,5-c]pyridin-2-yl)methanol | 265 | 2.031, 495, L | 1H NMR (300 MHz, CDCl3) δ 8.71 (s, 1H), 8.66 (s, 1H), 8.46 (s, 1H), 8.38 (m, 2H), 8.21 (s, 1H), 6.90-6.88 (d, J = 6.0 Hz, 1H), 4.98 (s, 2H), 4.30 (s, 1H), 2.87-2.78 (m, 1H), 2.56-2.52 (m, 2H), 2.40-2.37 (m, 2H), 2.01-1.97 (m, 4H), 1.64 (s, 3H), 1.55-1.46 (m, 2H), 1.44-1.30 (m, 2H) |
| 478 | (6-(2-(1-(cyclopropylsulfonyl)-1H-pyrazol-4-yl)pyrimidin-4-ylamino)-1-(4-methylpentan-2-yl)-1H-imidazo[4,5-c]pyridin-2-yl)methanol | 265 | 1.748, 497, R | 1H NMR (300 MHz, DMSO-d6): δ 10.26 (s, 1H), 8.70 (s, 1H), 8.38-8.48 (m, 3H), 7.32 (d, J = 9 Hz, 3H), 5.77-5.74 (m, 1H), 4.86-4.84 (m, 1H), 4.73 (d, J = 6 Hz, 1H), 3.25-3.23 (m, 1H), 2.12-2.10 (m, 1H), 1.82-1.80 (m, 1H), 1.62 (m, 3H), 1.34-1.28 (m, 5H), 0.90 (m, 3H), 0.77 (m, 3H). |
| 479 | (1-cyclohexyl-6-(2-(1-(cyclopropylsulfonyl)-1H-pyrazol-4-yl)pyrimidin-4-ylamino)-1H-imidazo[4,5-c]pyridin-2-yl)methanol | 265 | 1.358, 495, R | 1H NMR (300 MHz, DMSO-d6): δ 10.14 (s, 1H), 8.65-8.63 (s, 2H), 8.45-8.40 (m, 2H), 8.19 (s, 1H), 7.38 (s, 1H), 5.72 (m, 1H), 4.74 (m, 2H), 4.52 (s, 1H), 3.33 (s, 1H), 2.27-2.22 (m, 6H), 1.67 (m, 1H), 1.42-1.23 (m, 7H). |
| 480 | (6-(2-(1-(cyclopropylsulfonyl)-1H-pyrazol-4-yl)pyrimidin-4-ylamino)-1-(3,3-difluoroCyclobutyl)-1H-imidazo[4,5-c]pyridin-2-yl)methanol | 265 | 1.444, 503, R | 1H NMR (300 MHz, DMSO-d6): δ 10.24 (s, 1H), 7.69 (d, 2H), 8.45-8.43 (m, 2H), 8.02 (s, 1 H), 7.41 (d, J = 6 Hz, 1H), 5.78 (m, 1H), 5.24-5.16 (m, 1H), 4.76 (m, 2H), 3.52-3.46 (m, 2H), 3.31-3.22 (m, 3H), 1.35-1.31 (m, 2H), 1.28-1.21 (m, 2H). |

TABLE 4-continued

| Example | Structure/Name | Synthesis Method/ Example # | LCMS R$_T$ (min), [M + H]$^+$, method | $^1$H NMR (ppm) |
|---|---|---|---|---|
| 481 | (1-cyclopentyl-6-(2-(1-(cyclopropylsulfonyl)-1H-pyrazol-4-yl) pyrimidin-4-ylamino)-1H-imidazo[4,5-c]pyridin-2-yl)methanol | 265 | 1.491, 481, R | $^1$H NMR (300 MHz, DMSO-d$_6$): δ 10.19 (s, 1H), 8.67 (s, 1H), 8.42-8.41 (s, 1H), 8.42 (m, 2H), 8.00 (s, 1H), 7.41 (s, 1H), 5.71 (m, 1H), 5.11-5.05 (m, 1H), 4.74 (d, J = 5.7 Hz, 2H), 3.22-3.16 (m, 1H), 4.22 (m, 4H), 1.91 (m, 2H), 1.71 (m, 2H), 1.30 (m, 4H). |
| 482 | (6-((2-(1-(cyclopropylsulfonyl)-1H-pyrazol-4-yl)pyrimidin-4-yl)amino)-1-(3,3-difluorocyclopentyl)-1H-imidazo[4,5-c]pyridin-2-yl)methanol | 265 | 1.451, 517, R | $^1$H NMR (300 MHz, DMSO-d$_6$): δ 10.19 (s, 1H), 8.69 (s, 1H), 8.62 (s, 1H), 8.42 (m, 2H), 7.93 (s, 1H), 7.45 (s, 1H), 5.77 (m, 1H), 5.36 (m, 1H), 4.77 (d, J = 5.7 Hz, 2H), 3.32-3.20 (m, 1H), 2.74-2.68 (m, 2H), 2.50-2.44 (m, 4H), 1.34-1.25 (m, 4H). |
| 483 | (6-(2-(1-(cyclopropylsulfonyl)-1H-pyrazol-4-yl)pyrimidin-4-ylamino)-1-(3,3,3-trifluoropropyl)-1H-imidazo[4,5-c]pyridin-2-yl)methanol | 265 | 1.409, 509, N | $^1$H NMR (300 MHz, DMSO-d$_6$): δ 10.30 (s, 1H), 8.73 (s, 1H), 8.66 (s, 1H), 8.49 (s, 1H), 8.40 (d, J = 5.7 Hz, 1H), 8.34 (s, 1H), 7.24 (d, J = 5.7 Hz, 1H), 5.84 (m, 1H), 4.77 (m, 2H), 4.64 (m, 2H), 3.32-3.29 (m, 1H), 3.00-2.89 (m, 2H), 1.38-1.32 (m, 2H), 1.29-1.25 (m, 2H) |
| 484 | (6-(2-(1-(cyclopropylsulfonyl)-1H-pyrazol-4-yl)pyrimidin-4-ylamino)-1-(1-methylcyclobutyl)-1H-imidazo[4,5-c]pyridin-2-yl)methanol | 265 | 1.466, 481, R | $^1$H NMR (400 MHz, DMSO-d$_6$): δ 10.20 (s, 1H), 8.65 (s, 2H), 8.46 (s, 1H), 8.39 (d, J = 4.5 Hz, 1H), 8.07 (s, 1H), 7.27 (s, 1H), 5.57 (m, 1H), 4.66 (d, J = 4.2 Hz, 2H), 3.32-3.22 (m, 1H), 2.92-2.85 (m, 2H), 2.50 (s, 2H), 2.10-1.99 (m, 1H), 1.95-1.82 (m, 1H), 1.76 (s, 3H), 1.33-1.32 (m, 2H), 1.30-1.22 (m, 2H) |

TABLE 4-continued

| Example | Structure/Name | Synthesis Method/ Example # | LCMS R$_T$ (min), [M + H]$^+$, method | $^1$H NMR (ppm) |
|---|---|---|---|---|
| 485 | (1-tert-butyl-6-(2-(1-(cyclopropylsulfonyl)-1H-pyrazol-4-yl)pyrimidin-4-ylamino)-1H-imidazo[4,5-c]pyridin-2-yl)methanol | 265 | 1.457, 469, R | $^1$H NMR (400 MHz, DMSO-d$_6$): δ 10.22 (s, 1H), 8.66 (s, 2H), 8.61 (s, 1H), 8.04 (s, 1H), 8.40 (d, J = 5.6 Hz, 1H), 7.29 (s, 1H), 5.65 (m, 1H), 4.83 (d, J = 5.6 Hz, 2H), 3.32-3.29 (m, 1H), 1.90 (s, 9H), 1.36-1.32 (m, 2H), 1.30-1.26 (m, 2H) |
| 486 | (6-(2-(1-(cyclopropylsulfonyl)-1H-pyrazol-4-yl)pyrimidin-4-ylamino)-1-phenethyl-1H-imidazo[4,5-c]pyridin-2-yl)methanol | 265 | 1.596, 517, R | $^1$H NMR (300 MHz, DMSO-d$_6$): δ 10.23 (s, 1H), 8.74 (s, 1H), 8.64 (d, J = 0.6 Hz, 1H), 8.52 (s, 1H), 8.40 (d, J = 5.7 Hz, 1H), 8.25 (s, 1H), 7.25-7.16 (m, 4H), 7.07-7.04 (m, 2H), 5.68 (m, 1H), 4.57 (m, 2H), 4.40 (d, J = 5.7 Hz, 2H), 3.31-3.21 (m, 1H), 3.19-3.11 (m, 2H), 1.38-1.32 (m, 2H), 1.29-1.20 (m, 2H) |
| 487 | (6-(2-(1-(cyclopropylsulfonyl)-1H-pyrazol-4-yl)pyrimidin-4-ylamino)-1-(3-methylbutan-2-yl)-1H-imidazo[4,5-c]pyridin-2-yl)methanol | 265 | 1.978, 483, M | $^1$H NMR (300 MHz, DMSO-d$_6$) δ 10.20 (s, 1H), 8.67-8.62 (m, 2H), 8.45 (s, 1H), 8.41-8.37 (m, 2H), 7.27 (s, 1H), 5.74-5.69 (m, 1H), 4.79-4.66 (m, 2H), 4.40-4.34 (m, 1H), 3.26 (s, 1H), 2.51-2.42 (m, 1H), 1.65 (d, J = 6.9 Hz, 3H), 1.37-1.26 (m, 7H), 0.62 (m, 3H) |
| 488 | (1-(1-cyclopropylpropan-2-yl)-6-(2-(1-(cyclopropylsulfonyl)-1H-pyrazol-4-yl)pyrimidin-4-ylamino)-1H-imidazo[4,5-c]pyridin-2-yl)methanol | 265 | 2.036, 495, M | $^1$H NMR (300 MHz, DMSO-d$_6$) δ 10.20 (s, 1H), 8.66 (s, 1H), 8.64 (s, 1H), 8.46 (s, 1H), 8.41 (s, 1H), 8.39 (s, 1H), 7.29 (s, 1H), 5.72 (m, 1H), 4.91-4.74 (m, 3H), 3.31-3.23 (m, 1H), 2.51-2.06 (m, 1H), 1.82-1.75 (m, 1H), 1.68-1.66 (m, 1H), 1.66 (d, J = 6.9 Hz, 3H), 1.33-1.24 (m, 4H), 0.46-0.44 (m, 1H), 0.35-0.33 (m, 1H), 0.21-0.18 (m, 1H), 0.11-0.08 (m, 1H), −0.20- −0.23 (m, 1H) |

TABLE 4-continued

| Example | Structure/Name | Synthesis Method/ Example # | LCMS R$_T$ (min), [M + H]$^+$, method | $^1$H NMR (ppm) |
|---|---|---|---|---|
| 489 | 2-{6-[2-(4-Methoxypiperidin-1-yl)pyrimidin-4-ylamino]-2-methyl-imidazo[4,5-c]pyridin-1-yl}propan-1-ol | 268 | 1.97, 398.2, F | $^1$H NMR (DMSO-d$_6$) δ 9.67 (1H, s), 8.49 (1H, s), 8.32 (1H, br s), 7.94 (1H, d, J = 5.6 Hz), 6.40 (1H, br d, J = 5.6 Hz), 5.04 (1H, t, J = 5.3 Hz), 4.58-4.49 (1H, m), 4.26-4.21 (2H, m), 3.92-3.86 (1H, m), 3.76-3.71 (1H, m), 3.48-3.42 (1H, m), 3.39-3.35 (1H, m), 3.30 (3H, s), 2.54 (3H, s), 1.94-1.87 (2H, m), 1.52 (3H, d, J = 7.1 Hz), 1.46-1.38 (2H, m). |
| 490 | [1-((S)-2-Methoxy-1-methylethyl)-2-methyl-1H-imidazo[4,5-c]pyridin-6-yl]-[2-(4-methoxypiperidin-1-yl)pyrimidin-4-yl]amine | 268 | 2.25, 412.2, F | $^1$H NMR (DMSO-d$_6$) δ 9.69 (1H, s), 8.50 (1H, s), 8.33 (1H, br s), 7.95 (1H, d, J = 5.7 Hz), 6.41 (1H, br d, J = 5.7 Hz), 4.77-4.69 (1H, m), 4.27-4.21 (2H, m), 3.83 (1H, t, J = 9.5 Hz), 3.68 (1H, dd, J = 10.0, 4.7 Hz), 3.49-3.43 (1H, m), 3.40-3.34 (2H, m), 3.30 (3H, s), 3.19 (3H, s), 2.54 (3H, s), 1.94-1.88 (2H, m), 1.56 (3H, d, J = 7.1 Hz), 1.48-1.39 (2H, m). |
| 491 | [1-(3-Methoxy-1-methylpropyl)-2-methyl-1H-imidazo[4,5-c]pyridin-6-yl]-[2-(4-methoxypiperidin-1-yl)pyrimidin-4-yl]amine | 268 | 2.33, 426.2, F | $^1$H NMR (DMSO-d$_6$) 9.71 (1H, s), 8.51 (1H, s), 8.35 (1H, br s), 7.95 (1H, d, J = 5.7 Hz), 6.40 (1H, br d, J = 5.7 Hz), 4.69-4.60 (1H, m), 4.27-4.21 (2H, m), 3.49-3.43 (1H, m), 3.40-3.34 (2H, m), 3.30 (3H, s), 3.27-3.22 (1H, m), 3.15 (3H, s), 2.95-2.89 (1H, m), 2.53 (3H, s), 2.29-2.21 (1H, m), 2.15-2.07 (1H, m), 1.94-1.88 (2H, m), 1.58 (3H, d, J = 7.0 Hz), 1.47-1.38 (2H, m). |

TABLE 4-continued

| Example | Structure/Name | Synthesis Method/ Example # | LCMS $R_T$ (min), [M + H]+, method | $^1$H NMR (ppm) |
|---|---|---|---|---|
| 492 | 3-{6-[2-(4-Methoxypiperidin-1-yl)pyrimidin-4-ylamino]-2-methylimidazo[4,5-c]pyridin-1-yl}butan-1-ol | 268 | 2.02, 412.2, F | $^1$H NMR (DMSO-d$_6$) δ 9.70 (1H, s), 8.50 (1H, s), 8.35 (1H, br s), 8.17 (1H, s), 7.95 (1H, d, J = 5.6 Hz), 6.39 (1H, br d, J = 5.6 Hz), 4.75-4.66 (1H, m), 4.27-4.21 (2H, m), 3.49-3.43 (1H, m), 3.40-3.32 (3H, m), 3.30 (3H, s), 3.07-3.01 (1H, m), 2.55 (3H, s), 2.25-2.17 (1H, m), 2.03-1.88 (3H, m), 1.57 (3H, d, J = 7.0 Hz), 1.47-1.38 (2H, m). |
| 493 | (1-Isopropyl-2-methyl-1H-imidazo[4,5-c]pyridin-6-yl)-[2-((1RS,3RS,5SR)-3-methoxy-8-azabicyclo[3.2.1]oct-8-yl)pyrimidin-4-yl]amine | 46 | 2.54, 408.2, F | $^1$H NMR (DMSO-d$_6$) δ 9.69 (1H, s), 8.50 (1H, s), 8.44 (1H, br s), 8.18 (1H, s), 7.95 (1H, d, J = 5.7 Hz), 6.40 (1H, br d, J = 5.7 Hz), 4.72 (1H, septet, J = 6.9 Hz), 4.66 (2H, br s), 3.47-3.45 (1H, m), 3.25 (3H, s), 2.56 (3H, s), 2.11-1.82 (8H, m), 1.58 (6H, d, J = 6.9 Hz). |
| 494 | N-(2-(4-Methoxypiperidin-yl)pyrimidin-4-yl)-2-methyl-1-phenyl-1H-imidazo[4,5-c]pyridin-6-amine | 18 | 2.71, 416.1, F | $^1$H NMR (DMSO-d$_6$) δ 9.80 (1 H, s), 8.60 (1H, s), 8.11 (1 H, s), 7.90 (1 H, d, J = 5.6 Hz), 7.56-7.70 (5 H, m), 6.29 (1 H, d, J = 5.7 Hz), 3.74-3.87 (2 H, m), 3.39-3.34 (1 H, m), 3.27 (3H, s), 2.96-3.12 (2 H, m), 2.40 (3 H, s), 1.52-1.64 (2H, s), 1.07-1.22 (2 H, m). |
| 495 | N-(2-(1-Oxa-7-azaspiro[3.5]nonan-7-yl)pyrimidin-4-yl)-1-isopropyl-2-methyl-1H-imidazo[4,5-c]pyridin-6-amine | 46 | 2.16, 394.3, F | $^1$H NMR (DMSO-d$_6$) δ 9.66 (1H, s), 8.50 (1H, d, J = 1 Hz), 8.36 (1H, s), 7.95 (1H, d, J = 5.6 Hz), 6.42 (1H, d, J = 5.6 Hz), 4.72 (1H, sept, J = 6.9 Hz), 4.45 (2H, t, J = 7.9 Hz), 3.70-3.87 (4H, m), 2.56 (3H, s), 2.41 (2H, J = 7.9 Hz), 1.75-1.87 (4H, m), 1.58 (6H, d, J = 7.9 Hz). |

TABLE 4-continued

| Example | Structure/Name | Synthesis Method/ Example # | LCMS $R_T$ (min), $[M+H]^+$, method | $^1$H NMR (ppm) |
|---|---|---|---|---|
| 496 | 1-Isopropyl-2-methyl-N-(2-(pyrrolo[3,4-c]pyrazol-5(2H,4H,6H)-yl)pyrimidin-4-yl)-1H-imidazo[4,5-c]pyridin-6-amine | 46 | 2.01, 376.2, F | $^1$H NMR (DMSO-$d_6$) δ 12.71 (1H, s), 9.78 (1H, s), 8.65 (1H, s), 8.51 (1H, s), 8.01 (1H, s), 7.60 (1H, br s), 6.48 (1H, d, J = 5.6 Hz), 4.77 (1H, septet, J = 6.9 Hz), 4.51-4.78 (4H, m), 2.58 (3H, s), 1.64 (6H, d, J = 6.9 Hz). |
| 497 | 3-(1-(4-((1-Isopropyl-2-methyl-1H-imidazo[4,5-c]pyridin-6-yl)amino)pyrimidin-2-yl)-4-methoxypiperidin-4-yl)propan-1-ol | 46 | 2.15, 440.2, F | $^1$H NMR (DMSO-$d_6$) δ 9.67 (1H, s), 8.50 (1H, d, J = 0.9 Hz), 8.39 (1H, s), 7.95 (1H, d, J = 5.6 Hz), 6.39 (1H, d, J = 5.6 Hz), 4.71 (1H, septet, J = 6.9 Hz), 4.40 (1H, d, J = 5.2 Hz), 4.29-4.37 (2H, m), 3.39 (1H, q, J = 5.2 Hz), 3.17-3.24 (2H, m), 3.12 (3H, s), 2.56 (3H, s), 1.71-1.79 (2H, m), 1.56 (6H, d, J = 6.9 Hz), 1.35-1.52 (7H, m) |
| 498 | (±)-(cis)-5-(4-((1-Isopropyl-2-methyl-1H-imidazo[4,5-c]pyridin-6-yl)amino)pyrimidin-2-yl)hexahydrooxazolo[4,5-c]pyridin-2(3H)-one | 46 | 1.82, 409.1, F | $^1$H NMR (DMSO-$d_6$) δ 9.74 (1H, s), 8.51 (1H, br s), 8.50 (1H, s), 7.96 (1H, d, J = 5.6 Hz), 7.69 (1H, s), 6.42 (1H, d, J = 5.6 Hz), 4.89-4.95 (1H, m), 4.72 (1H, septet, J = 6.9 Hz), 4.32 (1H, dd, J = 14.0, 2.8 Hz), 4.08-4.14 (1H, m), 3.57-3.76 (2H, m), 3.47 (1H, dd, J = 14.0, 2.8 Hz), 2.56 (3H, s), 2.13-2.24 (1H, m), 1.99-2.09 (1H, m), 1.56 (6H, d, J = 6.9 Hz). |
| 499 | N$^4$-(1-Isopropyl-2-methyl-1H-imidazo[4,5-c]pyridin-6-yl)-N2-(2-methyl-2-(methylsulfonyl)propyl)pyrimidine-2,4-diamine | 17 | 2.01, 418.1, F | $^1$H NMR (DMSO-$d_6$) δ 9.57 (1H, s), 8.50 (1H, s), 8.14 (1H, br s), 7.93 (1H, d, J = 5.6 Hz), 6.71 (1H, d, J = 5.6 Hz), 6.41 (1H, br s), 4.68 (1H, septet, J = 6.9 Hz), 3.77 (2H, d, J = 6.0 Hz), 2.98 (3H, s), 2.56 (3H, s), 1.56 (6H, d, J = 6.9 Hz), 1.33 (6H, s). |

TABLE 4-continued

| Example | Structure/Name | Synthesis Method/ Example # | LCMS R_T (min), [M + H]+, method | 1H NMR (ppm) |
|---|---|---|---|---|
| 500 | 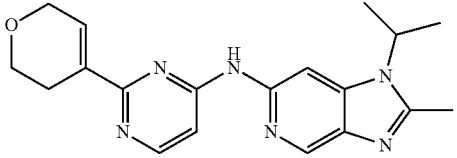 [SMILES: Cc1nc2cnc(Nc3ccnc(C4=CCOCC4)n3)cc2n1C(C)C]<br>N-(2-(3,6-Dihydro-2H-pyran-4-yl)pyrimidin-4-yl)-1-isopropyl-2-methyl-1H-imidazo[4,5-c]pyridin-6-amine | 269 | 2.25, 351.2, F | 1H NMR (DMSO-d6) δ 10.02 (1H, s), 8.54 (1H, s), 8.52 (1H, br s), 8.33 (1H, d, J = 5.6 Hz), 7.18-7.22 (1H, m), 7.10 (1H, d, J = 5.6 Hz), 4.73 (1H, septet, J = 6.9 Hz), 4.30-4.34 (1H m), 3.85 (2H, t, J = 5.3 Hz), 2.61-2.69 (2H, m), 2.57 (3H, s), 1.58 (6H, d, J = 6.9 Hz). |
| 501 | 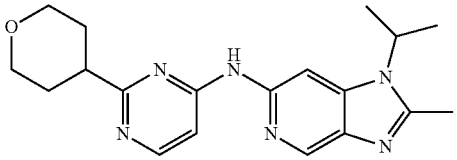 [SMILES: Cc1nc2cnc(Nc3ccnc(C4CCOCC4)n3)cc2n1C(C)C]<br>1-Isopropyl-2-methyl-N-(2-(tetrahydro-2H-pyran-4-yl)pyrimidin-4-yl)-1H-imidazo[4,5-c]pyridin-6-amine | 269 | 2.05, 353.2, F | 1H NMR (DMSO-d6) δ 10.01 (1H, s), 8.61 (1H, br s), 8.52 (1H, d, J = 0.9 Hz), 8.27 (1H, d, J = 5.6 Hz), 7.08 (1H, br d, J = 5.6 Hz), 4.73 (1H, septet, J = 6.9 Hz), 3.93-4.00 (2H, m), 3.42 (2H, m), 2.89-2.99 (1H, m), 2.56 (3H, s), 1.83-1.95 (4H, m), 6H, d, J = 6.9 Hz). |
| 502 | 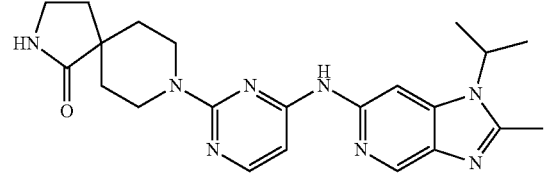 [SMILES: Cc1nc2cnc(Nc3ccnc(N4CCC5(CCNC5=O)CC4)n3)cc2n1C(C)C]<br>8-(4-((1-Isopropyl-2-methyl-1H-imidazo[4,5-c]pyridin-6-yl)amino) pyrimidin-2-yl)-2,8-diazaspiro[4.5]decan-1-one | 46 | 2.02, 421.2, F | 1H NMR (DMSO-d6) δ 9.69 (1H, s), 8.50 (1H, d, J = 0.9 Hz), 8.37 (1H, s), 7.96 (1H, d, J = 5.6 Hz), 7.59 (1H, s), 6.43 (1H, d, J = 5.6 Hz), 4.70 (1H, septet, J = 6.9 Hz), 4.51-4.59 (2H, m), 4.04-4.11 (1H, m), 3.22 (2H, t, J = 6.7 Hz), 3.10-3.19 (4H, m), 2.06 (2H, t, J = 6.7 Hz), 1.61-1.71 (2H, m), 1.55 (6H, d, J = 6.9 Hz), 1.38-1.45 (2H, m). |
| 503 | 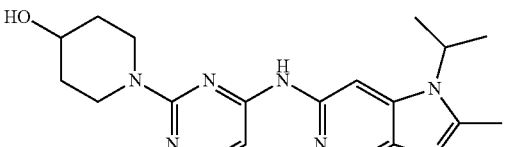<br>1-(4-((1-Isopropyl-2-methyl-1H-imidazo[4,5-c]pyridin-6-yl)amino)pyrimidin-2-yl)piperidin-4-ol | 46 | 1.92, 368.2, F | 1H NMR (DMSO-d6) δ 9.69 (1H, s), 8.50 (1H, s), 8.39 (1H, s), 7.94 (1H, d, J = 5.6 Hz), 6.38 (1H, d, J = 5.6 Hz), 4.66-4.76 (2H, m), 4.25-4.33 (2H, m), 3.69-3.78 (1H, m), 3.23-3.31 (2H, m), 2.56 (3H, s), 1.75-1.85 (2H, m), 1.56 (6H, d, J = 6.9 Hz) 1.31-1.43 (2H, m). |

TABLE 4-continued

| Example | Structure/Name | Synthesis Method/ Example # | LCMS R_T (min), [M + H]+, method | 1H NMR (ppm) |
|---|---|---|---|---|
| 504 | 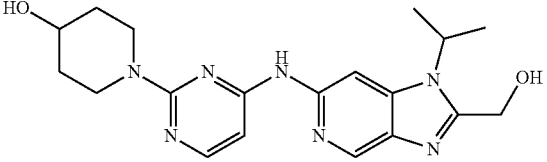 [SMILES: CC(C)n1c(CO)nc2cnc(Nc3ccnc(N4CCC(O)CC4)n3)cc21] 1-(4-((2-(Hydroxymethyl)-isopropyl-1H-imidazo[4,5-c]pyridin-6-yl)amino)pyrimidin-2-yl)piperidin-4-ol | 273 | 1.86, 384.1, F | 1H NMR (DMSO-$d_6$) δ 9.74 (1H, s), 8.59 (1H, s), 8.46 (1H, s), 7.95 (1H, d, J = 5.6 Hz), 6.39 (1H, d, J = 5.6 Hz), 5.68 (1H, t, J = 6.0 Hz), 4.96 (1H, septet, J = 6.9 Hz), 4.68-4.73 (3H, m), 4.30-4.39 (2H, m), 3.69-3.79 (1H, m), 3.24-3.32 (2H, m), 1.75-1.85 (2H, m), 1.58 (6H, d, J = 6.9 Hz) 1.31-1.43 (2H, m). |
| 505 | 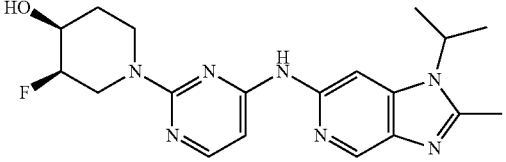 [SMILES: Cc1nc2cnc(Nc3ccnc(N4CC[C@H](O)[C@H](F)C4)n3)cc2n1C(C)C] (±)-3-Fluoro-1-(4-((1-isopropyl-2-methyl-1H-imidazo[4,5-c]pyridin-6-yl)amino)pyrimidin-2-yl)piperidin-4-ol | 46 | 1.87, 386.1, F | 1H NMR (DMSO-$d_6$) δ 9.72 (1H, s), 8.51 (1H, s), 8.35 (1H, s), 7.95 (1H, d, J = 5.6 Hz), 6.43 (1H, d, J = 5.6 Hz), 5.11 (1H, d, J = 5.4 Hz), 4.52-4.77 (3H, m), 4.31-4.39 (1H, m), 3.78-3.91 (1H, m), 3.45-3.59 (1H, m), 2.56 (3H, s), 1.66-1.76 (2H, m), 1.57 (6H, 2xd, J = 6.9 Hz) |
| 506 | 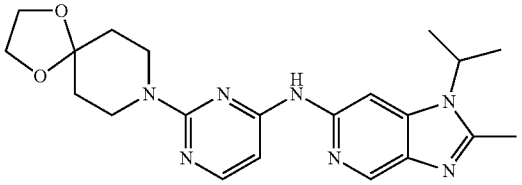 [SMILES: Cc1nc2cnc(Nc3ccnc(N4CCC5(CC4)OCCO5)n3)cc2n1C(C)C] N-(2-(1,4-Dioxa-8-azaspiro[4.5]decan-8-yl)pyrimidin-4-yl)-1-isopropyl-2-methyl-1H-imidazo[4,5-c]pyridin-6-amine | 46 | 2.29, 410.2, F | 1H NMR (DMSO-$d_6$) δ 9.70 (1H, s), 8.50 (1H, s), 8.33 (1H, s), 7.96 (1H, d, J = 5.6 Hz), 6.44 (1H, d, J = 5.6 Hz), 4.71 (1H, septet, J = 6.9 Hz), 3.95 (4H, br s), 3.85-3.91 (4H, m), 2.56 (3H, s), 1.62-1.68 (4H, m), 1.55 (6H, d, J = 6.9 Hz) |
| 507 | 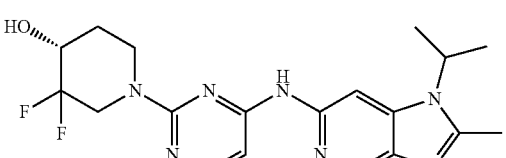 (±)-3,3-Difluoro-1-(4-((1-isopropyl-2-methyl-1H-imidazo[4,5-c]pyridin-6-yl)amino)pyrimidin-2-yl)piperidin-4-ol | 46 | 2.08, 404.1, F | 1H NMR (DMSO-$d_6$) δ 9.78 (1H, s), 8.52 (1H, s), 8.28 (1H, s), 7.95 (1H, d, J = 5.6 Hz), 6.51 (1H, d, J = 5.6 Hz), 5.73 (1H, d, J = 5.4 Hz), 4.73 (1H, septet, 6.9 Hz), 4.23-4.37 (1H, m), 3.86-4.10 (3H, m), 3.68-3.78 (1H, m), 2.56 (3H, s), 1.82-1.92 (1H, m), 1.63-1.74 (1H, m), 1.57 (6H, d, J = 6.9 Hz) |

TABLE 4-continued

| Example | Structure/Name | Synthesis Method/ Example # | LCMS $R_T$ (min), [M + H]$^+$, method | $^1$H NMR (ppm) |
|---|---|---|---|---|
| 508 | (±)-1-(4-((1-Isopropyl-2-methyl-1H-imidazo[4,5-c]pyridin-6-yl)amino)pyrimidin-2-yl)-4-methoxypiperidin-3-ol | 46 | 1.97, 398.1, F | $^1$H NMR (DMSO-$d_6$) δ 9.67 (1H, s), 8.49 (1H, s), 8.34 (1H, s), 7.94 (1H, d, J = 5.6 Hz), 6.43 (1H, d, J = 5.6 Hz), 5.05 (1H, d, J = 5.1 Hz), 4.72 (1H, septet, 6.9 Hz), 4.27-4.39 (2H, m), 3.37 (3H, s), 3.34-3.42 (1H, m), 3.15-3.28 (2H, m), 3.04-3.12 (1H, m), 2.56 (3H, s), 1.99-2.07 (1H, m), 1.57 (3H, d, J = 6.9 Hz), 1.56 (3H, d, J = 6.9 Hz), 1.28-1.39 (1H, m) |
| 509 | (±)-1-(4-((1-Isopropyl-2-methyl-1H-imidazo[4,5-c]pyridin-6-yl)amino)pyrimidin-2-yl)-3-methoxypiperidin-4-ol | 46 | 1.90, 398.1, F | $^1$H NMR (DMSO-$d_6$) δ 9.66 (1H, s), 8.50 (1H, s), 8.32 (1H, s), 7.95 (1H, d, J = 5.6 Hz), 6.43 (1H, d, J = 5.6 Hz), 4.96 (1H, d, J = 5.1 Hz), 4.72 (1H, septet, 6.9 Hz), 4.20 (1H, dd, J = 12.6, 3.6 Hz), 4.01-4.10 (1H, m), 3.59-3.66 (1H, m), 3.43-3.57 (2H, m), 3.34 (3H, s), 3.00-3.05 (1H, m), 2.56 (3H, s), 1.89-1.80 (1H, m), 1.57 (6H, 2xd, J = 6.9 Hz), 1.37-1.47 (1H, m) |
| 510 | (±)-3-Fluoro-1-(4-((2-(hydroxymethyl)-1-isopropyl-1H-imidazo[4,5-c]pyridin-6-yl)amino)pyrimidin-2-yl)piperidin-4-ol | 273 | 1.75, 402.1, F | $^1$H NMR (DMSO-$d_6$) δ 9.77 (1H, s), 8.60 (1H, s), 8.41 (1H, s), 7.96 (1H, d, J = 5.6 Hz), 6.43 (1H, d, J = 5.6 Hz), 5.68 (1H, br s), 5.12 (1H, br s), 4.96 (1H, septet, 6.9 Hz), 4.53-4.77 (4H, m), 4.33-4.42 (1H, m), 3.78-3.91 (1H, m), 3.45-3.58 (1H, m), 1.66-1.78 (2H, m), 1.60 (3H, d, J = 6.9 Hz), 1.59 (3H, d, J = 6.9 Hz) |

TABLE 4-continued

| Example | Structure/Name | Synthesis Method/ Example # | LCMS R$_T$ (min), [M + H]$^+$, method | $^1$H NMR (ppm) |
|---|---|---|---|---|
| 511 | (±)-1-Isopropyl-N-(2-(4-methoxy-2-methylpiperidin-1-yl)pyrimidin-4-yl)-2-methyl-1H-imidazo[4,5-c]pyridin-6-amine | 46 | 2.42, 396.2, F | $^1$H NMR (CDCl$_3$) δ 8.61 (1H, s), 8.38 (1H, s), 8.03 (1H, d, J = 6.9 Hz), 7.39 (1H, br s), 5.97 (1H, d, J = 5.6 Hz), 5.02-5.11 (1H, m), 4.58-4.71 (2H, m), 3.66 (1H, pentet, J = 3.1 Hz), 3.40 (3H, s), 3.35 (1H, dt, J = 13.2, 2.9 Hz), 2.62 (3H, s), 1.91-1.99 (2H, m), 1.67-1.87 (2H, m), 1.67 (3H, d, J = 6.9 Hz), 1.66 (3H, d, J = 6.9 Hz), 1.39 (3H, d, J = 6.9 Hz) |
| 512 | (1-Isopropyl-6-((2-(4-(trifluoromethyl)piperidin-1-yl)pyrimidin-4-yl)amino)-imidazo[4,5-c]pyridin-2-yl)methanol | 273 | 2.64, 436.2, F | $^1$H NMR (DMSO-d$_6$) δ 9.79 (1H, s), 8.60 (1H, s), 8.38 (1H, s), 7.99 (1H, d, J = 5.6 Hz), 6.48 (1H, d, J = 5.6 Hz), 5.68 (1H, t, J = 5.7 Hz), 4.95 (1H, septet, J = 6.9 Hz), 4.80-4.88 (2H, m), 4.71 (2H, d, J = 5.7 Hz), 2.94 (2H, br t, J = 12.6 Hz), 2.57-2.75 (1H, m), 1.84-1.94 (2H, m), 1.58 (6H, d, J = 6.9 Hz) 1.43 (2H, ddd, 12.5 Hz, 12.4, 4.4 Hz) |
| 513 | (6-((2-(4-Ethylpiperidin-1-yl)pyrimidin-4-yl)amino)-1-isopropyl-1H-imidazo[4,5-c]pyridin-2-yl)methanol | 273 | 2.72, 396.3, F | $^1$H NMR (DMSO-d$_6$) δ 9.73 (1H, s), 8.59 (1H, d, J = 0.9 Hz), 8.46 (1H, s), 7.95 (1H, d, J = 5.6 Hz), 6.38 (1H, d, J = 5.6 Hz), 5.68 (1H, t, J = 5.7 Hz), 4.95 (1H, septet, J = 6.9 Hz), 4.78-4.68 (4H, m), 4.71 (2H, d, J = 5.7 Hz), 2.86 (2H, dt, J = 12.6, 2.7 Hz), 2.57-2.75 (2H, m), 1.70-1.79 (2H, m), 1.58 (6H, d, J = 6.9 Hz) 1.37-1.48 (1H, m), 1.27 (2H, pentet, J = 6.9 Hz), 1.08 (2H, ddd, 12.3, 12.3, 4.0 Hz). |

TABLE 4-continued

| Example | Structure/Name | Synthesis Method/ Example # | LCMS R$_T$ (min), [M + H]$^+$, method | $^1$H NMR (ppm) |
|---|---|---|---|---|
| 514 | (1-Isopropyl-2-methyl-1H-imidazo[4,5-c]pyridin-6-yl)[2-(2-methyl-2,4,6,7-tetrahydropyrazolo[4,3-c]pyridin-5-yl)-pyrimidin-4-yl]amine | 46 | 2.14, 404, F | $^1$H NMR (DMSO-d$_6$) δ 9.74 (s, 1H), 8.51 (s, 1H), 8.40 (s, 1H), 7.99 (d, J = 5.7 Hz, 1H), 7.47 (s, 1H), 6.47 (d, J = 5.7 Hz, 1H), 4.78 (s, 2H), 4.78-4.70 (m, 1H), 4.11 (t, J = 5.7 Hz, 2H), 3.77 (s, 3H), 2.70 (t, J = 5.7 Hz, 2H), 2.58 (s, 3H), 1.63 (d, J = 6.9 Hz, 6H) |
| 515 | [2-(4-Dimethylaminomethyl-4-methoxypiperidin-1-yl)pyrimidin-4-yl](1-isopropyl-2-methyl-1H-imidazo[4,5-c]pyridin-6-yl)amine | 46 | 1.74, 439, F | $^1$H NMR (DMSO-d$_6$) δ 9.68, (s, 1H), 8.50 (s, 1H), 8.39 (s, 1H), 7.95 (d, J = 5.7 Hz, 1H), 6.39 (d, J = 5.7 Hz, 1H), 4.77-4.67 (m, 1H), 4.29-4.24 (m, 2H), 3.31-3.26 (m, 2H), 3.17 (s, 3H), 2.56 (s, 3H), 2.32 (s, 2H), 2.22 (s, 6H), 1.81-1.75 (m, 2H), 1.56 (d, J = 6.8 Hz, 6H), 1.55-1.48 (m, 2H) |
| 516 | (1-Isopropyl-2-methyl-1H-imidazo[4,5-c]pyridin-6-yl)[2-(4-methoxy-4-methoxymethylpiperidin-1-yl)pyrimidin-4-yl]amine | 46 | 2.32, 426, F | $^1$H NMR (DMSO-d$_6$) δ 9.69 (s, 1H), 8.50 (s, 1H), 8.39 (s, 1H), 7.95 (d, J = 5.7 Hz, 1H), 6.40 (d, J = 5.7 Hz, 1H), 4.77-4.66 (m, 1H), 4.39-4.33 (m, 2H), 3.34 (s, 2H), 3.27 (s, 3H), 3.27-3.20 (m, 2H), 3.20 (s, 3H), 2.56 (s, 3H), 1.77-1.72 (m, 2H), 1.56 (d, J = 7.0 Hz, 6H), 1.55-1.47 (m, 2H) |
| 517 | {1-[4-(1-Isopropyl-2-methyl-1H-imidazo[4,5-c]pyridin-6-ylamino)pyrimidin-2-yl]-4-methoxypiperidin-4-yl}methanol | 46 | 1.97, 412, F | $^1$H NMR (DMSO-d$_6$) δ 9.68 (s, 1H), 8.50 (s, 1H), 8.41 (s, 1H), 7.95 (d, J = 5.7 Hz, 1H), 6.39 (d, J = 5.7 Hz, 1H), 4.77-4.67 (m, 1H), 4.57 (t, J = 5.3 Hz, 1H), 4.40-4.35 (m, 2H), 3.39 (d, J = 5.3 Hz, 2H), 3.27-3.18 (m, 2H), 3.20 (s, 3H), 2.56 (s, 3H), 1.74-1.69 (m, 2H), 1.56 (d, J = 6.8 Hz, 6H), 1.52-1.45 (m, 2H) |

TABLE 4-continued

| Example | Structure/Name | Synthesis Method/ Example # | LCMS R$_T$ (min), [M + H]$^+$, method | $^1$H NMR (ppm) |
|---|---|---|---|---|
| 518 | N$^2$-(3-Amino-2,2-dimethylpropyl)-N$^4$-(1-isopropyl-2-methyl-1H-imidazo[4,5-c]pyridin-6-yl)pyrimidine-2,4-diamine | 46 | 1.68, 369, F | $^1$H NMR (DMSO-d$_6$) δ 9.50 (s, 1H), 8.48 (s, 1H), 8.30 (s, 1H), 7.86 (d, J = 5.8 Hz, 1H), 6.91-6.87 (m, 1H), 6.48 (d, J = 5.8 Hz, 1H), 4.77-4.66 (m, 1H), 3.26 (s, 2H), 2.56 (s, 3H), 2.42 (s, 2H), 1.57 (d, J = 6.9 Hz, 6H), 0.87 (s, 6H) |
| 519 | 3-[4-(1-Isopropyl-2-methyl-1H-imidazo[4,5-c]pyridin-6-ylamino)pyrimidin-2-ylamino]-2,2-dimethylpropan-1-ol | 46 | 2.10, 370, F | $^1$H NMR (DMSO-d$_6$) δ 9.54 (s, 1H), 8.49 (s, 1H), 8.24 (s, 1H), 7.87 (d, J = 5.7 Hz, 1H), 6.54 (d, J = 5.7 Hz, 1H), 6.46 (bs, 1H), 4.89 (bs, 1H), 4.77-4.67 (m, 1H), 3.24-3.17 (m, 4H), 2.56 (s, 3H), 1.57 (d, J = 6.8 Hz, 6H), 0.87 (s, 6H) |
| 520 | 2-{1-[4-(1-Isopropyl-2-methyl-1H-imidazo[4,5-c]pyridin-6-ylamino)pyrimidin-2-yl]-4-methoxypiperidin-4-yl}ethanol | 46 | 2.07, 426, F | $^1$H NMR (DMSO-d$_6$) δ 9.67 (s, 1H), 8.50 (s, 1H), 8.39 (s, 1H), 7.94 (d, J = 5.6 Hz, 1H), 6.39 (d, J = 5.6 Hz, 1H), 4.75-4.67 (m, 1H), 4.34-4.30 (m, 3H), 3.51-3.45 (m, 2H), 3.27-3.19 (m, 2H), 3.14 (s, 3H), 2.56 (s, 3H), 1.78-1.68 (m, 4H), 1.56 (d, J = 6.9 Hz, 6H), 1.54-1.45 (m, 2H) |
| 521 | {2-[4-(2-Dimethylaminoethyl)-4-methoxypiperidin-1-yl]pyrimidin-4-yl}-(1-isopropyl-2-methyl-1H-imidazo[4,5-c]pyridin-6-yl)amine | 46 | 1.78, 453, F | $^1$H NMR (400 MHz, CDCl$_3$): δ 8.61 (s, 1H), 8.34 (s, 1H), 8.03 (d, J = 5.7 Hz, 1H), 7.34 (s, 1H), 6.04 (d, J = 5.7 Hz, 1H), 4.70-4.59 (m, 1H), 4.50-4.45 (m, 2H), 3.38-3.31 (m, 2H), 3.26 (s, 3H), 2.62 (s, 3H), 2.53-2.44 (m, 2H), 2.35 (s, 6H), 1.89-1.82 (m, 2H), 1.81-1.74 (m, 2H), 1.66 (d, J = 6.8 Hz, 6H), 1.59-1.52 (m, 2H) |
| 522 | N$^4$-(1-Isopropyl-2-methyl-1H-imidazo[4,5-c]pyridin-6-yl)-N$^2$-(3-methoxy-2,2-dimethylpropyl)pyrimidine-2,4-diamine | 46 | 2.51, 384, F | $^1$H NMR (DMSO-d$_6$) δ 9.52 (s, 1H), 8.49 (s, 1H), 8.29 (s, 1H), 7.88 (d, J = 5.8 Hz, 1H), 6.50 (d, J = 5.8 Hz, 1H), 6.25 (bs, 1H), 4.78-4.67 (m, 1H), 3.30 (s, 2H), 3.23 (s, 3H), 3.15 (s, 2H), 2.56 (s, 3H), 1.57 (d, J = 6.9 Hz, 6H), 0.92 (s, 6H) |

TABLE 4-continued

| Example | Structure/Name | Synthesis Method/ Example # | LCMS $R_T$ (min), $[M + H]^+$, method | $^1$H NMR (ppm) |
|---|---|---|---|---|
| 523 | 3-[4-(1-Isopropyl-2-methyl-1H-imidazo[4,5-c]pyridin-6-ylamino)pyrimidin-2-ylamino]-2,2-dimethylpropionitrile; formate salt | 46 | 2.22, 365, F | $^1$H NMR (DMSO-$d_6$) δ 9.55 (s, 1H), 8.50 (s, 1H), 8.16 (s, 1H), 8.10 (s, 1H), 7.93 (d, J = 5.7 Hz, 1H), 6.89 (bs, 1H), 6.69 (d, J = 5.7 Hz, 1H), 4.78-4.68 (m, 1H), 3.61 (d, J = 6.5 Hz, 2H), 2.57 (s, 3H), 1.58 (d, J = 6.8 Hz, 6H), 1.33 (s, 6H) |
| 524 | (±)-[2-((cis)-3-Fluoro-4-methoxypiperidin-1-yl)pyrimidin-4-yl](1-isopropyl-2-methyl-1H-imidazo[4,5-c]pyridin-6-yl)amine; formate salt | 46 | 2.18, 400, F | $^1$H NMR (400 MHz, CDCl$_3$): δ 8.61 (s, 1H), 8.33 (s, 1H), 8.03 (d, J = 5.7 Hz, 1H), 7.56 (s, 1H), 6.09 (d, J = 5.7 Hz, 1H), 4.87-4.72 (m, 1H), 4.70-4.60 (m, 1H), 4.48-4.41 (m, 1H), 4.19-4.12 (m, 1H), 3.90 (ddd, J = 22.4, 13.9, 2.6 Hz, 1H), 3.72-3.59 (m, 2H), 3.51 (s, 3H), 2.63 (s, 3H), 2.08-1.98 (m, 1H), 1.85-1.78 (m, 1H), 1.67 (d, J = 6.9 Hz, 6H) |
| 525 | (±)-[2-((trans)-3-Fluoro-4-methoxypiperidin-1-yl)pyrimidin-4-yl]-(1-isopropyl-2-methyl-1H-imidazo[4,5-c]pyridin-6-yl)amine | 46 | 2.39, 400, F | $^1$H NMR (DMSO-$d_6$) δ 9.73 (bs, 1H), 8.50 (s, 1H), 8.31 (s, 1H), 7.97 (d, J = 5.8 Hz, 1H), 6.49 (d, J = 5.8 Hz, 1H), 4.77-4.67 (m, 1H), 4.60-4.37 (m, 2H), 4.20-4.14 (m, 1H), 3.61-3.51 (m, 2H), 3.47-3.39 (m, 1H), 3.40 (s, 3H), 2.56 (s, 3H), 2.07-1.99 (m, 1H), 1.57 (d, J = 6.9 Hz, 3H), 1.56 (d, J = 6.9 Hz, 3H), 1.53-1.49 (m, 1H) |
| 526 | (±)-{6-[2-((cis)-3-Fluoro-4-methoxypiperidin-1-yl)pyrimidin-4-ylamino]-1-isopropyl-1H-imidazo[4,5-c]pyridin-2-yl}methanol; formate salt | 46 | 2.10, 416, F | $^1$H NMR (DMSO-$d_6$) δ 9.78 (s, 1H) 8.60 (s, 1H), 8.39 (s, 1H), 8.17 (s, 1H), 7.97 (d, J = 5.8 Hz, 1H), 6.46 (d, J = 5.8 Hz, 1H), 5.69 (bs, 1H), 5.02-4.87 (m, 2H), 4.76-4.68 (m, 1H), 4.71 (s, 2H), 4.51-4.44 (m, 1H), 3.62-3.21 (m, 3H), 3.36 (s, 3H), 1.85-1.79 (m, 1H), 1.77-1.67 (m, 1H), 1.60 (2 x d, J = 6.9 Hz, 6H), |

TABLE 4-continued

| Example | Structure/Name | Synthesis Method/ Example # | LCMS $R_T$ (min), $[M + H]^+$, method | $^1$H NMR (ppm) |
|---|---|---|---|---|
| 527 | 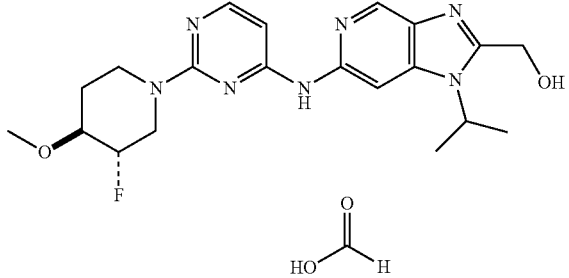 [SMILES: CO[C@H]1CCN(c2nccc(Nc3cc4c(cn3)nc(CO)n4C(C)C)n2)C[C@@H]1F ; O=CO]<br>(±)-{6-[2-((trans)-3-Fluoro-4-methoxypiperidin-1-yl)pyrimidin-4-ylamino]-1-isopropyl-1H-imidazo[4,5-c]pyridin-2-yl}methanol; formate salt | 46 | 2.29, 416, F | $^1$H NMR (DMSO-$d_6$) δ 9.81 (s, 1H), 8.60 (s, 1H), 8.37 (s, 1H), 8.16 (s, 1H), 7.98 (d, J = 5.7 Hz, 1H), 6.49 (d, J = 5.7 Hz, 1H), 5.68 (bs, 1H), 5.01-4.91 (m, 1H), 4.72 (s, 2H), 4.61-4.37 (m, 2H), 4.20-4.13 (m, 1H), 3.66-3.52 (m, 2H), 3.49-3.43 (m, 1H), 3.40 (s, 3H), 2.08-1.99 (m, 1H), 1.59 (d, J = 6.9 Hz, 3H) 1.58 (d, J = 6.9 Hz, 3H), 1.54-1.45 (m, 1H) |
| 528 | 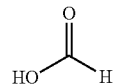<br>(±)-[2-(3,3-Difluoro-4-methoxypiperidin-1-yl)pyrimidin-4-yl](1-isopropyl-2-methyl-1H-imidazo[4,5-c]pyridin-6-yl)amine; formate salt | 46 | 2.63, 418, F | $^1$H NMR (DMSO-$d_6$) δ 9.79 (s, 1H), 8.52 (s, 1H), 8.25 (s, 1H), 8.19 (s, 1H), 7.98 (d, J = 5.7 Hz, 1H), 6.53 (d, J = 5.7 Hz, 1H), 4.78-4.67 (m, 1H), 4.34-4.24 (m, 1H), 4.07-3.97 (m, 2H), 3.80-3.69 (m, 2H), 3.46 (s, 3H), 2.57 (s, 3H), 2.00-1.91 (m, 1H), 1.78-1.69 (m, 1H), 1.57 (d, J = 6.9 Hz, 6H) |
| 529 | 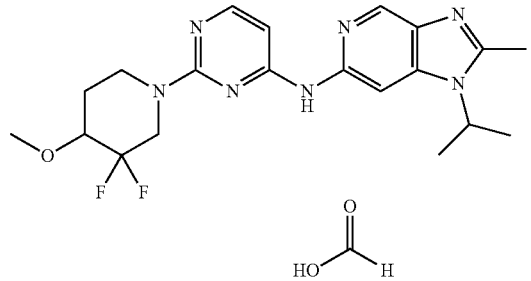<br>(±)-{6-[2-(3,3-Difluoro-4-methoxypiperidin-1-yl)pyrimidin-4-ylamino]-1-isopropyl-1H-imidazo[4,5-c]pyridin-2-yl}methanol; formate salt | 273 | 2.50, 434, F | $^1$H NMR (DMSO-$d_6$) δ 9.85 (s, 1H), 8.61 (s, 1H), 8.31 (s, 1H), 8.19 (s, 1H), 8.00 (d, J = 5.7 Hz, 1H), 6.54 (d, J = 5.7 Hz, 1H), 5.69 (bs, 1H), 5.01-4.90 (m, 1H), 4.72 (s, 2H), 4.34-4.25 (m, 1H), 4.08-3.98 (m, 2H), 3.80-3.71 (m, 2H), 3.46 (s, 3H), 2.01-1.92 (m, 1H), 1.79-1.70 (m, 1H), 1.59 (d, J = 6.9 Hz, 6H) |
| 530 | 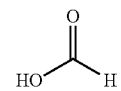<br>(±)-(1-Isopropyl-2-methyl-1H-imidazo[4,5-c]pyridin-6-yl)[2-(2-trifluoromethyl-piperidin-1-yl)pyrimidin-4-yl]amine | 46 | 3.34, 420, F | $^1$H NMR (DMSO-$d_6$) δ 8.62 (s, 1H), 8.17 (bs, 1H), 8.06 (d, J = 5.7 Hz, 1H), 7.41 (s, 1H), 6.15 (d, J = 5.7 Hz, 1H), 5.74-5.66 (m, 1H), 4.96-4.91 (m, 1H), 4.71-4.60 (m, 1H), 3.19-3.12 (m, 1H), 2.64 (s, 3H), 2.13-2.06 (m, 1H), 1.89-1.72 (m, 4H), 1.69-1.48 (m, 1H), 1.65 (2 × d, J = 6.9 Hz, 6H) |

TABLE 4-continued

| Example | Structure/Name | Synthesis Method/ Example # | LCMS $R_T$ (min), $[M + H]^+$, method | $^1$H NMR (ppm) |
|---|---|---|---|---|
| 531 | 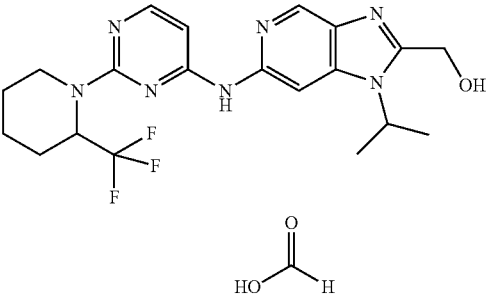 [SMILES: CC(C)n1c(CO)nc2cnc(Nc3ccnc(N4CCCCC4C(F)(F)F)n3)cc21 ; O=CO]<br>(±)-{1-Isopropyl-6-[2-(2-trifluoromethylpiperidin-1-yl)pyrimidin-4-ylamino]-1H-imidazo[4,5-c]pyridin-2-yl}methanol; formate salt | 273 | 3.14, 436, F | $^1$H NMR (DMSO-$d_6$): δ 9.83 (s, 1H), 8.57 (s, 1H), 8.24 (bs, 1H), 8.21 (s, 1H), 7.99 (d, J = 5.7 Hz, 1H), 6.56 (bs, 1H), 5.72-5.62 (m, 1H), 4.96-4.82 (m, 2H), 4.68 (s, 2H), 3.03-2.92 (1H, m), 2.01-1.95 (m, 1H), 1.82-1.61 (m, 4H), 1.54 (d, J = 6.9 Hz, 3H), 1.53 (d, J = 6.9 Hz, 3H), 1.49-1.37 (m, 2H) |
| 532 | 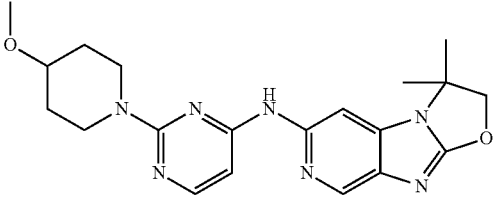 [SMILES: COC1CCN(c2nccc(Nc3cc4c(cn3)nc3n4C(C)(C)CO3)n2)CC1]<br>N-(2-(4-methoxypiperidin-1-yl)pyrimidin-4-yl)-3,3-dimethyl-2,3-dihydrooxazolo[3',2':1,2]imidazo[4,5-c]pyridin-6-amine | 280 | 2.30, 396, F | $^1$H NMR (DMSO-$d_6$): 10.04 (1H, br s), 8.34 (1H, s), 8.18 (1H, s), 7.95 (1H, d, J = 5.9 Hz), 6.45-6.35 (1H, m), 4.93 (2H, s), 4.20-4.09 (1H, m), 3.52-3.38 (4H, m), 3.29 (3H, s), 1.95-1.86 (2H, m), 1.64 (6H, s), 1.53-1.41 (2H, m). |
| 533 | 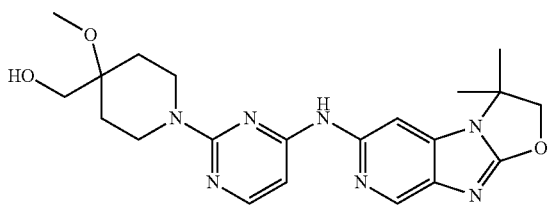 [SMILES: COC1(CO)CCN(c2nccc(Nc3cc4c(cn3)nc3n4C(C)(C)CO3)n2)CC1]<br>(1-(4-((3,3-dimethyl-2,3-dihydrooxazolo[3',2':1,2]imidazo[4,5-c]pyridin-6-yl)amino)pyrimidin-2-yl)-4-methoxypiperidin-4-yl)methanol | 280 | 2.04, 426, F | $^1$H NMR (DMSO-$d_6$): 9.69 (1H, br s), 8.25 (1H, s), 8.19 (1H, s), 7.90 (1H, d, J = 5.7 Hz), 6.28 (1H, d, J = 5.7 Hz), 4.87 (2H, s), 4.52 (1H, t, J = 5.5 Hz), 4.31-4.22 (2H, m), 3.32 (2H, d, J = 5.4 Hz), 3.22-3.13 (2H, m), 3.15 (3H, s), 1.70-1.60 (2H, m), 1.59 (6H, s), 1.50-1.39 (2H, m). |
| 534 | 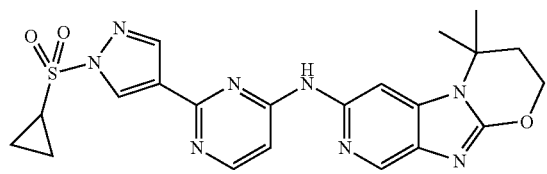 [SMILES: CC1(C)CCOc2nc3cnc(Nc4ccnc(-c5cnn(S(=O)(=O)C6CC6)c5)n4)cc3n21]<br>[2-(1-Cyclopropanesulfonyl-1H-pyrazol-4-yl)-pyrimidin-4-yl]-(4,4-dimethyl-3,4-dihydro-2H-1-oxa-4a,7,9-triazafluoren-6-yl)amine | 279 | 2.78, 467, F | $^1$H NMR (DMSO-$d_6$): 10.05 (1H, br s), 8.59 (1H, s), 8.40 (1H, s), 8.35-8.31 (2H, m), 8.23 (1H, br s), 7.22 (1H, br s), 4.49 (2H, t, J = 5.2 Hz), 3.24-3.16 (1H, m), 2.19 (2H, J = 5.2 Hz), 1.69 (6H, s), 1.32-1.17 (4H, m). |

TABLE 4-continued

| Example | Structure/Name | Synthesis Method/ Example # | LCMS R$_T$ (min), [M + H]$^+$, method | $^1$H NMR (ppm) |
|---|---|---|---|---|
| 535 | (R)-1-{(S)-1-sec-Butyl-6-[2-(1-ethanesulfonyl-1H-pyrazol-4-yl)-pyrimidin-4-ylamino]-1H-imidazo[4,5-c]pyridin-2-yl}-ethanol | 281 | 3.00, 471, F | $^1$H NMR 400 MHz (CDCl$_3$): δ 8.72 (1H, s), 8.69 (1H, s), 8.47 (1H, s), 8.39 (1H, br s), 8.36 (1H, d, J = 5.8 Hz), 7.74 (1H, br s), 6.81 (1H, d, J = 5.8 Hz), 5.10 (1H, q, J = 6.5 Hz), 4.71-4.60 (1H, m), 3.55 (2H, q, J = 7.4 Hz), 2.32-2.19 (1H, m), 2.16-2.02 (1H, m), 1.76 (3H, d, J = 6.5 Hz), 1.72 (3H, d, J = 6.8 Hz), 1.28 (3H, t, J = 7.4 Hz), 0.86 (3H, t, J = 7.3 Hz). |
| 536 | [2-(1-Cyclopropanesulfonyl-1H-pyrazol-4-yl)-pyrimidin-4-yl]-[1-isopropyl-2-(2-methoxy-ethoxy)-1H-imidazo[4,5-c]pyridin-6-yl]amine | 280 | 3.12, 499, F | $^1$H NMR 400 MHz (CDCl$_3$): δ 8.64 (1H, s), 8.43 (2H, s), 8.34 (1H, d, J = 5.8 Hz), 8.12 (1H, br s), 7.75 (1H, br s), 6.85 (1H, d, J = 5.8 Hz), 4.74-4.64 (3H, m), 3.82-3.77 (2H, m), 3.42 (3H, s), 2.83-2.76 (1H, m), 1.62 (6H, d, J = 6.9 Hz), 1.52-1.46 (2H, m), 1.21-1.15 (2H, m). |
| 537 | N$^6$-[2-(1-cyclopropanesulfonyl-1H-pyrazol-4-yl)-pyrimidin-4-yl]-1-isopropyl-N$^2$-(2-methoxyethyl)-1H-imidazo[4,5-c]pyridine-2,6-diamine | 283 | 2.81, 498, F | $^1$H NMR 400 MHz δ (CDCl$_3$): 8.62 (1H, s), 8.43 (1H, s), 8.36-8.30 (2H, m), 8.25 (1H, s), 6.86 (1H, d, J = 5.8 Hz), 4.79 (1H, br s), 4.40 (1H, sept, J = 6.9 Hz), 3.76-3.68 (2H, m), 3.67-3.62 (2H, m), 3.41 (3H, s), 2.83-2.76 (1H, m), 1.68 (6H, d, J = 6.9 Hz), 1.52-1.46 (2H, m), 1.23-1.14 (2H, m). |
| 538 | [2-(1-Cyclopropanesulfonyl-1H-pyrazol-4-yl)-pyrimidin-4-yl]-(4,4-dimethyl-3,4-dihydro-1H-2-oxa-4a,7,9-triazafluoren-6-yl)amine | 280 | 3.05, 467, F | $^1$H NMR 400 MHz δ (CDCl$_3$): 8.66 (1H, s), 8.65 (1H, s), 8.48 (1H, br s), 8.45 (1H, s), 8.37 (1H, d, J = 5.9 Hz), 7.95 (1H, br s), 6.78 (1H, d, J = 5.8 Hz), 4.97 (2H, s), 3.86 (2H, s), 2.84-2.76 (1H, m), 1.76 (6H, s), 1.53-1.47 (2H, m), 1.24-1.16 (2H, m). |

TABLE 4-continued

| Example | Structure/Name | Synthesis Method/ Example # | LCMS $R_T$ (min), [M + H]$^+$, method | $^1$H NMR (ppm) |
|---|---|---|---|---|
| 539 | 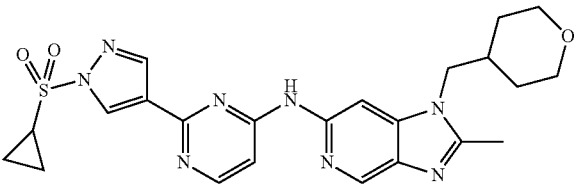 [SMILES: Cc1nc2cnc(Nc3ccnc(-c4cnn(S(=O)(=O)C5CC5)c4)n3)cc2n1CC1CCOCC1]<br>[2-(1-Cyclopropanesulfonyl-1H-pyrazol-4-yl)-pyrimidin-4-yl]-[2-methyl-1-(tetrahydropyran-4-ylmethyl)-1H-imidazo[4,5-c]pyridin-6-yl]amine | 18 | 2.75, 495, F | $^1$H NMR 400 MHz δ (CDCl$_3$): 8.66 (1H, s), 8.58 (1H, s), 8.42 (1H, s), 8.37 (1H, d, J = 5.9 Hz), 8.34 (1H, br s), 8.21 (1H, br s), 6.88 (1H, d, J = 5.8 Hz), 4.04 (2H, d, J = 7.4 Hz), 3.94 (2H, dd, J = 11.2, 3.1 Hz), 3.29 (2H, td, J = 11.5, 2.2 Hz), 2.86-2.78 (1H, m), 2.63 (3H, s), 2.20-2.07 (1H, m), 1.59-1.41 (6H, m), 1.23-1.16 (2H, m). |
| 540 | 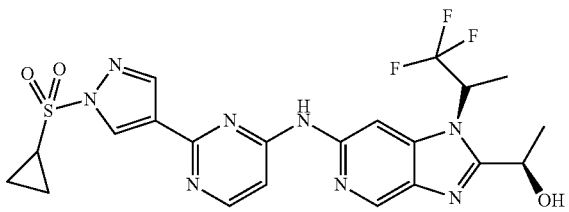<br>(R)-1-[(R)-6-[2-(1-Cyclopropanesulfonyl-1H-pyrazol-4-yl)pyrimidin-4-ylamino]-1-(2,2,2-trifluoro-1-methyl-ethyl)-1H-imidazo[4,5-c]pyridin-2-yl]ethanol | 286 | 3.32, 523, F | $^1$H NMR 400 MHz δ (CDCl$_3$): 8.72 (1H, s), 8.64 (1H, s), 8.44 (1H, s), 8.38 (1H, d, J = 5.9 Hz), 8.36 (1H, br s), 7.74 (1H, br s), 6.85 (1H, d, J = 5.8 Hz), 5.57-5.45 (1H, m), 5.17 (1H, q, J = 6.7 Hz), 2.84-2.77 (1H, m), 1.95 (3H, d, J = 7.2 Hz), 1.75 (3H, d, J = 6.7 Hz), 1.54-1.45 (2H, m), 1.24-1.12 (2H, m). |
| 541 | 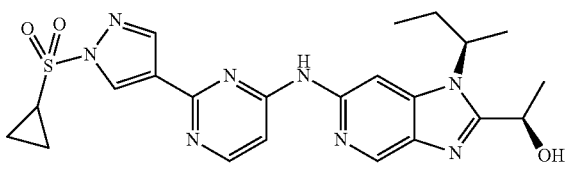 [SMILES: CC[C@@H](C)n1c([C@@H](C)O)nc2cnc(Nc3ccnc(-c4cnn(S(=O)(=O)C5CC5)c4)n3)cc21]<br>(R)-1-{1-((R)-sec-Butyl)-6-[2-(1-cyclopropanesulfonyl-1H-pyrazol-4-yl)pyrimidin-4-ylamino]-1H-imidazo[4,5-c]pyridin-2-yl}ethanol | 286 | 3.03, 483, F | $^1$H NMR 400 MHz δ (CDCl$_3$): 8.68 (1H, s), 8.64 (1H, s), 8.47 (1H, br s), 8.45 (1H, s), 8.37 (1H, br s), 8.35 (1H, d, J = 5.8 Hz), 6.81 (1H, d, J = 5.8 Hz), 5.08 (1H, q, J = 6.5 Hz), 4.56-4.45 (1H, m), 2.84-2.76 (1H, m), 2.31-2.19 (1H, m), 2.13-2.01 (1H, m), 1.73 (3H, d, J = 6.9 Hz), 1.69 (3H, d, J = 6.5 Hz), 1.52-1.46 (2H, m), 1.22-1.53 (2H, m), 0.84 (3H, t, J = 7.4 Hz). |

TABLE 4-continued

| Example | Structure/Name | Synthesis Method/ Example # | LCMS R_T (min), [M + H]+, method | 1H NMR (ppm) |
|---|---|---|---|---|
| 542 | 3-Fluoro-1-{4-[2-((R)-1-hydroxyethyl)-1-((R)-2,2,2-trifluoro-1-methylethyl)-1H-imidazo[4,5-c]pyridin-6-ylamino]pyrimidin-2-yl}-piperidin-4-ol | 286 | 2.20, 470, F | 1H NMR 400 MHz δ (CDCl$_3$): 8.71 (1H, s), 8.34 (1H, d, Hz), 8.06 (1H, d, J = 5.6 Hz), 7.41 (1H, br s), 6.14-6.09 (1H, m), 5.57-5.45 (1H, m), 5.18 (1H, q, J = 6.7 Hz), 4.83-4.75 (0.5H, m), 4.71-4.63 (0.5H, m), 4.52-4.42 (0.5H, m), 4.35-4.25 (0.5H, m), 4.25-3.97 (3H, m), 3.85-3.74 (0.5H, m), 3.69-3.60 (0.5H, m), 2.74 (1H, br s), 2.10 (1H, br s), 2.02-1.83 (2H, m), 1.90 (3H, d, J = 6.1 Hz), 1.77 (3H, d, J = 7.12 Hz). |
| 543 | (R)-1-[6-[2-(3-Fluoro-4-methoxypiperidin-1-yl)-pyrimidin-4-ylamino]-1-((S)-2,2,2-trifluoro-1-methyl-ethyl)-1H-imidazo[4,5-c]pyridin-2-yl]ethanol | 286 | 2.58, 484, F | 1H NMR 400 MHz δ (DMSO-d$_6$): 9.84 (1H, s), 8.68 (1H, s), 8.33 (1H, br s), 7.98 (1H, d, J = 5.8 Hz), 6.52 (1H, br s), 5.96 (1H, d, J = 5.8 Hz), 5.94-5.83 (1H, m), 5.03 (1H, quin, J = 6.6 Hz), 5.00-4.94 (0.5H, m), 4.87-4.82 (0.5H, m), 4.75-4.61 (1H, m), 4.49-4.39 (1H, m), 3.64-3.50 (1H, m), 3.50-3.36 (1H, m), 3.36 (3H, s), 3.28-3.16 (1H, m), 1.86 (3H, d, J = 6.6 Hz), 1.83-1.66 (2H, m), 1.63 (3H, d, J = 6.6 Hz). |
| 544 | 2-{4-[4-(1-Isopropyl-2-methyl-1H-imidazo[4,5-c]pyridin-6-ylamino)pyrimidin-2-yl]piperaziN-1-yl}isobutyramide | 292 | 1.78, 438.2, F | 1H NMR (400 MHz, DMSO-d$_6$) δ 9.66 (1H, s), 8.46 (1H, s), 8.30 (1H, s), 7.91 (1H, d, J = 5.7 Hz), 7.19 (1H, s), 6.97 (1H, s), 6.39 (1H, d, J = 5.7 Hz), 4.70-4.62 (1H, m), 3.74-3.73 (4H, m), 2.51 (3H, s), 2.46-2.44 (4H, m), 1.49 (6H, d, J = 7.1 Hz), 1.06 (6H, s). |
| 545 | (1-Isopropyl-2-methyl-1H-imidazo[4,5-c]pyridin-6-yl)-[2-(4-methanesulfonylpiperidin-1-yl)pyrimidin-4-yl]amine | 292 | 1.97, 430.1, F | 1H NMR (400 MHz, DMSO-d$_6$) δ 9.68 (1H, s), 8.46 (1H, s), 8.26 (1H, s), 7.93 (1H, d, J = 5.7 Hz), 6.44 (1H, d, J = 5.7 Hz), 4.84-4.80 (2H, m), 4.71-4.64 (1H, m), 3.39-3.31 (1H, m), 2.94-2.87 (5H, m), 2.51 (3H, s), 2.05-2.02 (2H, m), 1.57-1.47 (8H, m). |

TABLE 4-continued

| Example | Structure/Name | Synthesis Method/ Example # | LCMS $R_T$ (min), $[M+H]^+$, method | $^1$H NMR (ppm) |
|---|---|---|---|---|
| 546 | 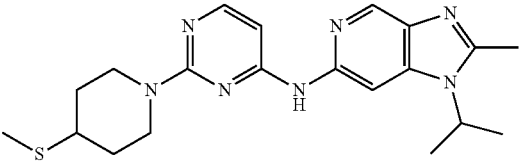<br>(1-Isopropyl-2-methyl-1H-imidazo[4,5-c]pyridin-6-yl)-[2-(4-methylsulfanylpiperidin-1-yl)pyrimidin-4-yl]amine | 292 | 2.55, 398.1, F | $^1$H NMR (400 MHz, DMSO-d$_6$) δ 9.65 (1H, s), 8.45 (1H, s), 8.30 (1H, s), 7.90 (1H, d, J = 5.7 Hz), 6.38 (1H, d, J = 5.7 Hz), 4.68-4.61 (1H, m), 4.54-4.50 (2H, m), 3.10-3.04 (2H, m), 2.86-2.79 (1H, m), 2.51 (3H, s), 2.04 (3H, s), 1.94-1.90 (2H, m), 1.51 (6H, d, J = 7.1 Hz), 1.44-1.34 (2H, m). |
| 547 | 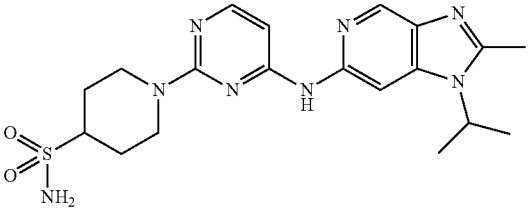 [SMILES: Cc1nc2cnc(Nc3ccnc(N4CCC(S(N)(=O)=O)CC4)n3)cc2n1C(C)C]<br>1-[4-(1-Isopropyl-2-methyl-1H-imidazo[4,5-c]pyridin-6-ylamino)pyrimidin-2-yl]piperidine-4-sulfonic acid amide | 292 | 1.90, 431.2, F | $^1$H NMR (400 MHz, DMSO-d$_6$) δ 9.69 (1H, s), 8.46 (1H, s), 8.30 (1H, s), 7.92 (1H, d, J = 5.7 Hz), 6.72 (2H, s), 6.41 (1H, d, J = 5.7 Hz), 4.81-4.78 (2H, m), 4.72-4.65 (1H, m), 3.14-3.08 (1H, m), 2.94-2.87 (2H, m), 2.52 (3H, s), 2.02-2.00 (2H, m), 1.56-1.48 (2H, m), 1.53 (6H, d, J = 7.0 Hz). |
| 548 | 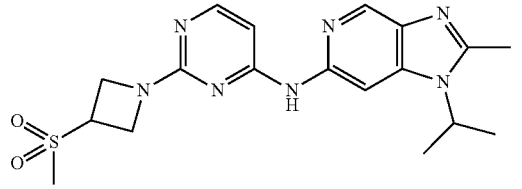 [SMILES: Cc1nc2cnc(Nc3ccnc(N4CC(S(C)(=O)=O)C4)n3)cc2n1C(C)C]<br>(1-Isopropyl-2-methyl-1H-imidazo[4,5-c]pyridin-6-yl)-[2-(3-methanesulfonylazetidin-1-yl)pyrimidin-4-yl]amine | 292 | 1.93, 402.1, F | $^1$H NMR (400 MHz, DMSO-d$_6$) δ 9.81 (1H, s), 8.46 (1H, s), 8.43 (1H, s), 7.94 (1H, d, J = 5.7 Hz), 6.52 (1H, d, J = 5.7 Hz), 4.71-4.64 (1H, s), 4.42-4.36 (1H, m), 4.32-4.27 (2H, m), 4.22-4.19 (2H, m), 3.00 (3H, s), 2.51 (3H, s), 1.52 (6H, d, J = 7.0 Hz). |
| 549 | 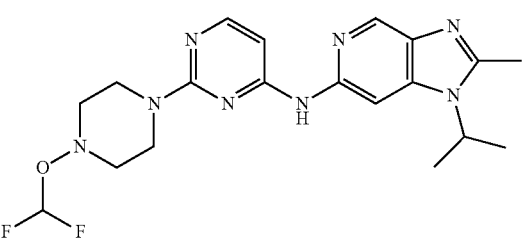 [SMILES: Cc1nc2cnc(Nc3ccnc(N4CCN(OC(F)F)CC4)n3)cc2n1C(C)C]<br>[2-(4-Difluoromethoxypiperidin-1-yl)pyrimidin-4-yl]-(1-isopropyl-2-methyl-1H-imidazo[4,5-c]pyridin-6-yl)amine | 292 | 2.60, 418.2, F | $^1$H NMR (400 MHz, DMSO-d$_6$) δ 9.67 (1H, s), 8.45 (1H, s), 8.29 (1H, s), 7.92 (1H, d, J = 5.7 Hz), 6.75 (1H, t, J = 76.5 Hz), 6.39 (1H, d, J = 5.7 Hz), 4.71-4.64 (1H, m), 4.39-4.33 (1H, m), 4.23-4.18 (2H, m), 3.45-3.39 (2H, m), 2.51 (3H, s), 1.92-1.88 (2H, m), 1.50-1.53 (2H, m), 1.51 (6H, d, J = 7.1 Hz). |

TABLE 4-continued

| Example | Structure/Name | Synthesis Method/ Example # | LCMS R_T (min), [M + H]+, method | 1H NMR (ppm) |
|---|---|---|---|---|
| 550 | (3aR,5R,6aS)-2-[4-(1-Isopropyl-2-methyl-1H-imidazo[4,5-c]pyridin-6-ylamino)pyrimidin-2-yl]octahydro-cyclopenta[c]pyrrol-5-ol | 292 | 2.07, 394.2, F | 1H NMR (400 MHz, DMSO-d6) δ 9.68 (1H, s), 8.65 (1H, s), 8.49 (1H, s), 7.92 (1H, d, J = 5.7 Hz), 6.33 (1H, d, J = 5.7 Hz), 4.77-4.70 (1H, m), 4.63 (1H, d, J = 3.8 Hz), 4.19-4.11 (1H, m), 3.77-3.72 (2H, m), 3.60-3.57 (2H, m), 2.73-2.64 (2H, m), 2.56 (3H, s), 2.14-2.07 (2H, m), 1.58 (6H, d, J = 6.9 Hz), 1.44-1.38 (2H, m). |
| 551 | 1-Isopropyl-N-(2-((3aR,5r,6aS)-5-methoxyhexahydrocyclopenta[c]pyrrol-2(1H)-yl)pyrimidin-4-yl)-2-methyl-1H-imidazo[4,5-c]pyridin-6-amine | 292 | 2.40, 408.2, F | 1H NMR (400 MHz, DMSO-d6) δ 9.68 (1H, s), 8.64 (1H, s), 8.49 (1H, s), 7.92 (1H, d, J = 5.7 Hz), 6.34 (1H, d, J = 5.7 Hz), 4.78-4.68 (1H, m), 3.89-3.84 (1H, m), 3.80-3.75 (2H, m), 3.53-3.49 (2H, m), 3.17 (3H, s), 2.77-2.68 (2H, m), 2.56 (3H, s), 2.18-2.11 (2H, m), 1.58 (6H, d, J = 6.9 Hz), 1.55-1.49 (2H, m). |
| 552 | 1-{[4-(1-Isopropyl-2-methyl-1H-imidazo[4,5-c]pyridin-6-ylamino)pyrimidin-2-ylamino]methyl}cyclopropane carboxylic acid amide | 292 | 1.87, 381.2, F | 1H NMR (400 MHz, DMSO-d6) δ 9.63 (1H, s), 8.49 (1H, s), 8.24 (1H, s), 7.90 (1H, d, J = 5.7 Hz), 7.31 (1H, s), 6.92 (1H, s), 6.69 (1H, s), 6.57-6.52 (1H, m), 4.78-4.67 (1H, m), 3.62 (1H, d, J = 6.2 Hz), 2.56 (3H, s), 1.56 (6H, d, J = 6.9 Hz), 0.97-0.94 (2H, m), 0.81-0.78 (2H, m). |
| 553 | (1-Isopropyl-2-methyl-1H-imidazo[4,5-c]pyridin-6-yl)-{2-[4-(propane-2-sulfonyl)piperidin-1-yl]pyrimidin-4-yl}amine | 292 | 2.29, 458.2, F | 1H NMR (400 MHz, DMSO-d6) δ 10.12 (1H, s), 8.50 (1H, s), 8.30 (1H, s), 7.98 (1H, d, J = 5.7 Hz), 6.49 (1H, d, J = 5.7 Hz), 4.86-4.80 (2H, m), 4.76-4.69 (1H, m), 3.64-3.57 (1H, m), 3.42-3.35 (1H, m), 3.04-2.98 (2H, m), 2.56 (3H, s), 2.05-1.99 (2H, m), 1.62-1.52 (8H, m), 1.26 (6H, d, J = 6.7 Hz). |

TABLE 4-continued

| Example | Structure/Name | Synthesis Method/ Example # | LCMS R_T (min), [M + H]+, method | 1H NMR (ppm) |
|---|---|---|---|---|
| 554 | (1-Isopropyl-6-{2-[4-(propane-2-sulfonyl)piperidin-1-yl]pyrimidin-4-ylamino}-1H-imidazo[4,5-c]pyridin-2-yl)methanol | 273 | 2.21, 474.2, F | $^1$H NMR (400 MHz, DMSO-$d_6$) δ 9.78 (1H, s), 8.60 (1H, s), 8.36 (1H, s), 7.99 (1H, d, J = 5.6 Hz), 6.50 (1H, d, J = 5.7 Hz), 5.68 (1H, t, J = 4.8 Hz), 4.99-4.92 (1H, m), 4.85-4.82 (2H, m), 4.72 (2H, d, J = 4.8 Hz), 3.65-3.57 (1H, m), 3.43-3.36 (1H, m), 3.05-2.99 (2H, m), 2.05-1.99 (2H, m), 1.62-1.52 (8H, m), 1.26 (6H, d, J = 6.6 Hz). |
| 555 | 1-[4-(1-Isopropyl-2-methyl-1H-imidazo[4,5-c]pyridin-6-ylamino)pyrimidin-2-yl]-1H-imidazole-4-sulfonic acid cyclopropylamide | 292 | 2.78, 454.3, F | $^1$H NMR (400 MHz, DMSO-$d_6$) δ 10.50 (1H, s), 8.63 (1H, d, J = 1.3 Hz), 8.56 (1H, d, J = 0.8 Hz), 8.35 (1H, d, J = 5.7 Hz), 8.22 (1H, d, J = 1.3 Hz), 8.19-8.11 (1H, m), 8.02-7.92 (1H, m), 7.36-7.20 (1H, m), 4.76-4.70 (1H, m), 2.55 (3H, s), 2.26-2.21 (1H, m), 1.57 (6H, d, J = 6.8 Hz), 0.45-0.35 (4H, m). |
| 556 | $N^2$-[2-(1-Cyclopropanesulfonyl-1H-pyrazol-4-yl)-pyrimidin-4-yl]-N2-ethyl-1-isopropyl-1H-imidazo[4,5-c]pyridine-2,6-diamine | 293 | 2.80, 468.2, F | $^1$H NMR (400 MHz, DMSO-$d_6$) δ 9.89 (1H, s), 8.58 (1H, s), 8.39 (1H, s), 8.30 (1H, d, J = 6.1 Hz), 8.29 (1H, s), 8.12 (1H, s), 7.27-7.22 (1H, m), 6.77-6.74 (1H, t, J = 5.3 Hz), 4.63-4.56 (1H, m), 3.24-3.17 (3H, m), 1.50 (6H, d, J = 7.3 Hz), 1.30-1.19 (4H, m), 1.17 (3H, t, J = 7.0 Hz). |
| 557 | 2-{6-[2-(1-Cyclopropanesulfonyl-1H-pyrazol-4-yl)pyrimidin-4-ylamino]-1-isopropyl-1H-imidazo[4,5-c]pyridin-2-ylmethoxy}ethanol | 293 | 2.82, 499.2, F | $^1$H NMR (400 MHz, DMSO-$d_6$) δ 10.21 (1H, s), 8.65 (1H, d, J = 0.9 Hz), 8.62 (1H, s), 8.46 (1H, s), 8.43 (1H, s), 8.36 (1H, d, J = 5.8 Hz), 7.20-7.18 (1H, m), 4.95-4.85 (1H, m), 4.75 (2H, s), 4.63 (1H, t, J = 5.2 Hz), 3.51-3.44 (4H, m), 3.24-3.18 (1H, m), 1.61 (6H, d, J = 6.7 Hz), 1.33-1.18 (4H, m). |

TABLE 4-continued

| Example | Structure/Name | Synthesis Method/ Example # | LCMS R_T (min), [M + H]+, method | 1H NMR (ppm) |
|---|---|---|---|---|
| 558 | [2-(1-Cyclopropanesulfonyl-1H-pyrazol-4-yl)-pyrimidin-4-yl]-[1-isopropyl-2-(2,2,2-trifluoro-ethyl)-1H-imidazo[4,5-c]pyridin-6-yl]amine | 293 | 3.72, 507.1, F | 1H NMR (400 MHz, DMSO-$d_6$) δ 10.23 (1H, s), 8.68 (1H, d, J = 0.9 Hz), 8.63 (1H, s), 8.49 (1H, s), 8.44 (1H, s), 8.37 (1H, d, J = 6.1 Hz), 7.23-7.17 (1H, m), 4.93-4.85 (1H, m), 4.23 (2H, q, J = 11.0 Hz), 3.24-3.18 (1H, m), 1.60 (6H, d, J = 6.8 Hz), 1.33-1.18 (4H, m). |
| 559 | {6-[2-(4-Hydroxymethyl-4-methoxypiperidin-1-yl)pyrimidin-4-ylamino]-1-isopropyl-1H-imidazo[4,5-c]pyridin-2-yl}methanol | 273 | 1.93, 428.2, F | 1H NMR (400 MHz, DMSO-$d_6$) δ 9.74 (1H, s), 8.59 (1H, s), 8.47 (1H, s), 7.95 (1H, d, J = 5.7 Hz), 6.39 (1H, d, J = 5.7 Hz), 5.69 (1H, s), 5.00-4.90 (1H, m), 4.71 (2H, s), 4.57 (1H, m), 4.40-4.36 (2H, m), 3.39 (2H, s), 3.25-3.16 (2H, m), 3.20 (3H, s), 1.74-1.70 (2H, m), 1.58 (6H, d, J = 6.7 Hz), 1.55-1.45 (2H, m). |
| 560 | 3-[4-(2-Hydroxymethyl-1-isopropyl-1H-imidazo[4,5-c]pyridin-6-ylamino)pyrimidin-2-ylamino]-2,2-dimethylpropionic acid methyl ester | 293 | 2.27, 414.1, F | 1H NMR (400 MHz, DMSO-$d_6$) δ 9.52 (1H, s), 8.53 (1H, s), 8.20 (1H, s), 7.84 (1H, d, J = 5.7 Hz), 6.52 (1H, d, J = 5.7 Hz), 6.32 (1H, s), 5.62 (1H, m), 4.94-4.80 (1H, m), 4.67-4.66 (2H, d, J = 3.6 Hz), 3.52 (2H, d, J = 6.4 Hz), 3.49 (3H, s), 1.55 (6H, d, J = 6.9 Hz), 1.12 (6H, s). |
| 561 | (R)-1-{6-[2-(1-Cyclopropanesulfonyl-1H-pyrazol-4-yl)pyrimidin-4-ylamino]-1-isopropyl-1H-imidazo[4,5-c]pyridin-2-yl}ethanol | 293 | 2.88, 469.2, F | 1H NMR (400 MHz, DMSO-$d_6$) δ 10.14 (1H, s), 8.61 (2H, s), 8.42 (1H, s), 8.40 (1H, bs), 8.34 (1H, d, J = 6.2 Hz), 7.21-7.19 (1H, m), 5.67 (1H, d, J = 4.5 Hz), 5.13-5.07 (1H, m), 5.03-4.98 (1H, m), 3.22-3.17 (1H, m), 1.60, 1.58 (6H, 2 x d, J = 6.4 Hz), 1.55 (3H, d, J = 6.6 Hz), 1.31-1.17 (4H, m). |

TABLE 4-continued

| Example | Structure/Name | Synthesis Method/ Example # | LCMS R_T (min), [M + H]+, method | 1H NMR (ppm) |
|---|---|---|---|---|
| 562 | (S)-1-{6-[2-(1-Cyclopropanesulfonyl-1H-pyrazol-4-yl) pyrimidin-4-ylamino]-1-isopropyl-1H-imidazo[4,5-c] pyridin-2-yl}ethanol | 293 | 2.88, 469.2, F | $^1$H NMR (400 MHz, DMSO-d$_6$) δ 10.14 (1H, s), 8.61 (2H, s), 8.42 (1H, s), 8.40 (1H, bs), 8.34 (1H, d, J = 6.2 Hz), 7.21-7.19 (1H, m), 5.67 (1H, d, J = 4.5 Hz), 5.13-5.07 (1H, m), 5.03-4.98 (1H, m), 3.22-3.17 (1H, m), 1.60, 1.58 (6H, 2 x d, J = 6.4 Hz), 1.55 (3H, d, J = 6.6 Hz), 1.31-1.17 (4H, m). |
| 563 | 2-{6-[2-(1-Cyclopropanesulfonyl-1H-pyrazol-4-yl)pyrimidin-4-ylamino]-1-isopropyl-1H-imidazo[4,5-c]pyridin-2-yl} propan-2-ol | 293 | 3.11, 483.2, F | $^1$H NMR (400 MHz, DMSO-d$_6$) δ 10.18 (1H, s), 8.67 (1H, s), 8.65 (1H, d, J = 0.8 Hz), 8.48 (1H, s), 8.46 (1H, bs), 8.40 (1H, d, J = 6.0 Hz), 7.30-7.26 (1H, m), 5.78 (1H, s), 5.75-5.67 (1H, m), 3.28-3.23 (1H, m), 1.66 (6H, d, J = 7.0 Hz), 1.65 (6H, s), 1.36-1.23 (4H, m). |
| 564 | [2-(1-Cyclopropanesulfonyl-1H-pyrazol-4-yl)-pyrimidin-4-yl]-(2-cyclopropyl-1-isopropyl-1H-imidazo[4,5-c]pyridin-6-yl)amine | 293 | 3.21, 465.2, F | $^1$H NMR (400 MHz, DMSO-d$_6$) δ 10.11 (1H, s), 8.61 (1H, s), 8.48 (1H, d, J = 0.8 Hz), 8.42 (1H, s), 8.35 (1H, bs), 8.33 (1H, d, J = 6.1 Hz), 7.22-7.15 (1H, m), 5.09-4.99 (1H, m), 3.23-3.18 (1H, m), 2.28-2.22 (1H, m), 1.62 (6H, d, J = 6.6 Hz), 1.31-1.18 (4H, m), 1.00-0.97 (4H, m). |
| 565 | (±)-[2-(1-Cyclopropanesulfonyl-1H-pyrazol-4-yl)-pyrimidin-4-yl]-[1-isopropyl-2-(tetrahydro-furan-2-yl)-1H-imidazo[4,5-c]pyridin-6-yl]amine | 293 | 3.40, 495.2, F | $^1$H NMR (400 MHz, DMSO-d$_6$) δ 10.22 (1H, s), 8.69 (1H, d, J = 0.8 Hz), 8.67 (1H, s), 8.48 (2H, s), 8.40 (1H, d, J = 6.1 Hz), 7.29-7.21 (1H, m), 5.29 (1H, t, J = 6.7 Hz), 5.09-4.99 (1H, m), 3.89-3.77 (2H, m), 3.30-3.23 (1H, m), 2.74-2.66 (1H, m), 2.29-2.20 (1H, m), 2.12-1.94 (2H, m), 1.66, 1.64 (6H, 2 x d, J = 6.9 Hz), 1.36-1.23 (4H, m). |

TABLE 4-continued

| Example | Structure/Name | Synthesis Method/ Example # | LCMS $R_T$ (min), $[M + H]^+$, method | $^1$H NMR (ppm) |
|---|---|---|---|---|
| 566 | (±)-[2-(1-Cyclopropanesulfonyl-1H-pyrazol-4-yl)pyrimidin-4-yl]-[1-isopropyl-2-(1-methoxy-ethyl)-1H-imidazo[4,5-c]pyridin-6-yl]amine | 293 | 3.41, 483.2, F | $^1$H NMR (400 MHz, DMSO-$d_6$) δ 10.23 (1H, s), 8.69 (1H, d, J = 0.8 Hz), 8.67 (1H, s), 8.49 (1H, bs), 8.48 (1H, s), 8.40 (1H, d, J = 6.0 Hz), 7.29-7.22 (1H, m), 5.08-4.98 (1H, m), 4.90 (1H, q, J = 6.6 Hz), 3.28 (3H, s), 3.26-3.23 (1H, m), 1.66, 1.65 (6H, 2 x d, J = 7.0 Hz), 1.60 (3H, d, J = 6.5 Hz), 1.36-1.23 (4H, m). |
| 567 | [2-((S)-1-Aminoethyl)-1-isopropyl-1H-imidazo[4,5-c]pyridin-6-yl]-[2-(1-cyclopropanesulfonyl-1H-pyrazol-4-yl)pyrimidin-4-yl]amine | 293 | 2.41, 468.2, F | $^1$H NMR (400 MHz, DMSO-$d_6$) δ 10.12 (1H, s), 8.60 (1H, s), 8.57 (1H, d, J = 0.8 Hz), 8.42 (1H, s), 8.39 (1H, bs), 8.34 (1H, d, J = 5.7 Hz), 7.22-7.16 (1H, m), 5.11-5.01 (1H, m), 4.25 (1H, q, J = 6.6 Hz), 3.23-3.17 (1H, m), 2.00 (2H, bs), 1.60, 1.59 (6H, 2 x d, J = 7.0 Hz), 1.42 (3H, d, J = 6.6 Hz), 1.30-1.17 (4H, m). |
| 568 | [2-((R)-1-Aminoethyl)-1-isopropyl-1H-imidazo[4,5-c]pyridin-6-yl]-[2-(1-cyclopropanesulfonyl-1H-pyrazol-4-yl)pyrimidin-4-yl]amine | 293 | 2.41, 468.2, F | $^1$H NMR (400 MHz, DMSO-$d_6$) δ 10.12 (1H, s), 8.60 (1H, s), 8.57 (1H, d, J = 0.8 Hz), 8.42 (1H, s), 8.39 (1H, bs), 8.34 (1H, d, J = 5.7 Hz), 7.22-7.16 (1H, m), 5.11-5.01 (1H, m), 4.25 (1H, q, J = 6.6 Hz), 3.23-3.17 (1H, m), 2.00 (2H, bs), 1.60, 1.59 (6H, 2 x d, J = 7.0 Hz), 1.42 (3H, d, J = 6.6 Hz), 1.30-1.17 (4H, m). |
| 569 | (S)-1-{6-[2-(1-Cyclopropanesulfonyl-1H-pyrazol-4-yl)pyrimidin-4-ylamino]-1-isopropyl-1H-imidazo[4,5-c]pyridin-2-yl}ethane-1,2-diol | 293 | 2.64, 485.1, F | $^1$H NMR (400 MHz, DMSO-$d_6$) δ 10.15 (1H, s), 8.61 (2H, s), 8.42 (2H, s), 8.35 (1H, d, J = 6.0 Hz), 7.23-7.18 (1H, m), 5.80 (1H, d, J = 6.1 Hz), 5.15-5.08 (1H, m), 4.86-4.81 (2H, m), 3.89-3.73 (2H, m), 3.23-3.17 (1H, m), 1.60, 1.59 (6H, 2 x d, J = 7.0 Hz), 1.30-1.17 (4H, m). |

TABLE 4-continued

| Example | Structure/Name | Synthesis Method/ Example # | LCMS $R_T$ (min), $[M + H]^+$, method | $^1$H NMR (ppm) |
|---|---|---|---|---|
| 570 | (±)-[2-(1-Cyclopropanesulfonyl-1H-pyrazol-4-yl)pyrimidin-4-yl]-(1-isopropyl-2-oxetan-2-yl-1H-imidazo[4,5-c]pyridin-6-yl)amine | 293 | 3.13, 481.1, F | $^1$H NMR (400 MHz, DMSO-d$_6$) δ 10.25 (1H, s), 8.75 (1H, d, J = 0.8 Hz), 8.66 (1H, s), 8.49 (1H, bs), 8.47 (1H, s), 8.41 (1H, d, J = 5.7 Hz), 7.27-7.23 (1H, m), 6.14-6.10 (1H, m), 4.76-4.69 (2H, m), 4.61-4.56 (1H, m), 3.48-3.39 (1H, m), 3.29-3.22 (1H, m), 3.07-2.99 (1H), m), 1.63, 1.61 (6H, 2 x d, J = 6.9 Hz), 1.35-1.23 (4H, m). |
| 571 | [6-[2-(1-Cyclopropanesulfonyl-1H-pyrazol-4-yl)pyrimidin-4-ylamino]-1-((S)-2,2,2-trifluoro-1-methyl-ethyl)-1H-imidazo[4,5-c]pyridin-2-yl]methanol | 293 | 3.16, 509.0, F | $^1$H NMR (400 MHz, DMSO-d$_6$) δ 10.31 (1H, s), 8.72 (1H, s), 8.62 (1H, s), 8.46 (1H, s), 8.44 (1H, bs), 8.42 (1H, d, J = 5.9 Hz), 7.31-7.25 (1H, m), 5.91 (1H, bs), 5.78-5.70 (1H, m), 4.79 (2H, 2 x d, J = 14.7 Hz), 3.26-3.21 (1H, m), 1.91 (3H, d, J = 7.0 Hz), 1.35-1.23 (4H, m). |
| 572 | (R)-1-[6-[2-(1-Cyclopropanesulfonyl-1H-pyrazol-4-yl)-pyrimidin-4-ylamino]-1-((S)-2,2,2-trifluoro-1-methylethyl)-1H-imidazo[4,5-c]pyridin-2-yl]-ethanol | 293 | 3.36, 523.1, F | $^1$H NMR (400 MHz, CDCl$_3$) δ 8.72 (1H, d, J = 0.8 Hz), 8.63 (1H, s), 8.43 (1H, s), 8.39 (1H, bs), 8.37 (1H, d, J = 5.9 Hz), 7.99 (1H, bs), 6.85 (1H, d, J = 5.8 Hz), 5.63-5.56 (1H, m), 5.14-5.09 (1H, m), 2.84-2.77 (1H, m), 1.97 (3H, d, J = 7.3 Hz), 1.83 (3H, d, J = 6.4 Hz), 1.51-1.47 (1H, m), 1.21-1.16 (4H, m). |
| 573 | {6-[2-(3,6-Dihydro-2H-pyran-4-yl)pyrimidin-4-ylamino]-1-isopropyl-1H-imidazo[4,5-c]pyridin-2-yl}methanol | 294 | 2.14, 367.1, F | $^1$H NMR (400 MHz, DMSO-d$_6$) δ 10.08 (1H, s), 8.63 (1H, s), 8.59 (1H, s), 8.34 (1H, d, J = 5.8 Hz), 7.21-7.19 (1H, m), 7.10 (1H, d, J = 5.8 Hz), 5.62 (1H, t, J = 4.8 Hz), 5.01-4.91 (1H, m), 4.72 (2H, d, J = 4.7 Hz), 4.34-4.32 (2H, m), 3.85 (2H, t, J = 5.5 Hz), 2.68-2.63 (2H, m), 1.60 (6H, d, J = 7.0 Hz). |

TABLE 4-continued

| Example | Structure/Name | Synthesis Method/ Example # | LCMS R$_T$ (min), [M + H]$^+$, method | $^1$H NMR (ppm) |
|---|---|---|---|---|
| 574 | {1-Isopropyl-6-[2-(tetrahydropyran-4-yl)pyrimidin-4-ylamino]-1H-imidazo[4,5-c]pyridin-2-yl}methanol | 294 | 1.96, 369.1, F | $^1$H NMR (400 MHz, DMSO-d$_6$) δ 10.08 (1H, s), 8.69 (1H, s), 8.62 (1H, s), 8.28 (1H, d, J = 5.8 Hz), 7.08 (1H, d, J = 5.7 Hz), 5.69 (1H, s), 5.01-4.93 (1H, m), 4.72 (2H, s), 3.99-3.95 (2H, m), 3.50-3.43 (2H, m), 2.99-2.91 (1H, m), 1.94-1.88 (4H, m), 1.63 (6H, d, J = 7.0 Hz). |
| 575 | [2-(2,5-Dihydrofuran-3-yl)pyrimidin-4-yl]-(1-isopropyl-2-methyl-1H-imidazo[4,5-c]pyridin-6-yl)amine | 294 | 2.29, 337.1, F | $^1$H NMR (400 MHz, DMSO-d$_6$) δ 10.00 (1H, s), 8.69 (1H, s), 8.28 (1H, d, J = 5.8 Hz), 8.25 (1H, s), 7.19-7.16 (1H, m), 6.87-6.85 (1H, m), 4.97-4.92 (2H, m), 4.78-4.74 (2H, m), 4.71-4.64 (1H, m), 2.51 (3H, s), 1.53 (6H, d, J = 7.0 Hz). |
| 576 | (±)-(1-Isopropyl-2-methyl-1H-imidazo[4,5-c]pyridin-6-yl)-[2-(tetrahydrofuran-3-yl)pyrimidin-4-yl]amine | 294 | 2.03, 339.2, F | $^1$H NMR (400 MHz, DMSO-d$_6$) δ 10.04 (1H, s), 8.52 (1H, s), 8.44 (1H, s), 8.27 (1H, d, J = 6.0 Hz), 7.17 (1H, d, J = 5.9 Hz), 4.77-4.60 (1H, m), 4.13-4.09 (1H, m), 3.98-3.78 (3H, m), 3.59-3.51 (1H, m), 2.57 (3H, s), 2.39-2.24 (2H, m), 1.58 (6H, d, J = 7.0 Hz). |
| 577 | 5-[4-(1-Isopropyl-2-methyl-1H-imidazo[4,5-c]pyridin-6-ylamino)pyrimidin-2-yl]pyridine-2-carboxylic acid methylamide | 294 | 2.57, 403.1, F | $^1$H NMR (400 MHz, DMSO-d$_6$) δ 10.23 (1H, s), 9.51-9.50 (1H, m), 8.82 (1H, q, J = 4.8 Hz), 8.79-8.77 (1H, m), 8.54 (1H, d, J = 0.8 Hz), 8.48 (1H, d, J = 6.1 Hz), 8.32 (1H, s), 8.13-8.11 (1H, m), 7.41-7.36 (1H, m), 4.76-4.68 (1H, m), 2.82 (3H, d, J = 4.8 Hz), 2.55 (3H, s), 1.59 (6H, d, J = 6.6 Hz). |
| 578 | 5-[4-(1-Isopropyl-2-methyl-1H-imidazo[4,5-c]pyridin-6-ylamino)pyrimidin-2-yl]pyridine-2-carboxylic acid dimethylamide | 294 | 2.41, 417.2, F | $^1$H NMR (400 MHz, DMSO-d$_6$) δ 10.23 (1H, s), 9.52-9.51 (1H, m), 8.76-8.74 (1H, m), 8.59 (1H, d, J = 0.8 Hz), 8.51 (1H, d, J = 6.1 Hz), 8.47 (1H, s), 7.73-7.71 (1H, m), 7.38-7.33 (1H, m), 4.80-4.73 (1H, m), 3.05 (3H, s), 2.99 (3H, s), 2.59 (3H, s), 1.62 (6H, d, J = 6.6 Hz). |

TABLE 4-continued

| Example | Structure/Name | Synthesis Method/ Example # | LCMS R$_T$ (min), [M + H]$^+$, method | $^1$H NMR (ppm) |
|---|---|---|---|---|
| 579 | {6-[2-(2-Ethylaminothiazol-5-yl)-pyrimidin-4-ylamino]-1-isopropyl-1H-imidazo[4,5-c]pyridin-2-yl}methanol | 295 | 2.34, 411.1, F | $^1$H NMR (400 MHz, DMSO-d$_6$) δ 10.05 (1H, s), 8.63 (1H, d, J = 0.8 Hz), 8.45 (1H, bs), 8.23 (1H, d, J = 5.8 Hz), 8.11 (1H, t, J = 5.4 Hz), 7.89 (1H, s), 7.06-6.91 (1H, m), 5.70 (1H, t, J = 4.1 Hz), 5.03-4.95 (1H, m), 4.73 (2H, d, J = 4.1 Hz), 3.31-3.25 (2H, m), 1.68 (6H, d, J = 7.0 Hz), 1.21 (3H, t, J = 7.1 Hz). |
| 580 | 3-[4-(1-Isopropyl-2-methyl-1H-imidazo[4,5-c]pyridin-6-ylamino)pyrimidin-2-ylamino]-2-methylpropionamide | 298 | 1.79, 369.1, F | $^1$H NMR (400 MHz, DMSO-d$_6$) δ 9.56 (1H, br s), 8.48 (1H, s), 8.33 (1H, br s), 7.88 (1H, d, J = 5.6 Hz), 7.30 (1H, br s), 6.83 (1H, br s), 6.50 (1H, br s), 6.35 (1H, br s), 4.72 (1H, septet, J = 6.9 Hz), 3.53 (1H, br s), 2.62 (1H, sextet, J = 6.9 Hz), 2.56 (3H, s), 1.56 (6H, d, J = 6.9 Hz), 1.07 (3H, d, J = 6.9 Hz). |
| 581 | 3-[4-(1-Isopropyl-2-methyl-1H-imidazo[4,5-c]pyridin-6-ylamino)pyrimidin-2-ylamino]-2-methoxymethyl-2-methylpropionamide | 298 | 1.97, 413.2, F | $^1$H NMR (400 MHz, DMSO-d$_6$) δ 9.71 (1H, br s), 8.50 (1H, s), 8.30 (1H, br s), 7.88 (1H, d, J = 5.8 Hz), 7.18 (1H, br s), 7.06 (1H, br s), 6.54 (1H, br d, J = 5.4 Hz), 6.15 (1H, brs), 4.73 (1H, septet, J = 6.9 Hz), 3.60 (1H, dd, J = 13.1, 5.9 Hz), 3.51 (1H, dd, J = 13.1, 5.9 Hz), 3.44 (2H, s), 3.21 (3H, s), 2.57 (3H, s), 1.57 (6H, d, J = 6.9 Hz), 1.12 (3H, s). |
| 582 | 2-Hydroxy-3-[4-(1-isopropyl-2-methyl-1H-imidazo[4,5-c]pyridin-6-ylamino)pyrimidin-2-ylamino]-2-methylpropionamide | 303 | 1.73, 385.1, F | $^1$H NMR (400 MHz, DMSO-d$_6$) δ 9.68 (1H, br s), 8.49 (1H, s), 8.30 (1H, br s), 7.88 (1H, d, J = 5.7 Hz), 7.26 (1H, br s), 7.17 (1H, br s), 6.56 (1H, br s), 6.16 (1H, br s), 4.75 (1H, septet, J = 6.9 Hz), 3.39 (1H, dd, J = 12.9, 4.3 Hz), 2.57 (3H, s), 1.57 (6H, d, J = 6.9 Hz), 1.28 (3H, s). |

TABLE 4-continued

| Example | Structure/Name | Synthesis Method/ Example # | LCMS R_T (min), [M + H]+, method | 1H NMR (ppm) |
|---|---|---|---|---|
| 583 | 4-[4-(1-Isopropyl-2-methyl-imidazo[4,5-c]pyridin-6-ylamino)pyrimidin-2-ylamino]butyramide | 298 | 1.76, 369.2, F | 1H NMR (400 MHz, DMSO-d6) δ 9.54 (1H, br s), 8.48 (1H, s), 8.36 (1H, br s), 7.87 (1H, d, J = 5.8 Hz), 7.27 (1H, br s), 6.71 (2H, br s), 6.46 (1H, br s), 4.71 (1H, septet, J = 6.9 Hz), 3.38-3.34 (2H, m), 2.56 (3H, s), 2.15 (2H, t, J = 7.5 Hz), 1.80 (2H, quintet, J = 7.3 Hz), 1.57 (6H, d, J = 6.9 Hz). |
| 584 | 3-{[4-(1-Isopropyl-2-methyl-1H-imidazo[4,5-c]pyridin-6-ylamino)pyrimidin-2-yl]methylamino}-2,2-dimethylpropionamide | 303 | 1.95, 397, F | 1H NMR (400 MHz, DMSO-d6) δ 9.60 (1H, br s), 8.49 (1H, s), 8.34 (1H, br s), 7.94 (1H, d, J = 5.6 Hz), 7.18 (1H, br s), 6.92 (1H, br s), 6.47 (1H, br s), 4.70 (1H, septet, J = 6.9 Hz), 3.89 (2H, s), 3.15 (3H, s), 2.55 (3H, s), 1.54 (6H, d, J = 6.9 Hz), 1.07 (3H, s). |
| 585 | (1-Isopropyl-2-methyl-1H-imidazo[4,5-c]pyridin-6-yl)-(2-pyridin-4-ylpyrimidin-4-yl)amine | 309 | 2.09, 346.1, F | 1H NMR (400 MHz, DMSO-d6) δ 10.30 (1H, s), 8.79-8.77 (2H, m), 8.59 (1H, s), 8.52 (1H, d, J = 6.0 Hz), 8.51 (1H, br s), 8.27-8.25 (2H, m), 7.37 (1H, br s), 4.78 (1H, septet, J = 6.9 Hz), 2.59 (3H, s), 1.65 (6H, d, J = 6.9 Hz). |
| 586 | [2-(6-Aminopyridin-3-yl)pyrimidin-4-yl]-(1-isopropyl-2-methyl-1H-imidazo[4,5-c]pyridin-6-yl)amine | 309 | 1.89, 361.1, F | 1H NMR (400 MHz, DMSO-d6) δ 10.01 (1H, s), 8.99 (1H, d, J = 2.3 Hz), 8.55 (1H, s), 8.50 (1H, br s), 8.34 (1H, d, J = 5.8 Hz), 8.31 (1H, dd, J = 8.7, 2.3 Hz), 7.11 (1H, br s), 6.52 (1H, d, J = 8.7 Hz), 6.44 (2H, s), 4.77 (1H, septet, J = 6.9 Hz), 2.58 (3H, s), 1.63 (6H, d, J = 6.9 Hz). |

TABLE 4-continued

| Example | Structure/Name | Synthesis Method/ Example # | LCMS R$_T$ (min), [M + H]$^+$, method | $^1$H NMR (ppm) |
|---|---|---|---|---|
| 587 | (1-Isopropyl-2-methyl-1H-imidazo[4,5-c]pyridin-6-yl)-[2-(6-methanesulfonylpyridin-3-yl)pyrimidin-4-yl]amine | 309 | 2.62, 424.2, F | $^1$H NMR (400 MHz, DMSO-d$_6$) δ 10.33 (1H, s), 9.64 (1H, dd, J = 2.2, 0.8 Hz), 8.94 (1H, dd, J = 8.3, 12 Hz), 8.59 (1H, s), 8.55 (1H, d, J = 5.9 Hz), 8.31 (1H, br s), 8.21 (1H, dd, J = 8.1, 0.8 Hz), 7.49 (1H, br s), 4.77 (1H, septet, J = 6.9 Hz), 3.36 (3H, s), 2.59 (3H, s), 1.61 (6H, d, J = 6.9 Hz). |
| 588 | {1-Isopropyl-6-[2-(2-methylaminothiazol-5-yl)pyrimidin-4-ylamino]-1H-imidazo[4,5-c]pyridin-2-yl}methanol | 312 | 2.17, 397.1, F | $^1$H NMR (400 MHz, DMSO-d$_6$) δ 10.06 (1H, s), 8.64 (1H, d, J = 0.9 Hz), 8.47 (1H, br s), 8.23 (1H, d, J = 5.8 Hz), 8.05 (1H, q, J = 4.8 Hz), 7.91 (1H, s), 7.02 (1H, br s), 5.70 (1H, t, J = 5.6 Hz), 4.99 (1H, septet, J = 6.9 Hz), 4.73 (2H, d, J = 5.4 Hz), 2.89 (3H, d, J = 4.7 Hz), 1.68 (6H, d, J = 6.9 Hz). |
| 589 | N-{(E)-3-[4-(1-Isopropyl-2-methyl-1H-imidazo[4,5-c]pyridin-6-ylamino)pyrimidin-2-yl]-1,1-dimethylallyl}acetamide | 315 | 2.15, 394.2, F | $^1$H NMR (400 MHz, DMSO-d$_6$) δ 10.00 (1H, s), 8.53 (1H, s), 8.41 (1H, br s), 8.28 (1H, d, J = 5.8 Hz), 7.87 (1H, s), 7.15 (1H, br s), 7.15 (1H, d, J = 15.8 Hz), 6.32 (1H, d, J = 15.8 Hz), 4.74 (1H, septet, J = 6.9 Hz), 2.57 (3H, s), 1.82 (3H, s), 1.60 (6H, d, J = 6.9 Hz), 1.43 (6H, s). |
| 590 | [2-(3-Fluoropiperidin-1-yl)pyrimidin-4-yl]-(1-isopropyl-2-methyl-1H-imidazo[4,5-c]pyridin-6-yl)amine | 46 | 2.31, 370.1, F | $^1$H NMR (400 MHz, DMSO-d$_6$) δ 9.74 (1H, br s), 8.51 (1H, s), 8.36 (1H, br s), 7.96 (1H, d, J = 5.7 Hz), 6.44 (1H, d, J = 5.7 Hz), 4.87-4.67 (2H, m), 4.19-4.12 (1H, m), 4.04-3.98 (1H, m), 3.91-3.80 (1H, m), 3.63-3.56 (1H, m), 2.56 (3H, s), 2.02-1.72 (3H, m), 1.57 (7H, 2d + m, J = 6.9 Hz). |

TABLE 4-continued

| Example | Structure/Name | Synthesis Method/ Example # | LCMS R$_T$ (min), [M + H]$^+$, method | $^1$H NMR (ppm) |
|---|---|---|---|---|
| 591 | [2-(4-Fluoropiperidin-1-yl)pyrimidin-4-yl]-(1-isopropyl-2-methyl-1H-imidazo[4,5-c]pyridin-6-yl)amine | 46 | 2.31, 370.1, F | $^1$H NMR (400 MHz, DMSO-d$_6$) δ 9.72 (1H, s), 8.50 (1H, s), 8.35 (1H, br s), 7.97 (1H, d, J = 5.7 Hz), 6.44 (1H, d, J = 5.7 Hz), 5.02-4.85 (1H, m), 4.72 (1H, septet, J = 6.9 Hz), 4.02-3.95 (2H, m), 3.79-3.72 (2H, m), 2.56 (3H, s), 2.01-1.88 (2H, m), 1.78-1.67 (2H, m), 1.56 (6H, d, J = 6.9 Hz). |
| 592 | [2-((S)-3-Fluoropyrrolidin-1-yl)pyrimidin-4-yl]-(1-isopropyl-2-methyl-1H-imidazo[4,5-c]pyridin-6-yl)amine | 46 | 2.16, 356.1, F | $^1$H NMR (400 MHz, DMSO-d$_6$) δ 9.73 (1H, s), 8.57 (1H, br s), 8.50 (1H, s), 7.96 (1H, d, J = 5.7 Hz), 6.44 (1H, d, J = 5.7 Hz), 5.47 (1H, br d, J = 53.5 Hz), 4.73 (1H, septet, J = 6.9 Hz), 3.92-3.56 (4H, m), 2.56 (3H, s), 2.33-2.11 (2H, m), 1.58 (6H, d, J = 6.9 Hz). |
| 593 | [2-((R)-3-Fluoropyrrolidin-1-yl)pyrimidin-4-yl]-(1-isopropyl-2-methyl-1H-imidazo[4,5-c]pyridin-6-yl)amine | 46 | 2.16, 356.1, F | $^1$H NMR (400 MHz, DMSO-d$_6$) δ 9.73 (1H, s), 8.58 (1H, br s), 8.50 (1H, s), 7.96 (1H, d, J = 5.7 Hz), 6.44 (1H, d, J = 5.7 Hz), 5.47 (1H, br d, J = 53.5 Hz), 4.73 (1H, septet, J = 6.9 Hz), 3.92-3.57 (4H, m), 2.56 (3H, s), 2.33-2.11 (2H, m), 1.58 (6H, d, J = 6.9 Hz). |
| 594 | {6-[2-(2-Dimethylaminothiazol-5-yl)pyrimidin-4-ylamino]-1-isopropyl-1H-imidazo[4,5-c]pyridin-2-yl}methanol | 312 | 2.35, 411.1, F | $^1$H NMR (400 MHz, DMSO-d$_6$) δ 10.09 (1H, s), 8.64 (1H, s), 8.46 (1H, br s), 8.24 (1H, d, J = 5.8 Hz), 7.97 (1H, s), 7.01 (1H, br s), 5.70 (1H, t, J = 5.7 Hz), 5.00 (1H, septet, J = 6.9 Hz), 4.74 (2H, d, J = 5.7 Hz), 3.14 (6H, s), 1.69 (6H, d, J = 6.9 Hz). |
| 595 | [2-(2-Ethylthiazol-5-yl)pyrimidin-4-yl]-(1-isopropyl-2-methyl-1H-imidazo[4,5-c]pyridin-6-yl)amine | 312 | 2.86, 380.2, F | $^1$H NMR (400 MHz, DMSO-d$_6$) δ 10.21 (1H, s), 8.57 (1H, d, J = 0.9 Hz), 8.40 (1H, br s), 8.36 (1H, s), 8.35 (1H, d, J = 5.9 Hz), 7.20 (1H, br s), 4.79 (1H, septet, J = 6.9 Hz), 3.06 (2H, q, J = 7.5 Hz), 2.59 (3H, s), 1.66 (6H, d, J = 6.9 Hz), 1.37 (3H, t, J = 7.5 Hz). |

TABLE 4-continued

| Example | Structure/Name | Synthesis Method/ Example # | LCMS R$_T$ (min), [M + H]$^+$, method | $^1$H NMR (ppm) |
|---|---|---|---|---|
| 596 | {1-[4-(1-Isopropyl-2-methyl-1H-imidazo[4,5-c]pyridin-6-ylamino)pyrimidin-2-yl]piperidin-4-yl}methylcarbamic acid tert-butyl ester | 46 | 2.98, 481.3, F | $^1$H NMR (400 MHz, DMSO-d$_6$) δ 9.71 (1H, s), 8.50 (1H, s), 8.37 (1H, br s), 7.96 (1H, d, J = 5.7 Hz), 6.42 (1H, br d, J = 5.6 Hz), 4.86 (2H, br d, J = 12.7 Hz), 4.72 (1H, septet, J = 6.9 Hz), 4.07 (1H, br s), 2.92-2.83 (2H, m), 2.66 (3H, s), 2.56 (3H, s), 1.66-1.60 (4H, m), 1.56 (6H, d, J = 6.9 Hz), 1.41 (9H, s). |
| 597 | 1-{1-[4-(1-Isopropyl-2-methyl-1H-imidazo[4,5-c]pyridin-6-ylamino)pyrimidin-2-yl]piperidin-4-yl}pyrrolidin-2-one | 46 | 2.09, 435.2, F | $^1$H NMR (400 MHz, DMSO-d$_6$) δ 9.72 (1H, s), 8.50 (1H, s), 8.37 (1H, br s), 7.96 (1H, d, J = 5.7 Hz), 6.42 (1H, br d, J = 5.6 Hz), 4.86 (2H, br d, J = 12.9 Hz), 4.71 (1H, septet, J = 6.9 Hz), 4.10-4.02 (1H, m), 3.31-3.26 (2H, m), 2.97-2.90 (2H, m), 2.56 (3H, s), 2.23 (2H, t, J = 8.1 Hz), 1.89 (2H, pentet, J = 7.4 Hz), 1.65-1.59 (4H, m), 1.56 (6H, d, J = 6.9 Hz). |
| 598 | (1-Isopropyl-2-methyl-1H-imidazo[4,5-c]pyridin-6-yl)-[2-(4-oxetan-3-ylpiperidin-1-yl)pyrimidin-4-yl]amine | 46 | 2.08, 394.2, F | $^1$H NMR (400 MHz, DMSO-d$_6$) δ 9.70 (1H, s), 8.50 (1H, s), 8.38 (1H, br s), 7.95 (1H, d, J = 5.7 Hz), 6.41 (1H, br d, J = 5.7 Hz), 4.73 (1H, septet, J = 6.9 Hz), 4.38 (4H, s), 3.75-3.72 (4H, m), 2.57 (3H, s), 1.84-1.81 (4H, m), 1.59 (6H, d, J = 6.9 Hz). |
| 599 | (2-Imidazol-1-ylpyrimidin-4-yl)-(1-isopropyl-2-methyl-1H-imidazo[4,5-c]pyridin-6-yl)amine | 46 | 1.93, 335.1, F | $^1$H NMR (400 MHz, DMSO-d$_6$) δ 10.41 (1H, s), 8.60 (1H, s), 8.52 (1H, s), 8.36 (1H, d, J = 5.9 Hz), 8.16 (1H, br s), 7.89 (1H, s), 7.36 (1H, br s), 7.15 (1H, s), 4.77 (1H, septet, J = 6.9 Hz), 2.59 (3H, s), 1.60 (6H, d, J = 6.9 Hz). |

Each compound in Table 5. below was prepared following the general method as described below:

General Method:

The appropriately substituted amine (1 equiv., 0.13 mmol) was weighed out into a 1 dram conical vial. To this vial was added N-(2-chloropyrimidin-4-yl)-1-isopropyl-imidazo[4,5-c]pyridin-6-amine (0.667 equiv., 0.087 mmol) dissolved in boiling isopropanol to a concentration of approximately 35 mM. Triethylamine (2 equiv., 0.26 mmol) was then added. The reaction was allowed to proceed at 110° C. overnight or until UPLC analysis indicated complete conversion. The reaction mixture was concentrated under reduced pressure. Any Boc-protected materials were optionally deprotected by shaking in 4M HCl for 2 hours, and acidic solvent then removed under reduced pressure. Following the removal of all volatiles the crude products were dissolved in dichloromethane (2 mL) and washed with sodium bicarbonate (2×1 mL). The organic portion was separated and concentrated under reduced pressure. The crude product was purified via reverse-phase HPLC and lyophilized to yield the desired product.

| Example | Structure/Name | LCMS $R_T$ (min), [M + H]+, method | 1H NMR (ppm) |
|---|---|---|---|
| 600 | (cis)-1-(4-((1-isopropyl-2-methyl-1H-imidazo[4,5-c]pyridin-6-yl)amino)pyrimidin-2-yl)-2-methylpiperidin-4-ol (enantiomer 1) | 3.67, 382.2, B | 1H NMR (400 MHz, DMSO-$d_6$) δ 9.72 (s, 1H), 8.50 (d, J = 0.6 Hz, 1H), 8.39 (s, 1H), 7.93 (d, J = 5.7 Hz, 1H), 6.36 (d, J = 5.5 Hz, 1H), 5.06-4.88 (m, 1H), 4.73 (m, 1H), 4.65 (d, J = 2.3 Hz, 1H), 4.49 (d, J = 13.0 Hz, 1H), 4.03 (d, J = 2.5 Hz, 1H), 2.56 (s, 3H), 1.74 (m, 4H), 1.57 (m, 6H), 1.34 (d, J = 7.0 Hz, 3H). |
| 601 | (cis)-1-(4-((1-isopropyl-2-methyl-1H-imidazo[4,5-c]pyridin-6-yl)amino)pyrimidin-2-yl)-2-methylpiperidin-4-ol (enantiomer 2) | 3.64, 382.3, B | 1H NMR (400 MHz, DMSO-$d_6$) δ 9.68 (s, 1H), 8.50 (s, 1H), 8.39 (s, 1H), 7.94 (m, 1H), 6.35 (d, J = 5.7 Hz, 1H), 5.05-4.89 (m, 1H), 4.73 (m, 1H), 4.64 (d, J = 2.3 Hz, 1H), 4.50 (d, J = 13.2 Hz, 1H), 4.03 (d, J = 2.8 Hz, 1H), 2.56 (s, 3H), 1.80 (s, 4H), 1.57 (m, 6H), 1.33 (d, J = 7.0 Hz, 3H). |
| 602 | N-(2-(3-amino-1H-pyrazol-1-yl)pyrimidin-4-yl)-1-isopropyl-2-methyl-1H-imidazo[4,5-c]pyridin-6-amine | 3.35, 350.2, B | 1H NMR (400 MHz, DMSO-$d_6$) δ 10.24 (s, 1H), 8.74 (s, 1H), 8.53 (d, J = 0.7 Hz, 1H), 8.29 (d, J = 2.7 Hz, 1H), 8.22 (d, J = 5.8 Hz, 1H), 7.04 (s, 1H), 5.87 (d, J = 2.7 Hz, 1H), 4.98 (s, 2H), 4.73 (m, 1H), 2.57 (s, 3H), 1.68 (d, J = 6.9 Hz, 5H). |
| 603 | N4-(1-isopropyl-2-methyl-1H-imidazo[4,5-c]pyridin-6-yl)-N2-(1H-pyrazol-3-yl)pyrimidine-2,4-diamine | 3.26, 350.2, B | n/a |
| 604 | (1-isopropyl-2-methyl-N-(2-(3-methylmorpholino)pyrimidin-4-yl)-1H-imidazo[4,5-c]pyridin-6-amine (enantiomer 1) | 3.32, 368.2, B | 1H NMR (400 MHz, DMSO-$d_6$) δ 9.72 (s, 1H), 8.50 (d, J = 0.7 Hz, 1H), 8.34 (s, 1H), 7.98 (d, J = 5.6 Hz, 1H), 6.46 (d, J = 5.6 Hz, 1H), 4.70 (m, 2H), 4.29 (m, 1H), 3.93 (m, 1H), 3.74 (d, J = 11.2 Hz, 1H), 3.62 (m, 1H), 3.46 (m, 1H), 3.20 (m, 1H), 2.56 (s, 3H), 1.55 (d, 6H), 1.22 (d, J = 6.7 Hz, 3H). |

| Example | Structure/Name | LCMS R$_T$ (min), [M + H]$^+$, method | $^1$H NMR (ppm) |
|---|---|---|---|
| 605 | 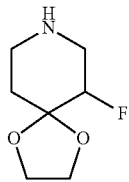 [SMILES: FC1CNCCC12OCCO2]<br>(1-isopropyl-2-methyl-N-(2-(3-methylmorpholino)pyrimidin-4-yl)-1H-imidazo[4,5-c]pyridin-6-amine (enantiomer 2) | 3.34, 368.3, B | $^1$H NMR (400 MHz, DMSO-d$_6$) δ 9.72 (s, 1H), 8.50 (d, J = 0.8 Hz, 1H), 8.34 (s, 1H), 7.98 (d, J = 5.6 Hz, 1H), 6.46 (d, J = 5.7 Hz, 1H), 4.79-4.62 (m, 2H), 4.29 (m, 1H), 3.93 (m, 1H), 3.74 (d, J = 11.2 Hz, 1H), 3.64 (d, J = 3.1 Hz, 1H), 3.46 (m, 1H), 3.22-3.15 (m, 1H), 2.56 (s, 3H), 1.55 (m, 6H), 1.22 (d, J = 6.7 Hz, 3H). |
| 606 | 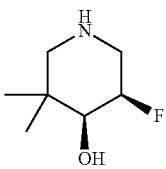<br>N-(2-(2,4-dimethyl-1H-imidazol-1-yl)pyrimidin-4-yl)-1-isopropyl-2-methyl-1H-imidazo[4,5-c]pyridin-6-amine | 3.64, 363.2, B | $^1$H NMR (400 MHz, DMSO-d$_6$) δ 10.27 (s, 1H), 8.58 (d, J = 0.9 Hz, 1H), 8.35 (d, J = 5.9 Hz, 1H), 8.16 (s, 1H), 7.53 (d, J = 1.2 Hz, 1H), 7.26 (s, 1H), 4.75 (m, 1H), 2.65 (s, 3H), 2.58 (s, 3H), 2.10 (d, J = 1.0 Hz, 3H), 1.59 (d, J = 6.9 Hz, 6H). |

Example A90: (±)-6-Fluoro-1,4-dioxa-8-azaspiro[4.5]decane

A mixture of (±)-6-fluoro-1,4-dioxa-8-azaspiro[4.5]decane-8-carboxylic acid benzyl ester (Tetrahedron Letters, 53, (2012), 2971-2975)(1.29 g, 4.37 mmol) and 10% palladium on carbon (129 mg) in industrial methylated spirit (25 mL) was stirred under a hydrogen atmosphere for 16 h, then filtered through a Celite pad. The filtrate was concentrated in vacuo to give a colorless oil (672 mg, 95%). LCMS (ESI): [M+H]$^+$ 162.

Example A91: (±)-cis-5-Fluoro-3,3-dimethylpiperidin-4-ol

Step 1: 3,3-Dimethyl-4-trimethylsilanyloxy-3,6-dihydro-2H-pyridine-1-carboxylic acid tert-butyl ester

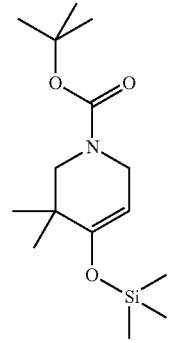

Trimethylsilyl chloride (0.74 mL, 5.9 mmol), and then triethylamine (1.6 mL, 12 mmol) were added to a mixture of 3,3-dimethyl-4-oxopiperidine-1-carboxylic acid tert-butyl ester (1.1 g, 4.9 mmol) in N,N-dimethylformamide (20 mL). The reaction mixture was heated at 80° C. under nitrogen for 16 h. The reaction mixture was cooled to room temperature and diluted with aqueous sodium hydrogen carbonate (50 mL). The aqueous mixture was extracted with cyclohexane (2×50 mL). The organic extracts were combined, washed with brine, dried over magnesium sulfate, filtered and concentrated in vacuo. The crude residue was purified by chromatography (silica, gradient: 0-20% ethyl acetate in cyclohexane) to give a colorless oil (781 mg, 53%). $^1$H NMR (400 MHz, CDCl$_3$) δ 4.60-4.53 (m, 1H), 3.92-3.85 (m, 2H), 3.26 (bs, 2H), 1.46 (s, 9H), 1.00 (s, 6H), 0.20 (s, 9H).

Step 2: 5-Fluoro-3,3-dimethyl-4-oxopiperidine-1-carboxylic acid tert-butyl ester

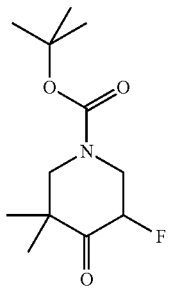

SelectFluor® (970 mg, 2.7 mmol) was added gradually in portions to a solution of 3,3-dimethyl-4-trimethylsilanyloxy-3,6-dihydro-2H-pyridine-1-carboxylic acid tert-butyl ester (781 mg, 2.6 mmol) in acetonitrile (13 mL) at 0° C. After stirring for 2 h the reaction mixture was concentrated in vacuo. The residue was taken up in brine (50 mL) and extracted with ethyl acetate (2×50 mL). The organic extracts were combined, dried over magnesium sulfate, filtered and concentrated in vacuo to give a colorless oil (620 mg, 97%). $^1$H NMR (400 MHz, CDCl$_3$) δ 5.11 (ddd, J=47.7, 10.6, 7.24, 1H), 4.83-4.52 (m, 1H), 4.07-3.85 (m, 1H), 3.21-2.84 (m, 2H), 1.50 (s, 9H), 1.19 (s, 3H), 1.12 (s, 3H).

Step 3: (±)-cis-5-Fluoro-4-hydroxy-3,3-dimethylpiperidine-1-carboxylic acid tert-butyl ester

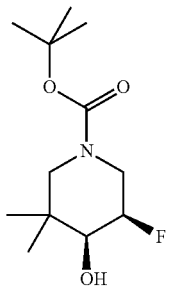

L-Selectride® (1.0 M solution in tetrahydrofuran)(3.0 mL, 3.0 mmol) was added dropwise to a solution of 5-fluoro-3,3-dimethyl-4-oxopiperidine-1-carboxylic acid tert-butyl ester (620 mg, 2.5 mmol) in anhydrous tetrahydrofuran (10 mL) at 0° C. and the mixture was stirred for 2 h. The reaction mixture was gradually quenched with 6M sodium hydroxide (3 mL) and stirred vigorously for 1 h. The reaction mixture was concentrated in vacuo. The residue was taken up in water (50 mL) and extracted with ethyl acetate (3×50 mL). The organic extracts were combined, washed with brine, dried over magnesium sulfate, filtered and concentrated in vacuo to give a colorless oil. The oil was purified by chromatography (silica, solvent gradient: 20-60% ethyl acetate in cyclohexane) to give a colorless oil (401 mg, 64%) as a racemic mixture. $^1$H NMR (400 MHz, CDCl$_3$) δ 4.78-4.56 (m, 1H), 4.27-2.93 (m, 6H), 1.46 (s, 9H), 1.43 (s, 6H).

Step 4: (±)-cis-5-Fluoro-3,3-dimethylpiperidin-4-ol

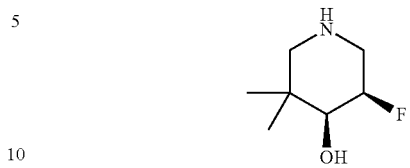

Trifluoroacetic acid (2 mL) was added to a solution of (±)-cis-5-fluoro-4-hydroxy-3,3-dimethylpiperidine-1-carboxylic acid tert-butyl ester (474 mg, 1.9 mmol) in dichloromethane (2 mL). After stirring at room temperature for 30 min the reaction mixture was loaded onto an SCX column. The column was washed with methanol and then eluted with 2M ammonia in methanol. The basic fraction was concentrated in vacuo to give a mixture of enantiomers as a colorless oil (282 mg, 99%). $^1$H NMR (400 MHz, CDCl$_3$) δ 4.73-4.58 (m, 1H), 3.45-3.38 (m, 1H), 3.24-3.17 (m, 1H), 2.85 (ddd, J=28.1, 14.0, 3.0 Hz, 1H), 2.74 (dd, J=13.4, 1.2 Hz, 1H), 2.35 (dd, J=13.4, 1.4 Hz, 1H), 1.88 (bs, 2H), 1.00 (d, J=2.1 Hz, 3H), 0.98 (s, 3H).

Example A92: (3RS,4SR)-3-Fluoro-4-hydroxy-4-methylpiperidine-1-carboxylic acid benzyl ester (mixture of enantiomers)

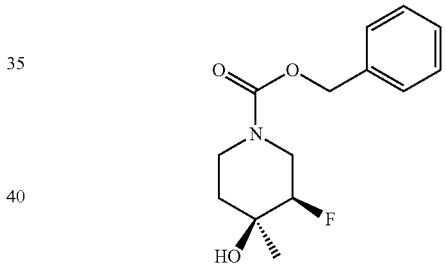

And

Example A93: (3RS,4RS)-3-Fluoro-4-hydroxy-4-methylpiperidine-1-carboxylic acid benzyl ester (mixture of enantiomers)

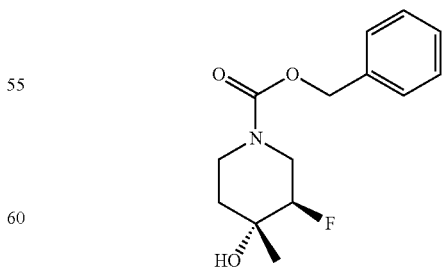

Methylmagnesium bromide (1.4 M in tetrahydrofuran: toluene, 1:3)(61 mL, 85.4 mmol) was added over 15 min to a solution of 3-fluoro-4-oxopiperidine-1-carboxylic acid benzyl ester (*J. Med. Chem.*, 2008, 51, 4239)(16.5 g, 65.6 mmol) in tetrahydrofuran (200 mL) at −78° C. The mixture was allowed to warm to −20° C. over 2 h then quenched by addition of saturated ammonium chloride. The aqueous phase was extracted twice with ethyl acetate, and the combined organic extracts were washed with brine, dried over anhydrous sodium sulfate, filtered and concentrated in vacuo. The residue was purified by chromatography on silica (solvent gradient: 50-100% diethyl ether in pentane) to afford the title compounds as colorless oils.

Example A92 (mixture of enantiomers with known relative stereochemistry): (3RS,4SR)-3-fluoro-4-hydroxy-4-methylpiperidine-1-carboxylic acid benzyl ester (8.0 g, 46%). $^1$H NMR (CDCl$_3$): δ 7.37-7.32 (5H, m), 5.13 (2H, s), 4.28 (1H, br d, J=47 Hz), 4.04-3.88 (1H, m), 3.69-3.64 (1H, m), 3.52-3.33 (2H, m), 2.00 (1H, br s), 1.82-1.77 (1H, m), 1.59-1.51 (1H, m), 1.31 (3H, d, J=0.8 Hz). Example A93 (mixture of enantiomers with known relative stereochemistry): (3RS,4RS)-3-fluoro-4-hydroxy-4-methylpiperidine-1-carboxylic acid benzyl ester (3.33 g, 19%). $^1$H NMR (CDCl$_3$): δ 7.36-7.35 (5H, m), 5.13 (2H, br s), 4.29-4.07 (2H, m), 3.92-3.80 (1H, m), 3.55-3.43 (1H, m), 3.30-3.17 (1H, m), 1.90-1.80 (1H, m), 1.75 (1H, br s), 1.52-1.46 (1H, m), 1.32 (3H, d, J=2.2 Hz).

Examples A94 and A95: (3R*,4S*)-3-Fluoro-4-hydroxy-4-methylpiperidine-1-carboxylic acid benzyl ester (enantiomer 1) and (3R*,4S*)-3-Fluoro-4-hydroxy-4-methylpiperidine-1-carboxylic acid benzyl ester (enantiomer 2)

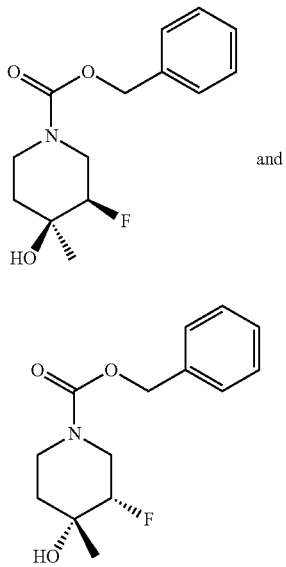

The enantiomers of Example A92 (7.72 g) were separated by chiral supercritical fluid chromatography:

Example A94 (as a single unknown enantiomer with known relative stereochemistry and absolute stereochemistry arbitrarily assigned): (3.4 g) [α]$_D$ +0.6° (c 3.2, methanol).

Example A95 (as a single unknown enantiomer with known relative stereochemistry and absolute stereochemistry arbitrarily assigned): (2.84 g) [α]$_D$ 0.0° (c 6.2, methanol).

Example A96: (3RS,4SR)-3-Fluoro-4-methylpiperidin-4-ol (mixture of enantiomers)

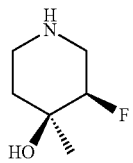

(3RS,4SR)-3-Fluoro-4-hydroxy-4-methylpiperidine-1-carboxylic acid benzyl ester (Example A92, 3.8 g, 14.2 mmol) was dissolved in ethanol (100 mL) and the mixture was purged with nitrogen. Palladium hydroxide on carbon (20%, 0.3 g) was added and the mixture was stirred under an atmosphere of hydrogen for 16 h. The mixture was purged with nitrogen, filtered through a Celite pad and the filtrate was concentrated in vacuo to give the title compound as a colorless gum as a mixture of enantiomers (quantitative). $^1$H NMR (CDCl$_3$): δ 4.29 (1H, ddd, J=48.4, 7.2, 3.5 Hz), 3.13-3.06 (1H, m), 3.00-2.91 (2H, m), 2.71-2.64 (1H, m), 2.18 (2H, br s), 1.80-1.72 (1H, m), 1.60-1.53 (1H, m), 1.28 (3H, d, J=1.3 Hz).

Example A97: (+)-(3R*,4S*)-3-Fluoro-4-methylpiperidin-4-ol (absolute stereochemistry unknown)

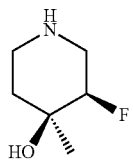

The title compound was prepared with known relative stereochemistry and absolute stereochemistry arbitrarily assigned from the earlier eluting enantiomer of (3R*,4S*)-3-fluoro-4-hydroxy-4-methylpiperidine-1-carboxylic acid benzyl ester (Example A94)(3.4 g, 12.72 mmol) by a procedure analogous to that described in Example A96. [α]$_D$ +16.9° (c 2.6, methanol). $^1$H NMR (CDCl$_3$): δ 4.29 (1H, ddd, J=48.4, 7.2, 3.5 Hz), 3.13-3.06 (1H, m), 3.00-2.91 (2H, m), 2.71-2.64 (1H, m), 2.10 (2H, br s), 1.80-1.72 (1H, m), 1.60-1.53 (1H, m), 1.28 (3H, d, J=1.2 Hz).

Example A98: (−)-(3R*,4S*)-3-Fluoro-4-methylpiperidin-4-ol (absolute stereochemistry unknown)

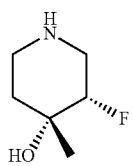

The title compound was prepared with known relative stereochemistry and absolute stereochemistry arbitrarily assigned from the later eluting enantiomer of (3R*,4S*)-3-fluoro-4-hydroxy-4-methylpiperidine-1-carboxylic acid benzyl ester (Example A95)(2.846 g, 10.64 mmol) by a procedure analogous to that described in Example A96. [α]$_D$ −13.7° (c 3.35, methanol). $^1$H NMR (CDCl$_3$): δ 4.30 (1H, ddd, J=48.4, 7.2, 3.5 Hz), 3.14-3.07 (1H, m), 3.01-2.92 (2H, m), 2.72-2.65 (1H, m), 1.92 (2H, br s), 1.80-1.73 (1H, m), 1.60-1.54 (1H, m), 1.29 (3H, d, J=1.3 Hz).

Example A99: (3RS,4SR)-1-(4-Aminopyrimidin-2-yl)-3-fluoro-4-methylpiperidin-4-ol (mixture of enantiomers)

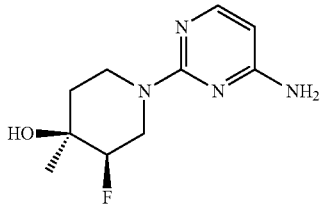 [SMILES: C[C@]1(O)CCN(c2nccc(N)n2)C[C@H]1F]

A mixture of (3RS,4SR)-3-fluoro-4-methylpiperidin-4-ol (1.89 g, 14.2 mmol)(Example A96), 2-chloro-4-aminopyrimidine (1.838 g, 14.2 mmol) and triethylamine (3.9 mL, 28 mmol) in isopropanol (30 mL) was heated under microwave irradiation at 150° C. for 1 h. The cooled reaction mixture was concentrated in vacuo. The residue was dissolved in a mixture of dichloromethane and methanol (30:1, 124 mL), to which potassium carbonate (5.5 g) was added and the mixture stirred for 10 min. The mixture was filtered and the filtrate concentrated in vacuo. Purification by chromatography on silica (solvent gradient 50-100% isopropyl acetate in dichloromethane, then 50-100% ethyl acetate in isopropyl acetate) gave the product as a mixture of enantiomers as a white solid (2.09 g, 65%). $^1$H NMR (CDCl$_3$): δ 7.92 (1H, d, J=5.6 Hz), 5.76 (1H, d, J=5.6 Hz), 4.56 (2H, br s), 4.48-4.40 (1H, m), 4.33 (1H, ddd, J=47, 9.1, 4.5 Hz), 4.15-4.09 (1H, m), 3.59 (1H, ddd, J=12.6, 8.8, 5.4 Hz), 3.47 (1H, ddd, J=13.4, 10.6, 3.3 Hz), 1.95 (1H, dd, J=2.7, 1.9 Hz), 1.88-1.81 (1H, m), 1.62-1.55 (1H, m), 1.33 (3H, t, J=1.0 Hz).

Example A100: (−)-(3R*,4S*)-1-(4-Aminopyrimidin-2-yl)-3-fluoro-4-methylpiperidin-4-ol (absolute stereochemistry unknown)

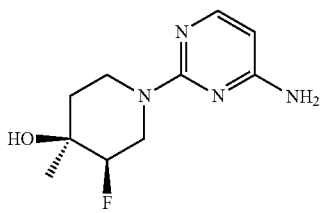 [SMILES: C[C@]1(O)CCN(c2nccc(N)n2)C[C@H]1F]

The title compound (2.093 g, 73%) was prepared as a single unknown stereoisomer with known relative stereochemistry and absolute stereochemistry arbitrarily assigned from (+)-(3R*,4S*)-3-fluoro-4-methylpiperidin-4-ol (Example A97) 1.679 g, 12.6 mmol) by a procedure analogous to that described in Example A99. [α]$_D$ −16° (c 1.16, methanol). $^1$H NMR (CDCl$_3$): δ 7.93 (1H, d, J=5.6 Hz), 5.76 (1H, d, J=5.6 Hz), 4.55 (2H, br s), 4.48-4.26 (2H, m), 4.16-4.09 (1H, m), 3.63-3.56 (1H, m), 3.51-3.44 (1H, m), 1.94 (1H, dd, J=2.7, 1.9 Hz), 1.88-1.81 (1H, m), 1.63-1.55 (1H, m), 1.33 (3H, t, J=0.9 Hz).

Example A101: (+)-(3R*,4S*)-1-(4-Aminopyrimidin-2-yl)-3-fluoro-4-methylpiperidin-4-ol (absolute stereochemistry unknown)

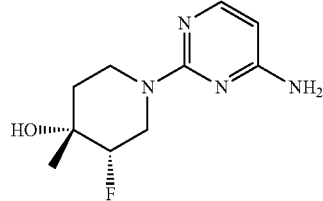 [SMILES: C[C@@]1(O)CCN(c2nccc(N)n2)C[C@@H]1F]

The title compound (1.684 g, 70%) was prepared as a single unknown stereoisomer with known relative stereochemistry and absolute stereochemistry arbitrarily assigned from (−)-(3R*,4S*)-3-fluoro-4-methylpiperidin-4-ol (Example A98) 1.417 g, 10.64 mmol) by a procedure analogous to that described in Example A99. [α]$_D$ +17° (c 1.17, methanol). $^1$H NMR (CDCl$_3$): δ 7.93 (1H, d, J=5.6 Hz), 5.76 (1H, d, J=5.6 Hz), 4.55 (2H, br s), 4.48-4.26 (2H, m), 4.16-4.09 (1H, m), 3.63-3.56 (1H, m), 3.51-3.44 (1H, m), 1.94 (1H, dd, J=2.7, 1.9 Hz), 1.88-1.81 (1H, m), 1.63-1.55 (1H, m), 1.33 (3H, t, J=0.9 Hz).

Example A102: (3RS,4SR)-3-Fluoro-4-methoxy-4-methylpiperidine-1-carboxylic acid benzyl ester (mixture of enantiomers)

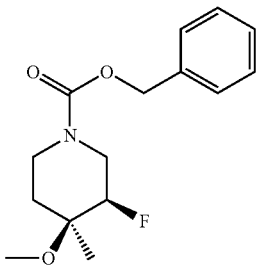 [SMILES: CO[C@@]1(C)CCN(C(=O)OCc2ccccc2)C[C@H]1F]

Sodium hydride (60 wt % dispersion in mineral oil)(0.16 g, 4.0 mmol) was added portion-wise to a solution of (3RS,4SR)-3-fluoro-4-hydroxy-4-methylpiperidine-1-carboxylic acid benzyl ester (Example A92)(0.27 g, 1.0 mmol), dimethyl sulfate (0.38 mL, 4.0 mmol) and 18-crown-6 (10 mg) in tetrahydrofuran (8 mL). The reaction mixture was stirred at room temperature for 16 h then quenched by addition of saturated ammonium chloride. The aqueous phase was extracted twice with ethyl acetate, and the combined organic extracts were washed with brine, dried over anhydrous sodium sulfate, filtered and concentrated in vacuo. The residue was purified by chromatography on silica (solvent gradient: 5-25% ethyl acetate in cyclohexane) to afford the title compound as a mixture of enantiomers colorless oil (quantitative). $^1$H NMR (CDCl3): δ 7.37-7.31 (5H, m), 5.13 (2H, br s), 4.29 (1H, br d, J=47 Hz), 3.96 (1H, br s), 3.68 (1H, br s), 3.50 (1H, br s), 3.30 (3H, s), 3.27-3.20 (1H, m), 1.92 (1H, br s), 1.41 (1H, br s), 1.30 (3H, s).

Example A103: (3RS,4SR)-3-Fluoro-4-methoxy-4-methylpiperidine (mixture of enantiomers)

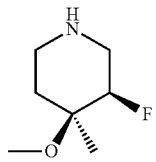

The title compound (51.4 mg, 35% 2 steps) was prepared as a mixture of enantiomers from (3RS,4SR)-3-fluoro-4-methoxy-4-methylpiperidine-1-carboxylic acid benzyl ester (Example A102) by a procedure analogous to that described in Example A96. $^1$H NMR (CDCl$_3$): δ 4.33 (1H, ddd, J=48, 7.2, 3.2 Hz), 3.30 (3H, s), 3.19-3.12 (1H, m), 2.95-2.86 (2H, m), 2.69-2.63 (1H, m), 1.92-1.85 (1H, m), 1.76 (1H, br s), 1.47-1.40 (1H, m), 1.27 (3H, d, J=1.1 Hz).

Example A104: 1-(4-Aminopyrimidin-2-yl)-4-methylpiperidin-4-ol

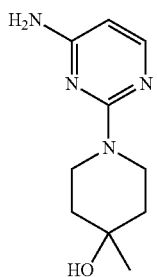

To a solution of 4-hydroxy-4-methylpiperidine-1-carboxylic acid tert-butyl ester (3.2 g, 14.9 mmol) in dichloromethane (100 mL) was added trifluoroacetic acid (5 mL) and the reaction mixture stirred at room temperature for 2 h. The reaction mixture was loaded onto an SCX-2 cartridge and washed with methanol. The product was eluted with a solution of ammonia in methanol (2M). The eluent was concentrated in vacuo and the residue was dissolved in isopropanol (20 mL). 2-Chloro-4-aminopyrimidine (1.83 g, 14.1 mmol) and triethylamine (4.14 mL, 29.7 mmol) were added and the reaction mixture was heated in a sealed vial at 120° C. for 48 h. The reaction mixture was purified via flash chromatography on silica gel (solvent gradient: 0-10% methanol in ethyl acetate). LCMS (ESI): [M+H]$^+$ 209.

Example A105: 6-Chloro-2-[(S)-1-(tetrahydropyran-2-yloxy)ethyl]-1-((S)-2,2,2-trifluoro-1-methylethyl)-1H-imidazo[4,5-c]pyridine

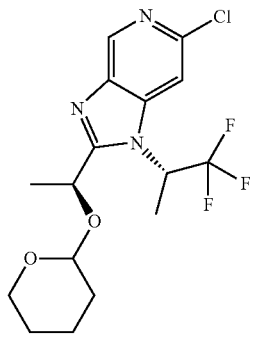 [SMILES: C[C@H](OC1CCCCO1)c1nc2cnc(Cl)cc2n1[C@@H](C)C(F)(F)F]

The title compound (1.1 g, 95%) was prepared from (S)-lactamide (558 mg, 6.26 mmol) and 6-chloro-N$^4$—((S)-2,2,2-trifluoro-1-methylethyl)pyridine-3,4-diamine (Example A82, step 2) (1 g, 4.17 mmol) according to a procedure analogous to that described for Example A72. LCMS (ESI): [M+H]$^+$ 378.

Example A106: 6-Chloro-2-[(R)-1-(tetrahydropyran-2-yloxy)ethyl]-1-((R)-2,2,2-trifluoro-1-methylethyl)-1H-imidazo[4,5-c]pyridine

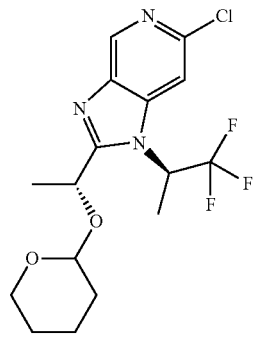 [SMILES: C[C@@H](OC1CCCCO1)c1nc2cnc(Cl)cc2n1[C@H](C)C(F)(F)F]

The title compound (2.1 g, 91%) was prepared from (R)-lactamide (2.5 g, 10.4 mmol) and 6-chloro-N$^4$—((R)-2,2,2-trifluoro-1-methylethyl)pyridine-3,4-diamine (Example A60, step 2) (1.4 g, 15.6 mmol) according to a procedure analogous to that described for Example A72. LCMS (ESI): [M+H]$^+$ 378.

Example A107: 6-Chloro-2-[(S)-1-(tetrahydropyran-2-yloxy)ethyl]-1-((R)-2,2,2-trifluoro-1-methylethyl)-1H-imidazo[4,5-c]pyridine

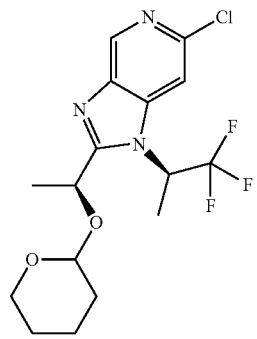 [SMILES: C[C@H](OC1CCCCO1)c1nc2cnc(Cl)cc2n1[C@H](C)C(F)(F)F]

The title compound (0.8 g, 99%) was prepared from (S)-lactamide (2.5 g, 10.4 mmol) and 6-chloro-N$^4$—((R)-2,2,2-trifluoro-1-methylethyl)pyridine-3,4-diamine (Example 60, step 2) (1.4 g, 15.6 mmol) according to a procedure analogous to that described for Example A72. LCMS (ESI): [M+H]$^+$ 378

Example A108 and A109: (5RS,6SR)-tert-butyl 6-fluoro-1-oxa-8-azaspiro[4.5]decane-8-carboxylate (mixture of enantiomers) and (5RS,6SR)-tert-butyl 6-fluoro-1-oxa-8-azaspiro[4.5]decane-8-carboxylate (mixture of enantiomers)

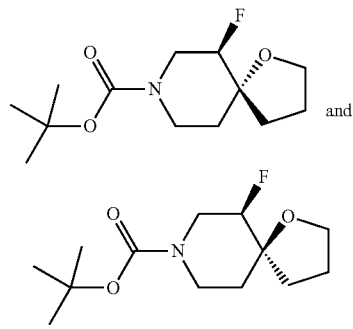

Step 1: 2-(Prop-2-yn-1-yloxy)tetrahydro-2H-pyran

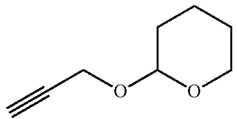

Into a 3000-mL 4-necked round-bottom flask purged and maintained with an inert atmosphere of nitrogen was placed a solution of prop-2-yn-1-ol (100 g, 1.78 mol) in dichloromethane (1000 mL), followed by the addition of camphorsulfonic acid (20 g, 86.21 mmol) with stirring at 0° C. To this was added a solution of 3,4-dihydro-2H-pyran (158 g, 1.88 mol) in dichloromethane (500 mL) dropwise with stirring at 0° C. The resulting solution was stirred overnight at room temperature, quenched by the addition of 2000 mL of water/ice and extracted with 3×2000 mL of dichloromethane. The combined organic layers were washed with 3×1000 mL saturated aqueous sodium bicarbonate and 3×1000 mL of brine, dried over anhydrous sodium sulfate, filtered and concentrated in vacuo. The crude product was purified by distillation under reduced pressure (10 mm Hg) and the fractions were collected at 84° C. to afford 152 g (61%) of the title compound as a colorless oil.

Step 2: tert-Butyl 3-fluoro-4-hydroxy-4-(3-((tetrahydro-2H-pyran-2-yl)oxy)prop-1-yn-1-yl)piperidine-1-carboxylate

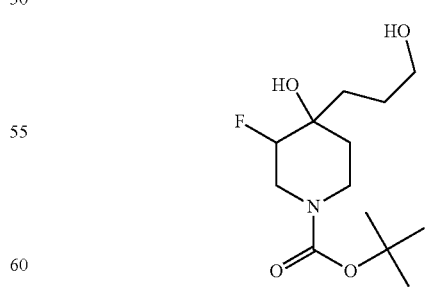

Into a 3000-mL 4-necked round-bottom flask purged and maintained under an inert atmosphere of nitrogen was placed a solution of 2-(prop-2-yn-1-yloxy)tetrahydro-2H-pyran (77.4 g, 552.15 mmol) in tetrahydrofuran (1000 mL), followed by the addition of n-butyllithium (2.5 M)(221.2 mL, 1.20 equiv) dropwise with stirring at −78° C. The mixture was stirred at −20° C. for 30 min. To this was added a solution of tert-butyl 3-fluoro-4-oxopiperidine-1-carboxylate (100 g, 460.33 mmol) in tetrahydrofuran (500 mL) dropwise with stirring at −20° C. The resulting solution was stirred at −20° C. for 1 h, quenched by the addition of 1000 mL of aqueous ammonium chloride and extracted with 3×1000 mL of ethyl acetate. The combined organic layers were washed with 2×1000 mL of brine, dried over anhydrous sodium sulfate, filtered and concentrated under vacuum. The residue was purified on a silica gel column (solvent gradient: 5%-20% ethyl acetate in petroleum ether) to afford 101 g (61%) of the title compound as a colorless oil.

Step 3: tert-Butyl 3-fluoro-4-hydroxy-4-(3-((tetrahydro-2H-pyran-2-yl)oxy)propyl)piperidine-1-carboxylate

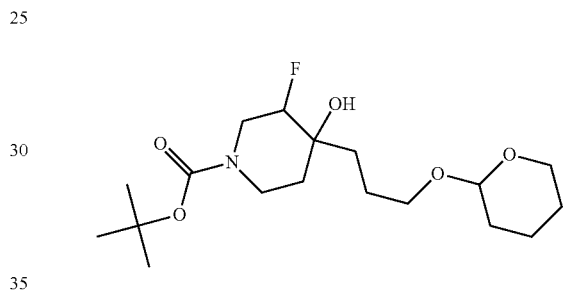

Into a 2000-mL 3-necked round-bottom flask purged and maintained under an inert atmosphere of nitrogen was placed tert-butyl 3-fluoro-4-hydroxy-4-(3-((tetrahydro-2H-pyran-2-yl)oxy)prop-1-yn-1-yl)piperidine-1-carboxylate (101 g, 282.58 mmol), methanol (1000 mL), and palladium on carbon (40 g). To the above was introduced $H_2$ (gas) and the resulting solution was stirred overnight at room temperature. The reaction was filtered and concentrated in vacuo to afford 91 g (89%) of the title compound as a colorless oil.

Step 4: tert-Butyl 3-fluoro-4-hydroxy-4-(3-hydroxypropyl)piperidine-1-carboxylate

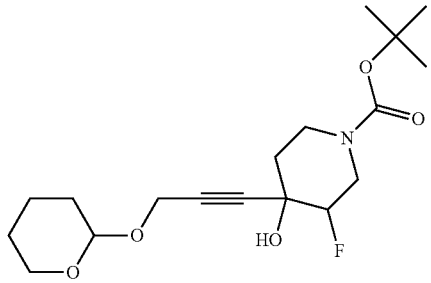 [SMILES: CC(C)(C)OC(=O)N1CCC(O)(C#CCOC2CCCCO2)C(F)C1]

Into a 5000-mL 4-necked round-bottom flask was placed a solution of tert-butyl 3-fluoro-4-hydroxy-4-(3-((tetrahydro-2H-pyran-2-yl)oxy)propyl)piperidine-1-carboxylate (91 g, 251.76 mmol) in dichloromethane (1000 mL). To the above solution was introduced hydrogen chloride (gas) at 0°

C. The mixture was stirred for 2 h under hydrogen chloride (gas) at 0° C. The solids were collected by filtration. The solids were diluted with 1000 mL of dichloromethane and to the mixture was added triethylamine (76.4 g, 755.02 mmol) and di-tert-butyl dicarbonate (60.4 g, 276.75 mmol). The resulting solution was stirred overnight at room temperature and then diluted with 1000 mL of dichloromethane. The resulting mixture was washed with 1×1000 mL of aqueous (1 N) hydrochloric acid, 1×1000 mL of aqueous sodium bicarbonate, 1×1000 mL of brine, dried over anhydrous sodium sulfate, filtered and concentrated in vacuo to afford 31 g (44%) of the title compound as a colorless oil.

Step 5: (5RS,6SR)-tert-butyl 6-fluoro-1-oxa-8-azaspiro[4.5]decane-8-carboxylate (mixture of enantiomers) and (5RS,6SR)-tert-butyl 6-fluoro-1-oxa-8-azaspiro[4.5]decane-8-carboxylate (mixture of enantiomers)

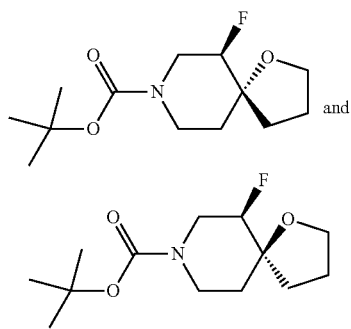

Into a 500-mL 3-necked round-bottom flask purged and maintained with an inert atmosphere of nitrogen was placed a solution of tert-butyl 3-fluoro-4-hydroxy-4-(3-hydroxypropyl)piperidine-1-carboxylate (31 g, 111.78 mmol) in dichloromethane (300 mL), triethylamine (33.9 g, 335.01 mmol), 4-dimethylaminopyridine (700 mg, 5.73 mmol), followed by the addition of 4-methylbenzene-1-sulfonyl chloride (25.5 g, 133.76 mmol) in several batches at 0° C. The resulting solution was stirred overnight at room temperature and then diluted with 1000 mL of dichloromethane. The resulting mixture was washed with 1×1000 mL of aqueous 1N HCl, 1×1000 mL of aqueous sodium bicarbonate, 1×1000 mL of brine, dried over anhydrous sodium sulfate, filtered and concentrated under vacuum. The residue was purified by silica gel column chromatography (solvent gradient: 10%-20% ethyl acetate in petroleum ether). The crude product was purified by preparative HPLC to afford each of the two title compounds each as a mixture of enantiomers with relative stereochemistry arbitrarily assigned.

Example A108: (5RS,6SR)-tert-butyl 6-fluoro-1-oxa-8-azaspiro[4.5]decane-8-carboxylate (10.04 g, 35%) as a white solid. $^1$H NMR (300 MHz, CDCl$_3$): δ 1.4 (s, 9H), 1.5-1.6 (m, 1H), 1.72-1.80 (m, 2H), 1.92-2.08 (m, 3H), 3.21-3.30 (m, 1H), 3.43-3.45 (m, 1H), 3.59-3.63 (m, 1H), 3.88-3.93 (m, 3H), 4.19-4.24 (m, 0.5H), 4.35-4.40 (m, 0.5H).

Example A109: (5RS,6SR)-tert-butyl 6-fluoro-1-oxa-8-azaspiro[4.5]decane-8-carboxylate (4.937 g, 17%) as a white solid. $^1$H NMR (300 MHz, CDCl$_3$): δ 1.4 (s, 9H), 1.5 (m, 1H), 1.6-1.7 (m, 1H), 1.86-1.98 (m, 3H), 2.00-2.13 (m, 1H), 3.15-3.22 (m, 1H), 3.23-3.49 (m, 1H), 3.75 (m, 1H), 3.84-3.89 (m, 2H), 3.95-4.02 (m, 1H), 4.12 (m, 0.5H), 4.25 (m, 0.5H).

Example A110:
meso-(3R,4s,5S)-3,5-Difluoro-4-hydroxypiperidine

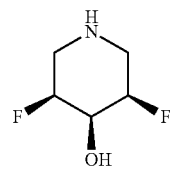

Step 1: 3-Fluoro-4-oxopiperidine-1,3-dicarboxylic acid 1-tert-butyl ester 3-methyl ester

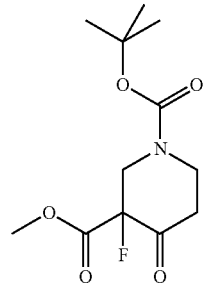 [SMILES: COC(=O)C1(F)CN(C(=O)OC(C)(C)C)CCC1=O]

4-Oxopiperidine-1,3-dicarboxylic acid 1-tert-butyl ester 3-methyl ester (2.65 g, 10.3 mmol)(WO 2005077369 A1) in tetrahydrofuran (30 mL) was added to a slurry of 60% sodium hydride in mineral oil (453 mg, 11.3 mmol) at 0° C. and stirred for 30 min. The reaction mixture was warmed to room temperature and stirred for a further hour. N,N-Dimethylformamide (30 mL) was then added, followed by SelectFluor® (3.65 g, 10.3 mmol). After stirring at room temperature for 2 h the reaction mixture was diluted with brine (300 mL). The mixture was extracted with ethyl acetate (5×30 mL). The organic extracts were combined, dried over sodium sulfate, filtered and concentrated in vacuo. The crude residue was purified by chromatography (silica, solvent gradient: 20-100% ethyl acetate in cyclohexane) to give the title compound as a mixture of enantiomers (2.42 g, 85%) as a colorless oil: $^1$H NMR (400 MHz, CDCl$_3$): δ 4.52-4.19 (m, 1H), 4.05-3.49 (m, 3H), 3.85 (s, 3H), 2.99-2.65 (m, 2H), 1.48 (s, 9H).

Step 2: 3,5-Difluoro-4-oxopiperidine-1,3-dicarboxylic acid 1-tert-butyl ester 3-methyl ester

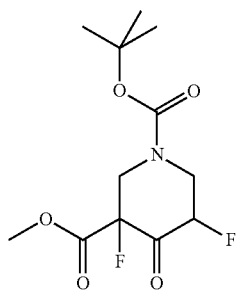 [SMILES: COC(=O)C1(F)CN(C(=O)OC(C)(C)C)CC(F)C1=O]

Trimethylsilyl chloride (1.34 mL, 10.5 mmol), followed by triethylamine (2.94 mL, 21.1 mmol) were added to a mixture of 3-fluoro-4-oxopiperidine-1,3-dicarboxylic acid 1-tert-butyl ester 3-methyl ester (2.42 g, 8.80 mmol) in N,N-dimethylformamide (9 mL). A precipitate formed immediately and further N,N-dimethylformamide (5 mL) was added to aid stirring. The reaction mixture was stirred for a further 10 min at room temperature and diluted with aqueous sodium hydrogen carbonate (50 mL). The aqueous mixture was extracted with cyclohexane (2×50 mL). The organic extracts were combined, washed with brine, dried over magnesium sulfate, filtered and concentrated in vacuo to give a pale yellow oil. The oil was dissolved in acetonitrile (35 mL) and SelectFluor® (3.27 g, 9.20 mmol) was added. After stirring at room temperature for 16 h, the reaction mixture was concentrated in vacuo. The residue was taken up in brine (50 mL) and extracted with ethyl acetate (2×50 mL). The organic extracts were combined, dried over magnesium sulfate, filtered and concentrated in vacuo. The crude residue was purified by chromatography (silica, solvent gradient: 15-100% ethyl acetate/cyclohexane) to give the title compound as a mixture of two diastereoisomers.

First eluting diastereoisomer (643 mg, 25%) as colourless oil: $^1$H NMR (400 MHz, CDCl$_3$) δ 4.76-4.58 (m, 1H), 4.57-4.19 (m, 2H), 3.92 (s, 3H), 3.62-3.30 (m, 1H), 3.09-2.98 (m, 1H), 1.47 (s, 9H).

Second eluting diastereoisomer was isolated as the hydrate (930 mg, 36%) as a white solid: $^1$H NMR (400 MHz, CDCl$_3$) δ 5.12-4.93 (m, 1H), 4.56-4.21 (m, 3H), 3.91 (s, 3H), 3.62-3.33 (m, 3H), 1.47 (s, 9H).

Step 3: 3,5-Difluoro-4-oxopiperidine-1-carboxylic acid tert-butyl ester

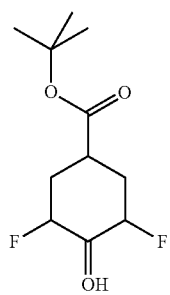 [SMILES: CC(C)(C)OC(=O)C1CC(F)C(=O)C(F)C1]

Lithium hydroxide monohydrate (184 mg, 4.39 mmol), was added to a solution of the first eluting diastereoisomer of 3,5-difluoro-4-oxopiperidine-1,3-dicarboxylic acid 1-tert-butyl ester 3-methyl ester (Step 2, 643 mg, 2.19 mmol) in methanol (20 mL) and water (20 mL). After stirring at room temperature for 30 min the reaction mixture was concentrated in vacuo to remove methanol. The aqueous residue was diluted with 0.2 M hydrochloric acid (25 mL, 5 mmol) and extracted with diethyl ether (2×50 mL). The organic extracts were combined, dried over magnesium sulfate, filtered and concentrated in vacuo to give 3,5-difluoro-4-oxopiperidine-1,3-dicarboxylic acid 1-tert-butyl ester as a pale yellow oil (566 mg, 92%). The crude acid (298 mg, 0.11 mmol) in acetonitrile (15 mL) was heated at 80° C. under microwave irradiation for 5 min. The reaction solution was then used immediately in the next step. An aliquot was concentrated in vacuo which gave the title compound as a pale yellow oil. $^1$H NMR (400 MHz, acetonitrile-d$_3$) δ 6.52 (bs, 1H), 5.07-4.92 (m, 1H), 4.44-4.20 (m, 2H), 3.80-3.60 (m, 1H), 3.27-2.99 (m, 1H), 1.44 (s, 9H).

Step 4: meso-(3R,4s,5S)-3,5-Difluoro-4-hydroxypiperidine-1-carboxylic acid tert-butyl ester and (±)-(3RS,5RS)-3,5-Difluoro-4-hydroxypiperidine-1-carboxylic acid tert-butyl ester

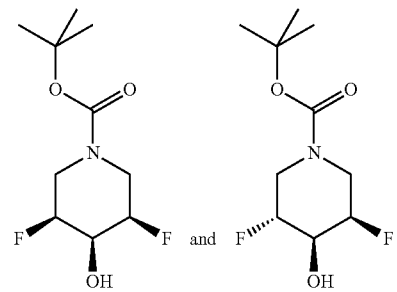

The solution of 3,5-difluoro-4-oxopiperidine-1-carboxylic acid tert-butyl ester (~0.11 mmol) from Step 3 was diluted with methanol (15 mL) and cooled to 0° C. Sodium borohydride (48 mg, 0.13 mmol) was added slowly to the solution and the mixture was stirred at 0° C. for 2 h. A few drops of saturated aqueous ammonium chloride were added to quench the reaction solution and the resulting mixture was concentrated in vacuo. The residue was taken up in saturated aqueous ammonium chloride (30 mL) and extracted with ethyl acetate (2×50 mL). The organic extracts were combined, dried over magnesium sulphate, filtered and concentrated in vacuo. The crude residue was purified by chromatography (silica, solvent gradient: 50-75% diethyl ether/cyclohexane) to give the title compounds.

First eluting compound, (±)-(3RS,5RS)-3,5-Difluoro-4-hydroxypiperidine-1-carboxylic acid tert-butyl ester, as a mixture of enantiomers (80 mg, 31%): $^1$H NMR (400 MHz, CDCl$_3$) δ 4.89-4.57 (m, 2H), 4.11-3.17 (m, 5H), 2.33 (bs, 1H), 1.47 (s, 9H).

Second eluting compound, meso-(3R,4s,5S)-3,5-Difluoro-4-hydroxypiperidine-1-carboxylic acid tert-butyl ester, as a single meso isomer (68 mg, 27%): $^1$H NMR (400 MHz, CDCl$_3$) δ 4.73-4.53 (m, 2H), 4.18-4.04 (m, 2H), 4.00-3.85 (m, 1H), 3.36 (ddd, J=26.4, 14.3, 2.7 Hz, 2H), 2.69 (d, J=8.3 Hz, 1H), 1.47 (s, 9H).

Step 5: meso-(3R,4s,5S)-3,5-Difluoro-4-hydroxypiperidine

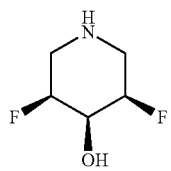

meso-(3R,4s,5S)-3,5-Difluoro-4-hydroxypiperidine-1-carboxylic acid tert-butyl ester from Step 4 (80 mg, 0.34 mmol) in hydrochloric acid (4 M in dioxane, 10 mL) was stirred for 1 h at room temperature. The reaction mixture was concentrated in vacuo to give a white solid. The solid was dissolved in methanol and loaded onto an SCX column. The column was washed with methanol and then eluted with 2M ammonia in methanol. The basic fraction was concentrated in vacuo and the residue was purified by chromatography (silica, solvent gradient: 5-15% 2M ammonia in methanol in dichloromethane) to give the title meso compound (21 mg, 54%) as a white solid: 1H NMR (400 MHz, pyridine-$d_5$) δ 7.55 (bs, 1H), 4.87-4.70 (m, 2H), 4.36-4.25 (m, 1H), 3.45-3.38 (m, 2H), 3.01-2.91 (m, 2H).

Example A111: (±)-(3RS,5RS)-3,5-Difluoropiperidin-4-ol (mixture of enantiomers)

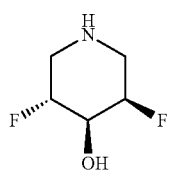

(±)-(3RS,5RS)-3,5-Difluoro-4-hydroxypiperidine-1-carboxylic acid tert-butyl ester (Example A110, step 4) (80 mg, 0.34 mmol) in hydrochloric acid (4 M in dioxane, 10 mL) was stirred for 1 h at room temperature. The reaction mixture was concentrated in vacuo to give a white solid. The solid was dissolved in methanol and loaded onto an SCX column. The title compound was washed with methanol and then eluted with 2M ammonia in methanol. The basic fraction was concentrated in vacuo to give a white solid. The solid was purified by chromatography (silica, solvent gradient: 5-15% 2M ammonia in methanol in ethyl acetate) to give the title compound as a mixture of enantiomers (22 mg, 48%) as a white solid: 1H NMR (400 MHz, pyridine-$d_5$) δ 7.76 (bs, 1H), 5.11-4.90 (m, 2H), 4.26-4.15 (m, 1H), 3.49-3.41 (m, 1H), 3.40-3.32 (m, 1H), 2.95-2.80 (m, 2H), 2.66 (bs, 1H).

Examples 607 and 608: Enantiomers of [2-((3RS,4SR)-3-Fluoro-4-methoxypiperidin-1-yl)pyrimidin-4-yl]-(1-isopropyl-2-methyl-1H-imidazo[4,5-c]pyridin-6-yl)amine (absolute stereochemistry unknown)

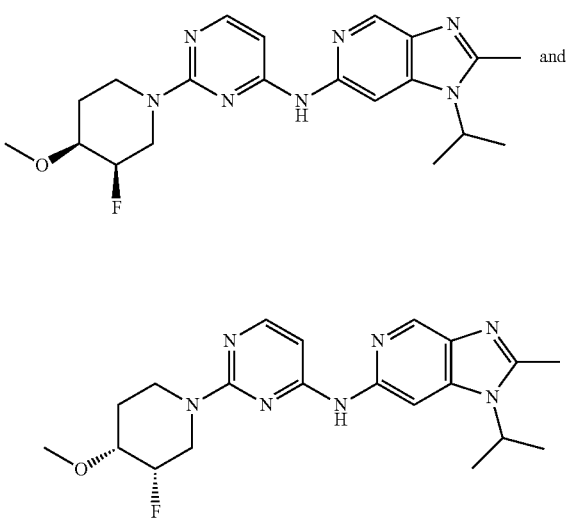

(±)-[2-((cis)-3-Fluoro-4-methoxypiperidin-1-yl)pyrimidin-4-yl]-(1-isopropyl-2-methyl-1H-imidazo[4,5-c]pyridin-6-yl)amine (Example 524) was separated via preparatory chiral SFC to yield the title compounds as single stereoisomers with known relative stereochemistry and absolute stereochemistry arbitrarily assigned. LCMS (ESI): $R_T$ 2.14 min [M+H]+ 400, Method F. 1H NMR (400 MHz, DMSO-$d_6$): δ 9.72 (s, 1H), 8.50 (s, 1H), 8.33 (bs, 1H) 7.95 (d, J=5.7 Hz, 1H), 6.45 (d, J=5.7 Hz, 1H), 5.00-4.86 (m, 1H), 4.77-4.66 (m, 1H), 4.48-4.43 (m, 1H), 3.62-3.18 (m, 4H), 3.36 (s, 3H), 2.56 (s, 3H), 1.84-1.66 (m, 2H), 1.57 (d, J=6.9 Hz, 6H).

Example 609: (R)-1-[6-[2-(2-Methanesulfonyl-2-methylpropoxy)pyrimidin-4-ylamino]-1-((S)-2,2,2-trifluoro-1-methylethyl)-1H-imidazo[4,5-c]pyridin-2-yl]ethanol

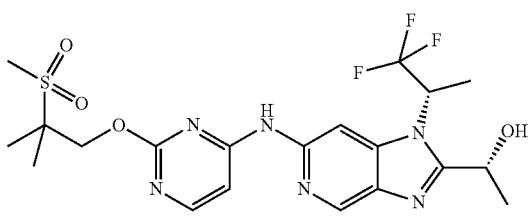 [SMILES: C[C@H](n1c([C@@H](C)O)nc2cnc(Nc3ccnc(OCC(C)(C)S(C)(=O)=O)n3)cc21)C(F)(F)F]

Step 1: 2-(2-Methanesulfonyl-2-methylpropoxy)pyrimidin-4-ylamine

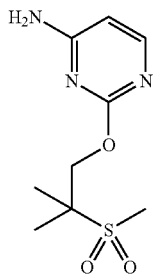

A microwave reaction vessel was charged with 4-amino-2-chloropyrimidine (100 mg, 0.774 mmol, 1.0 eq), 2-methanesulfonyl-2-methylpropan-1-ol (353 mg, 2.33 mmol, 3.0 eq), and potassium carbonate (160.3 mg, 1.16 mmol, 1.5 eq) in propan-2-ol (1 mL). The reaction was stirred at room temperature for 1 min and next heated under microwave irradiation at 200° C. for 2.5 h (Biotage Initiator, maximum pressure set at 22 bar). The reaction mixture was cooled and purified by flash column chromatography (solvent gradient: 0-10% 2M ammonia in methanol in ethyl acetate) to afford the title compound (163 mg, 86%). LCMS (ESI): [M+H]$^+$ 246.3.

Step 2: [2-(2-Methanesulfonyl-2-methylpropoxy)pyrimidin-4-yl]-[2-[(R)-1-(tetrahydropyran-2-yloxy)ethyl]-1-((S)-2,2,2-trifluoro-1-methylethyl)-1H-imidazo[4,5-c]pyridin-6-yl]amine

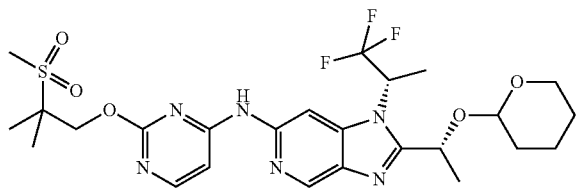 [SMILES: C[C@H](n1c([C@@H](C)OC2CCCCO2)nc2cnc(Nc3ccnc(OCC(C)(C)S(C)(=O)=O)n3)cc21)C(F)(F)F]

A reaction vessel was charged with 6-chloro-2-[(R)-1-(tetrahydropyran-2-yloxy)ethyl]-1-((S)-2,2,2-trifluoro-1-methylethyl)-1H-imidazo[4,5-c]pyridine (Example A83), (200 mg, 0.529 mmol), 2-(2-methanesulfonyl-2-methylpropoxy)pyrimidin-4-ylamine (130.1 mg, 0.529 mmol), 2-dicyclohexylphosphino-2',4',6'-triisopropylbiphenyl (50.4 mg, 0.106 mmol), tris(dibenzylideneacetone)dipalladium(0) (24.2 mg, 0.0265 mmol), cesium carbonate (344.9 mg, 1.06 mmol) and dioxane (5 ml). The reaction mixture was degassed, placed under argon and heated at 110° C. for 3 h. The reaction mixture was allowed to cool to room temperature, filtered and the filtrate partitioned between ethyl acetate and water. The organic layer was separated, dried over anhydrous magnesium sulfate, filtered and concentrated in vacuo. The residue was purified by flash column chromatography (solvent gradient: 0-10% methanol in ethyl acetate) to afford the title compound (110.5 mg, 36%). LCMS (ESI): [M+H]$^+$ 587.6.

Step 3: (R)-1-[6-[2-(2-Methanesulfonyl-2-methylpropoxy)pyrimidin-4-ylamino]-1-((S)-2,2,2-trifluoro-1-methylethyl)-1H-imidazo[4,5-c]pyridin-2-yl]ethanol

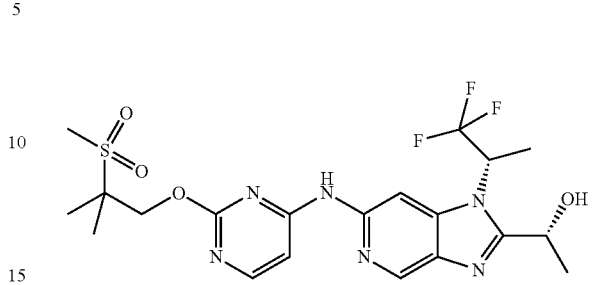

[2-(2-Methanesulfonyl-2-methylpropoxy)pyrimidin-4-yl]-[2-[(R)-1-(tetrahydropyran-2-yloxy)ethyl]-1-((S)-2,2,2-trifluoro-1-methylethyl)-1H-imidazo[4,5-c]pyridin-6-yl]amine (111 mg, 0.19 mmol) was dissolved in hydrochloric acid in methanol (2 ml, 1.25 M) and the reaction mixture was stirred at room temperature for 3 h. The reaction mixture was diluted with saturated aqueous sodium bicarbonate and the product extracted with ethyl acetate (3×15 ml). The combined organic extracts were washed with brine, dried over anhydrous magnesium sulfate, filtered and concentrated in vacuo. The resultant residue was subjected to preparative reverse phase-HPLC to yield the title compound as a white solid (55 mg, 57%). LCMS (ESI): $R_T$=2.86 min, [M+H]$^+$ 503, Method F; $^1$H NMR (400 MHz, DMSO-d$_6$) δ 10.32 (1H, br s), 8.72 (1H, s), 8.46 (1H, br s), 8.17 (1H, d, J=5.9 Hz), 7.06 (1H, br s), 5.97 (1H, d, J=7.1 Hz), 5.92-5.84 (1H, m), 5.07-5.01 (1H, m), 4.46 (2H, dd, J=11.3 Hz), 3.06 (3H, s), 1.84 (3H, d, J=7.1 Hz), 1.63 (3H, d, J=6.3 Hz), 1.42 (3H, s), 1.41 (3H, 2 s).

Example 610: 2,2-Difluoro-3-[4-(1-isopropyl-2-methyl-1H-imidazo[4,5-c]pyridin-6-ylamino)pyrimidin-2-ylamino]propionamide

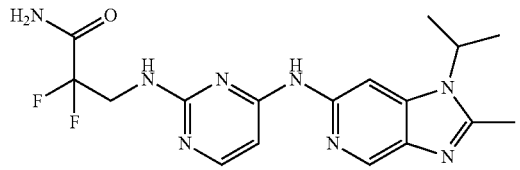 [SMILES: Cc1nc2cnc(Nc3ccnc(NCC(F)(F)C(N)=O)n3)cc2n1C(C)C]

Step 1: 2,2-Difluoro-3-[4-(1-isopropyl-2-methyl-1H-imidazo[4,5-c]pyridin-6-ylamino)pyrimidin-2-ylamino]propionic acid ethyl ester

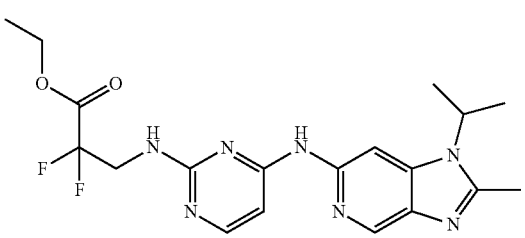 [SMILES: CCOC(=O)C(F)(F)CNc1nccc(Nc2cc3c(cn2)nc(C)n3C(C)C)n1]

The title compound (390 mg, quantitative) was prepared from (2-chloropyrimidin-4-yl)-(1-isopropyl-2-methyl-1H-imidazo[4,5-c]pyridin-6-yl)amine (275 mg, 0.908 mmol) using a method analogous to Example 46. LCMS (ESI): [M+H]+ 420.4.

Step 2: 2,2-Difluoro-3-[4-(1-isopropyl-2-methyl-1H-imidazo[4,5-c]pyridin-6-ylamino)pyrimidin-2-ylamino]propionic acid

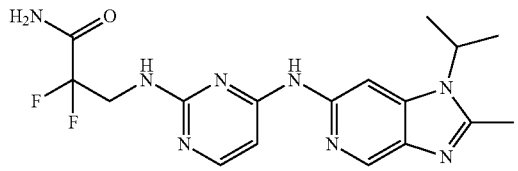 [SMILES: Cc1nc2cnc(Nc3ccnc(NCC(F)(F)C(N)=O)n3)cc2n1C(C)C]

A reaction vessel was charged with 2,2-difluoro-3-[4-(1-isopropyl-2-methyl-1H-imidazo[4,5-c]pyridin-6-ylamino)pyrimidin-2-ylamino]propionic acid ethyl ester (394 mg, 0.908 mmol) and lithium hydroxide hydrate (114 mg, 2.72 mmol) in tetrahydrofuran:water (3:1 ml respectively). The reaction mixture was stirred at room temperature for 1 minute then heated under microwave irradiation at 120° C. for 3 h. The reaction was concentrated in vacuo and purified by reverse phase HPLC and subsequently lyophilized to afford the title compound (95.3 mg, 27%). LCMS (ESI): [M+H]+ 392.4.

Step 3: 2,2-Difluoro-3-[4-(1-isopropyl-2-methyl-1H-imidazo[4,5-c]pyridin-6-ylamino)pyrimidin-2-ylamino]propionamide

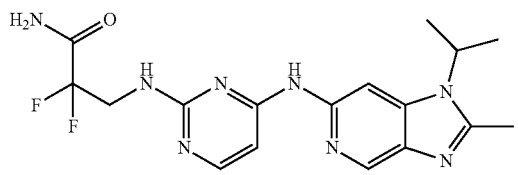 [SMILES: Cc1nc2cnc(Nc3ccnc(NCC(F)(F)C(N)=O)n3)cc2n1C(C)C]

A reaction vessel was charged with 2,2-difluoro-3-[4-(1-isopropyl-2-methyl-1H-imidazo[4,5-c]pyridin-6-ylamino)pyrimidin-2-ylamino]propionic acid (95.3 mg, 0.243 mmol) in N,N-dimethylformamide (5.0 ml). Ammonium chloride (26 mg, 0.487 mmol), 2-(1H-7-azabenzotriazol-1-yl)-1,1,3,3-tetramethyluronium hexafluorophosphate (138.8 mg, 0.365 mmol) and N,N-diisopropylethylamine (187 µl, 0.365 mmol) were added and the reaction mixture was stirred at room temperature for 24 h. The reaction mixture was concentrated in vacuo and purified by flash column chromatography (solvent gradient: 0-10% methanol in ethyl acetate). The product was further purified by preparative reverse phase HPLC and subsequently lyophilized to afford the title compound (42.6 mg, 45%). LCMS (ESI): R$_T$ 1.92 min, [M+H]+ 391.4, Method F; $^1$H NMR (400 MHz, DMSO-d$_6$) δ 9.63 (1H, s), 8.49 (1H, s), 8.23 (1H, br s), 8.15 (1H, br s), 7.94 (1H, br s), 7.92 (1H, d, J=5.8 Hz), 6.77 (1H, br s), 6.62 (1H, br s), 4.80-4.70 (1H, m), 4.12-4.03 (2H, m), 2.57 (3H, s), 1.55 (6H, d, J=7.0 Hz).

Example 611: (1-Isopropyl-2-methyl-1H-imidazo[4,5-c]pyridin-6-yl)-[2-(4-methyl-2-methylaminothiazol-5-yl)pyrimidin-4-yl]amine

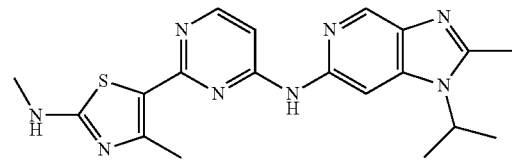

Step 1: Methyl-(4-methylthiazol-2-yl)amine

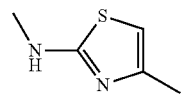

A mixture of chloroacetone (3.0 mL, 36.1 mmol) and N-methylthiourea (3.26 g, 36.1 mmol) in ethanol (40 mL) was heated at 75° C. for 3 h. The mixture was allowed to cool to room temperature and then concentrated in vacuo. The residue was partitioned between diethyl ether and aqueous ammonia. The aqueous phase was extracted with additional diethyl ether and the combined organic extracts were washed with brine, dried over anhydrous sodium sulfate, filtered and concentrated in vacuo. The residue was purified by chromatography on silica (solvent gradient: 30-100% ethyl acetate in cyclohexane) to afford the title compound as a colorless solid (3.97 g, 86%). $^1$H NMR (400 MHz, CDCl$_3$): δ 6.05 (1H, q, J=1.1 Hz), 5.79 (1H, br s), 2.95 (3H, s), 2.23 (3H, d, J=1.1 Hz).

Step 2: Methyl-(4-methyl-5-tributylstannanylthiazol-2-yl)carbamic acid tert-butyl ester

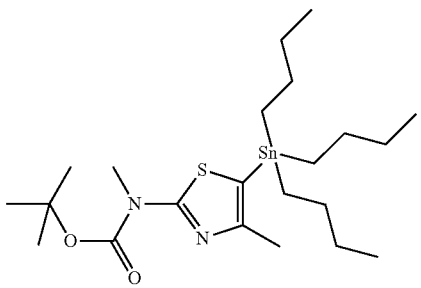 [SMILES: CCC[CH2][Sn]([CH2]CCC)([CH2]CCC)[c]1sc(N(C)C(=O)OC(C)(C)C)nc1C]

The title compound was prepared from methyl-(4-methylthiazol-2-yl)amine by an analogous method to that described for methyl-(5-tributylstannanylthiazol-2-yl)carbamic acid tert-butyl ester in Org. Lett., 2002, 4, 4209. $^1$H NMR (400 MHz, CDCl$_3$): δ 3.55 (3H, s), 2.36 (3H, s), 1.58 (9H, s), 1.55-1.49 (6H, m), 1.37-1.28 (6H, m), 1.13-1.08 (6H, m), 0.88 (9H, t, J=7.3 Hz).

Step 3: (1-Isopropyl-2-methyl-1H-imidazo[4,5-c]
pyridin-6-yl)-[2-(4-methyl-2-methylaminothiazol-5-
yl)pyrimidin-4-yl]amine

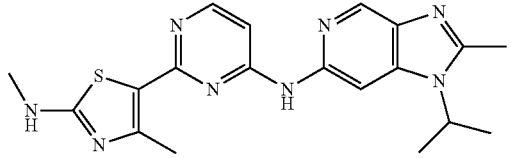

The title compound was prepared from N-(2-chloropyrimidin-4-yl)-1-isopropyl-2-methyl-1H-imidazo[4,5-c]pyridin-6-amine (Example 46, Step 7) and methyl-(4-methyl-5-tributylstannanylthiazol-2-yl)carbamic acid tert-butyl ester by an analogous method to that described in Example 312. LCMS (ESI): $R_T$ 2.20 min; [M+H]$^+$ 395.1, Method F. $^1$H NMR (400 MHz, DMSO-d$_6$) δ 9.86 (1H, s), 8.54 (1H, s), 8.26 (1H, d, J=5.8 Hz), 8.16 (1H, br s), 7.85 (1H, q, J=4.7 Hz), 7.06 (1H, br s), 4.75 (1H, septet, J=6.9 Hz), 2.86 (3H, d, J=4.7 Hz), 2.63 (3H, s), 2.58 (3H, s), 1.63 (6H, d, J=6.9 Hz).

Example 612: {1-Isopropyl-6-[2-(4-methyl-2-methylaminothiazol-5-yl)pyrimidin-4-ylamino]-1H-imidazo[4,5-c]pyridin-2-yl}methanol

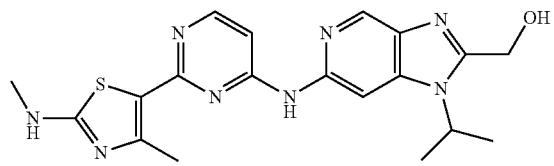 [SMILES: CNc1nc(C)c(-c2nccc(Nc3cc4c(cn3)nc(CO)n4C(C)C)n2)s1]

The title compound was prepared from (2-chloropyrimidin-4-yl)-[1-isopropyl-2-(tetrahydropyran-2-yloxymethyl)-1H-imidazo[4,5-c]pyridin-6-yl]amine (Example A49) and methyl-(4-methyl-5-tributylstannanylthiazol-2-yl)carbamic acid tert-butyl ester by an analogous method to that described in Example 312. LCMS (ESI): $R_T$ 2.13; min [M+H]$^+$ 411.1, Method F. $^1$H NMR (400 MHz, DMSO-d$_6$) δ 9.91 (1H, s), 8.63 (1H, s), 8.27 (1H, d, J=5.8 Hz), 8.21 (1H, br s), 7.86 (1H, q, J=4.7 Hz), 7.08 (1H, br s), 5.69 (1H, t, J=5.8 Hz), 4.96 (1H, septet, J=6.9 Hz), 4.73 (2H, d, J=5.8 Hz), 2.86 (3H, d, J=4.8 Hz), 2.63 (3H, s), 1.66 (6H, d, J=6.9 Hz).

Example 613: {1-Isopropyl-6-[2-(3-methyl-2-methylamino-3H-imidazol-4-yl)pyrimidin-4-ylamino]-1H-imidazo[4,5-c]pyridin-2-yl}methanol

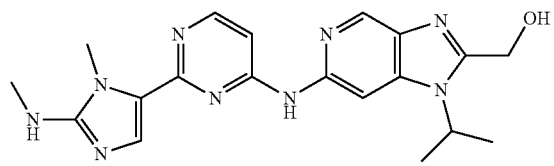 [SMILES: CNc1ncc(-c2nccc(Nc3cc4c(cn3)nc(CO)n4C(C)C)n2)n1C]

Step 1: (1-Methyl-1H-imidazol-2-yl)carbamic acid tert-butyl ester

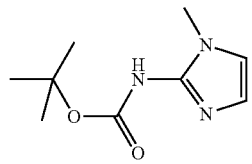

A solution of di-tert-butyl dicarbonate (1.07 g, 4.88 mmol) in tetrahydrofuran (6 mL) was added to a suspension of 1-methyl-1H-imidazol-2-ylamine (WO2011/071716) (0.395 g, 4.07 mmol) in tetrahydrofuran (4 mL). The mixture was stirred at room temperature for 16 h and then concentrated in vacuo. The residue was purified by chromatography on silica (solvent gradient 2-8% methanol in ethyl acetate) to afford the title compound as a cream solid (0.615 g, 77%). $^1$H NMR (400 MHz, CDCl$_3$): δ 11.11 (1H, br s), 6.67 (1H, br s), 6.54 (1H, br s), 3.50 (3H, s), 1.52 (9H, s).

Step 2:
Methyl-(1-methyl-1H-imidazol-2-yl)carbamic acid tert-butyl ester

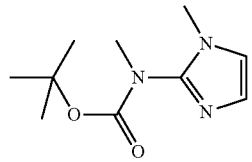

Sodium hydride (60 wt % dispersion in mineral oil)(187 mg, 4.67 mmol) was added portionwise to a solution of (1-methyl-1H-imidazol-2-yl)carbamic acid tert-butyl ester (0.615 g, 3.12 mmol) in N,N-dimethylformamide (15 mL). The resulting suspension was stirred at room temperature for 30 min and then cooled to 0° C. A solution of iodomethane (0.233 mL, 3.74 mmol) in N,N-dimethylformamide (2 mL) was added over 2 min and then the mixture was stirred at room temperature for 16 h. The reaction mixture was concentrated in vacuo. The residue was partitioned between aqueous ammonium chloride and ethyl acetate. The aqueous phase was extracted with additional ethyl acetate, and the combined organic extracts were dried over anhydrous sodium sulfate, filtered and concentrated in vacuo. The residue was purified by chromatography on silica (solvent gradient: 0-4% methanol in ethyl acetate) to afford the title compound as a cream solid (0.279 g, 42%). $^1$H NMR (400 MHz, CDCl$_3$): δ 6.91 (1H, d, J=1.4 Hz), 6.76 (1H, d, J=1.4 Hz), 3.48 (3H, s), 3.22 (3H, s), 1.43 (9H, br s).

Step 3: Methyl-(1-methyl-5-tributylstannanyl-1H-imidazol-2-yl)carbamic acid tert-butyl ester

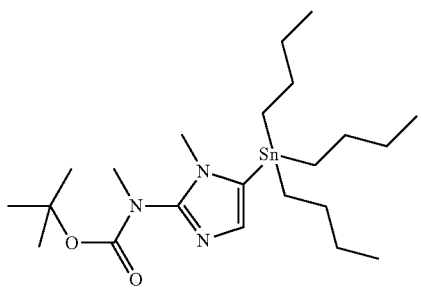 [SMILES: CCC[CH2][Sn]([CH2]CCC)([CH2]CCC)[c]1cnc(N(C)C(=O)OC(C)(C)C)n1C]

tert-Butyllithium (1.7M in pentane)(0.274 mL, 0.466 mmol) was added dropwise to a solution of methyl-(1-methyl-1H-imidazol-2-yl)carbamic acid tert-butyl ester (89.6 mg, 0.424 mmol) in tetrahydrofuran (3 mL) at −78° C. The mixture was stirred at −78° C. for 30 min and then tributyltin chloride (0.114 mL, 0.424 mmol) was added. The reaction mixture was allowed to warm to 0° C. over 90 min. Saturated ammonium chloride solution was added and the reaction mixture was partitioned between water and ethyl acetate. The aqueous phase was extracted with additional ethyl acetate, The combined organic layers were washed with brine, dried over anhydrous sodium sulfate and concentrated in vacuo to afford the title compound. LCMS (ESI): [M-$^t$Bu$^+$+2H$^+$] 446.

Step 4: {1-Isopropyl-6-[2-(3-methyl-2-methyl-amino-3H-imidazol-4-yl)pyrimidin-4-ylamino]-1H-imidazo[4,5-c]pyridin-2-yl}methanol

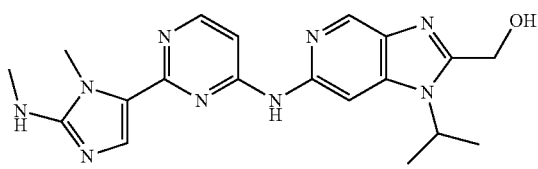 [SMILES: CNc1ncc(-c2nccc(Nc3cc4c(cn3)nc(CO)n4C(C)C)n2)n1C]

The title compound was prepared from (2-chloropyrimidin-4-yl)-[1-isopropyl-2-(tetrahydropyran-2-yloxymethyl)-1H-imidazo[4,5-c]pyridin-6-yl]amine (Example A49) and methyl-(1-methyl-5-tributylstannanyl-1H-imidazol-2-yl)carbamic acid tert-butyl ester by an analogous method to that described in Example 312. LCMS (ESI): R$_T$ 1.84 min; [M+H]$^+$ 394.2, Method F. $^1$H NMR (400 MHz, DMSO-d$_6$) δ 9.92 (1H, s), 8.63 (1H, s), 8.34 (1H, br s), 8.26 (1H, d, J=5.8 Hz), 7.50 (1H, s), 7.11 (1H, br s), 6.14 (1H, br s), 5.70 (1H, t, J=5.8 Hz), 4.97 (1H, septet, J=6.9 Hz), 4.73 (2H, d, J=5.7 Hz), 3.77 (3H, s), 2.84 (3H, d, J=4.8 Hz), 1.63 (6H, d, J=6.9 Hz).

Example 614: [2-(2-Aminothiazol-5-yl)pyrimidin-4-yl]-(1-isopropyl-2-methyl-1H-imidazo[4,5-c]pyridin-6-yl)amine

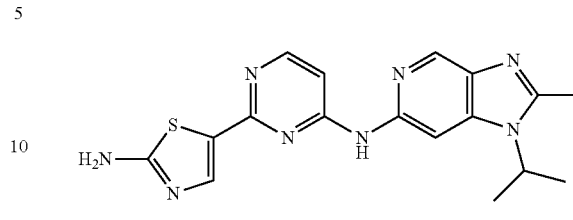

Step 1: Thiazol-2-yl-(2-trimethylsilanylethoxymethyl)carbamic acid tert-butyl ester

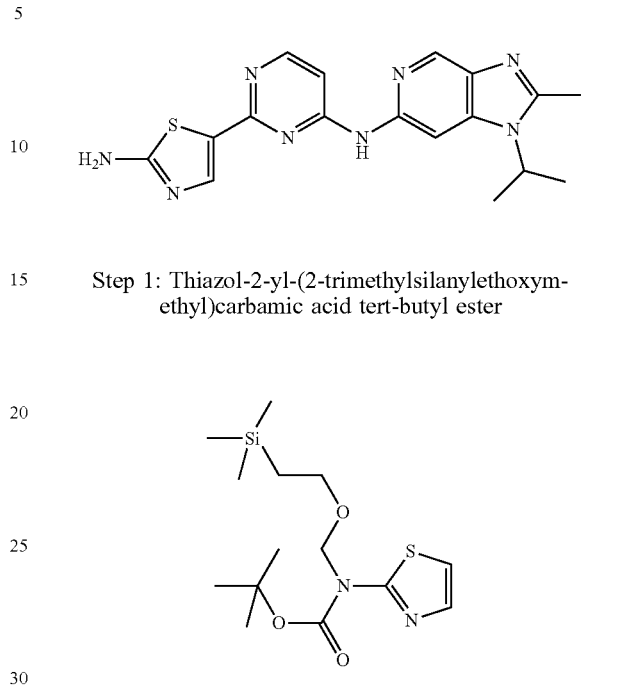

Sodium hydride (60 wt % dispersion in mineral oil)(80 mg, 2.0 mmol) was added portionwise to a solution of thiazol-2-yl-carbamic acid tert-butyl ester (0.266 g, 1.33 mmol) in N,N-dimethylformamide (3 mL). The mixture was stirred at room temperature for 30 min and then cooled to 0° C. 2-Trimethylsilanylethoxymethyl chloride (0.282 mL, 1.6 mmol) was added and then the mixture was stirred at room temperature for 16 h. The reaction mixture was partitioned between aqueous ammonium chloride and ethyl acetate. The aqueous phase was extracted with additional ethyl acetate, and the combined organic extracts were washed with water, then brine, dried over anhydrous sodium sulfate, filtered and concentrated in vacuo. The residue was purified by chromatography on silica (solvent gradient 2-10% ethyl acetate in cyclohexane) to afford the title compound as a colorless solid (0.389 g, 88%). $^1$H NMR (400 MHz, CDCl$_3$): δ 7.47 (1H, d, J=3.6 Hz), 6.97 (1H, d, J=3.6 Hz), 5.59 (2H, s), 3.72-3.68 (2H, m), 1.61 (9H, s), 1.00-0.96 (2H, m), 0.00 (9H, s).

Step 2: (5-Tributylstannanylthiazol-2-yl)-(2-trimethylsilanylethoxymethyl)carbamic acid tert-butyl ester

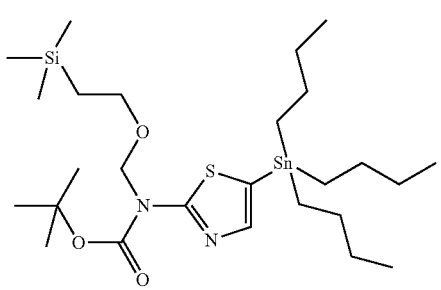 [SMILES: CCC[CH2][Sn]([CH2]CCC)([CH2]CCC)[c]1cnc(N(COCC[Si](C)(C)C)C(=O)OC(C)(C)C)s1]

n-Butyllithium (2.5M in hexanes)(0.466 mL, 1.165 mmol) was added dropwise to a solution of thiazol-2-yl-(2-trimethylsilanylethoxymethyl)carbamic acid tert-butyl ester (0.35 g, 1.059 mmol) in tetrahydrofuran (4 mL) at −78° C. The mixture was stirred at −78° C. for 30 min and then tributyltin chloride (0.288 mL, 1.059 mmol) in tetrahydrofuran (1 mL) was added. The reaction mixture was allowed to warm to 0° C. over 1 h. Saturated ammonium chloride solution was added and the reaction mixture was partitioned between water and ethyl acetate. The aqueous phase was extracted with additional ethyl acetate, The combined organic layers were washed with brine, dried over anhydrous sodium sulfate, filtered and concentrated in vacuo to afford a mixture of the title compound and tetrabutyltin (0.911 g). $^1$H NMR (400 MHz, CDCl$_3$): δ 7.38 (1H, s), 5.60 (2H, s), 3.73-3.68 (2H, m), 1.62 (9H, s), 1.61-1.53 (6H, m), 1.41-1.30 (12H, m), 1.14-1.10 (2H, m), 0.97-0.89 (9H, m), 0.00 (9H, s).

Step 3: [2-(2-Aminothiazol-5-yl)pyrimidin-4-yl]-(1-isopropyl-2-methyl-1H-imidazo[4,5-c]pyridin-6-yl)amine

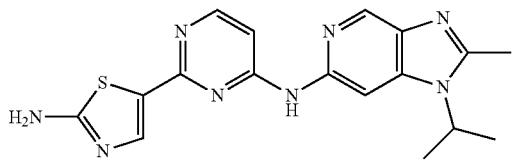 [SMILES: Cc1nc2cnc(Nc3ccnc(-c4cnc(N)s4)n3)cc2n1C(C)C]

The title compound was prepared from N-(2-chloropyrimidin-4-yl)-1-isopropyl-2-methyl-1H-imidazo[4,5-c]pyridin-6-amine (Example 46, Step 7) and (5-tributylstannanylthiazol-2-yl)-(2-trimethylsilanylethoxymethyl)carbamic acid tert-butyl ester by an analogous method to that described in Example 312. LCMS (ESI): R$_T$ 2.02 min; [M+H]$^+$ 367.1, Method F. $^1$H NMR (400 MHz, DMSO-d$_6$) δ 10.00 (1H, s), 8.54 (1H, s), 8.41 (1H, br s), 8.22 (1H, d, J=5.7 Hz), 7.82 (1H, s), 7.48 (2H, br s), 7.04 (1H, br s), 4.76 (1H, septet, J=6.9 Hz), 2.58 (3H, s), 1.65 (6H, d, J=6.9 Hz).

Example 615: {6-[2-(2-Aminothiazol-5-yl)pyrimidin-4-ylamino]-1-isopropyl-1H-imidazo[4,5-c]pyridin-2-yl}methanol

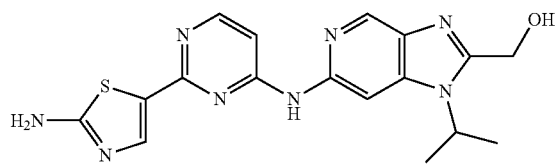 [SMILES: CC(C)n1c(CO)nc2cnc(Nc3ccnc(-c4cnc(N)s4)n3)cc21]

The title compound was prepared from (2-chloropyrimidin-4-yl)-[1-isopropyl-2-(tetrahydropyran-2-yloxymethyl)-1H-imidazo[4,5-c]pyridin-6-yl]amine (Example A49) and (5-tributylstannanylthiazol-2-yl)-(2-trimethylsilanylethoxymethyl)carbamic acid tert-butyl ester by an analogous method to that described in Example 312. LCMS (ESI): R$_T$ 1.94 min [M+H]$^+$ 383.0, Method F. $^1$H NMR (400 MHz, DMSO-d$_6$) δ 10.10 (1H, s), 8.64 (1H, s), 8.47 (1H, br s), 8.24 (1H, d, J=5.9 Hz), 7.85 (1H, s), 7.54 (2H, br s), 7.04 (1H, br s), 5.71 (1H, s), 4.99 (1H, septet, J=6.9 Hz), 4.74 (2H, s), 1.67 (6H, d, J=6.9 Hz).

Example 616: [2-(±)-(trans-3-Fluoro-4-methanesulfonylpiperidin-1-yl)pyrimidin-4-yl]-(1-isopropyl-2-methyl-1H-imidazo[4,5-c]pyridin-6-yl)amine (mixture of enantiomers)

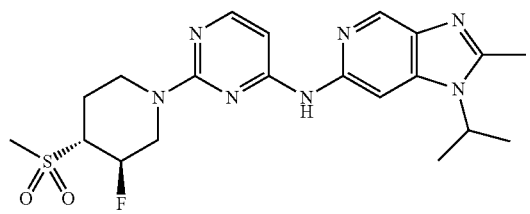

Step 1: (±)-cis-3-Fluoro-4-(toluene-4-sulfonyloxy)piperidine-1-carboxylic acid tert-butyl ester

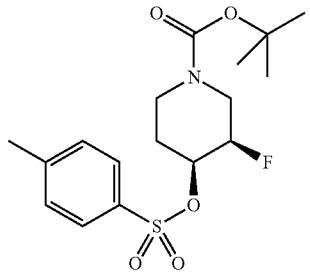 [SMILES: Cc1ccc(S(=O)(=O)O[C@H]2CCN(C(=O)OC(C)(C)C)C[C@H]2F)cc1]

p-Toluenesulfonyl chloride (0.442 g, 2.32 mmol) was added over 5 min to a solution of cis-3-fluoro-4-hydroxypiperidine-1-carboxylic acid tert-butyl ester (0.484 g, 2.2 mmol) in pyridine (1 mL) at 0° C. The mixture was stirred at room temperature for 5 h then diluted with ethyl acetate. The mixture was washed with ice-cooled 1M HCl. The aqueous phase was extracted with additional ethyl acetate, and the combined organic extracts were washed with water, then saturated sodium bicarbonate, dried over anhydrous sodium sulfate, filtered and concentrated in vacuo. The residue was purified by chromatography on silica (solvent gradient 10-60% ethyl acetate in cyclohexane) to afford the title compound as a white solid (0.573 g, 70%). $^1$H NMR (CDCl$_3$): δ 7.81 (2H, d, J=8.3 Hz), 7.35 (2H, d, J=8.3 Hz), 4.75-4.52 (2H, m), 3.94-3.68 (2H, m), 3.39-3.07 (2H, m), 2.45 (3H, s), 2.12-2.04 (1H, m), 1.74-1.68 (1H, m), 1.44 (9H, s).

Step 2: (±)-trans-3-Fluoro-4-methylsulfanylpiperidine-1-carboxylic acid tert-butyl ester (mixture of enantiomers)

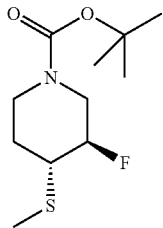 [SMILES: CS[C@@H]1CCN(C(=O)OC(C)(C)C)C[C@H]1F]

Sodium thiomethoxide (0.189 g, 2.69 mmol) was added over 3 min to a solution of cis-3-fluoro-4-(toluene-4-sulfonyloxy)piperidine-1-carboxylic acid tert-butyl ester (0.502 g, 1.34 mmol) in N,N-dimethylformamide (1.5 mL) at 0° C. The mixture was stirred at room temperature for 16 h then diluted with cyclohexane. The mixture was purified by chromatography on silica (solvent gradient: 2-20% ethyl acetate in cyclohexane) to afford the title compound as a colorless oil (0.288 g, 86%). $^1$H NMR (CDCl$_3$): δ 4.52-4.35 (1H, m), 4.06-3.93 (1H, m), 3.70-3.64 (1H, m), 3.32-3.14 (2H, m), 2.86-2.79 (1H, m), 2.21 (3H, s), 2.14-2.06 (1H, m), 1.61-1.52 (1H, m), 1.46 (9H, s).

Step 3: (±)-trans-3-Fluoro-4-methanesulfonylpiperidine-1-carboxylic acid tert-butyl ester (mixture of enantiomers)

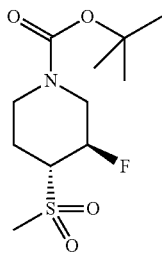 [SMILES: CC(C)(C)OC(=O)N1CC[C@@H](S(C)(=O)=O)[C@H](F)C1]

3-Chloroperbenzoic acid (77%, 0.648 g, 2.89 mmol) in dichloromethane (2 mL) was added to a solution of (±)-trans-3-fluoro-4-methylsulfanylpiperidine-1-carboxylic acid tert-butyl ester (0.288 g, 1.15 mmol) in dichloromethane (8 mL) at 0° C. The mixture was stirred at room temperature for 2 h then diluted with dichloromethane. The mixture washed successively with sodium metabisulfite solution, then sodium carbonate solution, dried over anhydrous sodium sulfate, filtered and concentrated in vacuo. The residue was purified by chromatography on silica (solvent gradient: 20-60% ethyl acetate in cyclohexane) to afford the title compound as a colorless solid (0.322 g, 90%). $^1$H NMR (CDCl$_3$): δ 4.92-4.73 (1H, m), 4.53 (1H, br s), 4.25 (1H, br s), 3.21-3.08 (1H, m), 3.03 (3H, d, J=1.8 Hz), 2.82-2.70 (2H, m), 2.33-2.26 (1H, m), 1.82-1.71 (1H, m), 1.47 (9H, s).

Step 4: (±)-trans-3-Fluoro-4-methanesulfonylpiperidine (mixture of enantiomers)

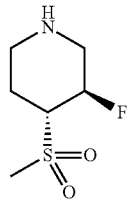

To a solution of (±)-trans-3-fluoro-4-methanesulfonylpiperidine-1-carboxylic acid tert-butyl ester (0.322 g, 1.14 mmol) in dichloromethane (2 mL) at 0° C. was added trifluoroacetic acid (1 mL). The mixture was allowed to warm to room temperature and stirred for 2 h. Toluene was added and the reaction mixture was concentrated in vacuo (2×). The residue was dissolved in methanol and loaded on to an SCX cartridge. The cartridge was washed with methanol, then eluted with 1M ammonia in methanol to give the title compound as a colorless solid (0.197 g, 95%). $^1$H NMR (CDCl$_3$): δ 4.81 (1H, dtd, J=48.6, 10.0, 5.3 Hz), 3.51-3.46 (1H, m), 3.23-3.17 (1H, m), 3.16-3.07 (1H, m), 3.02 (3H, d, J=1.8 Hz), 2.65 (1H, ddd, J=15.6, 10.2, 5.4 Hz), 2.58 (1H, td, J=12.6, 2.7 Hz), 2.35-2.28 (1H, m), 1.78-1.66 (1H, m), 1.52 (1H, br s).

Step 5: [2-(±)-(trans-3-Fluoro-4-methanesulfonylpiperidin-1-yl)pyrimidin-4-yl]-(1-isopropyl-2-methyl-1H-imidazo[4,5-c]pyridin-6-yl)amine (mixture of enantiomers)

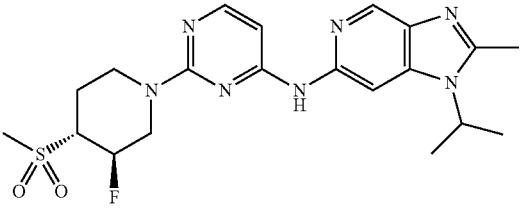

The title compound was prepared from N-(2-chloropyrimidin-4-yl)-1-isopropyl-2-methyl-1H-imidazo[4,5-c]pyridin-6-amine (Example 46, Step 7) and (±)-trans-3-fluoro-4-methanesulfonylpiperidine by an analogous method to that described in Example 46. LCMS (ESI): R$_T$ 2.12 min; [M+H]$^+$ 448.2, Method F. $^1$H NMR (400 MHz, DMSO-d$_6$) δ 9.81 (1H, s), 8.52 (1H, s), 8.25 (1H, br s), 8.01 (1H, d, J=5.7 Hz), 6.57 (1H, br d, J=5.4 Hz), 5.00-4.70 (4H, m), 3.90-3.81 (1H, m), 3.23-3.16 (1H, m), 3.10-3.03 (4H, m), 2.56 (3H, s), 2.23-2.16 (1H, m), 1.67-1.58 (1H, m), 1.57 and 1.56 (6H, 2d, J=6.9 Hz).

Example 617: [2-(±)-(cis-3-Fluoro-4-methylsulfanylpiperidin-1-yl)pyrimidin-4-yl]-(1-isopropyl-2-methyl-1H-imidazo[4,5-c]pyridin-6-yl)amine (mixture of enantiomers)

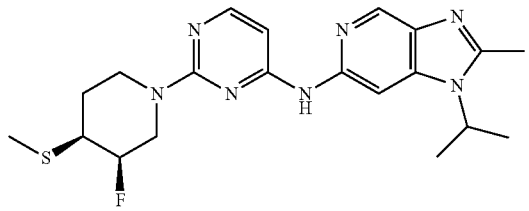

Step 1: (±)-cis-3-Fluoro-4-methylsulfanylpiperidine-1-carboxylic acid tert-butyl ester (mixture of enantiomers)

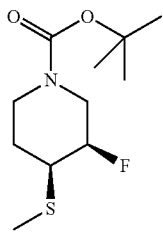 [SMILES: CS[C@H]1CCN(C(=O)OC(C)(C)C)C[C@H]1F]

Sodium thiomethoxide (0.146 g, 2.08 mmol) was added over 3 min to a solution of trans-3-fluoro-4-trifluoromethanesulfonyloxypiperidine-1-carboxylic acid tert-butyl ester (WO2011/084402)(0.366 g, 1.04 mmol) in N,N-dimethylformamide (1.5 mL) at 0° C. The mixture was stirred at room temperature for 16 h then diluted with cyclohexane. The mixture was purified by chromatography on silica (solvent gradient: 2-25% ethyl acetate in cyclohexane) to afford the title compound as a colorless oil (0.249 g, 96%). $^1$H NMR (CDCl$_3$): δ 4.73 (1H, br d, J=47 Hz), 4.27 (1H, br s), 4.10-3.96 (1H, m), 3.14-3.02 (1H, m), 2.92 (1H, br s), 2.83-2.72 (1H, m), 2.17 (3H, s), 2.00-1.90 (1H, m), 1.83-1.77 (1H, m), 1.46 (9H, s).

Step 2: (±)-cis-3-Fluoro-4-methylsulfanylpiperidine (mixture of enantiomers)

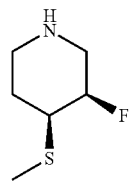

The title compound (121 mg, 88%) was prepared from (±)-cis-3-fluoro-4-methylsulfanylpiperidine-1-carboxylic acid tert-butyl ester (231 mg, 0.928 mmol) by a procedure analogous to that described in Example 616, step 4. $^1$H NMR (CDCl$_3$): δ 4.67 (1H, br d, J=48 Hz), 3.36-3.28 (1H, m), 3.15-3.10 (1H, m), 2.84-2.63 (3H, m), 2.17 (3H, s), 1.90-1.78 (3H, m).

Step 3: [2-(±)-(cis-3-Fluoro-4-methylsulfanylpiperidin-1-yl)pyrimidin-4-yl]-(1-isopropyl-2-methyl-1H-imidazo[4,5-c]pyridin-6-yl)amine (mixture of enantiomers)

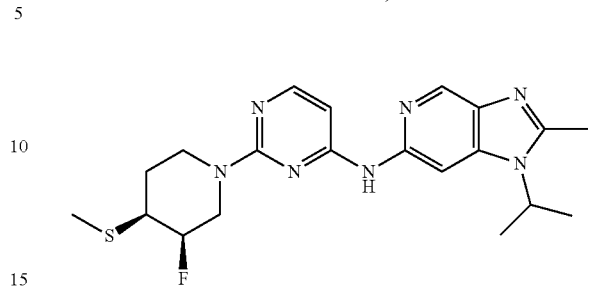

A mixture of N-(2-chloropyrimidin-4-yl)-1-isopropyl-2-methyl-1H-imidazo[4,5-c]pyridin-6-amine (Example 46, Step 7)(84.5 mg, 0.279 mmol), (±)-cis-3-fluoro-4-methylsulfanylpiperidine (50 mg, 0.335 mmol) and N,N-diisopropylethylamine (0.0726 mL, 0.419 mmol) in isopropanol (2 mL) was heated at 150° C. under microwave irradiation for 2 h. The cooled reaction mixture was diluted with methanol and loaded onto an SCX cartridge. The cartridge was washed with methanol and then eluted with 1M ammonia in methanol. After concentration in vacuo, the resulting residue was purified by chromatography on silica (solvent gradient: 2-7% 2M methanolic ammonia in dichloromethane) to afford the title compound as a white solid (107 mg, 93%). LCMS (ESI): R$_T$ 2.50 min; [M+H]$^+$ 416.1, Method F. $^1$H NMR (400 MHz, DMSO-d$_6$) δ 9.68 (1H, s), 8.46 (1H, s), 8.27 (1H, br s), 7.91 (1H, d, J=5.7 Hz), 6.41 (1H, br d, J=5.6 Hz), 4.96-4.79 (2H, m), 4.73-4.62 (2H, m), 3.25-2.98 (3H, m), 2.52 (3H, s), 2.10 (3H, s), 1.87-1.81 (1H, m), 1.77-1.67 (1H, m), 1.53 (6H, d, J=6.9 Hz).

Example 618: [2-(±)-(cis-3-Fluoro-4-methanesulfinylpiperidin-1-yl)pyrimidin-4-yl]-(1-isopropyl-2-methyl-1H-imidazo[4,5-c]pyridin-6-yl)amine (mixture of diastereoisomers)

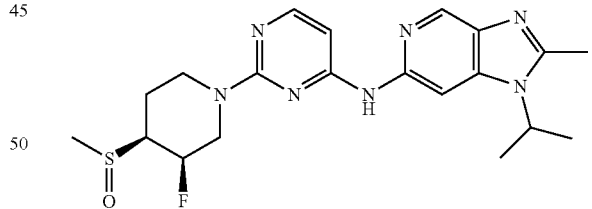

3-Chloroperbenzoic acid (77%, 53.7 mg, 0.24 mmol) in dichloromethane (1 mL) was added over 5 min to a solution of [2-(cis-3-fluoro-4-methylsulfanylpiperidin-1-yl)pyrimidin-4-yl]-(1-isopropyl-2-methyl-1H-imidazo[4,5-c]pyridin-6-yl)amine (99.6 mg, 0.24 mmol) in dichloromethane (5 mL) at 0° C. The mixture was stirred at 0° C. for 20 min then purified by chromatography on silica (solvent gradient: 2-12% 2M methanolic ammonia in dichloromethane) to afford the title compound as a white solid (70.1 mg, 68%). LCMS (ESI): R$_T$ 1.88 and 1.93 min; [M+H]$^+$ 432.1, Method F. $^1$H NMR (400 MHz, DMSO-d$_6$) δ 9.76 (1H, s), 8.52 (1H, s), 8.33 (1H, br d, J=5.8 Hz), 7.98 (1H, d, J=5.6 Hz), 6.50 (1H, br s), 5.28-5.07 (2H, m), 4.99-4.92 (1H, m), 4.79-4.68

(1H, m), 3.29-2.96 (3H, m), 2.66 and 2.65 (3H, 2s), 2.57 (3H, s), 2.00-1.65 (2H, m), 1.58 (6H, br d, J=6.8 Hz).

Example 619: (3RS,4SR)-3-Fluoro-1-[4-(2-hydroxymethyl-1-isopropyl-1H-imidazo[4,5-c]pyridin-6-ylamino)pyrimidin-2-yl]-4-methylpiperidin-4-ol (mixture of enantiomers)

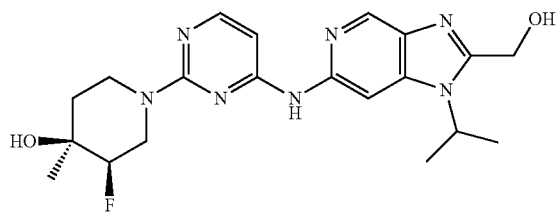 [SMILES: CC(C)n1c(CO)nc2cnc(Nc3ccnc(N4CC[C@](C)(O)[C@H](F)C4)n3)cc21]

Step 1: [6-(2-Chloropyrimidin-4-ylamino)-1-isopropyl-1H-imidazo[4,5-c]pyridin-2-yl]methanol

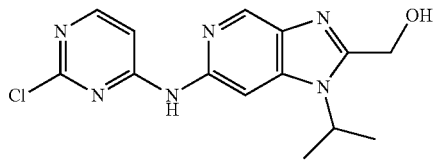 [SMILES: CC(C)n1c(CO)nc2cnc(Nc3ccnc(Cl)n3)cc21]

Hydrochloric acid (1.25M in methanol)(8 mL) was added to a suspension of (2-chloropyrimidin-4-yl)-[1-isopropyl-2-(tetrahydropyran-2-yloxymethyl)-1H-imidazo[4,5-c]pyridin-6-yl]amine (Example A49)(0.527 g, 1.308 mmol) in methanol (2 mL) at 0° C. The mixture was stirred at room temperature for 4.5 h and then concentrated in vacuo. The residue was dissolved in a mixture of methanol and water (40 mL, 4:1) and loaded onto an SCX cartridge. The cartridge was washed with a mixture of methanol and water (4:1), then methanol and then eluted with 1M ammonia in methanol in dichloromethane (3:1). Concentration in vacuo gave the title compound as a white solid (0.398 g, 96%). LCMS (ESI): [M+H]⁺=319 and 321.

Step 2: (3RS,4SR)-3-Fluoro-1-[4-(2-hydroxymethyl-1-isopropyl-1H-imidazo[4,5-c]pyridin-6-ylamino)pyrimidin-2-yl]-4-methylpiperidin-4-ol (mixture of enantiomers)

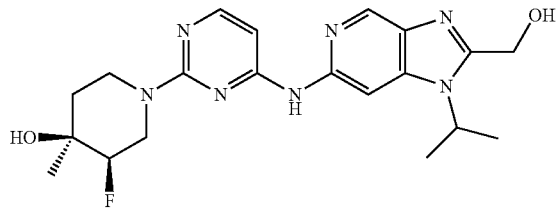 [SMILES: CC(C)n1c(CO)nc2cnc(Nc3ccnc(N4CC[C@](C)(O)[C@H](F)C4)n3)cc21]

A mixture of [6-(2-chloropyrimidin-4-ylamino)-1-isopropyl-1H-imidazo[4,5-c]pyridin-2-yl]methanol (63.8 mg, 0.20 mmol), (3RS,4SR)-3-fluoro-4-methylpiperidin-4-ol (Example A96)(40.3 mg, 0.30 mmol) and N,N-diisopropylethylamine (0.0595 mL, 0.34 mmol) in isopropanol (3 mL) was heated at 150° C. under microwave irradiation for 2 h. The cooled reaction mixture was diluted with methanol and loaded onto an SCX cartridge. The cartridge was washed with methanol and then eluted with 1M ammonia in methanol. After concentration, the resulting residue was purified by chromatography on silica (solvent gradient: 2-14% 2M methanolic ammonia in dichloromethane) to afford the title compound as a mixture of enantiomers as a white solid (64.5 mg, 78%). LCMS (ESI): $R_T$ 1.92 min; [M+H]⁺ 416.1, Method F. ¹H NMR (400 MHz, DMSO-$d_6$) δ 9.79 (1H, s), 8.60 (1H, s), 8.41 (1H, br s), 7.97 (1H, d, J=5.7 Hz), 6.46 (1H, br d, J=5.5 Hz), 5.68 (1H, t, J=5.8 Hz), 4.96 (1H, septet, J=6.9 Hz), 4.82 (1H, s), 4.71 (2H, d, J=5.7 Hz), 4.43-4.26 (2H, m), 4.16-4.10 (1H, m), 3.66-3.59 (1H, m), 3.53-3.46 (1H, m), 1.75-1.67 (1H, m), 1.59 and 1.58 (6H, 2d, J=6.9 Hz), 1.58-1.50 (1H, m), 1.25 (3H, s).

Example 620: (3R*,4S*)-3-Fluoro-1-{4-[2-((R)-1-hydroxyethyl)-1-((S)-2,2,2-trifluoro-1-methylethyl)-1H-imidazo[4,5-c]pyridin-6-ylamino]pyrimidin-2-yl}-4-methylpiperidin-4-ol (absolute stereochemistry unknown)

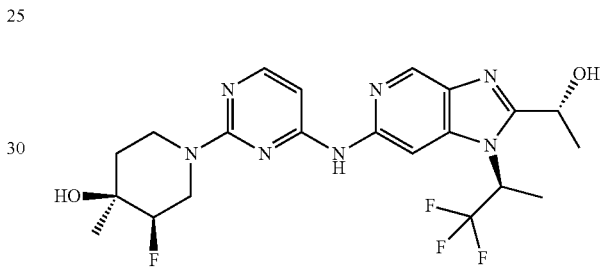

Step 1: (3R*,4S*)-3-Fluoro-4-methyl-1-{4-[2-[(R)-1-(tetrahydropyran-2-yloxy)ethyl]-1-((S)-2,2,2-trifluoro-1-methylethyl)-1H-imidazo[4,5-c]pyridin-6-ylamino]pyrimidin-2-yl}piperidin-4-ol (absolute stereochemistry unknown)

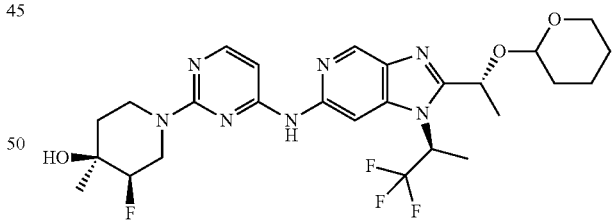

A mixture of 6-chloro-2-[(R)-1-(tetrahydropyran-2-yloxy)ethyl]-1-((S)-2,2,2-trifluoro-1-methylethyl)-1H-imidazo[4,5-c]pyridine (Example A83)(391 mg, 1.035 mmol), (−)-(3R*,4S*)-1-(4-aminopyrimidin-2-yl)-3-fluoro-4-methylpiperidin-4-ol (Example A100)(233 mg, 1.035 mmol), 2-dicyclohexylphosphino-2',4',6'-triisopropylbiphenyl (99 mg, 0.207 mmol), tris(dibenzylideneacetone)dipalladium(0) (47.4 mg, 0.052 mmol), cesium carbonate (673 mg, 2.07 mmol) and dioxane (10 mL) was heated in a sealed vial at 110° C. for 4 h. The cooled reaction mixture was partitioned between ethyl acetate and water. The aqueous phase was extracted with additional ethyl acetate and the combined organic phases were washed with brine, dried over anhydrous sodium sulfate and concentrated in vacuo. The residue was purified by chromatography on silica (solvent gradient: 2-8% 2M methanolic ammonia in dichloromethane) to afford the title compound (quantitative) as a single unknown stereoisomer with known relative stereochemistry and absolute stereochemistry arbitrarily assigned. LCMS (ESI): [M+H]$^+$ 568.

Step 2: (3R*,4S*)-3-Fluoro-1-{4-[2-((R)-1-hydroxyethyl)-1-((S)-2,2,2-trifluoro-1-methylethyl)-1H-imidazo[4,5-c]pyridin-6-ylamino]pyrimidin-2-yl}-4-methylpiperidin-4-ol (absolute stereochemistry unknown)

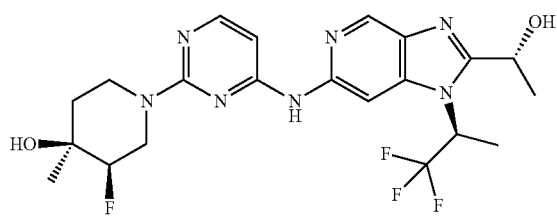 [SMILES: C[C@H](n1c([C@@H](C)O)nc2cnc(Nc3ccnc(N4CC[C@](C)(O)[C@H](F)C4)n3)cc21)C(F)(F)F]

To a solution of (3R*,4S*)-3-fluoro-4-methyl-1-{4-[2-[(R)-1-(tetrahydropyran-2-yloxy)ethyl]-1-((S)-2,2,2-trifluoro-1-methylethyl)-1H-imidazo[4,5-c]pyridin-6-ylamino]pyrimidin-2-yl}piperidin-4-ol (1.035 mmol) in dichloromethane (15 mL) at 0° C. was added trifluoroacetic acid (1.5 mL). The mixture was allowed to warm to room temperature and stirred for 1 h. Toluene was added and the reaction mixture was concentrated in vacuo (2×). To the residue was added 3% acetonitrile in water (50 mL) and 4 drops of trifluoroacetic acid. The resulting solution was loaded on to a C18 cartridge and eluted with 3-21% acetonitrile in 0.5% trifluoroacetic acid in water. The product containing fractions were partially concentrated in vacuo, then diluted with methanol and loaded on to an SCX cartridge. The cartridge was washed with methanol, and then eluted with 1M ammonia in methanol to give the title compound as a white solid (0.249 g, 50%, 2 steps) as a single unknown stereoisomer with known relative stereochemistry and absolute stereochemistry arbitrarily assigned. LCMS (ESI): R$_T$ 2.39 min; [M+H]$^+$ 484.2, Method F. $^1$H NMR (400 MHz, DMSO-d$_6$) δ 9.85 (1H, s), 8.69 (1H, s), 8.36 (1H, br s), 7.99 (1H, d, J=5.7 Hz), 6.52 (1H, br d, J=5.6 Hz), 5.96 (1H, d, J=7.1 Hz), 5.89 (1H, septet, J=8.0 Hz), 5.02 (1H, quintet, J=6.7 Hz), 4.82 (1H, s), 4.43-4.24 (2H, m), 4.15-4.09 (1H, m), 3.61-3.53 (1H, m), 3.49-3.42 (1H, m), 1.85 (3H, d, J=7.2 Hz), 1.72-1.64 (1H, m), 1.63 (3H, d, J=6.5 Hz), 1.55-1.48 (1H, m), 1.24 (3H, s).

Example 621: (3R*,4S*)-3-Fluoro-1-{4-[2-((R)-1-hydroxyethyl)-1-((S)-2,2,2-trifluoro-1-methylethyl)-1H-imidazo[4,5-c]pyridin-6-ylamino]pyrimidin-2-yl}-4-methylpiperidin-4-ol (absolute stereochemistry unknown)

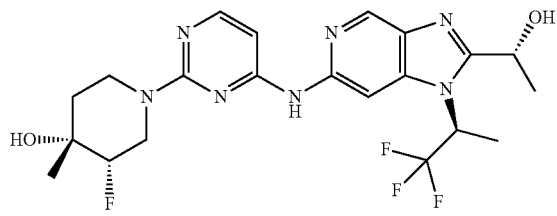 [SMILES: C[C@H](n1c([C@@H](C)O)nc2cnc(Nc3ccnc(N4CC[C@@](C)(O)[C@@H](F)C4)n3)cc21)C(F)(F)F]

The other diastereomer of the title compound was prepared by the reaction of 6-chloro-2-[(R)-1-(tetrahydropyran-2-yloxy)ethyl]-1-((S)-2,2,2-trifluoro-1-methylethyl)-1H-imidazo[4,5-c]pyridine (Example A83) and (+)-(3R*,4S*)-1-(4-aminopyrimidin-2-yl)-3-fluoro-4-methylpiperidin-4-ol (Example A101) by a procedure analogous to that described in Example 620. LCMS (ESI): R$_T$ 2.41 min; [M+H]$^+$ 484.2, Method F. $^1$H NMR (400 MHz, DMSO-d$_6$) δ 9.84 (1H, s), 8.69 (1H, s), 8.32 (1H, br s), 7.99 (1H, d, J=5.7 Hz), 6.52 (1H, br d, J=5.6 Hz), 5.96 (1H, d, J=6.9 Hz), 5.89 (1H, m), 5.02 (1H, quintet, J=6.6 Hz), 4.81 (1H, s), 4.38-4.23 (2H, m), 4.12-4.06 (1H, m), 3.65-3.58 (1H, m), 3.51-3.45 (1H, m), 1.85 (3H, d, J=7.2 Hz), 1.72-1.64 (1H, m), 1.63 (3H, d, J=6.4 Hz), 1.56-1.49 (1H, m), 1.24 (3H, s).

Example 622: (±)-{6-[2-(cis-3-Fluoro-4-methylsulfanylpiperidin-1-yl)pyrimidin-4-ylamino]-1-isopropyl-1H-imidazo[4,5-c]pyridin-2-yl}methanol (mixture of enantiomers)

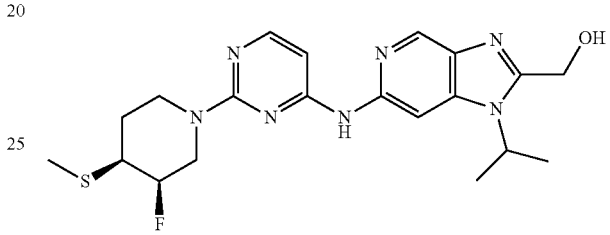

Step 1: (±)-[2-(cis-3-Fluoro-4-methylsulfanylpiperidin-1-yl)pyrimidin-4-yl]-[1-isopropyl-2-(tetrahydropyran-2-yloxymethyl)-1H-imidazo[4,5-c]pyridin-6-yl]amine (mixture of enantiomers)

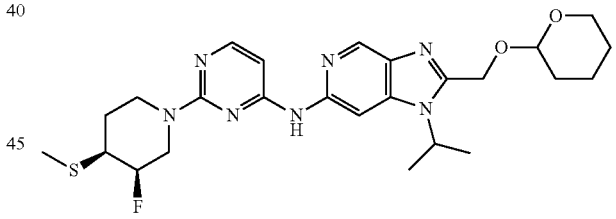

A mixture of (2-chloropyrimidin-4-yl)-[1-isopropyl-2-(tetrahydropyran-2-yloxymethyl)-1H-imidazo[4,5-c]pyridin-6-yl]amine (Example A49)(157 mg, 0.391 mmol), cis-3-fluoro-4-methylsulfanylpiperidine (Example 617, Step 2)(70 mg, 0.469 mmol) and N,N-diisopropylethylamine (0.101 mL, 0.586 mmol) in isopropanol (2 mL) was heated at 150° C. under microwave irradiation for 2 h. The cooled reaction mixture was partitioned between dichloromethane and dilute sodium bicarbonate. The aqueous phase was extracted with additional dichloromethane and the combined organic phases were washed with water, dried over anhydrous sodium sulfate and concentrated in vacuo. The residue was purified by chromatography on silica (solvent gradient: 2-7% 2M methanolic ammonia in dichloromethane) to afford the title compound as a colorless gum (167 mg, 83%). LCMS (ESI): [M+H]$^+$ 516.

Step 2: (±)-{6-[2-(cis-3-Fluoro-4-methylsulfanylpiperidin-1-yl)pyrimidin-4-ylamino]-1-isopropyl-1H-imidazo[4,5-c]pyridin-2-yl}methanol (mixture of enantiomers)

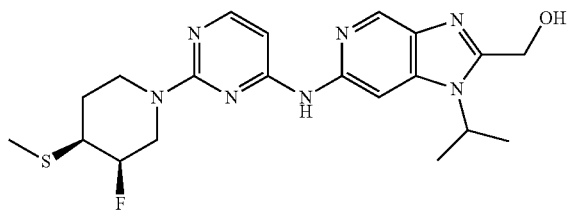 [SMILES: CS[C@H]1CCN(c2nccc(Nc3cc4c(cn3)nc(CO)n4C(C)C)n2)C[C@H]1F]

To a solution of (±)-[2-(cis-3-fluoro-4-methylsulfanylpiperidin-1-yl)pyrimidin-4-yl]-[1-isopropyl-2-(tetrahydropyran-2-yloxymethyl)-1H-imidazo[4,5-c]pyridin-6-yl]amine (50.6 mg, 0.098 mmol) in dichloromethane (3 mL) at 0° C. was added trifluoroacetic acid (1 mL). The mixture was allowed to warm to room temperature and stirred for 4 h. Toluene was added and the reaction mixture was concentrated in vacuo (2×). The residue was dissolved in methanol and loaded on to an SCX cartridge. The cartridge was washed with methanol, and then eluted with 1M ammonia in methanol. Further purification by chromatography on silica (solvent gradient: 2-10% 2M methanolic ammonia in dichloromethane) afforded the title compound as a colorless solid (30.8 mg, 73%) as a mixture of enantiomers. LCMS (ESI): $R_T$ 2.37 min; [M+H]$^+$ 432.1, Method F. $^1$H NMR (400 MHz, DMSO-d$_6$) δ 9.78 (1H, s), 8.60 (1H, s), 8.38 (1H, br s), 7.97 (1H, d, J=5.7 Hz), 6.46 (1H, br d, J=5.5 Hz), 5.68 (1H, t, J=5.8 Hz), 5.02-4.84 (3H, m), 4.76-4.71 (3H, m), 3.24-3.03 (3H, m), 2.15 (3H, s), 1.92-1.72 (2H, m), 1.60 (6H, 2d, J=6.8 Hz).

Example 623: {6-[2-(cis-3-Fluoro-4-methanesulfinylpiperidin-1-yl)pyrimidin-4-ylamino]-1-isopropyl-1H-imidazo[4,5-c]pyridin-2-yl}methanol (mixture of diastereoisomers)

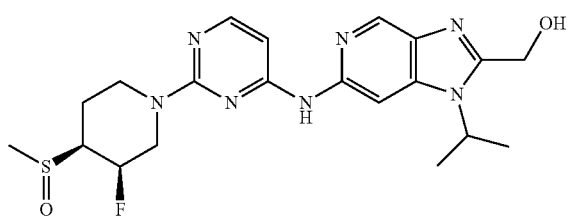 [SMILES: CC(C)n1c(CO)nc2cnc(Nc3ccnc(N4CC[C@H](S(C)=O)[C@H](F)C4)n3)cc21]

Step 1: [2-(cis-3-Fluoro-4-methylsulfinylpiperidin-1-yl)pyrimidin-4-yl]-[1-isopropyl-2-(tetrahydropyran-2-yloxymethyl)-1H-imidazo[4,5-c]pyridin-6-yl]amine

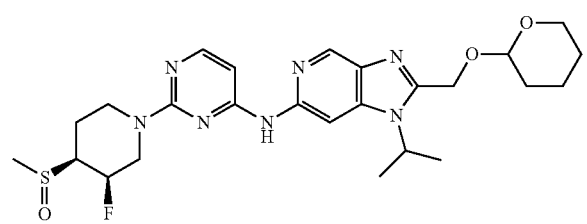 [SMILES: CC(C)n1c(COC2CCCCO2)nc2cnc(Nc3ccnc(N4CC[C@H](S(C)=O)[C@H](F)C4)n3)cc21]

3-Chloroperbenzoic acid (77%, 45.4 mg, 0.202 mmol) in dichloromethane (2 mL) was added to a solution of [2-(cis-3-fluoro-4-methylsulfanylpiperidin-1-yl)pyrimidin-4-yl]-[1-isopropyl-2-(tetrahydropyran-2-yloxymethyl)-1H-imidazo[4,5-c]pyridin-6-yl]amine (Example 622, step 1)(116 mg, 0.202 mmol) in dichloromethane (8 mL) at 0° C. The mixture was stirred at 0° C. for 15 min, then purified by chromatography on silica (solvent gradient: 2-10% 2M methanolic ammonia in dichloromethane) to afford the title compound as a colorless gum (91.7 mg, 85%). LCMS (ESI): [M+H]$^+$ 532.

Step 2: {6-[2-(cis-3-Fluoro-4-methylsulfinylpiperidin-1-yl)pyrimidin-4-ylamino]-1-isopropyl-1H-imidazo[4,5-c]pyridin-2-yl}methanol (mixture of diastereoisomers)

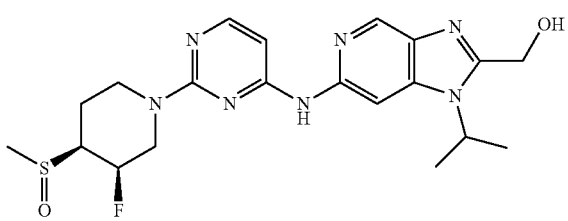 [SMILES: CC(C)n1c(CO)nc2cnc(Nc3ccnc(N4CC[C@H](S(C)=O)[C@H](F)C4)n3)cc21]

The title compound (35.5 mg, 46%) (mixture of diastereoisomers) was prepared from [2-(cis-3-fluoro-4-methylsulfinylpiperidin-1-yl)pyrimidin-4-yl]-[1-isopropyl-2-(tetrahydropyran-2-yloxymethyl)-1H-imidazo[4,5-c]pyridin-6-yl]amine (91.7 mg, 0.172 mmol) by a procedure analogous to that described in Example 622. LCMS (ESI): $R_T$ 1.81 and 1.86 min [M+H]$^+$ 448.2, Method F. $^1$H NMR (400 MHz, DMSO-d$_6$) δ 9.81 (1H, s), 8.61 (1H, s), 8.36 (1H, br d, J=5.4 Hz), 7.99 (1H, d, J=5.7 Hz), 6.51-6.49 (1H, m), 5.69 (1H, t, J=5.7 Hz), 5.28-5.22 (1H, m), 5.15-5.08 (1H, m), 5.00-4.93 (2H, m), 4.72 (2H, d, J=5.5 Hz), 3.29-2.97 (3H, m), 2.67 and 2.66 (3H, 2s), 2.01-1.68 (2H, m), 1.62-1.59 (6H, m).

Example 624: 4-(4-((2-(hydroxymethyl)-1-isopropyl-1H-imidazo[4,5-c]pyridin-6-yl)amino)pyrimidin-2-yl)cyclohex-3-enol

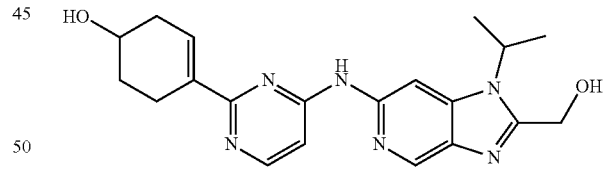

Step 1: N-(2-(1,4-dioxaspiro[4.5]dec-7-en-8-yl)pyrimidin-4-yl)-1-isopropyl-2-(((tetrahydro-2H-pyran-2-yl)oxy)methyl)-1H-imidazo[4,5-c]pyridin-6-amine

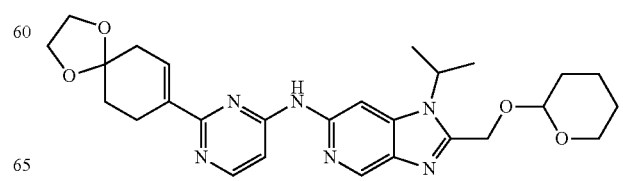

A mixture of N-(2-chloropyrimidin-4-yl)-1-isopropyl-2-(tetrahydropyran-2-yloxymethyl)imidazo[4,5-c]pyridin-6-amine (Example A49) (0.5099 g, 1.266 mmol), 2-(1,4-dioxaspiro[4.5]dec-8-en-8-yl)-4,4,5,5-tetramethyl-1,3,2-dioxaborolane (501.0 mg, 1.883 mmol), tetrakis(triphenylphosphine)palladium(0) (110.1 mg, 0.09528 mmol), cesium carbonate (685.9 mg, 2.08 mmol), 1,4-dioxane (4.0 mL, 47 mmol), and water (0.2 mL, 10 mmol) was stirred under nitrogen at 100° C. for 2 h and then at 110° C. overnight. The reaction mixture was diluted with ethyl acetate, washed with water and brine, dried over magnesium sulfate, filtered, and evaporated in vacuo. The crude product was purified via flash chromatography on silica gel (12 g silica, solvent gradient: 0-100% ethyl acetate in dichloromethane) to yield 442.8 mg (69%) of the title compound. LCMS (ESI): [M+H]$^+$=507.4; $^1$H NMR (400 MHz, DMSO-d$_6$) δ 10.10 (s, 1H), 8.69 (s, 1H), 8.66 (s, 1H), 8.32 (d, J=5.8 Hz, 1H), 7.12 (t, J=3.0 Hz, 1H), 7.04 (d, J=5.8 Hz, 1H), 4.99-4.86 (m, 2H), 4.82-4.69 (m, 2H), 3.99-3.88 (m, 4H), 3.84-3.72 (m, 1H), 3.61-3.48 (m, 1H), 2.86-2.71 (m, 2H), 2.49-2.45 (m, 2H), 1.84 (t, J=6.5 Hz, 2H), 1.74-1.65 (m, 2H), 1.63 (s, 6H), 1.51 (d, J=10.5 Hz, 4H).

Step 2: 4-(4-((2-(hydroxymethyl)-1-isopropyl-1H-imidazo[4,5-c]pyridin-6-yl)amino)pyrimidin-2-yl)cyclohex-3-enone

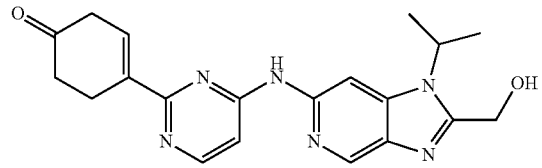 [SMILES: CC(C)n1c(CO)nc2cnc(Nc3ccnc(C4=CCC(=O)CC4)n3)cc21]

A mixture of N-(2-(1,4-dioxaspiro[4.5]dec-7-en-8-yl)pyrimidin-4-yl)-1-isopropyl-2-(((tetrahydro-2H-pyran-2-yl)oxy)methyl)-1H-imidazo[4,5-c]pyridin-6-amine (442.8 mg, 0.8741 mmol), ethanol (6.0 mL, 100 mmol), and hydrogen chloride (5 M in water) (1.5 mL, 7.5 mmol) was heated at 60° C. for 4 hours, and then cooled to room temperature. The reaction mixture was concentrated to remove the ethanol, diluted with dichloromethane, washed with saturated aqueous sodium bicarbonate, dried over magnesium sulfate, filtered, and evaporated in vacuo to give 280.9 mg (85%) of the title compound, which was carried forward without purification. LCMS (ESI): [M+H]$^+$=379.2.

Step 3: 4-(4-((2-(hydroxymethyl)-1-isopropyl-1H-imidazo[4,5-c]pyridin-6-yl)amino)pyrimidin-2-yl)cyclohex-3-enol

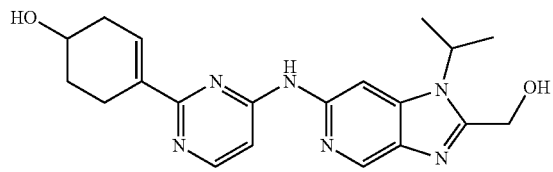 [SMILES: CC(C)n1c(CO)nc2cnc(Nc3ccnc(C4=CCC(O)CC4)n3)cc21]

To a solution of 4-(4-((2-(hydroxymethyl)-1-isopropyl-1H-imidazo[4,5-c]pyridin-6-yl)amino)pyrimidin-2-yl)cyclohex-3-enone (60.4 mg, 0.160 mmol) in methanol (3.0 mL, 70 mmol) was added sodium borohydride (13.9 mg, 0.364 mmol). The reaction mixture was stirred at room temperature for 1 h. The reaction mixture was diluted with dichloromethane, washed with saturated aqueous sodium bicarbonate, dried over magnesium sulfate, filtered, and evaporated in vacuo. The crude product was purified via reverse-phase HPLC and lyophilized to yield 20.3 mg (33%) of the title compound. LCMS (ESI): R$_T$ (min)=3.037, [M+H]$^+$=381.2, method=B; $^1$H NMR (400 MHz, DMSO-d$_6$) δ 10.01 (s, 1H), 8.68 (s, 1H), 8.62 (s, 1H), 8.30 (d, J=5.8 Hz, 1H), 7.16 (s, 1H), 7.01 (d, J=5.9 Hz, 1H), 5.68 (s, 1H), 4.98 (p, J=6.8 Hz, 1H), 4.73 (s, 2H), 4.69 (d, J=3.8 Hz, 1H), 3.86 (s, 1H), 2.86-2.75 (m, 1H), 2.52 (s, 2H), 2.21-2.10 (m, 1H), 1.96-1.86 (m, 1H), 1.70-1.54 (m, 7H).

Example 625: N-(2-(3-Chloro-1-(cyclopropylmethyl)-1H-pyrazol-4-yl)pyrimidin-4-yl)-1-isopropyl-2-methyl-1H-imidazo[4,5-c]pyridin-6-amine

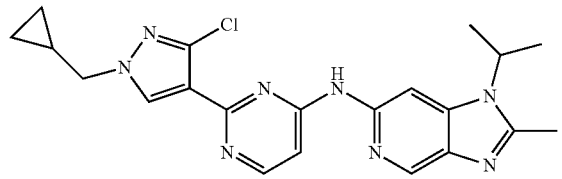 [SMILES: Cc1nc2cnc(Nc3ccnc(-c4cn(CC5CC5)nc4Cl)n3)cc2n1C(C)C]

Step 1: N-(2-(1-(Cyclopropylmethyl)-3-nitro-1H-pyrazol-4-yl)pyrimidin-4-yl)-1-isopropyl-2-methyl-1H-imidazo[4,5-c]pyridin-6-amine

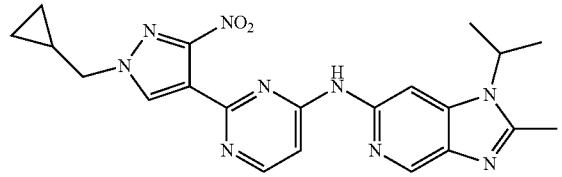 [SMILES: Cc1nc2cnc(Nc3ccnc(-c4cn(CC5CC5)nc4[N+](=O)[O-])n3)cc2n1C(C)C]

A mixture of 1-(cyclopropylmethyl)-3-nitro-1H-pyrazol-4-ylboronic acid (Example 251, step 3) (86 mg, 0.40 mmol), N-(2-chloropyrimidin-4-yl)-1-isopropyl-2-methyl-1H-imidazo[4,5-c]pyridin-6-amine (Example 46, step 7)(61.8 mg, 0.20 mmol), tetrakis(triphenylphosphine) palladium(0) (48 mg, 0.040 mmol) and sodium carbonate (130 mg, 1.23 mmol) in dioxane (8 mL) and water (0.1 mL) was heated at 90° C. for 5 h. The reaction was cooled to room temperature, filtered, and concentrated in vacuo. The residue was purified by silica gel chromatography (solvent gradient: 0-10% methanol in dichloromethane) to afford the title compound (80 mg, 45%) as a brown solid. LCMS (ESI): [M+H]$^+$=434.

Step 2: N-(2-(3-Amino-1-(cyclopropylmethyl)-1H-pyrazol-4-yl)pyrimidin-4-yl)-1-isopropyl-2-methyl-1H-imidazo[4,5-c]pyridin-6-amine

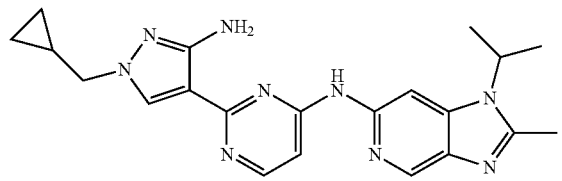 [SMILES: Cc1nc2cnc(Nc3ccnc(-c4cn(CC5CC5)nc4N)n3)cc2n1C(C)C]

To a reaction vessel was added N-(2-(1-(cyclopropylmethyl)-3-nitro-1H-pyrazol-4-yl)pyrimidin-4-yl)-1-isopropyl-2-methyl-1H-imidazo[4,5-c]pyridin-6-amine (120 mg, 0.28 mmol), iron powder (62 mg, 1.11 mmol), ammonium chloride (86 mg, 1.61 mmol), water (0.1 mL) and ethanol (7 mL). The reaction mixture was stirred for 8 h at 80° C. The reaction was cooled to room temperature, filtered, and concentrated in vacuo. The resulting residue was purified by silica gel chromatography (solvent gradient: 0-10% methanol in dichloromethane) to afford the title compound (80 mg, 72%) as white solid. LCMS (ESI): [M+H]$^+$=404.

Step 3: N-(2-(3-Chloro-1-(cyclopropylmethyl)-1H-pyrazol-4-yl)pyrimidin-4-yl)-1-isopropyl-2-methyl-1H-imidazo[4,5-c]pyridin-6-amine

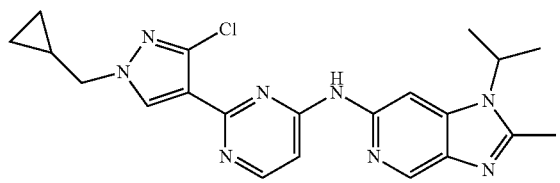 [SMILES: Cc1nc2cnc(Nc3ccnc(-c4cn(CC5CC5)nc4Cl)n3)cc2n1C(C)C]

A solution of N-(2-(3-amino-1-(cyclopropylmethyl)-1H-pyrazol-4-yl)pyrimidin-4-yl)-1-isopropyl-2-methyl-1H-imidazo[4,5-c]pyridin-6-amine (40 mg, 0.10 mmol) in acetonitrile (1 mL) was added dropwise to a precooled solution of tert-butyl nitrite (12.4 mg, 0.12 mmol), and copper (I) chloride (11.8 mg, 0.12 mmol) in acetonitrile (3 mL) at 0° C. The reaction mixture was stirred for 1 h at room temperature and 2 h at 60° C. in an oil bath. The reaction was cooled to room temperature, filtered, and concentrated in vacuo. The resulting residue was purified via reverse-phase HPLC and lyophilized to afford the title compound (2.2 mg, 5%) as an off-white solid. LCMS (ESI) [M+H]$^+$=423, $R_T$ (min)=1.470, Method=N; $^1$H NMR (400 MHz, DMSO-d$_6$) δ 9.95 (s, 1H), 8.55 (s, 1H), 8.35 (m, 2H), 8.18 (s, 1H), 7.34-7.32 (d, J=5.4 Hz, 1H), 4.78-4.69 (m, 1H), 4.01-3.98 (d, J=7.2 Hz, 2H), 2.58 (s, 3H), 1.57-1.55 (d, J=6.9 Hz, 6H), 1.31-1.28 (m, 1H), 0.59-0.56 (m, 2H), 0.42-0.39 (m, 2H).

Example 626 and Example 627: (±)-(cis)-1-(4-(2-(Hydroxymethyl)-1-isopropyl-1H-imidazo[4,5-c]pyridin-6-ylamino)pyrimidin-2-yl)-3-(trifluoromethyl)piperidin-4-ol and (±)-(trans)-1-(4-(2-(Hydroxymethyl)-1-isopropyl-1H-imidazo[4,5-c]pyridin-6-ylamino)pyrimidin-2-yl)-3-(trifluoromethyl)piperidin-4-ol

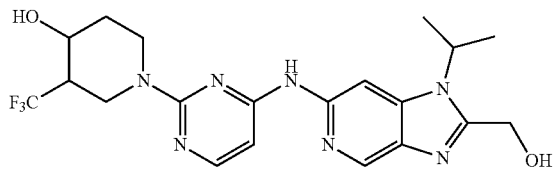 [SMILES: CC(C)n1c(CO)nc2cnc(Nc3ccnc(N4CCC(O)C(C(F)(F)F)C4)n3)cc21]

Step 1: 3-(Trifluoromethyl)pyridin-4-ol

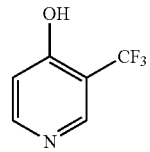 [SMILES: Oc1ccncc1C(F)(F)F]

A mixture of 4-bromo-3-(trifluoromethyl)pyridine hydrobromide (1.0 g, 3.26 mmol) and potassium acetate (1.6 g, 16.3 mmol) in acetic acid (11 mL) was heated under microwave irradiation at 160° C. for 3 h. After the reaction was cooled down to room temperature, the solution was diluted with water and the pH value was adjusted to 8 with aqueous sodium carbonate. The resulting solution was extracted with ethyl acetate (2×) and the combined organic layers were washed with brine, dried over anhydrous sodium sulfate, filtered, and concentrated in vacuo to afford the title compound (370 mg, 70%) as an off-white solid. LCMS (ESI): [M+H]$^+$=164.

Step 2: 3-(Trifluoromethyl)piperidin-4-ol hydrochloride

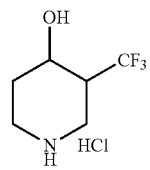

To a pressure tank reactor was added 3-(trifluoromethyl)pyridin-4-ol (100 mg, 0.61 mmol), platinum (IV) oxide (15 mg, 0.07 mmol), hydrochloric acid (0.1 mL) and methanol (6 mL). The reaction mixture was stirred under hydrogen (30 atm) for 5 h at 50° C. The reaction was cooled to room temperature, filtered, and concentrated in vacuo to afford the title compound (120 mg, 95%) as a white solid. LCMS (ESI): [M+H]$^+$=170.

Step 3: 1-(4-(1-Isopropyl-2-((tetrahydro-2H-pyran-2-yloxy)methyl)-1H-imidazo[4,5-c]pyridin-6-ylamino)pyrimidin-2-yl)-3-(trifluoromethyl)piperidin-4-ol

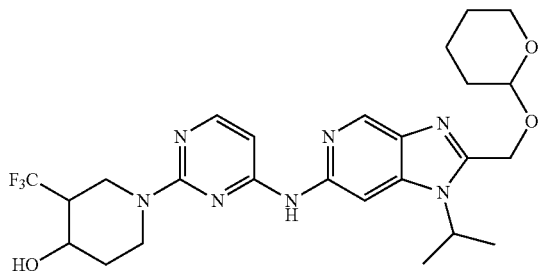 [SMILES: CC(C)n1c(COC2CCCCO2)nc2cnc(Nc3ccnc(N4CCC(O)C(C(F)(F)F)C4)n3)cc21]

A mixture of (2-chloropyrimidin-4-yl)-[1-isopropyl-2-(tetrahydropyran-2-yloxymethyl)-1H-imidazo[4,5-c]pyridin-6-yl]amine (Example A49)(238 mg, 0.59 mmol), 3-(trifluoromethyl)piperidin-4-ol hydrochloride (100 mg, 0.49 mmol), and potassium carbonate (205 mg, 1.48 mmol) in N,N-dimethylformamide (4 mL) was heated under microwave irradiation at 120° C. for 90 min. The reaction was cooled to room temperature, filtered, and concentrated in vacuo to afford the title compound (300 mg crude, 94%) as brown oil. LCMS (ESI): [M+H]$^+$=536.

Step 4: (±)-(cis)-1-(4-(2-(Hydroxymethyl)-1-isopropyl-1H-imidazo[4,5-c]pyridin-6-ylamino)pyrimidin-2-yl)-3-(trifluoromethyl)piperidin-4-ol and (±)-(trans)-1-(4-(2-(Hydroxymethyl)-1-isopropyl-1H-imidazo[4,5-c]pyridin-6-ylamino)pyrimidin-2-yl)-3-(trifluoromethyl)piperidin-4-ol

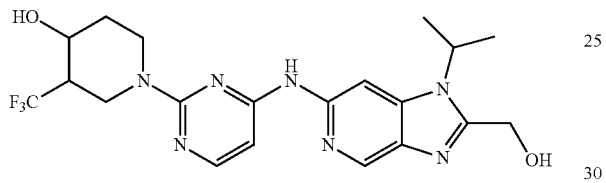

1-(4-(1-Isopropyl-2-((tetrahydro-2H-pyran-2-yloxy)methyl)-1H-imidazo[4,5-c]pyridin-6-ylamino)pyrimidin-2-yl)-3-(trifluoromethyl)piperidin-4-ol (320 mg, 0.60 mmol) was dissolved in HCl in 1,4-dioxane (4 M, 10 mL). The reaction mixture was stirred for 30 min at room temperature. The pH was adjusted to 10 with aqueous sodium carbonate and the resulting solution was extracted with ethyl acetate (2×) and the combined organic layers were washed with brine, dried over anhydrous sodium sulfate, filtered and concentrated in vacuo. The residue was purified via reverse-phase HPLC and lyophilized to afford the title compounds (55.7 mg, 21%) and (2.7 mg, 1%) each as a mixture of enantiomers with unknown stereochemistry as white solids.

Example 626 (isomer 1): LCMS (ESI) [M+H]$^+$=452, R$_T$ (min)=1.470, Method=M; $^1$H NMR (400 MHz, DMSO-d$_6$) δ 9.79 (s, 1H), 8.61 (s, 1H), 8.34 (s, 1H), 8.01 (d, J=5.6 Hz, 1H), 6.51 (d, J=5.6 Hz, 1H), 5.71-5.69 (m, 1H), 5.18-5.17 (d, J=4.0 Hz, 1H), 4.99-4.91 (m, 1H), 4.72-4.71 (d, J=6.0 Hz, 3H), 4.58-4.54 (d, J=16 Hz, 1H), 4.25 (s, 1H), 3.34-3.29 (m, 2H), 2.53-2.51 (m, 1H), 1.73-1.71 (m, 2H), 1.59-1.56 (m, 6H).

Example 627 (isomer 2): LCMS (ESI) [M+H]$^+$=452, R$_T$ (min)=1.70, Method=M; $^1$H NMR (400 MHz, DMSO-d$_6$) δ 9.80 (s, 1H), 8.61 (s, 1H), 8.30 (s, 1H), 8.02-8.00 (d, J=5.6 Hz, 1H), 6.56 (d, J=5.6 Hz, 1H), 5.69 (m, 1H), 5.17-5.16 (d, J=6.0 Hz, 1H), 4.99-4.91 (m, 1H), 4.76-4.71 (m, 3H), 4.56-4.52 (d, J=16 Hz, 1H), 3.88 (s, 1H), 3.22-3.09 (m, 2H), 2.33-2.25 (m, 1H), 1.96-1.93 (m, 1H), 1.59-1.57 (m, 6H), 1.52-1.44 (m, 1H).

Example 628 and Example 629: (1-Isopropyl-6-(2-((±)-cis)-4-methoxy-3-(trifluoromethyl)piperidin-1-yl)pyrimidin-4-ylamino)-1H-imidazo[4,5-c]pyridin-2-yl)methanol and (1-Isopropyl-6-(2-((±)-(trans)-4-methoxy-3-(trifluoromethyl)piperidin-1-yl)pyrimidin-4-ylamino)-1H-imidazo[4,5-c]pyridin-2-yl)methanol

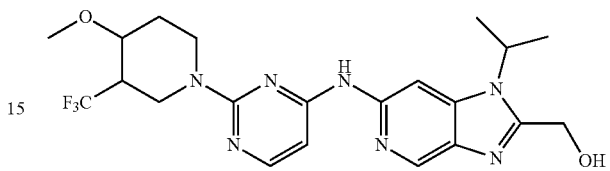

Step 1: tert-Butyl 4-hydroxy-3-(trifluoromethyl)piperidine-1-carboxylate

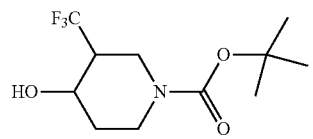 [SMILES: CC(C)(C)OC(=O)N1CCC(O)C(C(F)(F)F)C1]

A mixture of 3-(trifluoromethyl)piperidin-4-ol hydrochloride (Example 626, step 2)(350 mg, 1.70 mmol), di-tert-butyl dicarbonate (483 mg, 2.21 mmol), and N-ethyl-N-isopropylpropan-2-amine (881 mg, 6.82 mmol) in acetonitrile (5 mL) was stirred for 4 h at room temperature. The solvent was removed in vacuo and the resulting residue was purified by silica gel chromatography (solvent gradient: 0-20% EtOAc in petroleum) to afford the title compound (310 mg, 68%) as a white solid. LCMS (ESI): [M+H]$^+$=270.

Step 2: tert-Butyl-4-methoxy-3-(trifluoromethyl)piperidine-1-carboxylate

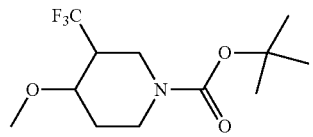 [SMILES: COC1CCN(C(=O)OC(C)(C)C)CC1C(F)(F)F]

A mixture of tert-butyl 4-hydroxy-3-(trifluoromethyl)piperidine-1-carboxylate (300 mg, 1.11 mmol) and sodium hydride (112 mg, 60% in oil, 4.67 mmol) in tetrahydrofuran (10 mL) was stirred for 1 h at 0° C. To the reaction mixture was added iodomethane (316 mg, 2.23 mmol) and the mixture was stirred at room temperature for 3 h. The reaction was quenched with water (5 mL), extracted with EtOAc (2×), washed with brine, dried over anhydrous sodium sulfate, filtered and concentrated in vacuo to afford the title compound (300 mg, 95%) as yellow oil. LCMS (ESI): [M+H]$^+$=284.

Step 3: 4-Methoxy-3-(trifluoromethyl)piperidine hydrochloride

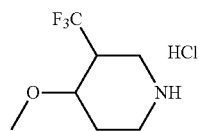

To a reaction vessel was added tert-butyl-4-methoxy-3-(trifluoromethyl)piperidine-1-carboxylate (300 mg, 1.06 mmol) and hydrogen chloride in 1,4-dioxane (4 M, 10 mL). The reaction mixture was stirred for 2 h at room temperature. The solvent was removed in vacuo to afford the title compound (190 mg, 82%) as an off-white solid, which was carried forward without purification.

Step 4: 1-Isopropyl-N-(2-(4-methoxy-3-(trifluoromethyl)piperidin-1-yl)pyrimidin-4-yl)-2-((tetrahydro-2H-pyran-2-yloxy)methyl)-1H-imidazo[4,5-c]pyridin-6-amine

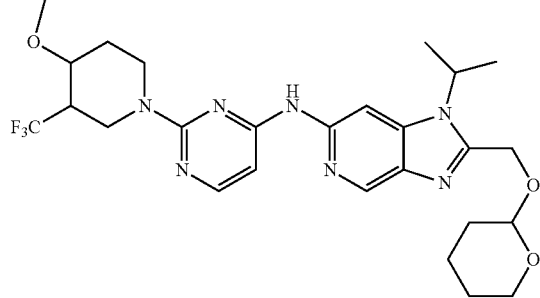 [SMILES: COC1CCN(c2nccc(Nc3cc4c(cn3)nc(COC3CCCCO3)n4C(C)C)n2)CC1C(F)(F)F]

The title compound (150 mg, 60%) was generated from 4-methoxy-3-(trifluoromethyl)piperidine hydrochloride (100 mg, 0.46 mmol) following a procedure analogous to Example 626, step 3. LCMS (ESI): [M+H]$^+$=550.

Step 5: (1-Isopropyl-6-(2-((±)-cis)-4-methoxy-3-(trifluoromethyl)piperidin-1-yl)pyrimidin-4-ylamino)-1H-imidazo[4,5-c]pyridin-2-yl)methanol and (1-Isopropyl-6-(2-((±)-(trans)-4-methoxy-3-(trifluoromethyl)piperidin-1-yl)pyrimidin-4-ylamino)-1H-imidazo[4,5-c]pyridin-2-yl)methanol

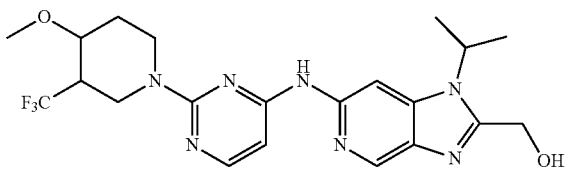 [SMILES: COC1CCN(c2nccc(Nc3cc4c(cn3)nc(CO)n4C(C)C)n2)CC1C(F)(F)F]

The title compounds (70.5 mg, 24% and 6.1 mg, 2%) were generated from 1-isopropyl-N-(2-(4-methoxy-3-(trifluoromethyl)piperidin-1-yl)pyrimidin-4-yl)-2-((tetrahydro-2H-pyran-2-yloxy)methyl)-1H-imidazo[4,5-c]pyridin-6-amine (340 mg, 0.62 mmol) following a procedure analogous to Example 626, step 4.

Example 628 (isomer 1): LCMS (ESI): [M+H]$^+$=466, R$_T$ (min)=1.743, Method=N; $^1$H NMR (400 MHz, DMSO-d$_6$) δ 9.78 (s, 1H), 8.61 (s, 1H), 8.29 (s, 1H), 8.02-8.00 (d, J=5.6 Hz, 1H), 6.56 (d, J=5.6 Hz, 1H), 5.71-5.68 (m, 1H), 4.97-4.92 (m, 1H), 4.72-4.66 (m, 3H), 4.53-4.49 (m, 1H), 3.85 (s, 1H), 3.35 (s, 3H), 3.32-3.16 (m, 2H), 2.87-2.68 (m, 1H), 2.04-2.00 (m, 1H), 1.63-1.57 (m, 7H).

Example 629 (isomer 2): LCMS (ESI): [M+H]$^+$=466, R$_T$ (min)=1.700, Method=N; $^1$H NMR (400 MHz, DMSO-d$_6$) δ 9.79 (s, 1H), 8.61 (s, 1H), 8.29 (s, 1H), 8.02-8.00 (d, J=5.6 Hz, 1H), 6.56 (s, 1H), 5.71-5.69 (m, 1H), 4.99-4.91 (m, 1H), 4.72-4.71 (d, J=6.0 Hz, 2H), 4.65-4.60 (m, 1H), 4.45-4.41 (m, 1H), 3.69-3.62 (m, 1H), 3.33 (s, 3H), 3.29 (m, 2H), 2.51-2.50 (m, 1H), 2.17-2.11 (m, 1H), 1.60-1.57 (m, 6H), 1.52-1.43 (m, 1H).

Example 630: (±)-(trans)-1-(4-(2-(Hydroxymethyl)-1-isopropyl-1H-imidazo[4,5-c]pyridin-6-ylamino)pyrimidin-2-yl)-3-methylpiperidin-4-ol (mixture of enantiomers)

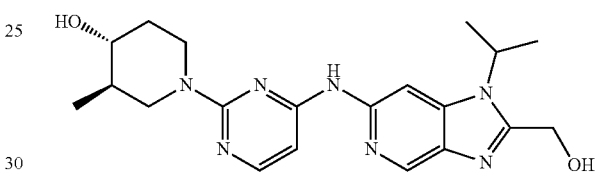

Step 1: (±)-(trans)-1-Benzyl-3-methylpiperidin-4-ol

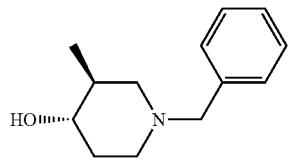

A mixture of 1-benzyl-3-methylpiperidin-4-one (10.0 g, 49.2 mmol), phosphoric acid (4.83 g, 49.3 mmol) and sodium tetrahydroborate (3.73 g, 98.6 mmol) in methanol (40 mL) and water (90 mL) was stirred for 8 h at room temperature. The solution was diluted with aqueous sodium hydroxide (4 M, 20 mL), extracted with ethyl acetate (2×), washed with brine, dried over anhydrous sodium sulfate, filtered, and concentrated in vacuo. The resulting residue was purified by silica gel chromatography (solvent gradient: 0-10% methanol in dichloromethane) to afford the title compound (8.5 g, 84%) as a yellow oil. LCMS (ESI): [M+H]$^+$=206.

Step 2: (±)-(trans)-3-Methylpiperidin-4-ol

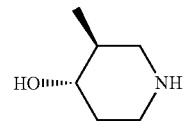

To a reaction vessel was added (±)-(trans)-1-benzyl-3-methylpiperidin-4-ol (800 mg, 3.90 mmol), methanol (15 mL) and palladium on carbon (100 mg, 20%). The reaction mixture was stirred under a hydrogen atmosphere (1 atm) for 8 h at room temperature. The reaction was filtered and concentrated in vacuo to afford the title compound (400 mg, 89%) as a colorless oil. LCMS (ESI): [M+H]$^+$=116.

Step 3: (±)-(trans)-1-(4-(1-Isopropyl-2-((tetrahydro-2H-pyran-2-yloxy)methyl)-1H-imidazo[4,5-c]pyridin-6-ylamino)pyrimidin-2-yl)-3-methylpiperidin-4-ol

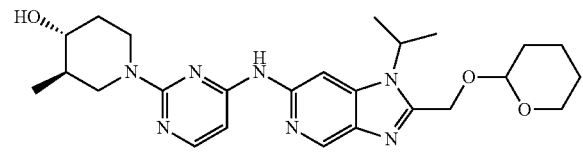 [SMILES: CC(C)n1c(COC2CCCCO2)nc2cnc(Nc3ccnc(N4CC[C@@H](O)[C@H](C)C4)n3)cc21]

The title compound (520 mg, 48%) was generated from (±)-(trans)-3-methylpiperidin-4-ol (260 mg, 2.26 mmol) following a procedure analogous to Example 626, step 3. LCMS (ESI): [M+H]$^+$=482.

Step 4: (±)-(trans)-1-(4-(2-(Hydroxymethyl)-1-isopropyl-1H-imidazo[4,5-c]pyridin-6-ylamino)pyrimidin-2-yl)-3-methylpiperidin-4-ol

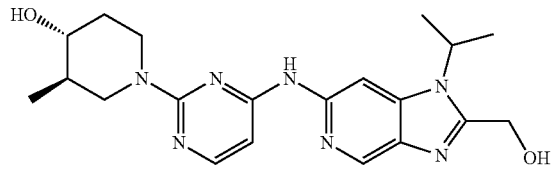 [SMILES: CC(C)n1c(CO)nc2cnc(Nc3ccnc(N4CC[C@@H](O)[C@H](C)C4)n3)cc21]

The title compound (115.8 mg, 47%) was generated from (±)-(trans)-1-(4-(1-isopropyl-2-((tetrahydro-2H-pyran-2-yloxy)methyl)-1H-imidazo[4,5-c]pyridin-6-ylamino)pyrimidin-2-yl)-3-methylpiperidin-4-ol (300 mg, 0.62 mmol) following a procedure analogous to Example 626, step 3. as a white solid. LCMS (ESI): [M+H]$^+$=398.1, R$_T$ (min)=2.02, Method=M; $^1$H NMR (400 MHz, DMSO-d$_6$) δ 9.72 (s, 1H), 8.60 (s, 1H), 8.38 (s, 1H), 7.97-7.95 (d, J=5.6 Hz, 1H), 6.44-6.43 (d, J=5.2 Hz, 1H), 5.72-5.69 (m, 1H), 4.97-4.94 (m, 1H), 4.72-4.70 (m, 3H), 4.67-4.64 (m, 1H), 4.57-4.56 (m, 1H), 3.23-3.19 (m, 1H), 3.06-2.99 (m, 1H), 2.66-2.60 (m, 1H), 1.90-1.86 (m, 1H), 1.61-1.58 (m, 6H), 1.40-1.35 (m, 2H), 0.97-0.95 (d, J=5.4 Hz, 3H).

Example 631: (±)-(cis)-1-(4-(2-(Hydroxymethyl)-1-isopropyl-1H-imidazo[4,5-c]pyridin-6-ylamino)pyrimidin-2-yl)-3-methylpiperidin-4-ol (mixture of enantiomers)

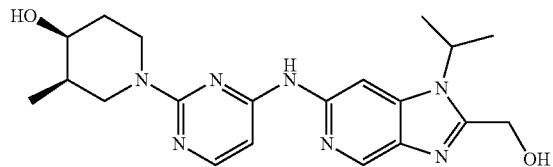 [SMILES: CC(C)n1c(CO)nc2cnc(Nc3ccnc(N4CC[C@H](O)[C@H](C)C4)n3)cc21]

Step 1: (±)-(cis)-1-Benzyl-3-methylpiperidin-4-ol

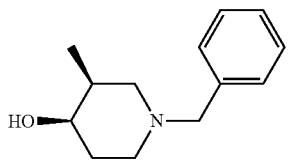

A solution of lithium tri-sec-butylhydroborate in tetrahydrofuran (1 M, 29.6 mL) was added dropwise to a precooled solution at 0° C. of 1-benzyl-3-methylpiperidin-4-one (5.0 g, 24.6 mmol) in tetrahydrofuran (20 mL). The reaction mixture was stirred for 3 h at 0° C. The resulting solution was diluted with water and extracted twice with ethyl acetate, washed with brine, dried over sodium sulfate and concentrated in vacuo. The resulting residue was purified by silica gel chromatography (solvent gradient 0-10% methanol in dichloromethane) to afford the title compound (3.7 g, 73%) as a yellow oil. LCMS (ESI): [M+H]$^+$=206.

Step 2: (±)-(cis)-3-Methylpiperidin-4-ol

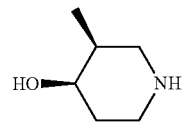

The procedure and purification method are similar to Example 630, step 2 using (±)-(cis)-1-benzyl-3-methylpiperidin-4-ol (500 mg, 2.44 mmol) to afford the title compound (200 mg, 71%) as colorless oil. LCMS (ESI): [M+H]$^+$=116

Step 3: (±)-(cis)-1-(4-(1-Isopropyl-2-((tetrahydro-2H-pyran-2-yloxy)methyl)-1H-imidazo[4,5-c]pyridin-6-ylamino)pyrimidin-2-yl)-3-methylpiperidin-4-ol

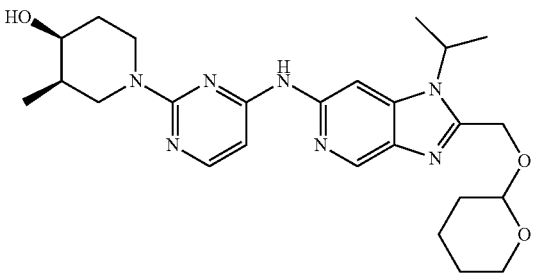 [SMILES: CC(C)n1c(COC2CCCCO2)nc2cnc(Nc3ccnc(N4CC[C@H](O)[C@H](C)C4)n3)cc21]

The procedure and purification method are similar to Example 626, step 3 using (±)-(cis)-3-methylpiperidin-4-ol (170 mg, 1.48 mmol) to afford the title compound (300 mg, 42%) as a yellow solid. LCMS (ESI): [M+H]$^+$=482.

Step 4: (±)-(cis)-1-(4-(2-(hydroxymethyl)-1-isopropyl-1H-imidazo[4,5-c]pyridin-6-ylamino)pyrimidin-2-yl)-3-methylpiperidin-4-ol (mixture of enantiomers)

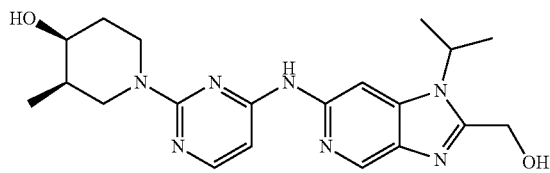 [SMILES: CC(C)n1c(CO)nc2cnc(Nc3ccnc(N4CC[C@H](O)[C@H](C)C4)n3)cc21]

The procedure and purification method are similar to Example 626, step 4 using (±)-(cis)-1-(4-(1-isopropyl-2-((tetrahydro-2H-pyran-2-yloxy)methyl)-1H-imidazo[4,5-c]pyridin-6-ylamino)pyrimidin-2-yl)-3-methylpiperidin-4-ol (300 mg, 0.62 mmol) to afford the title compound (61.4 mg, 25%) as a white solid. LCMS (ESI): [M+H]$^+$=398.1, R$_T$ (min)=1.25, Method=R; $^1$H NMR (400 MHz, DMSO-d$_6$) δ 9.71 (s, 1H), 8.59 (s, 1H), 8.42 (s, 1H), 7.94 (d, J=5.6 Hz, 1H), 6.38 (d, J=5.6 Hz, 1H), 5.70-5.67 (m, 1H), 4.98-4.94 (m, 1H), 4.71 (d, J=6 Hz, 2H), 4.63 (d, J=4 Hz, 1H), 4.09-4.01 (m, 1H), 3.99-3.92 (m, 1H), 3.75 (s, 1H), 3.68-3.61 (m, 1H), 3.41-3.35 (m, 1H), 1.65-1.58 (m, 3H), 1.58-1.57 (m, 6H), 0.87 (d, J=6.8 Hz, 3H).

Example 632: (1-Isopropyl-6-(2-((±)-cis)-4-methoxy-3-methylpiperidin-1-yl)pyrimidin-4-ylamino)-1H-imidazo[4,5-c]pyridin-2-yl)methanol (mixture of enantiomers)

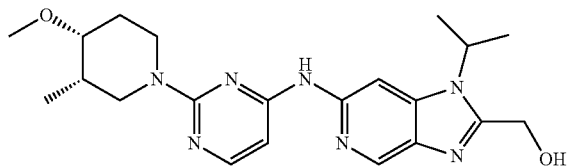 [SMILES: CO[C@@H]1CCN(c2nccc(Nc3cc4c(cn3)nc(CO)n4C(C)C)n2)C[C@@H]1C]

Step 1: (±)-(cis)-1-Benzyl-4-methoxy-3-methylpiperidine

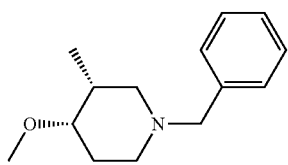 [SMILES: CO[C@H]1CCN(Cc2ccccc2)C[C@H]1C]

A mixture of (±)-(cis)-1-benzyl-3-methylpiperidin-4-ol (Example 631, step 1)(2.0 g, 9.74 mmol) and sodium hydride (500 mg, 60% in oil, 12.5 mmol) in tetrahydrofuran (30 mL) was stirred for 30 min at 0° C. Iodomethane (2.2 g, 15.5 mmol) was added and stirring continued at room temperature for 16 h. The reaction was quenched with water (5 mL), and the aqueous layer was extracted twice with ethyl acetate, washed with brine, dried over anhydrous sodium sulfate, filtered and concentrated in vacuo. The resulting residue was purified by silica gel chromatography (solvent gradient: 0-10% methanol in dichloromethane) to afford the title compound as a mixture of enantiomers (700 mg, 33%) as a yellow oil. LCMS (ESI): [M+H]$^+$=220.

Step 2: (±)-(cis)-4-Methoxy-3-methylpiperidine

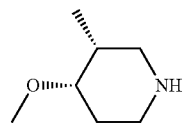

The procedure and purification method are similar to Example 630, step 2 using (±)-(cis)-1-benzyl-4-methoxy-3-methylpiperidine (500 mg, 2.28 mmol) to afford the title compound as a mixture of enantiomers (200 mg, 68%) as colorless oil. LCMS (ESI): [M+H]$^+$=130.

Step 3: 1-Isopropyl-N-(2-((±)-(cis)-4-methoxy-3-methylpiperidin-1-yl)pyrimidin-4-yl)-2-((tetrahydro-2H-pyran-2-yloxy)methyl)-1H-imidazo[4,5-c]pyridin-6-amine

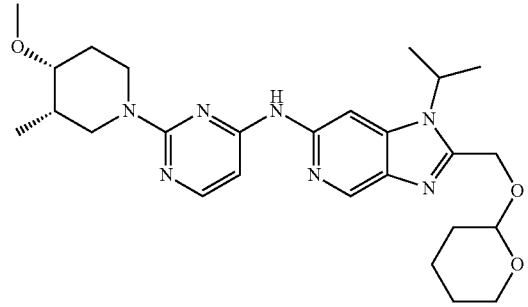 [SMILES: CO[C@@H]1CCN(c2nccc(Nc3cc4c(cn3)nc(COC3CCCCO3)n4C(C)C)n2)C[C@@H]1C]

The procedure and purification method are similar to Example 626, step 3 using (±)-(cis)-4-methoxy-3-methylpiperidine (150 mg, 1.16 mmol) to afford the title compound (200 mg, 35%) as a light yellow solid. LCMS (ESI): [M+H]$^+$=496.

Step 4: (1-Isopropyl-6-(2-((±)-(cis)-4-methoxy-3-methylpiperidin-1-yl)pyrimidin-4-ylamino)-1H-imidazo[4,5-c]pyridin-2-yl)methanol (mixture of enantiomers)

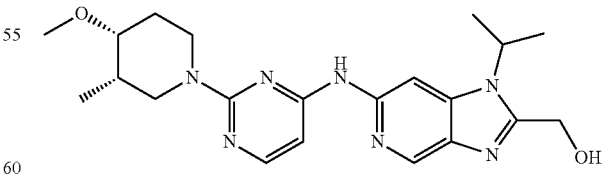

The procedure and purification method are similar to Example 626, step 4, using 1-isopropyl-N-(2-((±)-(cis)-4-methoxy-3-methylpiperidin-1-yl)pyrimidin-4-yl)-2-((tetrahydro-2H-pyran-2-yloxy)methyl)-1H-imidazo[4,5-c]pyridin-6-amine (200 mg, 0.4 mmol) to afford the title compound as a mixture of enantiomers (21.6 mg, 13%).

LCMS (ESI): [M+H]$^+$=412, R$_T$ (min)=1.17, Method=Q; $^1$H NMR (400 MHz, DMSO-d$_6$) δ 9.75 (s, 1H), 8.59 (s, 1H), 8.39 (s, 1H), 7.94 (d, J=5.6 Hz, 1H), 6.41 (d, J=5.6 Hz, 1H), 5.70-5.67 (m, 1H), 4.98-4.94 (m, 1H), 4.7 (d, J=5.6 Hz, 2H), 3.81-3.75 (m, 3H), 3.65-3.60 (m, 1H), 3.42-3.40 (m, 1H), 3.32-3.30 (m, 3H), 1.97-1.94 (m, 1H), 1.82-1.77 (m, 1H), 1.62-1.59 (m, 7H), 0.87 (d, J=6.8 Hz, 3H).

Example 633: (3RS,4RS)-4-cyclopropyl-3-fluoro-1-(4-((2-(hydroxymethyl)-1-isopropyl-1H-imidazo[4,5-c]pyridin-6-yl)amino)pyrimidin-2-yl)piperidin-4-ol (mixture of enantiomers)

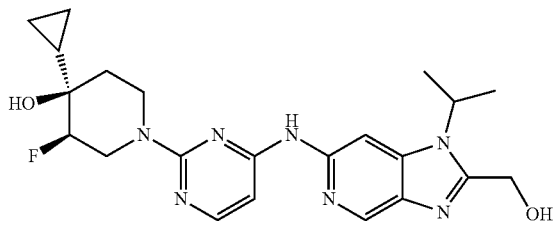 [SMILES: CC(C)n1c(CO)nc2cnc(Nc3ccnc(N4CC[C@@](O)(C5CC5)[C@H](F)C4)n3)cc21]

Step 1: (3RS,4RS)-tert-butyl 4-cyclopropyl-4-hydroxy-3-methylpiperidine-1-carboxylate (mixture of enantiomers)

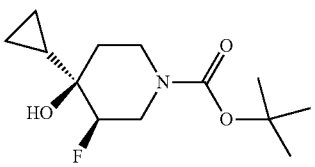 [SMILES: CC(C)(C)OC(=O)N1CC[C@@](O)(C2CC2)[C@H](F)C1]

A solution of cyclopropylmagnesium bromide in tetrahydrofuran (0.5 M, 9.2 mL) was added dropwise to a solution of tert-butyl 3-fluoro-4-oxopiperidine-1-carboxylate (500 mg, 2.3 mmol) in tetrahydrofuran (20 mL) at room temperature under nitrogen. The reaction mixture was stirred for 14 h at room temperature. The solution was quenched with saturated ammonium chloride, extracted twice with ethyl acetate, washed with brine, dried over sodium sulfate, filtered and concentrated in vacuo to afford the title compound (510 mg, crude, 85%) as a yellow oil. LCMS (ESI): [M+H]$^+$=260.

Step 2: (3RS,4RS)-4-cyclopropyl-3-fluoropiperidin-4-ol 2,2,2-trifluoroacetate (mixture of enantiomers)

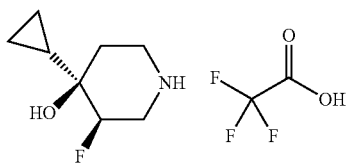

A mixture of tert-butyl 4-cyclopropyl-3-fluoro-4-hydroxypiperidine-1-carboxylate (510 mg, 1.97 mmol) and 2,2,2-trifluoroacetic acid (2 mL, 26.93 mmol) in dichloromethane (20 mL) was stirred for 2 h at room temperature. The solvent was removed in vacuo to afford the title compound (400 mg, crude, 74%) as a black oil. LCMS (ESI): [M+H]$^+$=160.

Step 3: (3RS,4RS)-4-cyclopropyl-3-fluoro-1-(4-((1-isopropyl-2-(((tetrahydro-2H-pyran-2-yl)oxy)methyl)-1H-imidazo[4,5-c]pyridin-6-yl)amino)pyrimidin-2-yl)piperidin-4-ol (mixture of enantiomers)

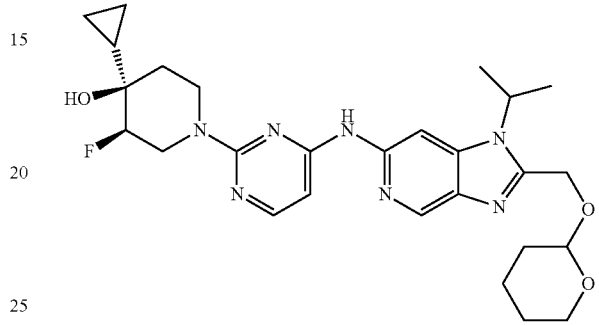

The procedure and purification method are similar to Example 626, step 3 using 4-cyclopropyl-3-fluoropiperidin-4-ol 2,2,2-trifluoroacetate salt (400 mg crude) to afford the title compound (100 mg) as a yellow solid. LCMS (ESI): [M+H]$^+$=526.

Step 4: (3RS,4RS)-4-cyclopropyl-3-fluoro-1-(4-((2-(hydroxymethyl)-1-isopropyl-1H-imidazo[4,5-c]pyridin-6-yl)amino)pyrimidin-2-yl)piperidin-4-ol (mixture of enantiomers)

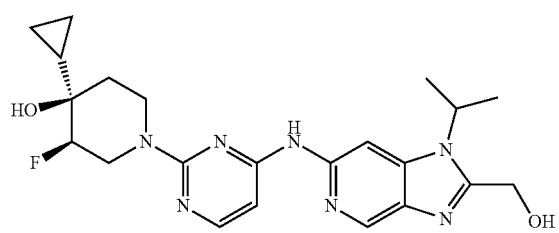 [SMILES: CC(C)n1c(CO)nc2cnc(Nc3ccnc(N4CC[C@@](O)(C5CC5)[C@H](F)C4)n3)cc21]

The procedure and purification method are similar to Example 626, step 4 using 4-cyclopropyl-3-fluoro-1-(4-(1-isopropyl-2-((tetrahydro-2H-pyran-2-yloxy)methyl)-1H-imidazo[4,5-c]pyridin-6-ylamino)pyrimidin-2-yl)piperidin-4-ol (100 mg, 0.19 mmol) to afford the title compound (16 mg, 19%) as a white solid as a mixture of enantiomers with known relative stereochemistry. LCMS (ESI): [M+H]$^+$=442.1, R$_T$ (min)=1.45, Method=R; $^1$H NMR (300 MHz, DMSO-d$_6$) δ 9.79 (s, 1H), 8.60 (s, 1H), 8.40 (s, 1H), 7.98-7.97 (d, J=5.7 Hz, 1H), 6.48-6.46 (d, J=5.7 Hz, 1H), 5.70-5.67 (m, 1H), 4.98-4.93 (m, 1H), 4.72-4.70 (d, J=5.4 Hz, 2H), 4.49-4.38 (m, 3H), 4.25-4.10 (m, 1H), 3.75-3.60 (m, 1H), 3.55-3.40 (m, 1H), 1.64-1.50 (m, 8H), 1.05-1.03 (m, 1H), 0.56-0.54 (m, 1H), 0.33-0.10 (m, 3H).

Example 634: (6-(2-((±)-(cis)-3-Chloro-4-methoxypiperidin-1-yl)pyrimidin-4-ylamino)-1-isopropyl-1H-imidazo[4,5-c]pyridin-2-yl)methanol (mixture of enantiomers)

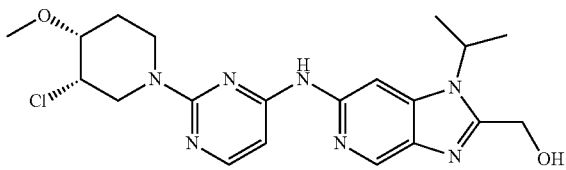 [SMILES: CO[C@@H]1CCN(c2nccc(Nc3cc4c(cn3)nc(CO)n4C(C)C)n2)C[C@@H]1Cl]

Step 1: tert-Butyl 4-(trimethylsilyloxy)-5,6-dihydropyridine-1(2H)-carboxylate

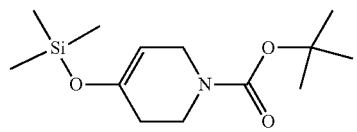 [SMILES: CC(C)(C)OC(=O)N1CC=C(O[Si](C)(C)C)CC1]

A mixture of tert-butyl 4-oxopiperidine-1-carboxylate (6.0 g, 30.1 mmol), triethylamine (9.14 g, 90.3 mmol) and trimethylsilyl trifluoromethanesulfonate (10.0 g, 45.2 mmol) in toluene (15 mL) was stirred for 30 min at 0° C. and 90 min at 25° C. The resulting solution was diluted with water and extracted twice with ethyl acetate, washed with brine, dried over sodium sulfate, filtered and concentrated in vacuo to afford the title compound (7.6 g, 93%) as a yellow oil. LCMS (ESI): [M+H]$^+$=272.

Step 2: tert-Butyl 3-chloro-4-oxopiperidine-1-carboxylate

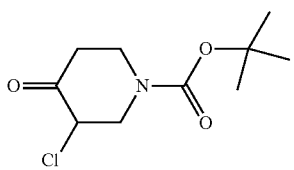

A mixture of tert-butyl 4-(trimethylsilyloxy)-5,6-dihydropyridine-1(2H)-carboxylate (500 mg, 1.84 mmol), 1-chloropyrrolidine-2,5-dione (500 mg, 3.74 mmol) and sodium acetate (270 mg, 3.29 mmol) in acetone (4 mL) and water (1 mL) was stirred for 2 h at 0° C. The solution was diluted with dichloromethane (20 mL) and washed with aqueous sodium sulfonate. The organic layer was concentrated in vacuo and the resulting residue was purified by silica gel chromatography (solvent gradient: 0-20% ethyl acetate in heptane) to afford the title compound (150 mg, 35%) as a yellow oil. LCMS (ESI): [M+H]$^+$=234.

Step 3: (±)-(cis)-tert-Butyl 3-chloro-4-hydroxypiperidine-1-carboxylate

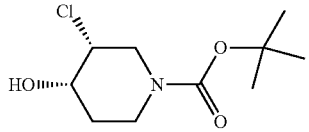

The procedure and purification method are similar to Example 631, step 1 using tert-butyl 3-chloro-4-oxopiperidine-1-carboxylate (2.5 g, 10.7 mmol) to afford the title compound (2 g, 79%) as a yellow oil. LCMS (ESI): [M+H]$^+$=236.

Step 4: (±)-(cis)-tert-Butyl 3-chloro-4-methoxypiperidine-1-carboxylate

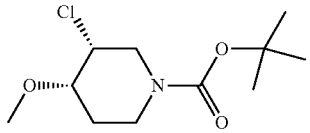 [SMILES: CO[C@H]1CCN(C(=O)OC(C)(C)C)C[C@H]1Cl]

The procedure and purification method are similar to Example 632, step 1 using (±)-(cis)-tert-butyl 3-chloro-4-hydroxypiperidine-1-carboxylate (850 mg, 3.61 mmol) to afford the title compound (300 mg, 33%) as a yellow oil. LCMS (ESI): [M+H]$^+$=250.

Step 5: (±)-(cis)-3-Chloro-4-methoxypiperidine 2,2,2-trifluoroacetate salt

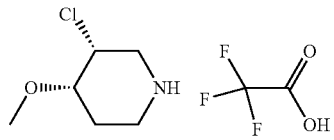

The procedure and purification method are similar to Example 633, step 2 using (±)-(cis)-tert-butyl 3-chloro-4-methoxypiperidine-1-carboxylate (300 mg, 1.2 mmol) to afford the title compound (500 mg, crude) as a yellow oil. LCMS (ESI): [M+H]$^+$=150.

Step 6: N-(2-((±)-(cis)-3-Chloro-4-methoxypiperidin-1-yl)pyrimidin-4-yl)-1-isopropyl-2-((tetrahydro-2H-pyran-2-yloxy)methyl)-1H-imidazo[4,5-c]pyridin-6-amine

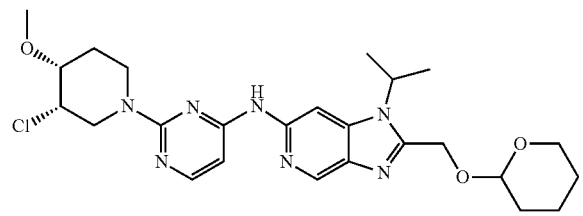 [SMILES: CO[C@@H]1CCN(c2nccc(Nc3cc4c(cn3)nc(COC3CCCCO3)n4C(C)C)n2)C[C@@H]1Cl]

The procedure and purification method are similar to Example 626, step 3 using (±)-(cis)-3-chloro-4-methoxypiperidine 2,2,2-trifluoroacetate salt (210 mg, 0.8 mmol) to afford the title compound (150 mg, 36%) as a yellow solid. LCMS (ESI): [M+H]⁺=516.

Step 7: (6-(2-((±)-(cis)-3-Chloro-4-methoxypiperidin-1-yl)pyrimidin-4-ylamino)-1-isopropyl-1H-imidazo[4,5-c]pyridin-2-yl)methanol (mixture of enantiomers)

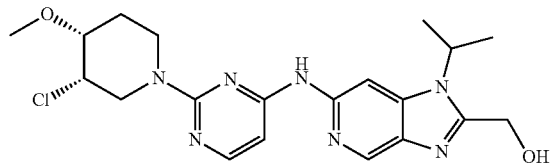 [SMILES: CO[C@@H]1CCN(c2nccc(Nc3cc4c(cn3)nc(CO)n4C(C)C)n2)C[C@@H]1Cl]

The procedure and purification method are similar to Example 626, step 4 using N-(2-((±)-(cis)-3-chloro-4-methoxypiperidin-1-yl)pyrimidin-4-yl)-1-isopropyl-2-((tetrahydro-2H-pyran-2-yloxy)methyl)-1H-imidazo[4,5-c]pyridin-6-amine (50 mg, 0.097 mmol) to afford the title compound (15 mg, 36%) as a white solid. LCMS (ESI): [M+H]⁺=432, $R_T$ (min)=2.92, Method=R; ¹H NMR (300 MHz, DMSO-$d_6$) δ 9.79 (s, 1H), 8.60 (s, 1H), 8.36 (s, 1H), 7.98-7.96 (d, J=6.0 Hz, 1H), 6.48-6.46 (d, J=6.0 Hz, 1H), 5.70-5.67 (m, 1H), 5.15-4.80 (m, 1H), 4.73-4.70 (d, J=6.0 Hz, 2H), 4.61-4.58 (m, 2H), 4.39-4.35 (m, 1H), 3.75-3.70 (m, 2H), 3.34 (s, 4H), 1.79-1.78 (m, 2H), 1.61-1.59 (d, J=6.0 Hz, 6H).

Example 635: 6-(2-(1-(Cyclopropylsulfonyl)-1H-pyrazol-4-yl)pyrimidin-4-ylamino)-N-(tetrahydro-2H-pyran-4-yl)-1-(1,1,1-trifluoropropan-2-yl)-1H-pyrrolo[3,2-c]pyridine-3-carboxamide

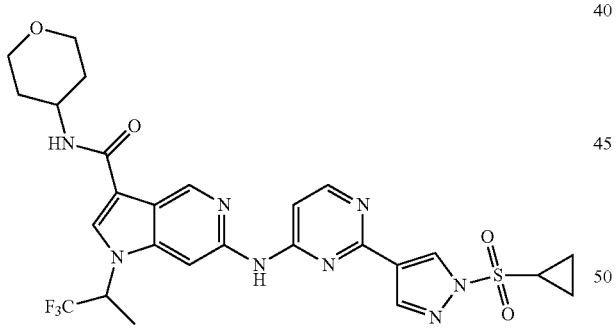

Step 1: 1,1,1-Trifluoropropan-2-yl 1,1,2,2,3,3,4,4,4-nonafluorobutane-1-sulfonate

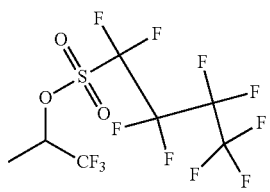 [SMILES: CC(OS(=O)(=O)C(F)(F)C(F)(F)C(F)(F)C(F)(F)F)C(F)(F)F]

1,1,2,2,3,3,4,4,4-nonafluorobutane-1-sulfonyl fluoride (72.7 g, 0.241 mol) was added dropwise to a pre-cooled solution at −40° C. of 1,1,1-trifluoropropan-2-ol (20 g, 0.175 mol) and triethylamine (17.7 g, 0.175 mol) in dichloromethane (200 mL). The resulting mixture was stirred for 16 hours at room temperature. The solvent was removed in vacuo and the resulting residue was purified by distillation under reduced pressure (2 mm Hg, collected 35° C. fraction) to afford the title compound (42 g, 60%) as a colorless liquid. ¹H NMR (300 MHz, CDCl₃) δ 5.22-5.10 (m, 1H), 1.69-1.67 (m, 3H).

Step 2: 6-Chloro-3-iodo-1-(1,1,1-trifluoropropan-2-yl)-1H-pyrrolo[3,2-c]pyridine

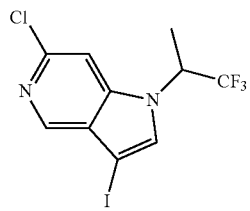 [SMILES: CC(n1cc(I)c2cnc(Cl)cc21)C(F)(F)F]

A mixture of 6-chloro-3-iodo-1H-pyrrolo[3,2-c]pyridine (Example 63, step 1) (2.00 g, 7.18 mmol), cesium carbonate (5.00 g, 15.3 mmol), 1,1,1-trifluoropropan-2-yl 1,1,2,2,3,3,4,4,4-nonafluorobutane-1-sulfonate (6.00 g, 15.2 mmol) in N,N-dimethylformamide (40 mL) was stirred for 16 h at room temperature. The solution was diluted with water and extracted twice with ethyl acetate. The combined organic layers were washed with brine, dried over anhydrous sodium sulfate, filtered and concentrated in vacuo. The resulting residue was purified by silica gel chromatography (solvent gradient: 0-10% ethyl acetate in petroleum ether) to afford the title compound (1.7 g, 63%) as a white solid. LCMS (ESI): [M+H]⁺=375.

Step 3: 6-Chloro-N-(tetrahydro-2H-pyran-4-yl)-1-(1,1,1-trifluoropropan-2-yl)-1H-pyrrolo[3,2-c]pyridine-3-carboxamide

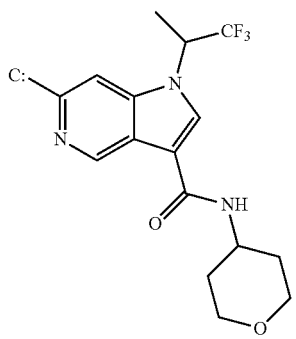

A mixture of 6-chloro-3-iodo-1-(1,1,1-trifluoropropan-2-yl)-1H-pyrrolo[3,2-c]pyridine (400 mg, 1.07 mmol), palladium acetate (24 mg, 0.11 mmol), (9,9-dimethyl-9H-xanthene-4,5-diyl)bis(diphenylphosphine) (64 mg, 0.11 mmol), oxan-4-amine (1.8 g, 17.8 mmol) and triethylamine (320 mg, 3.16 mmol) in N,N-dimethylformamide (10 mL) was stirred for 150 min at 60° C. under an atmosphere of carbon monoxide (1 atm). After cooling to room temperature, the solution was diluted with ethyl acetate and washed with brine, dried with anhydrous sodium sulfate, filtered and concentrated in vacuo. The resulting residue was purified by silica gel chromatography (solvent gradient: 0-75% ethyl acetate in petroleum ether) to afford the title compound (103 mg, 26%) as a yellow solid. LCMS (ESI): [M+H]$^+$=376. $^1$H NMR (300 MHz, DMSO-d$_6$) δ 9.13 (s, 1H), 8.40 (s, 1H), 8.10 (m, 1H), 8.01 (s, 1H), 5.87-5.80 (m, 1H), 4.06-3.98 (m, 1H), 3.92-3.89 (m, 2H), 3.43-3.38 (m, 2H), 1.84-1.81 (m, 2H), 1.76 (d, J=6.8 Hz, 3H), 1.59-1.53 (m, 2H).

Step 4: 6-(2-(1-(Cyclopropylsulfonyl)-1H-pyrazol-4-yl)pyrimidin-4-ylamino)-N-(tetrahydro-2H-pyran-4-yl)-1-(1,1,1-trifluoropropan-2-yl)-1H-pyrrolo[3,2-c]pyridine-3-carboxamide

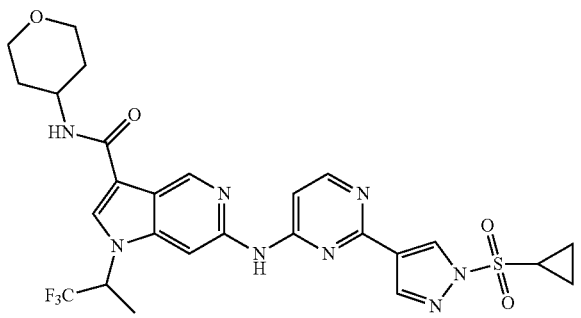 [SMILES: CC(n1cc(C(=O)NC2CCOCC2)c2cnc(Nc3ccnc(-c4cnn(S(=O)(=O)C5CC5)c4)n3)cc21)C(F)(F)F]

A mixture of 6-chloro-N-(tetrahydro-2H-pyran-4-yl)-1-(1,1,1-trifluoropropan-2-yl)-1H-pyrrolo[3,2-c]pyridine-3-carboxamide (50 mg, 0.13 mmol), 2-(1-cyclopropanesulfonyl-1H-pyrazol-4-yl)pyrimidin-4-ylamine (Example A62) (40 mg, 0.15 mmol), dicyclohexyl (2',4',6'-triisopropyl-3,6-dimethoxybiphenyl-2-yl)phosphine (15 mg, 0.03 mmol), 3$^{rd}$ Generation BrettPhos precatalyst (12 mg, 0.01 mmol), and cesium carbonate (80 mg, 0.25 mmol) in 1,4-dioxane (7 mL) was heated under microwave irradiation for 40 min at 100° C. After cooling to room temperature, the solution was concentrated in vacuo. The resulting residue was purified by silica gel chromatography (eluent: 100% EtOAc) to afford the title compound (18 mg, 22%) as a white solid. LCMS (ESI): [M+H]$^+$=605, R$_T$ (min)=1.48, Method=N; $^1$H NMR (400 MHz, DMSO-d$_6$) δ 10.31 (s, 1H), 9.12 (s, 1H), 8.72 (s, 1H), 8.48 (s, 2H), 8.39 (m, 1H), 8.34 (s, 1H), 8.03 (d, J=7.6 Hz, 1H), 7.10 (d, J=7.6 Hz, 1H), 5.77-5.74 (m, 1H), 4.05-4.01 (m, 1H), 3.93-3.90 (m, 2H), 3.44-3.32 (m, 2H), 3.26-3.22 (m, 1H), 1.85-1.80 (m, 5H), 1.60-1.54 (m, 2H), 1.38-1.34 (m, 2H), 1.28-1.21 (m, 2H).

Example 636: 6-(2-(4-Hydroxy-4-methylpiperidin-1-yl)pyrimidin-4-ylamino)-N-(tetrahydro-2H-pyran-4-yl)-1-(1,1,1-trifluoropropan-2-yl)-1H-pyrrolo[3,2-c]pyridine-3-carboxamide

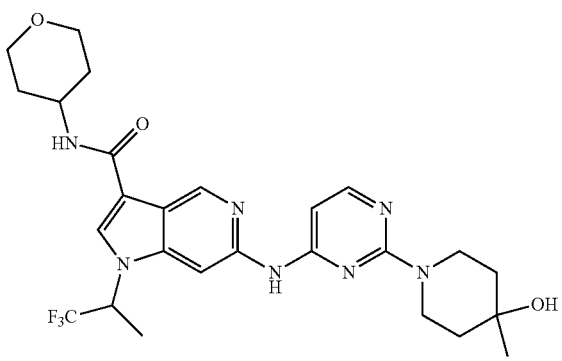 [SMILES: CC(n1cc(C(=O)NC2CCOCC2)c2cnc(Nc3ccnc(N4CCC(C)(O)CC4)n3)cc21)C(F)(F)F]

Step 1: 1-(4-Aminopyrimidin-2-yl)-4-methylpiperidin-4-ol

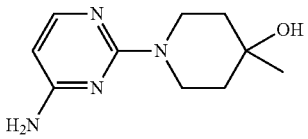

A mixture of 2-chloropyrimidin-4-amine (2.0 g, 15.4 mmol), 4-methylpiperidin-4-ol (1.94 g, 16.8 mmol), and potassium carbonate (6.36 g, 46.0 mmol) in dimethylsulfoxide (20 mL) was stirred for 8 h at 100° C. After cooling to room temperature, the solution was diluted with water (100 mL) and extracted ten times with ethyl acetate. The combined organic layers were washed with brine, dried over anhydrous sodium sulfate, filtered and concentrated in vacuo. The resulting residue was purified by silica gel chromatography (solvent gradient: 0-10% methanol in dichloromethane) to afford the title compound (1.9 g, 59%) as a yellow solid. LCMS (ESI): [M+H]$^+$=209.

Step 2: 6-(2-(4-Hydroxy-4-methylpiperidin-1-yl)pyrimidin-4-ylamino)-N-(tetrahydro-2H-pyran-4-yl)-1-(1,1,1-trifluoropropan-2-yl)-1H-pyrrolo[3,2-c]pyridine-3-carboxamide

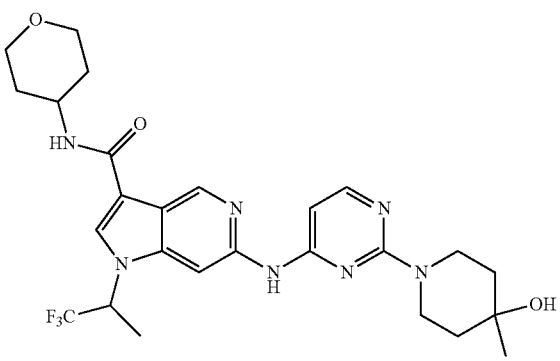 [SMILES: CC(n1cc(C(=O)NC2CCOCC2)c2cnc(Nc3ccnc(N4CCC(C)(O)CC4)n3)cc21)C(F)(F)F]

A mixture of 6-chloro-N-(tetrahydro-2H-pyran-4-yl)-1-(1,1,1-trifluoropropan-2-yl)-1H-pyrrolo[3,2-c]pyridine-3-carboxamide (Example 635, step 3) 40 mg, 0.11 mmol), 1-(4-aminopyrimidin-2-yl)-4-methylpiperidin-4-ol (32 mg, 0.15 mmol), dicyclohexyl(2',4',6'-triisopropyl-3,6-dimethoxybiphenyl-2-yl)phosphine (12 mg, 0.02 mmol), 3$^{rd}$ Generation BrettPhos precatalyst (10 mg, 0.01 mmol), and cesium carbonate (68 mg, 0.21 mmol) in 1,4-dioxane (6 mL) was stirred for 1.5 h at 120° C. After cooling to room temperature, the solution was concentrated in vacuo. The resulting residue was purified by silica gel chromatography (solvent gradient: 0-10% methanol in dichloromethane) to afford the title compound (25.6 mg, 44%) as a white solid. LCMS (ESI): [M+H]$^+$=548, R$_T$ (min)=1.83, Method=L; $^1$H NMR (400 MHz, DMSO-d$_6$) δ 9.80 (s, 1H), 9.04 (s, 1H), 8.43 (s, 1H), 8.28 (s, 1H), 8.05 (m, 1H), 7.94 (d, J=5.6 Hz, 1H), 6.29 (d, J=5.6 Hz, 1H), 5.46-5.43 (m, 1H), 4.38 (s, 1H), 4.17-4.16 (m, 2H), 4.03-4.00 (m, 1H), 3.92-3.89 (m, 2H), 3.56-3.34 (m, 4H), 1.84-1.77 (m, 5H), 1.56-1.50 (m, 6H), 1.15 (s, 3H).

Example 637: 1-(sec-butyl)-6-((2-((3S,4R)-3-fluoro-4-hydroxypiperidin-1-yl)pyrimidin-4-yl)amino)-N-((3SR, 4SR)-3-fluorotetrahydro-2H-pyran-4-yl)-1H-pyrrolo[3,2-c]pyridine-3-carboxamide (mixture of 4 diastereomers)

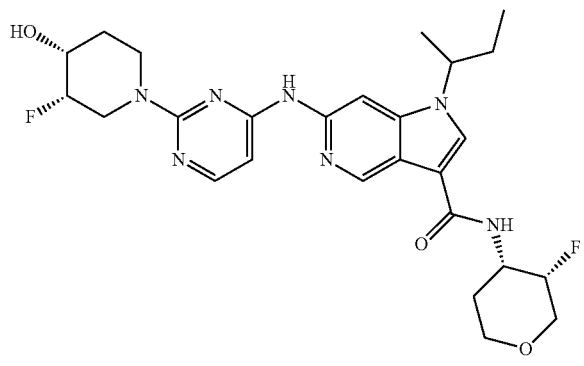 [SMILES: CCC(C)n1cc(C(=O)N[C@H]2CCOC[C@H]2F)c2cnc(Nc3ccnc(N4CC[C@@H](O)[C@@H](F)C4)n3)cc21]

The title compound was prepared in a manner analogous to Example 323. LCMS (ESI): $R_T$ 3.23 min, [M+H]$^+$ 530.3, method=B; $^1$H NMR (400 MHz, DMSO-d$_6$) δ 9.77 (s, 1H), 9.03 (s, 1H), 8.34 (s, 2H), 8.02 (d, J=7.7 Hz, 1H), 7.95 (d, J=5.7 Hz, 1H), 6.36 (d, J=5.6 Hz, 1H), 5.10 (d, J=5.1 Hz, 1H), 4.71 (m, 2H), 4.51 (m, 1H), 4.44-4.15 (m, 3H), 3.95 (m, 3H), 3.69-3.46 (m, 3H), 3.39 (m, 1H), 1.93 (m, 3H), 1.68 (m, 3H), 1.49 (m, 3H), 0.80 (m, 3H).

Example 638: 1-(sec-butyl)-6-((2-(4-hydroxy-4-methylpiperidin-1-yl)pyrimidin-4-yl)amino)-N-(tetrahydro-2H-pyran-4-yl)-1H-pyrrolo[3,2-c]pyridine-3-carboxamide

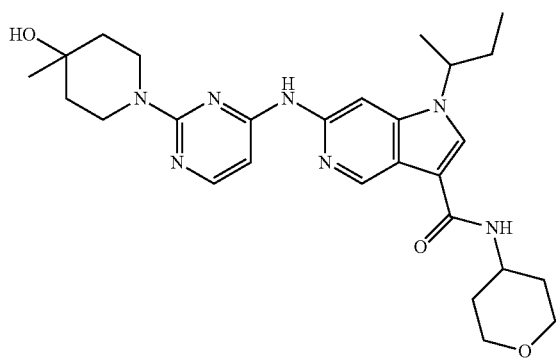 [SMILES: CCC(C)n1cc(C(=O)NC2CCOCC2)c2cnc(Nc3ccnc(N4CCC(C)(O)CC4)n3)cc21]

To a microwave reaction vessel was added 6-bromo-1-(sec-butyl)-N-(tetrahydro-2H-pyran-4-yl)-1H-pyrrolo[3,2-c]pyridine-3-carboxamide (0.19 g, 0.50 mmol), 1-(4-aminopyrimidin-2-yl)-4-methylpiperidin-4-ol (Example 636, Step 1)(0.10 g, 0.50 mmol), sodium tert-butoxide (0.15 g, 1.5 mmol), chloro{[BrettPhos][2-(2-aminoethylphenyl]palladium(II)]}/[BrettPhos] admixture (molar PdP/P=1:1, 50 mg) and tert-butanol (4 mL). The reaction was degassed by nitrogen bubbling for 20 min, sealed and stirred at 100° C. for 60 min. The reaction was cooled to room temperature, filtered and concentrated in vacuo. The crude products were purified by supercritical fluid chromatography to give the title compound as a mixture of enantiomers (158 mg, 62%). LCMS (ESI): $R_T$ 3.35 min, [M+H]$^+$ 508.4, method=B; $^1$H NMR (400 MHz, DMSO-d$_6$) δ 9.72 (s, 1H), 9.01 (s, 1H), 8.37 (s, 1H), 8.15 (s, 1H), 7.93 (d, J=5.6 Hz, 1H), 7.85 (d, J=7.7 Hz, 1H), 6.31 (d, J=5.6 Hz, 1H), 4.43-4.29 (m, 2H), 4.19 (m, 2H), 4.00 (s, 1H), 3.90 (m, 2H), 3.42 (m, 5H), 1.95-1.77 (m, 3H), 1.51 (m, 7H), 1.17 (s, 3H), 0.80 (t, J=7.3 Hz, 3H).

Example 639 and Example 640: The two stereoisomers of 6-((2-((3S,4R)-3-fluoro-4-hydroxypiperidin-1-yl)pyrimidin-4-yl)amino)-N-(tetrahydro-2H-pyran-4-yl)-1-(1,1,1-trifluoropropan-2-yl)-1H-pyrrolo[3,2-c]pyridine-3-carboxamide

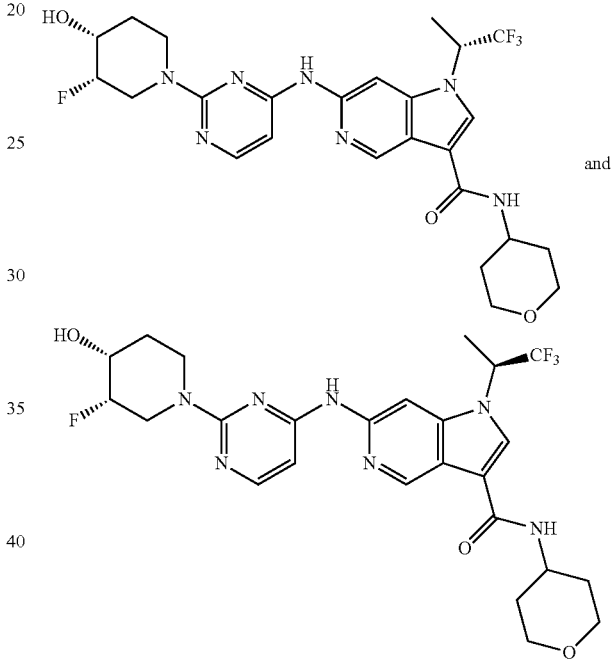

and

To a microwave reaction vessel was added 6-chloro-N-(tetrahydro-2H-pyran-4-yl)-1-(1,1,1-trifluoropropan-2-yl)-1H-pyrrolo[3,2-c]pyridine-3-carboxamide (Example 635, step 3)(0.10 g, 0.27 mmol), (+)-(3S,4R)-1-(4-aminopyrimidin-2-yl)-3-fluoropiperidin-4-ol (Example A66)(0.10 g, 0.47 mmol), sodium tert-butoxide (79 mg, 0.80 mmol), chloro{[BrettPhos][2-(2-aminoethylphenyl]palladium(II)]}/[BrettPhos] admixture (molar PdP/P=1:1, 60 mg) and tert-butanol (4 mL). The reaction was degassed by nitrogen bubbling for 5 min. The reaction was sealed and stirred at 100° C. for 30 min. The reaction was filtered and the filtrate was concentrated in vacuo. The crude mixture was purified by supercritical fluid chromatography to give the two title compounds as single unknown stereoisomers (22 mg, 15%).

Stereoisomer 1 (11 mg): LCMS (ESI): $R_T$ (min)=3.39, [M+H]=552.2, method=B; $^1$H NMR (400 MHz, DMSO-d$_6$) δ 9.85 (s, 1H), 9.05 (s, 1H), 8.41 (s, 1H), 8.28 (s, 1H), 7.97 (m, 2H), 6.34 (d, J=5.7 Hz, 1H), 5.55-5.37 (m, 1H), 5.09 (d, J=5.1 Hz, 1H), 4.69 (m, 1H), 4.57 (m, 2H), 4.33 (d, J=13.4

Hz, 1H), 4.02 (d, J=7.3 Hz, 1H), 3.90 (m, 3H), 3.52 (m, 1H), 3.41 (m, 2H), 1.90-1.47 (m, 8H).

Stereoisomer 2 (11 mg); LCMS (ESI): $R_T$ (min)=3.41, [M+H]=552.23, method=B; $^1$H NMR (400 MHz, DMSO-$d_6$) δ 9.83 (s, 1H), 9.05 (s, 1H), 8.35 (s, 1H), 8.27 (s, 1H), 7.97 (m, 2H), 6.35 (d, J=5.7 Hz, 1H), 5.43 (m, 1H), 5.09 (d, J=5.1 Hz, 1H), 4.70 (m, 1H), 4.58 (m, 2H), 4.27 (m, 1H), 4.02 (d, J=7.3 Hz, 1H), 3.90 (m, 3H), 3.52 (m, 1H), 3.41 (m, 2H), 1.79 (m, 4H), 1.68 (m, 2H), 1.55 (m, 2H).

Example 641: 1-(1-(sec-butyl)-6-((2-((3S,4R)-3-fluoro-4-hydroxypiperidin-1-yl)pyrimidin-4-yl)amino)-1H-pyrrolo[3,2-c]pyridin-3-yl)pyrrolidin-2-one

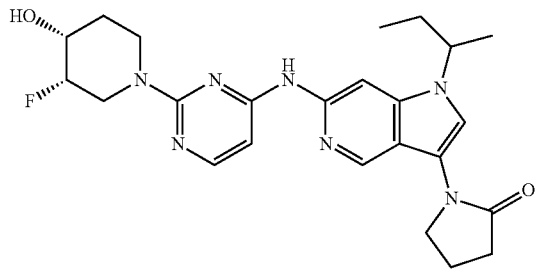 [SMILES: CCC(C)n1cc(N2CCCC2=O)c2cnc(Nc3ccnc(N4CC[C@@H](O)[C@@H](F)C4)n3)cc21]

Step 1: 1-(6-chloro-1-isopropyl-pyrrolo[3,2-c]pyridin-3-yl)-3-hydroxy-pyrrolidin-2-one

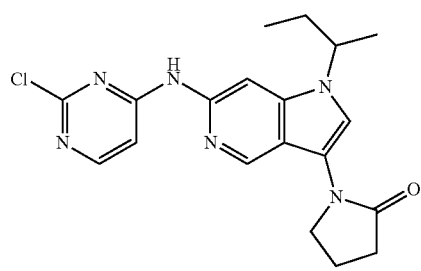 [SMILES: CCC(C)n1cc(N2CCCC2=O)c2cnc(Nc3ccnc(Cl)n3)cc21]

To a microwave reaction vessel was added 6-chloro-3-iodo-1-sec-butyl-pyrrolo[3,2-c]pyridine (0.40 g, 1.2 mmol), pyrrolidin-2-one (0.12 g, 1.4 mmol), copper(I) iodide (0.11 g, 0.60 mmol), (trans)-N,N'-dimethylcyclohexane-1,2-diamine (87 mmol, 0.60 mmol), potassium triphosphate (0.86 g, 1.8 mmol) and 1,4-dioxane (3 mL). The reaction vessel was sealed and degassed by nitrogen bubbling for 20 min. The reaction was then stirred at 100° C. for 2 h. The mixture was filtered and concentrated. The crude product was purified by silica gel chromatography (solvent gradient: 0-100% ethyl acetate in heptane) to give the title compound as a mixture of enantiomers (0.21 g, 60%). LCMS (ESI): [M+H]$^+$=382. $^1$H NMR (400 MHz, DMSO-$d_6$) δ 8.80 (s, 1H), 7.75 (s, 1H), 7.72 (s, 1H), 4.58 (m, 1H), 3.94 (t, J=7.0 Hz, 2H), 2.16 (m, 2H), 1.85-1.72 (m, 2H), 1.42 (d, J=6.7 Hz, 3H), 0.71-0.65 (m, 3H).

Step 2: 1-(1-(sec-butyl)-6-((2-((3S,4R)-3-fluoro-4-hydroxypiperidin-1-yl)pyrimidin-4-yl)amino)-1H-pyrrolo[3,2-c]pyridin-3-yl)pyrrolidin-2-one

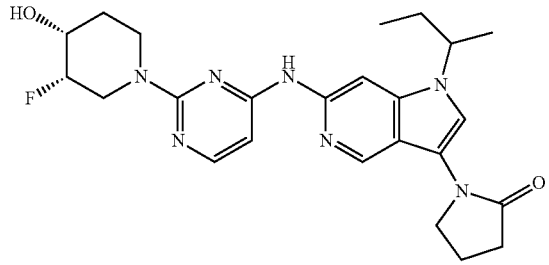 [SMILES: CCC(C)n1cc(N2CCCC2=O)c2cnc(Nc3ccnc(N4CC[C@@H](O)[C@@H](F)C4)n3)cc21]

To a microwave reaction vessel was added 1-(6-chloro-1-isopropyl-pyrrolo[3,2-c]pyridin-3-yl)-3-hydroxy-pyrrolidin-2-one (0.20 g, 0.69 mmol), (+)-(3S,4R)-1-(4-aminopyrimidin-2-yl)-3-fluoropiperidin-4-ol (Example A66)(0.10 g, 0.47 mmol), sodium tert-butoxide (0.20 g, 2.1 mmol), chloro{[BrettPhos][2-(2-aminoethylphenyl]palladium(II)]}/[BrettPhos] admixture (molar PdP/P=1:1, 60 mg) and tert-butanol (4 mL). The reaction was degassed by nitrogen bubbling for 5 min. The reaction was sealed and stirred at 120° C. for 1.5 h. The reaction was filtered and concentrated in vacuo. The crude product was purified by supercritical fluid chromatography to give the title compound as a mixture of two diastereoisomers (0.11 g, 32%). LCMS (ESI): $R_T$ (min)=3.01, [M+H]=468.2, method=B. $^1$H NMR (400 MHz, DMSO-$d_6$) δ 9.71 (s, 1H), 8.75 (s, 1H), 8.28 (s, 1H), 7.94 (s, 1H), 7.58 (s, 1H), 6.35 (d, J=5.5 Hz, 1H), 5.11 (d, J=5.1 Hz, 1H), 4.67 (m, 1H), 4.52 (m, 1H), 4.42-4.21 (m, 2H), 3.96 (t, J=7.0 Hz, 2H), 3.87 (m, 1H), 3.60 (m, 1H), 3.39 (m, 1H), 2.46 (m, 2H), 2.21-2.10 (m, 2H), 1.92-1.79 (m, 2H), 1.70 (m, 2H), 1.44 (m, 3H), 0.75 (m, 3H).

Example 642 and Example 643: The two enantiomers of 1-(1-(4-((1-isopropyl-2-methyl-1H-imidazo[4,5-c]pyridin-6-yl)amino)pyrimidin-2-yl)-1H-imidazol-4-yl)ethanol

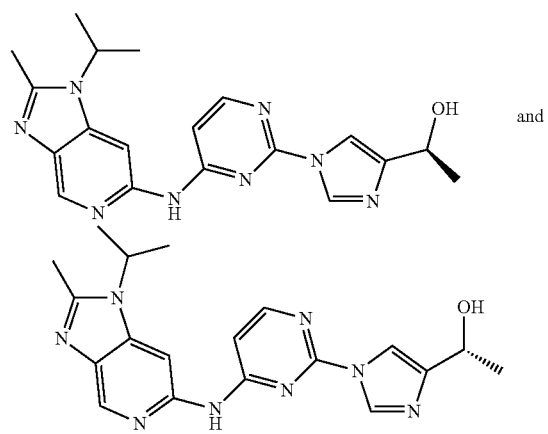

A mixture of N-(2-chloropyrimidin-4-yl)-1-isopropyl-2-methyl-1H-imidazo[4,5-c]pyridin-6-amine (215 mg, 0.71 mmol), 4-acetylimidazole (0.1 g, 0.89 mmol) and cesium carbonate (0.44 g, 1.3 mmol) in tert-butanol (2.5 mL) was heated in a microwave at 150° C. for 30 min. The reaction was diluted with saturated sodium bicarbonate and extracted with ethyl acetate (3×). The combined extracts were washed with brine, dried over sodium sulfate, filtered and concentrated. The crude product was filtered through a silica gel cartridge (eluted with ethyl acetate) and concentrated in vacuo. To the residue was added 10 mL of methanol and sodium borohydride (50 mg, 1.3 mmol) at 0° C. The reaction was stirred at room temperature for 15 min. The reaction was diluted with saturated sodium bicarbonate and extracted with ethyl acetate (3×). The combined extracts were washed with brine, dried over sodium sulfate, filtered and concentrated. The crude product was purified by supercritical fluid chromatography to give the title compounds as single enantiomers with absolute stereochemistry unknown (combined yield: 23 mg, 7.4%).

Example 642 (Enantiomer 1)(12 mg): LCMS (ESI): $R_T$ (min)=3.69, [M+H]=379.2, method=B. $^1$H NMR (400 MHz, DMSO) δ 10.39 (s, 1H), 8.59 (d, J=0.8 Hz, 1H), 8.43 (d, J=1.3 Hz, 1H), 8.33 (d, J=5.9 Hz, 1H), 8.21 (s, 1H), 7.70 (t, J=1.1 Hz, 1H), 7.27 (s, 1H), 5.04 (d, J=4.8 Hz, 1H), 4.77 (m, 1H), 4.71 (m, 1H), 2.59 (s, 3H), 1.62 (d, J=6.9 Hz, 6H), 1.39 (d, J=6.5 Hz, 3H).

Example 643 (Enantiomer 2)(11 mg): LCMS (ESI): $R_T$ (min)=3.69, [M+H]=379.2, method=B. $^1$H NMR (400 MHz, DMSO) δ 10.39 (s, 1H), 8.59 (d, J=0.8 Hz, 1H), 8.43 (d, J=1.3 Hz, 1H), 8.34 (d, J=5.9 Hz, 1H), 8.21 (s, 1H), 7.70 (t, J=1.1 Hz, 1H), 7.28 (s, 1H), 5.04 (d, J=4.8 Hz, 1H), 4.89-4.60 (m, 2H), 2.59 (s, 3H), 1.62 (d, J=6.9 Hz, 6H), 1.39 (d, J=6.5 Hz, 3H).

Example 644: (±)-(cis)-1-(4-(1-((S)-3,3-Difluorobutan-2-yl)-2-(hydroxymethyl)-1H-imidazo[4,5-c]pyridin-6-ylamino)pyrimidin-2-yl)-3-fluoropiperidin-4-ol

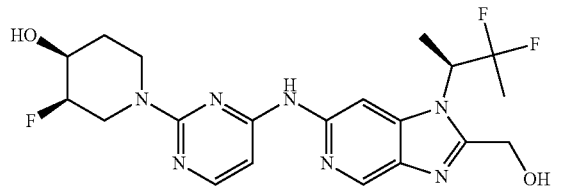 [SMILES: C[C@H](n1c(CO)nc2cnc(Nc3ccnc(N4CC[C@H](O)[C@H](F)C4)n3)cc21)C(C)(F)F]

Step 1: (S)-tert-Butyl 1-(methoxy(methyl)amino)-1-oxopropan-2-ylcarbamate

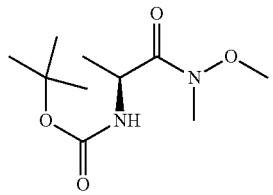 [SMILES: CON(C)C(=O)[C@H](C)NC(=O)OC(C)(C)C]

A mixture of (S)-2-(tert-butoxycarbonylamino) propanoic acid (20.0 g, 106 mmol), O-(7-aza-1H-benzotriazol-1-yl)-N,N,N',N'-tetramethyluronium hexafluorophosphate (80.0 g, 210 mmol), N-ethyl-N-isopropylpropan-2-amine (54.6 g, 422 mmol) and O,N-dimethylhydroxylamine hydrochloride (15.6 g, 160 mmol) in N,N-dimethylformamide (200 mL) was stirred for 2 days at room temperature. The solution was diluted with water (300 mL) and petroleum ether (200 mL). The solid was collected by filtration and dissolved in dichloromethane (200 mL), dried over anhydrous sodium sulfate, filtered and concentrated in vacuo to afford the title compound (17 g, 63%) as an off-white solid. LCMS (ESI): [M+H]$^+$=233.

Step 2: (S)-tert-Butyl 3-oxobutan-2-ylcarbamate

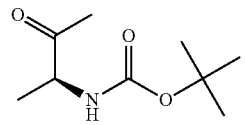

A solution of methylmagnesium bromide (3 M, 168 mmol) in tetrahydrofuran (56 mL) was added dropwise to a solution of (S)-tert-butyl 1-(methoxy(methyl)amino)-1-oxopropan-2-ylcarbamate (14.0 g, 60.3 mmol) in tetrahydrofuran (200 mL) at −16° C. under a nitrogen atmosphere. The resulting mixture was stirred overnight at room temperature. The solution was cooled to 0° C. and quenched with saturated ammonium chloride and extracted twice with ethyl acetate. The combined organic layers were washed with brine, dried over sodium sulfate, filtered and concentrated in vacuo to afford the title compound (10.0 g, 89%) as a yellow oil. LCMS (ESI): [M+H]$^+$=188.

Step 3: tert-Butyl (2S)-3-hydroxybutan-2-ylcarbamate

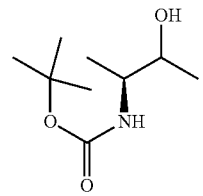

A mixture of (S)-tert-butyl 3-oxobutan-2-ylcarbamate (5.0 g, 26.7 mmol) and sodium borohydride (1.12 g, 29.5 mmol) in tetrahydrofuran (65 mL) and methanol (20 mL) was stirred for 1 h at room temperature. The solution was diluted with ether (200 mL) and citric acid (10%, 100 mL). The resulting solution was extracted with ethyl acetate (2×) and the combined organic layers were washed with sodium bicarbonate (aq.) and brine, dried over anhydrous sodium sulfate, filtered and concentrated in vacuo to afford the title compound (5.03 g, 99%) as a yellow crude oil. LCMS (ESI): [M+H]$^+$=190.

Step 4: (3S)-3-Aminobutan-2-ol hydrochloride

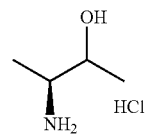

To a reaction vessel was added tert-butyl (2S)-3-hydroxybutan-2-ylcarbamate (5.0 g, 26.4 mmol), ether (22 mL) and hydrochloric acid in 1,4-dioxane (4 M, 8 mL). The reaction mixture was stirred for 36 h at room temperature. The resulting solution was concentrated in vacuo to afford the title compound (3.0 g, 90%) as an off-white solid. LCMS (ESI): [M+H]$^+$=90.

Step 5: (3S)-3-(2-Bromo-5-nitropyridin-4-ylamino) butan-2-ol

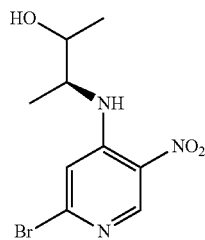 [SMILES: CC(O)[C@H](C)Nc1cc(Br)ncc1[N+](=O)[O-]]

A mixture of 2,4-dibromo-5-nitropyridine (5.43 g, 19.3 mmol), (3S)-3-aminobutan-2-ol hydrochloride (3.61 g, 28.7 mmol) and triethylamine (14 mL) in tetrahydrofuran (50 mL) was stirred for 8 h at room temperature. The solution was diluted with water (50 mL) and extracted with dichloromethane (2×) and the combined organic layers were washed with brine, dried over anhydrous sodium sulfate, filtered and concentrated in vacuo. The resulting residue was purified by silica gel chromatography (solvent gradient: 0-30% ethyl acetate in petroleum ether) to afford the title compound (4.92 g, 88%) as a yellow solid. LCMS (ESI): [M+H]$^+$=290.

Step 6: (S)-3-(2-Bromo-5-nitropyridin-4-ylamino) butan-2-one

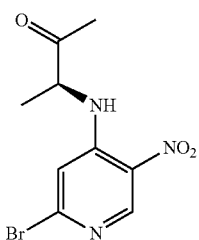 [SMILES: CC(=O)[C@H](C)Nc1cc(Br)ncc1[N+](=O)[O-]]

A mixture of (3S)-3-(2-bromo-5-nitropyridin-4-ylamino) butan-2-ol (3 g, 10.3 mmol) and Dess-Martin periodinane (8.8 g, 20.8 mmol) in dichloromethane (30 mL) was stirred for 3 h at room temperature. The solution was quenched with sodium bisulfite (50 mL) and sodium bicarbonate (50 mL) and extracted with dichloromethane (2×). The combined organic layers were washed with brine, dried over sodium sulfate, filtered and concentrated in vacuo to afford the title compound (2.5 g, 86%) as a yellow solid. LCMS (ESI): [M+H]$^+$=288.

Step 7: (S)-2-Bromo-N-(3,3-difluorobutan-2-yl)-5-nitropyridin-4-amine

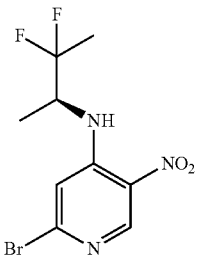 [SMILES: C[C@H](Nc1cc(Br)ncc1[N+](=O)[O-])C(C)(F)F]

A mixture of (S)-3-(2-bromo-5-nitropyridin-4-ylamino) butan-2-one (4.90 g, 17.0 mmol) and diethylaminosulfurtrifluoride (13.2 g, 81.7 mmol) in dichloromethane (50 mL) was stirred overnight at room temperature. The solution was quenched with sodium bicarbonate, extracted with dichloromethane (2×). The combined organic layers were washed with brine, dried over anhydrous sodium sulfate, filtered and concentrated in vacuo to afford the title compound (4.0 g, 75%) as a yellow solid. LCMS (ESI): [M+H]$^+$=310.

Step 8: (S)-6-Bromo-N$^4$-(3,3-difluorobutan-2-yl) pyridine-3,4-diamine

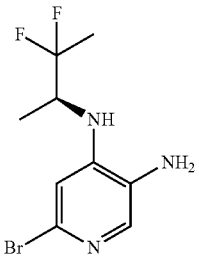

The title compound (0.75 g, 46%) was synthesized from (S)-2-bromo-N-(3,3-difluorobutan-2-yl)-5-nitropyridin-4-amine (1.8 g, 5.80 mmol) following a procedure similar to Example 265, step 2. LCMS (ESI): [M+H]$^+$=280.

Step 9: (S)-2-(6-Bromo-4-(3,3-difluorobutan-2-ylamino)pyridin-3-ylamino)-2-oxoethyl acetate

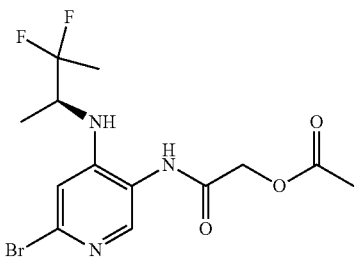 [SMILES: CC(=O)OCC(=O)Nc1cnc(Br)cc1N[C@@H](C)C(C)(F)F]

The title compound (0.9 g, 94%) was synthesized from (S)-6-bromo-N$^4$-(3,3-difluorobutan-2-yl)pyridine-3,4-diamine (0.7 g, 2.50 mmol) following a procedure similar to Example 265, step 3. LCMS (ESI): [M+H]$^+$=380.

Step 10: (S)-(6-Bromo-1-(3,3-Difluorobutan-2-yl)-1H-imidazo[4,5-c]pyridin-2-yl)methyl acetate

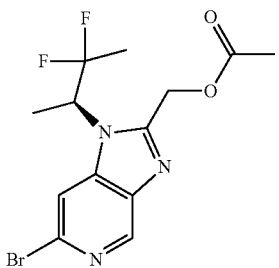 [SMILES: CC(=O)OCc1nc2cnc(Br)cc2n1[C@@H](C)C(C)(F)F]

The title compound (295 mg, 62%) was synthesized from (S)-2-(6-bromo-4-(3,3-difluorobutan-2-ylamino)pyridin-3-ylamino)-2-oxoethyl acetate (500 mg, 1.32 mmol) following a procedure analogous to Example 265, step 4. LCMS (ESI): [M+H]$^+$=362.

Step 11: (S)-(6-Bromo-1-(3,3-Difluorobutan-2-yl)-1H-imidazo[4,5-c]pyridin-2-yl)methanol

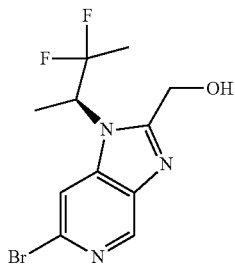

The title compound (210 mg, 81%) was synthesized from (S)-(6-bromo-1-(3,3-difluorobutan-2-yl)-1H-imidazo[4,5-c]pyridin-2-yl)methyl acetate (295 mg, 0.81 mmol) following a procedure analogous to Example 265, step 5. LCMS (ESI): [M+H]$^+$=320.

Step 12: (±)-(cis)-1-(4-(1-((S)-3,3-Difluorobutan-2-yl)-2-(hydroxymethyl)-1H-imidazo[4,5-c]pyridin-6-ylamino)pyrimidin-2-yl)-3-fluoropiperidin-4-ol

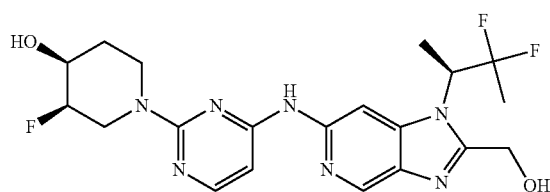 [SMILES: C[C@H](n1c(CO)nc2cnc(Nc3ccnc(N4CC[C@H](O)[C@H](F)C4)n3)cc21)C(C)(F)F]

The title compound (88.9 mg, 33%) was synthesized from (S)-(6-bromo-1-(3,3-difluorobutan-2-yl)-1H-imidazo[4,5-c]pyridin-2-yl) methanol (190 mg, 0.59 mmol) and (±)-cis-1-(4-aminopyrimidin-2-yl)-3-fluoropiperidin-4-ol (Example A 85) (126 mg, 0.59 mmol) following a procedure similar to Example 636, step 2. LCMS (ESI): [M+H]$^+$=452.2, R$_T$ (min)=1.469, Method=L; $^1$H NMR (300 MHz, DMSO-d$_6$) δ 9.80 (s, 1H), 8.63 (s, 1H), 8.36 (s, 1H), 7.97-7.95 (d, J=5.7 Hz, 1H), 6.46-6.44 (d, J=5.7 Hz, 1H), 5.85 (s, 1H), 5.29-5.11 (m, 2H), 4.76-4.52 (m, 4H), 4.34 (m, 1H), 3.88 (m, 1H), 3.58-3.40 (m, 1H), 3.25 (m, 1H), 1.73 (m, 8H).

Example 645: (3RS,4SR)-3-Fluoro-1-(4-((2-(hydroxymethyl)-1-isopropyl-1H-imidazo[4,5-c]pyridin-6-yl)amino)pyrimidin-2-yl)-3-methylpiperidin-4-ol (mixture of enantiomers)

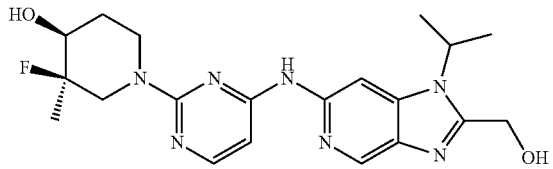 [SMILES: CC(C)n1c(CO)nc2cnc(Nc3ccnc(N4CC[C@H](O)[C@](C)(F)C4)n3)cc21]

Step 1: tert-Butyl-3-methyl-4-(trimethylsilyloxy)-5,6-dihydropyridine-1(2H)-carboxylate

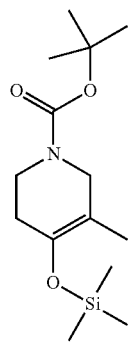 [SMILES: CC1=C(O[Si](C)(C)C)CCN(C(=O)OC(C)(C)C)C1]

Trimethylsilyl trifluoromethanesulfonate (25 g, 112 mmol) was added dropwise to a pre-cooled solution at 0° C. of tert-butyl-3-methyl-4-oxopiperidine-1-carboxylate (20 g, 93.8 mmol) and triethylamine (22 g, 223 mmol) in toluene (200 mL). The resulting mixture was stirred for 4 h at 0° C. The solution was quenched with water (100 mL) and extracted twice with ethyl acetate. The combined organic layers were combined, washed with brine, dried over anhydrous sodium sulfate and concentrated in vacuo to afford the title compound (25 g, 75%) as yellow oil. LCMS (ESI): [M+H]$^+$=286.

Step 2: tert-Butyl 3-fluoro-3-methyl-4-oxopiperidine-1-carboxylate

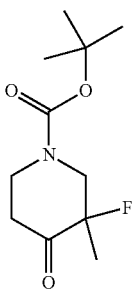 [SMILES: CC(C)(C)OC(=O)N1CCC(=O)C(C)(F)C1]

A mixture of tert-butyl 3-methyl-4-(trimethylsilyloxy)-5,6-dihydropyridine-1(2H)-carboxylate (1.14 g, 3.99 mmol) and SelectFluor® (1.56 g, 4.40 mmol) in acetonitrile (20 mL) was stirred for 1 h at 0° C. The solution was diluted with water (20 mL) and extracted with of ethyl acetate (2×). The combined organic layers were washed with brine, dried over anhydrous sodium sulfate, filtered and concentrated in vacuo. The resulting residue was purified by silica gel chromatography (solvent gradient: 0-10% ethyl acetate in petroleum ether) to afford the title compound (0.7 g, 76%) as a colorless oil. LCMS (ESI): [M+H]$^+$=232.

Step 3: tert-Butyl 3-fluoro-4-hydroxy-3-methylpiperidine-1-carboxylate

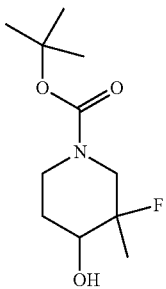 [SMILES: CC(C)(C)OC(=O)N1CCC(O)C(C)(F)C1]

A mixture of tert-butyl 3-fluoro-3-methyl-4-oxopiperidine-1-carboxylate (600 mg, 2.59 mmol) and sodium borohydride (118 mg, 3.11 mmol) in methanol (15 mL) was stirred for 3 h at room temperature. The solution was quenched with sodium hydroxide (4 M, 4 mL) and extracted with ether (3×). The combined organic layers were washed with brine, dried over anhydrous sodium sulfate, filtered and concentrated in vacuo to afford the title compound (490 mg, 80%) as a colorless oil. LCMS (ESI): [M+H]$^+$=234.

Step 4: 3-Fluoro-3-methylpiperidin-4-ol hydrochloride

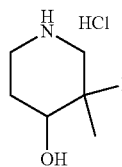

To a reaction vessel was added tert-butyl 3-fluoro-4-hydroxy-3-methylpiperidine-1-carboxylate (490 mg, 2.10 mmol), ether (15 mL) and hydrochloric acid (4 M in dioxane, 3 mL). The resulting mixture was stirred overnight at room temperature. The reaction precipitate was collected by filtration to afford the title compound (300 mg, 84%) as a white solid. LCMS (ESI): [M+H]$^+$=134.

Step 5: (3RS,4SR)-1-(4-Aminopyrimidin-2-yl)-3-fluoro-3-methylpiperidin-4-ol (mixture of enantiomers) and (3RS,4RS)-1-(4-Aminopyrimidin-2-yl)-3-fluoro-3-methylpiperidin-4-ol (mixture of enantiomers)

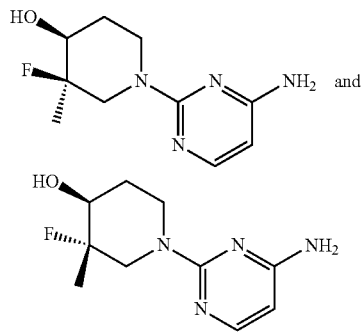

A mixture of 3-fluoro-3-methylpiperidin-4-ol hydrochloride (3 g, 17.7 mmol), 2-chloropyrimidin-4-amine (1.76 g, 13.6 mmol) and N-ethyl-N-isopropylpropan-2-amine (5.29 g, 40.9 mmol) in DMSO (15 mL) was stirred for 20 h at 80° C. The resulting mixture was concentrated in vacuo. The resulting residue was purified via reverse-phase HPLC and lyophilized to afford the two title compounds as off-white solid mixtures of enantiomers with known relative stereochemistry.

(3RS,4SR)-1-(4-Aminopyrimidin-2-yl)-3-fluoro-3-methylpiperidin-4-ol (mixture of enantiomers)(500 mg, 16%): LCMS (ESI): [M+H]$^+$=227.1, $R_T$ (min)=1.126, Method=R; $^1$H NMR (300 MHz, DMSO-d$_6$) δ 7.71-7.69 (d, J=5.7 Hz, 1H), 6.36 (s, 2H), 5.69-5.67 (d, J=5.7 Hz, 1H), 4.93-4.91 (d, J=6.6 Hz, 1H), 4.69-4.51 (m, 2H), 3.50-3.30 (m, 1H), 2.96-2.81 (m, 2H), 1.63-1.60 (m, 2H), 1.33-1.26 (d, J=21 Hz, 3H).

(3RS,4RS)-1-(4-Aminopyrimidin-2-yl)-3-fluoro-3-methylpiperidin-4-ol (mixture of enantiomers)(100 mg, 3%): LCMS (ESI): [M+H]$^+$=227.1, $R_T$ (min)=1.359, Method=L; $^1$H NMR (300 MHz, DMSO-d$_6$) δ 7.71-7.70 (d, J=5.4 Hz, 1H), 6.36 (s, 2H), 5.69-5.68 (d, J=5.4 Hz, 1H), 5.23-5.21 (d, J=4.5 Hz, 1H), 3.77-3.62 (m, 5H), 1.81-1.73 (m, 1H), 1.46-1.38 (m, 1H), 1.27-1.19 (d, J=22.5 Hz, 3H).

Step 6: (3RS,4SR)-3-Fluoro-1-(4-((2-(hydroxymethyl)-1-isopropyl-1H-imidazo[4,5-c]pyridin-6-yl)amino)pyrimidin-2-yl)-3-methylpiperidin-4-ol (mixture of enantiomers)

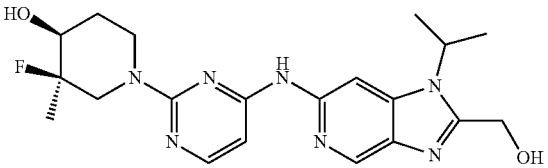 [SMILES: CC(C)n1c(CO)nc2cnc(Nc3ccnc(N4CC[C@H](O)[C@](C)(F)C4)n3)cc21]

The title compound (25.5 mg, 30%) was synthesized from (3RS,4SR)-1-(4-aminopyrimidin-2-yl)-3-fluoro-3-methylpiperidin-4-ol isomer 1 (46.6 mg, 0.206 mmol) and (6-bromo-1-isopropyl-1H-imidazo[4,5-c]pyridin-2-yl)methanol (Example A 49, step 2) (73 mg, 0.206 mmol)

following a procedure similar to Example 636, step 2. LCMS (ESI): [M+H]$^+$=416.1, R$_T$(min)=1.049, Method=N; $^1$H NMR (300 MHz, DMSO-d$_6$) δ 9.75 (s, 1H), 8.60 (s, 1H), 8.35 (s, 1H), 7.96-7.95 (d, J=5.7 Hz, 1H), 6.47-6.45 (d, J=5.7 Hz, 1H), 5.68 (m, 1H), 5.03-4.94 (m, 2H), 4.75-4.64 (m, 4H), 3.59-3.48 (m, 1H), 3.18-3.04 (m, 2H), 1.72 (m, 2H), 1.60 (m, 6H), 1.31-1.39 (d, J=24 Hz, 3H).

Example 646: 1-sec-Butyl-6-(2-((±)-cis-5-fluoro-4-hydroxy-3,3-dimethylpiperidin-1-yl)pyrimidin-4-ylamino)-N-(tetrahydro-2H-pyran-4-yl)-1H-pyrrolo[3,2-c]pyridine-3-carboxamide

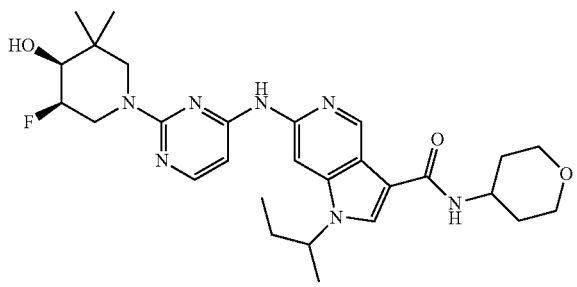 [SMILES: CCC(C)n1cc(C(=O)NC2CCOCC2)c2cnc(Nc3ccnc(N4C[C@@H](F)[C@@H](O)C(C)(C)C4)n3)cc21]

Step 1: tert-Butyl 5,5-dimethyl-4-(trimethylsilyloxy)-5,6-dihydropyridine-1(2H)-carboxylate

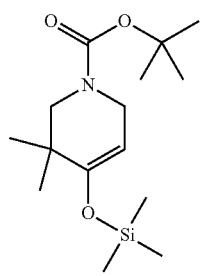 [SMILES: CC(C)(C)OC(=O)N1CC=C(O[Si](C)(C)C)C(C)(C)C1]

The title compound (7.5 g, 77%) was synthesized from tert-butyl 3,3-dimethyl-4-oxopiperidine-1-carboxylate (7.35 g, 32.4 mmol) following a procedure similar to Example 645, step 1. LCMS (ESI): [M+H]$^+$=300.

Step 2: tert-Butyl-5-fluoro-3,3-dimethyl-4-oxopiperidine-1-carboxylate

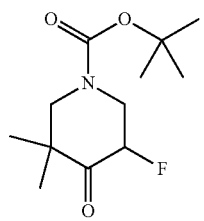 [SMILES: CC(C)(C)OC(=O)N1CC(F)C(=O)C(C)(C)C1]

The title compound (1.4 g, 23%) was synthesized from tert-butyl 5,5-dimethyl-4-(trimethylsilyloxy)-5,6-dihydropyridine-1(2H)-carboxylate (7.5 g, 25.0 mmol) following a procedure similar to Example 645, step 2. LCMS (ESI): [M+H]$^+$=246.

Step 3: (±)-(cis)-tert-Butyl 5-fluoro-4-hydroxy-3,3-dimethylpiperidine-1-carboxylate

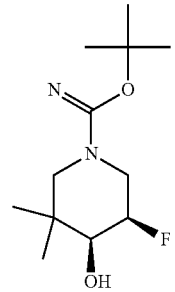 [SMILES: CC(C)(C)OC(=N)N1C[C@@H](F)[C@@H](O)C(C)(C)C1]

The title compound (1.0 g, 71%) was synthesized as a mixture of enantiomers from tert-butyl-5-fluoro-3,3-dimethyl-4-oxopiperidine-1-carboxylate (1.4 g, 5.71 mmol) following a procedure similar to Example 631, step 1. LCMS (ESI): [M+H]$^+$=248.

Step 4: (±)-(cis)-5-Fluoro-3,3-dimethylpiperidin-4-ol hydrochloride

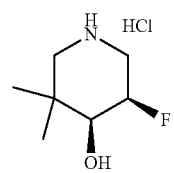

The title compound (1.36 g, 57%) was synthesized from (±)-(cis)-tert-butyl 5-fluoro-4-hydroxy-3,3-dimethylpiperidine-1-carboxylate (3.2 g, 12.9 mmol) as a mixture of enantiomers following a procedure similar to Example 645, step 4. LCMS (ESI): [M+H]$^+$=148.

Step 5: (±)-(cis)-1-(4-Aminopyrimidin-2-yl)-5-fluoro-3,3-dimethylpiperidin-4-ol

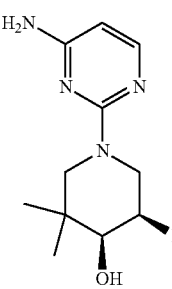

The title compound (700 mg, 43%) was synthesized from (±)-(cis)-5-fluoro-3,3-dimethylpiperidin-4-ol hydrochloride (1.36 g, 7.41 mmol) as a mixture of enantiomers following a procedure similar to Example 645, step 5. LCMS (ESI): [M+H]$^+$=241.

Step 6: 1-sec-Butyl-6-(2-((±)-cis-5-fluoro-4-hydroxy-3,3-dimethylpiperidin-1-yl)pyrimidin-4-ylamino)-N-(tetrahydro-2H-pyran-4-yl)-1H-pyrrolo[3,2-c]pyridine-3-carboxamide

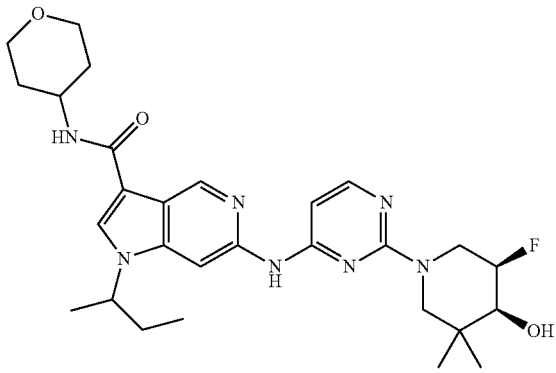 [SMILES: CCC(C)n1cc(C(=O)NC2CCOCC2)c2cnc(Nc3ccnc(N4C[C@@H](F)[C@@H](O)C(C)(C)C4)n3)cc21]

The title compound (43.9 mg, 55%) was synthesized as a mixture of two diastereomers from (±)-(cis)-1-(4-aminopyrimidin-2-yl)-5-fluoro-3,3-dimethylpiperidin-4-ol (30 mg, 0.12 mmol) and 6-Bromo-1-(sec-butyl)-N-(tetrahydro-2H-pyran-4-yl)-1H-pyrrolo[3,2-c]pyridine-3-carboxamide (Example 321, step 2) (47.5 mg, 0.12 mmol) following a procedure similar to Example 636, step 2. LCMS (ESI): [M+H]$^+$=540.2, R$_T$ (min)=1.548, Method=N; $^1$H NMR (300 MHz, DMSO-d$_6$) δ 9.80 (s, 1H), 9.02 (s, 1H), 8.33 (s, 1H), 8.18 (s, 1H), 7.94 (d, J=5.7 Hz, 1H), 7.87 (m, 1H), 6.35 (d, J=5.7 Hz, 1H), 5.16-5.13 (m, 1H), 4.89-4.66 (m, 1H), 4.48-4.31 (m, 1H), 4.29-3.89 (m, 5H), 3.83-3.68 (m, 1H), 3.50-3.30 (m, 4H), 1.90-1.80 (m, 4H), 1.57-1.48 (m, 5H), 0.98-0.90 (m, 6H), 0.80-0.71 (m, 3H).

Each compound in Table 5 below was prepared following a similar experimental procedure (using appropriately substituted reagents) as described in another Example herein, such Example being referenced in the Synthesis Method column.

TABLE 5

| Example | Structure/Name | Synthesis Method | LCMS R$_T$ (min), [M + H]$^+$, method | $^1$H NMR (ppm) |
|---|---|---|---|---|
| 647 | 1-isopropyl-2-methyl-N-(2-(4-(methylsulfonyl)phenyl)pyrimidin-4-yl)-1H-imidazo[4,5-c]pyridin-6-amine | 52 | 3.90, 423.2, B | $^1$H NMR (400 MHz, DMSO) δ 10.25 (s, 1H), 8.68-8.60 (m, 2H), 8.58 (d, J = 0.7 Hz, 1H), 8.52 (d, J = 5.9 Hz, 1H), 8.42 (s, 1H), 8.07 (d, J = 8.6 Hz, 2H), 7.39 (s, 1H), 4.78 (m, 1H), 2.59 (s, 3H), 1.64 (d, J = 6.9 Hz, 6H). |
| 648 | [2-(1,5-Dioxa-9-azaspiro[5.5]undec-9-yl)pyrimidin-4-yl]-(1-isopropyl-2-methyl-1H-imidazo[4,5-c]pyridin-6-yl)amine | 46 | 2.27, 424, F | $^1$H NMR (400 MHz, DMSO-d$_6$) δ 9.70 (s, 1H), 8.50 (s, 1H), 8.35 (bs, 1H), 7.95 (d, J = 5.7 Hz, 1H), 6.42 (d, J = 5.7 Hz, 1H), 4.76-4.66 (m, 1H), 3.89-3.87 (m, 4H), 3.81-3.78 (m, 4H), 2.56 (s, 3H), 1.85-1.83 (m, 4H), 1.67-1.62 (m, 2H), 1.56 (d, J = 6.9 Hz, 6H) |
| 649 | (±)-cis-5-Fluoro-1-[4-(1-isopropyl-2-methyl-1H-imidazo[4,5-c]pyridin-6-ylamino)pyrimidin-2-yl]-3,3-dimethylpiperidin-4-ol; formate salt | 46 | 2.01, 430, F | $^1$H NMR (400 MHz, DMSO-d$_6$) δ 9.68 (s, 1H), 8.50 (s, 1H), 8.27 (bs, 1H), 8.16 (s, 1H), 7.94 (d, J = 5.7 Hz, 1H), 6.47 (d, J = 5.7 Hz, 1H), 5.10 (bs, 1H), 4.82-4.67 (m, 2H), 4.25-4.18 (m, 1H), 3.98-3.89 (m, 1H), 3.79 (d, J = 13.0 Hz, 1H), 3.49-3.36 (m, 2H), 2.56 (s, 3H), 1.57 (d, J = 6.8 Hz, 3H), 1.56 (d, J = 6.8 Hz, 3H), 0.93 (d, J = 1.7 Hz, 3H), 0.91 (s, 3H) |

TABLE 5-continued

| Example | Structure/Name | Synthesis Method | LCMS R$_T$ (min), [M + H]$^+$, method | $^1$H NMR (ppm) |
|---|---|---|---|---|
| 650 | (±)-cis-5-Fluoro-1-[4-(2-hydroxymethyl-1-isopropyl-1H-imidazo[4,5-c]pyridin-6-ylamino)pyrimidin-2-yl]-3,3-dimethylpiperidin-4-ol | 273 | 2.01, 430, F | $^1$H NMR (400 MHz, DMSO-d$_6$) δ 9.73 (s, 1H), 8.60 (d, J = 0.98 Hz, 1H), 8.32 (bs, 1H), 7.95 (d, J = 5.7 Hz, 1H), 6.48 (d, J = 5.7 Hz, 1H), 5.68 (t app, J = 5.8 Hz, 1H), 5.11 (d, J = 5.4 Hz, 1H), 5.00-4.90 (m, 1H), 4.82-4.67 (m, 1H), 4.71 (d, J = 5.7 Hz, 1H), 4.28-4.20 (m, 1H), 3.93 (ddd, J = 23.4, 13.0, 2.8 Hz, 1H), 3.81 (d, J = 12.8 Hz, 1H), 3.46 (ddd, J = 22.5, 5.3, 2.7 Hz, 1H), 3.37 (d, J = 12.98 Hz, 1H), 1.60 (d, J = 6.8 Hz, 3H), 1.59 (d, J = 6.8 Hz, 3H), 0.93 (d, J = 1.6 Hz, 3H), 0.91 (s, 3H) |
| 651 | (1-Isopropyl-2-methyl-1H-imidazo[4,5-c]pyridin-6-yl)[2-(1,4,5,7-tetrahydropyrazolo[3,4-c]pyridin-6-yl)pyrimidin-4-yl]amine | 46 | 1.98, 390, F | $^1$H NMR (400 MHz, DMSO-d$_6$) δ 12.50 (bs, 1H), 9.73 (s, 1H), 8.51 (s, 1H), 8.40 (bs, 1H), 7.99 (d, J = 5.6 Hz, 1H), 7.42 (s, 1H), 6.47 (d, J = 5.6 Hz, 1H), 4.80 (s, 2H), 4.80-4.70 (m, 1H), 4.12 (t app, J = 5.8 Hz, 2H), 2.75 (t app, J = 5.8 Hz, 2H), 2.58 (s, 3H), 1.64 (d, J = 6.9 Hz, 6H) |
| 652 | N$^2$-(1,1-Dioxotetrahydrothiophen-3-ylmethyl)-N$^4$-(1-isopropyl-2-methyl-1H-imidazo[4,5-c]pyridin-6-yl)pyrimidine-2,4-diamine | 46 | 1.85, 416, F | $^1$H NMR (400 MHz, CDCl$_3$) δ 8.65 (s, 1H), 8.01 (d, J = 5.8 Hz, 1H), 7.84 (bs, 1H), 7.79 (bs, 1H), 6.48 (d, J = 5.8 Hz, 1H), 5.54 (bs, 1H), 4.71-4.60 (m, 1H), 3.69-3.57 (m, 2H), 3.30-3.20 (m, 2H), 3.10-3.02 (m, 1H), 2.93-2.83 (m, 2H), 2.63 (s, 3H), 2.42-2.34 (m, 1H), 2.06-1.95 (m, 1H), 1.66 (d, J = 6.9 Hz, 6H) |
| 653 | [2-(6-Fluoro-1,4-dioxa-8-azaspiro[4.5]dec-8-yl)pyrimidin-4-yl](1-isopropyl-2-methyl-1H-imidazo[4,5-c]pyridin-6-yl)amine | 46 | 2.30, 428, F | $^1$H NMR (400 MHz, DMSO-d$_6$) δ 9.74 (s, 1H), 8.50 (d, J = 0.9 Hz, 1H), 8.28 (bs, 1H), 7.97 (d, J = 5.6 Hz, 1H), 6.49 (d, J = 5.6 Hz, 1H), 4.76-4.65 (m, 1H), 4.58-4.44 (m, 1H), 4.41-4.34 (m, 1H), 4.20-4.14 (m, 1H), 4.05-3.94 (m, 4H), 3.83 (ddd, J = 27.3, 13.9, 2.6 Hz, 1H), 3.63 (ddd, J = 13.0, 9.2, 3.4 Hz, 1H), 2.56 (s, 3H), 1.92-1.85 (m, 1H), 1.67-1.62 (m, 1H), 1.56 (2 × d, J = 6.7 Hz, 6H) |
| 654 | {6-[2-(6-Fluoro-1,4-dioxa-8-azaspiro[4.5]dec-8-yl)pyrimidin-4-ylamino]-1-isopropyl-1H-imidazo[4,5-c]pyridin-2-yl}methanol | 273 | 2.20, 444, F | $^1$H NMR (400 MHz, DMSO-d$_6$) δ 9.80 (s, 1H), 8.60 (d, J = 0.9 Hz, 1H), 8.35 (bs, 1H), 7.98 (d, J = 5.7 Hz, 1H), 6.50 (d, J = 5.7 Hz, 1H), 5.69 (1H, bs), 5.00-4.89 (1H, m), 4.71 (s, 2H), 4.59-4.36 (m, 2H), 4.22-4.16 (m, 1H), 4.05-3.94 (4H, m), 3.82 (ddd, J = 27.7, 13.8, 2.6 Hz, 1H), 3.62 (ddd, J = 13.2, 9.36, 3.4 Hz, 1H), 1.93-1.85 (m, 1H), 1.68-1.62 (m, 1H), 1.58 (2 × d, J = 6.7 Hz, 6H) |

TABLE 5-continued

| Example | Structure/Name | Synthesis Method | LCMS R$_T$ (min), [M + H]$^+$, method | $^1$H NMR (ppm) |
|---|---|---|---|---|
| 655 | {6-[2-((3*,4*)-3-Fluoro-4-methoxypiperidin-1-yl)pyrimidin-4-ylamino]-1-isopropyl-1H-imidazo[4,5-c]pyridin-2-yl}methanol (single stereoisomer known relative stereochemistry, absolute configuration arbitrarily drawn) | 273 | 2.03, 416, F | $^1$H NMR (DMSO-d$_6$) δ 9.78 (s, 1H) 8.60 (d, J = 0.8, 1H), 8.39 (bs, 1H), 7.97 (d, J = 5.8 Hz, 1H), 6.46 (d, J = 5.8 Hz, 1H), 5.69 (t, J = 5.4 Hz, 1H), 5.02-4.87 (m, 2H), 4.76-4.68 (m, 1H), 4.71 (d, J = 5.4 Hz, 2H), 4.51-4.44 (m, 1H), 3.62-3.21 (m, 3H), 3.36 (s, 3H), 1.85-1.79 (m, 1H), 1.77-1.67 (m, 1H), 1.60 (2 × d, J = 6.9 Hz, 6H), |
| 656 | (1-Isopropyl-2-methyl-1H-imidazo[4,5-c]pyridin-6-yl)-[2-(2-methanesulfonyl-2-methylpropoxy)pyrimidin-4-yl]amine | 609 | 2.32, 419.1, F | $^1$H NMR (400 MHz, CDCl$_3$) δ 8.64 (1H, s), 8.21 (1H, s), 8.15 (1H, d, J = 5.8 Hz), 8.08 (1H, br s), 6.70 (1H, d, J = 5.7 Hz), 4.70-4.62 (1H, m), 4.59 (2H, s), 3.10 (3H, s), 2.64 (3H, s), 1.67 (6H, d, J = 6.6 Hz), 1.56 (6H, s). |
| 657 | [6-[2-((3RS,4SR)-3-Fluoro-4-methoxypiperidin-1-yl)pyrimidin-4-ylamino]-1-((S)-2,2,2-trifluoro-1-methylethyl)-1H-imidazo[4,5-c]pyridin-2-yl]methanol (mixture of diastereoisomers) | 286 | 2.37, 470.2, F | $^1$H NMR (400 MHz, CDCl$_3$) δ 8.66 (2H, 2 × s), 8.38, 8.35 (2H, 2 × s), 8.04 (2H, 2 × d, J = 5.7 Hz), 7.42 (2H, 2 × s), 6.08, 6.06 (2H, 2 × d, J = 5.7 Hz), 5.41-5.32 (2H, 2 × m), 4.99-4.89 (4H, 2 × m), 4.87-4.77 (2H, 2 × m), 4.69-4.60 (1H, m), 4.52-4.46 (1H, m), 4.39-4.30 (1H, m), 4.26-4.18 (1H, m), 3.83-3.68 (2H, m), 3.65-3.53 (3H, m), 3.52-3.35 (3H, m), 3.50 (6H, 2 × s), 2.05-1.96 (2H, 2 × m), 1.93 (3H, d, J = 7.1 Hz), 1.92 (3H, d, J = 6.8 Hz), 1.88-1.78 (2H, 2 × m). |
| 658 | (3RS,4SR)-3-Fluoro-1-{4-[2-((R)-1-hydroxyethyl)-1-isopropyl-1H-imidazo[4,5-c]pyridin-6-ylamino]pyrimidin-2-yl}piperidin-4-ol (mixture of diastereoisomers) | 288 | 1.93, 416.1, F | $^1$H NMR (400 MHz, DMSO-d$_6$) δ 9.76 (1H, s), 8.61 (1H, s), 8.41 (1H, s), 7.97 (1H, d, J = 5.7 Hz), 6.45 (1H, d, J = 5.7 Hz), 5.72 (1H, d, J = 6.1 Hz), 5.16-5.01 (3H, m), 4.77-4.56 (2H, m), 4.41-4.36 (1H, m), 3.90-3.79 (1H, m), 3.58-3.47 (1H, m), 3.32-3.29 (1H, m), 1.75-1.69 (2H, m), 1.61-1.58 (9H, m). |
| 659 | (R)-1-{6-[2-((3RS,4SR)-3-Fluoro-4-methoxypiperidin-1-yl)pyrimidin-4-ylamino]-1-isopropyl-1H-imidazo[4,5-c]pyridin-2-yl}ethanol (mixture of diastereoisomers) | 288 | 2.21, 430.2, F | $^1$H NMR (400 MHz, DMSO-d$_6$) δ 9.75 (1H, m), 8.61 (1H, m), 8.38 (1H, m), 7.96 (1H, d, J = 5.5 Hz), 6.46 (1H, d, J = 5.7 Hz), 5.71 (1H, d, J = 6.6 Hz), 5.15-5.09 (1H, m), 5.07-5.02 (1H, m), 5.01-4.87 (1H, m), 4.76-4.69 (1H, m), 4.51-4.45 (1H, m), 3.62-3.21 (3H, m), 3.35 (3H, s), 1.84-1.69 (2H, m), 1.60-1.58 (9H, m). |

TABLE 5-continued

| Example | Structure/Name | Synthesis Method | LCMS R$_T$ (min), [M + H]$^+$, method | $^1$H NMR (ppm) |
|---|---|---|---|---|
| 660 | {1-Isopropyl-6-[2-(2-methanesulfonyl-2-methylpropoxy)pyrimidin-4-ylamino]-1H-imidazo[4,5-c]pyridin-2-yl}methanol | 609 | 2.21, 435.1, F | $^1$H NMR (400 MHz, DMSO-d$_6$) δ 10.24 (1H, s), 8.63 (1H, s), 8.41 (1H, br s), 8.16 (1H, d, J = 5.7 Hz), 7.03 (1H, s), 5.69 (1H, s), 4.97-4.90 (1H, m), 4.72 (2H, s), 4.48 (2H, s), 3.10 (3H, s), 1.58 (6H, d, J = 6.8 Hz), 1.42 (6H, s). |
| 661 | {1-Isopropyl-6-[2-(4-methanesulfonylpiperidin-1-yl)pyrimidin-4-ylamino]-1H-imidazo[4,5-c]pyridin-2-yl}methanol | 273 | 1.87, 446.1, F | $^1$H NMR (400 MHz, DMSO-d$_6$) δ 9.80 (1H, s), 8.61 (1H, s), 8.38 (1H, br s), 7.99 (1H, d, J = 5.7 Hz), 6.49 (1H, d, J = 5.7 Hz), 5.68 (1H, t, J = 5.3 Hz), 4.99-4.93 (1H, m), 4.90-4.87 (2H, m), 4.72 (2H, d, J = 5.3 Hz), 3.45-3.37 (1H, m), 3.00-2.93 (2H, m), 2.96 (3H, s), 2.11-2.07 (2H, m), 1.63-1.53 (2H, m), 1.59 (6H, d, J = 7.0 Hz). |
| 662 | (R)-1-[6-[2-(4-Methanesulfonylpiperidin-1-yl)pyrimidin-4-ylamino]-1-((S)-2,2,2-trifluoro-1-methylethyl)-1H-imidazo[4,5-c]pyridin-2-yl]ethanol | 288 | 2.37, 514.1, F | $^1$H NMR (400 MHz, DMSO-d$_6$) δ 9.80 (1H, s), 8.64 (1H, s), 8.28 (1H, br s), 7.95 (1H, d, J = 5.7 Hz), 6.50 (1H, d, J = 5.7 Hz), 5.93 (1H, d, J = 6.9 Hz), 5.88-5.80 (1H, m), 5.01-4.94 (1H, m), 4.82-4.78 (2H, m), 3.42-3.23 (1H, m), 2.93-2.85 (2H, m), 2.89 (3H, s), 2.03-2.00 (2H, m), 1.80 (3H, d, J = 7.0 Hz), 1.58 (3H, d, J = 6.6 Hz), 1.54-1.45 (2H, m). |
| 663 | (R)-1-[6-[2-(2-Methanesulfonyl-2-methyl-propylamino)pyrimidin-4-ylamino]-1-((S)-2,2,2-trifluoro-1-methylethyl)-1H-imidazo[4,5-c]pyridin-2-yl]ethanol | 288 | 2.39, 502.2, F | $^1$H NMR (400 MHz, DMSO-d$_6$) δ 9.71 (1H, s), 8.67 (1H, s), 8.20 (1H, br s), 7.97 (1H, d, J = 5.7 Hz), 6.78 (1H, br s), 6.26 (1H, br s), 5.99 (1H, d, J = 7.2 Hz), 5.89-5.81 (1H, m), 5.05-4.99 (1H, m), 3.84-3.69 (2H, m), 2.98 (3H, s), 1.86 (3H, d, J = 7.1 Hz), 1.62 (3H, d, J = 6.4 Hz), 1.33, 1.32 (6H, 2 × s). |
| 664 | 1-Isopropyl-6-[2-(2-methanesulfonyl-2-methylpropylamino)pyrimidin-4-ylamino]-1H-pyrrolo[3,2-c]pyridine-3-carboxylic acid (tetrahydropyran-4-yl)amide | 57 | 2.34, 530.2, F | $^1$H NMR (400 MHz, DMSO-d$_6$) δ 9.70 (1H, s), 9.01 (1H, s), 8.25 (1H, br s), 8.14 (1H, s), 7.91 (1H, d, J = 5.8 Hz), 7.86 (1H, d, J = 7.5 Hz), 6.68 (1H, t, J = 6.1 Hz), 6.48 (1H, d, J = 5.7 Hz), 4.82-4.75 (1H, m), 4.06-3.96 (1H, m), 3.92-3.88 (2H, m), 3.81 (2H, d, J = 6.2 Hz), 3.43-3.67 (2H, m), 2.97 (3H, s), 1.83-1.79 (2H, m), 1.60-1.53 (2H, m), 1.49 (6H, d, J = 6.7 Hz), 1.34 (6H, s). |

TABLE 5-continued

| Example | Structure/Name | Synthesis Method | LCMS R<sub>T</sub> (min), [M + H]<sup>+</sup>, method | $^1$H NMR (ppm) |
|---|---|---|---|---|
| 665 | (R)-1-[6-[2-(4-Hydroxymethyl-4-methoxypiperidin-1-yl)pyrimidin-4-ylamino]-1-((S)-2,2,2-trifluoro-1-methylethyl)-1H-imidazo[4,5-c]pyridin-2-yl]ethanol | 288 | 2.36, 496.2, F | $^1$H NMR (400 MHz, DMSO-d$_6$) δ 9.79 (1H, s), 8.67 (1H, s), 8.43 (1H, br s), 7.97 (1H, d, J = 5.7 Hz), 6.45 (1H, d, J = 5.6 Hz), 5.95 (1H, d, J = 7.0 Hz), 5.93-5.86 (1H, m), 5.06-4.99 (1H, m), 4.57 (1H, t, J = 5.7 Hz), 4.38-4.34 (2H, m), 3.38 (2H, d, J = 5.7 Hz), 3.24-3.15 (2H, m), 3.20 (3H, s), 1.84 (3H, d, J = 7.0 Hz), 1.72-1.69 (2H, m), 1.62 (3H, d, J = 6.4 Hz), 1.51-1.43 (2H, m). |
| 666 | (3S,4R)-3-Fluoro-1-{4-[2-hydroxymethyl-1-((S)-2,2,2-trifluoro-1-methylethyl)-1H-imidazo[4,5-c]pyridin-6-ylamino]pyrimidin-2-yl}piperidin-4-ol | 288 | 2.05, 456.2, F | $^1$H NMR (400 MHz, DMSO-d$_6$) δ 9.86 (1H, s), 8.66 (1H, s), 8.37 (1H, br s), 7.98 (1H, d, J = 5.7 Hz), 6.48 (1H, d, J = 5.6 Hz), 5.89 (1H, t, J = 5.6 Hz), 5.75-5.68 (1H, m), 5.12 (1H, d, J = 5.0 Hz), 4.77 (2H, d, J = 5.8 Hz), 4.72-4.58 (1H, m), 4.56-4.50 (1H, m), 4.36-4.30 (1H, m), 3.90-3.79 (1H, m), 3.57-3.46 (1H, m), 3.31-3.27 (1H, m), 1.86 (3H, d, J = 7.0 Hz), 1.70-1.67 (2H, m). |
| 667 | (3R,4S)-3-Fluoro-1-{4-[2-hydroxymethyl-1-((S)-2,2,2-trifluoro-1-methylethyl)-1H-imidazo[4,5-c]pyridin-6-ylamino]pyrimidin-2-yl}piperidin-4-ol | 286 | 2.05, 456.2, F | $^1$H NMR (400 MHz, DMSO-d$_6$) δ 9.86 (1H, s), 8.67 (1H, s), 8.38 (1H, br s), 7.98 (1H, d, J = 5.7 Hz), 6.48 (1H, d, J = 5.6 Hz), 5.90 (1H, br s), 5.76-5.68 (1H, m), 5.12 (1H, br s), 4.77 (2H, s), 4.73-4.56 (2H, m), 4.39-4.33 (1H, m), 3.89-3.79 (1H, m), 3.52-3.41 (1H, m), 3.32-3.25 (1H, m), 1.86 (3H, d, J = 7.0 Hz), 1.72-1.67 (2H, m). |
| 668 | (±)-2-{1-[4-(2-Hydroxymethyl-1-isopropyl-1H-imidazo[4,5-c]pyridin-6-ylamino)pyrimidin-2-yl]piperidin-2-yl}ethanol | 273 | 2.20, 412.2, F | $^1$H NMR (400 MHz, DMSO-d$_6$) δ 9.72 (1H, s), 8.59 (1H, s), 8.41 (1H, br s), 7.94 (1H, d, J = 5.7 Hz), 6.36 (1H, d, J = 5.6 Hz), 5.68 (1H, t, J = 5.7 Hz), 5.06-5.01 (1H, m), 4.98-4.91 (1H, m), 4.75-4.73 (1H, m), 4.71 (2H, d, J = 5.8 Hz), 4.44-4.38 (1H, m), 2.97-2.90 (1H, m), 2.00-1.92 (1H, m), 1.71-1.60 (8H, m), 1.59 (6H, d, J = 6.9 Hz), 1.45-1.35 (1H, m). |
| 669 | 1-[4-(2-Hydroxymethyl-1-isopropyl-1H-imidazo[4,5-c]pyridin-6-ylamino)pyrimidin-2-yl]-4-trifluoromethylpiperidin-4-ol | 273 | 2.31, 452.2, F | $^1$H NMR (400 MHz, DMSO-d$_6$) δ 9.79 (1H, s), 8.60 (1H, s), 8.41 (1H, br s), 7.99 (1H, d, J = 5.6 Hz), 6.46 (1H, d, J = 5.7 Hz), 6.12 (1H, br s), 5.69 (1H, br s), 5.00-4.93 (1H, m), 4.72 (2H, s), 4.70-4.67 (2H, m), 3.19-3.12 (2H, m), 1.77-1.64 (4H, m), 1.58 (6H, d, J = 6.7 Hz). |

TABLE 5-continued

| Example | Structure/Name | Synthesis Method | LCMS R$_T$ (min), [M + H]$^+$, method | $^1$H NMR (ppm) |
|---|---|---|---|---|
| 670 | 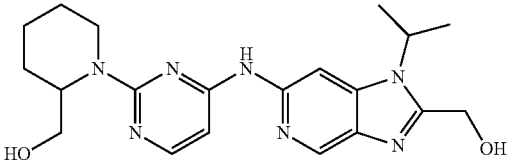<br>{6-[2-(2-Hydroxymethylpiperidin-1-yl)pyrimidin-4-ylamino]-1-isopropyl-1H-imidazo[4,5-c]pyridin-2-yl}methanol | 273 | 2.11, 398.2, F | $^1$H NMR (400 MHz, DMSO-d$_6$) δ 9.70 (1H, s), 8.59 (1H, s), 8.44 (1H, br s), 7.94 (1H, d, J = 5.6 Hz), 6.37 (1H, d, J = 5.7 Hz), 5.68 (1H, t, J = 5.8 Hz), 4.98-4.91 (2H, m), 4.71 (2H, d, J = 5.7 Hz), 4.69-4.67 (1H, m), 3.66-3.48 (2H, m), 2.98-2.91 (1H, m), 1.94-1.91 (1H, m), 1.71-1.37 (6H, m), 1.58 (6H, d, J = 7.0 Hz). |
| 671 | 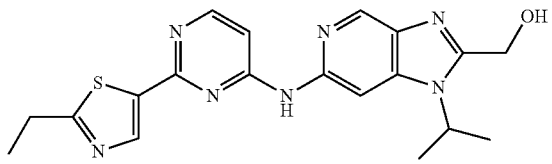<br>{6-[2-(2-Ethylthiazol-5-yl)pyrimidin-4-ylamino]-1-isopropyl-1H-imidazo[4,5-c]pyridin-2-yl}methanol | 312 | 2.79, 396.3, F | $^1$H NMR (400 MHz, DMSO-d$_6$) δ 10.26 (1H, s), 8.66 (1H, s), 8.47 (1H, br s), 8.38 (1H, s), 8.37 (1H, d, J = 6.0 Hz), 7.20 (1H, br s), 5.72 (1H, t, J = 5.8 Hz), 5.01 (1H, septet, J = 6.9 Hz), 4.75 (2H, d, J = 5.7 Hz), 3.06 (2H, q, J = 7.5 Hz), 1.69 (6H, d, J = 6.9 Hz), 1.37 (3H, t, J = 7.5 Hz). |
| 672 | 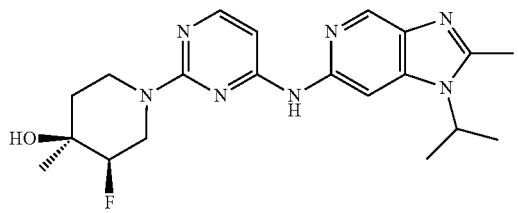<br>(3RS,4SR)-3-Fluoro-1-[4-(1-isopropyl-2-methyl-1H-imidazo[4,5-c]pyridin-6-ylamino)pyrimidin-2-yl]-4-methylpiperidin-4-ol<br>(Mixture of enantiomers) | 46 | 1.98, 400.2, F | $^1$H NMR (400 MHz, DMSO-d$_6$) δ 9.73 (1H, s), 8.51 (1H, s), 8.35 (1H, br s), 7.96 (1H, d, J = 5.6 Hz), 6.45 (1H, br d, J = 5.5 Hz), 4.81 (1H, s), 4.72 (1H, septet, J = 6.9 Hz), 4.43-4.26 (2H, m), 4.16-4.11 (1H, m), 3.64-3.57 (1H, m), 3.51-3.45 (1H, m), 2.56 (3H, s), 1.73-1.67 (1H, m), 1.57 and 1.56 (6H, 2d, J = 6.9 Hz), 1.56-1.50 (1H, m), 1.24 (3H, s). |
| 673 | 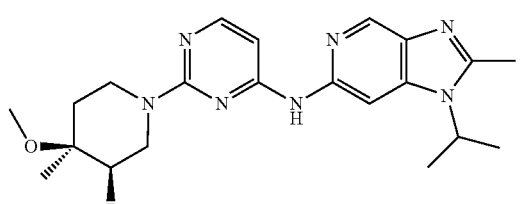<br>[((3RS,4SR)-3-Fluoro-4-methoxy-4-methylpiperidin-1-yl)pyrimidin-4-yl]-(1-isopropyl-2-methyl-1H-imidazo[4,5-c]pyridin-6-yl)amine<br>(Mixture of enantiomers) | 46 | 2.34, 414.2, F | $^1$H NMR (400 MHz, DMSO-d$_6$) δ 9.74 (1H, s), 8.51 (1H, s), 8.33 (1H, br s), 7.97 (1H, d, J = 5.7 Hz), 6.47 (1H, br d, J = 5.5 Hz), 4.72 (1H, septet, J = 6.9 Hz), 4.53 (1H, ddd, J = 46.8, 8.5, 3.9 Hz), 4.30-4.22 (1H, m), 4.04-3.98 (1H, m), 3.81-3.75 (1H, m), 3.55-3.48 (1H, m), 3.24 (3H, s), 2.56 (3H, s), 1.96-1.89 (1H, m), 1.56 (6H, d, J = 6.9 Hz), 1.52-1.45 (1H, m), 1.28 (3H, s). |
| 674 | 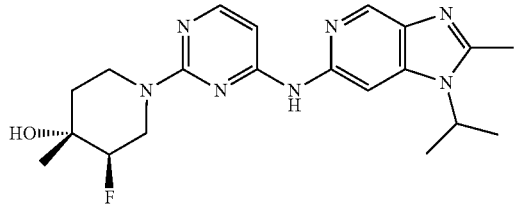<br>(3RS,4RS)-3-Fluoro-1-[4-(1-isopropyl-2-methyl-1H-imidazo[4,5-c]pyridin-6-ylamino)pyrimidin-2-yl]-4-methylpiperidin-4-ol<br>(Mixture of enantiomers) | 46 | 2.16, 400.1, F | $^1$H NMR (400 MHz, DMSO-d$_6$) δ 9.70 (1H, s), 8.50 (1H, s), 8.37 (1H, br s), 7.94 (1H, d, J = 5.7 Hz), 6.41 (1H, br d, J = 5.7 Hz), 5.01 (1H, s), 4.73 (1H, septet, J = 6.9 Hz), 4.69-4.61 (1H, m), 4.40-4.24 (2H, m), 3.63-3.50 (1H, m), 3.37-3.33 (1H, m), 2.56 (3H, s), 1.73-1.65 (1H, m), 1.57 (6H, 2d, J = 6.9 Hz), 1.55-1.50 (1H, m), 1.22 (3H, d, J = 2.1 Hz). |

TABLE 5-continued

| Example | Structure/Name | Synthesis Method | LCMS R_T (min), [M + H]+, method | 1H NMR (ppm) |
|---|---|---|---|---|
| 675 | (3RS,4RS)-3-Fluoro-1-[4-(2-hydroxymethyl-1-isopropyl-1H-imidazo[4,5-c]pyridin-6-ylamino)pyrimidin-2-yl]-4-methylpiperidin-4-ol (Mixture of enantiomers) | 619 | 2.09, 416.1, F | 1H NMR (400 MHz, DMSO-d6) δ 9.81 (1H, s), 8.61 (1H, s), 8.42 (1H, br s), 7.95 (1H, d, J = 5.7 Hz), 6.43 (1H, br d, J = 5.5 Hz), 5.69 (1H, t, J = 5.7 Hz), 5.03 (1H, s), 4.97 (1H, septet, J = 6.9 Hz), 4.72 (2H, d, J = 5.3 Hz), 4.70-4.63 (1H, m), 4.41-4.24 (2H, m), 3.63-3.51 (1H, m), 3.37-3.33 (1H, m), 1.74-1.66 (1H, m), 1.60 and 1.59 (6H, 2d, J = 6.9 Hz), 1.56-1.51 (1H, m), 1.22 (3H, d, J = 2.1 Hz). |
| 676 | (3RS,4SR)-3-Fluoro-1-{4-[2-((R)-1-hydroxyethyl)-1-((S)-2,2,2-trifluoro-1-methylethyl)-1H-imidazo[4,5-c]pyridin-6-ylamino]pyrimidin-2-yl}-4-methylpiperidin-4-ol (Mixture of diastereoisomers) | 620 | 2.40 and 2.42, 484.2, F | 1H NMR (400 MHz, DMSO-d6) δ 9.85 and 9.84 (1H, 2s), 8.69 (1H, s), 8.37 and 8.35 (1H, 2br s), 7.99 (1H, d, J = 5.6 Hz), 6.53-6.51 (1H, m), 5.96 (1H, d, J = 7.0 Hz), 5.89 (1H, septet, J = 7.8 Hz), 5.03 (1H, quintet, J = 6.7 Hz), 4.82 (1H, s), 4.43-4.23 (2H, m), 4.15-4.06 (1H, m), 3.65-3.42 (2H, m), 1.85 (3H, 2d, J = 7.2 Hz), 1.72-1.63 (1H, m), 1.63 (3H, d, J = 6.5 Hz), 1.56-1.48 (1H, m), 1.24 (3H, s). |
| 677 | [2-(4,4-Difluoropiperidin-1-yl)pyrimidin-4-yl]-(1-isopropyl-2-methyl-1H-imidazo[4,5-c]pyridin-6-yl)amine | 46 | 2.50, 388.2, F | 1H NMR (400 MHz, DMSO-d6) δ 9.77 (1H, s), 8.51 (1H, s), 8.28 (1H, br s), 8.00 (1H, d, J = 5.7 Hz), 6.53 (1H, br d, J = 5.6 Hz), 4.71 (1H, septet, J = 6.9 Hz), 3.95-3.93 (4H, m), 2.56 (3H, s), 2.08-1.98 (4H, m), 1.56 (6H, d, J = 6.9 Hz). |
| 678 | (R)-1-[4-(1-Isopropyl-2-methyl-1H-imidazo[4,5-c]pyridin-6-ylamino)pyrimidin-2-yl]pyrrolidine-3-carbonitrile | 46 | 2.00, 363.1, F | 1H NMR (400 MHz, DMSO-d6) δ 9.82 (1H, s), 8.56 (1H, br s), 8.51 (1H, s), 7.97 (1H, d, J = 5.7 Hz), 6.46 (1H, br d, J = 5.6 Hz), 4.75 (1H, septet, J = 6.9 Hz), 3.96 (1H, br s), 3.79-3.69 (2H, m), 3.62-3.55 (2H, m), 2.56 (3H, s), 2.45-2.37 (1H, m), 2.32-2.23 (1H, m), 1.58 (6H, d, J = 6.9 Hz). |
| 679 | (S)-1-[4-(1-Isopropyl-2-methyl-1H-imidazo[4,5-c]pyridin-6-ylamino)pyrimidin-2-yl]pyrrolidine-3-carbonitrile | 46 | 2.01, 363.2, F | 1H NMR (400 MHz, DMSO-d6) δ 9.79 (1H, s), 8.57 (1H, br s), 8.50 (1H, s), 7.97 (1H, d, J = 5.7 Hz), 6.45 (1H, br d, J = 5.6 Hz), 4.75 (1H, septet, J = 6.9 Hz), 3.96 (1H, br s), 3.79-3.69 (2H, m), 3.62-3.55 (2H, m), 2.56 (3H, s), 2.45-2.37 (1H, m), 2.31-2.23 (1H, m), 1.58 (6H, d, J = 6.9 Hz). |
| 680 | (R)-1-[4-(1-Isopropyl-2-methyl-1H-imidazo[4,5-c]pyridin-6-ylamino)pyrimidin-2-yl]pyrrolidin-3-ol | 46 | 1.79, 354.1, F | 1H NMR (400 MHz, DMSO-d6) δ 9.69 (1H, s), 8.64 (1H, br s), 8.49 (1H, s), 7.93 (1H, d, J = 5.7 Hz), 6.37 (1H, br d, J = 5.7 Hz), 4.97 (1H, br d, J = 3.6 Hz), 4.72 (1H, septet, J = 6.9 Hz), 4.40 (1H, br s), 3.72-3.47 (4H, br m), 2.56 (3H, s), 2.08-2.00 (1H, m), 1.93-1.87 (1H, m), 1.58 (6H, d, J = 6.9 Hz). |

TABLE 5-continued

| Example | Structure/Name | Synthesis Method | LCMS R_T (min), [M + H]+, method | ¹H NMR (ppm) |
|---|---|---|---|---|
| 681 | (S)-1-[4-(1-Isopropyl-2-methyl-1H-imidazo[4,5-c]pyridin-6-ylamino)pyrimidin-2-yl]pyrrolidin-3-ol | 46 | 1.79, 354.1, F | ¹H NMR (400 MHz, DMSO-d₆) δ 9.70 (1H, s), 8.63 (1H, br s), 8.49 (1H, s), 7.93 (1H, d, J = 5.7 Hz), 6.37 (1H, br d, J = 5.7 Hz) 4.97 (1H br d, J = 3.6, Hz), 4.72 (1H, septet, J = 6.9 Hz), 4.40 (1H, br s), 3.70-3.49 (4H, br m), 2.56 (3H, s), 2.08-2.00 (1H, m), 1.94-1.87 (1H, m), 1.58 (6H, d, J = 6.9 Hz). |
| 682 | 1-[4-(1-Isopropyl-2-methyl-1H-imidazo[4,5-c]pyridin-6-ylamino)pyrimidin-2-yl]-4-methylpiperidin-4-ol | 46 | 2.11, 382, F | ¹H NMR 400 MHz δ (CDCl₃): 8.51 (1H, s), 8.35 (1H, s), 7.99 (1H, d, J = 5.6 Hz), 7.43 (1H, br s), 5.99 (1H, d, J = 5.7 Hz), 4.61 (1H, sept, J = 7.0 Hz), 4.35 (1H, dt, J = 13.4, 4.2 Hz), 3.54 (2H, ddd, J = 13.8, 9.9, 4.4 Hz), 2.59 (3H, s), 1.71-1.57 (11H, m), 1.29 (3H, s). |
| 683 | 4-[2-((R)-1-hydroxyethyl)-1-((S)-2,2,2-trifluoro-1-methylethyl)-1H-imidazo[4,5-c]pyridin-6-ylamino]pyrimidin-2-yl}-4-methypiperidin-4-ol | 291 | 2.54, 466, F | ¹H NMR 400 MHz δ (CDCl₃): 8.68 (1H, s), 8.39 (1H, s), 8.02 (1H, d, J = 5.4 Hz), 7.27 (1H, br s), 6.00 (1H, d, J = 5.5 Hz), 5.56 (1H, sept, J = 7.6 Hz), 5.13-5.03 (1H, m), 4.32 (1H, dt, J = 13.3, 4.1 Hz), 3.56-3.47 (2H, m), 2.13 (1H, d, J = 8.2 Hz), 1.88 (3H, d, J = 7.2 Hz), 1.82 (3H, d, J = 6.5 Hz), 1.68-1.60 (4H, m), 1.30 (3H, s). |
| 684 | (S)-1-[6-[2-((cis)-3-Fluoro-4-methoxypiperidin-1-yl)pyrimidin-4-ylamino]-1-((S)-2,2,2-trifluoro-1-methylethyl)-1H-imidazo[4,5-c]pyridin-2-yl]ethanol (Mixture of diastereoisomers) | 291 | 2.52, 484, F | ¹H NMR 400 MHz δ (CDCl₃): 8.65 (1H, s), 8.33 (0.5H, s), 8.29 (0.5H, s), 8.01 (1H, d, J = 5.6 Hz), 7.39 (1H, br s), 6.08 (0.5H, d, J = 5.9 Hz) 6.06 (0.5H, d, J = 5.9 Hz), 5.53-5.40 (1H, m), 5.19-5.09 (1H, m), 4.88-4.79 (0.5H, m), 4.76-4.67 (0.5H, m), 4.64-4.54 (0.5H, m), 4.49-4.38 (0.5H, m), 4.34-4.24 (0.5H, m), 4.22-4.11 (0.5H, m), 3.84-3.49 (4H, m), 3.47 (3H, s), 2.04-1.75 (5H, m), 1.73 (3H, d, J = 6.9 Hz). |

TABLE 5-continued

| Example | Structure/Name | Synthesis Method | LCMS R$_T$ (min), [M + H]$^+$, method | $^1$H NMR (ppm) |
|---|---|---|---|---|
| 685 | (3S,4R)-3-Fluoro-1-{4-[2-((S)-1-hydroxyethyl)-1-((S)-2,2,2-trifluoro-1-methylethyl)-1H-imidazo[4,5-c]pyridin-6-ylamino]pyrimidin-2-yl}piperidin-4-ol | 291 | 2.21, 470, F | $^1$H NMR 400 MHz δ (CDCl$_3$): 8.66 (1H, s), 8.29 (1H, s), 8.01 (1H, d, J = 5.6 Hz), 7.41 (1H, br s), 6.08 (1H, d, J = 5.6 Hz), 5.49 (1H, sept, J = 7.5 Hz), 5.15 (1H, quin, J = 6.7 Hz), 4.77-4.71 (0.5H, m), 4.64-4.59 (0.5H, m), 4.32-4.20 (1H, m), 4.11-3.91 (3H, m), 3.80-3.70 (1H, m), 2.86 (1H, d, J = 5.9 Hz), 2.13 (1H, d, J = 5.1 Hz), 1.98-1.78 (5H, m), 1.73 (3H, d, J = 6.7 Hz). |
| 686 | (3R,4S)-3-Fluoro-1-{4-[2-((S)-1-hydroxyethyl)-1-((S)-2,2,2-trifluoro-1-methylethyl)-1H-imidazo[4,5-c]pyridin-6-ylamino]pyrimidin-2-yl}piperidin-4-ol | 291 | 2.21, 470, F | $^1$H NMR 400 MHz δ (CDCl$_3$): 8.66 (1H, s), 8.32 (1H, s), 8.02 (1H, d, J = 5.6 Hz), 7.39 (1H, br s), 6.08 (1H, d, J = 5.6 Hz), 5.55-5.41 (1H, m), 5.14 (1H, q, J = 6.6 Hz) 4.80-4.75 (0.5H m), 4.68-4.62 (0.5H, m), 4.51-4.38 (1H, m), 4.23-4.12 (1H, m), 4.09-4.12 (1H, m), 4.08-3.96 (1H, m), 3.92-3.77 (1H, m), 3.66-3.55 (1H, m), 1.98-1.79 (6H, m), 1.73 (3H, d, J = 6.6 Hz). |
| 687 | (3S,4R)-3-Fluoro-1-{4-[2-((R)-1-hydroxyethyl)-1-((R)-2,2,2-trifluoro-1-methylethyl)-1H-imidazo[4,5-c]pyridin-6-ylamino]pyrimidin-2-yl}piperidin-4-ol | 291 | 2.21, 470, F | $^1$H NMR 400 MHz δ (CDCl$_3$): 8.66 (1H, s), 8.32 (1H, s), 8.02 (1H, d, J = 5.6 Hz), 7.31 (1H, br s), 6.08 (1H, d, J = 5.6 Hz), 5.55-5.41 (1H, m), 5.14 (1H, q, J = 6.6 Hz), 4.80-4.75 (0.5H, m), 4.68-4.62 (0.5H, m), 4.51-4.38 (1H, m), 4.23-4.12 (1H, m), 4.09-4.12 (1H, m), 4.08-3.96 (1H, m), 3.92-3.77 (1H, m), 3.66-3.55 (1H, m), 1.98-1.79 (6H, m), 1.73 (3H, d, J = 6.6 Hz). |
| 688 | (3R,4S)-3-Fluoro-1-{4-[2-((R)-1-hydroxyethyl)-1-((R)-2,2,2-trifluoro-1-methylethyl)-1H-imidazo[4,5-c]pyridin-6-ylamino]pyrimidin-2-yl}piperidin-4-ol | 291 | 2.21, 470, F | $^1$H NMR 400 MHz δ (CDCl$_3$): 8.66 (1H, s), 8.29 (1H, s), 8.01 (1H, d, J = 5.6 Hz), 7.41 (1H, br s), 6.08 (1H, d, J = 5.6 Hz), 5.49 (1H, sept, J = 7.5 Hz), 5.15 (1H, quin, J = 6.7 Hz), 4.77-4.71 (0.5H, m), 4.64-4.59 (0.5H, m), 4.32-4.20 (1H, m), 4.11-3.91 (3H, m), 3.80-3.70 (1H, m), 2.86 (1H, d, J = 5.9 Hz), 2.13 (1H, d, J = 5.1 Hz), 1.98-1.78 (5H, m), 1.73 (3H, d, J = 6.7 Hz). |

TABLE 5-continued

| Example | Structure/Name | Synthesis Method | LCMS R$_T$ (min), [M + H]$^+$, method | $^1$H NMR (ppm) |
|---|---|---|---|---|
| 689 | (3S,4R)-3-Fluoro-1-{4-[2-((S)-1-hydroxyethyl)-1-((R)-2,2,2-trifluoro-1-methylethyl)-1H-imidazo[4,5-c]pyridin-6-ylamino]pyrimidin-2-yl}piperidin-4-ol | 291 | 2.29, 470, F | $^1$H NMR 400 MHz δ (CDCl$_3$): 8.68 (1H, s), 8.33 (1H, s), 8.02 (1H, d, J = 5.6 Hz), 7.38 (1H, br s), 6.06 (1H, d, J = 5.6 Hz), 5.68 (1H, sept, J = 7.5 Hz), 5.13-5.03 (1H, m), 4.80-4.74 (0.5H, m), 4.67-4.63 (0.5H, m), 4.51-4.41 (1H, m), 4.24-4.15 (1H, m), 4.04-3.95 (1H, m), 3.80 (1H, ddd, J = 23.6, 13.6, 2.5 Hz), 3.62-3.52 (1H, m), 2.26 (1H, d, J = 8.1 Hz), 2.07 (1H, d, J = 7.0 Hz), 1.93-1.77 (8H, m). |
| 690 | (3R,4S)-3-Fluoro-1-{4-[2-((S)-1-hydroxyethyl)-1-((R)-2,2,2-trifluoro-1-methylethyl)-1H-imidazo[4,5-c]pyridin-6-ylamino]pyrimidin-2-yl}piperidin-4-ol | 291 | 2.29, 470, F | $^1$H NMR 400 MHz δ (CDCl$_3$): 8.70 (1H, s), 8.31 (1H, s), 8.02 (1H, d, J = 5.6 Hz), 7.31 (1H, br s), 6.08 (1H, d, J = 5.6 Hz), 5.57 (1H, sept, J = 7.5 Hz), 5.13-5.04 (1H, m), 4.76-4.71 (0.5H, m), 4.64-4.59 (0.5H, m), 4.32-4.23 (1H, m), 4.11-3.91 (3H, m), 3.79-3.69 (1H, m), 2.14 (1H, d, J = 8.1 Hz), 2.04 (1H, d, J = 5.1 Hz), 1.98-1.78 (9H, m). |
| 691 | (6-((2-((1S,4S)-2-oxa-5-azabicyclo[2.2.1]heptan-5-yl)pyrimidin-4-yl)amino)-1-isopropyl-1H-imidazo[4,5-c]pyridin-2-yl)methanol | 273 | 0.55, 382.2 B | $^1$H NMR (400 MHz, DMSO-d$_6$) δ 9.79 (s, 1H), 8.59 (s, 1H), 7.95 (d, J = 5.7 Hz, 1H), 6.46 (s, 1H), 5.68 (s, 1H), 5.03-4.87 (m, 2H), 4.71 (s, 3H), 3.88-3.67 (m, 2H), 3.66-3.44 (m, 2H), 1.99-1.83 (m, 2H), 1.59 (dd, J = 11.4, 6.9 Hz, 6H). |
| 692 | (6-((2-(2-azabicyclo[2.1.1]hexan-2-yl)pyrimidin-4-yl)amino)-1-isopropyl-1H-imidazo[4,5-c]pyridin-2-yl)methanol | 273 | 3.080, 366.2, B | $^1$H NMR (400 MHz, DMSO-d$_6$) δ 9.74 (s, 1H), 8.63 (s, 1H), 8.59 (d, J = 0.8 Hz, 1H), 7.94 (d, J = 5.7 Hz, 1H), 6.41 (d, J = 5.7 Hz, 1H), 5.69 (s, 1H), 4.96 (p, J = 6.9 Hz, 1H), 4.86 (s, 1H), 4.71 (s, 2H), 3.54 (s, 2H), 3.03-2.89 (m, 1H), 2.00 (s, 2H), 1.61 (d, J = 6.9 Hz, 6H), 1.39 (dd, J = 4.4, 1.9 Hz, 2H). |
| 693 | 9-(4-((2-(hydroxymethyl)-1-isopropyl-1H-imidazo[4,5-c]pyridin-6-yl)amino)pyrimidin-2-yl)-1-oxa-4,9-diazaspiro[5.5]undecan-3-one | 273 | 5.470, 453.2, A | $^1$H NMR (400 MHz, DMSO-d$_6$) δ 9.73 (s, 1H), 8.59 (s, 1H), 8.40 (s, 1H), 8.21 (s, 0H), 7.97 (t, J = 5.0 Hz, 2H), 6.45 (d, J = 5.7 Hz, 1H), 5.65 (s, 1H), 4.95 (p, J = 6.8 Hz, 1H), 4.71 (s, 2H), 4.39 (dt, J = 13.0, 4.1 Hz, 2H), 4.04 (s, 2H), 3.16 (d, J = 2.7 Hz, 2H), 1.84 (d, J = 13.6 Hz, 2H), 1.70-1.60 (m, 2H), 1.57 (d, J = 6.9 Hz, 6H). |

TABLE 5-continued

| Example | Structure/Name | Synthesis Method | LCMS R_T (min), [M + H]+, method | ¹H NMR (ppm) |
|---|---|---|---|---|
| 694 | 4-(6-(2-(1-(Cyclopropylsulfonyl)-1H-pyrazol-4-yl)pyrimidin-4-ylamino)-2-(hydroxymethyl)-1H-imidazo[4,5-c]pyridin-1-yl)pyrrolidin-2-one | 265 | 1.468, 496.15, L | ¹H NMR (300 MHz, DMSO-d₆) δ 10.19 (s, 1H), 8.71 (s, 1H), 8.63 (s, 1H), 8.44-8.41 (d, J = 6.6 Hz, 2H), 7.97 (s, 1H), 7.70 (m, 2H), 5.77 (m, 1H), 5.65 (m, 1H), 4.78-4.76 (d, J = 5.7 Hz, 2H), 3.85 (m, 1H), 3.62 (m, 1H), 2.50 (m, 1H), 2.80 (m, 2H), 1.35 (m, 2H), 1.25 (m, 2H) |
| 695 | (6-(2-(1-(Cyclopropylsulfonyl)-1H-pyrazol-4-yl)pyrimidin-4-ylamino)-1-(4-methoxy-2-methylbutan-2-yl)-1H-imidazo[4,5-c]pyridin-2-yl)methanol | 265 | 1.660, 513.3, L | ¹H NMR (400 MHz, DMSO-d₆) δ 10.22 (s, 1H), 8.67 (d, J = 2 Hz, 2H), 8.42 (m, 3H), 7.35 (m, 1H), 5.69 (m, 1H), 4.82-4.80 (d, J = 5.6 Hz, 2H), 3.27 (m, 1H), 3.18 (m, 2H), 3.02 (s, 3H), 2.44 (m, 2H), 1.95 (s, 6H), 1.34 (m, 2H), 1.27 (m, 2H) |
| 696 | (6-(2-(1-(Cyclopropylsulfonyl)-1H-pyrazol-4-yl)pyrimidin-4-ylamino)-1-(4,4,4-trifluorobutan-2-yl)-1H-imidazo[4,5-c]pyridin-2-yl)methanol | 265 | 1.785, 523, N | ¹H NMR (400 MHz, DMSO-d₆) δ 10.19 (s, 1H), 8.69 (s, 1H), 8.66 (s, 1H), 8.42 (m, 2H), 8.32 (s, 1H), 7.31 (s, 1H), 5.88 (m, 1H), 5.22 (m, 1H), 4.74 (m, 2H), 3.21 (m, 2H), 3.02 (m, 1H), 1.75-1.73 (d, J = 6.8 Hz, 3H), 1.34 (m, 4H) |
| 697 | (6-(2-(1-(Cyclopropylsulfonyl)-1H-pyrazol-4-yl)pyrimidin-4-ylamino)-1-(3-methylcyclopentyl)-1H-imidazo[4,5-c]pyridin-2-yl)methanol | 265 | 1.815, 495, N | ¹H NMR (400 MHz, DMSO-d₆) δ 10.19 (s, 1H), 8.65 (m, 2H), 8.44 (m, 2H), 7.72 (m, 2H), 5.72 (s, 1H), 5.18 (m, 1H), 4.75 (s, 2H), 3.37 (m, 1H), 2.00 (m, 7H), 1.31 (m, 2H), 1.23 (m, 2H), 1.04 (m, 3H). |
| 698 | (6-(2-(1-(Cyclopropylsulfonyl)-1H-pyrazol-4-yl)pyrimidin-4-ylamino)-1-(2-methylcyclopropyl)-1H-imidazo[4,5-c]pyridin-2-yl)methanol | 265 | 1.658, 467, N | ¹H NMR (300 MHz, DMSO-d₆) δ 10.28 (s, 1H), 8.73 (s, 1H), 8.63 (s, 1H), 8.50 (s, 1H), 8.42-8.40 (d, J = 6.0 Hz 1H) 8.32 (s, 1H) 7.28 (d, J = 6.0 Hz, 1H), 5.56 (m, 1H), 4.77-4.75 (d, J = 4.8 Hz, 2H), 3.28 (m, 1H), 3.16 (m, 1H), 1.50 (m, 1H), 1.34 (m, 2H), 1.27 (m, 6H), 1.08 (m, 1H) |

TABLE 5-continued

| Example | Structure/Name | Synthesis Method | LCMS R$_T$ (min), [M + H]$^+$, method | $^1$H NMR (ppm) |
|---|---|---|---|---|
| 699 | (1-Isopropyl-6-(2-((±)-(trans)-4-methoxy-3-methylpiperidin-1-yl)pyrimidin-4-ylamino)-1H-imidazo[4,5-c]pyridin-2-yl)methanol | 632 | 1.516, 412.15, R | $^1$H NMR (400 MHz, DMSO-d$_6$) δ 9.75 (s, 1H), 8.60 (s, 1H), 8.36 (s, 1H), 7.97-7.96 (d, J = 6.0 Hz, 1H), 6.46-6.45 (d, J = 6.0 Hz, 1H), 5.71-5.69 (m, 1H), 4.99-4.92 (m, 1H), 4.72-4.71 (d, J = 5.6 Hz, 2H), 4.58-4.54 (m, 1H), 4.47-4.43 (m, 1H), 3.33 (s, 3H), 3.17-3.11 (m, 1H), 3.03-2.99 (m, 1H), 2.84-2.78 (m, 1H), 2.11-2.07 (m, 1H), 1.61-1.51 (m, 7H), 1.33-1.25 (m, 1H), 0.97-0.95 (d, J = 6.8 Hz, 3H). |
| 700 | 1-sec-Butyl-6-(2-(1-(cyclopropylsulfonyl)-1H-pyrazol-4-yl)pyrimidin-4-ylamino)-N-(1,4-dioxepan-6-yl)-1H-pyrrolo[3,2-c]pyridine-3-carboxamide | 321 | 1.685, 581, R | $^1$H NMR (400 MHz, DMSO-d$_6$) δ 10.28 (s, 1H), 9.07 (s, 1H), 8.70 (s, 1H), 8.48 (s, 2H), 8.39-8.37 (d, J = 6.0 Hz, 1H), 8.24 (s, 1H), 8.16-8.12 (m, 1H), 7.12-7.10 (d, J = 6.0 Hz, 1H), 4.59-4.52 (m, 1H), 3.81-3.71 (m, 2H), 3.70-3.58 (m, 3H), 3.58-3.48 (m, 1H), 3.30-3.25 (m, 4H), 1.95-1.93 (m, 2H), 1.56-1.54 (d, J = 6.0 Hz, 3H), 1.35-1.30 (m, 4H), 0.86-0.74 (m, 3H). |
| 701 | (3S,4S,5R)-3,5-Difluoro-1-{4-[2-((R)-1-hydroxyethyl)-1-((S)-2,2,2-trifluoro-1-methylethyl)-1H-imidazo[4,5-c]pyridin-6-ylamino]pyrimidin-2-yl}piperidin-4-ol (Single diastereoisomer) | 291 | 2.25, 488, F | $^1$H NMR 400 MHz (DMSO-d$_6$) δ 9.83 (1H, s), 8.65 (1H, s), 8.25 (1H, s), 7.95 (1H, d, J = 5.6 Hz), 6.53 (1H, d, J = 5.3 Hz), 5.90 (1H, br s), 5.84 (1H, sept, J = 7.9 Hz), 5.51 (1H, br s), 5.01-4.94 (1H, m), 4.60 (2H, d, J = 47.1 Hz), 4.33-4.21 (2H, m), 3.99 (1H, t, J = 47.2 Hz), 3.77 (2H, dd, J = 22.4, 13.2 Hz), 1.91 (3H, d, J = 7.2 Hz), 1.58 (3H, d, J = 6.5 Hz). |
| 702 | (3SR,4SR)-3-fluoro-1-(4-((2-(hydroxymethyl)-1-isopropyl-1H-imidazo[4,5-c]pyridin-6-yl)amino)pyrimidin-2-yl)-3-methylpiperidin-4-ol (mixture of enantiomers) | 645 | 1.154, 416.2, M | $^1$H NMR (300 MHz, DMSO-d$_6$) δ 9.78 (s, 1H), 8.61 (s, 1H), 8.38 (s, 1H), 7.97-7.95 (d, J = 5.4 Hz, 1H), 6.46-6.44 (d, J = 5.4 Hz, 1H), 5.70 (m, 1H), 5.35-5.33 (d, J = 4.5 Hz, 1H), 4.96 (m, 1H), 4.73-4.71 (m, 2H), 3.80 (m, 5H), 1.89 (m, 1H), 1.61 (m, 7H), 1.33-1.25 (d, J = 22.5 Hz, 3H) |

TABLE 5-continued

| Example | Structure/Name | Synthesis Method | LCMS R_T (min), [M + H]+, method | 1H NMR (ppm) |
|---|---|---|---|---|
| 703 | 1-sec-Butyl-6-(2-(1-(cyclopropylsulfonyl)-1H-pyrazol-4-yl)pyrimidin-4-ylamino)-N-(2-hydroxyethyl)-1H-pyrrolo[3,2-c]pyridine-3-carboxamide | 321 | 2.137, 525.2, M | $^1$H NMR (300 MHz, DMSO-d$_6$) δ 10.28 (s, 1H), 9.08 (s, 1H), 8.70 (s, 1H), 8.48 (s, 2H), 8.39-8.37 (m, 1H), 8.23 (s, 1H), 8.05 (m, 1H), 7.12 (s, 1H), 4.76 (m, 1H), 4.57 (m, 1H), 3.53 (m, 2H), 3.37 (m, 1H), 3.28 (m, 2H), 1.93 (m, 2H), 1.56-1.53 (d, J = 6.6 Hz, 3H), 1.28 (m, 4H), 0.79 (m, 3H) |
| 704 | 1-sec-Butyl-6-(2-(1-(cyclopropylsulfonyl)-1H-pyrazol-4-yl)pyrimidin-4-ylamino)-N-(2,2,2-trifluoroethyl)-1H-pyrrolo[3,2-c]pyridine-3-carboxamide | 321 | 1.712, 563.15, M | $^1$H NMR (300 MHz, DMSO-d$_6$) δ 10.32 (s, 1H), 9.08 (s, 1H), 8.71 (s, 1H), 8.67-8.64 (m, 1H), 8.50-8.49 (m, 2H), 8.40-8.38 (m, 1H), 8.34 (s, 1H), 7.13 (s, 1H), 4.60-4.58 (m, 1H), 4.15-4.10 (m, 2H), 3.33-3.26 (m, 1H), 1.96-1.92 (m, 2H), 1.57-1.55 (d, J = 6.4 Hz, 3H), 1.36-1.27 (m, 4H), 0.83-0.80 (m, 3H). |
| 705 | 1-sec-Butyl-6-(2-(1-(cyclopropylsulfonyl)-1H-pyrazol-4-yl)pyrimidin-4-ylamino)-N-(4-hydroxycyclohexyl)-1H-pyrrolo[3,2-c]pyridine-3-carboxamide | 321 | 2.222, 579.25, M | $^1$H NMR (300 MHz, DMSO-d$_6$) δ 10.25 (s, 1H), 9.07 (s, 1H), 8.69 (s, 1H), 8.47-8.42 (m, 2H), 8.37 (d, J = 5.7 Hz, 1H), 8.20 (s, 1H), 7.77-7.74 (m, 1H), 7.12 (d, J = 5.7 Hz, 1H), 4.57-4.55 (m, 2H), 3.74-3.72 (m, 1H), 3.47-3.40 (m, 1H), 3.29-3.25 (m, 1H), 1.97-1.89 (m, 6H), 1.54 (d, J = 6.6 Hz, 3H), 1.37-1.23 (m, 8H), 0.84-0.77 (m, 3H) |

TABLE 5-continued

| Example | Structure/Name | Synthesis Method | LCMS R$_T$ (min), [M + H]$^+$, method | $^1$H NMR (ppm) |
|---|---|---|---|---|
| 706 | (±)-(3RS,5RS)-3,5-Difluoro-1-[4-(1-isopropyl-2-methyl-1H-imidazo[4,5-c]pyridin-6-ylamino)pyrimidin-2-yl]piperidin-4-ol (mixture of enantiomers) | 46 | 1.97, 404, F | $^1$H NMR (400 MHz, DMSO-d$_6$) δ 9.79 (s, 1H), 8.52 (s, 1H), 8.27 (s, 1H), 7.98 (d, J = 5.6 Hz, 1H), 6.52 (d, J = 5.6 Hz, 1H), 5.77 (bs, 1H), 4.90-4.51 (m, 5H), 3.97-3.86 (m, 1H), 3.59 (dd, J = 31.0, 13.9 Hz, 1H), 3.48-3.39 (m, 1H), 2.57 (s, 3H), 1.58 (d, J = 6.5 Hz, 3H), 1.57 (d, J = 6.5 Hz, 3H) |
| 707 | (3R,4s,5S)-3,5-Difluoro-1-[4-(1-isopropyl-2-methyl-1H-imidazo[4,5-c]pyridin-6-ylamino)pyrimidin-2-yl]piperidin-4-ol (Meso single isomer) | 46 | 1.79, 404, F | n/a |

BIOCHEMICAL ASSAYS

The exemplified compounds described herein were tested according to the assay below. The enzyme data reported in Tables 4-5 is generally a representative of multiple experiments.

EGFR T790M L858R:

Ten nM EGFR T790M L858R enzyme (Life Technologies, PV4879) phosphorylates 1 μM 5-FAM-EEPLYWSF-PAKKK-CONH$_2$ peptide substrate (FL-Peptide 22, Caliper Life Sciences, 760366) in the presence of 5 μM adenosine-5'-triphosphate (ATP) and varying concentrations of test compound in 50 mM 2-[4-(2-hydroxyethyl)piperazin-1-yl]ethanesulfonic acid (HEPES), pH 7.5, 10 mM MgCl$_2$, 4 mM MnCl$_2$, 0.01% Brij-35, 1 mM dithiothreitol (DTT), 0.5% dimehylsulfoxide (DMSO). Reactions proceed for 30 minutes at room temperature (22° C.) and are terminated with 80 mM 2,2',2'',2'''-(ethane-1,2-diyldinitrilo)tetraacetic acid (EDTA). Product is detected using the Caliper mobility shift detection method where product and substrate are electrophoretically separated and measured. Percent activity is plotted against log concentration of compound and points are fit to the Morrison equation (shown below) to generate an apparent K$_i$. This apparent K$_i$ is further converted to K$_i$ using a Cheng-Prusoff conversion for competitive inhibitors: K$_i$=apparent K$_i$/(1+[ATP]/K$_m$ of ATP) where [ATP]=5 μM and K$_m$ of ATP=1.3 μM.

Morrison Equation:

$$v = v_0 \frac{[E] - [I] - K + \sqrt{([E] - [I] - K)^2 + 4[E]K}}{2[E]}$$

EGFR del746-750 T790M

Five nM EGFR del746-750 T790M enzyme (Carna Biosciences, 08-528) phosphorylates 1 μM 5-FAM-EEPLYWS-FPAKKK-CONH$_2$ peptide substrate (FL-Peptide 22, Caliper Life Sciences, 760366) in the presence of 5 μM adenosine-5'-triphosphate (ATP) and varying concentrations of test compound in 50 mM 2-[4-(2-hydroxyethyl)piperazin-1-yl]ethanesulfonic acid (HEPES), pH 7.5, 10 mM MgCl$_2$, 4 mM MnCl$_2$, 0.01% Brij-35, 1 mM dithiothreitol (DTT), 0.5% dimehylsulfoxide (DMSO). Reactions proceed for 30 minutes at room temperature (22° C.) and are terminated with 80 mM 2,2',2'',2'''-(ethane-1,2-diyldinitrilo)tetraacetic acid (EDTA). Product is detected using the Caliper mobility shift detection method where product and substrate are electrophoretically separated and measured. Percent activity is plotted against log concentration of compound and points are fit to the Morrison equation (shown below) to generate an apparent K$_i$. This apparent K$_i$ is further converted to K$_i$ using a Cheng-Prusoff conversion for competitive inhibitors: K$_i$=apparent K$_i$/(1+[ATP]/K$_m$ of ATP) where [ATP]=5 μM and K$_m$ of ATP=2.1 μM Morrison Equation:

$$v = v_0 \frac{[E] - [I] - K + \sqrt{([E] - [I] - K)^2 + 4[E]K}}{2[E]}$$

DATA TABLE I

EGFR(T790M/L858R) Biochemical activity

| Example | EGFR(T790M/L858R) Ki (μM) |
|---|---|
| 1 | 0.0936 |
| 2 | 0.0124 |
| 3 | 0.0308 |
| 4 | 0.0174 |
| 5 | 0.0177 |

DATA TABLE I-continued

EGFR(T790M/L858R) Biochemical activity

| Example | EGFR(T790M/L858R) Ki (μM) |
|---|---|
| 6 | 0.0105 |
| 7 | 0.1110 |
| 8 | 0.0244 |
| 9 | 0.1778 |
| 10 | 0.0186 |
| 11 | 0.0412 |
| 12 | 0.0445 |
| 13 | 0.0970 |
| 14 | 0.0843 |
| 15 | 1.3866 |
| 16 | 0.2923 |
| 17 | 1.2967 |
| 18 | 0.1871 |
| 19 | 0.0828 |
| 20 | 0.1227 |
| 21 | 0.2581 |
| 22 | 1.0414 |
| 23 | 0.0761 |
| 24 | 0.0138 |
| 25 | 1.0118 |
| 26 | 0.0200 |
| 27 | 0.1581 |
| 28 | 0.3346 |
| 29 | 0.5572 |
| 30 | 1.4359 |
| 31 | 0.1918 |
| 32 | 0.0194 |
| 33 | 0.0225 |
| 34 | 0.1128 |
| 35 | 0.2115 |
| 36 | 0.3227 |
| 37 | 0.1832 |
| 38 | 1.8262 |
| 39 | 1.0790 |
| 40 | 0.8198 |
| 41 | 0.1186 |
| 42 | 0.1734 |
| 43 | 0.3119 |
| 44 | 0.5875 |
| 45 | 0.6685 |
| 46 | 0.0122 |
| 47 | 0.5222 |
| 48 | 1.6189 |
| 49 | 0.4737 |
| 51 | 0.0010 |
| 52 | 0.0041 |
| 53 | 0.0310 |
| 54 | 0.0418 |
| 55 | 0.4676 |
| 56 | 0.2468 |
| 57 | 0.0054 |
| 58 | 0.0097 |
| 59 | 0.0119 |
| 60 | 0.0057 |
| 61 | 0.7869 |
| 62 | >0.229 |
| 63 | 0.0088 |
| 64 | 0.0010 |
| 65 | 0.5793 |
| 66 | 0.5935 |
| 67 | 1.4864 |
| 68 | 1.7141 |
| 69 | 0.3844 |
| 70 | 0.2161 |
| 71 | 0.3864 |
| 72 | 0.1734 |
| 73 | 0.1100 |
| 74 | 0.1010 |
| 75 | 0.5743 |
| 76 | 1.1614 |
| 77 | 0.4939 |
| 78 | 0.4280 |
| 79 | 0.4256 |
| 80 | 1.6896 |
| 81 | 1.0041 |
| 82 | 0.7561 |
| 83 | 0.2433 |
| 84 | 0.1114 |
| 85 | 0.0452 |
| 86 | 1.6717 |
| 87 | 1.4188 |
| 88 | 0.2408 |
| 89 | 0.4386 |
| 90 | 0.3269 |
| 91 | 0.0178 |
| 92 | 0.1946 |
| 93 | 0.0023 |
| 94 | 0.4336 |
| 95 | 0.2322 |
| 96 | 0.1113 |
| 97 | 0.0035 |
| 98 | 0.1823 |
| 99 | 0.3606 |
| 100 | 0.1154 |
| 101 | 0.4886 |
| 102 | 0.2545 |
| 103 | 1.4383 |
| 104 | 0.2066 |
| 105 | 0.3106 |
| 106 | 1.3201 |
| 107 | 0.2412 |
| 108 | 0.4325 |
| 109 | 0.6368 |
| 110 | 0.0429 |
| 111 | 0.0744 |
| 112 | 1.3490 |
| 113 | 0.0240 |
| 114 | 0.0012 |
| 115 | 0.0040 |
| 116 | 0.0247 |
| 117 | 0.0037 |
| 118 | 0.0886 |
| 119 | 0.0172 |
| 120 | 0.0054 |
| 121 | 0.0075 |
| 122 | 0.0442 |
| 123 | 0.0148 |
| 124 | 0.0255 |
| 125 | 0.0203 |
| 126 | 0.3725 |
| 127 | 0.3552 |
| 128 | 0.0593 |
| 129 | 0.0261 |
| 130 | 0.0979 |
| 131 | 0.1099 |
| 132 | 0.9884 |
| 133 | 0.5508 |
| 134 | 0.1088 |
| 135 | 0.1007 |
| 136 | 1.6800 |
| 137 | 0.1577 |
| 138 | 1.5390 |
| 139 | 0.2694 |
| 140 | 0.1555 |
| 141 | 0.0205 |
| 142 | 1.1152 |
| 143 | 0.5125 |
| 144 | 0.0326 |
| 145 | 1.0682 |
| 146 | 0.6216 |
| 147 | 1.1883 |
| 148 | 0.2835 |
| 149 | 0.0833 |
| 150 | 0.0977 |
| 151 | 0.0412 |
| 152 | 0.0113 |
| 153 | 0.0091 |
| 154 | 0.1710 |
| 155 | 0.7339 |
| 156 | 0.1662 |

DATA TABLE I-continued

EGFR(T790M/L858R) Biochemical activity

| Example | EGFR(T790M/L858R) Ki (μM) |
|---|---|
| 157 | 0.0281 |
| 158 | 0.4518 |
| 159 | 0.3541 |
| 160 | 0.0693 |
| 161 | 0.5770 |
| 162 | 1.1690 |
| 163 | 0.0175 |
| 164 | 0.0626 |
| 165 | 0.6142 |
| 166 | 0.5687 |
| 167 | 0.2054 |
| 168 | 0.3111 |
| 169 | 0.1485 |
| 170 | 0.2291 |
| 171 | 0.6036 |
| 172 | 0.5035 |
| 173 | 0.7088 |
| 174 | 0.5729 |
| 175 | 0.5083 |
| 176 | 0.2791 |
| 177 | 1.3541 |
| 178 | 1.0507 |
| 179 | 0.1641 |
| 180 | 0.3095 |
| 181 | 0.1183 |
| 182 | 0.5416 |
| 183 | 1.6372 |
| 184 | 1.0771 |
| 185 | 0.1906 |
| 186 | 0.2478 |
| 187 | 0.1359 |
| 188 | 0.8158 |
| 189 | 1.1743 |
| 190 | 0.1216 |
| 191 | 0.0708 |
| 192 | 1.2762 |
| 193 | 0.7025 |
| 194 | 0.2156 |
| 195 | 0.1812 |
| 196 | 1.0275 |
| 197 | 1.8027 |
| 198 | 1.2413 |
| 199 | 0.7345 |
| 200 | 1.1887 |
| 201 | 1.2235 |
| 202 | 0.4293 |
| 203 | 0.4221 |
| 204 | 1.8573 |
| 205 | 1.1560 |
| 206 | 0.9748 |
| 207 | 1.5476 |
| 208 | 1.0203 |
| 209 | 0.3790 |
| 210 | 1.3532 |
| 211 | 0.5508 |
| 212 | 0.6426 |
| 213 | 0.8121 |
| 214 | 1.1686 |
| 215 | 0.8322 |
| 216 | 0.4430 |
| 217 | 0.7584 |
| 218 | 0.3527 |
| 219 | 1.7784 |
| 220 | 0.8431 |
| 221 | 1.0527 |
| 222 | 1.6884 |
| 223 | 1.4642 |
| 224 | 1.7775 |
| 225 | 0.9983 |
| 226 | 1.2479 |
| 227 | 1.5761 |
| 228 | 0.5481 |
| 229 | 0.1052 |
| 230 | 0.1154 |
| 231 | 0.7603 |
| 232 | 1.1975 |
| 233 | 1.0615 |
| 234 | 0.0919 |
| 235 | 0.9890 |
| 236 | 1.7198 |
| 237 | 1.7785 |
| 238 | 1.7326 |
| 239 | 0.5595 |
| 240 | 0.2236 |
| 241 | 0.7451 |
| 242 | 0.1730 |
| 243 | 0.0113 |
| 244 | 0.0126 |
| 245 | 0.0071 |
| 246 | 0.0102 |
| 247 | 0.0062 |
| 248 | 0.0030 |
| 249 | 0.0028 |
| 250 | 0.0054 |
| 287 | 0.614 |
| 269 | 0.514 |
| 514 | 0.0726 |
| 489 | 0.0841 |
| 268 | 0.0092 |
| 598 | 0.331 |
| 318 | 0.462 |
| 599 | 0.328 |
| 515 | 0.464 |
| 516 | 0.064 |
| 517 | 0.0135 |
| 508 | 0.0242 |
| 490 | 0.0848 |
| 341 | 0.107 |
| 394 | 0.0761 |
| 422 | 0.0607 |
| 423 | 0.169 |
| 333 | 0.0443 |
| 449 | 0.00406 |
| 463 | 0.345 |
| 367 | 0.433 |
| 491 | 0.0692 |
| 267 | 0.193 |
| 544 | 0.787 |
| 292 | 0.294 |
| 399 | 0.0604 |
| 398 | 0.27 |
| 332 | 0.0825 |
| 425 | 0.0658 |
| 424 | 0.105 |
| 400 | 0.0219 |
| 366 | 0.0467 |
| 342 | 0.0807 |
| 401 | 0.00195 |
| 492 | 0.0498 |
| 494 | 0.00851 |
| 606 | 0.235 |
| 403 | 0.00728 |
| 402 | 0.00231 |
| 395 | 0.0321 |
| 237 | 0.507 |
| 368 | 1.08 |
| 493 | 0.0398 |
| 546 | 0.0239 |
| 545 | 0.0608 |
| 279 | 0.00663 |
| 360 | 0.089 |
| 404 | 0.0879 |
| 405 | 0.00561 |
| 426 | 0.449 |
| 266 | 0.275 |
| 272 | 0.00355 |
| 407 | 0.201 |
| 406 | 0.0137 |
| 409 | 0.00195 |
| 547 | 0.108 |

DATA TABLE I-continued

EGFR(T790M/L858R) Biochemical activity

| Example | EGFR(T790M/L858R) Ki (µM) |
|---|---|
| 518 | 0.243 |
| 519 | 0.191 |
| 496 | 0.0566 |
| 410 | 0.00207 |
| 411 | 0.00259 |
| 365 | 0.0739 |
| 261 | 0.435 |
| 462 | 0.137 |
| 277 | 0.0945 |
| 278 | 0.0481 |
| 495 | 0.0139 |
| 412 | 0.00307 |
| 293 | 0.00268 |
| 556 | 0.00347 |
| 548 | 0.347 |
| 298 | 0.161 |
| 498 | 0.694 |
| 520 | 0.0509 |
| 521 | 0.169 |
| 270 | 0.0277 |
| 319 | 0.525 |
| 320 | 0.329 |
| 364 | 0.0939 |
| 361 | 0.633 |
| 461 | 0.0829 |
| 263 | 0.0157 |
| 469 | 0.0159 |
| 299 | 0.353 |
| 580 | 0.126 |
| 549 | 0.0347 |
| 550 | 0.161 |
| 280 | 0.0108 |
| 497 | 0.0769 |
| 393 | 0.000812 |
| 396 | 0.00106 |
| 386 | 0.000731 |
| 331 | 0.000828 |
| 257 | 0.00194 |
| 294 | 0.00351 |
| 551 | 0.0979 |
| 532 | 0.0515 |
| 533 | 0.0785 |
| 522 | 0.194 |
| 552 | 0.0343 |
| 499 | 0.0378 |
| 300 | 0.0224 |
| 397 | 0.00621 |
| 523 | 0.287 |
| 301 | 0.325 |
| 302 | 0.243 |
| 343 | 0.621 |
| 258 | 0.00381 |
| 445 | 0.00346 |
| 446 | 0.0023 |
| 581 | 0.108 |
| 557 | 0.0127 |
| 392 | 0.00166 |
| 259 | 0.0132 |
| 441 | 0.00201 |
| 452 | 0.00166 |
| 448 | 0.0016 |
| 558 | 0.0127 |
| 303 | 0.179 |
| 582 | 0.287 |
| 559 | 0.0426 |
| 377 | 0.0028 |
| 378 | 0.00244 |
| 379 | 0.00221 |
| 362 | 0.355 |
| 560 | 1.03 |
| 427 | 0.0249 |
| 438 | 0.00121 |
| 437 | 0.00173 |
| 583 | 0.672 |
| 584 | 0.313 |
| 428 | 0.639 |
| 388 | 0.0146 |
| 467 | 0.00629 |
| 466 | 0.0381 |
| 443 | 0.00129 |
| 255 | 0.000919 |
| 444 | 0.00114 |
| 447 | 0.00106 |
| 468 | 0.0563 |
| 470 | 0.0758 |
| 390 | 0.0412 |
| 534 | 0.00754 |
| 304 | 0.116 |
| 306 | 0.0664 |
| 344 | 0.0455 |
| 416 | 0.152 |
| 334 | 0.0279 |
| 305 | 0.983 |
| 561 | 0.00216 |
| 562 | 0.00834 |
| 500 | 0.0842 |
| 408 | 0.0497 |
| 464 | 0.0172 |
| 471 | 0.0675 |
| 307 | 0.133 |
| 308 | 0.323 |
| 501 | 0.484 |
| 276 | 0.536 |
| 573 | 0.235 |
| 563 | 0.0125 |
| 574 | 0.65 |
| 415 | 0.866 |
| 414 | 0.19 |
| 430 | 0.0398 |
| 429 | 0.22 |
| 327 | 0.000702 |
| 413 | 0.0774 |
| 253 | 0.00197 |
| 435 | 0.00214 |
| 436 | 0.00126 |
| 264 | 0.00172 |
| 576 | 0.611 |
| 564 | 0.00307 |
| 309 | 0.0181 |
| 387 | 0.0207 |
| 254 | 0.0033 |
| 431 | 0.0949 |
| 585 | 0.159 |
| 586 | 0.00789 |
| 565 | 0.00879 |
| 575 | 0.258 |
| 363 | 0.0487 |
| 442 | 0.00133 |
| 604 | 0.0745 |
| 605 | 0.0699 |
| 566 | 0.0119 |
| 310 | 0.0706 |
| 285 | 0.0742 |
| 311 | 0.334 |
| 312 | 0.00174 |
| 567 | 0.0623 |
| 432 | 0.342 |
| 602 | 1.1 |
| 603 | 0.465 |
| 281 | 0.00474 |
| 313 | 0.266 |
| 587 | 1.03 |
| 421 | 0.403 |
| 439 | 0.000946 |
| 601 | 0.0296 |
| 600 | 0.0602 |
| 314 | 0.0325 |
| 282 | 0.0032 |
| 536 | 0.00646 |
| 553 | 0.357 |

DATA TABLE I-continued

EGFR(T790M/L858R) Biochemical activity

| Example | EGFR(T790M/L858R) Ki (μM) |
|---|---|
| 568 | 0.0622 |
| 569 | 0.00476 |
| 502 | 0.118 |
| 525 | 0.0426 |
| 526 | 0.00285 |
| 528 | 0.00588 |
| 529 | 0.00718 |
| 527 | 0.0542 |
| 330 | 0.0034 |
| 335 | 0.00147 |
| 336 | 0.0378 |
| 328 | 0.000928 |
| 420 | 0.0302 |
| 329 | 0.174 |
| 260 | 0.00588 |
| 440 | 0.00123 |
| 256 | 0.00548 |
| 315 | 0.0205 |
| 530 | 0.092 |
| 271 | 0.0749 |
| 274 | 0.122 |
| 535 | 0.00247 |
| 283 | 0.00668 |
| 284 | 0.00226 |
| 554 | 0.317 |
| 578 | 0.697 |
| 524 | 0.00273 |
| 460 | 0.0905 |
| 295 | 0.00146 |
| 579 | 0.00179 |
| 588 | 0.00135 |
| 577 | 0.514 |
| 537 | 0.00249 |
| 503 | 0.0334 |
| 589 | 0.201 |
| 419 | 0.0723 |
| 465 | 0.00224 |
| 504 | 0.0436 |
| 505 | 0.0116 |
| 555 | 0.135 |
| 418 | 0.0384 |
| 355 | 0.046 |
| 356 | 0.0477 |
| 434 | 0.0674 |
| 345 | 0.0145 |
| 385 | 0.0027 |
| 391 | 0.0015 |
| 483 | 0.0186 |
| 477 | 0.00163 |
| 454 | 0.000548 |
| 252 | 0.000205 |
| 453 | 0.000489 |
| 538 | 0.00461 |
| 590 | 0.0519 |
| 591 | 0.027 |
| 592 | 0.0385 |
| 593 | 0.0596 |
| 316 | 0.836 |
| 539 | 0.0629 |
| 506 | 0.00978 |
| 321 | 0.00096 |
| 322 | 0.00101 |
| 383 | 0.000842 |
| 384 | 0.00238 |
| 417 | 0.0441 |
| 482 | 0.138 |
| 484 | 0.00124 |
| 476 | 0.0909 |
| 456 | 0.000728 |
| 457 | 0.000528 |
| 455 | 0.000736 |
| 382 | 0.000573 |
| 485 | 0.0026 |
| 450 | 0.000779 |
| 451 | 0.000674 |
| 353 | 0.0393 |
| 352 | 0.107 |
| 357 | 0.141 |
| 570 | 0.00445 |
| 507 | 0.00615 |
| 571 | 0.00153 |
| 572 | 0.00111 |
| 286 | 0.00236 |
| 540 | 0.00149 |
| 347 | 0.00576 |
| 433 | 0.0265 |
| 273 | 0.0489 |
| 480 | 0.471 |
| 262 | 0.00116 |
| 481 | 0.0104 |
| 475 | 0.00344 |
| 458 | 0.00139 |
| 346 | 0.00421 |
| 317 | 0.00178 |
| 594 | 0.00256 |
| 595 | 0.00556 |
| 541 | 0.00217 |
| 542 | 0.0174 |
| 543 | 0.00116 |
| 531 | 0.148 |
| 510 | 0.0135 |
| 509 | 0.0634 |
| 296 | 0.00225 |
| 297 | 0.00725 |
| 354 | 0.305 |
| 359 | 0.148 |
| 358 | 0.201 |
| 380 | 0.00143 |
| 381 | 0.00178 |
| 486 | 0.17 |
| 459 | 0.00060 |
| 349 | 0.0609 |
| 350 | 0.269 |
| 351 | 0.114 |
| 473 | 0.0112 |
| 479 | 0.00466 |
| 474 | 0.0105 |
| 511 | 0.011 |
| 375 | 0.00107 |
| 376 | 0.000695 |
| 373 | 0.00178 |
| 374 | 0.00159 |
| 339 | 0.00108 |
| 372 | 0.00111 |
| 340 | 0.0010 |
| 513 | 0.149 |
| 371 | 0.00137 |
| 348 | 0.00296 |
| 472 | 0.0291 |
| 251 | 0.0338 |
| 487 | 0.00895 |
| 325 | 0.00177 |
| 326 | 0.00204 |
| 478 | 0.0257 |
| 265 | 0.00612 |
| 290 | 0.00142 |
| 512 | 0.0803 |
| 369 | 0.00163 |
| 370 | 0.00136 |
| 288 | 0.00161 |
| 488 | 0.00303 |
| 291 | 0.00124 |
| 289 | 0.00135 |
| 324 | 0.00101 |
| 323 | 0.00115 |
| 389 | 0.00163 |
| 50 | 0.0314 |
| 647 | 0.158 |
| 642 | 0.11 |
| 643 | 0.098 |

DATA TABLE I-continued

EGFR(T790M/L858R) Biochemical activity

| Example | EGFR(T790M/L858R) Ki (μM) |
|---|---|
| 607 | 0.00363 |
| 655 | 0.0047 |
| 608 | 0.00365 |
| 671 | 0.00622 |
| 275 | 0.0164 |
| 612 | 0.000779 |
| 613 | 0.218 |
| 656 | 0.0507 |
| 611 | 0.000792 |
| 677 | 0.0783 |
| 326 | 0.00204 |
| 614 | 0.00327 |
| 615 | 0.00365 |
| 610 | 0.0266 |
| 657 | 0.00164 |
| 694 | 0.993 |
| 658 | 0.00784 |
| 659 | 0.00354 |
| 672 | 0.0254 |
| 619 | 0.0302 |
| 637 | 0.00169 |
| 696 | 0.0101 |
| 630 | 0.0532 |
| 660 | 0.0454 |
| 673 | 0.00554 |
| 674 | 0.0254 |
| 675 | 0.0372 |
| 625 | 0.0251 |
| 697 | 0.0198 |
| 631 | 0.0767 |
| 661 | 0.0897 |
| 648 | 0.0245 |
| 649 | 0.00883 |
| 650 | 0.0153 |
| 662 | 0.00817 |
| 699 | 0.0659 |
| 641 | 0.00142 |
| 663 | 0.0122 |
| 651 | 0.0114 |
| 632 | 0.0295 |
| 698 | 0.0106 |
| 617 | 0.0143 |
| 618 | 0.0344 |
| 622 | 0.0184 |
| 623 | 0.0465 |
| 691 | 0.219 |
| 692 | 0.119 |
| 664 | 0.00617 |
| 665 | 0.00331 |
| 616 | 0.0601 |
| 653 | 0.00461 |
| 654 | 0.00524 |
| 652 | 0.864 |
| 609 | 0.00417 |
| 693 | 0.0976 |
| 624 | 0.111 |
| 626 | 0.306 |
| 627 | 0.70 |
| 633 | 0.0767 |
| 666 | 0.00318 |
| 682 | 0.0436 |
| 683 | 0.00511 |
| 636 | 0.00736 |
| 667 | 0.00336 |
| 668 | 0.345 |
| 676 | 0.00358 |
| 684 | 0.00274 |
| 695 | 0.0418 |
| 634 | 0.00828 |
| 635 | 0.00249 |
| 669 | 0.149 |
| 628 | 0.0817 |
| 629 | 0.50 |
| 685 | 0.00558 |
| 686 | 0.00577 |
| 678 | 0.141 |
| 679 | 0.112 |
| 680 | 0.297 |
| 681 | 0.165 |
| 670 | 0.193 |
| 639 | 0.00227 |
| 640 | 0.00323 |
| 687 | 0.0159 |
| 688 | 0.0208 |
| 689 | 0.0464 |
| 690 | 0.0609 |
| 620 | 0.00413 |
| 621 | 0.00518 |
| 703 | 0.00264 |
| 700 | 0.0017 |
| 705 | 0.00251 |
| 638 | 0.00435 |
| 645 | 0.0178 |
| 646 | 0.00232 |
| 704 | 0.00344 |
| 644 | 0.00165 |
| 702 | 0.0912 |
| 701 | 0.00235 |

Data Table II: EGFR(T790M/d746-750) Biochemical activity

| Example | EGFR(T790M/d746-750) Ki (μM) |
|---|---|
| 3 | 0.1270 |
| 5 | 0.0477 |
| 6 | 0.0633 |
| 8 | 0.1061 |
| 9 | 0.4175 |
| 10 | 0.0632 |
| 11 | 0.0984 |
| 12 | 0.0192 |
| 23 | 0.0350 |
| 24 | 0.0152 |
| 26 | 0.0252 |
| 46 | 0.0082 |
| 52 | 0.0018 |
| 57 | 0.0202 |
| 58 | 0.0609 |
| 59 | 0.0287 |
| 63 | 0.0101 |
| 64 | 0.0012 |
| 66 | 0.1380 |
| 85 | 0.0208 |
| 91 | 0.0035 |
| 97 | 0.0019 |
| 110 | 0.1439 |
| 111 | 0.0189 |
| 114 | 0.0021 |
| 115 | 0.0285 |
| 120 | 0.0102 |
| 121 | 0.0244 |
| 122 | 0.1001 |
| 129 | 0.0363 |
| 141 | 0.0555 |
| 163 | 0.0149 |
| 191 | 0.0547 |
| 268 | 0.00688 |
| 599 | 0.02750 |
| 508 | 0.35936 |
| 490 | 0.74638 |
| 399 | 0.01413 |
| 366 | 0.01469 |
| 401 | 0.00266 |
| 494 | 0.03040 |
| 402 | 0.00084 |

Data Table II: EGFR(T790M/d746-750) Biochemical activity

| Example | EGFR(T790M/d746-750) Ki (μM) |
|---|---|
| 337 | 0.52369 |
| 545 | 0.50089 |
| 279 | 0.00687 |
| 360 | 0.02974 |
| 272 | 0.00212 |
| 409 | 0.00197 |
| 410 | 0.00486 |
| 411 | 0.00313 |
| 365 | 0.04646 |
| 495 | 0.07175 |
| 556 | 0.00385 |
| 549 | 0.14268 |
| 280 | 0.00886 |
| 393 | 0.00112 |
| 396 | 0.00147 |
| 386 | 0.00111 |
| 331 | 0.00283 |
| 532 | 0.51878 |
| 499 | 0.05167 |
| 397 | 0.01449 |
| 258 | 0.00425 |
| 392 | 0.00141 |
| 441 | 0.00080 |
| 448 | 0.00062 |
| 427 | 0.11905 |
| 438 | 0.00106 |
| 437 | 0.00121 |
| 388 | 0.02900 |
| 467 | 0.00577 |
| 534 | 0.00561 |
| 561 | 0.00173 |
| 562 | 0.01403 |
| 563 | 0.01115 |
| 430 | 0.04774 |
| 327 | 0.00053 |
| 253 | 0.00182 |
| 435 | 0.00236 |
| 436 | 0.00118 |
| 363 | 0.03098 |
| 442 | 0.00081 |
| 312 | 0.00084 |
| 281 | 0.00237 |
| 601 | 0.05054 |
| 600 | 0.07578 |
| 525 | 0.22197 |
| 526 | 0.05046 |
| 528 | 0.04330 |
| 529 | 0.08383 |
| 527 | 0.23873 |
| 335 | 0.00228 |
| 524 | 0.05090 |
| 295 | 0.00177 |
| 503 | 0.12838 |
| 505 | 0.04283 |
| 418 | 0.16918 |
| 356 | 0.56241 |
| 385 | 0.00647 |
| 590 | 0.09346 |
| 591 | 0.05499 |
| 592 | 0.05750 |
| 593 | 0.11775 |
| 506 | 0.11710 |
| 321 | 0.00145 |
| 322 | 0.00134 |
| 383 | 0.00281 |
| 384 | 0.00539 |
| 507 | 0.02163 |
| 347 | 0.02051 |
| 433 | 0.01724 |
| 273 | 0.02370 |
| 262 | 0.00148 |
| 458 | 0.00135 |
| 346 | 0.00307 |
| 317 | 0.00297 |

| Example | EGFR(T790M/d746-750) Ki (μM) |
|---|---|
| 595 | 0.00962 |
| 542 | 0.10101 |
| 543 | 0.00581 |
| 509 | 0.34812 |
| 296 | 0.00504 |
| 297 | 0.04004 |
| 380 | 0.00696 |
| 381 | 0.00929 |
| 349 | 0.69220 |
| 375 | 0.00341 |
| 376 | 0.00288 |
| 373 | 0.00444 |
| 374 | 0.00331 |
| 339 | 0.00412 |
| 372 | 0.00108 |
| 340 | 0.00333 |
| 371 | 0.00116 |
| 348 | 0.01960 |
| 325 | 0.00335 |
| 326 | 0.00383 |
| 478 | 0.03242 |
| 265 | 0.00563 |
| 290 | 0.00465 |
| 512 | 0.13262 |
| 369 | 0.00547 |
| 370 | 0.00402 |
| 288 | 0.00400 |
| 488 | 0.00217 |
| 291 | 0.00359 |
| 289 | 0.00335 |
| 324 | 0.00239 |
| 323 | 0.00341 |
| 389 | 0.00403 |
| 607 | 0.0411 |
| 655 | 0.0608 |
| 608 | 0.0483 |
| 671 | 0.0126 |
| 656 | 0.214 |
| 611 | 0.000773 |
| 326 | 0.00383 |
| 614 | 0.00334 |
| 615 | 0.00338 |
| 610 | 0.0132 |
| 657 | 0.0174 |
| 694 | 0.709 |
| 658 | 0.0443 |
| 659 | 0.0393 |
| 672 | 0.135 |
| 619 | 0.146 |
| 637 | 0.00401 |
| 696 | 0.00767 |
| 630 | 0.202 |
| 660 | 0.171 |
| 673 | 0.0971 |
| 674 | 0.073 |
| 675 | 0.112 |
| 625 | 0.0386 |
| 697 | 0.0169 |
| 631 | 0.351 |
| 661 | 0.90 |
| 648 | 0.219 |
| 649 | 0.0435 |
| 650 | 0.092 |
| 662 | 0.0684 |
| 699 | 0.305 |
| 641 | 0.00402 |
| 663 | 0.0145 |
| 651 | 0.00914 |
| 632 | 0.326 |
| 698 | 0.00702 |
| 617 | 0.115 |
| 618 | 0.236 |
| 622 | 0.17 |
| 623 | 0.393 |

Data Table II: EGFR(T790M/d746-750) Biochemical activity

| Example | EGFR(T790M/d746-750) Ki (μM) |
|---|---|
| 691 | 0.736 |
| 692 | 0.14 |
| 664 | 0.00568 |
| 665 | 0.0115 |
| 616 | 0.483 |
| 653 | 0.0343 |
| 654 | 0.036 |
| 652 | 1.16 |
| 609 | 0.0131 |
| 693 | 0.572 |
| 624 | 0.0678 |
| 626 | 1.25 |
| 627 | 1.57 |
| 633 | 0.21 |
| 666 | 0.00726 |
| 682 | 0.135 |
| 683 | 0.0132 |
| 636 | 0.0144 |
| 667 | 0.00565 |
| 668 | 0.451 |
| 676 | 0.00818 |
| 684 | 0.00767 |
| 695 | 0.0688 |
| 634 | 0.146 |
| 635 | 0.00453 |
| 669 | 0.234 |
| 628 | 1.19 |
| 629 | 2.96 |
| 685 | 0.0266 |
| 686 | 0.0185 |
| 678 | 0.20 |
| 679 | 0.168 |
| 680 | 0.395 |
| 681 | 0.189 |
| 670 | 0.273 |
| 639 | 0.015 |
| 640 | 0.0153 |
| 687 | 0.107 |
| 688 | 0.107 |
| 689 | 0.23 |
| 690 | 0.387 |
| 650 | 0.020 |
| 621 | 0.0217 |
| 703 | 0.0025 |
| 700 | 0.00165 |
| 705 | 0.00237 |
| 638 | 0.0149 |
| 645 | 0.0687 |
| 646 | 0.00372 |
| 704 | 0.00335 |
| 644 | 0.00345 |
| 702 | 0.239 |
| 701 | 0.0044 |

H1975 pEGFR MSD Cellular Assays
Background:
These assays are intended for determining cellular. Potency of compounds to inhibit phosphor-EGFR in H1975 (L585R/T790M) mutant EGFR expressing cells is determined using the Meso Scale Discovery 384 well pEGFR Tyr1068 assay kits. (Meso Scale Discovery Catalog# N31CB-1).
Cell Culture:
NCI-H1975 (ATCC Catalog# CRL-5908) cells are maintained in medium containing RPMI 1640, 10% FBS, 4 mM L-Glutamine, 1% Penicillin-Streptomycin, and 4.5 g/L Glucose. All cell culture reagents were purchased from Invitrogen/Gibco. Cells are cultured at 37° C. at 5% $CO_2$ and split as recommended by ATCC.
Cell Plating and Serum Starvation:
H1975 cells are harvested and plated into sterile cell culture treated 384 well plates (Greiner catalog #781091) at a density of 30,000 cells/well in 50 ul culture medium and placed in a 37° C. at 5% $CO_2$ incubator for six hours. After six hours, culture medium is aspirated and replaced with serum-free culture medium. Cells are then incubated with the serum-free medium overnight at 37° C. and 5% $CO_2$.
Assay Procedure:
The following day, test compounds are serially diluted in dimethyl sulfoxide (DMSO) and added to cells in serum free medium (final DMSO concentration 0.5%). Assay plates are then incubated for 1 hour at 37° C. and 5% $CO_2$. Following 1 hour of compound incubation cells are then lysed and processed as per the MSD pEGFR assay kit protocol. Cell lysates are added to assay plates pre-coated with antibodies against phosphorylated EGFR. Phosphorylated EGFR in samples are allowed to bind to the capture antibodies overnight at 4° C. The detection antibody (anti-total EGFR, labeled with an electrochemiluminescent SULFO-TAG) is added to the bound lysate and incubated for 1 hour at room temperature. The MSD Read Buffer is added such that when a voltage is applied to the plate electrodes, the labels bound to the electrode surface emit light. The MSD Sector Instrument measures the intensity of the light, and quantitatively measures the amount of phosphorylated-EGFR in the sample. Percent inhibition of EGFR phosphorylation by varying concentrations of test compounds is calculated relative to untreated controls. $EC_{50}$ values are calculated using the 4 parameter logistic nonlinear regression dose-response model.

H1975 Proliferation Assays
Background:
This assay is intended for determining the potency of compounds H1975 (EGFR T790M/L858R) cell proliferation.
Cell Culture:
NCI-H1975 (ATCC Catalog# CRL-5908) cells are maintained in medium containing RPMI 1640, 10% FBS, 4 mM L-Glutamine, 1% Penicillin-Streptomycin, and 4.5 g/L Glucose. All cell culture reagents were purchased from Invitrogen/Gibco. Cells are cultured at 37° C. at 5% $CO_2$ and split as recommended by ATCC.
Assay Procedure:
H1975 cells are harvested and plated into sterile cell culture treated 384 well plates (Greiner catalog #781091) at a density of 1000 cells/well in 50 μL culture medium and placed in a 37° C. at 5% $CO_2$ incubator overnight. The following day, test compounds are serially diluted in dimethyl sulfoxide (DMSO) and added to cells in culture medium (final DMSO concentration 0.5%, final assay volume 50 μL). Assay plates are then incubated for 72 hour at 37° C. and 5% $CO_2$. After 72 hours, 25 μL of reconstituted Promega Cell Titer-Glo reagent (Promega Catalog# G7572) is added to all wells. Plates are then read on a Perkin Elmer Envision Multi-label plate reader using luminescence mode. Percent inhibition of proliferation by varying concentrations of test compounds is calculated relative to untreated controls. $EC_{50}$ values are calculated using the 4 parameter logistic nonlinear regression dose-response model.

Data Table III: H1975 pEGFR MSD activity

| Example | H1975 pEGFR $EC_{50}$ (μM) |
|---|---|
| 24 | 0.792 |
| 26 | 1.19 |
| 2 | 0.872 |

Data Table III: H1975 pEGFR MSD activity

| Example | H1975 pEGFR EC$_{50}$ (μM) |
| --- | --- |
| 57 | 0.236 |
| 8 | 0.585 |
| 5 | 0.871 |
| 115 | 0.71 |
| 58 | 1.41 |
| 54 | 3.57 |
| 59 | 0.583 |
| 110 | 0.623 |
| 52 | 0.254 |
| 51 | 0.181 |
| 164 | 4.71 |
| 395 | 1.34 |
| 280 | 1.74 |
| 393 | 0.0109 |
| 396 | 0.0769 |
| 445 | 0.831 |
| 378 | 0.177 |
| 534 | 1.37 |
| 327 | 0.105 |
| 565 | 1.16 |
| 312 | 0.112 |
| 282 | 0.414 |
| 529 | 0.66 |
| 335 | 0.252 |
| 256 | 1.05 |
| 271 | 5.75 |
| 295 | 0.0806 |
| 538 | 0.838 |
| 322 | 0.0609 |
| 383 | 0.0347 |
| 572 | 0.167 |
| 433 | 2.19 |
| 262 | 0.0577 |
| 475 | 1.81 |
| 543 | 0.0247 |
| 296 | 0.189 |
| 376 | 0.0145 |
| 373 | 0.0673 |
| 369 | 0.239 |

Data Table IV: H1975 Antiproliferative activity

| Example | H1975 antiproliferative EC$_{50}$ (μM) |
| --- | --- |
| 26 | 4.88 |
| 57 | 2.96 |
| 8 | 6.26 |
| 5 | 7.01 |
| 115 | 3.41 |
| 59 | 4.43 |
| 110 | 3.36 |
| 52 | 3.04 |
| 51 | 1.22 |
| 164 | 9.0 |
| 395 | 5.0 |
| 280 | 0.808 |
| 393 | 0.209 |
| 396 | 0.548 |
| 445 | 7.3 |
| 378 | 1.06 |
| 534 | 0.732 |
| 327 | 0.44 |
| 565 | 2.52 |
| 312 | 0.587 |
| 282 | 1.58 |
| 529 | 2.51 |
| 335 | 0.876 |
| 256 | 1.03 |
| 271 | 9.65 |
| 295 | 0.588 |
| 538 | 1.91 |
| 322 | 0.487 |
| 383 | 1.27 |
| 572 | 0.346 |
| 433 | 9.84 |
| 262 | 0.357 |
| 475 | 0.739 |
| 543 | 0.121 |
| 296 | 0.783 |
| 376 | 0.139 |
| 369 | 0.581 |

The invention claimed is:

1. A compound of Formula (I)

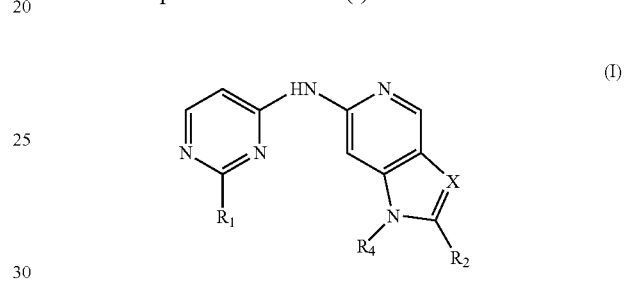

wherein,
X is CR$_3$ or N;
R$_1$ is C$_3$-C$_7$heterocycloalkyl, heteroaryl, aryl, —O(C$_1$-C$_6$alkyl), —O(C$_3$-C$_7$cycloalkyl) or —NR$_a$R$_b$, wherein said C$_3$-C$_7$heterocycloalkyl and heteroaryl may be further substituted with one to five R$_f$ groups;
R$_2$ is hydrogen, —(CH$_2$)$_m$aryl, —(CH$_2$)$_m$ heteroaryl, —(CH$_2$)$_m$C$_4$-C$_7$heterocycloalkyl, C$_1$-C$_6$alkyl, alkylamino, alkoxy or —CH$_2$O(C$_1$-C$_3$alkyl);
R$_3$ is hydrogen, C$_1$-C$_3$alkyl, CN, COOH, C$_3$-C$_7$cycloalkyl, heterocycloalkyl, —NHC(O)C$_1$-C$_6$alkyl, (CH$_2$)$_m$C(O)NR$_a$R$_b$ or heteroaryl;
R$_4$ is hydrogen, C$_3$-C$_7$heterocycloalkyl, C$_3$-C$_7$cycloalkyl, C$_1$-C$_6$alkyl, —(CH$_2$)$_m$phenyl or —(CH$_2$)$_m$heteroaryl;
wherein each R$_a$ is independently H or C$_1$-C$_6$alkyl; each R$_b$ is independently H, C$_1$-C$_6$alkyl, alkoxy, amino, —(CH$_2$)$_m$C$_3$-C$_7$cycloalkyl, —(CH$_2$)$_m$C$_3$-C$_7$heteocycloalkyl or —(CH$_2$)$_m$heteroaryl, wherein said C$_3$-C$_7$heterocycloalkyl and heteroaryl may be further substituted with one to three groups selected from the group consisting of halo, hydroxy, C$_1$-C$_3$alkyl, amino, oxo, amide, sulfonyl, sulfoxide, sulfoximinyl, alkoxy, CN and acyl; R$_a$ and R$_b$ together may form a C$_3$-C$_7$cycloalkyl, C$_3$-C$_7$heterocycloalkyl, or heteroaryl ring;
wherein each R$_f$ is independently selected from the group consisting of C$_1$-C$_3$alkyl, alkoxy, amino, hydroxyl, alkylamino, amide, urea, oxo, halo, pyrazolyl, imidazolyl, triazolyl, CN, NHC(O)(C$_1$-C$_3$alkyl), acyl, sulfonyl, sulfoxide, sulfoximinyl, sulfonamide, amide, —(CH$_2$)$_m$C$_3$-C$_7$heterocycloalkyl, —O(C$_1$-C$_6$alkyl), —C(O)OR$_a$;
each m is independently 0, 1, 2 or 3;
or a pharmaceutically acceptable salt thereof.

2. The compound of claim 1, wherein X is N; or a pharmaceutically acceptable salt thereof.

3. The compound of claim 1, wherein X is $CR_3$; or a pharmaceutically acceptable salt thereof.

4. The compound according to claim 1, wherein $R_1$ is $C_3$-$C_7$heterocycloalkyl; on a pharmaceutically acceptable salt thereof.

5. The compound according to claim 1, wherein $R_1$ is heteroaryl; or a pharmaceutically acceptable salt thereof.

6. The compound according to claim 1, wherein $R_1$ is —$NR_aR_b$; or a pharmaceutically acceptable salt thereof.

7. The compound according to claim 1, wherein $R_2$ is $C_1$-$C_6$alkyl; or a pharmaceutically acceptable salt thereof.

8. The compound according to claim 1, wherein $R_2$ is hydrogen, —$(CH_2)_m$aryl, heteroaryl, $C_4$-$C_7$heterocycloalkyl, alkylamino, alkoxy or —$(CH_2)_mO(C_1$-$C_3$alkyl); or a pharmaceutically acceptable salt thereof.

9. The compound according to claim 1, wherein $R_4$ is hydrogen or $C_1$-$C_6$alkyl.

10. The compound according to claim 1, wherein $R_3$ is hydrogen, $C_1$-$C_3$alkyl, heteroaryl or —$(CH_2)_mC(O)NR_aR_b$; or a pharmaceutically acceptable salt thereof.

11. The compound according to claim 1, wherein $R_1$ is a $C_3$-$C_7$heterocycloalkyl selected from the group consisting of piperidinyl, piperizinyl, pyrazolyl and pyrrolidinyl, wherein said $C_3$-$C_7$heterocycloalkyl may be further substituted with one to five $R_f$ groups selected from $C_1$-$C_6$alkyl, alkoxy, halo, hydroxy, sulfonyl, and sulfonamide; or a pharmaceutically acceptable salt thereof.

12. The compound according to claim 1, wherein $R_2$ is hydrogen or $C_1$-$C_3$alkyl; or a pharmaceutically acceptable salt thereof.

13. The compound according to claim 10, wherein $R_3$ is hydrogen, $C_1$-$C_3$alkyl or —$C(O)NH_2$; or a pharmaceutically acceptable salt thereof.

14. The compound according to claim 1, wherein $R_4$ is hydrogen or isopropyl; $R_f$ is F, or a pharmaceutically acceptable salt thereof.

15. A pharmaceutical composition comprising a compound according to claim 1 and a pharmaceutically acceptable carrier.

16. The compound according to claim 1, wherein said compound is:
N-(2-(4-Methoxypiperidin-1-yl)pyrimidin-4-yl)-2-(1H-pyrazol-4-yl)-1H-pyrrolo[3,2-c]pyridin-6-amine;
1-Isopropyl-N-(2-(4-methoxypiperidin-1-yl)pyrimidin-4-yl)-2-(1H-pyrazol-4-yl)-1H-pyrrolo[3,2-c]pyridin-6-amine;
(1-Isopropyl-1H-imidazo[4,5-c]pyridin-6-yl)-[2-(4-methoxypiperidin-1-yl)pyrimidin-4-yl]amine formate salt;
(2-Ethyl-1-isopropyl-1H-imidazo[4,5-c]pyridin-6-yl)-[2-(4-methoxypiperidin-1-yl)pyrimidin-4-yl]amine;
(1-Isopropyl-2-methyl-1H-imidazo[4,5-c]pyridin-6-yl)-[2-(4-methoxypiperidin-1-yl)pyrimidin-4-yl]amine;
1-Isopropyl-$N^6$-[2-(4-methoxypiperidin-1-yl)pyrimidin-4-yl]-$N^2$-methyl-1H-imidazo[4,5-c]pyridine-2,6-diamine;
[2-(2-Ethoxyethoxymethyl)-1-isopropyl-1H-imidazo[4,5-c]pyridin-6-yl]-[2-(4-methoxypiperidin-1-yl)pyrimidin-4-yl]amine;
[2-(2-Dimethylaminoethoxymethyl)-1-isopropyl-1H-imidazo[4,5-c]pyridin-6-yl]-[2-(4-methoxypiperidin-1-yl)pyrimidin-4-yl]amine;
(2-Dimethylaminomethyl-1-isopropyl-1H-imidazo[4,5-c]pyridin-6-yl)-[2-(4-methoxypiperidin-1-yl)pyrimidin-4-yl]amine formate salt;
(1-Isopropyl-6-[2-(4-methoxypiperidin-1-yl)pyrimidin-4-ylamino]-1H-imidazo[4,5-c]pyridin-2-yl)methanol;
(1-Isopropyl-2-methoxy-1H-imidazo[4,5-c]pyridin-6-yl)-[2-(4-methoxypiperidin-1-yl)pyrimidin-4-yl]amine;
(1-Isopropyl-1H-imidazo[4,5-c]pyridin-6-yl)-[2-(1,4,6,7-tetrahydropyrazolo[4,3-c]pyridin-5-yl)pyrimidin-4-yl]amine;
1-[4-(1-Isopropyl-1H-imidazo[4,5-c]pyridin-6-ylamino)pyrimidin-2-yl]piperidin-4-ol;
8-[4-(1-Isopropyl-1H-imidazo[4,5-c]pyridin-6-ylamino)pyrimidin-2-yl]-1-oxa-3,8-diazaspiro[4.5]decan-2-one;
[2-(5,6-Dihydro-8H-imidazo[1,2-a]pyrazin-7-yl)pyrimidin-4-yl]-(1-isopropyl-1H-imidazo[4,5-c]pyridin-6-yl)amine;
(1-Isopropyl-1H-imidazo[4,5-c]pyridin-6-yl)-[2-(4-methanesulfonylpiperazin-1-yl)pyrimidin-4-yl]-amine;
(1-Isopropyl-1H-imidazo[4,5-c]pyridin-6-yl)-[2-(3-methoxyazetidin-1-yl)pyrimidin-4-yl]amine;
[2-(4-Methoxypiperidin-1-yl)pyrimidin-4-yl]-[1-(tetrahydrofuran-3-yl)-1H-imidazo[4,5-c]pyridin-6-yl]amine;
[2-(4-Methoxypiperidin-1-yl)pyrimidin-4-yl]-[1-(tetrahydropyran-4-yl)-1H-imidazo[4,5-c]pyridin-6-yl]amine;
(1-Ethyl-1H-imidazo[4,5-c]pyridin-6-yl)-[2-(4-methoxypiperidin-1-yl)pyrimidin-4-yl]amine;
[2-(4-Methoxypiperidin-1-yl)pyrimidin-4-yl]-[1-methyl-2-(1H-pyrazol-4-yl)-1H-imidazo[4,5-c]pyridin-6-yl]amine;
[2-(2-Fluorobenzyl)-3-methyl-3H-imidazo[4,5-c]pyridin-6-yl]-[2-(4-methoxypiperidin-1-yl)pyrimidin-4-yl]amine;
[2-(4-Methoxypiperidin-1-yl)pyrimidin-4-yl]-[2-(1H-pyrazol-4-yl)-3H-imidazo[4,5-c]pyridin-6-yl]amine;
(1-Cyclopentyl-1H-pyrrolo[3,2-c]pyridin-6-yl)-[2-(4-methoxypiperidin-1-yl)pyrimidin-4-yl]amine;
[2-(4-Methoxypiperidin-1-yl)pyrimidin-4-yl]-[3-methyl-2-(1 H-pyrazol-4-yl)-3H-imidazo[4,5-c]pyridin-6-yl]amine dihydrochloride;
(1-Cyclopentyl-1H-imidazo[4,5-c]pyridin-6-yl)-[2-(4-methoxy-piperidin-1-yl)-pyrimidin-4-yl]amine;
(1-Isopropyl-1H-imidazo[4,5-c]pyridin-6-yl)-[2-(1-methanesulfonyl-1,2,3,6-tetrahydropyridin-4-yl)pyrimidin-4-yl]amine;
(1-Isopropyl-1H-imidazo[4,5-c]pyridin-6-yl)-(2-morpholin-4-ylpyrimidin-4-yl)amine;
4-(4-((1-isopropyl-1H-imidazo[4,5-c]pyridin-6-yl)amino)pyrimidin-2-yl)thiomorpholine 1-oxide;
4-(4-((1-isopropyl-1H-imidazo[4,5-c]pyridin-6-yl)amino)pyrimidin-2-yl)thiomorpholine 1,1-dioxide;
3-{6-[2-(4-Methoxypiperidin-1-yl)pyrimidin-4-ylamino]pyrrolo[3,2-c]pyridin-1-yl}-2,2-dimethylpropionamide;
((R) or (S) 1-sec-Butyl-1H-imidazo[4,5-c]pyridin-6-yl)-[2-(4-methoxypiperidin-1-yl)pyrimidin-4-yl]amine;
1-[4-(1-Isopropyl-2-methyl-1H-imidazo[4,5-c]pyridin-6-ylamino)pyrimidin-2-yl]piperidine-3,4-diol;
N-(2-(8-Oxa-3-aza-bicyclo[3.2.1]octan-3-yl)pyrimidin-4-yl)-1-isopropyl-l H imidazo[4,5-c]pyridin-6-amine;
(R or S)—N-(2-2-oxa-7-azaspiro[4.4]nonan-7-yl)pyrimidin-4-yl)-1-isopropyl-1H-imidazo[4,5-c]pyridin-6-amine;
1-Isopropyl-N-(2-(6-(methylsulfonyl)-2,6-diazaspiro[3.3]heptan-2-yl)pyrimidin-4-yl)-1H-imidazo[4,5-c]pyridin-6-amine;
$N^4$-(1-isopropyl-1H-imidazo[4,5-c]pyridin-6-yl)-N2-(2-(methylsulfonyl)ethyl)pyrimidine-2,4-diamine;
$N^4$-(1-Isopropyl-1H-imidazo[4,5-c]pyridin-6-yl)-$N^2$-(1-methyl-1H-pyrazol-4-yl)pyrimidine-2,4-diamine;

1-Isopropyl-N-(2-(4-methoxypiperidin-1-yl)pyrimidin-4-yl)-2-(trifluoromethyl)-1H-imidazo[4,5-c]pyridin-6-amine;
$N^4$-(1-Isopropyl-1H-imidazo[4,5-c]pyridin-6-yl)-$N^2$-(1H-pyrazol-4-yl)pyrimidine-2,4-diamine;
1-Isopropyl-N-(2-(4-(trifluoromethoxy)piperidin-1-yl)pyrimidin-4-yl)-1H-imidazo[4,5-c]pyridin-6-amine;
N-(2-((1R,5S,6s)-6-Amino-3-azabicyclo[3.1.0]hexan-3-yl)pyrimidin-4-yl)-1-isopropyl-1H-imidazo[4,5-c]pyridin-6-amine;
1-Isopropyl-N-(2-((1R,5S,6s)-6-(methylamino)-3-azabicyclo[3.1.0]hexan-3-yl)pyrimidin-4-yl)-1H-imidazo[4,5-c]pyridin-6-amine;
N-(2-(6,7-Dihydro-1H-pyrazolo[4,3-c]pyridin-5(4H)-yl)pyrimidin-4-yl)-1-isopropyl-2-methyl-1H-imidazo[4,5-c]pyridin-6-amine;
((1R,5 S,6r)-3-(4-((1-isopropyl-1H-imidazo[4,5-c]pyridin-6-yl)amino)pyrimidin-2-yl)-3-azabicyclo[(3.1.0] hexan-6-yl)methanol;
1-isopropyl-N-(2-((I R,5S,6r)-6-(methoxymethyl)-3-azabicyclo[3.1.0]hexan-3-yl)pyrimidin-4-yl)-1H-imidazo[4,5-c]pyridin-6-amine;
$N^2$-(1-Benzyl-1H-pyrazol-3-yl)-N4-(1-isopropyl-1H-imidazo[4,5-c]pyridin-6-yl)pyrimidine-2,4-diamine;
3-((4-((1-Isopropyl-2-methyl-1H-imidazo[4,5-c]pyridin-6-yl)amino)pyrimidin-2-yl)amino)tetrahydrothiophene 1,1-dioxide;
6-((2-(1-(Cyclopropylsulfonyl)-1H-pyrazol-4-yl)pyrimidin-4-yl)amino)-1-isopropyl-1H-pyrrolo[3,2-c]pyridine-3-carboxamide; or
N-(2-(1-(Cyclopropylsulfonyl)-1H-pyrazol-4-yl)pyrimidin-4-yl)-1-isopropyl-2-methyl-1H-imidazo[4,5-c]pyridin-6-amine.

17. The compound according to claim 1, wherein said compound is:

1-Isopropyl-N-(2-(4-methoxyphenyl)pyrimidin-4-yl)-1H-imidazo[4,5-c]pyridin-6-amine;
1-Isopropyl-N-(2-(6-methoxypyridin-3-yl)pyrimidin-4-yl)-1H-imidazo[4,5-c]pyridin-6-amine;
N-(2'-Ethoxy-[2,5'-bipyrimidin]-4-yl)-1-isopropyl-1H-imidazo[4,5-c]pyridin-6-amine;
N-(2-(4-Isopropoxypiperidin-1-yl)pyrimidin-4-yl)-1-isopropyl-1H-imidazo[4,5-c]pyridin-6-amine;
N-Ethyl-1-isopropyl-6-((2-(4-methoxypiperidin-1-yl)pyrimidin-4-yl)amino)-1H-pyrrolo[3,2-c]pyridine-3-carboxamide;
1-Isopropyl-6-((2-(4-methoxypiperidin-1-yl)pyrimidin-4-yl)amino)-1H-pyrrolo[3,2-c]pyridine-3-carbonitrile;
1-Isopropyl-N-(2-(4-methoxypiperidin-1-yl)pyrimidin-4-yl)-3-(5-methyl-1,3,4-oxadiazol-2-yl)-1H-pyrrolo[3,2-c]pyridin-6-amine;
6-((2-(6,7-Dihydro-1H-pyrazolo[4,3-c]pyridin-5(4H)-yl)pyrimidin-4-yl)amino)-1-isopropyl-1H-pyrrolo[3,2-c]pyridine-3-carboxamide;
1-(4-((1-Isopropyl-2-methyl-1H-imidazo[4,5-c]pyridin-6-yl)amino)pyrimidin-2-yl)-N-methyl-1H-imidazole-4-carboxamide;
5-(4-((1-Isopropyl-1H-imidazo[4,5-c]pyridin-6-yl)amino)pyrimidin-2-yl)pyridin-2-ol;
N-(2-(1H-Imidazol-1-yl)ethyl)-1-isopropyl6(2-(4-methoxypiperidin-1-yl)pyrimidin-4-ylamino)-1H-pyrrolo[3,2-c]pyridine-3-carboxamide;
N-Ethyl-1-isopropyl-6-((2-(4-methoxypiperidin-1-yl)pyrimidin-4-yl)amino)-1H-pyrrolo[3,2-c]pyridine-3-carboxamide;
1-isopropyl-N-(2-(3-methoxypyrrolidin-1-yl)pyrimidin-4-yl)-1H-imidazo[4,5-c]pyridin-6-amine;
1-(4-(1-isopropyl-1H-imidazo[4,5-c]pyridin-6-ylamino) pyrimidin-2-yl)piperidine-3-carboxamide;
N-(1-(4-(1-isopropyl-1H-imidazo[4,5-c]pyridin-6-ylamino) pyrimidin-2-yl)azetidin-3-yl)acetamide;
1-(5-(4-(1-isopropyl-1H-imidazo[4,5-c]pyridin-6-ylamino) pyrimidin-2-yl)-hexahydropyrrolo[3,4-c]pyrrol-2(1H)-yl)ethanone;
1-isopropyl-N-(2-(5-(methylsulfonyl)-hexahydropyrrolo [3,4-c]pyrrol-2(1H)-yl) pyrimidin-4-yl)-1H-imidazo[4,5-c]pyridin-6-amine;
4-(4-(1-isopropyl-1H-imidazo[4,5-c]pyridin-6-ylamino) pyrimidin-2-yl)piperazine-1-carboxamide;
1-isopropyl-N-(2-(7-(methylsulfonyl)-2,7-diazaspiro[4.4] nonan-2-yl)pyrimidin-4-yl)-1H-imidazo[4,5-c]pyridin-6-amine;
1-isopropyl-N-(2-(3-methoxypiperidin-1-yl)pyrimidin-4-yl)-1H-imidazo[4,5-c]pyridin-6-amine;
1-(1-(4-(1-isopropyl-1H-imidazo[4,5-c]pyridin-6-ylamino)pyrimidin-2-yl)piperidin-4-yl)urea;
1-(4-(1-isopropyl-1H-imidazo[4,5-c]pyridin-6-ylamino) pyrimidin-2-yl)-4-methylpiperidine-4-carboxamide;
N-(1-(4-(1-isopropyl-1H-imidazo[4, 5-c]pyridin-6-ylamino)pyrimidin-2-yl)azetidin-3-yl)methanesulfonamide;
1-(1-(4-(1-isopropyl-1H-imidazo[4,5-c]pyridin-6-ylamino)pyrimidin-2-yl)azetidin-3-yl)urea;
1-(4-(1-isopropyl-1H-imidazo[4,5-c]pyridin-6-ylamino) pyrimidin-2-yl)pyrrolidine-3-carboxamide;
N-(1-(4-(1-isopropyl-1H-imidazo[4,5-c]pyridin-6-ylamino)pyrimidin-2-yl)piperidin-4-yl)methanesulfonamide;
N-(2-(3-aminoazetidin-1-yl)pyrimidin-4-yl)-1-isopropyl-1H-imidazo[4,5-c]pyridin-6-amine;
1-(4-(1-isopropyl-1H-imidazo[4,5-c]pyridin-6-ylamino) pyrimidin-2-yl)-N,N-dimethylpyrrolidine-3-carboxamide;
1-isopropyl-N-(2-(4-(oxetan-3-yl)piperazin-1-yl)pyrimidin-4-yl)-1H-imidazo[4,5-c]pyridin-6-amine;
N4-(1-isopropyl-1H-imidazo[4,5-c]pyridin-6-yl)-N2-(3-methoxypropyl)pyrimidine-2,4-diamine;
4-(4-(1-isopropyl-1H-imidazo[4,5-c]pyridin-6-ylamino) pyrimidin-2-yl)-1-methylpiperazine-2-carboxamide;
N4-(1-isopropyl-1H-imidazo[4,5-c]pyridin-6-yl)-2,5'-bipyrimidine-2',4-diamine;
3-(4-(1-isopropyl-1H-imidazo[4,5-c]pyridin-6-ylamino) pyrimidin-2-ylamino)-2,2-dimethylpropanamide;
3-(4-(1-isopropyl-1H-imidazo[4,5-c]pyridin-6-ylamino) pyrimidin-2-yloxy)propan-1-ol;
7-(4-(1-isopropyl-1H-imidazo[4,5-c]pyridin-6-ylamino) pyrimidin-2-yl)-tetrahydro-1H-oxazolo[3,4-a]pyrazin-3(5H)-one;
2-(1-(4-(1-isopropyl-1H-imidazo[4,5-c]pyridin-6-ylamino)pyrimidin-2-yl)piperidin-4-yloxy)acetamide;
3-(4-(1-isopropyl-1H-imidazo[4,5-c]pyridin-6-ylamino) pyrimidin-2-ylamino)propanamide;
3-(4-(1-isopropyl-1H-imidazo[4,5-c]pyridin-6-ylamino) pyrimidin-2-yloxy)-2,2-dimethylpropan-1-ol;
1-isopropyl-2-methyl-N-(2-(1-(methylsulfonyl)-1H-pyrazol-4-yl)pyrimidin-4-yl)-1H-imidazo[4,5-c]pyridin-6-amine;
1-isopropyl-2-methyl-N-(2-(3-(methylsulfonyl)phenyl) pyrimidin-4-yl)-1H-imidazo[4,5-c]pyridin-6-amine;
1-isopropyl-N-(2-(1-((2-methoxyethyl)sulfonyl)-1H-pyrazol-4-yl)pyrimidin-4-yl)-2-methyl-1H-imidazo[4, 5-c]pyridin-6-amine;
4-((1-isopropyl-1H-imidazo[4,5-c]pyridin-6-yl)amino)-[2,5'-bipyrimidin]-2'-ol;

2-(4-(4-((1-isopropyl-1H-imidazo[4,5-c]pyridin-6-yl)
amino)pyrimidin-2-yl)-1H-pyrazol-1-yl)ethanol;

N-(2-(1H-pyrazol-4-yl)pyrimidin-4-yl)-1-isopropyl-1H-
imidazo[4,5-c]pyridin-6-amine;

N-(2-(1-(cyclopropylsulfonyl)-1H-pyrazol-4-yl)pyrimi-
din-4-yl)-1-isopropyl-1H-imidazo[4,5-c]pyridin-6-
amine;

1-isopropyl-N-(2-(1-isopropyl-1H-pyrazol-4-yl)pyrimi-
din-4-yl)-1H-imidazo[4,5-c]pyridin-6-amine;

1-isopropyl-N-(2'-methoxy-[2,5'-bipyrimidin]-4-yl)-1H-
imidazo[4,5-c]pyridin-6-amine;

N-(2-(4-ethoxypiperidin-1-yl)pyrimidin-4-yl)-1-isopro-
pyl-1H-imidazo[4,5-c]pyridin-6-amine;

N-(2-(1-oxa-7-azaspiro[4.4]nonan-7-yl)pyrimidin-4-yl)-
1-isopropyl-1H-imidazo[4,5-c]pyridin-6-amine; or N-(2-(7-oxa-2-azaspiro[3.5]nonan-2-yl)pyrimidin-4-yl)-
1-isopropyl-1H-imidazo[4,5-c]pyridin-6-amine.

18. The compound according to claim 1, wherein said compound is:

1-isopropyl-N-(2-(3-(methylsulfonyl)pyrrolidin-1-yl)py-
rimidin-4-yl)-1H-imidazo[4,5-c]pyridin-6-amine;

3-((4-((1-isopropyl-1H-imidazo[4,5-c]pyridin-6-yl)
amino)pyrimidin-2-yl)amino)tetrahydro-2H-thiopyran
1,1-dioxide;

N-(2-(2-oxa-6-azaspiro[3.4]octan-6-yl)pyrimidin-4-yl)-
1-isopropyl-1H-imidazo[4,5-c]pyridin-6-amine;

3-((4-((1-isopropyl-1H-imidazo[4,5-c]pyridin-6-yl)
amino)pyrimidin-2-yl)amino)cyclobutanol;

3-((4-((1-isopropyl-1H-imidazo[4,5-c]pyridin-6-yl)
amino)pyrimidin-2-yl)amino)tetrahydrothiophene 1,1-
dioxide;

2-(difluoromethyl)-1-isopropyl-N-(2-(4-methoxypiperi-
din-1-yl)pyrimidin-4-yl)-1H-imidazo[4,5-c]pyridin-6-
amine;

N-(2-(7,7-dimethyl-6,7-dihydro-1H-pyrazolo[4,3-c]pyri-
din-5(4H)-yl)pyrimidin-4-yl)-1-isopropyl-2-methyl-
1H-imidazo[4,5-c]pyridin-6-amine;

2-((4-((1-isopropyl-1H-imidazo[4,5-c]pyridin-6-yl)
amino)pyrimidin-2-yl)amino)-N-methyl ethanesulfo-
namide;

3-((4-((1-isopropyl-2-methyl-1H-imidazo[4,5-c]pyridin-
6-yl)amino)pyrimidin-2-yl)amino)-2,2-dimethylpro-
panamide;

1-isopropyl-6-((2-(4-methoxypiperidin-1-yl)pyrimidin-4-
yl)amino)-N-(1-methylpiperidin-4-yl)-1H-pyrrolo[3,2-
c]pyridine-3-carboxamide;

1-isopropyl-6-((2-(4-methoxypiperidin-1-yl)pyrimidin-4-
yl)amino)-1H-pyrrolo[3,2-c]pyridine-3-carboxamide;

1-isopropyl-6-((2-(4-methoxypiperidin-1-yl)pyrimidin-4-
yl)amino)-1H-pyrrolo[3,2-c]pyridine-3-carboxylic
acid;

1-isopropyl-6-((2-(4-methoxypiperidin-1-yl)pyrimidin-4-
yl)amino)-N-(tetrahydro-2H-pyran-4-yl)-1H-pyrrolo
[3,2-c]pyridine-3-carboxamide;

(1-isopropyl-6-((2-(4-methoxypiperidin-1-yl)pyrimidin-
4-yl)amino)-1H-pyrrolo[3,2-c]pyridin-3-yl)(mor-
pholino)methanone;

(1-isopropyl-6-((2-(4-methoxypiperidin-1-yl)pyrimidin-
4-yl)amino)-1H-pyrrolo[3,2-c]pyridin-3-yl)(pyrroli-
din-1-yl)methanone;

N,1-diisopropyl-6-((2-(4-methoxypiperidin-1-yl)pyrimi-
din-4-yl)amino)-1H-pyrrolo[3,2-c]pyridine-3-carbox-
amide;

N-(2-hydroxyethyl)-1-isopropyl-6-((2-(4-methoxypiperi-
din-1-yl)pyrimidin-4-yl)amino)-1H-pyrrolo[3,2-c]
pyridine-3-carboxamide;

(4-ethylpiperazin-1-yl)(1-isopropyl-6-((2-(4-methoxypi-
peridin-1-yl)pyrimidin-4-yl)amino)-1H-pyrrolo[3,2-c]
pyridin-3-yl)methanone;

6-((2-(4-ethoxypiperidin-1-yl)pyrimidin-4-yl)amino)-1-
isopropyl-1H-pyrrolo[3,2-c]pyridine-3-carboxamide;

6-((2-(4-isopropoxypiperidin-1-yl)pyrimidin-4-yl)
amino)-1-isopropyl-1H-pyrrolo[3,2-c]pyridine-3-car-
boxamide;

6-((2-(4-cyclopropoxypiperidin-1-yl)pyrimidin-4-yl)
amino)-1-isopropyl-1H-pyrrolo[3,2-c]pyridine-3-car-
boxamide;

6-((2-(((1,1-dioxidotetrahydrothiophen-3-yl)amino)py-
rimidin-4-yl)amino)-1-isopropyl-1H-pyrrolo[3,2-c]
pyridine-3-carboxamide;

2-{[4-(1-Isopropyl-1H-pyrrolo[3,2-c]pyridin-6-ylamino)
pyrimidin-2-yl]methylamino}ethanol;

2-{Methyl-[4-(1-phenyl-1H-pyrrolo[3,2-c]pyridin-6-
ylamino)pyrimidin-2-yl]amino}ethanol;

(1-Isopropyl-1H-pyrrolo[3,2-c]pyridin-6-yl)-[2-(4-
methoxypiperidin-1-yl)pyrimidin-4-yl]amine formate
salt;

(1-Isopropyl-1H-imidazo[4,5-c]pyridin-6-yl)-(2-piperi-
din-1-yl-pyrimidin-4-yl)amine;

1-[4-(1-Isopropyl-1H-imidazo[4,5-c]pyridin-6-ylamino)
pyrimidin-2-yl]piperidine-4-carboxylic acid amide;

4-[4-(1-Isopropyl-1H-imidazo[4,5-c]pyridin-6-ylamino)
pyrimidin-2-yl]piperazin-2-one;

(1-Isopropyl-1H-imidazo[4,5-c]pyridin-6-yl)-[2-(4-pyra-
zol-1-ylpiperidin-1-yl)pyrimidin-4-yl]amine;

[2-(4-Imidazol-1-yl-piperidin-1-yl)pyrimidin-4-yl]-(1-
isopropyl-1H-imidazo[4,5-c]pyridin-6-yl)amine;

(1-Isopropyl-1H-imidazo[4,5-c]pyridin-6-yl)-[2-(4-[1,2,
4]triazol-1-ylpiperidin-1-yl)pyrimidin-4-yl]amine;

(1-Isopropyl-1H-imidazo[4,5-c]pyridin-6-yl)-(2-[1,2]ox-
azinan-2-ylpyrimidin-4-yl)amine;

(1-Isopropyl-1H-imidazo[4,5-c]pyridin-6-yl)-(2-thiomor-
pholin-4-ylpyrimidin-4-yl)amine;

{1-[4-(1-isopropyl-1H-imidazo[4,5-c]pyridin-6-ylamino)
pyrimidin-2-yl]piperidin-4-
ylmethyl}dimethylammonium formate;

2-{1-[4-(1-Isopropyl-1H-imidazo[4,5-c]pyridin-6-
ylamino)pyrimidin-2-yl]piperidin-4-yl}ethanol;

2-{[4-(1-Cyclopentyl-1H-pyrrolo[3,2-c]pyridin-6-
ylamino)pyrimidin-2-yl]methylamino}ethanol formate
salt;

(1-Isopropyl-1H-imidazo[4,5-c]pyridin-6-yl)-[2-(1-oxa-
8-azaspiro[4.5]dec-8-yl)pyrimidin-4-yl]amine formate
salt;

1-{4-[4-(1-Isopropyl-1H-imidazo[4,5-c]pyridin-6-
ylamino)pyrimidin-2-yl]piperazin-1-yl}ethanone for-
mate salt;

2-{1-[4-(1-Isopropyl-1H-imidazo[4,5-c]pyridin-6-
ylamino)-pyrimidin-2-yl]-piperidin-4-yl}-propan-2-ol;

(1-Isopropyl-1H-imidazo[4,5-c]pyridin-6-yl)-[2-(4-
methoxy-4-methylpiperidin-1-yl)pyrimidin-4-yl]
amine;

1-[4(1-Isopropyl-1H-imidazo[4,5-c]pyridin-6-ylamino)
pyrimidin-2-yl]azetidine-3-carbonitrile;

1-[4-(1-Isopropyl-1H-imidazo[4,5-c]pyridin-6-ylamino)
pyrimidin-2-yl]azetidin-3-ol;

N4-(1-Isopropyl-1H-imidazo[4,5-c]pyridin-6-yl)-N2-
(R)-tetrahydrofuran-3-ylpyrimidine-2,4-diamine;

1-[4-(1-Isopropyl-1H-imidazo[4,5-c]pyridin-6-ylamino)
pyrimidin-2-yl]piperidine-4-carbonitrile;

[2-(4-Methoxypiperidin-1-yl)-pyrimidin-4-yl]-[1-(2,2,2-
trifluoroethyl)-1H-imidazo[4,5-c]pyridin-6-yl]amine
formate salt;

(1-Cyclopropyl-1H-imidazo[4,5-c]pyridin-6-yl)-[2-(4-methoxypiperidin-1-yl)pyrimidin-4-yl]amine formate salt;
(1-Cyclobutyl-1H-imidazo[4,5-c]pyridin-6-yl)-[2-(4-methoxypiperidin-1-yl)pyrimidin-4-yl]amine formate salt;
(1-Cyclohexyl-1H-imidazo[4,5-c]pyridin-6-yl)-[2-(4-methoxypiperidin-1-yl)pyrimidin-4-yl]amine;
±(1-sec-butyl-1H-imidazo[4,5-c]pyridin-6-yl)-[2-(4-methoxypiperidin-1-yl)pyrimidin-4-yl]amine; or
(1-Isopropyl-1H-imidazo[4,5-c]pyridin-6-yl)-[2-(1,4,6,7-tetrahydroimidazo[4,5-c]pyridin-5-yl)pyrimidin-4-yl]amine.

19. The compound according to claim 1, wherein said compound is:
{2-[4-(1,1-Dioxo-1lambda6-isothiazolidin-2-yl)piperidin-1-yl]pyrimidin-4-yl}-(1-isopropyl-1H-imidazo[4,5-c]pyridin-6-yl)amine formate salt;
(1-Isopropyl-1H-imidazo[4,5-c]pyridin-6-yl)-{2-[4-(2-methoxyethoxy)piperidin-1-yl]pyrimidin-4-yl}amine;
[2-(4-Methoxypiperidin-1-yl)pyrimidin-4-yl]-[1-(2,2,2-trifluoro-1-methylethyl)-1H-imidazo[4,5-c]pyridin-6-yl]amine formate salt;
2-{1-[4-(1-Isopropyl-1H-imidazo[4,5-c]pyridin-6-ylamino)pyrimidin-2-yl]piperidin-4-yl}isobutyramide;
(1-Isopropyl-1H-imidazo[4,5-c]pyridin-6-yl)-[2-(3-methyl-3,4,6,7-tetrahydroimidazo[4,5-c]pyridin-5-yl)pyrimidin-4-yl]amine;
[2-(3,6-Dihydro-2H-pyridin-1-yl)-pyrimidin-4-yl]-(1-isopropyl-2-methyl-1H-imidazo[4,5-c]pyridin-6-yl)amine;
{2-[4-(2-Dimethylaminoethoxy)piperidin-1-yl]pyrimidin-4-yl}-(1-isopropyl-1H-imidazo[4,5-c]pyridin-6-yl)amine;
{2-[4-(2-Dimethylaminoethyl)-piperidin-1-yl]pyrimidin-4-yl}-(1-isopropyl-1H-imidazo[4,5-c]pyridin-6-yl)amine;
(1-tert-butyl-2-methyl-1H-imidazo[4,5-c]pyridin-6-yl)-[2-(4-methoxypiperidin-1-yl)pyrimidin-4-yl]amine;
[1-(2-Methoxy-1,1-dimethylethyl)-2-methyl-1H-imidazo[4,5-c]pyridin-6-yl]-[2-(4-methoxypiperidin-1-yl)pyrimidin-4-yl]amine;
(1-Isopropyl-1H-imidazo[4,5-c]pyridin-6-yl)-[2-(1-methanesulfonylpiperidin-4-yl)pyrimidin-4-yl]amine;
1-((4-(1-isopropyl-1H-imidazo[4,5-c]pyridin-6-yl)amino)pyrimidin-2-yl)amino)-2-methylpropan-2-ol;
N2-(cyclopropylmethyl)-N4-(1-isopropyl-1H-imidazo[4,5-c]pyridin-6-yl)pyrimidine-2,4-diamine;
1-(4-((1-isopropyl-1H-imidazo[4,5-c]pyridin-6-yl)amino)pyrimidin-2-yl)piperidin-3-ol;
4-(4-((1-isopropyl-1H-imidazo[4,5-c]pyridin-6-yl)amino)pyrimidin-2-yl)morpholine-2-carboxamide;
N-(2-(hexahydro-1H-pyrido[1,2-a]pyrazin-2(6H)-yl)pyrimidin-4-yl)-1-isopropyl-1H-imidazo[4,5-c]pyridin-6-amine;
4-(4-((1-isopropyl-1H-imidazo[4,5-c]pyridin-6-yl)amino)pyrimidin-2-yl)-1,4-diazepan-2-one;
2-(4-(4-((1-isopropyl-1H-imidazo[4,5-c]pyridin-6-yl)amino)pyrimidin-2-yl)piperazin-1-yl)ethanol;
N4-(1-isopropyl-1H-imidazo[4,5-c]pyridin-6-yl)-N2-methyl-N2-((tetrahydrofuran-2-yl)$_m$ethyl)pyrimidine-2,4-diamine;
1-isopropyl-N-(2-(4-(2-methoxyethyl)piperazin-1-yl)pyrimidin-4-yl)-1H-imidazo[4,5-c]pyridin-6-amine;
3-((4-((1-isopropyl-1H-imidazo[4,5-c]pyridin-6-yl)amino)pyrimidin-2-yl)amino)cyclohexanol;
N-(2-(2-azabicyclo[2.1.1]hexan-2-yl)pyrimidin-4-yl)-1-isopropyl-1H-imidazo[4,5-c]pyridin-6-amine;
1-((1-(4-((1-isopropyl-1H-imidazo[4,5-c]pyridin-6-yl)amino)pyrimidin-2-yl)piperidin-4-yl)methyl)pyrrolidin-2-one;
1-(4-((4-((1-isopropyl-1H-imidazo[4,5-c]pyridin-6-yl)amino)pyrimidin-2-yl)amino)piperidin-1-yl)ethanone;
4-(4-((1-isopropyl-1H-imidazo[4,5-c]pyridin-6-yl)amino)pyrimidin-2-yl)-N,2-dimethylmorpholine-2-carboxamide;
tert-butyl 4-(4-((1-isopropyl-1H-imidazo[4,5-c]pyridin-6-yl)amino)pyrimidin-2-yl)-2-methylpiperazine-1-carboxylate;
tert-butyl 4-(4-((1-isopropyl-1H-imidazo[4,5-c]pyridin-6-yl)amino)pyrimidin-2-yl)piperazine-1-carboxylate;
1-isopropyl-N-(2-(7-methoxy-2-azabicyclo[2.2.1]heptan-2-yl)pyrimidin-4-yl)-1H-imidazo[4,5-c]pyridin-6-amine;
1-(4-((1-isopropyl-1H-imidazo[4,5-c]pyridin-6-yl)amino)pyrimidin-2-yl)-N-methylpyrrolidine-3-carboxamide;
1-(4-4-((1-isopropyl-1H-imidazo[4, 5-c]pyridine-6-yl)amino)pyrimidin-2-yl)-1,4-diazepan-1-yl)ethanone;
N-(2-3,3-difluoropyrrolidin-1-yl)pyrimidin-4-yl)-1-isopropyl-1H-imidazo[4,5-c]pyridine-6-amine;
3-(4-((1-isopropyl-1H-imidazo[4,5-c]pyridine-6-yl)amino)pyrimidin-2-yl)-3-azabicyclo[3.1.0]hexane-6-carboxamide;
(1-(4-((1-isopropyl-1H-imidazo[4,5-c]pyridin-6-yl)amino)pyrimidin-2-yl)piperidin-4-yl)methanol;
N-(2-(5-oxa-2-azaspiro[3.5]nonan-2-yl)pyrimidin-4-yl)-1-isopropyl-1H-imidazo[4,5-c]pyridin-6-amine;
N-(2-(4-cyclopropylpiperazin-1-yl)pyrimidin-4-yl)-1-isopropyl-1H-imidazo[4,5-c]pyridin-6-amine;
N-(2-(3,4-difluoropyrrolidin-1-yl)pyrimidin-4-yl)-1-isopropyl-1H-imidazo[4,5-c]pyridin-6-amine;
N-(2-(5-fluoro-2-azabicyclo[2.2.1]heptan-2-yl)pyrimidin-4-yl)-1-isopropyl-1H-imidazo[4,5-c]pyridin-6-amine;
7-(4-((1-isopropyl-1H-imidazo[4,5-c]pyridin-6-yl)amino)pyrimidin-2-yl)-2,7-diazaspiro[4.4]nonan-1-one;
N4-(1-isopropyl-1H-imidazo[4,5-c]pyridin-6-yl)-N2-(2-methoxy-2-methylpropyl)pyrimidine-2,4-diamine;
N-(2-(hexahydrofuro[3,2-c]pyridin-5(6H)-yl)pyrimidin-4-yl)-1-isopropyl-1H-imidazo[4,5-c]pyridin-6-amine;
N-(2-(hexahydrofuro[3,4-c]pyridin-5(3H)-yl)pyrimidin-4-yl)-1-isopropyl-1H-imidazo[4,5-c]pyridin-6-amine;
3-(4-((1-isopropyl-1H-imidazo[4,5-c]pyridin-6-yl)amino)pyrimidin-2-yl)-N-methyl-3-azabicyclo[3.1.0]hexane-6-carboxamide;
1-(4-((1-isopropyl-1H-imidazo[4,5-c]pyridin-6-yl)amino)pyrimidin-2-yl)-N-methylazetidine-3-carboxamide;
(1-(4-((1-isopropyl-1H-imidazo[4,5-c]pyridin-6-yl)amino)pyrimidin-2-yl)azetidin-3-yl)(morpholino)methanone;
2-(1-(4-((1-isopropyl-1H-imidazo[4,5-c]pyridin-6-yl)amino)pyrimidin-2-yl)piperidin-4-yl)-N,N-dimethylacetamide;
1-(4-((1-isopropyl-1H-imidazo[4,5-c]pyridin-6-yl)amino)pyrimidin-2-yl)azepan-4-ol;
tert-butyl (1-(4-((1-isopropyl-1H-imidazo[4,5-c]pyridin-6-yl)amino)pyrimidin-2-yl)pyrrolidin-3-yl)(methyl)carbamate;

1-(4-((1-isopropyl-1H-imidazo[4,5-c]pyridin-6-yl)
amino)pyrimidin-2-yl)-N,4-dimethylpiperidine-4-carboxamide;

(1-(4-((1-isopropyl-1H-imidazo[4,5-c]pyridin-6-yl)
amino)pyrimidin-2-yl)pyrrolidin-2-yl)methanol;

N2-((1-ethylpyrrolidin-3-yl)methyl)-N4-(1-isopropyl-1H-imidazo[4,5-c]pyridin-6-yl)-N2-methylpyrimidine-2,4-diamine; or N-(2-(hexahydropyrrolo[1,2-a]pyrazin-2(1H)-yl)pyrimidin-4-yl)-1-isopropyl-1H-imidazo[4,5-c]pyridin-6-amine.

20. The compound according to claim 1, wherein said compound is:

N4-(1-isopropyl-1H-imidazo[4,5-c]pyridin-6-yl)-N2-((tetrahydro-2H-pyran-3-yl)methyl)pyrimidine-2,4-diamine;

N-(2-(4-(2-(dimethylamino)ethyl)piperazin-1-yl)pyrimidin-4-yl)-1-isopropyl-1H-imidazo[4,5-c]pyridin-6-amine;

N4-(1-isopropyl-1H-imidazo[4,5-c]pyridin-6-yl)-N2-((tetrahydro-2H-pyran-4-yl)methyl)pyrimidine-2,4-diamine;

1-(4-((1-isopropyl-1H-imidazo[4,5-c]pyridin-6-yl)
amino)pyrimidin-2-yl)-4-methylpyrrolidin-3-ol;

N4-(1-isopropyl-1H-imidazo[4,5-c]pyridin-6-yl)-N2-(2-(4-methylpiperidin-1-yl)ethyl)pyrimidine-2,4-diamine;

N-(2-(2,6-dioxa-9-azaspiro[4.5]decan-9-yl)pyrimidin-4-yl)-1-isopropyl-1H-imidazo[4,5-c]pyridin-6-amine;

1-isopropyl-N-(2-(tetrahydro-2H-furo[2,3-c]pyrrol-5(3H)-yl)pyrimidin-4-yl)-1H-imidazo[4,5-c]pyridin-6-amine;

N-(2-(6-oxa-2-azaspiro [3.5]nonan-2-yl)pyrimidin-4-yl)-1-isopropyl-1H-imidazo[4, 5-c]pyridin-6-amine;

7-(4-((1-isopropyl-1H-imidazo[4,5-c]pyridin-6-yl)
amino)pyrimidin-2-yl)-7-azabicyclo[2.2.1]heptane-2-carboxamide;

1-(4-((1-isopropyl-1H-imidazo[4,5-c]pyridin-6-yl)
amino)pyrimidin-2-yl)-3-methylpyrrolidin-3-ol;

N-(2-(3-azabicyclo[3.1.0]hexan-3-yl)pyrimidin-4-yl)-1-isopropyl-1H-imidazo[4,5-c]pyridin-6-amine;

N-(2-(2-azabicyclo[3.1.0]hexan-2-yl)pyrimidin-4-yl)-1-isopropyl-1H-imidazo[4,5-c]pyridin-6-amine;

1-isopropyl-N-(2-(tetrahydro-1H-furo[3,4-c]pyrrol-5(3H)-yl)pyrimidin-4-yl)-1H-imidazo[4,5-c]pyridin-6-amine;

N-(2-(3-(aminomethyl)pyrrolidin-1-yl)pyrimidin-4-yl)-1-isopropyl-1H-imidazo[4,5-c]pyridin-6-amine;

N-(2-(4-(aminomethyl)piperidin-1-yl)pyrimidin-4-yl)-1-isopropyl-1H-imidazo[4,5-c]pyridin-6-amine;

N2-ethyl-N4-(1-isopropyl-1H-imidazo[4,5-c]pyridin-6-yl)pyrimidine-2,4-diamine;

N-(2-(2,7-diazaspiro[3.5]nonan-7-yl)pyrimidin-4-yl)-1-isopropyl-1H-imidazo[4,5-c]pyridin-6-amine;

N-(2-(2,6-diazaspiro[3.5]nonan-2-yl)pyrimidin-4-yl)-1-isopropyl-1H-imidazo[4,5-c]pyridin-6-amine;

N-(2-(2,8-diazaspiro[4.5]decan-2-yl)pyrimidin-4-yl)-1-isopropyl-1H-imidazo[4,5-c]pyridin-6-amine;

N-(2-(1,8-diazaspiro[4.6]undecan-8-yl)pyrimidin-4-yl)-1-isopropyl-1H-imidazo[4,5-c]pyridin-6-amine;

N-(2-(2,6-diazaspiro[4.5]decan-2-yl)pyrimidin-4-yl)-1-isopropyl-1H-imidazo[4,5-c]pyridin-6-amine;

N-(2-(3,9-diazaspiro[5.5]undecan-3-yl)pyrimidin-4-yl)-1-isopropyl-1H-imidazo[4,5-c]pyridin-6-amine;

N-(2-(1,7-diazaspiro[3.5]nonan-7-yl)pyrimidin-4-yl)-1-isopropyl-1H-imidazo[4,5-c]pyridin-6-amine;

N4-(1-isopropyl-1H-imidazo[4,5-c]pyridin-6-yl)-N2-(1-oxa-8-azaspiro[4.5]decan-3-yl)pyrimidine-2,4-diamine;

N-(2-(2-oxa-4,9-diazaspiro[5.5]undecan-9-yl)pyrimidin-4-yl)-1-isopropyl-1H-imidazo[4,5-c]pyridin-6-amine;

N-(2-(1-oxa-4,9-diazaspiro[5.5]undecan-4-yl)pyrimidin-4-yl)-1-isopropyl-1H-imidazo[4,5-c]pyridin-6-amine;

N-(2-(1-oxa-4,8-diazaspiro[5.5]undecan-8-yl)pyrimidin-4-yl)-1-isopropyl-1H-imidazo[4,5-c]pyridin-6-amine;

N-(2-(2-amino-7-azaspiro[3.5]nonan-7-yl)pyrimidin-4-yl)-1-isopropyl-1H-imidazo[4,5-c]pyridin-6-amine;

N2-(6-azaspiro[2.5]octan-1-ylmethyl)-N4-(1-isopropyl-1H-imidazo[4,5-c]pyridin-6-yl)pyrimidine-2,4-diamine;

N-(2-(1-amino-3-azabicyclo[3.1.0]hexan-3-yl)pyrimidin-4-yl)-1-isopropyl-1H-imidazo[4,5-c]pyridin-6-amine;

N-(2-(hexahydropyrrolo[3,4-b]pyrrol-5(1H)-yl)pyrimidin-4-yl)-1-isopropyl-1H-imidazo[4,5-c]pyridin-6-amine;

N-(2-(9-oxa-3,7-diazabicyclo[3.3.1]nonan-3-yl)pyrimidin-4-yl)-1-isopropyl-1H-imidazo[4,5-c]pyridin-6-amine;

N4(2-(1-(aminomethyl)-2-azabicyclo[2.1.1]hexan-2-yl)pyrimidin-4-yl)-1-isopropyl-1H-imidazo[4,5-c]pyridin-6-amine;

(1R,5S,6r)-3-(4-((1-isopropyl-1H-imidazo[4,5-c]pyridin-6-yl)amino)pyrimidin-2-yl)-3-azabicyclo[3.1.0]
hexane-6-carboxamide;

N-(2-(2-aminopyridin-4-yl)pyrimidin-4-yl)-1-isopropyl-1H-imidazo[4,5-c]pyridin-6-amine;

1-isopropyl-N-(2-(3-(methoxymethyl)piperazin-1-yl)pyrimidin-4-yl)-1H-imidazo[4,5-c]pyridin-6-amine;

3-(4-(1-isopropyl-1H-imidazo[4,5-c]pyridin-6-ylamino)
pyrimidin-2-yloxy)-2,2-dimethylpropanamide;

N-(3-hydroxypropyl)-1-isopropyl-6-2-(4-methoxypiperidin-1-yl)pyrimidin-4-ylamino)-1H-pyrrolo[3,2-c]pyridine-3-carboxamide;

1-isopropyl-6-(2-(4-methoxypiperidin-1-yl)pyrimidin-4-ylamino)-N-(3-morpholinopropyl)-1H-pyrrolo[3,2-c]pyridine-3-carboxamide;

1-isopropyl-6-(2-(4-methoxypiperidin-1-yl)pyrimidin-4-ylamino)-N-(2-(4-methylpiperazin-1-yl)ethyl)-1H-pyrrolo[3,2-c]pyridine-3-carboxamide;

1-isopropyl-6-(2-(4-methoxypiperidin-1-yl)pyrimidin-4-ylamino)-N-(2-(pyrrolidin-1-yl)ethyl)-1H-pyrrolo[3,2-c]pyridine-3-carboxamide;

1-isopropyl-6-(2-(4-methoxypiperidin-1-yl)pyrimidin-4-ylamino)-N-(2-(piperazin-1-yl)ethyl)-1H-pyrrolo[3,2-c]pyridine-3-carboxamide;

1-isopropyl-6-(2-(4-methoxypiperidin-1-yl)pyrimidin-4-ylamino)-N-(piperidin-4-ylmethyl)-1H-pyrrolo[3,2-c]pyridine-3-carboxamide;

1-isopropyl-6-(2-(4-methoxypiperidin-1-yl)pyrimidin-4-ylamino)-N-(2-(methylsulfonyl)ethyl)-1H-pyrrolo[3,2-c]pyridine-3-carboxamide;

N-(azetidin-3-yl)-1-isopropyl-6-(2-(4-methoxypiperidin-1-yl)pyrimidin-4-ylamino)-1H-pyrrolo[3,2-c]pyridine-3-carboxamide;

(6-(2-(3-Amino-1-(cyclopropylmethyl)-1H-pyrazol-4-yl)pyrimidin-4-ylamino)-1-isopropyl-1H-imidazo[4,5-c]pyridin-2-yl)methanol;

N-(4-Cyanocyclohexyl)-6-((2-(1-(cyclopropyl sulfonyl)-1H-pyrazol-4-yl)pyrimidin-4-yl)amino)-1-isopropyl-1H-pyrrolo[3,2-c]pyridine-3-carboxamide;

2-(3-(6-(2-(1-(Cyclopropylsulfonyl)-1H-pyrazol-4-yl)pyrimidin-4-ylamino)-1-isopropyl-1H-pyrrolo[3,2-c]pyridin-3-yl)-4-methyl-1H-pyrazol-1-yl)ethanol; or N-(2-(1H-pyrazol-4-yl)pyrimidin-4-yl)-1-isopropyl-3-(2H-1,2,3-triazol-4-yl)-1H-pyrrolo[3,2-c]pyridin-6-amine;

21. The compound according to claim 1, wherein said compound is:

2-(4-(6-(2-(1-(Ethylsulfonyl)-1H-pyrazol-4-yl)pyrimidin-4-ylamino)-1-isopropyl-1H-pyrrolo[3,2-c]pyridin-3-yl)-1H-pyrazol-1-yl)-N-(oxetan-3-yl)acetamide;

4-(6-(2-(1-(Cyclopropylsulfonyl)-1H-pyrazol-4-yl)pyrimidin-4-ylamino)-1-isopropyl-1H-pyrrolo[3,2-c]pyridin-3-yl)pyrrolidin-2-one;

N-(2-(1-(Cyclopropylsulfonyl)-1H-pyrazol-4-yl)pyrimidin-4-yl)-2-methyl-1-(1,1,1-trifluoropropan-2-yl)-1H-imidazo[4,5-c]pyridin-6-amine;

1-Isopropyl-2-methyl-N-(2-(1-(pyrrolidin-3-ylsulfonyl)-1H-pyrazol-4-yl)pyrimidin-4-yl)-1H-imidazo[4,5-c]pyridin-6-amine;

1-(3-(4-(4-(1-Isopropyl-2-methyl-1H-imidazo[4,5-c]pyridin-6-ylamino)pyrimidin-2-yl)-1H-pyrazol-1-ylsulfonyl)pyrrolidin-1-yl)ethanone;

1-Isopropyl-2-methyl-N-(2-(1-(oxetan-3-ylsulfonyl)-1H-pyrazol-4-yl)pyrimidin-4-yl)-1H-imidazo[4,5-c]pyridin-6-amine;

(1-Isopropyl-6-(2-(4-methoxypiperidin-1-yl)pyrimidin-4-ylamino)-1H-imidazo[4,5-c]pyridin-2-yl)(4-m ethyl-piperazin-1-yl)methanone;

2-Chloro-6-(2-(1-(cyclopropylsulfonyl)-1H-pyrazol-4-yl)pyrimidin-4-ylamino)-1-isopropyl-N-(tetrahydro-2H-pyran-4-yl)-1H-pyrrolo[3,2-c]pyridine-3-carboxamide;

N-(2-(1-(Cyclopropylsulfonyl)-1H-pyrazol-4-yl)pyrimidin-4-yl)-2-(difluoromethyl)-1-isopropyl-1H-imidazo[4,5-c]pyridin-6-amine;

6-(2-(1-(Cyclopropylsulfonyl)-1H-pyrazol-4-yl)pyrimidin-4-ylamino)-1-isopropyl-1H-imidazo[4,5-c]pyridine-2-carbaldehyde;

(6-(2-(1-(Cyclopropylsulfonyl)-1H-pyrazol-4-yl)pyrimidin-4-ylamino)-1-(pentan-2-yl)-1H-imidazo[4,5-c]pyridin-2-yl)methanol;

(trans)-N-{1-[4-(1-Isopropyl-2-methyl-1H-imidazo[4,5-c]pyridin-6-ylamino)pyrimidin-2-yl]-4-methoxypiperidin-3-yl}methanesulfonamide formate salt;

(trans)-[2-(3-Amino-4-methoxypiperidin-1-yl)pyrimidin-4-yl]-(1-isopropyl-2-methyl-1H-imidazo[4,5-c]pyridin-6-yl)amine;

[1-(1-Cyclopropylethyl)-2-methyl-1H-imidazo[4,5-c]pyridin-6-yl]-[2-(4-methoxypiperidin-1-yl)pyrimidin-4-yl]amine;

(2-Cyclohexylpyrimidin-4-yl)-(1-isopropyl-1H-imidazo[4,5-c]pyridin-6-yl)amine;

{2-[4-(2-Aminoethyl)-4-methoxypiperidin-1-yl]pyrimidin-4-yl}(1-isopropyl-2-methyl-1H-imidazo[4,5-c]pyridin-6-yl)amine;

[2-(4-Aminomethyl-4-methoxypiperidin-1-yl)pyrimidin-4-yl](1-isopropyl-2-methyl-1H-imidazo[4,5-c]pyridin-6-yl)amine;

{6-[2-(1-Cyclopropanesulfonyl-1H-pyrazol-4-yl)pyrimidin-4-ylamino]-1-isopropyl-1H-imidazo[4,5-c]pyridin-2-yl}methanol;

(1-Isopropyl-6-((2-((1R,5R,8r)-8-methoxy-3-azabicyclo[3.2.1]octan-3-yl)pyrimidin-4-yl)amino)-1H-imidazo[4,5-c]pyridin-2-yl)methanol;

{6-[2-(4-Aminomethyl-4-methoxypiperidin-1-yl)pyrimidin-4-ylamino]-1-isopropyl-1H-imidazo[4,5-c]pyridin-2-yl}methanol;

(2-Cyclohex-1-enylpyrimidin-4-yl)-(1-isopropyl-2-methyl-1H-imidazo[4,5-c]pyridin-6-yl)amine;

4-(1-Isopropyl-2-methyl-1H-imidazo[4,5-c]pyridin-6-ylamino)pyrimidine-2-carbonitrile;

2-1{6-[4-(1-Isopropyl-2-methyl-1H-imidazo[4,5-c]pyridin-6-ylamino)pyrimidin-2-yl]-4,5,6,7-tetrahydropyrazolo[3,4-c]pyridin-1-yl}ethanol;

2-{6-[4-(1-Isopropyl-2-methyl-1H-imidazo[4,5-c]pyridin-6-ylamino)pyrimidin-2-yl]-4,5,6,7-tetrahydropyrazolo[3,4-c]pyridin-2-yl}ethanol;

[2-(1-Cyclopropanesulfonyl-1H-pyrazol-4-yl)-pyrimidin-4-yl]-(1-isopropyl-2-methoxymethyl-1H-imidazo[4,5-c]pyridin-6-yl)amine;

[2-(1-Cyclopropanesulfonyl-1H-pyrazol-4-yl)-pyrimidin-4-yl]-(3,3-dimethyl-2,3-dihydro-1-oxa-3a,6,8-triazacyclopenta[a]inden-5-yl)-amine;

(R)-1-{1-((R)-sec-Butyl)-6-[2-(1-ethanesulfonyl-1H-pyrazol-4-yl)-pyrimidin-4-ylamino]-1H-imidazo[4,5-c]pyridin-2-yl}ethanol;

2-{6-[2-(1-Cyclopropanesulfonyl-1H-pyrazol-4-yl)pyrimidin-4-ylamino]-1-isopropyl-1H-imidazo[4,5-c]pyridin-2-yloxy}ethanol;

$N^6$-[2-(1-Cyclopropanesulfonyl-1H-pyrazol-4-yl)-pyrimidin-4-yl]-1-isopropyl-$N^2,N^2$-dim ethyl-1H-imidazo[4,5-c]pyridine-2,6-diamine;

[2-(Azetidin-3-yloxy)-1-isopropyl-1H-imidazo[4,5-c]pyridin-6-yl]-[2-(1-cyclopropanesulfonyl-1H-pyrazol-4-yl)pyrimidin-4-yl]amine;

[2-(Azetidin-3-yloxy)-1-isopropyl-1H-imidazo[4,5-c]pyridin-6-yl]-[2-(1H-pyrazol-4-yl)pyrimidin-4-yl]amine;

[(R)-6-[2-(1-Cyclopropanesulfonyl-1H-pyrazol-4-yl)pyrimidin-4-ylamino]-1-(2,2,2-trifluoro-1-methylethyl)-1H-imidazo[4,5-c]pyridin-2-yl]methanol;

(1-Isopropyl-1H-imidazo[4,5-c]pyridin-6-yl)-[2-(1-methanesulfonylpiperidin-4-yl)pyrimidin-4-yl]amine;

(R)-1-[6-[2-((3R,4S)-3-Fluor o-4-methoxypiperidin-1-yl)-pyrimidin-4-ylamino]-1-((S)-2,2,2-trifluoro-1-methylethyl)-1H-imidazo[4,5-c]pyridin-2-yl]ethanol;

(3R,4S)-3-Fluoro-1-{4-[2-((R)-1-hydroxyethyl)-1-((S)-2,2,2-trifluoro-1-methylethyl)-1H-imidazo[4,5-c]pyridin-6-ylamino]pyrimidin-2-yl}-piperidin-4-ol;

(R)-1-[6-[2-((3S,4R)-3-Fluoro-4-methoxypiperidin-1-yl)-pyrimidin-4-ylamino]-1-((S)-2,2,2-trifluoro-1-methylethyl)-1H-imidazo[4,5-c]pyridin-2-yl]ethanol;

(3S,4R)-3-Fluoro-1-{4-[2-((R)-1-hydroxyethyl)-1-((S)-2,2,2-trifluoro-1-methyl ethyl)-1H-imidazo[4,5-c]pyridin-6-ylamino]pyrimidin-2-yl}-piperidin-4-ol;

1-[4-(1-Isopropyl-2-methyl-1H-imidazo[4,5-c]pyridin-6-ylamino)pyrimidin-2-yl]piperidine-3-carbonitrile;

$N^6$-[2-(1-Cyclopropanesulfonyl-1H-pyrazol-4-yl)pyrimidin-4-yl]-1-isopropyl-$N^2$-methyl-1H-imidazo[4,5-c]pyridine-2,6-diamine;

(±)-1-{6-[2-(1-Cyclopropanesulfonyl-1H-pyrazol-4-yl)pyrimidin-4-ylamino]-1-isopropyl-1H-imidazo[4,5-c]pyridin-2-yl}ethanol;

[2-(2-Ethylaminothiazol-5-yl)pyrimidin-4-yl](1-isopropyl-2-methyl-1H-imidazo[4,5-c]pyridin-6-yl)amine;

cis-3-Fluoro-1-{4-[2-((R)-1-hydroxyethyl)-1-((S)-2,2,2-trifluoro-1-methylethyl)-1H-imidazo[4,5-c]pyridin-6-ylamino]pyrimidin-2-yl}piperidin-4-ol;

(R)-1-[6-[2-(cis-3-Fluoro-4-methoxypiperidin-1-yl)pyrimidin-4-ylamino]-1-((R)-2,2,2-trifluoro-1-methylethyl)-1H-imidazo[4,5-c]pyridin-2-yl]ethanol;

3-[4-(1-Isopropyl-2-methyl-1H-imidazo[4,5-c]pyridin-6-ylamino)pyrimidin-2-ylamino]propionamide;

2-{[4-(1-Isopropyl-2-methyl-1H-imidazo[4,5-c]pyridin-6-ylamino)pyrimidin-2-ylamino]methyl}-2-methylbutyric acid;

2-{[4(1-Isopropyl-2-methyl-1H-imidazo[4,5-c]pyridin-6-ylamino)pyrimidin-2-ylamino]methyl}-2-methylbutyramide;

2-Hydroxy-3-[4-(1-isopropyl-2-methyl-1H-imidazo[4,5-c]pyridin-6-ylamino)pyrimidin-2-ylamino]propionamide;

3-[4-(1-Isopropyl-2-methyl-1H-imidazo[4,5-c]pyridin-6-ylamino)pyrimidin-2-ylamino]-2,2-dimethylpropionic acid; or 2-Hydroxymethyl-3-[4-(1-isopropyl-2-methyl-1H-imidazo[4,5-c]pyridin-6-ylamino)pyrimidin-2-ylamino]-2-methylpropionamide.

22. The compound according to claim 1, wherein said compound is:

(1-Isopropyl-2-methyl-1H-imidazo[4,5-c]pyridin-6-yl)-[2-(3-methoxy-3-methylbut-1-ynyl)pyrimidin-4-yl]amine;

(1-Isopropyl-2-methyl-1H-imidazo[4,5-c]pyridin-6-yl)-[2-(3-methoxy-3-methylbutyl)pyrimidin-4-yl]amine;

1-[4-(1-Isopropyl-2-methyl-1H-imidazo[4,5-c]pyridin-6-ylamino)pyrimidin-2-yl]-3-methylpyrrolidine-3-carboxylic acid amide;

(1-Isopropyl-2-methyl-1H-imidazo[4,5-c]pyridin-6-yl)-[((E)-2-pent-1-enyl)pyrimidin-4-yl]amine;

(E)-4-[4-(1-Isopropyl-2-methyl-1H-imidazo[4,5-c]pyridin-6-ylamino)pyrimidin-2-yl]-2-methylbut-3-en-2-ol;

(1-Isopropyl-2-methyl-1H-imidazo[4,5-c]pyridin-6-yl)-(2-pyridin-3-ylpyrimidin-4-yl)amine;

(E)-4-[4-(1-Isopropyl-2-methyl-1H-imidazo[4,5-c]pyridin-6-ylamino)pyrimidin-2-yl]-2,2-dimethylbut-3-enoic acid amide;

(1-Isopropyl-2-methyl-1H-imidazo[4,5-c]pyridin-6-yl)-[2-(3-methyl-3H-imidazol-4-yl)pyrimidin-4-yl]amine;

(1-Isopropyl-2-methyl-1H-imidazo[4,5-c]pyridin-6-yl)-[2-(2-methylaminothiazol-5-yl)pyrimidin-4-yl]amine;

5-[4-(1-Isopropyl-2-methyl-1H-imidazo[4,5-c]pyridin-6-ylamino)pyrimidin-2-yl]pyridine-2-carboxylic acid amide;

(1-Isopropyl-2-methyl-1H-imidazo[4,5-c]pyridin-6-yl)-[12-(6-methylaminopyridin-3-yl)pyrimidin-4-yl]amine;

N-{5-[4-(1-Isopropyl-2-methyl-1H-imidazo[4,5-c]pyridin-6-ylamino)pyrimidin-2-yl]thiazol-2-yl}-N-methyl-acetamide;

[2-(2-Benzenesulfonyl-3-methyl-3H-imidazol-4-yl)pyrimidin-4-yl]-(1-isopropyl-2-methyl-1H-imidazo[4,5-c]pyridin-6-yl)amine;

[2-(2-Dimethylaminothiazol-5-yl)pyrimidin-4-yl]-(1-isopropyl-2-methyl-1H-imidazo[4,5-c]pyridin-6-yl)amine;

1-[4(1-Isopropyl-2-methyl-1H-imidazo[4,5-c]pyridin-6-ylamino)pyrimidin-2-yl]imidazolidin-one;

N-(2-(4-methoxypiperidin-1-yl)pyrimidin-4-yl)-3H-imidazo[4,5-c]pyridin-6-amine;

N-(2-4-Methoxypiperidin-1-yl)pyrimidin-4-yl)-3H-imidazo[4,5-c]pyridin-6-amine;

(+)-1-(sec-Butyl)-6-((2-(1-(cyclopropylsulfonyl)-1H-pyrazol-4-yl)pyrimidin-4-yl)amino)-N-(tetrahydro-2H-pyran-4-yl)-1H-pyrrolo[3,2-c]pyridine-3-carboxamide;

(−)-1-(sec-butyl)-6-((2-(1-(cyclopropylsulfonyl)-1H-pyrazol-4-yl)pyrimidin-4-yl)amino)-N-(tetrahydro-2H-pyran-4-yl)-1H-pyrrolo[3,2-c]pyridine-3-carboxamide;

1-(sec-butyl)-6-((2-((3S,4R)-3-fluoro-4-hydroxypiperidin-1-yl)pyrimidin-4-yl)amino)-N-(tetrahydro-2H-pyran-4-yl)-1H-pyrrolo[3,2-c]pyridine-3-carboxamide;

1-(sec-butyl)-6-((2-((3S,4R)-3-fluoro-4-hydroxypiperidin-1-yl)pyrimidin-4-yl)amino)-N-(tetrahydro-2H-pyran-4-yl)-1H-pyrrolo[3,2-c]pyridine-3-carboxamide;

1-(sec-butyl)-6-((2-((3 S,4R)-3-fluoro-4-methoxypiperidin-1-yl)pyrimidin-4-yl)amino)-N-(1-(oxetan-3-yl)piperidin-4-yl)-1H-pyrrolo[3,2-c]pyridine-3-carboxamide;

1-(sec-butyl)-6-((2-((3S,4R)-3-fluoro-4-methoxypiperidin-1-yl)pyrimidin-4-yl)amino)-N-(1-(oxetan-3-yl)piperidin-4-yl)-1H-pyrrolo[3,2-c]pyridine-3-carboxamide N-(6-((2-(1-(Cyclopropylsulfonyl)-1H-pyrazol-4-yl)pyrimidin-4-yl)amino)-1-isopropyl-1H-pyrrolo[3,2-c]pyridin-3-yl)acetamide;

N-(6-((2-(1-(Cyclopropylsulfonyl)-1H-pyrazol-4-yl)pyrimidin-4-yl)amino)-1-isopropyl-1H-pyrrolo[3,2-c]pyridin-3-yl)-2-hydroxyacetamide;

$N^4$-(Isopropyl-2-methyl-1H-imidazo[4,5-c]pyridin-6-yl)-$N^2$-(2-methyl-2-(4H-1,2,4-triazol-3-yl)propyl)pyrimidine-2,4-diamine;

N-(2-(1-(Cyclopropylsulfonyl)-1H-pyrazol-4-yl)pyrimidin-4-yl)-1-isopropyl-3-morpholino-1H-pyrrolo[3,2-c]pyridin-6-amine;

2-(4-(6-((2-(1-(Cyclopropylsulfonyl)-1H-pyrazol-4-yl)pyrimidin-4-yl)amino)-1-isopropyl-1H-pyrrolo[3,2-c]pyridin-3-yl)-1H-pyrazol-1-yl)acetamide;

(+/−)-1-(1-(4-((1-Isopropyl-2-methyl-1H-imidazo[4,5-c]pyridin-6-yl)amino)pyrimidin-2-yl)-1H-imidazol-4-yl)ethanol;

1-Isopropyl-N-(2-(4-methoxypiperidin-1-yl)pyrimidin-4-yl)-3-(methylsulfonyl)-1H-pyrrolo[3,2-c]pyridin-6-amine;

(6-((2-(1-(1-Fluorovinyl)-1H-pyrazol-4-yl)pyrimidin-4-yl)amino)-1-isopropyl-1H-imidazo[4,5-c]pyridin-2-yl)methanol;

6-((2-(1-(Cyclopropylsulfonyl)-1H-pyrazol-4-yl)pyrimidin-4-yl)amino)-1-isopropyl-2-methyl-N-(tetrahydro-2H-pyran-4-yl)-1H-pyrrolo[3,2-c]pyridine-3-carboxamide;

N-(2-(5-Chloro-1-(cyclopropylmethyl)-1H-pyrazol-4-yl)pyrimidin-4-yl)-1-isopropyl-2-methyl-1H-imidazo[4,5-c]pyridin-6-amine;

1-Isopropyl-2-methyl-N-(2-(4-(methyl sulfonyl)-1H-imidazol-1-yl)pyrimidin-4-yl)-1H-imidazo[4,5-c]pyridin-6-amine;

1-Isopropyl-2-methyl-N-(2-(4-(methylsulfinyl)-1H-imidazol-1-yl)pyrimidin-4-yl)-1H-imidazo[4,5-c]pyridin-6-amine;

1-((R)-sec-butyl)-6-((2-((3R,4S)-3-fluoro-4-methoxypiperidin-1-yl)pyrimidin-4-yl)amino)-N-(tetrahydro-2H-pyran-4-yl)-1H-pyrrolo[3,2-c]pyridine-3-carboxamide;

1-((S)-sec-butyl)-6-((2-((3R,4S)-3-fluoro-4-methoxypiperidin-1-yl)pyrimidin-4-yl)amino)-N-(tetrahydro-2H-pyran-4-yl)-1H-pyrrolo[3,2-c]pyridine-3-carboxamide;

1-(4-(4-((1-Isopropyl-2-methyl-1H-imidazo[4,5-c]pyridin-&-yl)amino)pyrimidin-2-yl)-1H-pyrazol-1-yl)-2-methylpropan-2-ol;

2-(4-(4-((1-Isopropyl-2-methyl-1H-imidazo[4,5-c]pyridin-6-yl)amino)pyrimidin-2-yl)-1H-pyrazol-1-yl)-2-methylpropan-1-ol;

3-((4-((1-Isopropyl-2-methyl-1H-imidazo[4,5-c]pyridin-6-yl)amino)pyrimidin-2-yl)thio)-2,2-dimethylpropanamide;
1-Isopropyl-2-methyl-N-(2-(1-(pyrrolidin-3-ylmethyl)-1H-pyrazol-4-yl)pyrimidin-4-yl)-1H-imidazo[4,5-c]pyridin-6-amine;
N-(2-(1-(Cyclopropylsulfonyl)-1H-pyrazol-4-yl)pyrimidin-4-yl)-3-(3, 5-dimethyl-1H-pyrazol-4-yl)-1-isopropyl-1H-pyrrolo[3,2-c]pyridin-6-amine;
N-(2-(1-(cyclopropylsulfonyl)-1H-pyrazol-4-yl)pyrimidin-4-yl)-1-isopropyl-3-(4-methyl-1H-pyrazol-5-yl)-1H-pyrrolo[3,2-c]pyridin-6-amine;
1-(4-((1-Isopropyl-3-(4-methyl-1H-pyrazol-5-yl)-1H-pyrrolo[3,2-c]pyridin-6-yl)amino)pyrimidin-2-yl)-3,3-dimethylpiperidin-4-ol;
2-(3-(6-((2-((3R,4S)-3-Fluoro-4-methoxypiperidin-1-yl)pyrimidin-4-yl)amino)-1-isopropyl-1H-pyrrolo[3,2-c]pyridin-3-yl)-4-methyl-1H-pyrazol-1-yl)ethanol;
3-(6-((2-(4-Methoxypiperidin-1-yl)pyrimidin-4-yl)amino)-2-methyl-1H-imidazo[4,5-c]pyridin-1-yl)butanenitrile;
(cis)-3-(6 ((2-(4-methoxypiperidin-1-yl)pyrimidin-4-yl)amino)-2-methyl-1H-imidazo[4,5-c]pyridin-1-yl)cyclopentanecarbonitrile;
(trans)-3-(6-((2-(4-methoxypiperidin-1-yl)pyrimidin-4-yl)amino)-2-methyl-1H-imidazo[4,5-c]pyridin-1-yl)cyclopentanecarbonitrile;
3-(6-((2-(4-Methoxypiperidin-1-yl)pyrimidin-4-yl)amino)-2-methyl-1H-imidazo[4,5-c]pyridin-1-yl)butanamide; or
4-(1-(6-((2-(4Methoxypiperidin-1-yl)pyrimidin-4-yl)amino)-2-methyl-1H-imidazo[4,5-c]pyridin-1-yl)ethyl)benzonitrile.

23. The compound according to claim 1, wherein said compound is:
4-(1-(6-((2-(4-Methoxypiperidin-1-yl)pyrimidin-4-yl)amino)-2-methyl-1H-imidazo[4,5-c]pyridin-1-yl)ethyl)benzamide;
1-(1H-Indazol-4-ylmethyl)-N-[2-(4-methoxy-1-piperidyl)pyrimidin-4-yl]-2-methyl-imidazo[4,5-c]pyridin-6-amine;
1-Benzyl-N-[2-(4-methoxy-1-piperidyl)pyrimidin-4-yl]-2-methyl-imidazo[4,5-c]pyridin-6-amine;
1-[(1S)-1-(1H-Benzimidazol-5-yl)ethyl]-N-[2-(4-methoxy-1-piperidyl)pyrimidin-4-yl]-2-methyl-imidazo[4,5-c]pyridin-6-amine;
1-((1H-Benzo[d]imidazol-4-yl)methyl)-N-(2-(4-methoxypiperidin-1-yl)pyrimidin-4-yl)-2-methyl-1H-imidazo[4,5-c]pyridin-6-amine;
1-((1H-Benzo[d]imidazol-5-yl)methyl)-N-(2-(4-methoxypiperidin-1-yl)pyrimidin-4-yl)-2-methyl-1H-imidazo[4,5-c]pyridin-6-amine;
1-Isopropyl-2-methyl-N-(2-(3-methylisothiazol-5-yl)pyrimidin-4-yl)-1H-imidazo[4,5-c]pyridin-6-amine;
(5-(4-((1-Isopropyl-2-methyl-1H-imidazo[4,5-c]pyridin-6-yl)amino)pyrimidin-2-yl)thiazol-2-yl)methanol;
N-(2-(3,5-Di methyl-1H-pyrazol-4-yl)pyrimidin-4-yl)-1-isopropyl-2-methyl-1H-imidazo[4,5-c]pyridin-6-amine;
N-(2-(3-Amino-1-methyl-1H-pyrazol-4-yl)pyrimidin-4-yl)-1-isopropyl-2-methyl-1H-imidazo[4,5-c]pyridin-6-amine;
N-(2-(3-(1I-Pyrazol-5-yl)piperadine-1-yl)pyrimidin-4-yl)-1-isopropyl-2-methyl-1H-imidazo[4,5-c]pyridin-6-amine;
1-Isopropyl-2-methyl-N-(2-(1-methyl-1H-pyrazol-4-yl)pyrimidin-4-yl)-1H-imidazo[4,5-c]pyridin-6-amine;
1-Isopropyl-N-(2-isoxazol-4-yl)pyrimidin-4-yl)-2-methyl-1H-imidazo[4,5-c]pyridin-6-amine;
N-(2-(2H-1,2,3-triazol-2-yl)pyrimidin-4-yl)-1-isopropyl-2-methyl-1H-imidazo[4,5-c]pyridine-6-amine;
1-Isopropyl-2-methyl-N-(2-(3-methyl-1H-1,2,4-triazol-5-yl)pyrimidin-4-yl)-1H-imidazo[4,5-c]pyridine-6-amine;
[2-((3RS,4SR)-3-Fluoro-4-methoxypiperidin-1-yl)pyrimidin-4-yl]-(1-isopropyl-2-methyl-1H-imidazo[4,5-c]pyridin-6-yl)amine;
(R)-1-[6-[2-(2-Methanesulfonyl-2-methylpropoxy)pyrimidin-4-ylamino]-1-((S)-2,2,2-trifluoro-1-methylethyl)-1H-imidazo[4,5-c]pyridin-2-yl]ethanol;
2,2-Difluoro-3-[4-(1-isopropyl-2-methyl-1H-imidazo[4,5-c]pyridin-6-ylamino)pyrimidin-2-ylamino]propionamide;
(1-Isopropyl-2-methyl-1H-imidazo[4,5-c]pyridin-6-yl)-[2-(4-methyl-2-methylaminothiazol-5-yl)pyrimidin-4-yl]amine;
{Isopropyl-6-[2-(4-methyl-2-methylaminothiazol-5-yl)pyrimidin-4-ylamino]-1H-imidazo[4,5-c]pyridin-2-yl}methanol;
{1-Isopropyl-6-[2-(3-methyl-2-methylamino-3H-imidazol-4-yl)pyrimidin-4-ylamino]-1H-imidazo[4,5-c]pyridin-2-yl}methanol;
[2-(2-Aminothiazol-5-yl)pyrimidin-4-yl]-(1-isopropyl-2-methyl-1H-imidazo[4,5-c]pyridin-6-yl)amine;
{6-[2-(2-Aminothiazol-5-yl)pyrimidin-4-ylamino]-1-isopropyl-1H-imidazo[4,5-c]pyridin-2-yl}methanol;
[2-(±z)-(trans-3-Fluoro-4-methanesulfonylpiperidin-1-yl)pyrimidin-4-yl]-(1-isopropyl-2-methyl-1H-imidazo[4,5-c]pyridin-6-yl)amine;
[2-(±)-(cis-3-Fluoro-4-methylsulfanylpiperidin-1-yl)pyrimidin-4-yl]-(1-isopropyl-2-methyl-1H-imidazo[4,5-c]pyridin-6-yl)amine;
[2-(±)-(cis-3-Fluoro-4-methanesulfinylpiperidin-1-yl)pyrimidin-4-yl]-(1-isopropyl-2-methyl-1H-imidazo[4,5-c]pyridin-6-yl)amine;
(3RS,4SR)-3-Fluoro-1-[4-(2-hydroxymethyl-1-isopropyl-1H-imidazo[4,5-c]pyridin-6-ylamino)pyrimidin-2-yl]-4-methylpiperidin-4-ol;
(3R*,4S*)-3-Fluoro-1-{4-[2-((R)-1-hydroxyethyl)-1-((S)-2,2,2-trifluoro-1-methylethyl)-1H-imidazo[4,5-c]pyridin-6-ylamino]pyrimidin-2-yl}-4-methylpiperidin-4-ol;
(3R*,4S*)-3-Fluoro-1-{4-[2-((R)-1-hydroxyethyl)-1-((S)-2,2,2-trifluoro-1-methylethyl)-1H-imidazo[4,5-c]pyridin-6-ylamino]pyrimidin-2-yl}-4-methylpiperidin-4-ol;
(±)-(6-[2-(cis-3-Fluoro-4-methylsulfanylpiperidin-1-yl)pyrimidin-4-ylamino]-1-isopropyl-1H-imidazo[4,5-c]pyridin-2-yl)methanol;
{6-[2-(cis-3-Fluoro-4-methanesulfinylpiperidin-1-yl)pyrimidin-4-ylamino]-1-isopropyl-1H-imidazo[4,5-c]pyridin-2-yl}methanol;
4-(4-((2-(hydroxymethyl)-1-isopropyl-1H-imidazo[4,5-c]pyridin-6-yl)amino)pyrimidin-2-yl)cyclohex-3-enol;
N-(2-(3-Chloro-1-(cyclopropylmethyl)-1H-pyrazol-4-yl)pyrimidin-4-yl)-1-isopropyl-2-methyl-1H-imidazo[4,5-c]pyridin-6-amine;
(±)-(cis)-1-(4-(2-(Hydroxymethyl)-1-isopropyl-1H-imidazo[4,5-c]pyridin-6-ylamino)pyrimidin-2-yl)-3-(trifluoromethyl)piperidin-4-ol;
(−)-(trans)-1-(4-(2-(Hydroxymethyl)-1-isopropyl-1H-imidazo[4,5-c]pyridin-6-ylamino)pyrimidin-2-yl)-3-(trifluoromethyl)piperidin-4-ol;

(1-Isopropyl-6-(2-((±)-cis)-4-methoxy-3-(trifluorom-ethyl)piperidin-1-yl)pyrimidin-4-ylamino)-1H-imi-dazo[4,5-c]pyridin-2-yl)methanol;

(1-Isopropyl-6-(2-((±)-(trans)-4-methoxy-3-(trifluorom-ethyl)piperidin-1-yl)pyrimidin-4-ylamino)-1H-imi-dazo[4,5-c]pyridin-2-yl)methanol;

(±)-(trans)-1-(4-(2-(Hydroxymethyl)-1-isopropyl-1H-imidazo[4,5-c]pyridin-6-ylamino)pyrimidin-2-yl)-3-methylpiperidin-4-ol;

(±)-(cis)-1-(4-(2-(Hydroxymethyl)-1-isopropyl-1H-imidazo[4,5-c]pyridin-6-ylamino)pyrimidin-2-yl)-3-methylpiperidin-4-ol;

(1-Isopropyl-6-(2-((±)-cis)-4-methoxy-3-methylpiperi-din-1-yl)pyrimidin-4-ylamino)-1H-imidazo[4,5-c]pyridin-2-yl)methanol;

(3RS,4RS)-4-cyclopropyl-3-fluoro-1-(4-((2-(hydroxym-ethyl)-1-isopropyl-1H-imidazo[4,5-c]pyridin-6-yl)amino)pyrimidin-2-yl)piperidin-4-ol;

(6-(2-(cis)-3-Chloro-4-methoxypiperidin-1-yl)pyrimidin-4-ylamino)-1-isopropyl-1H-imidazo[4,5-c]pyridin-2-yl)methanol;

6-(2-(1-(Cyclopropylsulfonyl)-1H-pyrazol-4-yl)pyrimi-din-4-ylamino)-N-(tetrahydro-2H-pyran-4-yl)-1-(1,1,1-trifluoropropan-2-yl)-1H-pyrrolo[3,2-c]pyridine-3-carboxamide;

6-(2-(4-Hydroxy-4-methylpiperidin-1-yl)pyrimidin-4-ylamino)-N-(tetrahydro-2H-pyran-4-yl)-1-(1,1,1-trif-luoropropan-2-yl)-1H-pyrrolo[3,2-c]pyridine-3-car-boxamide;

1-(sec-butyl)-6-((2-((3S,4R)-3-fluoro-4-hydroxypiperi-din-1-yl)pyrimidin-4-yl)amino)-N-((3SR,4SR)-3-fluo-rotetrahydro-2 1-pyran-4-yl)-1H-pyrrolo[3,2-c]pyri-dine-3-carboxamide;

1-(sec-butyl)-6-((2-(4-hydroxy-4-methylpiperidin-1-yl)pyrimidin-4-yl)amino)-N-(tetrahydro-2H-pyran-4-yl)-1H-pyrrolo[3,2-c]pyridine-3-carboxamide;

6-((2-((3S,4R)-3-fluoro-4-hydroxypiperidin-1-yl)pyrimi-din-4-yl)amino)-N-(tetrahydro-2H-pyran-4-yl)-1-(1,1,1-trifluoropropan-2-yl)-1H-pyrrolo[3,2-c]pyridine-3-carboxamide;

1-(1-(sec-butyl)-6-((2-((3S,4R)-3-fluoro-4-hydroxypip-eridin-1-yl)pyrimidin-4-yl)amino)-1H-pyrrolo[3,2-c]pyridin-3-yl)pyrrolidin-2-one;

1-(1-(4-((1-isopropyl-2-methyl-1H-imidazo[4,5-c]pyri-din-6-yl)amino)pyrimidin-2-yl)-1H-imidazol-4-yl)ethanol; or (±)-(cis)-1-(4-(1-((S)-3,3-Difluorobutan-2-yl)-2-(hy-droxymethyl)-1H-imidazo[4,5-c]pyridin-6-ylamino)pyrimidin-2-yl)-3-fluoropiperidin-4-ol.

24. The compound according to claim 1, wherein said compound is:

(3RS,4SR)-3-Fluoro-1-(4-((2-(hydroxymethyl)-1-isopro-pyl-1H-imidazo[4,5-c]pyridin-6-yl)amino)pyrimidin-2-yl)-3-methylpiperidin-4-ol;

1-sec-Butyl-6-(2-((±)-cis-5-fluoro-4-hydroxy-3,3-dim-ethylpiperidin-1-yl)pyrimidin-4-ylamino)-N-(tetra-hydro-2H-pyran-4-yl)-1H-pyrrolo[3,2-c]pyridine-3-carboxamide;

1-(sec-butyl)-N-ethyl-6-((2-((3S,4R)-3-fluoro-4-hy-droxypiperidin-1-yl)pyrimidin-4-yl)amino)-1H-pyr-rolo[3,2-c]pyridine-3-carboxamide;

1-(sec-butyl)-N-ethyl-6-((2-((3 S,4R)-3-fluoro-4-hy-droxypiperidin-1-yl)pyrimidin-4-yl)amino)-1H-pyr-rolo[3,2-c]pyridine-3-carboxamide;

(±)-1-(sec-butyl)-6-((2-(1-(cyclopropylsulfonyl)-1H-pyrazol-4-yl)pyrimidin-4-yl)amino)-N-(1-(oxetan-3-yl)piperidin-4-yl)-1H-pyrrolo[3,2-c]pyridine-3-car-boxamide;

(±)-6-((2-(1-(cyclopropylsulfonyl)-1H-pyrazol-4-yl)py-rimidin-4-yl)amino)-N-((cis)-3-fluoro-1-(oxetan-3-yl)piperidin-4-yl)-1-isopropyl-1H-pyrrolo[3,2-c]pyri-dine-3-carboxamide;

1-(sec-butyl)-6-((2-(4-hydroxy-3,3-dimethylpiperidin-1-yl)pyrimidin-4-yl)amino)-N-(tetrahydrofuran-3-yl)-1H-pyrrolo[3,2-c]pyridine-3-carboxamide;

1-(sec-butyl)-6-((2-(4-hydroxy-3,3-dimethylpiperidin-1-yl)pyrimidin-4-yl)amino)-N-(tetrahydro-2H-pyran-3-yl)-1H-pyrrolo[3,2-c]pyridine-3-carboxamide;

1-(sec-butyl)-6-((2-((3 S,4R)-3-fluoro-4-methoxypiperi-din-1-yl)pyrimidin-4-yl)amino)-N-(tetrahydro-2H-pyran-4-yl)-1H-pyrrolo[3,2-c]pyridine-3-carboxam-ide;

1-(sec-butyl)-6-((2-((3S,4R)-3-fluoro-4-methoxypiperi-din-1-yl)pyrimidin-4-yl)amino)-N-(tetrahydro-2H-pyran-4-yl)-1H-pyrrolo[3,2-c]pyridine-3-carboxam-ide;

6-((2-(1-(N,N-dimethylsulfamoyl)-1H-pyrazol-4-yl)py-rimidin-4-yl)amino)-N-ethyl-1-isopropyl-1H-pyrrolo[3,2-c]pyridine-3-carboxamide;

6-((2-(1-(N,N-dimethylsulfamoyl)-1H-pyrazol-4-yl)py-rimidin-4-yl)amino)-1-isopropyl-N-(oxetan-3-yl)-1H-pyrrolo[3,2-c]pyridine-3-carboxamide;

6-((2-(1-(cyclopropylsulfonyl)-1H-pyrazol-4-yl)pyrimi-din-4-yl)amino)-1-isopropyl-N-(oxetan-3-yl)-1H-pyr-rolo[3,2-c]pyridine-3-carboxamide;

6-((2-((3 S,4R)-3-fluoro-4-methoxypiperidin-1-yl)py-rimidin-4-yl)amino)-1-isopropyl-N-(tetrahydro-2H-pyran-4-yl)-1H-pyrrolo[3,2-c]pyridine-3-carboxam-ide;

6-((2-((3R,4S)-3-fluoro-4-methoxypiperidin-1-yl)pyrimi-din-4-yl)amino)-1-isopropyl-N-(tetrahydro-2H-pyran-4-yl)-1H-pyrrolo[3,2-c]pyridine-3-carboxamide;

1-(sec-butyl)-6-((2-(1-(cyclopropylsulfonyl)-1H-pyrazol-4-yl)pyrimidin-4-yl)amino)-N-(tetrahydrofuran-3-yl)-1H-pyrrolo[3,2-c]pyridine-3-carboxamide;

1-(sec-butyl)-6-((2-(4-hydroxy-3,3-dimethylpiperidin-1-yl)pyrimidin-4-yl)amino)-N-(tetrahydro-2H-pyran-4-yl)-1H-pyrrolo[3,2-c]pyridine-3-carboxamide;

1-(sec-butyl)-6-((2-(4-hydroxy-3,3-dimethylpiperidin-1-yl)pyrimidin-4-yl)amino)-N-(tetrahydro-2H-pyran-4-yl)-1H-pyrrolo[3,2-c]pyridine-3-carboxamide;

(±)-6-((2-(4-hydroxy-3,3-dimethylpiperidin-1-yl)pyrimi-din-4-yl)amino)-1-isopropyl-N-(tetrahydro-2H-pyran-4-yl)-1H-pyrrolo[3,2-c]pyridine-3-carboxamide;

6-((2-(1-(cyclopropylsulfonyl)-1H-pyrazol-4-yl)pyrimi-din-4-yl)amino)-1-isopropyl-N-(oxetan-3-yl)-1H-pyr-rolo[3,2-c]pyridine-3-carboxamide;

N-(6-((2-(1-(cyclopropylsulfonyl)-1H-pyrazol-4-yl)py-rimidin-4-yl)amino)-1-isopropyl-1H-pyrrolo[3,2-c]pyridin-3-yl)-N-methylacetamide;

1-isopropyl-N-(oxetan-3-yl)-6-((2-(1-(pyrrolidin-1-ylsul-fonyl)-1H-pyrazol-4-yl)pyrimidin-4-yl)amino)-1H-pyrrolo[3,2-c]pyridine-3-carboxamide;

1-(sec-butyl)-6-((2-((3R,4S)-3-fluoro-4-hydroxypiperi-din-1-yl)pyrimidin-4-yl)amino)-N-(1-(oxetan-3-yl)pi-peridin-4-yl)-1H-pyrrolo[3,2-c]pyridine-3-carboxam-ide;

N-(6-((2-(1-(cyclopropylsulfonyl)-1H-pyrazol-4-yl)py-rimidin-4-yl)amino)-1-isopropyl-1H-pyrrolo[3,2-c]pyridin-3-yl)-2-hydroxy-N-methylacetamide;

N-(6-((2-(1-(cyclopropylsulfonyl)-1H-pyrazol-4-yl)pyrimidin-4-yl)amino)-1-isopropyl-1H-pyrrolo[3,2-c]pyridin-3-yl)-2-hydroxy-2-methylpropanamide;

N-(2-(1-(ethylsulfonyl)-1H-pyrazol-4-yl)pyrimidin-4-yl)-1-isopropyl-3-(1-(2-(methylsulfonyl)ethyl)-1H-pyrazol-4-yl)-1H-pyrrolo[3,2-c]pyridin-6-amine;

2-(4-(6-((2-(1-(cyclopropylsulfonyl)-1H-pyrazol-4-yl)pyrimidin-4-yl)amino)-1-isopropyl-1H-pyrrolo[3,2-c]pyridin-3-yl)-1H-pyrazol-1-yl)ethanol;

1-isopropyl-2-methyl-N-(2-(1-(((1-methyl-1H-pyrazol-3-yl)sulfonyl)-1H-pyrazol-4-yl)pyrimidin-4-yl)-1H-imidazo[4,5-c]pyridin-6-amine;

N-(2-(1-(cyclopropylmethyl)-1H-pyrazol-4-yl)pyrimidin-4-yl)-1-isopropyl-2-methyl-1H-imidazo[4,5-c]pyridin-6-amine;

6-((2-(1-(cyclopropylsulfonyl)-1H-pyrazol-4-yl)pyrimidin-4-yl)amino)-1-isopropyl-N-(tetrahydro-2H-pyran-4-yl)-1H-pyrrolo[3,2-c]pyridine-3-carboxamide;

4-(4-(((1-isopropyl-2-methyl-1H-imidazo[4,5-c]pyridin-6-yl)amino)pyrimidin-2-yl)-N,N-dimethyl-1H-pyrazole-1-sulfonamide;

(±)-1-isopropyl-2-methyl-N-(2-(1-(pyrrolidin-3-yl)-1H-pyrazol-4-yl)pyrimidin-4-yl)-1H-imidazo[4,5-c]pyridin-6-amine;

1-isopropyl-2-methyl-N-(2-(3-methyl-1H-pyrazol-4-yl)pyrimidin-4-yl)-1H-imidazo[4,5-c]pyridin-6-amine;

N-(2-(1-(cyclopropylsulfonyl)-3-methyl-1H-pyrazol-4-yl)pyrimidin-4-yl)-1-isopropyl-2-methyl-1H-imidazo[4,5-c]pyridin-6-amine;

1-isopropyl-N-(2-(4-methoxypiperidin-1-yl)pyrimidin-4-yl)-3-(1H-pyrazol-4-yl)-1H-pyrrolo[3,2-c]pyridin-6-amine;

2-(4-(1-isopropyl-6-((2-(4-methoxypiperidin-1-yl)pyrimidin-4-yl)amino)-1H-pyrrolo[3,2-c]pyridin-3-yl)-1H-pyrazol-1-yl)ethanol;

3-(1H-imidazol-4-yl)-1-isopropyl-N-(2-(4-methoxypiperidin-1-yl)pyrimidin-4-yl)-1H-pyrrolo([3,2-c]pyridin-6-amine;

(±)-N-(2-(1-(((1,4-dioxan-2-yl)methyl)sulfonyl)-1H-pyrazol-4-yl)pyrimidin-4-yl)-1-isopropyl-2-methyl-1H-imidazo[4,5-c]pyridin-6-amine;

N-(2-(1-((2-ethoxyethyl)sulfonyl)-1H-pyrazol-4-yl)pyrimidin-4-yl)-1-isopropyl-2-methyl-1H-imidazo[4,5-c]pyridin-6-amine;

(±)-1-isopropyl-2-methyl-N-(2-(1-(((tetrahydrofuran-3-yl)sulfonyl)-1H-pyrazol-4-yl)pyrimidin-4-yl)-1H-imidazo[4,5-c]pyridin-6-amine;

N-(2-(1-(((1-ethyl-1H-pyrazol-4-yl)sulfonyl)-1H-pyrazol-4-yl)pyrimidin-4-yl)-1-isopropyl-2-methyl-1H-imidazo[4,5-c]pyridin-6-amine;

(6-((2-(1-(difluoromethyl)-1H-pyrazol-4-yl)pyrimidin-4-yl)amino)-1-isopropyl-1H-imidazo[4,5-c]pyridin-2-yl)methanol;

1-isopropyl-N-(2-(1-(isopropylsulfonyl)-1H-pyrazol-4-yl)pyrimidin-4-yl)-2-methyl-1H-imidazo[4,5-c]pyridin-6-amine;

2-(4-(1-isopropyl-6-((2-(4-methoxypiperidin-1-yl)pyrimidin-4-yl)amino)-1H-pyrrolo[3,2-c]pyridin-3-yl)-1H-pyrazol-1-yl)acetamide;

2-(3-(1-isopropyl-6-((2(4-methoxypiperidin-1-yl)pyrimidin-4-yl)amino)-1H-pyrrolo[3,2-c]pyridin-3-yl)-1H-pyrazol-1-yl)acetamide;

1-isopropyl-N-(2-(4-methoxypiperidin-1-yl)pyrimidin-4-yl)-3-(1-(2-morpholinoethyl)-1H-pyrazol-4-yl)-1H-pyrrolo[3,2-c]pyridin-6-amine;

2-(4-(4-((1-isopropyl-2-methyl-1H-imidazo[4,5-c]pyridin-6-yl)amino)pyrimidin-2-yl)-1H-pyrazol-1-yl)acetamide;

1-isopropyl-2-methyl-N-(2-(1-(1-(2,2,2-trifluoroethyl)azetidin-3-yl)-1H-pyrazol-4-yl)pyrimidin-$^4$-yl)-1H-imidazo[4,5-c]pyridin-6-amine; or N4-(1-isopropyl-2-methyl-1H-imidazo[4,5-c]pyridin-6-yl)-N2-(1-methyl-1H-pyrazol-3-yl)pyrimidine-2,4-diamine.

25. The compound according to claim 1, wherein said compound is:

N-(2-(1-(azetidin-3-yl)-1H-pyrazol-4-yl)pyrimidin-4-yl)-1-isopropyl-2-methyl-1H-imidazo[4,5-c]pyridin-6-amine;

(+)-3-((4-((1-isopropyl-2-methyl-1H-imidazo[4,5-c]pyridin-6-yl)amino)pyrimidin-2-yl)amino)-2,2-dimethylbutanamide;

1-(4-((2-(hydroxymethyl)-1-isopropyl-1H-imidazo[4,5-c]pyridin-6-yl)amino)pyrimidin-2-yl)-4-methylpiperidin-4-ol;

(±)-N-(2-(3-ethylmorpholino)pyrimidin-4-yl)-1-isopropyl-2-methyl-1H-imidazo[4,5-c]pyridin-6-amine;

N2-(2-(1H-pyrazol-4-yl)ethyl)-N4-(1-isopropyl-2-methyl-1H-imidazo[4,5-c]pyridin-6-yl)pyrimidine-2,4-diamine;

N-(2-(4-methoxypiperidin-1-yl)pyrimidin-4-yl)-1-(2-(methylsulfonyl)ethyl)-1H-pyrrolo[3,2-c]pyridin-6-amine;

1-isopropyl-2-methyl-N-(2-(4-(methylthio)-1H-imidazol-1-yl)pyrimidin-4-yl)-1H-imidazo[4,5-c]pyridin-6-amine;

2-(1-(4-(1-isopropyl-2-methyl-1H-imidazo[4,5-c]pyridin-6-yl)amino)pyrimidin-2-yl)-1H-imidazol-4-yl)propan-2-ol;

2-(4-(4-((1-isopropyl-2-methyl-1H-imidazo[4,5-c]pyridin-6-yl)amino)pyrimidin-2-yl)-1H-pyrazol-1-yl)-2-methylpropanamide;

2-(4-(4-((1-isopropyl-2-methyl-1H-imidazo[4,5-c]pyridin-6-yl)amino)pyrimidin-2-yl)-1H-pyrazol-1-yl)propanenitrile;

2-(4-(4-((1-isopropyl-2-methyl-1H-imidazo[4,5-c]pyridin-6-yl)amino)pyrimidin-2-yl)-1H-pyrazol-1-yl)-N,2-dimethylpropanamide;

1-(4-((1-isopropyl-2-methyl-1H-imidazo[4,5-c]pyridin-6-yl)amino)pyrimidin-2-yl)-3,3-dimethylpiperidin-4-ol;

N-(2-(4-amino-3,3-di methylpiperidin-1-yl)pyrimidin-4-yl)-1-isopropyl-2-methyl-1H-imidazo[4,5-c]pyridin-6-amine;

N-(2-(1-(azetidin-3-ylmethyl)-1H-pyrazol-4-yl)pyrimidin-4-yl)-1-isopropyl-2-methyl-1H-imidazo[4,5-c]pyridin-6-amine;

N-(2-(1-(3-aminopropyl)-1H-pyrazol-4-yl)pyrimidin-4-yl)-1-isopropyl-2-methyl-1H-imidazo[4,5-c]pyridin-6-amine;

1-isopropyl-2-methyl-N-(2-(1-((3-methyloxetan-3-yl)methyl)-1H-pyrazol-4-yl)pyrimidin-4-yl)-1H-imidazo[4,5-c]pyridin-6-amine;

3-(4-(4-((1-isopropyl-2-methyl-1H-imidazo[4,5-c]pyridin-6-yl)amino)pyrimidin-2-yl)-1H-pyrazol-1-yl)tetrahydrothiophene 1,1-dioxide;

(1R,5S,8r)-3-(4-((2-(hydroxymethyl)-1-isopropyl-1H-imidazo[4,5-c]pyridin-6-yl)amino)pyrimidin-2-yl)-3-azabicyclo[3.2.1]octan-8-ol;

N-(2-(1-(cyclopropylsulfonyl)-1H-pyrazol-yl)pyrimidin-yl)-3-(1,4-dimethyl-1H-pyrazol-5-yl)-1-isopropyl-1H-pyrrolo[3,2-c]pyridin-6-amine;

2-(3-(6-(2-(1-(cyclopropylsulfonyl)-1H-pyrazol-4-yl)pyrimidin-4-ylamino)-1-isopropyl-1H-pyrrolo[3,2-c]pyridin-3-yl)-5-methyl-1H-pyrazol-1-yl)ethanol;
2-(5-(6-(2-(1-(cyclopropylsulfonyl)-1H-pyrazol-4-yl)pyrimidin-4-ylamino)-1-isopropyl-1H-pyrrolo[3,2-c]pyridin-3-yl)-3-methyl-1H-pyrazol-1-yl)ethanol;
2-(4-(6-(2-(1-(cyclopropylsulfonyl)-1H-pyrazol-4-yl)pyrimidin-4-ylamino)-1-isopropyl-1H-pyrrolo[3,2-c]pyridin-3-yl)-3-methyl-1H-pyrazol-1-yl)ethanol;
2-(4-(6-(2-(1-(cyclopropylsulfonyl)-1H-pyrazol-4-yl)pyrimidin-4-ylamino)-1-isopropyl-1H-pyrrolo[3,2-c]pyridin-3-yl)-5-methyl-1H-pyrazol-1-yl)ethanol;
2-(4-(6-(2-(1-(cyclopropyl sulfonyl)-1H-pyrazol-4-yl)pyrimidin-4-ylamino)-1-isopropyl-1H-pyrrolo[3,2-c]pyridin-3-yl)-1H-pyrazol-1-yl)propane-1,3-diol;
3-((4-(6-(2-(1-(cyclopropylsulfonyl)-1H-pyrazol-4-yl)pyrimidin-4-ylamino)-1-isopropyl-1H-pyrrolo[3,2-c]pyridin-3-yl)-1H-pyrazol-1-yl)methyl)oxetan-3-ol;
N-(2-(1-(cyclopropylsulfonyl)-1H-pyrazol-4-yl)pyrimidin-4-yl)-1-isopropyl-3-(1-(oxetan-3-yl)-1H-pyrazol-4-yl)-1H-pyrrolo[3,2-c]pyridin-6-amine;
N-(2-(1-(cyclopropylsulfonyl)-1H-pyrazol-4-yl)pyrimidin-4-yl)-1-isopropyl-3-(5,6,7,8-tetrahydroimidazo[1,2-a]pyrazin-2-yl)-1H-pyrrolo[3,2-c]pyridin-6-amine;
2-(4-(6-(2-(1-(cyclopropylsulfonyl)-1H-pyrazol-4-yl)pyrimidin-4-ylamino)-1-isopropyl-1H-pyrrolo[3,2-c]pyridin-3-yl)-1H-pyrazol-1-yl)-1-(4-methylpiperazin-1-yl)ethanone;
2-(4-(6-(2-(1-(ethylsulfonyl)-1H-pyrazol-4-yl)pyrimidin-4-ylamino)-1-isopropyl-1H-pyrrolo[3,2-c]pyridin-3-yl)-1H-pyrazol-1-yl)-N-(tetrahydro-2H-pyran-4-yl)acetamide;
2-(4-(6-(2-(4-(hydroxymethyl)-4-methoxypiperidin-1-yl)pyrimidin-4-ylamino)-1-isopropyl-1H-pyrrolo[3,2-c]pyridin-3-yl)-1H-pyrazol-1-yl)-2-methylpropanamide;
2-(4-(6-(2-(4-(hydroxymethyl)-4-methoxypiperidin-1-yl)pyrimidin-4-ylamino)-1-isopropyl-1H-pyrrolo[3,2-c]pyridin-3-yl)-1H-pyrazol-1-yl)acetamide;
N-ethyl-2-(4-(6-(2-(1-(ethylsulfonyl)-1H-pyrazol-4-yl)pyrimidin-4-ylamino)-1-isopropyl-1H-pyrrolo[3,2-c]pyridin-3-yl)-1H-pyrazol-1-yl)acetamide;
6-(2-(1-(ethylsulfonyl)-1H-pyrazol-4-yl)pyrimidin-4-ylamino)-1-isopropyl-N-(oxetan-3-yl)-1H-pyrrolo[3,2-c]pyridine-3-carboxamide;
1-isopropyl-6-(2-(4-methoxypiperidin-1-yl)pyrimidin-4-ylamino)-N-(1-(oxetan-3-yl)piperidin-4-yl)-1H-pyrrolo[3,2-c]pyridine-3-carboxamide;
6-(2-(1-(cyclopropylsulfonyl)-1H-pyrazol-4-yl)pyrimidin-4-ylamino)-N-((1s,3S,4R)-3,4-dihydroxycyclopentyl)-1-isopropyl-1H-pyrrolo[3,2-c]pyridine-3-carboxamide;
6-(2-(1-(cyclopropylsulfonyl)-1H-pyrazol-4-yl)pyrimidin-4-ylamino)-N-((1r,3R,4S)-3,4-dihydroxycyclopentyl)-1-isopropyl-1H-pyrrolo[3,2-c]pyridine-3-carboxamide;
6-(2-(1-(cyclopropylsulfonyl)-1H-pyrazol-4-yl)pyrimidin-4-ylamino)-1-isopropyl-N-(2-(methylsulfonyl)ethyl)-1H-pyrrolo[3,2-c]pyridine-3-carboxamide;
6-(2-(1-(cyclopropylsulfonyl)-1H-pyrazol-4-yl)pyrimidin-4-ylamino)-1-isopropyl-N-(tetrahydrofuran-3-yl)-1H-pyrrolo[3,2-c]pyridine-3-carboxamide;
6-(2-(1-(cyclopropylsulfonyl)-1H-pyrazol-4-yl)pyrimidin-4-ylamino)-N-(4-hydroxycyclohexyl)-1-isopropyl-1H-pyrrolo[3,2-c]pyridine-3-carboxamide;
6-((2-(1-(cyclopropylsulfonyl)-1H-pyrazol-4-yl)pyrimidin-4-yl)amino)-1-isopropyl-N-(1-oxidotetrahydro-2H-thiopyran-4-yl)-1H-pyrrolo[3,2-c]pyridine-3-carboxamide;
6-((2-(1-(cyclopropylsulfonyl)-1H-pyrazol-4-yl)pyrimidin-4-yl)amino)-1-isopropyl-N-(1-oxidotetrahydro-2H-thiopyran-4-yl)-1H-pyrrolo[3,2-c]pyridine-3-carboxamide;
6-((2-(1-(cyclopropylsulfonyl)-1H-pyrazol-4-yl)pyrimidin-4-yl)amino)-N-(1,1-dioxidotetrahydro-2H-thiopyran-4-yl)-1-isopropyl-1H-pyrrolo[3,2-c]pyridine-3-carboxamide;
6-(2-(1-(cyclopropylsulfonyl)-1H-pyrazol-4-yl)pyrimidin-4-ylamino)-1-isopropyl-N-(tetrahydro-2H-thiopyran-4-yl)-1H-pyrrolo[3,2-c]pyridine-3-carboxamide;
6-(2-(1-(cyclopropylsulfonyl)-1H-pyrazol-4-yl)pyrimidin-4-ylamino)-1-isopropyl-N-(tetrahydro-2H-pyran-3-yl)-1H-pyrrolo[3,2-c]pyridine-3-carboxamide;
4-(6-(2-(1-(cyclopropylsulfonyl)-1H-pyrazol-4-yl)pyrimidin-4-ylamino)-1-isopropyl-1H-pyrrolo[3,2-c]pyridin-3-yl)-1-(2-hydroxyethyl)pyrrolidin-2-one;
N-(2-(1-(cyclopropylsulfonyl)-1H-pyrazol-4-yl)pyrimidin-4-yl)-2-methyl-1H-imidazo[4,5-c]pyridin-6-amine;
3-(4-(1-isopropyl-2-methyl-1H-imidazo[4,5-c]pyridin-6-ylamino)pyrimidin-2-ylamino)-N,N,2,2-tetramethylpropanamide;
3-(4-(1-isopropyl-2-methyl-1H-imidazo[4,5-c]pyridin-6-ylamino)pyrimidin-2-ylamino)-N,2,2-trimethylpropanamide;
(24(4-(4-(1-isopropyl-2-methyl-1H-imidazo[4,5-c]pyridin-6-ylamino)pyrimidin-2-yl)-1H-pyrazol-1-ylsulfonyl)cyclopropyl)methanol; or
4-(4-(4-(1-isopropyl-2-methyl-1H-imidazo[4,5-c]pyridin-6-ylamino)pyrimidin-2-yl)-1H-pyrazol-1-ylsulfonyl)pyrrolidin-2-one.

26. The compound according to claim 1, wherein said compound is:
1-(3-(4-(4-(1-isopropyl-2-methyl-1H-imidazo[4,5-c]pyridin-6-ylamino)pyrimidin-2-yl)-1H-pyrazol-1-ylsulfonyl)azetidin-1-yl)ethanone;
N-(2-(1-(azetidin-3-ylsulfonyl)-1H-pyrazol-4-yl)pyrimidin-4-yl)-1-isopropyl-2-methyl-1H-imidazo[4,5-c]pyridin-6-amine;
1-isopropyl-2-methyl-N-(2-(1-(1-methylazetidin-3-ylsulfonyl)-1H-pyrazol-4-yl)pyrimidin-4-yl)-1H-imidazo[4,5-c]pyridin-6-amine;
2-(difluoromethyl)-1-isopropyl-N-(2-(1-(isopropylsulfonyl)-1H-pyrazol-4-yl)pyrimidin-4-yl)-1H-imidazo[4,5-c]pyridin-6-amine;
3-(4-(4-(2-(hydroxymethyl)-1-isopropyl-1H-imidazo[4,5-c]pyridin-6-ylamino)pyrimidin-2-yl)-1H-pyrazol-1-yl)-2,2-dimethylpropan-1-ol;
3-(44(4-(2-(hydroxymethyl)-1-isopropyl-1H-imidazo[4,5-c]pyridin-6-ylamino)pyrimidin-2-yl)-1H-pyrazol-1-yl)-2,2-dimethylpropanamide;
3-(6-(2-(1-(cyclopropylsulfonyl)-1H-pyrazol-4-yl)pyrimidin--ylamino)-2-(hydroxymethyl)-1H-imidazo[4,5-c]pyridin-1-yl)-3-methylbutan-1-ol;
(6-(2-(1-(cyclopropylsulfonyl)-1H-pyrazol-4-yl)pyrimidin-4-ylamino)-1-(1R,2R)-2-methylcyclopentyl)-1H-imidazo[4,5-c]pyridin-2-yl)methanol;
(6-(2-(1-(cyclopropylsulfonyl)-1H-pyrazol-4-yl)pyrimidin-4-ylamino)-1-((1R,2R)-2-methylcyclopentyl)-1H-imidazo[4,5-c]pyridin-2-yl)methanol;

(6-(2-(1-(cyclopropylsulfonyl)-1H-pyrazol-4-yl)pyrimidin-4-ylamino)-1-phenyl-1H-imidazo[4,5-c]pyridin-2-yl)methanol;

4-(6-(2-(1-(cyclopropylsulfonyl)-1H-pyrazol-4-yl)pyrimidin-4-ylamino)-2-(hydroxymethyl)-1H-imidazo[4,5-c]pyridin-1-yl)-1-methylpyrrolidin-2-one;

(6-(2-(1-(cyclopropylsulfonyl)-1H-pyrazol-4-yl)pyrimidin-4-ylamino)-1-(1-methyl cyclopentyl)-1H-imidazo[4,5-c]pyridin-2-yl)methanol;

(6-(2-(1-(cyclopropylsulfonyl)-1H-pyrazol-4-yl)pyrimidin-4-ylamino)-1-(4-methylpentan-2-yl)-1H-imidazo[4,5-c]pyridin-2-yl)methanol;

(1-cyclohexyl-6-(2-(1-(cyclopropylsulfonyl)-1H-pyrazol-4-yl)pyrimidin-4-ylamino)-1H-imidazo[4,5-c]pyridin-2-yl)methanol;

(6-(2-(1-(cyclopropylsulfonyl)-1H-pyrazol-4-yl)pyrimidin-4-ylamino)-1-(3,3-difluoroCyclobutyl)-1H-imidazo[4,5-c]pyridin-2-yl)methanol;

(1-cyclopentyl-6-(2-(1-(cyclopropylsulfonyl)-1H-pyrazol-4-yl)pyrimidin-4-ylamino)-1H-imidazo[4,5-c]pyridin-2-yl)methanol;

(6-((2-(1-(cyclopropylsulfonyl)-1H-pyrazol-4-yl)pyrimidin-4-yl)amino)-1-(3,3-difluorocyclopentyl)-1H-imidazo[4,5-c]pyridin-2-yl)methanol;

(6-(2-(1-(cyclopropylsulfonyl)-1H-pyrazol-4-yl)pyrimidin-4-ylamino)-1-(3,3,3-trifluoropropyl)-1H-imidazo[4,5-c]pyridin-2-yl)methanol;

(6-(2-(1-(cyclopropylsulfonyl)-1H-pyrazol-4-yl)pyrimidin-4-ylamino)-1-(1-methylcyclobutyl)-1H-imidazo[4,5-c]pyridin-2-yl)methanol;

(1-tert-butyl-6-(2-(1-(cyclopropylsulfonyl)-1H-pyrazol-4-yl)pyrimidin-4-ylamino)-1H-imidazo[4,5-c]pyridin-2-yl)methanol;

(6-(2-(1-(cyclopropylsulfonyl)-1H-pyrazol-4-yl)pyrimidin-4-ylamino)-1-phenethyl-1H-imidazo[4,5-c]pyridin-2-yl)methanol;

(6-(2-(1-(cyclopropylsulfonyl)-1H-pyrazol-4-yl)pyrimidin-4-ylamino)-1-(3-methylbutan-2-yl)-1H-imidazo[4,5-c]pyridin-2-yl)methanol;

(1-(1-cyclopropylpropan-2-yl)-6-(2-(1-(cyclopropylsulfonyl)-1H-pyrazol-4-yl)pyrimidin-4-ylamino)-1H-imidazo[4,5-c]pyridin-2-yl)methanol;

2-{6-[2-(4-Methoxypiperidin-1-yl)pyrimidin-4-ylamino]-2-methyl-imidazo[4,5-c]pyridin-1-yl}propan-1-ol;

[1-((S)-2-Methoxy-1-methylethyl)-2-methyl-1H-imidazo[4,5-c]pyridin-6-yl]-[2-(4-methoxypiperidin-1-yl)pyrimidin-4-yl]amine;

[1-(3-Methoxy-1-methylpropyl)-2-methyl-1H-imidazo[4,5-c]pyridin-6-yl]-[2-(4-methoxypiperidin-1-yl)pyrimidin-4-yl]amine;

3-{6-[2-(4-Methoxypiperidin-1-yl)pyrimidin-4-ylamino]-2-methylimidazo[4,5-c]pyridin-1-yl}butan-1-ol;

(1-Isopropyl-2-methyl-1H-imidazo[4,5-c]pyridin-6-yl)-[2-((1 RS,3RS,5SR)-3-methoxy-8-azabicyclo[3.2.1]oct-8-yl)pyrimidin-4-yl]amine;

N-2-(4-Methoxypiperidin-1-yl)pyrimidin-4-yl)-2-methyl-1-phenyl-1H-imidazo[4,5-c]pyridin-6-amine;

N-(2-(1-Oxa-7-azaspiro[3.5]nonan-7-yl)pyrimidin-4-yl)-1-isopropyl-2-methyl-1H-imidazo[4,5-c]pyridin-6-amine;

1-Isopropyl-2-methyl-N-(2-(pyrrolo[3,4-c]pyrazol-5(2H,4H,6H)-yl)pyrimidin-4-yl)-1H-imidazo[4,5-c]pyridin-6-amine;

3-(1-(4-((1-Isopropyl-2-methyl-1H-imidazo[4,5-c]pyridin-6-yl)amino)pyrimidin-2-yl)-4-methoxypiperidin-4-yl)propan-1-ol;

(±)-(cis)-5-(4-((1-Isopropyl-2-methyl-1H-imidazo[4,5-c]pyridin-6-yl)amino)pyrimidin-2-yl)hexahydrooxazolo[4,5-c]pyridin-2(3H)-one;

N4-(1-Isopropyl-2-methyl-1H-imidazo[4,5-c]pyridin-6-yl)-N2-(2-methyl-2-(methylsulfonyl)propyl)pyrimidine-2,4-diamine;

N-(2-(3,6-Dihydro-2H-pyran-4-yl)pyrimidin-4-yl)-1-isopropyl-2-methyl-1H-imidazo[4,5-c]pyridin-6-amine;

1-Isopropyl-2-methyl-N-(2-(tetrahydro-2H-pyran-4-yl)pyrimidin-4-yl)-1H-imidazo[4,5-c]pyridin-6-amine;

8-(4-((1-Isopropyl-2-methyl-1H-imidazo[4,5-c]pyridin-6-yl)amino)pyrimidin-2-yl)-2,8-diazaspiro[4.5]decan-1-one;

1-(4-((1-Isopropyl-2-methyl-1H-imidazo[4,5-c]pyridin-6-yl)amino)pyrimidin-2-yl)piperidin-4-ol;

1-(4-((2-(Hydroxymethyl)-1-isopropyl-1H-imidazo[4,5-c]pyridin-6-yl)amino)pyrimidin-2-yl)piperidin-4-ol;

(±)-3-Fluoro-1-(4-((1-isopropyl-2-methyl-1H-imidazo[4,5-c]pyridin-6-yl)amino)pyrimidin-2-yl)piperidin-4-ol;

N-(2-(1,4-Dioxa-8-azaspiro[4.5]decan-8-yl)pyrimidin-4-yl)-1-isopropyl-2-methyl-1H-imidazo[4,5-c]pyridin-6-amine;

(±)-3,3-Difluoro-11-(4-((1-isopropyl-2-methyl-1H-imidazo[4,5-c]pyridin-6-yl)amino)pyrimidin-2-yl)piperidin-4-ol;

(±)-1-(4-((1-Isopropyl-2-methyl-1H-imidazo[4,5-c]pyridin-6-yl)amino)pyrimidin-2-yl)-4-methoxypiperidin-3-ol;

(±)-1-(4-((1-Isopropyl-2-methyl-1H-imidazo[4,5-c]pyridin-6-yl)amino)pyrimidin-2-yl)-3-methoxypiperidin-4-ol;

(±)-3-Fluoro-1-(4-((2-(hydroxymethyl)-1-isopropyl-1H-imidazo[4,5-c]pyridin-6-yl)amino)pyrimidin-2-yl)piperidin-4-ol;

(±)-1-Isopropyl-N-(2-(4-methoxy-2-methylpiperidin-1-yl)pyrimidin-4-yl)-2-methyl-1H-imidazo[4,5-c]pyridin-6-amine;

(1-Isopropyl-6-((2-(4-(trifluoromethyl)piperidin-1-yl)pyrimidin-4-yl)amino)-1H-imidazo[4,5-c]pyridin-2-yl)methanol;

(6-((2-(4-Ethylpiperidin-1-yl)pyrimidin-4-yl)amino)-1-isopropyl-1H-imidazo[4,5-c]pyridin-2-yl)methanol;

(1-Isopropyl-2-methyl-1H-imidazo[4,5-c]pyridin-6-yl)[2-(2-methyl-2,4,6,7-tetrahydropyrazolo[4,3-c]pyridin-5-yl)-pyrimidin-4-yl]amine; or

[2-(4-Dimethylaminomethyl-4-methoxypiperidin-1-yl)pyrimidin-4-yl](1-isopropyl-2-methyl-1H-imidazo[4,5-c]pyridin-6-yl)amine.

27. The compound according to claim 1, wherein said compound is:

(1-Isopropyl-2-methyl-1H-imidazo[4,5-c]pyridin-6-yl)[2-(4-methoxy-4-methoxymethylpiperidin-1-yl)pyrimidin-4-yl]amine;

{1-[4-(1-Isopropyl-2-methyl-1H-imidazo[4,5-c]pyridin-6-ylamino)pyrimidin-2-yl]-4-methoxypiperidin-4-yl}methanol;

N2-(3-Amino-2,2-dimethylpropyl)-N4-(1-isopropyl-2-methyl-1H-imidazo[4,5-c]pyridin-6-yl)pyrimidine-2,4-diamine;

3-[4-(1-Isopropyl-2-methyl-1H-imidazo[4,5-c]pyridin-6-ylamino)pyrimidin-2-ylamino]-2,2-dimethylpropan-1-ol;

2-(1-[4-(1-Isopropyl-2-methyl-1H-imidazo[4,5-c]pyridin-6-ylamino)pyrimidin-2-yl]-4-methoxypiperidin-4-yl) ethanol;
{2-[4-(2-Dimethylaminoethyl)-4-methoxypiperidin-1-yl]pyrimidin-4-yl}-(1-isopropyl-2-methyl-1H-imidazo[4,5-c]pyridin-6-yl)amine;
N4-(1-Isopropyl-2-methyl-1H-imidazo[4,5-c]pyridin-6-yl)-N2-(3-methoxy-2,2-dimethylpropyl)pyrimidine-2,4-diamine;
3-[4-(1-Isopropyl-2-methyl-1H-imidazo[4,5-c]pyridin-6-ylamino)pyrimidin-2-ylamino]-2,2-dimethylpropionitrile; formate salt;
(±)-[2-((cis)-3-Fluoro-4-methoxypiperidin-1-yl)pyrimidin-4-yl](1-isopropyl-2-methyl-1H-imidazo[4,5-c]pyridin-6-yl)amine; formate salt;
(±)-[2-((trans)-3-Fluoro-4-methoxypiperidin-1-yl)pyrimidin-4-yl]-(1-isopropyl-2-methyl-1H-imidazo[4,5-c]pyridin-6-yl)amine;
(±)-{6-[2-((cis)-3-Fluoro-4-methoxypiperidin-1-yl)pyrimidin-4-ylamino]-1-isopropyl-1H-imidazo[4,5-c]pyridin-2-yl}methanol; formate salt;
(±)-{6-[2-((trans)-3-Fluoro-4-methoxypiperidin-1-yl)pyrimidin-4-ylamino]-1-isopropyl-1H-imidazo[4,5-c]pyridin-2-yl}methanol; formate salt;
(±)-[2-(3,3-Difluoro-4-methoxypiperidin-1-yl)pyrimidin-4-yl](1-isopropyl-2-methyl-1H-imidazo[4,5-c]pyridin-6-yl)amine; formate salt;
(±)-{6-[2-(3,3-Difluoro-4-methoxypiperidin-1-yl)pyrimidin-4-ylamino]-1-isopropyl-1H-imidazo[4,5-c]pyridin-2-yl}methanol; formate salt;
(±)-(1-Isopropyl-2-methyl-1H-imidazo[4,5-c]pyridin-6-yl)[2-(2-trifluoromethyl-piperidin-1-yl)pyrimidin-4-yl]amine;
(±)-{1-Isopropyl-6-[2-(2-trifluoromethylpiperidin-1-yl)pyrimidin-4-ylamino]-1H-imidazo[4,5-c]pyridin-2-yl}methanol; formate salt;
N-(2-(4-methoxypiperidin-11-yl)pyrimidin-4-yl)-3,3-dimethyl-2,3-dihydrooxazolo[3',2': 1,2]imidazo[4,5-c]pyridin-6-amine;
(1-(4-((3,3-dimethyl-2,3-dihydrooxazolo[3',2': 1,2]imidazo[4,5-c]pyridin-6-yl)amino)pyrimidin-2-yl)-4-methoxypiperidin-4-yl)methanol;
[2-(1-Cyclopropanesulfonyl-1H-pyrazol-4-yl)-pyrimidin-4-yl]-(4,4-dimethyl-3,4-dihydro-2H-1-oxa-4a,7,9-triazafluoren-6-yl)amine;
(R)-1-{(S)-1-sec-Butyl-6-[2-(1-ethanesulfonyl-1H-pyrazol-4-yl)-pyrimidin-4-ylamino]-1H-imidazo[4,5-c]pyridin-2-yl}-ethanol;
[2-(1-Cyclopropanesulfonyl-1H-pyrazol-4-yl)-pyrimidin-4-yl]-[1-isopropyl-2-(2-methoxy-ethoxy)-1H-imidazo[4,5-c]pyridin-6-yl]amine;
N6-[2-(1-Cyclopropanesulfonyl-1H-pyrazol-4-yl)-pyrimidin-4-yl]-1-isopropyl-N2-(2-methoxyethyl)-1H-imidazo[4,5-c]pyridine-2,6-di amine;
[2-(1-Cyclopropanesulfonyl-1H-pyrazol-4-yl)-pyrimidin-4-yl]-(4,4-dimethyl-3,4-dihydro-1H-2-oxa-4a,7,9-triazafluoren-6-yl)amine;
[2-(1-Cyclopropanesulfonyl-1H-pyrazol-4-yl)-pyrimidin-4-yl]-[2-methyl-1-(tetrahydropyran-4-ylmethyl)-1H-imidazo[4,5-c]pyridin-6-yl]amine;
(R)-1-[(R)-6-[2-(1-Cyclopropanesulfonyl-1H-pyrazol-4-yl)pyrimidin-4-ylamino]-1-(2,2,2-trifluoro-1-methyl-ethyl)-1H-imidazo[4,5-c]pyridin-2-yl]ethanol;
(R)-1-{(1-((R)-sec-Butyl)-6-[2-(1-cyclopropanesulfonyl-1H-pyrazol-4-yl)pyrimidin-4-ylamino]-1H-imidazo[4,5-c]pyridin-2-yl}ethanol;
3-Fluoro-1-(4-[2-((R)-1-hydroxyethyl)-1-((R)-2,2,2-trifluoro-1-methylethyl)-1H-imidazo[4,5-c]pyridin-6-ylamino]pyrimidin-2-yl)-piperidin-4-ol;
(R)-1-[6-[2-(3-Fluoro-4-methoxypiperidin-1-yl)-pyrimidin-4-ylamino]-1-((S)-2,2,2-trifluoro-1-methyl-ethyl)-1H-imidazo[4,5-c]pyridin-2-yl]ethanol;
2-{4-[4-(1-Isopropyl-2-methyl-1H-imidazo[4,5-c]pyridin-6-ylamino)pyrimidin-2-yl]piperaziN-1-yl}isobutyramide;
(1-Isopropyl-2-methyl-1H-imidazo[4,5-c]pyridin-6-yl)-[2-(4-methanesulfonylpiperidin-1-yl)pyrimidin-4-yl]amine;
(1-isopropyl-2-methyl-1H-imidazo[4,5-c]pyridin-6-yl)-[2-(4-methylsulfanylpiperidin-1-yl)pyrimidin-4-yl]amine;
1-[4-(1-Isopropyl-2-methyl-1H-imidazo[4,5-c]pyridin-6-ylamino)pyrimidin-2-yl]piperidine-4-sulfonic acid amide;
(1-Isopropyl-2-methyl-1H-imidazo[4,5-c]pyridin-6-yl)-[2-(3-methanesulfonylazetidin-1-yl)pyrimidin-4-yl]amine;
[2-(4-Difluoromethoxypiperidin-1-yl)pyrimidin-4-yl]-(1-isopropyl-2-methyl-1H-imidazo[4,5-c]pyridin-6-yl)amine;
(3aR,5R,6aS)-2-[4-(1-Isopropyl-2-methyl-1H-imidazo[4,5-c]pyridin-6-ylamino)pyrimidin-2-yl]octahydro-cyclopenta[c]pyrrol-5-ol;
1-Isopropyl-N-(2-((3aR,5r,6aS)-5-methoxyhexahydrocyclopenta[c]pyrrol-2(1H)-yl)pyrimidin-4-yl)-2-methyl-1H-imidazo[4,5-c]pyridin-6-amine;
1-{[4-(1-isopropyl-2-methyl-1H-imidazo[4,5-c]pyridin-6-ylamino)pyrimidin-2-ylamino]methyl}cyclopropane carboxylic acid amide;
(1-Isopropyl-2-methyl-1H-imidazo[4,5-c]pyridin-6-yl)-{2-[4-(propane-2-sulfonyl)piperidin-1-yl]pyrimidin-4-yl}amine;
(1-Isopropyl-6-{2-[4-(propane-2-sulfonyl)piperidin-1-yl]pyrimidin-4-ylamino}-1H-imidazo[4,5-c]pyridin-2-yl)methanol;
1-[4-(1-Isopropyl-2-methyl-1H-imidazo[4,5-c]pyridin-6-ylamino)pyrimidin-2-yl]-1H-imidazole-4-sulfonic acid cyclopropylamide;
N2-[2-(1-Cyclopropanesulfonyl-1H-pyrazol-4-yl)-pyrimidin-4-yl]-N2-ethyl-1-isopropyl-1H-imidazo[4,5-c]pyridine-2,6-diamine;
2-{6-[2-(1-Cyclopropanesulfonyl-1H-pyrazol-4-yl)pyrimidin-4-ylamino]-1-isopropyl-1H-imidazo[4,5-c]pyridin-2-ylmethoxy}ethanol;
[2-(1-Cyclopropanesulfonyl-1H-pyrazol-4-yl)-pyrimidin-4-yl]-[1-isopropyl-2-(2,2,2-trifluoroethyl)-1H-imidazo[4,5-c]pyridin-6-yl]amine;
{6-[2-(4-Hydroxymethyl-4-methoxypiperidin-1-yl)pyrimidin-4-ylamino]-1-isopropyl-1H-imidazo[4,5-c]pyridin-2-yl}methanol;
3-[4-(2-Hydroxymethyl-1-isopropyl-1H-imidazo[4,5-c]pyridin-6-ylamino)pyrimidin-2-ylamino]-2,2-dimethylpropionic acid methyl ester;
(R)-1-{6-[2-(1-Cyclopropanesulfonyl-1H-pyrazol-4-yl)pyrimidin-4-ylamino]-1-isopropyl-1H-imidazo[4,5-c]pyridin-2-yl}ethanol;
(S)-1-{6-[2-(1-Cyclopropanesulfonyl-1H-pyrazol-4-yl)pyrimidin-4-ylamino]-1-isopropyl-1H-imidazo[4,5-c]pyridin-2-yl}ethanol;
2-{6-[2-(1-Cyclopropanesulfonyl-1H-pyrazol-4-yl)pyrimidin-4-ylamino]-1-isopropyl-1H-imidazo[4,5-c]pyridin-2-yl}propan-2-ol; or

[2-(1-Cyclopropanesulfonyl-1H-pyrazol-4-yl)-pyrimidin-4-yl]-(2-cyclopropyl-1-isopropyl-1H-imidazo[4,5-c]pyridin-6-yl)amine.

28. The compound according to claim 1, wherein said compound is:
- (±)-[2-(1-Cyclopropanesulfonyl-1H-pyrazol-4-yl)-pyrimidin-4-yl]-[1-isopropyl-2-(tetrahydrofuran-2-yl)-1H-imidazo[4,5-c]pyridin-6-yl]amine;
- (4)-[2-(1-Cyclopropanesulfonyl-1H-pyrazol-4-yl)pyrimidin-4-yl]-[1-isopropyl-2-(1-methoxyethyl)-1H-imidazo[4,5-c]pyridin-6-yl]amine;
- [2-((S)-1-Aminoethyl)-1-isopropyl-1H-imidazo[4,5-c]pyridin-6-yl]-[2-(1-cyclopropanesulfonyl-1H-pyrazol-4-yl)pyrimidin-4-yl]amine;
- [2-((R)-1-Aminoethyl)-1-isopropyl-1H-imidazo[4,5-c]pyridin-6-yl]-[2-(1-cyclopropanesulfonyl-1H-pyrazol-4-yl)pyrimidin-4-yl]amine;
- (S)-i-{6-[2-(1-Cyclopropanesulfonyl-1H-pyrazol-4-yl)pyrimidin-4-ylamino]-1-isopropyl-1H-imidazo[4,5-c]pyridin-2-yl}ethane-1,2-diol;
- (±)-[2-(1-Cyclopropanesulfonyl-1H-pyrazol-4-yl)pyrimidin-4-yl]-(1-isopropyl-2-oxetaN-2-yl-1H-imidazo[4,5-c]pyridin-6-yl)amine;
- [6-[2-(1-Cyclopropanesulfonyl-1H-pyrazol-4-yl)pyrimidin-4-ylamino]-1-((S)-2,2,2-trifluoro-1-methyl-ethyl)-1H-imidazo[4,5-c]pyridin-2-yl]methanol;
- (R)-1-[6-[2-(1-Cyclopropanesulfonyl-1H-pyrazol-4-yl)-pyrimidin-4-ylamino]-1-((S)-2,2,2-trifluoro-1-methyl-ethyl)-1H-imidazo[4,5-c]pyridin-2-yl]-ethanol;
- {6-[2-(3,6-Dihydro-2H-pyran-4-yl)pyrimidin-4-ylamino]-1-isopropyl-1H-imidazo[4,5-c]pyridin-2-yl}methanol;
- {1-Isopropyl-6-[2-(tetrahydropyran-4-yl)pyrimidin-4-ylamino]-1H-imidazo[4,5-c]pyridin-2-yl}methanol;
- [2-(2,5-Dihydrofuran-3-yl)pyrimidin-4-yl]-(1-isopropyl-2-methyl-1H-imidazo[4,5-c]pyridin-6-yl)amine;
- (±)(1-Isopropyl-2-methyl-1H-imidazo[4,5-c]pyridin-6-yl)-[2-(tetrahydrofuran-3-yl)pyrimidin-4-yl]amine;
- 5-(1-Isopropyl-2-methyl-1H-imidazo[4,5-c]pyridin-6-ylamino)pyrimidin-2-yl]pyridine-2-carboxylic acid methylamide;
- 5-[4-(1-Isopropyl-2-methyl-1H-imidazo[4,5-c]pyridin-6-ylamino)pyrimidin-2-yl]pyridine-2-carboxylic acid dimethylamide;
- {6-[2-(2-Ethylaminothiazol-5-yl)-pyrimidin-4-ylamino]-1-isopropyl-1H-imidazo[4,5-c]pyridin-2-yl}methanol;
- 3-[4-(1-Isopropyl-2-methyl-1H-imidazo[4,5-c]pyridin-6-ylamino)pyrimidin-2-ylamino]-2-methylpropionamide;
- 3-[4-(1-Isopropyl-2-methyl-1H-imidazo[4,5-c]pyridin-6-ylamino)pyrimidin-2-ylamino]-2-methoxymethyl-2-methylpropionamide;
- 2-Hydroxy-3-[4-(1-isopropyl-2-methyl-1H-imidazo[4,5-c]pyridin-6-ylamino)pyrimidin-2-ylamino]-2-methyl-propionamide;
- 4-[4-(1-Isopropyl-2-methyl-1H-imidazo[4,5-c]pyridin-6-ylamino)pyrimidin-2-ylamino]butyramide;
- 3-{[4-(1-Isopropyl-2-methyl-1H-imidazo[4,5-c]pyridin-6-ylamino)pyrimidin-2-yl]methylamino}-2,2-dimethylpropionamide;
- (1-Isopropyl-2-methyl-1H-imidazo[4,5-c]pyridin-6-yl)-(2-pyridin-4-ylpyrimidin-4-yl)amine;
- [2-(6-Aminopyridin-3-yl)pyrimidin-4-yl]-(1-isopropyl-2-methyl-1H-imidazo[4,5-c]pyridin-6-yl)amine;
- (1-Isopropyl-2-methyl-1H-imidazo[4,5-c]pyridin-6-yl)-[2-(6-methanesulfonylpyridin-3-yl)pyrimidin-4-yl]amine;
- {1-Isopropyl-6-[2-(2-methylaminothiazol-5-yl)pyrimidin-4-ylamino]-1H-imidazo[4,5-c]pyridin-2-yl}methanol;
- N-{(E)-3-[4-(1-Isopropyl-2-methyl-1H-imidazo[4,5-c]pyridin-6-ylamino)pyrimidin-2-yl]-1,1-dimethylallyl}acetamide;
- [2-(3-Fluoropiperidin-1-yl)pyrimidin-4-yl]-(1-isopropyl-2-methyl-1H-imidazo[4,5-c]pyridin-6-yl)amine;
- [2-(4-Fluoropiperidin-1-yl)pyrimidin-4-yl]-(1-isopropyl-2-methyl-1H-imidazo[4,5-c]pyridin-6-yl)amine;
- [2-((S)-3-Fluoropyrrolidin-1-yl)pyrimidin-4-yl]-(1-isopropyl-2-methyl-1H-imidazo[4,5-c]pyridin-6-yl)amine;
- [2-((R)-3-Fluoropyrrolidin-1-yl)pyrimidin-4-yl]-(1-isopropyl-2-methyl-1H-imidazo[4,5-c]pyridin-6-yl)amine;
- {6-[2-(2-Dimethylaminothiazol-5-yl)pyrimidin-4-ylamino]-1-isopropyl-1H-imidazo[4,5-c]pyridin-2-yl}methanol;
- [2-(2-Ethylthiazol-5-yl)pyrimidin-4-yl]-(1-isopropyl-2-methyl-1H-imidazo[4,5-c]pyridin-6-yl)amine;
- {1-[4-(1-Isopropyl-2-methyl-1H-imidazo[4,5-c]pyridin-6-ylamino)pyrimidin-2-yl]piperidin-4-yl}methylcarbamic acid tert-butyl ester;
- 1-(1-[4-(1-Isopropyl-2-methyl-1H-imidazo[4,5-c]pyridin-6-ylamino)pyrimidin-2-yl]piperidin-4-yl}pyrrolidin-2-one;
- (1-Isopropyl-2-methyl-1H-imidazo[4,5-c]pyridin-6-yl)-[2-(4-oxetan-3-ylpiperidin-1-yl)pyrimidin-4-yl]amine;
- (2-Imidazol-1-ylpyrimidin-4-yl)-(1-isopropyl-2-methyl-1H-imidazo[4,5-c]pyridin-6-yl)amine;
- (cis)-1-(4-((1-isopropyl-2-methyl-1H-imidazo[4,5-c]pyridin-6-yl)amino)pyrimidin-2-yl)-2-methylpiperidin-4-ol;
- N-(2-(3-amino-1H-pyrazol-1-yl)pyrimidin-4-yl)-1-isopropyl-2-methyl-1H-imidazo[4,5-c]pyridin-6-amine;
- N4-(1-isopropyl-2-methyl-1H-imidazo[4,5-c]pyridin-6-yl)-N2-(1H-pyrazol-3-yl)pyrimidine-2,4-di amine;
- (1-isopropyl-2-methyl-N-(2-(3-methylmorpholino)pyrimidin-4-yl)-1H-imidazo[4,5-c]pyridin-6-amine;
- N-(2-(2,4-dimethyl-1H-imidazol-1-yl)pyrimidin-4-yl)-1-isopropyl-2-methyl-1H-imidazo[4,5-c]pyridin-6-amine;
- 1-isopropyl-2-methyl-N-(2-(4-(methylsulfonyl)phenyl)pyrimidin-4-yl)-1H-imidazo[4,5-c]pyridin-6-amine;
- [2-(1,5-Dioxa-9-azaspiro[5.5]undec-9-yl)pyrimidin-4-yl]-(1-isopropyl-2-methyl-1H-imidazo[4,5-c]pyridin-6-yl)amine;
- (±)-cis-5-Fluoro-1-[4-(1-isopropyl-2-methyl-1H-imidazo[4,5-c]pyridin-6-ylamino)pyrimidin-2-yl]-3,3-dimethylpiperidin-4-ol; formate salt;
- (±)-cis-5-Fluoro-1-[4-(2-hydroxymethyl-1-isopropyl-1H-imidazo[4,5-c]pyridin-6-ylamino)pyrimidin-2-yl]-3,3-dimethylpiperidin-4-ol;
- (1-Isopropyl-2-methyl-1H-imidazo[4,5-c]pyridin-6-yl)[2-(1,4,5,7-tetrahydropyrazolo[3,4-c]pyridin-6-yl)pyridin-4-yl]amine;
- N2-(1,1-Dioxotetrahydrothiophen-3-ylmethyl)-N4-(1-isopropyl-2-methyl-1H-imidazo[4,5-c]pyridin-6-yl)pyrimidine-2,4-diamine;
- [2-(6-Fluoro-1,4-dioxa-8-azaspiro[4.5]dec-8-yl)pyrimidin-4-yl](1-isopropyl-2-methyl-1H-imidazo[4,5-c]pyridin-6-yl)amine;
- {6-[2-(6-Fluoro-1,4-dioxa-8-azaspiro[4.5]dec-8-yl)pyrimidin-4-ylamino]-1-isopropyl-1H-imidazo[4,5-c]pyridin-2-yl}methanol;

{6-[2-((3*,4*)-3-Fluoro-4-methoxypiperidin-1-yl)pyrimidin-4-ylamino]-1-isopropyl-1H-imidazo[4,5-c]pyridin-2-yl}methanol; or (1-Isopropyl-2-methyl-1H-imidazo[4,5-c]pyridin-6-yl)-[2-(2-methanesulfonyl-2-methylpropoxy)pyrimidin-4-yl]amine.

29. The compound according to claim 1, wherein said compound is:

[6-[2-((3 RS,4 SR)-3-Fluoro-4-methoxypiperidin-1-yl)pyrimidin-4-ylamino]-1-((S)-2,2,2-trifluoro-1-methylethyl)-1H-imidazo[4,5-c]pyridin-2-yl]methanol;

(3RS,4SR)-3-Fluoro-1-{4-[2-((R)-1-hydroxyethyl)-1-isopropyl-1H-imidazo[4,5-c]pyridin-6-ylamino]pyrimidin-2-yl}piperidin-4-ol;

(R)-1-{6-[2-((3RS,4SR)-3-Fluoro-4-methoxypiperidin-1-yl)pyrimidin-4-ylamino]-1-isopropyl-1H-imidazo[4,5-c]pyridin-2-yl}ethanol;

{1-Isopropyl-6-[2-(2-methanesulfonyl-2-methylpropoxy)pyrimidin-4-ylamino]-1H-imidazo[4,5-c]pyridin-2-yl}methanol;

{1-Isopropyl-6-[2-(4-methanesulfonylpiperidin-1-yl)pyrimidin-4-ylamino]-1H-imidazo[4,5-c]pyridin-2-yl}methanol;

(R)-1-[6-[2-(4-Methanesulfonylpiperidin-1-yl)pyrimidin-4-ylamino]-1-((S)-2,2,2-trifluoro-1-methylethyl)-1H-imidazo[4,5-c]pyridin-2-yl]ethanol;

(R)-1-[6-[2-(2-Methanesulfonyl-2-methyl-propylamino)pyrimidin-4-ylamino]-1-((S)-2,2,2-trifluoro-1-methylethyl)-1H-imidazo[4,5-c]pyridin-2-yl]ethanol;

1-Isopropyl-6-[2-(2-methanesulfonyl-2-methylpropylamino)pyrimidin-4-ylamino]-1H-pyrrolo[3,2-c]pyridine-3-carboxylic acid (tetrahydropyran-4-yl)amide;

(R)-1-[6-[2-(4-Hydroxymethyl-4-methoxypiperidin-1-yl)pyrimidin-4-ylamino]-1-((S)-2,2,2-trifluoro-1-methylethyl)-1H-imidazo[4,5-c]pyridin-2-yl]ethanol;

(3S,4R)-3-Fluoro-1-(4-[2-hydroxymethyl-1-((S)-2,2,2-trifluoro-1-methylethyl)-1H-imidazo[4,5-c]pyridin-6-ylamino]pyrimidin-2-yl) piperidin-4-ol;

(3R,4S)-3-Fluoro-1-{4-[2-hydroxymethyl-1-((S)-2,2,2-trifluoro-1-methylethyl)-1H-imidazo[4,5-c]pyridin-6-ylamino]pyrimidin-2-yl}piperidin-4-ol;

(±)-2-({1-[4-(2-Hydroxymethyl-1-isopropyl-1H-imidazo[4,5-c]pyridin-6-ylamino)pyrimidin-2-yl]piperidin-2-yl}ethanol;

1-[4-(2-Hydroxymethyl-1-isopropyl-1H-imidazo[4,5-c]pyridin-6-ylamino)pyrimidin-2-yl]-4-trifluoromethyl-piperidin-4-ol;

{6-[2-(2-Hydroxymethylpiperidin-1-yl)pyrimidin-4-ylamino]-1-isopropyl-1H-imidazo[4,5-c]pyridin-2-yl}methanol;

{6-[2-(2-Ethylthiazol-5-yl)pyrimidin-4-ylamino]-1-isopropyl-1H-imidazo[4,5-c]pyridin-2-yl}methanol;

(3RS,4SR)-3-Fluoro-1-[4-(1-isopropyl-2-methyl-1H-imidazo[4,5-c]pyridin-6-ylamino)pyrimidin-2-yl]-4-methylpiperidin-4-ol;

[((3RS,4SR)-3-Fluoro-4-methoxy-4-methylpiperidin-1-yl)pyrimidin-4-yl]-(1-isopropyl-2-methyl-1H-imidazo[4,5-c]pyridin-6-yl)amine;

(3RS,4RS)-3-Fluoro-1-[4-(1-isopropyl-2-methyl-1H-imidazo[4,5-c]pyridin-6-ylamino)pyrimidin-2-yl]-4-methylpiperidin-4-ol;

(3RS,4RS)-3-Fluoro-1-[4-(2-hydroxymethyl-1-isopropyl-1H-imidazo[4,5-c]pyridin-6-ylamino)pyrimidin-2-yl]-4-methylpiperidin-4-ol;

(3RS,4SR)-3-Fluoro-1-{4-[2-((R)-1-hydroxyethyl)-1-((S)-2,2,2-trifluoro-1-methylethyl)-1H-imidazo[4,5-c]pyridin-6-ylamino]pyrimidin-2-yl}-4-methylpiperidin-4-ol;

[2-(4,4-Difluoropiperidin-1-yl)pyrimidin-4-yl]-(1-isopropyl-2-methyl-1H-imidazo[4,5-c]pyridin-6-yl)amine;

(R)-1-[4-(1-Isopropyl-2-methyl-1H-imidazo[4,5-c]pyridin-6-ylamino)pyrimidin-2-yl]pyrrolidine-3-carbonitrile;

(S)-1-[4-(1-Isopropyl-2-methyl-1H-imidazo[4,5-c]pyridin-6-ylamino)pyrimidin-2-yl]pyrrolidine-3-carbonitrile;

(R)-1-[4-(1-Isopropyl-2-methyl-1H-imidazo[4,5-c]pyridin-6-ylamino)pyrimidin-2-yl]pyrrolidin-3-ol;

(S)-1-[4-(1-Isopropyl-2-methyl-1H-imidazo[4,5-c]pyridin-6-ylamino)pyrimidin-2-yl]pyrolidin-3-ol;

1-[4-(1-Isopropyl-2-methyl-1H-imidazo[4,5-c]pyridin-6-ylamino)pyrimidin-2-yl]-4-methylpiperidin-4-ol;

4-[2-((R)-1-hydroxyethyl)-1-((S)-2,2,2-trifluoro-1-methylethyl)-1H-imidazo[4,5-c]pyridin-6-ylamino]pyrimidin-2-yl}-4-methylpiperidin-4-ol;

(S)-1-[6-[2-((cis)-3-Fluoro-4-methoxypiperidin-1-yl)pyrimidin-4-ylamino]-1-((S)-2,2,2-trifluoro-1-methylethyl)-1H-imidazo[4,5-c]pyridin-2-yl]ethanol;

(3S,4R)-3-Fluoro-1-{4-[2-((S)-1-hydroxyethyl)-1-((S)-2,2,2-trifluoro-1-methylethyl)-1H-imidazo[4,5-c]pyridin-6-ylamino]pyrimidin-2-yl}piperidin-4-ol;

(3R,4S)-3-Fluoro-1-{4-[2-((S)-1-hydroxyethyl)-1-((S)-2,2,2-trifluoro-1-methylethyl)-1H-imidazo[4,5-c]pyridin-6-ylamino]pyrimidin-2-yl}piperidin-4-ol;

(3 S,4R)-3-Fluoro-1-{4-[2-((R)-1-hydroxyethyl)-1-((R)-2,2,2-trifluoro-1-methylethyl)-1H-imidazo[4,5-c]pyridin-6-ylamino]pyrimidin-2-yl}piperidin-4-ol;

(3R,4S)-3-Fluoro-I 1-{4-[2-((R)-1-hydroxyethyl)-1-((R)-2,2,2-trifluoro-1-methyl ethyl)-1H-imidazo[4,5-c]pyridin-6-ylamino]pyrimidin-2-yl}piperidin-4-ol;

(3S,4R)-3-Fluoro-1-{4-[2-((S)-1-hydroxyethyl)-1-((R)-2,2,2-trifluoro-1-methylethyl)-1H-imidazo[4,5-c]pyridin-6-ylamino]pyrimidin-2-yl}piperidin-4-ol;

(3R,4S)-3-Fluoro-1-{4-[2-((S)-1-hydroxyethyl)-1-((R)-2,2,2-tri fluoro-1-methylethyl)-1H-imidazo[4,5-c]pyridin-6-ylamino]pyrimidin-2-yl}piperidin-4-ol;

(6-((2-((1S,4S)-2-oxa-5-azabicyclo[2.2.1]heptan-5-yl)pyrimidin-4-yl)amino)-1-isopropyl-1H-imidazo[4, 5-c]pyridin-2-yl)methanol;

(6-((2-(2-azabicyclo[2.1.1]hexan-2-yl)pyrimidin-4-yl)amino)-1-isopropyl-1H-imidazo[4,5-c]pyridin-2-yl)methanol;

9-(4-((2-(hydroxymethyl)-1-isopropyl-1H-imidazo[4,5-c]pyridin-6-yl)amino)pyrimidin-2-yl)-1-oxa-4,9-diazaspiro[5.5]undecan-3-one;

4-(6-(2-(1-(Cyclopropylsulfonyl)-1H-pyrazol-4-yl)pyrimidin-4-ylamino)-2-(hydroxymethyl)-1H-imidazo[4, 5-c]pyridin-1-yl)pyrrolidin-2-one;

(6-(2-(1-(Cyclopropylsulfonyl)-1H-pyrazol-4-yl)pyrimidin-4-ylamino)-1-(4-methoxy-2-methylbutan-2-yl)-1H-imidazo[4,5-c]pyridin-2-yl)methanol;

(6-(2-(1-(Cyclopropylsulfonyl)-1H-pyrazol-4-yl)pyrimidin-4-ylamino)-1-(4,4,4-trifluorobutan-2-yl)-1H-imidazo[4,5-c]pyridin-2-yl)methanol;

(6-(2-(1-(Cyclopropylsulfonyl)-1H-pyrazol-4-yl)pyrimidin-4-ylamino)-1-(3-methylcyclopentyl)-1H-imidazo[4,5-c]pyridin-2-yl)methanol;

(6-(2-(1-(Cyclopropylsulfonyl)-1H-pyrazol-4-yl)pyrimidin-4-ylamino)-1-(2-methylcyclopropyl)-1H-imidazo[4,5-c]pyridin-2-yl)methanol;

(1-Isopropyl-6-(2-((±)-(trans)-4-methoxy-3-methylpiperidin-1-yl)pyrimidin-4-ylamino)-1H-imidazo[4,5-c]pyridin-2-yl)methanol;

1-sec-Butyl-6-(2-(1-(cyclopropylsulfonyl)-1H-pyrazol-4-yl)pyrimidin-4-ylamino)-N-(1,4-dioxepan-6-yl)-1H-pyrrolo[3,2-c]pyridine-3-carboxamide;

(3S,4S,5R)-3,5-Difluoro-1-{4-[2-((R)-1-hydroxyethyl)-1-((S)-2,2,2-trifluoro-1-methyl ethyl)-1H-imidazo[4,5-c]pyridin-6-ylamino]pyrimidin-2-yl}piperidin-4-ol;

(3SR,4SR)-3-fluoro-1-(4-((2-(hydroxymethyl)-1-isopropyl-1H-imidazo[4,5-c]pyridin-6-yl)amino)pyrimidin-2-yl)-3-methylpiperidin-4-ol;

1-sec-Butyl-6-(2-(1-(cyclopropylsulfonyl)-1H-pyrazol-4-yl)pyrimidin-4-ylamino)-N-(2-hydroxyethyl)-1H-pyrrolo[3,2-c]pyridine-3-carboxamide;

1-sec-Butyl-6-(2-(1-(cyclopropylsulfonyl)-1H-pyrazol-4-yl)pyrimidin-4-ylamino)-N-(2,2,2-trifluoroethyl)-1H-pyrrolo[3,2-c]pyridine-3-carboxamide;

1-sec-Butyl-6-(2-(1-(cyclopropylsulfonyl)-1H-pyrazol-4-yl)pyrimidin-4-ylamino)-N-(4-hydroxycyclohexyl)-1H-pyrrolo[3,2-c]pyridine-3-carboxamide;

(±)-(3RS,5RS)-3,5-Difluoro-1-[4-(1-isopropyl-2-methyl-1H-imidazo[4,5-c]pyridin-6-ylamino)pyrimidin-2-yl]piperidin-4-ol; or (3R,4s,5S)-3,5-Difluoro-1-[4-(1-isopropyl-2-methyl-1H-imidazo[4,5-c]pyridin-6-ylamino)pyrimidin-2-yl]piperidin-4-ol.

* * * * *